US011324827B2

(12) United States Patent
Weng et al.

(10) Patent No.: US 11,324,827 B2
(45) Date of Patent: *May 10, 2022

(54) MULTIFUNCTIONALIZED POLYETHYLENE GLYCOL DERIVATIVE AND PREPARATION METHOD THEREFOR

(71) Applicant: XIAMEN SINOPEG BIOTECH CO., LTD., Xiamen (CN)

(72) Inventors: Wengui Weng, Xiamen (CN); Chao Liu, Xiamen (CN); Ce Yan, Xiamen (CN); Shaofeng Wu, Xiamen (CN); Chun Zhou, Xiamen (CN)

(73) Assignee: Xiamen Sinopeg Biotech Co., Ltd., Fujian (CN)

( * ) Notice: Subject to any disclaimer, the term of this patent is extended or adjusted under 35 U.S.C. 154(b) by 83 days.

This patent is subject to a terminal disclaimer.

(21) Appl. No.: 15/516,259

(22) PCT Filed: Sep. 30, 2015

(86) PCT No.: PCT/CN2015/091193
§ 371 (c)(1),
(2) Date: Jun. 19, 2017

(87) PCT Pub. No.: WO2016/050210
PCT Pub. Date: Apr. 7, 2016

(65) Prior Publication Data
US 2017/0312363 A1  Nov. 2, 2017

(30) Foreign Application Priority Data

Oct. 1, 2014   (CN) .......................... 201410526707.6
Jun. 23, 2015  (CN) .......................... 201510349134.9

(51) Int. Cl.
  A61K 47/10   (2017.01)
  C08G 65/334  (2006.01)
  C08G 65/323  (2006.01)
  C08G 65/08   (2006.01)
  C08G 65/329  (2006.01)
  C08G 65/00   (2006.01)

(52) U.S. Cl.
  CPC ............ A61K 47/10 (2013.01); C08G 65/002 (2013.01); C08G 65/08 (2013.01); C08G 65/323 (2013.01); C08G 65/329 (2013.01); C08G 65/334 (2013.01); C08G 2650/36 (2013.01); C08G 2650/58 (2013.01)

(58) Field of Classification Search
  CPC ..................................................... A61K 47/10
  See application file for complete search history.

(56) References Cited

U.S. PATENT DOCUMENTS 5,811,510 A     9/1998  Papisov
6,458,953 B1 * 10/2002  Jones ................... C07C 233/69
                                                       530/402
7,144,978 B2   12/2006  Huang et al.
7,790,150 B2    9/2010  Papisov et al.
7,838,619 B2   11/2010  Papisov
2014/0073810 A1  3/2014  Urban et al.
2016/0326317 A1 11/2016  Yoshioka et al.
2017/0312363 A1 11/2017  Weng et al.
2018/0214561 A1  8/2018  Weng et al.

FOREIGN PATENT DOCUMENTS

| CN | 1569892 A   | 1/2005 |
| CN | 101831065 A | 9/2010 |
| CN | 103044675 A | 4/2013 |
| CN | 103881084 A | 6/2014 |
| CN | 104530413 A | 4/2015 |
| CN | 104530415 A | 4/2015 |

(Continued)

OTHER PUBLICATIONS

CAS Registry No. 641632-679, which entered STN on Jan. 26, 2004 (Year: 2004).*
Zacchigna et al. European Journal of Pharmaceutical Sciences 2007, 30, 343-350 (Year: 2007).*
Song et al. Soft Matter, 2012, 8 3419-3428 (Year: 2012).*
Abbasi et al., Nanoscale Research Letters, 9(247):1-10 (2014).
Ahmed and Tanaka, J. Org. Chem., 71:9884-86 (2006).
Albertazzi et al., Biomacromolecules, 13:4089-97 (2012).
Brocchini et al., Advanced Drug Delivery Reviews, 60:3-12 (2008).
Chan et al., Macromolecules, 43:4937-42 (2010).
Chang et al., Macromolecules, 33:4496-500 (2000).
Cheng et al., Chem. Soc. Rev., 40:2673-703 (2011).
Conte et al., Chem. Commun., 47:11086-88 (2011).
French et al., Angew. Chem., 121:1274-78 (2009).

(Continued)

Primary Examiner — Matthew P Coughlin
(74) Attorney, Agent, or Firm — RatnerPrestia

(57) ABSTRACT

Disclosed are a multifunctionalized polyethylene glycol derivative and a preparation method therefor. The derivative has an H-shaped structure as represented by formula (1) and comprises one linear core LPEG and four PEG branch chains, where $n_1$, $n_2$, $n_3$, and $n_4$ respectively are the degrees of polymerization of the branch chains, $U_1$ and $U_2$ are trivalent branching groups connecting the core LPEG to two of the PEG branch chains, $F_1$ and $F_2$ contain a functional group or a protected form $R_{01}$ thereof and may or may not contain a branched group G, correspondingly, the number of $R_{01}$ is one or more, $F_1$ and $F_2$ are either identical or different, any one linking group in the molecule or any linking group formed with an adjacent heteroatom group can either remain stable or be degraded, and any one PEG segment in the molecule is discretely polydispersed or monodispersed. The multifunctional polyethylene glycol is flexible and diverse in terms of branch structures and the lengths of branching arms, has various parameters and performance indicators that are adjustable and easy to control, and has a broad applicability.

36 Claims, No Drawings

(56) References Cited

FOREIGN PATENT DOCUMENTS

| | | | |
|---|---|---|---|
| CN | 104530417 A | 4/2015 | |
| CN | 104877127 A | 9/2015 | |
| EP | 2360203 A1 | 8/2011 | |
| EP | 2518098 A1 | 10/2012 | |
| EP | 3315531 A1 | 5/2018 | |
| WO | 2008066787 A1 | 6/2008 | |
| WO | WO 2011/123031 A1 | 10/2011 | |
| WO | WO 2012/158622 A2 | 11/2012 | |
| WO | WO 2013/147015 A1 | 10/2013 | |
| WO | 2016050208 A1 | 4/2016 | |
| WO | 2016050209 A1 | 4/2016 | |
| WO | 2016050210 A1 | 4/2016 | |
| WO | 2016206540 A1 | 12/2016 | |

OTHER PUBLICATIONS

Geschwind and Frey, Macromolecules, 46:3280-87 (2013).
Greenwald et al., J. Org. Chem., 60:331-36 (1995).
Hoogenboom, Angew. Chem. Int. Ed., 49:3415-17 (2010).
Ihre et al., J. Am. Chem. Soc., 123:5908-17 (2001).
Kahveci et al., Macromol. Chem. Phys., 215:566-71 (2014).
Khire et al., J. Polymer Science: Part A: Polymer Chemistry, 46:6896-906 (2008).
Kim et al., Bioorg. Med. Chem. Lett., 25:38-42 (2015).
Li et al., Macromol. Biosci., 11:1570-78 (2011).
Mangold et al., Polym. Chem., 3:1714-21 (2012).
Mommer et al., Macromol. Rapid Commun., 35:1986-93 (2014).
Monfardini et al., Bioconjugate Chem., 6:62-69 (1995).
Movellan et al., Biomaterials, 35:7940-50 (2014).
Povoski et al., Expert Rev. Mol. Diagn., 13(4):315-19 (2013).
Rajan et al., J. Controlled Release, 194:301-9 (2014).
Schömer et al., J. Polymer Science: Part A: Polymer Chemistry, 51:995-1019 (2013).
Schömer and Frey, Macromolecules, 45:3039-46 (2012).
Wang et al., Macromol. Biosci., 11:1553-62 (2011).
Wilms et al., Macromol. Rapid Commun., 31:1811-15 (2010).
Xi et al., Adv. Funct. Mater., 24:2572-90 (2014).
Zhang et al., Angew. Chem. Int. Ed., 54:3763-67 (2015).
Zhu et al., Langmuir, 26(11):8875-81 (2010).
PCT/CN2015/091193 International Search Report issued by Chinese Patent Office dated Jan. 6, 2015.
Im et al., Biomaterials, 34(8):2098-106 (2013).

* cited by examiner

MULTIFUNCTIONALIZED POLYETHYLENE GLYCOL DERIVATIVE AND PREPARATION METHOD THEREFOR

CROSS-REFERENCE TO RELATED APPLICATIONS

This application is a U.S. National Phase Application of International Application No. PCT/CN2015/091193, filed Sep. 30, 2015 which claims priority to Chinese Application Nos. 201410526707.6, filed Oct. 1, 2014 and 201510349134.9, filed Jun. 23, 2015.

TECHNICAL FIELD

The present invention relates to the field of polymer synthesis, especially a multifunctionalized polyethylene glycol compound, substance thereof and production methods thereof.

BACKGROUND OF THE INVENTION

PEGylation has been widely recognized as one of the most important approaches for drug modification. Wherein, Functionalized PEGs, owing to their active groups, are capable of modifying therapeutic drugs and bio-related substances by covalently binding to target molecules, normally small molecule organic drugs or biomolecules, including proteins, peptides, saccharides, lipids, oligonucleotides, affinity ligands, cofactors, liposomes, biomaterials and the like. The pegylated drugs would be endowed with many beneficial properties with respect to hydrophilicity, flexibility, antithrombogenicity, etc. Meanwhile, due to the steric repulsion effect, pharmaceutical drugs modified with polyethylene glycol can avoid the filtration through glomeruli in the kidney and bio-reactions such as immunoreactions, so that longer half-life in blood is achieved compared with the unmodified forms. For example, it has been shown that the water-insoluble drug paclitaxel, when coupled to polyethylene glycol, becomes water-soluble (Greenwald et al., J. Org. Chem. 1995, 331-336).

In 1995, Monfardini and coworkers synthesized a branched polyethylene glycol with two arms, also denoted as "V-shaped" PEG, wherein two linear monomethoxy polyethylene glycol chains were directly linked to the two amino groups of lysine followed by activation of the carboxyl group as succinimidyl ester, and furthermore modification of enzymes with the branched polyethylene glycol was investigated (Bioconjugate Chem. 1995, 6, 62-69). Since then, it has gained popularity as a tool to produce a monofunctional branched PEG and drug derivatives thereof, and has already been applied in three commercially available pharmaceutical products. Compared with a linear polyethylene glycol having the same molecular weight, a branched polyethylene glycol, in virtue of its particular molecular structure, can provide an "umbrella-like" protective coverage around protein surface which increases steric hindrance around the drug molecule, inhibit attack from other macromolecules in vivo more effectively so as to decrease inactivation and enzymolysis in body, and therefore enable a more prolonged circulation time of pegylated drugs.

The conventionally commercial branched polyethylene glycol derivatives with two polyethylene glycol chains, representively "V-shaped", only has a single active group capable of reacting with drug molecules, which result in low drug loading and very limited applications.

Furthermore, with respect to pegylated drugs, because the binding site may be located at or nearby the active moiety, or because of the introduction of steric effect, it is most likely to result in decrease or disappearance of activities of pegylated drugs. What's more, for conventional administration methods, such as parenteral administration, oral administration, etc., the drug molecules not only act on the lesion site, but also accumulate in normal tissues, and thus cause somewhat or very severe toxic side effects. Although the toxic side effects can be greatly reduced via pegylation for many drugs, the biosafety requirement for some drugs especially for anticancer drugs still cannot be satisfied by using available pegylation technique.

Therefore, it is necessary to develop a novel multifunctionalized polyethylene glycol, also termed as multifunctional polyethylene glycol, to achieve flexible and diverse characteristics in terms of branched structures, the length of branch arms, initiators, production methods, etc., adjustable and controllable parameters and properties as well as broad applications, and also to effectively combine high drug loading, impactful protection of drug molecules and high modification efficiency during pegylating. Furthermore, problems such as how to improve the maintenance of drug activity, or how to realize release of highly active drugs are urgently to be improved or resolved. It is also necessary to further reduce the toxic side effects of drugs, or increase the distribution of drugs in lesion tissues.

SUMMARY OF THE INVENTION

The aim of the present invention is to overcome the above-mentioned shortcomings of the prior art, and to provide an H-shaped multifunctionalized polyethylene glycol compound and production methods thereof.

The above-mentioned aim can be achieved as follows.

The H-shaped multifunctionalized polyethylene glycol compound is represented by the following general formula (1):

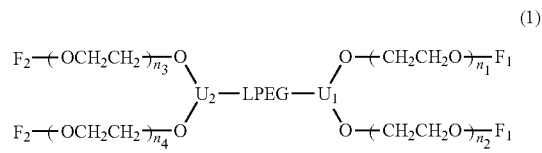

said H-shaped structure consists of one linear main chain LPEG and four branch chains, and the total number of oxyethylene units of the linear PEG main chain and four PEG branch chains is no more than 5000;

wherein, LPEG is the linear main chain; LPEG is a polyethylene glycol segment which contains one, two, three or 4 to 150 polyethylene glycol blocks; the number of oxyethylene units of LPEG is an integer from 2 to 2000;

wherein, $n_1$, $n_2$, $n_3$ and $n_4$ represent the degree of polymerization of the four PEG branch chains, respectively, are each independently a value from 2 to 2000, and can be the same or different in one molecule; LPEG and PEG branch chains corresponding to $n_1$, $n_2$, $n_3$ and $n_4$ are each independently polydisperse or monodisperse;

wherein, $U_1$ and $U_2$ are trivalent branching groups connecting LPEG and respective two PEG branch chains; the structure of $U_1$ is

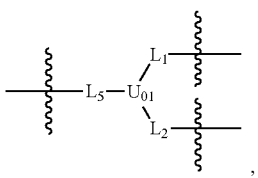

and the structure of $U_2$ is

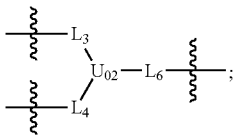

$U_{01}$ and $U_{02}$ are each independently a trivalent group; wherein, $L_1$, $L_2$, $L_3$ and $L_4$ are linking groups that connect PEG moieties with a corresponding oxyethylene-unit number of $n_1$, $n_2$, $n_3$ and $n_4$, respectively; $L_5$ and $L_6$ are linking groups that connect with linear PEG main chain, respectively; $L_1$, $L_2$, $L_3$, $L_4$, $L_5$ and $L_6$ are each independently present or absent, and can be the same or different in one molecule;

wherein, $F_1$ and $F_2$ are each independently an unprotected or protected functional group;

wherein, $F_1$ and $F_2$ are each independently and correspondingly represented as respective

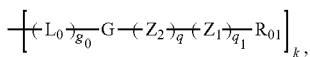

and can be the same or different from each other in one molecule;

wherein,

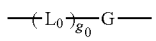

is a linking group that connects with corresponding PEG moiety; wherein, k is an integer of 1 or from 2 to 250; g is 0 or 1; G is a linking group of trivalence or higher valence; when g is 0, k would be equal to 1; when g is 1, k would be an integer from 2 to 250, and the valence of corresponding G is k+1; $L_0$ is a divalent linking group; $g_0$ is 0 or 1, or an integer from 2 to 1000; q and $q_1$ are each independently 0 or 1; $Z_1$ and $Z_2$ are each independently a divalent linking group; $R_{01}$ is an unprotected or protected functional end-group; in one molecule, k, G, g, $L_0$, $g_0$, $Z_2$, q, $Z_1$, $q_1$ and $R_{01}$ of $F_1$ are each independently the same as or different from that of $F_2$.

Wherein, in one molecule, LPEG, $U_1$, $U_2$, $U_{01}$, $U_{02}$, $L_1$, $L_2$, $L_3$, $L_4$, $L_5$, $L_6$, $L_0(F_1)$, $G(F_1)$, $Z_1(F_1)$, $Z_2(F_1)$, $L_0(F_2)$, $G(F_2)$, $Z_1(F_2)$, $Z_2(F_2)$, and the joint linking group formed by any said group with its adjacent heterosubstituted group can be each independently either stable or degradable;

Compared with the prior art, the present invention brings the following beneficial effects:

For translation, the phrase "be different" used in the present invention means "be not identical" and allows the presence of two identical objects as far as that there exist at least two different objects.

(1) The application of initiators based on linear polyethylene glycols can take full advantage of the adjustability of the molecular weight, diversity of molecular structures, and variousness of different molecular weights and molecular structures, and thus synthesize novel initiators with diverse structures and characteristics. (2) Compared with conventional small molecular initiators, initiators based on linear polyethylene glycols provide more manners and advantages in the aspect of isolation and purification. (3) The H-shaped design can modulate the distance between branch chains of two sides via changing the length of linear main chain, and help control properties of H-shaped multifunctionalized polyethylene glycols of a given molecular weight by regulating respective lengths of main chain and branch chains. (4) With respect to one terminal functional group, the functional end-groups thereof could be one or more in quantities, which increases the number of active groups contained in polyethylene glycol derivatives, improves the drug loading greatly and broadens applications. (5) The reaction efficiency would be increased when modifying drugs. (6) The combination of diversity in production methods and quantity in active sites, allows modification of two different drugs in one molecule or introduction of functional moieties capable of promoting pharmaceutical efficacy, so as that the drug loading can be raised, and meanwhile the function of efficacy-promoting moieties can also be significantly exerted. (7) With respect to an H-shaped functionalized polyethylene glycol in the present invention, degradable groups can be flexibly introduced into its structure or a pegylated bio-related substance thereof in the subsequent applications. It allows weakening of steric effect through the breakage of modified forms into low-molecular-weight moieties under stimulation of enzyme, light illumination, temperature, an acidic condition, a basic condition, an oxidation-reduction condition, etc. It also allows generation of highly active drug molecules via the dissociation of bio-related substances within pegylated forms from polyethylene glycol moieties. What's more, the pharmacokinetics and tissue distribution profile can also be improved. (8) A heterofunctionalized design can be introduced in the present invention, which allows unpegylated bio-related substance to be terminated by hydroxyl groups in place of methoxy groups in order to reduce the immunogenicity of pegylated drugs. (9) The heterofunctionalized design in the present invention also allows one PEG derivative to be connected with two kinds of bio-related substances in one molecule. As a result, functional moieties, such as targeting factors, fluorescent groups and the like can also be introduced while the drugs are pegylated. The introduction of targeting factors can improve tissue distribution profile of drugs, weaken adverse effects against normal tissues, and thus decrease toxic side effects. The introduction of fluorescent groups can facilitate the detection of pharmacokinetics, tissue distribution of drugs, etc.

DETAILED DESCRIPTION OF THE INVENTION

The related terms of the present invention are defined as follows.

In the present invention, hydrocarbons refer to a class of compounds that contain only carbon atoms and hydrogen atoms.

In the present invention, hydrocarbons include aliphatic hydrocarbons and aromatic hydrocarbons (also referred to as arenes, or aromatics, or aryl hydrocarbons). Hydrocarbons containing neither phenyl rings nor hydrocarbyl-substituted phenyl rings are defined as aliphatic hydrocarbons. Hydrocarbons containing at least one phenyl ring or hydrocarbyl-substituted phenyl ring are defined as aromatic hydrocarbons. An aromatic hydrocarbon can contain one or more aliphatic hydrocarbyl groups, such as toluene, diphenylmethane, 2,3-dihydroindene, etc.

Hydrocarbons include saturated hydrocarbons and unsaturated hydrocarbons. All aromatic hydrocarbons are unsaturated hydrocarbons. Saturated aliphatic hydrocarbons are also termed as alkanes. The degree of unsaturation of unsaturated aliphatic hydrocarbons is not particularly limited. For example, examples of unsaturated aliphatic hydrocarbons include but are not limited to alkenes containing a carbon-carbon double-bond, alkynes containing a carbon-carbon triple-bond, dienes containing two conjugated carbon-carbon double-bonds, and the like. Aromatic hydrocarbons with their aliphatic moiety to be saturated are also termed as arylalkanes, such as toluene.

The structures of hydrocarbons are not particularly limited. They can be linear structures (or straight chains) which have no pendant groups, branched structures which bear pendant groups, cyclic structures which contain at least one ring, dendritic structures, comb-like structures, hyperbranched structures, etc. If no particular definitions are concerned, preferable structures include linear structures without pendant groups, branched structures bearing pendant groups and cyclic structures containing at least one ring, corresponding to linear hydrocarbons (acyclic unbranched hydrocarbons), branched hydrocarbons and cyclic hydrocarbons (also cyclohydrocarbons), respectively. Wherein, hydrocarbons that contain no rings are termed as open-chain hydrocarbons (acyclic hydrocarbons), including but not limited to linear chain structures without pendant groups, and branched structures bearing pendant groups. Open-chain hydrocarbons fall into the scope of aliphatic hydrocarbons, so linear hydrocarbons are also referred to as linear aliphatic hydrocarbons, while branched hydrocarbons are also referred to as branched aliphatic hydrocarbons.

In the present invention, a ring structure, also referred to as a cyclic structure or a cyclic unit or a ring unit, is not particularly limited, as long as it contains at least one closed-end ring. Ring-membering atoms that are linked together end-to-end in a ring construct the ring skeleton.

Hydrocarbons containing at least one cyclic unit are termed as cyclic hydrocarbons, wherein the corresponding cyclic unit is a full-carbon ring completely composed of carbon atoms.

According to difference of source, cyclic hydrocarbons include aliphatic cyclic hydrocarbons (also referred to as alicyclic hydrocarbons or aliphatic cyclohydrocarbons) and aromatic hydrocarbons (also referred to as aromatic cyclic hydrocarbons).

Wherein, aliphatic hydrocarbons containing closed-end carbon rings are termed as aliphatic cyclic hydrocarbons (also alicyclic hydrocarbons), and the corresponding cyclic unit is an alicyclic ring (or an aliphatic ring). Aliphatic cyclic hydrocarbons include saturated aliphatic cyclic hydrocarbons and unsaturated aliphatic cyclic hydrocarbons. Saturated aliphatic cyclic hydrocarbons are also referred to as cycloalkanes. According to the difference of the degree of unsaturation, unsaturated aliphatic cyclic hydrocarbons can include cycloalkenes (or cycloolefins; or cyclic alkenes), cycloalkynes (cyclic alkynes), cyclodienes (cyclic dienes), etc.

All the aromatic hydrocarbons belong to cyclic hydrocarbons and contain at least one phenyl ring or a substituted phenyl ring, wherein alicyclic rings can be present or absent.

In the present invention, an aromatic ring (also referred to as an aryl ring) is particularly referred to as a phenyl ring or a fused ring formed by two or more joint phenyl groups.

The structural units to constitute ring skeletons are not particularly limited, and they can have nested cyclic structures or not. Examples of structural units without nested cyclic structures include cyclopentane, cyclohexane, cycloheptane, benzene, furan, pyridine, benzotriazole, fluorene and so on, while cyclodextrins have a nested cyclic structure made up of several D-glucopyranose monocyclic ring unit (D-glucopyranoside unit) bound together end-to-end in a ring.

Non-carbon atoms except a hydrogen atom are defined as heteroatoms. In the present invention, heteroatoms are not particularly limited, including but not limited to O, S, N, P, Si, F, Cl, Br, I, B, etc.

Relative to the carbon rings, cyclic structures containing ring-membering heteroatoms are termed as heterorings (or heterocycles). Alicyclic rings with any ring-membering atom to be replaced by heteroatoms correspond to heteroalicyclic rings, and aromatic rings with any ring-membering atom to be replaced by heteroatoms correspond to heteroaromatic rings (heteroaryl rings).

According to heteroatoms of the ring skeleton (ring-membering heteroatoms), heterorings include different types, including but not limited to oxa-, aza-, thia-, phospha-, etc.

Examples of aza-compounds include pyridine, pyran, pyrrole, carbazole, indole, isoindole, pyrimidine, imidazole, purine, pyrazole, pyrazine, pyridazine, indazole, quinolinoazole (azole fused quinoline), triazole, tetraazafluorene and the like.

Examples of oxa-compounds include ethylene oxide, furan, tetrahydrofuran, pyran, tetrahydropyran, dioxane, propylene oxide and the like.

Examples of thia-compounds include thiophene and the like.

The number of heteroatoms is not particularly limited, and can be one or more. For example, heterorings that contain only one heteroatom include furan, tetrahydrofuran, pyridine, pyran, pyrrole, tetrahydropyran, carbazole, indole, isoindole and the like, heterorings that contain two heteroatoms include pyrimidine, isoxazole, imidazole, pyrazole, pyrazine, pyridazine, thiazole, isothiazole, indazole, quinolinoazole and the like, heterorings that contain three heteroatoms include triazole and triazine, and heterorings containing four heteroatoms include tetraazafluorene, purine, etc.

When heterorings contain two or more heteroatoms, heteroatoms therein can be identical or different.

Examples of heterorings containing two or more identical heteroatoms include but are not limited to above-mentioned aza-, oxa-, and thia-compounds.

Examples of heterorings containing different species of heteroatoms include aza-oxa compounds such as oxazole, isoxazole, aza-oxa-cyclopropane and the like, and aza-thia-compounds such as thiazole, isothiazole and the like.

When polycyclic compounds contain two or more heteroatoms, the positions of heteroatoms are not particularly limited. They can be located within one ring, e.g., benzotriazole, or be positioned among different rings, e.g., purine. A heteroatom herein can also be situated at the common bond shared by adjacent rings, e.g.,

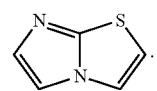

The number of cyclic units of a molecule is not particularly limited. Compounds having only one closed cyclic unit are defined as monocyclic compounds. For compounds having at least two rings which share at least one atom, are defined as polycyclic compounds (or polycycles). According to the number of rings, polycyclic compounds can be included by bicyclic compounds (e.g., norbornene, naphthalene, indole, isoindole, indazole, benzotriazole, benzopyran, benzothiophene and quinolinoazole), tricyclic compounds (e.g., adamantane, anthracene, phenanthrene and fluorene), tetracyclic compounds (e.g., pyrene), and so on.

The linking manner between two or more cyclic rings of polycyclic rings is not particularly limited. Two rings to be connected by sharing only one common atom would form a spirocyclic ring. Two rings to be connected by sharing a common edge (meaning that they share two adjacent skeleton atoms) would form a condensed ring (also a fused ring), e.g., anthracene, and a benzoheteroring. Two rings to be connected by sharing a bridge consisting of two bridged atoms would form a spiro-ring, wherein the bridgehead atoms are defined as any atom that is not a hydrogen, and that is part of the skeletal framework of the molecule that is bonded to three or more other skeletal atoms, e.g., norbornene, adamantine. What's more, diphenyl which has two phenyl rings possesses no shared atoms and thus does not fall into the scope of polycyclic compounds. The shared common atoms can be shared by two or more rings, e.g., pyrene.

Any two connected rings of polycyclic rings can each independently be an alicyclic ring or a hetero-alicyclic ring, or each independently be an aromatic ring (an aryl ring) or a heteroaromatic ring (a heteroaryl ring), or each independently be an alicyclic ring, an aromatic ring, a heteroalicyclic ring or a heteroaromatic ring.

Monocyclic rings being heterosubstituted which have ring-membering heteroatoms are termed as heterosubstituted monocyclic rings (or heterosubstituted monorings or heteromonorings), such as furan, tetrahydrofuran, pyridine, pyran, dioxane, cyclic isomers of glucose, and the like.

Polycyclic rings being heterosubstituted which have ring-membering heteroatoms are termed as heterosubstituted polycyclic rings (or heteropolycyclic rings or heteropolyrings). According to structural difference, heteropolycyclic rings include heterospirocyclic rings, heterobridged cyclic rings, and hetero-condensed cyclic rings (or heterosubstituted condensed rings or heterosubstituted fused rings), correspond to those rings with ring-membering atoms to be replaced by heteroatoms including spirocyclic rings (spirorings), bridged cyclic rings (bridged rings) and condensed cyclic rings (condensed rings), respectively.

Condensed rings include condensed aromatic rings (or condensed aryl rings, or fused aromatic rings, or fused aryl rings) and condensed heterorings (or fused heterorings). Wherein, condensed aryl rings correspond to the combination of two or more phenyl rings. Wherein, heterocondensed rings are condensed rings that contain heterorings, also referred to as condensed heterorings, and include aromatic condensed heterorings (or aryl-condensed heterorings) and heterocondensed heterorings (or heterofused heterorings). Wherein, aryl-condensed heterorings, also referred to as aryloheterorings, are condensed by aromatic rings and heterorings, representative examples including benzoheterorings, such as benzotriazole. Heterocondensed heterorings are condensed by heterorings and heterorings.

Heterosubstituted condensed aromatic rings which have one or more ring-membering heteroatoms correspond to heterocondensed aromatic rings.

In the present invention, rings deriving from hydrocarbons include but are not limited to cyclic structures selected from the group consisting of alicyclic rings, aromatic rings, monocyclic rings, polycyclic rings, spirorings, bridged rings, condensed rings, condensed aryl rings, condensed heterorings, aryl-condensed heterorings, aryloheterorings, benzoheterorings, heterocondensed heterorings, carbon rings, heterorings, aliphatic-derived heterorings, aromatic-derived heterorings, heterosubstituted monocyclic rings, heterosubstituted polycyclic rings, hetero-spirorings, hetero-bridged rings, hetero-condensed rings, hetero-alicyclic rings, hetero-aromatic rings, saturated alicyclic rings, unsaturated alicyclic rings, the like, and the combination of any two or more types of rings thereof. Generally, according to whether or not containing aromatic rings or heteroaromatic rings, those rings can be categorized into two types as follows:

Wherein, cyclic hydrocarbons include monocyclohydrocarbons (or monocyclic hydrocarbons) and polycyclohydrocarbons (or polycyclic ring hydrocarbons). Wherein, examples of monocyclic hydrocarbons include cyclobutane, cyclopentane, cyclohexane, benzene, etc., while examples of polycyclic hydrocarbons include anthracene, fluorine, etc. Polycyclic hydrocarbons include spiro-hydrocarbons, bridged hydrocarbons and condensed cyclic hydrocarbons (also referred to as condensed ring hydrocarbons, fused ring hydrocarbons, or fused cyclic hydrocarbons).

Wherein, with respect to polycyclic hydrocarbons, any two condensed rings thereof can be both alicyclic rings, such as norbornene, or be both phenyl rings, such as naphthalene, anthracene, pyrene and phenanthrene, or be the combination of an alicyclic ring and a phenyl ring, for example, such as 2,3-dihydroindene and the like. Condensed cyclic hydrocarbons (also referred to as condensed cyclic hydrocarbons, condensed ring hydrocarbons, fused ring hydrocarbons, or fused cyclic hydrocarbons) which are condensed by two or more phenyl rings are referred to as condensed aromatic hydrocarbons (or fused aromatic hydrocarbons).

According to the degree of unsaturation, cyclic hydrocarbons can also be categorized into saturated cyclic hydrocarbons and unsaturated cyclic hydrocarbons. Wherein, saturated cyclic hydrocarbons are cycloalkanes. Unsaturated cyclic hydrocarbons include unsaturated alicyclic hydrocarbons and aromatic hydrocarbons.

In the present invention, hydrocarbons with any atom to be replaced by heteroatoms are generally referred to as heterosubstituted hydrocarbons (or heterohydrocarbons). For translation, the term of "heterosubstituted" means a carbon atom to be replaced into a heteroatom, referred to as a skeleton-membering heteroatom, typically a ring-membering heteroatom. What should be noted is that, a hydrogen atom to be replaced into a substituent is described as "substituted"; when said substituent contains a heteroatom, it is also referred to as "heterosubstituted". In summary, "heterosubstituted" include substitution of a hydrogen atom with a heteroatom-containing substituent and replacement of a carbon atom with a heteroatom, and can generally refer to structural changes with introduction of heteroatoms.

According to the species difference of hydrocarbons to be heterosubstituted, heterosubstituted hydrocarbons include aliphatic-derived heterosubstituted hydrocarbons (or heterosubstituted aliphatic hydrocarbons) and aromatic-derived heterosubstituted hydrocarbons (or heterosubstituted aromatic hydrocarbons).

Aliphatic-derived heterosubstituted hydrocarbons refer to those derive from aliphatic hydrocarbons, including aliphatic-derived heterocyclic hydrocarbons (aliphatic-derived heterocyclohydrocarbons or heterosubstituted aliphatic cyclohydrocarbons) and aliphatic-derived open-chain heterosubstituted hydrocarbons (heterosubstituted aliphatic open-chain hydrocarbons). Saturated aliphatic-derived heterohydrocarbons are also termed as heteroalkanes.

Aromatic-derived heterosubstituted hydrocarbons refer to heterosubstituted hydrocarbons that derive from aromatic hydrocarbons, including but not limited to heteroaromatics (or heteroaryl hydrocarbons) and condensed heterosubstituted hydrocarbons (or condensed heterohydrocarbons, or fused heterohydrocarbons). Wherein, condensed heterocyclic hydrocarbons (or condensed heterocyclohydrocarbons, or fused heterocyclohydrocarbons) refer to condensed cyclohydrocarbons with ring-membering atoms to be replaced by heteroatoms, including aromatic condensed heterocyclic hydrocarbons (aryl-condensed heterocyclic hydrocarbons) and heterocondensed heterocyclic hydrocarbons, etc. Heterosubstituted arylalkanes (or aralkanes) which have heteroatoms refer to heteroarylalkanes.

Heterosubstituted hydrocarbons without ring units are generally referred to as open-chain heterohydrocarbons. All open-chain heterosubstituted hydrocarbons fall into the scope of aliphatic-derived heterosubstituted hydrocarbons (heterosubstituted aliphatic hydrocarbons).

Heterorings formed by substituting or replacing ring-membering atoms of cyclohydrocarbons (or cyclic hydrocarbons) with heteroatoms are referred to as heterocyclic hydrocarbons (or cyclic heterohydrocarbons). According to the species difference of cyclic hydrocarbons to be substituted or replaced, heterocyclic hydrocarbons (or cyclic heterohydrocarbons) include aliphatic-derived heterocyclic hydrocarbons (aliphatic-derived heterocyclohydrocarbons, or heterosubstituted aliphatic cyclohydrocarbons, or heterosubstituted alicyclic hydrocarbons) and aromatic-derived heterohydrocarbons.

Aliphatic-derived heterocyclic hydrocarbons are heterocyclic hydrocarbons derived from alicyclic hydrocarbons, such as 1,4-oxetane and 1,4-dioxane.

The heteroatoms of aromatic-derived heterosubstituted hydrocarbons can participate in forming the aromatic ring skeletal framework, also corresponding to heteroaromatics, such as pyridine and pyrimidine.

All condensed heterocyclic hydrocarbons fall into the scope of heterocyclic hydrocarbons, including but not limited to aryl-condensed heterocyclic hydrocarbons (e.g., benzotriazole), heterocondensed heterocyclic hydrocarbons, etc.

The term "group" in the present invention contains at least one atom, also referring to the residue radical of a compound molecule after removing one or more atoms. With respect to a compound, the residue group formed by removal of a group moiety is also denoted as "a residue". The valence of a group is not particularly limited, and examples include a monovalent group, a divalent group, a trivalent group, a tetravalent group, . . . , a hectovalent group, etc. Wherein, groups of valence equal to or greater than two are collectively defined as linkages (e.g., linking groups). A linkage can also contain only one atom, such as a divalent oxygen atom (an oxy group), a divalent sulfur atom (a thioxy group).

A hydrocarbon group represents the residue of a hydrocarbon molecule by removing at least one hydrogen atom. According to the number of removed hydrogen, hydrocarbon groups can include monovalent hydrocarbon groups (removing one hydrogen atom, also denoted as hydrocarbyl groups), divalent hydrocarbon groups (removing two hydrogen atoms, also referred to as hydrocarbylene groups), trivalent hydrocarbon groups (removing three hydrogen atoms) and the like. Accordingly, when removing n hydrogen atoms, the valence of the resulting hydrocarbon group is n. Hydrocarbon groups in the present invention particularly refer to monovalent hydrocarbon groups, also denoted as hydrocarbyl groups, if without particular instructions.

One or more hydrogen atoms of the above-described hydrocarbons, including aliphatic hydrocarbons, aromatic hydrocarbons (or aromatics, aryl hydrocarbons, arenes), arylalkanes (or aralkanes), saturated hydrocarbons, alkanes, unsaturated hydrocarbons, alkenes, alkynes, dienes, open-chain hydrocarbons, linear hydrocarbons (linear aliphatic hydrocarbons), branched hydrocarbons (branched aliphatic hydrocarbons), cyclohydrocarbons (or cyclic hydrocarbons), alicyclic hydrocarbons (or aliphatic cyclohydrocarbons), cycloalkanes, unsaturated alicyclic hydrocarbons, cycloalkenes (or cycloolefins, or cyclic alkenes), cycloalkynes (or cyclic alkynes), cyclodienes (or cyclic dienes), monocyclohydrocarbons (or monocyclic hydrocarbons), polycyclohydrocarbons (or polycyclic hydrocarbons), spirohydrocarbons, bridged hydrocarbons, condensed cyclic hydrocarbons (or condensed cyclohydrocarbons, or condensed ring hydrocarbons, or fused cyclic hydrocarbons, or fused ring hydrocarbons), condensed aromatic hydrocarbons (or condensed aryl hydrocarbons, or fused aromatic hydrocarbons), heterosubstituted hydrocarbons (or heterosubstituted hydrocarbons), aliphatic-derived heterosubstituted hydrocarbons (or heterosubstituted aliphatic hydrocarbons), open-chain heterohydrocarbons, heterocyclic hydrocarbons (or cyclic heterohydrocarbons, or heterocyclohydrocarbons), aliphatic-derived heterocyclic hydrocarbons (or heterosubstituted alicyclic hydrocarbons, heterosubstituted aliphatic cyclohydrocarbons), aromatic-derived heterosubstituted hydrocarbons (or heterosubstituted aromatic hydrocarbons), heteroaromatics (or heteroarylhydrocarbons), condensed heterocyclic hydrocarbons (condensed heterocyclohydrocarbons, or fused heterocyclic hydrocarbons), aromatic condensed heterocyclic hydrocarbons (or aromatic condensed heterocyclohydrocarbons, or aryl-fused heterocyclic hydrocarbons), heterocondensed heterocyclic hydrocarbons (heterocondensed heterocyclohydrocarbons, or heterofused heterocyclic hydrocarbons) and the like, can be substituted by any substituent (a heteroatom substituent or a group substituent), corresponding to substituted hydrocarbons, substituted aliphatic hydrocarbons, substituted aromatic hydrocarbons, substituted arylalkanes, substituted saturated hydrocarbons, substituted alkanes, substituted unsaturated hydrocarbons, substituted alkenes, substituted alkynes, substituted dienes, substituted open-chain hydrocarbons, substituted linear hydrocarbons (substituted linear aliphatic hydrocarbons), substituted branched hydrocarbons (substituted branched aliphatic hydrocarbons), substituted cyclohydrocarbons, substituted alicyclic hydrocarbons, substituted cycloalkanes, substituted unsaturated alicyclic hydrocarbons, substituted cycloalkenes, substituted cycloalkynes, substituted cyclodienes, substituted monocyclohydrocarbons, substituted polycyclohydrocarbons substituted spirohydrocarbons, substituted bridged hydrocarbons, substituted condensed cyclic hydrocarbons, substituted condensed aromatic hydrocarbons, substituted heterohydrocarbons, substituted aliphatic-derived heterohydrocarbons, substituted open-chain heterohydrocarbons, substituted heterocyclic hydrocarbons, substituted aliphatic-derived heterocyclic hydrocarbons, substituted aromatic-derived heterohydrocarbons, substituted heteroaromatics, substituted condensed heterocyclic hydrocarbons, substituted aryl-condensed heterocyclic hydrocarbons, substituted heterocondensed heterocyclic hydrocarbons and the like, respectively. In the present invention, the heteroatom used for substituting is referred to as "an atom substituent" (or "a substituting atom"), and the group used for substituting is referred to as "a group substituent" (or "a substituting group"). A substituent can be an atom substituent or a group substituent.

The above-mentioned heteroatom is not particularly limited and is preferably a halogen atom.

The group substituent is not particularly limited and can be a hydrocarbon group substituent or a heteroatom-containing group substituent. In the present invention, the group substituent can contain heteroatoms or not if without particular definitions.

Wherein the two hydrogen atoms of a secondary carbon atom can be independently substituted by two identical or different substituents (heteroatom-containing substituents or monovalent hydrocarbon groups), e.g., —C(CH$_3$)$_2$—, —CH(OCH$_3$)—, —CF(OCH$_3$)—, or be substituted by a common ring structure, e.g., 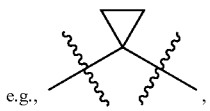

or be meanwhile substituted by only one heteroatom to form a linkage selected from, but not limited to, a carbonyl group, a thiocarbonyl group, an imino group and the like, e.g., an adenine group, a guanine group, a cytosine group, a uracil group, a thymine group, a N,N-dimethylguanine group, a 1-methylguanine group, a hypoxanthine group, a 1-methylhypoxanthine group and the like.

Wherein, when the hydrogen atom of a secondary or tertiary carbon of a linear hydrocarbon is substituted by a hydrocarbon group, the resulting compound is a branched hydrocarbon and the corresponding monovalent hydrocarbyl group serves as a pendant group (or a side group).

Deriving from a hydrocarbon selected from the group consisting of those above-described hydrocarbons, aliphatic hydrocarbons, aromatic hydrocarbons, arylalkanes (or aralkanes), saturated hydrocarbons, alkanes, unsaturated hydrocarbons, alkenes, alkynes, dienes (or alkadienes), open-chain hydrocarbons, linear hydrocarbons, branched hydrocarbons, cyclohydrocarbons (or cyclic hydrocarbons), alicyclic hydrocarbons (or aliphatic cyclohydrocarbons), cycloalkanes, unsaturated alicyclic hydrocarbons, monocyclohydrocarbons (or monocyclic hydrocarbons), polycyclohydrocarbons (or polycyclic hydrocarbons), heterohydrocarbons, aliphatic-derived heterohydrocarbons, heteroalkanes, open-chain heterohydrocarbons, heterocyclic hydrocarbons (or heterocyclohydrocarbons), aliphatic-derived heterocyclic hydrocarbons, aromatic-derived heterohydrocarbons, heteroaromatics, heteroarylalkanes (or heteroaralkanes), condensed cyclic hydrocarbons (or condensed cyclohydrocarbons, or condensed ring hydrocarbons, or fused ring hydrocarbons, or fused cyclic hydrocarbons), condensed aromatic hydrocarbons (or fused aryl hydrocarbons), condensed heterocyclic hydrocarbons (or condensed heterocyclohydrocarbons), aromatic condensed heterocyclic hydrocarbons (or aryl-condensed heterocyclic hydrocarbons), heterocondensed heterocyclic hydrocarbons (heterofused heterocyclic hydrocarbons) and the like, can correspondingly obtain a hydrocarbon substituent selected from residues including but not limited to hydrocarbon groups (hydrocarbyl groups), aliphatic groups, aryl groups, aryl-hydrocarbyl groups, aralkyl groups (or arylalkyl groups), saturated hydrocarbon groups, alkyl groups, unsaturated hydrocarbon groups, alkenyl groups, alkynyl groups, dienyl groups (or alkadienyl groups), alkenyl-hydrocarbyl groups, alkynyl-hydrocarbyl groups, dienyl-hydrocarbyl groups, open-chain hydrocarbon groups, linear hydrocarbon groups, branched hydrocarbon groups, cyclohydrocarbon groups (or cyclic hydrocarbon groups, or cyclohydrocarbyl groups, or cyclic hydrocarbyl groups), alicyclic hydrocarbon groups, cycloalkyl groups, unsaturated alicyclic hydrocarbon groups, monocyclohydrocarbon groups (or monocyclic hydrocarbon groups), polycyclohydrocarbon groups (or polycyclic hydrocarbon groups), condensed cyclic hydrocarbon groups, condensed aromatic hydrocarbon groups, heterohydrocarbon groups, heterocyclohydrocarbon groups, aliphatic-derived heterohydrocarbon groups, heteroalkyl groups, open-chain heterohydrocarbon groups, aliphatic-derived heterocyclohydrocarbon groups, aromatic-derived heterohydrocarbon groups, heteroaralkyl groups (or heteroarylalkyl groups), heteroaryl groups, heteroaryl-hydrocarbyl groups, condensed cyclohydrocarbon groups, condensed aryl groups, condensed heterocyclohydrocarbon groups, aryl-condensed heterocyclic hydrocarbon groups, heterocondensed heterocyclic hydrocarbon groups and the like.

Group substituents without heteroatoms are hydrocarbon groups, including but not limited to substituents selected from the group consisting of an aliphatic group, an aryl group, an aryl-hydrocarbyl group, an arylalkyl group (an aralkyl group), a saturated hydrocarbon group, an alkyl group, an unsaturated hydrocarbon group, an alkenyl group, an alkynyl group, a dienyl group, an alkenyl-hydrocarbyl group, an alkynyl-hydrocarbyl group, a dienyl-hydrocarbyl group, an open-chain hydrocarbon group, a linear hydrocarbon group (a linear aliphatic hydrocarbon group), a branched hydrocarbon group (a branched aliphatic hydrocarbon group), a cyclohydrocarbon group, an alicyclic hydrocarbon group, a cycloalkyl group, an unsaturated alicyclic hydrocarbon group, a monocyclohydrocarbon group, a polycyclohydrocarbon, a condensed cyclohydrocarbon group and a condensed aryl group. For specific examples, a hydrocarbon group can be but not limited to a methyl group, an ethyl group, a vinyl group (an ethenyl group), a propyl group, an allyl group, a propenyl group, a propargyl group, a propynyl group, an isopropyl group, a butyl group, a t-butyl group, a pentyl group, a heptyl group, a 2-ethylhexyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, a cyclopropyl group, a cyclopentyl group, a cyclohexyl group, a cycloheptyl group, a cyclooctyl group, a phenyl group, a benzyl group, a p-methylphenyl group, a butylphenyl group, an alkynyl group or the like.

In the present invention, besides heterohydrocarbon groups, heteroatom-containing group substituents also include but are not limited to substituents selected from the group consisting of a haloalkyl group, a nitro group, a silyl group (a trimethylsilyl group, a t-butyldimethylsilyl group, a trimethoxysilyl group, etc.) and a group substituent derived from a hydrocarbon group or a heterohydrocarbon group being directly linked with a heteroatom-containing linkage such as an oxy group (a divalent oxygen linkage), a thioxy group (a divalent sulfur linkage), an acyl linkage, an acyloxy linkage, an oxyacyl linkage, —NH—C(=O)—, —C(=O)—NH— and the like. Take a hydrocarbyl group for example, the resulting substituent is a hydrocarbyloxy group (or a hydrocarbonoxy group), a hydrocarbylthio group (or a hydrocarbylthioxy group), an acyl group, an acyloxy group, a hydrocarbyloxy-acyl group, an aminoacyl group, an acylamino group and the like, respectively.

The acyl group in the present invention can be a carbonyl group or a non-carbonyl acyl group. For example, The acyl group can be but not particularly limited to a carbonyl group, a sulfonyl group, a sulfinyl group, a phosphoryl group, a phosphiryl group, a phosphinyl group, a nitroxyl group, a nitrosyl group, a thiocarbonyl group, an imidoyl group, a thiophosphoryl group, a dithiophosphoryl group, a trithiophosphoryl group, a thiophosphiryl group, a dithiophosphiryl group, a thiophosphinyl group, a thiophosphono group, a dithiophosphono group, a thiophosphino group or the like, preferably a carbonyl group, a thiocarbonyl group, a sulfonyl group or sulfinyl group. Herein, an acyl group particularly refers to a carbonyl group if without particular illustrations.

Hydrocarbyloxy groups, include, e.g., alkoxy groups (also alkoxyl groups, e.g. a methoxy group (or a methyloxy group), an ethoxy group (or an ethyloxy group), a tert-butoxy group (or a t-butyloxy group), etc.) formed by an alkyl group and an oxy group, an aryloxy group (e.g., a phenoxy group, etc.) formed by an aryl group and an oxy group, an arylhydrocarbyloxy group (e.g., a benzyloxy group, etc.) formed by an arylhydrocarbyl group and an oxy group, an alkenyloxy group formed by an alkenyl group and an oxy group, an alkynyloxy group formed by an alkynyl group and an oxy group, etc.

Examples of a hydrocarbylthio group include an alkylthio group, an arylthio group, an arylhydrocarbylthio group, an alkenylthio group, and an alkynylthio group, etc.

Acyloxy groups, also denoted as acyloxyl group, corresponding to the above-described acyl groups, similarly include a sulfonyloxy group, a sulfinyloxy group and the like besides a carbonyloxy group, no more repeated here.

Oxyacyl groups also include an oxysulfonyl group and the like besides an oxycarbonyl group, corresponding to the above-described acyl groups, no more repeated here.

Aminoacyl groups and acylamino group, also respectively include a sulfamoyl group, a sulfonylamino group and the like besides an aminocarbonyl group and a carbonylamino group, corresponding to the above-described acyl groups, no more repeated here.

The above-mentioned substituted hydrocarbon groups include both hydrocarbyl-substituted hydrocarbon groups (still falling into the scope of hydrocarbon groups), and heterohydrocarbyl-substituted hydrocarbon groups (falling into the scope of heterohydrocarbon groups).

According to the species difference, heterohydrocarbon groups include aliphatic-derived heterohydrocarbon groups and aromatic-derived heterohydrocarbon groups. According to the structural difference, heterohydrocarbon groups include but are not limited to open-chain heterohydrocarbon groups, heterocyclic hydrocarbon groups (or heterocyclohydrocarbon groups), heterring-substituted hydrocarbon groups. Aliphatic-derived heterohydrocarbon groups include open-chain heterohydrocarbon groups and aliphatic-derived heterocyclohydrocarbon groups. Aromatic-derived heterohydrocarbon groups include but are not limited to heteroaryl groups, heteroarylhydrocarbon groups and aryl-condensed heterocyclohydrocarbon groups, etc. Heterocyclic hydrocarbon groups (or heterocyclohydrocarbon groups) include but are not limited to aliphatic-derived heterocyclic hydrocarbon groups and aromatic-derived heterohydrocarbon groups.

With respect to a compound, a group or an atom, it can be substituted or heterosubstituted meanwhile, e.g., a nitrophenyl substituent, or —$CH_2$—S—$CH(CH_3)$— replacing —$CH_2$—$CH_2$—$CH_2$—.

Wherein, hydrocarbon groups derived from aliphatic hydrocarbons are aliphatic hydrocarbon groups.

Hydrocarbon groups derived from alkanes are alkyl groups. Unsaturated hydrocarbons after removal of hydrogen atoms result in unsaturated hydrocarbon groups.

The hydrocarbon groups formed by removing hydrogen atoms bound to unsaturated carbon atoms of unsaturated hydrocarbons, can include alkenyl groups, alkynyl groups, dienyl groups, and the like, for example, e.g., a propenyl group and a propynyl group. According to the difference of unsaturated bond, the hydrocarbon groups formed by removing hydrogen atoms bound to saturated carbon atoms of unsaturated hydrocarbons, include, e.g., alkenylhydrocarbyl groups, alkynylhydrocarbyl groups, dienylhydrocarbyl groups and the like, with specific examples such as an allyl group and a propargyl group. Wherein, alkenyl-hydrocarbyl groups also belong to the scope of alkenyl groups.

Open-chain hydrocarbon groups are residue groups derived from open-chain hydrocarbons after removal of hydrogen atoms.

Linear hydrocarbons after removing a hydrogen atom linked with a primary carbon atom turn into linear hydrocarbyl groups. Linear hydrocarbons after removing a hydrogen atom linked with a secondary or tertiary carbon atom turn into branched hydrocarbyl groups. Branched hydrocarbons after removing a hydrogen atom of any position turn into branched hydrocarbyl groups.

Hydrocarbon groups formed from cyclic hydrocarbons (or cyclohydrocarbons) after removing a hydrogen atom are regarded as cyclic hydrocarbyl groups (or cyclohydrocarbyl groups).

Alicyclic hydrocarbons after removing a hydrogen atom turn into alicyclic hydrocarbyl groups.

Aromatic hydrocarbon groups derived from aromatic hydrocarbons include aryl groups and arylhydrocarbyl groups. Wherein, aryl-hydrocarbyl groups also fall into the scope of aryl groups.

Aromatic hydrocarbons after removing a hydrogen atom on the aromatic ring turn into aryl groups. Aromatic hydrocarbons after removing non-ring hydrogen atoms turn into aryl-hydrocarbyl groups; wherein, aryl-hydrocarbyl groups also fall into the scope of aryl groups. Arylalkanes (or aralkanes) after removing non-ring hydrogen atoms turn into arylalkyl groups (aralkyl groups). Aralkyl groups fall into the scope of the aryl-hydrocarbyl groups. For example, most typical examples of aryl groups include a phenyl group, and a phenylene group, and the typical example of aryl-hydrocarbyl groups is a benzyl group.

Heterosubstituted hydrocarbons after removing hydrogen atoms turn into heterohydrocarbon groups. Heteroalkanes can turn into heteroalkyl groups.

Aliphatic-derived heterosubstituted hydrocarbons after removing hydrogen atoms turn into aliphatic-derived heterohydrocarbon groups. Aromatic-derived heterosubstituted hydrocarbons after removing hydrogen atoms turn into aromatic-derived heterohydrocarbon groups.

Open-chain heterosubstituted hydrocarbons after removing hydrogen atoms turn into open-chain heterohydrocarbon groups.

Heterocyclic hydrocarbons (or cyclic heterohydrocarbons) after removing hydrogen atoms on the ring turn into heterocyclic hydrocarbon groups (or heterocyclohydrocarbon groups).

Aliphatic-derived heterocyclic hydrocarbons after removing hydrogen atoms on the alicyclic ring turn into aliphatic-derived heterocyclohydrocarbon groups.

Aromatic-derived heterosubstituted hydrocarbons after removing hydrogen atoms on the aromatic ring turn into heteroaryl groups. Aromatic heterosubstituted hydrocarbons after removing non-ring hydrogen atoms turn into heteroarylhydrocarbyl groups; wherein, heteroarylhydrocarbyl groups also belong to the scope of heteroaryl groups. Heteroaralkanes after removing non-ring hydrogen atoms turn into heteroaralkyl groups.

Condensed cyclic hydrocarbons after removing hydrogen atoms on a ring turn into condensed cyclic hydrocarbon groups. Wherein, condensed aryl hydrocarbons removing hydrogen atoms on the aryl ring turn into condensed aryl hydrocarbon groups.

With respect to condensed heterocyclic hydrocarbons, aryl-condensed heterocyclic hydrocarbons after removing hydrogen atoms turn into aryl-condensed heterocyclohydrocarbon groups. Heterocondensed heterocyclic hydrocarbons after removing hydrogen atoms turn into heterocondensed heterocyclohydrocarbon groups.

Heterohydrocarbon groups in the present invention are not particularly limited, for example, including but not limited to groups containing heteroatoms such as aliphatic-derived heterohydrocarbon groups, open-chain heterohydrocarbon groups, aliphatic-derived heterocyclohydrocarbon groups, aromatic-derived heterohydrocarbon groups, heteroaryl groups, heteroarylhydrocarbyl groups, aryl-condensed heterocyclohydrocarbon groups, heterocondensed heterocyclohydrocarbon groups, oxa-hydrocarbyl groups, aza-hydrocarbyl groups, thia-hydrocarbyl groups, phospha-hydrocarbyl groups, monoheterosubstituted hydrocarbyl groups, diheterosubstituted hydrocarbyl groups, multiheterosubstituted hydrocarbyl groups and the like.

In the present invention, the sources of divalent hydrocarbon groups, also termed as hydrocarbylene groups, are not particularly limited. For example, they can be derived from aliphatic hydrocarbons or aromatic hydrocarbons, or be derived from saturated hydrocarbons or unsaturated hydrocarbons, or be derived from linear-chain hydrocarbons, branched hydrocarbons or cyclic hydrocarbons, or be derived from hydrocarbons or heterohydrocarbons, etc. According to the degree of saturation, e.g., they can be derived from alkanes, alkenes, alkynes, dienes, etc. With respect to cyclic hydrocarbons, e.g., they can be derived from alicyclic hydrocarbons or aromatic hydrocarbons, monocyclic hydrocarbons or polycyclic hydrocarbons. With respect to heterocyclic hydrocarbons, e.g., they can be derived from aliphatic-derived heterocyclic hydrocarbons or aromatic-derived heterocyclic hydrocarbons.

Hydrocarbylene groups formed from alkanes are also termed as alkylene groups. Generally, an alkylene groups include but are not limited to a methylene group, a 1,2-ethylene group, a 1,3-propylene group, a 1,2-propyene group, an isopropylene group, a butylene group, a pentylene group, a hexylene group, a heptylene group, an octylene group, a nonylene group, a decylene group, and the like.

Hydrocarbylene groups derived from unsaturated aliphatic hydrocarbons contain basic units such as —CH=CH— and —C≡C—, etc.

For cyclohydrocarbylene groups, the positions of hydrogen atoms to be removed are not particularly limited, as long as they are not connected to a common carbon atom. When the two removed hydrogen atoms are connected to a common carbon atom, the resulting cyclic structure serves as a group substituent of this carbon atom. Alicyclic hydrocarbons with removal of two hydrogen atoms of a common ring can generate alicyclic hydrocarbylene groups, such as

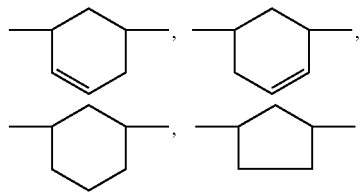

and the like. Aromatic hydrocarbons with removal of two hydrogen atoms of a common ring can generate arylene groups, such as phenylene groups including a p-phenylene group

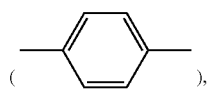

an m-phenylene group

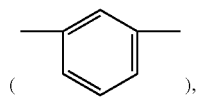

or an o-phenylene group

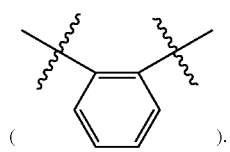 [SMILES: *c1ccccc1*]

When one of the two hydrogen atoms of aromatic hydrocarbons to be removed is on the aromatic ring, and the other one is located at the aliphatic moiety, the resulting hydrocarbylene group is an arylhydrocarbylene group, such as,

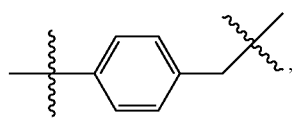

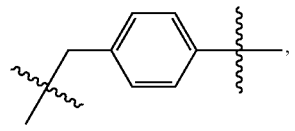

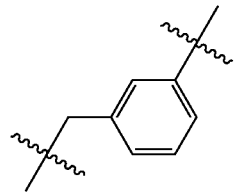

and so on. Examples of a cyclic structure as a group substituent include

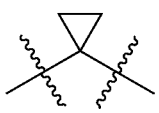 [SMILES: *C1(*)CC1]

and the like.

Hydrocarbylene may contain or do not contain substituting groups or pendant groups. Said pendant groups include but are not limited to straight chains

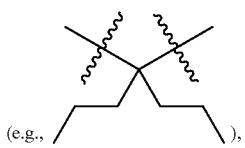

(e.g., ）， branched chains

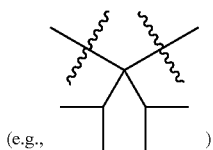 [SMILES: *C(*)(C(C)C)C(C)C]

(e.g., ） or cyclic structures (e.g.,

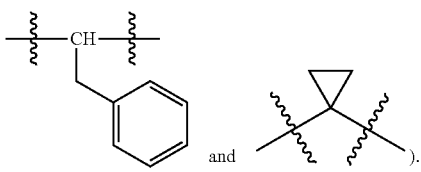 [SMILES: *C(*)Cc1ccccc1 ; *C1(*)CC1]

and ）.

The two radical positions of hydrocarbylene groups to connect with other groups are not particularly limited if without particular illustrations. For example, a phenylene group may be a p-phenylene group, an o-phenylene, or an m-phenylene, and a propylene group may be a 1,3-propyldene group, a 1,2-propylene group, a 1,1-propylene group, an isopropylene group and the like.

Examples of condensed cyclic compounds also include phthalimide, phthalic hydrazide and phthalic anhydride besides the above-described examples.

The protecting groups (protective groups) involved in the present invention, such as mercapto protecting groups (or thiol protecting groups), alkynyl protecting groups, hydroxyl protecting groups, amino protecting groups, etc., are not particularly limited. All the above-mentioned protecting groups in the prior art can be incorporated into the present invention by reference. Wherein, said hydroxyl groups to be protected are not particularly limited, e.g., alcoholic hydroxyl groups, phenolic hydroxyl groups and the like. Wherein, said amino groups to be protected are not particularly limited, e.g., primary amines, secondary amines, hydrazines, amides and the like.

The amino group in the present invention is not particularly limited, can be but not limited to a primary amino group, a secondary amino group or a tert-amino group.

For simplicity, the value range of the carbon-atom number of a group can also be marked as a subscript of a carbon atom ("C") to represent available number of carbon atoms. For example, $C_{1-10}$ represents "having 1 to 10 carbon atoms", $C_{3-20}$ indicates "having 3 to 20 carbon atoms". "Substituted $C_{3-20}$ hydrocarbyl groups" means the resulting groups after substituting hydrogen atoms of $C_{3-20}$ hydrocarbyl groups. "$C_{3-20}$ substituted hydrocarbyl groups" means that the resulting groups after hydrogen atoms being substituted have 3 to 20 carbon atoms.

Regarding the divalent linking groups in the present invention, e.g., a hydrocarbylene group, an alkylene group, an arylene group, an amide bond and the like, either radical terminus could be available when connecting to another group, if without particular limitations. For example, when an amide bond serves as a divalent linking group between A-CH$_2$CH$_2$— and —CH$_2$—B, both A-CH$_2$CH$_2$—C(=O)NH—CH$_2$—B and A-CH$_2$CH$_2$—NHC(=O)—CH$_2$—B could be a candidate. Some chemical formulas are marked with asterisks to denote an oriented terminus and to indicate the available radical ends to be connected towards a given direction.

When a structure has isomers, it may refer to any form of the isomers if without particular instructions. For example, when cis- and trans-isomers are present, it can refer to either a cis-structure or a trans-structure. Regarding an alkyl group, if without particular instructions, it refers to a hydrocarbyl group which is formed via removing hydrogen atoms from any position. Specific examples include that a propyl group refers to either a 1-propyl group or an isopropyl group, and a propylene group can refer to a 1,3-propylene group, or a 1,2-propylene group (an isopropylene group).

Concerning a structural formula, if it is not easy to unquestionably make clear the two radical termini of a divalent linkage,

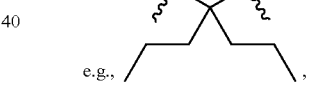

e.g., we use "〜〜" to mark the radical positions for connecting with other groups. In most cases, formulas are not particularly marked, such as phenylene groups of

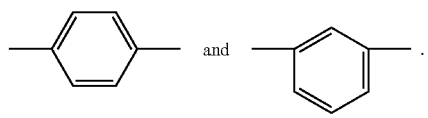

and .

In the production method section of the present invention, in the formula of some skeleton groups, dashed lines means that the involved skeleton group would be directly connecting with the shown structure in given compounds.

In the present invention, cyclic structures are represented by circles, and are marked respectively according to different cyclic types. For examples,

represents a cyclic structure of any type;

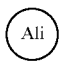

represents a cyclic structure of aliphatics which contain neither aromatic rings nor heteroaromatic rings of any type, and is also denoted as an alicyclic ring or an aliphatic ring;

represents a cyclic structure of aromatics which contains at least one aromatic ring or heteroaromatic ring, and is also denoted as an aromatic ring or an aryl ring.

represents a skeleton of saccharides or derivatives thereof which contains one or more cyclic monosaccharide skeletons, and is also denoted as a sugar ring.

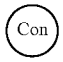

represents a ring which contains at least one type of chemical bonds selected from the group consisting of an amide bond, an ester bond, an imide bond, an anhydride and the like, and is also denoted as a condensed ring.

is a cyclic skeleton of watersoluble polymers, and is also denoted as a polymeric ring. The molecular weight of said watersoluble polymers is not particularly limited.

Examples of rings including

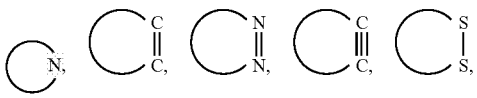

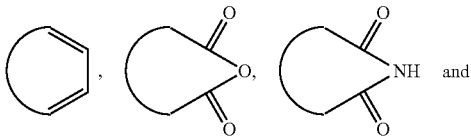

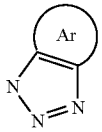

correspond to cyclic structures which contain a nitrogen atom, a double carbon-carbon bond, an azo group, a triple carbon-carbon bond, a disulfide bond, a conjugated dienyl bond, an anhydride bond, an imide bond and a triazole moiety, respectively.

If without particular illustrations, cyclic structures in the present invention include but are not limited to alicyclic rings

, aromatic rings

, sugar rings

, condensed rings

and polymeric rings

.

Alicyclic rings include alicyclic rings and aliphatic-derived heterorings, including but not limited to cyclic structures selected from the group consisting of monocyclic rings, polycyclic rings, spirocyclic rings, bridged cyclic rings, condensed rings (fused rings), carbon rings, heterorings, aliphatic-derived heterorings, heterosubstituted monocyclic rings, heterosubstituted polycyclic rings, heterospirorings, hetero-bridged rings, hetero-alicyclic rings, and the combination of any two or any two more cyclic structures of the foregoing. Wherein, cyclic structures such as a triazole ring can be generated via a chemical reaction. What should be noted is that although

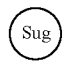

is an alicyclic ring, it is sometimes regarded as one individual type owing to its particular characteristics.

Examples of alicyclic rings include but are not limited to:

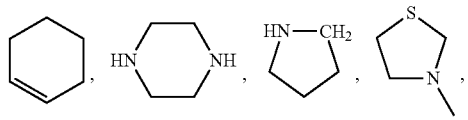

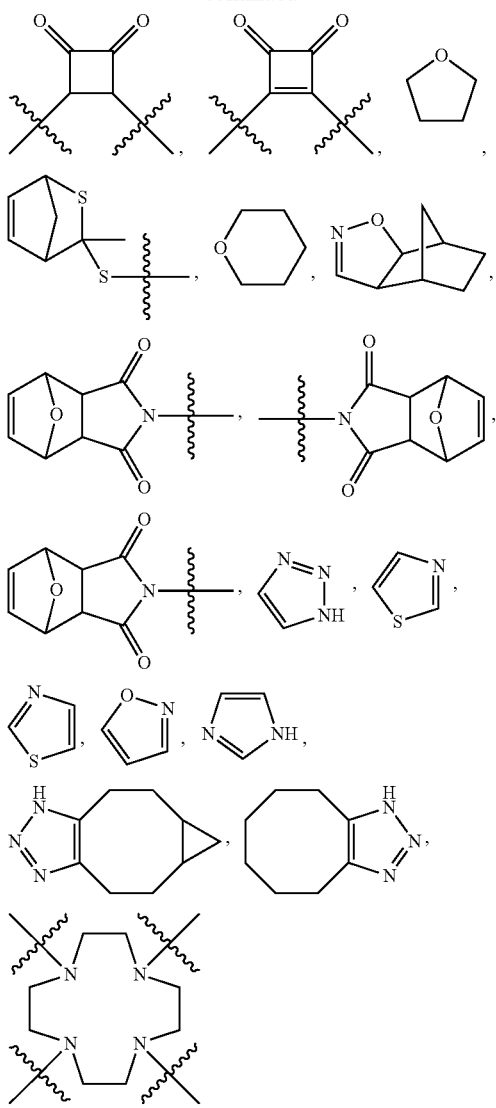

and the like.

Examples of sugar rings include the following structures:

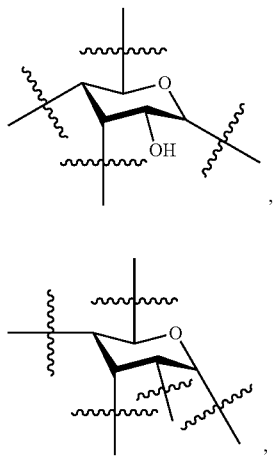

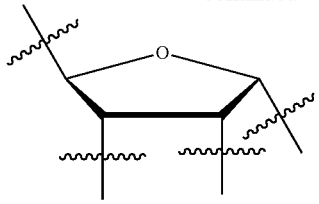

cyclodextrins, etc.

Aromatic rings include aromatic rings and aromatic heterorings, including but not limited to cyclic structures selected from the group consisting of monocyclic rings, polycyclic rings, condensed rings, condensed aryl rings, condensed heterorings, aryl-condensed heterorings, arylo-heterorings, benzoheterorings, heterocondensed heterorings, carbon rings, heterocyclic rings, aromatic-derived heterocyclic rings, heterosubstituted monocyclic rings (or hetero-monorings), heterosubstituted polycyclic rings, heterosubstituted condensed rings (or hetero-condensed rings), heteroaryl rings and the combination of any two or more cyclic structures thereof. Specific examples include and are not limited to the following structures:

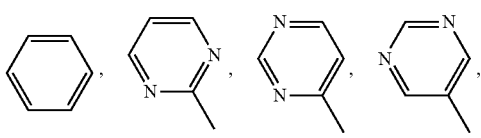

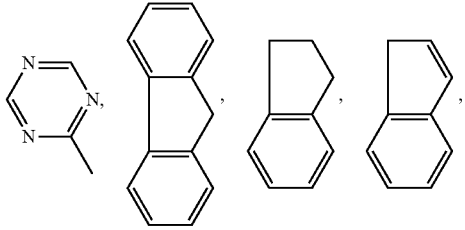

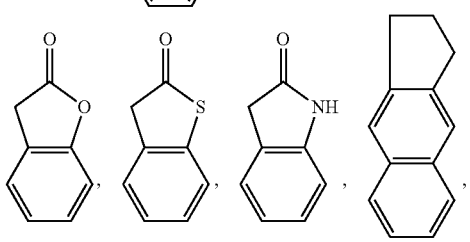

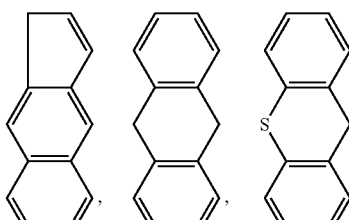

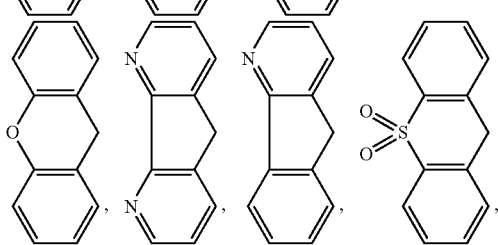

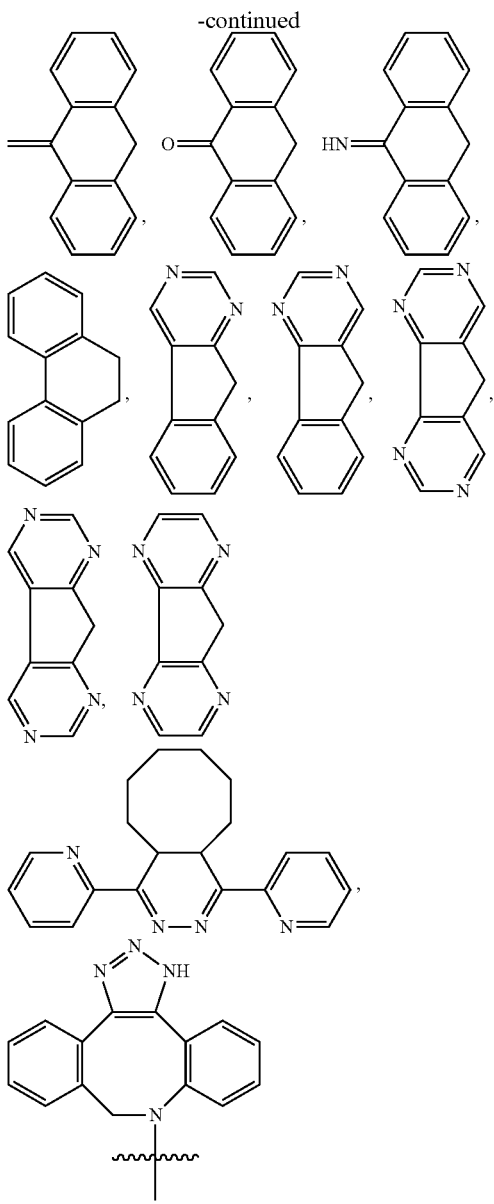

and the like.

Specific examples of condensed rings are as follows:

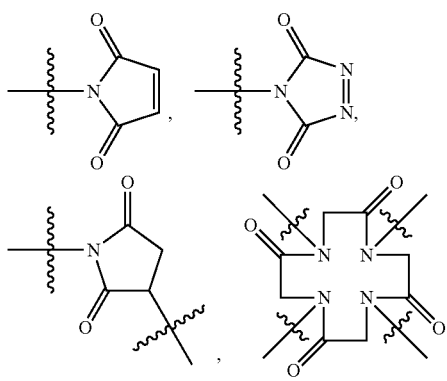

and the like.

Regarding the term "substituted" in the present invention, take "substituted hydrocarbyl groups" for example, means that any one or more hydrogen atoms at any position of said hydrocarbyl groups to be substituted can be substituted by any atom or group substituent. The atom substituent is not particularly limited and is preferably a halogen atom, if without particular limitations. The group substituents are not particularly limited, including but not limited to all the above-listed substituting groups in the terminology section, and could be selected from all above-mentioned hydrocarbon substituents or heteroatom-containing substituents, if without particular limitations. When describing, we directly illustrate available combination of atom substituents and group substituents such as "the atom or group substituent can be a halogen atom, a hydrocarbyl substituent, or a heteroatom-containing substituent."

The terms "be stable" (or "can remain stable") and "be degradable" (or "can be degraded") regarding a group is a couple of relatively opposite concepts in the present invention.

The term "degradation", the noun form of the term "degradable", means the breakage of chemical bonds into at least two individual residues. If a linking group remains as a whole linkage after undergoing structural change via chemical reactions, such a linking group still falls into the scope of "stable groups". The condition "to be degradable" or "to degrade" or "to be degraded" is not particularly limited, including but not limited to conditions such as light illumination, heat, an enzymatic condition, an oxidation-reduction condition, an acidic condition, a basic condition, a physiological condition, a simulated physiological environment in vitro, etc., preferably conditions such as light illumination, heat, an enzymatic condition, an oxidation-reduction condition, an acidic condition, a basic condition, etc. Said light illumination condition includes but is not limited to visible light, ultraviolet light, infrared light, near-infrared light, mid-infrared light, etc. Said heat condition means a temperature higher than normal physiological temperature, and normally means a temperature higher than 37° C. and also normally below 45° C., preferably below 42° C. Said enzymatic condition is not particularly limited, and all enzymes that can be physiologically generated are incorporated, e.g., peptidases, proteases and lyases. Said oxidation-reduction condition is not particularly limited, such as a redox transition between a mercapto group and a disulfide bond. Said physiological condition is not particularly limited, including but not limited to physiological environments of serum, heart, liver, spleen, lung, kidney, bone, muscle, fat, brain, lymph node, small intestine, gonads, etc. The above-listed physiological condition could be intracellular or in the extracellular matrix, be in normal tissues or in pathologic tissues (such as tumor, inflammation, etc.). Said simulated physiological environment in vitro is not particularly limited, including but not limited to physiological saline, buffer, culture medium and the like. The rate of degradation is not particularly limited, e.g., rapid degradation via enzymolysis, or slow degradation via physiological hydrolysis, etc.

In contrast, as long as a linking group can keep as a whole linking group (i.e., a linking group which can keep covalently linking the adjacent groups being connected), it would be defined as "a stable group", and herein chemical changes through which the wholeness of the linking group is still maintained are allowed. The chemical changes are not particularly limited, including but not limited to isomerization transition, protonation, substitution reactions, etc. The condition "to be stable" or "to remain stable" is not particularly limited, including but not limited to conditions such as light illumination, heat, an enzymatic condition, oxidation-reduction, a neutral condition, an acid condition, a basic condition, a physiological condition, a simulated physiological environment in vitro, etc.

In addition, for one linking group, the concept of "stable" is not strictly absolute. For example, an amide bond is much more stable than an ester bond under an acidic or basic condition. Accordingly, "stable" linking groups in the present invention include amide bonds. However, an amide bond (typically a peptide bond) could also be broken when suffering from specific enzymatic conditions, and therefore it can also fall into the scope of "degradable" linking groups. Similarly, a urethane group, a thiourethane group and the like could be either a "stable" linking group or a "degradable" linking group.

In the present invention, the structure type of an amino acid is not particularly limited, and can be either of $_L$-type or of $_D$-type if without particular illustrations.

In the present invention, the amino acid skeleton refers to a residue group having typical characteristics of amino acid, and specifically means a residue group formed after removal of carboxylic hydroxyl group (including all the C-terminal carboxylic hydroxyl groups as well as carboxylic hydroxyl group of the pendant group of aspartic acid and glutamic acid), hydrogen atom of hydroxyl group, hydrogen atom of phenolic hydroxyl group (e.g. tyrosine), hydrogen atom of mercapto group (e.g., cysteine), hydrogen atoms bonded to nitrogen atoms (including all the N-terminal hydrogen atoms as well as hydrogen atoms of pendant amino groups, such as hydrogen atoms of ε-amino group of lysine, hydrogen atoms of amino group of pendant ring of histidine and tryptophan, and the like), amino group of terminal amide group (e.g., asparagine, glutamine, etc.), amino group or hydrogen atoms of amino group of pendant guanidino group. For example, the skeleton structure of glycine is

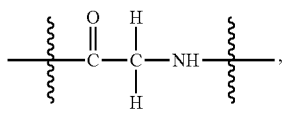 [SMILES: *NCC(*)=O], the skeleton of lysine is

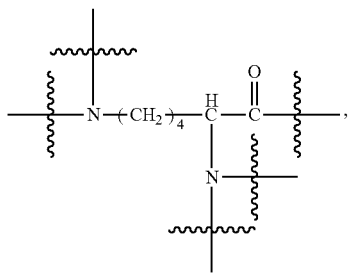, no more specifically listing.

Similarly, in the present invention, the skeleton of an amino acid derivative refers to a skeleton that contains characteristic atoms or groups besides amino acid skeleton. For example, the skeleton of hydroxyproline is

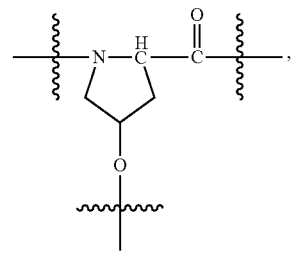 [SMILES: *OC1CC(C(*)=O)N(*)C1], and the skeleton of sarcosine (also termed as N-methyl-glycine) is

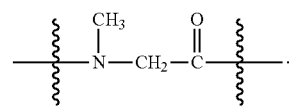.

In the present invention, the skeleton of a cyclic monosaccharide refers to the residue group formed by removal of all hydroxyl groups. In the present invention, regarding the description for the degree of polymerization of any PEG chain or PEG segment or PEG block of the H-shaped multifunctionalized polyethylene glycol corresponding to $n_1$, $n_2$, $n_3$, $n_4$, $m_1$, $m_2$ and $m_3$, description such as "a range from 2 to 2000" or "an integer from 2 to 2000" can be used. The resulting substance produced by using the methods described in the present invention is composed of molecules. For an individual molecule thereof, taking $n_1$ for instance, it should be an integer which corresponds to the number of EO units (the oxyethylene-unit number or the EO-unit number). As for the substance, $n_1$ would represent the number-average value of a series of integers and is allowed to be a non-integer value among a given value range, referring to the EXAMPLEs of the present invention. For further translation explanation, a substance of the present invention is a population of molecules corresponding to the same general formula wherein the molecular weight of either oligomeric or polymeric block can be variable among these molecules. In one substance of the present invention, the molecular weights among all said molecules of either PEG block or chain selected from LPEG and the four branch chains can vary between a value range, and said value range for one PEG block, segment or chain is determined by corresponding number average degree of polymerization and corresponding PDI value, wherein either PDI value is equal to 1 or greater than 1 in the present invention. Furthermore, well known to one person in the art, the terms and phrases including "polydisperse", "monodisperse", "polydispersity", "polydispersity index", "PDI", "number average molecular weight", "number average degree of polymerization", "distribution of molecular weight" and the like are used to describe a substance or a matter rather than a compound. As a result, such terms and phrases should not be regarded as limitation to the scope of compounds in the present invention.

In addition, the content of the patent document including application No. CN 201510349134.9 (publication No. CN104877127A, publication date 2 Sep. 2015) and cited references therein are incorporated into the present invention by reference, particularly involving branch centers (or branching centers), branched structures, cyclic structures (including but not limited to alicyclic rings, aromatic rings, sugar rings, condensed rings, polymeric rings, etc.), "stable", "degradable", "cyclic monosaccharide", "polydisperse" and "monodisperse", trivalent groups and examples thereof, tetravalent groups and examples thereof, pentavalent groups and examples thereof, hexavalent groups and examples thereof, groups of higher valence and examples thereof, trivalent groups wherein the non-core moiety beyond core structure contains no heteroatoms and examples thereof, trivalent groups wherein the non-core moiety beyond core structure contain heteroatoms and examples thereof, trivalent branched structures, examples of functional groups and protected forms thereof, stable divalent linking groups, degradable divalent linking groups, degradable multivalent groups, terminal branch structures and examples thereof (including but not limited to ring-containing structures, comb-like structures, dendritic structures, hyperbranched structures, branched structures, etc.), targeting factors, photosensitive groups (including fluorescent substances), pairs of heterofunctional groups allowed to be present meanwhile, small molecules containing two identical or different functional groups, heterofunctional small molecules containing trivalent core structure, end-functionalization methods (linear-functionalized and branched-functionalized) and reagent materials to be used, etc. What should be noted is that preferable structures of above-involved structures are also incorporated by reference into the present invention.

1.1. In the present invention, the H-shaped multifunctionalized polyethylene glycol compound is represented by the following general formula (1):

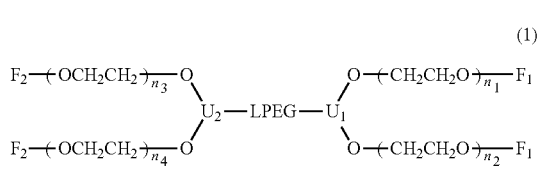

(1)

The H-shaped structure consists of one linear main chain LPEG and four PEG branch chains, and the total number of oxyethylene units of the linear PEG main chain and four branch chains is no more than 5000, preferably no more than 4000, more preferably no more than 3000, more preferably no more than 2500, more preferably no more than 2000, and more preferably no more than 1500.

Wherein, LPEG is the linear main chain, and can be a polyethylene glycol segment which contains one, two, three or 4 to 150 polyethylene glycol blocks.

Wherein, the number of oxyethylene units of LPEG is an integer from 2 to 2000, preferably an integer from 5 to 2000, more preferably an integer from 5 to 1000, more preferably an integer from 10 to 1000, more preferably an integer from 10 to 500, more preferably an integer from 20 to 500, more preferably an integer from 20 to 250, and more preferably an integer from 50 to 250.

Wherein, $n_1$, $n_2$, $n_3$ and $n_4$ represent the degree of polymerization of the four PEG branch chains, respectively, and are each independently selected from the value range of 2 to 2000; in one molecule, $n_1$, $n_2$, $n_3$ and $n_4$ can be the same or different; $n_1$, $n_2$, $n_3$ and $n_4$ are each independently preferably a value from 5 to 2000, more preferably a value from 5 to 1000, more preferably a value from 10 to 1000, more preferably a value from 20 to 1000, more preferably a value from 20 to 500, and more preferably a value from 50 to 500.

In the H-shaped multifunctionalized polyethylene glycol of the present invention, all the PEG blocks are each independently polydisperse or monodisperse. As long as LPEG has at least one polydisperse PEG block, LPEG is regarded as polydisperse. Only when all the PEG blocks contained in LPEG are monodisperse, LPEG is regarded as monodisperse. In the present invention, LPEG and four PEG branch chains corresponding to $n_1$, $n_2$, $n_3$ and $n_4$ are each independently polydisperse or monodisperse.

Wherein, $U_1$ and $U_2$ are trivalent branching groups connecting LPEG and respective two PEG branch chains; the structure of $U_1$ is

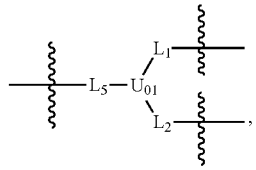

and the structure of $U_2$ is

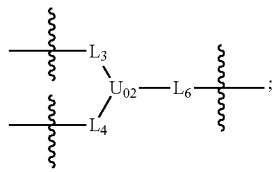

$U_{01}$ and $U_{02}$ are each independently a trivalent group; wherein, $L_1$, $L_2$, $L_3$ and $L_4$ are linking groups that connect corresponding PEG moieties with a corresponding number of oxyethylene units of $n_1$, $n_2$, $n_3$ and $n_4$, respectively; $L_5$ and $L_6$ are linking groups that connect with linear PEG main chain; $L_1$, $L_2$, $L_3$, $L_4$, $L_5$ and $L_6$ are each independently present or absent, and can be the same or different in one molecule.

Wherein, $F_1$ and $F_2$ are each independently a functional group in an unprotected or protected form.

Wherein, $F_1$ and $F_2$ are each independently and correspondingly represented as respective

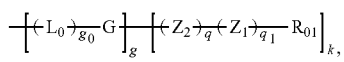

and can be the same or different from each other in one molecule. In one molecule, the two $F_1$ groups have the same $g$, $L_0$, $g_0$, $Z_2$, $q$, $Z_1$, $q_1$ and $R_{01}$, and the two $F_2$ groups have the same $g$, $L_0$, $g_0$, $Z_2$, $q$, $Z_1$, $q_1$ and $R_{01}$.

wherein,

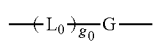

is a linking group that connects with corresponding PEG moiety; wherein, k is an integer of 1 or from 2 to 250; g is 0 or 1; G is a linking group of trivalence or higher valence; when g is 0, k would be equal to 1; when g is 1, k would be an integer from 2 to 250, and the valence of corresponding G is k+1; $L_0$ is a divalent linking group; $g_0$ is 0 or 1, or an integer from 2 to 1000; q and $q_1$ are each independently 0 or 1; $Z_1$ and $Z_2$ are each independently a divalent linking group; $R_{01}$ is an unprotected or protected functional end-group (also referred to as functional end-group in the invention); in one molecule, k, G, g, $L_0$, $g_0$, $Z_2$, q, $Z_1$, $q_1$ and $R_{01}$ of $F_1$ and $F_2$ are each independently the same or different.

Wherein, in one molecule, LPEG, $U_1$, $U_2$, $U_{01}$, $U_{02}$, $L_1$, $L_2$, $L_3$, $L_4$, $L_5$, $L_6$, $L_0(F_1)$, $G(F_1)$, $Z_1(F_1)$, $Z_2(F_1)$, $L_0(F_2)$, $G(F_2)$, $Z_1(F_2)$, $Z_2(F_2)$, and the joint linking group formed by any said group with its adjacent heterosubstituted group can be each independently either stable or degradable. The condition "to be stable" ("to remain stable") or "to be degradable" ("to be degraded") is not particularly limited, including but not limited to conditions such as light illumination, heat, an enzymatic condition, an oxidation-reduction condition, an acidic condition, a basic condition, a physiological condition, a simulated physiological environment in vitro, etc., preferably conditions such as light illumination, heat, an enzymatic condition, an oxidation-reduction condition, an acidic condition, a basic condition, etc.

In the present invention, the position of one linking group to remain stable or be degraded include the linking group itself as well as the joint linking group of it and its adjacent heterosubstituted groups.

The number and position of the degradable sites of H-shaped multifunctionalized polyethylene glycols play an important role in the stability of polymer and the releasability of modified drugs thereof. (1) When a degradable position occurs between the functional end-group and its corresponding polyethylene glycol branch chain, including positions at $L_0(F_1)$, $L_0(F_2)$, $Z_1(F_1)$, $Z_1(F_2)$, $Z_2(F_1)$, $Z_2(F_2)$, $G(F_1)$ and $G(F_2)$, the pegylated drug molecule can be separated from the polyethylene glycol moiety to expose its active site to a maximum extent; especially with respect to a position at $Z_1(F_1)$, $Z_1(F_2)$, $Z_2(F_1)$ or $Z_2(F_2)$, more especially a position at $Z_1(F_1)$ or $Z_1(F_2)$, the drug molecule can turn towards its unmodified form to a maximum extent when undergoing degradation. (2) When a degradable reaction occurs in the middle position of the H-shaped structure, including positions at $U_1$ (including positions at $U_{01}$, $L_1$, $L_2$ and $L_5$), $U_2$ (including positions at $U_{02}$, $L_3$, $L_4$ and $L_6$) and LPEG (including positions at $W_0$, $W_{01}$ and $W_{02}$), the molecular weight of polyethylene glycol moiety connected with the drug molecule decreases, and thus the shielding effect for the drug molecule is reduced and drug efficacy increases; wherein, when degradation reaction occur at $L_1$, $L_2$, $L_3$ or $L_4$, the drug molecule grafted at the corresponding terminus can only carry a linear remaining polyethylene glycol chain; when degradation reaction occur at $L_5$, $L_6$, $W_0$, $W_{01}$ or $W_{02}$, V- or Y-shaped polyethylene glycol bearing drug molecules at the ends of two branch chains can be obtained.

According to the number of polyethylene glycol blocks of the linear main chain (LPEG), the structure of LPEG can be but not limited to

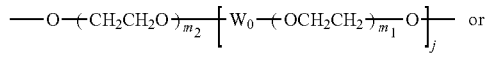   or

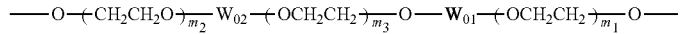

Wherein, $W_0$, $W_{01}$ and $W_{02}$ are each independently a linking group containing 1 to 100 atoms; $W_0$, $W_{01}$ and $W_{02}$ are each independently either stable or degradable;

$m_1$, $m_2$ and $m_3$ are the degree of polymerization of corresponding PEG blocks, respectively, each independently selected from 0 to 2000, and in one molecule, they can be the same or different; $m_1$, $m_2$ and $m_3$ are each independently preferably a value from 0 to 1000; the PEG blocks corresponding to $m_1$, $m_2$ and $m_3$ are each independently polydisperse or monodisperse;

j is an integer of 1 or from 2 to 100.

LPEG is preferably

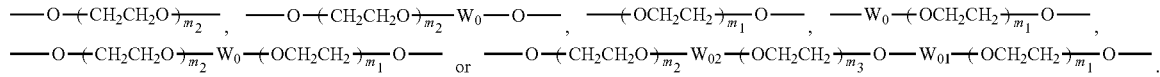

With respect to

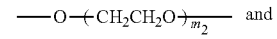 and

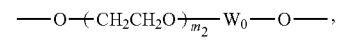, $m_2$ is a value from 2 to 2000 (the intersection of 0 to 2000 for $m_2$ and 2 to 2000 for LPEG). $m_2$ is more preferably a value from 5 to 2000, more preferably from 5 to 1000, more preferably from 10 to 1000, more preferably from 10 to 500, more preferably from 20 to 500, more preferably from 20 to 250, and more preferably from 50 to 250.

LPEG is most preferably

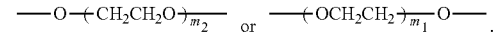

The H-shaped multifunctionalized polyethylene glycol represented by general formula (1) can has a structure represented by general formula (2) or general formula (3) shown as follows.

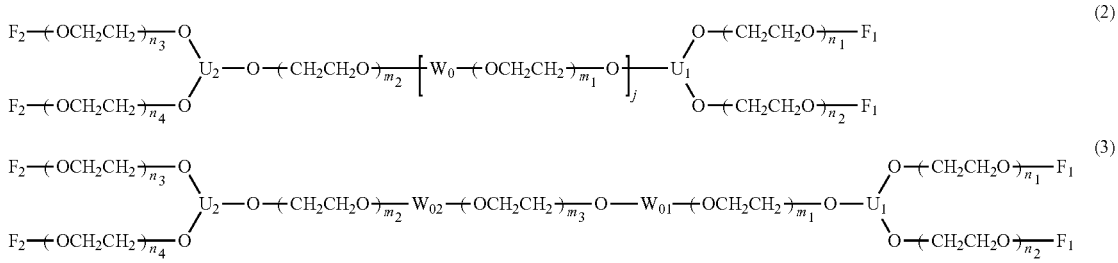

(2)

(3)

wherein, the definitions of $n_1$, $n_2$, $n_3$, $n_4$, $F_1$, $F_2$, $U_1$, $U_2$, $W_0$, $W_{01}$, $W_{02}$, $m_1$, $m_2$, $m_3$ and j are the same as above-defined, no more repeated here.

Wherein, general formula (2) is preferably a structure represented by general formula (4), general formula (4b), general formula (5), general formula (5b) or general formula (6).

atoms, more preferably has 1 to 20 non-hydrogen atoms and further preferably has 1 to 10 non-hydrogen atoms.

1.1.1. The Degree of Polymerization and Dispersity of Polyethylene Glycol Chains What should be noted is that the "molecular weight" in the present invention also refers to "number average molecular weight" ($M_n$) for a substance. A molecular weight can refer

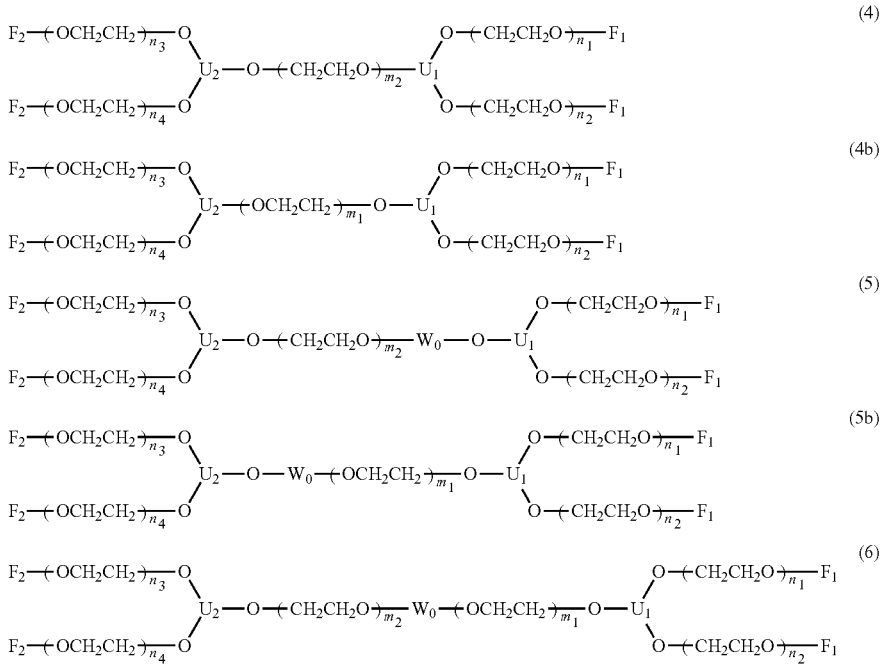

(4)

(4b)

(5)

(5b)

(6)

In the present invention, preferable structures of LPEG including

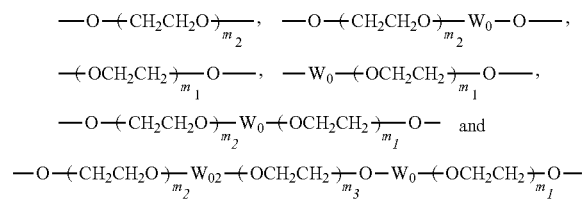

correspond to general formula (4), general formula (5), general formula (4b), general formula (5b), general formula (6) and general formula (3), respectively. Wherein, in general formula (6), $W_0$ preferably has 1 to 50 non-hydrogen to a PEG block, chain or segment of polydisperse blocks or substances, or refer to that of a PEG block, chain or segment of monodisperse blocks or substances. Herein, the molecular weight generally corresponds to polydisperse polymer if without particular limitations for a substance.

With respect to a polydisperse PEG chain ($n_1$, $n_2$, $n_3$, $n_4$, $m_1$, $m_2$, $m_3$, LPEG, etc) of the substance, the number average degree of polymerization is preferably a value from 2 to about 1000, more preferably a value from 2 to about 500, more preferably a value from 5 to about 500, more preferably a value from 11 to about 500, more preferably a value from 22 to about 500, more preferably a value from 30 to about 250, and more preferably a value from 34 to about 150. With respect to these preferable ranges, the more common the corresponding molecular weight of PEG segment is, the simpler and more controllable the production method is, also the narrower the PDI (polydispersity index)

of molecular weight would be, and also the more uniform the performance is. The number average molecular weight of linear PEG chain obtained by mostly common polymerization method is about 2 kDa to 40 kDa.

With respect to a monodisperse PEG block of the substance, the molecular weight is described by the number of oxyethylene units (also referred to as EO-unit number, or oxyethylene-unit number). The EO-unit number of monodisperse polyethylene glycol by common prior art is about 1 to 70, including but not limited to EO-unit numbers listed or disclosed in references of "Expert Rev. Mol. Diagn. 2013, 13 (4), 315-319", "J. Org. Chem. 2006, 71, 9884-9886", "Angew. Chem. 2009, 121, 1274-1278", "Bioorganic & Medicinal Chemistry Letters, 2015, 25: 38-42", "Angew. Chem Int Ed, 2015, 54: 3763-3767", and cited literatures by these references. Typical EO-unit number of monodisperse PEGs could be but not limited to 1, 2, 3, 4, 5, 6, 7, 8, 9, 10, 12, 13, 16, 20, 22, 24, 27, 29, 36, 44, 48, 56, 62, 64, 67, etc. What should be noted is that, monodispersity herein not only can refer to a single component having only one kind of EO-unit number, but also can refer to a monodisperse mixture. With respect to a monodisperse mixture, the relative percentages of different components should be a fixed value in order to generate a PDI of 1 for the mixture as a whole, and herein the corresponding number average degree of polymerization can be either an integer or a non-integer. For a mixture matter composed of monodisperse blocks or substances, if the percentage of each component is not fixed, then the whole PDI would be greater than unity and corresponds to a polydisperse mixture. The EO-unit number of a monodisperse PEG block is preferably from 2 to 70, more preferably from 3 to 70, more preferably from 3 to 50, and more preferably from 3 to 25. The more preferable the EO-unit number is, the more diverse production methods thereof are.

According to the difference of dispersity of PEG chains, the H-shaped multifunctionalized polyethylene glycols represented by general formula (1) include but are not limited to the following embodiments:

(1) Wherein, LPEG is polydisperse.

The corresponding number average molecular weight in units of Da is preferably about 500, 600, 700, 800, 900, 1000, 1500, 2000, 2500, 3000, 3350, 3500, 4000, 5000, 5500, 6000, 6500, 7000, 7500, 8000, 8500, 9000, 9500, 10000, 11000, 12000, 13000, 14000, 15000, 16000, 17000, 18000, 19000, 20000, 25000, 30000, 35000, 40000, 50000 or 60000 Da, and more preferably about 1000, 1500, 2000, 2500, 3000, 3350, 3500, 4000, 5000, 5500, 6000, 6500, 7000, 7500, 8000, 8500, 9000, 9500, 10000, 11000, 12000, 13000, 14000, 15000, 16000, 17000, 18000, 19000 or 20000 Da, and more preferably about 1000, 2000, 3000, 3350, 3500, 4000, 5000, 6000, 7000, 8000, 9000, 10000, 12000, 13000, 14000, 15000, 16000, 17000, 18000, 19000 or 20000 Da, and more preferably about 1000, 2000, 3350, 3500, 4000, 5000, 6000, 8000, 9000, 10000, 12000, 15000 or 20000 Da.

(2) Wherein, LPEG is monodisperse.

In the present invention, LPEG is allowed to have one, two, three or more PEG blocks, when LPEG is monodisperse, all the PEG blocks should be monodisperse.

When containing one PEG block, the EO-unit number of LPEG is preferably an integer from 2 to 70, more preferably an integer from 3 to 70, more preferably an integer from 5 to 70, and more preferably an integer from 5 to 50.

When containing two PEG blocks, the total EO-unit number of LPEG is preferably an integer from 2 to 140, more preferably an integer from 3 to 140, more preferably an integer from 5 to 140, more preferably an integer from 5 to 70, and more preferably an integer from 5 to 50.

When containing three PEG blocks, the total EO-unit number of LPEG is preferably an integer from 3 to 210, more preferably an integer from 5 to 210, more preferably an integer from 5 to 150, more preferably an integer from 5 to 100, more preferably an integer from 5 to 70, and more preferably an integer from 5 to 50.

When containing four or more PEG blocks, the total EO-unit number of LPEG is preferably an integer from 4 to 500, more preferably an integer from 5 to 500, more preferably an integer from 5 to 250, more preferably an integer from 5 to 200, more preferably an integer from 5 to 100, and more preferably an integer from 5 to 50.

(3) Wherein, one PEG branch chain corresponding to $n_1$, $n_2$, $n_3$ or $n_4$ is polydisperse.

The number average molecular weight of corresponding PEG branch chain is preferably about 500, 600, 700, 800, 900, 1000, 1500, 2000, 2500, 3000, 3350, 3500, 4000, 5000, 5500, 6000, 6500, 7000, 7500, 8000, 8500, 9000, 9500, 10000, 11000, 12000, 13000, 14000, 15000, 16000, 17000, 18000, 19000, 20000, 25000, 30000, 35000, 40000, 50000 or 60000 Da, more preferably about 1000, 1500, 2000, 2500, 3000, 3350, 3500, 4000, 5000, 5500, 6000, 6500, 7000, 7500, 8000, 8500, 9000, 9500, 10000, 11000, 12000, 13000, 14000, 15000, 16000, 17000, 18000, 19000 or 20000 Da, more preferably about 1000, 2000, 3000, 3350, 3500, 4000, 5000, 6000, 7000, 8000, 9000, 10000, 12000, 13000, 14000, 15000, 16000, 17000, 18000, 19000 or 20000 Da, and more preferably about 1000, 2000, 3350, 3500, 4000, 5000, 6000, 8000, 9000, 10000, 12000, 15000 or 20000 Da.

(4) Wherein, one PEG branch chain corresponding to $n_1$, $n_2$, $n_3$ or $n_4$ is monodisperse.

The EO-unit number of corresponding PEG branch chain is preferably an integer from 2 to 70, more preferably an integer from 3 to 70, more preferably an integer from 5 to 70, and more preferably an integer from 5 to 50.

(5) Wherein, all the PEG branch chains corresponding to $n_1$, $n_2$, $n_3$ and $n_4$ are polydisperse, and LPEG is monodisperse. Wherein, the PEG-block number of LPEG is not particularly limited. LPEG is preferably a monodisperse monoblock, diblock or triblock.

(6) Wherein, two of the PEG branch chains corresponding to $n_1$, $n_2$, $n_3$ and $n_4$ are polydisperse, and the other two are monodisperse. LPEG is polydisperse or monodisperse.

(7) Wherein, all the PEG branch chains corresponding to $n_1$, $n_2$, $n_3$ and $n_4$ are monodisperse, and LPEG is polydisperse. Wherein, the PEG-block number of LPEG is not particularly limited, LPEG is preferably a monoblock, diblock or triblock, and contains at least one polydisperse block.

(8) Wherein, all the PEG branch chains corresponding to $n_1$, $n_2$, $n_3$ and $n_4$ and LPEG are polydisperse.

(9) Wherein, all the PEG branch chains corresponding to $n_1$, $n_2$, $n_3$ and $n_4$ and LPEG are monodisperse.

1.1.2. Branching Groups $U_1$, $U_2$ (SemiH-Branching) and G (End-Branching)

$U_1$ and $U_2$ each independently is identical to or contains $U_{01}$ and $U_{02}$, respectively.

$U_1$ and $U_2$ are each independently symmetrical or asymmetrical in terms of structure, i.e., $U_1$ and $U_2$ are each independently of a symmetrical or asymmetrical type; wherein, said symmetrical type means that corresponding two PEG branches connect to the common branching core via identical linkages; said asymmetrical type means that corresponding two PEG branches connect to the common branching core via different linkages.

With respect to trivalent groups $U_{01}$ and $U_{02}$, any of its radical ends can be directed to the PEG main chain if without special instructions. When a mark of asterisk "*" is used, the marked end would be directed to PEG main chain. The asterisk "*" in the structural formulas of the present invention indicates the available radical ends to be connected towards LPEG.

Take a trivalent group

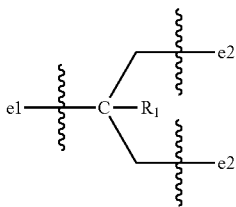

for example, it has two types of radical ends, marked by e1 and e2, respectively. As for a trivalent group $U_{01}$ or $U_{02}$, if the radical end "e1" is directed to the PEG main chain, $U_{01}$ or $U_{02}$ corresponds to a symmetrical type, and if any radical end "e2" is directed to the PEG main chain, $U_{01}$ or $U_{02}$ corresponds to an asymmetrical type.

$U_{01}$ and $U_{02}$ are each independently a trivalent group selected from the set $G^3$ consisting of trivalent groups.

In one molecule, $U_{01}$ and $U_{02}$ are each independently symmetrical or asymmetrical.

When $U_{01}$ or $U_{02}$ is symmetrical, the corresponding $U_1$ or $U_2$ would be symmetrical or asymmetrical. With respect to symmetrical $U_{01}$ or $U_{02}$, when $L_1=L_2$ or $L_3=L_4$, the corresponding $U_1$ or $U_2$ would be symmetrical. When $L_1$ is different from $L_2$, or $L_3$ is different from $L_4$, the corresponding $U_1$ or $U_2$ would be asymmetrical.

When $U_{01}$ or $U_{02}$ is asymmetrical, the corresponding $U_1$ or $U_2$ would be of an asymmetrical type.

The stability of $U_1$ and $U_2$ are not particularly limited, each independently stable or degradable.

The structure of $U_1$ and $U_2$ are not particularly limited, each independently including but not limited to a branched structure and a ring-containing structure.

The stability of $U_{01}$ and $U_{02}$ are not particularly limited, each independently stable or degradable.

The structure of $U_{01}$ and $U_{02}$ are not particularly limited, each independently including but not limited to a branched structure and a ring-containing structure.

As for a group G with the valence of k+1 (k=2 to 250), any one of its radical ends can be directed to corresponding PEG branch chain. When an asterisk mark is used, the marked radical end would direct to the corresponding PEG branch chain if without particular instructions.

The structure of G is not particularly limited, including but not limited to a branched type, a ring-containing type, a comb-like type, a dendritic type, a hyperbranched type, etc.

k represents the number of unprotected or protected functional end-groups of a PEG branch chain terminal. Wherein, k is an integer of 1 or from 2 to 250, representing the available number of unprotected or protected functional end-groups ($R_{01}$) to be contained in one terminal functional group.

When k=1, g would be zero and G would be absent.

When k is an integer from 2 to 250, g would be 1 and G would be present. G is a linking group with the valence of k+1. Herein, k can be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or an integer from 33 to 250. Correspondingly, the valence of G is from 3 to 251, selected from 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33 and integers from 34 to 251.

Wherein, k is preferably selected from 1 to 100; specifically, k is preferably 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or an integer from 33 to 100, more preferably 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or an integer from 33 to 64, and more preferably 1, 2, 3, 4, 5, 6, 7, 8, 9, 10, 11, 12, 13, 14, 15, 16, 17, 18, 19 or 20.

For any k selected from 2 to 250, the corresponding G can be any (k+1)-valent group selected from the set of $G^{k+1}$ consisting of groups with valence of k+1.

The stability of any (k+1)-valent group in the set of $G^{k+1}$ is not particularly limited and can be stable or be degradable. The condition "to be stable" is not particularly limited, including but not limited to conditions such as light illumination, heat, an enzymatic condition, an oxidation-reduction condition, an acidic condition, a basic condition, a physiological condition, a simulated physiological environment in vitro, etc., preferably conditions such as light illumination, heat, an enzymatic condition, an oxidation-reduction condition, an acidic condition, a basic condition, etc. The condition "to be degradable" or "to degrade" is not particularly limited, including but not limited to conditions such as light illumination, heat, an enzymatic condition, an oxidation-reduction condition, an acidic condition, a basic condition, a physiological condition, a simulated physiological environment in vitro, etc., preferably conditions such as light illumination, heat, an enzymatic condition, an oxidation-reduction condition, an acidic condition, a basic condition, etc.

$U_{01}$, $U_{02}$ and trivalent G could be each independently any trivalent group selected from the set $G^3$ consisting of trivalent groups. They can be the same or different in one molecule.

1.1.2.1. Trivalent Groups

Trivalent groups in the set of $G^3$ containing a trivalent core structure. Said trivalent core structure can be an atom $CM_3$, an unsaturated bond $CB_3$ or a cyclic structure $CC_3$.

Wherein, said trivalent atom core ($CM_3$) is not particularly limited as long as it can provide three covalent single bonds individually. Examples of $CM_3$ include a trivalent nitrogen-atom core, a trivalent carbon-atom core, a trivalent silicon-atom core, a trivalent phosphorus-atom core, etc. The trivalent core atom can connect with no other atom or group substituents, such as a trivalent nitrogen atom core of

or can connect with other atom or group substituents, e.g., a trivalent carbon atom core of

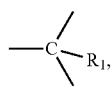

a trivalent silicon atom core of

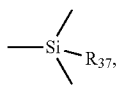

a trivalent phosphorous atom core of

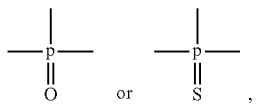

etc.

Wherein, $R_1$ is a hydrogen atom or a substituent bound to a carbon atom or a silicon atom.

When as a group substituent, $R_1$ is not particularly limited, but preferably a group substituent that can remain stable under anionic polymerization conditions.

When as a group substituent, the carbon-atom number of $R_1$ is not particularly limited, preferably from 1 to 20, and more preferably from 1 to 10.

When as a group substituent, $R_1$ can contain heteroatoms or not.

When as a group substituent, the structure of $R_1$ is not particularly limited, including but not limited to a linear structure, a branched structure which bearing one or more pendant groups and a ring-containing structure. Wherein the type of cyclic structure is not particularly limited, including but not limited to all the above-listed cyclic structures in the terminology section.

$R_1$ is a hydrogen atom or a group substituent selected from the group consisting of $C_{1-20}$ hydrocarbyl groups, substituted $C_{1-20}$ hydrocarbyl groups and the like. Wherein, the atom or group substituent of $R_1$ is not particularly limited. Examples of $R_1$ include but are not limited to all the above-listed substituting atoms and substituting groups in the terminology section. $R_1$ can be selected from the group consisting of halogen atoms, hydrocarbyl substituents and heteroatom-containing substituents.

$R_1$ is preferably a hydrogen atom or a group substituent selected from the group consisting of a $C_{1-20}$ alkyl group, an arylalkyl group, a $C_{1-20}$ open-chain heterohydrocarbyl group, a heteroarylhydrocarbyl group, a substituted $C_{1-20}$ alkyl group, a substituted arylhydrocarbyl group, a substituted $C_{1-20}$ open-chain heterohydrocarbyl group, a substituted heteroarylhydrocarbyl group and the like.

Specific examples of $R_1$ can be a hydrogen atom or a group substituent selected from, but not limited to, a methyl group, an ethyl group, a 1-propyl group (or an n-octyl group), an isopropyl group, a butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, a benzyl group, a substituted $C_{1-20}$ alkyl group, a substituted arylhydrocarbyl group, a substituted $C_{1-20}$ open-chain heterohydrocarbyl group, a substituted heteroarylhydrocarbyl group and the like. Wherein, the butyl group includes but is not limited to an n-butyl group and a t-butyl group. The octyl group includes but is not limited to an n-octyl group and a 2-ethylhexyl group. Wherein, the atom or group substituent can be a halogen atom, a hydrocarbyl substituent or a heteroatom-containing substituent, and preferably a fluorine atom, a chlorine atom, a bromine atom, an iodine atom, a $C_{1-6}$ alkyl group, an alkoxy group or a nitro group.

$R_1$ is preferably a hydrogen atom, a methyl group, an ethyl group, an n-propyl group, an isopropyl group, a butyl group, a pentyl group, a hexyl group, a heptyl group, an octyl group, a nonyl group, a decyl group, a $C_{1-10}$ halogenated hydrocarbyl group (or a halohydrocarbyl group), a halogenated acetyl group or an alkoxy-substituted $C_{1-10}$ aliphatic hydrocarbyl group. Wherein, the halogen atom is F, Cl, Br or I.

$R_1$ is most preferably a hydrogen atom, a methyl group or an ethyl group.

Wherein, $R_{37}$ is the substituent of a trivalent silicon-branching center, selected from hydrocarbyl groups, preferably a $C_{1-20}$ hydrocarbyl group, more preferably a $C_{1-20}$ alkyl group, and most preferably a methyl group.

Wherein, $CB_3$, said trivalent unsaturated-bond core structure is not particularly limited, as long as it can provide three covalent single bonds individually. The bond-membering atoms of said unsaturated bond can be two or two more, preferably two or three, and more preferably two. For example,

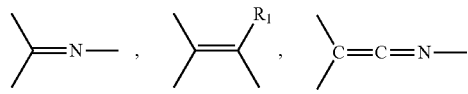

and the like.

Wherein, said trivalent cyclic core structure, $CC_3$, is not particularly limited, as long as it can protrude three covalent single bonds individually. The ring-membering atoms to form a covalent single bond radical are not particularly limited, including but not limited to N, C, Si, P, etc. The cyclic structure can be but not limited to an alicyclic ring, an aromatic ring, a sugar ring or a condensed ring. The cyclic structure can be a monocyclic ring, e.g.,

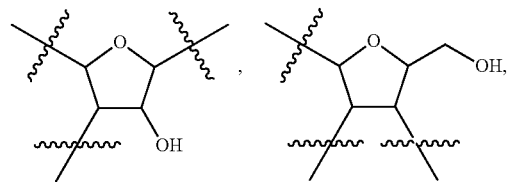

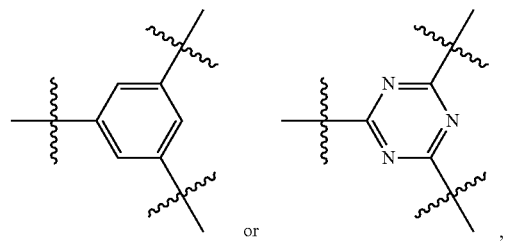

or be a polycyclic ring, e.g.,

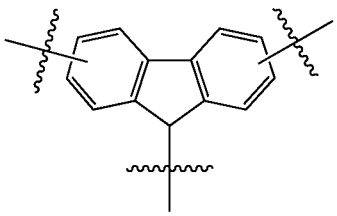

The cyclic structure can come from natural source, such as originating from a trivalent monocyclic ring of a cyclic monosaccharide, e.g.,

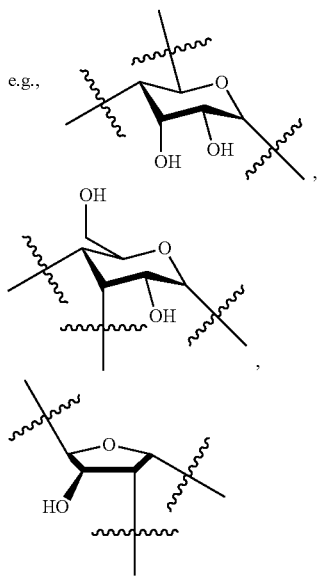

and the like. The cyclic structure can also be a synthesized ring formed via chemical reactions, such as a cyclopeptide, a lactone, a lactam, a lactide,

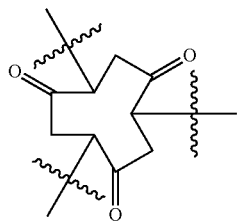

The covalent single bond can protrude directly from a ring-membering atom, or via an unsaturated bond. It also allows three covalent single bonds to protrude from three ring-membering atoms respectively,

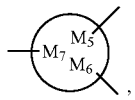

or two of the three covalent single bonds to derive from one ring-membering atom together,

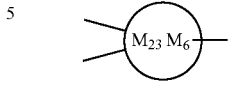

Wherein, $M_5$, $M_6$, $M_7$ and $M_{23}$ are ring-membering atoms, i.e., constituting the ring skeleton. $M_5$, $M_6$, $M_7$ and $M_{23}$ are each independently a carbon atom or a heteroatom, and they can be the same or different in one molecule. $M_5$, $M_6$, $M_7$ and $M_{23}$ are each independently preferably a carbon atom, a nitrogen atom, a phosphorus atom or a silicon atom. The number of ring-membering atoms of a ring containing $M_5$, $M_6$, $M_7$ or $M_{23}$ is not particularly limited, preferably from 3 to 50, more preferably from 3 to 32, and more preferably from 3 to 18. $M_{23}$ is a carbon atom, a nitrogen atom, a phosphorus atom or a silicon atom which protrudes two single bonds. Concerning a nitrogen atom, the ring-membering nitrogen atom is in a form of quaternary ammonium cation.

$M_5$, $M_6$, $M_7$ and $M_{23}$ can each independently be a carbon atom or a heteroatom of a 3- to 50-membered ring, preferably a carbon atom or a heteroatom of a 3- to 32-membered ring, preferably a carbon atom, a nitrogen atom, a phosphorus atom or a silicon atom of a 3- to 32-membered ring, more preferably a carbon atom, a nitrogen atom, a phosphorus atom or a silicon atom of a 3- to 18-membered ring.

The ring containing any of $M_5$, $M_6$ and $M_7$, the ring containing $M_5$, $M_6$ and $M_7$, and the ring containing $M_{23}$ and $M_6$ are not particularly limited, including but not limited to

and the like.
Wherein,

is an alicyclic ring or an aliphatic-derived heteroring of any type, and the ring-membering atoms are each independently a carbon atom or a heteroatom; said heteroatom is not particularly limited, including but not limited to a nitrogen atom, an oxygen atom, a sulfur atom, a phosphorus atom, a silicon atom, a boron atom and the like. The hydrogen linked to a ring-membering atom can be substituted by any heteroatom or group substituent, or be not substituted. Said heteroatom or group substituent is not particularly limited, including but not limited to all substituents above-listed in the terminology section, and is selected from the group consisting of a halogen atom, a hydrocarbyl substituent and a heteroatom-containing substituent. The definition of said alicyclic ring and said aliphatic-derived heteroring are defined in detail in the terminology section, no more repeated here. Generally speaking, said alicyclic ring and said aliphatic-derived heteroring include but are not limited to cyclic structures selected from the group consisting of a monocyclic ring, a polycyclic ring, a spirocyclic ring, a bridged cyclic ring, a condensed ring, a carbon ring, a heteroring, an aliphatic-derived heteroring, a heteromonocyclic ring, a heteropolycyclic ring, a hetero-spiroring, a hetero-bridged ring, a hetero-aliphatic ring, and the combination of any two or more cyclic structures of the foregoing.

Wherein, (Ar)

is an aromatic ring or an aromatic-derived heteroring, and the ring-membering atoms are each independently a carbon atom or a heteroatom; said heteroatom is not particularly limited, and can be, but not limited to, a nitrogen atom, a phosphorus atom, a silicon atom, a boron atom or the like. The hydrogen linked to the arylring-membering atoms can be substituted with any heteroatom or group substituent, or be not substituted. Said heteroatom or group substituent is not particularly limited, including but not limited to all heteroatom or group substituents above-listed in the terminology section, and selected from the group consisting of halogen atoms, hydrocarbyl substituents, and heteroatom-containing substituents. The substituting atom is preferably a halogen atom and the substituting group is preferably a group that can favor inductive effect, conjugation effect, or both inductive and conjugation effects of electrons of unsaturated bonds. The definition of said aromatic ring and said aromatic-derived heteroring are defined in detail in the terminology section, no more repeated here. Generally speaking, said aromatic ring and said aromatic-derived heteroring include but are not limited to cyclic structures selected from the group consisting of a monocyclic ring, a polycyclic ring, a condensed ring, a condensed aryl ring, a condensed heteroring, an aryl-condensed heteroring, an aryloheteroring, a benzoheteroring, a heterocondensed heteroring, a carbon ring, a heteroring, an aromatic-derived heteroring, a heteromonocyclic ring, a heteropolycyclic ring, a heterosubstituted condensed ring, a heteroaromatic ring, and the combination of any two or two more cyclic structures thereof. The aromatic ring is preferably derived from any cyclic compound selected from the group consisting of benzene, pyridine, pyridazine, pyrimidine, pyrazine, 1,3,5-triazine, tetrazine (three isomers of 1,2,3,4-, 1,2,4,5- and 1,2,3,5-), indene, indane, indole, isoindole, purine, naphthalene, dihydroanthracene, xanthene, thioxanthene, dihydrophenanthrene, 10,11-dihydro-5H-dibenzo[a,d]cycloheptane, dibenzocycloheptene, 5-dibenzosuberenone, quinoline, isoquinoline, fluorene, carbazole, iminodibenzyl, acenaphthene (or 1,2-dihydroacena-phthylene), dibenzocyclooctyne, aza-dibenzocyclooctyne and the like, or any substituted form thereof, or any heterosubstituted form of the foregoing.

Wherein, (Sug)

is the skeleton of a saccharide and derivative thereof which contains a cyclic monosaccharide skeleton. Said saccharide or derivative thereof can be derived from natural or unnatural monosaccharides. The structure of said cyclic monosaccharide can be any form selected from the group consisting of isomers, enantiomers, optical isomers, conformational isomers, rotamers and the combination of two or two more thereof.

(Sug)

is selected from skeletons of cyclic monosaccharides and derivatives thereof, skeletons of oligosaccharides and derivatives thereof, and skeletons of polysaccharides and derivatives thereof.

Said skeleton of a cyclic monosaccharide or derivative thereof is represented as (MSug), and the carbon-atom number is 3, 4, 5, 6 or 7. It can be an isomer, an enantiomer, an optical isomer, a conformational isomer, a rotamer or the combination of any two or two more thereof. It is preferably a skeleton of $C_6$ monosaccharide or derivative thereof selected from the group including but not limited to, for example, glucose, allose, altrose, mannose, gulose, idose, galactose, talose, psicose, fructose, sorbose, tagatose and inositol.

Said skeleton of an oligosaccharide or derivative thereof is represented as (OSug), the combination manners between the cyclic monosaccharide skeletons include but are not limited to linear, branched, hyperbranched, dendritic, comb-like and cyclic manners. The number of monosaccharide units is from 2 to 10. Take the cyclic manner for example, it can be combined into a cyclodextrin or derivative thereof selected from α-cyclodextrin, β-cyclodextrin and γ-cyclodextrin and derivatives thereof.

Said the skeleton of a polysaccharide or derivative thereof is represented as (PSug), the combination manners between the cyclic monosaccharide skeletons include but are not limited to linear, branched, hyperbranched, dendritic, comb-like and cyclic manners. The number of monosaccharide units is more than 10. For example, D-glucopyranose units can be linked in sequence via α-1,4-glycosidic bonds to form a linear combination, and said linear structure can further be interconnected end-to-end to form a cyclic combination. For another example, when at least one D-glucopyranose unit is bound together with its adjacent glucopyranose units via at least two glycosidic bonds selected from types of a α-1,2-glycosidic bond, a α-1,3 glycosidic bond, a α-1,4-glycosidic bond and a α-1,6-glycosidic bond, a branched or hyperbranched combination can be achieved. When all the glucose units are bound together via more than three given glycosidic bonds in a regular and repeated manner, a comb-like combination can be obtained. Specifically, for example, said polysaccharide or derivative thereof can be starch, chitin, cellulose or glucan.

Wherein,

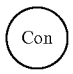

represents a ring containing at least one chemical bond by condensation reaction selected from an amide bond, an ester bond, an imide bond, an anhydride bond and the like. Specific examples can be a lactone, a lactam, a cycloimide, a cycloanhydride, a cyclopeptide or the like.

$CC_3$ can be any trivalent cyclic core structure selected from the group consisting of, but not limited to,

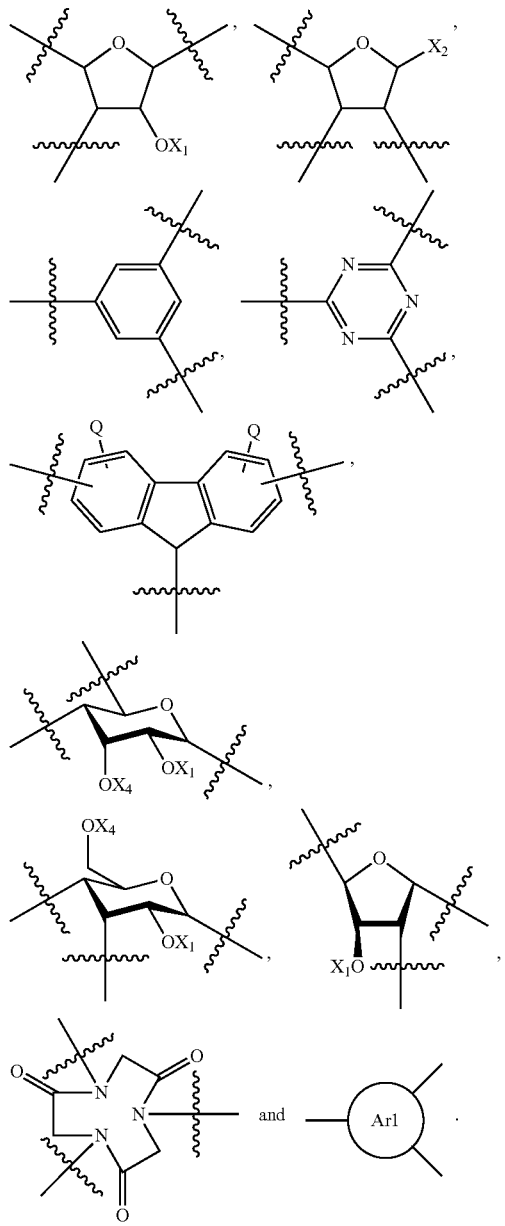

Wherein, $X_1$ and $X_4$ connect to an oxy group, and are each independently a hydrogen atom, a hydroxyl protecting group or a group $LG_4$.

When as a hydroxyl protecting group, $X_1$ and $X_4$ are selected from hydroxyl protecting groups listed for $PG_4$. A protected hydroxyl group is denoted as $OPG_4$. The type of hydroxyl protecting groups is not particularly limited.

Wherein, the carbon-atom number of $LG_4$ is not particularly limited, preferably from 1 to 20, and more preferably from 1 to 10.

The structure of $LG_4$ is not particularly limited, can be, but not limited to, a linear type, a branched type bearing pendant groups or a ring-containing type. Wherein, said ring is not particularly limited, including but not limited to all the above-listed cyclic structures in the terminology section.

$LG_4$ can contain heteroatoms, or do not contain heteroatoms.

$LG_4$ can be a $C_{1-20}$ hydrocarbyl group, a $C_{1-20}$ heterohydrocarbyl group, a substituted $C_{1-20}$ hydrocarbyl group or a substituted heterohydrocarbyl group. Wherein, the heteroatom or group substituent of $LG_4$ is not particularly limited, including but not limited to all the above-listed substituting heteroatoms and substituting groups in the terminology section, and can be a halogen atom, a hydrocarbyl substituent, or a heteroatom-containing substituent.

$LG_4$ is preferably selected from the group consisting of a $C_{1-20}$ alkyl group, a $C_{1-20}$ unsaturated aliphatic hydrocarbyl group, an aryl group, an arylhydrocarbyl group, a $C_{1-20}$ heterohydrocarbyl group, a $C_{1-20}$ aliphatic hydrocarbyl-acyl group, a $C_{1-20}$ aliphatic-derived heterohydrocarbyl-acyl group, an aryl-acyl group, a heteroaryl-acyl group, a $C_{1-20}$ hydrocarbyloxy-acyl group, a $C_{1-20}$ hydrocarbylthio-acyl group, a $C_{1-20}$ hydrocarbylamino-acyl group, a $C_{1-20}$ heterohydrocarbyloxy-acyl group, a $C_{1-20}$ heterohydrocarbylthio-acyl group, a $C_{1-20}$ heterohydrocarbylamino-acyl group and substituted forms thereof. Wherein, said acyl group of $LG_4$ is not particularly limited, can be but not limited to any of all the above-listed acyl groups in the terminology section. For examples, the acyl group within $LG_4$ can be selected from the group consisting of a carbonyl group, a sulfonyl group, a sulfinyl group, a phosphoryl group, a phosphiryl group, a phosphinyl group, a nitroxyl group, a nitrosyl group, a thiocarbonyl group, an imidoyl group, a thiophosphoryl group, a dithiophosphoryl group, a trithiophosphoryl group, a thiophosphiryl group, a dithiophosphiryl group, a thiophosphinyl group, a thiophosphono group, a dithiophosphono group, a thiophosphino group and the like. The acyl group of $LG_4$ is preferably a carbonyl group, a thiocarbonyl group, a sulfonyl group or a sulfinyl group, and more preferably a carbonyl group, a thiocarbonyl group or a sulfonyl group.

$LG_4$ is more preferably selected from the group consisting of a $C_{1-20}$ alkyl group, a $C_{3-20}$ alkenylhydrocarbyl group, an aryl group, an aralkyl group (or an arylalkyl group), a $C_{1-20}$ heteroalkyl group, a heteroaryl group, a heteroarylalkyl group, a $C_{1-20}$ alkylcarbonyl group, an arylcarbonyl group, an arylalkylcarbonyl group (or an aralkylcarbonyl group), a $C_{1-20}$ heteroalkylcarbonyl group, a heteroarylcarbonyl group, a heteroarylalkylcarbonyl group (or a heteroaralkylcarbonyl group), a $C_{1-20}$ alkoxycarbonyl group (or an alkyloxycarbonyl group, alkyl-O—CO—), an aryloxycarbonyl group (or an aroxycarbonyl group, aryl-O—CO—), an arylalkoxycarbonyl group (or an aralkyloxycarbonyl group, arylalkyl-O—CO—), a $C_{1-20}$ (alkylthio)carbonyl group (or an alkylthio-carbonyl group, alkyl-S—CO—), an (arylthio)carbonyl group (or an (arthio)carbonyl group, aryl-S—CO—), an (arylalkylthio)carbonyl group (or an (aralkylthio)

carbonyl group, arylalkyl-S—CO—), a $C_{1-20}$ alkylaminocarbonyl group (e.g., alkyl-NH—CO—, alkyl-N (alkyl)-CO—, etc), an arylaminocarbonyl group (or an araminocarbonyl group), an arylalkylaminocarbonyl group (or an aralkylaminocarbonyl group), a $C_{1-20}$ heteroalkoxycarbonyl group, a heteroaryloxycarbonyl group, a heteroarylalkoxycarbonyl group (or a heteroaralkoxycarbonyl group), a $C_{1-20}$ hetero(alkylthio)carbonyl group, a hetero(arylthio)carbonyl group, a hetero(arylalkylthio)carbonyl group (or a hetero(aralkylthio)carbonyl group), a $C_{1-20}$ heteroalkylaminocarbonyl group, a heteroarylaminocarbonyl group, a heteroarylalkylaminocarbonyl group (or a heteroaralkylaminocarbonyl group), a $C_{1-20}$ alkyl-thiocarbonyl group (or an alkyl-thioxocarbonyl group, alkyl-CS—), an aryl-thiocarbonyl group (or an aryl-thioxocarbonyl group aryl-CS—), an arylalkyl-thiocarbonyl group (or an aralkyl-thiocarbonyl group, arylalkyl-CS—), a $C_{1-20}$ heteroalkyl-thiocarbonyl group, a heteroaryl-thiocarbonyl group, a heteroarylalkyl-thiocarbonyl group (or a heteroaralkyl-thiocarbonyl group), a $C_{1-20}$ alkoxy-thiocarbonyl group (or alkyloxy-thiocarbonyl group, alkyl-O—CS—), an aroxy-thiocarbonyl group (or an aryloxy-thiocarbonyl group, aryl-O—CS—), an arylalkoxy-thiocarbonyl group (or an aralkyloxy-thiocarbonyl group, aralkyl-O—CS—), a $C_{1-20}$ (alkylthio)thiocarbonyl group (alkyl-S—CS—), an (arylthio)thiocarbonyl group (aryl-S—CS—), an (arylalkylthio)thiocarbonyl group (or an (aralkylthio)thiocarbonyl group, aralkyl-S—CS—), a $C_{1-20}$ alkylaminothiocarbonyl group (e.g., alkyl-NH—CS—, alkyl-N(alkyl)-CS—, etc), an arylaminothiocarbonyl group (e.g., aryl-NH—CO—, etc), an arylalkylaminothiocarbonyl group (or an aralkylaminothiocarbonyl group), a $C_{1-20}$ heteroalkyloxy-thiocarbonyl group (or a $C_{1-20}$ heteroalkoxy-thiocarbonyl group), a heteroaryloxy-thiocarbonyl group (or a heteroaroxy-thiocarbonyl group), a heteroarylalkoxy-thiocarbonyl group (or a heteroarylalkyloxy-thiocarbonyl group), a $C_{1-20}$ hetero(alkylthio)thiocarbonyl group, a hetero(arylthio)thiocarbonyl group, a hetero(arylalkylthio)thiocarbonyl group (or a hetero(aralkylthio)thiocarbonyl group), a $C_{1-20}$ heteroalkylaminothiocarbonyl group, a heteroarylaminothiocarbonyl group (or a heteroaraminothiocarbonyl group), a heteroarylalkylaminothiocarbonyl group (or a heteroaralkylaminothiocarbonyl group) and substituted forms of the foregoing.

$LG_4$ is more preferably selected from the group consisting of a $C_{1-20}$ alkyl group, a $C_{3-20}$ alkenylhydrocarbyl group, an aryl group, an arylalkyl group, a $C_{1-20}$ heteroalkyl group, a heteroaryl group, a heteroarylalkyl group and substituted forms of the foregoing.

Specifically, $LG_4$ can be but not limited to a methyl group, an ethyl group, an n-propyl group, an isopropyl group, a butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, an allyl group, a trityl group, a benzyl group, a methylbenzyl group, a 1-ethoxyethyl group, a methoxyethoxymethyl group, a benzyloxymethyl group, a (methylthio)methyl group, a tetrahydropyranyl group, an acetyl group, a benzoyl group, a methoxy-acyl group, an ethoxy-acyl group, a t-butyloxy-acyl group, a phenoxy-acyl group, a benzyloxy-acyl group, a (methylthio)acyl group (a methylthio-acyl group, a $CH_3S$-acyl group), an ethylthio-acyl group, a t-butylthio-acyl group, a phenylthio-acyl group, a benzylthio-acyl group, a methylamino-acyl group, an ethylamino-acyl group, a t-butylamino-acyl group, a benzylamino-acyl group, the like or the substituted form of any said group thereof. Wherein, butyl group includes but is not limited to an n-butyl group and a t-butyl group. Octyl group includes but is not limited to an n-octyl group and a 2-ethylhexyl group. Wherein, the atom or group substituent can be a halogen atom, a hydrocarbyl substituent or a heteroatom-containing substituent, and preferably a fluorine atom, a chlorine atom, a bromine atom, an iodine atom, an alkoxy group, an alkenyl group or a nitro group.

$LG_4$ is further preferably a methyl group, an ethyl group, an n-propyl group, an isopropyl group, a t-butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, an allyl group, a trityl group, a phenyl group, a benzyl group, a methylbenzyl group, a 1-ethoxyethyl group, a methoxyethoxymethyl group, a benzyloxymethyl group, a (methylthio)methyl group, a tetrahydropyranyl group, an acetyl group, a benzoyl group, a methoxycarbonyl group (or methyloxycarbonyl group), an ethoxycarbonyl group (ethyloxycarbonyl group), t-butoxycarbonyl group (or t-butyloxycarbonyl group), a phenoxycarbonyl group (or phenyloxycarbonyl group), a benzyloxycarbonyl group (or benzoxycarbonyl), a (methylthio)carbonyl group ($CH_3$—S—CO—), an (ethylthio)carbonyl group ($CH_3CH_2$—S—CO—), (t-butylthio)carbonyl group, a (phenylthio)carbonyl group, a (benzylthio)carbonyl group, a methylaminocarbonyl group, an ethylaminocarbonyl group, a t-butylaminocarbonyl group, a benzylaminocarbonyl group, an (ethyl)thiocarbonyl group ($CH_3CH_2$—CS—), a (phenyl)thiocarbonyl group (Ph-CS—), a methoxy-thiocarbonyl group ($CH_3$—O—CS—), an ethoxy-thiocarbonyl group, a t-butyloxy-thiocarbonyl group (or t-butoxy-thiocarbonyl group), a phenoxy-thiocarbonyl group, a benzyloxy-thiocarbonyl group (or benzoxy-thiocarbonyl group), a (methylthio)thiocarbonyl group ($CH_3$—S—CS—), an (ethylthio)thiocarbonyl group ($CH_3CH_2$—S—CS—), a (t-butylthio)thiocarbonyl group, a (phenylthio)thiocarbonyl group, a (benzylthio)thiocarbonyl group, a (methylamino)thiocarbonyl group, an (ethylamino)thiocarbonyl group, a (t-butylamino)thiocarbonyl group, a (benzylamino)thiocarbonyl group, a $C_{1-10}$ halohydrocarbyl group, a trifluoroacetyl group, a halogenated phenyl group (or a halophenyl group), a halogenated benzyl group (or a halobenzyl group), a nitrobenzyl group, a p-methoxybenzyl group, a trifluoromethyl benzyl group or the substituted form of any said group of the foregoing. Wherein, the atom or group substituent is preferably a fluorine atom, an alkoxy group or a nitro group.

$LG_4$ is more preferably a methyl group, an ethyl group, an n-propyl group, an isopropyl group, a t-butyl group, a pentyl group, a hexyl group, an allyl group, a trityl group, a phenyl group, a benzyl group, a 1-ethoxyethyl group, a 2-ethoxyethyl group, a methoxyethoxymethyl group, a benzyloxymethyl group, a (methylthio)methyl group, a tetrahydropyranyl group, a nitrobenzyl group, a p-methoxybenzyl group, a trifluoromethyl benzyl group, a t-butoxycarbonyl group, a phenoxycarbonyl group, a benzyloxycarbonyl group, an acetyl group, a trifluoroacetyl group or the like.

$LG_4$ is more preferably a methyl group, an ethyl group, an n-propyl group, an isopropyl group, a t-butyl group, a pentyl group, a hexyl group, an allyl group, a trityl group, a phenyl group, a benzyl group, a nitrobenzyl group, a p-methoxy benzyl group, a trifluoromethyl benzyl group or the like.

$LG_4$ is most preferably a methyl group, an ethyl group, an allyl group or a benzyl group.

Wherein, $X_2$ is an atom or a group that connects to a carbon atom. It can be a hydrogen atom, a hydroxyl group, a protected hydroxyl group $OPG_4$, $R_1$ or —$CH_2$—$OX_1$. Wherein, the definitions of $R_1$ and $X_1$ are the same as above defined, no more repeated here.

Wherein, Q is not particularly limited as long as it favors inductive effect, conjugation effect, or both inductive and conjugation effects of electrons of unsaturated bonds.

When Q is on the ring, it can be one or more. When the number of Q is more than one, they can have the same structure or be a combination of two or two more different structures.

Q can be an atom substituent or a group substituent.

When as an atom substituent, Q can be a hydrogen atom or a halogen atom, and preferably a hydrogen atom or a fluorine atom.

When as a group substituent, examples of Q include but are not limited to all the above-listed substituting groups in the terminology section. Q can contain carbon atoms or not. One examples of Q without carbon atoms is a nitro group. When containing carbon atoms, the carbon-atom number of Q is not particularly limited, preferably from 1 to 20, and more preferably from 1 to 10.

When as a group substituent, the structure of Q is not particularly limited, including but not limited to a linear structure, a branched structure bearing pendant groups or a ring-containing structure. Wherein, said ring is not particularly limited, including but not limited to all the above-listed cyclic structures in the terminology section.

Q can be a hydrogen atom, a halogen atom, a carbon-free substituent, a hydrocarbyl group, a heterohydrocarbyl group, a substituted hydrocarbyl group or a substituted heterohydrocarbyl group.

Q is preferably a hydrogen atom, a halogen atom, a nitro group, a nitro-containing substituent, an acyl-containing substituent, a $C_{1-20}$ haloalkyl group, a $C_{1-20}$ alkyl group, a $C_{2-20}$ alkenyl group, a $C_{3-20}$ open-chain alkenyl-hydrocarbyl group, a $C_{3-20}$ cycloalkenyl group, an aryl group, an arylhydrocarbyl group, a $C_{1-20}$ heteroalkyl group, a heteroaryl group, a heteroarylalkyl group, or a $C_{1-20}$ alkoxy group, an aryloxy group, an arylhydrocarbyloxy group, a $C_{1-20}$ heteroalkoxy group, a heteroaryloxy group (or heteroaroxy group), a heteroarylhydrocarbyloxy group, a $C_{1-20}$ alkylthio group, an arylthio group, an arylhydrocarbylthio group, a $C_{1-20}$ heteroalkylthio group, a heteroarylthio group, a heteroarylhydrocarbylthio group or any substituted form thereof. Wherein, the atom or group substituents within Q are not particularly limited, including but not limited to all the above-listed substituting heteroatoms and substituting groups in the terminology section, and can be selected from halogen atoms, hydrocarbyl substituents, and heteroatom-containing substituents.

Q is more preferably a hydrogen atom, a halogen atom, a nitro group, a nitro-containing substituent, an acyl group, a ester-terminated substituent, a thioester-terminated substituent, an amide-terminated substituent, a $C_{1-20}$ haloalkyl group, a $C_{2-20}$ alkenyl group, a $C_{3-20}$ open-chain alkenyl-hydrocarbyl group, a $C_{3-20}$ cycloalkenyl group, an aryl group, an arylhydrocarbyl group, a $C_{1-20}$ heteroalkyl group, a heteroaryl group, a heteroarylalkyl group, a $C_{1-20}$ alkoxy group, an aryloxy group, an arylhydrocarbyloxy group, a $C_{1-20}$ heteroalkoxy group, a heteroaryloxy group, a heteroarylhydrocarbyloxy group, a $C_{1-20}$ alkylthio group, an arylthio group, an arylhydrocarbylthio group, a $C_{1-20}$ heteroalkylthio group, a heteroarylthio group, a heteroarylhydrocarbylthio group or any substituted form thereof. Wherein, said acyl group is not particularly limited, can be but not limited to any of all the above-listed acyl groups in the terminology section. For example, said acyl group within Q can be a carbonyl group, a sulfonyl group, a sulfinyl group, a phosphoryl group, a phosphiryl group, a phosphinyl group, a nitroxyl group, a nitrosyl group, a thiocarbonyl group, an imidoyl group, a thiophosphoryl group, a dithiophosphoryl group, a trithiophosphoryl group, a thiophosphiryl group, a dithiophosphiryl group, a thiophosphinyl group, a thiophosphono group, a dithiophosphono group, a thiophosphino group or the like. Said acyl group is more preferably a carbonyl group, a thiocarbonyl group, a sulfonyl group, a sulfinyl group or the like, and more preferably a carbonyl group, a thiocarbonyl group, a sulfinyl group or a sulfonyl group.

Q is more preferably a hydrogen atom, a halogen atom, a nitro group, a nitro-containing substituent, a $C_{1-20}$ carbonyl group, a $C_{1-20}$ (alkyl)thiocarbonyl group (alkyl-CS—), a $C_{1-20}$ sulfonyl group, a $C_{1-20}$ alkoxycarbonyl group, a $C_{1-20}$ (alkylthio)carbonyl group (alkyl-S—CO—), a $C_{1-20}$ alkylaminocarbonyl group, a $C_{1-20}$ (alkoxy)thiocarbonyl group, a $C_{1-20}$ (alkylthio)thiocarbonyl group (alkyl-S—CS—), a $C_{1-20}$ (alkylamino)thiocarbonyl group, a $C_{1-20}$ alkylsulfonate group, a $C_{1-20}$ alkylsulfinate group, an (aryl)thiocarbonyl group (aryl-CS—), an aryloxycarbonyl group, an (arylthio)carbonyl group, an arylaminocarbonyl group, an aryloxy-thiocarbonyl group, an (arylthio)thiocarbonyl group, an (arylamino)thiocarbonyl group, an aryl-sulfonate group (an aryloxy-sulfonyl group), an arylsulfinate group, an (arylalkyl)thiocarbonyl group, an arylalkoxycarbonyl group, an (arylalkylthio)carbonyl group, an arylalkylaminocarbonyl group, an arylalkoxy-thiocarbonyl group, an (arylalkylthio)thiocarbonyl group, an (arylalkylamino)thiocarbonyl group, an arylalkylsulfonate group (an arylalkoxy-sulfonyl group), an arylalkylsulfinate group, a $C_{1-20}$ alkyl group, a $C_{2-20}$ alkenyl group, a $C_{3-20}$ open-chain alkenyl-hydrocarbyl group, a $C_{3-20}$ cycloalkenyl group, an aryl group, an arylhydrocarbyl group, a $C_{1-20}$ heteroalkyl group, a heteroaryl group, a heteroarylalkyl group, a $C_{1-20}$ alkoxy group, an aryloxy group, an arylhydrocarbyloxy group, a $C_{1-20}$ heteroalkoxy group, a heteroaryloxy group, a heteroarylhydrocarbyloxy group, a $C_{1-20}$ alkylthio group, an arylthio group, an arylhydrocarbylthio group, a $C_{1-20}$ heteroalkylthio group, a heteroarylthio group, a heteroarylhydrocarbylthio group, a $C_{1-20}$ haloalkyl group, or the like, or any substituted form thereof.

Q is more preferably a hydrogen atom, a halogen atom, a nitro group, a nitro-containing substituent, a $C_{1-10}$ carbonyl group, a $C_{1-10}$ (alkyl)thiocarbonyl group, a $C_{1-10}$ sulfonyl group, a $C_{1-10}$ alkoxycarbonyl group, a $C_{1-10}$ (alkylthio)carbonyl group, a $C_{1-10}$ alkylaminocarbonyl group, a $C_{1-10}$ alkoxy-thiocarbonyl group, a $C_{1-10}$ (alkylthio)thiocarbonyl group, a $C_{1-10}$ (alkylamino)thiocarbonyl group, a $C_{1-10}$ alkylsulfonate group, a $C_{1-10}$ alkylsulfinate group, an (aryl)thiocarbonyl group, an aryloxycarbonyl group, an (arylthio)carbonyl group, an arylaminocarbonyl group, an aryloxy-thiocarbonyl group, an (arylthio)thiocarbonyl group, an (arylamino)thiocarbonyl group, an arylsulfonate group, an arylsulfinate group, an (arylalkyl)thiocarbonyl group, an arylalkoxycarbonyl group, an (arylalkylthio)carbonyl group, an arylalkylaminocarbonyl group, an arylalkoxy-thiocarbonyl group, an (aralkylthio)thiocarbonyl group, an (arylalkylamino)thiocarbonyl group, an arylalkylsulfonate group, an arylalkylsulfinate group, a $C_{1-20}$ alkyl group, a $C_{2-10}$ alkenyl group, a $C_{3-10}$ open-chain alkenyl-hydrocarbyl group, a $C_{3-10}$ cycloalkenyl group, an aryl group, an arylhydrocarbyl group, a $C_{1-10}$ heteroalkyl group, a heteroaryl group, a heteroaralkyl group, a $C_{1-10}$ alkoxy group, an aryloxy group, an arylhydrocarbyloxy group, a $C_{1-10}$ heteroalkoxy group, a heteroaryloxy group, a heteroarylhydrocarbyloxy group, a $C_{1-10}$ alkylthio group, an arylthio group, an arylhydrocarbylthio group, a $C_{1-10}$ heteroalkylthio group, a heteroarylthio group, a heteroarylhydrocarbylthio group, a $C_{1-10}$ haloalkyl group, or the like, or any substituted form thereof.

Specifically, Q can be a hydrogen atom, a fluorine atom, a chlorine atom, a bromine atom, an iodine atom, a nitro group, a nitrophenyl group, an acetyl group, a benzoyl group, a tosyl, a mesyl group, a methoxycarbonyl group, an ethoxycarbonyl group, a t-butoxycarbonyl group, a phenoxycarbonyl group, a benzyloxycarbonyl group, a (methylthio)carbonyl group, an (ethylthio)carbonyl group, a (t-butylthio)carbonyl group, a (phenylthio)carbonyl group, a (benzylthio)carbonyl group, an ethylaminocarbonyl group, a t-butylaminocarbonyl group, a phenylaminocarbonyl group, a benzylaminocarbonyl group, a methoxy-thiocarbonyl group, an ethoxy-thiocarbonyl group, a t-butoxy-thiocarbonyl group, a phenoxy-thiocarbonyl group, a benzyloxy-thiocarbonyl group, a (methylthio)thiocarbonyl group, an (ethylthio)thiocarbonyl group, a (t-butylthio)thiocarbonyl group, a (phenylthio)thiocarbonyl group, a (benzylthio)thiocarbonyl group, an ethylaminothiocarbonyl group, a t-butylaminothiocarbonyl group, a phenylaminothiocarbonyl group, a benzylaminothiocarbonyl group, a methyl group, an ethyl group, an n-propyl group, an isopropyl group, a butyl group, a pentyl group, a hexyl group, a heptyl group, a 2-ethylhexyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, an ethenyl group, a propenyl group, an allyl group, a propynyl group, a propargyl group, a cyclopropyl group, a cyclopropenyl group, a phenyl group, a benzyl group, a butylphenyl group, a p-methylphenyl group, a methoxy group (or a methyloxy group), an ethoxy group (or an ethyloxy group), a phenoxy group (or a phenyloxy group), a benzyloxy group (or a benzoxy group), a methylthio group, an ethylthio group, a phenylthio group, a benzylthio group, a $C_{1-20}$ haloalkyl group, the like, or any substituted form thereof. Wherein, butyl group includes but is not limited to an n-butyl group and a t-butyl group. Octyl group includes but is not limited to an n-octyl group and a 2-ethylhexyl group. Wherein, the atom or group substituent is a halogen atom, a hydrocarbyl substituent or a heteroatom-containing substituent, and preferably a halogen atom, an alkoxy group, an alkenyl group, an aryl group or a nitro group.

Q is preferably a hydrogen atom, a fluorine atom, a chlorine atom, a bromine atom, an iodine atom, a nitro group, a nitrophenyl group, an acetyl group, a benzoyl group, a tosyl group, a mesyl group, a methoxy-acyl group, an ethoxy-acyl group, a t-butoxycarbonyl group, a phenoxycarbonyl group, a benzyloxycarbonyl group, a (methylthio)acyl group, an (ethylthio)acyl group, a (t-butylthio)carbonyl group, a (phenylthio)carbonyl group, a (benzylthio)carbonyl group, an ethylamino-acyl group, a t-butylaminocarbonyl group, a phenylaminocarbonyl group, a benzylaminocarbonyl group, a methyl group, an ethyl group, an n-propyl group, an isopropyl group, a butyl group, a pentyl group, a hexyl group, a heptyl group, an octyl group, a nonyl group, a decyl group, an ethenyl group (also termed as a vinyl group), a propenyl group, an allyl group, a propynyl group, a propargyl group, a cyclopropyl group, a cyclopropenyl group, a phenyl group, a benzyl group, a butylphenyl group, a p-methylphenyl group, a methoxy group, an ethoxy group, a phenoxy group, a benzyloxy group, a methylthio group, an ethylthio group, a phenylthio group, a benzylthio group, a trifluoromethyl group, a 2,2,2-trifluoroethyl group, or any substituted form thereof. Wherein, the atom or group substituent is preferably a fluorine atom, an alkoxy group, an alkenyl group, an aryl group or a nitro group.

Q is more preferably a hydrogen atom, a fluorine atom, a methyl group, a trifluoromethyl group, a methoxy group, a methoxycarbonyl group, a tosyl group, a mesyl group or the like.

Q is more preferably a hydrogen atom, a fluorine atom, a methyl group, a trifluoromethyl group, a methoxy group, a methoxycarbonyl group or the like.

Wherein,

can be selected from but is not limited to the following structures and substituted forms thereof:

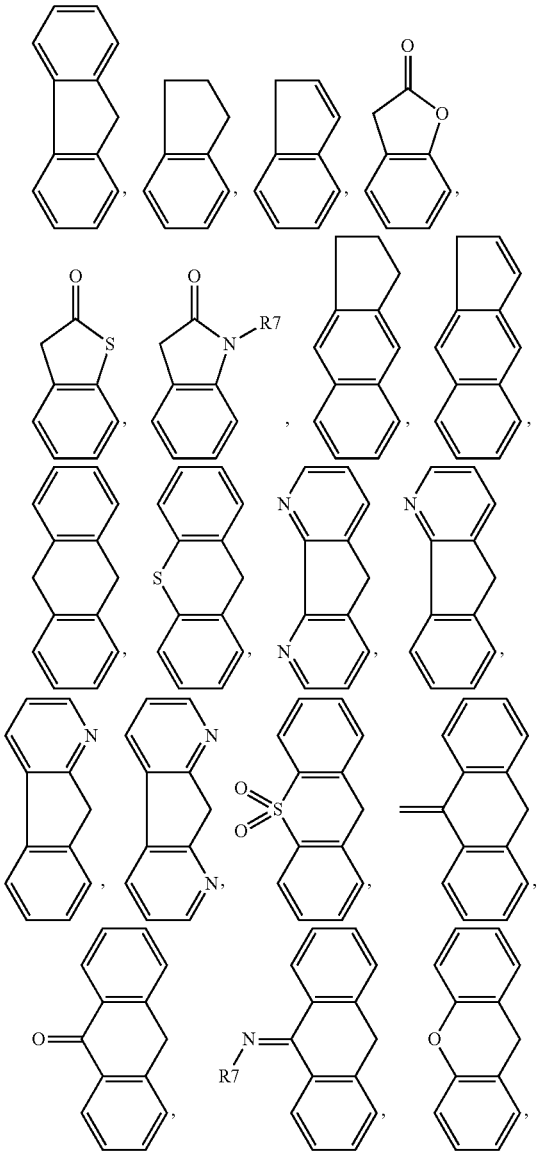

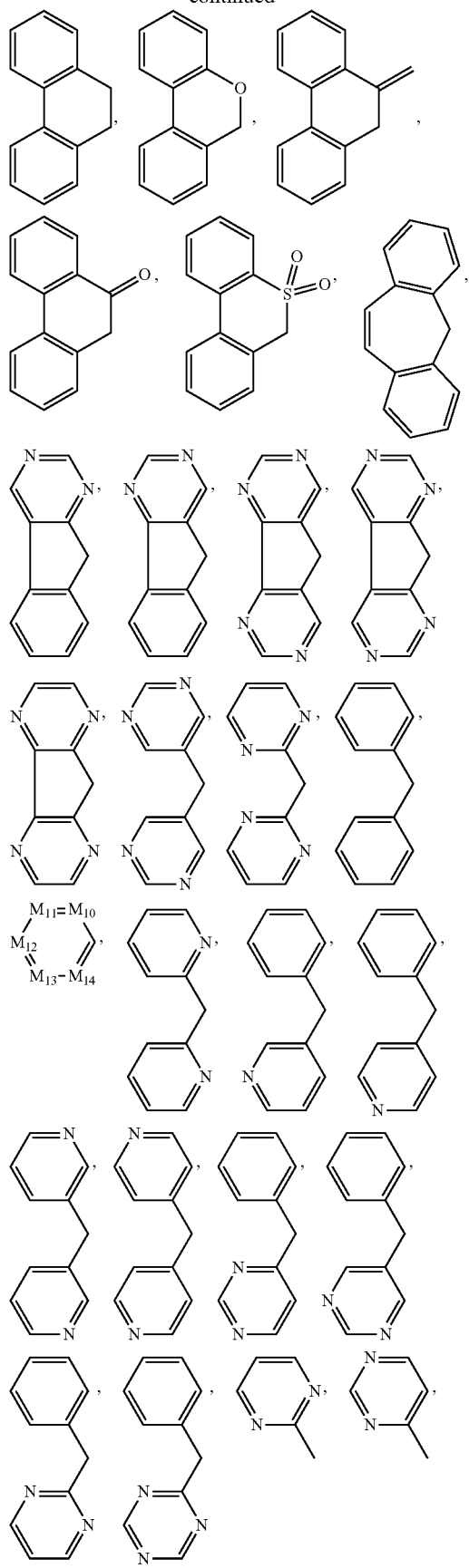

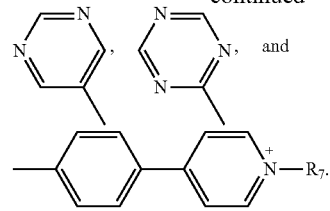

Wherein, $M_{10}$, $M_{11}$, $M_{12}$, $M_{13}$ and $M_{14}$ are each independently a nitrogen atom or a carbon atom. When any one of $M_{10}$, $M_{11}$, $M_{12}$, $M_{13}$ and $M_{14}$ is a nitrogen atom, its adjacent ring-membering atom should be a carbon atom.

Wherein, atom or group substituents of

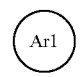

are not particularly limited, including but not limited to all the above-listed substituting atoms and substituting groups in the terminology section, and can be halogen atoms, hydrocarbyl substituents, or heteroatom-containing substituents. The substituting atom is preferably a halogen atom, and the substituting group is preferably a group that can favor inductive effect, conjugation effect, or both inductive and conjugation effects of electrons of unsaturated bonds.

Wherein, $R_7$ connects with an oxy group, and can be a hydrogen atom, an amino protecting group or a group $LG_5$.

Wherein, the carbon-atom number of $LG_5$ is not particularly limited, preferably from 1 to 20, and more preferably from 1 to 10.

The structure of $LG_5$ is not particularly limited, including but not limited to a linear structure, a branched structure bearing pendant groups or a ring-containing structure. Wherein, said ring is not particularly limited, including but not limited to all the above-listed cyclic structures in the terminology section.

$LG_5$ can contain heteroatoms, or does not contain heteroatoms.

$LG_5$ is a $C_{1-20}$ hydrocarbyl group, a $C_{1-20}$ heterohydrocarbyl group, a substituted $C_{1-20}$ hydrocarbyl group or a substituted heterohydrocarbyl group. Wherein, the heteroatom or group substituent of $LG_5$ is not particularly limited, including but not limited to all the above-listed substituting heteroatoms and substituting groups in the terminology section, and can be a halogen atom, a hydrocarbyl substituent, or a heteroatom-containing substituent.

$LG_5$ is more preferably a $C_{1-20}$ alkyl group, a $C_{1-20}$ unsaturated aliphatic hydrocarbyl group, an aryl group, an arylhydrocarbyl group, a $C_{1-20}$ heterohydrocarbyl group, a $C_{1-20}$ aliphatic hydrocarbyl-acyl group, a $C_{1-20}$ aliphatic-derived heterohydrocarbyl-acyl group, an aryl-acyl group, a heteroaryl-acyl group, a $C_{1-20}$ hydrocarbyloxy-acyl group, a $C_{1-20}$ hydrocarbylthio-acyl group, a $C_{1-20}$ hydrocarbylamino-acyl group, a $C_{1-20}$ heterohydrocarbyloxy-acyl group, a $C_{1-20}$ heterohydrocarbylthio-acyl group, a $C_{1-20}$ heterohydrocarbylamino-acyl group, the like, or any substituted form thereof. Wherein, the acyl group within $LG_5$ is not particularly limited, including but not limited to all the above-listed acyl groups in the terminology section. For example, the acyl group within $LG_5$ can be a carbonyl group, a sulfonyl group, a sulfinyl group, a phosphoryl group, a phosphiryl group, a phosphinyl group, a nitroxyl group, a nitrosyl group, a thiocarbonyl group, an imidoyl group, a thiophosphoryl group, a dithiophosphoryl group, a trithiophosphoryl group, a thiophosphiryl group, a dithiophosphiryl group, a thiophosphinyl group, a thiophosphono group, a dithiophosphono group, a thiophosphino group, or the like. $LG_5$ is preferably a carbonyl group, a thiocarbonyl group, a sulfonyl group or a sulfinyl group, and more preferably a carbonyl group, a thiocarbonyl group or a sulfonyl group.

$LG_5$ is more preferably a $C_{1-20}$ alkyl group, a $C_{2-20}$ alkenyl group, a $C_{3-20}$ alkenylhydrocarbyl group, an aryl group, an arylalkyl group, a $C_{1-20}$ heteroalkyl group, a heteroaryl group, a heteroarylalkyl group, a $C_{1-20}$ alkylcarbonyl group, an arylcarbonyl group, an arylalkylcarbonyl group, a $C_{1-20}$ heteroalkylcarbonyl group, a heteroarylcarbonyl group, a heteroarylalkylcarbonyl group, a $C_{1-20}$ alkoxycarbonyl group, an aryloxycarbonyl group, an arylalkoxycarbonyl group, a $C_{1-20}$ (alkylthio)carbonyl group, an (arylthio)carbonyl group, an (arylalkylthio)carbonyl group, a $C_{1-20}$ alkylaminocarbonyl group, an arylaminocarbonyl group, an arylalkylaminocarbonyl group, a $C_{1-20}$ heteroalkoxycarbonyl group, a heteroaryloxycarbonyl group, a heteroarylalkoxycarbonyl group, a $C_{1-20}$ hetero(alkylthio) carbonyl group, a hetero(arylthio)carbonyl group, a hetero (arylalkylthio)carbonyl group, a $C_{1-20}$ heteroalkylaminocarbonyl group, a heteroarylaminocarbonyl group, a heteroarylalkylaminocarbonyl group, a $C_{1-20}$ (alkyl)thiocarbonyl group, an (aryl)thiocarbonyl group, an (arylalkyl) thiocarbonyl group, a $C_{1-20}$ hetero(alkyl)thiocarbonyl group, a hetero(aryl)thiocarbonyl group, a hetero(arylalkyl)thiocarbonyl group, a $C_{1-20}$ alkoxy-thiocarbonyl group, an aryloxy-thiocarbonyl group, an arylalkoxy-thiocarbonyl group, a $C_{1-20}$ (alkylthio)thiocarbonyl group, an (arylthio)thiocarbonyl group, an (arylalkylthio)thiocarbonyl group, a $C_{1-20}$ alkylaminothiocarbonyl group, an arylaminothiocarbonyl group, an arylalkylaminothiocarbonyl group, a $C_{1-20}$ heteroalkyloxy-thiocarbonyl group, a heteroaryloxy-thiocarbonyl group, a heteroarylalkoxy-thiocarbonyl group, a $C_{1-20}$ hetero(alkylthio)thiocarbonyl group, a hetero(arylthio)thiocarbonyl group, a hetero(arylalkylthio)thiocarbonyl group, a $C_{1-20}$ heteroalkylaminothiocarbonyl group, a heteroarylaminothiocarbonyl group, a heteroarylalkylaminothiocarbonyl group, the like or any substituted form thereof.

$LG_5$ is more preferably a $C_{1-20}$ alkyl group, a $C_{2-20}$ alkenyl group, a $C_{3-20}$ alkenyl-hydrocarbyl group, an aryl group, an arylalkyl group, a $C_{1-20}$ heteroalkyl group, a heteroaryl group, a heteroarylalkyl group or any substituted form thereof.

Specifically, $LG_5$ can be, but not limited to, a methyl group, an ethyl group, an n-propyl group, an isopropyl group, a butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, an allyl group, a trityl group, a benzyl group, a methylbenzyl group, 1,3,5-dioxo-azacyclohexyl group, a formyl group, an acetyl group, a benzoyl group, a methoxy-acyl group, an ethoxy-acyl group, a t-butyloxy-acyl group, a phenoxy-acyl group, a benzyloxy-acyl group, a 9-fluorenylmethoxycarbonyl group (Fmoc group), a 2-(methylsulfonyl)ethylcarbonyl group, a 2-(p-toluenesulfonyl)ethoxycarbonyl group, a methylthio-acyl group, an ethylthio-acyl group, a t-butylthio-acyl group, a phenylthio-acyl group, a benzylthio-acyl group, a methylamino-acyl group, an ethylamino-acyl group, a t-butylamino-acyl group, a benzylamino-acyl group, the like, or any substituted form thereof. Wherein, said butyl group includes but is not limited to an n-butyl group and a t-butyl group. Said octyl group includes but is not limited to an n-octyl group and a 2-ethylhexyl group. Wherein, the atom or group substituent is a halogen atom, a hydrocarbyl substituting group or a heteroatom-containing substituent, and preferably a fluorine atom, a chlorine atom, a bromine atom, an iodine atom, an alkoxy group, an alkenyl group or a nitro group.

$LG_5$ is further preferably a methyl group, an ethyl group, an n-propyl group, an isopropyl group, a t-butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, an allyl group, a trityl group, a phenyl group, a benzyl group, a methylbenzyl group, a 1,3,5-dioxo-azacyclohexyl group, a formyl group, an acetyl group, a benzoyl group, a methoxycarbonyl group, an ethoxycarbonyl group, a t-butoxycarbonyl group, a phenoxycarbonyl group, a benzyloxycarbonyl group, a 9-fluorenylmethoxycarbonyl group, a 2-(methylsulfonyl) ethylcarbonyl group, a 2-(p-toluenesulfonyl)ethyloxycarbonyl group, a (methylthio)carbonyl group, an (ethylthio) carbonyl group, a (t-butylthio)carbonyl group, a (phenylthio)carbonyl group, a (benzylthio)carbonyl group, a methylaminocarbonyl group, an ethylaminocarbonyl group, a t-butylaminocarbonyl group, a benzylaminocarbonyl group, an (ethyl)thiocarbonyl group, a (phenyl)thiocarbonyl group, a methoxy-thiocarbonyl group, an ethoxy-thiocarbonyl group, a t-butyloxy-thiocarbonyl group, a phenoxy-thiocarbonyl group, a benzyloxy-thiocarbonyl group, a (methylthio)thiocarbonyl group, an (ethylthio)thiocarbonyl group, a (t-butylthio)thiocarbonyl group, a (phenylthio)thiocarbonyl group, a (benzylthio)thiocarbonyl group, a methylaminothiocarbonyl group, an ethylaminothiocarbonyl group, a t-butylaminothiocarbonyl group, a benzylaminothiocarbonyl group, [2-(methylsulfonyl)ethoxy]carbonyl group, a $C_{1-10}$ halohydrocarbyl group, a trifluoroacetyl group, 2-iodoethoxycarbonyl group, a halophenyl group, a halobenzyl groups, a nitrobenzyl group, a p-methoxybenzyl group, a trifluoromethylbenzyl group, the like, or any substituted form thereof. Wherein, the atom or group substituent is preferably a fluorine atom, an alkoxy group or a nitro group.

$LG_5$ is more preferably a methyl group, an ethyl group, an n-propyl group, an isopropyl group, a t-butyl group, a pentyl group, a hexyl group, an allyl group, a trityl group, a phenyl group, a benzyl group, a nitrobenzyl group, a p-methoxybenzyl group, a trifluoromethylbenzyl group, a 1,3,5-dioxo-azacyclohexyl group, a 9-fluorenylmethoxycarbonyl group, a 2-(methylsulfonyl)ethylcarbonyl group, a 2-(p-toluenesulfonyl)ethyloxycarbonyl group, a t-butoxycarbonyl group, a benzyloxycarbonyl group, a formyl group, an acetyl group, a trifluoroacetyl group or the like.

$LG_5$ is more preferably a methyl group, an ethyl group, an n-propyl group, an isopropyl group, a t-butyl group, a pentyl group, a hexyl group, an allyl group, a trityl group, a phenyl group, a benzyl group, a nitrobenzyl group, a p-methoxybenzyl group, a (trifluoromethyl)benzyl group or the like.

$LG_5$ is most preferably a methyl group, an ethyl group, an allyl group or a benzyl group.

$R_7$ is most preferably a hydrogen atom, a methyl group, an ethyl group or a benzyl group.

The trivalent cyclic structure of $CC_3$ is preferably deriving from but not limited to a furanose ring, a pyranose ring, benzene, tetrahydrofuran, pyrrolidine, thiazolidine, cyclohexane, cyclohexene, tetrahydropyran, piperidine, 1,4-dioxane, pyridine, pyridazine, pyrimidine, pyrazine, 1,3,5-triazine, 1,4,7-triazacyclononane, cyclotripeptides, indene, indane, indole, isoindole, purine, naphthalene, dihydroanthracene, xanthene, thioxanthene, dihydrophenanthrene, 10,11-dihydro-5H-dibenzo[a,d]cycloheptane, dibenzocycloheptene, 5-dibenzosuberenone, quinoline, isoquinoline, fluorene, carbazole, iminodibenzyl, acenaphthene (or 1,2-dihydroacena-phthylene), dibenzocyclooctyne, aza-dibenzocyclooctyne, the like, the substituted form of any said cyclic structure thereof, or the heterosubstituted form of any said cyclic structure of the foregoing.

1.1.2.2. The Tetravalent Group

The tetravalent groups in set $G^4$ have a combination of two trivalent core structures or a tetravalent core structure.

Said trivalent core structure is defined as that in the above-mentioned set of $G^3$, no more repeated here.

The tetravalent core structure can be an atom $CM_4$, an unsaturated bond $CB_4$ or a cyclic structure $CC_4$.

Wherein, tetravalent core-atom $CM_4$ is not particularly limited, as long as it can provide four covalent single bonds individually, such as a tetravalent carbon-atom core, a tetravalent silicon-atom core, a tetravalent phosphorus-atom core and the like. The tetravalent core-atom can connect with no other atoms or groups, such as tetravalent atom cores of

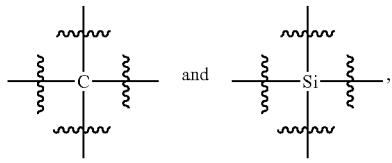 [SMILES: *C(*)(*)* ; *[Si](*)(*)*]

or can connect with other atoms or groups.

Wherein, the core structure $CB_4$ of a tetravalent unsaturated bond type is not particularly limited, as long as it can provide four covalent single bonds individually. The bond-membering atoms of the unsaturated bond can be two or two more, preferably two or three, and more preferably two. For example,

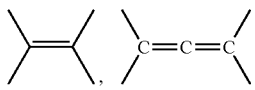

and the like.

Wherein, the tetravalent cyclic core structure $CC_4$ is not particularly limited, as long as it can protrude individually four covalent single bonds. The ring-membering atoms that provide covalent bond radicals are not particularly limited, including but not limited to N, C, Si, P, etc. The cyclic structure can be an aliphatic ring or an aromatic ring, e.g.,

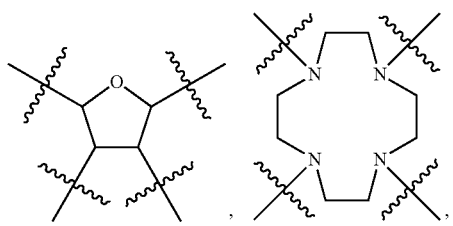

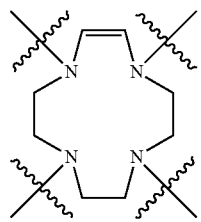

and the like, or be a sugar ring, e.g., 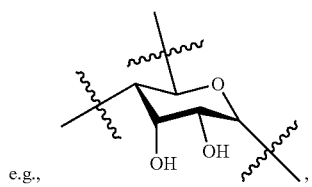

and the like, or be a condensed ring, e.g., 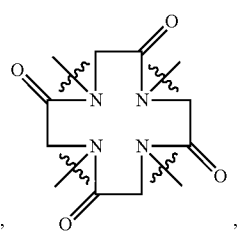

etc. The cyclic structures that can come from natural sources, such as a sugar ring, or be formed via chemical reactions, such as

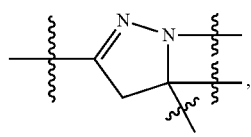 [SMILES: *C1=NN(*)C(*)(*)C1]

etc. The covalent single bond can protrude directly from a ring-membering atom, or from an unsaturated bond. Each covalent single bond protrudes individually from a ring-membering atom, or two covalent single bonds protrude from one ring-membering atom together. Typical structure of $CC_4$ is that four covalent single bonds protrude from four ring-membering atoms respectively.

$CC_4$ can be but not limited to

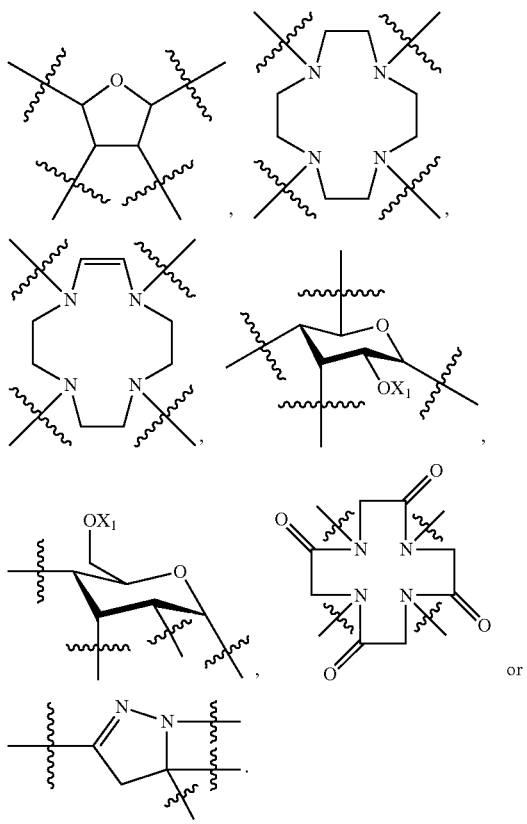

The tetravalent cyclic core structure also can be but not limited to

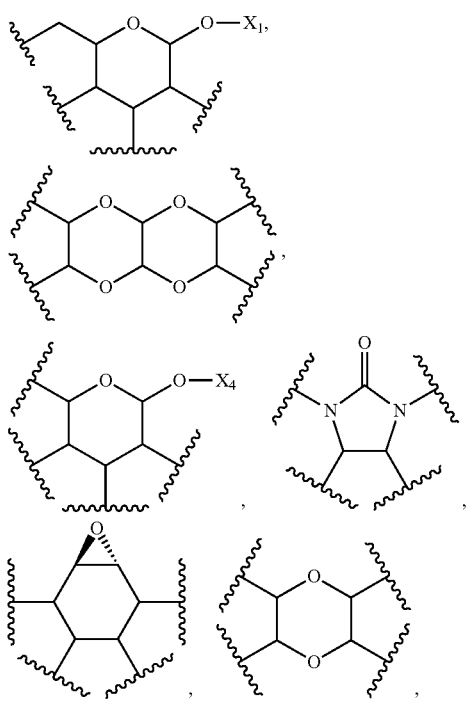

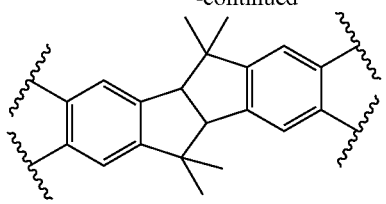

or the like.

The tetravalent cyclic structure of $CC_4$ is preferably deriving from but not limited to a furanose ring, a pyranose ring, cycleanine, a cyclic tetrapeptide, tetrahydrofuran, pyrrolidine, thiazolidine, cyclohexane, benzene, cyclohexene, tetrahydropyran, piperidine, 1,4-dioxane, pyridine, pyridazine, pyrimidine, pyrazine, indene, indane, indole, isoindole, purine, naphthalene, dihydroanthracene, xanthene, thioxanthene, dihydrophenanthrene, 10,11-5H-dihydro-dibenzo[a,d]cycloheptane, dibenzocycloheptene, 5-dibenzosuberenone, quinoline, isoquinoline, fluorene, carbazole, iminodibenzyl, tetramethyl tetrahydroindene, dipyridamole skeleton, tetravalent triethanedial dehydrate skeleton, tetravalent six-membered ring of D-sorbitol skeleton with 2-, and 4-hydroxyl groups being protected, the like, the substituted form of any said cyclic structure thereof, or the heterosubstituted form of any said cyclic structure of the foregoing.

1.1.2.3. (k+1)-Valent Groups (k≥4)

Any (k+1)-valent group in the set $G^{k+1}$(k≥4) can contain a (k+1)-valent cyclic core structure as $CC_{k+1}$, or contain a combination of two or two more lower-valent cyclic core structures with the valence of 3 to k. For example, When k=4, in the set of $G^5$, each $CC_5$ is a cyclic core structure wherein five covalent single bonds protrude from five ring-membering atoms, respectively. $CC_5$ can be but not limited to a cyclic monosaccharide core structure, a cyclopeptide, an azacycloalkane or the like, such as

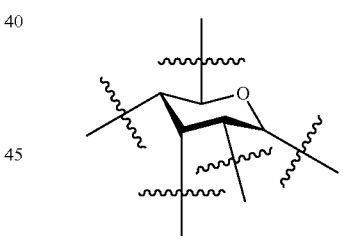

that derives from a cyclic monosaccharide core structure, or

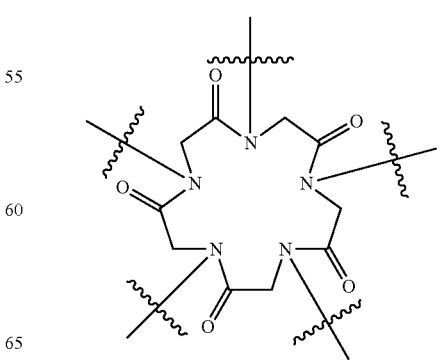

that derives from a cyclopeptide, etc.

When k≥5, in the set of $G^{k+1}(k≥5)$, cyclic core structures include but are not limited to a cyclopeptide, an azacycloalkane, a polymeric ring, and the like. Take the set $G^6$ for example, $CC_6$ is a cyclic core structure, wherein six ring-membering atoms protrude six covalent single bonds, respectively, such as

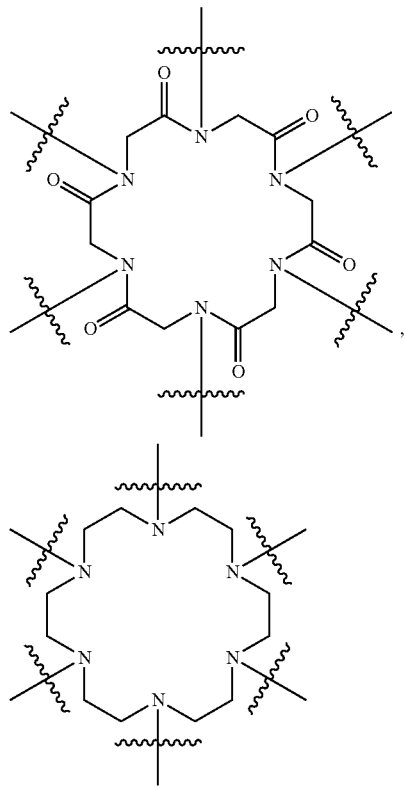

and the like.

1.1.2.4. Examples of (k+1)-Valent Groups in the Set of $G^{k+1}(k≥2)$

Any (k+1)-valent group in the set of $G^{k+1}(k≥2)$, when containing a core structure with the valence of 3 to k+1, can contain or do not contain non-core moieties beyond (3 to k+1)-valent core structure.

Take k=2 for example, then $U_{01}$ and $U_{02}$ each independently can contain any of the above-mentioned trivalent core structures, and preferably contains

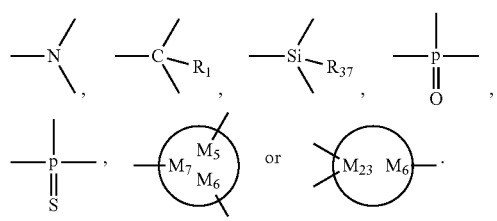

When containing non-core moieties, said non-core moieties can contain carbon atoms or not, also can contain heteroatoms or not. Said non-core moieties beyond the (k+1)-valent core structure can be heteroatom-containing groups, or hydrocarbylene groups without heteroatoms. Said heteroatoms include but are not limited to O, S, N, P, Si, F, Cl, Br, I, B and the like. Wherein, the heteroatom-number can be one, two or two more. A heteroatom can be present as an individual divalent linking group, e.g., —O— (an oxy group or an ether bond), —S— (a thioxy group or a thioether bond), —N($R_7$)— (a secondary amino group or a divalent t-amino group) or the like, or be present as a divalent substituent, such as —C(=O)—, —C(=S)—, —P(=O)—, —S(=O)$_2$—, —S(=O)— or the like, or participate in combining into some specific covalent bonds, such as —C(=O)—N($R_7$)—, —N($R_7$)—C(=O)—, —S—S—, —C(=O)—O—, —O—C(=O)—, —C(=O)—S—, —S—C(=O)—, —C(=S)—O—, —O—C(=S)—, —C(=S)—S—, —S—C(=S)—, —O—C(=O)—O—, —S—C(=O)—O—, —O—C(=S)—O—, —O—C(=O)—S—, —S—C(=S)—O—, —O—C(=S)—S—, —S—C(=O)—S—, —S—C(=S)—S—, —N($R_7$)—C(=O)—O—, —O—C(=O)—N($R_7$)—, —N($R_7$)—C(=S)—O—, —O—C(=S)—N($R_7$)—, —N($R_7$)—C(=O)—S—, —S—C(=O)—N($R_7$)—, —N($R_7$)—C(=S)—S—, —S—C(=S)—N($R_7$)—, —N($R_{19}$)—N($R_{18}$)—, —N($R_{19}$)—C(=O)—N($R_{18}$)—, —N($R_{19}$)—C(=S)—N($R_{18}$)—, —N($R_{18}$)—N($R_{19}$)—C(=O)—, —C(=O)—N($R_{19}$)—N($R_{18}$)—, —N($R_{18}$)—N($R_{19}$)—C(=S)—, —C(=S)—N($R_{19}$)—N($R_{18}$)—, —($R_{15}$)C=N—, —N=C($R_{15}$)—, —($R_{15}$)C=N—N($R_7$)—, —N($R_7$)—N=C($R_{15}$)—, —($R_{15}$)C=N—N($R_7$)—C(=O)—, —C(=O)—N($R_7$)—N=C($R_{15}$)—, —($R_{15}$)C=N—O—, —O—N=C($R_{15}$)—, —($R_{15}$)C=N—S—, —S—N=C($R_{15}$)—, —N=N—, —N($R_{18}$)—N($R_{19}$)—C(=O)—N=N—, —N=N—C(=O)—N($R_{19}$)—N($R_{18}$)—, —N($R_{18}$)—C(=O)—N($R_{19}$)—, —C(=NR$_7$)—N($R_{23}$)—, —N($R_{23}$)—C(=NR$_7$)—, —N($R_7$)—C(=NH$_2^+$)—, —C(=NH$_2^+$)—N($R_7$)—, —C(=NR$_7$)—O—, —O—C(=NR$_7$)—, —O—C(=NH$_2^+$)—, —C(=NH$_2^+$)—O—, —C(=NR$_7$)—S—, —S—C(=NR$_7$)—, —S—C(=NH$_2^+$)—, —C(=NH$_2^+$)—S—, —S(=O)$_2$—O—, —O—S(=O)$_2$—, —S(=O)—O—, —O—S(=O)—, —S(=O)$_2$—N($R_7$)—, —N($R_7$)—S(=O)$_2$—, —S(=O)$_2$—N($R_{18}$)—N($R_{19}$)—, —N($R_{19}$)—N($R_{18}$)—S(=O)$_2$— or the like. Said hydrocarbylene group without heteroatoms is not particularly limited, and preferably a $C_{1-10}$ hydrocarbylene group.

The non-core moiety beyond the core structure is preferably a $C_{1-6}$ alkylene group, an ether bond, a thioether bond, a secondary amino group, a divalent t-amino group, an amide bond, a carbamate bond, a thiocarbamate bond or a divalent linking group as a combination of a $C_{1-6}$ alkylene group and any above-listed divalent linking group, and more preferably a $C_{1-6}$ alkylene group, —O—, —N($R_7$)—, —C(=O)—N($R_7$)—, —N($R_7$)—C(=O)—, —N($R_7$)—C(=O)—O— or —O—C(=O)—N($R_7$)—.

Wherein, the definitions of $R_7$, $R_{18}$, $R_{19}$ and $R_{23}$ are the same as above defined $R_7$, no more repeated here. In one molecule, $R_7$, $R_{18}$, $R_{19}$ and $R_{23}$ can be the same or different.

$R_{15}$ is linked to the carbon atom of structures containing a C=N bond, and can be a hydrogen atom, an atom substituent or a group substituent. Examples of said structures containing a C=N bond include but are not limited to —C=N—, —C=N$^+$=N$^-$, —C=N—NH—, —C=N—NH—C(=O)— and the like. C=N is termed as an imine bond or an imino bond in the present invention.

When as an atom substituent, $R_{15}$ can be a halogen atom, and preferably a fluorine atom.

When as a group substituent, the carbon-atom number of $R_{15}$ is not particularly limited, preferably from 1 to 20, and more preferably from 1 to 10.

When as a group substituent, the structure of $R_{15}$ is not particularly limited, including but not limited to a linear structure, a branched structure bearing pendant groups or a ring-containing structure. Said ring is not particularly limited, including but not limited to all the above-listed cyclic structures in the terminology section.

When as a group substituent, $R_{15}$ can contain or do not contain heteroatoms.

$R_{15}$ is a hydrogen atom, a halogen atom, a $C_{1-20}$ hydrocarbyl group, a $C_{1-20}$ heterohydrocarbyl group, a substituted $C_{1-20}$ hydrocarbyl group or a substituted heterohydrocarbyl group. Wherein, the atom or group substituent of $R_{15}$ is not particularly limited, including but not limited to all substituting atoms and substituting groups listed in the terminology section, and can be a halogen atom, a hydrocarbyl substituent or a heteroatom-containing substituent.

$R_{15}$ is preferably a hydrogen atom, a halogen atom, a $C_{1-20}$ hydrocarbyl group, a $C_{1-20}$ heterohydrocarbyl group, a substituted $C_{1-20}$ hydrocarbyl group or a substituted heterohydrocarbyl group.

$R_{15}$ is more preferably a hydrogen atom, a halogen atom, a $C_{1-20}$ alkyl group, a $C_{1-20}$ unsaturated aliphatic hydrocarbyl group, an aryl group, an arylhydrocarbyl group, a $C_{1-20}$ heterohydrocarbyl group, a $C_{1-20}$ hydrocarbyloxy-acyl group, a $C_{1-20}$ hydrocarbylthio-acyl group, a $C_{1-20}$ hydrocarbylamino-acyl group, or any substituted form thereof. Wherein, said acyl group within $R_{15}$ is not particularly limited, including but not limited to all the above-listed acyl groups in the terminology section. For examples, said acyl group within $R_{15}$ can be a carbonyl group, a sulfonyl group, a sulfinyl group, a phosphoryl group, a phosphiryl group, a phosphinyl group, a nitroxyl group, a nitrosyl group, a thiocarbonyl group, an imidoyl group, a thiophosphoryl group, a dithiophosphoryl group, a trithiophosphoryl group, a thiophosphiryl group, a dithiophosphiryl group, a thiophosphinyl group, a thiophosphono group, a dithiophosphono group, a thiophosphino group or the like. Said acyl group within $R_{15}$ is preferably a carbonyl group, a thiocarbonyl group, a sulfonyl group or a sulfinyl group, and more preferably a carbonyl group or a thiocarbonyl group.

$R_{15}$ is more preferably a hydrogen atom, a halogen atom, a $C_{1-20}$ alkyl group, a $C_{1-20}$ alkenyl group, an aryl group, an arylhydrocarbyl group, a $C_{1-20}$ aliphatic-derived heterohydrocarbyl group, a heteroaryl group, a heteroarylhydrocarbyl group, a $C_{1-20}$ alkoxy-acyl group, an aryloxy-acyl group, a $C_{1-20}$ alkylthio-acyl group, an arylthio-acyl group, a $C_{1-20}$ alkylamino-acyl group, an arylamino-acyl group, the like, or any substituted form thereof. Wherein, the atom or group substituent can be a halogen atom, a hydrocarbyl substituent or a heteroatom-containing substituent, and preferably a halogen atom, an alkenyl group or a nitro group.

$R_{15}$ is more preferably a hydrogen atom, a halogen atom, a $C_{1-20}$ alkyl group, a $C_{1-20}$ alkenyl group, an aryl group, an arylhydrocarbyl group, a $C_{1-20}$ aliphatic-derived heterohydrocarbyl group, a heteroaryl group, a heteroarylhydrocarbyl group, a $C_{1-20}$ alkoxycarbonyl group, an aryloxycarbonyl group, a $C_{1-20}$ (alkylthio)carbonyl group, an (arylthio)carbonyl group, a $C_{1-20}$ alkylaminocarbonyl group, an arylaminocarbonyl group, a $C_{1-20}$ alkoxy-thiocarbonyl group, an aryloxy-thiocarbonyl group, a $C_{1-20}$ (alkylthio)thiocarbonyl group, an (arylthio)thiocarbonyl group, a $C_{1-20}$ alkylaminothiocarbonyl group, an arylaminothiocarbonyl group, the like, or any substituted form thereof. Wherein, the atom or group substituent is a halogen atom, a hydrocarbyl substituent or a heteroatom-containing substituent, and preferably a fluorine atom, a chlorine atom, a bromine atom, an iodine atom, an alkenyl group or a nitro group.

Specifically, $R_{15}$ can be but not limited to a hydrogen atom, a fluorine atom, a chlorine atom, a bromine atom, an iodine atom, a methyl group, an ethyl group, an n-propyl group, an isopropyl group, a butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, an allyl group, a propenyl group, an ethenyl group, a phenyl group, a methylphenyl group, a butylphenyl group, a benzyl group, a methoxycarbonyl group, an ethoxycarbonyl group, a phenoxycarbonyl group, a benzyloxycarbonyl group, a (methylthio)carbonyl group, an (ethylthio)carbonyl group, a (phenylthio)carbonyl group, a (benzylthio)carbonyl group, an ethylaminocarbonyl group, a benzylaminocarbonyl group, a methoxy-thiocarbonyl group, an ethoxy-thiocarbonyl group, a phenoxy-thiocarbonyl group, a benzyloxy-thiocarbonyl group, a (methylthio)thiocarbonyl group, an (ethylthio)thiocarbonyl group, a (phenylthio)thiocarbonyl group, a (benzylthio)thiocarbonyl group, an ethylaminothiocarbonyl group, a benzylaminothiocarbonyl group, a substituted $C_{1-20}$ alkyl group, a substituted $C_{1-20}$ alkenyl group, a substituted aryl group, a substituted arylhydrocarbyl group, a substituted $C_{1-20}$ aliphatic-derived heterohydrocarbyl group, a substituted heteroaryl group, a substituted heteroarylhydrocarbyl group, a substituted $C_{1-20}$ alkoxycarbonyl group, a substituted aryloxycarbonyl group, a substituted $C_{1-20}$ (alkylthio)carbonyl group, a substituted (arylthio)carbonyl group, a substituted $C_{1-20}$ alkylaminocarbonyl group, a substituted arylaminocarbonyl group, a substituted $C_{1-20}$ alkoxy-thiocarbonyl group, a substituted aryloxy-thiocarbonyl group, a substituted $C_{1-20}$ (alkylthio)thiocarbonyl group, a substituted (arylthio)thiocarbonyl group, a substituted $C_{1-20}$ alkylaminothiocarbonyl group, a substituted arylaminothiocarbonyl group or the like. Wherein, said butyl group includes but is not limited to an n-butyl group and a t-butyl group. Said octyl groups includes but is not limited to an n-octyl group and a 2-ethylhexyl group. Wherein, the atom or group substituent is a halogen atom, a hydrocarbyl substituent or a heteroatom-containing substituent, and preferably a fluorine atom, a chlorine atom, a bromine atom, an iodine atom or a nitro group.

$R_{15}$ is further preferably a hydrogen atom, a fluorine atom, a methyl group, an ethyl group, an n-propyl group, an isopropyl group, a butyl group, a pentyl group, a hexyl group, a heptyl group, an octyl group, a nonyl group, a decyl group, an allyl group, a propenyl group, an ethenyl group, a phenyl group, a methylphenyl group, a butylphenyl group, a benzyl group, a $C_{1-10}$ halohydrocarbyl group, a halophenyl group, a halobenzyl group, a nitrophenyl group, a methoxycarbonyl group, an ethoxycarbonyl group, a phenoxycarbonyl group, a benzyloxycarbonyl group, a (methylthio)carbonyl group, an (ethylthio)carbonyl group, a (phenylthio)carbonyl group, a (benzylthio)carbonyl group, an ethylaminocarbonyl group, a benzylaminocarbonyl group, a methoxy-thiocarbonyl group, an ethoxy-thiocarbonyl group, a phenoxy-thiocarbonyl group, a benzyloxy-thiocarbonyl group, a (methylthio)thiocarbonyl group, an (ethylthio)thiocarbonyl group, a (phenylthio)thiocarbonyl group, a (benzylthio)thiocarbonyl group, an ethylaminothiocarbonyl group, a benzylaminothiocarbonyl group, the like, or any substituted form thereof.

$R_{15}$ is most preferably a hydrogen atom, a fluorine atom or a methyl group.

For example, when k=2, examples of trivalent groups wherein the non-core moiety contains no heteroatoms include as follows:

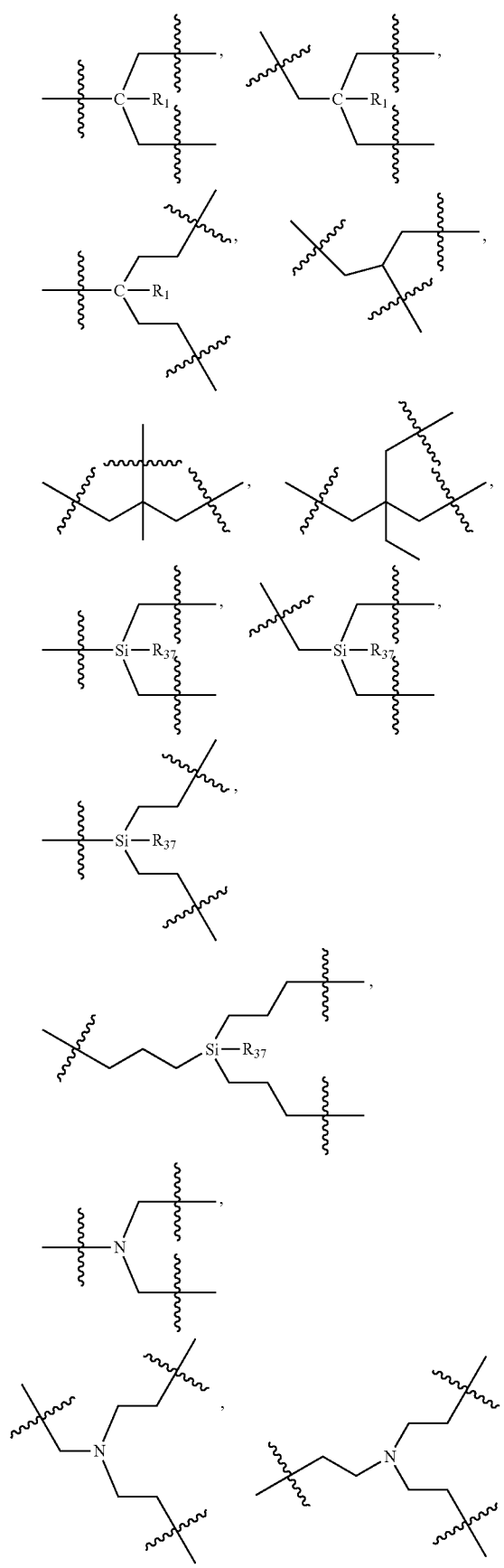
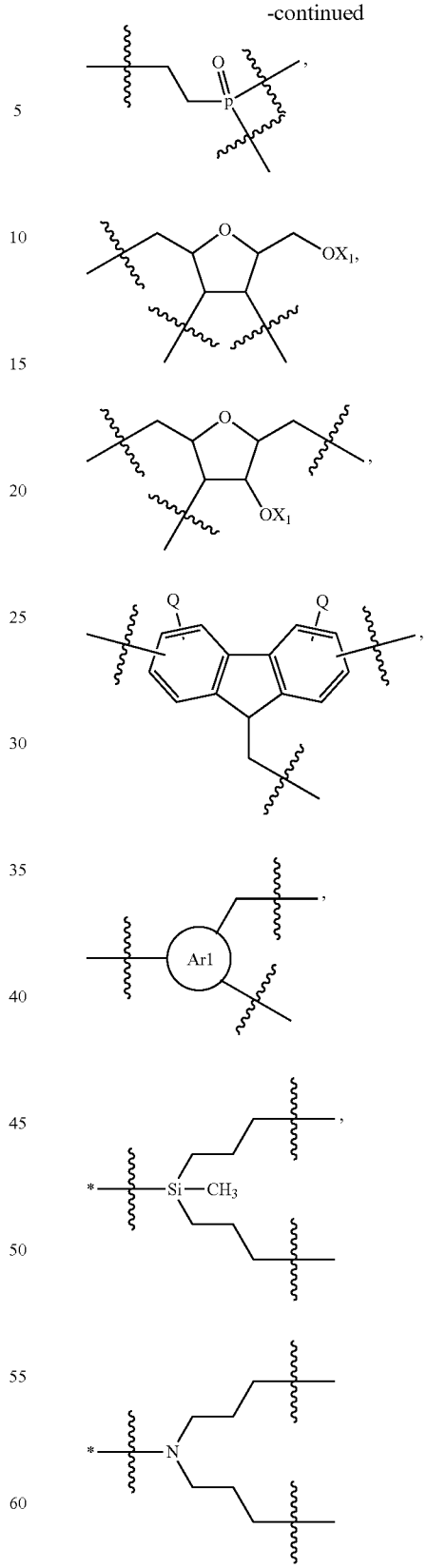
and the like. Examples also include but are not limited to the following structures disclosed in the patent document CN104877127A paragraph [0199]:

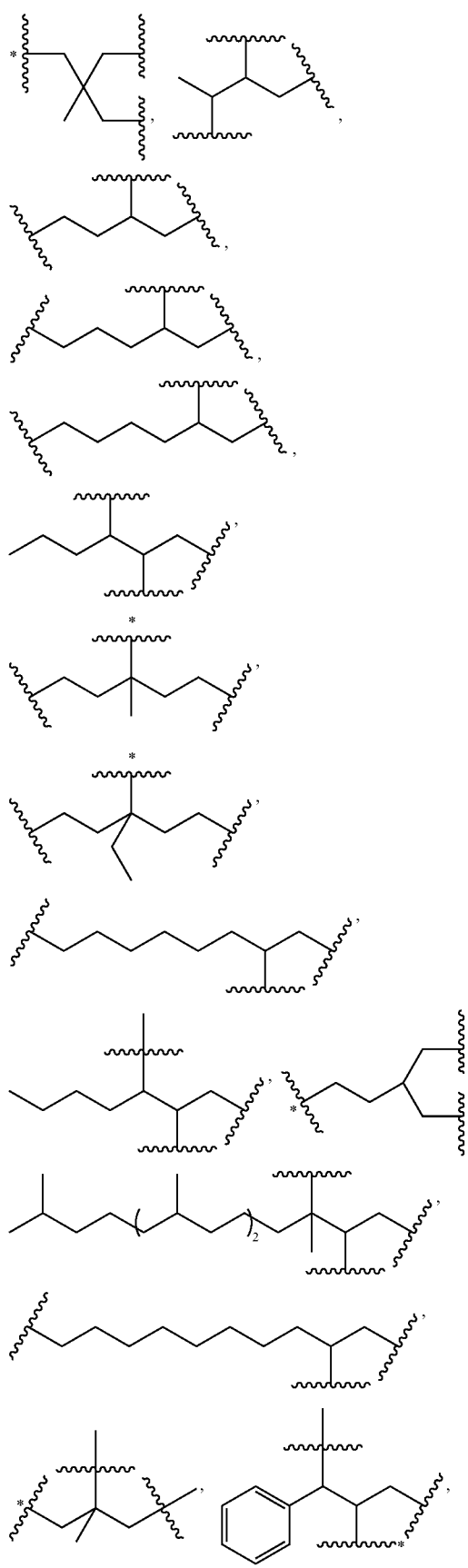
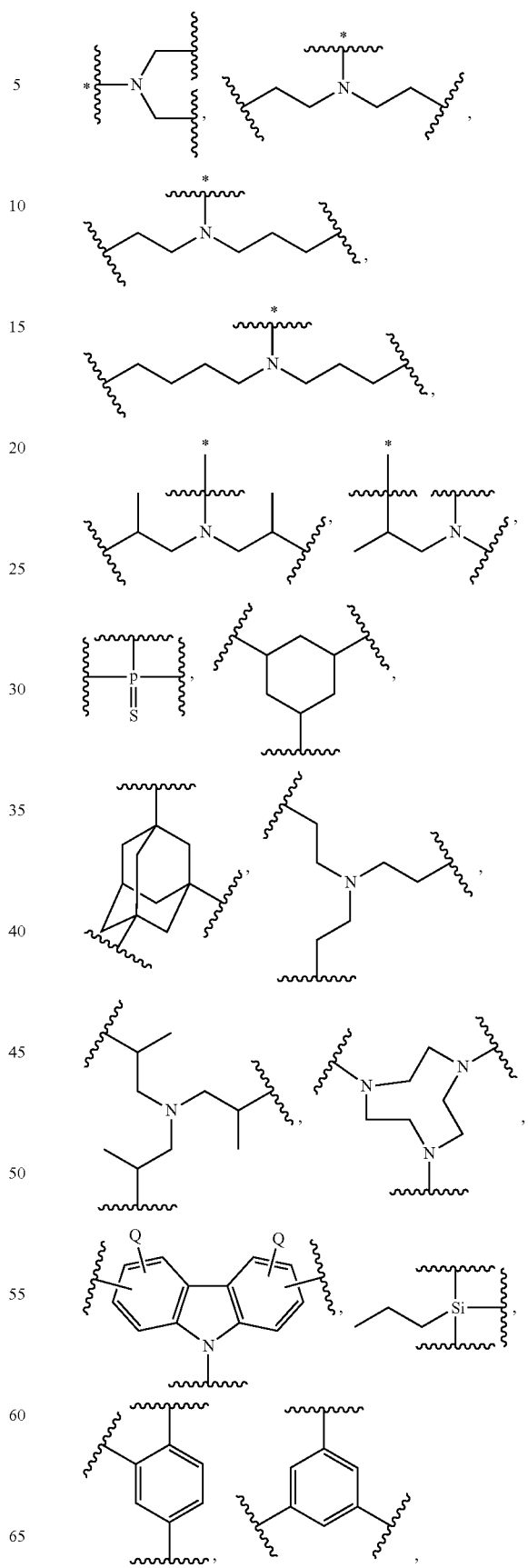

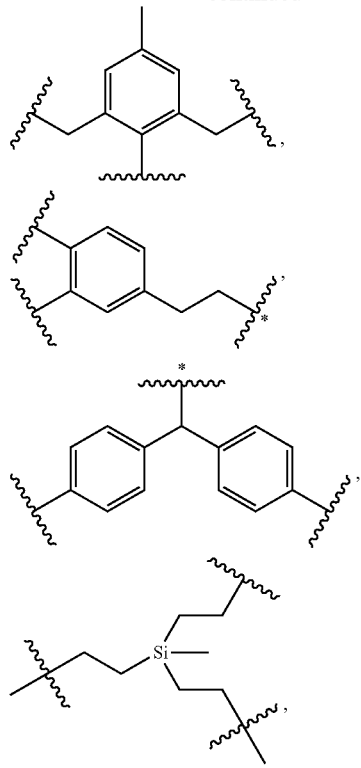
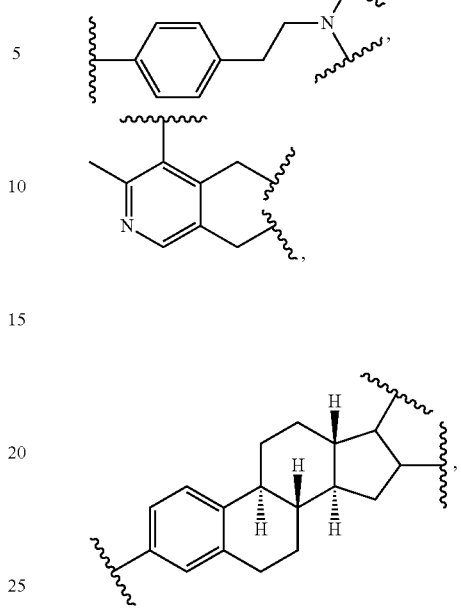
etc.
Examples of trivalent groups wherein the non-core moiety contains heteroatoms include as follows:

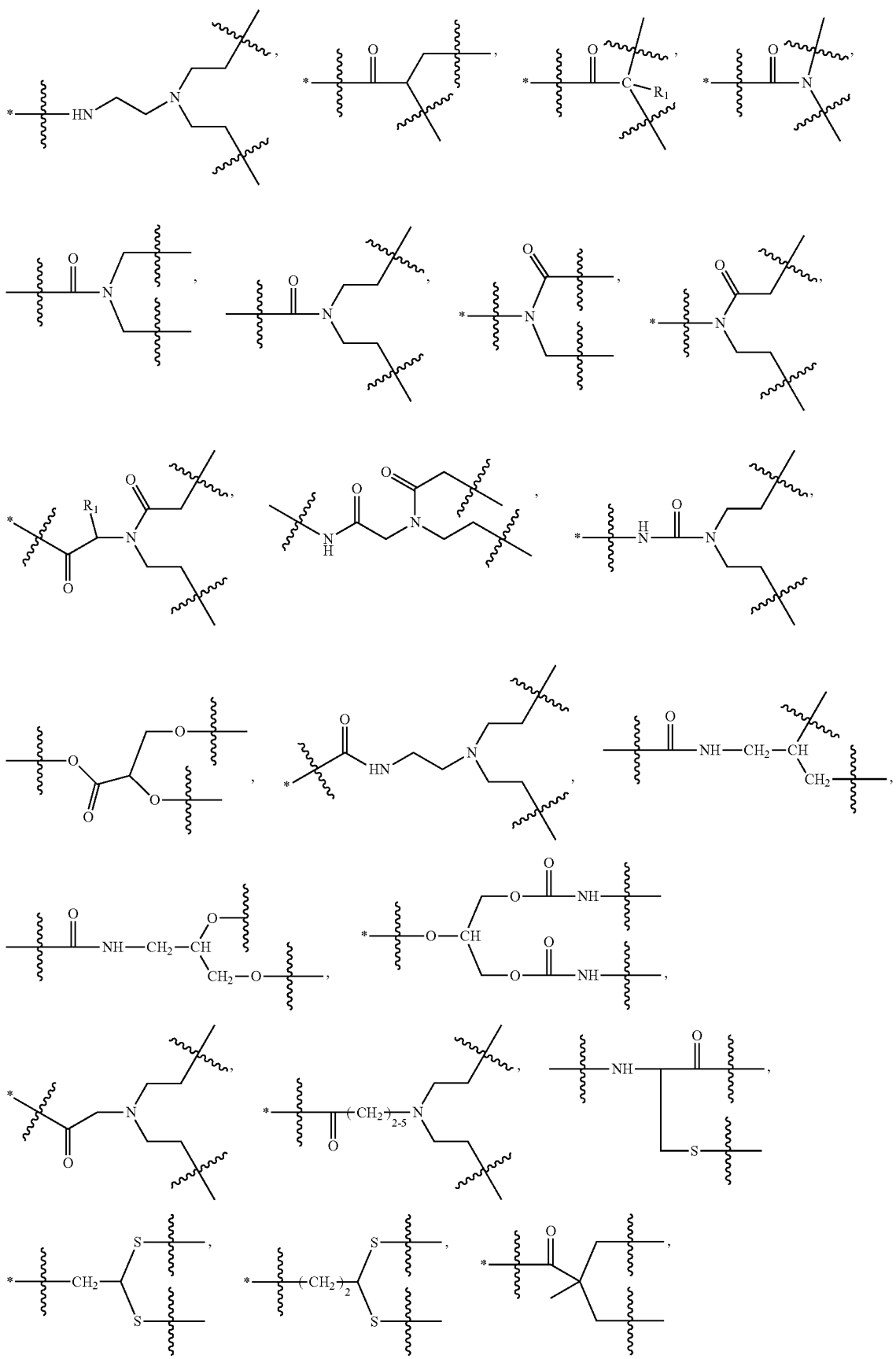

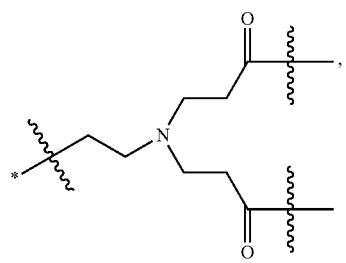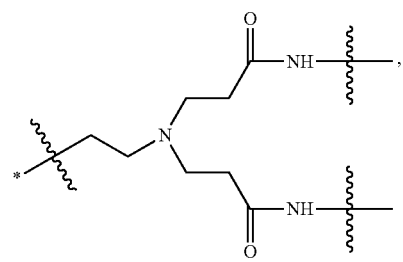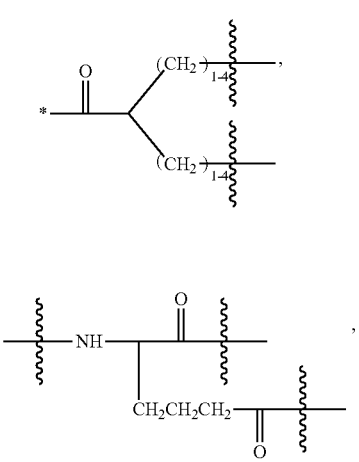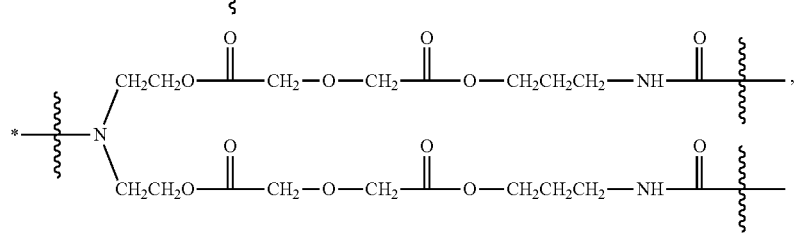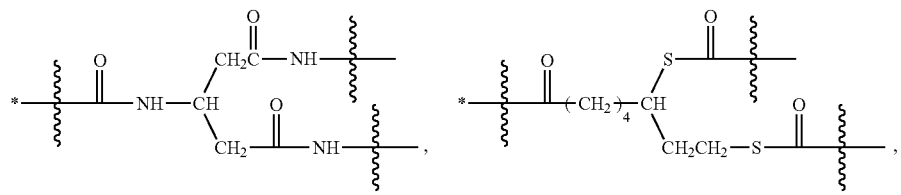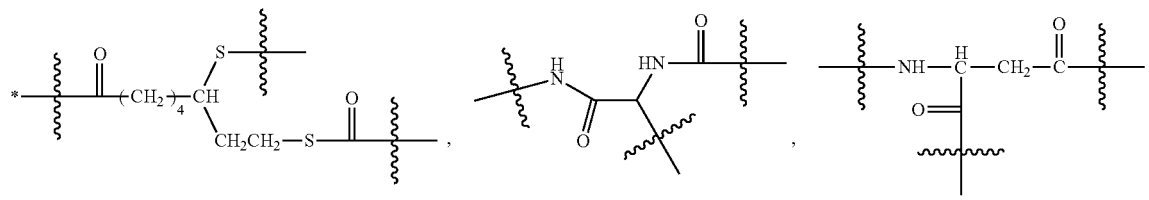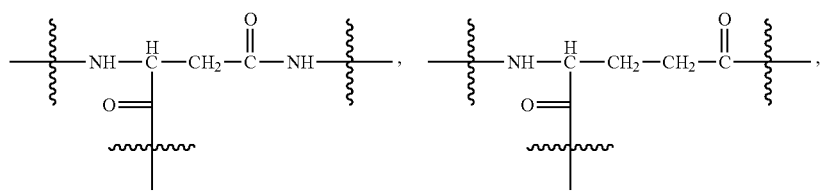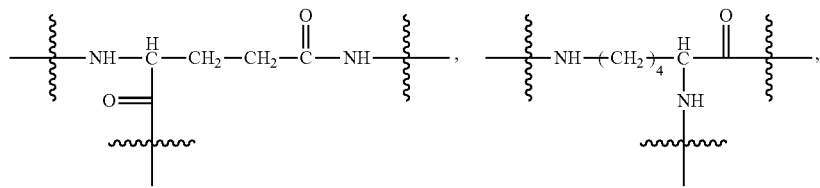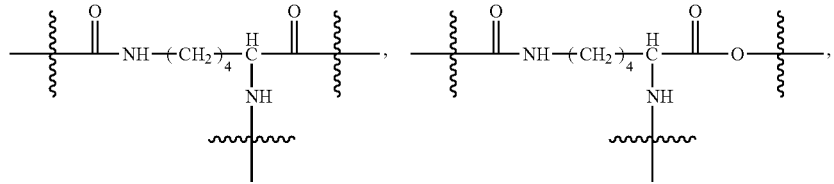

-continued
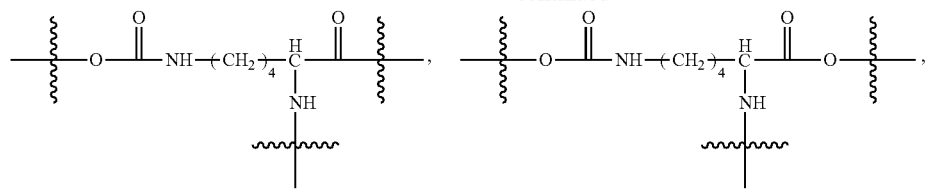
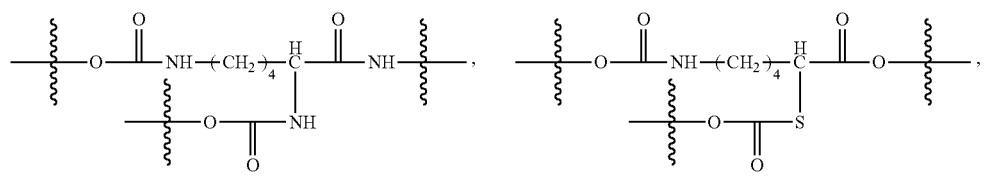
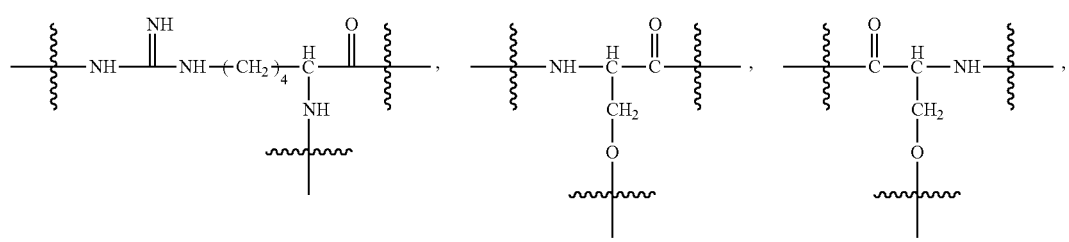
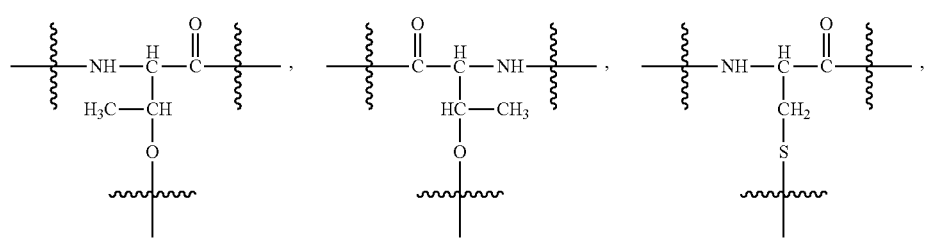
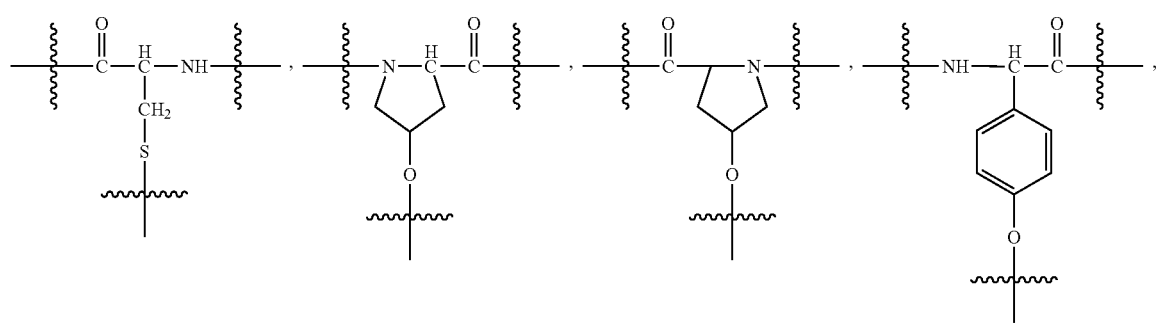
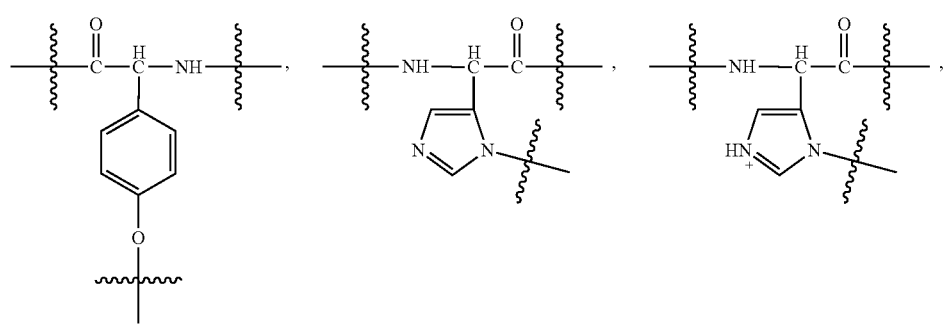

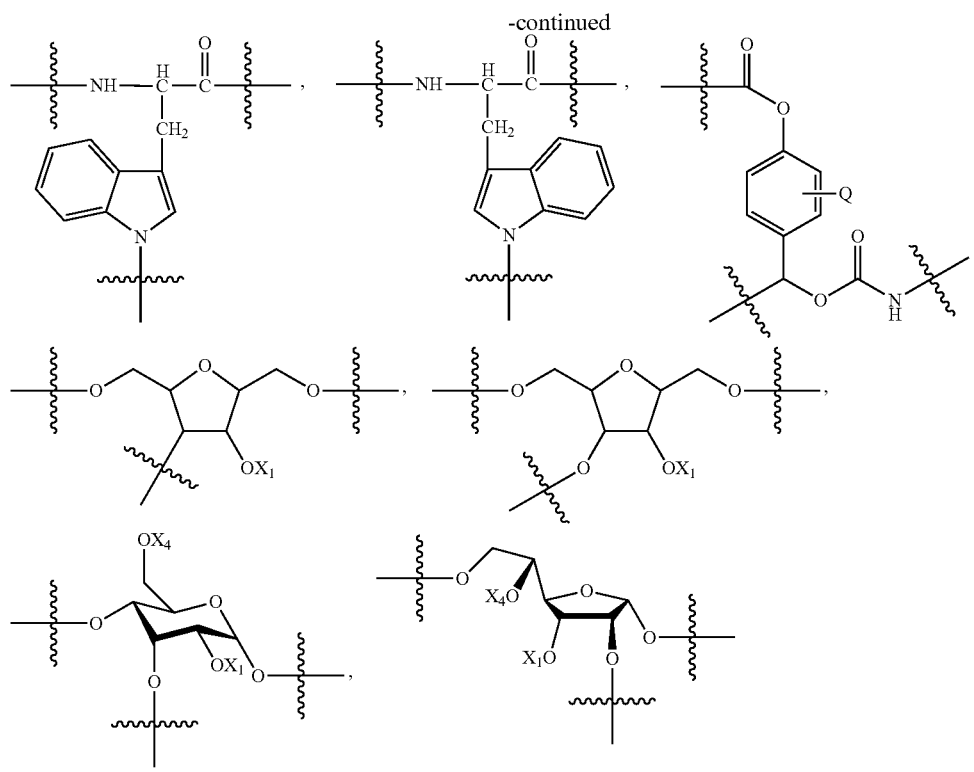
and the like. Examples also include but are not limited to the following structures disclosed in the patent document CN104877127A paragraphs [0201] to [0202]:
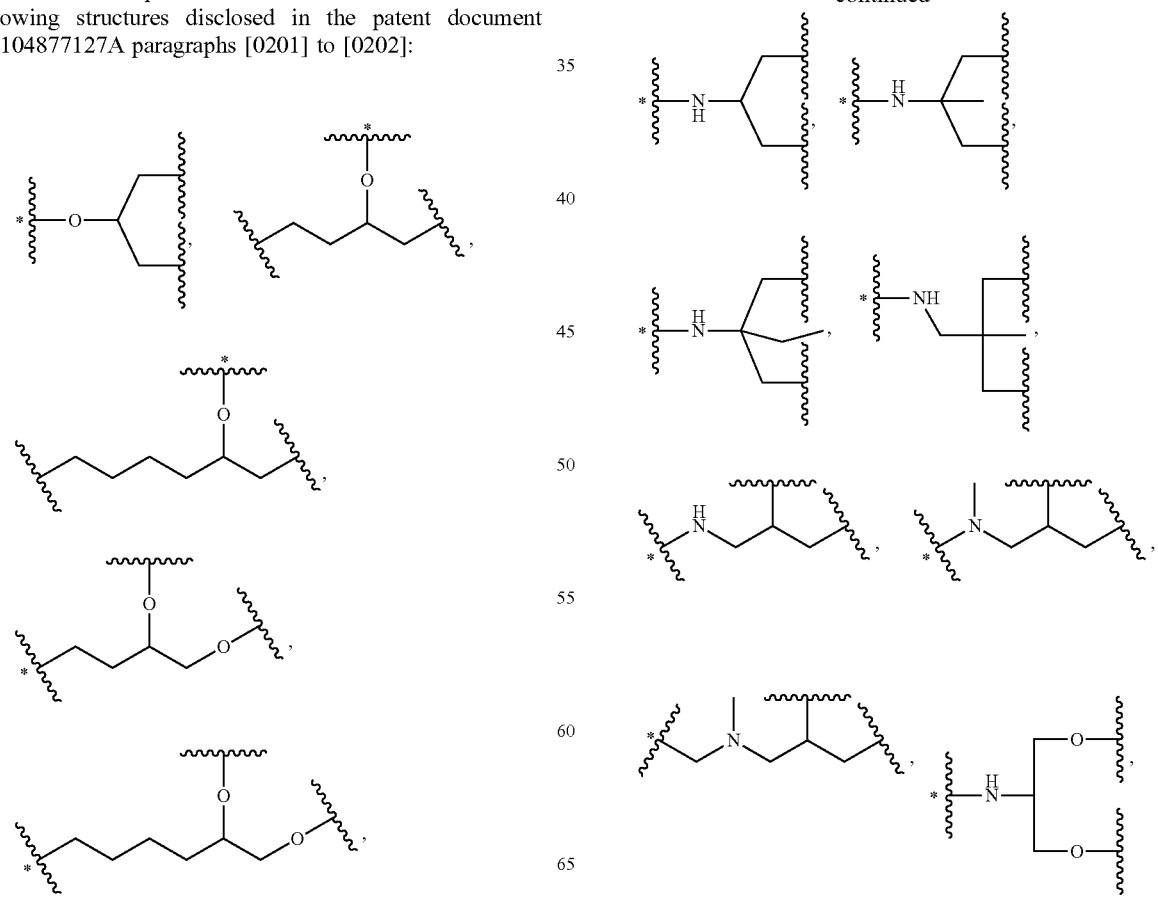

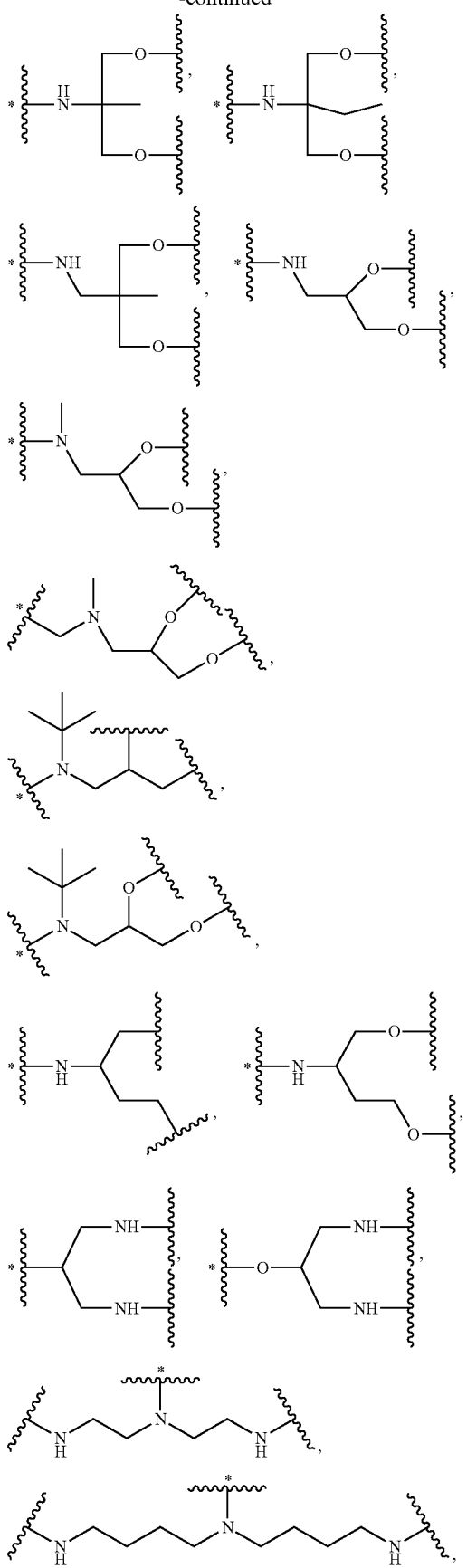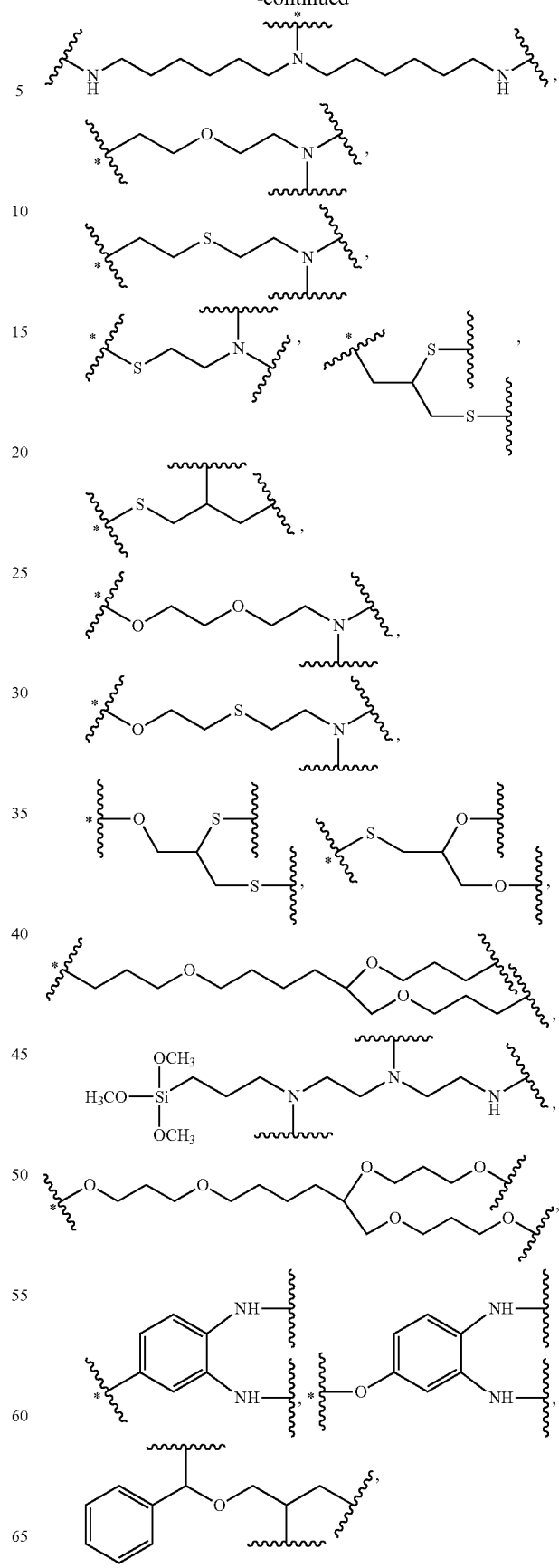

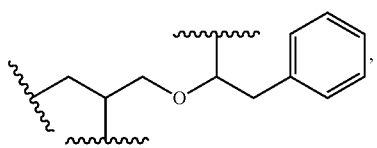
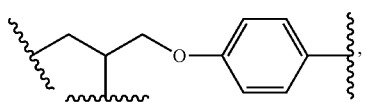
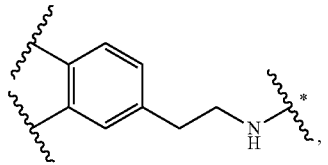
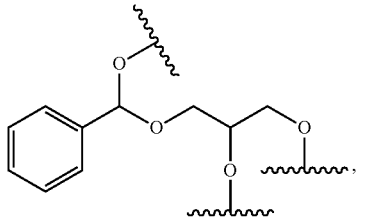
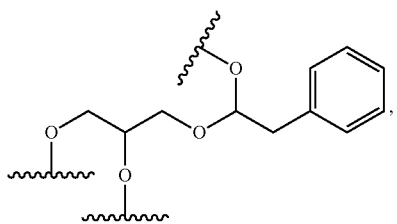
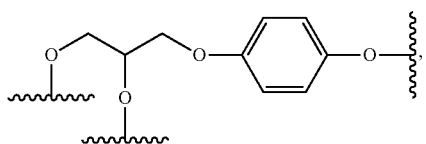
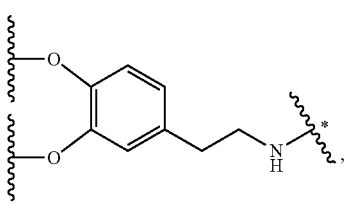
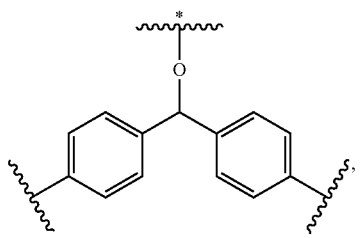
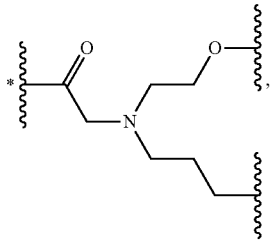
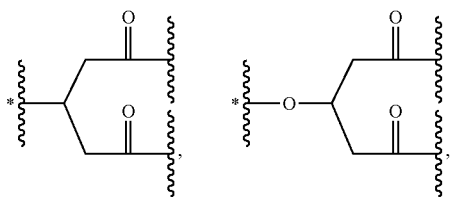
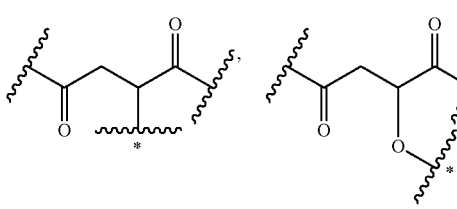
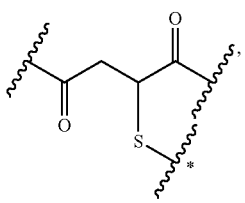
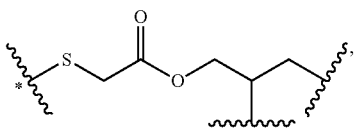
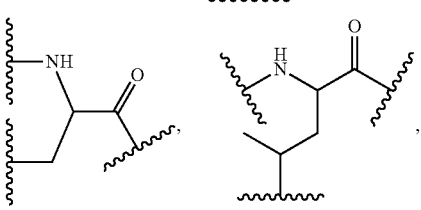
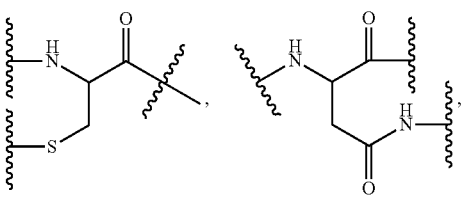
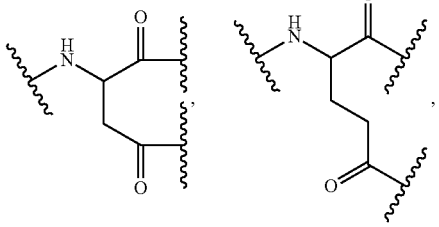

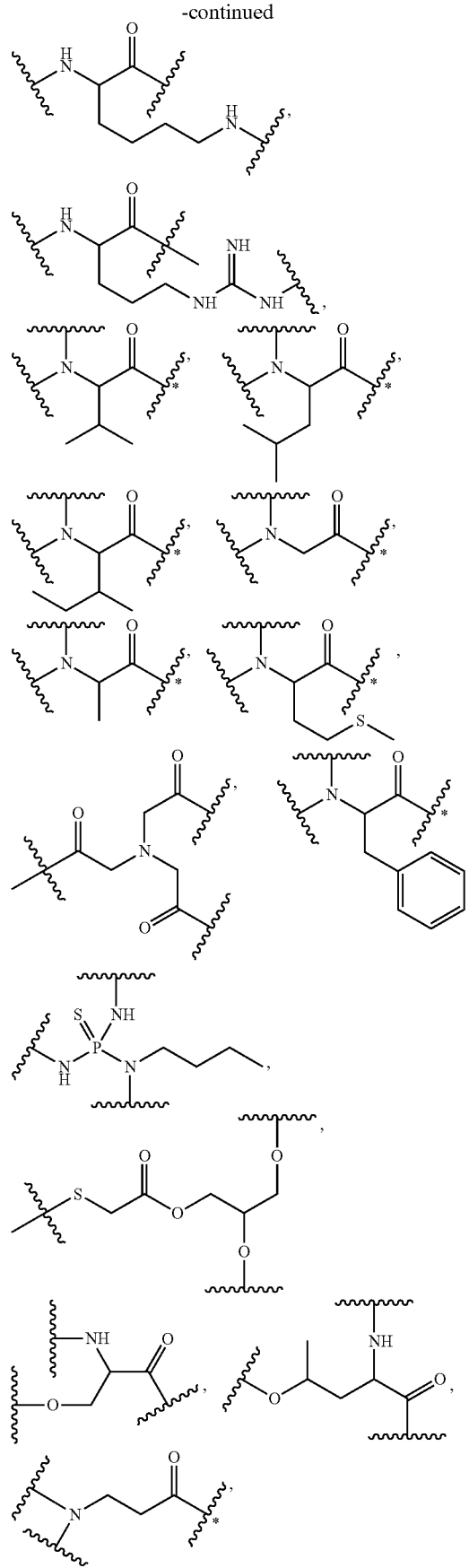
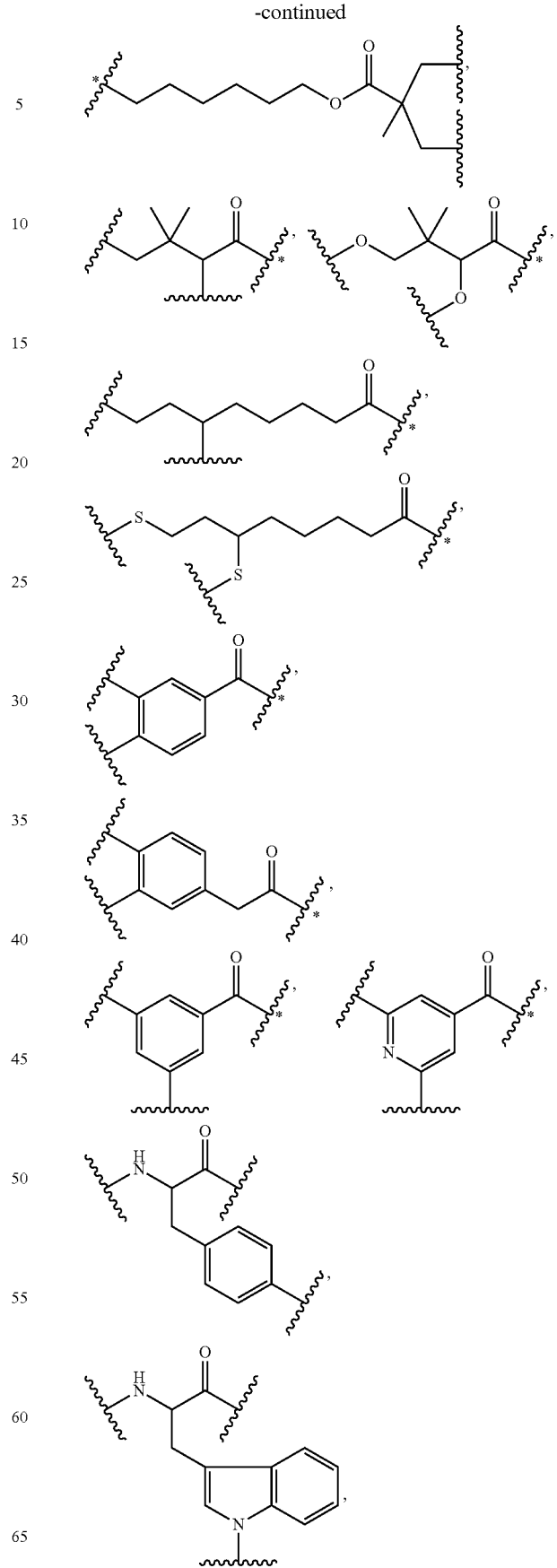

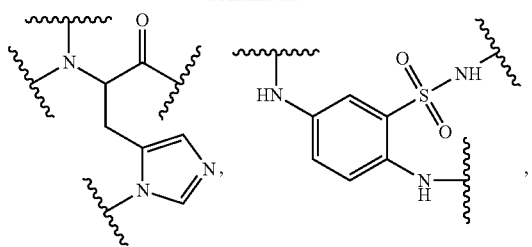
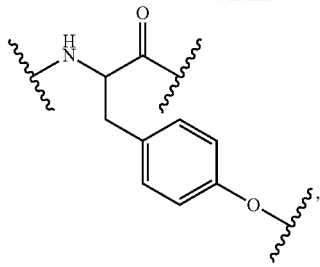
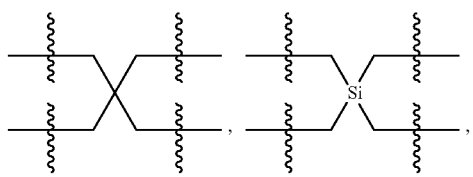

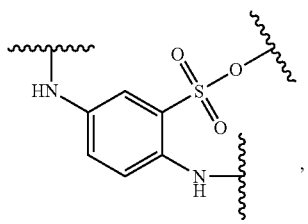

and the like.

Wherein, the definitions of $R_1$, $R_{37}$, $X_1$, $X_2$, $X_4$ and Q are the same as above-described, no more repeated here.

The above-listed examples are to illustrate the characteristics of the trivalent groups in the set $G^3$ much better, and would not confine the scope of set $G^3$.

For example, when k=3, examples of tetravalent groups wherein the non-core moiety contains no heteroatoms include as follows:

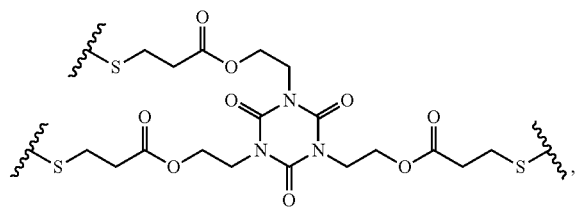

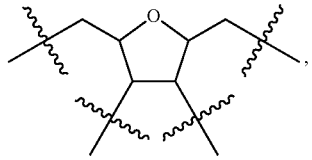

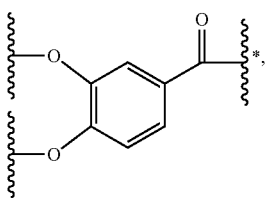

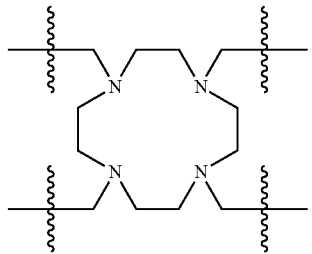

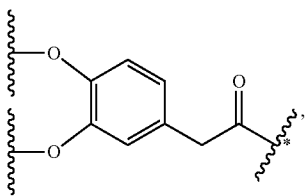

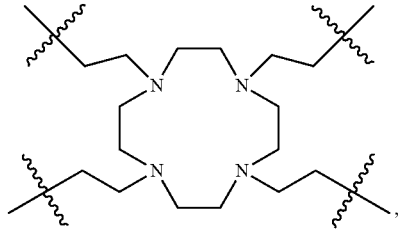

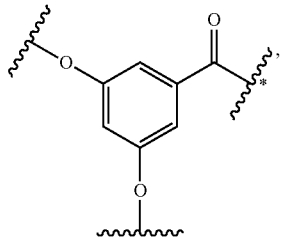

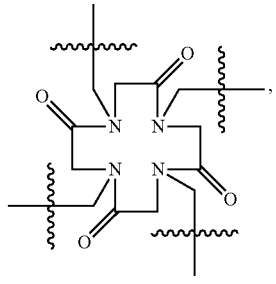

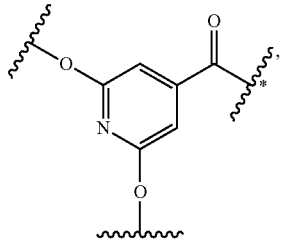

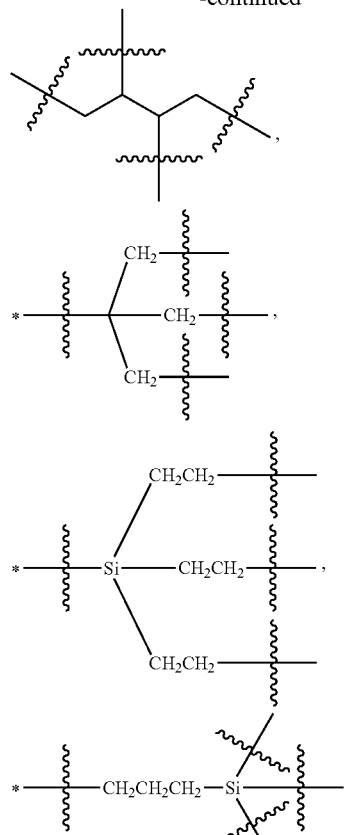
and the like.
Examples of tetravalent groups wherein the non-core moiety contains heteroatoms include as follows:
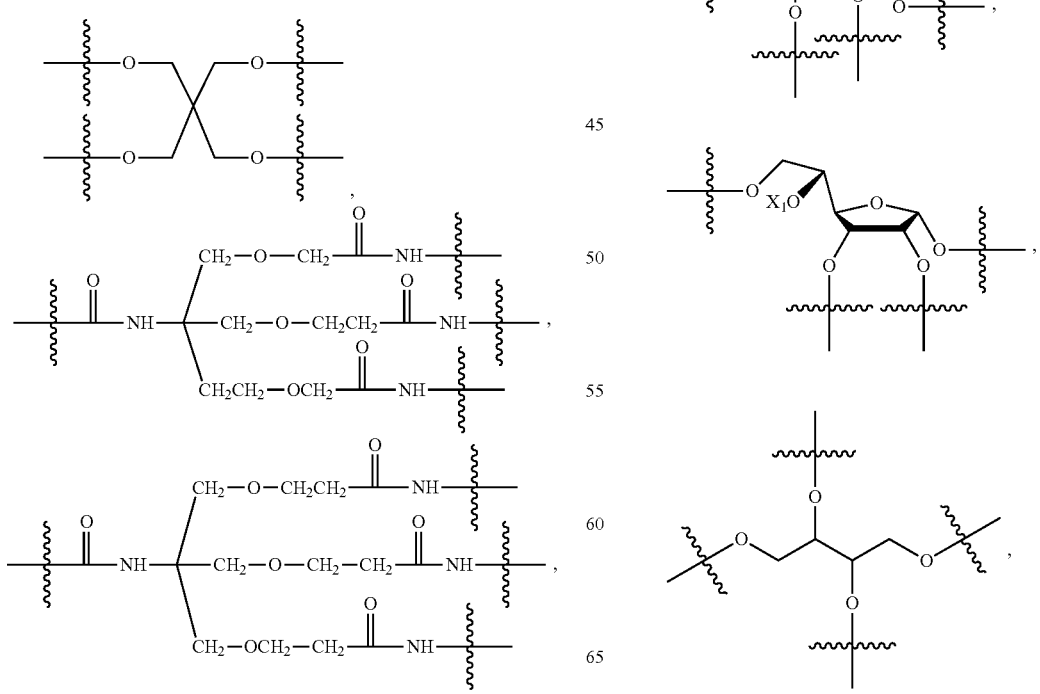
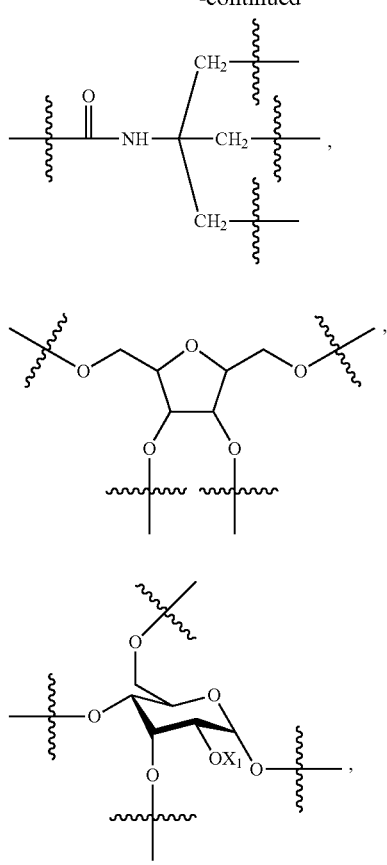

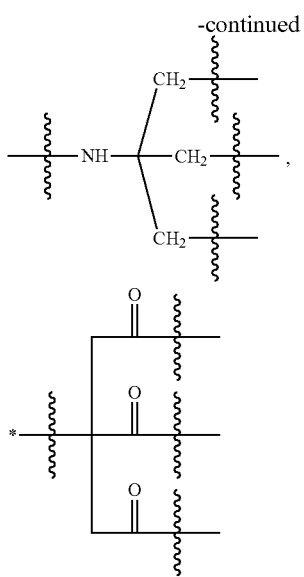

and the like.

When k≥3, that is when the valence of G is equal to or higher than 4, (k+1)-valent groups (groups with valence of k+1) in the set $G^{k+1}$ contain corresponding a (k+1)-valent cyclic core structure $CC_{k+1}$, or are combined directly by lower-valent groups with a valence from 3 to k in quantities of k−1, or are combined indirectly via one or more divalent spacer groups denoted as $L_{10}$. For example, when k is 3, a tetravalent group can be combined by two trivalent groups, and a pentavalent group can be combined by three trivalent groups, or be combined by a trivalent group and a tetravalent group.

When containing two or two more spacer groups $L_{10}$, they can be the same or different.

$L_{10}$ can contain carbon atoms or not, can contain heteroatoms or not, and can be a divalent group of a single atom or a divalent group formed by two or two more atoms.

$L_{10}$ can be a single-atom divalent group, such as —O— or —S—.

$L_{10}$ also can be a hydrocarbylene group that contain no heteroatoms, and preferably a $C_{1-20}$ alkylene group, a $C_{1-20}$ divalent alkenyl group, a $C_{1-20}$ divalent alkenyl-hydrocarbyl group, a $C_{1-20}$ divalent alkynyl group, a $C_{1-20}$ divalent alkynyl-hydrocarbyl group, a $C_{1-20}$ divalent cycloalkyl group, a $C_{1-20}$ divalent cycloalkyl-hydrocarbyl group, a phenylene group, a divalent condensed aryl group or a divalent arylhydrocarbyl group.

$L_{10}$ also can be —C(=O)—N(R₇)—, —N(R₇)—C(=O)—, —S—S—, —C(=O)—O—, —O—C(=O)—, —C(=O)—S—, —S—C(=O)—, —C(=S)—O—, —O—C(=S)—, —C(=S)—S—, —S—C(=S)—, —O—C(=O)—O—, —S—C(=O)—O—, —O—C(=S)—O—, —O—C(=O)—S—, —S—C(=S)—O—, —O—C(=S)—S—, —S—C(=O)—S—, —S—C(=S)—S—, —N(R₇)—C(=O)—O—, —O—C(=O)—N(R₇)—, —N(R₇)—C(=S)—O—, —O—C(=S)—N(R₇)—, —N(R₇)—C(=O)—S—, —S—C(=O)—N(R₇)—, —N(R₇)—C(=S)—S—, —S—C(=S)—N(R₇)—, —N(R₁₉)—N(R₁₈)—, —N(R₁₉)—C(=O)—N(R₁₈)—, —N(R₁₉)—C(=S)—N(R₁₈)—, —N(R₁₈)—N(R₁₉)—C(=O)—, —C(=O)—N(R₁₉)—N(R₁₈)—, —N(R₁₈)—N(R₁₉)—C(=S)—, —C(=S)—N(R₁₉)—N(R₁₈)—, —(R₁₅)C=N—, —N=C(R₁₅)—, —(R₁₅)C=N—N(R₇)—, —N(R₇)—N=C(R₁₅)—, —(R₁₅)C=N—N(R₇)—C(=O)—, —C(=O)—N(R₇)—N=C(R₁₅)—, —(R₁₅)C=N—O—, —O—N=C(R₁₅)—, —(R₁₅)C=N—S—, —S—N=C(R₁₅)—, —N=N—, —N(R₁₈)—N(R₁₉)—C(=O)—N=N—, —N=N—C(=O)—N(R₁₉)—N(R₁₈)—, —N(R₁₈)—C(=O)—N(R₁₉)—, —C(=NR₇)—N(R₂₃)—, —N(R₂₃)—C(=NR₇)—, —N(R₇)—C(=NH₂⁺)—, —C(=NH₂⁺)—N(R₇)—, —C(=NR₇)—O—, —O—C(=NR₇)—, —O—C(=NH₂⁺)—, —C(=NH₂⁺)—O—, —C(=NR₇)—S—, —S—C(=NR₇)—, —S—C(=NH₂⁺)—, —C(=NH₂⁺)—S—, —S(=O)₂—O—, —O—S(=O)₂—, —S(=O)—O—, —O—S(=O)—, —S(=O)₂—N(R₇)—, —N(R₇)—S(=O)₂—, —S(=O)₂—N(R₁₈)—N(R₁₉)—, —N(R₁₉)—N(R₁₈)—S(=O)₂—, —CH₂—O—, —O—CH₂—, —O—R₂₉—, —R₂₉—O—, —O—R₂₉—O—, the like, or any substituted form thereof, wherein all the above-listed divalent linkages contain heteroatoms.

Wherein, the definitions of $R_7$, $R_{18}$, $R_{19}$, $R_{23}$ and $R_{15}$ are the same as above, no more repeated here. Wherein, $R_{29}$ is a $C_{3-20}$ alkylene group, its structure is not particularly limited, and can be a linear-chain type, a branched-chain type or a ring-containing type; the carbon-atom number of $R_{29}$ is preferably $C_{3-12}$; the structure of $R_{29}$ is preferably a linear-chain type.

$L_{10}$ is more preferably an oxy group, a thioxy group, a secondary amino group or a divalent t-amino group corresponding to a stable connection.

$L_{10}$ is most preferably an oxy group such as an ether bond formed by the condensation between two alcoholic hydroxyl groups.

$L_{10}$ also can be a monodisperse multi-form of —CH₂CH₂—O—, —O—CH₂CH₂—, —O—R₂₉— or —R₂₉—O—, wherein the repeat-unit number is from 2 to 20, and preferably from 2 to 10. However, these structures should not occur in the branched central structure $U_{01}$ or $U_{02}$.

Take tetravalent groups with k in quantities of 3 for example, tetravalent groups in the set $G^4$ can both be based on a tetravalent core structure, and also can be a combination of any two trivalent groups in the set $G^3$.

The combination can be in a direct manner, e.g., tetravalent groups derived from erythritol can be regarded as a direct combination of two trivalent groups separated by a dashed line as follows:

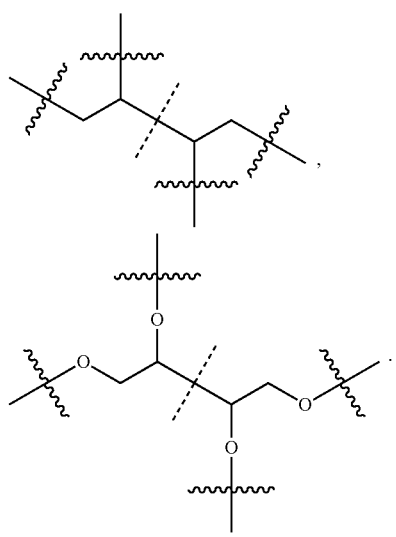

For another example, tetravalent groups which are formed by two amino acid skeletons via direct connections as follows,

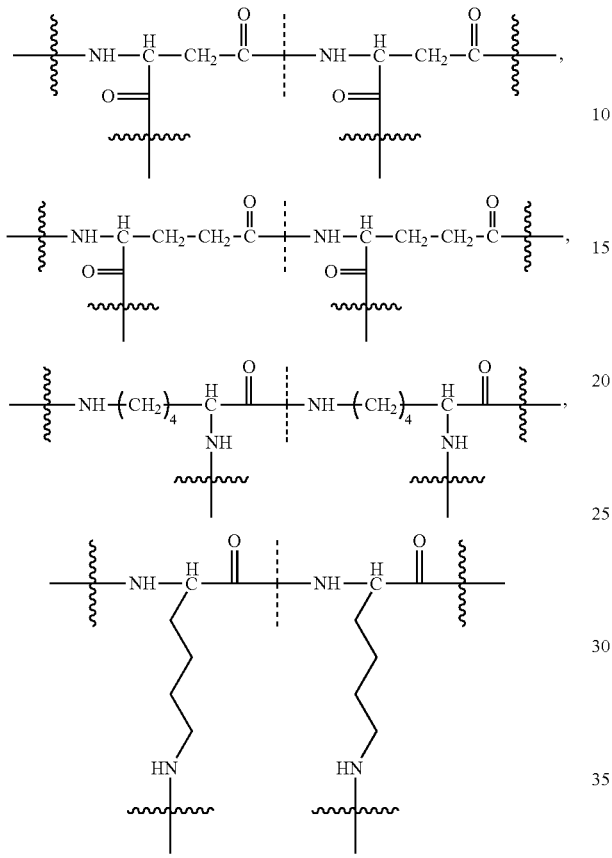

and the like.

The combination can also be in an indirect manner via one or one more divalent spacer groups $L_{10}$. When a tetravalent group in the set $G^4$ contains two or two more spacer groups $L_{10}$, they can be the same or different. Tetravalent groups formed by removing hydroxyl groups or hydrogen atoms of hydroxyl groups of tetraols which are formed by the condensation of two molecules of common triols belong to this manner. For example,

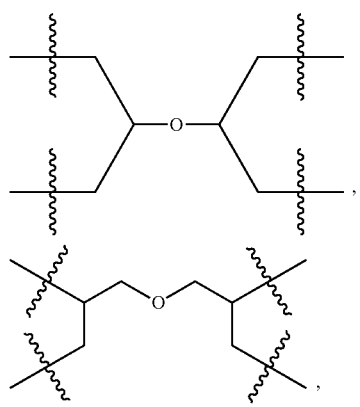

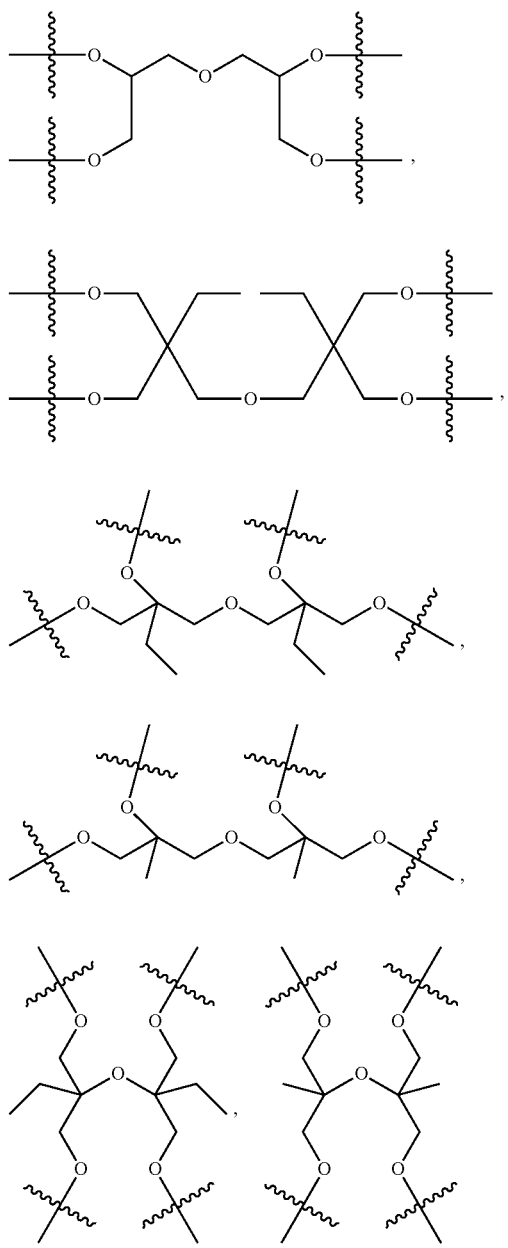

and the like.

The tetravalent G can be any tetravalent group selected from the above-mentioned set $G^4$. Examples of tetravalent G also include but are not limited to the following structures disclosed in the patent document CN104877127A paragraph [0231]:

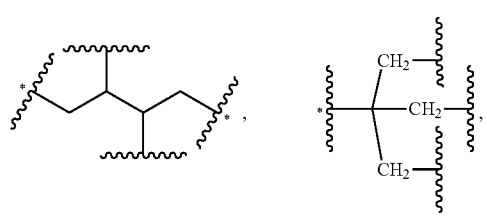

91
-continued
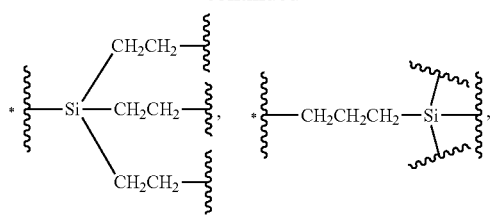 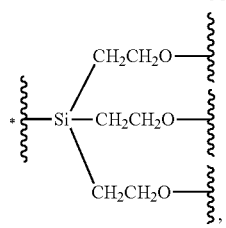
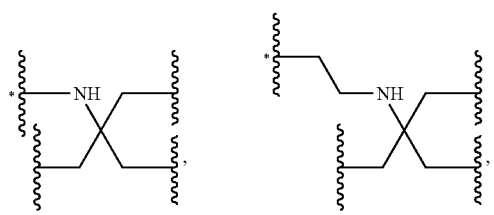
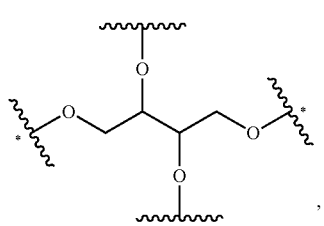
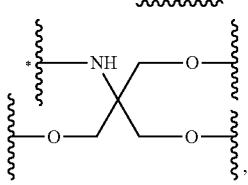
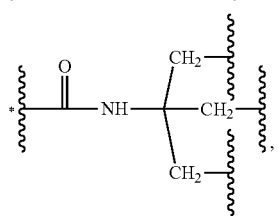
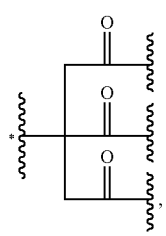
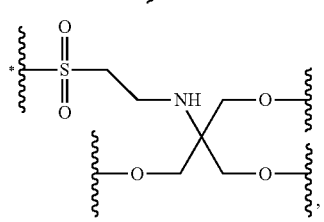
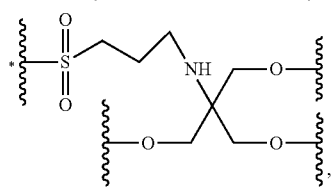
92
-continued
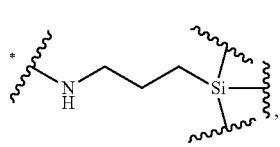
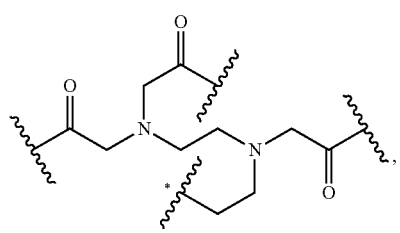
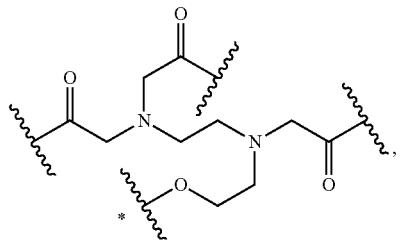
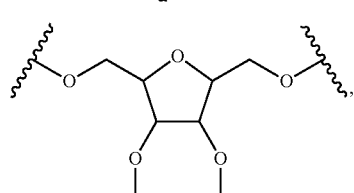
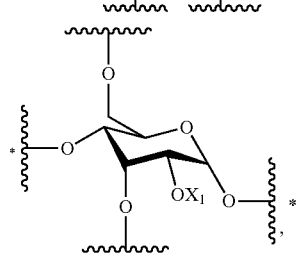
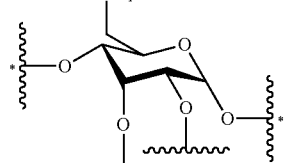
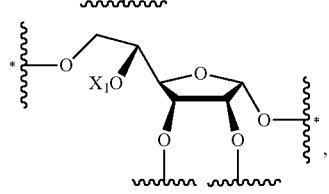

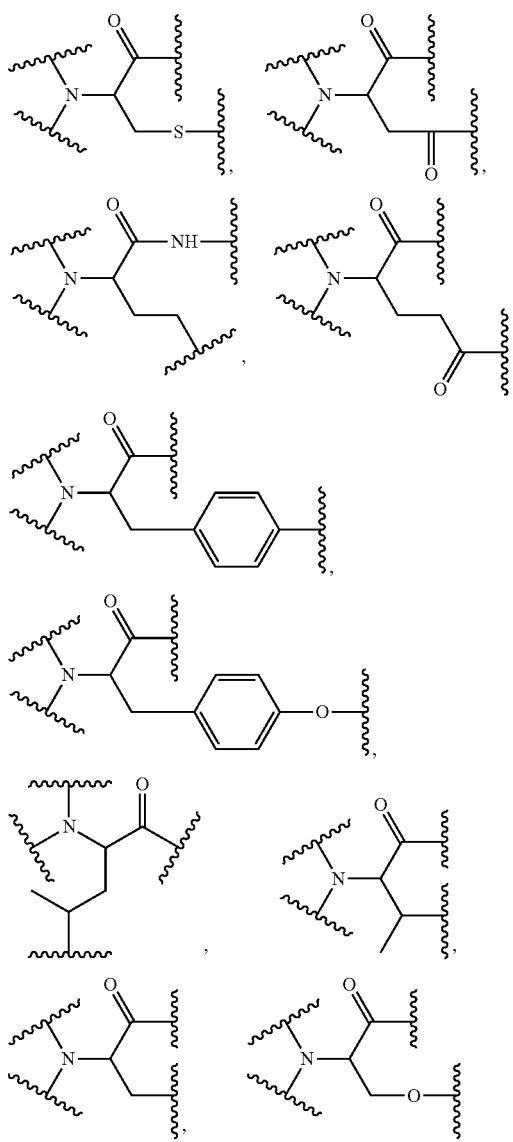
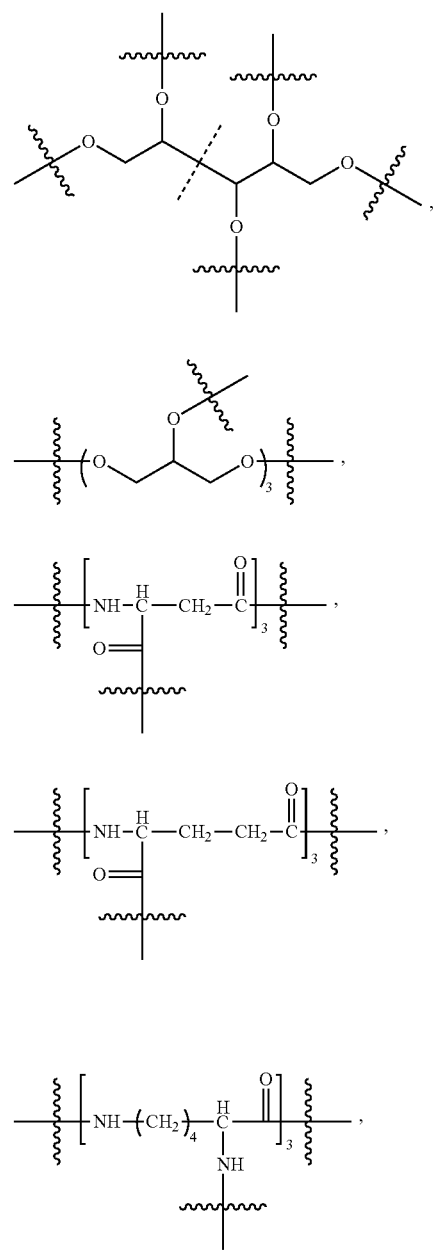
and the like. Wherein, the definition of $X_1$ is the same as above defined.
When k=4, examples of pentavalent groups include as follows:
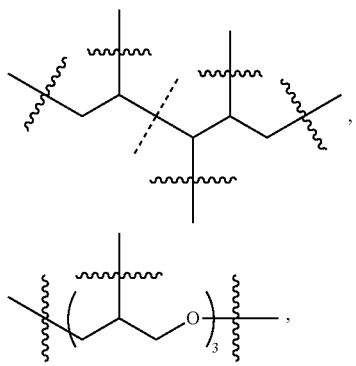
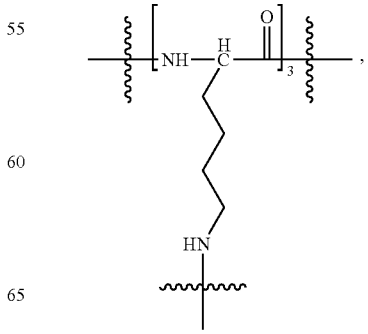

-continued
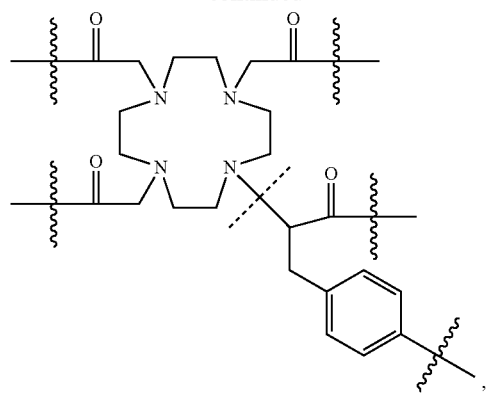
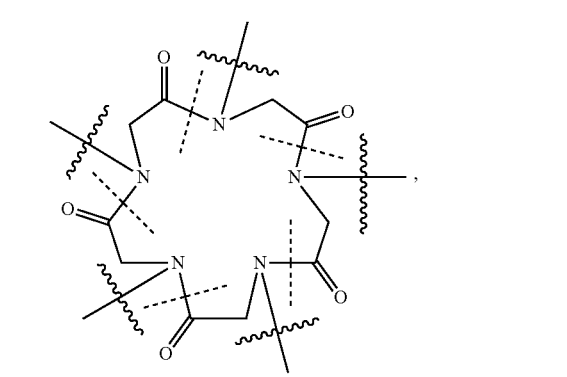
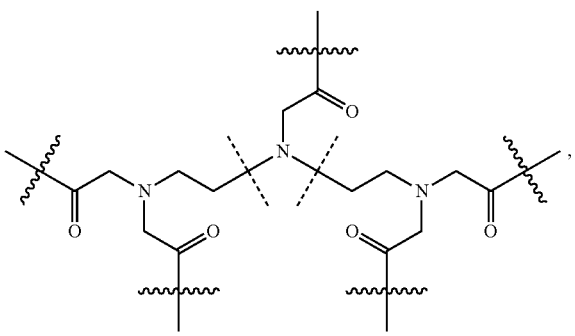
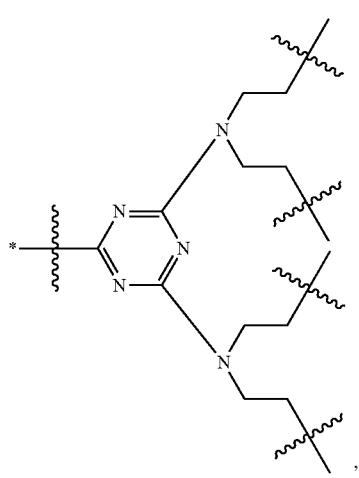
-continued
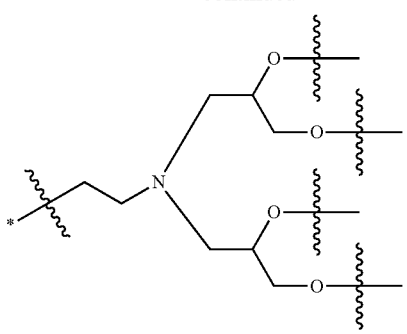
and the like.
Examples also include but are not limited to the following structures disclosed in the patent document CN104877127A paragraph [0233]:
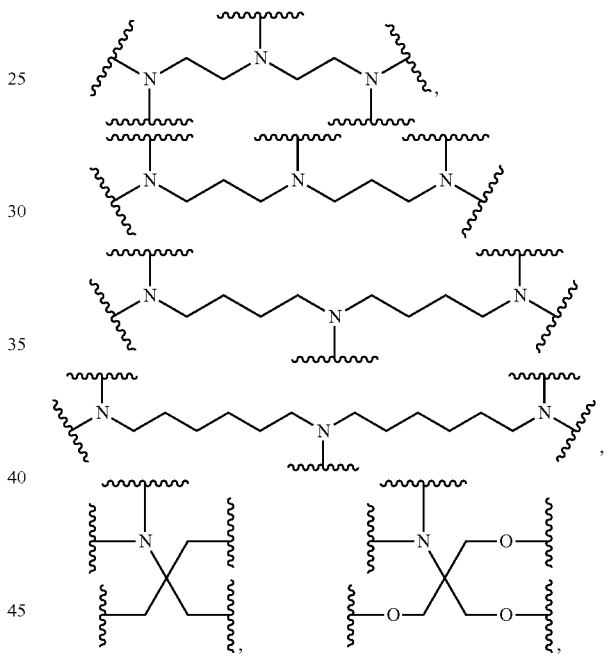
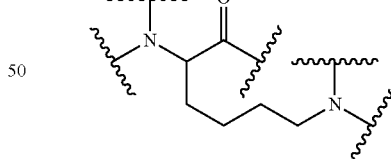
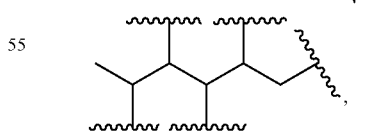
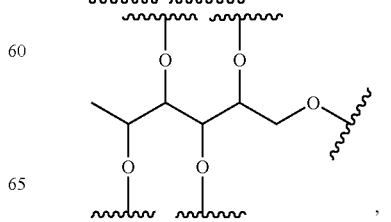

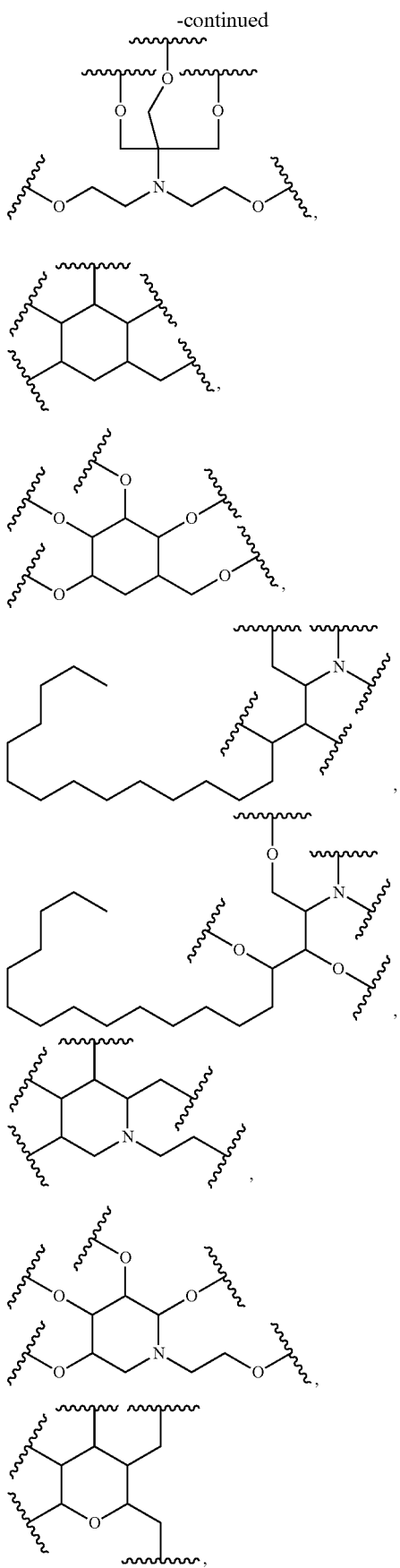
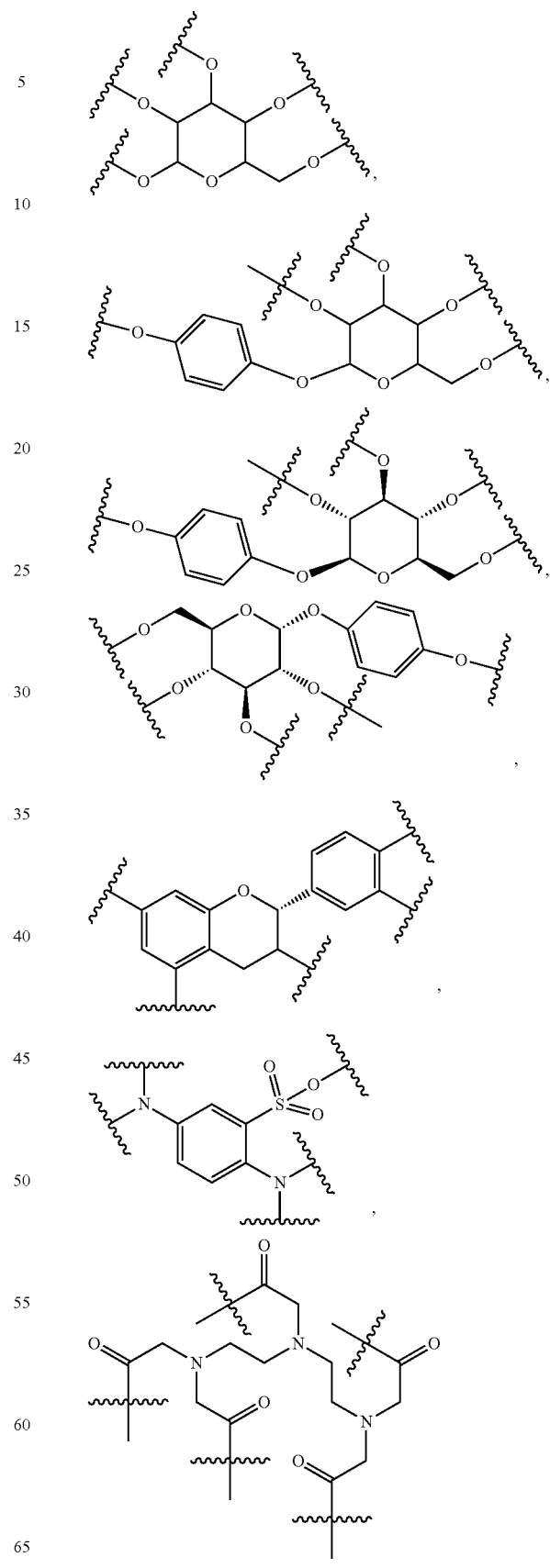

and the like. Wherein, the isomeric structures of

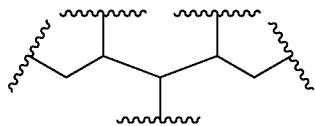 [SMILES: *CC(*)C(*)C(*)C*]

include but are not limited to pentavalent carbon skeletons of D-ribose, D-arabinose, D-xylose and D-lyxose. Pentavalent groups also include but are not limited to pentavalent skeleton structures of six-membered cyclic monosaccharide such as glucose, allose, altrose, mannose, gulose, idose, galactose, talose, psicose, fructose, sorbose, tagatose and the like.

When k=5, examples of hexavalent groups include as follows:

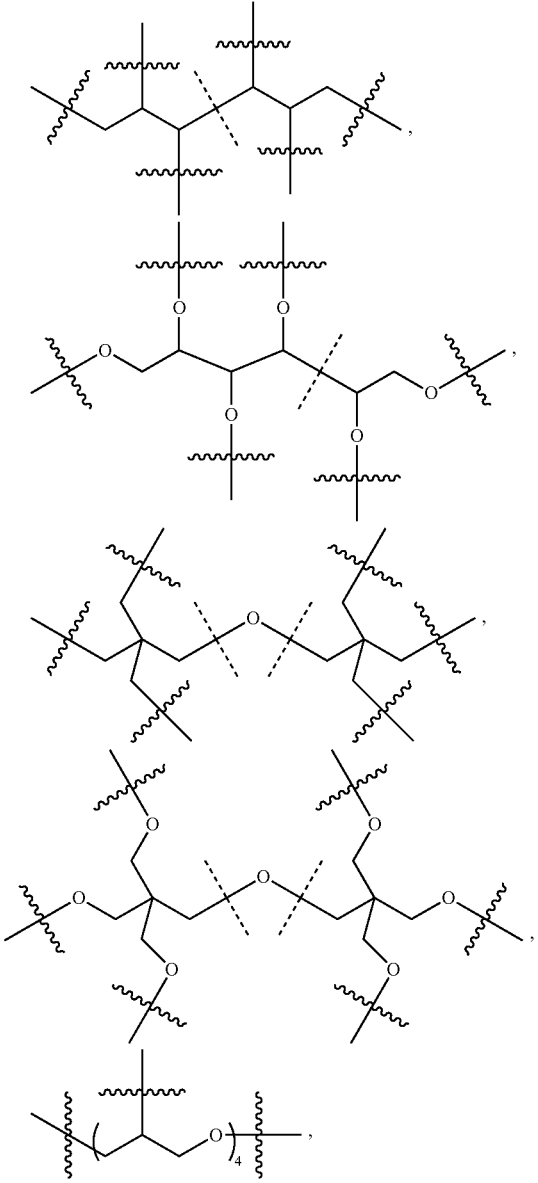

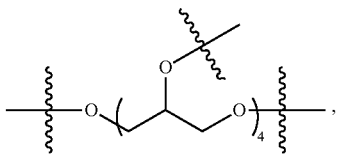

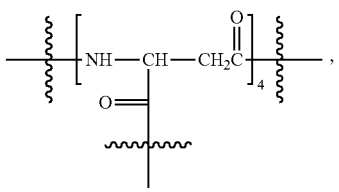

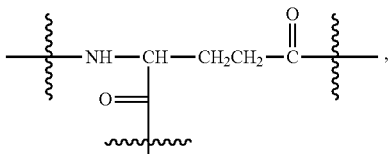

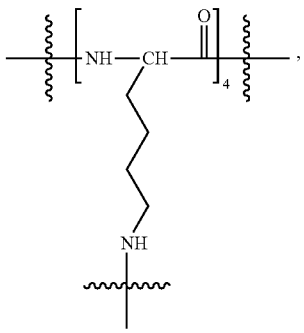

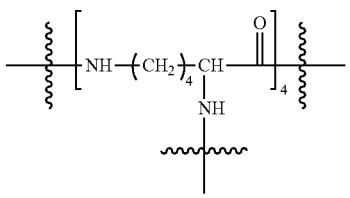

and the like. Hexavalent groups also include but are not limited to

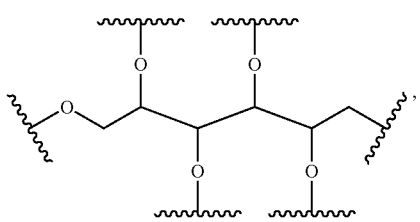 [SMILES: *CC(O*)C(O*)C(O*)C(CO*)O*]

hexavalent skeletons derived from inositol, sorbitol, mannitol, D-glucamine, 1-mercapto-sorbitol, N-methyl-D-glucamine, tris(2,3-dichloropropyl)phosphate ester and D-sorbitol-3-phosphate ester after removing six hydrogen atoms of hydroxyl groups, amino groups or/and mercapto groups, and hexavalent skeletons derived from D-allose, D-altrose, D-glucose, D-mannose, D-gulose, D-idose, D-galactose, D-talose and D-psicose.

When k=6, examples of heptavalent groups include as follows:

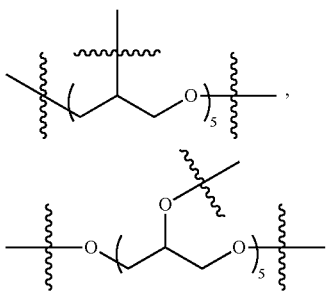

and the like.

When k=7, examples of octavalent groups include as follows:

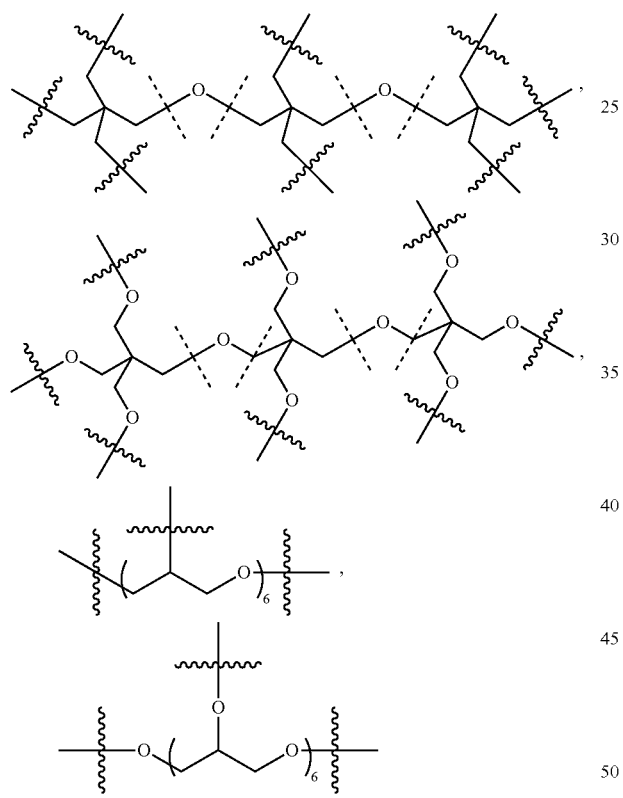

and the like.

When k is ≥4, the valence of G is ≥5. For (k+1)-valent groups in the set $G^{k+1}$ which are formed via a direct combination lower-valent (from 3- to k-valent) groups in quantities of 3 to k−1, or are combined indirectly via one or more divalent spacer groups $L_{10}$, the combination manner of the lower-valent (from 3- to k-valent) groups is not particularly limited, for example, including but not limited to a comb-like manner, a dendritic manner, a branched manner, a hyperbranched manner, a cyclic manner and the like. With respect to a group of the combination of several lower-valent groups in a comb-like, dendritic, branched or hyperbranched manner, said lower-valent groups in one molecule can be the same or different, and preferred to be the same.

For (k+1)-valent groups in the set $G^{k+1}$(k≥4) formed by combination of lower-valent groups in a comb-like manner, a dendritic manner, a branched manner, a hyperbranched manner or a cyclic manner, the number of said lower-valent groups is from 3 to 150, and preferably from 3 to 100.

The dendritic combinations have a generation from 2 to 6, preferably a generation from 2 to 5, and more preferably a generation of 2, 3 or 4.

The branched combinations include, such as

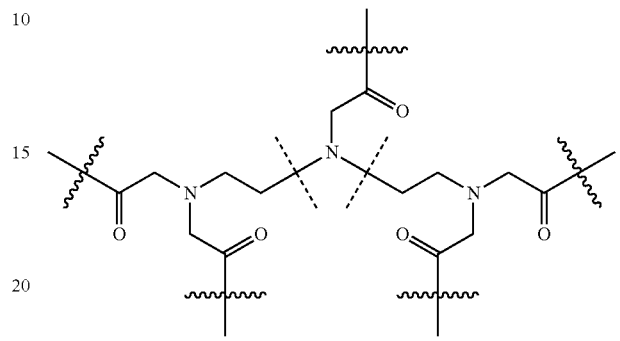

and the like. Examples of comb-like combinations include as follows:

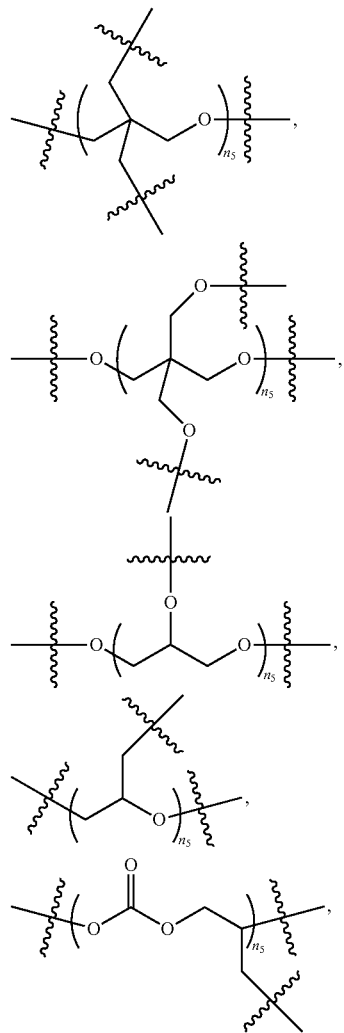

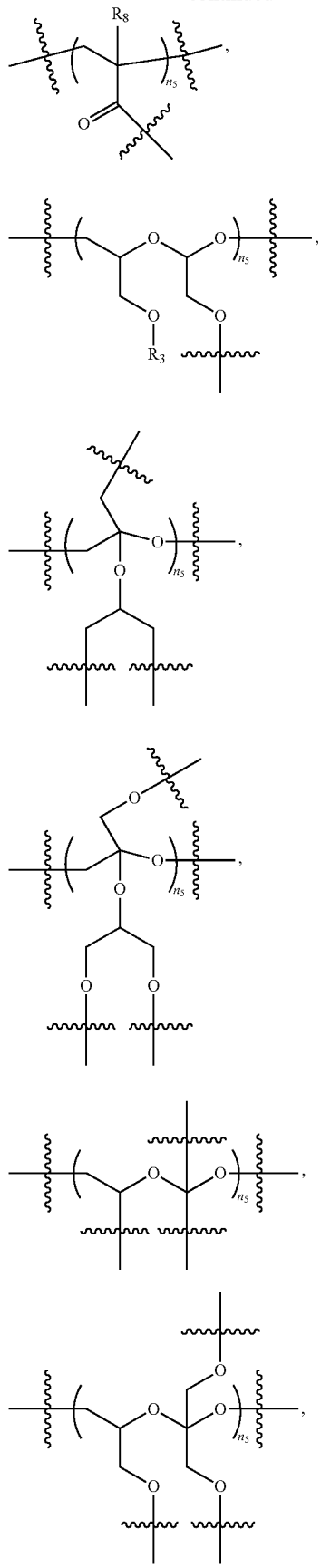
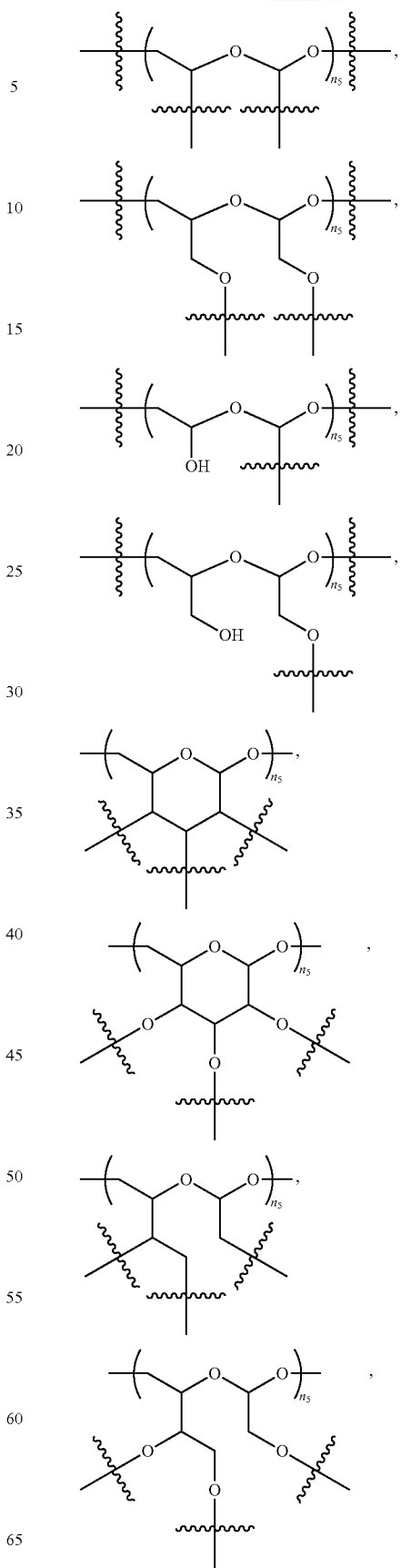

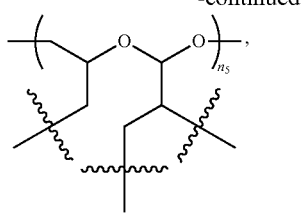
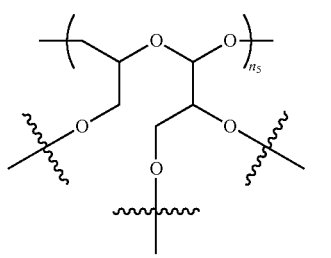
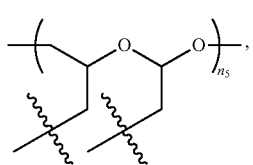
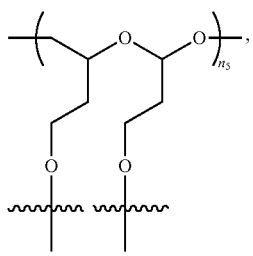
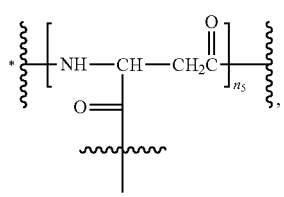
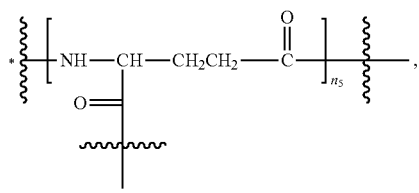
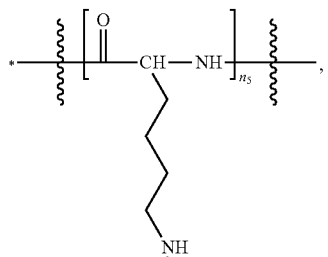
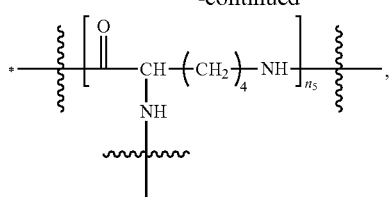
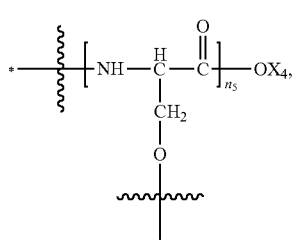
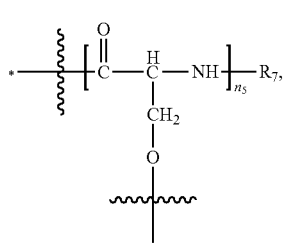
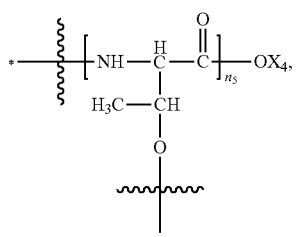
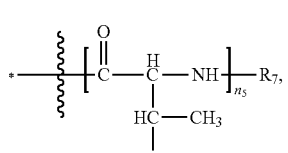
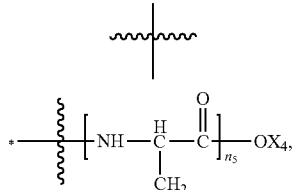
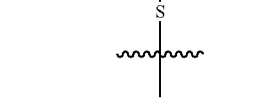
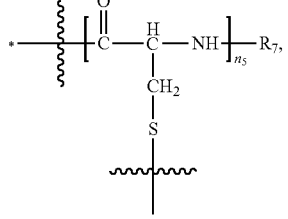

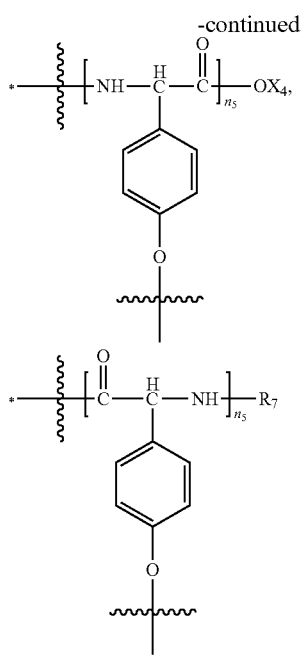

More typically, hexaglycerol, tripentaerythritol and the like.

The generations of dendritic combination is not particularly limited, preferably from 1 to 6, more preferably from 1 to 5, and most preferably 2, 3 or 4. Dendritic structures combined in a dendritic manner can also be denoted as DENR ($U_{denr}$, NONE, d), DENR ($U_{denr}$, $L_{10}$, d), or $[U_{denr}]_d$. Wherein, $U_{denr}$ represents the multivalent repeat unit; NONE represents direct connection between multivalent repeat units; $L_{10}$ serves as a divalent linking group for multivalent repeat units to be indirectly combined; d represents the generation of dendritic combination. For example,

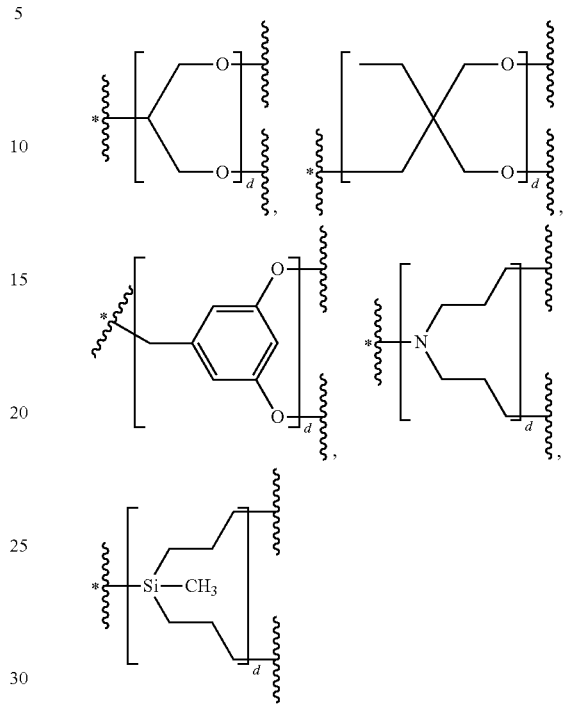

and the like. Wherein, ng is 1, 2, 3, 4, 5 or 6.

Examples of hyperbranched combination include hyperbranched structures containing repeat units such as

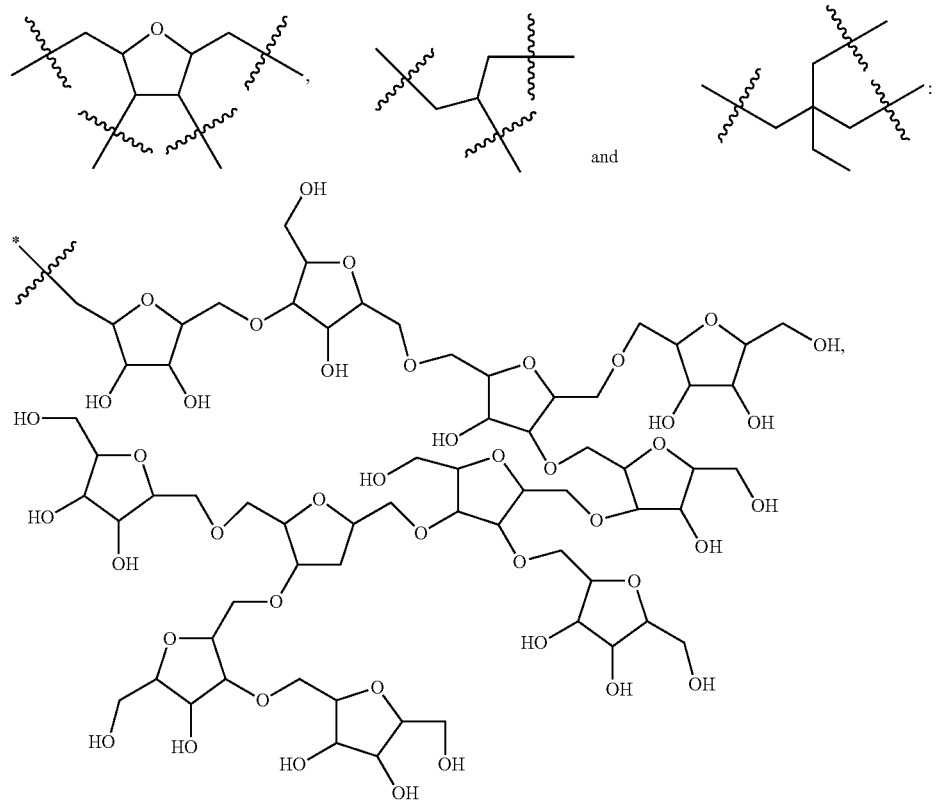

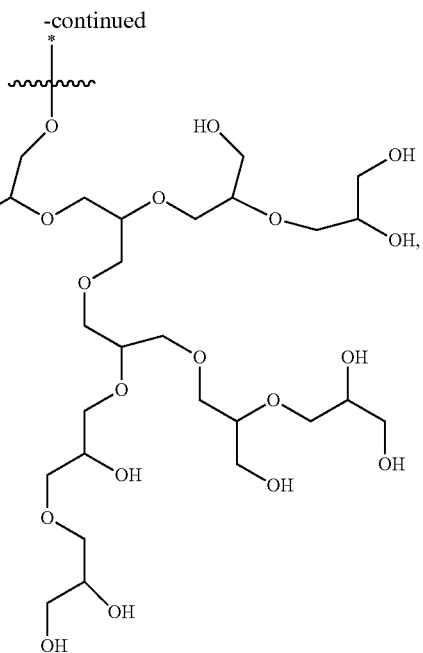
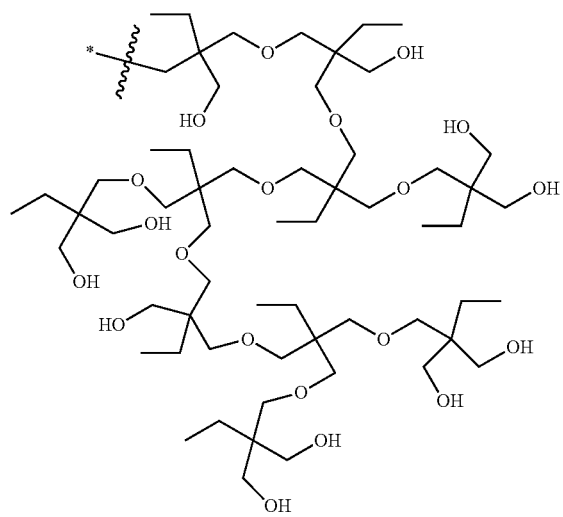
and the like.

Examples of cyclic combination include as follows,

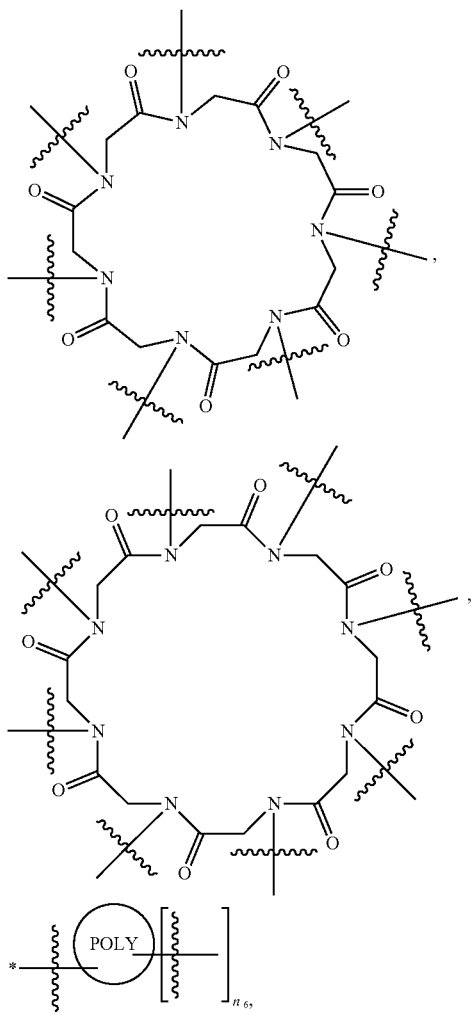

cyclodextrin skeletons and the like.

Wherein, $n_5$ is from 3 to 150, preferably from 3 to 100.
Wherein, $n_6$ is from 2 to 150, preferably from 5 to 100.
Wherein, $M_9$ is O, S or $NX_{10}$.
Wherein, $X_{10}$ is a hydrogen atom or a hydrocarbyl group containing 1 to 20 carbon atoms.

The structure of $X_{10}$ is not particularly limited, can be but not limited to a linear structure, a branched structure or a ring-containing structure.

The species of $X_{10}$ is not particularly limited, can be but not limited to a linear alkyl group, a branched alkyl group, a cycloalkyl group, an aryl group, an arylalkyl groups, a substituted cycloalkyl group, a substituted aryl group, a substituted arylalkyl group or the like.

$X_{10}$ is preferably a hydrogen atom, a methyl group, an ethyl group, a propyl group, an isopropyl group, a butyl group, a t-butyl group, a pentyl group, a hexyl group, a heptyl group, a 2-ethyl hexyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, a $C_{3-20}$ cycloalkyl group, an aryl group, a phenyl group, an arylhydrocarbyl group, an arylalkyl group, a benzyl group, a butylphenyl group, a substituted $C_{3-20}$ cycloalkyl group, a substituted aryl group, a substituted $C_{7-20}$ arylhydrocarbyl group, a substituted $C_{7-20}$ arylalkyl group or the like. It is more preferably a methyl group, an ethyl group, a propyl group, an isopropyl group, a butyl group, a t-butyl group, a pentyl group, a heptyl group, a 2-ethyl hexyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, a benzyl group, a butylphenyl group or the like.

$X_{10}$ is more preferably a hydrogen atom or a hydrocarbyl group containing 1 to 10 carbon atoms. Examples of $X_{10}$ include but are not limited to a hydrogen atom, a methyl group, an ethyl group, a propyl group, an isopropyl group, a butyl group, a t-butyl group, a pentyl group, a heptyl group, a 2-ethyl hexyl group, an octyl group, a nonyl group, a decyl group, a benzyl group, a butylphenyl group and the like.

$X_{10}$ is more preferably a hydrogen atom or a hydrocarbyl group containing 1 to 5 carbon atoms, being but not limited to a hydrogen atom, a methyl group, an ethyl group, a propyl group, an isopropyl group, a butyl group, a t-butyl group, a pentyl group or the like.

$X_{10}$ is more preferably a hydrogen atom or a methyl group.

Wherein, $R_3$ is a terminal group connecting with an oxy group or a thioxy group (—S—).

The carbon-atom number of $R_3$ is not particularly limited, preferably from 1 to 20, and more preferably from 1 to 10.

The structure of $R_3$ is not particularly restricted, including but not limited to a linear structure, a branched structure bearing pendant groups or a ring-containing structure. Said ring is not particularly limited, including but not limited to all the above-listed cyclic structures in the terminology section.

$R_3$ can contain heteroatoms or does not contain heteroatoms.

$R_3$ is a $C_{1-20}$ hydrocarbyl group, a $C_{1-20}$ heterohydrocarbyl group, a $C_{1-20}$ substituted hydrocarbyl group or a $C_{1-20}$ substituted heterohydrocarbyl group. The heteroatom or group substituent within $R_3$ is not particularly limited, including but not limited to all the above-listed heteroatoms and substituting groups in the terminology section, and preferably a halogen atom, a hydrocarbyl substituent, or a heteroatom-containing substituent.

$R_3$ is preferably a $C_{1-20}$ alkyl group, a $C_{3-20}$ alkenyl-hydrocarbyl group, an aryl group, an arylhydrocarbyl group, a $C_{1-20}$ aliphatic-derived heterohydrocarbyl group, a heteroaryl group, a heteroarylhydrocarbyl group, a substituted $C_{1-20}$ alkyl group, a substituted $C_{3-20}$ alkenyl-hydrocarbyl group, a substituted aryl group, a substituted arylhydrocarbyl group, a substituted $C_{1-20}$ aliphatic-derived heterohydrocarbyl group, a substituted heteroaryl group, or a substituted heteroarylhydrocarbyl group. Wherein, the atom or group substituent is a halogen atom, a hydrocarbyl substituent, or a heteroatom-containing substituent.

$R_3$ is preferably a $C_{1-20}$ linear alkyl group, a $C_{1-20}$ branched alkyl group, a $C_{3-20}$ cycloalkyl group, an aryl group, an arylhydrocarbyl group, a $C_{1-20}$ aliphatic-derived heterohydrocarbyl group, a heteroaryl group, a heteroarylhydrocarbyl group, a substituted $C_{1-20}$ linear alkyl group, a substituted $C_{1-20}$ branched alkyl group, a substituted $C_{3-20}$ cycloalkyl group, a substituted aryl group, a substituted arylhydrocarbyl group, a substituted $C_{1-20}$ aliphatic-derived heterohydrocarbyl group, a substituted heteroaryl group or a substituted heteroarylhydrocarbyl group. Wherein, the atom or group substituent is a halogen atom, a hydrocarbyl substituent, or a heteroatom-containing substituent, and preferably a halogen atom, an alkoxy group, a hydrocarbyl group, an aryl group or a nitro group.

$R_3$ is more preferably a $C_{1-10}$ linear alkyl group, a $C_{1-10}$ branched alkyl group, a $C_{3-10}$ cycloalkyl group, an aryl group, an arylhydrocarbyl group, a $C_{1-20}$ aliphatic-derived heterohydrocarbyl group, a heteroaryl group, a heteroarylhydrocarbyl group, a substituted $C_{1-10}$ linear alkyl group, a substituted $C_{1-10}$ branched alkyl group, a substituted $C_{3-10}$ cycloalkyl group, a substituted aryl group, a substituted arylhydrocarbyl group, a substituted $C_{1-10}$ aliphatic-derived heterohydrocarbyl group, a substituted heteroaryl group or a substituted heteroarylhydrocarbyl group. Wherein, the atom or group substituent is a halogen atom, a hydrocarbyl substituent or a heteroatom-containing substituent, preferably a fluorine atom, a chlorine atom, a bromine atom, an iodine atom, a hydrocarbyl group, an aryl group or a nitro group, and more preferably a halogen atom, an alkoxy group or a nitro group.

Specifically, $R_3$ can be a methyl group, an ethyl group, an n-propyl group, an isopropyl group, a butyl group, a pentyl group, a hexyl group, a heptyl group, an octyl group, a nonyl group, a decyl group, a benzyl group, an allyl group, the like, or any substituted form thereof. Wherein, said butyl group includes but is not limited to an n-butyl group and a t-butyl group. Said octyl group includes but is not limited to an n-octyl group and a 2-ethylhexyl group. Wherein, the atom or group substituent is a halogen atom, a hydrocarbyl substituent or a heteroatom-containing substituent, preferably a fluorine atom, a chlorine atom, a bromine atom, an iodine atom, a hydrocarbyl group, an aryl group or a nitro group, and more preferably a halogen atom, an alkoxy group or a nitro group.

$R_3$ is most preferably a methyl group, an ethyl group or a benzyl group.

Wherein, $R_8$ is a hydrogen atom, an atom substituent or a group substituent of carbon-carbon double bonds (—C=C—).

When as an atom substituent, $R_8$ is a halogen atom selected from F, Cl, Br and I, and preferably a fluorine atom.

When as a group substituent, the carbon-atom number of $R_8$ is not particularly limited, preferably from 1 to 20, and more preferably from 1 to 10.

When as a group substituent, the structure of $R_8$ is not particularly limited, can be but not limited to a linear structure, a branched structure bearing pendant groups or a ring-containing structure. Said ring is not particularly limited, including but not limited to all the above-listed cyclic structures in the terminology section.

When as a group substituent, $R_8$ can contain heteroatoms or not.

$R_8$ is a hydrogen atom, a halogen atom, a $C_{1-20}$ hydrocarbyl group, a $C_{1-20}$ heterohydrocarbyl group, a substituted $C_{1-20}$ hydrocarbyl group or a substituted heterohydrocarbyl group. Wherein, the atom or group substituent of $R_8$ is not particularly limited, including but not limited to all the above-listed substituting atoms and substituting groups in the terminology section, and can be a halogen atom, a hydrocarbyl substituent, or a heteroatom-containing substituent.

$R_8$ is more preferably a hydrogen atom, a halogen atom, a $C_{1-20}$ alkyl group, a $C_{1-20}$ unsaturated aliphatic hydrocarbyl group, an aryl group, an arylhydrocarbyl group, a $C_{1-20}$ heterohydrocarbyl group, a $C_{1-20}$ hydrocarbyloxy-acyl group, a $C_{1-20}$ hydrocarbylthio-acyl group, a $C_{1-20}$ hydrocarbylamino-acyl group, or any substituted form thereof. Wherein, said acyl group within $R_8$ is not particularly limited, including but not limited to all the above-listed acyl groups in the terminology section.

$R_8$ is more preferably a hydrogen atom, a halogen atom, a $C_{1-20}$ alkyl group, a $C_{1-20}$ alkenyl group, an aryl group, an arylhydrocarbyl group, a $C_{1-20}$ aliphatic-derived heterohydrocarbyl group, a heteroaryl group, a heteroarylhydrocarbyl group, a $C_{1-20}$ alkoxy-acyl group, an aryloxy-acyl group, a $C_{1-20}$ alkylthio-acyl group, an arylthio-acyl group, a $C_{1-20}$ alkylamino-acyl group, an arylamino-acyl group, or any substituted form thereof. The atom or group substituent is a halogen atom, a hydrocarbyl substituent, or a heteroatom-containing substituent, and preferably a halogen atom, an alkenyl group or a nitro group.

$R_8$ is more preferably a hydrogen atom, a halogen atom, a $C_{1-20}$ alkyl group, a $C_{1-20}$ alkenyl group, an aryl group, an arylhydrocarbyl group, a $C_{1-20}$ aliphatic-derived heterohydrocarbyl group, a heteroaryl group, a heteroarylhydrocarbyl group, a $C_{1-20}$ alkoxycarbonyl group, an aryloxycarbonyl group, a $C_{1-20}$ (alkylthio)carbonyl group, an (arylthio)carbonyl group, a $C_{1-20}$ alkylaminocarbonyl group, an arylaminocarbonyl group, a $C_{1-20}$ alkoxy-thiocarbonyl group, an aryloxy-thiocarbonyl group, a $C_{1-20}$ (alkylthio)thiocarbonyl group, an (arylthio)thiocarbonyl group, a $C_{1-20}$ alkylaminothiocarbonyl group, an arylaminothiocarbonyl group, or any substituted form thereof. Said acyl group within $R_8$ is more preferably a carbonyl group or a thiocarbonyl group. Wherein, the atom or group substituent is a halogen atom, a hydrocarbyl substituent, or a heteroatom-containing substituent, and preferably a fluorine atom, a chlorine atom, a bromine atom, an iodine atom, an alkenyl group or a nitro group.

Specifically, $R_8$ can be but not limited to a hydrogen atom, a fluorine atom, a chlorine atom, a bromine atom, an iodine atom, a methyl group, an ethyl group, an n-propyl group, an isopropyl group, a butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, an allyl group, a propenyl group, an ethenyl group, a phenyl group, a methylphenyl group, a butylphenyl group, a benzyl group, a methoxycarbonyl group, an ethoxycarbonyl group, a phenoxycarbonyl group, a benzyloxycarbonyl group, a (methylthio)carbonyl group, an (ethylthio)carbonyl group, a (phenylthio)carbonyl group, a (benzylthio)carbonyl group, an ethylaminocarbonyl group, a benzyl aminocarbonyl group, a methoxy-thiocarbonyl group, an ethoxy-thiocarbonyl group, a phenoxy-thiocarbonyl group, a benzyloxy-thiocarbonyl group, a (methylthio)thiocarbonyl group, an (ethylthio)thiocarbonyl group, a (phenylthio)thiocarbonyl group, a (benzylthio)thiocarbonyl group, an ethylaminothiocarbonyl group, a benzylaminothiocarbonyl group, a substituted $C_{1-20}$ alkyl group, a substituted $C_{1-20}$ alkenyl group, a substituted aryl group, a substituted arylhydrocarbyl group, a substituted $C_{1-20}$ aliphatic-derived heterohydrocarbyl group, a substituted heteroaryl group, a substituted heteroarylhydrocarbyl group, a substituted $C_{1-20}$ alkoxycarbonyl group, a substituted aryloxycarbonyl group, a substituted $C_{1-20}$ (alkylthio)carbonyl group, a substituted (arylthio)carbonyl group, a substituted $C_{1-20}$ alkylaminocarbonyl group, a substituted arylaminocarbonyl group, a substituted $C_{1-20}$ alkoxy-thiocarbonyl group, a substituted aryloxy-thiocarbonyl group, a substituted $C_{1-20}$ (alkylthio)thiocarbonyl group, a substituted (arylthio)thiocarbonyl group, a substituted $C_{1-20}$ alkylaminothiocarbonyl group, a substituted arylaminothiocarbonyl group or the like. Wherein, said butyl group includes but is not limited to an n-butyl group and a t-butyl group. Said octyl group includes but are not limited to an n-octyl group and a 2-ethylhexyl group. Wherein, the atom or group substituent is a halogen atom, a hydrocarbyl substituent or a heteroatom-containing substituent, and preferably a halogen atom, an alkenyl group or a nitro group.

$R_8$ is further preferably a hydrogen atom, a methyl group, an ethyl group, an n-propyl group, an isopropyl group, a butyl group, a pentyl group, a hexyl group, a heptyl group, an octyl group, a nonyl group, a decyl group, an allyl group, a propenyl group, an ethenyl group, a phenyl group, a methylphenyl group, a butylphenyl group, a benzyl group, a methoxycarbonyl group, an ethoxycarbonyl group, a phenoxycarbonyl group, a benzyloxycarbonyl group, a (methylthio)carbonyl group, an (ethylthio)carbonyl group, a (phenylthio)carbonyl group, a (benzylthio)carbonyl group, an ethylaminocarbonyl group, a benzylaminocarbonyl group, a methoxy-thiocarbonyl group, an ethoxy-thiocarbonyl group, a phenoxy-thiocarbonyl group, a benzyloxy-thiocarbonyl group, a (methylthio)thiocarbonyl group, an (ethylthio)thiocarbonyl group, a (phenylthio)thiocarbonyl group, a (benzylthio)thiocarbonyl group, an ethylaminothiocarbonyl group, a benzylaminothiocarbonyl group, a $C_{1-10}$ halohydrocarbyl group, a halophenyl group, a halobenzyl group, a nitrophenyl group, the like, or any substituted form thereof. Wherein, the atom or group substituent is a halogen atom, a hydrocarbyl substituent or a heteroatom-containing substituent, and preferably a fluorine atom, a chlorine atom, a bromine atom, an iodine atom, an alkenyl group or a nitro group.

$R_8$ is more preferably a hydrogen atom, a fluorine atom or a methyl group.

Wherein,

is a $(n_5+1)$-valent cyclic structure with water-soluble segments of the ring skeleton, and all the branching points come from ring-membering atoms.

The structure of said water-soluble segments is not particularly limited, preferably a linear structure.

The stability of said water-soluble segment is not particularly limited, either stable or degradable.

Said ring skeleton contains at least one water-soluble segment.

When the quantity of said water-soluble segments is more than 1, the species of water-soluble segments can be the same or different. Herein, the connection manner between the adjacent water-soluble segments is not particularly limited, and can be in a direct manner or in an indirect manner via suitable divalent linking groups. The stability of said divalent linking group is not particularly limited, either stable or degradable.

The water-soluble segments can be a water-soluble oligomer or a water-soluble polymer.

The source of water-soluble segments is not particularly limited, and it can be natural, or modified or synthesized oligomers or polymers.

The species of water-soluble polymer segments are not particularly limited, e.g., including but not limited to poly(alkylene oxide) and derivatives thereof (preferably poly(ethylene oxide) and derivatives thereof), polyvinyl alcohol, polyacrylic acid and derivatives thereof, poly(methyl methacrylate) and derivatives thereof, poly(ethyl methacrylate) and derivatives thereof, polyacrylamide, poly(N-isopropylacrylamide), poly(hydroxyethyl methacrylate), polyglycolic acid, poly(hydroxyl butyrate), poly(propylene fumarate), polyvinyl pyrrolidone, water-soluble polysaccharides, chitosan, dextran, poly(amino acid)s or peptides, polypeptides, carboxymethyl starch, starch acetate, hydroxymethyl cellulose, carboxymethyl cellulose, poly(hydroxyalkyl methacrylamide), poly(hydroxyalkyl methacrylate), poly($\alpha$-hydroxyacid), polyphosphazene, polyoxazoline, poly(N-acryloylmorpholine) and the like. It is preferably polyethylene glycol, a poly(amino acid), cyclodextrin or a peptide. Wherein, said poly(amino acid) is preferably polylysine.

Accordingly, monomer unit or "monomer unit pair" constituting water-soluble oligomeric or polymeric segments includes but is not limited to ethylene oxide, substituted ethylene oxide, ethylene glycol, vinyl alcohol, acrylic acid and derivatives thereof, methyl methacrylate and derivatives thereof, ethyl methacrylate and derivatives thereof, acrylamide, N-isopropyl acrylamide, hydroxyethyl methacrylate, glycolic acid, hydroxybutyric acid, fumaric acid and propylene glycol, vinyl pyrrolidone, open-chain glucose units, cyclic glucose units, watersoluble saccharides, natural amino acids and derivatives thereof, peptides, hydroxyalkyl methacrylamide, hydroxyalkyl methacrylate, $\alpha$-hydroxyacids, phosphazene, oxazoline, N-acryloyl morpholine, and combination or any two or more thereof.

Wherein, the structure formula of said substituted ethylene oxide is

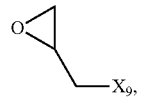

wherein $X_9$ is not particularly limited as long as it can remain stable during anionic polymerization.

Said water-soluble oligomer segments include but are not limited to cyclic oligomers (e.g., cyclodextrins) formed by above-mentioned monomer units. Another example can be a water-soluble cyclic peptide.

Specifically, water soluble segment of

can be derived from, but not limited to, the following oligomers and polymers: polyethylene glycol, polyvinyl alcohol, polyacrylic acid, poly(methyl methacrylate), poly(ethyl methacrylate), polyacrylamide, poly(N-isopropylacrylamide), poly(hydroxyethyl methacrylate), polyglycolic acid, polyhydroxybutyrate, poly(propylene fumarate), polyvinyl pyrrolidone, water-soluble polysaccharide, chitosan, dextran, poly(amino acid)s or peptides, polypeptides, carboxymethyl starch, starch acetate, hydroxymethyl cellulose, carboxymethyl cellulose, cyclodextrin, cyclic peptides and the like. It is preferably polyethylene glycol, a poly(amino acid) or a peptide, cyclodextrin, a polypeptide, cyclodextrin, a cyclic peptide, poly(hydroxyalkyl methacrylamide), poly(hydroxyalkyl methacrylate), poly($\alpha$-hydroxyacid), polyphosphazene, polyoxazoline, poly(N-acryloyl morpholine) or the like, and further preferably polyethylene glycol, substituted polyethylene glycol, polylysine, a polypeptide, cyclodextrin or a cyclic peptide.

1.1.3 Functional Groups or Protected Forms Thereof.

1.1.3.1 The definition of $R_{01}$, a Functional End-Group or Protected Form Thereof In formulas (1) to (6), $R_{01}$ is a functional end-group or protected form thereof, also referred to as a functional or protected functional end-group, an unprotected or protected functional end-group, a deprotected or protected functional end-group, or an active or protected functional end-group in the present invention.

$R_{01}$ is an unprotected or protected form of a functional end-group capable of interreacting with bio-related substances, or be a functional end-group or derivative form of a functional end-group which does not react with bio-related substances.

Unprotected or protected functional end-groups including reactive groups, variant forms of reactive groups, therapeutic targeting functional groups, fluorescent functional groups and the like, corresponding embodiments thereof as well as preferable structures thereof disclosed in paragraphs [0280] to [0506] of patent document CN104877127A are all incorporated into the scope of $R_{01}$ by reference in the present invention.

$R_{01}$ is the unprotected or protected form of a functional end-group capable of generating a covalent bond, a dynamic covalent bond, dihydrogen-bonding, multiple hydrogen bonding, therapeutic targeting binding or photoreactive response.

Wherein, said reactive groups are active and capable of bonding with bio-related substances to form chemical linkages, mainly referring to reactions involving forming covalent bonds, and dihydrogen-bonding or multiple hydrogen bonding are used for complexion when concerning non-covalent linkages.

Said covalent bonds include but are not limited to stable covalent bonds, degradable covalent bonds and dynamic covalent bonds.

Said reactive groups in the present invention refer to functional end-groups capable of forming covalent bonds, dynamic covalent bonds, dihydrogen-bonding or multiple hydrogen bonding.

Said variant forms of reactive groups include but are not limited to precursors of reactive groups, active forms with reactive groups as precursors, substituted active forms, protected forms, deprotected forms and the like.

Said precursor of a reactive group refers to a structure that can be converted into said reactive group after at least one process selected from oxidation, reduction, hydration, dehydration, electronic rearrangement, structural rearrangement, salt complex and decomplexation, ionization, protonation, deprotonation, etc. The precursor can be active or non-active.

The variant form of a reactive group refers to an active form (still a reactive group) of a given reactive group (also referred to as an objective reactive group) after undergoing at least one process selected from oxidation, reduction, hydration, dehydration, electronic rearrangement, structural rearrangement, salt complexation and decomplexation, ionization, protonation, deprotonation, being substituted, deprotection and the like, or refers to a non-active form of the given reactive group after being protected.

Said active forms means that such a form has the capability to generate a covalent bond, a dynamic covalent bond, dihydrogen-bonding, multiple hydrogen bonding, therapeutic targeting binding or photoreactive response.

As long as a functional group can generate fluorescence, or can generate fluorescence under the stimulus of microenvironment in vivo (such as fluorescein diacetate), or can generate fluorescence under clinical stimulus (such as light stimulation, thermal stimulation, etc.), it would fall into the scope of fluorescent functional groups.

When capable of reacting with bio-related substances, $R_{01}$ includes but not limited to functional groups selected from Group A to Group H, and Group (A-H)', and variant forms thereof, wherein, $R_{01}$ or the variant form of $R_{01}$ is a reactive group.

Group A: active ester groups including but not limited to a succinimidyl ester group, a p-nitrophenyl ester group, an o-nitrophenyl ester group, a benzotriazole ester group, a 1,3,5-trichlorophenyl ester group, a 1,3,5-trifluorophenyl ester group, a pentafluorophenyl ester group, an imidazole ester group, and the like, and analogs of said active ester groups such as a 2-thioxo-3-thiazolidine-formate group (a thiazolidine-2-thione-formate group), a 2-thioxo-thiazolidine-3-carboxylate group, a 2-thioxo-pyrrolidine-carboxylate group, a 2-thioxo-pyrrolidine-formate group, a 2-thioxo-benzothiazole-formate group, a 1-oxo-3-thioxoisoindoline-formate group, and the like.

Group B: a sulfonate group, a sulfinate group, a sulfonyl group, a sulfoxide group, a 1,3-disulfonyl-2-propylcarbonylphenyl group, a (2-sulfonylmethyl)acryl group, and the like;

Group C: a hydroxylamino group, a mercapto group, an amino group (a primary or secondary amino group), an azido group, a halohydrocarbyl group, a haloacetylamino group (e.g., an iodoacetylamino group), a tetramethylpiperidinyloxy group, a dioxapiperidinyloxy group (a 3,5-dioxa-1-cyclohexylamino-N-oxy group), an ammonia salt group (an amine salt group), a hydrazino group, a disulfide group (e.g., a lipoyl group as a cyclodisulfide group which is a disulfide-containing cyclic group, etc.) and the like;

Group D: an amido group (e.g. a carbonylamino group of $-CONH_2$ containing an $-NH_2$ terminus), a hydrazinocarbonyl group (an acylhydrozino group, $-CONHNH_2$), an aminooxycarbonyl group (an acyl-hydroxylamino group, $-COONH_2$), a carboxyl group, an aldehyde group, a glyoxal group, an acylhalide group (a haloacyl group), an acetal group, a hemiacetal group, a hydrated aldehyde group, a ketal group, a hemiketal group, a hydrated ketone group, an orthoester group, a cyanate group, an isocyanato group, an ester group (a carboxylate group), a silyloxy group, a silicate group, a silyl group, a thioester group (with a $-S-(C=O)-$ bond), a thiocarboxylate group (e.g., a thioate group with a $-O-(C=S)-$ bond), a dithioester group (a dithiocarboxylate group), a trithioester group (a trithiocarbonate group), a thiohemiacetal group (including a hemithioacetal group), a monothiohydrate group, a dithiohydrate group, a disulfide group (e.g. an orthopyridyl disulfide group also termed as o-pyridyl disulfide group or OPSS, etc.), a thiol hydrate group, a thione group (a thioketone group), a thioacetal group, a thione hydrate group, a thioketal group or a dithioketal group, a thiohemiketal group or a hemithioketal group, a dihydrooxazole group, an isothiocyanato group, a mercapto group (a thiol group), a ureido group, a thioureido group, a guanidino group (a guanidyl group), an anhydride group, a squaryl group, a square group and the like;

Group E: a maleimido group, an acrylamide group, an acrylate group, an N-methacrylamide group, a methacrylate group, a norbornenyl-2,3-dicarboximide group, a maleamic acid group, a protected maleimido group, a 1,2,4-triazoline-3,5-dione group, a substituted maleimido group and the like;

Group F: a cyano group, an alkenyl group (including an ethenyl group, a propenyl group, etc.), an alkenyl-hydrocarbyl groups (e.g., an allyl group), a cycloalkenyl group (e.g. a cyclooctenyl group, a norbornenyl group, etc.), an alkynyl group, an alkynyl-hydrocarbyl group (e.g., a propargyl group), an epoxy groups, an azo group (e.g. a linear azo compound, F10 of a cyclic structure, etc.), a diazo group, a dienyl group, a dienyl-hydrocarbyl group, a tetrazole group, a linear conjugated dienyl group (e.g., a linear butadienyl group), a nitrile oxide group (a cyano oxide group, —C≡N$^+$ O$^-$) and the like;

Group G: a cycloalkynyl group or a heterosubstituted cycloalkynyl group, a cyclodienyl group (e.g., a conjugated cyclopentadienyl, a 2,5-norbornadienyl group, a dicycloheptadienyl group, an 7-oxa-dicycloheptadienyl group, an 7-oxabicyclo[2.2.1]hept-5-en-2-yl, etc.), a heterosubstituted conjugated dienyl group with a skeleton-membering heteroatom (e.g. a furyl group with a ring-membering heteroatom), a 1,2,4,5-tetrazinyl group and the like;

Group H: a hydroxyl group (including but not limited to an alcoholic hydroxyl group, a phenolic hydroxyl group, an enolic hydroxyl group, the hydroxyl group of a hemiacetal, etc.), a protected hydroxyl group, a siloxy group, a protected dihydroxyl group, a trihydroxysilyl group, a protected trihydroxysilyl group and the like.

Group (A-H)': Additionally, examples of $R_{01}$ can also be but not limited to an imide group, a sulfonylhydrazino group, a hydrazone group, an imino group, an enamino group, an alkynylamino group, a xanthate group, a perthiocarbonate group, a dithiobis(thionoformate) group, a sulfonic acid group, a sulfenic acid group, a hydroxamic acid group, a thiohydroxamic acid group, a xanthogenic acid group, a chlorosulfonyl group, an orthoacid group, a cyanate group, a thiocyanate group, a thiocarboxylic acid group (a monothiocarboxylic acid group containing a thiocarbonyl group or a thiol group, a dithiocarboxylic acid group), an amidino group (e.g, —C(=NH)NH$_2$) and protonated form thereof, a semi-squaric acid group, a semi-squarate group, an N-carbamoyl-3-imidazole group or an N-carbamoyl-3-methylimidazolium iodide group, an imidic acid group, an imidic ester group, a nitrone group, an oxime group or an oximino group, a urea group, a thiourea group, a pseudourea group, an isocyano group, an aldoxime group, a diazo group, a diazonium group, an azoxy group, a nitrilimine group, an N-aldimine oxide group, a tetrazole group, a 4-acetyl-2-methoxy-5-nitrophenoxy group and its diazo form, etc. Other functional groups which can undergo 1,3-dipolar cycloaddition reactions are also incorporated into the present invention, and are classified into group (A-H)'.

In addition, the above-mentioned groups of Group A to Group H also include precursors, substituted forms and protected forms of any reactive group, such as a protected hydroxyl group, a protected mercapto group, a protected alkynyl group, a protected amino group, a protected carboxyl group and the like. Functional groups related to click reactions reported and cited by document "Adv. Funct. Mater., 2014, 24, 2572" are incorporated by reference into the present invention. CN is a precursor of its oxidized form C≡N$^+$O$^-$, —NH$_2$ is the precursor of ammonium ion —NH$_3^+$ and amine salt (—NH$_2$HCl), —COOH is the precursor of its sodium salt —COONa and anionic form —COO$^-$, etc.

Said protected forms include but are not limited to a protected hydroxyl group, a protected dihydroxyl group, a protected trihydroxyl group, a protected orthocarbonic acid, a protected mercapto group, a protected amino group, a protected carboxyl group, a protected aldehyde group, a protected maleimido group (such as E4), a protected alkynyl group (such as F4) and the like. A15, A16 and G4-G10 also include substituted forms thereof. —NH(C=NH$_2^+$)NH$_2$ is the protonated form of a guanidino group. A functional group can meanwhile belong to two subgroups, for example, the o-pyridyl disulfide group C13 is also a protected form of mercapto group. C9 is a protected amino group and meanwhile a protected dihydroxyl group. Esters (carboxylates), thioesters, thiocarboxylates (e.g., thioates, dithioesters), carbonates and thiocarbonates can also be regarded as protected hydroxyl groups or protected mercapto groups.

The applications of above-mentioned functional groups (with variant forms thereof included), for example, include but are not limited to:

Functional groups in Group A can undergo amino-modification (a reaction with an amino group) and form an amide bond or a urethane bond.

A sulfonate group or a sulfinate group in Group B can be used for alkylation, and functional groups containing a sulfonyl group or a sulfoxide group can be used for modification with a mercapto groups or a disulfide bond.

Group C: Some groups also frequently occur in bio-related substances as an active site to be modified, such as a mercapto group, an amino group, a disulfide bond and the like. Group C mainly refers to functional groups that have similar reactivity (e.g., a hydroxylamino group, a hydrazino group), protected forms, salt forms and the like. Leaving groups which are liable to leave such as a halogen atom and the like are also included. What's more, an iodoacetylamino group can also undergo thio-modification (a reaction with a thiol group).

Group D: Some functional groups or deprotected forms thereof can interreact with a hydroxyl group or a functional group selected from Group C and Group D. For example, an unprotected functional group such as a carboxyl group, a sulfonic acid group, a hydroxamic acid group, a haloacyl group, an aldehyde group, an isocyanato group, an isothiocyanato group, an oxycarbonyl halide group, a dihydrooxazole group, a thiocarboxylic acid group, a ureido group, a thioureido group, a guanidino group or protonated form thereof, an N-aminoformyl-3-imidazole group or an N-aminoformyl-3-methylimidazolium iodide group, or a deprotected form of an acetal group, a trihydroxyl protecting group, a carboxylate group (D11), a thiohemiacetal group, a squarate group, a semi-squarate group or a thiocarboxylate group, is capable of reacting with a suitable group selected from the group consisting of an amino group, a mercapto group, a hydroxyl group and a halide. E.g., an N-aminoformyl-3-imidazole group is capable of reacting with a carboxyl group, and a dihydrooxazole group is capable of reacting with a carboxyl group or an acyl halide. Wherein, a guanidino group is capable of reacting with the two carbonyl groups of tanshinone IIa to form dihydrogen bonding.

Functional groups in Group E contain an α,β-unsaturated bond, and thus can undergo 1,2-addition reactions, such as reactions with an amino group, a thiol group and a hydroxyl group. A dihalosubstituted maleimido group can also undergo substitution reaction with two mercapto groups.

Regarding functional groups in group F, several mostly common structures are similar in preparation methods, and can be obtained via a substitution reaction with a corresponding halide. For instance, an epoxy group can undergo reactions including but not limited to a ring-opening reaction to obtain an unprotected dihydroxyl group, and a ring-opening addition reaction with an amino group. An alkenyl group in F2 can undergo an addition reaction. The alkynyl group or deprotected form thereof is commonly used as a functional group for click reactions.

Functional groups of the present invention also include other active groups that can undergo click reactions. A cycloalkynes or precursor thereof, a conjugated diene, 1,2,4,5-tetrazine can undergo a cycloaddition reaction or Diels-Alder addition reaction. Functional groups such as an allyl group, a propargyl group and an allenyl group can undergo a 1,3-dipolar cycloaddition reaction. In addition, G10 can be converted into a reactive diazo group with the treatment of hydrozine and further react with a carboxyl group to generate an ester bond.

Functional groups in Group H including a hydroxyl group, a dihydroxyl group, a trihydroxyl group, and protected form of any type, are important starting groups for functionalization in the present invention (e.g., a hydroxyl group of the terminal end of a PEG chain). A functional group that contains a hydroxyl group or deprotonated form thereof is a necessary moiety of one initiator center in order to initiate the polymerization of ethylene oxide in the present invention. Hydroxyl groups in Group H could also occur in bio-related substances as a reactive site to be modified. Additionally, groups in group H6 and group H7 can be converted into an enolic hydroxyl form under light irradiation and further undergo an addition reaction with a functional group such as an α,β-unsaturated bond in group E.

"Functional groups that do not react with bio-related substances" means that no bonding reactions take place, and herein said functional groups should have special functions (meaning active). Functional group $R_{O1}$ of this type includes but is not limited to special functional moieties and derivatives thereof of a targeting moiety (e.g., folic acid, etc.), a light-sensitive group (e.g., a fluorescent group) and the like. A substituted form still bearing corresponding special function can correspondingly be classified as a targeting group or a light-sensitive group. $R_{O1}$ of this type includes but is not limited to functional groups selected from Group I and Group J and derivatives thereof:

Group I: Targeting groups and pharmaceutically acceptable salts thereof, such as a folic acid and derivatives thereof, cholesterol and derivatives thereof, biotins and derivatives thereof, and any functional derivative thereof. Examples of derivatives of biotin include D-desthiobiotin, 2-iminobiotin and the like.

Group J: Fluorescent groups, such as a fluorescein group, a rhodamine group, an anthracenyl group, a pyrenyl group, a coumarin group, a fluorescent yellow 3G group, a carbazole group, an imidazole group, an indole group, a galleinmonohydrate group, the like, and any functional derivative thereof. Wherein, derivatives of rhodamine include but are not limited to tetramethylrhodamine, tetraethyl rhodamine (rhodamine B, RB200), rhodamine 3G, rhodamine 6G (rhodamine 590), 5-carboxy-X-rhodamine, 6-carboxy-X-rhodamine, sulfonylrhodamine B, sulfonylrhodamine G, sulfonylrhodamine 101, rhodamine X (R101), rhodamine 101, rhodamine 110, rhodamine 123, rhodamine 700, rhodamine 800, etc., as well as derivatives of rhodamine disclosed in the literature "Progress in Chemistry, 2010, 22 (10): 1929-1939" and its cited references.

In the present invention, $—(Z_1)_{q1}—R_{O1}$ is regarded as a whole unprotected or protected functional group. For example, When $R_{O1}$ is an active ester group, $—(Z_1)_{q1}—R_{O1}$ can be but not limited to an active ester of one type selected from the group consisting of carbonate, acetate, propionate, butyrate, pentanoate (also valerate), hexanoate, heptanoate, octanoate, a nonanoate (e.g., pelargonate), a decanoate (e.g., caprate), oxalate, malonate, methylmalonate, ethylmalonate, butylmalonate, succinate, 2-methylsuccinate ester, 2,2-dimethylsuccinate, 2-ethyl-2-methylsuccinate, 2,3-dimethylsuccinate, glutarate, 2-methylglutarate, 3-methylglutarate, 2,2-dimethylglutarate, 2,3-dimethylglutarate, 3,3-dimethylglutarate, adipate, pimelate, suberate, azelate, sebacate, maleate, fumarate, an amino acid ester, a peptide ester, a poly(amino acid) ester and the like;

When $R_{O1}$ is an amino group, $—(Z_1)_{q1}—R_{O1}$ can be a primary amino residue formed by removing a non-amino hydrogen atom of a primary amine, or a secondary amino residue formed by removing a hydrogen atom within an amino group of a primary amine, or a secondary residue formed by removing a non-amino hydrogen atom of a secondary amine, wherein, said primary amine includes but is not limited to methylamine, ethylamine, propylamine, butylamine, pentylamine, hexylamine, heptylamine, octylamine, cyclohexylamine, aniline and the like, and said secondary amine includes but is not limited to dimethylamine, diethylamine, dipropylamine, dibutylamine, diamylamine, dihexylamine, diheptyl amine, dioctylamine, dicyclohexylamine, N-methylaniline, N-ethylaniline, N-propylaniline, N-isopropylaniline, N-butylaniline, N-cyclohexylaniline, azetidine, pyrrolidine, piperidine and the like. $—(Z_1)_{q1}—R_{O1}$ can also be a residue group formed by removing a hydroxyl group within the C-carboxyl group or a pendant carboxyl group deriving from an amino acid, a derivative of amino acids, an ω-amino acid (e.g., β-alanine, γ-piperidic acid, δ-norvaline, ε-norleucine, etc.), a peptide or a peptide derivative, wherein, and the resulting $R_{O1}$ is an N-amino group or a pendant amino group.

When $R_{O1}$ is an aldehyde group, $—(Z_1)_{q1}—R_{O1}$ can be the residue monovalent functional group formed by removing a non-aldehyde hydrogen atom of an aldehyde except formaldehyde, and said aldehyde can be but not limited to formaldehyde, acetaldehyde, propionaldehyde, butanal (also butyraldehyde), petanal (also pentanaldehyde, e.g., valeraldehyde), hexanal, heptanal, octanal (also octanaldehyde), nonanal, decanal, crotonaldehyde, acraldehyde (or acrolein, propenal), methacrolein, 2-ethylacraldehyde (or 2-ethylacrolein, 2-ethylpropenal), chloroacetaldehyde, iodoacetaldehyde, dichloroacetaldehyde, benzaldehyde, phenylacetaldehyde, tolualdehyde (also methylbenzaldehyde), cinnamaldehyde (or cinnamic aldehyde), nitrocinnamaldehyde, bromobenzaldehyde, chlorobenzaldehyde and the like, corresponding to a formaldehyde group, an acetaldehyde group, a propionaldehyde group, a butyraldehyde group, a pentanaldehyde group (e.g., a valeraldehyde group), a hexanal group, a heptanal group, an octanal group, a nonanal group, a decanal group, a crotonaldehyde group, an acraldehyde group (or an acrolein group, a propenal group), a methacrolein group, a 2-ethylacraldehyde group (or a 2-ethyl acrolein group, a 2-ethyl propenal group), a chloroacetaldehyde group, an iodoacetaldehyde group, a dichloroacetaldehyde group, a benzaldehyde group, a phenylacetaldehyde group, a methylbenzaldehyde group, a cinnamaldehyde group (or a cinnamic aldehyde group), a nitrocinnamaldehyde group, a bromobenzaldehyde group, a chlorobenzaldehyde group, the like, respectively. As described in the terminology section, when two or two more structural forms such as isomers exist, any structural form can be available. For example, butyraldehyde includes but is not limited to n-butyraldehyde, isobutyraldehyde, 2-methylpropanal and 2,2-dimethyl-acetaldehyde. Petanal includes but is not limited to n-petanal, 2-methylbutanal and isovaleraldehyde. Octanal includes but is not limited to n-octanal and 2-ethylhexanal. Methylbenzaldehyde includes but is not limited to o-methylbenzaldehyde, m-methylbenzaldehyde and p-methylbenzaldehyde. Cinnamaldehyde includes but is not limited to trans-cinnamaldehyde. Nitrocinnamaldehyde includes but is not limited to trans-2-nitrocinnamaldehyde. Bromobenzaldehyde can be 2-bromobenzaldehyde, 3-bromobenzaldehyde or 4-bromobenzaldehyde. Chlorobenzaldehyde can be 2-chlorobenzaldehyde, a3-chlorobenzaldehyde or 4-chlorobenzaldehyde. Wherein, said acraldehyde (or acrolein, propenal) is

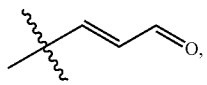 [SMILES: */C=C/C=O]

said benzaldehyde is

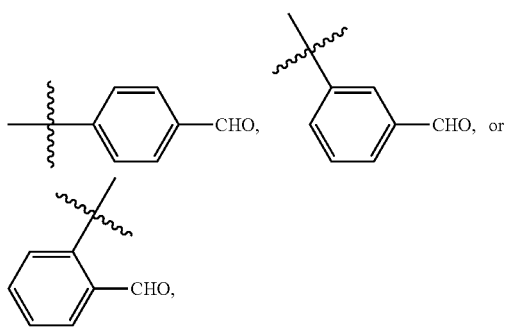

said m-methylbenzaldehyde is

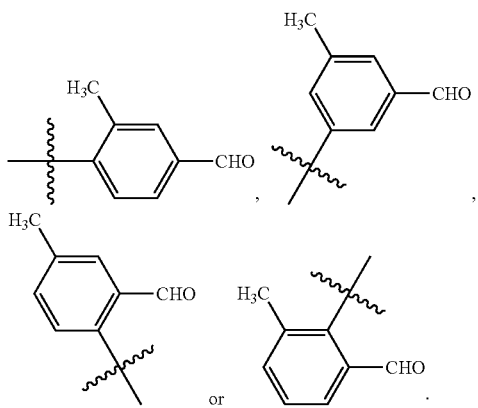

Trans-cinnamaldehyde includes but is not limited to

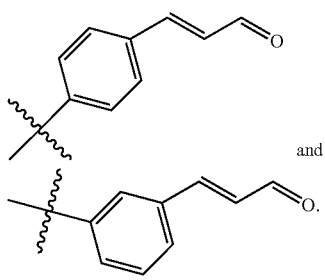

When $R_{O1}$ is a carboxyl group, $-(Z_1)_{q1}-R_{O1}$ can be a monovalent functional residue formed by removing a non-carboxyl hydrogen atom of a monocarboxylic acid, or by removing a hydroxyl group of a dicarboxylic acid. Said monocarboxylic acid includes but is not limited to formic acid, acetic acid, propionic acid, butanoic acid (butyric acid), pentanoic acid (e.g., valeric acid), hexanoic acid, heptanoic acid, octanoic acid, nonanoic acid, decanoic acid, lauric acid, myristic acid, palmitic acid, stearic acid, oleic acid, eicosanoic acid, heneicosanoic acid, docosanoic acid, isobutyric acid, 3-methylbutyric acid, acrylic acid, methacrylic acid, citric acid, vinylacetic acid, tiglic acid, 6-heptenoic acid, itaconic acid, citronellic acid, monochloroacetic acid, dichloroacetic acid, monofluoroacetic acid, difluoroacetic acid, benzoic acid, methylbenzoic acid, fluorobenzoic acid, ethoxybenzoic acid, methoxybenzoic acid, ethylbenzoic acid, vinylbenzoic acid, propylbenzoic acid, 2-isopropylbenzoic acid, 2-butylbenzoic acid, 2-isobutylbenzoic acid, N-carbamoylmaleamic acid, N-phenylmaleamic acid, maleamic acid, arachidonic acid, tetracosanoic acid, tetracosenoic acid (or nervonic acid), glycolic acid, lactic acid, isonicotinic acid, ascorbic acid, gentisic acid, gluconic acid, alduronic acid, sorbic acid, N-(ω-aminocarboxylic acid) and the like. Said dicarboxylic acid includes but is not limited to oxalic acid, malonic acid (propanedioic acid), methylmalonic acid, ethylmalonic acid, butylmalonic acid, succinic acid, 2-methylsuccinic acid, 2,2-dimethylsuccinic acid, 2-ethyl-2-methylsuccinic acid, 2,3-dimethylsuccinic acid, glutaric acid, 2-methylglutaric acid, 3-methylglutaric acid, 2,2-dimethylglutaric acid, 2,3-dimethylglutaric acid, 3,3-dimethylglutaric acid, adipic acid, pimelic acid, suberic acid, azelaic acid, sebacic acid, maleic acid, fumaric acid, oxaloacetic acid, dimethylmalonic acid, isopropylmalonic acid, benzylmalonic acid, 1,1-epoxy-dicarboxylic acid (1,1-cyclopropanedicarboxylic acid), 1,1-cyclobutanedicarboxylic acid, dibutylmalonic acid, ethyl(1-methylpropyl)malonic acid, ethyl(1-methylbutyl)malonic acid, ethyl(isopentyl)malonic acid, phenylmalonic acid, 2,2-dimethylsuccinic acid, 2-oxoglutaric acid, 3-oxoglutaric acid, 5-norbornene-endo-2,3-dicarboxylic acid, 1,4-cyclohexanedicarboxylic acid, 1,3-cyclohexanedicarboxylic acid, 1,2-cyclohexanedicarboxylic acid, pyrrolidine-3,4-dicarboxylic acid, camphoric acid, chlorendic acid, dibenzyl-2-oxoimidazolidine-4,5-dicarboxylic acid, 5-methyl-1,3-benzenedicarboxylic acid (5-methylisophthalic acid), phthalic acid, 4-methyl-1,2-benzenedicarboxylic acid, 4-chlorophthalic acid, 3,4-pyridinedicarboxylic acid, 2,3-pyridinedicarboxylic acid, 2,4-pyridinedicarboxylic acid, 3,5-pyridinedicarboxylic acid, 2,6-pyridinedicarboxylic acid, 2,4-dimethyl-1H-pyrrole-3,5-dicarboxylic acid, pyridine-2,3-dicarboxylic acid, 5-methylpyridine-2,3-dicarboxylic acid, 5-ethylpyridine-2,3-dicarboxylic acid, 5-methoxymethyl-2,3-pyridinedicarboxylic acid, pyridazine-4,5-dicarboxylic acid (4,5-pyridazinedicarboxylic acid), 2,3-pyrazinedicarboxylic acid (pyrazine-2,3-dicarboxylic acid), 5-methylpyrazine-2,3-dicarboxylic acid, 4,5-imidazoledic arboxylic acid, 2-propyl-1H-imidazo ledicarboxylic acid, biphenyldicarboxylic acid, 4,4'-stilbenedicarboxylic acid, 2,7-naphthalenedicarboxylic acid, 4,4'-oxybisbenzoic acid (4-(4-carboxyphenoxy)benzoic acid), 2,2'-bipyridine-5,5'-dicarboxylic acid, 2,2'-bipyridine-3,3'-dicarboxylic acid, 4-pyrone-2,6-dicarboxylic acid (chelidonic acid), 1,2-phenylenedioxydiacetic acid, thiophene-2,3-dicarboxylic acid (2-thiazolylisocyanate), thiophene-2,5-dicarboxylic acid, 2,5-dicarboxylic acid-3,4-ethylene dioxythiophene, 1,3-acetonedicarboxylic acid (3-ketoglutaric acid), itaconic acid, 2-methyl-2-butenedioic acid (citraconic acid and mesaconic acid), 1,3-butadiene-1, 4-dicarboxylic acid, butynedioic acid, norbornene-2,3-dicarboxylic acid (bicyclo[2.2.1]hept-5-ene-2,3-dicarboxylic acid), bicyclo[2.2.1]hept-2-ene-2,3-dicarboxylic acid, diglycolic acid, dithiodiglycolic acid, malic acid, tartaric acid, 2,3-dimercaptosuccinic acid, 2,3-dibromosuccinic acid, mefenpyr, 4,4'-dichlorodiphenic acid, 4,4'-dibromodiphenic acid, glucaric acid, saccharic acid, pamoic acid, 2-bromosuccinic acid, 2-mercaptosuccinic acid, 1,3-adamantanedicarboxylic acid, 2,6-dimethyl-1,4-dihydro-3,5-pyridinedicarboxylic acid, mesoxalic acid, 3-oxoglutaric acid, ethoxymethylenemalonic acid, 3,3'-dithiodipropionic acid, 5-exo-methyl-2-norbornene-5,6-endo-cis-dicarboxylicacid, acetylmalonic acid and the like. Wherein, for example, methylbenzoic acid includes o-methylbenzoic acid, m-methylbenzoic acid and p-methylbenzoic acid, monofluorobenzoic acid includes 2-fluorobenzoic acid, 3-fluorobenzoic acid and 4-fluorobenzoic acid, ethoxybenzoic acid includes o-ethoxybenzoic acid, m-ethoxybenzoic acid and p-ethoxybenzoic acid, methoxybenzoic acid includes o-methoxybenzoic acid, m-methoxybenzoic acid and p-methoxybenzoic acid, and ethylbenzoic acid includes o-ethylbenzoic acid, m-ethylbenzoic acid and p-ethylbenzoic acid. The examples of dicarboxylic acids removing a hydroxyl group are as follows: e.g., malonic acid corresponding to

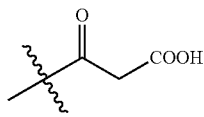 [SMILES: *C(=O)CC(=O)O]

for —$(Z_1)_{q1}$—$R_{01}$, succinic acid corresponding to

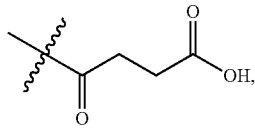 [SMILES: *C(=O)CCC(=O)O]

maleamic acid corresponding to

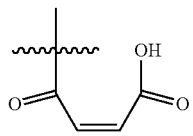

and the like. —$(Z_1)_{q1}$—$R_{01}$ also can be a residue group formed by removing an N-amino group or a pendant amino group from an amino acid, an amino acid derivative, a peptide or a peptide derivative, wherein, $R_{01}$ is a C-carboxyl group or a pendant carboxyl group.

When $R_{01}$ is a haloacyl group (or an acyl halide group), the halogen atom therein can be a fluorine atom, a chlorine atom, a bromine atom or an iodine atom, and preferably a chlorine atom or a bromine atom. Wherein, —$(Z_1)_{q1}$—$R_{01}$ can be a monovalent residue group obtained by removing a hydrogen atom of an acyl halide, or a combination of a diacyl group and a halogen atom. Said acyl halide can be but not limited to acetyl chloride, acetyl bromide, chloroacetyl chloride, dichloroacetyl chloride, propionyl chloride, propionyl bromide, butanoyl chloride (butyryl chloride), 3-cyclopentylpropionyl chloride, 2-chloropropionyl chloride, 3-chloropropionyl, t-butylacetyl chloride, pentanoyl chloride (e.g., valeroyl chloride, isovaleryl chloride), hexanoyl chloride, heptanoyl chloride, octanoyl chloride, nonanoyl chloride, decanoyl chloride, lauroyl chloride, myristoyl chloride, palmitoyl chloride, stearoyl chloride, oleoyl chloride, behenoyl chloride, cyclopentanecarbonyl chloride, methoxyacetyl chloride, acetoxyacetyl chloride or the like. Said diacyl group can be but not limited to an oxalyl group, a malonyl group, a methylmalonyl group, an ethylmalonyl group, a butylmalonyl group, a succinyl group, a 2-methylsuccinyl group, a 2,2-dimethylsuccinyl group, a 2-ethyl-2-methylsuccinyl group, a 2,3-dimethylsuccinyl group, a glutaryl group, a 2-methylglutaryl group, a 3-methylglutaryl group, a 2,2-dimethylglutaryl group, a 2,3-dimethylglutaryl group, a 3,3-methylglutaryl group, an adipoyl group, a pimeloyl group, an octanedioyl group, an azelaoyl group, a decanedioyl group, a maleoyl group, a fumaroyl group, or the like. Herein, the diacyl group of a dicarboxylic acid refers to the residue after removing two hydroxyl groups, for example, a malonyl group corresponding to

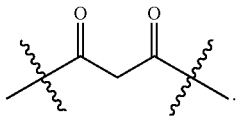 [SMILES: *C(=O)CC(*)=O]

When $R_{01}$ is an anhydride group, it can be an open-chain anhydride, or an intramolecular anhydride. For example, —$(Z_1)_{q1}$—$R_{01}$ can be the monovalent functional residue formed by removing a hydrogen atom of an anhydride, wherein said anhydride can be but not limited to acetic anhydride, propionic anhydride, butyric anhydride, pentanoic anhydride (also valeric anhydride), hexanoic anhydride, heptanoic anhydride, octanoic anhydride, nonanoic anhydride, decanoic anhydride, lauric anhydride, myristic anhydride, palmitic anhydride, stearic anhydride, behenic anhydride, crotonic anhydride, methacrylic anhydride, oleic anhydride, linoleic anhydride, chloroacetic anhydride, iodoacetic anhydride, dichloroacetic anhydride, succinic anhydride, methylsuccinic anhydride, 2,2-dimethylsuccinic anhydride, itaconic anhydride, maleic anhydride, glutaric anhydride, diglycolic anhydride, benzoic anhydride, phenylsuccinic anhydride, phenylmaleic anhydride, homophthalic anhydride, isatoic anhydride, phthalic anhydride or the like. Said intramolecular anhydride also can be but not limited to butanedioic anhydride, 2,2-dimethylsuccinic anhydride, cyclopentane-1,1-diacetic anhydride, 1,1-cyclohexane diacetic anhydride, 2-methylenesuccinic anhydride (or itaconic anhydride), glutaric anhydride, caronic anhydride, cyclobutane-1,2-dicarboxylic anhydride, hexahydrophthalic anhydride, methylhexahydrophthalic anhydride, 1,2,3,6-tetrahydrophthalic anhydride, 1,2,5,6-tetrahydrophthalic anhydride, 3-methyltetrahydrophthalic anhydride, methyltetrahydrophthalic anhydride, citraconic anhydride, 2,3-dimethylmaleic anhydride, 2,3-dichloromaleic anhydride, 3,4,5,6-tetrahydrophthalic anhydride, 3-methylphthalic anhydride, 4-t-butylphthalic anhydride, 1,8-naphthalic anhydride, 2,2'-diphenyldicarboxylic anhydride, 4-fluorophthalic anhydride, 3-fluorophthalic anhydride, 4-bromophthalic anhydride, 4-chlorophthalic anhydride, 3,6-dichlorophthalic anhydride, 3-nitrophthalic anhydride, 4-nitrophthalic anhydride, 4-bromo-1,8-naphthalic anhydride, 4,5-dichloro-1,8-naphthalic anhydride, 4-nitro-1,8-naphthalic anhydride, norbornene-dicarboxylic anhydride, methyl nadic anhydride (methylnorbornene-2,3-dicarboxylic anhydride), norcantharidin (7-oxabicyclo[2.2.1]heptane-2,3-dicarboxylic anhydride), 2,3-pyridinedicarboxylic anhydride, 2,3-pyrazinedicarboxylic anhydride, benzothioxanthenedicarboxylic anhydride or the like.

When $R_{01}$ is an intramolecular imide group, $-(Z_1)_{q1}-R_{01}$ can be but not limited to any corresponding imide form of the above-mentioned intramolecular anhydrides, such as succinic anhydride corresponding to succinimide, maleic anhydride corresponding to maleimide, phthalic anhydride corresponding to phthalimide, and the like, no more repeated here. Saccharin, also termed as o-sulfobenzimide, is also included.

When $R_{01}$ is a maleimido group, it can be the residue group deriving from the following compounds or groups, including but not limited to 3,4,5,6-tetrahydrophthalimide, a maleimidoacetyl group, a 3-maleimidopropionyl group, a 4-maleimidobutanoyl group, a 5-maleimidopentanoyl group (e.g., a 5-maleimidovaleryl group), a 6-maleimidohexanoyl group, a 3-maleimidobenzoyl group, a 4-maleimidobenzoyl group, a 4-(N-maleimidomethypcyclohexyl-1-formyl group, a 4-(4-maleimidophenyl)butanoyl group, a 11-maleimidoundecanoyl group, N-(2-aminoethyl)maleimide, N-(4-aminophenyl)maleimide, a 2-maleimidoethyl group and the like.

When $R_{01}$ is a cyano group, $-(Z_1)_{q1}-R_{01}$ can be the monovalent functional residue group formed by removing a hydrogen atom from one of the following cyano-containing cyanides including but not limited to formonitrile, acetonitrile, butyronitrile, pentanonitrile (also valeronitrile), hexanenitrile, heptanenitrile, octanenitrile, nonanenitrile (also nonanonitrile), decanenitrile, undecyl nitrile, allyl nitrile, acrylonitrile, crotononitrile, methacrylonitrile, dichloroacetonitrile, fluoroacetonitrile, benzenonitrile, benzyl nitrile, methylbenzyl nitrile, chlorobenzonitrile, methylbenzonitrile and the like.

When $R_{01}$ is an alkynyl group, $-(Z_1)_{q1}-R_{01}$ can be but not limited to an ethynyl group, a propynyl group, a propargyl group, a cycloalkynyl group, or the like.

When $R_{01}$ is a hydroxyl group, $-(Z_1)_{q1}-R_{01}$ can be the monovalent functional residue group formed by removing a non-hydroxyl hydrogen atom from one of the following mono-ols, including but not limited to methanol, ethanol, propanol, butanol, pentanol, hexanol, heptanol, octanol, nonanol, decanol, undecyl alcohol, lauryl alcohol (or dodecanol), tridecanol (or tridecyl alcohol), tetradecanol (or tetradecyl alcohol), pentadecanol (pentadecyl alcohol), hexadecanol (or hexadecyl alcohol), heptadecanol (or heptadecyl alcohol), octadecanol (or octadecyl alcohol), oleyl alcohol, benzyl alcohol, cumyl alcohol, phenol, cresol, stilboestol, propofol, cumylphenol, naphthol, cyclopentanol, cyclohexanol and the like.

When $R_{01}$ is a cholesterol moiety or derivative thereof, $-(Z_1)_{q1}-R_{01}$ includes but is not limited to the residue groups of cholesterol derivatives, cholesterol succinate and like after being connected at the terminal ends of PEG chains.

When $R_{01}$ is a biotin moiety or derivative thereof, $-(Z_1)_{q1}-R_{01}$ can be selected from the residue groups of biotin-containing compounds after being bound to the terminal ends of PEG chains, wherein said biotin-containing compounds include but are not limited to biotin N-hydroxysuccinimide ester (or biotin N-succinimidyl ester, or N-succinimidyl biotinate), succinimidyl 3-[3-[2-(biotinamido)ethyl]amino-3-oxopropyl]dithio]propionate, sulfosuccinimidyl 3-[[2-(biotinamido)ethyl]dithio]propionate, N-(3-azidopropyl)biotinamide, N-biotinyl-3,6-dioxaoctane-1,8-diamine, N-biotinyl-3,6,9-trioxaundecanediamine, biotinyl-6-aminoquinoline, N-(6-[biotinamido]hexyl)-3'-(2'-pyridyldithio)propionamide, 15-[D-(+)-biotinylamino]-4,7,10,13-tetraoxapentadecanoic acid, 3-(4-(N-biotinoyl-6-aminocaproyloxy)phenyl)propionic acid, N-Fmoc-N'-biotinyl-$_L$-lysine, D-biotin hydrazide, biotin-Asp-Glu-Val-Asp-aldehyde and the like.

When $R_{01}$ is a fluorescein moiety or derivative thereof, $-(Z_1)_{q1}-R_{01}$ can be the residue group of fluorescein-containing compounds after being bound to the terminal ends of PEG chains, wherein said fluorescein-containing compounds include but are not limited to 5-carboxyfluorescein succinimidyl ester, 6-carboxyfluorescein succinimidyl ester, 5-aminofluorescein, 6-aminofluorescein, 5-(aminomethyl)fluorescein hydrochloride, 6-(4,6-dichlorotriazin-2-yl]amino)fluorescein hydrochloride, 5'-fluorescein phosphoramidite, fluorescein-5-maleimide, fluorescein-6-maleimide, 5-carboxyfluorescein, 6-carboxylfluorescein, 2,7-bis(2-carboxyethyl)-5-carboxyfluorescein, 2,7-bis(2-carboxyethyl)-6-carboxyfluorescein, 5-(4,6-dichlorotriazinyl)aminofluorescein, CI 45350 and the like.

When $R_{01}$ is a rhodamine moiety or derivative thereof, $-(Z_1)_{q1}-R_{01}$ can be the residue group of rhodamine-containing compounds after being bound to the terminal ends of PEG chains, wherein said rhodamine-containing compounds include but are not limited to tetramethylrhodamine, rhodamine B (RB200), rhodamine 3G, rhodamine 6G (rhodamine 590), 5-carboxy-X-rhodamine, 6-carboxy-X-rhodamine, sulfonylrhodamine B, sulfonylrhodamine G, sulfonylrhodamine 101, rhodamine X (R101), rhodamine 101, rhodamine 110, rhodamine 123, rhodamine 700, rhodamine 800, 5-carboxytetramethylrhodamine, 6-carboxytetramethylrhodamine, 5-carboxytetramethylrhodamine succinimidyl ester, 6-carboxytetramethylrhodamine succinimidyl ester, 5-carboxyrhodamine 6G succinimidyl ester, 6-carboxyrhodamine 6G succinimidyl ester, tetramethylrhodamine-5-maleimide, tetramethylrhodamine-6-maleimide, 6-carboxy-X-rhodamine succinimidyl ester, tetramethylrhodamine-5-isothiocyanate, tetramethylrhodamine-6-isothiocyanate, tetramethylrhodamine B-5-isothiocyanate, tetramethylrhodamine B-6-isothiocyanate, chlororhodamine 101, sulforhodamine B and the like.

When $R_{01}$ is an anthracene moiety or derivative thereof, $-(Z_1)_{q1}-R_{01}$ can be the residue group of anthryl-containing compounds after being bound to the terminal ends of PEG chains, wherein said anthryl-containing compounds include but are not limited to 9-anthracenemethanol, 1-aminoanthracene, 2-aminoanthracene (2-anthracenamine), 9-anthraldehyde (anthracene-9-carboxaldehyde), 10-methyl-9-anthraldehyde, 9-anthroic acid, 9-anthracenylmethyl acrylate, 9-anthracenylmethyl methacrylate, 9-anthraldehyde oxime, 9-anthraceneacrolein and the like.

When $R_{01}$ is a pyrene moiety or derivative thereof, $-(Z_1)_{q1}-R_{01}$ can be the residue group of pyrenyl-containing compounds after being bound to the terminal ends of PEG chains, wherein said pyrenyl-containing compounds include but are not limited to 1-pyrenemethanol, 7,8,9,10-tetrahydrogenbenzo[a]pyren-7-ol, 1-pyrenebutyric acid N-hydroxysuccinimide ester, 1-pyrenecarboxaldehyde, 1-pyrenebutyrate (or 1-pyrenebutyric acid, or 1-pyrenebutanoic acid), 1-pyrenecarboxylic acid, 1-pyreneacetic acid, 10-(1-pyrene)decanoic acid, 1-pyrenedodecanoic acid, Fmoc-3-(1-pyrenyl)-L-alanine, Boc-3-(1-pyrenyl)-D-alanine, Boc-3-(1-pyrenyl)-L-alanine, 1-aminopyrene, 1,3-diaminopyrene, 1,8-diaminopyrene, 1,6-diaminopyrene, 1-pyrenylmethylamine, N-(1-pyrenyl)maleimide and the like.

When $R_{01}$ is a carbazole moiety or derivative thereof, —$(Z_1)_{q1}$—$R_{01}$ can be the residue group of carbazole-containing compounds after being bound to the terminal ends of PEG chains, wherein said carbazole-containing compounds include but are not limited to carbazole, carbazole-9-ethanol, 2-hydroxycarbazole, 2-(9H-carbazolyl)ethylboronic acid pinacol ester, 2-(9H-carbazolyl)ethylboronic acid diethanolamine ester, N-aminocarbazole, 9-(4-aminophenyl)carbazole, carbazole-9-acetic acid and the like.

When $R_{01}$ is an imidazole moiety or derivative thereof, —$(Z_1)_{q1}$—$R_{01}$ can be the residue group of imidazole-containing compounds after being bound to the terminal ends of PEG chains, wherein said imidazole-containing compounds includes but is not limited to 4-(hydroxymethyl)imidazole, 4-(hydroxyethyl)imidazole, 1-(2-hydroxyethyl)imidazole, 1-methyl-2-(hydroxymethyl)imidazole, 1-(2-hydroxypropyl)imidazole, 1-(2-hydroxyethyl)-2-methylimidazole, 4-hydroxymethyl-5-methyl-2-phenylimidazole, 1-hydroxyethyl-3-methylimidazole, 1-hydroxyethyl-3-methylimidazolium chloride, 4-hydroxymethyl-5-methylimidazole, 4-bromo-1H-imidazole, 2-bromo-1H-imidazole, 1-methyl-2-bromo-1H-imidazole (2-bromo-1-methyl-1H-imidazole), 5-chloro-1-methylimidazole, 2-aminoimidazole, 4-aminoimidazole, 1-(3-aminopropyl)imidazole, 1-methylimidazole-4-carboxylic acid, imidazole-4-carboxaldehyde (4-formylimidazole), 1-formylimidazole, 2-formylimidazole, 4-(imidazol-1-yl)benzaldehyde, 1-methyl-2-imidazolecarboxaldehyde, 2-butyl-1H-imidazole-4-carboxaldehyde, 5-methyl-4-imidazolecarboxaldehyde, 2-ethyl-4-formylimidazole, 2-ethyl-4-methyl-5-imidazolecarboxaldehyde, 1-benzyl-1H-imidazole-5-carboxaldehyde, 2-ethyl-4-formylimidazole, 5-amino-1H-imidazole-4-carbonitrile, histidine and the like.

When $R_{01}$ is an indole moiety or derivative thereof, —$(Z_1)_{q1}$—$R_{01}$ can be the residue group of indole-containing compounds after being bound to the terminal ends of PEG chains, wherein said indole-containing compounds include but are not limited to 4-hydroxyindole, 5-hydroxyindole, 6-hydroxyindole, 7-hydroxyindole, 5-hydroxy-2-methylindole, 4-hydroxy-2-methylindole, 3-(2-methylaminoethyl)indole, 2-(2-aminoethyl)indole, 3-(2-aminoethyl)-6-methoxyindole, 4-aminoindole, 5-aminoindole, 6-aminoindole, 7-aminoindole, 4-methyl-5-aminoindole, 3-bromoindole, 4-bromoindole, 5-bromoindole, 6-bromoindole, 7-bromoindole, 5-bromo-1-methyl-1H-indole, 3-(2-aminoethyl)indol-5-ol, 5-hydroxyindole-2-carboxylic acid, 6-hydroxyindole-2-carboxylic acid, 7-hydroxyindole-2-carboxylic acid, 5-bromoindole-2-carboxylic acid, 6-bromoindole-2-carboxylic acid, 7-bromoindole-2-carboxylic acid, 5-bromoindole-3-carboxylic acid, 6-bromoindole-3-carboxylic acid, 4-bromoindole-3-carbaldehyde, 6-bromoindole-3-carbaldehyde, 5-bromo-1H-indole-3-ethanol and the like.

1.1.3.2. Specific Structures of Functional End-Group in Unprotected or Protected Form ($R_{01}$)

$R_{01}$ can be selected from the group consisting of functional groups from Group A to Group J, variant forms of Group A to Group H and functional derivatives of Group I to Group J.

Specifically, $R_{01}$ can be but not limited to any structure from any of the following groups from Group A to Group H:

Group A:

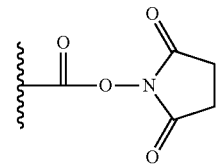
A1

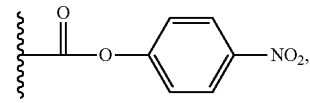
A2

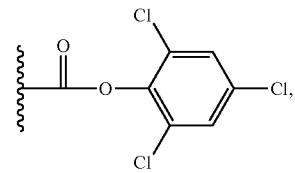
A3

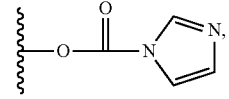
A4

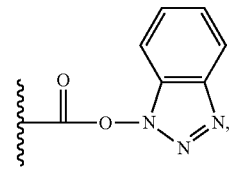
A5

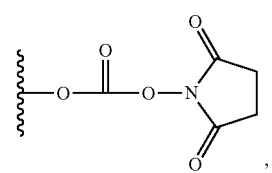
A6

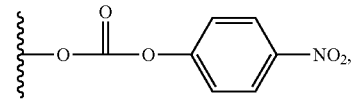
A7

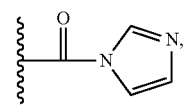
A8

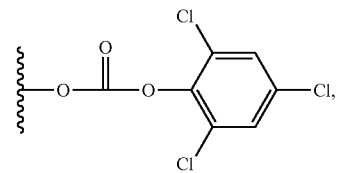
A9

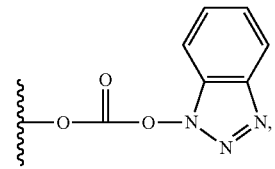
A10

-continued
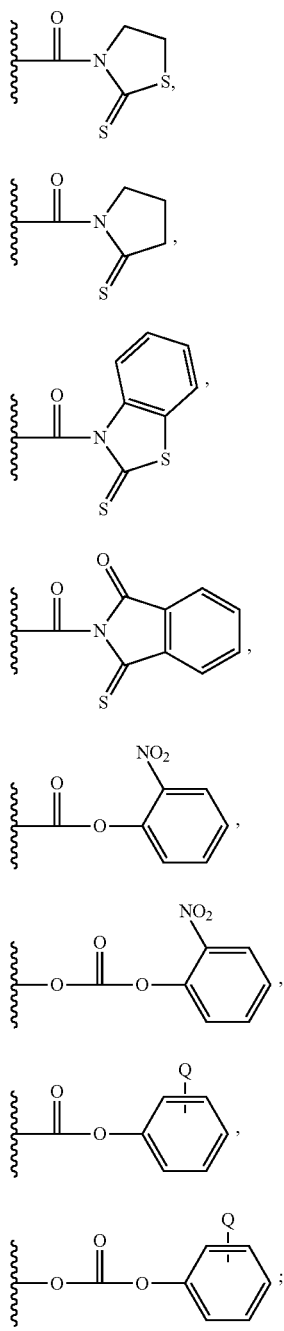
A11
A12
A13
A14
A15
A16
A17
A18
Group B:
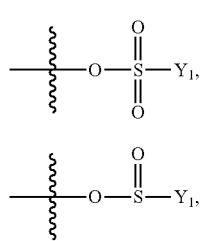
-continued
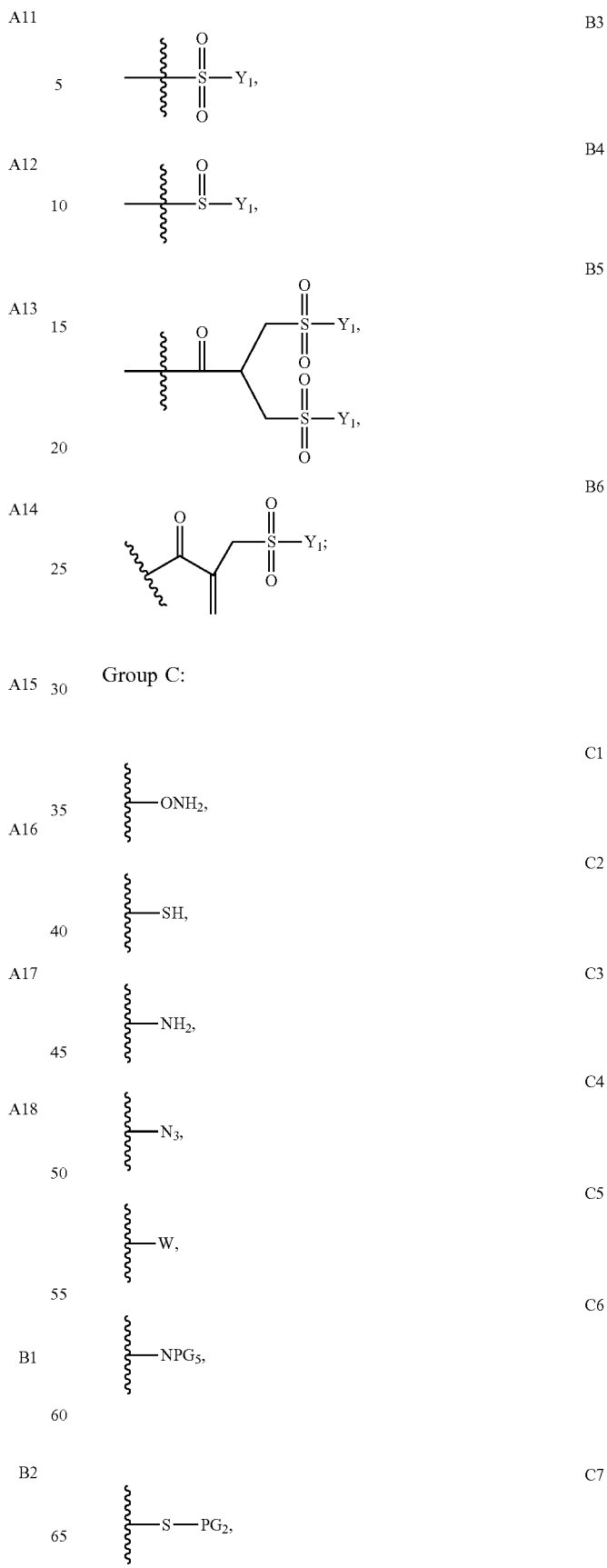
Group C:
B3
B4
B5
B6
C1
C2
C3
C4
C5
C6
C7

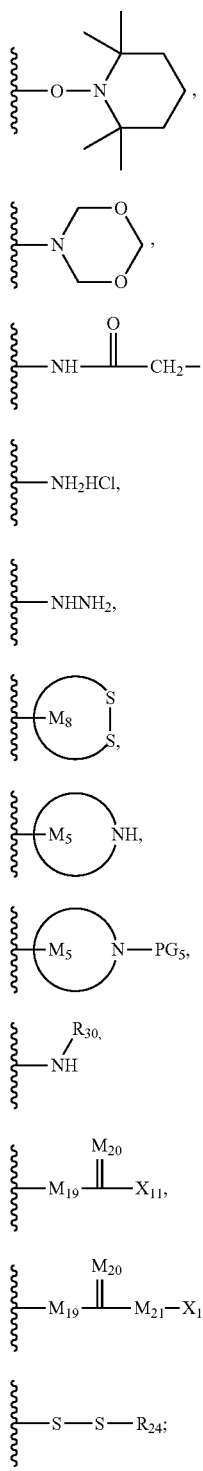
Group D:
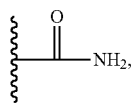
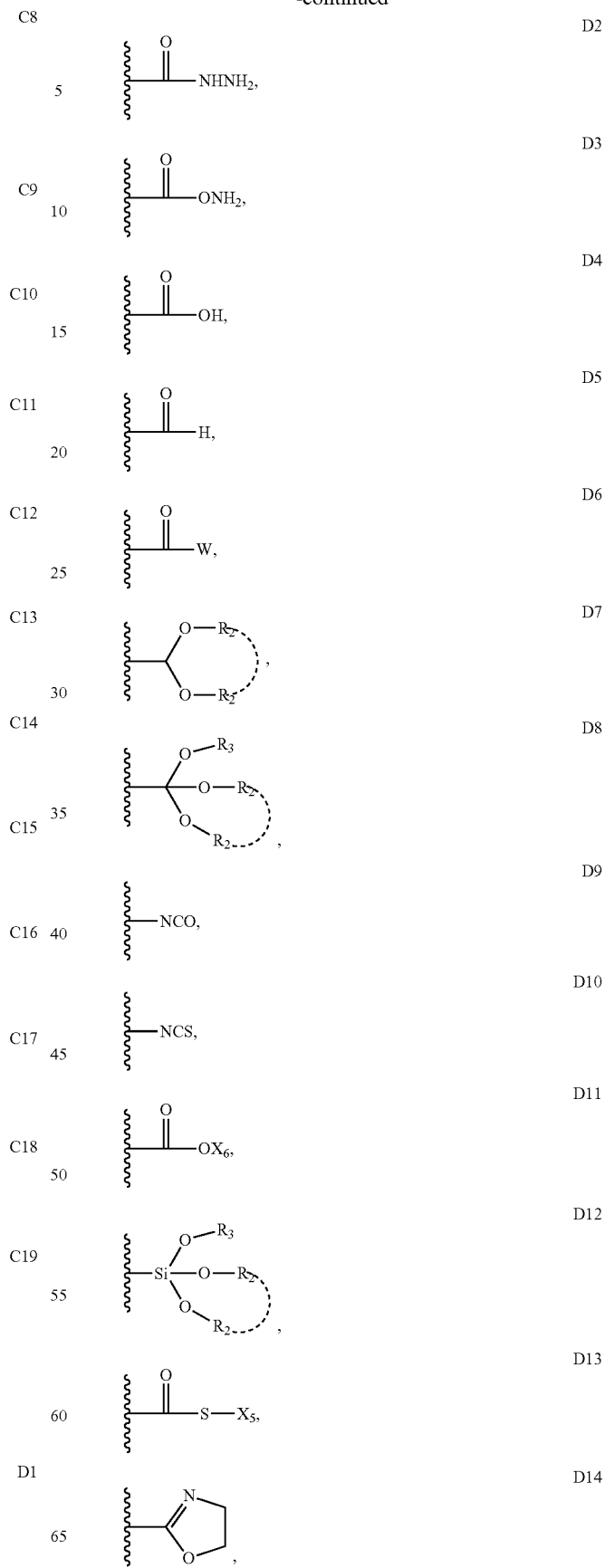

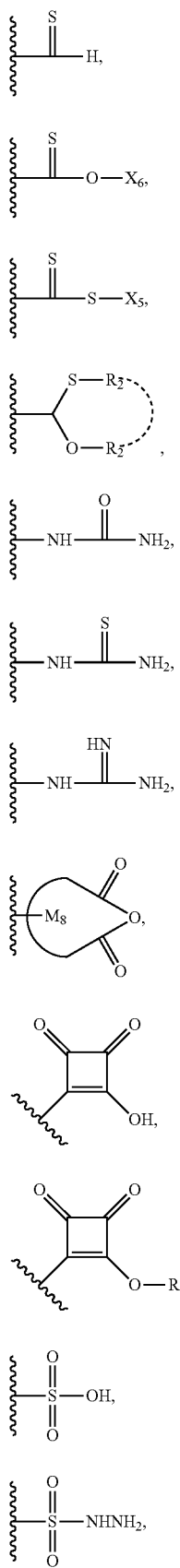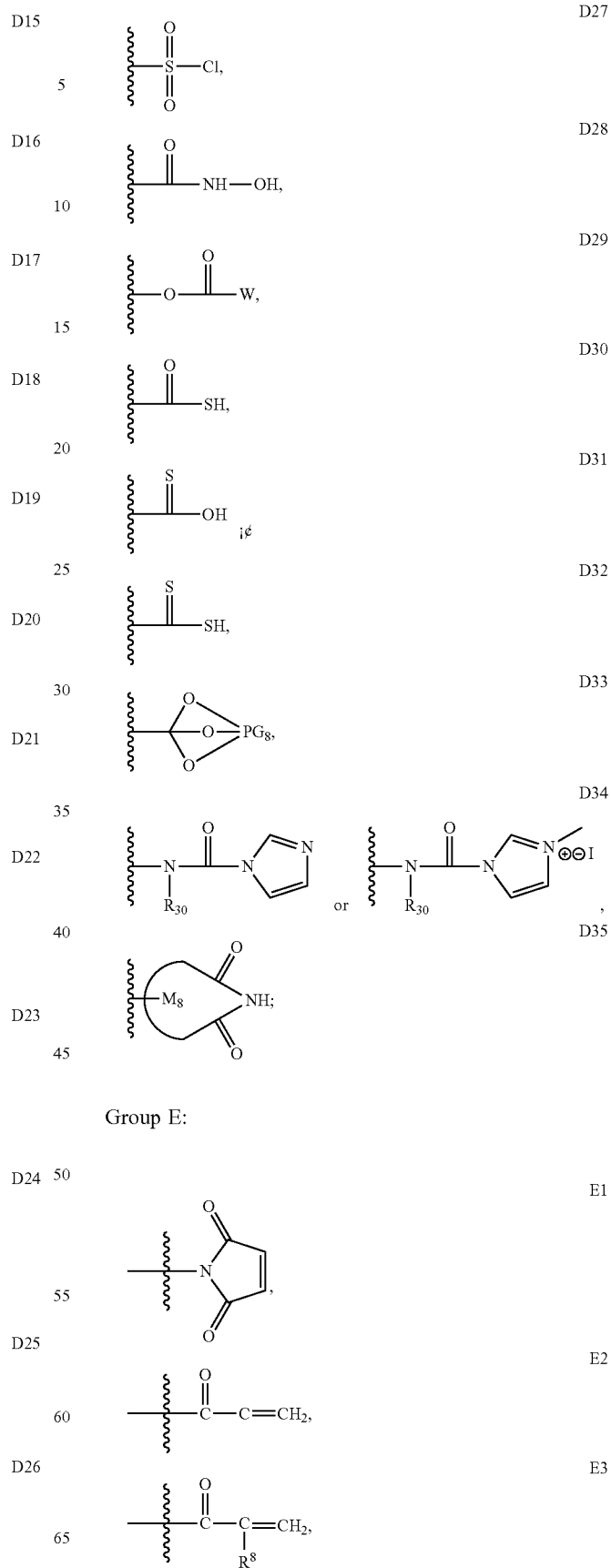
Group E:

-continued
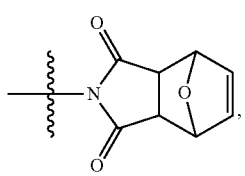
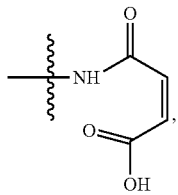
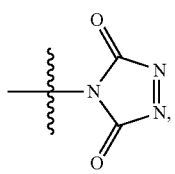
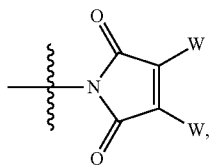
Group F:
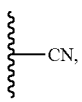 F1
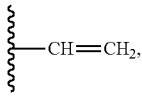 F2
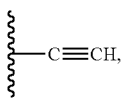 F3
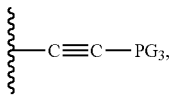 F4
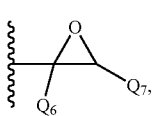 F5
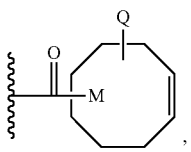 F6
-continued
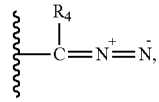 E4
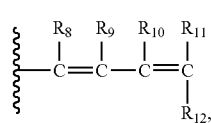 E6
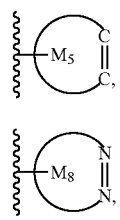 E6
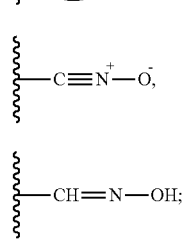 E8
Group G:
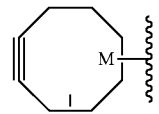 
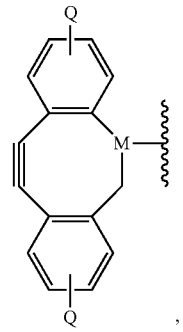 
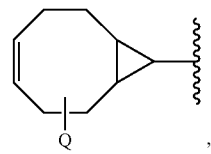 
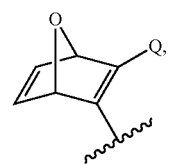 
F7
F8
F9
F10
F11
F12
G1
G2
G3
G4

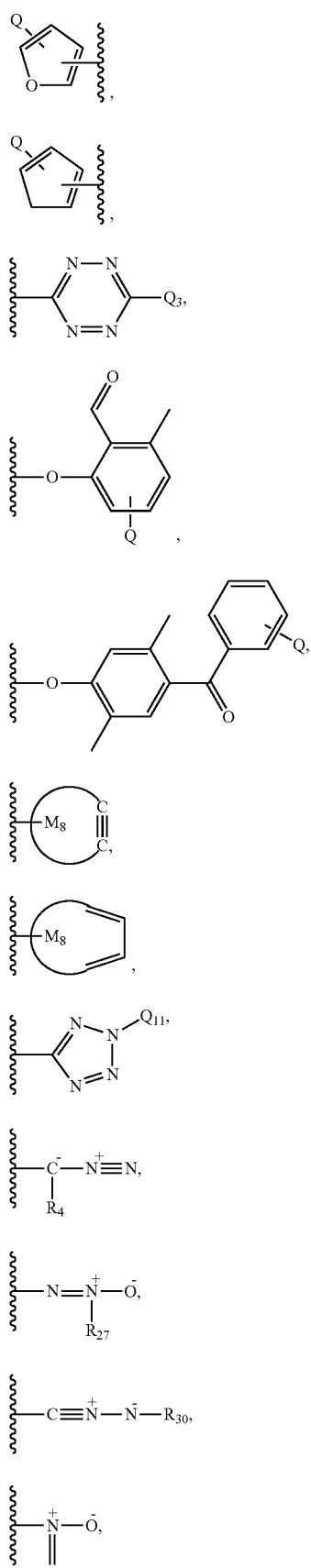
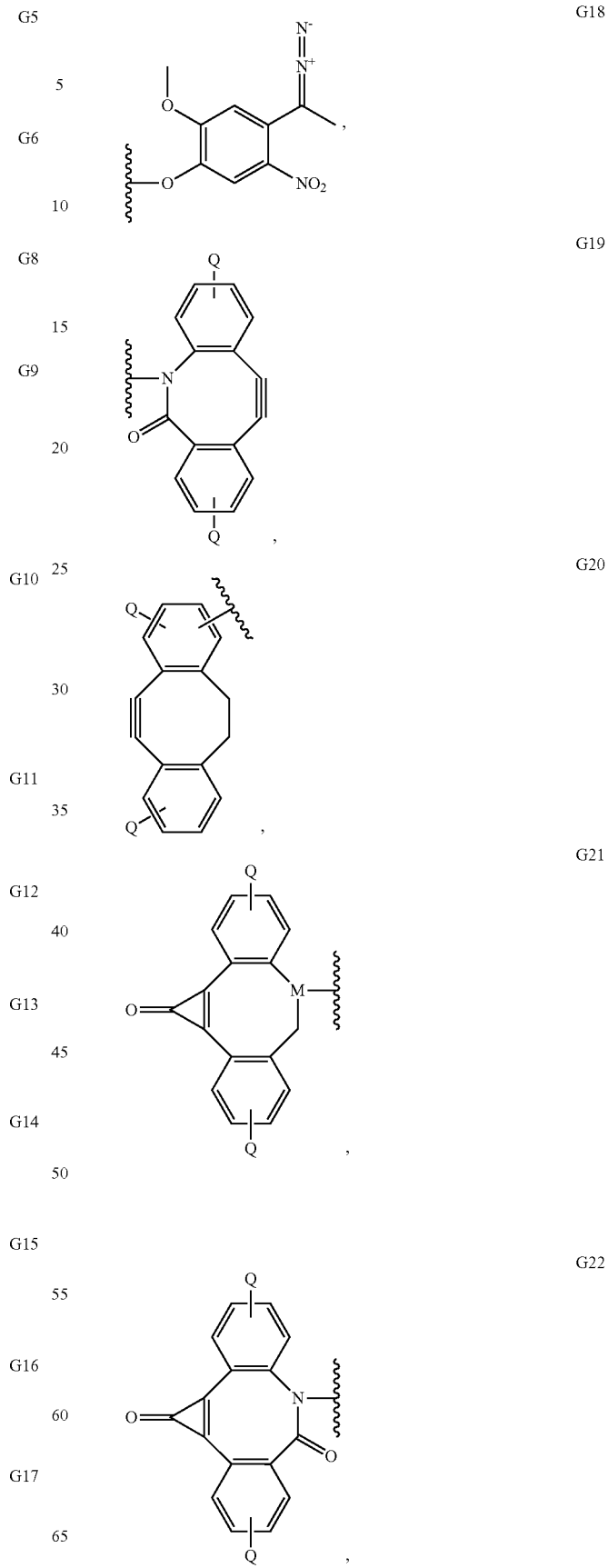

G23 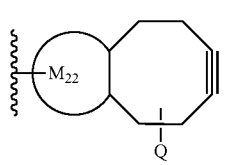
G24 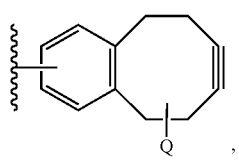
G25 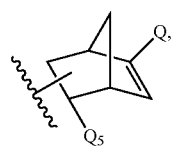
G26 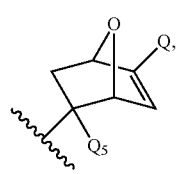
G27 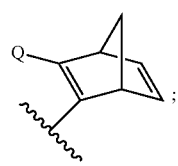
Group H:
H1 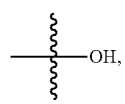
H2 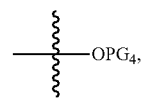
H3 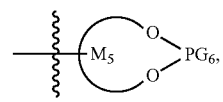
H4 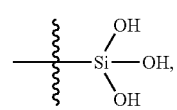
H5 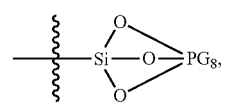
H6 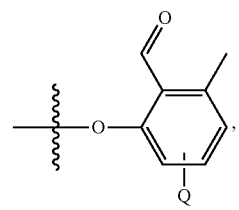
H7 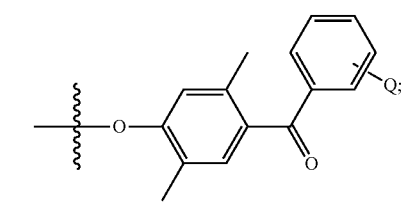
Group I:
I1 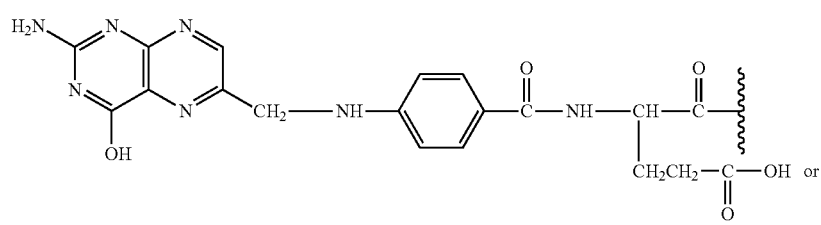
or
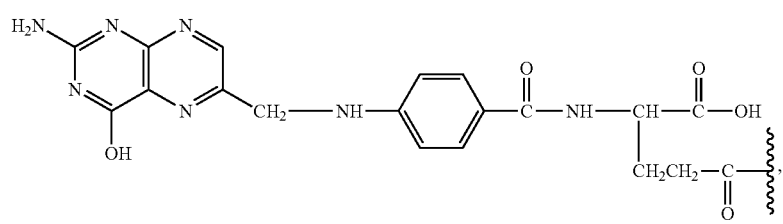

Group J:

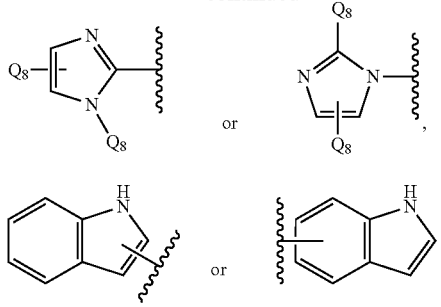

and the like.

Wherein, $X_6$ is a terminal group connected to the oxygen atom of an ester group or of a thiocarboxylate group, and can be a hydroxyl protecting group or a group $LG_4$. Wherein, the definitions of $R_3$, $LG_4$, Q, $M_5$ and $M_5$-membered rings are the same as above-defined, no more repeated here.

Wherein, $Y_1$ is a leaving group that connects to a sulfonyl group, a sulfinyl group, an oxysulfonyl group (a sulfonate group) or an oxysulfinyl group (a sulfinate group).

$Y_1$ is not particularly limited.

$Y_1$ is preferably a $C_{1-10}$ hydrocarbyl group or a fluorinated $C_{1-10}$ hydrocarbyl group.

$Y_1$ is more preferably a $C_{1-10}$ alkyl group, a $C_{1-10}$ alkenyl group, a phenyl group or any substituted form thereof. Wherein, the atom or group substituent is a halogen atom, an alkenyl group, an alkoxy group or a nitro group.

Specifically, for example, $Y_1$ can be but not limited to a methyl group, an ethyl group, an n-propyl group, an isopropyl group, a butyl group, a pentyl group, a hexyl group, a heptyl group, an octyl group, a nonyl group, a decyl group, a vinyl group, a phenyl group, a benzyl group, a p-methylphenyl group, a 4-(trifluoromethoxy)phenyl group, a trifluoromethyl group, a 2,2,2-trifluoroethyl group or the like. Wherein, said butyl group includes but is not limited to an n-butyl group and a t-butyl group. Said octyl group includes but is not limited to an n-octyl group and a 2-ethylhexyl group.

$Y_1$ is preferably a methyl group, a methylphenyl group, a 2,2,2-trifluoroethyl group, a trifluoromethyl group, a vinyl group or the like.

Wherein, W is F, Cl, Br or I, and preferably Br or Cl.

Wherein, $W_2$ is F, Cl, Br or I, and preferably I.

Wherein,

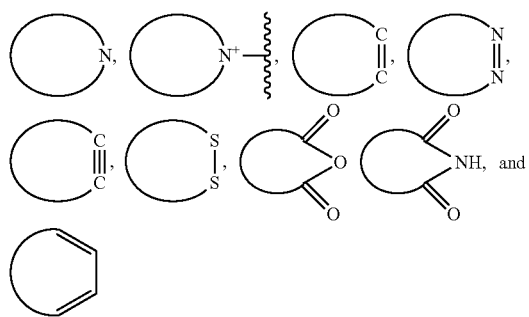

are cyclic structures, also denoted as ring structures, wherein the ring skeleton contains a nitrogen atom, a nitrogen cation, a carbon-carbon double bond, an azo bond, a carbon-carbon triple bond, a disulfide bond, an anhydride group, an imide group and a dienylene linkage, respectively, and said cyclic structures include but are not limited to a carbon ring, a heteroring, a benzoheteroring, a substituted carbon ring, a substituted heteroring, a substituted benzoheteroring and the like.

Wherein, M is a carbon atom or a heteroatom of the ring skeleton, i.e. a ring-membering atom, including but not limited to a carbon atom, a nitrogen atom, a phosphorus atom or a silicon atom.

Wherein, $M_8$ is a carbon atom or a heteroatom of the ring skeleton. $M_8$ is preferably a carbon atom, a nitrogen atom, a phosphorus atom or a silicon atom. The number of ring-membering atoms of $M_8$-membered rings is not particularly limited, preferably from 4 to 50, more preferably from 4 to 32, more preferably from 5 to 32, and more preferably from 5 to 18. $M_8$ can be a carbon atom or a heteroatom of a 4- to 50-membered ring skeleton, preferably a carbon atom, a nitrogen atom, a phosphorus atom or a silicon atom of a 4- to 32-membered ring skeleton, more preferably a carbon atom, a nitrogen atom, a phosphorus atom or a silicon atom of a 5- to 32-membered ring skeleton, and more preferably a carbon atom, a nitrogen atom, a phosphorus atom or a silicon atom of a 5- to 18-membered ring skeleton.

Wherein, the definitions of $R_8$, $R_9$, $R_{10}$, $R_{11}$ and $R_{12}$ are the same as above-defined $R_8$, no more repeated here. In one molecule, $R_8$, $R_9$, $R_{10}$, $R_{11}$ and $R_{12}$ can be identical or not identical.

For a functional group E3, $R_8$ is most preferably a methyl group.

Wherein, $R_2$ is a terminal group (a monovalent group) or a divalent linking group that connects with an oxygen atom or a sulfur atom of structures such as acetal, ketal, hemiacetal, hemiketal, orthoester, thioacetal, thioketal, thiohemiacetal, thiohemiketal, thioorthoester, etc., e.g., D7, D8, D12 and D18.

$R_2$ is a hydrogen atom, a divalent group $R_{21}$ or a monovalent group $R_3$.

Wherein, $R_{21}$ is a divalent linking group and participates in forming a ring (a ring-membering linking group).

The carbon-atom number of $R_{21}$ is not particularly limited, preferably from 1 to 20, and more preferably from 1 to 10.

The structure of $R_{21}$ is not particularly limited, including but not limited to a linear structure, a branched structure bearing pendant groups or a ring-containing structure. Wherein, Said ring is not particularly limited, including but not limited to all the above-listed cyclic structures in the terminology section, and preferably an aliphatic ring, an aromatic ring, a sugar ring or a condensed ring.

$R_{21}$ can contain heteroatoms, or not.

$R_{21}$ is a $C_{1-20}$ hydrocarbylene group, a divalent $C_{1-20}$ heterohydrocarbyl, a substituted $C_{1-20}$ hydrocarbylene group, a substituted divalent $C_{1-20}$ heterohydrocarbyl, or the combination of any two or three thereof. Wherein, the atom or group substituent is not particularly limited, including but not limited to all the above-listed substituting atoms and substituting groups in the terminology section, and can be a halogen atom, a hydrocarbyl substituent, and or a heteroatom-containing substituent.

$R_{21}$ is preferably a $C_{1-20}$ open-chain alkylene group, a $C_{2-20}$ open-chain alkenylene group, a $C_{3-20}$ cycloalkylene group, a $C_{3-20}$ cycloalkenylene group, an arylene group, an arylhydrocarbylene group, a divalent $C_{1-20}$ aliphatic-derived heteroalkyl group, a divalent $C_{2-20}$ aliphatic-derived heteroalkenyl group, a divalent heteroaryl group, a divalent heteroarylhydrocarbyl group, a substituted alkylene group, a substituted $C_{2-20}$ open-chain alkenylene group, a substituted $C_{3-20}$ cycloalkylene group, a substituted $C_{3-20}$ cycloalkenylene group, a substituted arylene group, a substituted arylhydrocarbylene group, a substituted divalent $C_{3-20}$ aliphatic-derived heteroalkyl group, a substituted divalent $C_{2-20}$ aliphatic-derived heteroalkenyl group, a substituted divalent hetero aryl group, a substituted divalent heteroarylhydrocarbyl group, or the combination of any two or three thereof. Wherein, the atom or group substituent is preferably a halogen atom, an alkoxy group or a nitro group.

$R_{21}$ is more preferably a $C_{1-10}$ open-chain alkylene group, a $C_{2-10}$ open-chain alkenylene group, a $C_{3-10}$ cycloalkylene group, a $C_{3-10}$ cycloalkenylene group, an arylene group, an arylhydrocarbylene group, a divalent $C_{1-10}$ aliphatic-derived heteroalkyl group, a divalent $C_{2-10}$ aliphatic-derived heteroalkenyl group, a divalent heteroaryl group, a divalent heteroarylhydrocarbyl group, a substituted alkylene group, a substituted $C_{2-20}$ open-chain alkenylene group, a substituted $C_{3-10}$ cycloalkylene group, a substituted $C_{3-10}$ cycloalkenylene group, a substituted arylene group, a substituted arylalkylene group, a substituted divalent $C_{1-10}$ aliphatic-derived heteroalkyl group, a substituted divalent $C_{2-10}$ aliphatic-derived heteroalkenyl group, a substituted divalent heteroaryl group, a substituted divalent heteroarylhydrocarbyl group, or the combination of any two or three thereof.

Specifically, $R_{21}$ can be a methylene group, an ethylene group, a propylene group, a butylene group, a pentylene group, a hexylene group, a heptylene group, an octylene group, a nonylene group, a decylene group, a 1,2-phenylene group, a benzylene group, a $C_{1-20}$ oxa-alkylene group, a $C_{1-20}$ thia-alkylene group, a $C_{1-20}$ aza-alkylene group, an aza-arylhydrocarbylene group, or any substituted form thereof, or the combination of any two or two more identical or different above-said groups or substituted forms thereof. Wherein, the atom or group substituent is a halogen atom, a hydrocarbyl substituent or a heteroatom-containing substituent, and preferably a halogen atom, an alkoxy group or a nitro group.

$R_{21}$ is preferably a methylene group, an ethylene group, a propylene group, a butylene group, a pentylene group, a hexylene group, a heptylene group, an octylene group, a nonylene group, a decylene group, a 1,2-phenylene group, a benzylene group, a $C_{1-20}$ oxa-alkylene group, a $C_{1-20}$ thia-alkylene group, a $C_{1-20}$ aza-alkylene group, an aza-arylhydrocarbylene group, or any substituted form thereof, or the combination of any two or two more identical or different above-said groups or substituted forms thereof. Wherein, the atom or group substituent is a halogen atom, a hydrocarbyl substituent or a heteroatom-containing substituent, and preferably a halogen atom, an alkoxy group or a nitro group.

$R_{21}$ is more preferably a 1,2-ethylene group or a 1,3-propylene group.

Wherein, $R_4$ is a hydrogen atom, an atom substituent or a group substituent linked to the carbon atom of a structure with the formula of $-(R_4)C=N^+=N^-$ or $-(R_4)C^--N^+\equiv N$.

When as an atom substituent, $R_4$ is a halogen atom, and preferably a fluorine atom.

When as a group substituent, the carbon-atom number of $R_4$ is not particularly limited, preferably from 1 to 20, and more preferably from 1 to 10.

When as a group substituent, the structure of $R_4$ is not particularly limited, including but not limited to a linear structure, a branched structure bearing pendant groups or a ring-containing structure. Wherein, said ring is not particularly limited, including but not limited to all the above-listed cyclic structures in the terminology section.

When as a group substituent, $R_4$ can contain heteroatoms, or not.

$R_4$ is a hydrogen atom, a halogen atom, a $C_{1-20}$ hydrocarbyl group, a $C_{1-20}$ heterohydrocarbyl group, a substituted $C_{1-20}$ hydrocarbyl group or a substituted heterohydrocarbyl group. Wherein, the atom or group substituent of $R_4$ is not particularly limited, including but not limited to all the above-listed substituting atoms and substituting groups in the terminology section, and can be a halogen atom, a hydrocarbyl substituent, or a heteroatom-containing substituent.

$R_4$ is more preferably a hydrogen atom, a halogen atom, a $C_{1-20}$ alkyl group, $C_{1-20}$ unsaturated aliphatic hydrocarbyl group, an aryl group, an arylhydrocarbyl group, a $C_{1-20}$ heterohydrocarbyl, a $C_{1-20}$ hydrocarbyloxy-acyl group, a $C_{1-20}$ hydrocarbylthio-acyl group, a $C_{1-20}$ hydrocarbylamino-acyl group, or any substituted form thereof. Wherein, said acyl group within $R_4$ is not particularly limited, including but not limited to all acyl types listed in the terminology section, and more preferably a carbonyl group or a thiocarbonyl group.

$R_4$ is more preferably a hydrogen atom, a halogen atom, a $C_{1-20}$ alkyl group, a $C_{1-20}$ alkenyl group, an aryl group, an arylhydrocarbyl group, a $C_{1-20}$ aliphatic-derived heterohydrocarbyl group, a heteroaryl group, a heteroarylhydrocarbyl group, a $C_{1-20}$ alkoxy-acyl group, an aryloxy-acyl group, a $C_{1-20}$ (alkylthio)acyl group, an (arylthio)acyl group, a $C_{1-20}$ alkylamino-acyl group, an arylamino-acyl group, or any substituted form thereof.

$R_4$ is more preferably a hydrogen atom, a halogen atom, a $C_{1-20}$ alkyl group, a $C_{1-20}$ alkenyl group, an aryl group, an arylhydrocarbyl group, a $C_{1-20}$ aliphatic-derived heterohydrocarbyl group, a heteroaryl group, a heteroarylhydrocarbyl group, a $C_{1-20}$ alkoxycarbonyl group, an aryloxycarbonyl group, a $C_{1-20}$ (alkylthio)carbonyl group, an (arylthio)carbonyl group, a $C_{1-20}$ alkylaminocarbonyl group, an arylaminocarbonyl group, a $C_{1-20}$ alkoxy-thiocarbonyl group, an aryloxy-thiocarbonyl group, a $C_{1-20}$ (alkylthio)thiocarbonyl group, an (arylthio)thiocarbonyl group, a $C_{1-20}$ alkylaminothiocarbonyl group, an arylaminothiocarbonyl group, or any substituted form thereof.

Specifically, $R_4$ can be a hydrogen atom, a fluorine atom, a chlorine atom, a bromine atom, an iodine atom, a methyl group, an ethyl group, an n-propyl group, an isopropyl group, a butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, an allyl group, a propenyl group, an ethenyl group, a phenyl group, a methylphenyl group, a butylphenyl group, a benzyl group, a methoxycarbonyl group, an ethoxycarbonyl group, a phenoxycarbonyl group, a benzyloxycarbonyl group, a (methylthio)carbonyl group, an (ethylthio)carbonyl group, a (phenylthio)carbonyl group, a (benzylthio)carbonyl group, an ethylaminocarbonyl group, a benzylaminocarbonyl group, a methoxy-thiocarbonyl group, an ethoxy-thiocarbonyl group, a phenoxy-thiocarbonyl group, a benzyloxy-thiocarbonyl group, a (methylthio)thiocarbonyl group, an (ethylthio)thiocarbonyl group, a (phenylthio)thiocarbonyl group, a (benzylthio)thiocarbonyl group, an ethylaminothiocarbonyl group, a benzylaminothiocarbonyl group, a substituted $C_{1-20}$ alkyl group, a substituted $C_{1-20}$ alkenyl group, a substituted aryl group, a substituted arylhydrocarbyl group, a substituted $C_{1-20}$ aliphatic-derived heterohydrocarbyl group, a substituted heteroaryl group, a substituted heteroarylhydrocarbyl group, a substituted $C_{1-20}$ alkoxycarbonyl group, a substituted aryloxycarbonyl group, a substituted $C_{1-20}$ (alkylthio)carbonyl group, a substituted (arylthio)carbonyl group, a substituted $C_{1-20}$ alkylaminocarbonyl group, a substituted arylaminocarbonyl group, a substituted $C_{1-20}$ alkoxy-thiocarbonyl group, a substituted aryloxy-thiocarbonyl group, a substituted $C_{1-20}$ (alkylthio)thiocarbonyl group, a substituted (arylthio)thiocarbonyl group, a substituted $C_{1-20}$ alkylaminothiocarbonyl group, a substituted arylaminothiocarbonyl group or the like. Wherein, butyl group includes but is not limited to an n-butyl group and a t-butyl group. Octyl group includes but is not limited to an n-octyl group and a 2-ethylhexyl group. Wherein, the atom or group substituent is a halogen atom, a hydrocarbyl substituent or a heteroatom-containing substituent, and preferably a fluorine atom, a chlorine atom, a bromine atom, an iodine atom, an alkenyl group or a nitro group.

$R_4$ is further preferably a hydrogen atom, a methyl group, an ethyl group, an n-propyl group, an isopropyl group, a butyl group, a pentyl group, a hexyl group, a heptyl group, an octyl group, a nonyl group, a decyl group, an allyl group, a propenyl group, an ethenyl group, a phenyl group, a methylphenyl group, a butylphenyl group, a benzyl group, a methoxycarbonyl group, an ethoxycarbonyl group, a phenoxycarbonyl group, a benzyloxycarbonyl group, a (methylthio)carbonyl group, an (ethylthio)carbonyl group, a (phenylthio)carbonyl group, a (benzylthio)carbonyl group, an ethylaminocarbonyl group, a benzylaminocarbonyl group, a methoxy-thiocarbonyl group, an ethoxy-thiocarbonyl group, a phenoxy-thiocarbonyl group, a benzyloxy-thiocarbonyl group, a (methylthio)thiocarbonyl group, an (ethylthio)thiocarbonyl group, a (phenylthio)thiocarbonyl group, a (benzylthio)thiocarbonyl group, an ethylaminothiocarbonyl group, a benzylaminothiocarbonyl group, a $C_{1-10}$ halohydrocarbyl group, a halophenyl group, a halobenzyl group, a nitrophenyl group, the like, or any substituted form thereof.

$R_4$ is preferably a hydrogen atom, a methyl group, an ethyl group, an n-propyl group, an isopropyl group, a butyl group, a pentyl group, a hexyl group, a heptyl group, an octyl group, a nonyl group, a decyl group, an allyl group, a propenyl group, an ethenyl group, a phenyl group, a methylphenyl group, a butylphenyl group or a benzyl group.

$R_4$ is most preferably a hydrogen atom, a methyl group or a benzyl group.

Wherein, $R_{24}$ is a terminal monovalent group connecting to a disulfide bond, and preferably a $C_{1-20}$ alkyl group, an aryl group, an arylhydrocarbyl group, a heterosubstituted phenyl group with one or more ring-membering heteroatoms or the like, such as an o-pyridyl group. Herein, said heterosubstituted phenyl group also allows presence or absence of heteroatom substituents.

Wherein, $R_{27}$ is a substituent connecting to an azo group, and preferably a phenyl group, a substituted phenyl group or a heterosubstituted phenyl group with one or more ring-membering heteroatoms. Herein, said heterosubstituted phenyl group also allows presence or absence of heteroatom substituents.

Wherein, $R_{30}$ is a hydrocarbyl group, and preferably a $C_{1-20}$ alkyl group, a benzyl group, or a benzyl group in which the benzene ring is substituted with $C_{1-20}$ hydrocarbyl groups.

Wherein, $M_{19}$, $M_{20}$ and $M_{21}$ are each independently an oxygen atom or a sulfur atom, and in one molecule they can be the same or different.

Wherein, $X_{11}$ is a terminal group connecting to a carbonyl group or a thiocarbonyl group, preferably a $C_{1-20}$ alkyl group, more preferably a methyl group, an ethyl group, an isopropyl group or a t-butyl group.

Wherein, $X_{12}$ is a terminal group connecting to a carbonate group or a thiocarbonate group, selected from hydrocarbyl groups with or without a phenyl ring, preferably a $C_{1-20}$ hydrocarbyl group, and more preferably a $C_{1-20}$ alkyl group, a phenylhydrocarbyl group or a phenyl group substituted with hydrocarbyl groups (a hydrocarbyl-substituted phenyl group).

Wherein, $X_5$ is a terminal monovalent group connecting to a thioxy group, and selected from a mercapto protecting group and a group $LG_2$.

When as a mercapto protecting group, $X_5$ can be any mercapto protecting group listed for $PG_2$.

Wherein, the carbon-atom number of $LG_2$ is not particularly limited, preferably from 1 to 20, and more preferably from 1 to 10.

The structure of $LG_2$ is not particularly limited, including but not limited to a linear structure, a branched structure bearing pendant groups or a ring-containing structure. Wherein, said ring is not particularly limited, including but not limited to all the above-listed cyclic structures in the terminology section.

$LG_2$ can contain heteroatoms, or do not contain heteroatoms.

$LG_2$ is a $C_{1-20}$ hydrocarbyl group, a $C_{1-20}$ heterohydrocarbyl group, a substituted $C_{1-20}$ hydrocarbyl group or a substituted heterohydrocarbyl group. Wherein, the heteroatom or group substituent within $LG_2$ is not particularly limited, including but not limited to all the above-listed substituting heteroatoms and substituting groups in the terminology section, and can be a halogen atom, a hydrocarbyl substituent, or a heteroatom-containing substituent.

$LG_2$ is more preferably a $C_{1-20}$ alkyl group, a $C_{1-20}$ unsaturated aliphatic hydrocarbyl group, an aryl group, an arylhydrocarbyl group, a $C_{1-20}$ heterohydrocarbyl group, a $C_{1-20}$ alkylthio group, a $C_{1-20}$ aliphatic-derived heterohydrocarbylthio group, an arylthio group, an arylhydrocarbylthio group, a $C_{1-20}$ aliphatic hydrocarbyl-acyl group, a $C_{1-20}$ aliphatic-derived heterohydrocarbyl-acyl group, an aryl-acyl group, a heteroaryl-acyl group, a $C_{1-20}$ hydrocarbyloxy-acyl group, a $C_{1-20}$ hydrocarbylthio-acyl group, a $C_{1-20}$ hydrocarbylamino-acyl group, a $C_{1-20}$ heterohydrocarbyloxy-acyl group, a $C_{1-20}$ heterohydrocarbylthio-acyl group and a $C_{1-20}$ heterohydrocarbylamino-acyl group, or any substituted form thereof. Wherein, said acyl group within $LG_2$ is not particularly limited, including but not limited to all the above-listed acyl groups in the terminology section, and more preferably a carbonyl group or a thiocarbonyl group. For examples, said acyl group within $LG_2$ can be a carbonyl group, a sulfonyl group, a sulfinyl group, a phosphoryl groups, a phosphiryl group, a phosphinyl group, a nitroxyl group, a nitrosyl group, a thiocarbonyl group, an imidoyl group, a thiophosphoryl group, a dithiophosphoryl group, a trithiophosphoryl group, a thiophosphiryl group, a dithiophosphiryl group, a thiophosphinyl group, a thiophosphono group, a dithiophosphono group, a thiophosphino group or the like, and preferably a carbonyl group, a thiocarbonyl group, a sulfonyl group or a sulfinyl group, and more preferably a carbonyl group, a thiocarbonyl group or a sulfonyl group.

$LG_2$ is more preferably a $C_{1-20}$ alkyl group, an aryl group, an arylalkyl group, a $C_{1-20}$ heteroalkyl group, a heteroaryl group, a heteroarylalkyl group, a $C_{1-20}$ alkylthio group, an arylthio group, an arylalkylthio group, a $C_{1-20}$ heteroalkyl thio group, a heteroarylthio group, a heteroarylalkylthio group, a $C_{1-20}$ alkylcarbonyl group, an arylcarbonyl group, an arylalkylcarbonyl group, a $C_{1-20}$ heteroalkylcarbonyl group, a heteroarylcarbonyl group, a heteroarylalkylcarbonyl group, a $C_{1-20}$ alkoxycarbonyl group, an aryloxycarbonyl group, an arylalkoxycarbonyl group, a $C_{1-20}$ (alkylthio)carbonyl group, an (arylthio)carbonyl group, an (arylalkylthio)carbonyl group, a $C_{1-20}$ alkylaminocarbonyl group, an arylaminocarbonyl group, an arylalkylaminocarbonyl group, a $C_{1-20}$ heteroalkoxycarbonyl group, a heteroaryloxycarbonyl group, a heteroarylalkoxycarbonyl group, a $C_{1-20}$ hetero(alkylthio)carbonyl group, a hetero(arylthio)carbonyl group, a hetero(arylalkylthio)carbonyl group, a $C_{1-20}$ heteroalkylaminocarbonyl group, a heteroarylaminocarbonyl group, a heteroarylalkylaminocarbonyl group, a $C_{1-20}$ alkyl-thiocarbonyl group, an aryl-thiocarbonyl group, an arylalkyl-thiocarbonyl group, a $C_{1-20}$ heteroalkyl-thiocarbonyl group, a heteroaryl-thiocarbonyl group, a heteroarylalkyl-thiocarbonyl group, a $C_{1-20}$ alkoxy-thiocarbonyl group, an aryloxy-thiocarbonyl group, an arylalkoxy-thiocarbonyl group, a $C_{1-20}$ (alkylthio)thiocarbonyl group, an (arylthio)thiocarbonyl group, an (arylalkylthio)thiocarbonyl group, a $C_{1-20}$ alkylaminothiocarbonyl group, an arylaminothiocarbonyl group, an arylalkylaminothiocarbonyl group, a $C_{1-20}$ heteroalkyloxy-thiocarbonyl group, a heteroaryloxy-thiocarbonyl group, a heteroarylalkyloxy-thiocarbonyl group, a $C_{1-20}$ hetero(alkylthio)thiocarbonyl group, a hetero(arylthio)thiocarbonyl group, a hetero(arylalkylthio)thiocarbonyl group, a $C_{1-20}$ heteroalkylaminothiocarbonyl group, a heteroarylaminothiocarbonyl group, a heteroarylalkylaminothiocarbonyl group, or any substituted form thereof.

$LG_2$ is more preferably a $C_{1-20}$ alkyl group, an aryl group, an arylalkyl group, a $C_{1-20}$ heteroalkyl group, a heteroaryl group and a heteroarylalkyl group, a $C_{1-20}$ alkylthio group, an arylthio group, an arylalkylthio group, a $C_{1-20}$ heteroalkylthio group, a heteroarylthio group, a heteroarylalkylthio group, or any substituted form thereof.

Specifically, $LG_2$ can be a methyl group, an ethyl group, an n-propyl group, an isopropyl group, a butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, an allyl group, a trityl group, a phenyl group, a benzyl group, a methylbenzyl group, a nitrobenzyl group, a t-butylthio group, a benzylthio group, a 2-pyridylthio group, an ethyl-acyl group, a benzoyl group, a methoxy-acyl group, an ethoxy-acyl group, a t-butyloxy-acyl group, a phenoxy-acyl group, a benzyloxy-acyl group, a methylthio-acyl group, an ethylthio-acyl group, a t-butylthio-acyl group, a phenylthio-acyl group, a benzylthio-acyl group, a 2-pyridyl-acyl group, a methylamino-acyl group, an ethylamino-acyl group, a t-butylamino-acyl group, a benzylamino-acyl group, the like, or any substituted form thereof. Wherein, butyl group includes but is not limited to an n-butyl group and a t-butyl group. Octyl group includes but is not limited to an n-octyl group and a 2-ethylhexyl group. Wherein, the atom or group substituent is a halogen atom, a hydrocarbyl substituent or a heteroatom-containing substituent, and preferably a fluorine atom, a chlorine atom, a bromine atom, an iodine atom or a nitro group.

$LG_2$ is further preferably a methyl group, an ethyl group, an n-propyl group, an isopropyl group, a t-butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, an allyl group, a trityl group, a phenyl group, a benzyl group, a methylbenzyl group, a nitrobenzyl group, a t-butylthio group, a benzylthio group, a 2-pyridylthio group, an acetyl group, a benzoyl group, a methoxycarbonyl group, an ethoxycarbonyl group, a t-butoxycarbonyl group, a phenoxycarbonyl group, a benzyloxycarbonyl group, a (methylthio)carbonyl group, an (ethylthio)carbonyl group, a (t-butylthio)carbonyl group, a (phenylthio)carbonyl group, a (benzylthio)carbonyl group, a 2-pyridylcarbonyl group, a methylaminocarbonyl group, an ethylaminocarbonyl group, a t-butylaminocarbonyl group, a benzylaminocarbonyl group, an ethyl-thiocarbonyl group, a phenyl-thiocarbonyl group, a methoxy-thiocarbonyl group, an ethoxy-thiocarbonyl group, a t-butyloxy-thiocarbonyl group, a phenoxy-thiocarbonyl group, a benzyloxy-thiocarbonyl group, a (methylthio)thiocarbonyl group, an (ethylthio)thiocarbonyl group, a (t-butylthio)thiocarbonyl group, a (phenylthio)thiocarbonyl group, a (benzylthio)thiocarbonyl group, a methylaminothiocarbonyl group, an ethylaminothiocarbonyl group, a t-butylaminothiocarbonyl group, a benzylaminothiocarbonyl group, a $C_{1-10}$ halohydrocarbyl group, a trifluoroacetyl group, a halophenyl group, a halobenzyl group, a nitrophenyl group, a nitrobenzyl group, the like, or any substituted form thereof. Wherein, the atom or group substituent is preferably a fluorine atom, an alkoxy group or a nitro group.

$LG_2$ is more preferably a t-butyl group, a trityl group, a phenyl group, a benzyl group, a methylbenzyl group, a t-butylthio group, a benzylthio group, a 2-pyridylthio group, a 2-pyridylcarbonyl group, a t-butoxycarbonyl group, a phenoxycarbonyl group, a benzyloxycarbonyl group, a t-butyloxy-thiocarbonyl group, a phenoxy-thiocarbonyl group, a benzyloxy-thiocarbonyl group, a (t-butylthio)thiocarbonyl group, a (phenylthio)thiocarbonyl group, a (benzylthio)thiocarbonyl group, a trifluoroacetyl group or the like.

$LG_2$ is more preferably a t-butyl group, a trityl group, a phenyl group, a benzyl group, a methylbenzyl group, a t-butylthio group, a benzylthio group, a 2-pyridylthio group or the like.

$LG_2$ is most preferably a methyl group, an ethyl group, an allyl group or a benzyl group.

Wherein, $Q_3$ is a hydrogen atom or a substituent that can favor inductive effect, conjugation effect, or both inductive and conjugation effects of electrons of unsaturated bonds.

$Q_3$ can be but not limited to any of all the above-listed substituting atoms and substituting groups in the terminology section, as long as it can favor inductive effect or/and conjugation effect.

$Q_3$ can contain carbon atoms or not. When containing no carbon atoms, for example, $Q_3$ can be a nitro group. When containing carbon atoms, the carbon-atom number is not particularly limited, preferably from 1 to 20, and more preferably from 1 to 10.

The structure of $Q_3$ is not particularly limited, including but not limited to a linear structure, a branched structure bearing pendant groups or a ring-containing structure. Wherein, said ring is not particularly limited, including but not limited to all the above-listed cyclic structures in the terminology section.

$Q_3$ can be a hydrogen atom, a halogen atom, a carbon-free substituent, a hydrocarbyl group, a heterohydrocarbyl group, a substituted hydrocarbyl group or a substituted heterohydrocarbyl group. Wherein, the heteroatom or group substituent within $Q_3$ is not particularly limited, including but not limited to all the above-listed substituting heteroatoms and substituting groups in the terminology section, and can be a halogen atom, a hydrocarbyl substituent, or a heteroatom-containing substituent.

$Q_3$ is more preferably a hydrogen atom, a halogen atom, a $C_{1-20}$ alkyl group, a $C_{2-20}$ alkenyl group, a $C_{3-20}$ open-chain alkenyl-hydrocarbyl group, a $C_{3-20}$ cycloalkenyl group, an aryl group, an arylhydrocarbyl group, a $C_{1-20}$ heteroalkyl group, a heteroaryl group, a heteroarylalkyl group (a heteroaralkyl group), a $C_{1-20}$ alkoxy group, an aryloxy group, an arylhydrocarbyloxy group, a $C_{1-20}$ heteroalkoxy group, a heteroaryloxy group, a heteroarylhydrocarbyloxy group, a $C_{1-20}$ heteroalkylthio group, a heteroarylthio group, a heteroarylhydrocarbylthio group, a $C_{1-20}$ haloalkyl group, the like, or any substituted form thereof.

$Q_3$ is more preferably a hydrogen atom, a halogen atom, a $C_{1-10}$ haloalkyl group, a $C_{1-10}$ alkyl group, a $C_{2-10}$ alkenyl group, a $C_{3-10}$ open-chain alkenyl-hydrocarbyl group, a $C_{3-10}$ cycloalkenyl group, an aryl group, an arylhydrocarbyl group, a $C_{1-10}$ heteroalkyl group, a heteroaryl group, a heteroarylalkyl group (a heteroaralkyl group), a $C_{1-10}$ alkoxy group, an aryloxy group, an arylhydrocarbyloxy group, a $C_{1-10}$ heteroalkoxy group, a heteroaryloxy group, a heteroarylhydrocarbyloxy group, the like, or any substituted form thereof.

Specifically, $Q_3$ can be a hydrogen atom, a fluorine atom, a chlorine atom, a bromine atom, an iodine atom, a methyl group, an ethyl group, an n-propyl group, an isopropyl group, a butyl group, a pentyl group, a hexyl group, a heptyl group, an octyl group (e.g., a 2-ethylhexyl group), a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, an ethenyl group, a propenyl group, an allyl group, a propynyl group, a propargyl group, a cyclopropyl group, a cyclopropenyl group, a phenyl group, a benzyl group, a butylphenyl group, a p-methylphenyl group, a nitrophenyl group, a p-methoxyphenyl group, an azaphenyl group, a methoxy group, an ethoxy group, a phenoxy group, a benzyloxy group, a methylthio group, an ethylthio group, a phenylthio group, a benzylthio group, a $C_{1-20}$ haloalkyl group, the like, or any substituted form thereof. Wherein, butyl group includes but is not limited to an n-butyl group and a t-butyl group. Octyl group includes but is not limited to an n-octyl group and a 2-ethylhexyl group. Wherein, the atom or group substituent is a halogen atom, a hydrocarbyl substituent or a heteroatom-containing substituent, and preferably a halogen atom, an alkoxy group, an alkenyl group or a nitro group.

$Q_3$ is preferably a hydrogen atom, a fluorine atom, a chlorine atom, a bromine atom, an iodine atom, a methyl group, an ethyl group, an n-propyl group, an isopropyl group, a butyl group, a pentyl group, a hexyl group, a heptyl group, an octyl group, a nonyl group, a decyl group, an ethenyl group, a propenyl group, an allyl group, a propynyl group, a propargyl group, a cyclopropyl group, a cyclopropenyl group, a phenyl group, a benzyl group, a butylphenyl group, a p-methylphenyl group, a p-nitrophenyl group, an o-nitrophenyl group, a p-methoxyphenyl group, an azaphenyl group (e.g., a pyridyl group), a methoxy group, an ethoxy group, a phenoxy group, a benzyloxy group, a methylthio group, an ethylthio group, a phenylthio group, a benzylthio group, a trifluoromethyl group, a 2,2,2-trifluoroethyl group, the like, or any substituted form thereof. Wherein, the atom or group substituent is preferably a fluorine atom, an alkoxy group, an alkenyl group or a nitro group.

$Q_3$ is more preferably a hydrogen atom, a methyl group, a trifluoromethyl group, a phenyl group, a p-nitro phenyl group, an o-nitro phenyl group, a pyridyl group or the like.

$Q_3$ is more preferably a hydrogen atom, a methyl group, a phenyl group, a pyridyl group, a diazaphenyl group or a triazaphenyl group.

$Q_3$ is more preferably a hydrogen atom, a methyl group, a phenyl group or a pyridyl group.

$Q_3$ is most preferably a hydrogen atom, a phenyl group or a pyridyl group.

Wherein, $Q_5$ is a hydrogen atom, a substituting atom (also an atom substituent) or a substituting group (also a group substituent), not particularly limited, but preferably a hydrogen atom, a methyl group, an ethyl group or a propyl group. When $Q_5$ is located at the ring, its number can be one or more. When the number is greater than one, they can have the same structure, or be a combination of two or two more different structures. The ring containing $Q_5$ includes but is not limited to fluorine, carbazole, norbornene or 7-oxabicyclo[2.2.1]hept-5-en-2-yl.

Wherein, $Q_6$ is a hydrogen atom or a methyl group. $Q_7$ is a hydrogen atom, a methyl group, a phenyl group, or a substituted phenyl group, and one example of said substituted phenyl group is a p-methoxyphenyl group. In one molecule, $Q_6$ and $Q_7$ can be identical or different from each other.

Wherein, $Q_8$ is an atom or group substituent of an imidazole group, not particularly limited, and preferably a hydrogen atom, a methyl group, an ethyl group, a propyl group, a butyl group or a phenyl group. $Q_8$ can be one or more in quantities. When the number is more than one, they can have the same structure, or be a combination of two or two more different structures.

Wherein, $Q_{11}$ is a group substituent on the nitrogen atom of a tetrazole group, and preferably a phenyl group, a substituted phenyl group or an azaphenyl group.

Wherein, $PG_2$ is a mercapto protecting group, and the protected mercapto group is represented as $SPG_2$.

Wherein, $PG_3$ is an alkynyl protecting group.

Wherein, $PG_4$ is a hydroxyl protecting group, and the protected hydroxyl group is represented as $OPG_4$.

Wherein, $PG_5$ is an amino protecting group, and the protected amino group is represented as $NPG_5$.

Wherein, $PG_6$ is a dihydroxyl protecting group, and forms an acetal structure in a five- or six-membered ring with two oxygen atoms. $PG_6$ is a methylene group or a substituted methylene group. The substituent of $PG_6$ is a hydrocarbyl substituent or a heteroatom-containing substituent, including but not limited to the following groups: a methylene group, a 1-methylmethylene group, a 1,1-dimethylmethylene group, a 1,1-cyclopentylene group, a 1,1-cyclohexylene group, a 1-phenylmethylene group, a 3,4-dimethylphenylmethylene group or the like.

Wherein, $PG_8$ is a protecting group for orthocarbonic acid or orthosilicic acid, wherein, the functional group D8 is the protected form of orthoacid, the functional group H5 is the protected form of orthosilicic acid. $PG_8$ can be an individual trivalent end-group such as

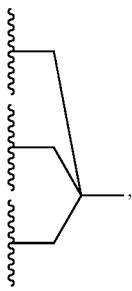 [SMILES: *CC(C)(C*)C*]

taking D8 for example, corresponding to

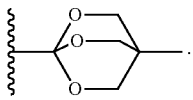.

PG₈ also can be the combination of two or three individual end-groups, e.g., corresponding to

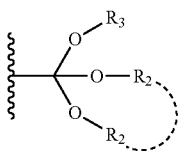

of D8 and

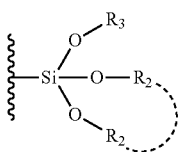

of D5.

Said PG$_2$ as a mercapto protecting group is not particularly limited. SPG$_2$ is the protected form of a mercapto group, not specifically limited, but preferably a sulfide (or a thioether), a disulfide, a silyl thioether, a thiocarboxylate (a thioester, a thioate, or —S—CS—), etc. SPG$_2$ can be but not limited to any of the following structures: a methyl sulfide, an ethyl sulfide, a propyl sulfide, a t-butyl thioether, a butyl thioether, an isobutyl thioether, a benzyl thioether, a p-methoxybenzyl thioether, an o-hydroxybenzyl thioether, a p-hydroxybenzyl thioether, an o-acetoxybenzyl thioether, a p-acetoxybenzyl thioether, a p-nitrobenzyl thioether, a 2,4,6-trimethylbenzyl thioether, a 2,4,6-trimethoxybenzyl thioether, a 4-pyridylmethyl thioether, a 2-quinolylmethyl thioether, a 2-pyridine-N-oxide-methyl thioether, a 9-anthracenemethyl thioether, a 9-fluorenylmethyl thioether, a S-ferrocenylmethyl ether, a diphenylmethyl thioether, a triphenylmethyl thioether (a trityl thioether), a bis(4-methoxyphenyl)methyl thioether, a bis(4-methoxyphenyl) benzyl thioether, a 5-dibenzosuberyl thioether, a diphenyl-4-pyridylmethyl thioether, a 2,4-dinitrophenyl thioether, a 1-adamantyl thioether, a methoxymethyl thioether, an isobutoxymethyl thioether, a benzyloxymethyl thioether, a 2-tetrahydrofuranyl thioether, benzylthiomethyl thioether, a phenylthiomethyl thioether, a tetrahydrothiazolo thioether, an acetamidomethyl thioether, a trimethylacetamidomethyl thioether, a benzamidomethyl thioether (a benzoylaminomethyl thioether), an allyloxycarbonylaminomethyl thioether, a phenylacetamidomethyl thioether, a phthalimidomethyl thioether, an acetylmethyl thioether, a (2-nitrophenyl)ethyl thioether, a 2-(2,4-dinitrophenyl)ethyl thioether, a 2(4'-pyridyl)ethyl thioether, a 2-cyanoethyl thioether, a 2-(trimethylsilyl)ethyl thioether, a 2,2-bis(ethoxycarbonyl)ethyl thioether, a 2-phenylsulphonylethyl thioether, a 1-(4-methylphenylsulphonyl)-2-methyl-2-propyl thioether, an acetyl thioester, a benzoyl thioester, a trifluoroacetyl thioester, an N-[[p-biphenylyl)isopropyloxy]carbonyl]-N-methyl-γ-aminothiobutyryl thioester, an N-[(t-butyloxy)carbonyl]-N-methyl-γ-aminothiobutyryl thioester, a 2,2,2-trichloroethoxycarbonyl thiocarbonate, a t-butyloxycarbonyl thiocarbonate, a benzyloxycarbonyl thiocarbonate, a p-methoxybenzyloxycarbonyl thiocarbonate, an N-ethyl carbamate, an N-methoxymethyl carbamate, an ethyl disulfide, a t-butyl disulfide, a substituted phenyl disulfide and a 2-pyridyl disulfide.

Said SPG$_2$ is preferably a t-butyl thioether, a triphenylmethyl thioether, a substituted triphenylmethyl thioether, a t-butyldimethylsilyl thioether, a triisopropylsilyl thioether, a benzyl thioether, a substituted benzyl thioether, a p-nitrobenzyl thioether, an o-nitrobenzyl thioether, an acetyl thioester, a benzoyl thioester, a trifluoroacetyl thioester, a t-butyl disulfide, a substituted phenyl disulfide, a 2-pyridyl disulfide or the like.

Said PG$_3$ is an alkynyl protecting group, not particularly limited, and preferably a silyl group. PG$_3$ includes but is not limited to the following structures: a trimethylsilyl group, a triethylsilyl group, a t-butyldimethylsilyl group, a dimethyl (1,1,2-trimethylpropypsilyl group, a dimethyl[1,1-dimethyl-3-(tetrahydro-pyran-2H-2-yloxy)propyl]silyl group, a biphenyldimethylsilyl group, a triisopropylsilyl group, a biphenyldiisopropylsilyl group, a t-butyldiphenylsilyl group, a 2-(2-hydroxyl) propylsilyl and the like.

Said PG$_4$ is a hydroxyl protecting group, not particularly limited, and can protect an alcoholic hydroxyl group or a phenolic hydroxyl group. OPG$_4$ is the protected form, not specifically limited, preferably an ether, a silyl ether, an ester, a carbonate, a sulfonate, or the like. OPG$_4$ includes but is limited to the following structures: a methyl ether, a methoxymethyl ether, a methylthiomethyl ether, a (phenyldimethylsilyl)methoxymethyl ether, a benzyloxymethyl ether, a p-methoxybenzyloxymethyl ether, a p-nitrobenzyloxymethyl ether, an o-nitrobenzyloxymethyl ether, a (4-methoxybenzyloxy)methyl ether, an o-methoxyphenol methyl ether, a t-butoxymethyl ether, a 4-pentenyloxymethyl ether, a siloxymethyl ether, a 2-methoxyethoxymethyl ether, a 2,2,2-trichloroethoxymethyl ether, a bis(2-chloroethoxy) methyl ether, a 2-(trimethylsilyl)ethoxymethyl ether, a methoxymethyl ether, a tetrahydropyranyl ether, a 3-bromotetrahydropyranyl ether, a 1-methoxycyclohexyl ether, a 4-methoxytetrahydropyranyl-cyclohexyl ether, a 4-methoxytetrahydrothiopyranyl-cyclohexyl ether, a S,S-dioxo-4-methoxytetrahydrothiopyranyl ether, a 1-[(2-chloro-4-methyl)phenyl]-4-methoxypiperidin-4-yl ether, a 1-(2-fluorophenyl)-4-methoxypiperidin-4-yl ether, a 1,4-dioxan-2-yl ether, a tetrahydrofuranyl ether, a tetrahydrothiofuranyl ether, an ethoxy ether, a 1-ethoxyethyl ether, a 1-(2-chloroethoxy)ethyl ether, a 1-[2-(trimethylsilyl)ethoxy]ethyl ether, a 1-methyl-1-methylethyl ether, a 1-methyl-1-benzylethyl ether, a 1-methyl-1-benzyl-2-fluoroethyl ether, a 1-methyl-1-phenoxyethyl ether, a 2,2,2-trichloroethyl ether, a 1,1-dimethoxyphenyl-2,2,2-trichloroethyl ether, a 1,1,1,3,3,3-hexafluoro-2-phenylisopropyl ether, a 2-(trimethylsilyl)

ethyl ether, a 2-(benzylthio)ethyl ether, a 2-phenylselenyl ether, a t-butyl ether, an allyl ether, a propargyl ether, a p-chlorophenyl ether, a p-methoxyphenyl ether, a p-nitrophenyl ether, a 2,4-dinitrophenyl ether, a 2,3,5,6-tetrafluoro-4-(trifluoromethyl)phenyl ether, a benzyl ether, a p-methoxybenzyl ether, a 3,4-dimethoxybenzyl ether, an o-nitrobenzyl ether, a p-nitrobenzyl ether, a p-bromobenzyl ether, a p-chlorobenzyl ether, a 2,6-dichlorobenzyl ether, a p-cyanobenzyl ether, a p-phenylbenzyl ether, a 2,6-difluorobenzyl ether, a p-acetamidobenzyl ether, a p-azidobenzyl ether, a 2-trifluoromethylbenzyl ether, a p-(methylsulfinyl) benzyl ether, a 2-pyridylmethyl ether, a 4-pyridylmethyl ether, a 3-methyl-2-pyridylmethyl-N-oxide ether, a 2-quinolylmethyl ether, a 1-pyrenylmethyl ether, a diphenylmethyl ether, a 5-dibenzosuberyl ether, a triphenylmethyl ether, an α-naphthyldiphenylmethyl ether, a p-methoxyphenyldiphenylmethyl ether, a di(p-nitrophenyl)methyl ether, a tri(p-methoxyphenyl)methyl ether, a 4-(4'-bromophenacyloxy)phenyldiphenylmethyl ether, a 4,4'4"-tri(4,5-dichlorophthalimidophenyl)methyl ether, a 4,4'4"-tri(levulinylphenyl)methyl ether, a 4,4'4"-tri(benzoylphenyl)methyl ether, a 4,4'-(dimethoxy-3"-N-imidazolylmethyl)trityl ether, a 4,4'-(dimethoxy-3"-[N-(imidazolylethyl)carbamoyl]trityl ether, a 1,1'-bis(4-methoxyphenyl)-1'-pyrenylmethyl ether, a 4-(17-tetrabenzo[a,c,g,i]fluorenylmethyl)-4,4'-dimethoxytrityl ether, a 9-anthryl ether, a 9-(9-phenyl-10-oxo)anthryl ether, a [1,3-benzodithiolan-2-yl] ether, a S,S-dioxo-benzisothiazolyl ether, a trimethylsilyl ether, a triethylsilyl ether, a triisopropylsilyl ether, a dimethylisopropylsilyl ether, a diethylisopropylsilyl ether, a 1,1,2-trimethylpropyldimethylsilyl ether, a t-butyldimethylsilyl ether, a t-butyldiphenylsilyl ether, a tribenzylsilyl ether, a tri-(p-methylbenzyl)silyl ether, a triphenylsilyl ether, a diphenylmethylsilyl ether, a di-t-butylmethylsilyl ether, a tri(trimethylsilyl)silyl ether, a (2-hydroxystyryl)dimethylsilyl ether, a 2-hydroxystyryldiisopropylsilyl ether, a t-butylmethoxyphenylsilyl ether, a t-butoxydiphenylsilyl ether, a formate, a benzoylformate, an acetate, a chloroacetate, a dichloroacetate, a trichloroacetate, a trifluoroacetate, a methoxyacetate, a triphenylmethoxyacetate, a phenoxyacetate, a p-chlorophenoxyacetate, a phenylacetate, a diphenylacetate, a nicotinate, a 3-phenylpropionate, a 4-pentenoate, a 4-levulinate, a 4,4-(ethylenedithio)pentanoate, a 5-[3-bis(4-methoxyphenyl)hydroxymethylphenoxy]levulinate, a pivalate, a 1-adamantylformate, a crotonate, a 4-methoxycrotonate, a benzoate, a p-phenylbenzoate, a 2,4,6-trimethylphenylbenzoate, an alkylmethyl carbonate, a methoxymethylcarbonate, a 9-fluorenylmethyl carbonate, an alkylethyl carbonate, a 2,2,2-trichloroethyl carbonate, a 1,1-dimethyl-2,2,2-trichloroethyl carbonate, a 2-(trimethylsilyl)ethyl carbonate, a 2-(phenylsulfonyl)ethyl carbonate, a 2-(triphenylphosphonio)ethyl carbonate, an isobutyl carbonate, a vinyl carbonate, an allylcarbonate, a p-nitrophenyl carbonate, a p-methoxybenzyl carbonate, a 3,4-dimethoxybenzyl carbonate, an o-nitrobenzyl carbonate, a p-nitrobenzyl carbonate, a 2-dansylethyl carbonate, a 2-(4-nitrophenyl)ethyl carbonate, a 2-(2,4-dinitrophenyl)ethyl carbonate, a 2-cyano-1-phenylethyl carbonate, a S-benzyl thiocarbonate, a 4-ethoxy-1-naphthyl carbonate, a methyl dithiocarbonate, 2-iodobenzoate, a 4-azidobutyrate, a 4-nitro-4-methylpentanoate, an o-(dibromomethyl)benzoate, a 2-formylbenzensulfonate, a 2-(methylthiomethoxy)ethyl carbonate, a 4-(methylthiomethoxy)butyrate, a 2-(methylthiomethoxymethyl)benzoate, a 2-(chlorohexanoyloxymethyl)benzoate, a 2-[2-(chloroacetyloxy)ethyl]benzoate, a 2-[2-(benzyloxy) ethyl]benzoate, a 2-[2-(4-methoxybenzyloxy)ethyl]benzoate, a 2,6-dichloro-4-methylphenoxyacetate, a 2,6-dichloro-4-(1,1,3,3-tetramethylbutyl)phenoxyacetate, a 2,4-di(1,1-dimethylpropyl)phenoxyacetate, a chlorodiphenylacetate, an isobutyrate, a monosuccinate, a (E)-2-methyl-2-butenoate, an o-(methoxycarbonyl)benzoate, a α-naphthoate, a nitrate, a N,N,N',N'-tetramethylphosphorodiamidate, a 2-chlorobenzoate, a 4-bromobenzoate, a 4-nitrobenzoate, a 3'-5'-dimethoxybenzoin carbonate, an N-phenyl carbamate, a borate, a dimethyl thiophosphinate, a 2,4-dinitrophenylsulfinate, a sulfate, an allylsulfonate, a methylsulfonate, a benzylsulfonate, a p-methylsulfonate, a 2-(4-nitrophenylethyl)sulfonate, and the like.

Said $OPG_4$ is preferably a methyl ether, a 1-ethoxyethyl ether, a t-butyl ether, an allyl ether, a benzyl ether, a p-methoxybenzyl ether, an o-nitrobenzyl ether, a p-nitrobenzyl ether, a 2-trifluoromethylbenzyl ether, a methoxymethyl ether, a 2-methoxyethoxymethyl ether, a benzyloxymethyl ether, a p-methoxybenzyloxymethyl ether, a (methylthio)methyl ether, a tetrahydropyranyl ether, a trimethylsilyl ether, a triethylsilyl ether, a triisopropylsilyl ether, a t-butyldimethylsilyl ether, an acetate, a chloroacetate, a trifluoroacetate, a carbonate or the like.

Said $PG_5$ is an amino protecting group, not particularly limited, and can protect a primary amine, a secondary amine, a hydrazine and the like. $NPG_5$ is protected form, not specifically limited, but preferably a carbamate, an amide, an imide, an N-alkyl amine, an N-aryl amine, an imine, an enamine, an imidazole, a pyrrole, an indole, or the like. Examples of $NPG_5$ include but are not limited to the following structures: a methyl carbamate, an ethyl carbamate, a 9-fluorenylmethyl carbamate, a 9-(2-sulfo)fluorenylmethyl carbamate, a 9-(2,7-dibromo)fluorenylmethyl carbamate, a 17-tetrabenzo[a,c,g,i]fluorenylmethyl carbamate, a 2-chloro-3-indenylmethyl carbamate, a 1,1-dioxobenzo[b]thiophene-2-ylmethyl carbamate, a 2,2,2-trichloroethyl carbamate, a 2-(trimethylsilyl)ethyl carbamate, a 2-phenylethyl carbamate, a 1,1-dimethyl-2-chloroethyl carbamate, a 1,1-dimethyl-2-bromoethyl carbamate, a 1,1-dimethyl-2-fluoroethyl carbamate, a 1,1-dimethyl-2,2-dibromoethyl carbamate, a 1,1-dimethyl-2,2,2-trichloroethyl carbamate, a 1-methyl-1-(4-biphenyl)-1-methylethyl carbamate, a 1-(3,5-di-t-butylphenyl)-1-methylethyl carbamate, a 2-(2',4'-pyridyl)ethyl carbamate, a 2,2-bis(4'-nitrophenyl)ethyl carbamate, an N-(2-pivalamido)-1,1-dimethylethyl carbamate, a 2-[(2-nitrophenyl)dithio]-1-phenylethyl carbamate, a 2-(N,N-dicyclohexylcarboxamido)ethyl carbamate, a t-butyl carbamate, a 1-adamantyl carbamate, a 2-adamantyl carbamate, a vinyl carbamate, an allyl carbamate, a 1-isopropylallyl carbamate, a cinnamyl carbamate, a 4-nitrocinnamyl carbamate, a 3-(3'-pyridyl)allyl carbamate, an 8-quinolyl carbamate, an N-hydroxypiperidinyl carbamate, a methyl dithiocarbamate, an ethyl dithiocarbamate, a t-butyl dithiocarbamate, an isopropyl dithiocarbamate, a phenyl dithiocarbamate, a benzyl carbamate, a p-methoxybenzyl carbamate, a p-nitrobenzyl carbamate, a p-bromobenzyl carbamate, a p-chlorobenzyl carbamate, a 2,4-dichlorobenzyl carbamate, a 4-methylsulfinylbenzyl carbamate, a 9-anthrylmethyl carbamate, a diphenylmethyl carbamate, a 2-methylthioethyl carbamate, a 2-methylsulfonylethyl carbamate, a 2-(p-toluenesulfonyl)ethyl carbamate, a [2-(1,3-dithianyl)]methyl carbamate, a 4-methylthiophenyl carbamate, a 2,4-dimethylthiophenyl carbamate, a 2-phosphonioethyl carbamate, a 1-methyl-1-(triphenylphosphonio)ethyl carbamate, a 1,1-dimethyl-2-cyanoethyl carbamate, a 2-dansylethyl carbamate, a 2-(4-nitrophenyl)ethyl carbamate, a 4-phenylacetoxybenzyl carbamate, a 4-azidomethoxybenzyl carbamate, a p-(dihydroxyboryl)benzyl carbamate, a 5-benzisoxazolylmethyl carbamate, a 2-(trifluoromethyl)-6-chromonylmethyl carbamate, an m-nitrophenyl carbamate, a 3,5-dimethylbenzyl carbamate, a 1-methyl-1-(3,5-dimethoxyphenyl)ethyl carbamate, an α-methylnitropiperonyl carbamate, an o-nitrobenzyl carbamate, a 3,4-dimethoxy-6-nitro-benzyl carbamate, an o-nitrophenylmethyl carbamate, a 2-(2-nitrophenyl)ethyl carbamate, a 6-nitro-3,4-dimethoxybenzyl carbamate, a 4-methoxybenzoylmethyl carbamate, a 3',5'-dimethoxybenzoin carbamate, a t-amyl carbamate, a S-benzyl thiocarbamate, a butynyl carbamate, a p-cyanobenzyl carbamate, a cyclobutyl carbamate, a cyclohexyl carbamate, a cyclopentyl carbamate, a cyclopropylmethyl carbamate, a diisopropyl carbamate, a 2,2-methoxycarbonylvinyl carbamate, an o-(N,N'-dimethylcarboxamido)propyl carbamate, a 1,1-dimethylpropynyl carbamate, a di(2-pyridyl)methyl carbamate, a 2-furylmethyl carbamate, a 2-iodoethyl carbamate, an isobornyl carbamate, an isonicotinyl carbamate, a p-(p-methoxyphenylazo)benzyl carbamate, a 1-methylcyclobutyl carbamate, a 1-methylcyclohexyl carbamate, a 1-methyl-1-cyclopropylmethyl carbamate, a 1-methyl-1-(p-phenylazophenyl)ethyl carbamate, a 1-methyl-1-phenylethyl carbamate, a 1-(4'-pyridyl)ethyl carbamate, a phenyl carbamate, a p-phenylazobenzyl carbamate, a 2,4,6-tri-t-butylphenyl carbamate, a 4-(trimethylamino)benzyl carbamate, a 2,4,6-trimethylbenzyl carbamate, a formamide, an acetamide, a chloroacetamide, a trichloroacetamide, a trifluoroacetamide, a phenylacetamide, a 3-phenylpropylamide, a 4-pentenylamide, a 2-pyridylamide, a 3-pyridylamide, a benzamide, a p-phenylbenzamide, an o-nitrophenylacetamide, an o-nitrophenoxyacetamide, a 3-(o-nitrophenyl)propionamide, a 2-methyl-2-(o-nitrophenoxy)propionamide, a 3-methyl-3-nitrobutyramide, an o-nitro-cinnamamide, an o-nitrobenzamide, a 2,2-dimethyl-3-(4-t-butyl-2,6-dinitrophenyl)propionamide, an o-(benzoyloxymethyl)benzamide, a (2-acetoxymethyl)benzamide, a 2-[(tert-butyldiphenylsilyloxy)methyl]benzamide, a 3-(3',6'-dioxo-2',3',5'-trimethylcyclohexa-1',4'-diene)-3,3-dimethylpropanamide; an o-hydroxy-trans-cinnamamide, a 2-methyl-2-(p-phenylazophenoxy)propionamide, a 4-chlorobutyramide, an acetylacetamide, a 3-(p-hydroxyphenyl)propionamide, a (N'-dithiobenzyloxycarbonylamino)acetamide, a phthalimide, a tetrachlorophthalimide, a 4-nitrophthalimide, a dithiasuccinimide, a 2,3-diphenylmaleimide, a 2,5-dimethylpyrrole, a 2,5-bis(triisopropylsilyloxy)pyrrole, a 1,1,4,4-tetramethyldisilylaza-cyclopentane, a 1,1,3,3-tetramethyl-1,3-disilaisoindoline, a 5-substituted-1,3-dimethyl-1,3,5-triazacyclopentan-2-one, a 5-substituted-1,3-dibenzyl-1,3,5-triazacyclopentan-2-one, a 1-substituted 3,5-dinitro-4-pyridone, a 1,3,5-dioxazine, a methylamine, a tert-butylamine, an allylamine, a [2-(trimethylsilyl)ethoxy]methylamine, a 3-acetoxypropylamine, a cyanomethylamine, an (1-isopropyl-4-nitro-2-oxo-3-pyrrolin-yl)amine, a 2-azanorbornenylamine, a 2,4-dinitrophenylamine, a quaternary ammonium salt, a benzylamine, a 4-methoxybenzylamine, a 2,4-dimethoxybenzylamine, a 2-hydroxylbenzylamine, a diphenylmethylamine, a bis(4-methoxyphenyl)methylamine, a 5-dibenzosuberylamine, a triphenylmethylamine, a (4-methoxyphenyl)diphenylmethylamine, a 9-phenylfluorenylamine, a ferrocenylmethylamine, a 2-pyridylmethylamine-N'-oxide, a 1,1-dimethylthiomethyleneamine, a benzylimine, a p-methoxybenzylimine, a diphenylmethyleneamine, a [(2-pyridyl)trimethylphenyl]methyleneamine (or a trimethylphenyl-pyridine-2-methyleneamine), a N',N'-dimethylaminomethyleneamine, a N',N'-dibenzylaminomethyleneamine, a N'-t-butylaminomethyleneamine, an isopropylenediamine, a p-nitrobenzylimine, a salicylaldimine, a 5-chlorosalicylaldimine, a (5-chloro-2-hydroxyphenyl) benzylimine, a cyclohexylimine, a t-butylmethyleneamine, an N-(5,5-dimethyl-3-oxo-1-cyclohexenyl)amine, an N-2,7-dichloro-9-fluorenylmethylamine, an N-1-(4,4-dimethyl-2, 6-dioxocyclohex-1-ylidene)ethylamine, an N-4,4,4-trifluoro-3-oxo-1-butenylamine, an N-(1-isopropyl-4-nitro-2-oxo-3-pyrrolin-3-yl)amine and the like.

The above-mentioned $NPG_5$ as a structure of protected amino group is preferably a formamide, an acetamide, a trifluoroacetamide, a t-butyl carbamate, a 2-iodoethyl carbamate, a benzyl carbamate, a 9-fluorenylmethyl carbamate, a 2-trimethylsilylethyl carbamate, a 2-methylsulfonylethyl carbamate, a 2-(p-toluenesulfonyl)ethyl carbamate, a phthalimide, a diphenylmethyleneamine, a 1,3,5-dioxazine, a methylamine, a triphenylmethylamine, a t-butylamine, an allylamine, a benzylamine, a 4-methoxybenzylamine, a benzylimine or the like.

1.1.3.3. Examples of $Z_1$-Containing Functional Groups and Protected Forms Thereof $Z_1$ is a divalent linking group, and will be defined in detail hereafter. For example, $-(Z_1)_{q1}-R_{O1}$ can be but not limited to any structure from any of the following groups from Group A to Group H:

Group A:

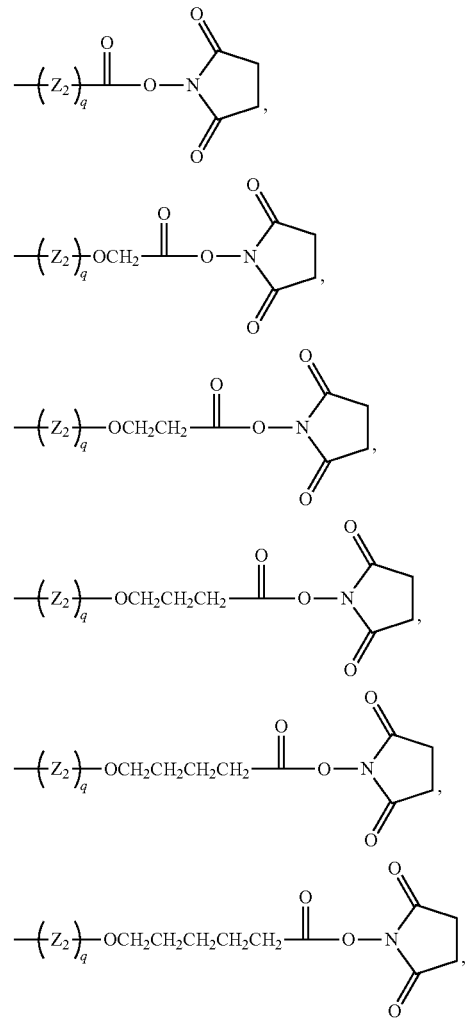

161
-continued
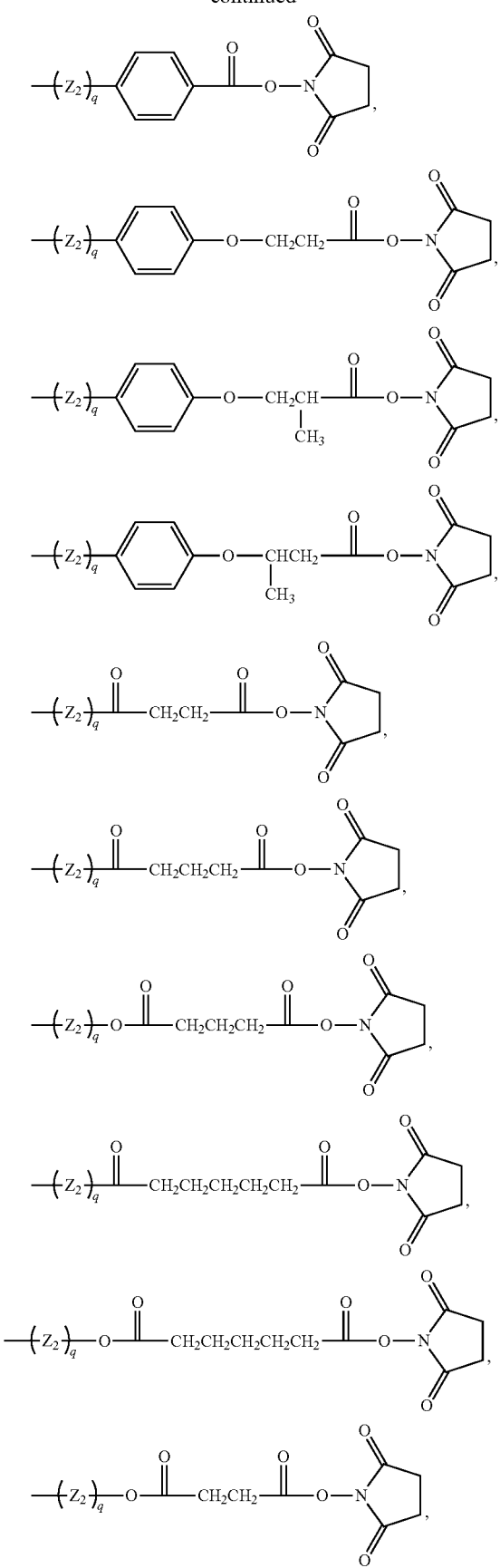
162
-continued
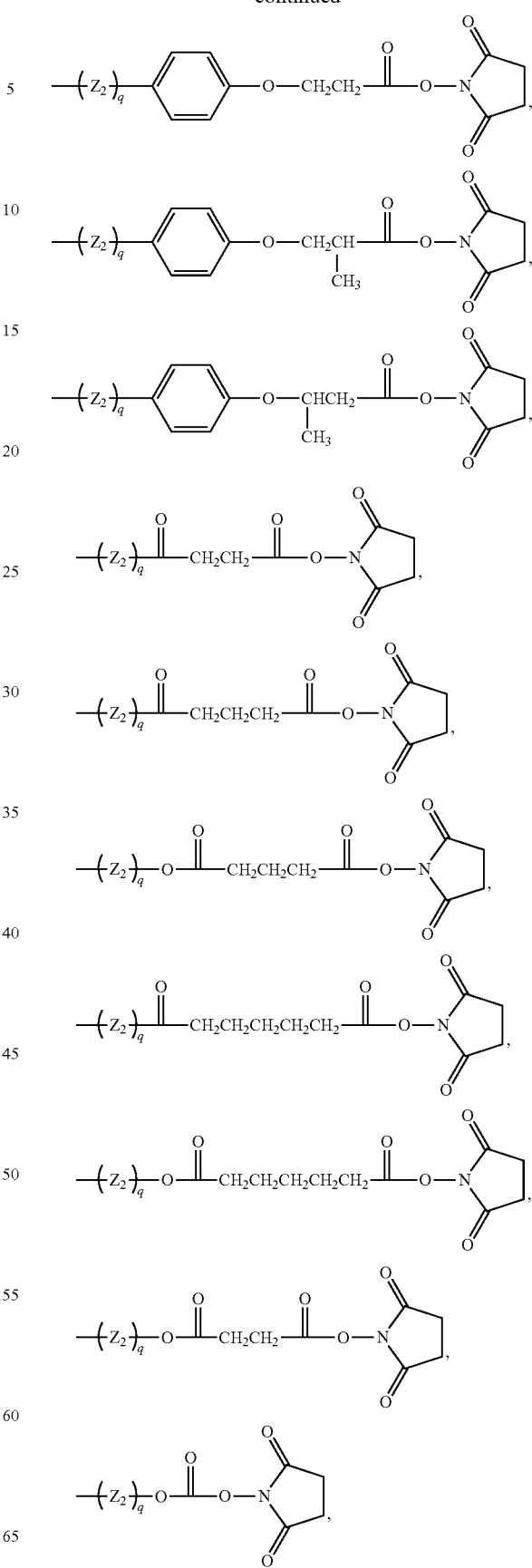

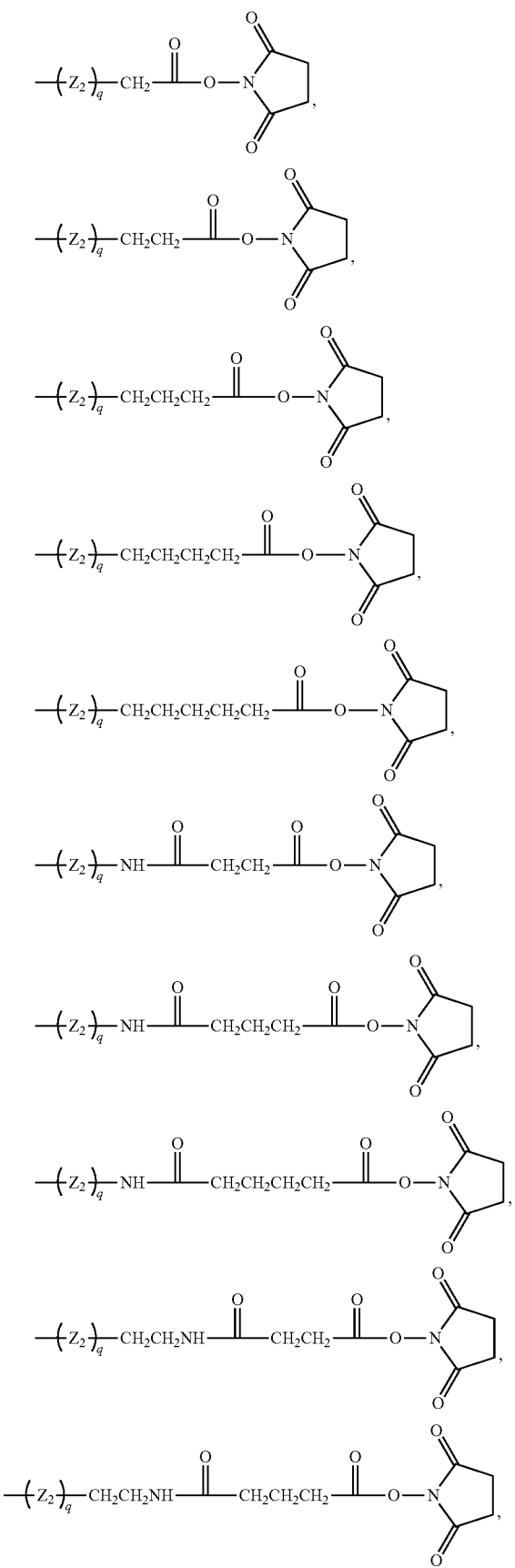
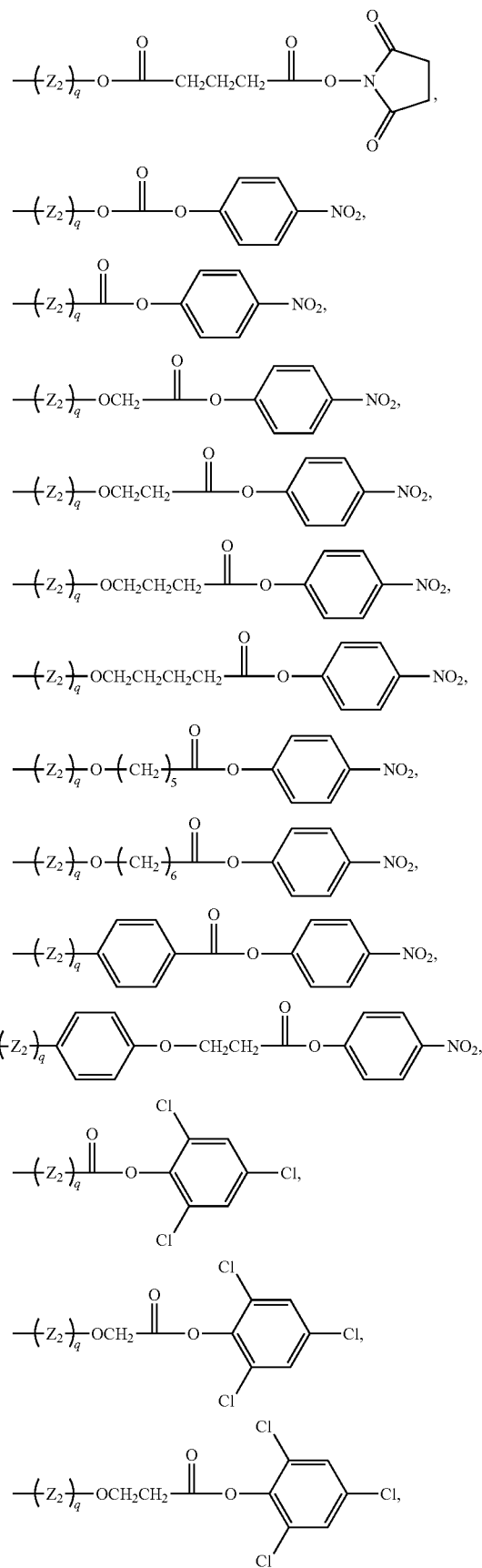

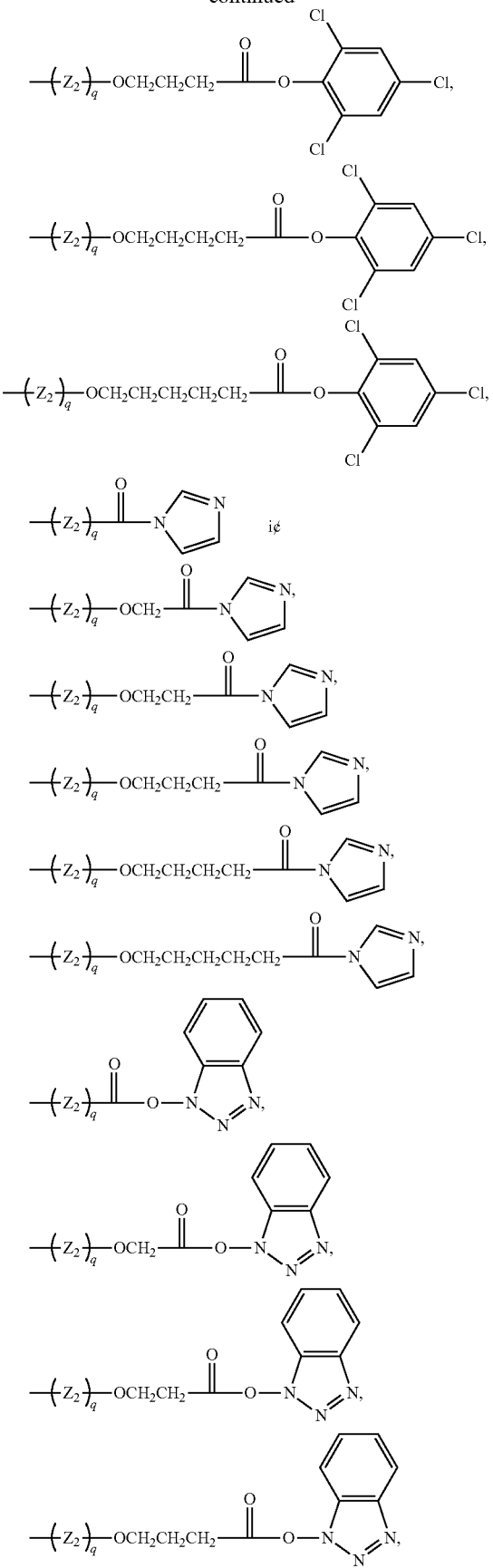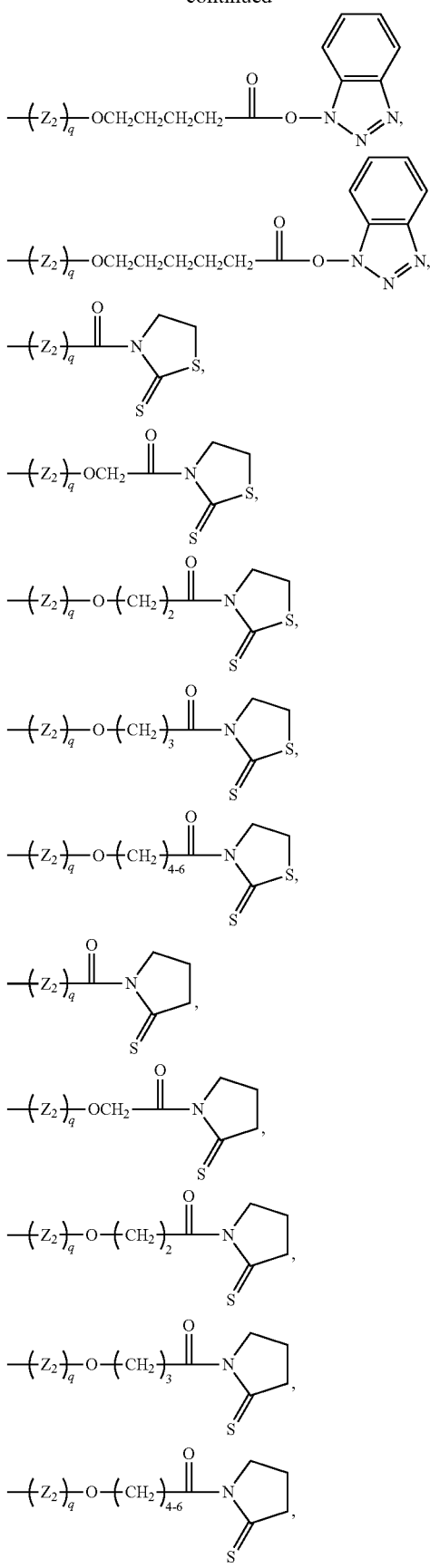

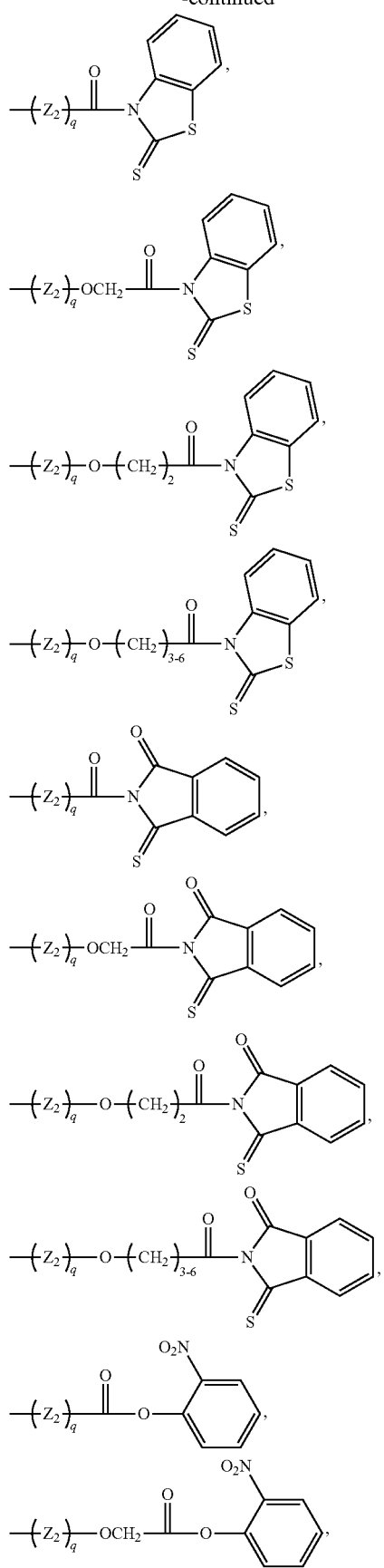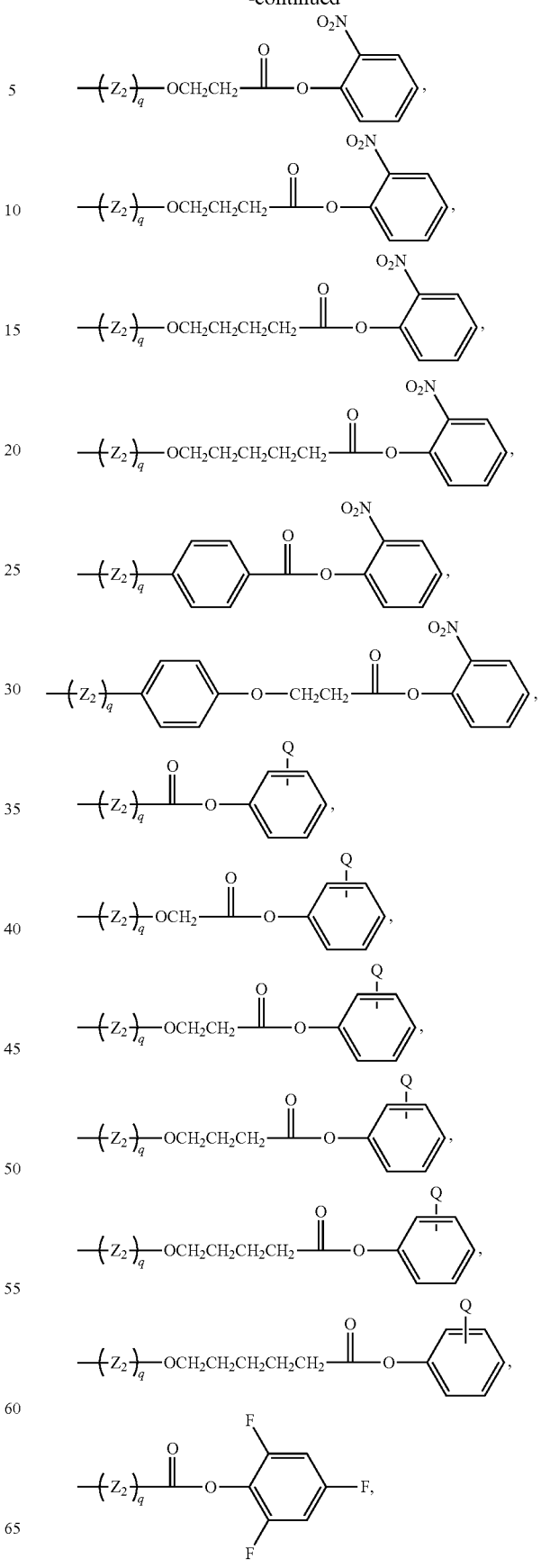

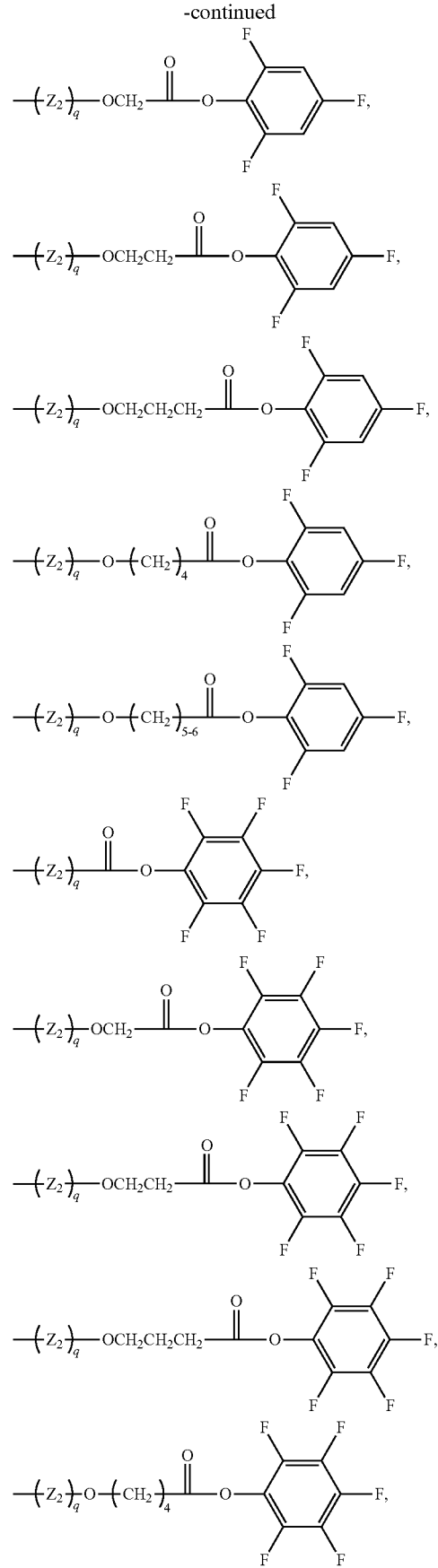
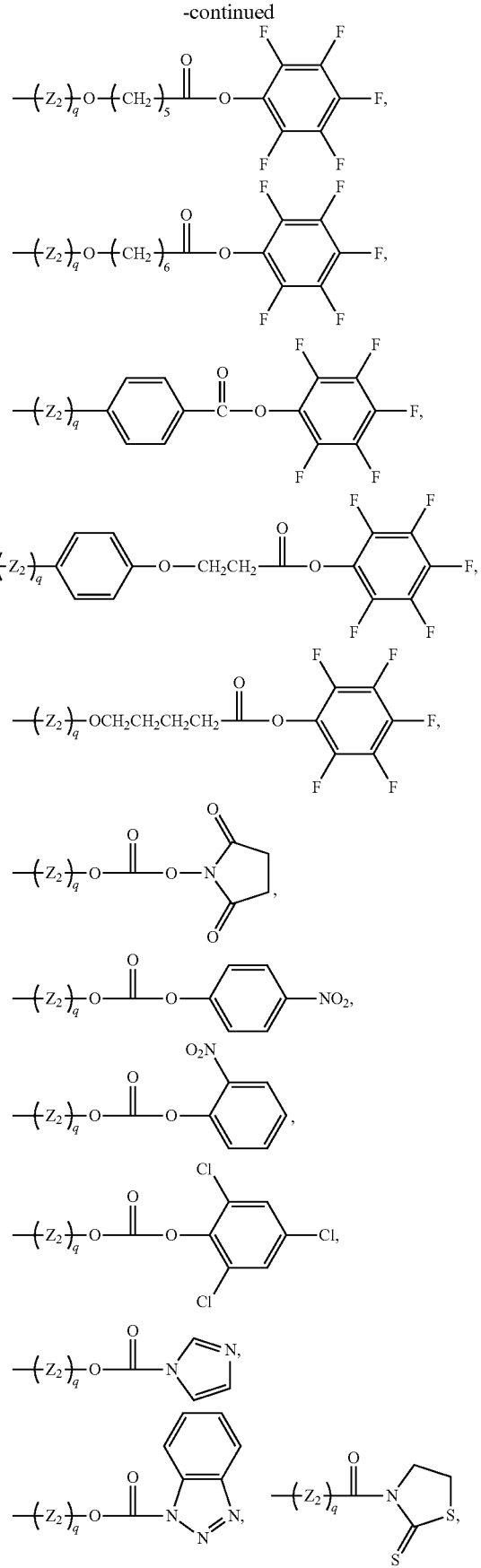

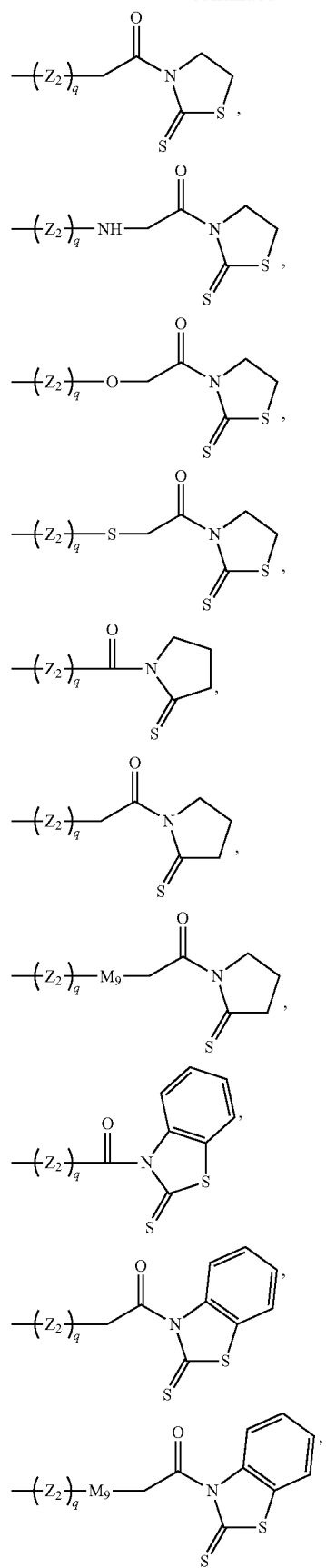
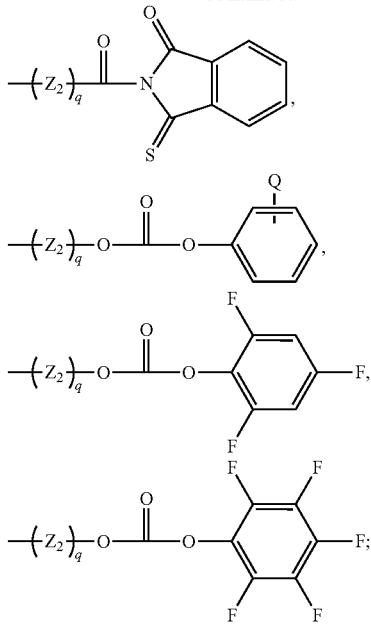
Group B:
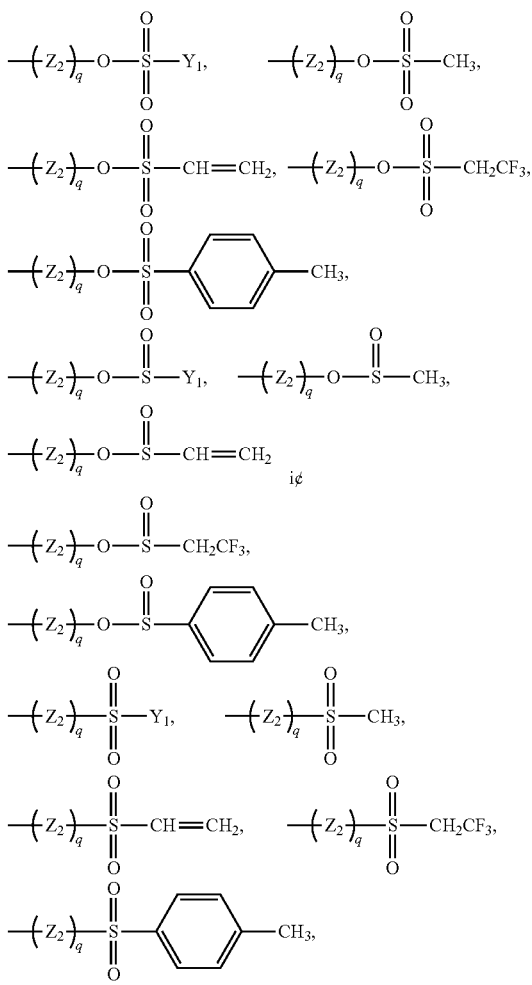

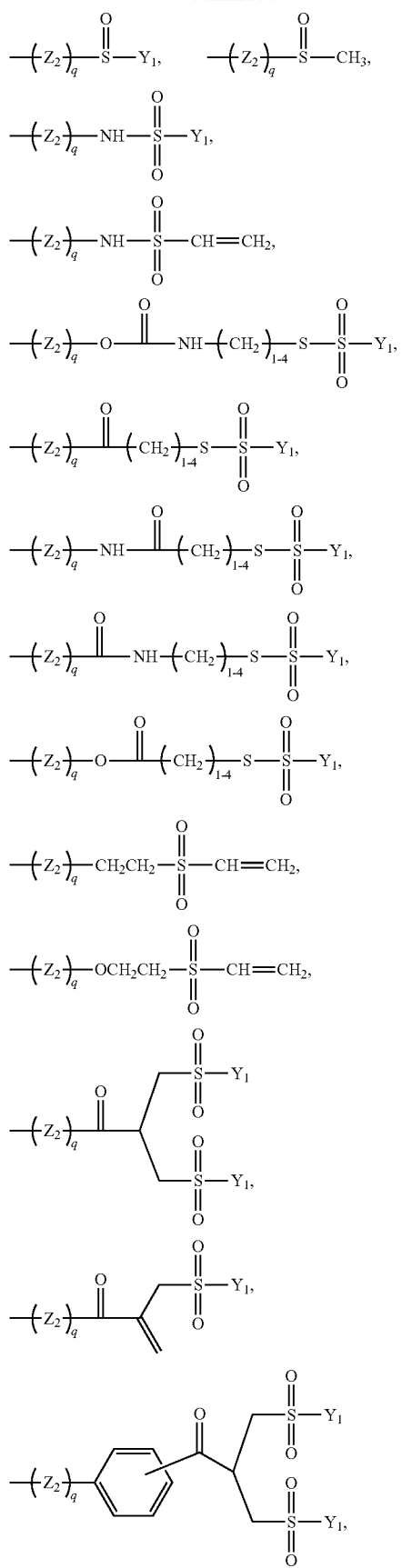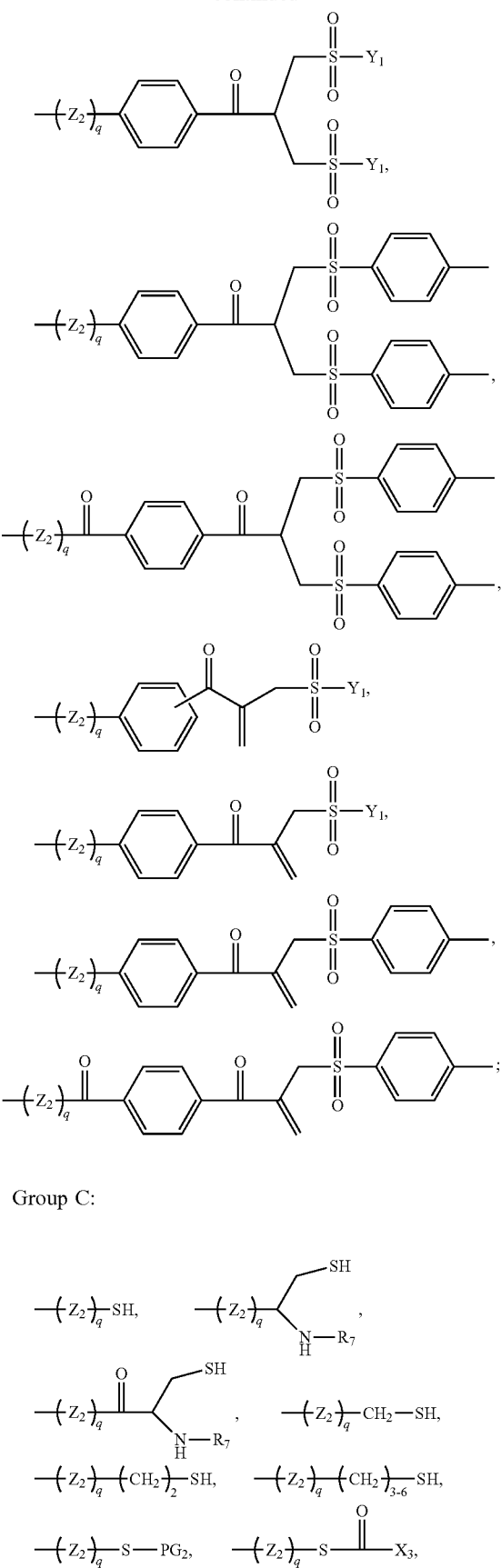
Group C:

-continued
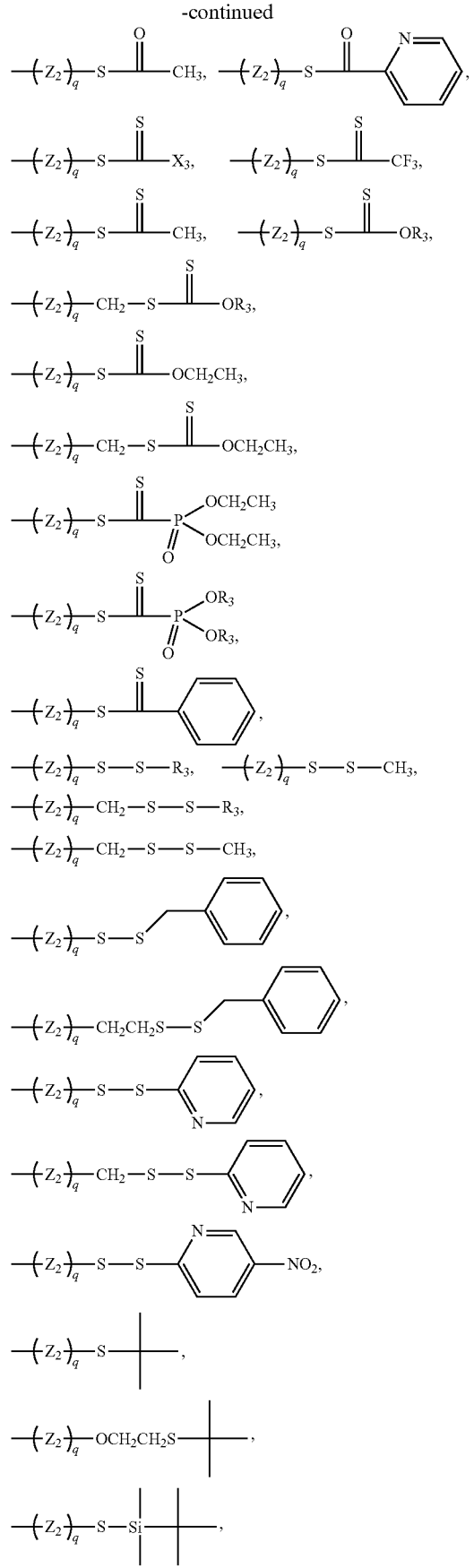
-continued
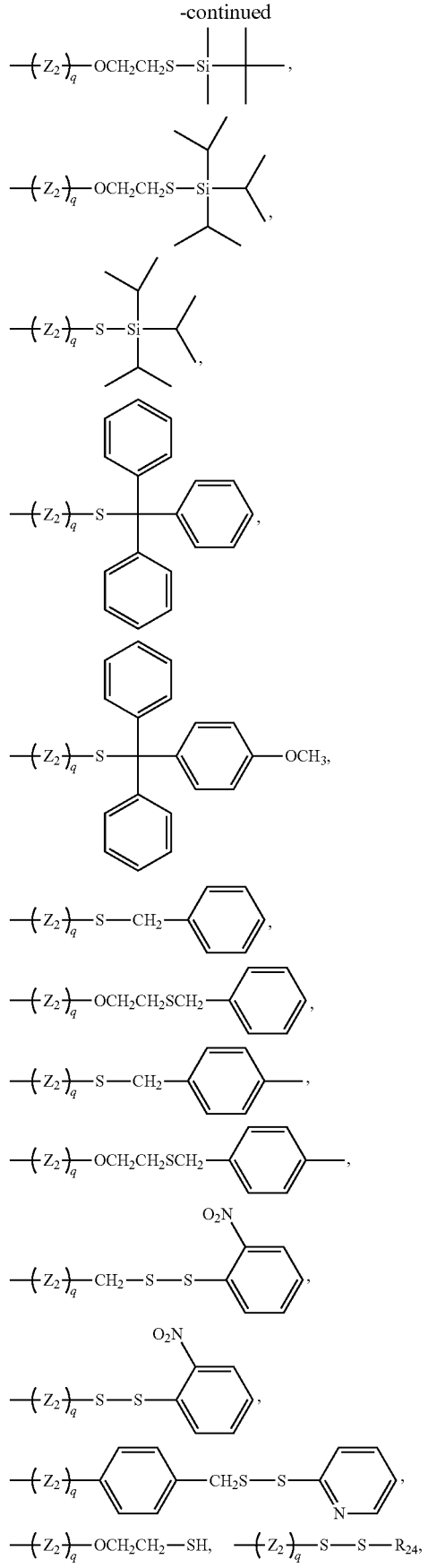

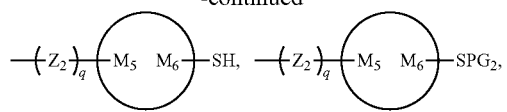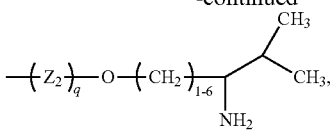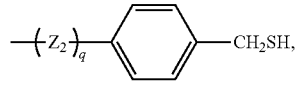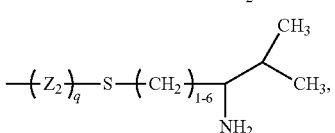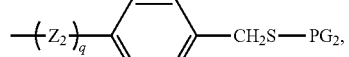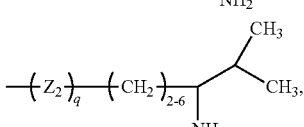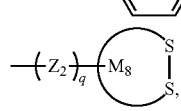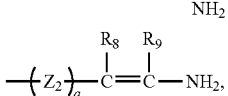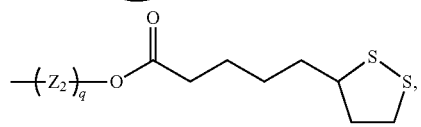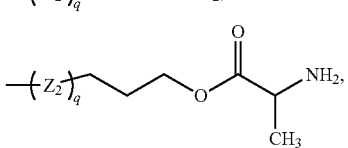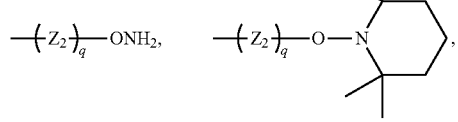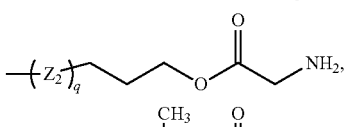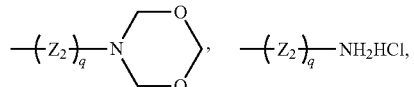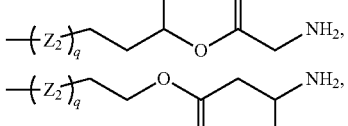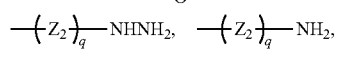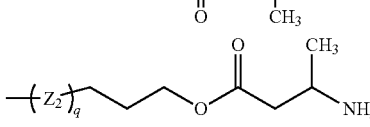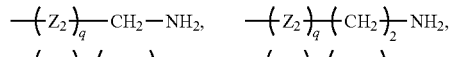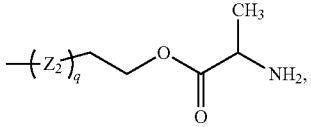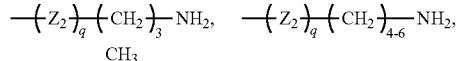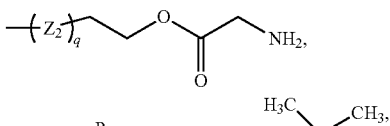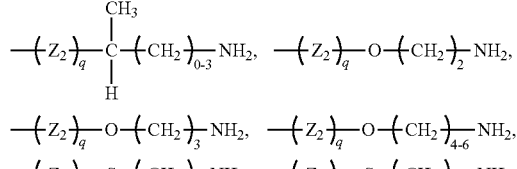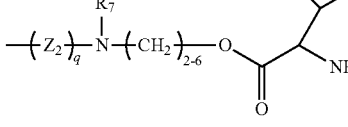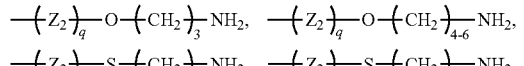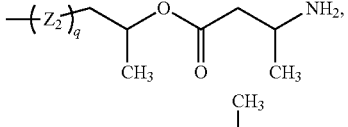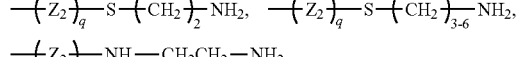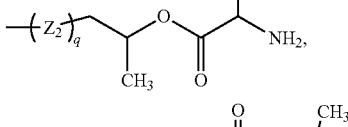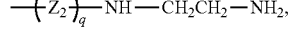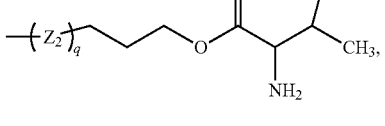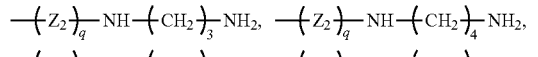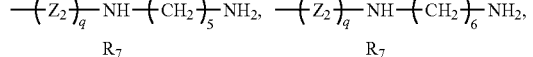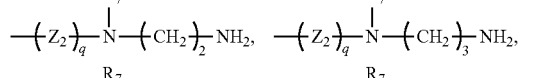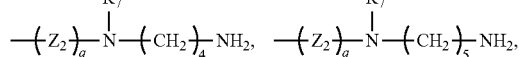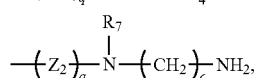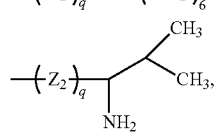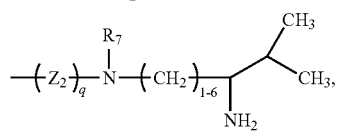

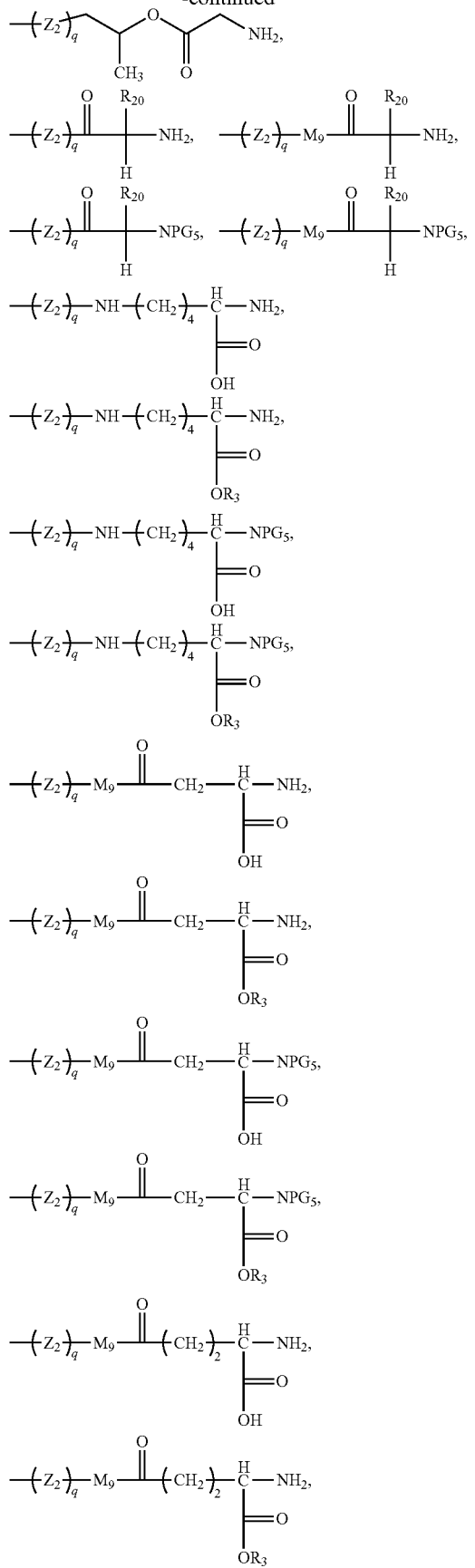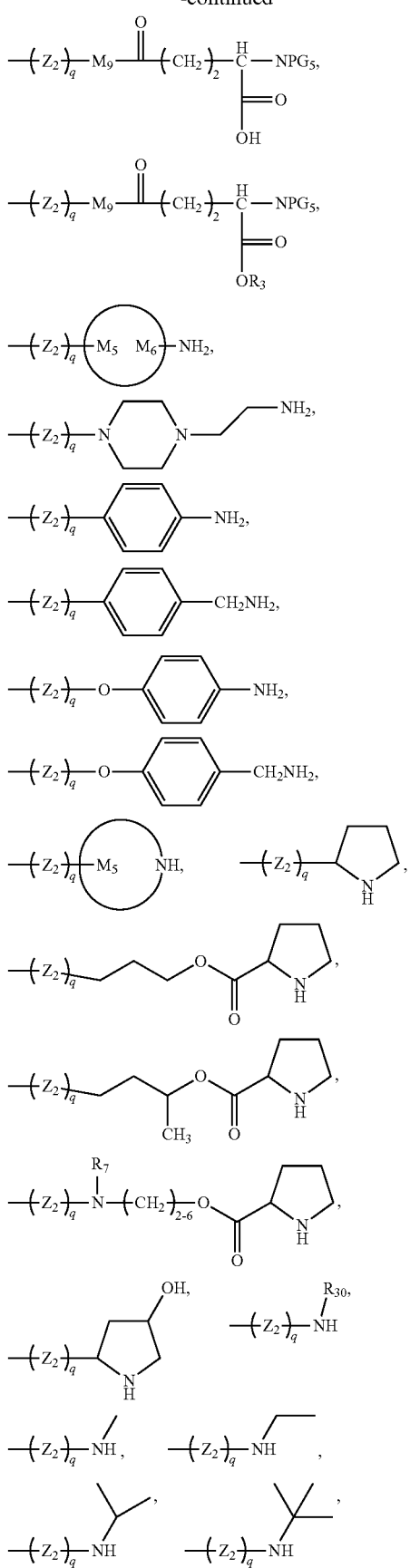

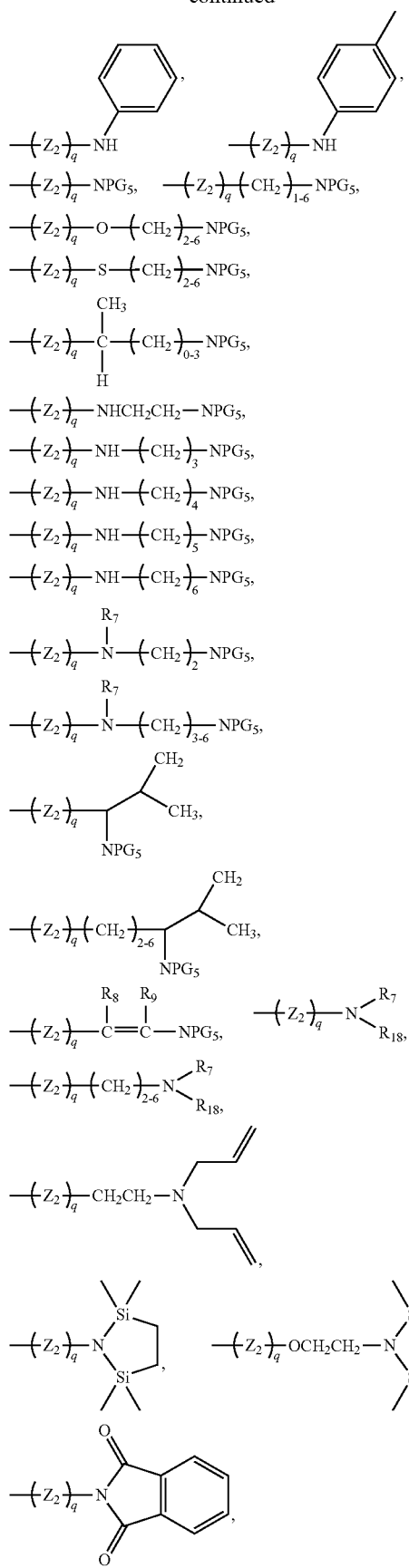
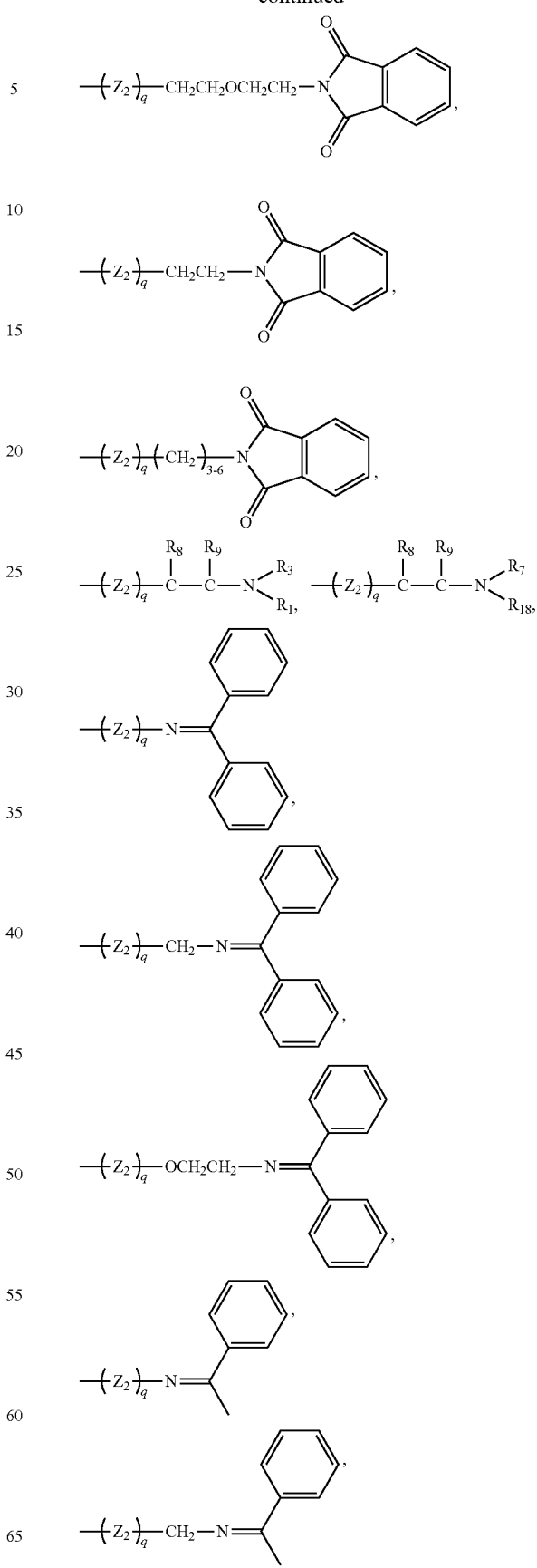

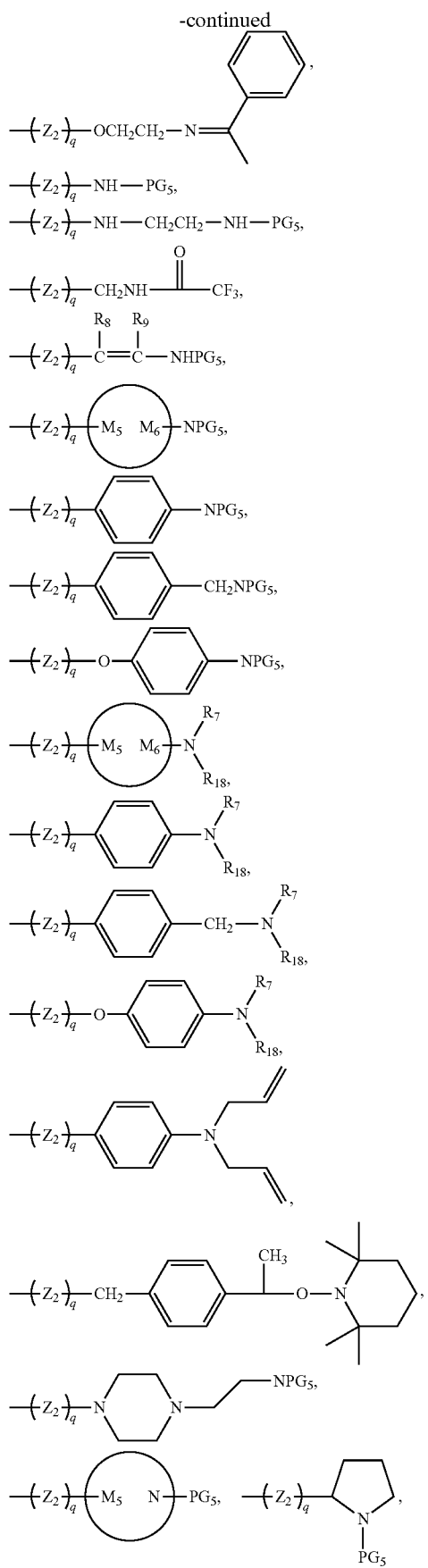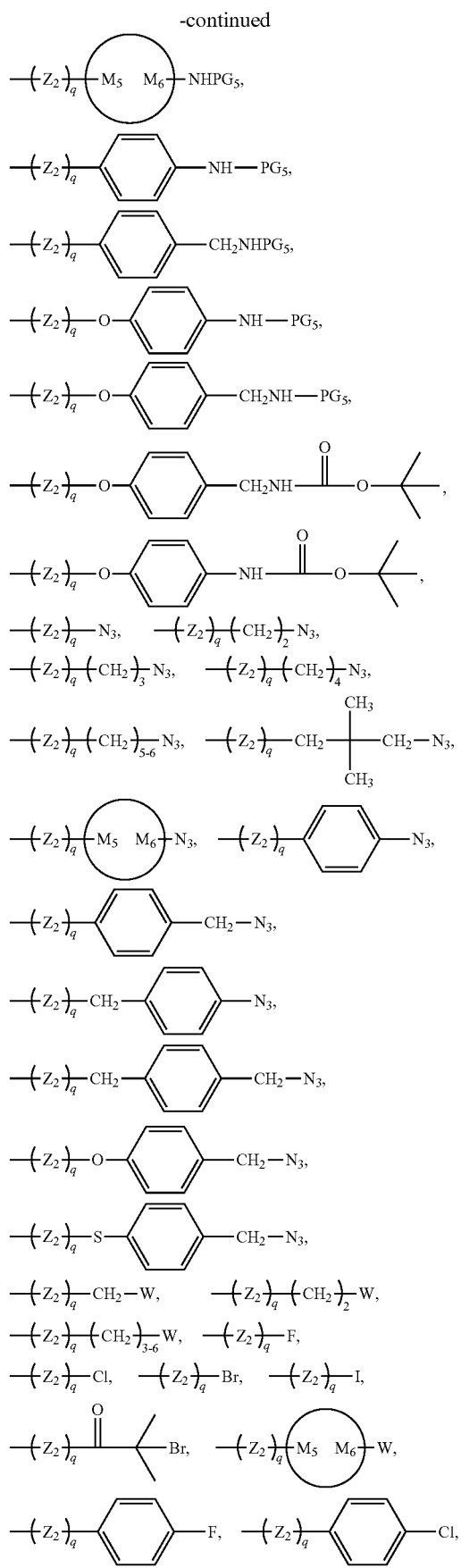

-continued
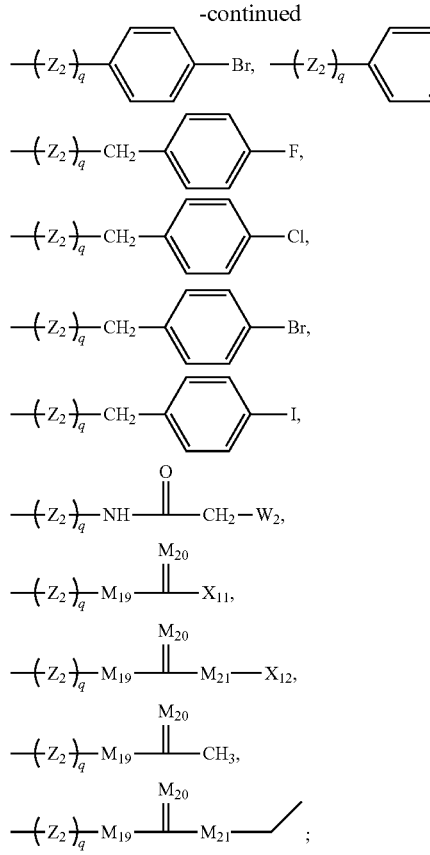
Group D:
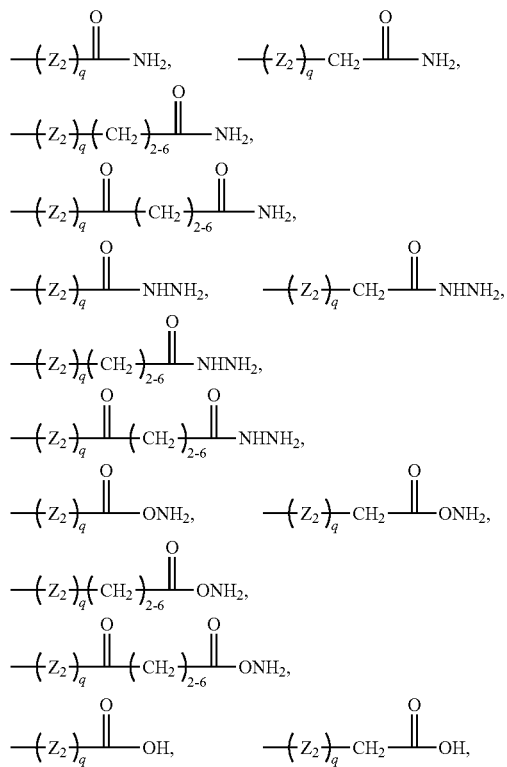
-continued
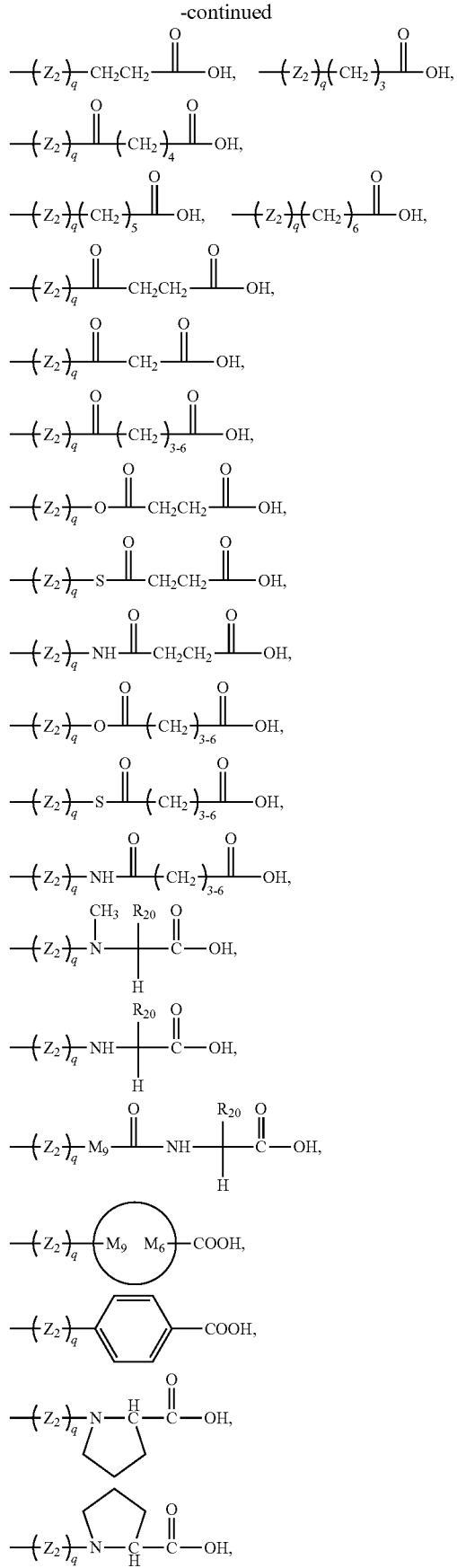

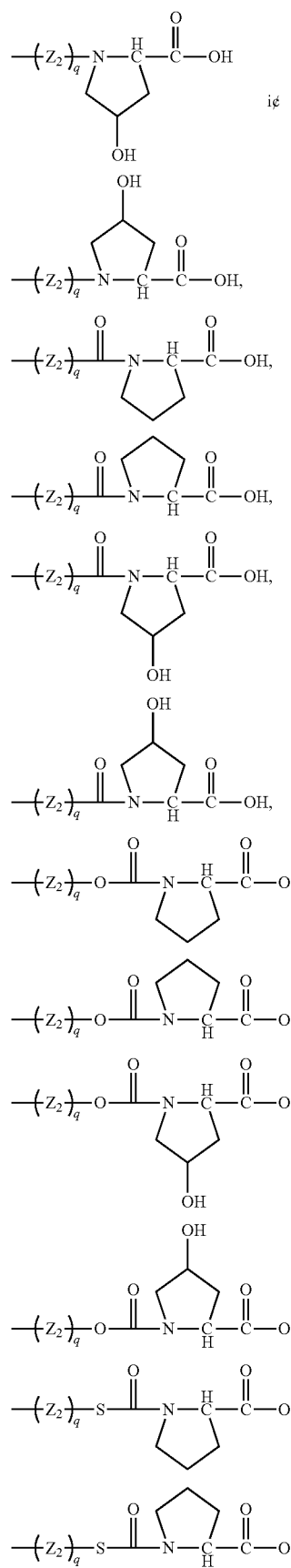
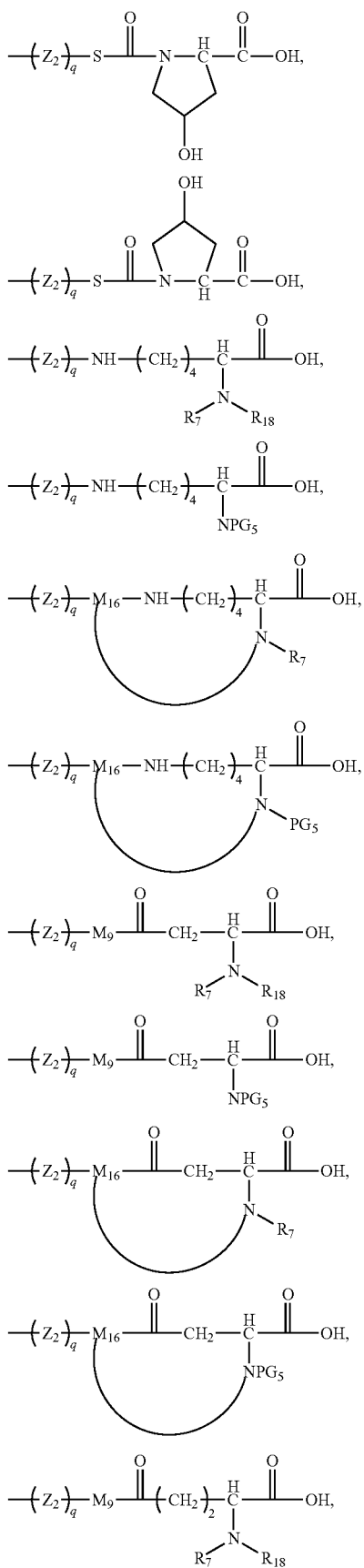

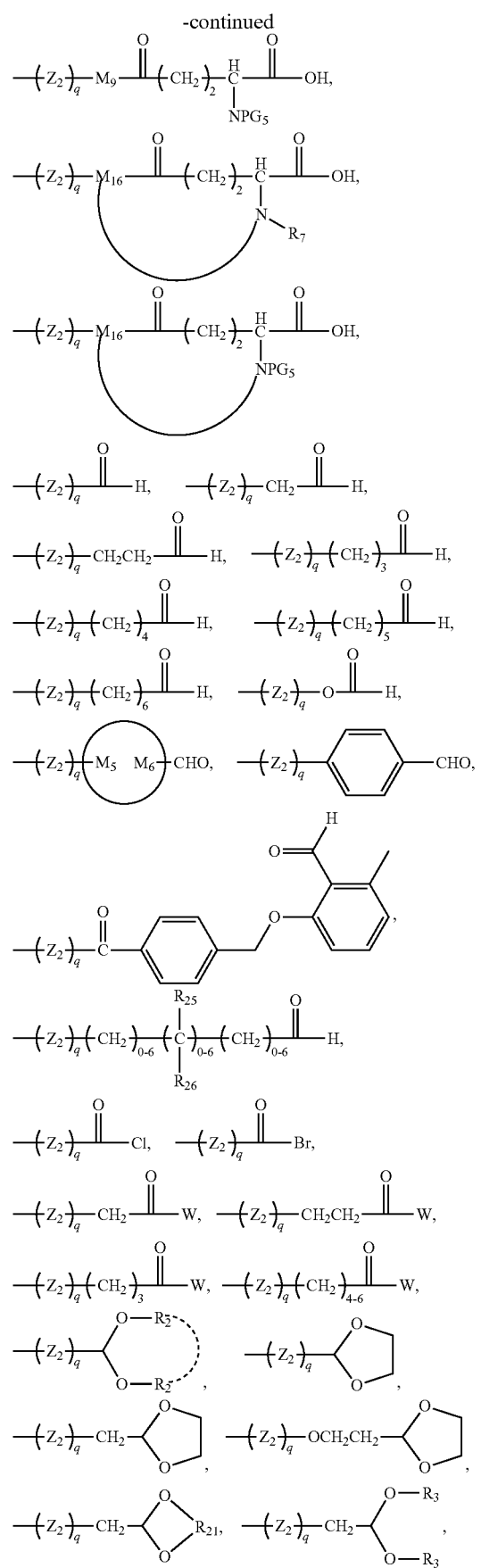
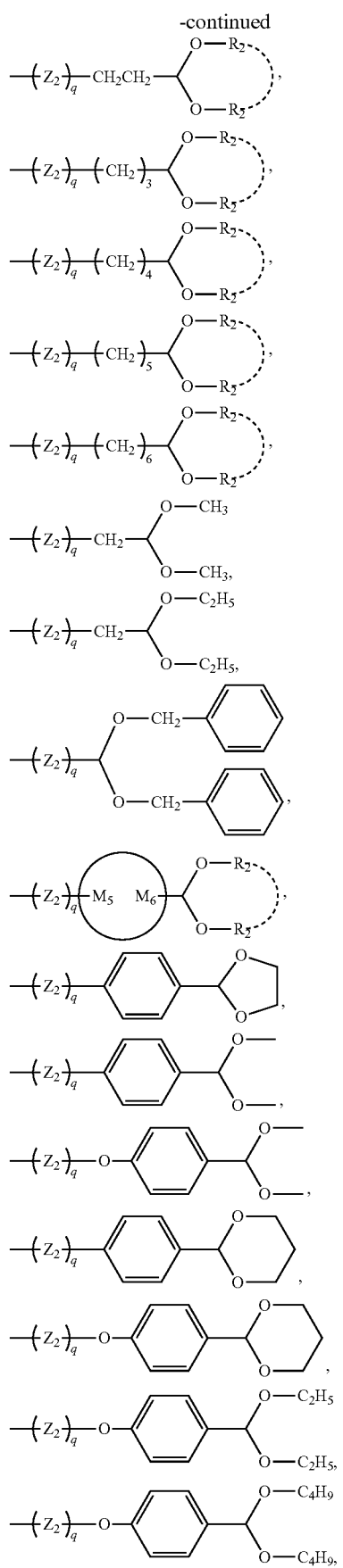

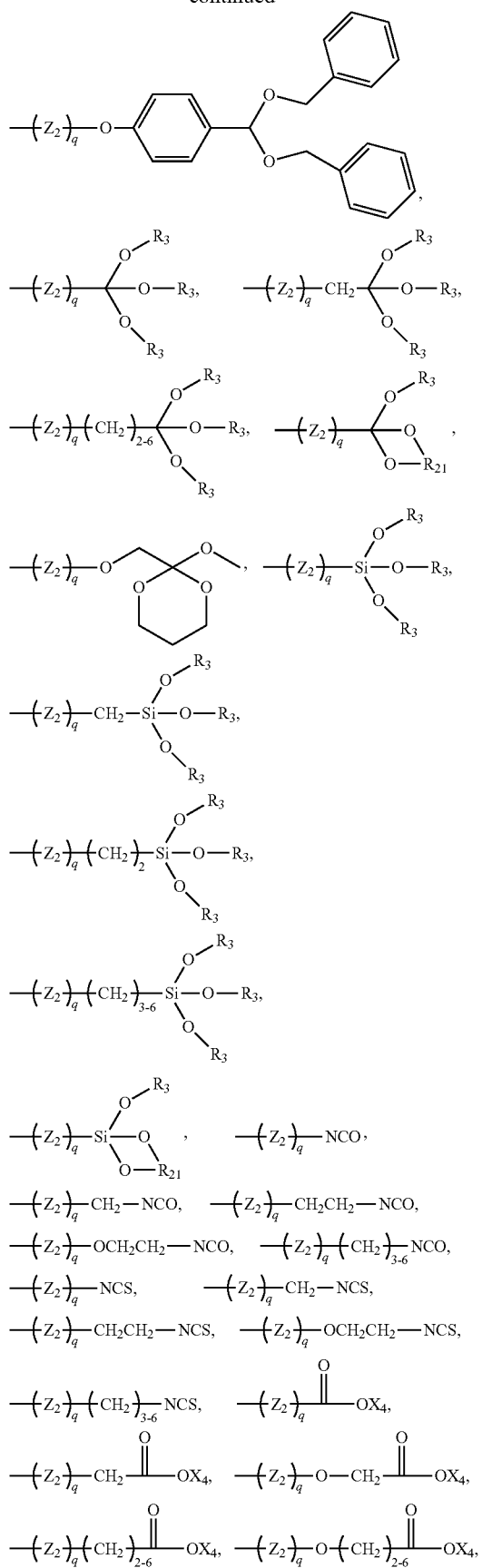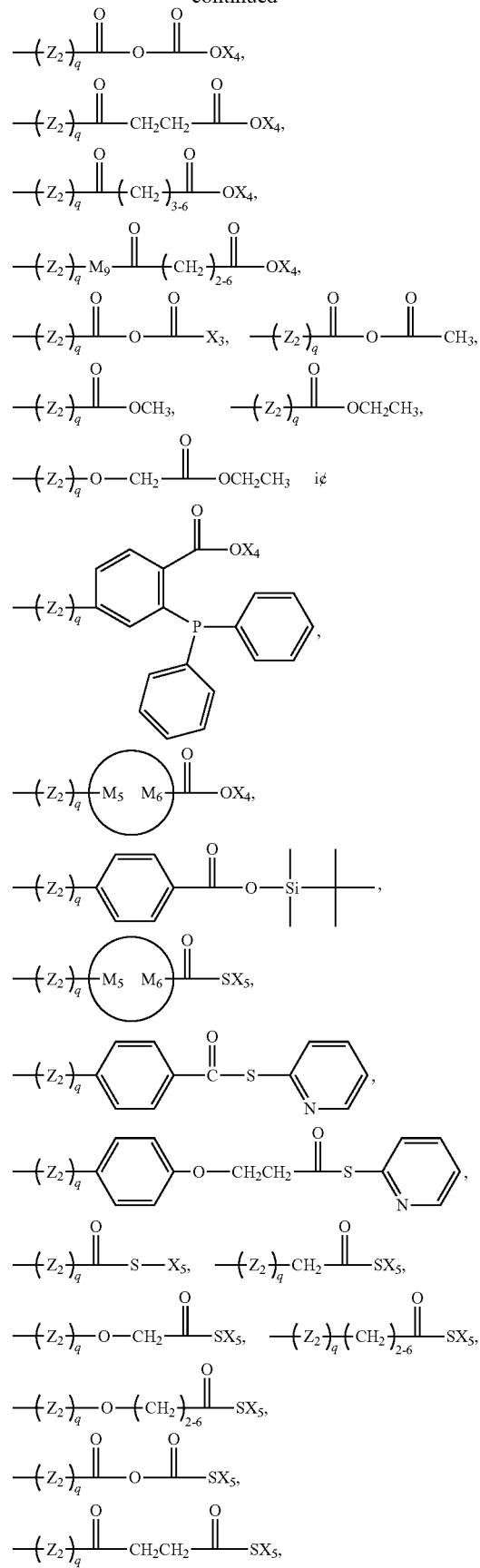

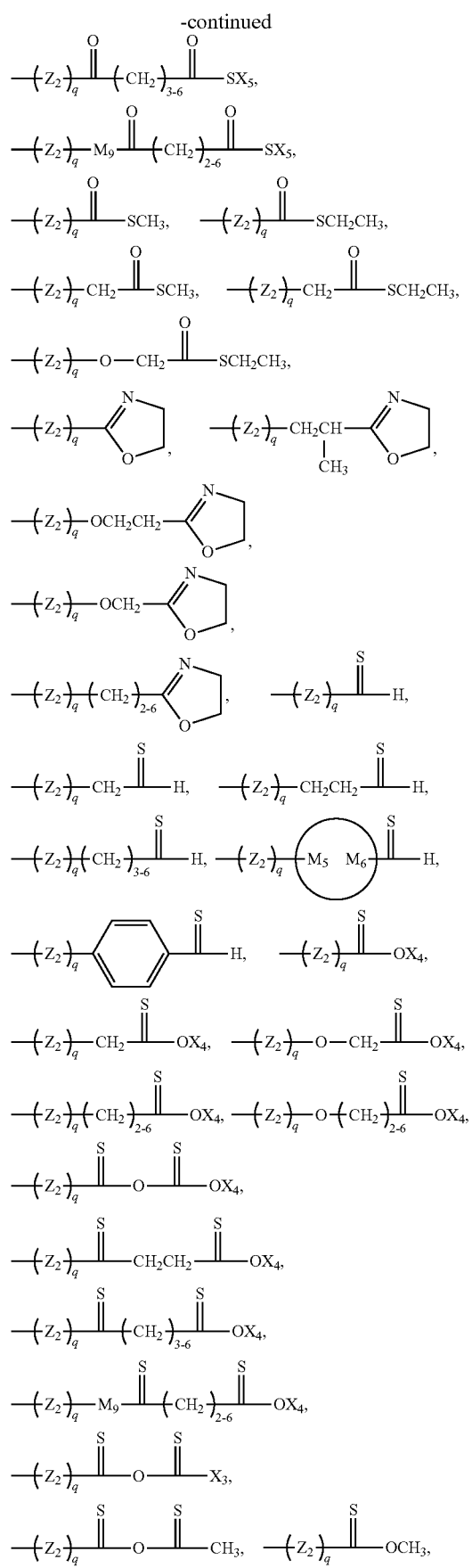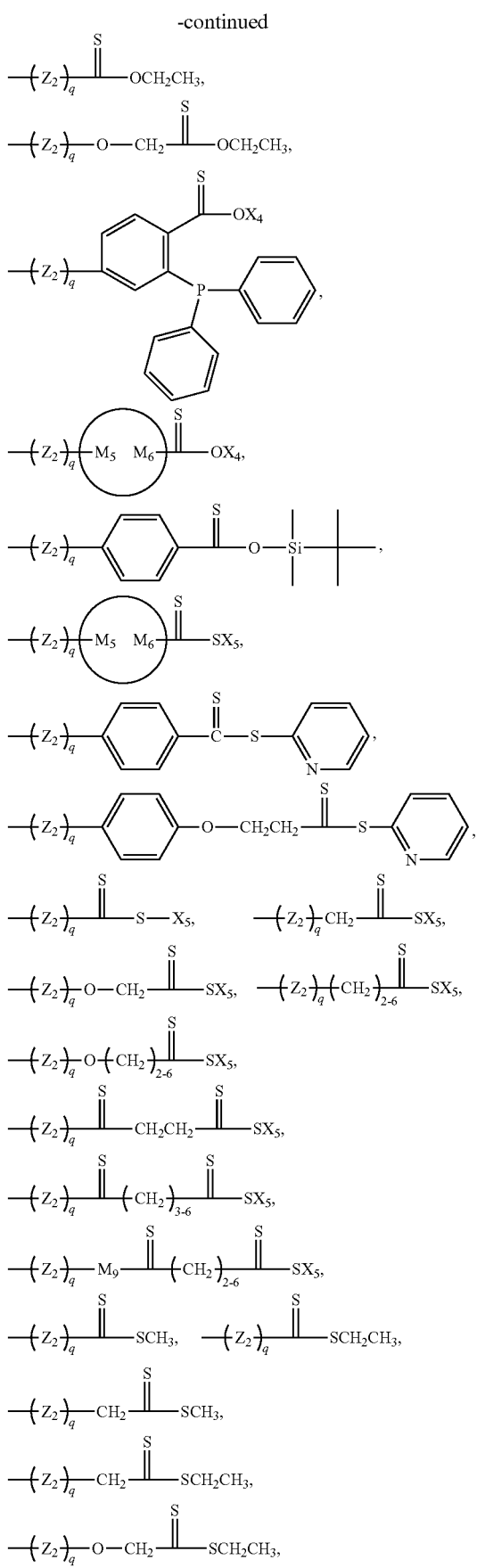

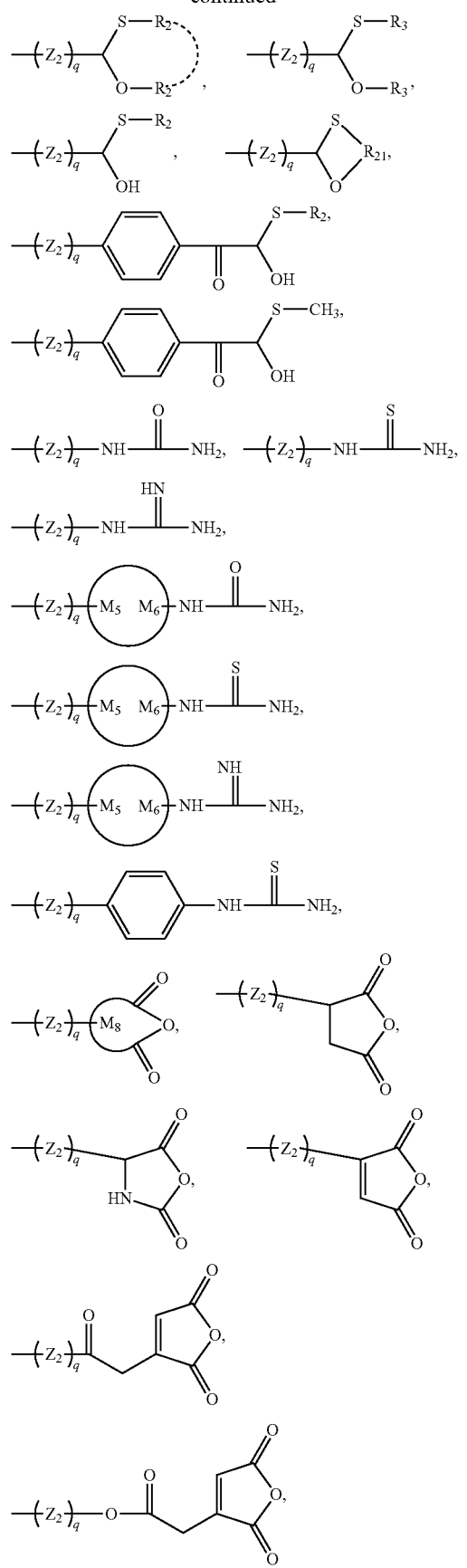
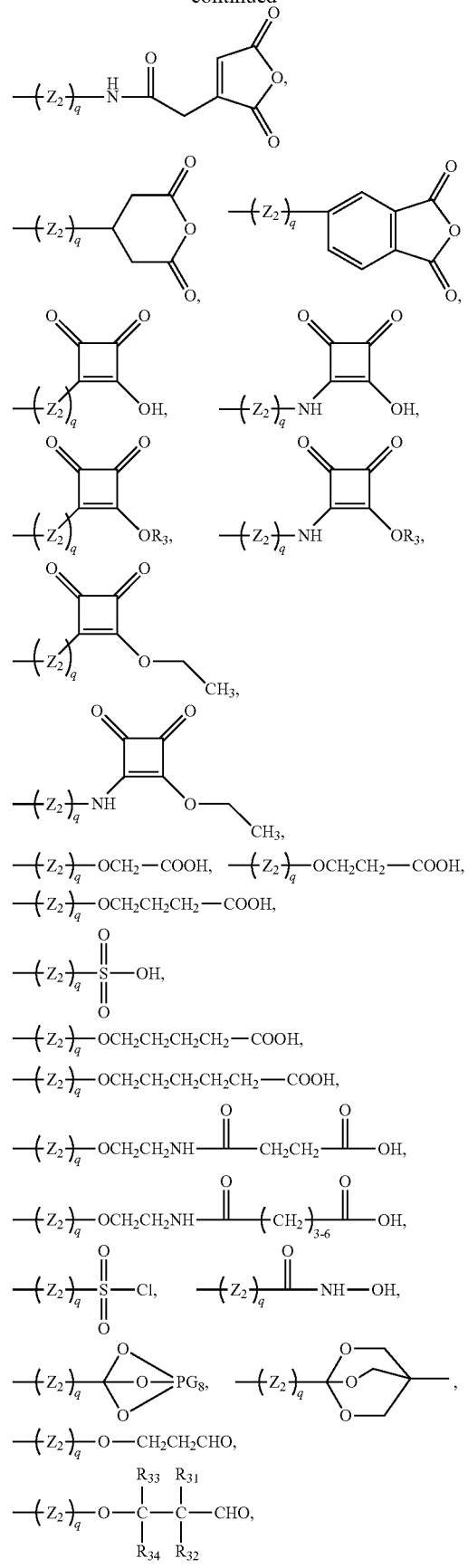

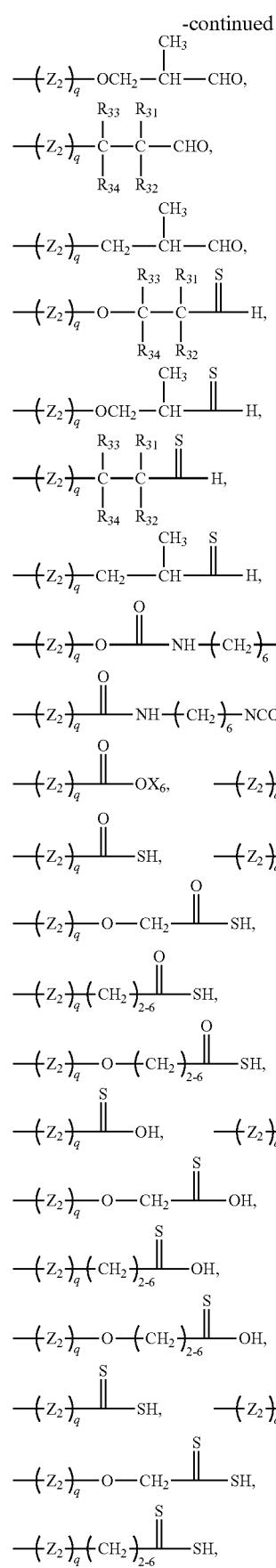
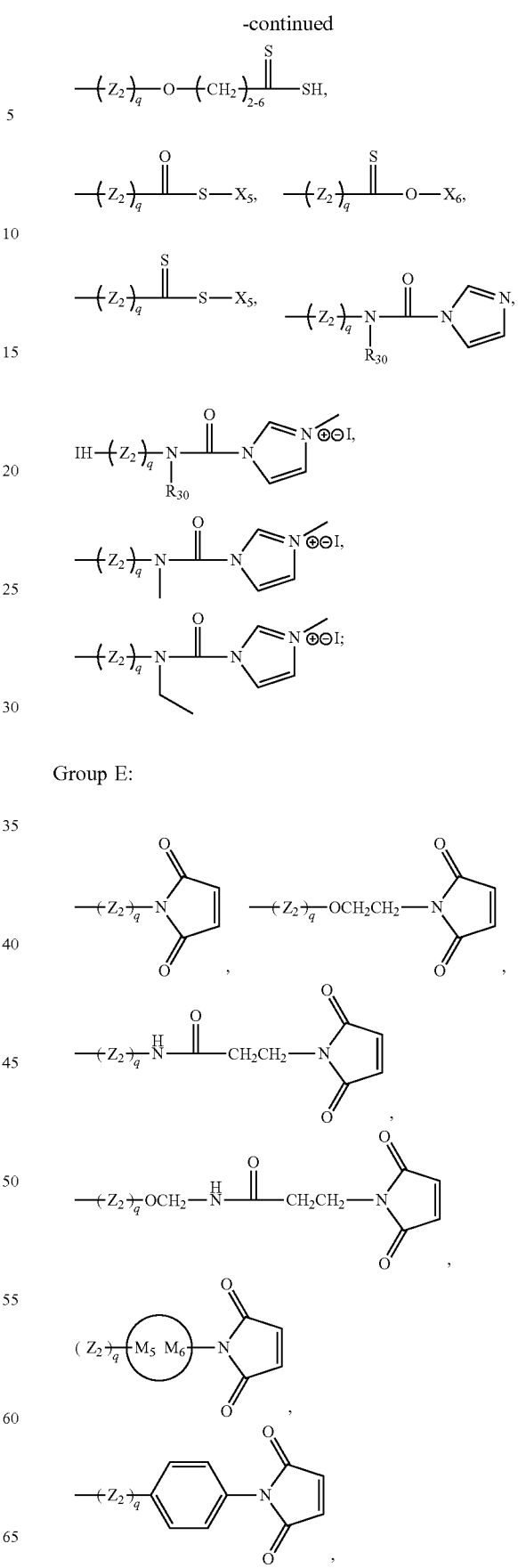
Group E:

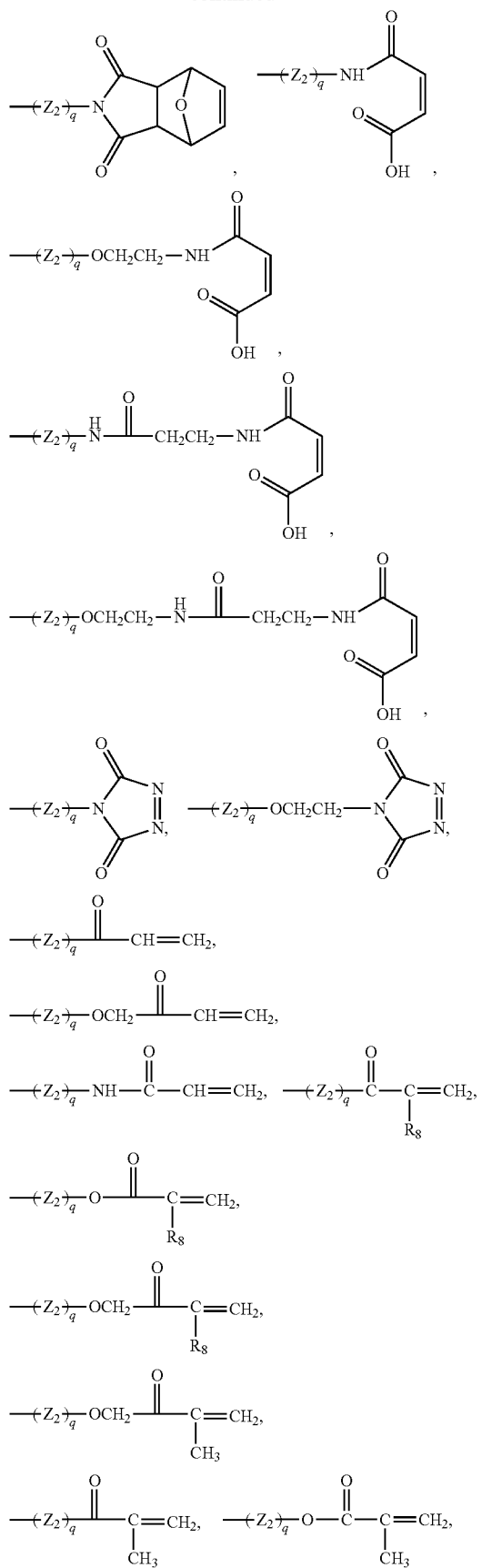
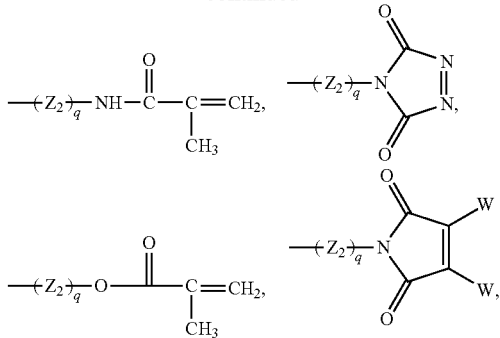
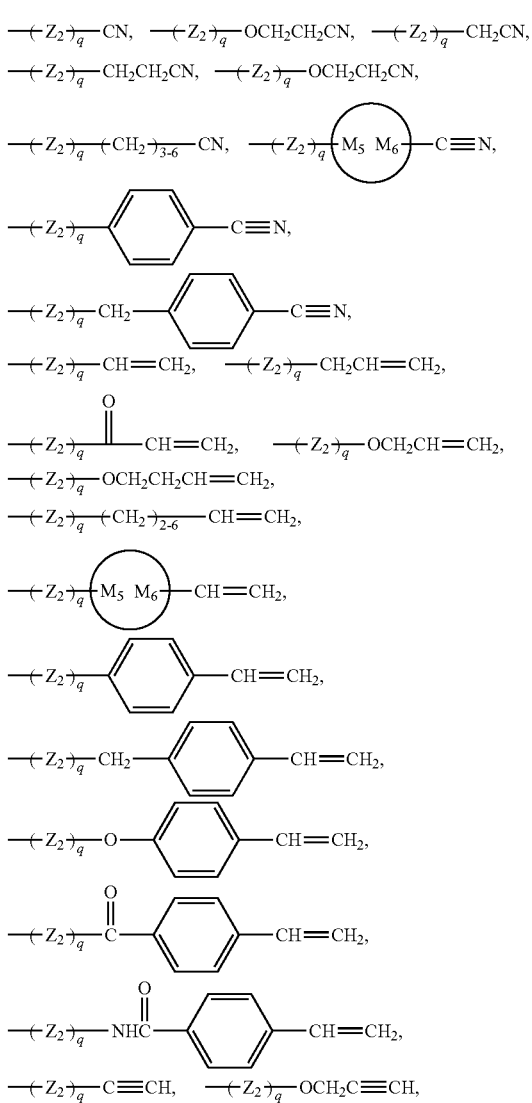
Group F:

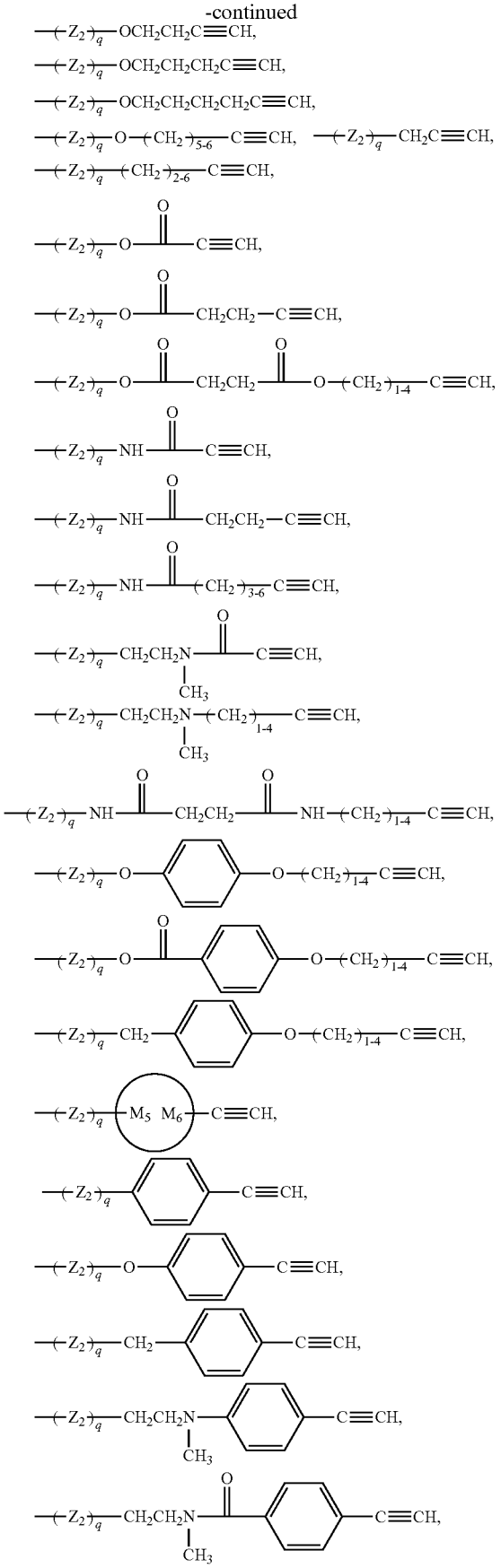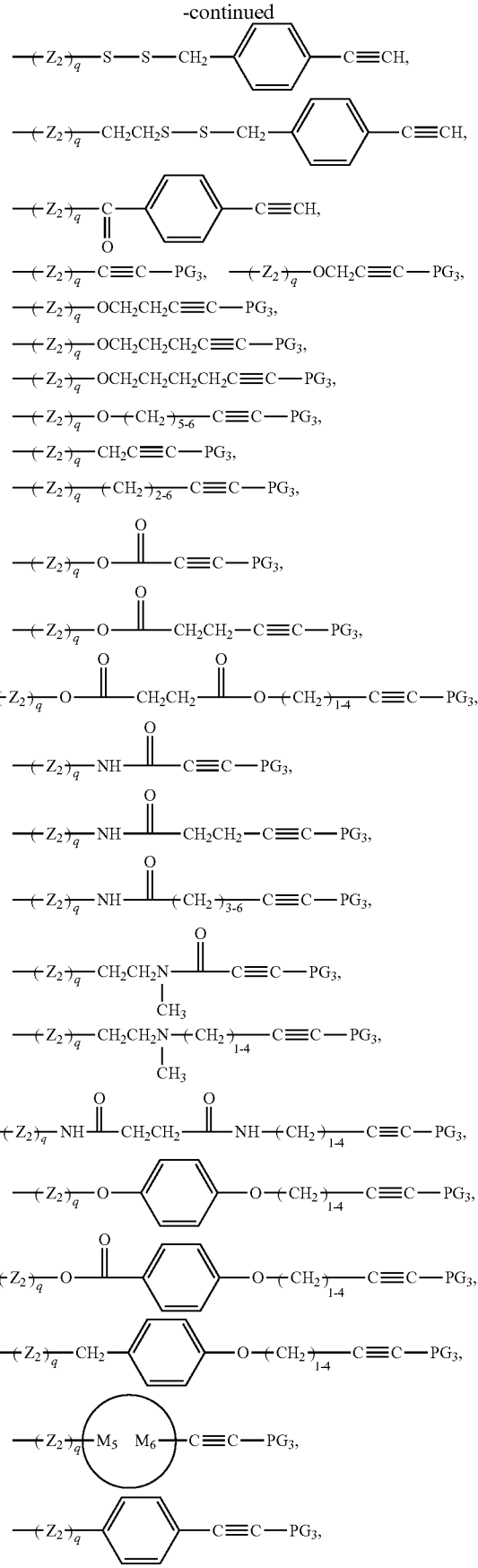

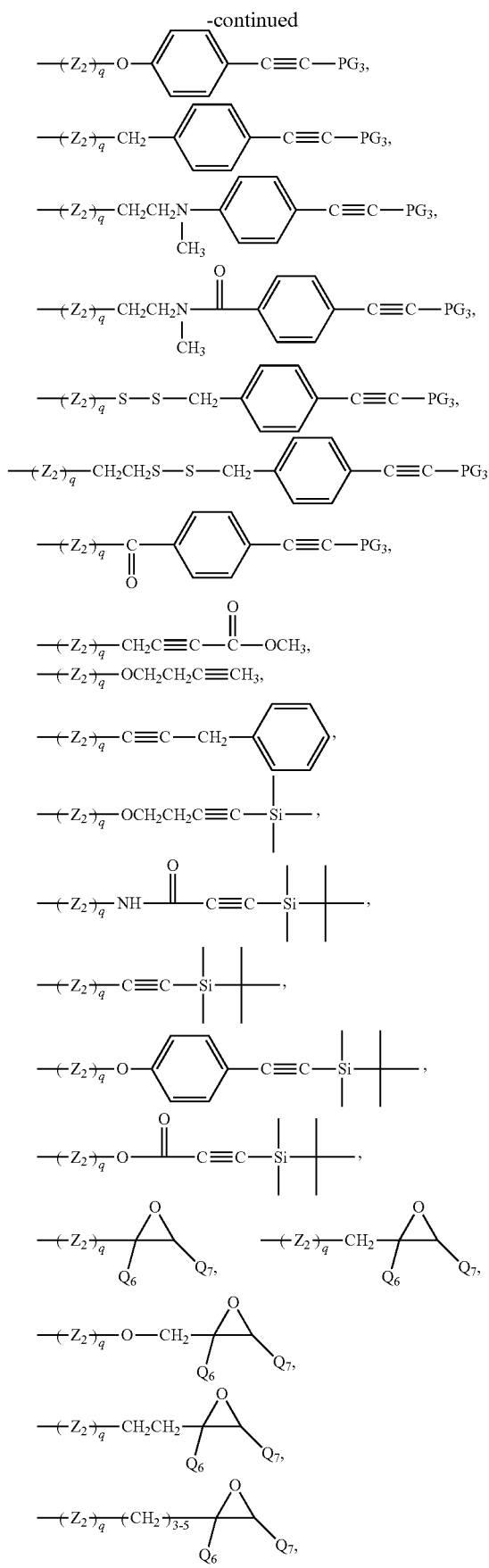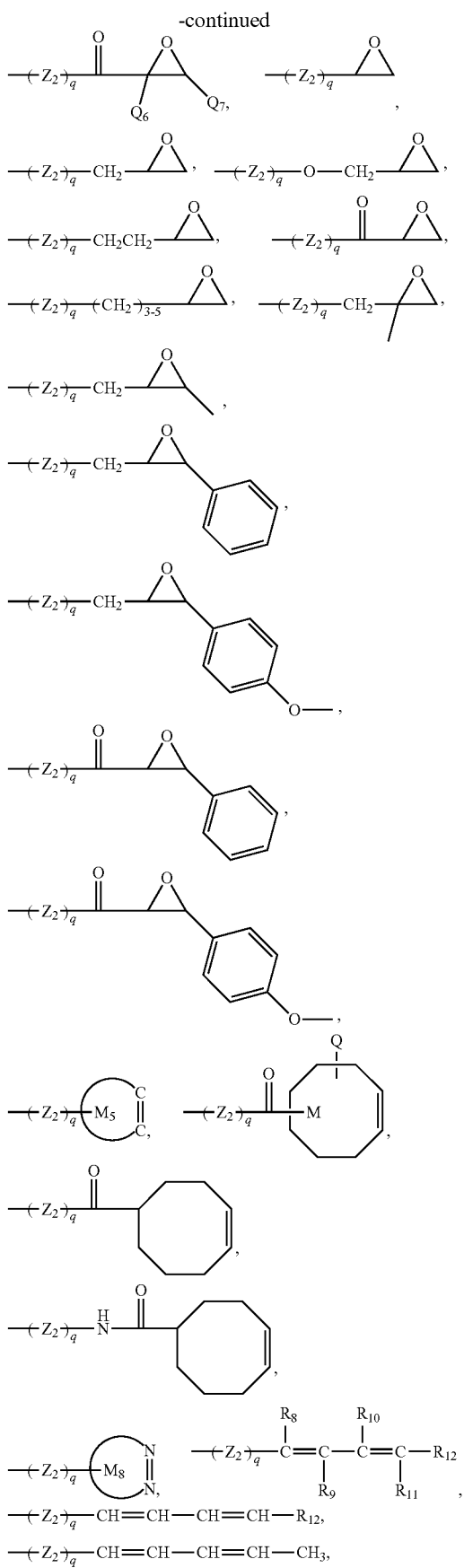

-continued
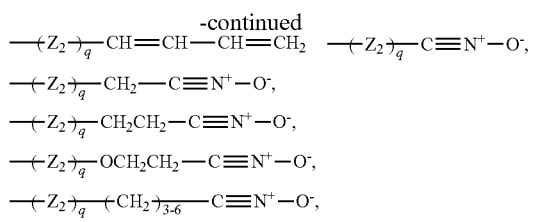
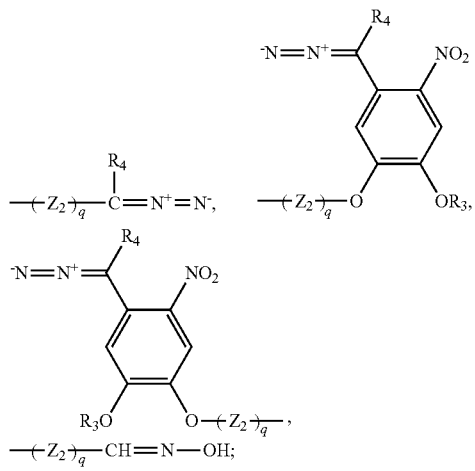
Group G:
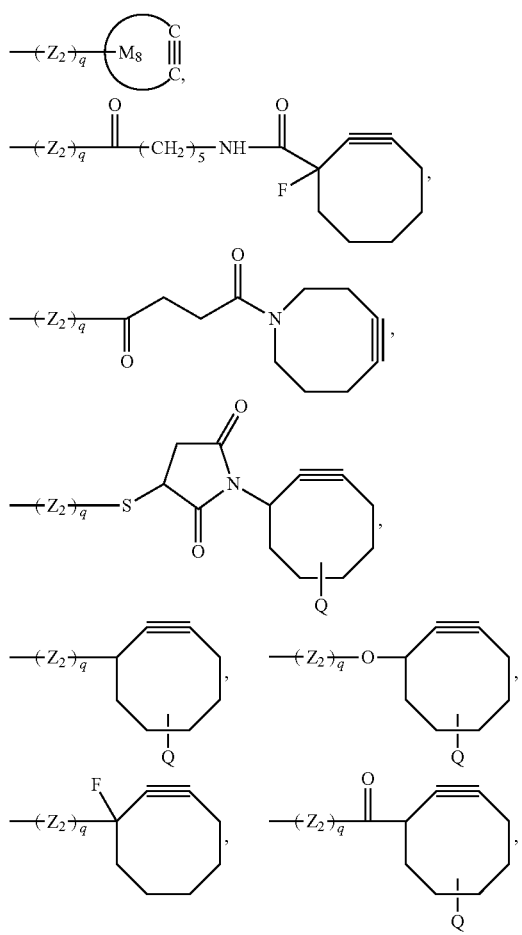
-continued
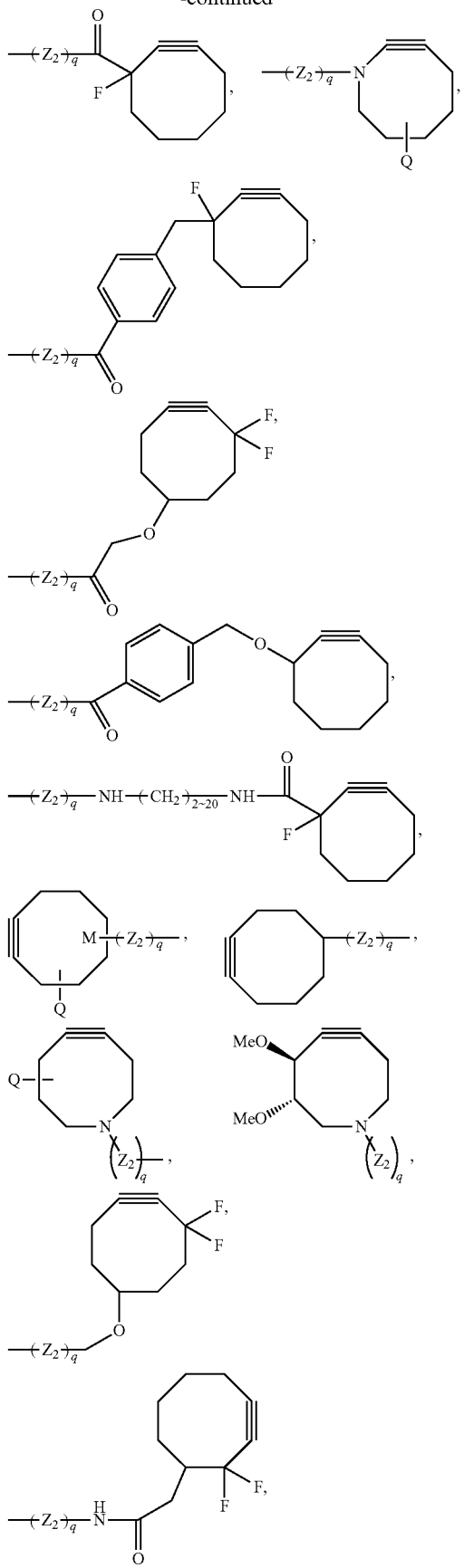

207
-continued
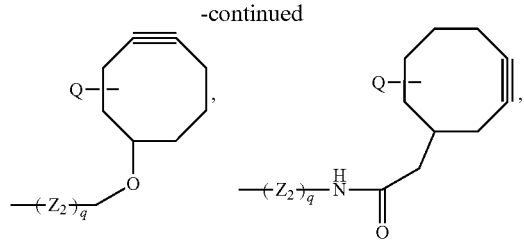
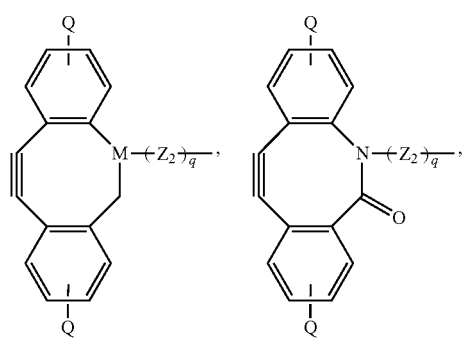
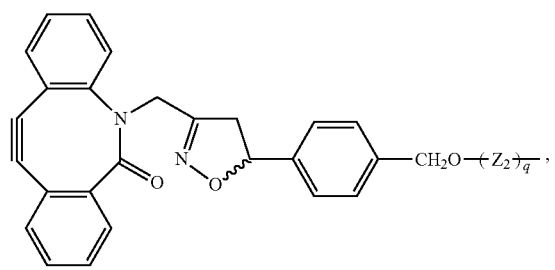
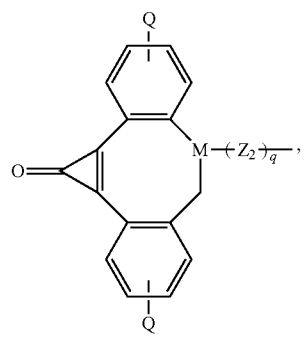
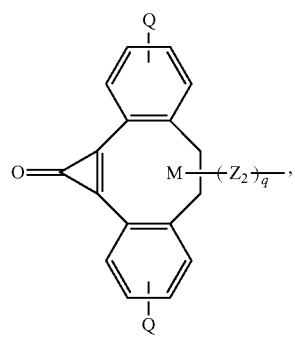
208
-continued
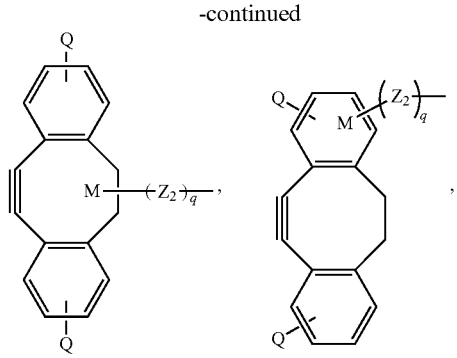
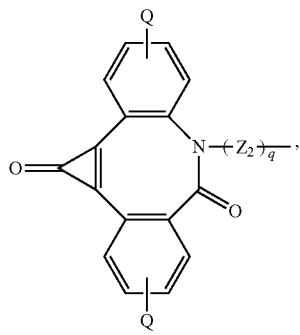
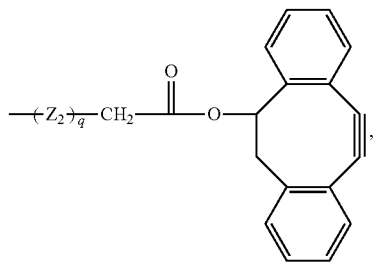
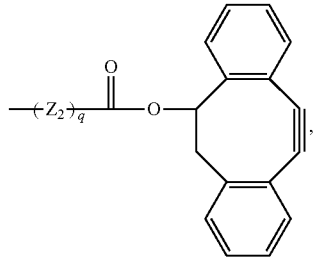
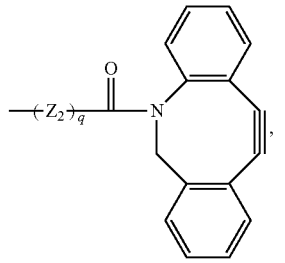
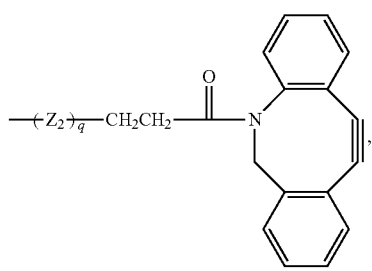

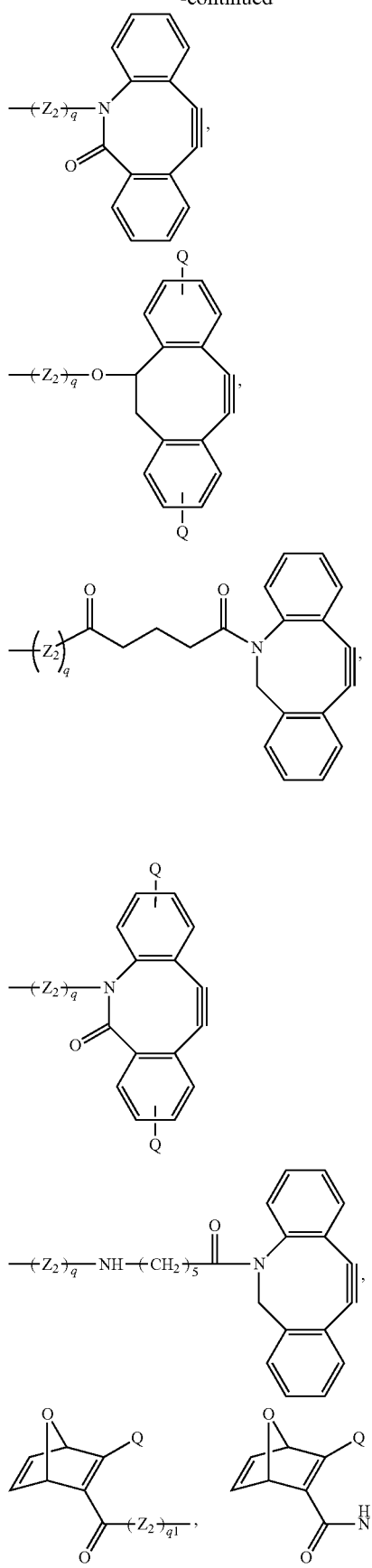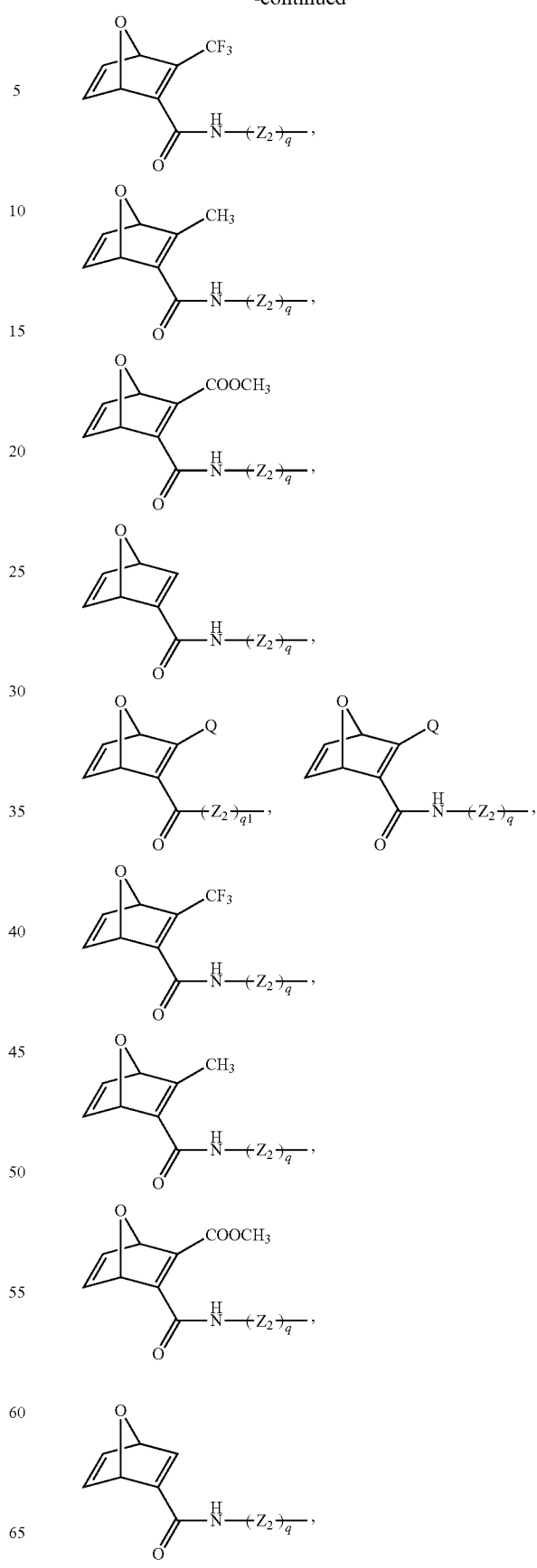

211
-continued
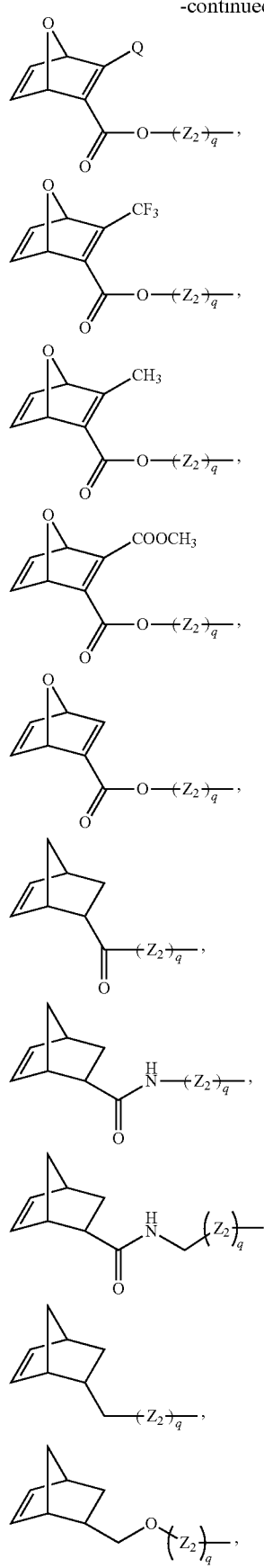
212
-continued
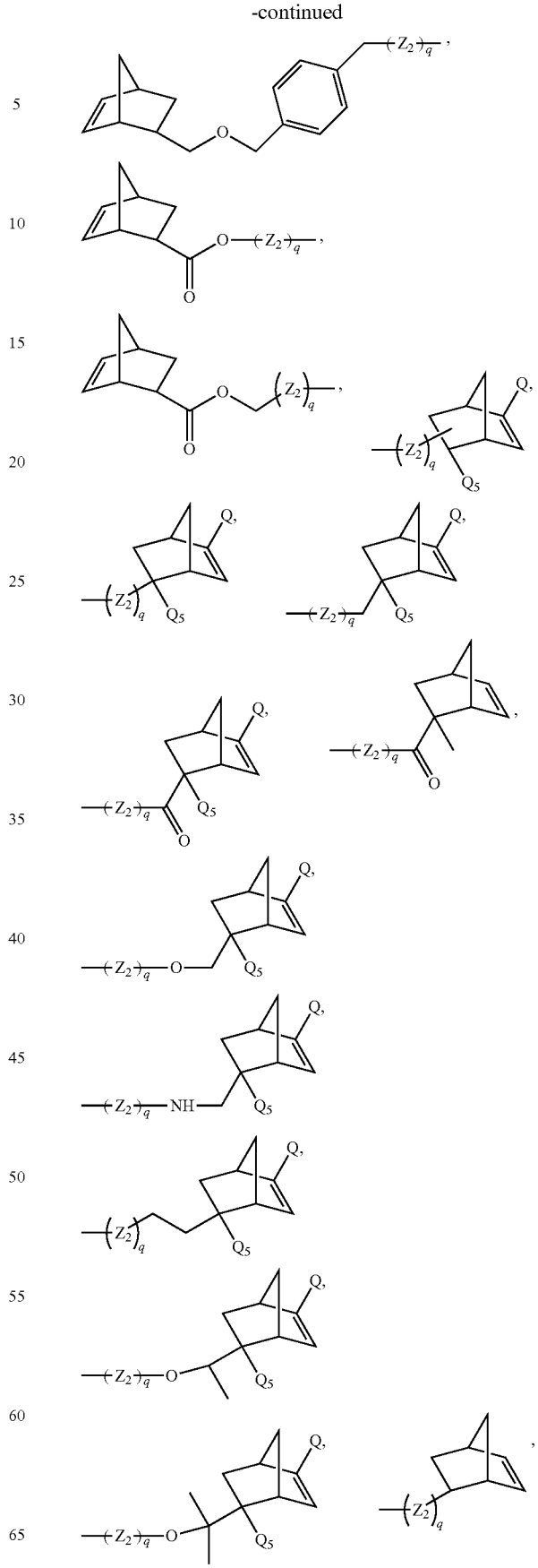

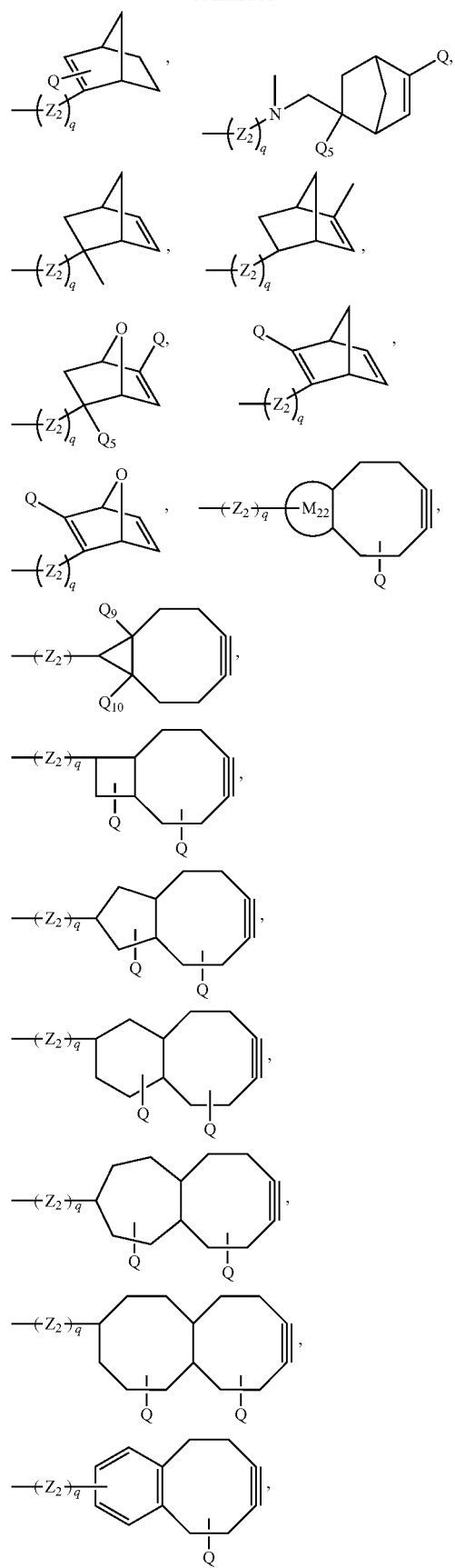
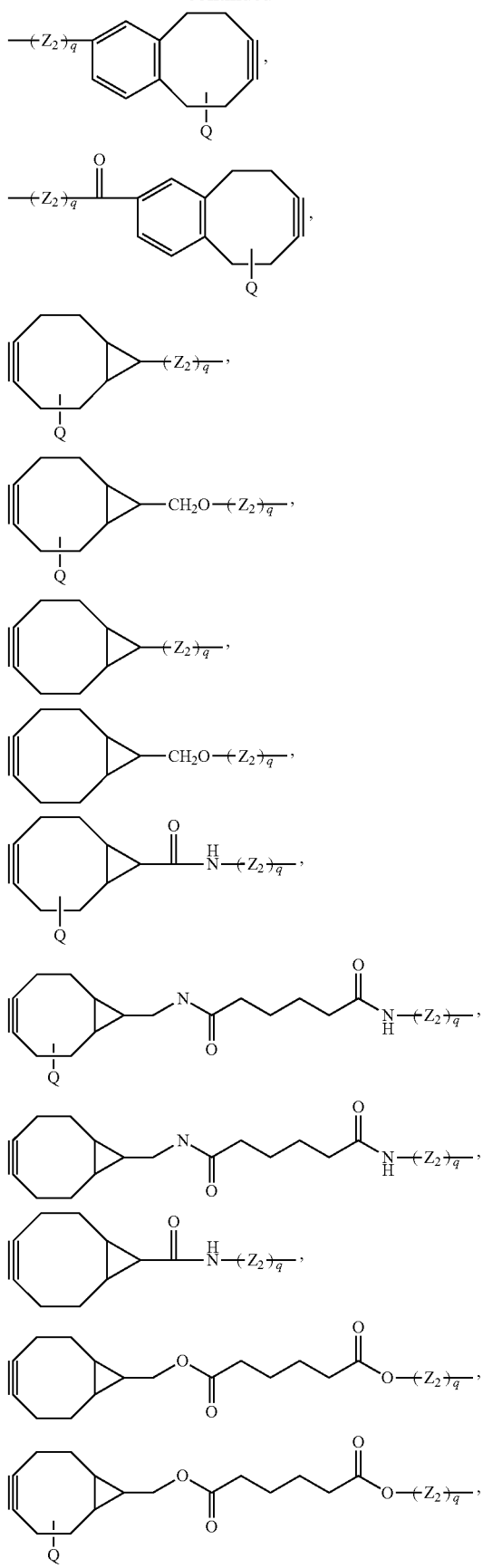

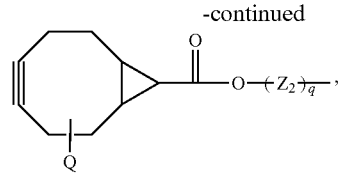
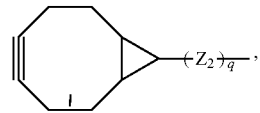
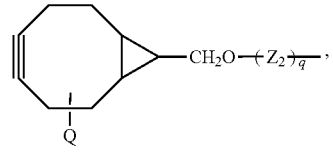
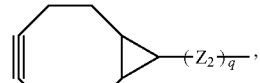
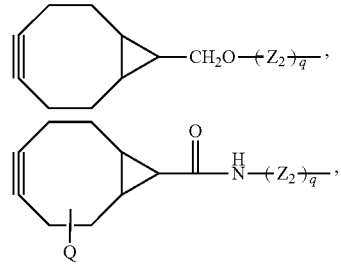
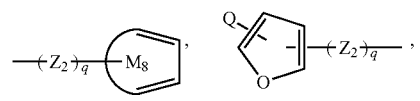
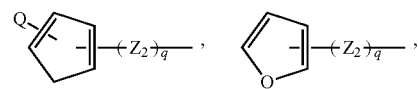
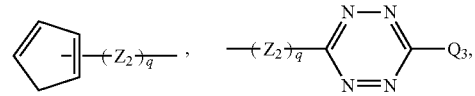
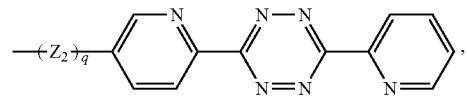

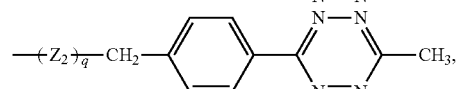
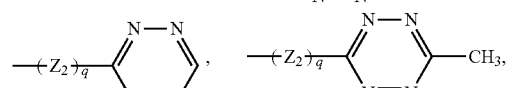
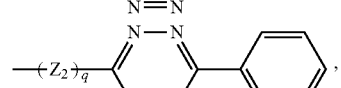
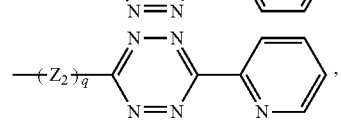
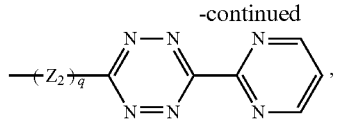
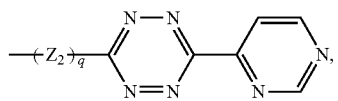
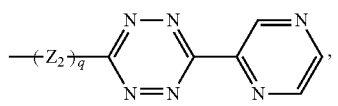
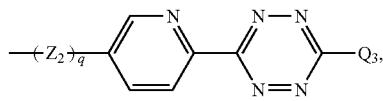
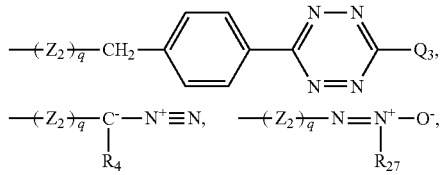
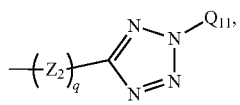
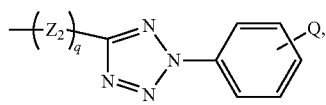
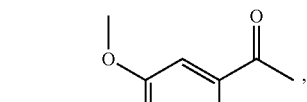
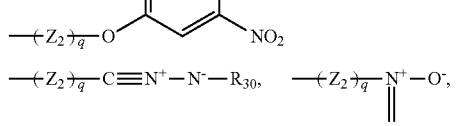
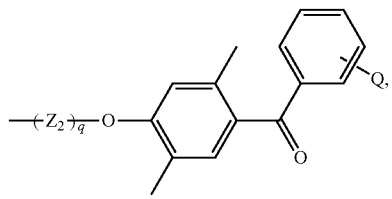
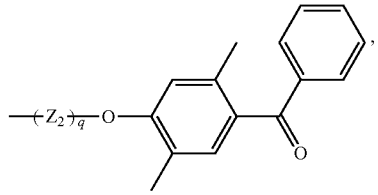
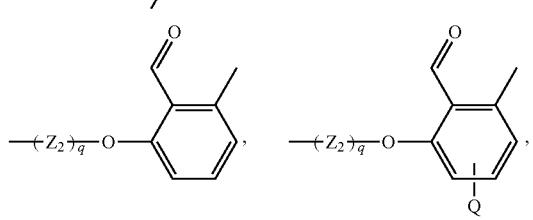

217

-continued

—(Z₂)_q—O—[4-methoxy-2-nitrophenyl with C(CH₃)=N⁺=N⁻ group];

Group H:

—(Z₂)_q—OH,  —(Z₂)_q—CH₂OH,  —(Z₂)_q—CH₂CH₂OH,

—(Z₂)_q—CH₂CH₂CH₂OH,  —(Z₂)_q—CH₂CH₂CH₂CH₂OH,

—(Z₂)_q—(CH₂)_{5-6}—OH,  —(Z₂)_q—CH₂CHOH(CH₃),

—(Z₂)_q—CH₂CH₂CHOH(CH₃),  —(Z₂)_q—C(R₈)=C(R₉)(R₇)—OH,

—(Z₂)_q—CH=CH—OH,  —(Z₂)_q—N(R)—(CH₂)_{2-6}—OH,

—(Z₂)_q—NH—(CH₂)_{2-6}—OH,

—(Z₂)_q—N(piperazine)N—CH₂CH₂—OH,

—(Z₂)_q—[M₅—M₆]—OH,  —(Z₂)_q—C₆H₄—OH (para),

—(Z₂)_q—CH₂—C₆H₄—OH,

—(Z₂)_q—O—CH₂—C₆H₄—OH,

—(Z₂)_q—O—PG₄,  —(Z₂)_q—CH₂O—PG₄,

—(Z₂)_q—CH₂CH₂O—PG₄,  —(Z₂)_q—CH₂CH₂CH₂O—PG₄,

—(Z₂)_q—CH₂CH₂CH₂CH₂O—PG₄,

—(Z₂)_q—CH₂CH(CH₃)O—PG₄,  —(Z₂)_q—CH₂CH₂CH(CH₃)O—PG₄,

—(Z₂)_q—C(R₈)=C(R₉)—O—PG₄,  —(Z₂)_q—N(R₇)—(CH₂)_{2-6}OPG₄,

—(Z₂)_q—NH—(CH₂)_{2-6}OPG₆,  —(Z₂)_q—O—(tetrahydropyran-2-yl),

—(Z₂)_q—CH₂O—(tetrahydropyran-2-yl),

—(Z₂)_q—CH₂CH₂O—(tetrahydropyran-2-yl),

—(Z₂)_q—CH₂CH₂CH₂O—(tetrahydropyran-2-yl),

—(Z₂)_q—CH₂CH₂CH₂CH₂O—(tetrahydropyran-2-yl),

218

-continued

—(Z₂)_q—O—CH(CH₃)—O—CH₂CH₃,  —(Z₂)_q—CH₂O—CH(CH₃)—O—CH₂CH₃,

—(Z₂)_q—CH₂CH₂O—CH(CH₃)—O—CH₂CH₃,  —(Z₂)_q—O—C(CH₃)₃,

—(Z₂)_q—OCH₂CH₂O—C(CH₃)₃,  —(Z₂)_q—O—Si(CH₃)₂C(CH₃)₃,

—(Z₂)_q—OCH₂CH₂O—Si(CH₃)₂C(CH₃)₃,

—(Z₂)_q—O—Si(iPr)₃,

—(Z₂)_q—OCH₂CH₂O—Si(iPr)₃,

—(Z₂)_q—O—C(C₆H₅)₃,

—(Z₂)_q—O—C(C₆H₅)₂(C₆H₄—OCH₃),

—(Z₂)_q—O—CH₂—C₆H₅,

—(Z₂)_q—O—CH₂—C₆H₄— (para),

—(Z₂)_q—O—CH₂—C₆H₄—CH=CH₂ (para),

—(Z₂)_q—O—CH₂—C₆H₄—NO₂ (ortho, with O₂N),

—(Z₂)_q—O—CH₂—C₆H₄—NO₂ (para),

—(Z₂)_q—O—CH₂—C₆H₄—CF₃ (para),

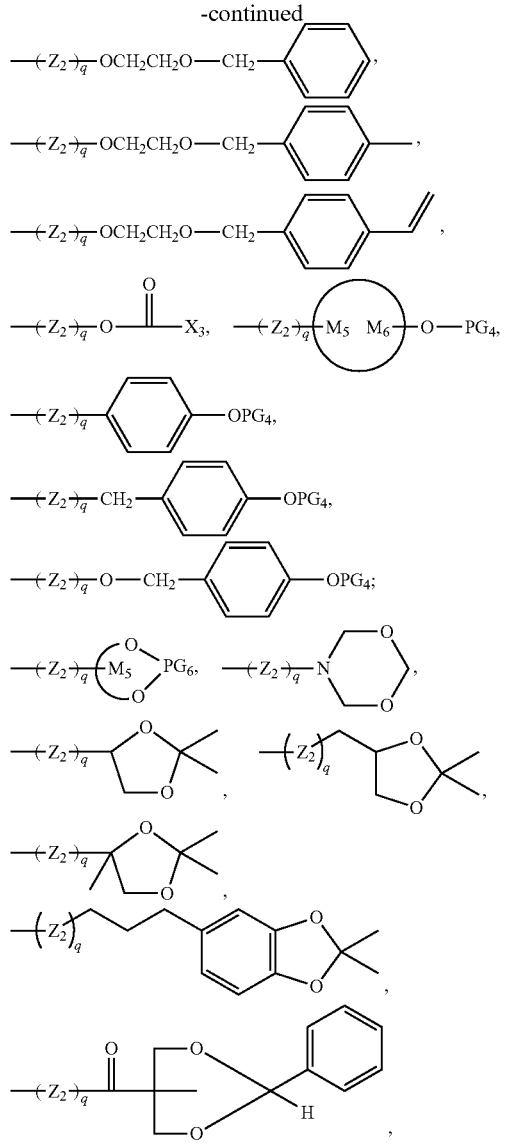
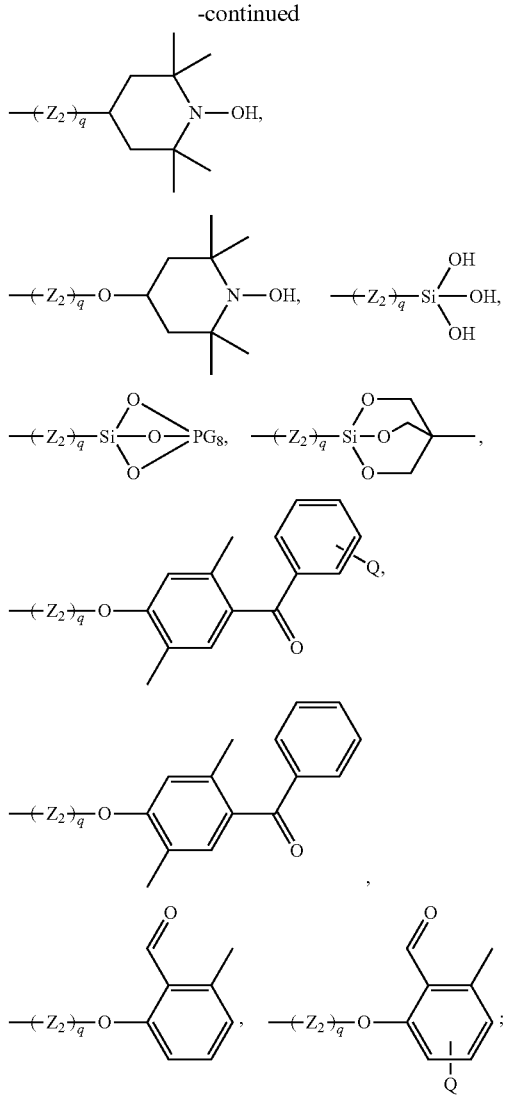
Group I:
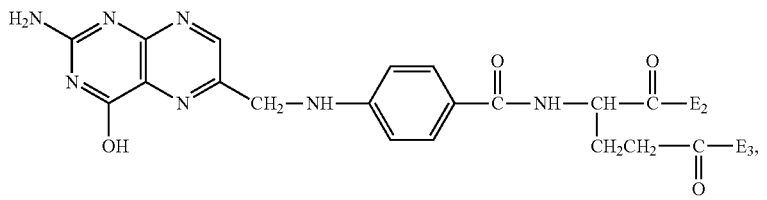
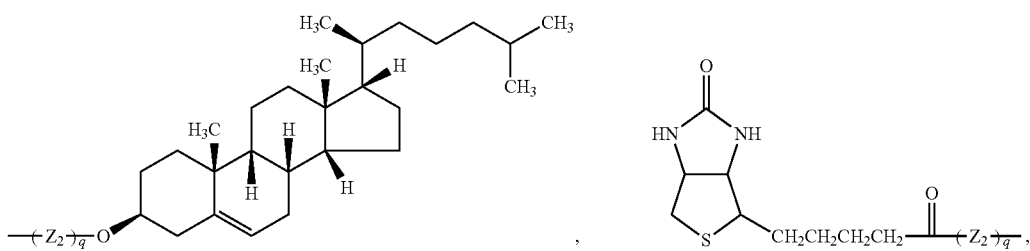

-continued
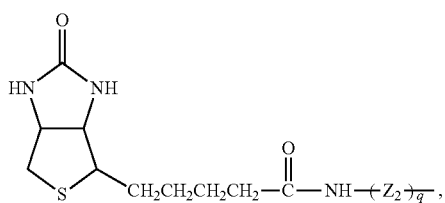
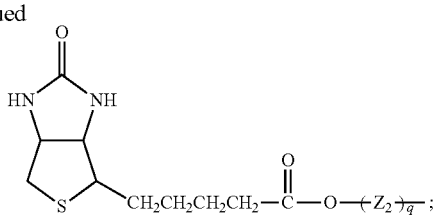
Group J:
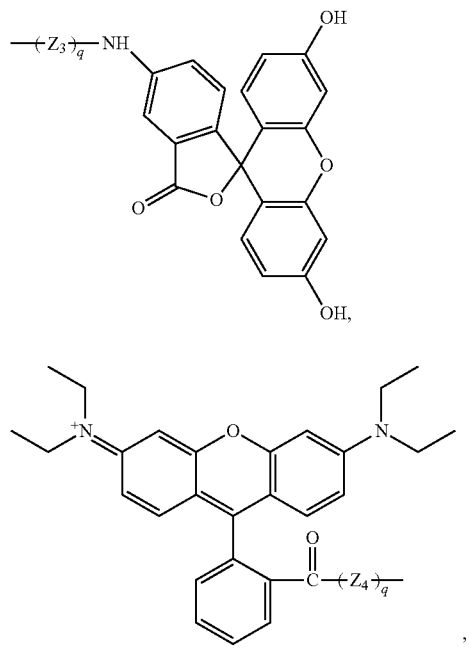
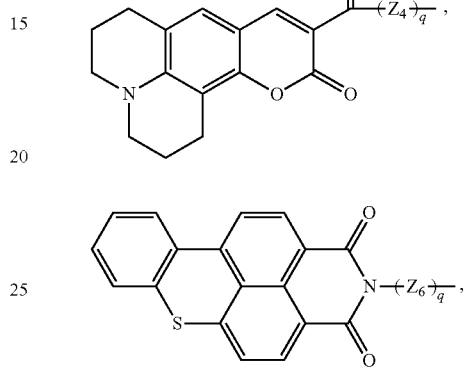
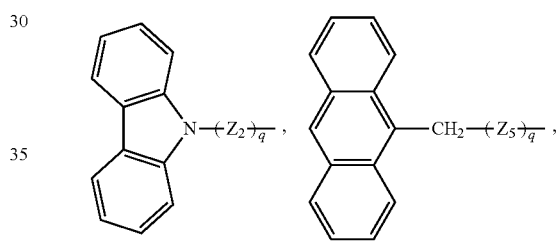
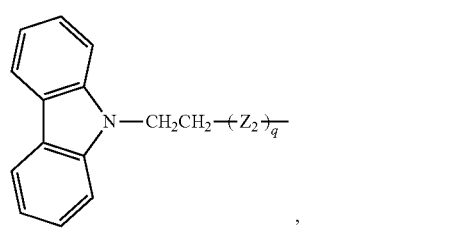
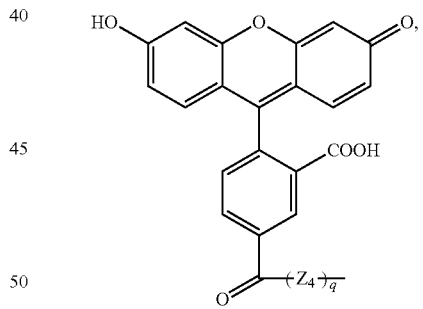
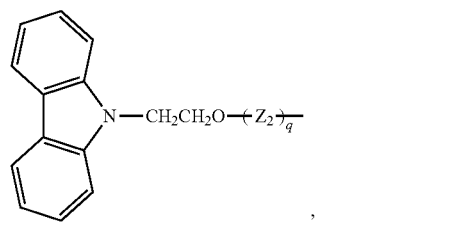
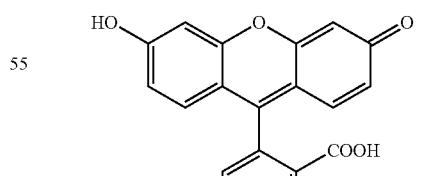
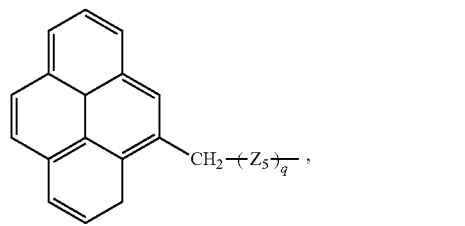

-continued

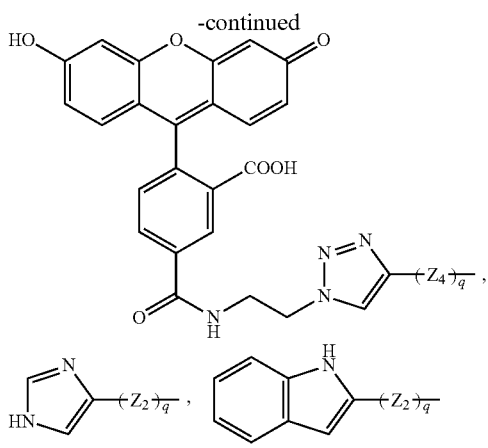

and the like.

With respect to above-said groups from Group A to Group J:

Wherein, any one of $E_2$ and $E_3$ is

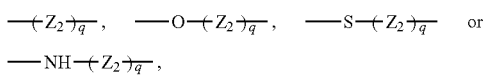

and the other is a hydroxyl group (—OH);

Wherein, $Z_3$ is

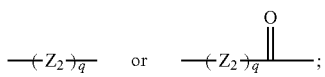

Wherein, $Z_4$ is

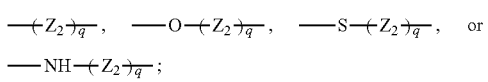

Wherein, $Z_5$ is

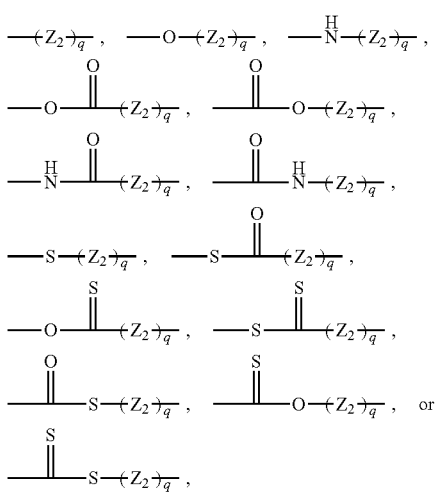

Wherein, $Z_6$ is

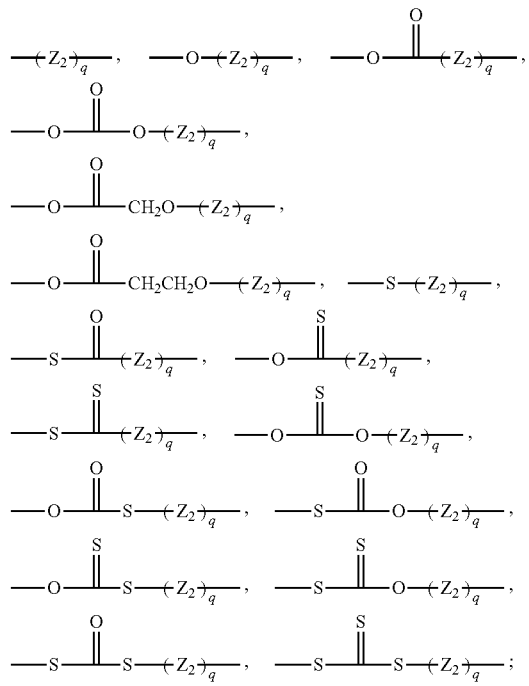

Wherein, q is 0 or 1.

Wherein, $Z_2$ is a divalent linking group that can be stable or degradable, defined in detail in the following text.

Wherein, $M_9$ is O, S or $NX_{10}$.

Wherein, the definitions of $Y_1$, $R_1$, $R_2$, $R_3$, $R_4$, $R_{21}$, $R_7$, $R_{18}$, $R_8$, $R_9$, $R_{10}$, $R_{11}$, $R_{12}$, $R_{24}$, $R_{27}$, $R_{30}$, $X_4$, $X_5$, $X_6$, Q, $Q_3$, $Q_5$, $Q_6$, $Q_7$, $Q_{11}$, W, $W_2$, $PG_2$, $PG_3$, $PG_4$, $PG_5$, $PG_6$, $PG_8$, $X_{10}$, $M_{19}$, $M_{20}$, $M_{21}$, $M_{22}$, M, $M_5$, $M_6$, $M_8$ and $M_5$-, $M_6$- or $M_8$-membered rings are the same as above, no more repeated here.

Wherein, $M_{16}$ is C, N, P or Si.

Wherein, $M_{22}$ is a carbon atom, a nitrogen atom, a phosphorus atom or a silicon atom of the alicyclic ring or an aliphatic-derived heteroring; the number of ring-membering atoms of $M_{22}$ membered rings is 4, 5, 6, 7 or 8.

Wherein, $Q_9$ and $Q_{10}$ are each independently a hydrogen atom, a $C_{1-20}$ alkyl group, a $C_{6-20}$ aryl group, a $C_{6-20}$ arylhydrocarbyl group, a heterosubstituted $C_{6-20}$ aryl group with a ring-membering heteroatom or a heterosubstituted $C_{6-20}$ arylhydrocarbyl group with a ring-membering heteroatom. In one molecule, $Q_9$ and $Q_{10}$ can be the same or different from each other. $Q_9$ and $Q_{10}$ are each independently preferably a hydrogen atom, a $C_{1-6}$ alkyl group, a phenyl group, a heterosubstituted phenyl group with a ring-membering heteroatom or a substituted phenyl group.

Wherein, $X_3$ is a hydrocarbyl group, a heterohydrocarbyl group, a substituted hydrocarbyl group or a substituted heterohydrocarbyl group within an acyl group.

The carbon-atom number of $X_3$ is not particularly limited, preferably from 1 to 20, and more preferably from 1 to 10.

The structure of $X_3$ is not particularly limited, including but not limited to a linear structure, a branched structure bearing pendant groups or a ring-containing structure. Wherein, said ring is not particularly limited, including but not limited to all the above-listed cyclic structures in the terminology section.

$X_3$ is a $C_{1-20}$ hydrocarbyl group, a $C_{1-20}$ heterohydrocarbyl group, a substituted $C_{1-20}$ hydrocarbyl group or a substituted heterohydrocarbyl group. Wherein, the heteroatom or group within $X_3$ is not particularly limited, including but not limited to all the above-listed substituting heteroatoms and substituting groups in the terminology section, and can be a halogen atom, a hydrocarbyl substituent, or a heteroatom-containing substituent.

$X_3$ is more preferably a $C_{1-20}$ alkyl group, a $C_{1-20}$ unsaturated aliphatic hydrocarbyl group, an aryl group, an arylhydrocarbyl group, a $C_{1-20}$ heterohydrocarbyl group, a $C_{1-20}$ hydrocarbyloxy group, an aryloxy group, an arylhydrocarbyloxy group, a $C_{1-20}$ aliphatic-derived heterohydrocarbyloxy group, a heteroaryloxy group, a heteroarylhydrocarbyloxy group, a $C_{1-20}$ hydrocarbylthio group, an arylthio group, an arylhydrocarbylthio group, a $C_{1-20}$ aliphatic-derived heterohydrocarbylthio group, a heteroarylthio group, a heteroarylhydrocarbylthio group, a $C_{1-20}$ hydrocarbylamino group, an arylamino group, an arylhydrocarbylamino group, a $C_{1-20}$ aliphatic-derived heterohydrocarbylamino group, a heteroarylamino group, a heteroarylhydrocarbylamino group, the like, or any substituted form thereof.

$X_3$ is more preferably a $C_{1-20}$ alkyl group, a $C_{3-20}$ alkenyl group, a $C_{3-20}$ alkynyl group, a $C_{5-20}$ dienyl group, a $C_{3-20}$ an alkenyl-hydrocarbyl group, a $C_{3-20}$ alkynyl-hydrocarbyl group, a $C_{5-20}$ dienyl-hydrocarbyl group, an aryl group, an arylhydrocarbyl group, a $C_{3-20}$ aliphatic-derived heterohydrocarbyl group, a heteroaryl group, a heteroarylhydrocarbyl group, a $C_{1-20}$ alkoxy group, a $C_{2-20}$ alkenyloxy group, a $C_{2-20}$ alkynyloxy group, a $C_{2-20}$ alkenyl-hydrocabyloxy group, a $C_{2-20}$ alkynyl-hydrocarbyloxy group, an aryloxy group, an arylhydrocarbyloxy group, a $C_{1-20}$ alkylthio group, a $C_{2-20}$ alkenylhydrocarbylthio group, a $C_{2-20}$ alkynylhydrocarbylthio group, an arylthio group, an arylhydrocarbylthio group, a $C_{1-20}$ alkylamino group, a $C_{2-20}$ alkenylamino group, a $C_{2-20}$ alkenyl-hydrocarbylamino group, an arylamino group, an arylhydrocarbylamino group, the like, or any substituted form thereof.

$X_3$ is more preferably a $C_{1-20}$ alkyl group, a $C_{3-20}$ alkenyl group, a $C_{3-20}$ alkynyl group, a $C_{5-20}$ dienyl group, a $C_{3-20}$ an alkenyl-hydrocarbyl group, a $C_{3-20}$ alkynyl group, a $C_{5-20}$ dienylhydrocarbyl group, an aryl group, an arylhydrocarbyl group, a $C_{3-20}$ aliphatic-derived heterohydrocarbyl group, a heteroaryl group, a heteroarylhydrocarbyl group, the like, or any substituted form thereof.

Specifically, for example, $X_3$ can be a methyl group, an ethyl group, an n-propyl group, an isopropyl group, a butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, a cyclopropyl group, a cyclohexyl group, an ethenyl group, a propenyl group, an allyl group, a propynyl group, a propargyl group, a phenyl group, a benzyl group, a butylphenyl group, a p-methylphenyl group, a methoxy group, an ethoxy group, a phenoxy group, a benzyloxy group, a methylthio group, an ethylthio group, a phenylthio group, a benzylthio group, a methylamino group, an ethylamino group, a benzylamino group, the like, or any substituted form thereof. Wherein, butyl group includes but is not limited to an n-butyl group and a t-butyl group. Octyl group includes but is not limited to an n-octyl group and a 2-ethylhexyl group. Wherein, the atom or group substituent is a halogen atom, a hydrocarbyl substituent or a heteroatom-containing substituent, and preferably a fluorine atom, an alkoxy group, an alkenyl group or a nitro group.

$X_3$ is more preferably a methyl group, an ethyl group, an n-propyl group, an isopropyl group, an n-butyl group, a t-butyl group, an ethenyl group, an allyl group, a phenyl group, a benzyl group, a butylphenyl group, a p-methylphenyl group, a $C_{1-10}$ fluoroalkyl group, a nitrophenyl group, an ethenylphenyl group, a methoxyphenyl group, a fluorophenyl group or the like.

$X_3$ is most preferably a methyl group, a trifluoromethyl group, a 2,2,2-trifluoroethyl group, a p-methyl phenyl group or an ethenyl group.

Wherein, $R_{20}$ is a pendant group, a protected form thereof or a substituted form thereof within an amino acid or a derivative thereof.

Any amino acid as the source of $R_{20}$ can be itself or its derivative, and said amino acid can be of either $_L$- or $_D$-type.

For example, $R_{20}$ can be a pendant group, a protected form or a substituted form derived from any of the following amino acids and derivatives thereof of any Group:

Neutral amino acids and their derivatives: glycine, alanine, valine, leucine, isoleucine, phenylalanine, proline and sarcosine;

Hydroxyl-containing or mercapto-containing amino acids and their derivatives: serine, threonine, cysteine, methionine, tyrosine and hydroxyproline;

Acidic amino acids and their derivatives: aspartic acid, glutamic acid, asparagine and glutamine;

Basic amino acids and their derivatives: lysine, arginine, histidine and tryptophan.

Wherein, $R_{25}$ and $R_{26}$ are each independently a hydrogen atom or a methyl group.

Wherein, $R_{31}$, $R_{32}$, $R_{33}$ and $R_{34}$ are each independently a hydrogen atom or a $C_{1-6}$ hydrocarbyl group. In one molecule, they can be the same or different. $R_{31}$, $R_{32}$, $R_{33}$ and $R_{34}$ are each independently preferably a hydrogen atom or a methyl group.

Regarding said $Z_1$ in the above examples, taking —$(Z_2)$q-$CH_2$—$NH_2$ and —$(Z_2)$q-$(CH_2)_2$—$NH_2$ for example, herein, $R_{01}$ is $NH_2$ and $q_1$=1, while the former $Z_1$ is a methylene group, and the latter $Z_1$ is an ethylene group.

The connection between $Z_2$ and $Z_1$ is not particularly limited in the present invention. The terminal end of $Z_1$ directly connecting with $Z_2$ can be a heteroatom (such as —O—, —S—, —NH—, etc.), a heteroatom substituent (such as —S(=O)—, —S(=O)$_2$—, —P(=O)—, etc.), —$CH_2$—, —CH(LG$_5$)-, —$CR_{22}$—, a carbonyl group, a thiocarbonyl group, —C(=NR$_7$)—, etc. Wherein, the definition of LG$_5$ is defined as above, no more repeating here. Wherein, $R_{22}$ is a divalent linking group to form a ring substituent, wherein the number of ring-membering atoms is preferably from 3 to 8, and said ring substituent is preferably a $C_{3-8}$ ring, and more preferably a $C_{3-8}$ saturated ring. Take g=0 and also two identical $(R_{01})$s for example, such as pairs of $F_1$ and $F_2$ including a succinimidyl propionate group and a succinimidyl acetate group (corresponding to two functional A1 groups having the same $R_{01}$ of a succinimidyl group, and —$(Z_2)_q$—$(Z_1)_{q1}$— being a 1,2-ethylene group and a methylene group, respectively), a propionaldehyde group and a butyraldehyde group (corresponding to two functional D5 groups having the same $R_{01}$ of CHO, and —$(Z_2)_q$—$(Z_1)_{q1}$— being a 1,2-ethylene group and a 1,3-propylene group, respectively), an acetic acid group and a propionic acid group (corresponding to two functional D4 groups having the same $R_{01}$ of COOH, and —$(Z_2)_q$—$(Z_1)_{q1}$— being a methylene group and a 1,2-ethylene group, respectively), herein, q is 0, $q_1$ is 1, $Z_2$ is absent and two $(Z_1)$s are different, or q is 1, $q_1$ is 0, $Z_1$ is absent, and two $(Z_2)$s are different.

1.1.4. Heterofunctional Group Pairs ("$R_{01}$ Pair")

In one molecule, k, G, g, L$_0$, g$_0$, Z$_1$, Z$_2$, R$_{01}$, q, q$_1$ in F$_1$ are each independently the same as or different from that in F$_2$ in the general formulas (1) to (6).

For example, $F_1$ and $F_2$ can have the same or different $R_{01}$ groups.

As for the same $R_{01}$, take $R_{01}$ as a hydroxyl group (H1), an amino group (C3), an aldehyde group (D5) or a succinimide active ester group (A1 or A6) for example:

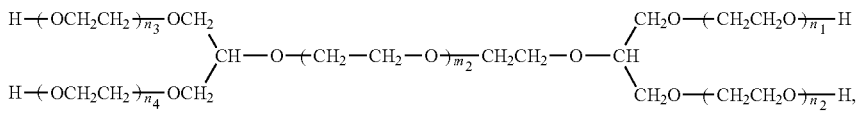

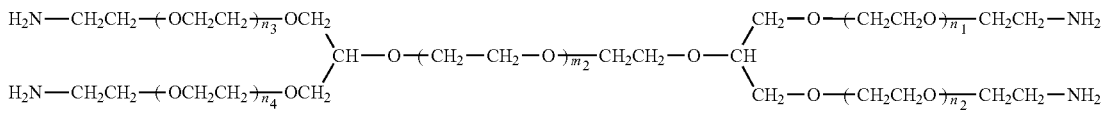


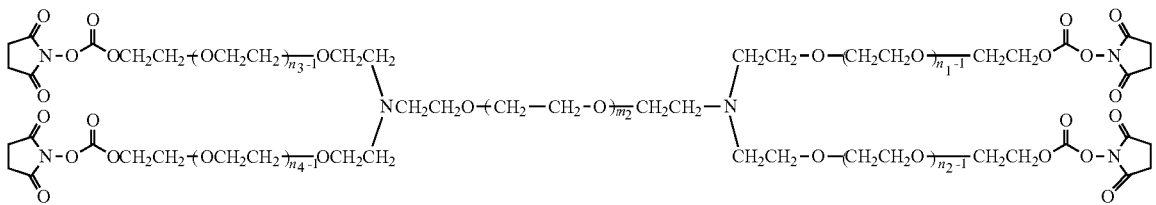

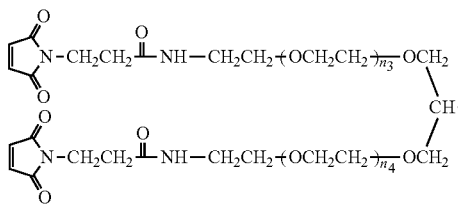

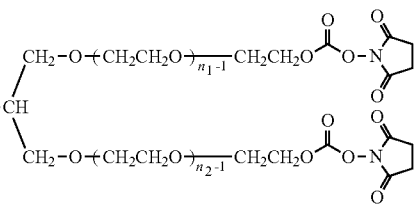

As for different $R_{01}$ groups, the two ($R_{01}$)s of "$R_{01}$ pair" are not particularly limited, and each independently can be any unprotected or protected functional end-group selected from Group A to group J, as long as they can stably exist meanwhile. What should be noted is that, the definition for the stability of a functional group is different from that for the stability of a linking group in the present invention. The stability of a functional group refers to being stable without chemical changes in structure. For example, a hydrochlorinated amino group is regarded as a different $R_{01}$ from the precursor amino group, meaning that the hydrochlorination of an amino group does not belong to a stable conversion. Take a $R_{01}$ pair consisting of a maleimido group with a succinimidyl active ester group for example as follows:

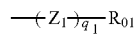

Wherein, when $q_1=1$, $$-(Z_1)_{\overline{q_1}}R_{01}$$

of $F_1$ and $F_2$ can be the same or different from each other in one molecule.

Take a $R_{01}$ pair having identical $R_{01}$ groups and different $Z_1$ groups for example as follows:

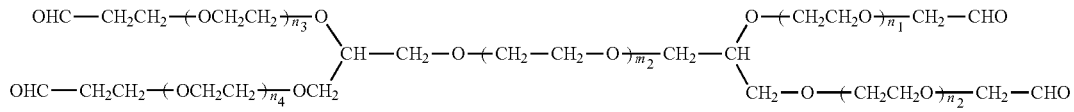

Wherein, $g=0$, $q=0$, $q_1=1$, the $Z_2$ within both $F_1$ and $F_2$ is absent, $Z_1$ of $F_1$ is a methylene group, $Z_1$ of $F_2$ is an ethylene group; both $R_{01}$ groups are an aldehyde group (D5). Meanwhile, in the above formula, $L_1 \ne L_2$ and $L_3 \ne L_4$.

Take a $R_{01}$ pair having the same $Z_1$ group and different $R_{01}$ groups for example,

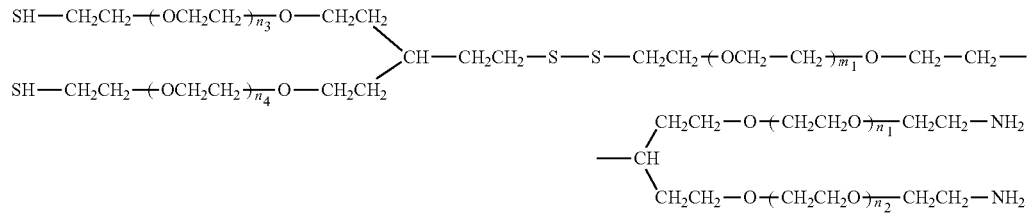

Wherein, $g=0$, $q=0$, $q_1=1$, the $Z_2$ within both $F_1$ and $F_2$ is absent, $Z_1$ is an ethylene group; the $R_{01}$ of $F_1$ is an amino group (C3), and the $R_{01}$ of $F_2$ is a mercapto group (C2).

Take a $R_{01}$ pair having different $Z_1$ groups and different $R_{01}$ groups for example,

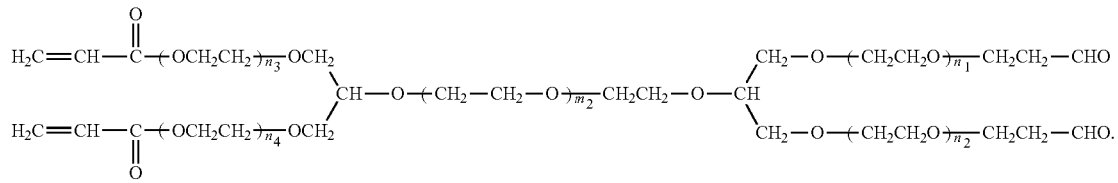

Wherein, $g=0$, $q=0$, $q_1=1$, the $Z_2$ within both $F_1$ and $F_2$ is absent, the $Z_1$ of $F_1$ is an ethylene group, the $Z_1$ of $F_2$ is absent; the $R_{01}$ of $F_1$ is an aldehyde group (D5), and the $R_{01}$ of $F_2$ is an acrylate group (E2).

In the present invention, heterofunctional group pair ($R_{01}$ pair) consisting of two kinds of functional end-groups which can stably exist meanwhile includes but is not limited to the group consisting of a hydroxyl group with a protected hydroxyl group, a hydroxyl group or a protected hydroxyl group with a non-hydroxyl reactive group belonging to Group A to Group H (e.g., an amino group, a protected amino group, an amine salt group, an aldehyde group, an active ester group, a maleimido group, a carboxyl group, a protected carboxyl group, an alkynyl group, a protected alkynyl group, an azido group, an alkenyl group, an acrylic acid group, an acrylate group, a methacrylate group, an epoxy group, an isocyanato group, etc.), a hydroxyl group or a protected hydroxyl group with a functional group or derivative thereof belonging to Group I to Group J (such as targeting group, a photosensitive group, etc.), an active ester group with a maleimido group, an active ester group with an aldehyde group, an active ester group with an azido group, an active ester group with an alkynyl group or a protected alkynyl group, an active ester group with an acrylate group, an active ester group with a methacrylate group, an active ester group with an acrylic acid group, a maleimido group with an azido group, a maleimido group with an alkynyl group or a protected alkynyl group, a maleimido group with an acrylate group, a maleimido group with a methacrylate group, a maleimido group with an acrylic acid group, a maleimido group with a carboxyl group, a maleimido group with an amino group or a protected amino group or an amine salt group, a maleimido group with an isocyanato group, a maleimido group with a protected mercapto group, an aldehyde group with an azido group, an aldehyde group with an acrylate group, an aldehyde group with a methacrylate group, an aldehyde group with an acrylic acid group, an aldehyde group with an epoxy group, an aldehyde group with a carboxyl group, an aldehyde group with an alkynyl group or a protected alkynyl group, an azido group with a mercapto group or a protected mercapto group, an azido group with an amino group or a protected amino group or an amine salt group, an azido group with an acrylate group, an azido group with a methacrylate group, an azido group with an acrylic acid group, an azido group with a carboxyl group, an acrylate group with an amino group or a protected amino group or an amine salt group, an acrylate group with an isocyanato group, an acrylate group with an epoxy group, an acrylate group with a methacrylate group, an acrylate group with a carboxyl group, a methacrylate group with a carboxyl group, a methacrylate group with an amino group or a protected amino group or an amine salt group, a methacrylate group with an isocyanato group, a methacrylate group with an epoxy group, an alkynyl group or a protected alkynyl group with an amino or a protected amino group or an amine salt group, an alkynyl group or a protected alkynyl group with an isocyanato group, an alkynyl group or a protected alkynyl group with an acrylate group, an alkynyl group or a protected alkynyl group with a methacrylate group, an alkynyl group or a protected alkynyl group with acrylic acid group, an alkynyl group or a protected alkynyl group with an epoxy group, an alkynyl group or a protected alkynyl group with a carboxyl group, a protected alkynyl group with an azido group, an acrylic acid group with an isocyanato group, an acrylic acid group with an acrylate group, an acrylic acid group with an epoxy group, an acrylic acid group with a carboxyl group, a carboxyl group with a mercapto group or a protected mercapto group, a carboxyl group with an amino group or a protected amino group or an amine salt group, a carboxyl group with an isocyanato group, a carboxyl group with an epoxy group, an amino group or a protected amino group or an amine salt group with a mercapto or a protected mercapto group, a targeting group with a non-hydroxyl reactive group, a photosensitive group with a non-hydroxyl reactive group, and the like.

Any of the above-said active ester groups can also be replaced by suitable analogs thereof, wherein, said active ester groups include but are not limited to all disclosed succinimidyl active esters groups (e.g. a succinimidyl carbonate group, etc.) in the present invention, a p-nitrophenyl active ester group, an o-nitrophenyl active ester group, a benzotriazole active ester group, a 1,3,5-trichlorobenzyl active ester group, a 1,3,5-fluorophenyl active ester group, a pentafluorophenyl active ester group, an imidazole active ester group and the like, and said analogs of active ester groups can be a 2-thioxo-3-thiazolidine-formate group, a 2-thioxo-thiazolidine-3-carboxylate group, a 2-thioxo-pyrrolidine-N-carboxylate group, a 2-thioxo-pyrrolidine-1-carboxylate group, a 2-thioxo-benzothiazole-N-carboxylate group, a 1-oxo-3-thioxo-isoindoline-formate or the like. Wherein said amino groups can be a primary amino group or a secondary amino group, and said amine salt is preferably a hydrochlorinated form thereof, such as $NH_2HCl$.

Wherein, a non-hydroxyl reactive group can be but not limited to an amino group, a protected amino group, an aldehyde group, and active ester group, a maleimido group, a carboxyl group, a protected carboxyl group, an alkynyl group, a protected alkynyl group, an azido group, an alkenyl group, an acrylic acid group, an acrylate group, a methacrylate group, an epoxy group, an isocyanato group, or the like; and said amino group can be a primary amino group or a secondary amino group.

1.1.5. Divalent Linking Groups

In general formula (1) to general formula (6), $L_0$, $L_1$, $L_2$, $L_3$, $L_4$, $L_5$, $L_6$, $W_0$, $W_{01}$, $W_{02}$, $Z_1$ and $Z_2$ are each independently a divalent group and can be each independently the same or different in one molecule. Wherein, the $L_0$ can be of $F_1$ or of $F_2$; the $Z_1$ can be of $F_1$ or of $F_2$, $Z_2$ can be of $F_1$ or of $F_2$, being denoted as $L_0(F_1)$, $L_0(F_2)$, $Z_1(F_1)$, $Z_1(F_2)$, $Z_2(F_1)$ and $Z_2(F_2)$, respectively.

The structure of $L_0$, $L_1$, $L_2$, $L_3$, $L_4$, $L_5$, $L_6$, $W_0$, $W_{01}$, $W_{02}$, $Z_1$ and $Z_2$ are not particularly limited, each independently can be but not limited to a linear structure, a branched structure or a ring-containing structure.

The non hydrogen atom number of $L_0$, $L_1$, $L_2$, $L_3$, $L_4$, $L_5$, $L_6$, $W_0$, $W_{01}$, $W_{02}$, $Z_1$ and $Z_2$ are not particularly limited, each independently preferably from 1 to 50, more preferably from 1 to 20, and more preferably from 1 to 10. Said non-hydrogen atom is a carbon atom or a heteroatom. Said heteroatom can be but not limited to O, S, N, P, Si, B or the like. When the non-hydrogen atom number is 1, it can be a carbon atom or a heteroatom. When more than 1, the species of non-hydrogen atoms are not particularly limited, and can be of merely one species, or be a combination of two or two more species, which can be any combination of carbon atoms with carbon atoms, carbon atoms with heteroatoms or heteroatoms with heteroatoms.

Preferably, the non-hydrogen atom number of $L_0$, $L_1$, $L_2$, $L_3$, $L_4$, $L_5$, $L_6$, $W_0$, $W_{01}$, $W_{02}$, $Z_1$ and $Z_2$ are each independently preferably from 1 to 50. Wherein, non-hydrogen atoms can be C, O, S, N, P, Si, B or the like; when the non-hydrogen atom number is more than 1, the species number of non-hydrogen atoms can be one, two, or two more; the non-hydrogen atoms can be any combination of carbon atoms with carbon atoms, carbon atoms with heteroatoms or heteroatoms with heteroatoms.

The stability of $L_0$, $L_1$, $L_2$, $L_3$, $L_4$, $L_5$, $L_6$, $W_0$, $W_{01}$, $W_{02}$, $Z_1$ and $Z_2$ are not particularly limited, wherein any divalent linking group thereof or any joint divalent linking group thereof formed together with its adjacent heterosubstituted group can be either a stable linking group denoted as STAG (i.e., a linking group which can remain stable, or a linking group which can keep covalently linking the adjacent groups along the backbone (not side groups or pendent groups) being connected under a certain condition) or a degradable linking group denoted as DEGG (i.e., a linking group which may be degraded, or a linking group which may be degraded into at least two separate individual subgroups). The condition "to remain stable" is not particularly limited, including but not limited to conditions such as light illumination, heat, an enzymatic condition, an oxidation-reduction condition, an acidic condition, a basic condition, a physiological condition, a simulated physiological environment in vitro, etc., and preferably conditions such as light illumination, heat, an enzymatic condition, an oxidation-reduction condition, an acidic condition, a basic condition, etc. The condition "to be degradable" or "to degrade" or "to be degraded" is not particularly limited, including but not limited to conditions such as light illumination, heat, an enzymatic condition, an oxidation-reduction condition, an acidic condition, a basic condition, a physiological condition, a simulated physiological environment in vitro, etc., and preferably conditions such as light illumination, heat, an enzymatic condition, an oxidation-reduction condition, an acidic condition, a basic condition, etc.

Divalent linking groups in quantities of zero, one, two or two more selected from $L_1$, $L_2$, $L_3$, $L_4$, $L_5$, $L_6$, $L_0(F_1)$, $L_0(F_2)$, $Z_1(F_1)$, $Z_1(F_2)$, $Z_2(F_1)$, $Z_2(F_2)$, $W_0$, $W_{01}$, $W_{02}$, and joint divalent linking groups formed by any thereof together with its adjacent heterosubstituted group can be stable linking groups denoted as STAG, the other divalent linking groups as well as joint divalent linking groups thereof with adjacent heterosubstituted group being degradable linking groups denoted as DEGG.

Examples of said adjacent heterosubstituted groups include an oxy group, a thioxy group, $-NX_{10}-$, a carbonyl group, a thiocarbonyl group, $-C(=NX_{10})-$, $-C(=NH_2^+)-$, $-S(=O)-$, $-S(=O)_2-$, $-P(=O)-$, $-Si(R_{37})_2-$, $-C(=O)-M_9-$, $-M_9-C(=O)-$, $-C(=S)-M_9-$, $-M_9-C(=S)-$, $-C(=NX_{10})-M_9-$, $-M_9-C(=NX_{10})-$, $-C(=NH_2^+)-M_9-$, $-M_9-C(=NH_2^+)$ and the like. Wherein, the definitions of $M_9$, $X_{10}$ and $R_{37}$ are the same as above-defined, no more repeated here.

The groups $U_1(O-)_3$ and $U_2(O-)_3$ in the present invention preferably exclude the repeat unit of $-OCH_2CH_2O-$.

The groups including $-O(L_0)_{g0}-$ and $-O(Z_2)_q$ $-(Z_1)_{q1}-$ in the present invention preferably contain no repeat units of $-OCH_2CH_2O-$.

1.1.6. Degradability

The H-shaped multifunctionalized polyethylene glycol derivative can be either stable or degradable. When being degradable, in one molecule, the number of degradable sites can be one or more. According to the difference in number and position of degradable sites, structures include but are not limited to the following cases:

(1) wherein, one position at $Z_1(F_1)$ or $Z_2(F_1)$ is degradable, and the other above-said positions each independently can be either stable or degradable; or when one position at $Z_1(F_2)$ or $Z_2(F_2)$ is degradable, and the other above-said positions each independently can be either stable or degradable;

(2) wherein, one position at $Z_1(F_1)$ or $Z_2(F_1)$, and one position at $Z_1(F_2)$ or $Z_2(F_2)$ are degradable, and the other above-said positions each independently can be either stable or degradable;

(3) wherein, one position at $L_0(F_1)$ or $L_0(F_2)$ is degradable, and the other positions each independently can be either stable or degradable;

(4) wherein, positions at both $L_0(F_1)$ and $L_0(F_2)$ are degradable, and the other positions each independently can be either stable or degradable;

(5) wherein, one position at $L_5$ or $L_6$ is degradable, and the other positions each independently can be either stable or degradable;

(6) wherein, positions at both $L_5$ and $L_6$ are degradable, and the other positions each independently can be either stable or degradable;

(7) wherein, one position at $W_0$, $W_{01}$ or $W_{02}$ is degradable, and the other positions each independently can be either stable or degradable.

With respect to the degradable position, it can occur within $U_{01}$, $U_{02}$, $L_1$, $L_2$, $L_3$, $L_4$, $L_5$, $L_6$, $W_0$, $W_{01}$, $W_{02}$, $(L_0)_{g0}$, G and $(Z_2)_q$—$(Z_1)_{q1}$; (2) or at the connection of any above-said group with its adjacent group, except that the degradability of the connection of $Z_1$—$R_{01}$ is not confined. In the first case, the degradable groups contain a degradable divalent linking group such as an ester group, a carbonate group, or the like. In the second case, connection positions selected from $U_{01}$-$L_i$ (i=1, 2 or 5), $U_{02}$-$L_i$ (i=3, 4 or 6), $L_i$ (i=1, 2, 3, 4, 5 or 6)-O, O-$(L_0)_{g0}$, $(L_0)_{g0}$-G, G-$Z_2$ and $Z_2$—$Z_1$ each independently can be degradable.

The number and position of degradable sites of H-shaped multifunctionalized polyethylene glycol derivatives have a great influence on the stability of polymer and releasability of modified drugs thereof. (1) When a degradable position occurs between the functional end-group and its corresponding polyethylene glycol chain, such as is at $(Z_2)_q$—$(Z_1)_{q1}$—, the pegylated drug molecule can be separated from the polyethylene glycol moiety to expose its active site to a maximum extent, and thus the drug molecule can turn towards its unmodified form to a maximum extent when undergoing degradation. (2) When a degradable position occurs at the trivalent branch center, including $U_{01}$, $U_{02}$, $L_1$, $L_2$, $L_3$, $L_4$, $L_5$, $L_6$, $U_{01}$-$L_i$ (i=1, 2 or 5), $U_{02}$-$L_i$ (i=3, 4 or 6) and $L_i$ (i=1, 2, 3, 4, 5 or 6)-O, the molecular weight of polyethylene glycol moiety connected with the drug molecule decreases, and thus the shielding effect for the drug molecule is reduced and drug efficacy increases.

Several typical degradation manners are as follows:

(a) wherein, g is equal to 0 or 1, the divalent connections between the trivalent core structure of trivalent semiH-branching structures and PEG branch chains can be degraded, at least one position of $U_{01}$-$L_1$-O and $U_{01}$-$L_2$-O at $U_1$(O—)$_3$ is degradable, and at least one position of $U_{02}$-$L_3$-O and $U_{02}$-$L_4$-O at $U_2$(O—)$_3$ is degradable;

(b) wherein, g is equal to 0 or 1, the divalent connections between the trivalent core structure of trivalent semiH-branching structures and PEG main chain can be degraded, and the position of $U_{01}$-$L_5$-O at $U_1$(O—)$_3$ is degradable, and the position of $U_{02}$-$L_6$-O at $U_2$(O—)$_3$ is degradable;

(c) wherein, g is equal to 0 or 1, the trivalent semiH-branching structure ($U_{01}$ or $U_{02}$) contains a cyclic trivalent core structure $CC_3$, and $CC_3$ is degradable;

(d) wherein, g is equal to 0 or 1, degradable reaction only occurs at LPEG, and $m_1 \times j \neq 0$ or $m_1+m_3 \neq 0$; when $m_1 \times j \neq 0$, degradable reaction only occurs at —$OW_0O$—; when $m_1+m_3 \neq 0$, at least one position at —$OW_{01}O$— and —$OW_{02}O$— is degradable;

(e) wherein, g is equal to 0 or 1, degradable reaction only occurs at —$(Z_2)_q$—$(Z_1)_{q1}$—, wherein the degradation position also includes the connection of —$(Z_2)_q$—$(Z_1)_{q1}$— with its adjacent group towards the PEG side;

(f) wherein, g is equal to 1, degradable reaction only occurs at $(L_0)_{g0}$, wherein the degradation positions include inside of $(L_0)_{g0}$, connection between O-$(L_0)_{g0}$ and connection between $(L_0)_{g0}$-G;

(g) wherein, g is equal to 1, degradable reaction only occurs at inside of G.

When $F_1$ and $F_2$ have identical $R_{01}$ groups, three degradation manners including (e), (f) or (g) can take place, and branch chains on different sides can be degraded in the same manner. When $U_1=U_2$ and if the degradation manner is (a), (b) or (c), the degradability at corresponding branching-center would be the same.

When $F_1$ and $F_2$ have different $R_{01}$ groups, the degradation manner of two sides are each independent, that is, the degradability of positions including trivalent core structures at two branching centers, the divalent linkages between trivalent core structures and PEG branch chains, the divalent linkages between trivalent core structures and PEG main chain, and $(L_0)_{g0}$-G-$((Z_2)_q$—$(Z_1)_{q1})_k$ at the terminal end of branch chains are each independent, and can be the same or different.

The H-shaped multifunctionalized polyethylene glycol derivative can involve one or one more degradation manners. When more than one degradation manner are concerned, gradient degradation may occur to more flexibly control the degradation kinetics of pegylated product; with respect to the pegylated drug, pharmacokinetics in body can be controlled more flexibly and more finely, and the requirement for therapeutic effect of more comprehensive treatment can be met better.

The combination of $U_1$ and $U_2$ is preferably selected from the following Groups:

Group (1): both $U_1$(O—)$_3$ and $U_2$(O—)$_3$ are stable;
Group (2): both $U_1$(O—)$_3$ and $U_2$(O—)$_3$ are degradable;
Group (3): $U_1$(O—)$_3$ is stable, and $U_2$(O—)$_3$ is degradable;
Group (4): $U_1$(O—)$_3$ is degradable, and $U_2$(O—)$_3$ is stable.

1.1.7. Description for Stable and Degradable Groups

In the present invention, a stable linking group denoted as STAG or a degradable linking group denoted as DEGG, can exist within any of the above-mentioned divalent linking groups including $L_1$, $L_2$, $L_3$, $L_4$, $L_6$, $Z_1$ and $Z_2$, or within the divalent linking group formed by any divalent linking group together with its adjacent heterosubstituted group, or within any of the branched core structures including $U_1$, $U_2$, $U_{01}$ and $U_{02}$, or within the terminal branched structure denoted as G, or within the divalent linking group formed by a multivalent group and its adjacent group.

1.1.7.1. Stable Divalent Linking Groups (Stable Divalent Linkages): STAG

The condition "to be stable" or "to remain stable" is not particularly limited, including but not limited to conditions such as light illumination, heat, an enzymatic condition, an oxidation-reduction condition, an acidic condition, a basic condition, a physiological condition, a simulated physiological environment in vitro, etc., preferably conditions such as light illumination, heat, an enzymatic condition, an oxidation-reduction condition, an acidic condition, a basic condition, etc.

The stability type of STAG is not particularly limited, can be but not limited to an alkylene group, a divalent heteroalkyl group, a carbon-carbon double bond, a carbon-carbon triple bond, a divalent dienyl group, a divalent cycloalkyl group, a divalent cycloalkenyl group, a divalent cycloalkenylhydrocarbyl group, a divalent cycloalkynyl group, an arylene group, an aliphatic-derived heteroring group, a heterophenylene group (with one or more heteroatoms as ring-membering atom), an aryloheteroring group, a hetero-condensed heteroring group, a substituted alkylene group, a substituted heteroalkylene group (or a substituted divalent heteroalkyl group), a substituted double bond (e.g., an amino-substituted double bond such as —$(R_8)C=C$ ($NR_7R_{39}$)—), a substituted divalent dienyl group, a substituted divalent cycloalkyl group, a substituted divalent cycloalkenyl group, a substituted divalent cycloalkenylhydrocarbyl group, a substituted divalent cycloalkynyl group, a substituted arylene group, a substituted aliphatic-derived heteroring group, a substituted heterophenylene group, a substituted aryloheterorings, a substituted heterocondensed heteroring group, an ether bond, a thioether bond, a urea bond, a thiourea bond, a carbamate bond, a thiocarbamate bond, —P(=O)—, —P(=S)—, a divalent silyl group without active hydrogen atoms, a boron-containing divalent linking group, a secondary amino bond, a tertiary amino bond, a carbonyl group, a thiocarbonyl group, a —S(=O)$_2$— linkage (a sulfuryl group), a —S(=O)— linkage, a 1,1-ring linkage such as -$M_{17}(R_{22})$—, an amide bond, a thioamide bond, a sulfonamide bond, an enamino group, a triazole linkage, a 4,5-dihydroisoxazole linkage, the skeleton of an amino acid or derivative thereof, the like or a divalent linking group by the combination of any two or two more linkages of the foregoing (e.g., —S—$CH_2C$(=O)N($R_7$)—).

Specifically, a STAG linkage can be but not limited to any of the following structures, or the combination of any two or two more thereof:

-$L_{11}$-, —$(R_5)_{r1}$—C($R_8$)=C($R_9$)—$(R_6)_{r2}$—, —$(R_5)_{r1}$—C≡C—$(R_6)_{r2}$—, —$(R_5)_{r1}$—C($R_8$)=C($R_9$)—C($R_{10}$)=C($R_{11}$)—$(R_6)_{r2}$—, —$(R_5)_{r1}$—O—$(R_6)_{r2}$—, —$(R_5)_{r1}$—S—$(R_6)_{r2}$—, —$(R_5)_{r1}$—N($R_{18}$)—C(=O)—N($R_{19}$)—$(R_6)_{r2}$—, —$(R_5)_{r1}$—N($R_{18}$)—C(=S)—N($R_{19}$)—$(R_6)_{r2}$—, —$(R_5)_{r1}$—N($R_7$)—C(=O)—O—$(R_6)_{r2}$—, —$(R_5)_{r1}$—O—C(=O)—N($R_7$)—$(R_6)_{r2}$—, —$(R_5)_{r1}$—N($R_7$)—C(=S)—O—$(R_6)_{r2}$—, —$(R_5)_{r1}$—O—C(=S)—N($R_7$)—$(R_6)_{r2}$—, —$(R_5)_{r1}$—N($R_7$)—C(=O)—S—$(R_6)_{r2}$—, —$(R_5)_{r1}$—S—C(=O)—N($R_7$)—$(R_6)_{r2}$—, —$(R_5)_{r1}$—N($R_7$)—C(=S)—S—$(R_6)_{r2}$—, —$(R_5)_{r1}$—S—C(=S)—N($R_7$)—$(R_6)_{r2}$—, —$(R_5)_{r1}$—N($R_7$)—$(R_6)_{r2}$—, —$(R_5)_{r1}$—C(=O)—$(R_6)_{r2}$—, —$(R_5)_{r1}$—C(=S)—$(R_6)_{r2}$—, —$(R_5)_{r1}$—P(=O)—$(R_6)_{r2}$—, —$(R_5)_{r1}$—$(R_{38})$P(=O)—$(R_6)_{r2}$—, —$(R_5)_{r1}$—$(R_{38}$O)P(=O)—$(R_6)_{r2}$—, —$(R_5)_{r1}$—P(=S)—$(R_6)_{r2}$—, —$(R_5)_{r1}$—$(R_{38})$P(=S)—$(R_6)_{r2}$—, —$(R_5)_{r1}$—$(R_{38}$O)P(=S)—$(R_6)_{r2}$—, —$(R_5)_{r1}$—C(=O)N($R_7$)—$(R_6)_{r2}$—, —$(R_5)_{r1}$—N($R_7$)C(=O)—$(R_6)_{r2}$—, —$(R_5)_{r1}$—$NHCH_2$—$(R_6)_{r2}$—, —$(R_5)_{r1}$—$CH_2NH$—$(R_6)_{r2}$—, —$(R_5)_{r1}$—$CH_2$—N($R_7$)—$CH_2$—$(R_6)_{r2}$—, —$(R_5)_{r1}$—C($R_8$)=C($R_9$)—$(R_6)_{r2}$—, —$(R_5)_{r1}$—C≡C—$(R_6)_{r2}$—, —$(R_5)_{r1}$—N($R_7$)C(=O)$CH_2$—S—$(R_6)_{r2}$—, —$(R_5)_{r1}$—S—$CH_2C$(=O)N($R_7$)—$(R_6)_{r2}$—, —$(R_5)_{r1}$—S(=O)$_2$—$(R_6)_{r2}$—, —$(R_5)_{r1}$—S(=O)—$(R_6)_{r2}$—, —$(R_5)_{r1}$—$(R_8)$C=C(N$R_7R_{39}$)—$(R_6)_{r2}$—, —$(R_5)_{r1}$—(N$R_7R_{39}$)C=C($R_8$)—$(R_6)_{r2}$—, —$(R_5)_{r1}$-$M_{17}(R_{22})$—$(R_6)_{r2}$—,

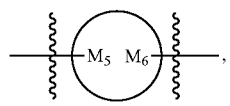

the skeleton of an ω-amino acid, and a divalent linking group containing at least one amino acid skeleton or one amino acid derivative skeleton from the set SG. Said ω-amino acids is preferably $H_2N(CH_2)_{j1}COOH$, wherein, $j_1$ is an integer from 2 to 20, preferably from 2 to 12, more preferably from 2 to 6, and most preferably 2.

Wherein, r1 and r2 are each independently 0 or 1 and typically r1 is 0.

Wherein, the definitions of $R_7$, $R_{18}$, $R_{19}$, $R_8$, $R_9$, $R_{10}$, $R_{11}$, $M_5$, $M_6$ and $M_5$- or $M_6$-membered rings are the same as above-defined, no more repeated here. Wherein, typical examples of STAG include but are not limited to: $R_1$ is a hydrogen atom, a methyl group or an ethyl group; $R_3$ is a methyl, an ethyl group or a benzyl group; $R_7$, $R_{18}$ and $R_{19}$ are each independently a methyl group, an ethyl group, an n-propyl group, an isopropyl group, an n-butyl group, a t-butyl group, a pentyl group, a hexyl group, an allyl group, a triphenylmethyl group (a trityl group), a phenyl group, a benzyl group, a nitrophenyl group, an o-methoxyphenyl group or a trifluoromethyl benzyl group; $R_8$, $R_9$, $R_{10}$ and $R_{11}$ are each independently a hydrogen atom or a methyl group.

Also preferably, all of $R_7$, $R_{18}$, $R_{19}$, $R_8$, $R_9$, $R_{10}$, $R_{11}$ and $R_{39}$ are a hydrogen atom.

Wherein, $L_{11}$ is a stable hydrocarbylene group or substituted hydrocarbylene group. Wherein, the heteroatom or group substituent is not particularly limited, including but not limited to all the above-listed substituting heteroatoms and substituting groups in the terminology section, and can be a halogen atom, a hydrocarbyl substituent, or a heteroatom-containing substituent.

The structure of $L_{11}$ is not particularly limited, including but not limited to a linear structure, a branched structure or a ring-containing structure.

The carbon-atom number of $L_{11}$ is not particularly limited, preferably from 1 to 20, and more preferably from 1 to 10.

$L_{11}$ is preferably a stable $C_{1-20}$ hydrocarbylene group or substituted $C_{1-20}$ hydrocarbylene group. The condition "to be stable" is not particularly limited, including but not limited to conditions such as light illumination, heat, an enzymatic condition, an oxidation-reduction condition, an acidic condition, a basic condition, a physiological condition, a simulated physiological environment in vitro, etc.

$L_{11}$ is more preferably a stable $C_{1-20}$ hydrocarbylene group or substituted $C_{1-20}$ hydrocarbylene group under the condition of light illumination, heat, an enzymatic condition, an oxidation-reduction condition, an acidic condition, a basic condition, a physiological condition, a simulated environment in vitro, or the like.

Take hydrocarbylene groups containing a cyclic structure for example, $L_{11}$ can be but not limited to

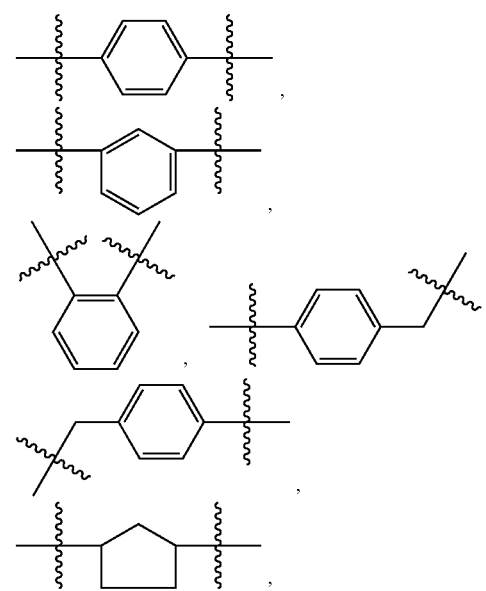

-continued

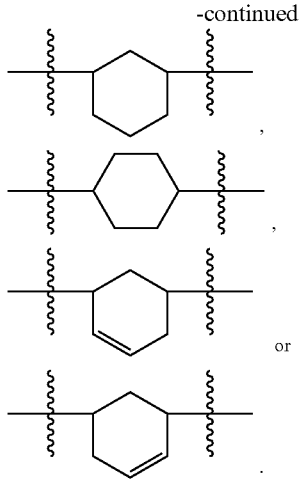

or

Take a methylene group or a substituted methylene group for example, the structure of $L_{11}$ includes but is not limited to:

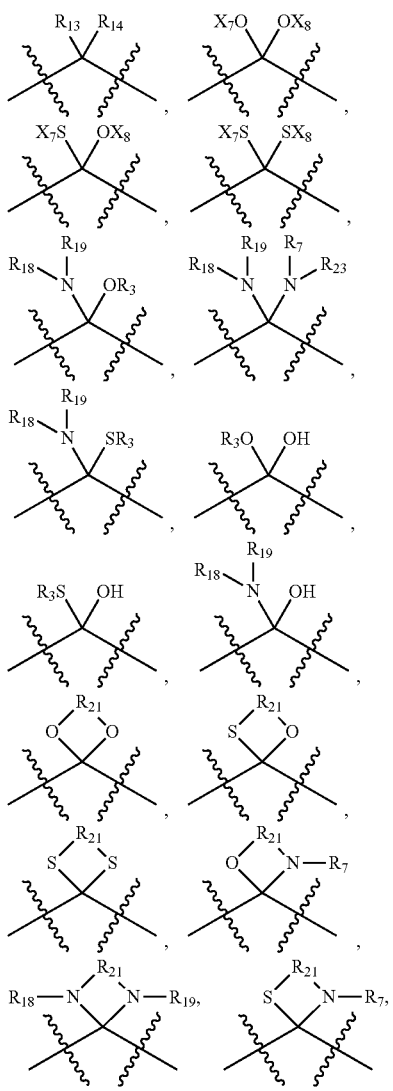

-continued

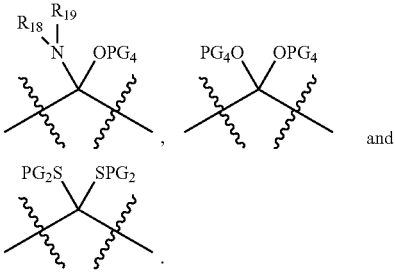

and

Wherein, the definitions of $R_3$, $R_7$, $R_{18}$, $R_{19}$, $R_{23}$, $R_{21}$, $PG_2$ and $PG_4$ are the same as above-defined, no more repeated here.

Wherein, for example,

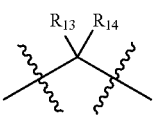

includes but is not limited to: a methylene group,

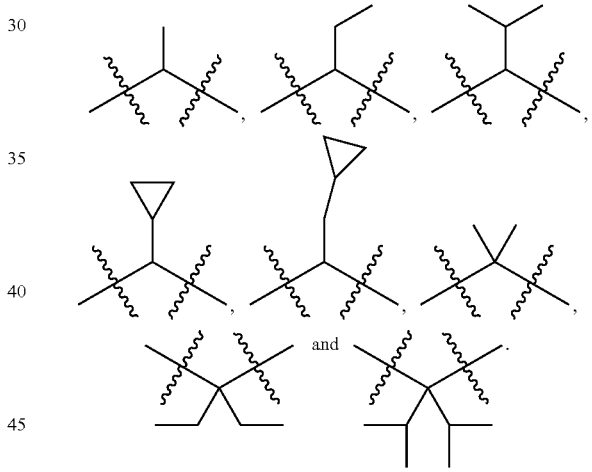

and $L_{11}$ is more preferably a methylene group, a 1,1-ethylene group, a 1,2-ethylene group, a 1,3-propylene group, a 1,2-propylene group, an isopropylene group, a butylene group, a pentylene group, a hexylene group, a heptylene group, an octylene group, a nonylene group, a decylene group, an undecylene group, a dodecylene group, a tridecylene group, a tetradecylene group, a pentadecylene group, a hexadecylene group, a heptadecylene group, an octadecylene group, a nonadecylene group, an eicosylene group, a cyclopropylene group, a cyclopentylene group, a cyclohexylene group, a cyclohexenylene group, a cyclooctylene group, a cyclodecylene group, an o-phenylene group, a p-phenylene group, an m-phenylene group, a benzylene group, any substituted form thereof, and the combination of any two or two more hydrocarbylene groups or substituted hydrocarbylene groups thereof. Wherein, the substituent is a $C_{1-6}$ alkyl group, a phenyl group, a benzyl group, a methylphenyl group or a butylphenyl group.

For example, —NR$_7$— includes but is not limited to —NH—,

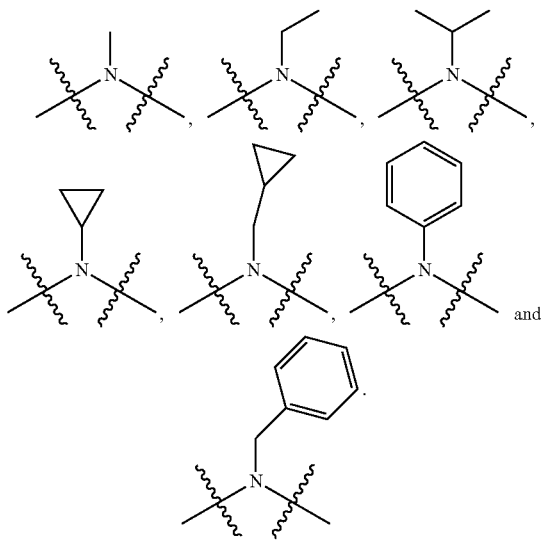

and

Wherein, X$_7$ and X$_8$ exist in one molecule and each independently connect to an oxy group or a thioxy group. Wherein, one of X$_7$ and X$_8$ is R$_3$, and the other is X$_4$ when connecting to an oxy group, or X$_5$ when connecting to a thioxy group. Wherein, the definitions of R$_3$, X$_4$ and X$_5$ are the same as above-defined, no more repeated here.

Wherein, R$_{13}$ and R$_{14}$ are each independently a hydrogen atom, a heteroatom or a substituting group linked to a secondary or tertiary carbon.

The heteroatom or group substituent of R$_{13}$ and R$_{14}$ is not particularly limited.

The carbon-atom number of R$_{13}$ and R$_{14}$ is not particularly limited. For aliphatic hydrocarbyl groups or aliphatic-derived heterohydrocarbyl groups, the carbon-atom number is preferably from 1 to 20, and more preferably 1 to 10. With respect to aryl groups, arylhydrocarbyl group, heteroaryl groups, heteroarylhydrocarbyl groups and condensed heterocyclohydrocarbyl groups, the carbon-atom number is not particularly limited.

R$_{13}$ and R$_{14}$ each independently can be but not limited to a hydrogen atom, a halogen atom, a C$_{1-20}$ hydrocarbyl group, a C$_{1-20}$ heterohydrocarbyl group, a substituted C$_{1-20}$ hydrocarbyl group, a substituted C$_{1-20}$ heterohydrocarbyl group, or the like.

Wherein, the atom or group substituent is not particularly limited, including but not limited to all the above-listed substituting atoms and substituting groups in the terminology section, and can be a halogen atom, a hydrocarbyl substituent, or a heteroatom-containing substituent.

R$_{13}$ and R$_{14}$ are each independently preferably a hydrogen atom, a halogen atom, a C$_{1-20}$ alkyl group, a C$_{3-20}$ unsaturated hydrocarbyl group, a C$_{1-20}$ linear aliphatic hydrocarbyl group, a C$_{3-20}$ branched aliphatic hydrocarbyl group, a C$_{3-20}$ alicyclic hydrocarbyl group, an aryl group, an arylhydrocarbyl group, a C$_{1-20}$ open-chain heterohydrocarbyl group, a C$_{3-20}$ aliphatic-derived heterocyclohydrocarbyl group, a heteroaryl group, a heteroarylhydrocarbyl group, a condensed heterocyclohydrocarbyl group, a C$_{1-20}$ hydrocarbyloxy group, C$_{1-20}$ hydrocarbylthio group, a C$_{1-20}$ hydrocarbylamino group, a C$_{1-20}$ aliphatic hydrocarbyl-acyl group, an aryl-acyl group, an arylhydrocarbyl-acyl group, a C$_{1-20}$ aliphatic-derived heterohydrocarbyl-acyl group, a heteroaryl-acyl group, a heteroarylhydrocarbyl-acyl group, a C$_{1-20}$ hydrocarbyloxy-acyl group, a C$_{1-20}$ hydrocarbylthio-acyl group, a C$_{1-20}$ hydrocarbylamino-acyl group, a C$_{1-20}$ hydrocarbyl-acyloxy group, a C$_{1-20}$ hydrocarbyl-acylthio group, a C$_{1-20}$ hydrocarbyl-acylamino group, the like, or any substituted form thereof. Wherein, the atom or group substituent is preferably a fluorine atom, a chlorine atom, a bromine atom, an iodine atom, a C$_{1-6}$ alkyl group, a C$_{1-6}$ alkenyl group, an aryl group, an alkoxy group or a nitro group.

Wherein, said acyl group is not particularly limited, including but not limited to all the above-listed acyl groups in the terminology section. Said acyl group is preferably a carbonyl group, a sulfonyl group, a sulfinyl group, a phosphoryl group, a phosphiryl group, a phosphinyl group, a nitroxyl group, a nitrosyl group, a thiocarbonyl group, an imidoyl group, a thiophosphoryl group, a dithiophosphoryl group, a trithiophosphoryl group, a thiophosphiryl group, a dithiophosphiryl group, a thiophosphinyl group, a thiophosphono group, a dithiophosphono group, a thiophosphino group or the like, and more preferably a carbonyl group, a thiocarbonyl group, a sulfonyl group or a sulfinyl group.

R$_{13}$ and R$_{14}$ are each independently preferably a hydrogen atom, a halogen atom, a C$_{1-20}$ alkyl group, a C$_{2-20}$ alkenyl group, a C$_{2-20}$ alkynyl group, a C$_{4-20}$ dienyl group, a C$_{3-20}$ alkenyl-hydrocarbyl group, a C$_{3-20}$ alkynyl-hydrocarbyl group, a C$_{5-20}$ dienyl-hydrocarbyl group, a C$_{1-20}$ linear aliphatic hydrocarbyl group, a C$_{3-20}$ branched aliphatic hydrocarbyl group, a C$_{3-20}$ cycloalkyl group, a C$_{3-20}$ cycloalkenyl group, a C$_{3-20}$ cycloalkynyl group, a C$_{5-20}$ cyclodienyl-hydrocarbyl group, a phenyl group, a condensed cyclohydrocarbyl group, an arylhydrocarbyl group, a C$_{1-20}$ open-chain heterohydrocarbyl group, a C$_{3-20}$ aliphatic-derived heterocyclohydrocarbyl group, a heteroaryl group, a heteroarylhydrocarbyl group, an aryl-condensed heterocyclic hydrocarbyl group, a heterocondensed heterocyclic hydrocarbyl group, a C$_{1-20}$ alkoxy group, a C$_{2-20}$ alkenyloxy group, a C$_{2-20}$ alkynyloxy group, an aryloxy, an arylhydrocarbyloxy group, a C$_{1-20}$ alkylthio group, a C$_{2-20}$ alkenylthio group, a C$_{2-20}$ alkynylthio group, an arylthio group, a C$_{1-20}$ alkylamino group, a C$_{2-20}$ alkenylamino group, a C$_{1-20}$ alkyl-acyl group, a C$_{2-20}$ alkenyl-acyl group, a C$_{2-20}$ alkynyl-acyl group, an aryl-acyl group, an arylhydrocarbyl-acyl group, a C$_{1-20}$ aliphatic-derived heterohydrocarbyl-acyl group, a heteroaryl-acyl group, a heteroarylhydrocarbyl-acyl group, a C$_{1-20}$ alkoxy-acyl group, an aryloxy-acyl group, a C$_{1-20}$ alkylthio-acyl group, an arylthio-acyl group, a C$_{1-20}$ alkylamino-acyl group, a C$_{1-20}$ alkyl-acyloxy group, an aryl-acyloxy, a C$_{1-20}$ alkyl-acylthio group, an aryl-acylthio group, a C$_{1-20}$ alkyl-acylamino group, the like, or any substituted form thereof.

Specifically, R$_{13}$ and R$_{14}$ can be each independently a hydrogen atom, a fluorine atom, a chlorine atom, a bromine atom, an iodine atom, a methyl group, an ethyl group, an n-propyl group, an isopropyl group, a butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, a cyclopropyl group, a cyclohexyl group, a phenyl group, a benzyl group, a butylphenyl group, a p-methylphenyl group, a vinyl group, a propenyl group, an allyl group, a propynyl group, a propargyl group, a methoxy group, an ethoxy group, a phenoxy group, a benzyloxy group, a methylthio group, an ethylthio group, a phenylthio group, a benzylthio group, a methylamino group, an ethylamino group, a benzylamino group, an acetyl group, a benzoyl group, a methoxy-acyl group, an ethoxy-acyl group, a phenoxy-acyl group, a benzyloxy-acyl group, a methylthio-acyl group, an ethylthio-acyl group, a phenylthio-acyl group, a benzylthio-acyl group, a methylamino-acyl group, an ethylamino-acyl group, a phenylamino-acyl group, a benzylamino-acyl group, an ethyl-acyloxy group, a phenyl-acyloxy group, an ethyl-acylthio group, a phenyl-acylthio group, an ethyl-acylamino group, a phenyl-acylamino group, a $C_{1-20}$ haloalkyl group, the like, or any substituted form thereof. Wherein, butyl group includes but is not limited to an n-butyl group and a t-butyl group. Octyl group includes but is not limited to an n-octyl group and a 2-ethylhexyl group. Said acyl group can be any one of the above-mentioned acyl groups. Wherein, the atom or group substituent can be a halogen atom, a hydrocarbyl substituent or a heteroatom-containing substituent, preferably a halogen atom, a $C_{1-6}$ alkyl group, an alkoxy group, a $C_{1-6}$ alkenyl group or a nitro group.

$R_{13}$ and $R_{14}$ are each independently more preferably a hydrogen atom, a fluorine atom, a chlorine atom, a bromine atom, an iodine atom, a methyl group, an ethyl group, an n-propyl group, an isopropyl group, a butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, a cyclopropyl group, a cyclohexyl group, a phenyl group, a benzyl group, a butylphenyl group, a p-methylphenyl group, a vinylphenyl group, a vinyl group, a propenyl group, an allyl group, a propynyl group, a propargyl group, a nitrophenyl group, a p-methoxyphenyl, a methoxy group, an ethoxy group, a phenoxy group, a benzyloxy group, a methylthio group, an ethylthio group, a phenylthio group, a benzylthio group, a methylamino group, an ethylamino group, a benzylamino group, an acetyl group, a benzoyl group, a methoxycarbonyl group, an ethoxycarbonyl group, a phenoxycarbonyl group, a benzyloxycarbonyl group, a (methylthio)carbonyl group, an (ethylthio)carbonyl group, a (phenylthio)carbonyl group, a (benzylthio)carbonyl group, a methylaminocarbonyl group, an ethylaminocarbonyl group, a phenylaminocarbonyl group, a benzylaminocarbonyl group, a methoxysulfonyl group, an ethoxysulfonyl group, a phenoxysulfonyl group, a benzyloxysulfonyl group, an acetyloxy group, a benzoyloxy group, an acetylthio group, a benzoylthio group, an acetylamino group, a benzoylamino group, an ethyl-thiocarbonyl group, a phenyl-thiocarbonyl group, a methoxy-thiocarbonyl group, an ethoxy-thiocarbonyl group, a phenoxy-thiocarbonyl group, a benzyloxy-thiocarbonyl group, a (methylthio)thiocarbonyl group, an (ethylthio)thiocarbonyl group, a (phenylthio)thiocarbonyl group, a (benzylthio)thiocarbonyl group, a methylaminothiocarbonyl group, an ethylaminothiocarbonyl group, a phenylaminothiocarbonyl group, a benzylaminothiocarbonyl group, an ethyl-thiocarbonyloxy group, a phenyl-thiocarbonyloxy group, an ethyl-thiocarbonylthio group, a phenyl-thiocarbonylthio group, an ethyl-thiocarbonylamino group, a phenyl-thiocarbonylamino group, a trifluoromethyl group, a 2,2,2-trifluoroethyl group, the like, or any substituted form thereof. Wherein, butyl group includes but is not limited to an n-butyl group and a t-butyl group. Octyl group includes but is not limited to an n-octyl group and a 2-ethylhexyl group.

$R_{13}$ and $R_{14}$ are each independently more preferably a hydrogen atom, a fluorine atom, a methyl group, an ethyl group, an n-propyl group, an isopropyl group, a butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, a cyclopropyl group, a cyclohexyl group, a phenyl group, a benzyl group, a butylphenyl group, a p-methylphenyl group, a vinylphenyl group, a vinyl group, a propenyl group, an allyl group, a nitrophenyl group, a p-methoxyphenyl, a methoxy group, an ethoxy group, a phenoxy group, a benzyloxy group, a methylthio group, an ethylthio group, a phenylthio group, a benzylthio group, a methylamino group, an ethylamino group, a benzylamino group, a trifluoromethyl group, a 2,2,2-trifluoroethyl group, the like, or any substituted form thereof. Wherein, the atom or group substituent is preferably a fluorine atom, a $C_{1-6}$ alkyl group, an alkoxy group, a $C_{1-6}$ alkenyl group or a nitro group.

$R_{13}$ and $R_{14}$ are each independently more preferably a hydrogen atom, a fluorine atom, a methyl group, an ethyl group, an n-propyl group, an isopropyl group, a butyl group, a phenyl group, a benzyl group, a butylphenyl group, a p-methylphenyl group, a trifluoromethyl group, a 2,2,2-trifluoroethyl group, the like, or any substituted form thereof.

$R_{13}$ and $R_{14}$ are each independently more preferably a hydrogen atom or a methyl group.

Wherein, $R_5$ and $R_6$ are each independently a stable hydrocarbylene group or substituted hydrocarbylene group. In one molecule, $R_5$ and $R_6$ can be the same or different from each other. The condition to be stable is not particularly limited.

The structure of $R_5$ and $R_6$ are not particularly limited, each independently including but not limited to a linear structure, a branched structure or a ring-containing structure.

The carbon-atom number of $R_5$ and $R_6$ are each independently preferably from 1 to 20, and more preferably from 1 to 10.

$R_5$ and $R_6$ are each independently a stable $C_{1-20}$ hydrocarbylene group or substituted form thereof. The condition "to be stable" is not particularly limited, preferably selected from conditions such as light illumination, heat, an enzymatic condition, an oxidation-reduction condition, an acidic condition, a basic condition, a physiological condition, a simulated physiological environment in vitro, etc.

$R_5$ and $R_6$ are each independently more preferably a linear alkylene group, a branched alkylene group, a cycloalkylene group, a phenylene group, a condensed arylhydrocarbylene group or an arylalkylene group, or a substituted form of any above-said hydrocarbylene group with a substituent of a $C_{1-6}$ alkyl group, a phenyl group, a benzyl group, a methylphenyl group or a butylphenyl group.

$R_5$ and $R_6$ each independently preferably have 1 to 10 carbon atoms.

Specifically, for example, $R_5$ and $R_6$ are each independently a methylene group, a 1,1-ethylene group, a 1,2-ethylene group, a 1,3-propylene group, a 1,2-propylene group, an isopropylene group, a butylene group, a pentylene group, a hexylene group, a heptylene group, an octylene group, a nonylene group, a decylene group, an undecylene group, a dodecylene group, a tridecylene group, a tetradecylene group, a pentadecylene group, a hexadecylene group, a heptadecylene group, an octadecylene group, a nonadecylene group, an eicosylene group, a cyclopropylene group, a cyclohexylene group, a cyclooctylene group, a cyclodecylene group, a p-phenylene group, an o-phenylene group, an m-phenylene group, a benzylene group, or any substituted form thereof, or a combination of any two or two more hydrocarbylene groups or substituted hydrocarbylene groups of the foregoing. Wherein, the substituent can be a $C_{1-6}$ alkyl group, a phenyl group, a benzyl group, a methylphenyl group or a butylphenyl group. Wherein, the pentylene group includes but is not limited to a 1,5-pentylene group and a 3,3-pentylene group. Wherein, heptylene group includes but is not limited to a 1,7-heptylene group and a 1,1-diisopropylmethylene group.

$R_5$ and $R_6$ are each independently more preferably a methylene group, a 1,2-ethylene group, a 1,3-propylene group, a 1,2-propylene group, an isopropylene group, a butylene group, a pentylene group, a hexylene group, a 1,7-heptylene group, a 1,1-diisopropylmethylene group, an octylene group, a cyclopropylene group, an o-phenylene group, a p-phenylene group, an m-phenylene group, a benzylene group, a 1-benzylmethylene group, a 1-phenylmethylene group or the like.

$R_5$ and $R_6$ are each independently most preferably a methylene group, a 1,2-ethylene group, a 1,3-propylene group, a 1,4-butylene group, a 1,5-pentylene group or a 1,6-hexylene group.

$-M_{17}(R_{22})-$ is a divalent 1,1-cyclic linking group, and the ring-membering atom number is preferably from 3 to 8 (3, 4, 5, 6, 7 or 8).

Wherein, $M_{17}$ is a carbon atom or heteroatom of the ring skeleton (i.e., a ring-membering atom), preferably a carbon atom, a phosphorus atom or a silicon atom of the ring. $-(R_5)_{r1}-M_{17}(R_{22})-(R_6)_{r2}-$ also can be represented by

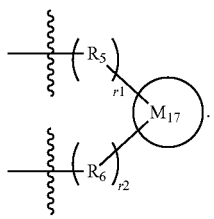

Wherein,

is a cyclic structure wherein $M_{17}$ is one of the ring-membering atoms, and can be a $C_{1-20}$ alicyclic ring, a $C_{1-20}$ aliphatic-derived heteroring, a $C_{1-20}$ condensed heteroring, or any substituted form thereof. Wherein, the heteroatom or group substituent is not particularly limited, including but not limited to all the above-listed substituting heteroatoms and substituting groups in the terminology section, and can be a halogen atom, a hydrocarbyl substituent, or a heteroatom-containing substituent.

Wherein, $R_{22}$ is a divalent linking group, and participates in forming a ring (i.e., a ring-membering divalent linking group).

The carbon-atom number of $R_{22}$ is not particularly limited, preferably from 1 to 20, and more preferably from 1 to 10.

The structure of $R_{22}$ is not particularly limited, including but not limited to a linear structure, a branched structure bearing pendent groups or a ring-containing structure.

Wherein, said ring is not particularly limited, including but not limited to all the above-listed cyclic structures in the terminology section.

$R_{22}$ can contain heteroatoms, or not.

$R_{22}$ can be a $C_{1-20}$ hydrocarbylene group, a $C_{1-20}$ divalent heterohydrocarbyl group, a substituted $C_{1-20}$ hydrocarbylene group, a substituted $C_{1-20}$ divalent heterohydrocarbyl group, or a combination of any two or three thereof. Wherein, the atom or group substituent is not particularly limited, including but not limited to, all the above-listed substituting atoms and substituting groups in the terminology section, and can be a halogen atom, a hydrocarbyl substituent, or a heteroatom-containing substituent.

$R_{22}$ is more preferably a $C_{1-20}$ open-chain alkylene group, a $C_{2-20}$ open-chain alkenylene group, a $C_{3-20}$ cycloalkylene group, a $C_{3-20}$ cycloalkenylene group, an arylene group, a $C_{1-20}$ divalent aliphatic-derived heteroalkyl group, a $C_{2-20}$ divalent aliphatic-derived heteroalkenyl group, a divalent heteroaryl group, a substituted alkylene group, a substituted $C_{2-20}$ open-chain alkenylene group, a substituted $C_{3-20}$ cycloalkylene group, a substituted $C_{3-20}$ cycloalkenylene group, a substituted arylene group, a substituted $C_{1-20}$ divalent aliphatic-derived heteroalkyl group, a substituted $C_{2-20}$ divalent aliphatic-derived heteroalkenyl group, a substituted divalent heteroaryl group, or a combination of any two or three thereof. Wherein, said heteroatom is not particularly limited, and preferably O, S, N, P or Si.

$R_{22}$ is more preferably a $C_{1-10}$ open-chain alkylene group, a $C_{2-10}$ open-chain alkenylene group, a $C_{3-10}$ cycloalkylene group, a $C_{3-10}$ cycloalkenylene group, an arylene group, a $C_{1-10}$ divalent aliphatic-derived heteroalkyl group, a $C_{2-10}$ divalent aliphatic-derived heteroalkenyl group, a divalent heteroaryl group, a substituted alkylene group, a substituted $C_{2-20}$ open-chain alkenylene group, a substituted $C_{3-10}$ cycloalkylene group, a substituted $C_{3-10}$ cycloalkenylene group, a substituted arylene group, a substituted $C_{1-10}$ divalent aliphatic-derived heteroalkyl group, a substituted $C_{2-10}$ divalent aliphatic-derived heteroalkenyl group, a substituted divalent heteroaryl group, or a combination of any two or three thereof.

Specifically, $R_{22}$ is a linking group selected from a methylene group, an ethylene group, a propylene group, a butylene group, a pentylene group, a hexylene group, a heptylene group, an octylene group, a nonylene group, a decylene group, a $C_{1-20}$ divalent oxa-alkyl group, a $C_{1-20}$ divalent thia-alkyl group, a $C_{1-20}$ divalent aza-alkyl group and a divalent aza-aryl group, or the substituted form of any linking group thereof, or a combination of any two or more identical or different linking groups or substituted linking groups thereof. Wherein, the atom or group substituent is a halogen atom, a hydrocarbyl substituent or a heteroatom-containing substituent, and preferably a halogen atom, an alkoxy group or a nitro group.

$R_{22}$ is preferably a 1,2-ethylene group, a 1,2-vinylene group (an ethenylene group) or a 1,3-propylene group.

Wherein, for example, when $R_{22}$ is a 1,2-ethylene group, it corresponds to

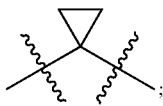 [SMILES: *C1(*)CC1];

when R$_{22}$ is a 1,2-vinylene group, it corresponds to

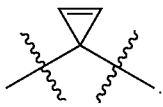

Wherein, R$_{38}$ is a hydrocarbyl group, preferably a C$_{1-20}$ hydrocarbyl group, more preferably a C$_{1-20}$ alkyl group, and more preferably a methyl group, an ethyl group, a propyl group, a butyl group, a pentyl group or a hexyl group.

Wherein, R$_{39}$ is a hydrogen atom or a substituting group connecting to a nitrogen atom, preferably a hydrogen atom or a C$_{1-20}$ hydrocarbyl group, and further preferably a hydrogen atom, a methyl group, an ethyl group, an n-propyl group, an isopropyl group, an n-butyl group or a benzyl group. In said —NR$_7$R$_{39}$, R$_7$ and R$_{39}$ can be the same or different from each other. NR$_7$R$_{39}$ is preferably NH$_2$, NHR$_{39}$ or N(R$_{39}$)$_2$.

Wherein, SG is a set consisting of amino acid skeletons. Each amino acid skeleton of SG is derived from an amino acid or derivative thereof, wherein said amino acid is of $_L$- or $_D$-type.

For example, amino acids of SG can be derived from, but not limited to, any of the following amino acids and derivatives thereof from any of the following Groups:

Neutral amino acids: glycine, alanine, valine, leucine, isoleucine, phenylalanine, proline and sarcosine;

Hydroxyl- or sulfur-containing amino acids: serine, threonine, cysteine, methionine, tyrosine and hydroxyproline;

Acidic amino acids: aspartic acid, glutamic acid, asparagine and glutamine;

Basic amino acids: lysine, arginine, histidine and tryptophan.

Wherein, SG includes but is not limited to the following amino acid skeletons:

Neutral Amino Acid Skeletons:

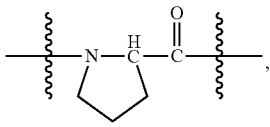

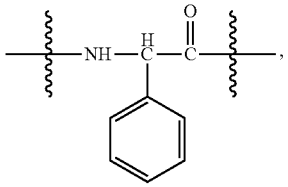

—C(=O)—CH(R$_{20}$)—NH—  or  —NH—CH(R$_{20}$)—C(=O)—; wherein, R$_{20}$ is —H, —CH$_3$, —CH(CH$_3$)$_2$, —CH$_2$—CH(CH$_3$)$_2$ and —CH(CH$_3$)—CH$_2$CH$_3$;

Hydroxyl- or Sulfur-Containing Amino Acid Skeletons:

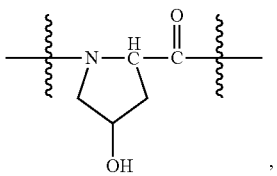

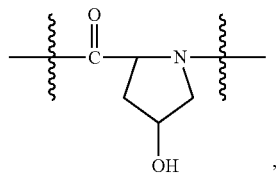

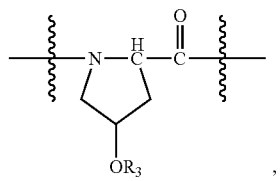

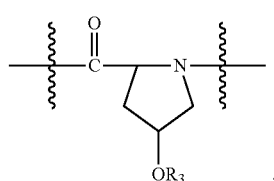

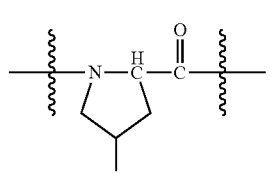

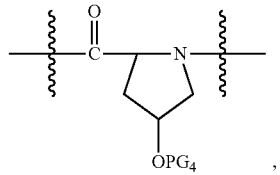

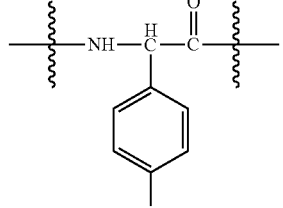

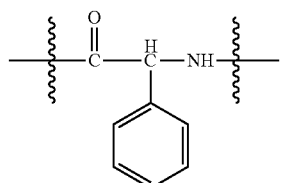

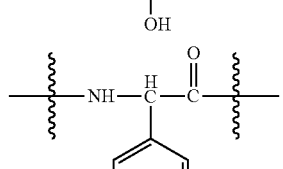

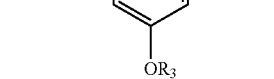

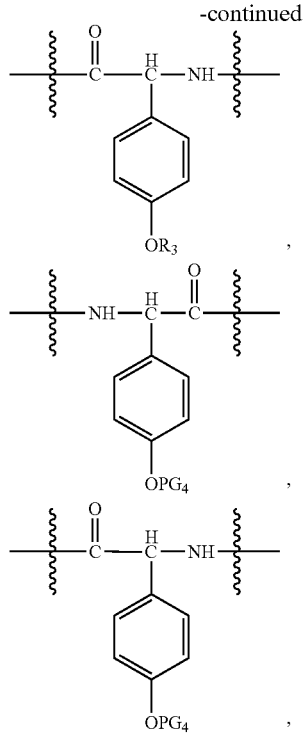

,

—C(=O)—CH(R$_{20}$)—NH— and —NH—CH(R$_{20}$)—C(=O)—; wherein, R$_{20}$ is —CH$_2$—OH, —CH$_2$—OPG$_4$, —CH$_2$—OR$_3$, —CH(CH$_3$)—OH, —CH(CH$_3$)—OPG$_4$, —CH(CH$_3$)—OR$_3$, —CH$_2$—SH, —CH$_2$—SPG$_2$, —CH$_2$—SR$_3$ or —CH$_2$CH$_2$—S—CH$_3$;

Acidic Amino Acid Skeletons:

—C(=O)—CH$_2$—CH(COOH)—NH—, —NH—CH(COOH)—CH$_2$—C(=O)—, —C(=O)—CH$_2$—CH(COOR$_3$)—NH—, —NH—CH(COOR$_3$)—CH$_2$—C(=O)—, —C(=O)—CH$_2$—CH$_2$—CH(COOH)—NH—, —NH—CH(COOH)—CH$_2$—CH$_2$—C(=O)—, —C(=O)—CH$_2$—CH$_2$—CH(COOR$_3$)—NH—, —NH—CH(COOR$_3$)—CH$_2$—CH$_2$—C(=O)—, —NH—C(=O)—CH$_2$—CH(COOH)—NH—, —NH—CH(COOH)—CH$_2$—C(=O)—NH—, —NH—C(=O)—CH$_2$—CH(COOR$_3$)—NH—, —NH—CH(COOR$_3$)—CH$_2$—C(=O)—NH—, —NH—C(=O)—CH$_2$—CH$_2$—CH(COOH)—NH—, —NH—CH(COOH)—CH$_2$—CH$_2$—C(=O)—NH—, —NH—C(=O)—CH$_2$—CH$_2$—CH(COOR$_3$)—NH—, —NH—CH(COOR$_3$)—CH$_2$—CH$_2$—C(=O)—NH—, —C(=O)—CH(R$_{20}$)—NH— or —NH—CH(R$_{20}$)—C(=O)—; wherein, R$_{20}$ is —CH$_2$—COOH, —CH$_2$—C(=O)—OR$_3$, —CH$_2$—CH$_2$—C(=O)—OR$_3$, —CH$_2$—C(=O)—NH$_2$ or —CH$_2$—CH$_2$—C(=O)—NH$_2$;

Basic Amino Acid Skeletons:

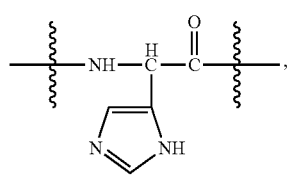

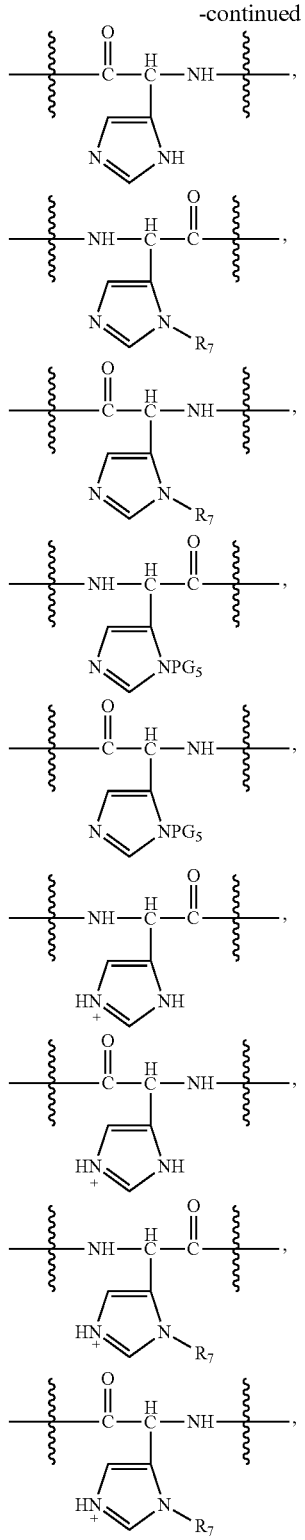

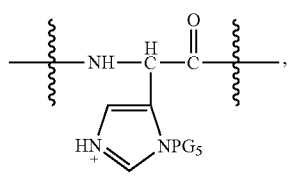

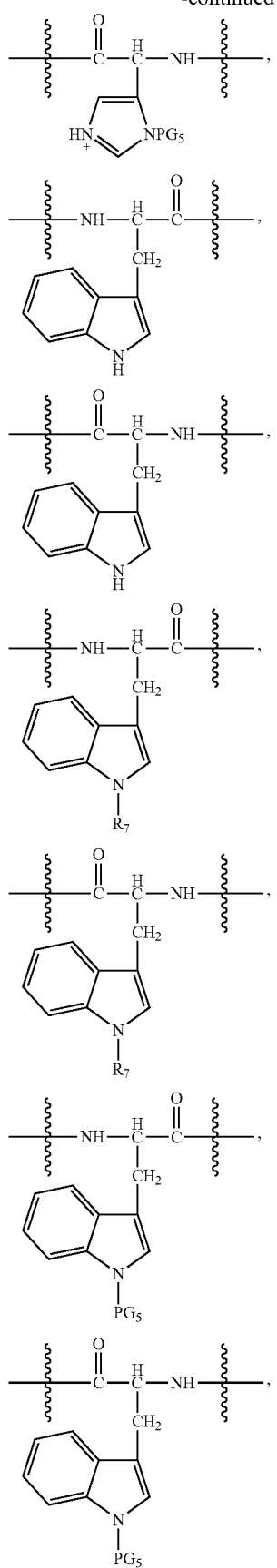
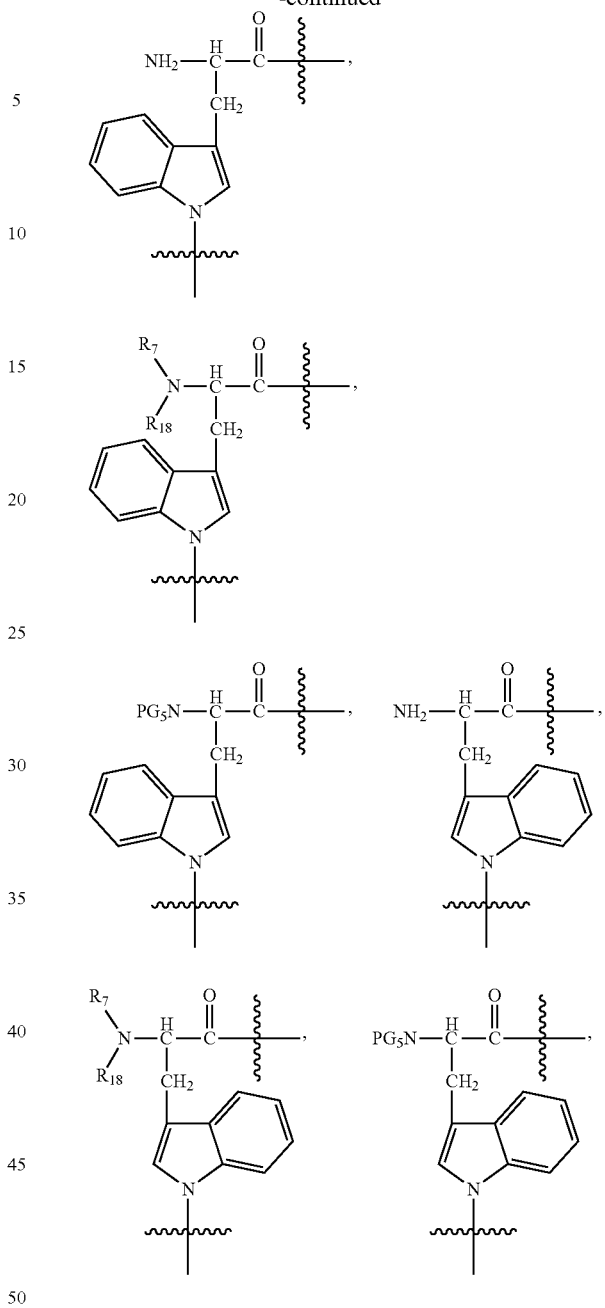

—C(=O)—CH(NH$_2$)—(CH$_2$)$_4$—NH—, —NH—(CH$_2$)$_4$—CH(NH$_2$)—C(=O)—, —C(=O)—CH(NH$_2$)—(CH$_2$)$_3$—NH—C(=NH)—NH—, —NH—C(=NH)—NH—(CH$_2$)$_3$—CH(NH$_2$)—C(=O)—, —C(=O)—CH(NH$_2$)—(CH$_2$)$_3$—NH—C(=NH$_2^+$)—NH—, —NH—C(=NH$_2^+$)—NH—(CH$_2$)$_3$—CH(NH$_2$)—C(=O)—, —C(=O)—CH(R$_{20}$)—NH— or —NH—CH(R$_{20}$)—C(=O)—;

Wherein, R$_{20}$ is —(CH$_2$)$_4$—NH$_2$, —(CH$_2$)$_4$—NH$_3^+$, —(CH$_2$)$_4$—NPG$_5$, —(CH$_2$)$_4$—NR$_7$(R$_{18}$), —(CH$_2$)$_3$—NH—C(=NH)—NH$_2$ or —(CH$_2$)$_3$—NH—C(=NH$_2^+$)—NH$_2$;

In the above-said amino acid skeletons, the definitions of R$_3$, R$_7$, R$_{18}$, PG$_4$ and PG$_5$ are the same as above-defined, no more repeated here.

For example,
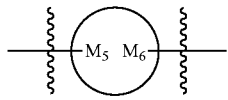
includes but is not limited to the following cyclic linking groups:
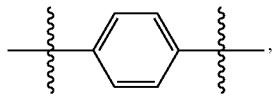
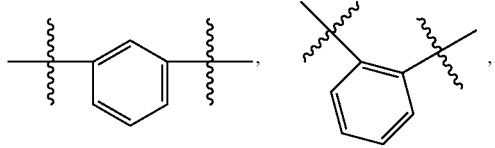
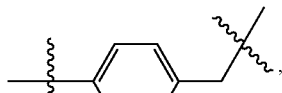
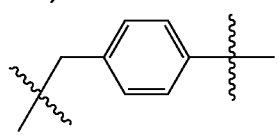
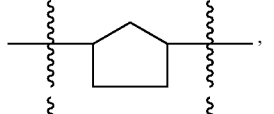
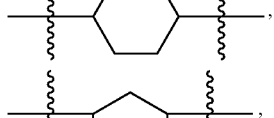
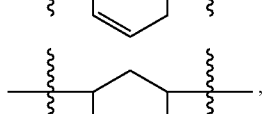
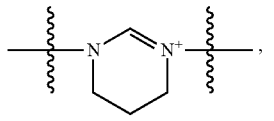
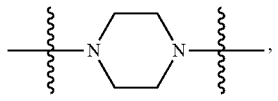
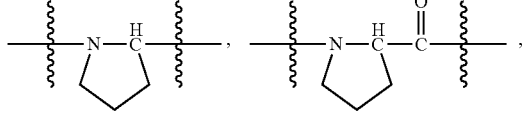
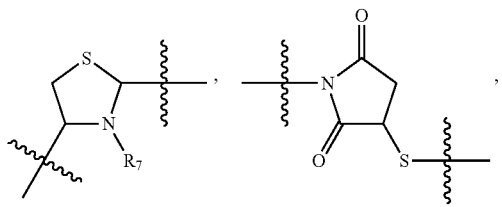
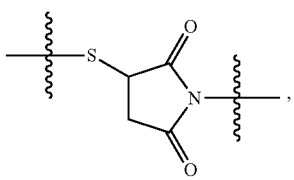
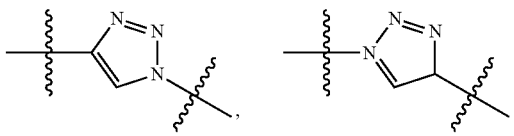
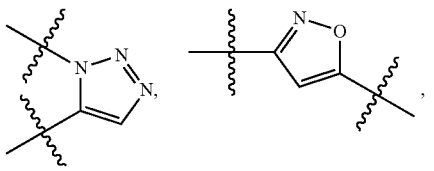
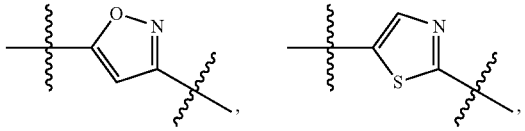
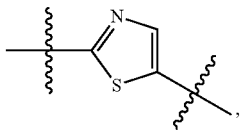
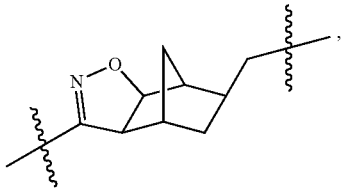
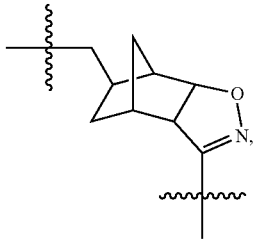
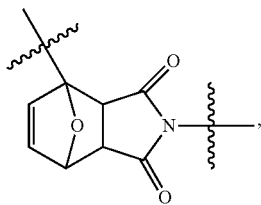

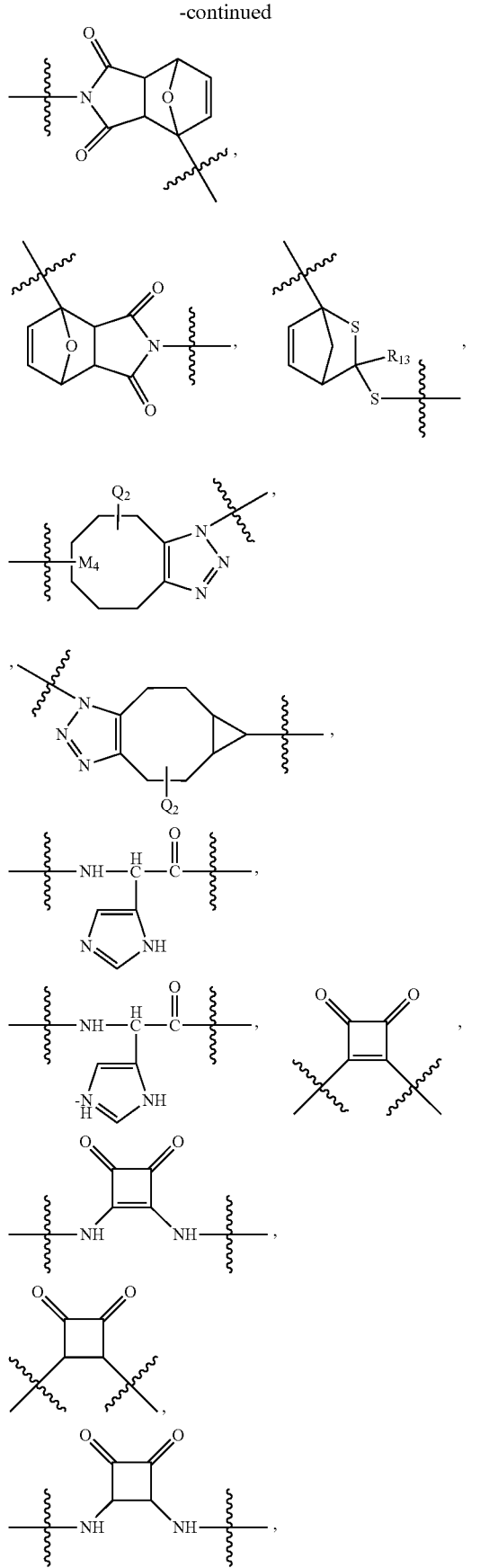
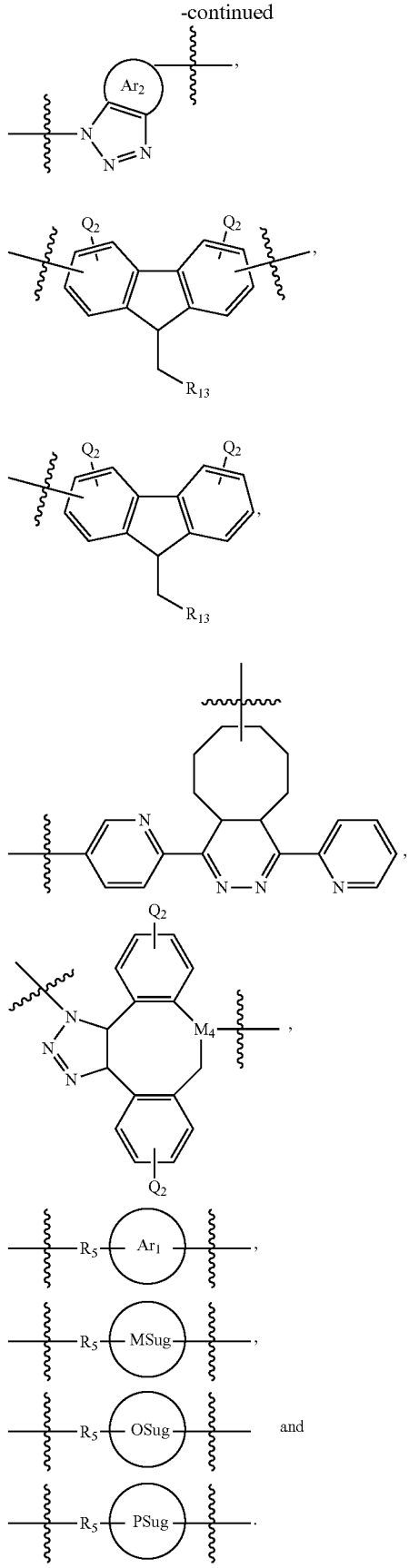

Wherein, the definitions of $R_5$, $R_{13}$,

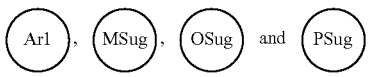

are the same as above-defined, no more repeated here.

Wherein, $R_7$ is a hydrogen atom, a group $PG_5$ or a group $LG_5$. Wherein, the definitions of $PG_5$ and $LG_5$ are the same as above-defined.

Wherein, the definition of $Q_2$ is the same as above-defined Q, no more repeated here.

Wherein, $M_4$ is a carbon atom or heteroatom of the ring skeleton, including but not limited to a carbon atom, a nitrogen atom, a phosphorus atom or a silicon atom.

Wherein,

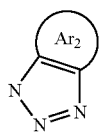

represents a heteroaryl ring, a condensed heteroring, a substituted heteroaryl ring or a substituted condensed heteroring which contains a triazole unit.

Examples of the combination of any two or two more above-said structures include —$CH_2O$—, —$OCH_2$—, —$CH_2CH_2O$—, —$OCH_2CH_2$—, —$OCH_2CH_2O$—, —$(CH_2)_3O$—, —$O(CH_2)_3$—, —$(CH_2)_3O$—, —$O(CH_2)_3$— and the like. For example, $L_0$ can contain an oligopeptide or peptide segment of amino acids that are linked together end-to-end via N-terminus and C-terminus, wherein said amino acids can be the same or different, but peptide fragments which can be enzymatically degraded should be excluded. In addition, $L_0$ can also contain a linkage selected from -$(L_{11}O)_{nj}$—, —$(OL_{11})_{nj}$-, —$(R_{29}O)_{nj}$—, —$(OR_{29})_{nj}$—, —$(CH_2CH_2O)_{nj}$—, —$(OCH_2CH_2)_{nj}$—, and the like. Wherein, the definitions of $L_{11}$ and $R_{29}$ are the same as above-defined. Wherein, nj is an integer representing the repeat unit number of a monodisperse structure, selected from 2 to 20, and preferably from 2 to 10.

Examples also include the following linkages,

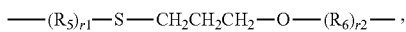

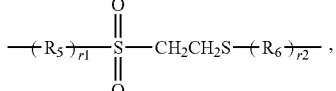

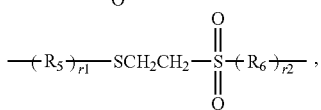

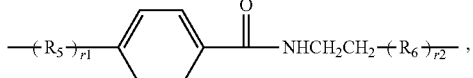

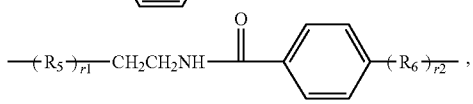

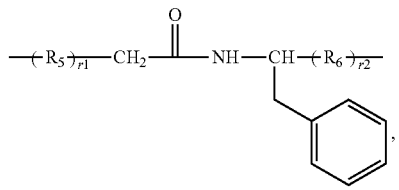

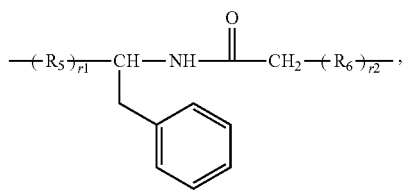

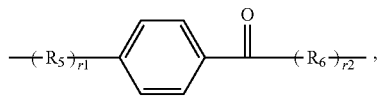

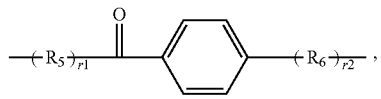

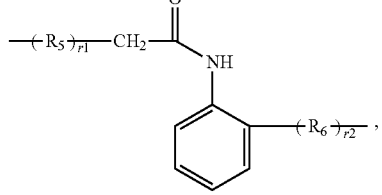

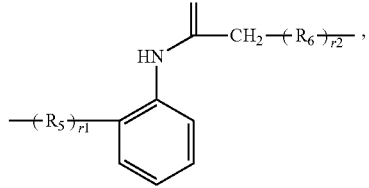

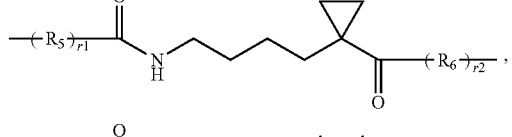

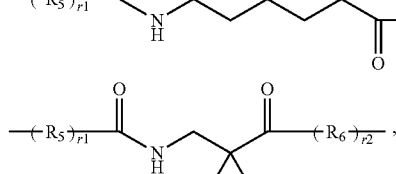

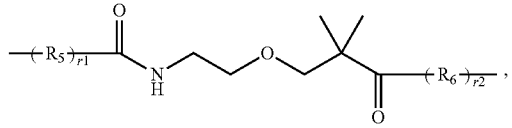

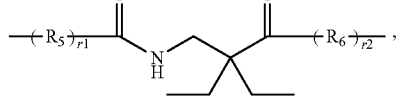

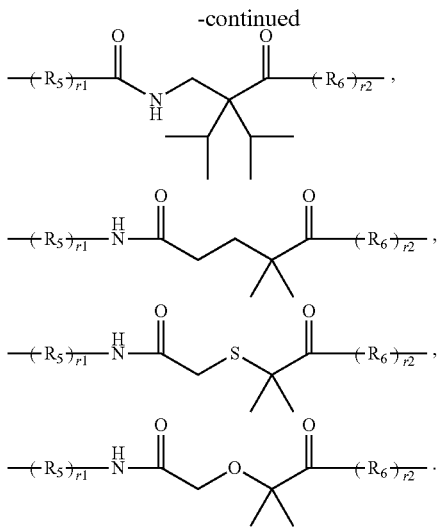

1.1.7.2. Degradable Divalent Linking Group (Degradable Divalent Linkage): DEGG The condition "to be degradable" or "to degrade" or "to be degraded" is not particularly limited, including but not limited to conditions such as light illumination, heat, an enzymatic condition, an oxidation-reduction condition, an acidic condition, a basic condition, a physiological condition, a simulated physiological environment in vitro, etc., preferably conditions such as light illumination, heat, an enzymatic condition, an oxidation-reduction condition, an acidic condition, a basic condition, etc.

The divalent linking group formed by the combination of a DEGG linkage and a STAG linkage is a degradable linking group.

The degradability type of DEGG linkage is not particularly limited, and should contain at least one degradable divalent linkage selected from the group consisting of, but not limited to, a disulfide bond, a vinylether bond, an ester bond (an ester linkage), a thioester bond (an thioester linkage), a thiocarboxylate linkage (e.g., a thioate bond, or a monothioester bond), a dithioester bond, a carbonate bond, a thiocarbonate bond, a dithiocarbonate bond, a trithiocarbonate bond, a carbamate bond, a thiocarbamate bond, a dithiocarbamate bond, an acetal linkage, a cycloacetal linkage, a mercaptal linkage, an azaacetal linkage, an azacycloacetal linkage, an azathiaacetal linkage, a dithioacetal linkage, a hemiacetal linkage, a thiohemiacetal linkage, an azahemiacetal linkage, a ketal linkage, a thioketal linkage, an azaketal linkage, an azacycloketal linkage, an azathiaketal linkage, an imine bond (e.g., —CH=N—), a hydrazone bond, an acylhydrazone bond, an oxime bond (e.g., —C(alkyl)=N—O—, or an iminoxy linkage, or an iminooxy linkage, or an oxyimino linkage, or an oximino bond, e.g., —O—N=CH—), a thiooxime bond (e.g., —C(alkyl)=N—S—), a semicarbazone bond, a thiosemicarbazone bond, a hydrazino bond, an acylhydrazino bond, a thiocarbonyl-hydrazino bond (—C(=S)—NH—NH—), an azocarbonyl-hydrazino linkage (e.g., —N=N—C(=O)—NH—NH—), an azo-thiocarbonyl-hydrazino linkage (e.g., —N=N—C(=S)—NH—NH—), a hydrazino formate linkage, a hydrazino thioformate linkage, a carbohydrazide bond, a thiocarbohydrazide bond, an azo bond, an isourea bond, an isothiourea bond, an allophanate linkage, a thioallophanate linkage, a guanidino linkage, an amidino linkage, an aminoguanidino linkage, an aminoamidino linkage, an iminocarbonyl-oxy linkage (e.g., —C(=NH)—O—), an iminocarbonyl-thioxy linkage (e.g., —C(=NH)—S—), a sulfonate linkage, a sulfinate linkage, a sulfonylhydrazino linkage, a sulfonylureido linkage, a maleimide linkage, an orthoester linkage, a phosphate linkage, a phosphirate linkage, a phosphinate linkage, a phosphonate linkage, a phosphosilicate linkage, a silicate linkage, an amide bond, a thioamide bond, a sulfonamide bond, a polyamide linkage, a phosphamide linkage, a phosphiramide linkage, a phosphinamide linkage, a phosphonamide linkage, a pyrophosphamide linkage, a cyclophosphamide linkage, an ifosfamide linkage, a thiophosphamide linkage, an aconityl linkage, a benzyloxycarbonyl linkage, a peptide fragment, the skeleton of a nucleotide and derivatives thereof, the skeleton of a deoxynucleotide and derivatives thereof, and divalent linking groups via the combination of any two or two more degradable linkages of the foregoing.

Herein, said carbamate group, thiocarbamate group, amide group, phosphamide group and the like, can exist as either a stable linking group or a degradable linking group.

Specifically, typical structures of DEGG can be but are not limited to any of the following structures, or the combination of any two or two more following structures, or the combination of any one or more following structures with a stable divalent linking group $L_9$:

—$(R_5)_{r1}$—S—S—$(R_6)_{r2}$—, —$(R_5)_{r1}$—C($R_8$)=C($R_9$)—O—$(R_6)_{r2}$—, —$(R_5)_{r1}$—O—C($R_9$)=C($R_8$)—$(R_6)_{r2}$—, —$(R_5)_{r1}$—C(=O)—O—$(R_6)_{r2}$—, —$(R_5)_{r1}$—O—C(=O)—$(R_6)_{r2}$—, —$(R_5)_{r1}$—C(=O)—S—$(R_6)_{r2}$—, —$(R_5)_{r1}$—S—C(=O)—$(R_6)_{r2}$—, —$(R_5)_{r1}$—C(=S)—O—$(R_6)_{r2}$—, —$(R_5)_{r1}$—O—C(=S)—$(R_6)_{r2}$—, —$(R_5)_{r1}$—C(=S)—S—$(R_6)_{r2}$—, —$(R_5)_{r1}$—S—C(=S)—$(R_6)_{r2}$—, —$(R_5)_{r1}$—O—C(=O)—O—$(R_6)_{r2}$—, —$(R_5)_{r1}$—S—C(=O)—O—$(R_6)_{r2}$—, —$(R_5)_{r1}$—O—C(=S)—O—$(R_6)_{r2}$—, —$(R_5)_{r1}$—O—C(=O)—S—$(R_6)_{r2}$—, —$(R_5)_{r1}$—S—C(=S)—O—$(R_6)_{r2}$—, —$(R_5)_{r1}$—O—C(=S)—S—$(R_6)_{r2}$—, —$(R_5)_{r1}$—S—C(=O)—S—$(R_6)_{r2}$—, —$(R_5)_{r1}$—S—C(=S)—S—$(R_6)_{r2}$—, —$(R_5)_{r1}$—N(R_7)—C(=O)—O—$(R_6)_{r2}$—, —$(R_5)_{r1}$—O—C(=O)—N(R_7)—$(R_6)_{r2}$—, —$(R_5)_{r1}$—N(R_7)—C(=S)—O—$(R_6)_{r2}$—, —$(R_5)_{r1}$—O—C(=S)—N(R_7)—$(R_6)_{r2}$—, —$(R_5)_{r1}$—N(R_7)—C(=O)—S—$(R_6)_{r2}$—, —$(R_5)_{r1}$—S—C(=O)—N(R_7)—$(R_6)_{r2}$—, —$(R_5)_{r1}$—N(R_7)—C(=S)—S—$(R_6)_{r2}$—, —$(R_5)_{r1}$—S—C(=S)—N(R_7)—$(R_6)_{r2}$—, —$(R_5)_{r1}$—CH(OR_3)—O—$(R_6)_{r2}$—, —$(R_5)_{r1}$—O—CH(OR_3)—$(R_6)_{r2}$—, —$(R_5)_{r1}$—CH(OR_3)—S—$(R_6)_{r2}$—, —$(R_5)_{r1}$—S—CH(OR_3)—$(R_6)_{r2}$—, —$(R_5)_{r1}$—CH(SR_3)—O—$(R_6)_{r2}$—, —$(R_5)_{r1}$—O—CH(SR_3)—$(R_6)_{r2}$—, —$(R_5)_{r1}$—CH(SR_3)—S—$(R_6)_{r2}$—, —$(R_5)_{r1}$—S—CH(SR_3)—$(R_6)_{r2}$—, —$(R_5)_{r1}$—CH(OR_3)—N(R_7)—$(R_6)_{r2}$—, —$(R_5)_{r1}$—N(R_7)—CH(OR_3)—$(R_6)_{r2}$—, —$(R_5)_{r1}$—CH(NR_{18}R_{19})—O—$(R_6)_{r2}$—, —$(R_5)_{r1}$—O—CH(NR_{18}R_{19})—$(R_6)_{r2}$—, —$(R_5)_{r1}$—CH(NR_{18}R_{19})—N(R_7)—$(R_6)_{r2}$—, —$(R_5)_{r1}$—N(R_7)—CH(NR_{18}R_{19})—$(R_6)_{r2}$—, —$(R_5)_{r1}$—(R_{18}R_{19}N)C(SR_3)—$(R_6)_{r2}$—, —$(R_5)_{r1}$—CH(SR_3)—N(R_7)—$(R_6)_{r2}$—, —$(R_5)_{r1}$—N(R_7)—CH(SR_3)—$(R_6)_{r2}$—, —$(R_5)_{r1}$—CH(NR_{18}R_{19})—S—$(R_6)_{r2}$—, —$(R_5)_{r1}$—S—CH(NR_{18}R_{19})—$(R_6)_{r2}$—, —$(R_5)_{r1}$—CH(OH)—O—$(R_6)_{r2}$—, —$(R_5)_{r1}$—O—CH(OH)—$(R_6)_{r2}$—, —$(R_5)_{r1}$—CH(OH)—S—$(R_6)_{r2}$—, —$(R_5)_{r1}$—S—CH(OH)—$(R_6)_{r2}$—, —$(R_5)_{r1}$—CH(OH)—N(R_7)—$(R_6)_{r2}$—, —$(R_5)_{r1}$—N(R_7)—CH(OH)—$(R_6)_{r2}$—, —$(R_5)_{r1}$—CR_{13}(OR_3)—O—$(R_6)_{r2}$—, —$(R_5)_{r1}$—O—CR_{13}(OR_3)—$(R_6)_{r2}$—, —$(R_5)_{r1}$—CR_{13}(OR_3)—S—$(R_6)_{r2}$—, —$(R_5)_{r1}$—S—CR_{13}(OR_3)—$(R_6)_{r2}$—, —$(R_5)_{r1}$—CR_{13}(SR_3)—O—$(R_6)_{r2}$—, —$(R_5)_{r1}$—O—CR_{13}(SR_3)—$(R_6)_{r2}$—, —$(R_5)_{r1}$—CR_{13}(SR_3)—S

—(R₆)ᵣ₂—, —(R₅)ᵣ₁—S—CR₁₃(SR₃)—(R₆)ᵣ₂—, —(R₅)ᵣ₁—CR₁₃(OR₃)—N(R₇)—(R₆)ᵣ₂—, —(R₅)ᵣ₁—N(R₇)—CR₁₃(OR₃)—(R₆)ᵣ₂—, —(R₅)ᵣ₁—CR₁₃(NR₁₈R₁₉)—O—(R₆)ᵣ₂—, —(R₅)ᵣ₁—O—CR₁₃(NR₁₈R₁₉)—(R₆)ᵣ₂—, —(R₅)ᵣ₁—CR₁₃(NR₁₈R₁₉)—N(R₇)—(R₆)ᵣ₂—, —(R₅)ᵣ₁—N(R₇)—CR₁₃(NR₁₈R₁₉)—(R₆)ᵣ₂—, —(R₅)ᵣ₁—CR₁₃(SR₃)—N(R₇)—(R₆)ᵣ₂—, —(R₅)ᵣ₁—N(R₇)—CR₁₃(SR₃)—(R₆)ᵣ₂—, —(R₅)ᵣ₁—CR₁₃(NR₁₈R₁₉)—S—(R₆)ᵣ₂—, —(R₅)ᵣ₁—S—CR₁₃(NR₁₈R₁₉)—(R₆)ᵣ₂—, —(R₅)ᵣ₁—CR₁₃(OH)—O—(R₆)ᵣ₂—, —(R₅)ᵣ₁—O—CR₁₃(OH)—(R₆)ᵣ₂—, —(R₅)ᵣ₁—CR₁₃(OH)—S—(R₆)ᵣ₂—, —(R₅)ᵣ₁—S—CR₁₃(OH)—(R₆)ᵣ₂—, —(R₅)ᵣ₁—CR₁₃(OH)—N(R₇)—(R₆)ᵣ₂—, —(R₅)ᵣ₁—N(R₇)—CR₁₃(OH)—(R₆)ᵣ₂—, —(R₅)ᵣ₁—(R₁₅)C=N—(R₆)ᵣ₂—, —(R₅)ᵣ₁—N=C(R₁₅)—(R₆)ᵣ₂—, —(R₅)ᵣ₁—(R₁₅)C=N—N(R₇)—(R₆)ᵣ₂—, —(R₅)ᵣ₁—N(R₇)—N=C(R₁₅)—(R₆)ᵣ₂—, —(R₅)ᵣ₁—(R₁₅)C=N—N(R₇)—C(=O)—(R₆)ᵣ₂—, —(R₅)ᵣ₁—C(=O)—N(R₇)—N=C(R₁₅)—(R₆)ᵣ₂—, —(R₅)ᵣ₁—(R₁₅)C=N—O—(R₆)ᵣ₂—, —(R₅)ᵣ₁—O—N=C(R₁₅)—(R₆)ᵣ₂—, —(R₅)ᵣ₁—(R₁₅)C=N—S—(R₆)ᵣ₂—, —(R₅)ᵣ₁—S—N=C(R₁₅)—(R₆)ᵣ₂—, —(R₅)ᵣ₁—N(R₇)—C(=O)—N(R₁₈)—N=C—(R₆)ᵣ₂—, —(R₅)ᵣ₁—C=N—N(R₁₈)—C(=O)—N(R₇)—(R₆)ᵣ₂—, —(R₅)ᵣ₁—N(R₇)—C(=S)—N(R₁₈)—N=C—(R₆)ᵣ₂—, —(R₅)ᵣ₁—C=N—N(R₁₈)—C(=S)—N(R₇)—(R₆)ᵣ₂—, —(R₅)ᵣ₁—N(R₇)—N(R₁₈)—(R₆)ᵣ₂—, —(R₅)ᵣ₁—N(R₇)—N(R₁₈)—C(=O)—(R₆)ᵣ₂—, —(R₅)ᵣ₁—C(=O)—N(R₁₈)—N(R₇)—(R₆)ᵣ₂—, —(R₅)ᵣ₁—N(R₇)—N(R₁₈)—C(=S)—(R₆)ᵣ₂—, —(R₅)ᵣ₁—C(=S)—N(R₁₈)—N(R₇)—(R₆)ᵣ₂—, —(R₅)ᵣ₁—N(R₇)—N(R₁₈)—C(=O)—N=N—(R₆)ᵣ₂—, —(R₅)ᵣ₁—N=N—C(=O)—N(R₁₈)—N(R₇)—(R₆)ᵣ₂—, —(R₅)ᵣ₁—N(R₇)—N(R₁₈)—C(=S)—N=N—(R₆)ᵣ₂—, —(R₅)ᵣ₁—N=N—C(=S)—N(R₁₈)—N(R₇)—(R₆)ᵣ₂—, —(R₅)ᵣ₁—N(R₇)—N(R₁₈)—N(R₇)—C(=O)—O—(R₆)ᵣ₂—, —(R₅)ᵣ₁—O—C(=O)—N(R₇)—N(R₁₈)—(R₆)ᵣ₂—, —(R₅)ᵣ₁—N(R₁₈)—N(R₇)—C(=S)—O—(R₆)ᵣ₂—, —(R₅)ᵣ₁—O—C(=S)—N(R₇)—N(R₁₈)—(R₆)ᵣ₂—, —(R₅)ᵣ₁—N(R₁₈)—N(R₇)—C(=O)—S—(R₆)ᵣ₂—, —(R₅)ᵣ₁—S—C(=O)—N(R₇)—N(R₁₈)—(R₆)ᵣ₂—, —(R₅)ᵣ₁—N(R₁₈)—N(R₇)—C(=S)—S—(R₆)ᵣ₂—, —(R₅)ᵣ₁—S—C(=S)—N(R₇)—N(R₁₈)—(R₆)ᵣ₂—, —(R₅)ᵣ₁—N(R₇)—N(R₁₈)—C(=O)—N(R₁₉)—N(R₂₃)—(R₆)ᵣ₂—, —(R₅)ᵣ₁—N(R₇)—N(R₁₈)—C(=S)—N(R₁₉)—N(R₂₃)—, —(R₅)ᵣ₁—N=N—(R₆)ᵣ₂—, —(R₅)ᵣ₁—O—C(=NR₁₈)—N(R₇)—(R₆)ᵣ₂—, —(R₅)ᵣ₁—N(R₇)—C(=NR₁₈)—O—(R₆)ᵣ₂—, —(R₅)ᵣ₁—O—C(=NH₂⁺)—N(R₇)—(R₆)ᵣ₂—, —(R₅)ᵣ₁—N(R₇)—C(=NH₂⁺)—O—(R₆)ᵣ₂—, —(R₅)ᵣ₁—N(R₇)—C(=NR₁₈)—S—(R₆)ᵣ₂—, —(R₅)ᵣ₁—S—C(=NR₁₈)—N(R₇)—(R₆)ᵣ₂—, —(R₅)ᵣ₁—N(R₇)—C(=NH₂⁺)—S—(R₆)ᵣ₂—, —(R₅)ᵣ₁—S—C(=NH₂⁺)—N(R₇)—(R₆)ᵣ₂—, —(R₅)ᵣ₁—N(R₁₈)—C(=O)—N(R₇)—C(=O)—O—(R₆)ᵣ₂—, —(R₅)ᵣ₁—O—C(=O)—N(R₇)—C(=O)—N(R₁₈)—(R₆)ᵣ₂—, —(R₅)ᵣ₁—N(R₁₈)—C(=S)—N(R₇)—C(=O)—O—(R₆)ᵣ₂—, —(R₅)ᵣ₁—O—C(=O)—N(R₇)—C(=S)—N(R₁₈)—(R₆)ᵣ₂—, —(R₅)ᵣ₁—N(R₁₈)—C(=NR₇)—N(R₁₉)—(R₆)ᵣ₂—, —(R₅)ᵣ₁—N(R₁₈)—C(=NH₂⁺)—N(R₁₉)—(R₆)ᵣ₂—, —(R₅)ᵣ₁—C(=NR₇)—N(R₁₉)—(R₆)ᵣ₂—, —(R₅)ᵣ₁—N(R₁₉)—C(=NR₇)—(R₆)ᵣ₂—, —(R₅)ᵣ₁—C(=NH₂⁺)—N(R₁₈)—(R₆)ᵣ₂—, —(R₅)ᵣ₁—C(=NH₂⁺)—N(R₁₈)—(R₆)ᵣ₂—, —(R₅)ᵣ₁—N(R₂₃)—N(R₁₈)—C(=NR₇)—N(R₁₉)—(R₆)ᵣ₂—, —(R₅)ᵣ₁—N(R₁₉)—C(=NR₇)—N(R₁₈)—N(R₂₃)—(R₆)ᵣ₂—, —(R₅)ᵣ₁—N(R₇)—N(R₁₈)—C(=NH₂⁺)—N(R₁₉)—(R₆)ᵣ₂—, —(R₅)ᵣ₁—N(R₁₉)—C(=NH₂⁺)—N(R₁₈)—N(R₇)—(R₆)ᵣ₂—, —(R₅)ᵣ₁—C(=NR₇)—N(R₁₈)—N(R₁₉)—(R₆)ᵣ₂—, —(R₅)ᵣ₁—N(R₁₉)—N(R₁₈)—C(=NR₇)—(R₆)ᵣ₂—, —(R₅)ᵣ₁—N(R₁₉)—N(R₁₈)—C(=NH₂⁺)—(R₆)ᵣ₂—, —(R₅)ᵣ₁—C(=NH₂⁺)—N(R₁₈)—N(R₁₉)—(R₆)ᵣ₂—, —(R₅)ᵣ₁—C(=NR₇)—O—(R₆)ᵣ₂—, —(R₅)ᵣ₁—O—C(=NR₇)—(R₆)ᵣ₂—, —(R₅)ᵣ₁—O—C(=NH₂⁺)—(R₆)ᵣ₂—, —(R₅)ᵣ₁—C(=NH₂⁺)—O—(R₆)ᵣ₂—, —(R₅)ᵣ₁—C(=NR₇)—S—(R₆)ᵣ₂—, —(R₅)ᵣ₁—S—C(=NR₇)—(R₆)ᵣ₂—, —(R₅)ᵣ₁—S—C(=NH₂⁺)—(R₆)ᵣ₂—, —(R₅)ᵣ₁—C(=NH₂⁺)—S—(R₆)ᵣ₂—, —(R₅)ᵣ₁—S(=O)₂—O—(R₆)ᵣ₂—, —(R₅)ᵣ₁—O—S(=O)₂—(R₆)ᵣ₂—, —(R₅)ᵣ₁—S(=O)—O—(R₆)ᵣ₂—, —(R₅)ᵣ₁—O—S(=O)—(R₆)ᵣ₂—, —(R₅)ᵣ₁—S(=O)₂—N(R₁₈)—N(R₁₉)—(R₆)ᵣ₂—, —(R₅)ᵣ₁—N(R₁₉)—N(R₁₈)—S(=O)₂—(R₆)ᵣ₂—, —(R₅)ᵣ₁—S(=O)₂—N(R₁₈)—C(=O)—N(R₇)—(R₆)ᵣ₂—, —(R₅)ᵣ₁—N(R₇)—C(=O)—N(R₁₈)—S(=O)₂—(R₆)ᵣ₂—, —(R₅)ᵣ₁—N(R₇)—(CH₂)ᵣ₃—O—C(=O)—, —(R₅)ᵣ₁—N(R₇)—(CH₂)ᵣ₃—O—C(=O)—(R₆)ᵣ₂—, —(R₅)ᵣ₁—O—Si(R₄₁R₄₂)—O—(R₆)ᵣ₂—, an orthoester linkage, a phosphate linkage, a phosphirate linkage, a phosphinate linkage, a phosphonate linkage, a phosphosilicate linkage, a silicate linkage, an amide bond, a thioamide bond, a sulfonamide bond, a polyamide linkage, a phosphamide linkage, a phosphiramide linkage, a pyrophosphamide linkage, a cyclophosphamide linkage, an ifosfamide linkage, a thiophosphamide linkage, an aconityl linkage, a benzyloxycarbonyl linkage, a peptide fragment, divalent linkages deriving from a nucleotide and derivatives thereof, divalent linkages deriving from a deoxynucleotide and derivatives thereof,

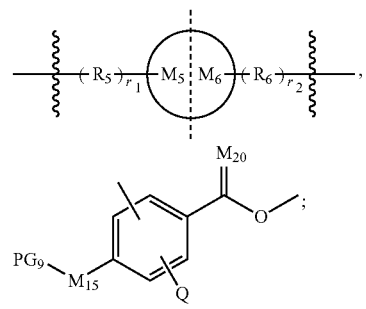

in addition, linking groups such as

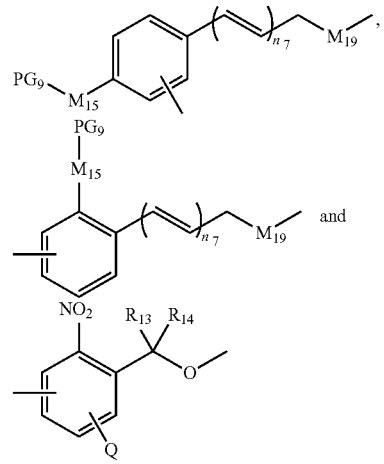

and can be stable under some physiological conditions, but can be degradable under special light illumination. Generally, ester bonds can be degraded under acidic or basic conditions, however ester groups from benzyloxycarbonyl group,

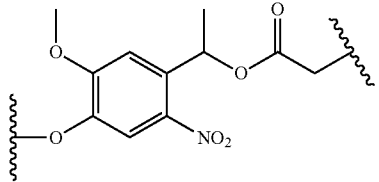 [SMILES: *CC(=O)OC(C)c1cc(OC)c(O*)cc1[N+](=O)[O-]]

and the like can also be degraded under some special light illumination ("Journal of Polymer Science: Part A: Polymer Chemistry, 2008, 46, 6896-6906").

Wherein, $L_9$ can be any stable divalent linking group, and can be any of the above-mentioned STAG linkages.

Wherein, r1 and r2 are each independently 0 or 1.

Wherein, r3 is 2, 3, 4, 5 or 6.

Wherein, the definitions of $R_3$, $R_5$, $R_6$, $R_7$, $R_{18}$, $R_{19}$, $R_{23}$, $R_8$, $R_9$, $R_{13}$, $R_{14}$, $R_{15}$, $M_5$ and $M_6$ are the same as above-defined, no more repeated here.

Wherein, $R_3$ is preferably a methyl group, an ethyl group or a benzyl group.

$R_7$, $R_{18}$, $R_{19}$ and $R_{23}$ are preferably the same and each independently a hydrogen atom or a methyl group.

$R_8$ and $R_9$ are preferably the same and each independently a hydrogen atom or a methyl group.

$R_{13}$ is preferably a hydrogen atom, a heteroatom or a substituting group linked to a secondary or tertiary carbon, and selected from the group consisting of a hydrogen atom, a fluorine atom, a methyl group, an ethyl group, an n-propyl group, an isopropyl group, a butyl group, a phenyl group, a benzyl group, a butylphenyl group, a p-methylphenyl group, a trifluoromethyl group, a 2,2,2-trifluoroethyl group, and any substituted form thereof.

$R_{15}$ is preferably a hydrogen atom or a methyl group.

Preferably, $M_5$ and $M_6$ are ring-membering atoms, and are each independingly a carbon atom, a nitrogen atom, a phosphorus atom or a silicon atom; the ring structure containing $M_5$ or $M_6$ is 3- to 50-membered; said ring structure is derived from one of the following cyclic structures, the substituted form of one cyclic structure thereof, or the heterosubstituted form of one cyclic structure thereof: a furanose ring, a pyranose ring, benzene, tetrahydrofuran, pyrrolidine, thiazolidine, cyclohexane, cyclohexene, tetrahydropyran, piperidine, 1,4-dioxane, pyridine, pyridazine, pyrimidine, pyrazine, 1,3,5-triazine, 1,4,7-triazacyclononane, cyclotripeptides, indene, indane, indole, isoindole, purine, naphthalene, dihydroanthracene, xanthene, thioxanthene, dihydrophenanthrene, 10,11-dihydro-5H-dibenzo[a,d]cycloheptane, dibenzocycloheptene, 5-dibenzosuberenone, quinolone, isoquinoline, fluorine, carbazole, iminodibenzyle, acenaphthene, dibenzocyclooctyne and aza-dibenzocyclooctyne.

Wherein, $R_{41}$ and $R_{42}$ are each independently a $C_{1-20}$ alkyl group, a phenyl group, a benzyl group, a phenyl group substituted with a $C_{1-20}$ alkyl substituent, a benzyl group substituted with a $C_{1-20}$ alkyl substituent or a $C_{1-20}$ alkoxy group, preferably a $C_{1-6}$ alkyl group, a phenyl group, a benzyl group, a phenyl group substituted with a $C_{1-6}$ alkyl substituent, a benzyl group substituted with a $C_{1-6}$ alkyl substituent or a $C_{1-6}$ alkoxy group, and more preferably a $C_{1-6}$ alkyl group, a phenyl group or a benzyl group.

Wherein, $M_{19}$ and $M_{20}$ are each independently an oxygen atom or a sulfur atom, and in one molecule, they can be the same or different from each other.

Wherein, $M_{15}$ is a heteroatom selected from an oxygen atom, a sulfur atom and a nitrogen atom; $PG_9$ is the protecting group for $M_{15}$ and can be deprotected under conditions of acid, base, enzyme, redox (also denoted as oxidation-reduction), light illumination or heat; when $M_{15}$ is an oxygen atom, $PG_9$ corresponds to a hydroxyl protecting group denoted as $PG_4$; when $M_{15}$ is a sulfur atom, $PG_9$ corresponds to a mercapto protecting group denoted as $PG_2$; when $M_{15}$ is a nitrogen atom, $PG_9$ corresponds to an amino protecting group denoted as $PG_5$.

Wherein, $n_7$ is the number of carbon-carbon double bonds, and can be 0 or an integer from 1 to 10.

Wherein,

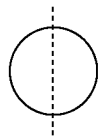

is a cyclic structure that can be degraded into at least two individual fragments. For example, a lactide ring.

Take r1=r2=0, $R_7$=$R_{18}$=$R_{19}$=$R_{23}$=$R_8$=$R_9$=$R_{13}$=$R_{14}$=$R_{15}$=H for example, a DEGG linkage can contain any of the following structures or the combination of any two or two more following structures: —S—S—, CH═CH—O—, —O—CH═CH—, —C(═O)—O—, —O—C(═O)—, —C(═O)—O—CH$_2$—, —CH$_2$—O—C(═O)—, —C(═O)—O—CH$_2$—O—C(═O)—, —C(═O)—O—CH$_2$—NH—C(═O)—, —O—C(═O)—R$_5$—C(═O)—O—, —C(═O)—S—, —S—C(═O)—, —C(═S)—O—, —O—C(═S)—, —C(═S)—S—, —S—C(═S)—, —O—C(═O)—O—, —S—C(═O)—O—, —O—C(═S)—O—, —O—C(═O)—S—, —S—C(═S)—O—, —O—C(═S)—S—, —S—C(═O)—S—, —S—C(═S)—S—, —NH—C(═O)—O—, —O—C(═O)—NH—, —NH—C(═S)—O—, —O—C(═S)—NH—, —NH—C(═O)—S—, —S—C(═O)—NH—, —NH—C(═S)—S—, —S—C(═S)—NH—, —CH(OR$_3$)—O—, —O—CH(OR$_3$)—, —CH(OR$_3$)—S—, —S—CH(OR$_3$)—, —CH(SR$_3$)—O—, —O—CH(SR$_3$)—, —CH(SR$_3$)—S—, —S—CH(SR$_3$)—, —CH(OR$_3$)—NH—, —NH—CH(OR$_3$)—, —CH(NPG$_5$)-O—, —O—CH(NH$_2$)—, —CH(NH$_2$)—NH—, —NH—CH(NH$_2$)—, —(NH$_2$)C(SR$_3$)—, —CH(SR$_3$)—NH—, —NH—CH(SR$_3$)—, —CH(NH$_2$)—S—, —S—CH(NH$_2$)—, —CH(OH)—NH—, —NH—CH(OH)—, —CH(OR$_3$)—O—, —O—CH(OR$_3$)—, —CH(OR$_3$)—S—, —S—CH(OR$_3$)—, —CH(SR$_3$)—O—, —O—CH(SR$_3$)—, —CH(SR$_3$)—S—, —S—CH(SR$_3$)—, —CH(OR$_3$)—NH—, —NH—CH(OR$_3$)—, —CH(NH$_2$)—O—, —O—CH(NH$_2$)—, —CH(NH$_2$)—NH—, —NH—CH(NH$_2$)—, —CH(SR$_3$)—NH—, —NH—CH(SR$_3$)—, —CH(NH$_2$)—S—, —S—CH(NH$_2$)—, —CH(OH)—O—, —O—CH(OH)—, —CH(OH)—S—, —S—CH(OH)—, —CH(OH)—NH—, —NH—CH(OH)—, —HC═N—, —N═CH—, —HC═N—NH—, —NH—N═CH—, —HC═N—NH—C(═O)—, —C(═O)—NH—N═CH—, —HC═N—O—, —O—N═CH—, —HC═N—S—, —S—N═CH—, —NH—C(═O)—NH—N═CH—, —HC=N—NH—C(=O)—NH—, —NH—C(=S)—NH—N=CH—, —HC=N—NH—C(=S)—NH—, —NH—NH—, —NH—NH—C(=O)—, —C(=O)—NH—NH—, —NH—NH—C(=S)—, —C(=S)—NH—NH—, —NH—NH—C(=O)—N=N—, —N=N—C(=O)—NH—NH—, —NH—NH—C(=S)—N=N—, —N=N—C(=S)—NH—NH—, —NH—NH—C(=O)—O—, —O—C(=O)—NH—NH—, —NH—NH—C(=S)—O—, —O—C(=S)—NH—NH—, —NH—NH—C(=O)—S—, —S—C(=O)—NH—NH—, —NH—NH—C(=S)—S—, —S—C(=S)—NH—NH—, —NH—NH—C(=O)—NH—NH—, —NH—NH—C(=S)—NH—NH—, —N=N—, —O—C(=NH)—NH—, —NH—C(=NH)—O—, —O—C(=NH$_2^+$)—NH—, —NH—C(=NH$_2^+$)—O—, —NH—C(=NH)—S—, —S—C(=NH)—NH—, —NH—C(=NH$_2^+$)—S—, —S—C(=NH$_2^+$)—NH—, —NH—C(=O)—NH—C(=O)—O—, —O—C(=O)—NH—C(=O)—NH—, —NH—C(=S)—NH—C(=O)—O—, —O—C(=O)—NH—C(=S)—NH—, —NH—C(=NH)—NH—, —NH—C(=NH$_2^+$)—NH—NH—C(=O)—NH—C(=O)—O—, —NH—C(=NH$_2^+$)—NH—, —C(=NH)—NH—, —NH—C(=NH)—, —NH—C(=NH$_2^+$)—, —C(=NH$_2^+$)—NH—, —NH—NH—C(=NH)—NH—, —NH—C(=NH)—NH—NH—, —NH—NH—C(=NH$_2^+$)—NH—, —NH—C(=NH$_2^+$)—NH—NH—, —C(=NH)—NH—NH—, —NH—NH—C(=NH)—, —NH—NH—C(=NH$_2^+$)—, —C(=NH$_2^+$)—NH—NH—, —C(=NH)—O—, —O—C(=NH)—, —O—C(=NH$_2^+$)—, —C(=NH$_2^+$)—O—, —C(=NH)—S—, —S—C(=NH)—, —S—C(=NH$_2^+$)—, —C(=NH$_2^+$)—S—, —S(=O)$_2$—O—, —O—S(=O)$_2$—, —S(=O)—O—, —O—S(=O)—, —S(=O)$_2$—NH—, —NH—S(=O)$_2$—, —NH—S(=O)$_2$—NH—, —S(=O)$_2$—NH—NH—, —NH—NH—S(=O)$_2$—, —S(=O)$_2$—NH—C(=O)—NH—, —NH—C(=O)—NH—S(=O)$_2$—, —NH—(CH$_2$)$_{r3}$—O—C(=O)—, —N(CH$_3$)—(CH$_2$)$_{r3}$—O—C(=O)—, —O—Si(R$_{41}$R$_{42}$)—O—, an orthocarbonate linkage, an orthosilicate linkage, an orthophosphate linkage, an orthosulfate linkage, an orthotellurate linkage, a phosphate linkage, a phosphirate linkage, a phosphinate linkage, a phosphonate linkage, phosphosilicate linkage, a silicate linkage, an amide bond, a thioamide bond, a sulfonamide bond, a polyamide linkage, a phosphamide linkage, a phosphiramide linkage, a phosphinamide linkage, a phosphonamide linkage, a pyrophosphamide linkage, a cyclophosphamide linkage, an ifosfamide linkage, a thiophosphamide linkage, an aconityl linkage, a benzyloxycarbonyl linkage, a peptide fragment, a nucleotide skeleton and derivatives thereof, a deoxynucleotide skeleton and derivatives thereof,

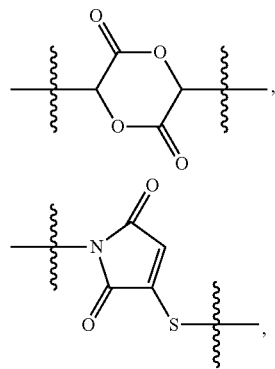

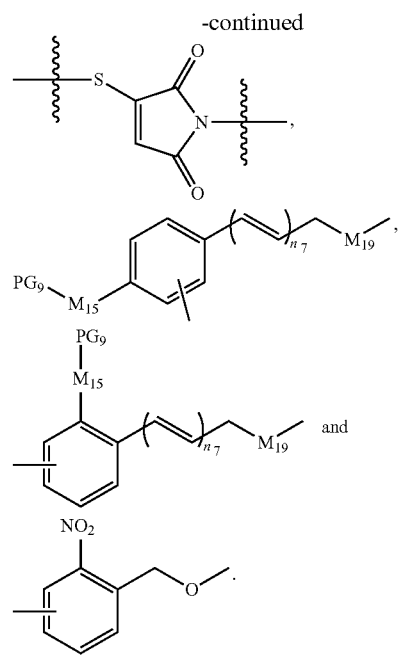

Wherein, r3 is 2, 3, 4, 5 or 6. R$_3$ is preferably a methyl group, an ethyl group or a phenyl group. Wherein, the definitions of M$_{15}$, PG$_9$, M$_{19}$, M$_{20}$ and n$_7$ are the same as above-defined, no more repeated here.

DEGG can also be the combination of any above-said degradable divalent linking group and any suitable stable divalent linking group.

Examples of the divalent linking group combined by one DEGG linkage and one above-said STAG linkage include as follows:

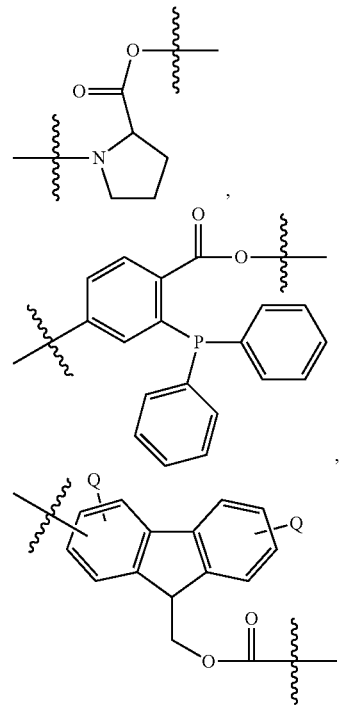

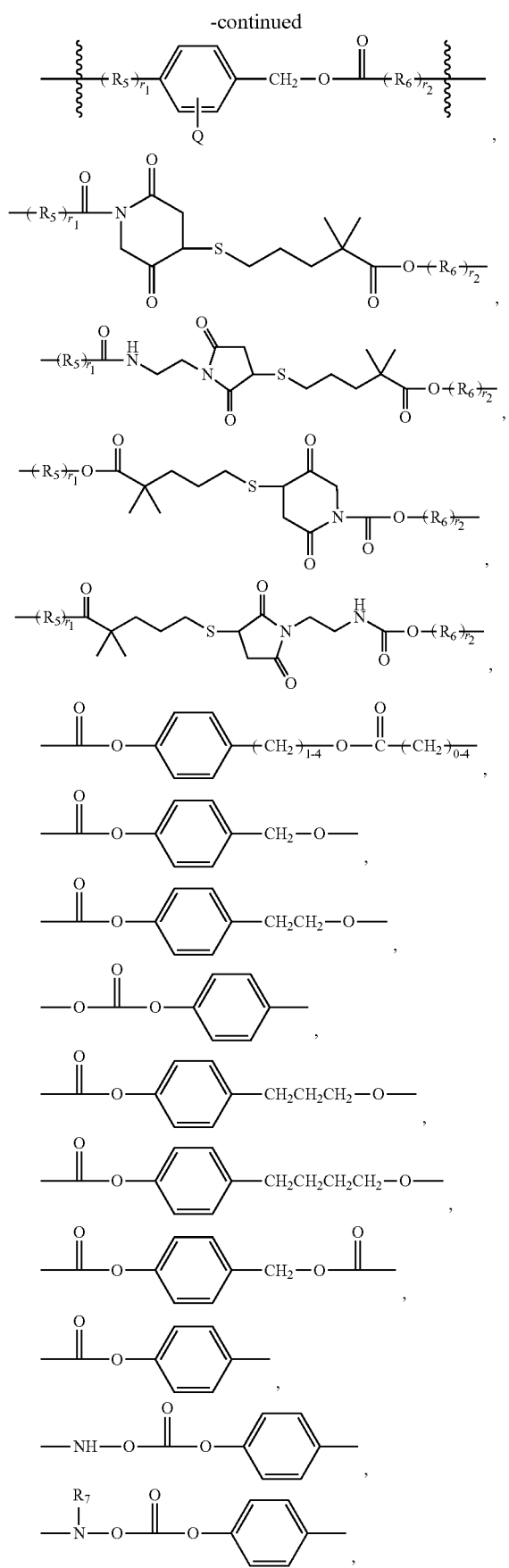
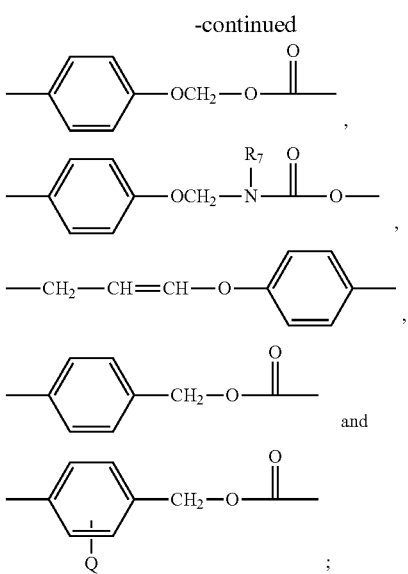
Wherein, r1 and r2 are each independently 0 or 1.
Wherein, the definitions of $R_5$, $R_6$, $R_7$ and Q are the same as above-mentioned, no more repeated here.
Degradable divalent linking groups bearing aryl rings can also be combined by aryl rings (such as
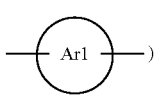)
and degradable divalent linking groups. For example,
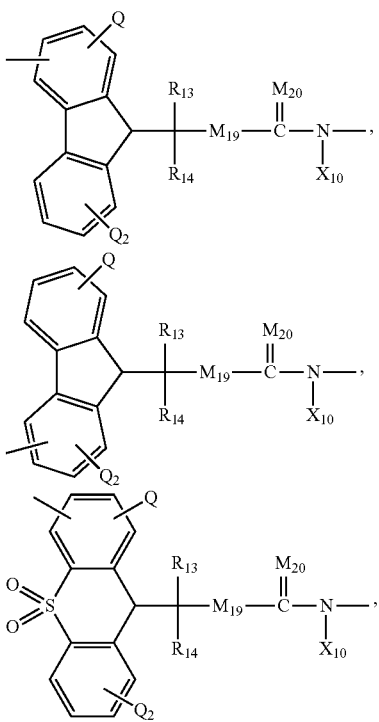

-continued

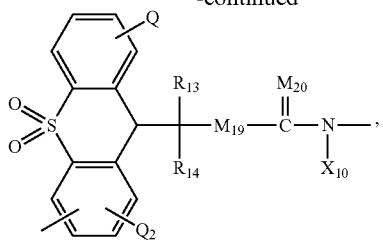

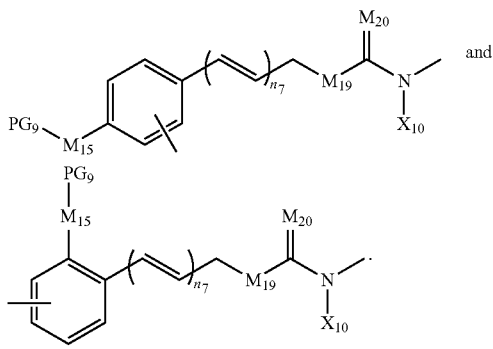

Wherein, the definitions of Q, $Q_2$, $R_{13}$, $R_{14}$, $X_{10}$, $M_{19}$, $M_{20}$, $M_{15}$, $PG_9$ and $n_7$ are the same as above, no more repeated here.

1.1.7.3. Degradable Multivalent Groups

A degradable trivalent, tetravalent, or higher valent group should contain at least one degradable divalent linking group DEGG.

The degradable trivalent groups include but not limited to the combination of a stable trivalent group containing a trivalent atom core structure together with a degradable divalent linking group, the combination of a trivalent aryl ring together with a degradable divalent linking group, the combination of a degradable trivalent cyclic structure together with a stable divalent linking group, the combination of a degradable trivalent cyclic structure together with a degradable divalent linking group, the trivalent form of any above-said degradable divalent linking group, and the like. Wherein, said degradable trivalent cyclic structure refers to a trivalent cyclic structure that can be degraded into at least two individual fragments. The typical example is trivalent closed cyclic structure formed by two or two more degradable groups that are connected in sequence, such as a cyclopeptide, or a cyclic structure formed via two or two more ester bonds in sequence.

The degradable trivalent group $U_1$, $U_2$ and G, can be the combination of a trivalent aryl ring and a degradable divalent linking group, the combination of a degradable trivalent cyclic structure and a stable or degradable divalent linking group, or the trivalent form of any above-said degradable divalent linking group.

Wherein examples of said degradable U groups ($U_1$, $U_2$, $U_{01}$ or $U_{02}$) formed by a trivalent aryl ring (such as

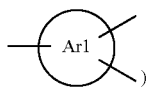

and a degradable divalent linking group include as follows:

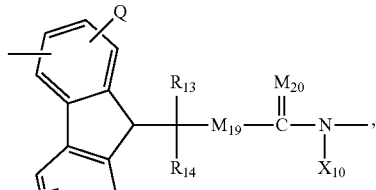

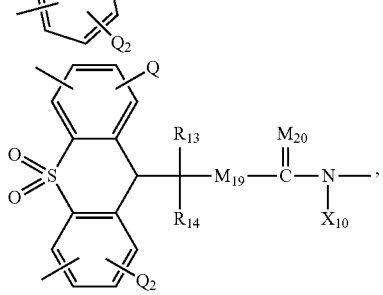

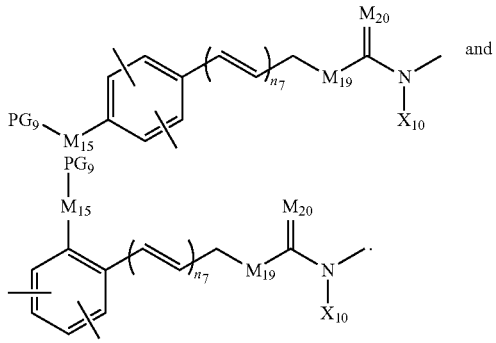

Wherein, the definitions of Q, $Q_2$, $R_{13}$, $R_{14}$, $X_{10}$, $M_{19}$, $M_{20}$, $M_{15}$, $PG_9$ and $n_7$ are the same as above-defined, no more repeated here.

Wherein, said degradable trivalent cyclic structures refer to trivalent cyclic structures that can be degraded into at least two individual fragments. They can be a trivalent closed cyclic structure formed by two or two more degradable groups that are linked in sequence, such as a cyclopeptide, or a cyclic structure formed via two or two more ester bonds connected in sequence.

Wherein, said trivalent forms of above-said degradable divalent linking groups, for example,

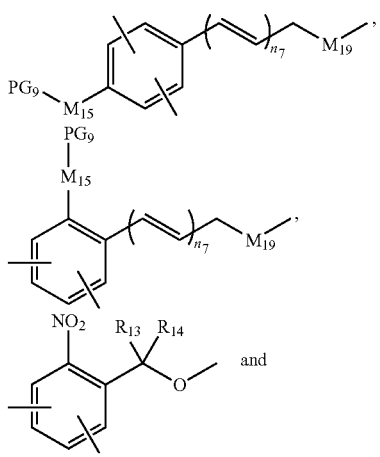

-continued
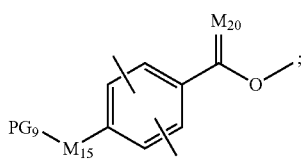
wherein, the definitions of $M_{19}$, $M_{20}$, $M_{15}$, $PG_9$ and $n_7$ are the same as above-mentioned, no more repeated here.
1.1.8. Preferable Structures of Trivalent SemiH-Branching Groups: $U_1$, $U_2$, $U_{01}$ and $U_{02}$
$U_{01}$ and $U_{02}$ each independently preferably can contain any of the following structures:
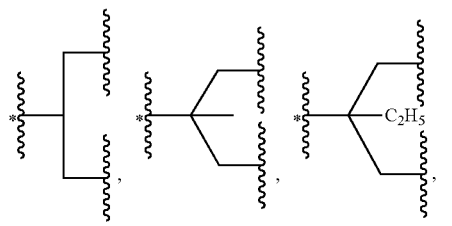
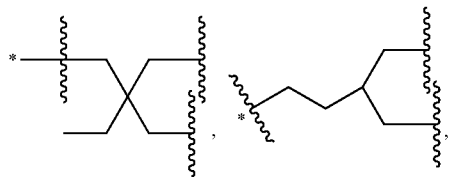
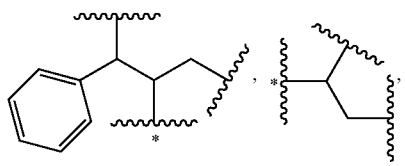
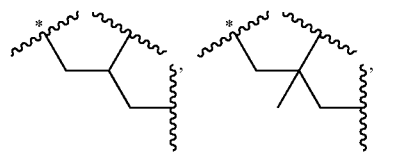
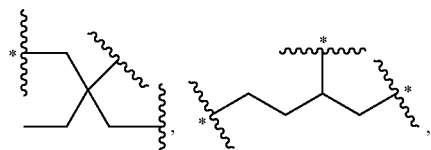
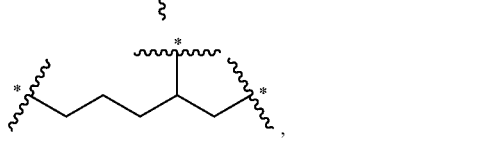
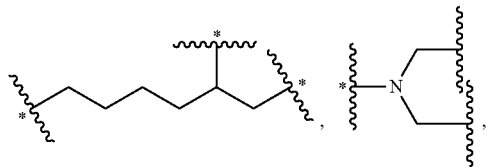
-continued
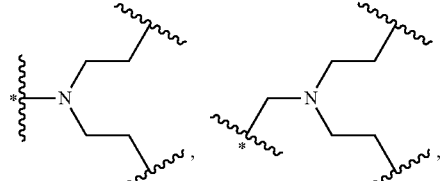
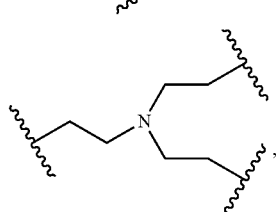
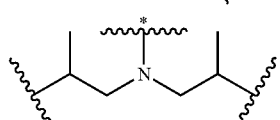
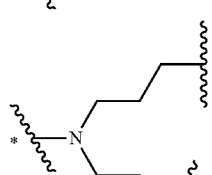
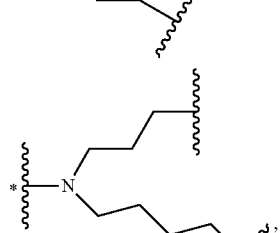
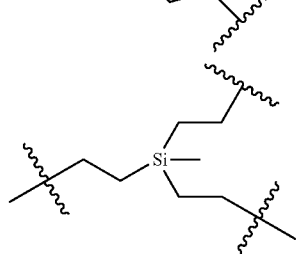
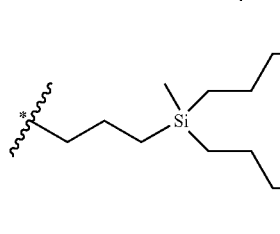
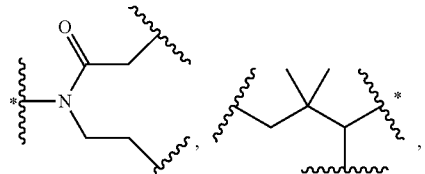
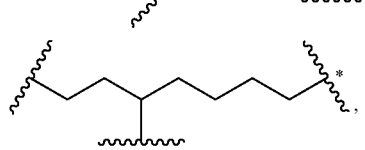

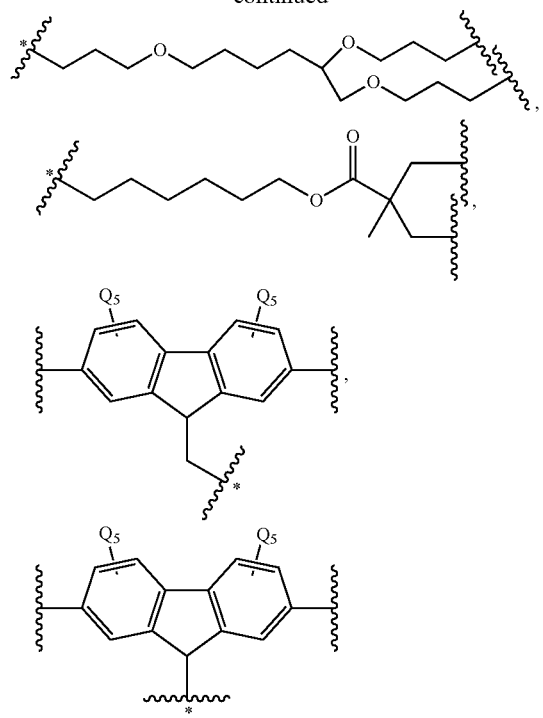

and the like. $U_{01}$ and $U_{02}$ each independently further preferably contain any above-said structure end-capped by one, two or three identical or different divalent linking groups selected from an oxy group, a thioxy group, a secondary amino group, a divalent t-amino group and a carbonyl group; when serving as a moiety of initiator molecules for living anionic polymerization, $U_{01}$ and $U_{02}$ each independently further preferably contains no carbonyl group and secondary amino group. For example, $U_{01}$ and $U_{02}$ can be each independently any of the following structures:

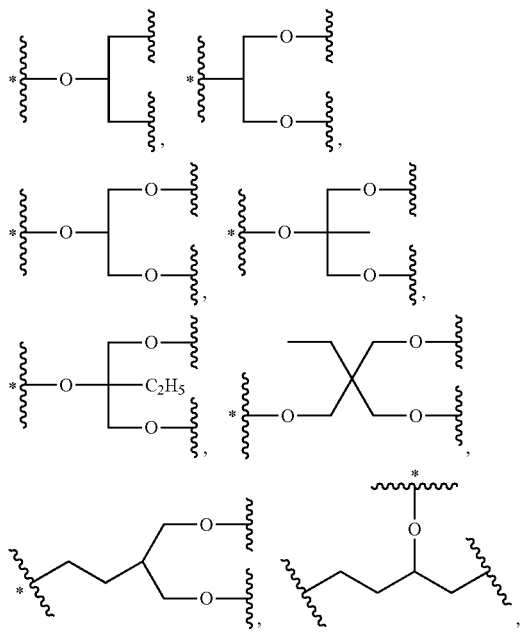

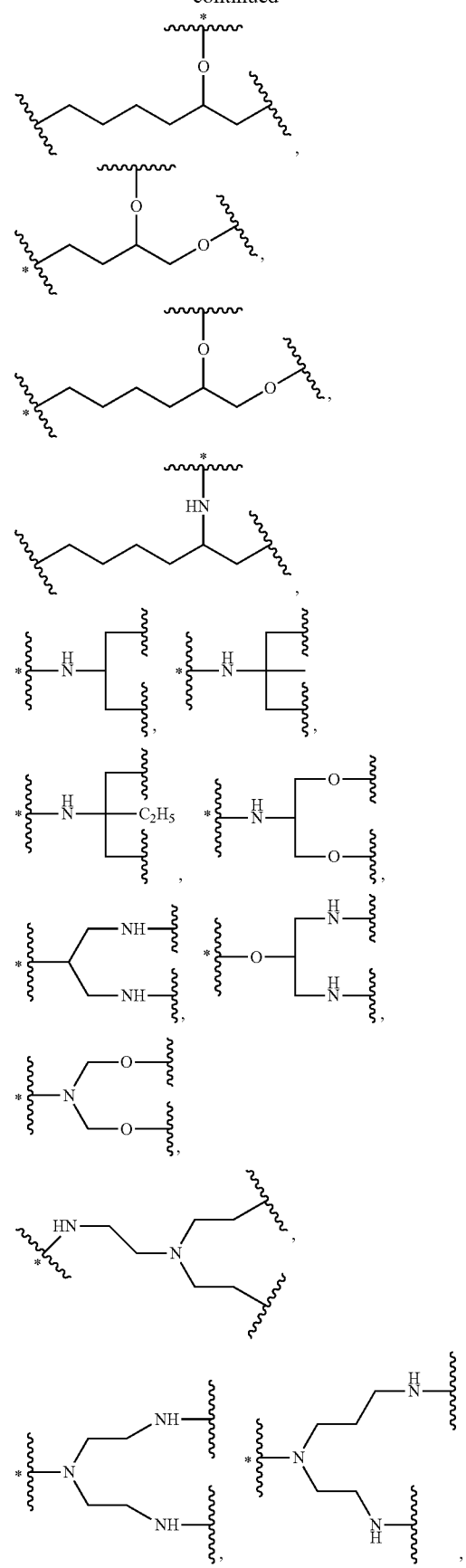

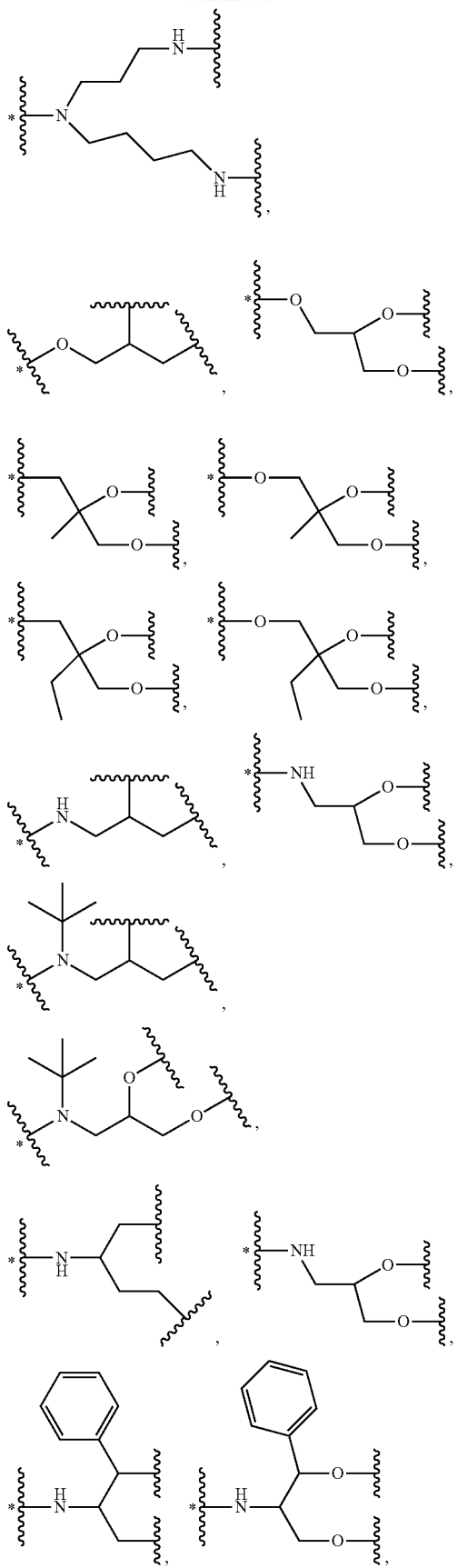
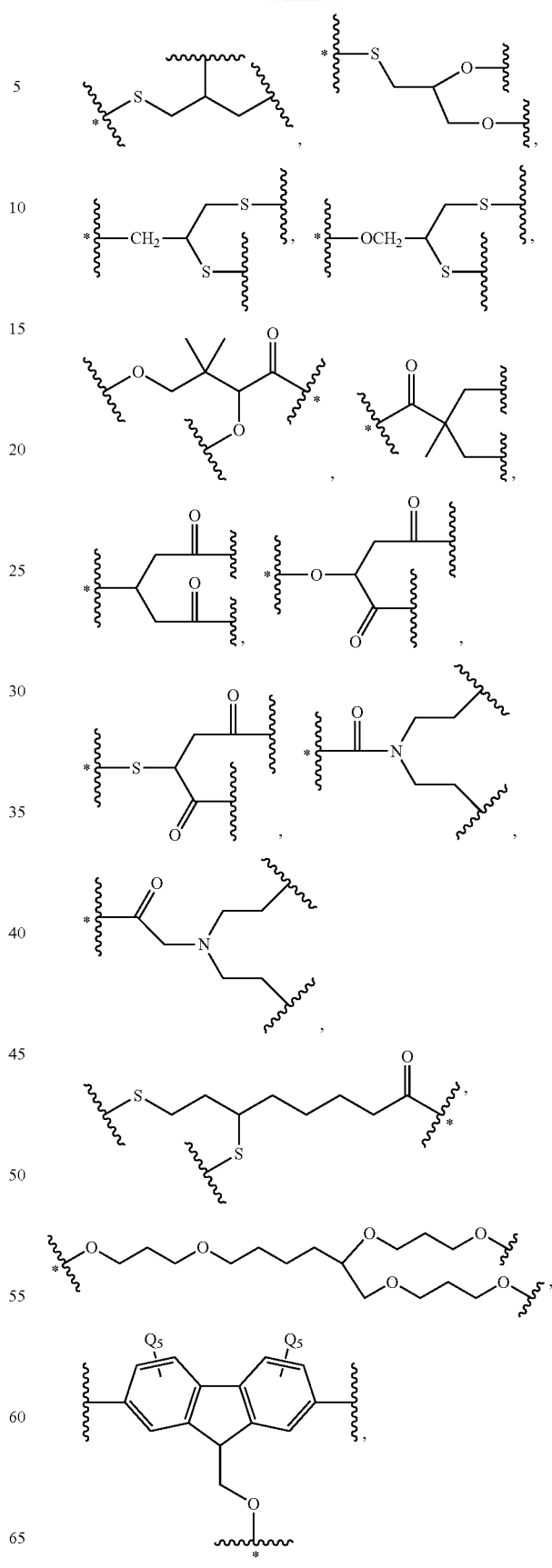

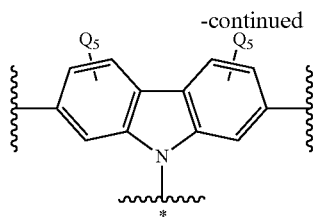

and the like. When contained in initiator molecules for living anionic polymerization, $U_{01}$ and $U_{02}$ each independently further preferably contains neither carbonyl group nor secondary amino group. The definition of $Q_5$ is the same as above-mentioned.

The semiH-branching groups $U_{01}$ and $U_{02}$ are each independently more preferably

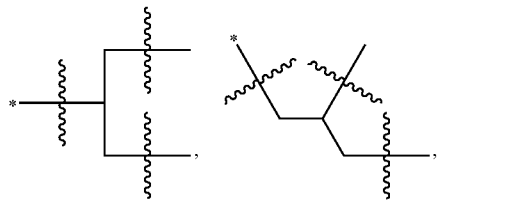

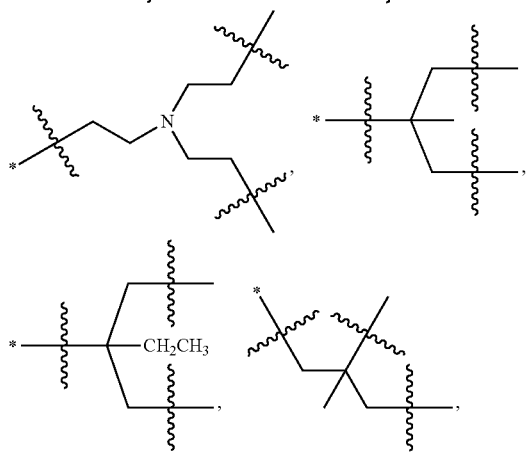

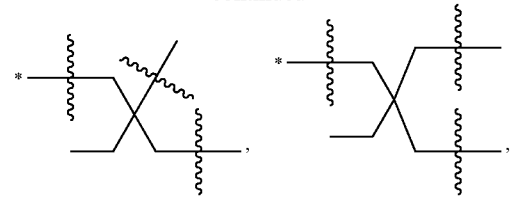

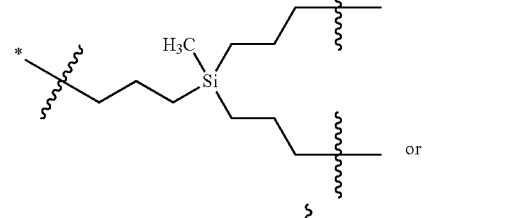

or

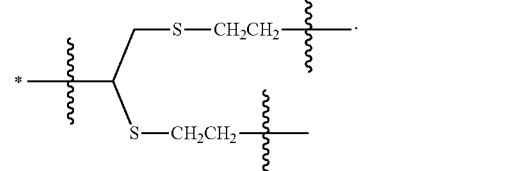

$U_{01}$ and $U_{02}$ can also be each independently the trivalent skeleton structure of amino acids and derivatives thereof, but would not participate in constructing initiator molecules of living anionic polymerization; wherein, said amino acids are of $_L$- or $_D$-type. For example, said amino acids can be derived from, but not limited to, the following amino acids and derivatives thereof: hydroxyl- or sulfur-containing amino acids such as serine, threonine, cysteine, tyrosine and hydroxyproline and derivatives thereof, acidic amino acids including aspartic acid, glutamic acid, asparagine and glutamine and derivatives thereof, basic amino acids including lysine, arginine, citrulline, histidine and tryptophan and derivatives thereof.

Specific examples of the branching groups $U_1$ and $U_2$ in the above general formula (1) to general formula (6) each independently include but are not limited to the following structures:

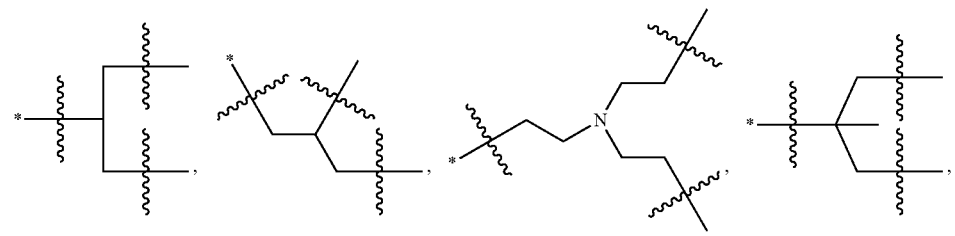

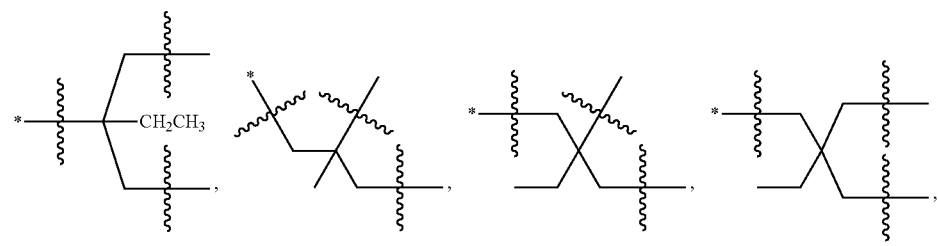

-continued
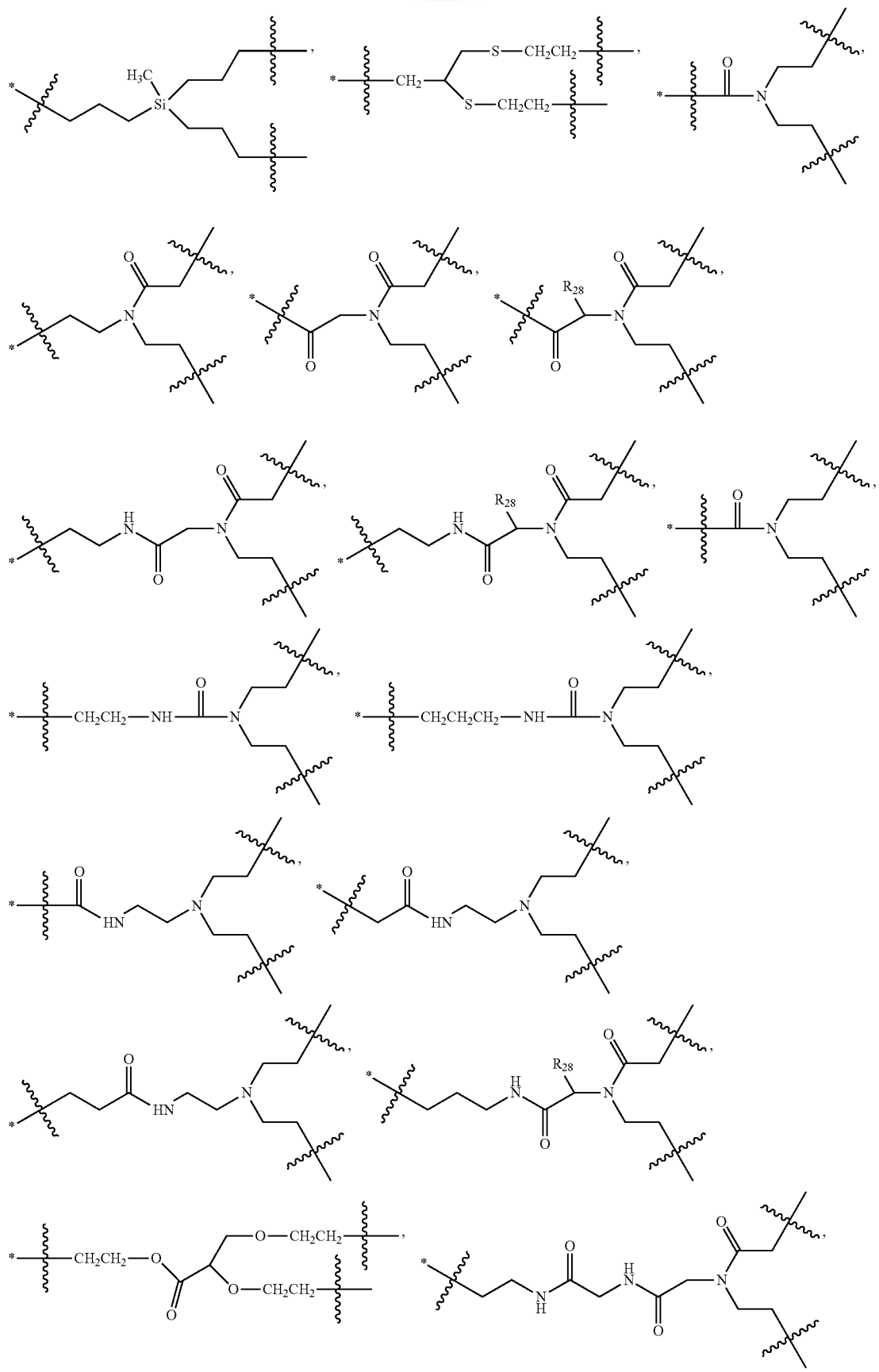

-continued
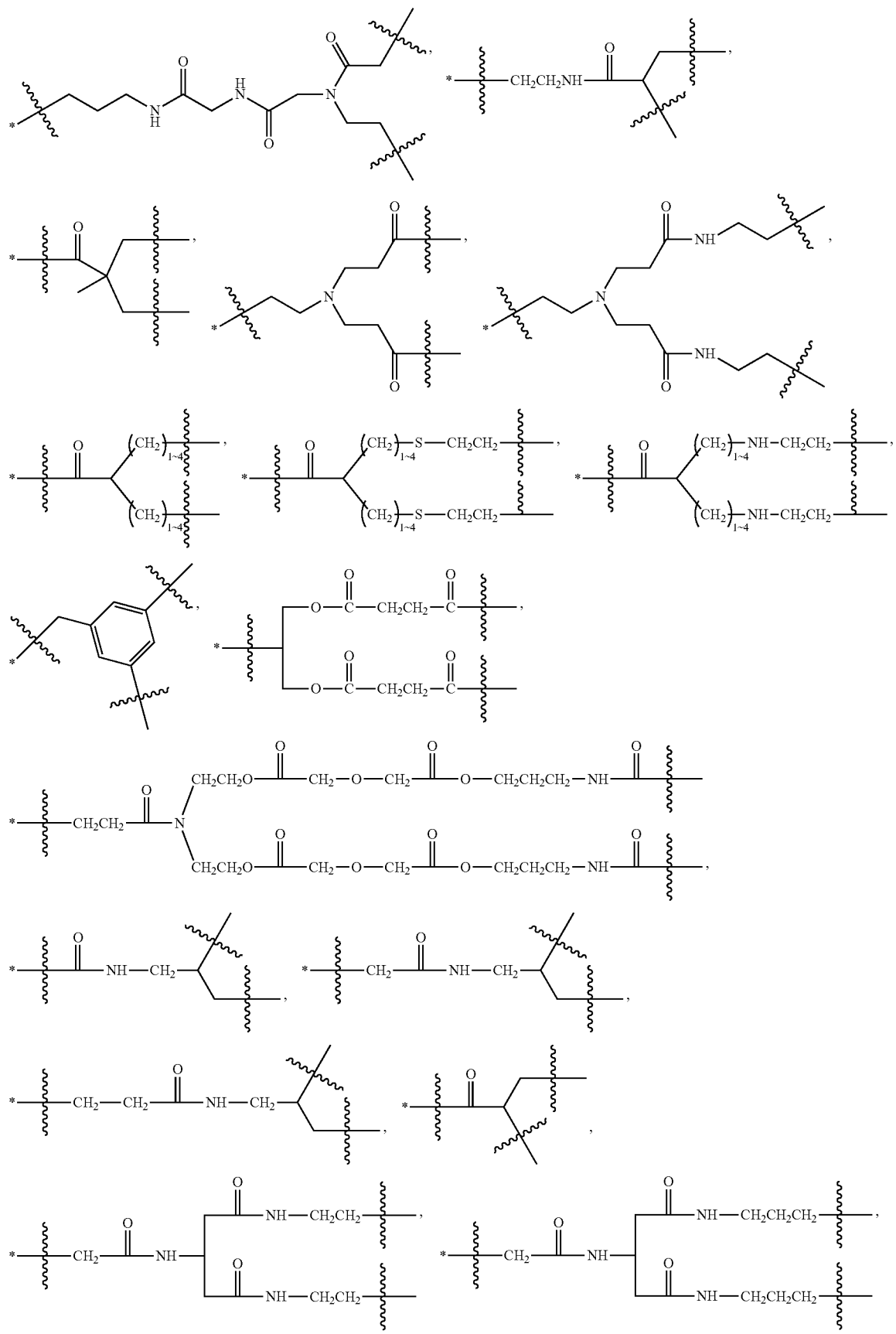

-continued
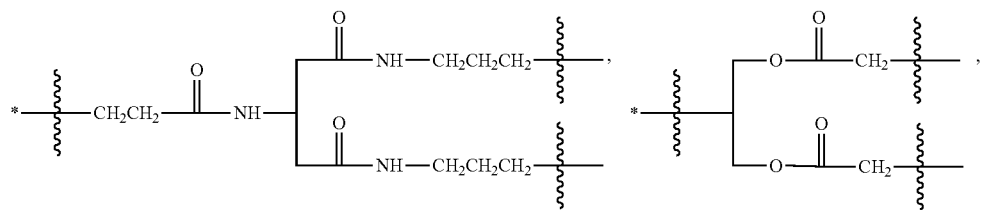
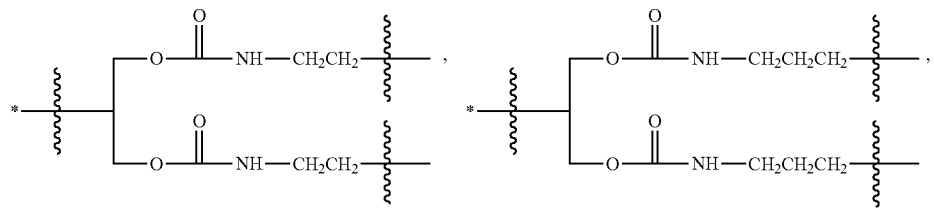
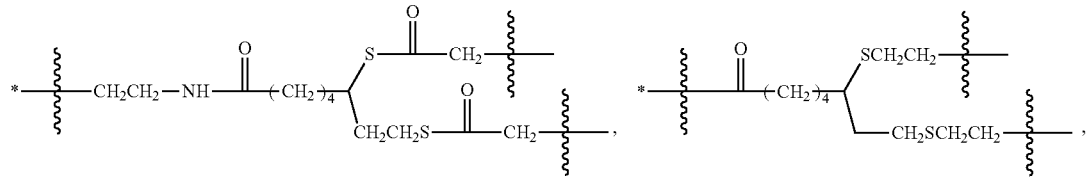
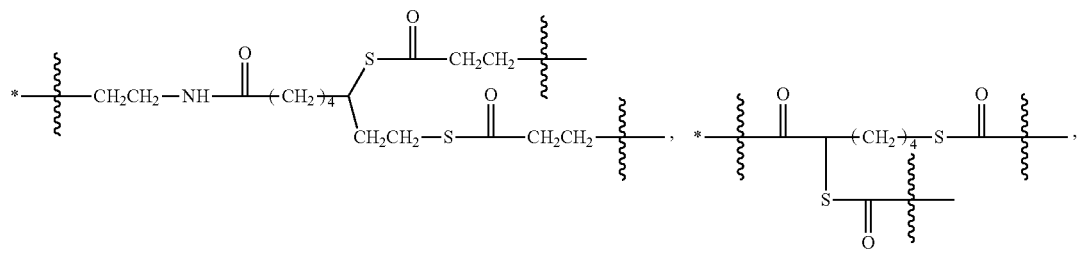
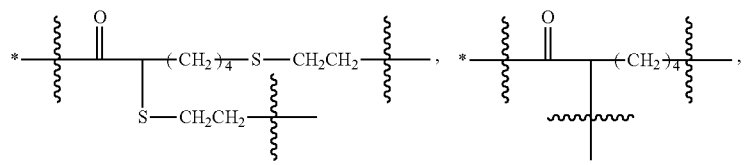
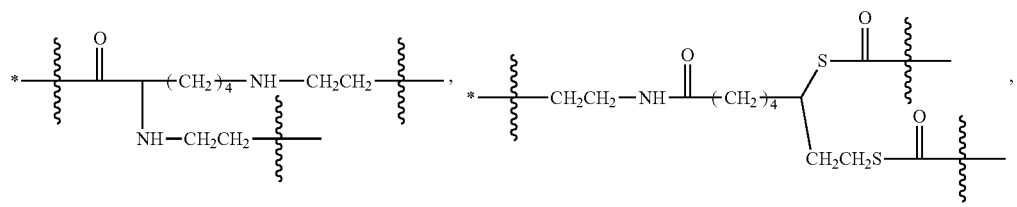
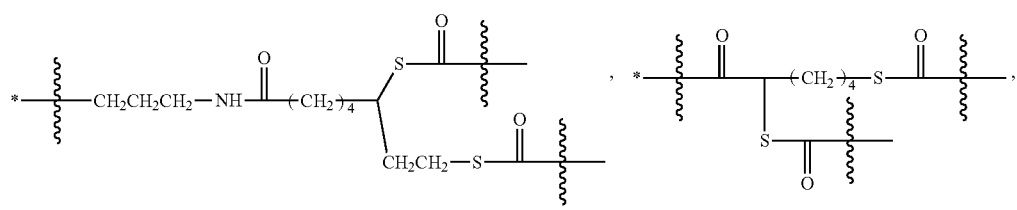

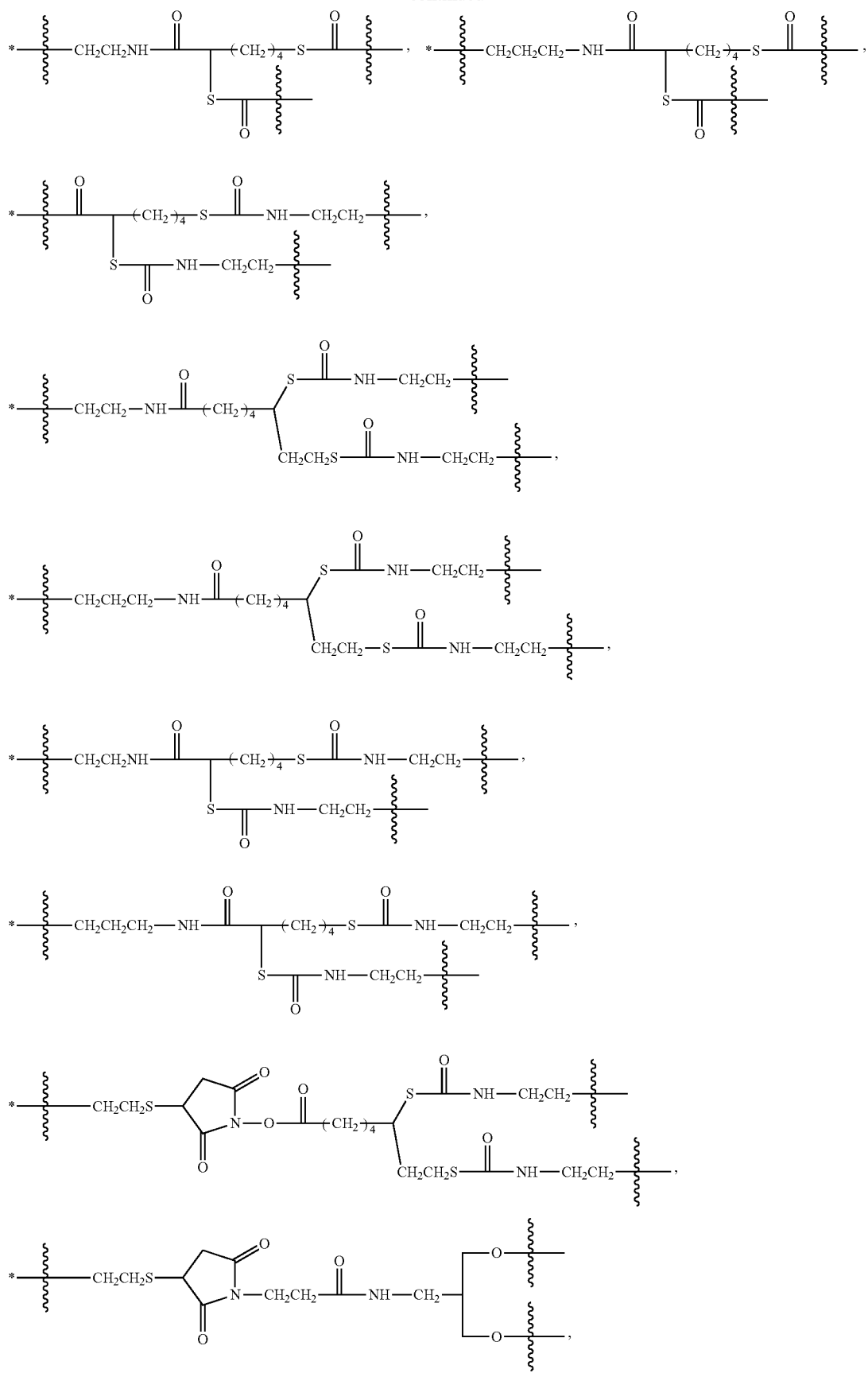

-continued
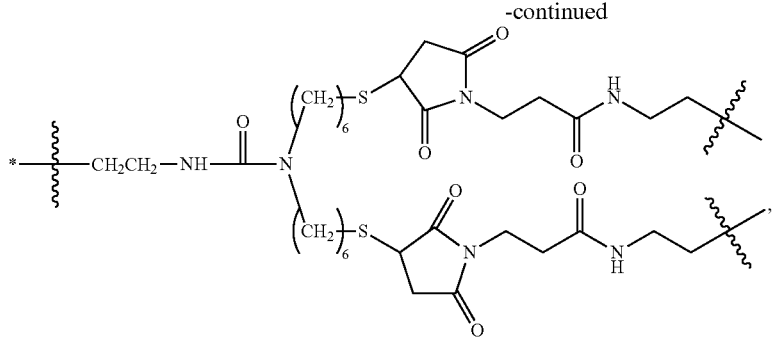
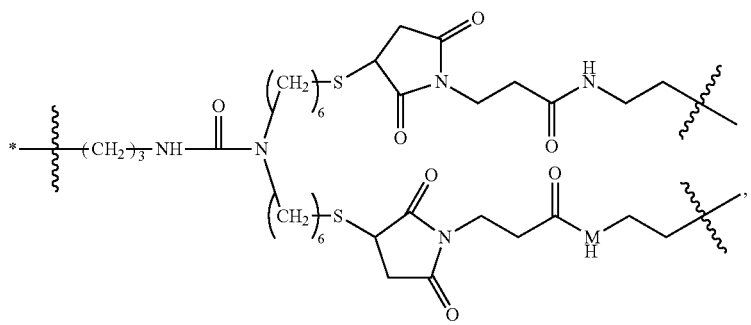
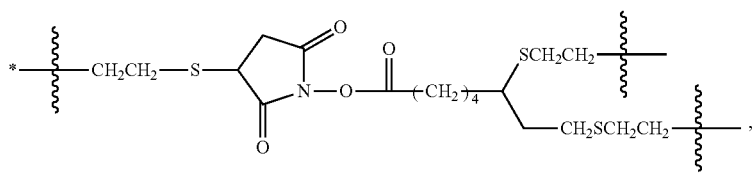
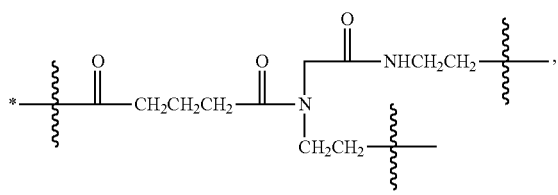
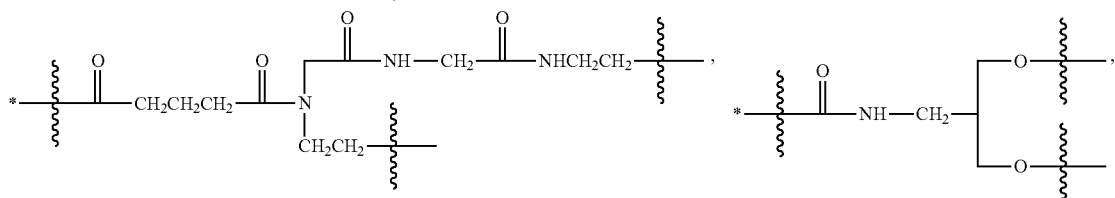
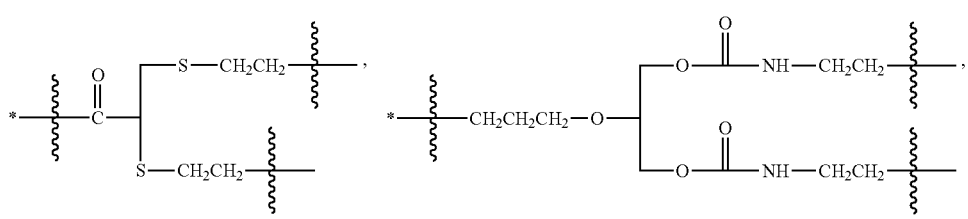
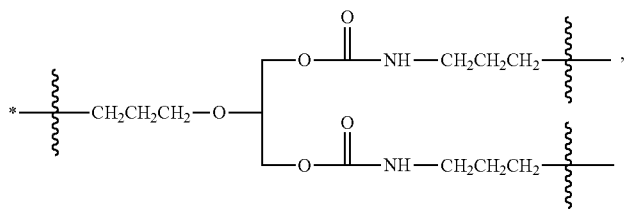

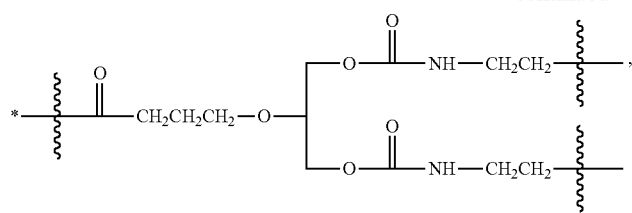
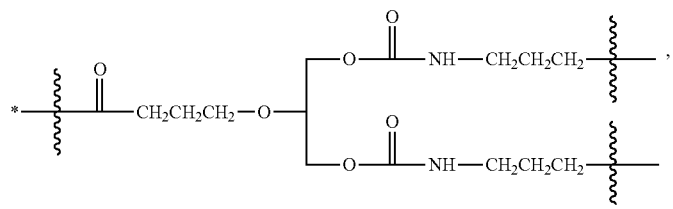
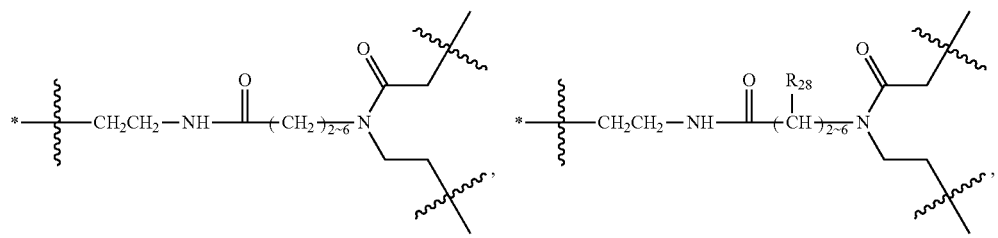
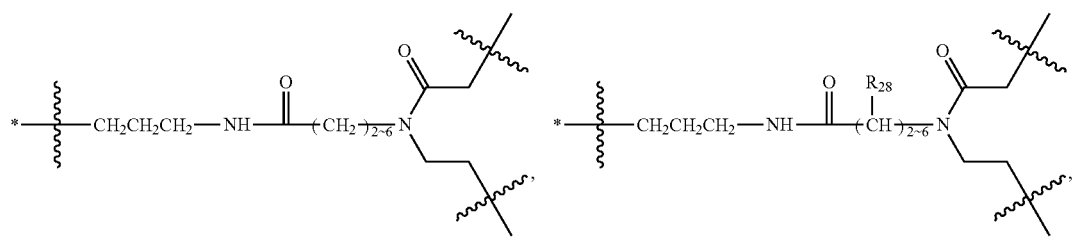
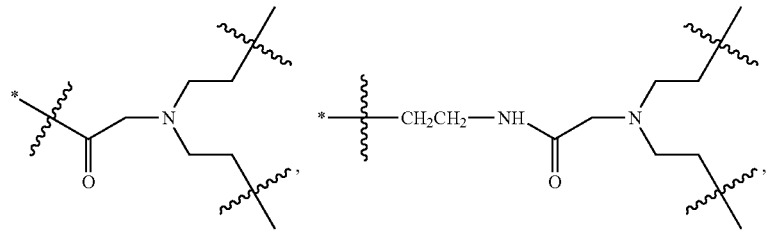
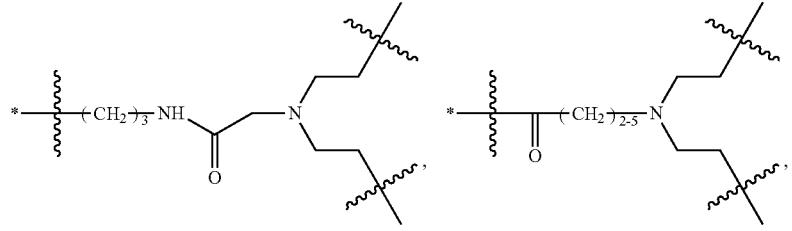
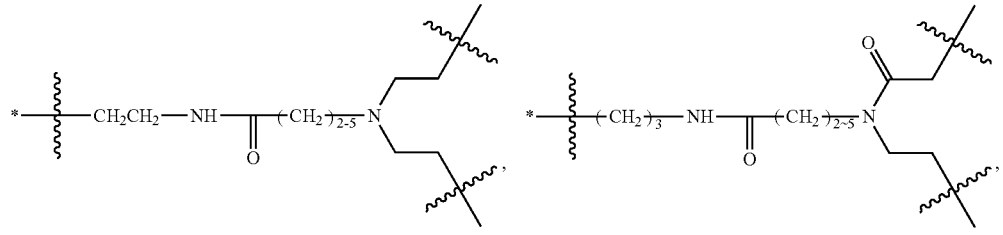

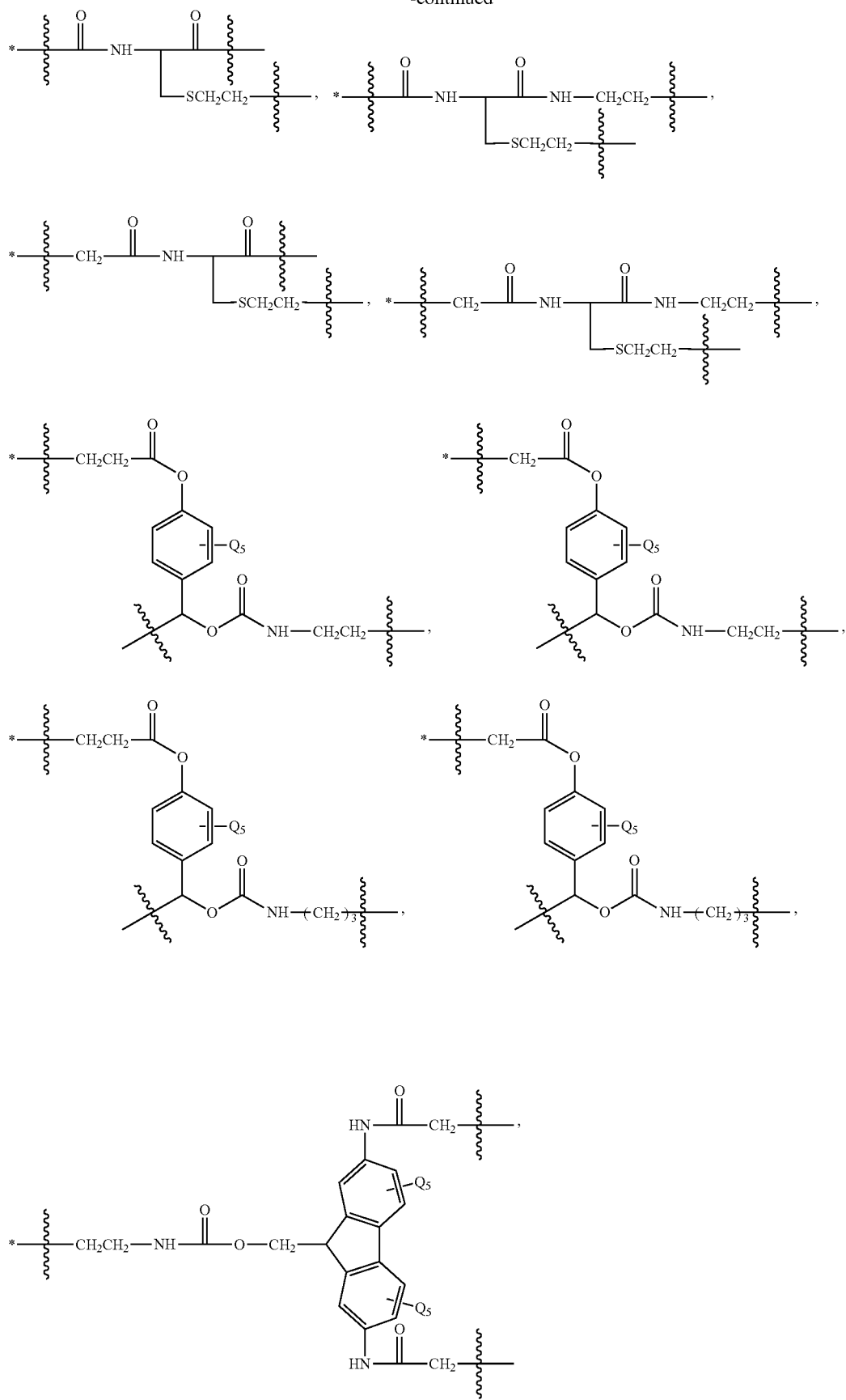

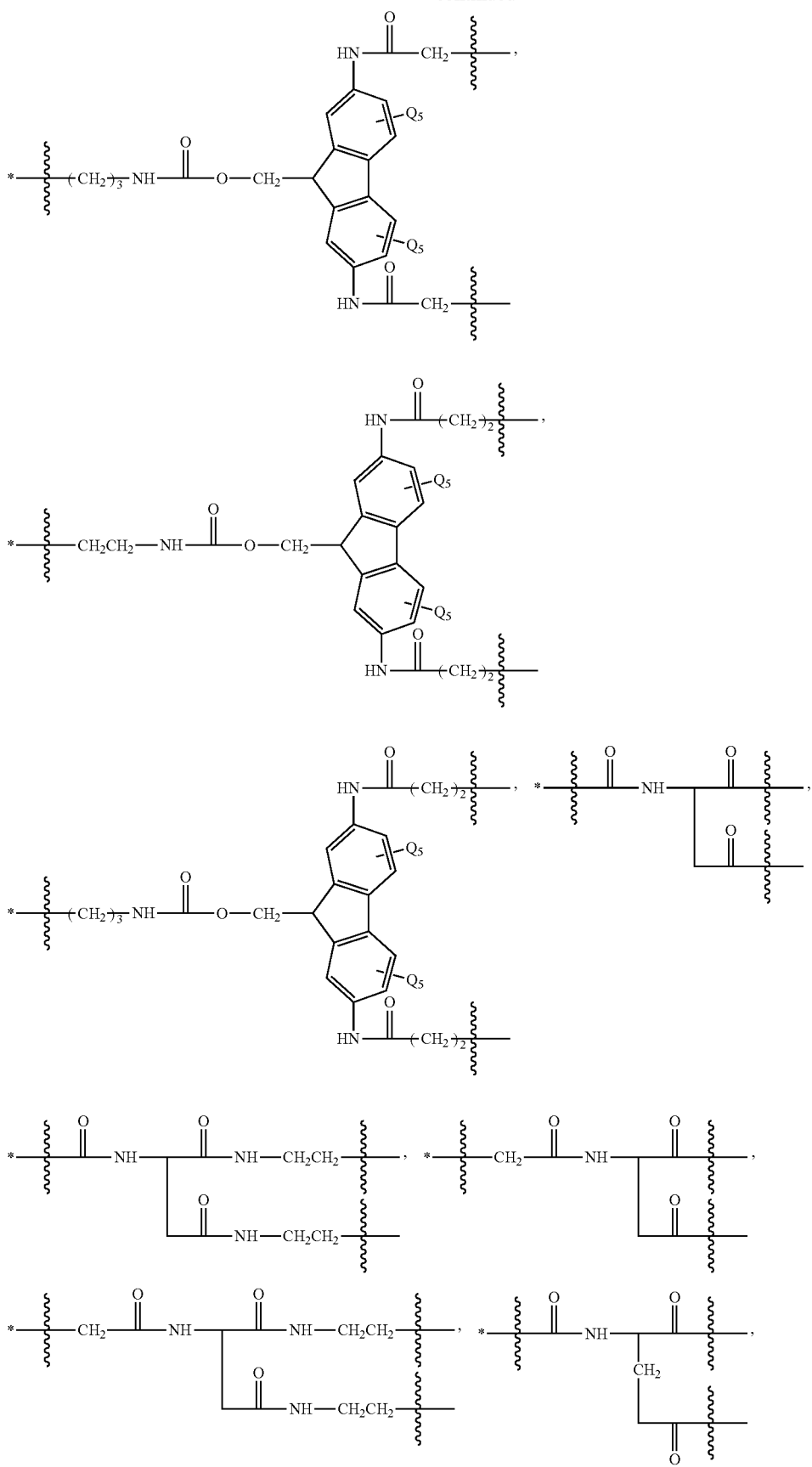

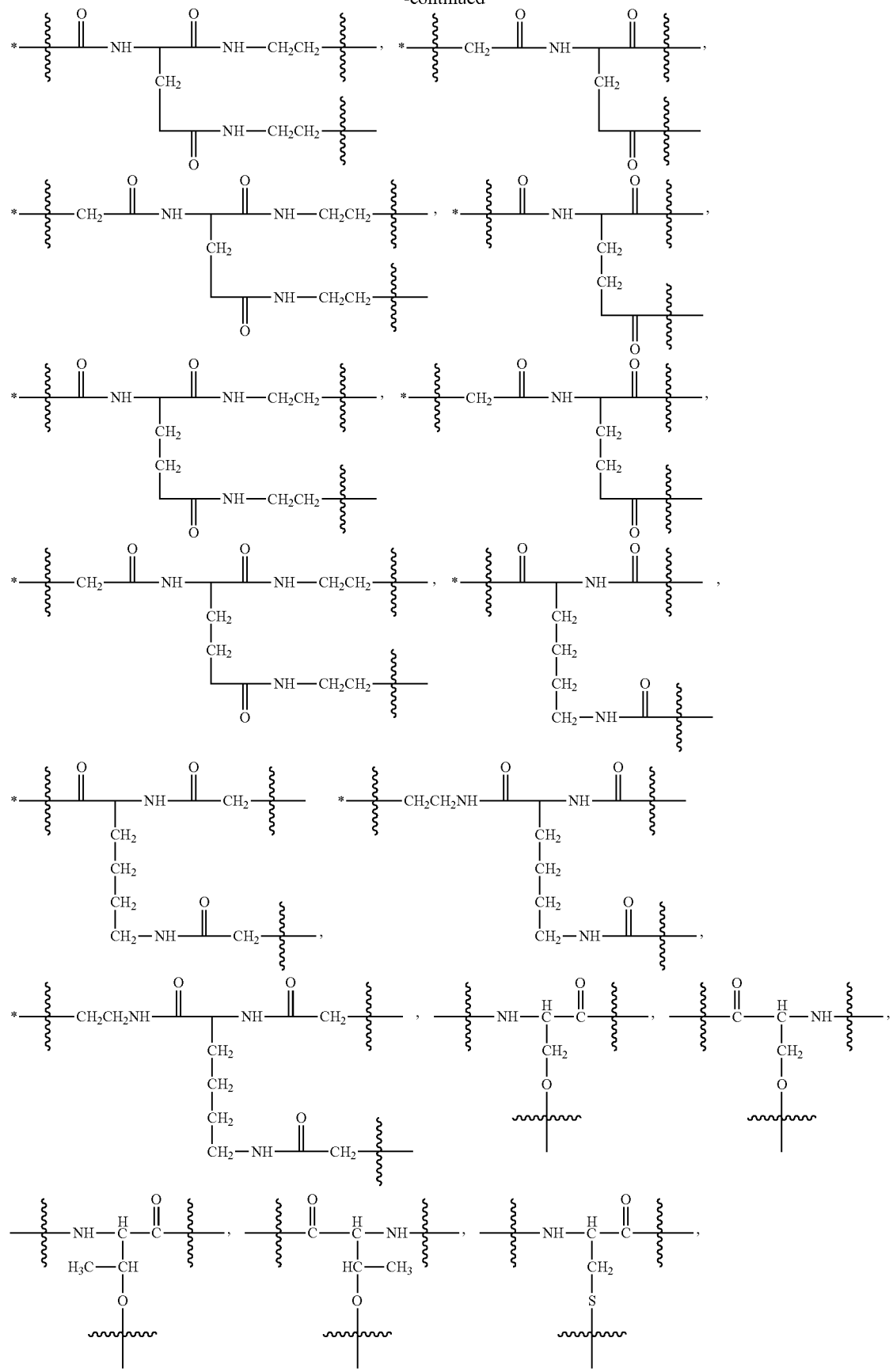

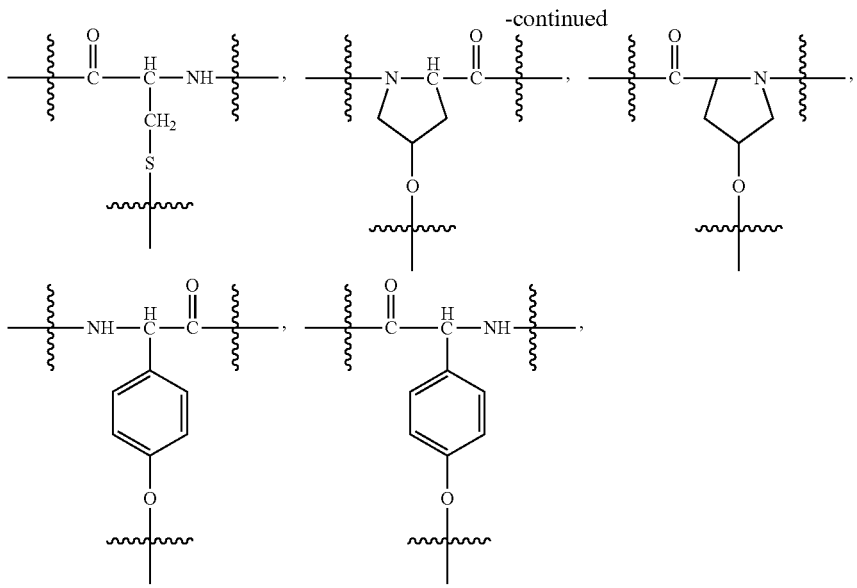

and the like. Wherein, $Q_5$ is a hydrogen atom, a methyl group, an ethyl group or a propyl group; $R_{28}$ is a methyl group, an isopropyl group or an isobutyl group.

The branched central structures of an H-shape including $U_1$ and $U_2$ are each independently preferably

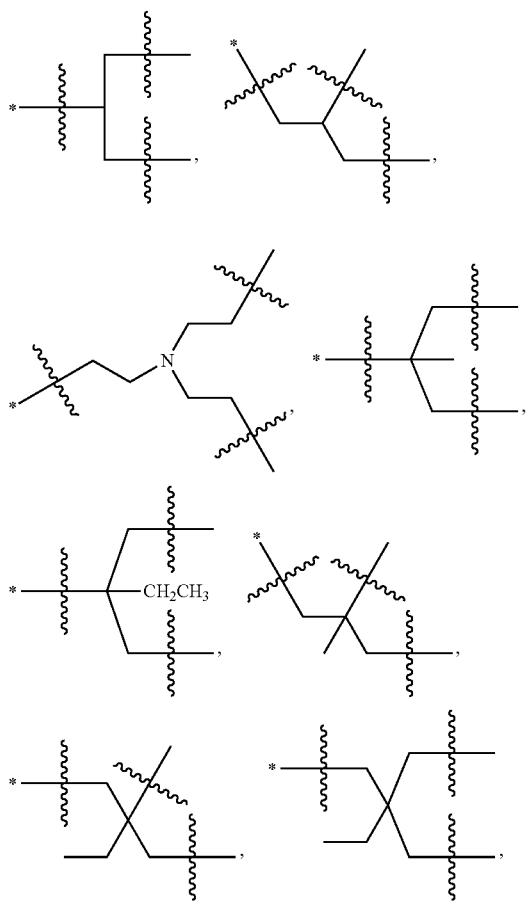

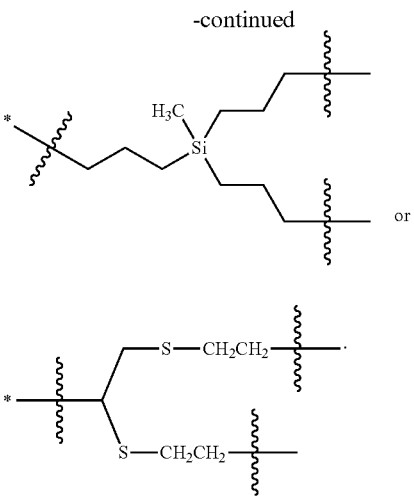

1.1.9. End-Branching Structure G and Examples Thereof

The structure of G is not particularly limited, each independently can be but not limited to a branched type, a ring-containing type, a comb-like type, a dendritic type, a hyperbranched type, or the like. G can be either degradable or stable.

$L_0$ is a divalent linking group that connects a PEG chain with corresponding end-branching structure G, and can be independently present or absent. $L_0$ is degradable or stable, and selected from the above-mentioned STAG linkages or DEGG linkages.

The branching type of end-branching groups (G) in one molecule can be the same or different. When having the same branching type, they can all be of a tribranched type, of a tetrabranched type, of a comb-like type, of a dendritic type, of a hyperbranched type, or of a ring-containing type. When having the same branching type, the chemical structure of PEG-chain termini can be not exactly the same, especially for special branching structures such as comb-like structures, dendritic structures, hyperbranched structures, cyclic structures, or the like. For instance, with respect to a comb-like branching type, different chemical structure can have different valences along with the number of repeat unit. With respect to a hyperbranched type, not only the number of branching unit can be not strictly identical, but also the branching units can be combined together randomly. Therefore, in one molecule, when the PEG chain termini are of a comb-like type or of a hyperbranched type, corresponding k can be different. However, with respect to a dendritic branching type or a cyclic branching type, chemical structures should be exactly the same, and corresponding k should be exactly equal.

When k (the number of functional end-groups $R_{01}$) is equal to 2, the corresponding G is a trivalent group, and allows structures include but not limited to trivalent groups of the above-said set $G^3$, all $U_{01}$ groups, all $U_{02}$ groups, all $U_1$ groups and all $U_2$ groups. Herein, $(L_0)_{g0}$-G preferably contains any of the following structures: all above-mentioned $U_{01}$ groups, all above-mentioned $U_{02}$ groups, all above-mentioned $U_1$ groups, all above-mentioned $U_2$ groups, When the terminal-reactive-site number k is equal to 3, the corresponding G is a tetravalent group, and allowed structures include but not limited to tetravalent groups of the above-said set $G^4$. A tetravalent G preferably contains a tetravalent core structure selected from an atom $CM_4$, an unsaturated bond $CB_4$ and a cyclic structure $CC_4$, or contains two trivalent core structures. $(L_0)_{g0}$-G further preferably contains any of the following structures:

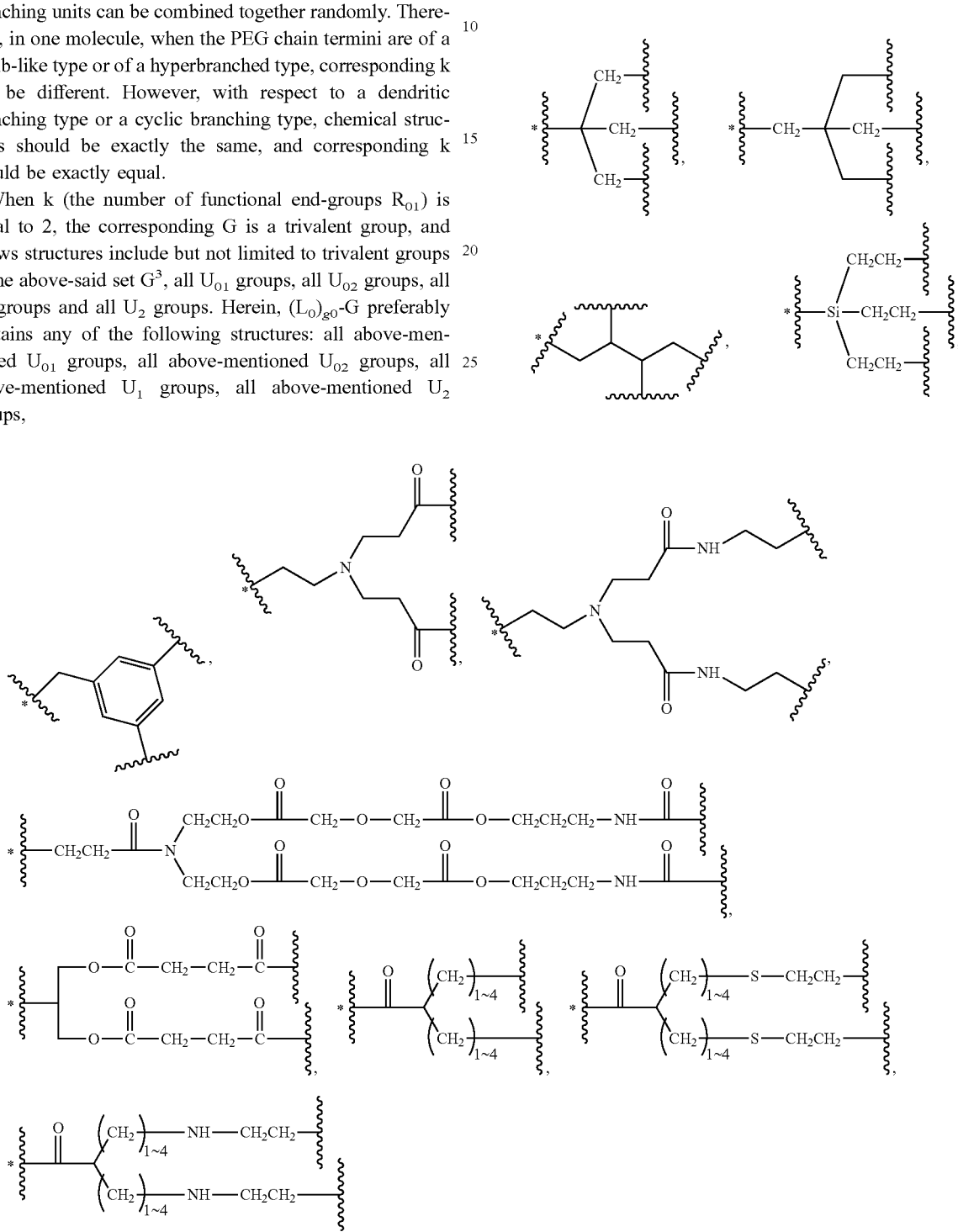

and the like.

299
-continued
300
-continued
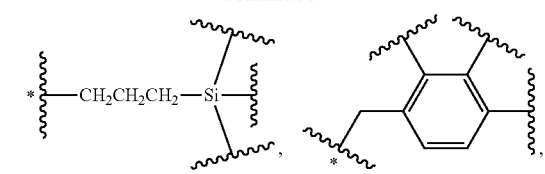
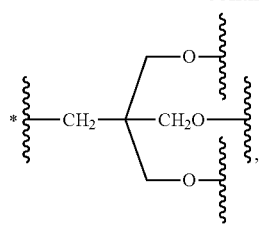
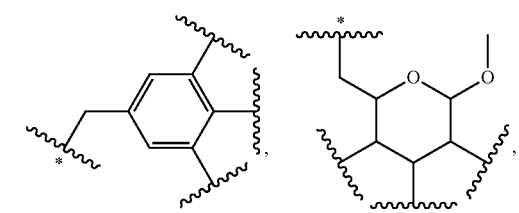
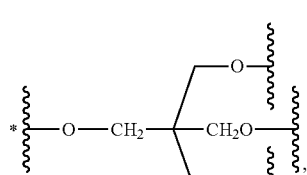
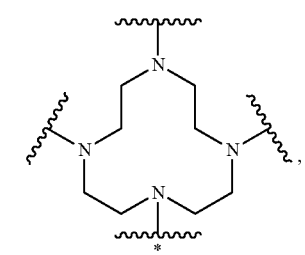
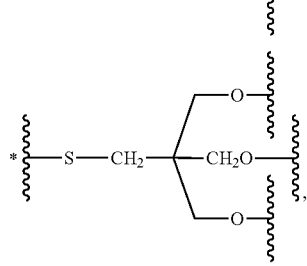
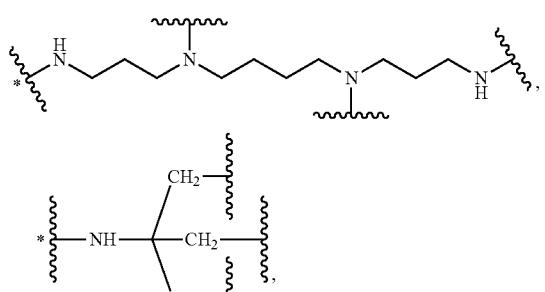
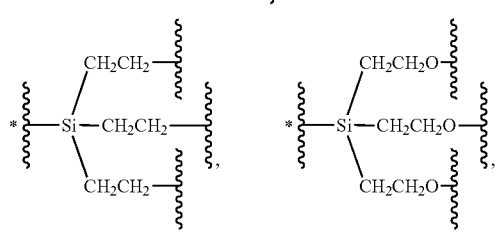
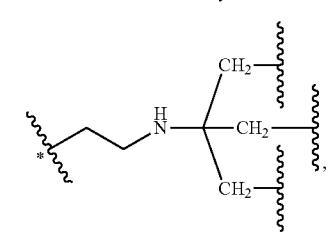
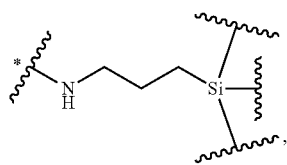
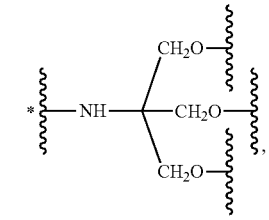
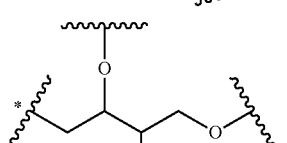
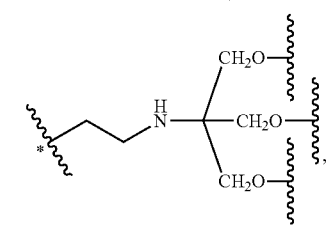
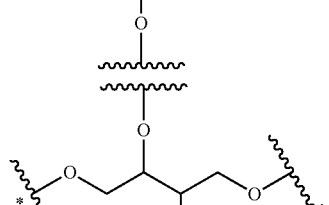
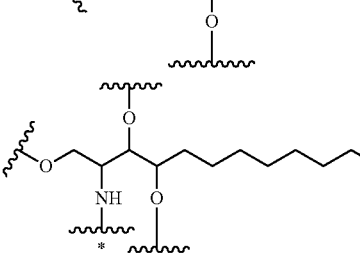

301
-continued
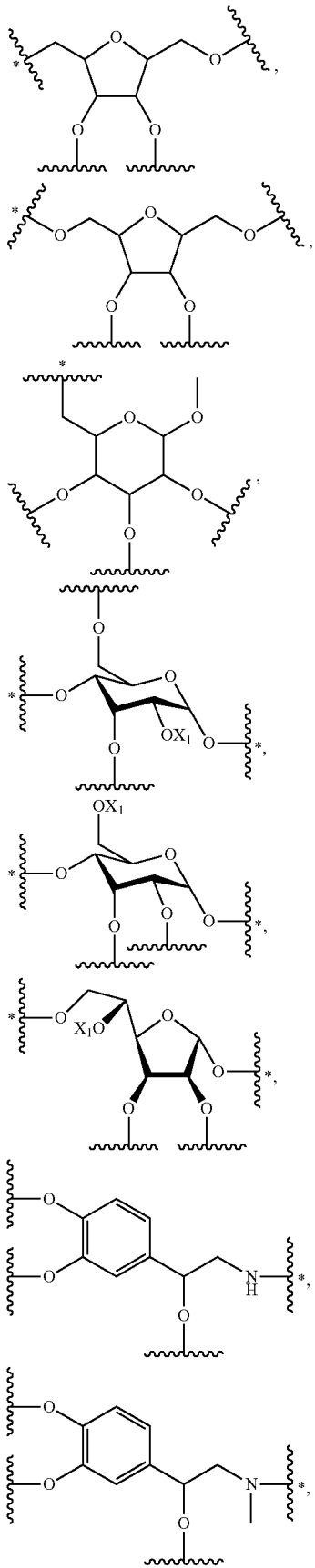
302
-continued
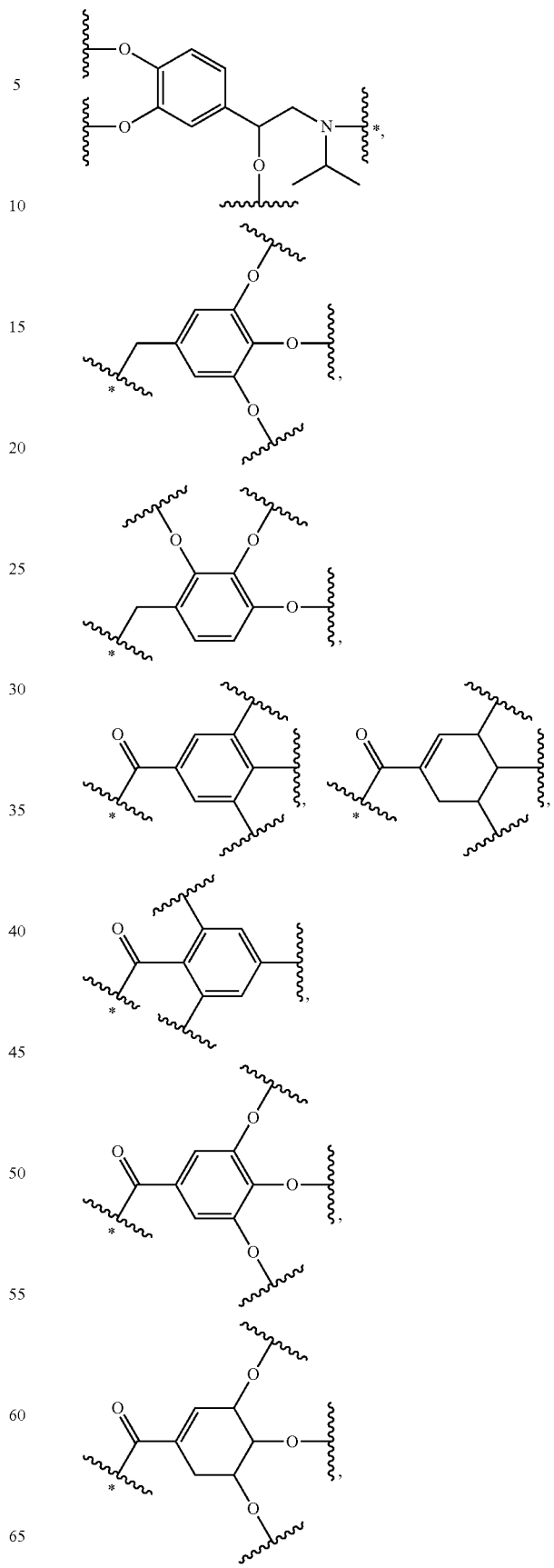

303
-continued
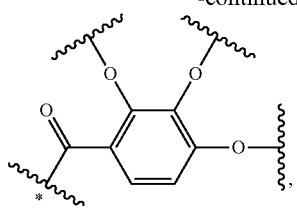
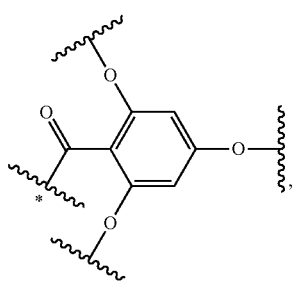
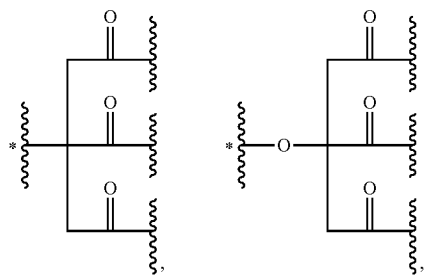
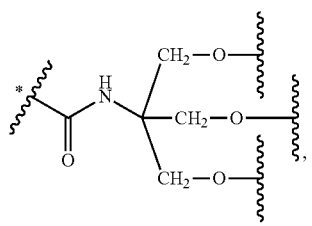
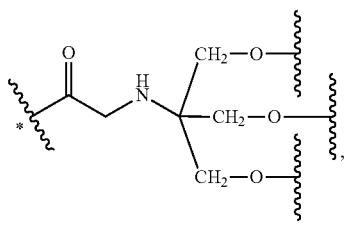
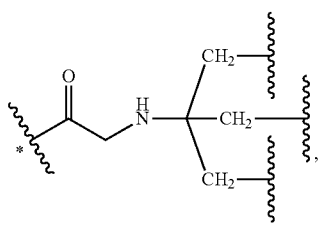
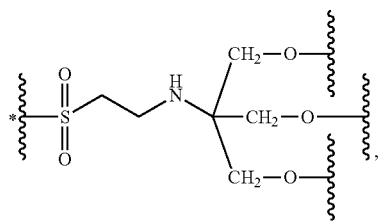
304
-continued
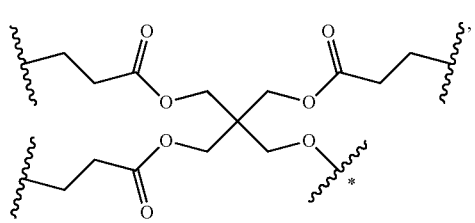
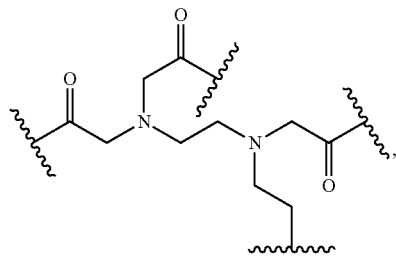
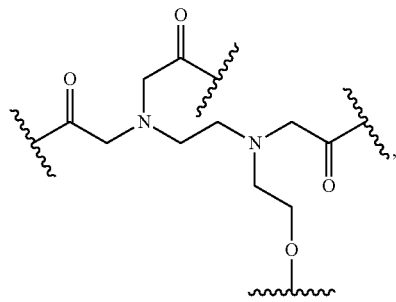
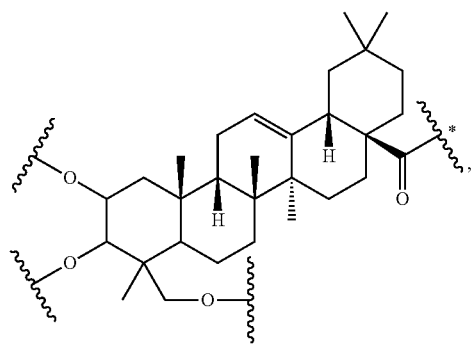

-continued

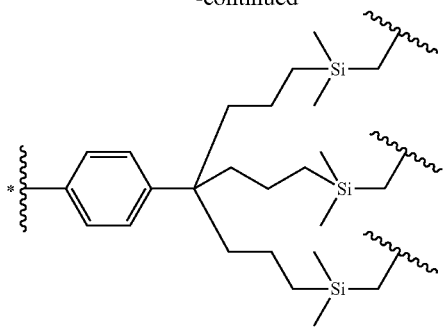

and the like.

When the terminal-reactive-site number k≥3, that is when the valence of G is equal to or higher than 4, then (k+1)-valent G groups include but are not limited to (k+1)-valent groups (groups with a valence of k+1) of the above-said set $G^{k+1}$. A (k+1)-valent G can contain a (k+1)-valent core structure, or be combined directly by lower-valent groups with a valence from 3 to k in quantities of 2 to k−1, or be combined indirectly via one or more divalent spacer groups denoted as $L_{10}$. Said lower-valent groups of 3- to k-valence can be identical or not identical in structure, and can also be identical or different in valence. For example, two different trivalent groups can form a structure shown as

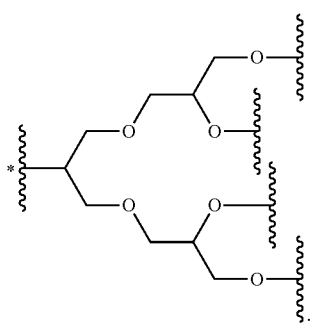 [SMILES: *OCC(COCC(*)COCC(CO*)O*)O*]

With respect to a (k+1)-valent core structure and k≥4, when containing a (k+1)-valent core, said (k+1)-valent core structure is preferably a cyclic structure. When containing two or two more spacer groups denoted as $L_{10}$ groups, these $L_{10}$ groups can be the same or not. The definition of $L_{10}$ is the same as the above-mentioned.

As for (k+1)-valent G groups (k≥4) formed via a direct or indirect combination, the combination manners include but are not limited to comb-like, dendritic, branched, hyperbranched, cyclic, etc. For example, with respect to groups formed by several lower-valent groups in a comb-like, dendritic or hyperbranched manner, the lower-valent groups can be identical or different, and are preferred to be identical.

Wherein, the branching unit of G to form a dendritic combination is preferably any of above-said trivalent G groups or any of above-said tetravalent G groups.

Examples of the dendritic combination are as follows:

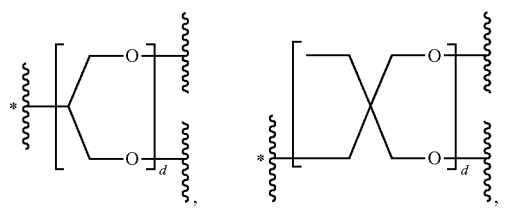

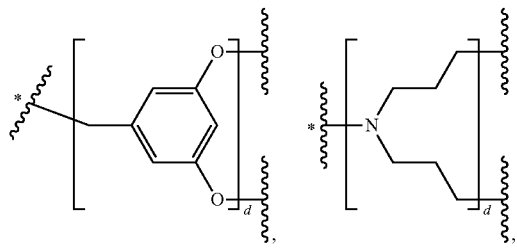

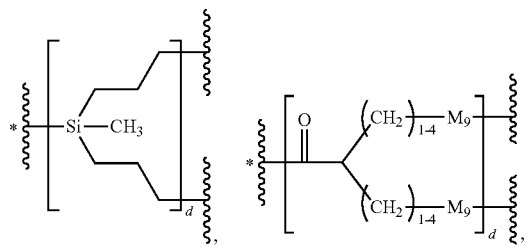

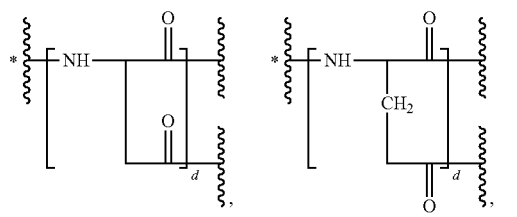

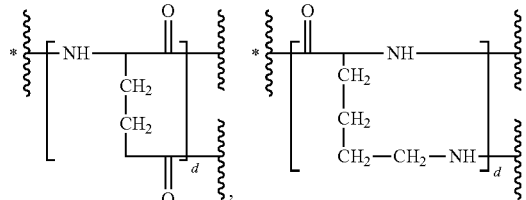

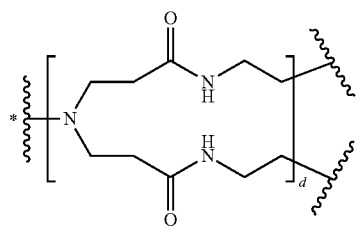

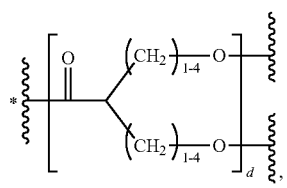

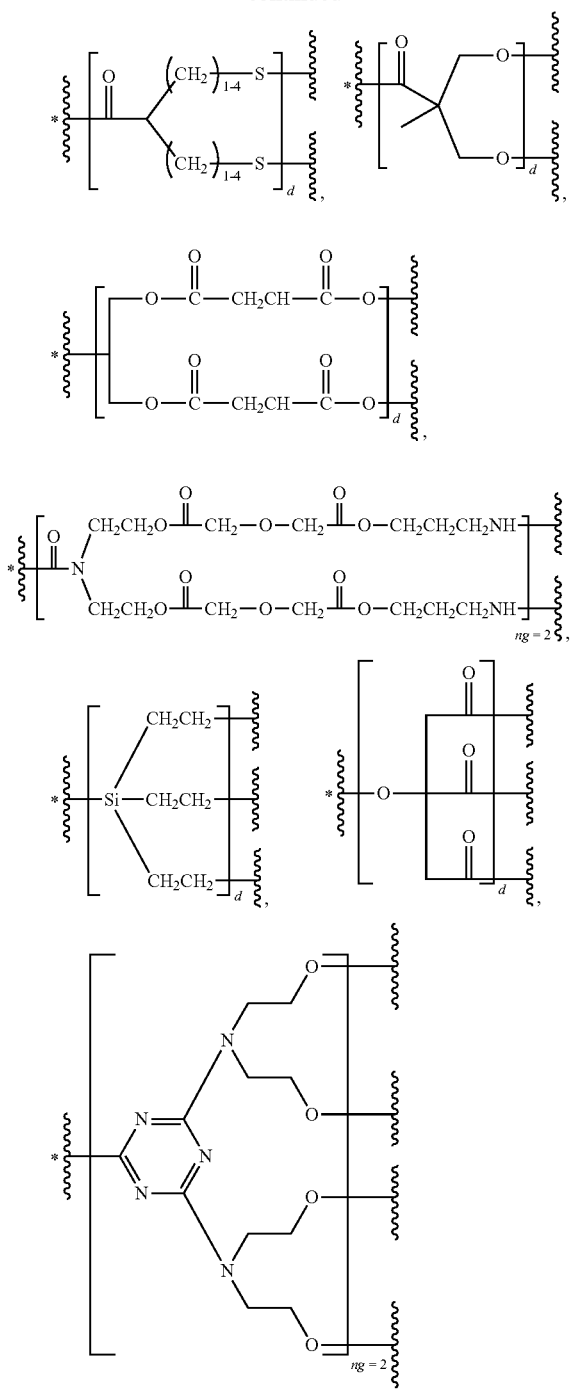

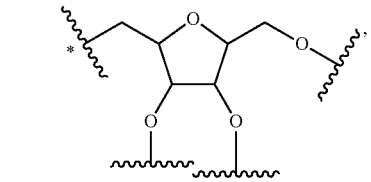 [SMILES: *CC1OC(CO*)C(O*)C1O*]

etc. The branched and hyperbranched combination are different from the above-described dendritic combination in that they can be a hybrid combination of the multivalent G together with lower-valent form thereof. Regarding the lower-valent form of multivalent G, for example, the lower-valent forms of

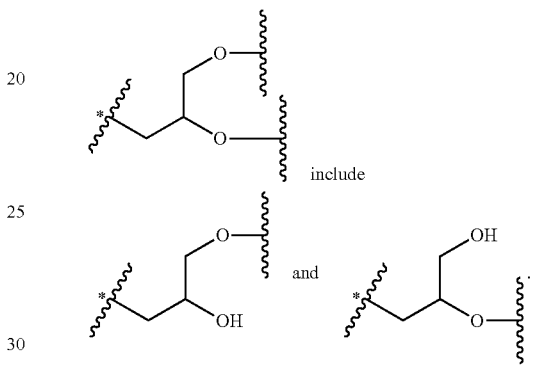

Wherein, structural units of multivalent G to form a comb-like combination is preferably a trivalent, tetravalent or pentavalent above-said G group, include but are not limited to glycerol, pentaerythritol, substituted epoxypropane, the combination of substituted epoxypropane with carbon dioxide, acrylate and derivatives thereof, methacrylate and derivatives thereof, acetal-containing structural units (such as (1→6)β-D glucopyranoside), hydroxyl- or mercapto-containing amino acids and derivatives thereof, acidic amino acids and derivatives thereof, basic amino acids and derivatives thereof, and the like. G also can be an acetalated-dextran structure formed by D-glucopyranose units that are linked end to end via any of the following glucosidic bonds: β-1,6-glucosidic bond, α-1,6-glucosidic bond, β-1,4-glucosidic bond, α-1,4-glucosidic bond, β-1,3-glycosidic bond, α-1,3-glycosidic bond, or an oxidized form of the above-said acetalated-dextran. The repeat unit of comb-like combination also can be suitable trihydric alcohols, suitable tetraols, open-chain pentitols or open-chain hexitols, and corresponding reagents are preferably in the form with all hydroxyl groups being protected except for those forming ether-bonds. Examples of above-said alcohols include glycerol, trihydroxyethylethane and trihydroxyethylpropane. Typical examples include but are not limited to the following structures:

and the like. Wherein, ng and d each independently represents the generation number of a dendritic combination, preferably a generation from 2 to 6, more preferably from 2 to 5, and most preferably 2, 3 or 4. Wherein, $M_9$ is O, S or $NX_{10}$, and the definition of $X_{10}$ is the same as above-mentioned.

Wherein, the structural unit of multivalent G to form a branched or hyperbranched combination is preferably any of above-said trivalent or tetravalent G groups. Preferable structural units include but are not limited to those for the above-mentioned dendritic combination,

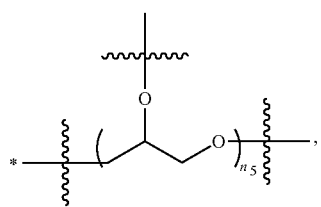

309
-continued
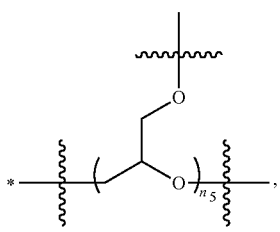
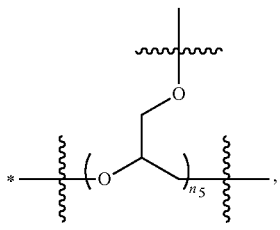
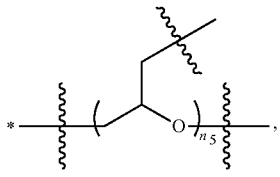
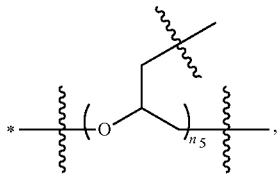
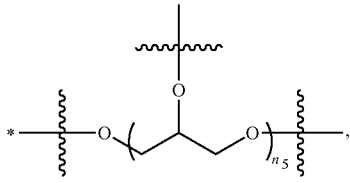
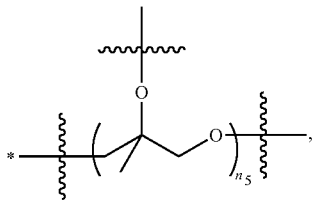
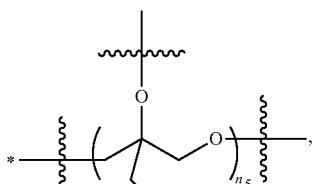
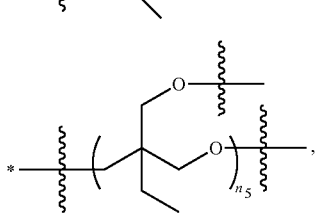
310
-continued
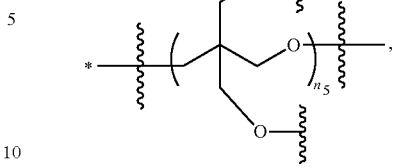
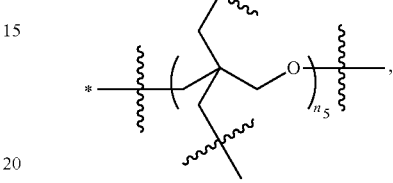
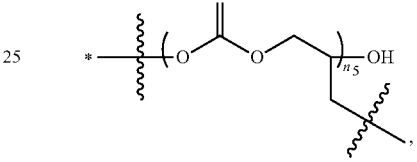
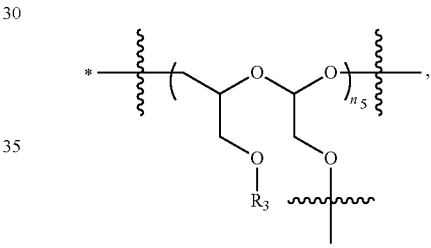
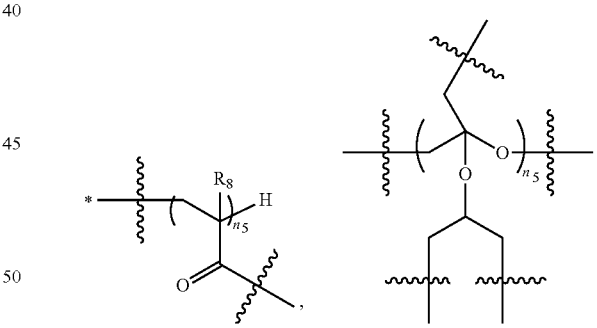
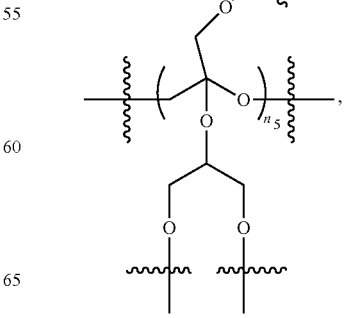

311
-continued
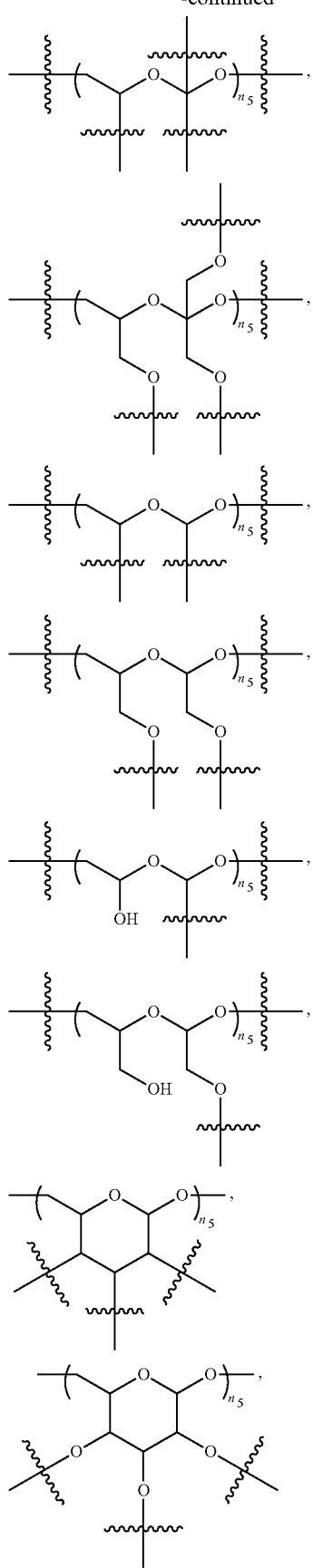
312
-continued
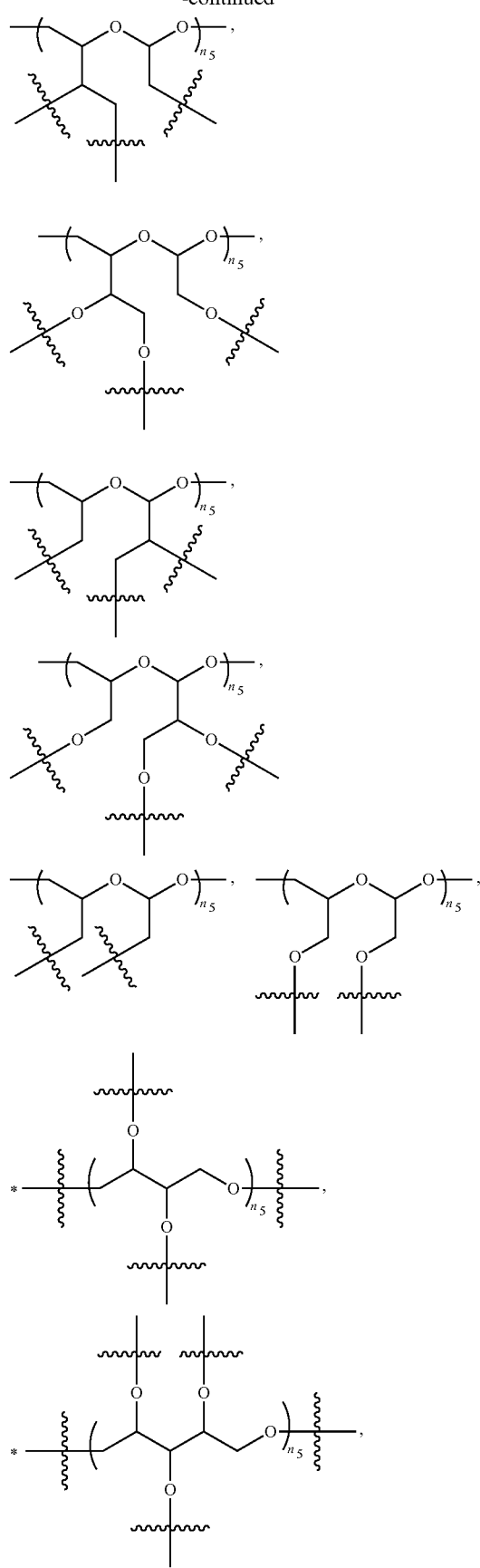

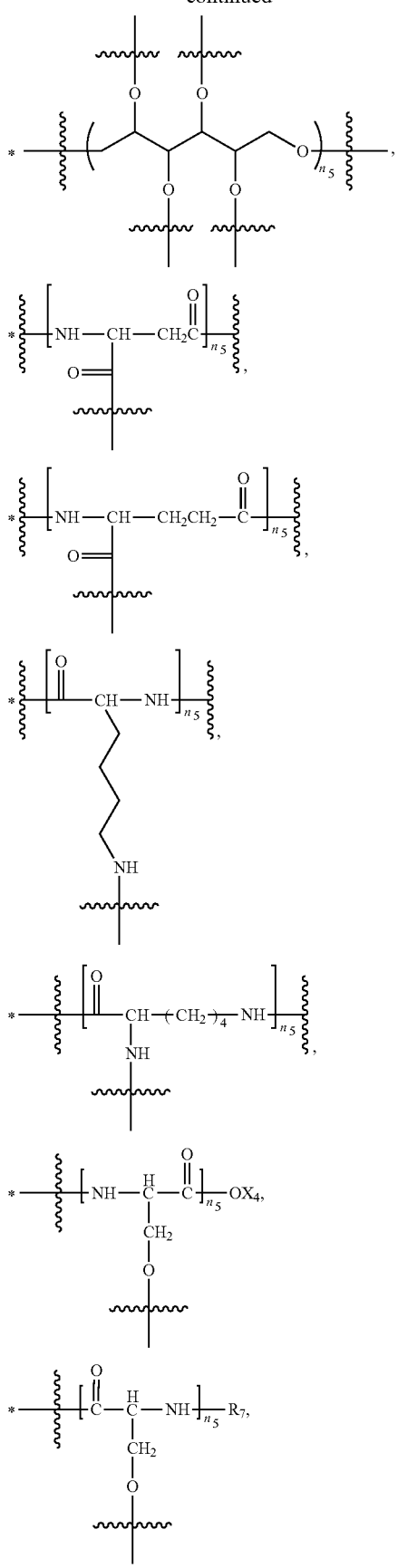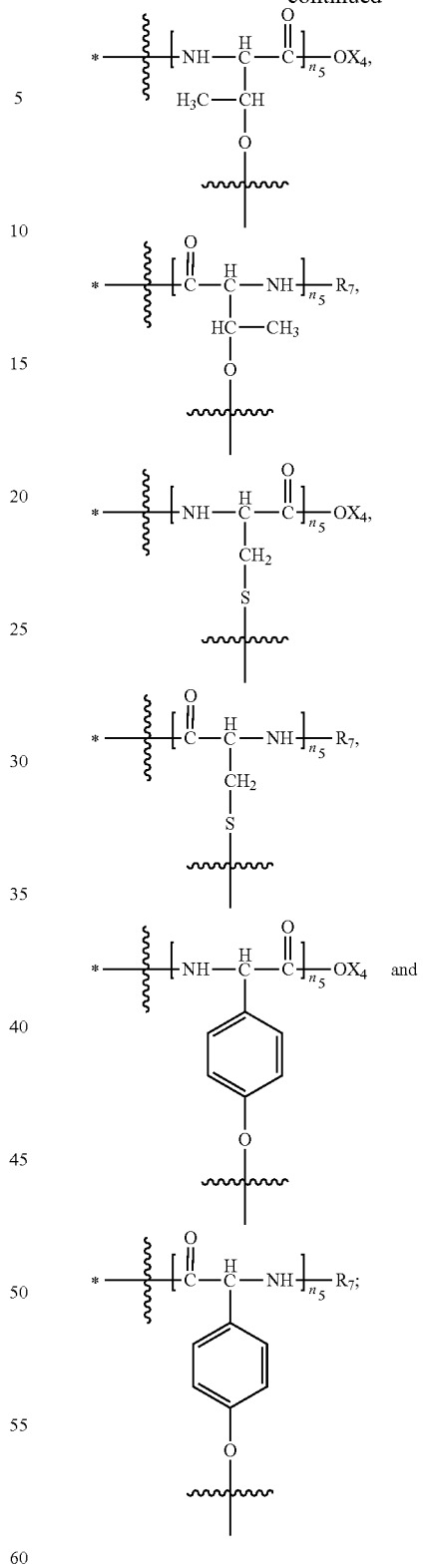

wherein, the definitions of $n_5$, $X_4$, $R_7$, $R_3$ and $R_8$ are the same as above-mentioned, wherein, $X_4$ is a hydrogen atom, a hydroxyl protecting group or a $LG_4$ group which connects to an oxy group; $R_7$ is a hydrogen atom, an amino protecting group or a $LG_5$ group which connects to an amino group.

Wherein, the multivalent G group via a cyclic combination is preferably or a residue of cyclopeptide or derivative thereof, a residue of monosaccharides or derivatives thereof, or a residue of polysaccharides or derivatives thereof (e.g., a functionalized derivative of cyclodextrin), the skeleton of 1,4,7-tri-t-butoxycarbonyl-1,4,7,10-tetraazacyclododecane, the skeleton of 2-hydroxymethylpiperidine-3,4,5-triol or the skeleton of 6-amino-4-(hydroxymethyl)-4-cyclohexyl-[4H, 5H]-1,2,3-triol.

For example, when the terminal-reactive-site number k is equal to 4, then G is a pentavalent group, including but not limited to pentavalent groups in the above-mentioned set $G^5$; pentavalent G groups can contain merely one pentavalent core structure, a combination of one tetravalent together with one trivalent core structure, or a combination of three trivalent core structures. $(L_o)_{g0}$-G preferably contains any of the following structures:

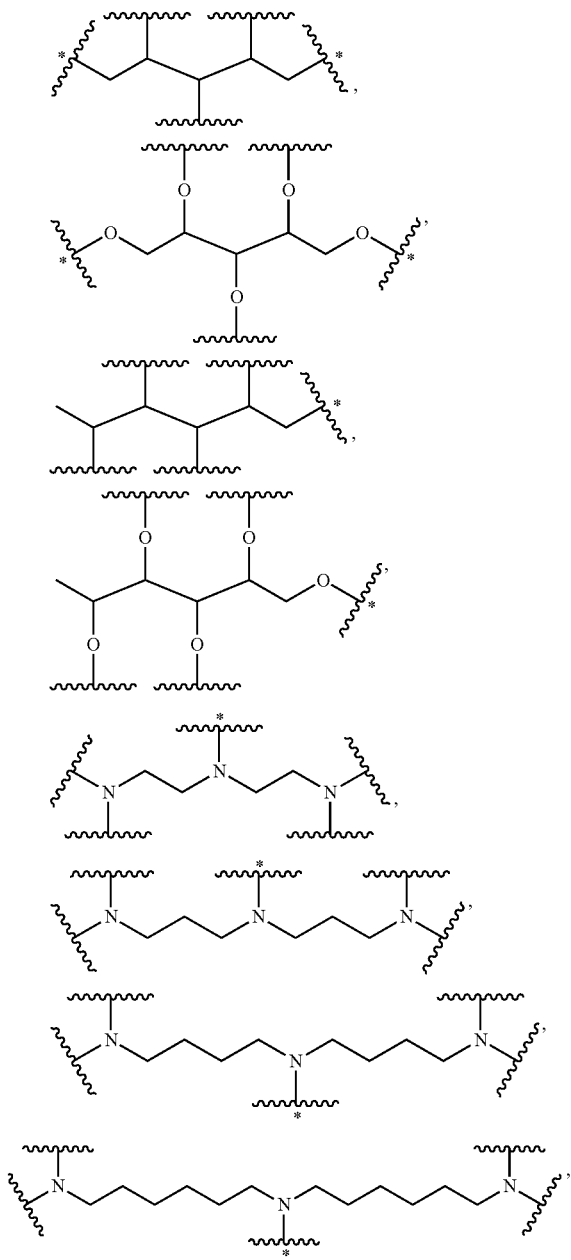
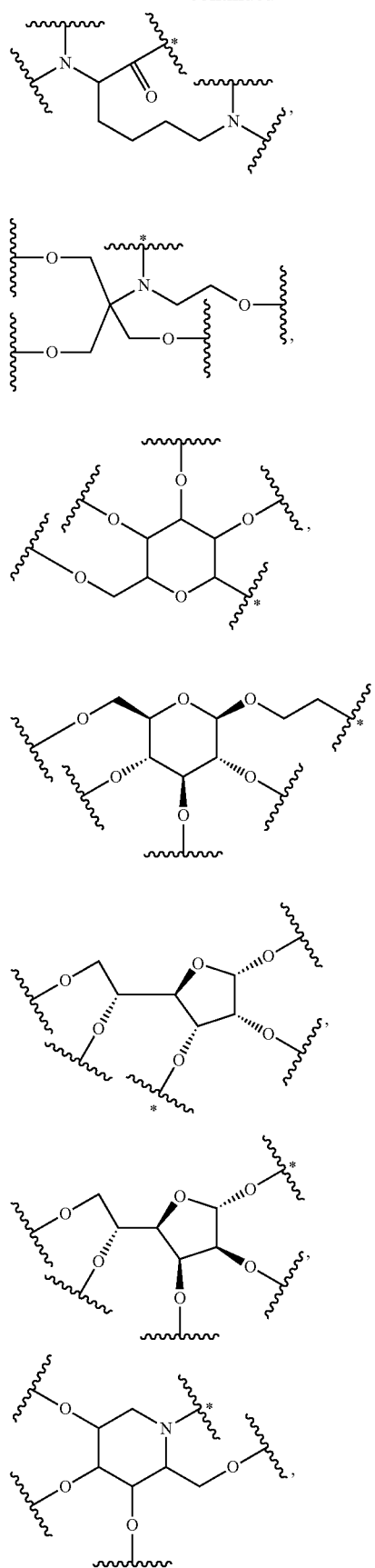

317
-continued

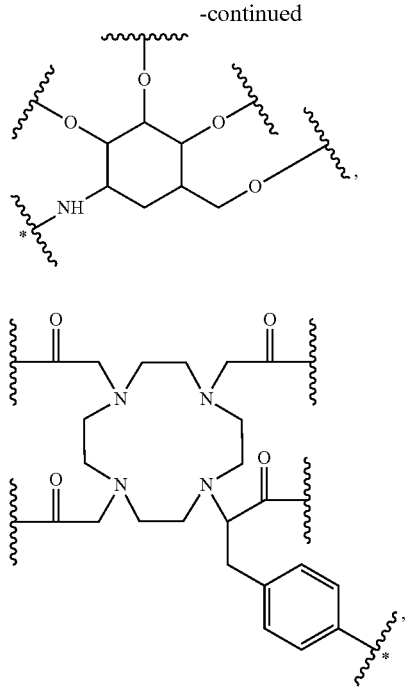

318
-continued

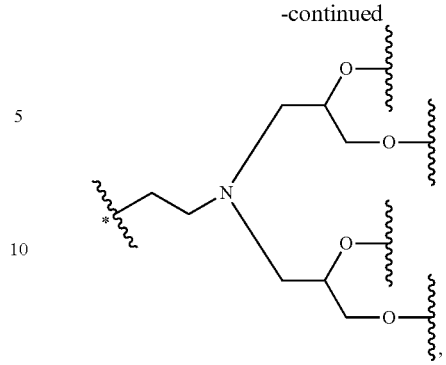

dendritic structures formed by three trivalent G groups via a direct or indirect combination, comb-like structures formed by three trivalent G groups via a direct or indirect combination, and the like. Wherein, examples of dendritic structures formed by three trivalent G groups via a direct or indirect combination include above-mentioned structures of generation number d=2. Comb-like structures formed by three trivalent G groups via a direct combination include but are not limited to a skeleton of trilysines, a skeleton of trimers of glutamic acid, a skeleton of trimers of aspartic acid, a skeleton of triglycerols and the like, such as

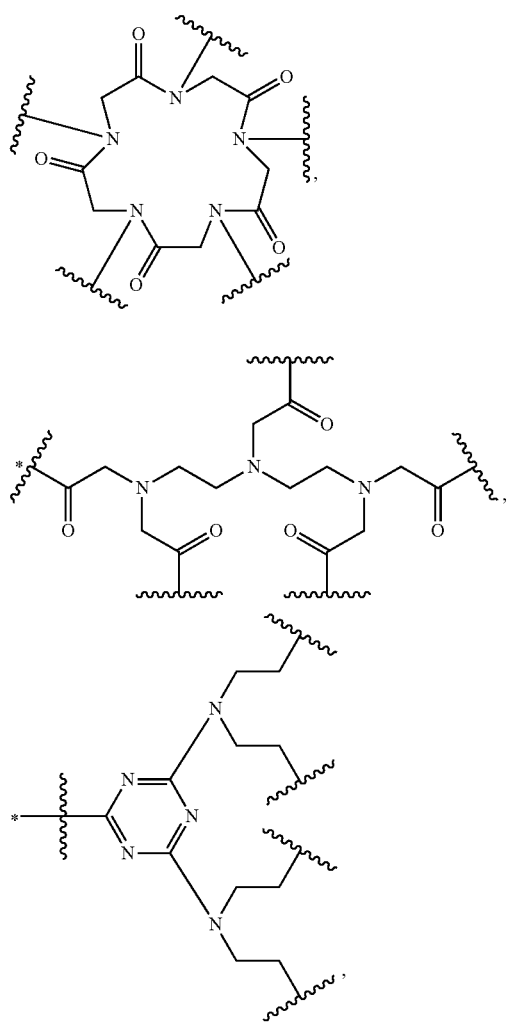

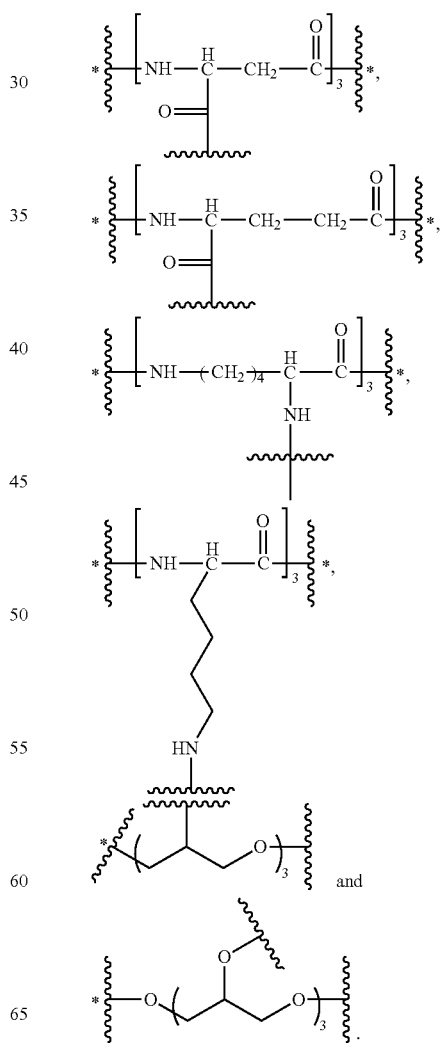

One typical example of comb-like structures formed by three trivalent groups via an indirect combination is the combination of three lysines by using amino acid spacers such as glycine, alanine, or the like.

For example, when the terminal-reactive-site number k is equal to 5, then G is a hexavalent group, including but not limited to hexavalent groups in the above-mentioned set $G^6$. The hexavalent G groups can contain merely one hexavalent core structure, a combination of one pentavalent core structure and one trivalent core structure, a combination of two tetravalent core structures, a combination of one tetravalent core structure and two trivalent core structures or a combination of four trivalent core structures. $(L_o)_{g0}$-G preferably contains any of the following structures: comb-like structures directly or indirectly combined by four trivalent G groups (e.g., tetraglycerol, tetralysine, tetramer of aspartic acid, tetramer of glutamic acid),

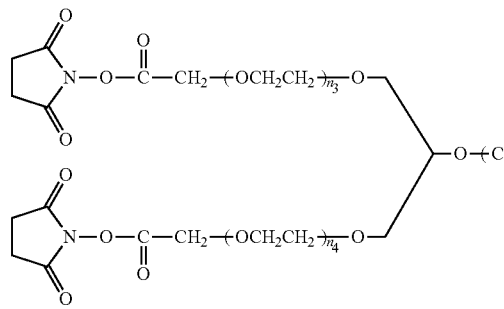

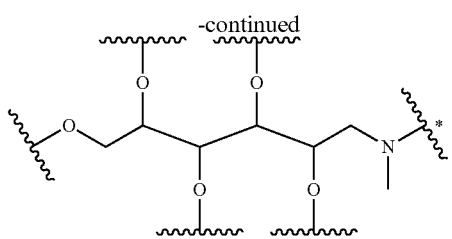

and the like.

1.1.10. Examples of H-Shaped Multifunctionalized Polyethylene Glycol

As for examples, H-shaped multifunctionalized polyethylene glycols in the present invention include but are not limited to the following structures:

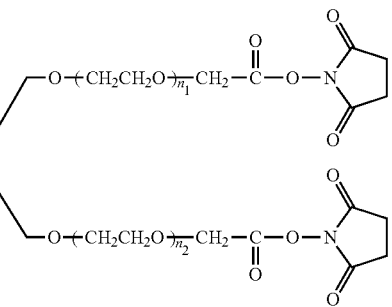

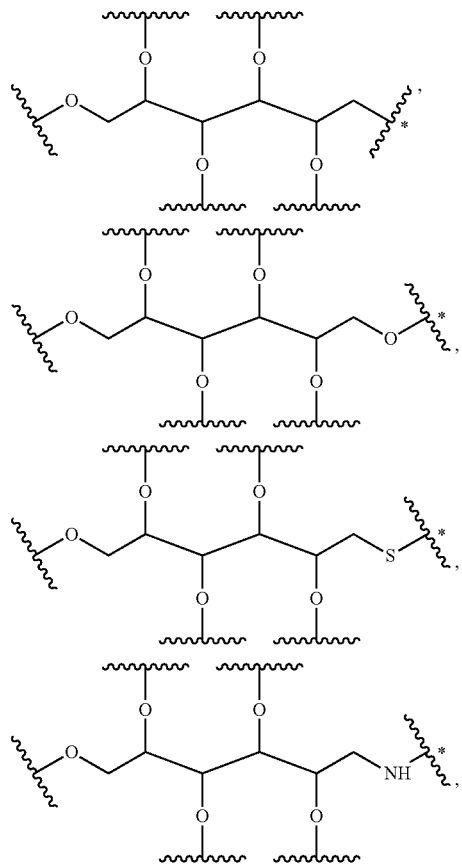

Wherein,

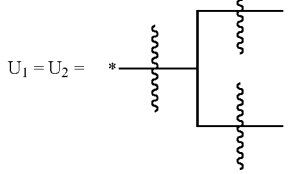

($U_1$ and $U_2$ are of a symmetrical type,

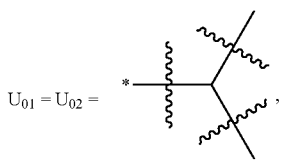

$L_1=L_2=L_3=L_4=CH_2$, without $L_5$ and $L_6$), $F_1=F_2=CH_2CONHS$ (g=0, k=1, q=0, $q_1$=1, $Z_1$=$CH_2CO$, $R_{01}$=NHS) and j=0. The designed total molecular weight is approximately 26 kDa, wherein, the molecular weight of four branch chains is approximately 4×5000=20000 Da corresponding to $n_1 \approx n_2 \approx n_3 \approx n_4 \approx 114$, and the molecular weight of the main chain is approximately 5000 Da corresponding to $m_2 \approx 114$.

321 322

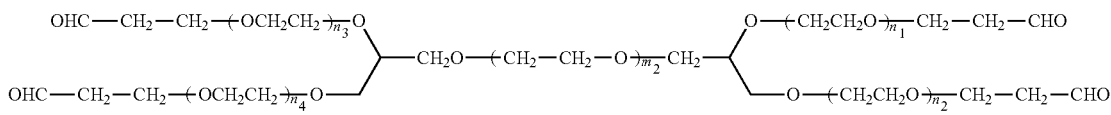

Wherein, ($U_1$ and $U_2$ are of a symmetrical type,

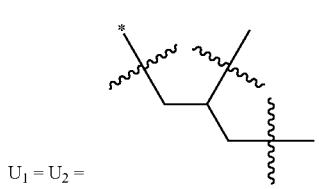

$U_1 = U_2 =$ ($U_1$ and $U_2$ are of an asymmetrical type, $U_{01} = U_{02} =$ $L_1=L_2=L_3=L_4=CH_2CH_2$, $L_5=L_6=CH_2CH_2$),

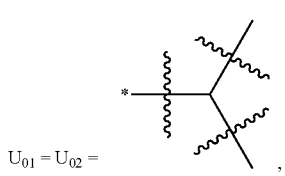

$U_{01} = U_{02} =$ $F_1 = F_2 =$ without $L_1$ and $L_3$, $L_2=L_4=CH_2$, $L_5=L_6=CH_2$), $F_1=F_2=CH_2CH_2CHO$ (g=0, k=1, q=0, $q_1=1$, $Z_1=CH_2CH_2$, $R_{01}=CHO$) and j=0. The designed total molecular weight is approximately 20 kDa, wherein, the molecular weight of four branch chains is approximately 4×4750=19000 Da corresponding to $n_1 \approx n_2 \approx n_3 \approx n_4 \approx 108$, and the main chain of the polyethylene glycol is monodisperse with an EO-unit number of $m_2=24$.

(g=0, k=1, q=1, $Z_2 =$ $q_1=1$,

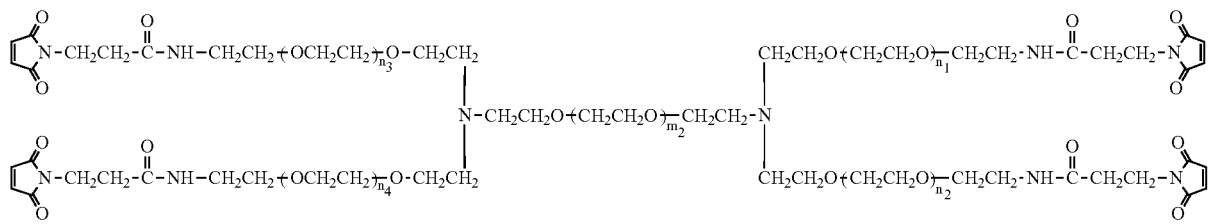

Wherein,

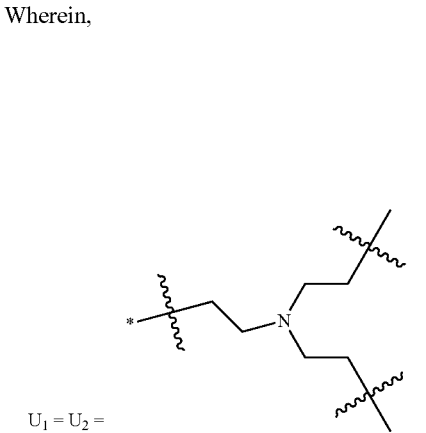

$U_1 = U_2 =$

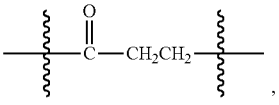

$Z_1 =$

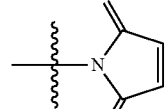

$R_{01} =$ and j=0. The designed total molecular weight is approximately 42 kDa, wherein, the molecular weight of four branch chains is approximately 4×10000=40000 Da corresponding to $n_1 \approx n_2 \approx n_3 \approx n_4 \approx 227$, and the molecular weight of the main chain is approximately 1000 Da corresponding to $m_2 \approx 23$.

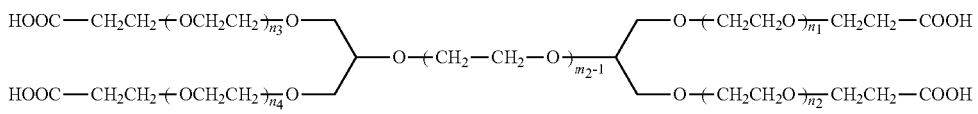

Wherein,

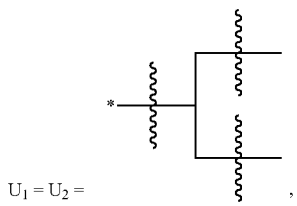

$U_1 = U_2 =$ $F_1=F_2=CH_2CH_2COOH$ (g=0, k=1, q=0, $q_1$=1, $Z_1=CH_2CH_2$, $R_{O1}=COOH$) and j=0. The designed total molecular weight is approximately 30 kDa, wherein, the molecular weight of four branch chains is approximately 4×6000=24000 Da corresponding to $n_1{\approx}n_2{\approx}n_3{\approx}n_4{\approx}136$, and the molecular weight of the main chain is approximately 6000 Da corresponding to $m_2{\approx}136$.

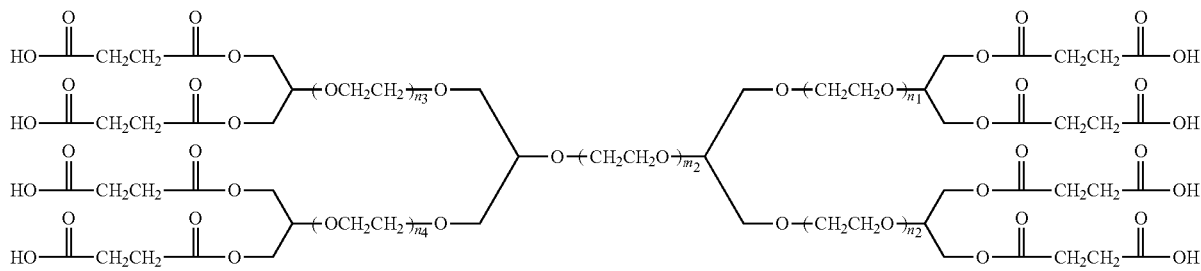

Wherein,

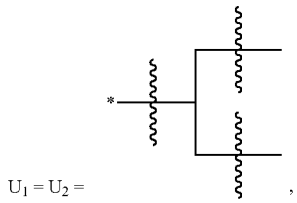

$U_1 = U_2 =$ $F_1=F_2$, g=1, k=2, $g_0$=0,

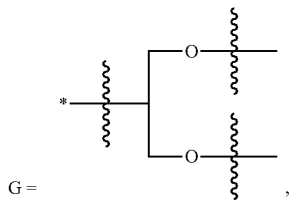

$G =$ q=1,

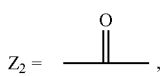

$Z_2 =$ $q_1$=1, $Z_1=CH_2CH_2$, $R_{O1}=COOH$ and j=0. The designed total molecular weight is approximately 30 kDa, wherein, the molecular weight of four branch chains is approximately 4×5000=20000 Da corresponding to $n_1{\approx}n_2{\approx}n_3{\approx}n_4{\approx}114$, and the molecular weight of the main chain is approximately 8750 Da corresponding to $m_2{\approx}199$.

325 326

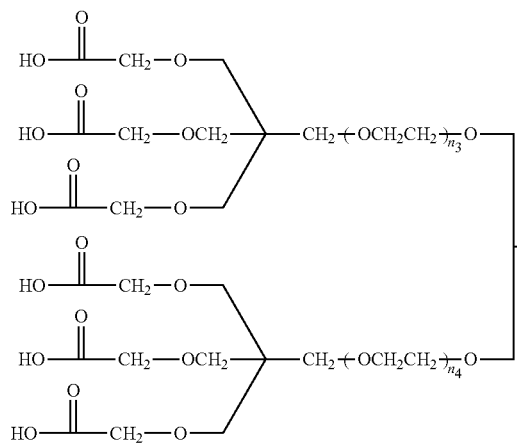 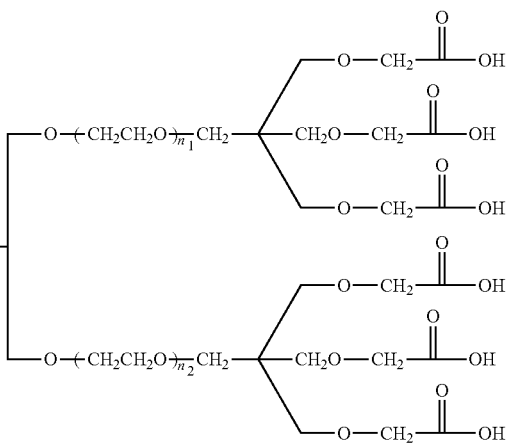

Wherein,

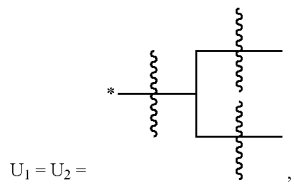

$U_1 = U_2 = $ $F_1 = F_2$, $g=1$, $k=3$, $g_0=0$,

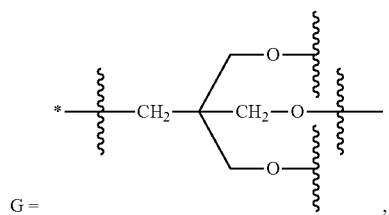

$G = $ $q=0$, $q_1=1$, $Z_1=CH_2$, $R_{01}=COOH$ and $j=0$. The designed total molecular weight is approximately 11 kDa, wherein, the molecular weight of four branch chains is approximately $4\times2000=8000$ Da corresponding to $n_1 \approx n_2 \approx n_3 \approx n_4 \approx 45$, and the main chain of the polyethylene glycol is monodisperse with an EO-unit number of $m_2=44$.

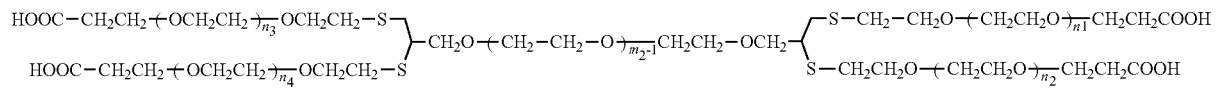

Wherein, in the compound D4-4,

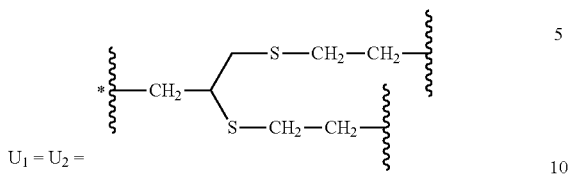

$U_1 = U_2 =$ ($U_1$ and $U_2$ are of an asymmetrical type,

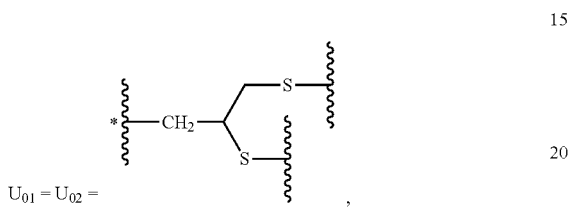

$U_{01} = U_{02} =$ , $L_1=L_3=CH_2CH_2$, $L_2=L_4=CH_2CH_2$, without $L_5$ and $L_6$), $F_1=F_2=CH_2CH_2COOH$ (g=0, k=1, q=0, $q_1$=1, $Z_1=CH_2CH_2$, $R_{01}=COOH$) and j=0. The designed total molecular weight is approximately 25 kDa, wherein, the four branch chains are monodisperse with an EO-unit number of $n_1=n_2=n_3=n_4=22$, and the molecular weight of main chain is 20000 Da corresponding to $m_2 \approx 455$.

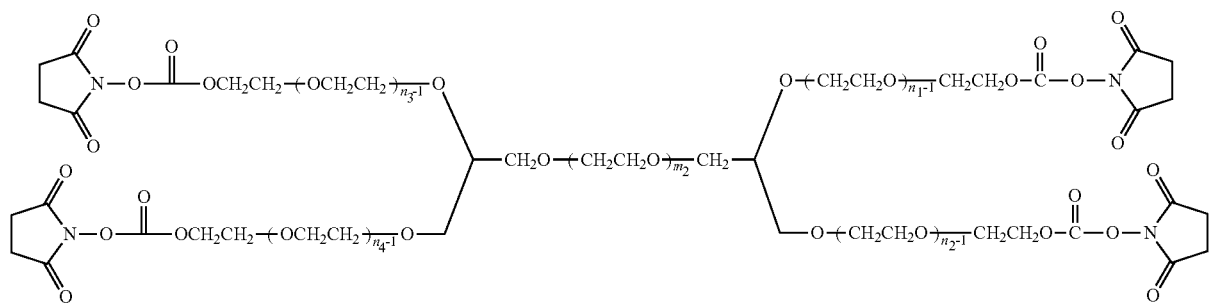

Wherein,

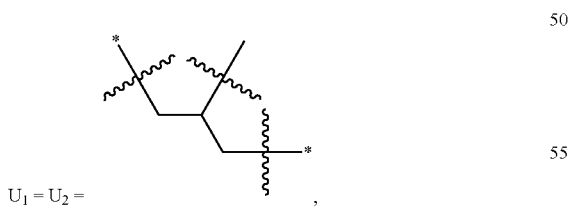

$U_1 = U_2 =$ , $F_1=F_2=CH_2CH_2OCONHS$ (g=0, k=1, q=1, $Z_2=CH_2CH_2$, $q_1$=1, $Z_1$ is $-OC(=O)-$, $R_{01}=NHS$) and j=0. The designed total molecular weight is approximately 40 kDa, wherein, the molecular weight of four branch chains is approximately 4×8000=32000 Da corresponding to $n_1 \approx n_2 \approx n_3 \approx n_4 \approx 182$, and the molecular weight of the main chain is approximately 8000 Da corresponding to $m_2 \approx 182$.

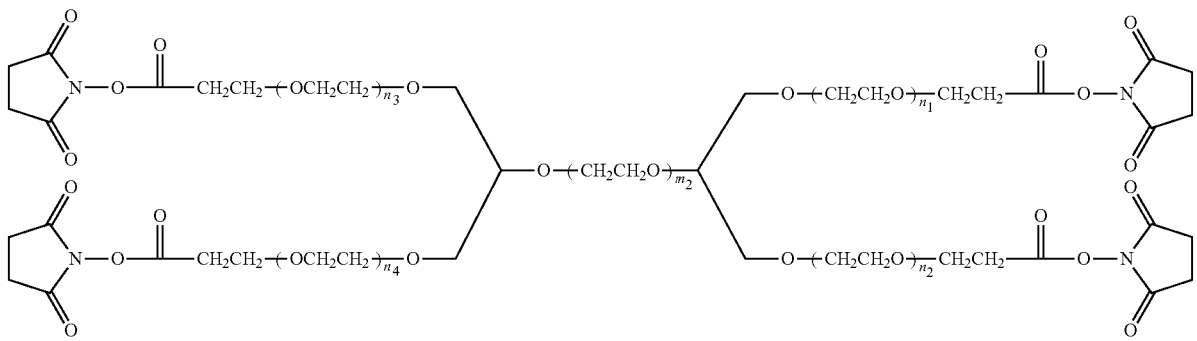

Wherein,

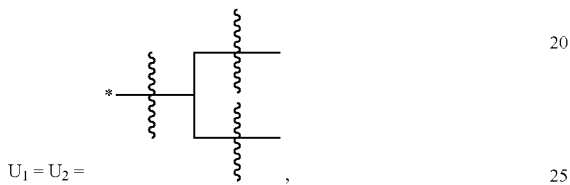

$U_1 = U_2 =$ $F_1=F_2=CH_2CH_2CONHS$ ($g=0$, $k=1$, $q=0$, $q_1=1$, $Z_1$ is $-CH_2CH_2C(=O)-$, $R_{01}=NHS$) and $j=0$. The designed total molecular weight is approximately 26 kDa, wherein, the molecular weight of four branch chains is approximately $4 \times 5000 = 20000$ Da corresponding to $n_1 \approx n_2 \approx n_3 \approx n_4 \approx 114$, and the molecular weight of the main chain is approximately 5000 Da corresponding to $m_2 \approx 114$.

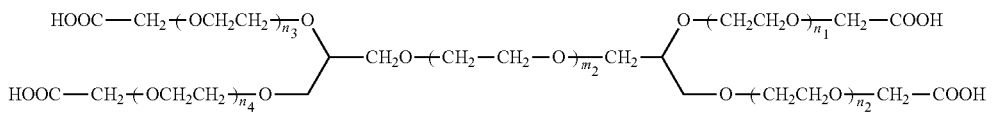

Wherein,

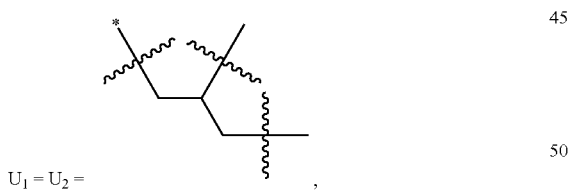

$U_1 = U_2 =$ $F_1=F_2=CH_2COOH$ ($g=0$, $k=1$, $q=0$, $q_1=1$, $Z_1=CH_2$, $R_{01}=COOH$) and $j=0$. The designed total molecular weight is approximately 40 kDa, wherein, the molecular weight of four branch chains is approximately $4 \times 8000 = 32000$ Da corresponding to $n_1 \approx n_2 \approx n_3 \approx n_4 \approx 182$, and the molecular weight of the main chain is approximately 8000 Da corresponding to $m_2 \approx 182$.

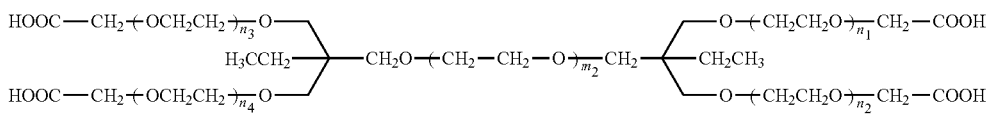

Wherein, $U_1 = U_2 =$ 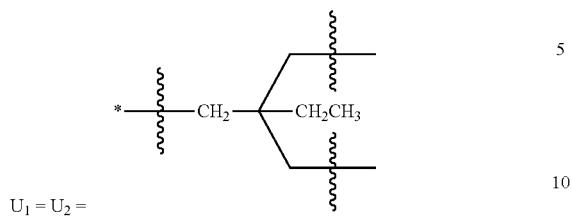

($U_1$ and $U_2$ are of a symmetrical type $U_{01} = U_{02} =$ 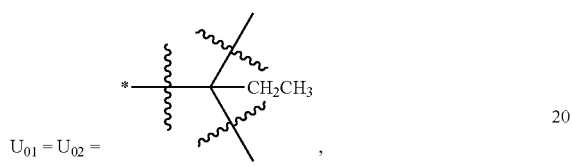, $L_1=L_3=CH_2$, $L_2=L_4=CH_2$, $L_5=L_6=CH_2$), $F_1=F_2=CH_2COOH$ (g=0, k=1, q=0, $q_1$=1, $Z_1$=$CH_2$, $R_{01}$=COOH) and j=0. The designed total molecular weight is approximately 20 kDa, wherein, the molecular weight of four branch chains is approximately 4×3000=12000 Da corresponding to $n_1 \approx n_2 \approx n_3 \approx n_4 \approx 68$, and the molecular weight of the main chain is approximately 8000 Da corresponding to $m_2 \approx 182$.

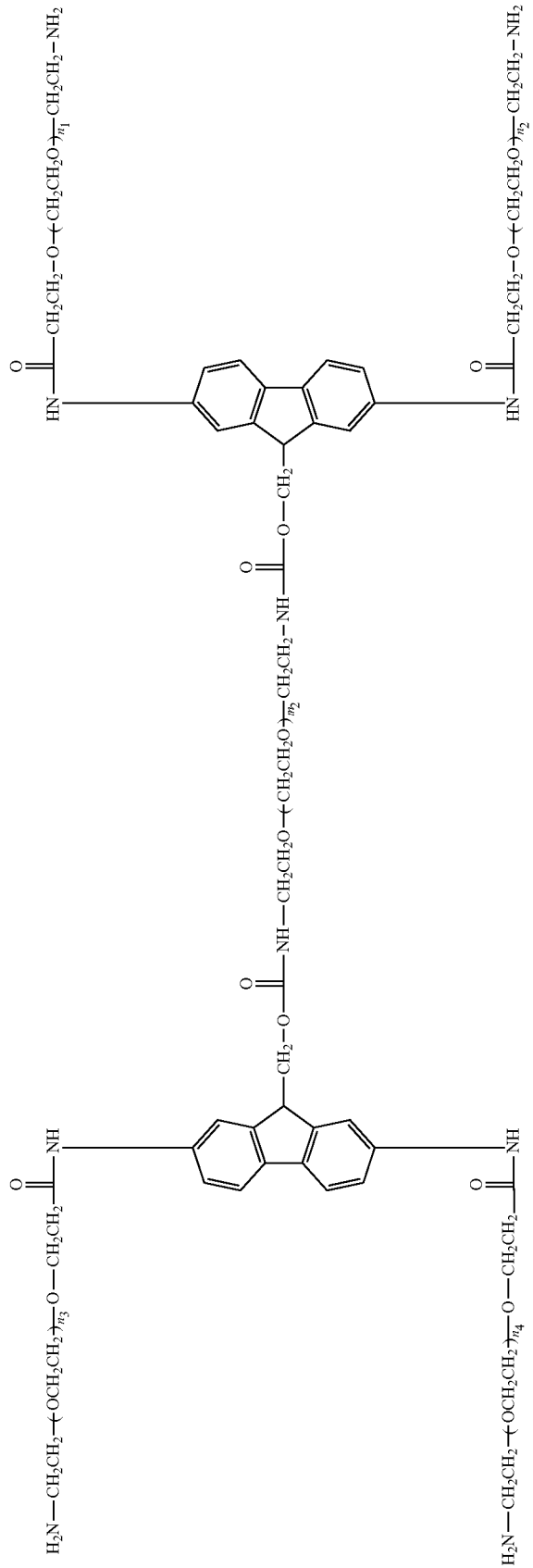

Wherein, $U_1$ and $U_2$ are of a symmetrical type, $U_{01} = U_{02} =$ 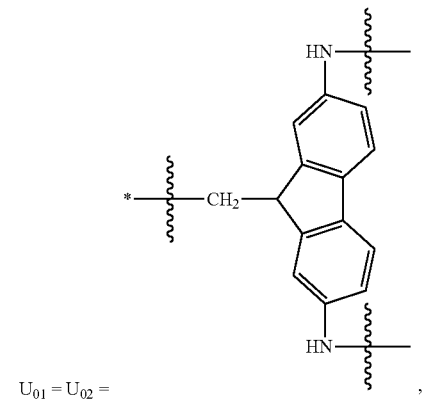

$L_1 = L_2 = L_3 = L_4 =$ 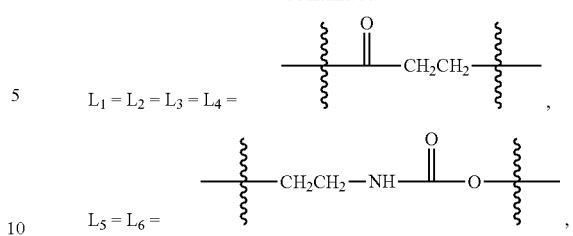

$L_5 = L_6 =$ $F_1 = F_2 = CH_2CH_2NH_2$ (g=0, k=1, q=0, $q_1$=1, $Z_1$=$CH_2CH_2$, $R_{01}$=$NH_2$) and j=0. The designed total molecular weight is approximately 52 kDa, wherein, the molecular weight of four branch chains is approximately 4×1200=48000 Da corresponding to $n_1 \approx n_2 \approx n_3 \approx n_4 \approx 273$, and the main chain of the polyethylene glycol is monodisperse with an EO-unit number of $m_2$=65.

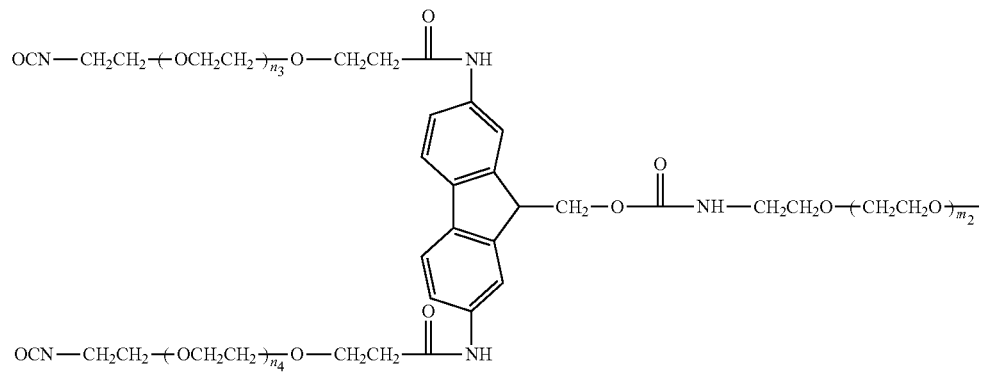

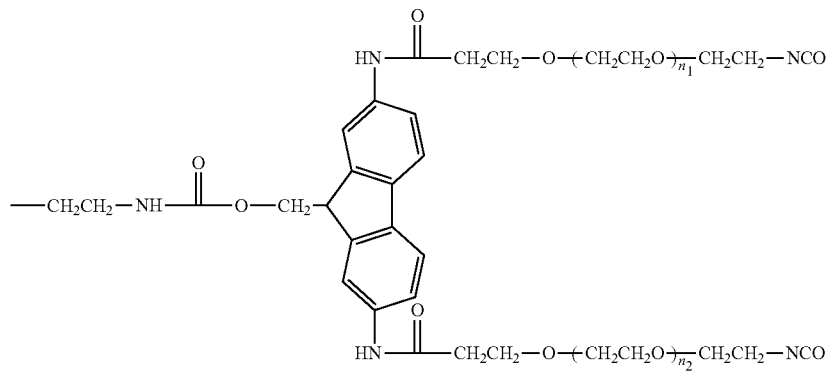

Wherein, $F_1=F_2=$—CH$_2$CH$_2$NCO (g=0, k=1, q=0, q$_1$=1, Z$_1$=CH$_2$CH$_2$, R$_{01}$=NCO). The designed total molecular weight is approximately 52 kDa, wherein, the molecular weight of four branch chains is approximately 4×12000=48000 Da corresponding to n$_1$≈n$_2$≈n$_3$≈n$_4$≈273, and the main chain of the polyethylene glycol is monodisperse with an EO-unit number of m$_2$=65.

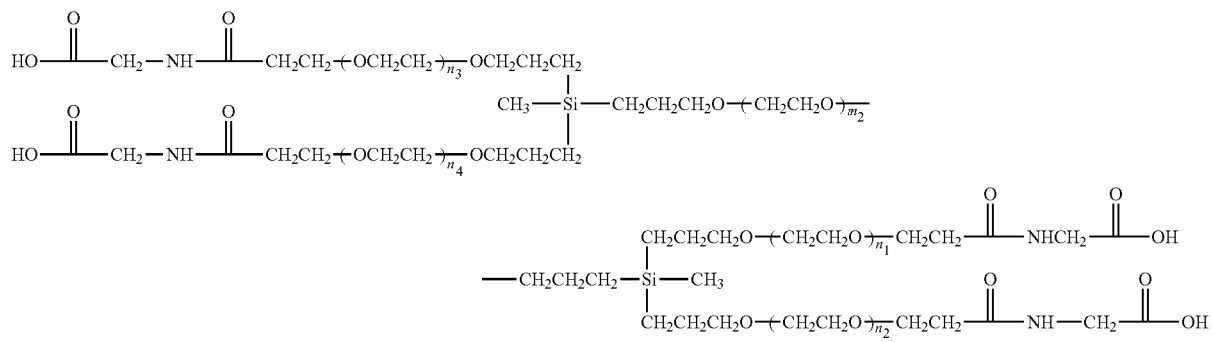

Wherein,

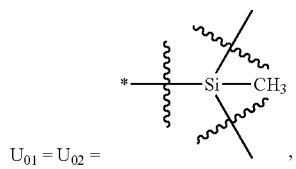

(U$_1$ and U$_2$ are of a symmetrical type,

L$_1$=L$_3$=CH$_2$CH$_2$CH$_2$, L$_2$=L$_4$=CH$_2$CH$_2$CH$_2$, L$_5$=L$_6$=CH$_2$CH$_2$CH$_2$),

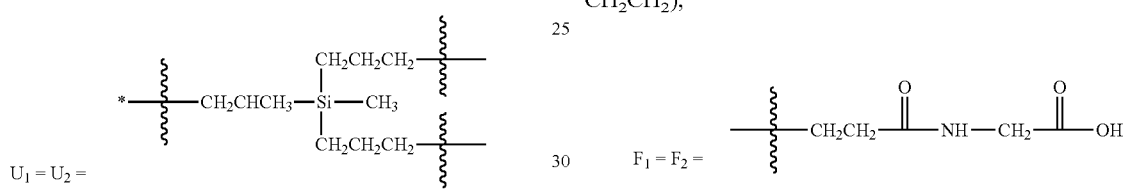

(g=0, k=1, q=1, Z$_2$=—CH$_2$CH$_2$C(=O)NH—, q$_1$=1, Z$_1$=—CH$_2$—, R$_{01}$=COOH) and j=0. The designed total molecular weight is approximately 40 kDa, wherein, the molecular weight of four branch chains is approximately 4×8000=32000 Da corresponding to n$_1$≈n$_2$≈n$_3$≈n$_4$≈182, and the molecular weight of the main chain is approximately 7100 Da corresponding to m$_2$≈161.

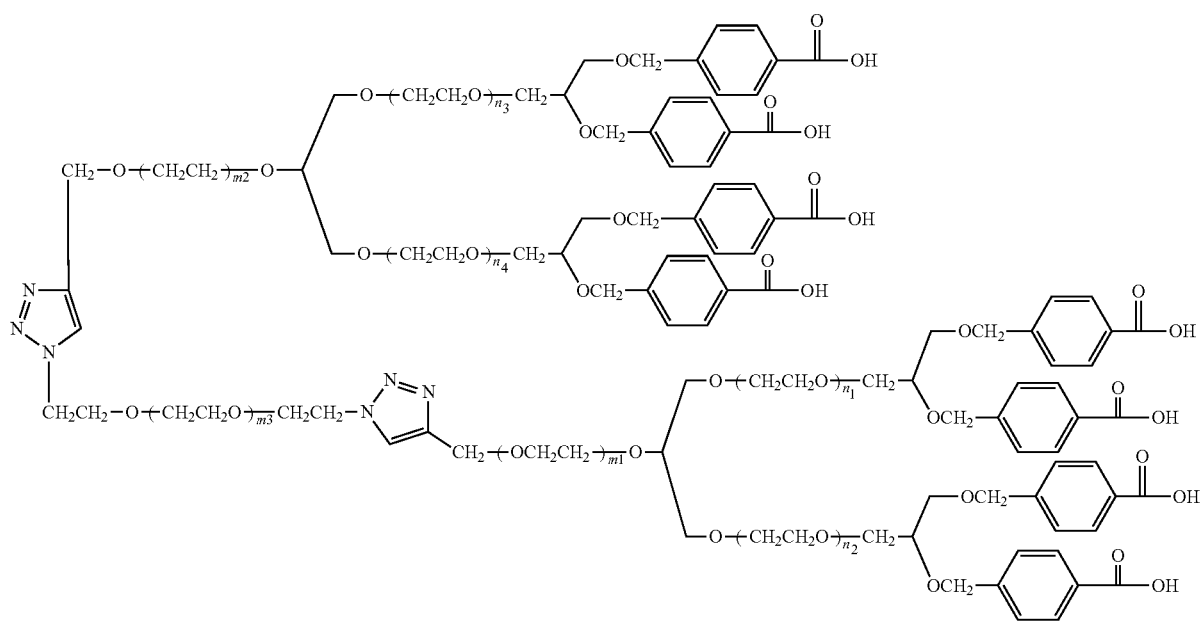

Wherein, $U_1 = U_2 =$ [structure], $F_1 = F_2 =$ —CH$_2$CH$_2$—C(O)—NH—CH$_2$—C(O)—OH $(g = 1, k = 2, g_0 = 0, G =$ [branched structure]$)$, $q = 0, q_1 = 1, Z_1 =$ —CH$_2$—C$_6$H$_4$— , HO—C(O)—CH$_2$CH$_2$—(OCH$_2$CH$_2$)$_{n_3}$—OCH$_2$CH$_2$CH$_2$—
HO—C(O)—(CH$_2$CH$_2$—OCH$_2$CH$_2$)$_{n_4}$—OCH$_2$CH$_2$CH$_2$—
CH$_3$—Si—CH$_2$CH$_2$CH$_2$O—(CH$_2$CH$_2$O)$_{m_2}$—CH$_2$CH$_2$CH$_2$—Si—CH$_3$
—CH$_2$CH$_2$CH$_2$O—(CH$_2$CH$_2$O)$_{n_2}$—CH$_2$CH$_2$CH$_2$—
CH$_2$CH$_2$CH$_2$O—(CH$_2$CH$_2$O)$_{n_1}$—CH$_2$CH$_2$—C(O)—OH
CH$_2$CH$_2$CH$_2$O—(CH$_2$CH$_2$O)$_{n_2}$—CH$_2$CH$_2$—C(O)—OH $R_{01} = COOH$), $W_{01} = W_{02} =$ —CH$_2$CH$_2$—[triazole]—CH$_2$— ;

the asterisk (*) for $U_1$ and $U_2$ pointing to the polyethylene glycol main chain, the asterisk for G and $Z_1$ pointing to polyethylene glycol branch chains, and the asterisk for $W_{01}$ and $W_{02}$ pointing to polyethylene glycol block corresponding to $m_3$. The designed total molecular weight is approximately 24 kDa, wherein, the molecular weight of four branch chains is approximately 4×3000=12000 Da corresponding to $n_1 \approx n_2 \approx n_3 \approx n_4 \approx 68$, and the molecular weight of three PEG blocks along the main chain is 2000 Da, 6000 Da and 2000 Da, respectively, corresponding to $m_1=44$, $m_3 \approx 136$ and $m_2=44$, wherein, the middle block is polydisperse, and the two side blocks are monodisperse.

Wherein,

[structure: —CH$_2$CHCH$_3$—Si(CH$_3$)(CH$_2$CH$_2$CH$_2$—)(CH$_2$CH$_2$CH$_2$—)]

($U_1$ and $U_2$ are of a symmetrical type, $U_{01} = U_{02} =$ [Si—CH$_3$ structure] , $L_1=L_3=$CH$_2$CH$_2$CH$_2$, $L_2=L_4=$CH$_2$CH$_2$CH$_2$, $L_5=L_6=$CH$_2$CH$_2$CH$_2$), $F_1=F_2=$CH$_2$CH$_2$COOH ($g=0$, $k=1$, $q=0$, $q_1=1$, $Z_1=$CH$_2$CH$_2$, $R_{01}=$COOH) and $j=0$. The designed total molecular weight is approximately 40 kDa, wherein, the molecular weight of four branch chains is approximately 4×8000=32000 Da corresponding to $n_1 \approx n_2 \approx n_3 \approx n_4 \approx 182$, and the molecular weight of the main chain is approximately 7300 Da corresponding to $m_2 \approx 161$.

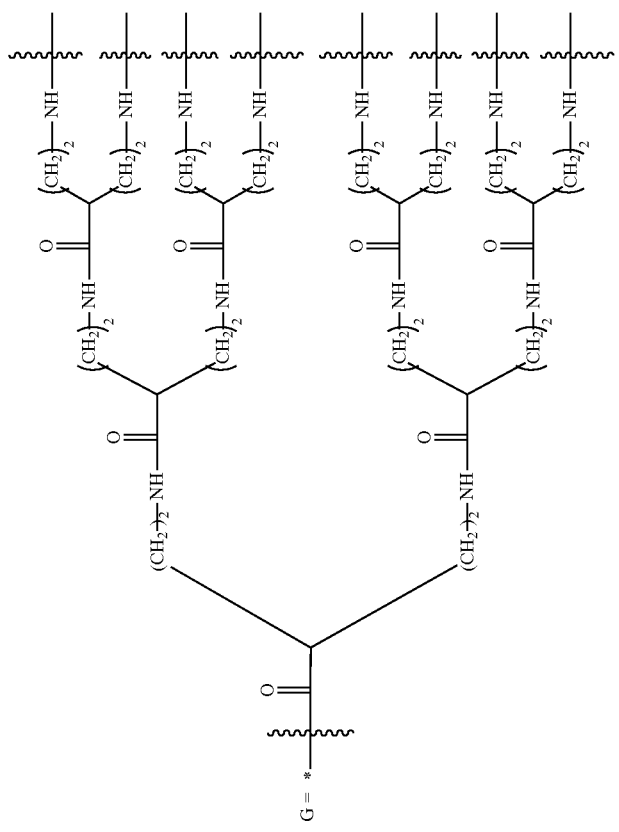
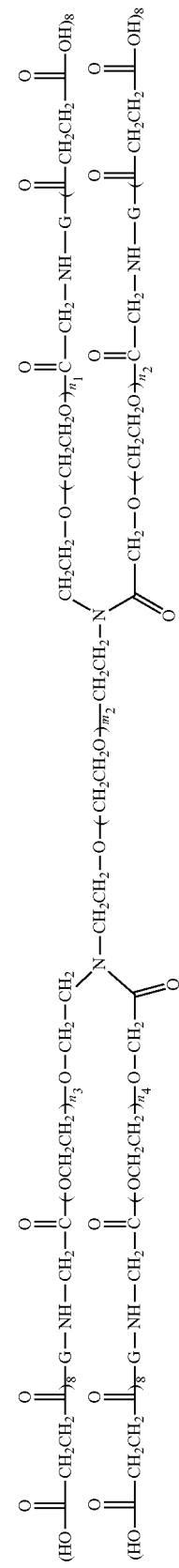

341

Wherein, $U_1 = U_2 =$ 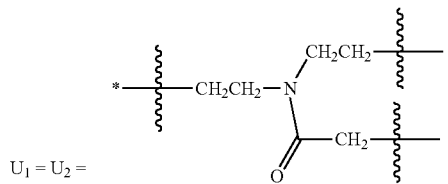

($U_1$ and $U_2$ are of an asymmetrical type,

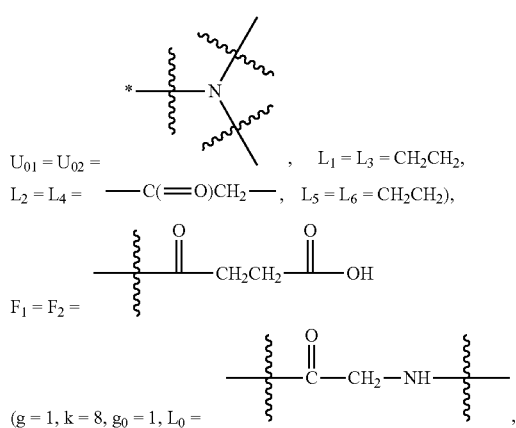

$U_{01} = U_{02} =$ , $L_1 = L_3 = CH_2CH_2$,
$L_2 = L_4 = -C(=O)CH_2-$, $L_5 = L_6 = CH_2CH_2$), $F_1 = F_2 =$ ($g = 1$, $k = 8$, $g_0 = 1$, $L_0 =$ $q=0$, $q_1=1$, $Z_1=-C(=O)CH_2CH_2-$, $R_{01}=COOH$) and $j=0$. The designed total molecular weight is approximately 60 kDa, wherein, the molecular weight of four branch chains is approximately 4×12000=48000 Da corresponding to $n_1 \approx n_2 \approx n_3 \approx n_4 \approx 273$, and the molecular weight of the main chain is approximately 7600 Da corresponding to $m_2 \approx 172$.

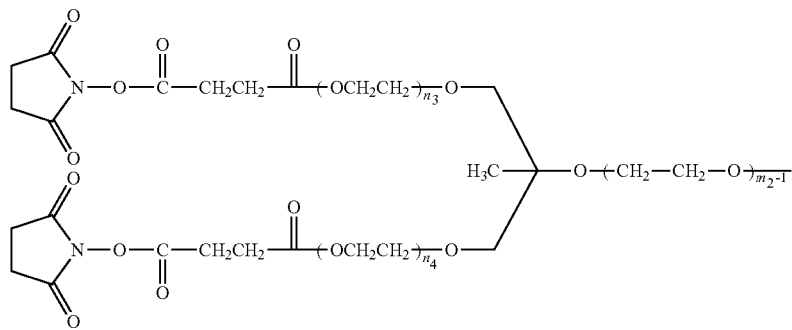

342

Wherein, $U_1 = U_2 =$ 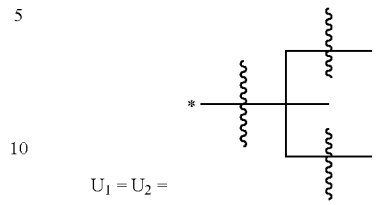

($U_1$ and $U_2$ are of a symmetrical type,

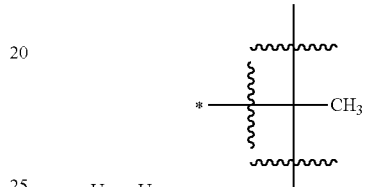

$U_{01} = U_{02} =$ , $L_1=L_2=L_3=L_4=CH_2$, without $L_5$ and $L_6$), $F_1=F_2=COCH_2CH_2CONHS$ ($g=0$, $k=1$, $q=0$, $q_1=1$, $Z_1=COCH_2CH_2CO$, $R_{01}=NHS$) and $j=0$. The designed total molecular weight is approximately 40 kDa, wherein, the molecular weight of four branch chains is approximately 4×7500=30000 Da corresponding to $n_1 \approx n_2 \approx n_3 \approx n_4 \approx 170$, and the molecular weight of the main chain is approximately 10000 Da corresponding to $m_2 \approx 227$.

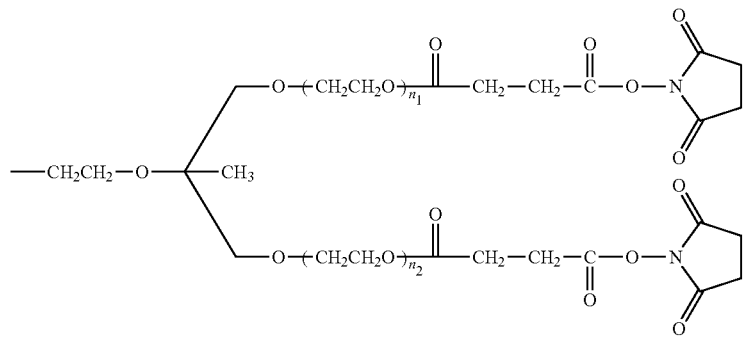

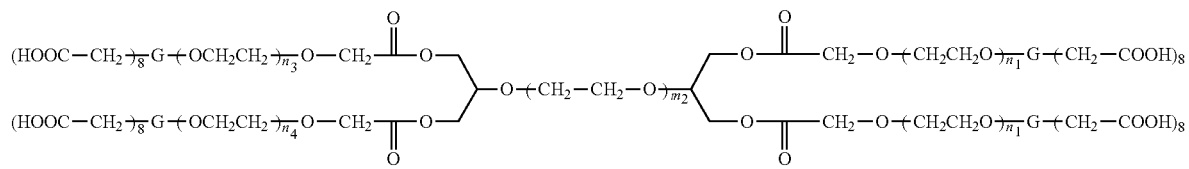

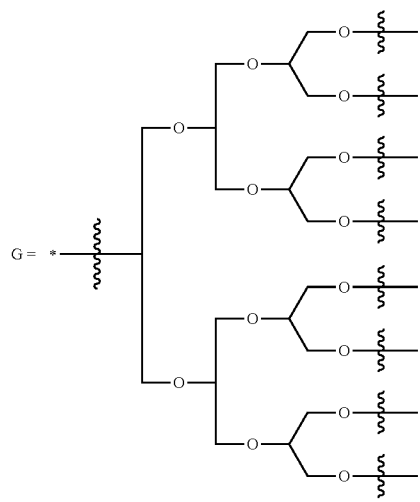

Wherein,

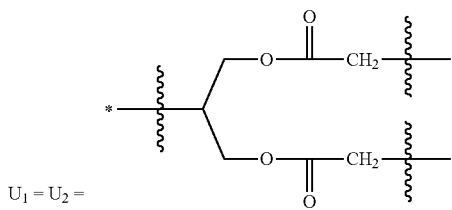 [SMILES: *CC(=O)OCC(*)COC(=O)C*]

($U_1$ and $U_2$ are of a symmetrical type,

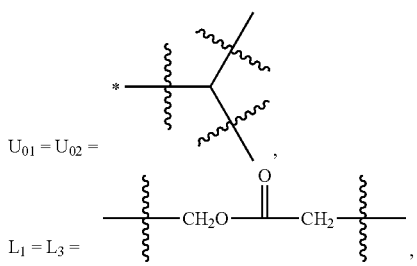

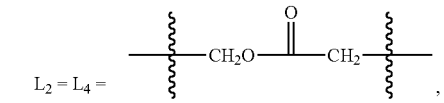

without $L_5$ and $L_6$), $F_1=F_2=G(CH_2COOH)_8$, $g=1$, $k=8$,

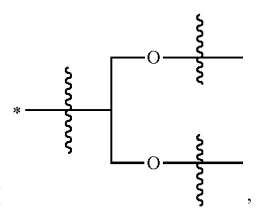

$G = DENR($ NONE, 3), $g_0=0$, $q=0$, $q_1=1$, $Z_1=CH_2$, $R_{O1}=COOH$ and $j=0$. The designed total molecular weight is approximately 80 kDa, wherein, the molecular weight of four branch chains is approximately $4\times16000=64000$ Da corresponding to $n_1 \approx n_2 \approx n_3 \approx n_4 \approx 364$, and the molecular weight of the main chain is approximately 16000 Da corresponding to $m_2 \approx 364$.

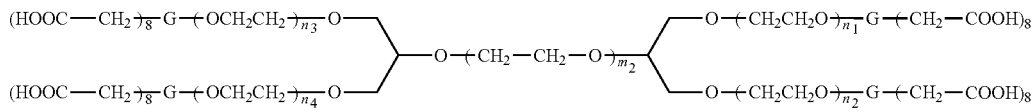

Wherein,

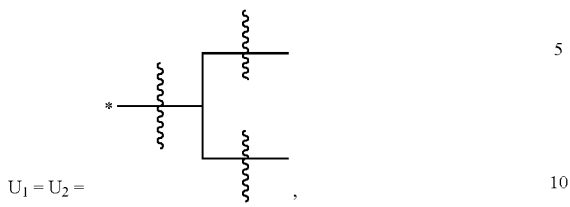

$U_1 = U_2 = $ $F_1 = F_2 = CH_2COOH$

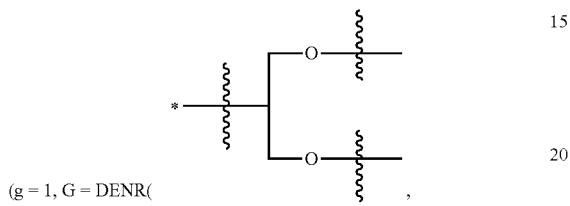

$(g = 1, G = DENR($

NONE, 3), $k=8$, $g_0=0$, $q=0$, $q_1=1$, $Z_1=CH_2$, $R_{01}=COOH$) and $j=0$. The designed total molecular weight is approximately 25 kDa, wherein, the molecular weight of four branch chains is approximately 3500 Da, 3500 Da, 4500 Da and 4500 Da, corresponding to $n_1 \approx n_2 \approx 80$, $n_3 \approx n_4 \approx 102$, and the molecular weight of the main chain is approximately 5000 Da corresponding to $m_2 \approx 114$.

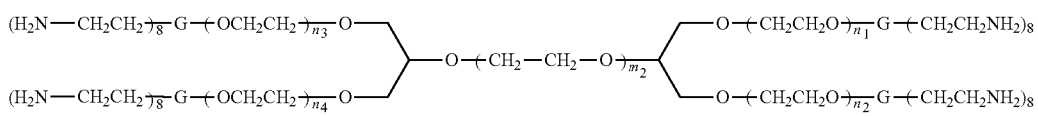

Wherein,

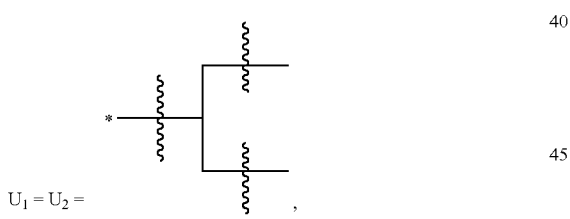

$U_1 = U_2 = $ $F_1 = F_2 = G(CH_2CH_2NH_2)_8$, $g=1$, $k=8$,

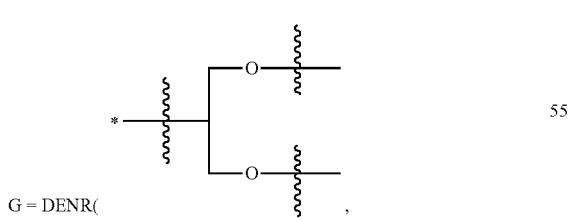

$G = DENR($

NONE, 3), $g_0=0$, $q=0$, $q_1=1$, $Z_1=CH_2CH_2$, $R_{01}=NH_2$ and $j=0$. The designed total molecular weight is approximately 31 kDa, wherein, the molecular weight of four branch chains is approximately 3500 Da, 4400 Da, 3500 Da and 4400 Da, corresponding to $n_1 \approx 80$, $n_2 \approx 80$, $n_3 \approx 100$, $n_4 \approx 100$, and the molecular weight of the main chain is approximately 12000 Da corresponding to $m_2 \approx 272$.

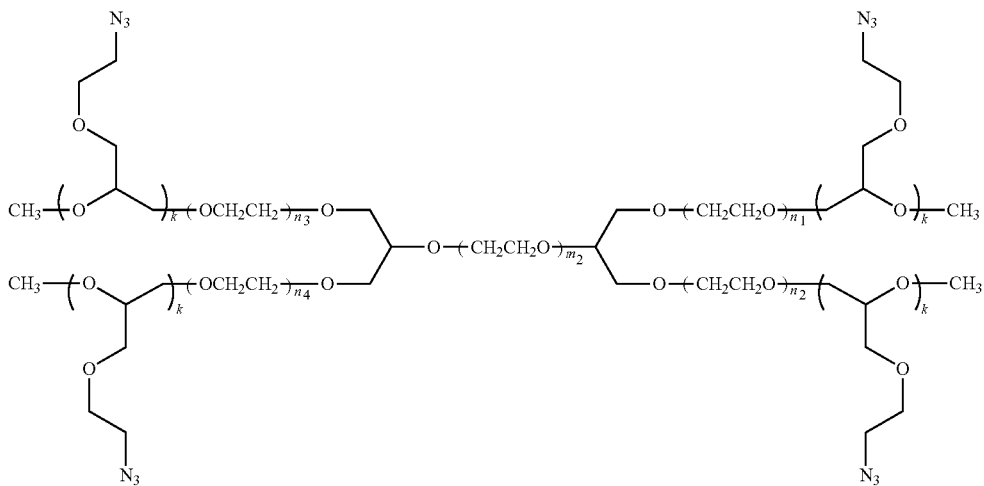

Wherein,

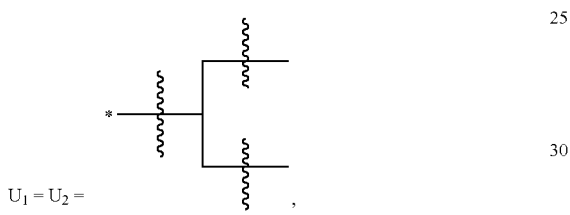

$F_1=F_2=G(CH_2CH_2N_3)_{25}$ ($g=1$, $k=25$, $g_0=0$, $q=0$, $q_1=1$, $Z_1=CH_2CH_2$, $R_{01}=N_3$) and $j=0$. The designed total molecular weight is approximately 40 kDa, wherein, the molecular weight of four branch chains is approximately $4\times5000=20000$ Da, corresponding to $n_1\approx n_2\approx n_3\approx n_4\approx 114$, and the molecular weight of the main chain is approximately 5000 Da corresponding to $m_2\approx 114$.

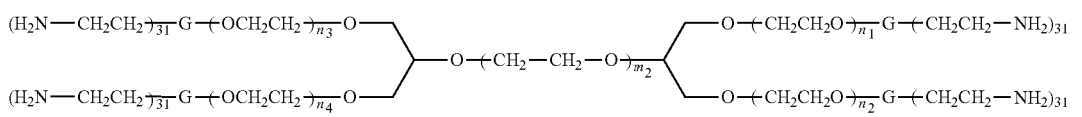

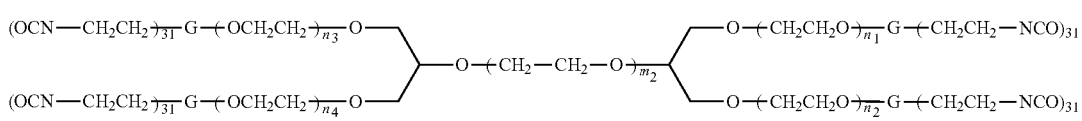

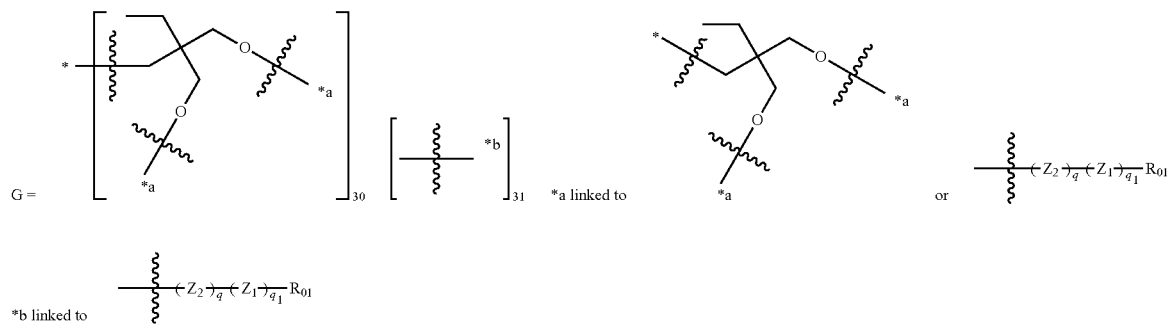

Wherein, * represents pointing to polyethylene glycol branch chains, *a represents connecting with repeat unit of

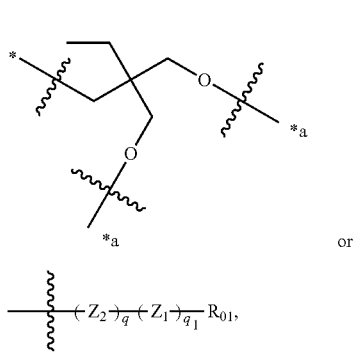 or 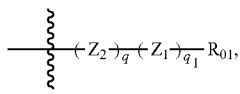

and *b represents connecting with

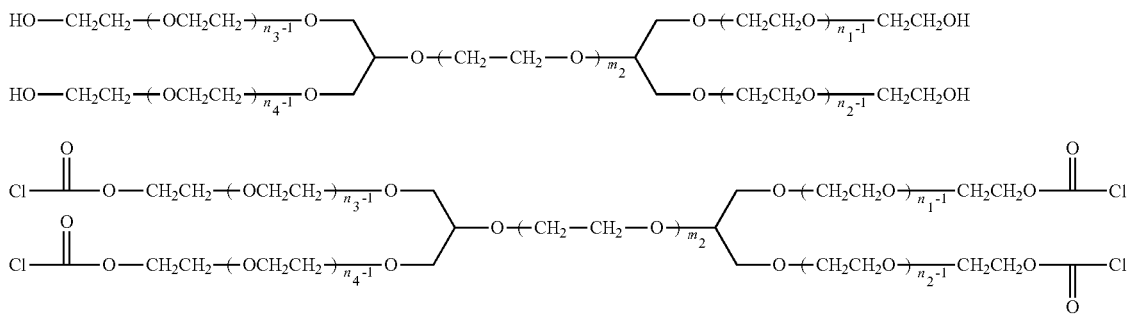

In the polyethylene glycol amine,

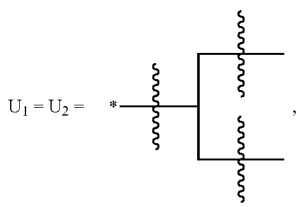

$F_1=F_2=G(CH_2CH_2NH_2)_{41}$ (g=1, k=31, $g_0=0$, G has a hyperbranched structure, q=0, $q_1=1$, $Z_1=CH_2CH_2$, $R_{01}=NH_2$) and j=0. The designed total molecular weight is approximately 40 kDa, wherein, the molecular weight of four branch chains is approximately 4×4000=16000 Da, corresponding to $n_1 \approx n_2 \approx n_3 \approx n_4 \approx 91$, and the molecular weight of the main chain is approximately 4000 Da corresponding to $m_2 \approx 91$.

In the polyethylene glycol isocyanate,

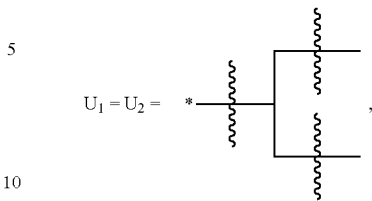

$F_1=F_2=CH_2CH_2NCO$ (g=1, k=31, $g_0=0$, q=0, $q_1=1$, $Z_1=CH_2CH_2$, $R_{01}=NCO$) and j=0. The designed total molecular weight is approximately 42 kDa, wherein, the molecular weight of four branch chains is approximately 4×4000=16000 Da, corresponding to $n_1 \approx n_2 \approx n_3 \approx n_4 \approx 91$, and the molecular weight of the main chain is approximately 4000 Da corresponding to $m_2 \approx 91$.

In the polyethylene glycol alcoholic derivative,

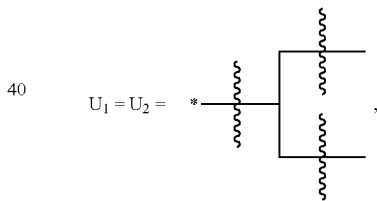

$F_1=F_2=H$ (g=0, $g_0=0$, q=0, $q_1=1$, $Z_1=CH_2CH_2$, $R_{01}=OH$) and j=0. The designed total molecular weight is approximately 30 kDa, wherein, the molecular weight of four branch chains is approximately 4×5000=20000 Da, corresponding to $n_1 \approx n_2 \approx n_3 \approx n_4 \approx 114$, and the molecular weight of the main chain is approximately 10000 Da corresponding to $m_2 \approx 227$.

In the polyethylene glycol acylchloride,

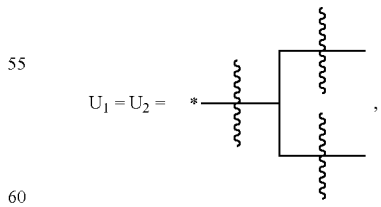

$F_1=F_2=CH_2CH_2OC(=O)Cl$ (g=0, q=0, $q_1=1$, $Z_1=CH_2CH_2$, $R_{01}$ is $OC(=O)Cl$). The designed total molecular weight is approximately 30 kDa, wherein, the molecular weight of four branch chains is approximately 4×5000=20000 Da, corresponding to $n_1 \approx n_2 \approx n_3 \approx n_4 \approx 114$, and the molecular weight of the main chain is approximately 10000 Da corresponding to $m_2 \approx 227$.

351 352

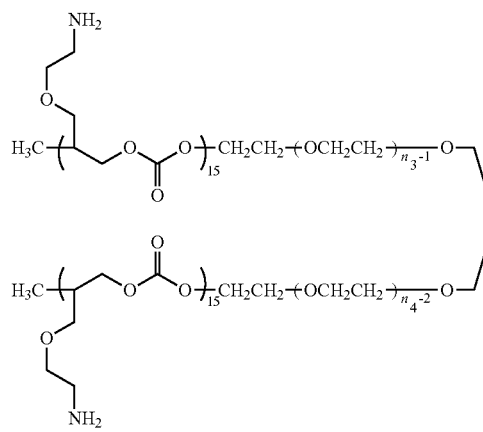
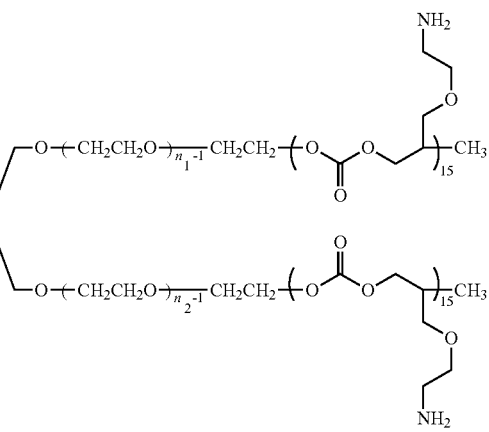

Wherein,

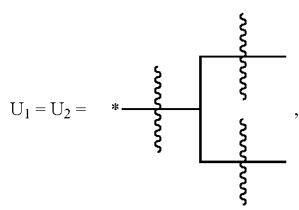

$U_1 = U_2 =$ $F_1=F_2=G(CH_2CH_2NH2)_{15}$ (g=1, k=15,

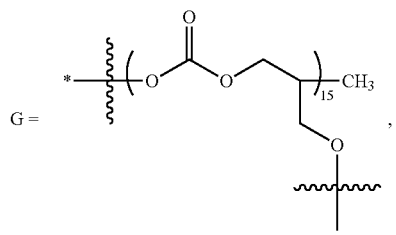

G =

$g_0=1$, $L_0=CH_2CH_2$, q=0, $q_1=1$, $Z_1=CH_2CH_2$, $R_{01}=NH_2$) and j=0. The designed total molecular weight is approximately 35 kDa, wherein, the molecular weight of four branch chains is approximately 4×5000=20000 Da corresponding to $n_1 \approx n_2 \approx n_3 \approx n_4 \approx 114$, and the molecular weight of the main chain is approximately 5000 Da corresponding to $m_2 \approx 114$.

Wherein,

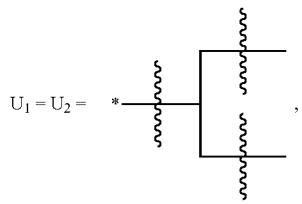

$F_1=F_2=CH_2CH_2NH_2$ ($g=0$, $k=1$, $q=0$, $q_1=1$, $Z_1=CH_2CH_2$, $R_{01}=NH_2$), $j=1$ and

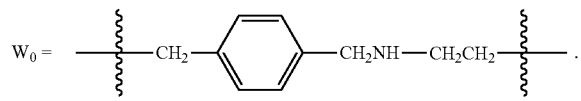

The designed total molecular weight is approximately 25 kDa, wherein, the molecular weight of four branch chains is approximately 4×5000=20000 Da, corresponding to $n_1 \approx n_2 \approx n_3 \approx n_4 \approx 114$, and the molecular weight of two PEG blocks of the main chain is approximately 2000 Da and 3000 Da, corresponding to $m_1 \approx 45$ and $m_2 \approx 68$.

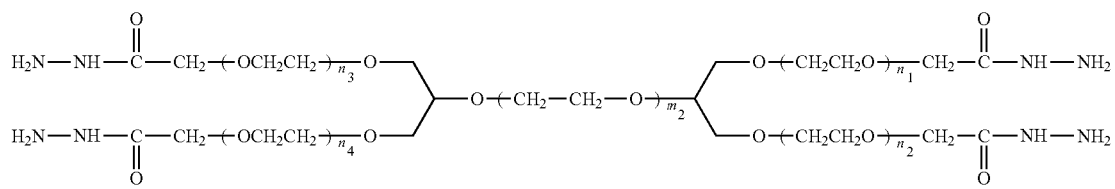

Wherein,

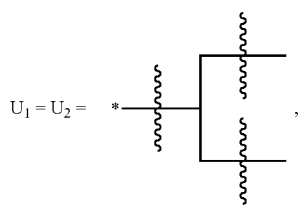

$F_1=F_2=CH_2CONH_2NH_2$ ($g=0$, $k=1$, $q=0$, $q_1=1$, $Z_1=CH_2$, $R_{01}=CONH_2NH_2$) and $j=0$. The designed total molecular weight is approximately 30 kDa, wherein, the molecular weight of four branch chains is approximately 4×6000=24000 Da, corresponding to $n_1 \approx n_2 \approx n_3 \approx n_4 \approx 136$, and the molecular weight of the main chain is approximately 6000 Da, corresponding to $m_2 \approx 136$.

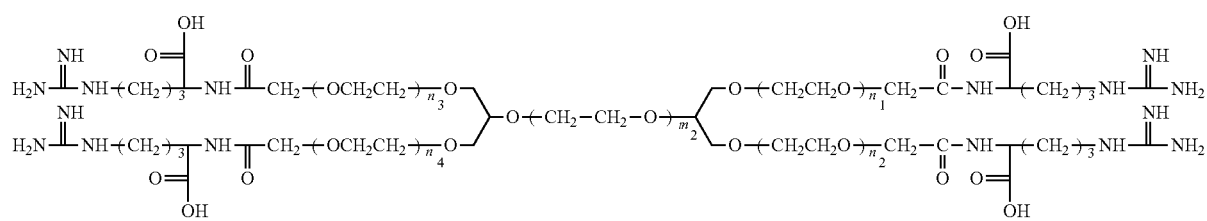

Wherein, $U_1 = U_2 =$ 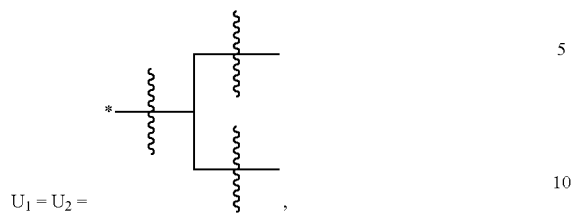, $F_1 = F_2 =$ 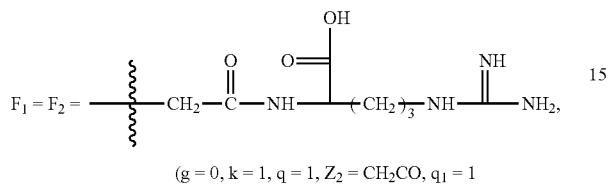, $(g=0, k=1, q=1, Z_2 = CH_2CO, q_1 = 1$ $Z_1 =$ 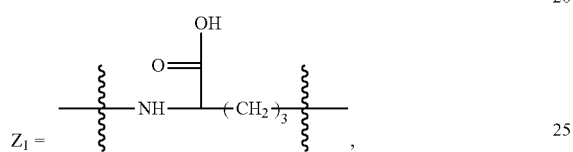, $R_{O1}$ is $NHC(=NH)NH_2$) and $j=0$. The designed total molecular weight is approximately 31 kDa, wherein, the molecular weight of four branch chains is approximately $4\times6000=24000$ Da, corresponding to $n_1 \approx n_2 \approx n_3 \approx n_4 \approx 136$, and the molecular weight of the main chain is approximately 6000 Da, corresponding to $m_2 \approx 136$.

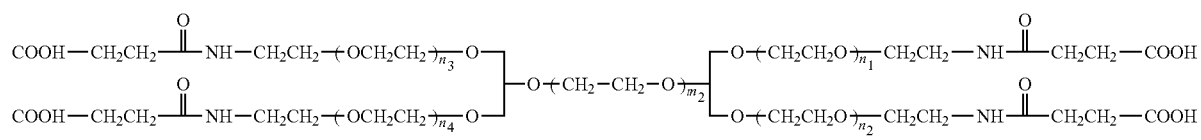

Wherein, $U_1 = U_2 =$ 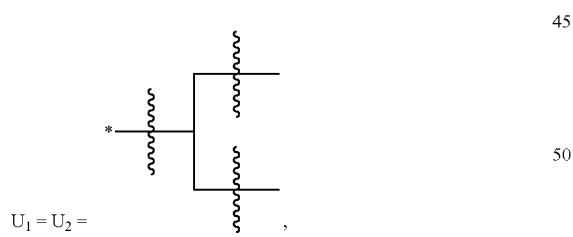, $F_1 = F_2 =$ 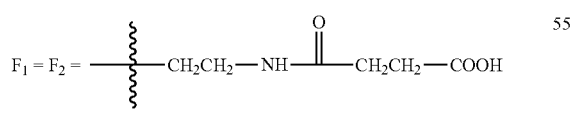, $(g=0, k=1, q=1, Z_2=CH_2CH_2NH, q_1=1, Z_1=COCH_2CH_2, R_{O1}=COOH)$ and $j=0$. The designed total molecular weight is approximately 33 kDa, wherein, the molecular weight of four branch chains is approximately $4\times6000=24000$ Da, corresponding to $n_1 \approx n_2 \approx n_3 \approx n_4 \approx 136$, and the molecular weight of the main chain is approximately 8000 Da, corresponding to $m_2 \approx 182$.

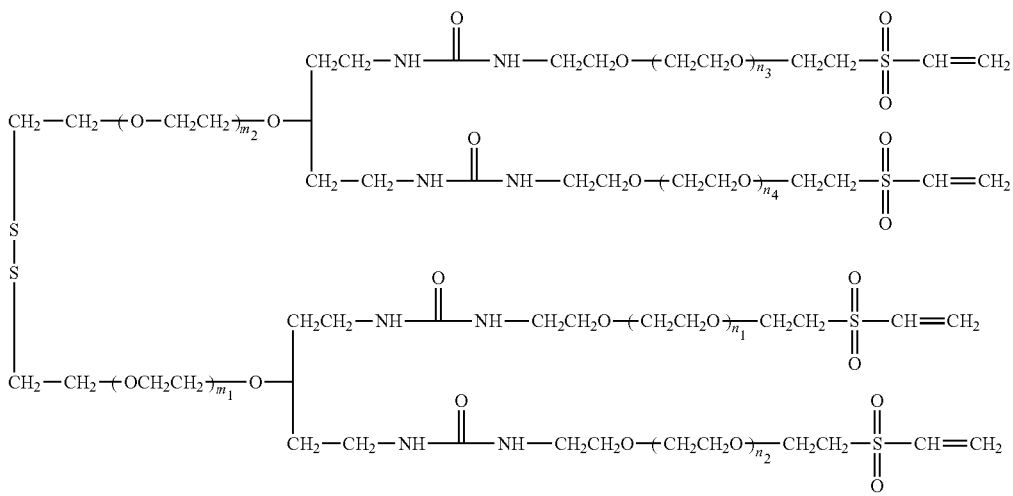

Wherein,

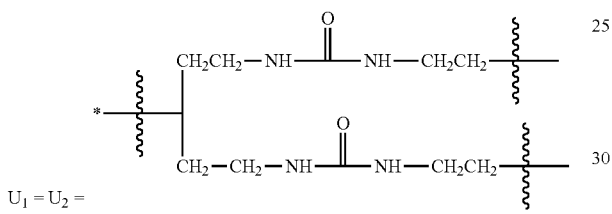

($U_1$ and $U_2$ are of a symmetrical type,

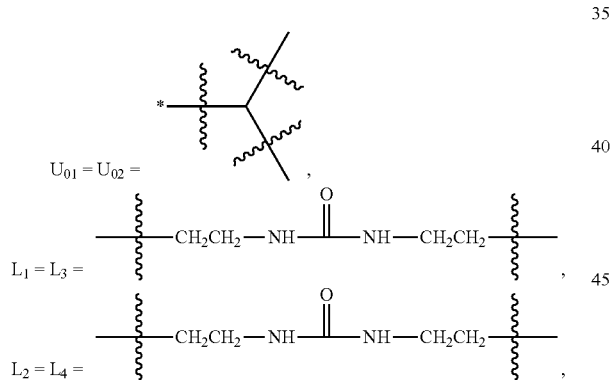

without $L_5$ and $L_6$), $F_1$ and $F_2$ are $-CH_2CH_2S(=O)_2CH=CH_2$ ($g=0$, $k=1$, $q=0$, $q_1=1$, $Z_1=CH_2CH_2$, $R_{01}$ is $-S(=O)_2CH=CH_2$), $j=1$ and $W_0$ is $-CH_2CH_2S-SCH_2CH_2-$. The designed total molecular weight is approximately 25 kDa, wherein, the molecular weight of four branch chains is approximately $4\times5000=20000$ Da, corresponding to $n_1 \approx n_2 \approx n_3 \approx n_4 \approx 114$, and the molecular weight of two PEG blocks of the main chain is approximately 2000 Da and 2000 Da, corresponding to $m_1 \approx 45$ and $m_2 \approx 45$ respectively.

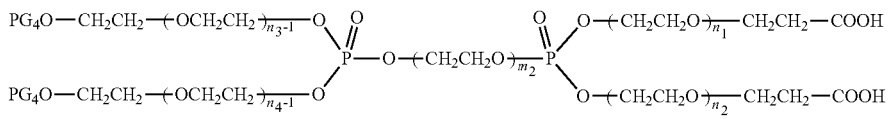

Wherein,

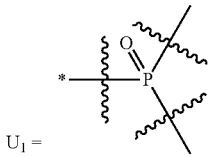

($U_1$ and $U_2$ being symmetrical structures,

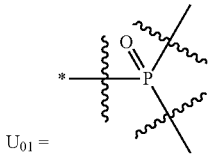

without $L_1$, $L_2$, $L_3$, $L_4$, $L_5$ and $L_6$), $F_1=CH_2CH_2COOH$ (g=0, k=1, q=0, $q_1$=1, $Z_1=CH_2CH_2$, $R_{01}=COOH$), $F_2=CH_2CH_2OPG_4$ (g=0, k=1, q=0, $q_1$=1, $Z_1=CH_2CH_2$, $R_{01}=OPG_4$, $PG_4$=Boc) and j=0. The designed total molecular weight is approximately 20 kDa, wherein, the molecular weight of four branch chains is approximately 4×4000=16000 Da, corresponding to $n_1 \approx n_2 \approx n_3 \approx n_4 \approx 91$, and the molecular weight of the main chain is approximately 4000 Da, corresponding to $m_2 \approx 91$. $PG_4$ also can be

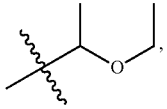 [SMILES: *C(C)OCC]

a t-butyldiphenylsilyl group, a t-butyldimethylsilyl group or other suitable hydroxyl protecting groups.

Wherein,

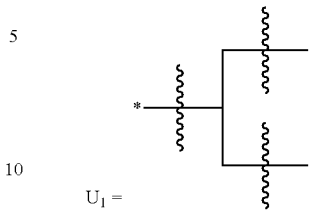

($U_1$ is of a symmetrical type,

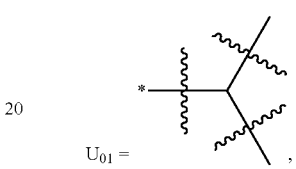

$L_1=CH_2$, $L_2=CH_2$, without $L_5$),

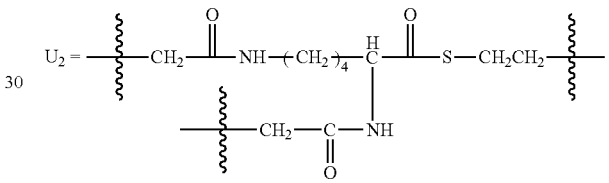

($U_2$ is of an asymmetrical type,

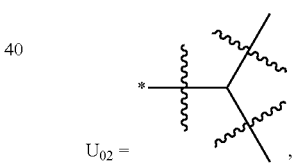

$L_3=(CH_2)_4NHCOCH_2$, $L_4=NHCOCH_2$, $L_6=SCH_2CH_2$), $F_1=CH_2CH_2COOH$ (g=0, k=1, q=0, $q_1$=1, $Z_1=CH_2CH_2$, $R_{01}=COOH$), $F_2=CH_2CH_2NPG_5$ (g=0, k=1, q=0, $q_1$=1, $Z_1=CH_2CH_2$, $R_{01}=NPG_5$, $PG_5$=Boc) and j=0. The designed total molecular weight is approximately 30 kDa, wherein, the molecular weight of four branch chains is approximately 8500 Da, 8500 Da, 1400 Da and 1400 Da, corresponding to $n_1 \approx 193$, $n_2 \approx 193$, $n_3=32$, $n_4=32$, and the molecular weight of the main chain is approximately 9000 Da, corresponding to $m_2 \approx 205$.

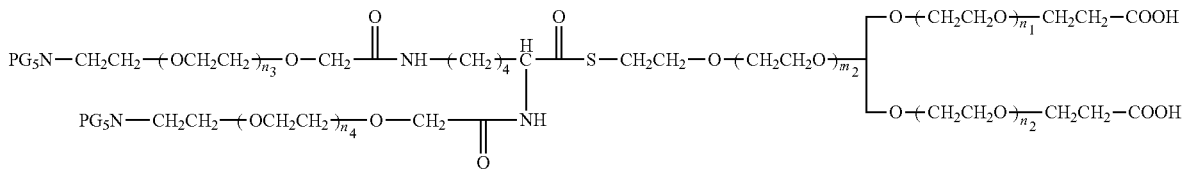

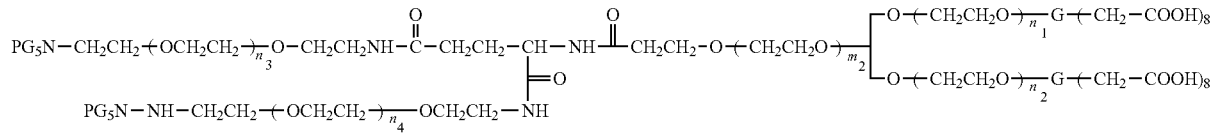

Wherein,

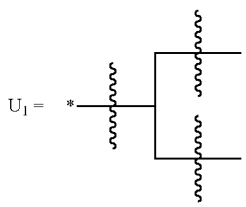

($U_1$ is of a symmetrical type,

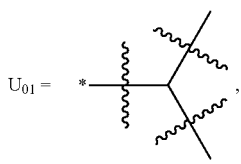

$L_1=CH_2$, $L_2=CH_2$, without $L_5$),

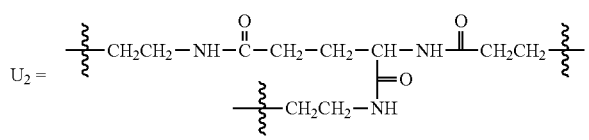

($U_2$ is of a symmetrical type,

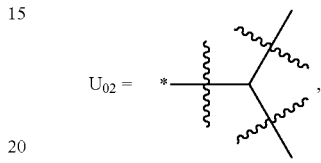

$L_3=(CH_2)_2CONHCH_2CH_2$, $L_4=CONHCH_2CH_2$, $L_6=NHCOCH_2CH_2$), $F_1=G(CH_2COOH)_8$ [g=1, k=8, G=DENR

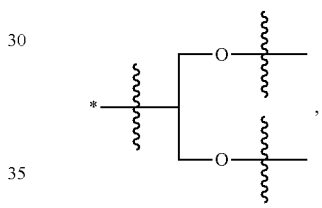

NONE, 3), q=0, $q_1=1$, $Z_1=CH_2$, $R_{01}=COOH$], $F_2=CH_2CH_2NPG_5$ (g=0, k=1, q=0, $q_1=1$, $Z_1=CH_2CH_2$, $R_{01}=NPG_5$, $PG_5=Fmoc$) and j=0. The designed total molecular weight is approximately 24.6 kDa, wherein, the molecular weight of four branch chains is approximately 10000 Da, 10000 Da, 700 Da and 700 Da, corresponding to $n_1\approx227$, $n_2\approx227$, $n_3=16$, $n_4=16$, wherein, the two branch chains terminated by protected glycine are monodisperse, and the polyethylene glycol main chain is monodisperse corresponding an EO-unit number of $m_2=9$.

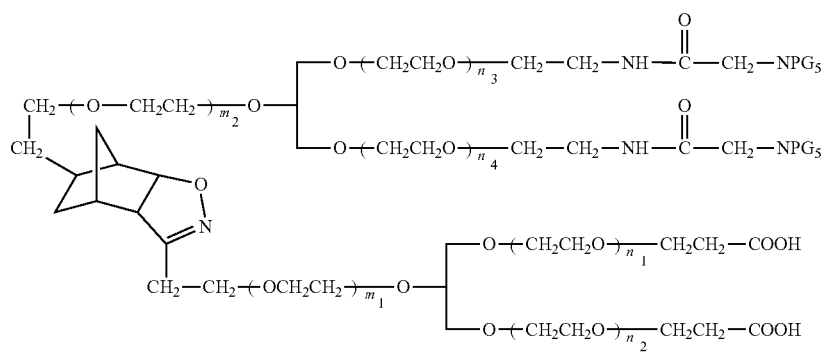

Wherein,

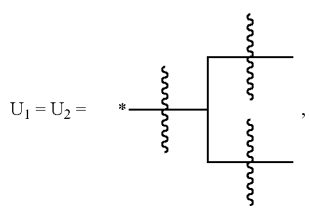

$U_1 = U_2 =$ $F_1=CH_2CH_2COOH$ (g=0, k=1, q=0, $q_1=1$, $Z_1=CH_2CH_2$, $R_{01}=COOH$), $F_2=CH_2CH_2NPG_5$ (g=0, k=1, q=0, $q_1=1$, $Z_1=CH_2CH_2$, $R_{01}=NPG_5$, $PG_5=Fmoc$), j=1 and $W_0 =$ The designed total molecular weight is approximately 20.1 kDa, wherein, the molecular weight of four branch chains is approximately 8000 Da, 8000 Da, 500 Da and 500 Da, corresponding to $n_1\approx182$, $n_2\approx182$, $n_3=12$, $n_4=12$, wherein, the two branch chains terminated by protected glycine are monodisperse, and the two PEG blocks of the main chain are monodisperse corresponding an EO-unit number of $m_1=16$ and $m_2=32$, respectively.

Wherein, $U_1 = U_2 =$ $F_1=CH_2CONHS$ (g=0, k=1, q=0, $q_1=1$, $Z_1=CH_2$, $R_{01}=CONHS$), $F_2=CH_2CH_2OPG_5$ (g=0, k=1, q=0, $q_1=1$, $Z_1=CH_2CH_2$, $R_{01}=OPG_5$, $PG_5$ is a hydroxyl protecting group) and j=0. Wherein, $n_1$, $n_2$, $n_3$ and $n_4$ are each independently an integer from 5 to 2000, and can be the same or different in one molecule. $m_2$ is an integer from 5 to 1000.

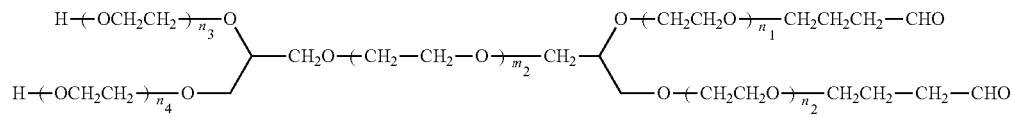

Wherein, $U_1 = U_2 = $ 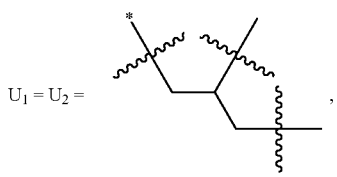, $F_1=CH_2CH_2CH_2CHO$ (g=0, k=1, q=0, $q_1$=1, $Z_1$=$CH_2CH_2CH_2$, $R_{01}$=CHO), $F_2$=$CH_2CH_2OH$ (g=0, k=1, q=0, $q_1$=1, $Z_1$=$CH_2CH_2$, $R_{01}$=OH) and j=0. Wherein, $n_1$, $n_2$, $n_3$ and $n_4$ are each independently an integer from 10 to 2000, and can be the same or different in one molecule, $m_2$ is an integer from 10 to 1000.

Examples of H-shaped multifunctionalized polyethylene glycol are as follows:

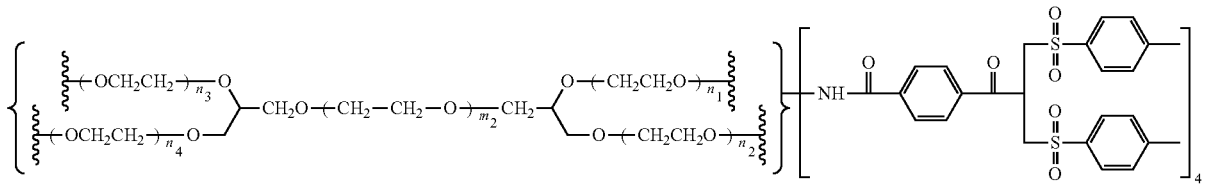

Wherein, $n_1$, $n_2$, $n_3$ and $n_4$ are each independently an integer from 10 to 2000, and can be the same or different in one molecule, $m_2$ is an integer from 5 to 1000.

For example, $F_1$ and $F_2$ have identical $R_{01}$ groups, and $F_1$ and $F_2$ are identical, then the structure of the H-shaped multifunctionalized polyethylene glycol represented by general formula (1) can be equivalent to the following formula (10):

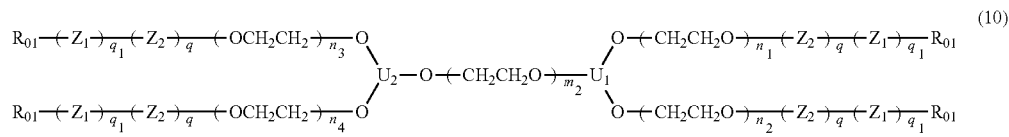

(10)

Wherein, the definitions of $U_1$, $U_2$, $n_1$, $n_2$, $n_3$, $n_4$, $m_2$, $Z_2$, q, $Z_1$, $q_1$ and $R_{01}$ are the same as above-mentioned, and no more repeated here. Wherein, in general formula (10), those in quantities of four or four more including $Z_2$, q, $Z_1$, $q_1$ and $R_{01}$ are each independently identical in one molecule.

Taking $U_1 = U_2 = $ 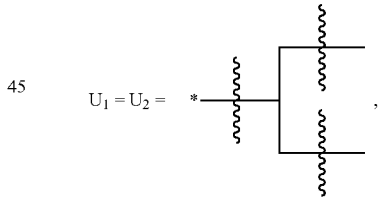,

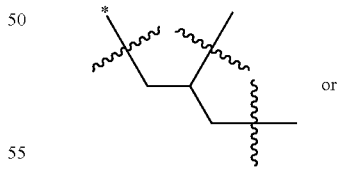 or

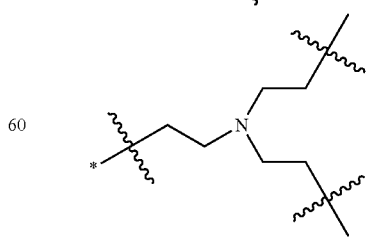

for example, the structure of H-shaped multifunctionalized polyethylene glycol is represented as follows, respectively.

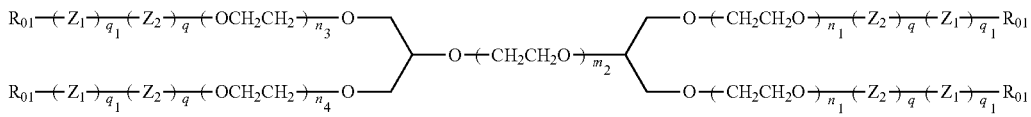

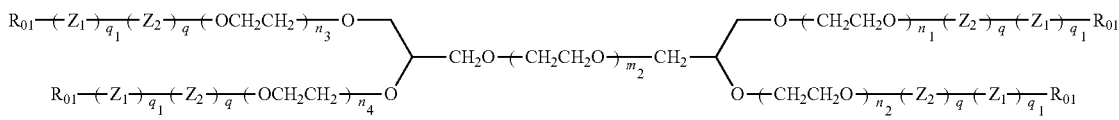

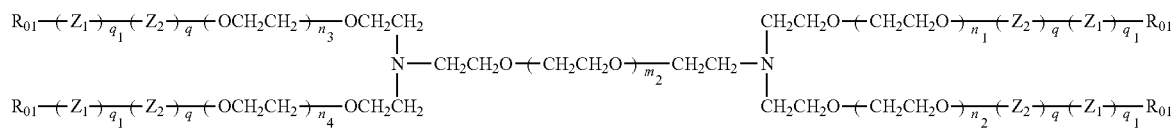

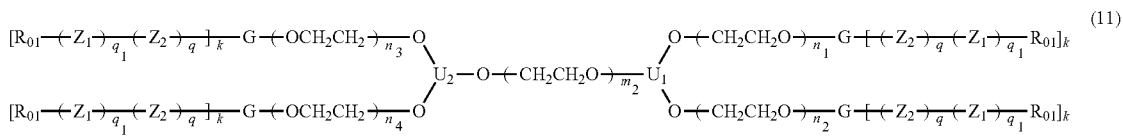

When $F_1=F_2$, for example, the structure of H-shaped multifunctionalized polyethylene glycol represented by general formula (1) is equivalent to the following formula (11):

$$[R_{01}-(Z_1)_{q_1}(Z_2)_{q}]_k-G-(OCH_2CH_2)_{n_3}O \qquad O-(CH_2CH_2O)_{n_1}-G-[(Z_2)_{q}(Z_1)_{q_1}R_{01}]_k$$
$$U_2-O-(CH_2CH_2O)_{m_2}-U_1 \qquad (11)$$
$$[R_{01}-(Z_1)_{q_1}(Z_2)_{q}]_k-G-(OCH_2CH_2)_{n_4}O \qquad O-(CH_2CH_2O)_{n_2}-G-[(Z_2)_{q}(Z_1)_{q_1}R_{01}]_k$$

Wherein, the definitions of $U_1$, $U_2$, $n_1$, $n_2$, $n_3$, $n_4$, $m_2$, $Z_2$, q, $Z_1$, $q_1$ and $R_{01}$ are the same as above-mentioned, and no more repeated here.

Wherein, those in quantities of four or four more including $Z_2$, q, $Z_1$, $q_1$ and $R_{01}$ are each independently identical in one molecule; four G groups have identical structure types; G is a tri-valent or higher-valent linking group with a valence of k+1; k is an integer from 2 to 250; G is selected from terminal branched structures in above-said part 1.1.9, preferably a trivalent group, a tetravalent group, a pentavalent group, a hexavalent group or a dendritic structure.

Take

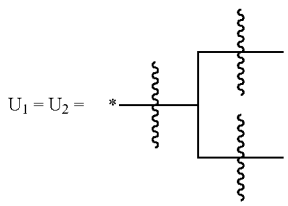

for example, when G is

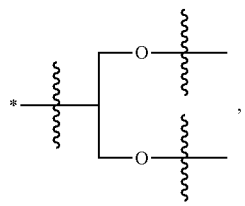

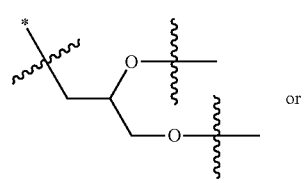

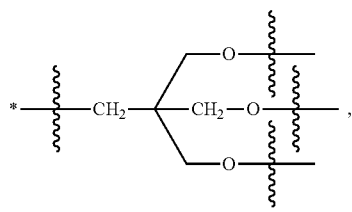

the structure of H-shaped multifunctionalized polyethylene glycol is as follows respectively.

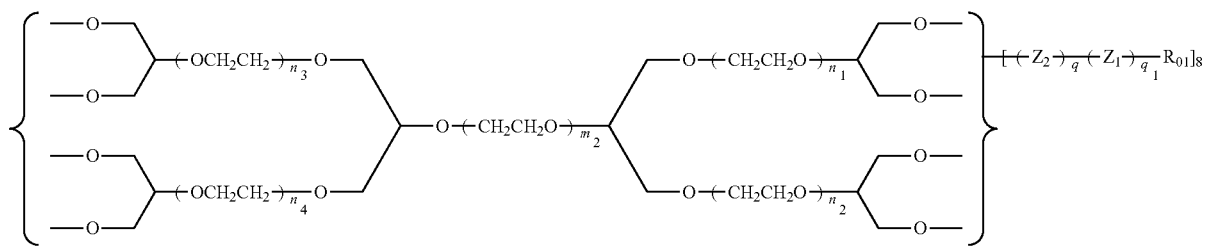
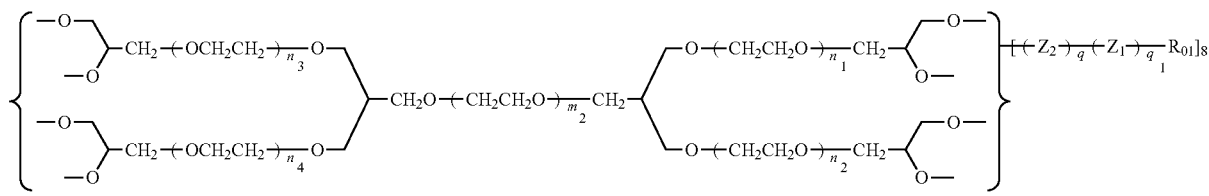
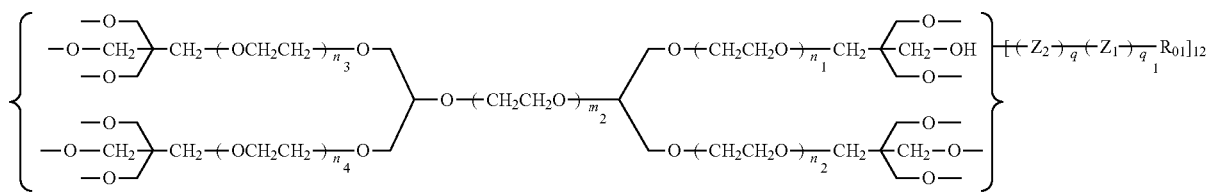
Take
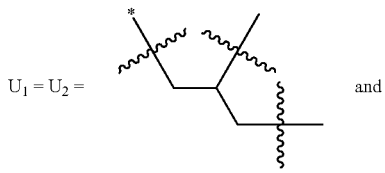
and
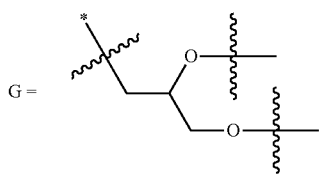
for another example, the structure of H-shaped multifunctionalized polyethylene glycol is as follows:
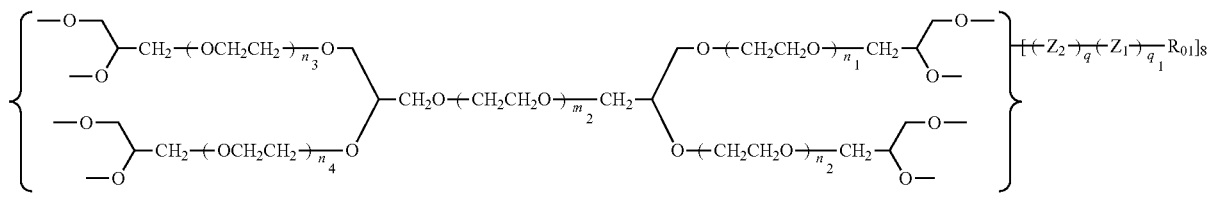

When the G group in $F_1$ and the G group in $F_2$ have identical structure types, the structure of H-shaped multifunctionalized polyethylene glycol represented by general formula (1) is equivalent to formula (12):

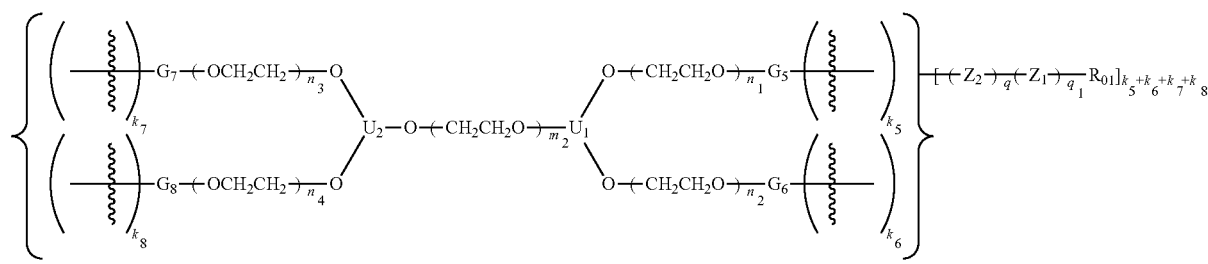

(12)

Wherein, the definitions of $U_1$, $U_2$, $n_1$, $n_2$, $n_3$, $n_4$, $m_2$, $Z_2$, q, $Z_1$, $q_1$ and $R_{01}$ are the same as above-mentioned, and no more repeated here.

Wherein, those in quantities of four or four more including $Z_2$, q, $Z_1$, $q_1$ and $R_{01}$ are each independently identical in one molecule; $k_5$, $k_6$, $k_7$ and $k_8$ are each independently an integer from 2 to 250, and can be identical or not identical in one molecule; the definitions of $G_5$, $G_6$, $G_7$ and $G_8$ are the same as G, and are each independently a linking group of trivalence or higher valence with a valence of $k_5+1$, $k_6+1$, $k_7+1$ and $k_8+1$, respectively.

Said identical structure types, for example, all are tri-branched, tetrabranched, comb-like, dendritic, hyperbranched, or ring-containing structures. In one molecule, the structure of $G_5$, $G_6$, $G_7$ and $G_8$ can be the same or different; preferably $G_5=G_6=G_7=G_8$, wherein, $k_5=k_6=k_7=k_8$ and the structure type of $G_5$, $G_6$, $G_7$ and $G_8$ are the same.

Wherein, for typical example, $G_5$, $G_6$, $G_7$ and $G_8$ are each independently of a comb-like structure or of a hyperbranched structure.

Wherein, $G_5$, $G_6$, $G_7$ and $G_8$ each independently includes but is not limited to all comb-like structures in the above-said part 1.1.9.

Wherein, $G_5$, $G_6$, $G_7$ and $G_8$ each independently includes but is not limited to all hyperbranched structures in the above-said part 1.1.9, typically and preferably a combination of any of the following structures or derivatives thereof together with corresponding lower-valent groups thereof in a direct manner or in an indirect manner via one or more divalent spacer groups ($L_{10}$):

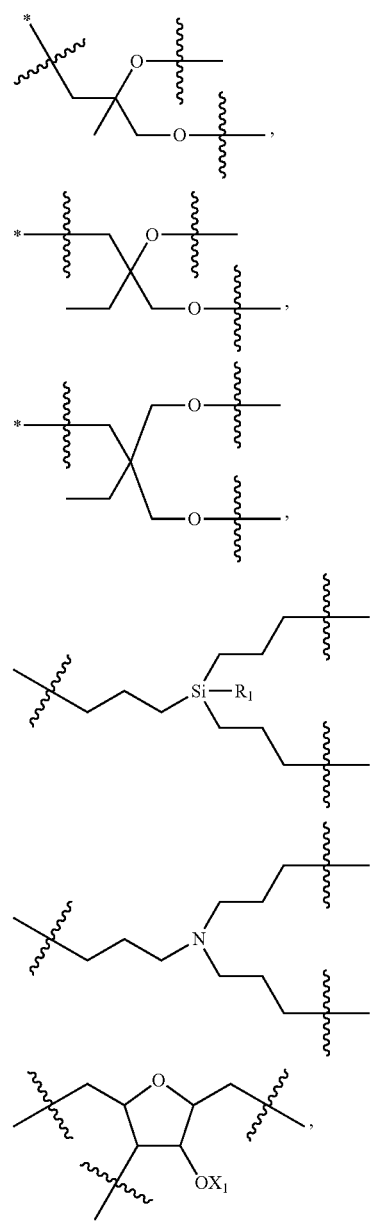

-continued

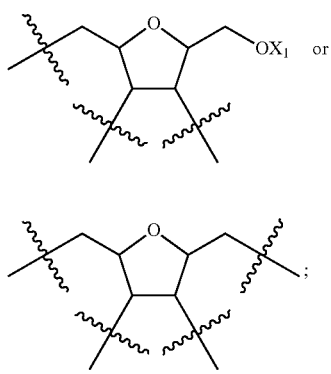

wherein, $X_1$ is a hydrogen atom or a $C_{1-6}$ alkyl group; $R_1$ is a $C_{1-6}$ alkyl group; wherein, the definition of $L_{10}$ is the same as above-mentioned, preferably an oxy group herein.

For example, as shown in the following structural units for a hyperbranched combination: the lower-valent groups of

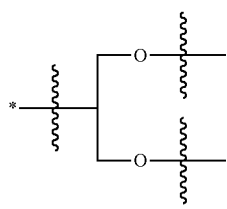

include

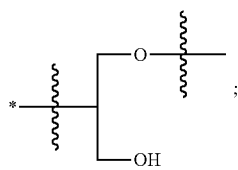

the lower-valent groups of

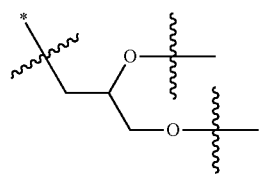

include

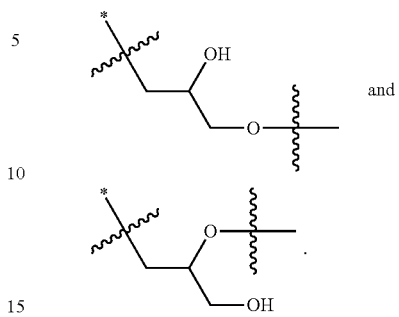

and

Examples also include hyperbranched structures with repeat units as follows:

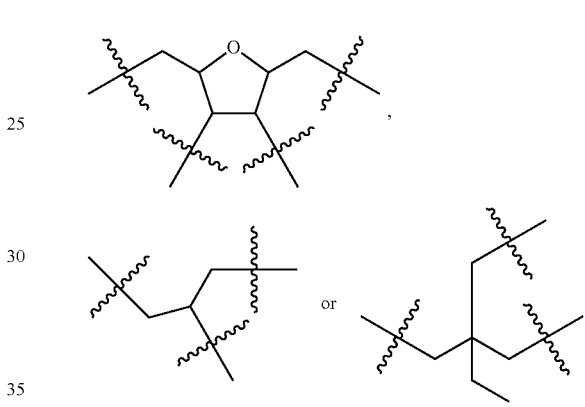

1.2. An H-Shaped Multifunctionalized Polyethylene Glycol is Disclosed in the Present Invention, and the General Formula is Represented by Formula (1).

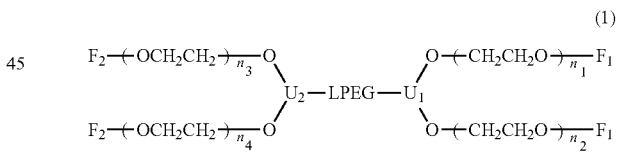

(1)

Wherein, the definitions of LPEG, $U_1$, $U_2$, $n_1$, $n_2$, $n_3$, $n_4$, $F_1$ and $F_2$ are the same as above-mentioned. PEG chains corresponding to $n_1$, $n_2$, $n_3$ and $n_4$ are polydisperse, and LPEG is monodisperse, and no more repeated here.

1.3. An H-Shaped Multifunctionalized Polyethylene Glycol is Disclosed in the Present Invention, and the General Formula is Represented by Formula (13).

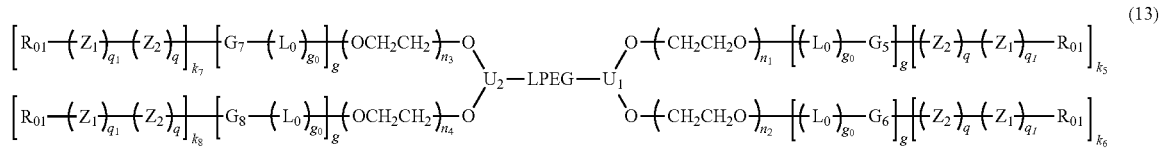

(13)

Wherein, the definitions of LPEG, $U_1$, $U_2$, $L_1$, $L_2$, $L_3$, $L_4$, $L_5$, $L_6$, $n_1$, $n_2$, $n_3$, $n_4$, $L_0$, $g_0$, $Z_2$, $q$, $Z_1$, $q_1$ and $R_{01}$ are the same as above-mentioned, and no more repeated here. Wherein, those in quantities of four or four more including $Z_2$, $q$, $Z_1$, $q_1$, $R_{01}$, $L_0$, $g_0$ and $g$ are each independently identical in one molecule; g is 0 or 1; $k_5$, $k_6$, $k_7$ and $k_8$ are each independently an integer of 1 or from 2 to 250, and can be identical or not identical in one molecule. The definitions of $G_5$, $G_6$, $G_7$ and $G_8$ are the same as G, each independently a linking group of trivalence or higher valence with a valence of $k_5+1$, $k_6+1$, $k_7+1$, $k_8+1$, respectively.

In one molecule, LPEG, $U_1$, $U_2$, $U_{01}$, $U_{02}$, $L_1$, $L_2$, $L_3$, $L_4$, $L_5$, $L_6$, $Z_1$, $Z_2$, $L_0$, $G_5$, $G_6$, $G_7$, $G_8$, and the joint linking group formed by any said group with its adjacent heterosubstituted group each independently can be either stable or degradable.

When g=0, then $k_5=k_6=k_7=k_8=1$, the structure can be represented by general formula (14), wherein $G_5$, $G_6$, $G_7$ and $G_8$ are absent; those in quantities of four or four more including $Z_2$, $q$, $Z_1$, $q_1$ and $R_{01}$ are each independently identical in one molecule.

When g=1, the structure can be represented by general formula (15), wherein, those in quantities of four or four more including $Z_2$, $q$, $Z_1$, $q_1$, $R_{01}$, $L_0$ and $g_0$ are each independently identical in one molecule; $k_5$, $k_6$, $k_7$ and $k_8$ are each independently an integer from 2 to 250; in one molecule, $G_5$, $G_6$, $G_7$ and $G_8$ have the same structure type.

When $G_5=G_6=G_7=G_8=G$ and $k_5=k_6=k_7=k_8=k$, general formula (15) can be equivalent to general formula (16), wherein, those in quantities of four or four more including $Z_2$, $q$, $Z_1$, $q_1$, $R_{01}$, $k$, $L_0$ and $g_0$ are each independently identical in one molecule; k is an integer from 2 to 250, and G is a linking group of trivalence or higher valence with a valence of k+1.

pyrrolidine-carboxylate group, an acetic acid, a propionic acid, a butyric acid, a pentanoic acid (also valeric acid), a hexanoic acid, an oxalic acid, a malonic acid, a methylmalonic acid, an ethylmalonic acid, a butylmalonic acid, a succinic acid, a 2-methylsuccinic acid, a 2,2-dimethylsuccinic acid, a 2-ethyl-2-methylsuccinic acid, a 2,3-dimethylsuccinic acid, a glutaric acid, a 2-methylglutaric acid, a 3-methylglutaric acid, a 2,2-dimethylglutaric acid, a 2,3-dimethylglutaric acid, a 3,3-dimethylglutaric acid, an adipic acid, a maleic acid, a fumaric acid, an amino acid (e.g., an amino-propionamide), a peptide acid, a poly(amino acid), a squaric acid (such as

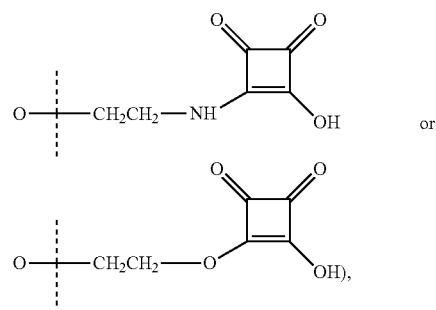

an acetaldehyde, a propionaldehyde, a butyraldehyde (also referred to a butanal), a pentanal, a hexanal, a benzaldehyde, a tolunaldehyde, a methanol, an ethanol, a propanol, a butanol, a pentanol, a hexanol, a propylene, a propyne, an ethanthiol, a propanthiol, a butanthiol, a pentanthiol, a hexanthiol, a propionitrile, a cyanacetic acid, a vinylsulfone,

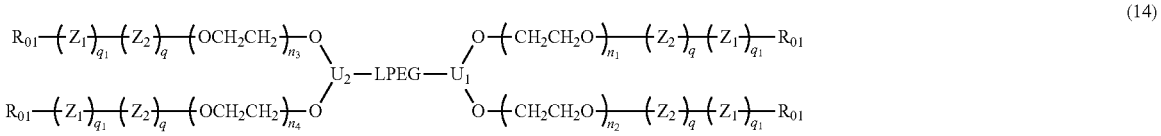

(14)

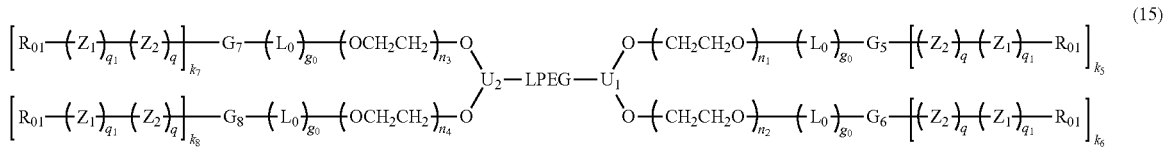

(15)

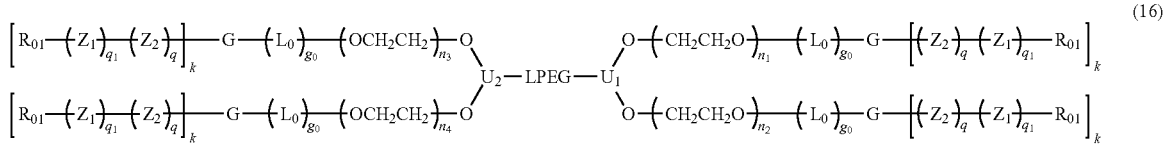

(16)

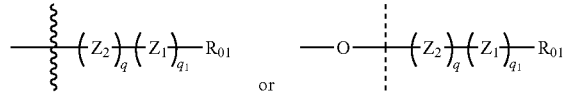

can be but is not limited to any functional group or protected form thereof, and the corresponding functionalized derivative is preferably the derivative of an active ester selected from the group consisting of a succinimidyl ester, a p-nitrophenyl ester, an o-nitrophenyl ester groups, a benzotriazole ester, a 1,3,5-trichlorophenyl ester, a 1,3,5-trifluorophenyl ester, a pentafluorophenyl ester, an imidazole ester, 2-thioxo-thiazolidine-3-carboxylate group and a 2-thioxoa vinyl sulfoxide, a p-methylphenylsulfone, a p-methylphenylsulfoxide, a vinylsulfonyl-ethyl group, a vinylsulfoxide-ethyl group, a p-methylphenylsulfonyl-ethyl group, a p-methylphenylsulfoxide-ethyl group, a p-methylbenzenesulfonate, a hydroxylamine, an azidoethyl group, an azidopropyl group, an azidobutyl group, an azidopentyl group, an azidohexyl group, an orthopyridyldisulfide group (such as

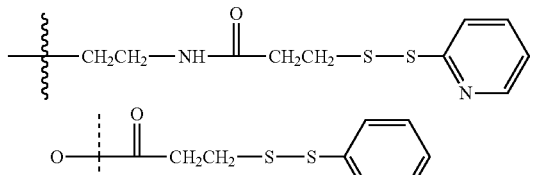

or a lipoic acid, an acetamide, a propanamide, a butyramide, a pentanamide, a hexanamide, an acethydrazide, a daminozide, a pentanehydrazide, a hexanohydrazide, an acetylhydroxylamine, a propionylhydroxylamine, a butyrylhydroxylamine, a pentanoylhydroxylamine, a hexanoylhydroxylamine, a heptanoylhydroxylamine, an isoxazolylethyl group, a tetrazolylethyl group, an isocyanatoethyl group, an isothiocyanatoethyl group, a glycidyl group

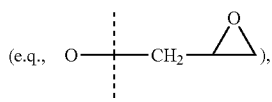

a maleimide (such as

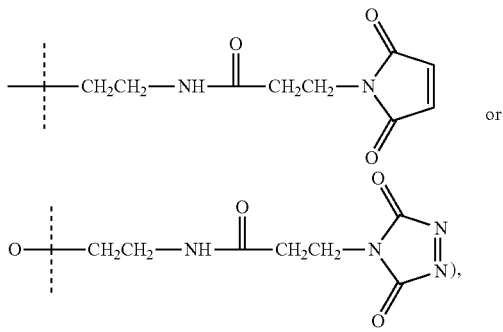

or an acrylate, a methyl acrylate, a propynoate, a squarate, a carbonate, a trithiocarbonate-ethyl group, an acetate, an ethanethioate, an alkyloxy(thiocarbonyl) group, an alkylthio(thiocarbonyl) group, a chloroformyloxy group, an acetylchloride, an acetylbromide, an iodoacetamidopropyl group, an ethylamine, a propylamine, a butylamine, a pentylamine, a hexylamine, amino acid esters (containing an N-amino group of amino acids) and the like containing a reactive group, or preferably contains a reactive group selected from the group consisting of a cyclooctenyl group, a norbornenyl-azo group, a diazo group (such as

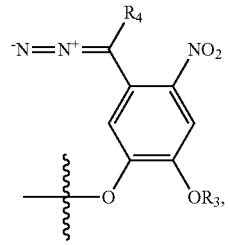

wherein, $R_3$ is a methyl group, and $R_4$ is a methyl group or a hydrogen atom), a dienyl group, a dienylhydrocarbyl group, a tetrazolyl group, a cyclopentadienyl group, a 2,5-norbomadienyl group, a dicycloheptadienyl group, a 7-oxabicyclo[2.2.1]hept-5-en-2-yl group, a furyl group, a 1,2,4,5-tetrazinyl group, a cycloalkynyl group, a benzocycloalkynyl group and the like containing an unsaturated group; wherein, said active ester can be but not limited to an active ester of a carbonate, an acetate, a propionate, a butyrate, a pentanoate, a hexanoate, a heptanoate, an octanoate, a nonanoate (e.g., pelargonate), a decanoate (e.g., caprate), an oxalate, a malonate, a methylmalonate, an ethylmalonate, a butylmalonate, a succinate, a 2-methylsuccinate, a 2,2-dimethylsuccinate, a 2-ethyl-2-methyl-succinate, a 2,3-dimethylsuccinate, a glutarate, a 2-methylglutarate, a 3-methylglutarate, a 2,2-dimethylglutarate, a 2,3-dimethylglutarate, a 3,3-dimethylglutarate, an adipate, a pimelate, a suberate, an azelate, a sebacate, a maleate, a fumarate, an amino acid ester, a peptide ester, a poly(amino acid) ester or the like.

1.4. An H-shaped multifunctionalized polyethylene glycol is disclosed in the present invention, and the general formula is represented by formula (10). Wherein, the definitions of $U_1$, $U_2$, $n_1$, $n_2$, $n_3$, $n_4$, $m_2$, $Z_2$, $q$, $Z_1$, $q_1$ and $R_{01}$ are the same as those in the general formula (4), and no more repeated here. Wherein, those in quantities of four or four more including $Z_2$, $q$, $Z_1$, $q_1$ and $R_{01}$ are each independently identical in one molecule.

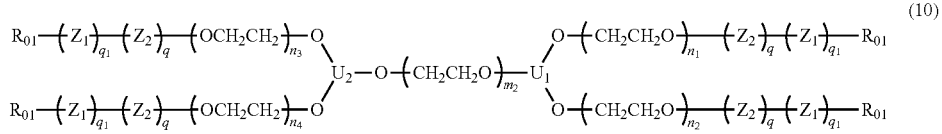

(10)

In one molecule, $U_1$, $U_2$, $U_{01}$, $U_{02}$, $L_1$, $L_2$, $L_3$, $L_4$, $L_5$, $L_6$, $Z_1$, $Z_2$, and the joint linking group formed by any said group with its adjacent heterosubstituted group each independently can be either stable or degradable.

1.5. An H-shaped multifunctionalized polyethylene glycol is disclosed in the present invention, and the general formula is represented by formula (17). Wherein, the definitions of $U_1$, $U_2$, $n_1$, $n_2$, $n_3$, $n_4$, $m_2$, $Z_2$, $q$, $Z_1$, $q_1$, $R_{01}$, $L_0$, $g_0$, $G$ and $k$ are the same as those in the general formula (4), and no more repeated here.

(17)

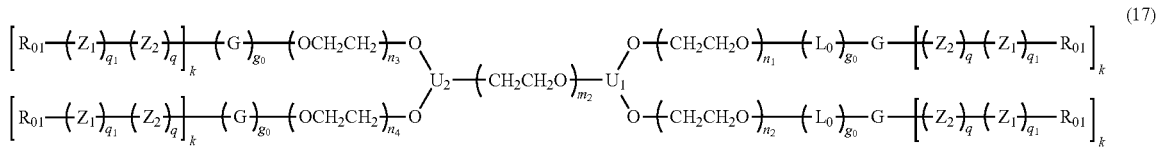

In one molecule, $U_1$, $U_2$, $U_{01}$, $U_{02}$, $L_1$, $L_2$, $L_3$, $L_4$, $L_5$, $L_6$, $Z_1$, $Z_2$, $L_0$, G, and the joint linking group formed by any said group with its adjacent heterosubstituted group each independently can be either stable or degradable. Wherein, those in quantities of four or four more including $Z_2$, q, $Z_1$, $q_1$, $R_{01}$ $L_0$, and k are each independently identical in one molecule; G is a linking group of trivalence or higher valence with a valence of k+1; k is an integer from 2 to 250.

1.6. An H-shaped multifunctionalized polyethylene glycol is disclosed in the present invention, and the general formula is represented by formula (18). Wherein, the definitions of $U_1$, $U_2$, $n_1$, $n_2$, $n_3$, $n_4$, $m_2$, $Z_2$, q, $Z_1$, $q_1$, $R_{01}$, $L_0$, $g_0$, G and k are the same as those in the general formula (4), and no more repeated here.

(18)

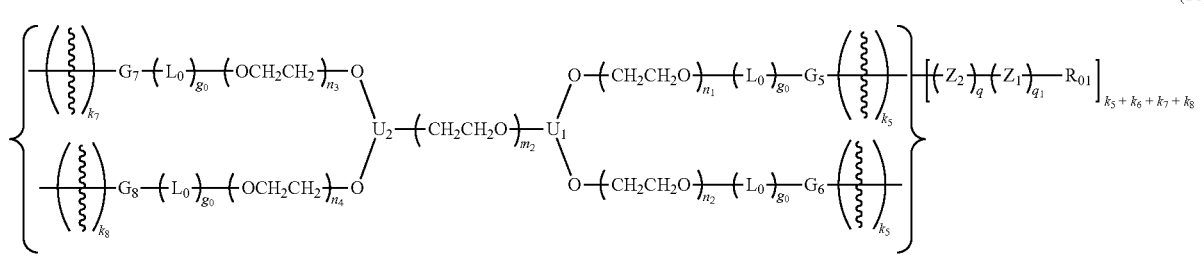

Wherein, the definitions of $U_1$, $U_2$, $n_1$, $n_2$, $n_3$, $n_4$, $m_2$, $Z_2$, q, $Z_1$, $q_1$ and $R_{01}$ are the same as those in the general formula (4), and no more repeated here. Wherein, those in quantities of four or four more including $Z_2$, q, $Z_1$, $q_1$, $R_{01}$, $L_0$ and $g_0$ are each independently identical in one molecule; $k_5$, $k_6$, $k_7$ and $k_8$ are each independently an integer from 2 to 250, and can be identical or not identical in one molecule; the definitions of $G_5$, $G_6$, $G_7$ and $G_8$ are the same as G, each independently a linking group of trivalence or higher valence with a valence of $k_5+1$, $k_6+1$, $k_7+1$, $k_8+1$, respectively; in one molecule, the structure type of $G_5$, $G_6$, $G_7$ and $G_8$ are the same.

In one molecule, $U_1$, $U_2$, $U_{01}$, $U_{02}$, $L_1$, $L_2$, $L_3$, $L_4$, $L_5$, $L_6$, $Z_1$, $Z_2$, $L_0$, $G_5$, $G_6$, $G_7$, $G_8$, and the joint linking group formed by any said group with its adjacent heterosubstituted group each independently can be either stable or degradable.

1.7. An H-shaped multifunctionalized polyethylene glycol is disclosed in the present invention, and the general formula is represented by formula (19), (20) or (21). Wherein, the definitions of LPEG, $U_1$, $U_2$, $L_1$, $L_2$, $L_3$, $L_4$, $L_5$, $L_6$, $n_1$, $n_2$, $n_3$, $n_4$, $L_0$, $g_0$, $Z_2$, q, $Z_1$, $q_1$ and $R_{01}$ are the same as above-mentioned, and no more repeated here. Wherein, the definitions of $L_{02}$, $g_{02}$, $Z_8$, $q_8$, $Z_7$, $q_7$ and $R_{02}$ are the same as $L_0$, $g_0$, $Z_2$, q, $Z_1$, $q_1$ and $R_{01}$, respectively. $k_5$, $k_6$, $k_7$ and $k_8$ are each independently an integer from 2 to 250, and can be identical or not identical in one molecule. The definitions of $G_5$, $G_6$, $G_7$ and $G_8$ are the same as G, each independently a linking group of trivalence or higher valence with a valence of $k_5+1$, $k_6+1$, $k_7+1$, $k_8+1$, respectively.

(19)

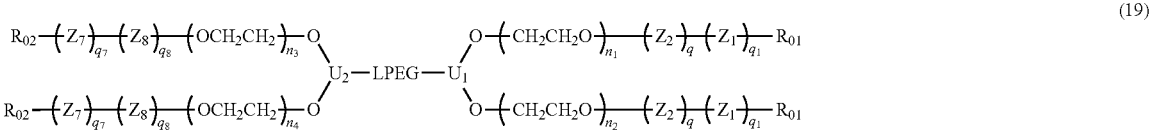

(20)

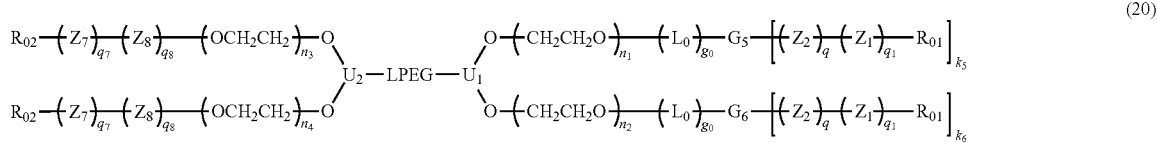

-continued

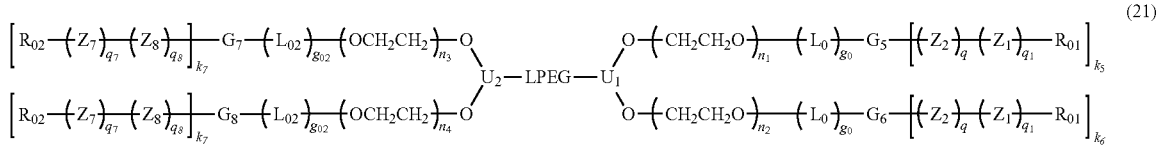
(21)

Wherein, in general formula (19), those in quantities of two or two more including $Z_2$, q, $Z_1$, $q_1$, $R_{O1}$, $Z_8$, $q_8$, $Z_7$, $q_7$ and $R_{O2}$ are each independently identical in one molecule.

Wherein, in general formula (20), those in quantities of two or two more including $Z_2$, q, $Z_1$, $q_1$, $R_{O1}$, $Z_8$, $q_8$, $Z_7$, $q_7$, $R_{O2}$, $L_0$ and $g_0$ are each independently identical in one molecule.

Wherein, in general formula (21), those in quantities of two or two more including $Z_2$, q, $Z_1$, $q_1$, $R_{O1}$, $Z_8$, $q_8$, $Z_7$, $q_7$, $R_{O2}$, $L_0$, $g_0$, $L_{O2}$ and $g_{O2}$ are each independently identical in one molecule.

In one molecule, the structure type of $G_5$ and $G_6$ are the same, and preferably $G_5$ is identical to $G_6$ wherein $k_5$ is equal to $k_6$; the structure type of $G_7$ and $G_8$ are the same, and preferably $G_7$ is identical to $G_8$ wherein $k_7$ is equal to $k_8$. The structure type of $G_5$ and $G_7$ can be the same or different from each other.

In one molecule, $L_{O2}$ and $L_0$, $g_{O2}$ and $g_0$, $Z_8$ and $Z_2$, $q_8$ and q, $Z_7$ and $Z_1$, $q_7$ and $q_1$, $R_{O2}$ and $R_{O1}$ are each independently the same or different from each other respectively, and

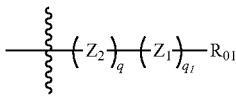

is different from

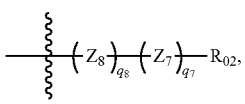

further preferably $R_{O1}$ is different from $R_{O2}$. Wherein, the heterofunctional-group pair ($R_{O1}$, $R_{O2}$) includes but is not limited to those listed in above-said part 1.1.4.

In one molecule, LPEG, $U_1$, $U_2$, $U_{O1}$, $U_{O2}$, $L_1$, $L_2$, $L_3$, $L_4$, $L_5$, $L_6$, $Z_1$, $Z_2$, $L_0$, $G_5$, $G_6$, $G_7$, $G_8$, $L_{O2}$, $Z_8$, $Z_7$, and the joint linking group formed by any said group with its adjacent heterosubstituted group each independently can be either stable or degradable.

1.8. An H-shaped multifunctionalized polyethylene glycol is disclosed in the present invention, and the general formula is represented by formula (22).

Wherein, the definitions of LPEG, $U_1$, $U_2$, $L_1$, $L_2$, $L_3$, $L_4$, $L_5$, $L_6$, $n_1$, $n_2$, $n_3$, $n_4$, $L_0$, $g_0$, $Z_2$, q, $Z_1$, $q_1$, $R_{O1}$, $L_{O2}$, $g_{O2}$, $Z_8$, $q_8$, $Z_7$, $q_7$ and $R_{O2}$ are the same as above-mentioned, and no more repeated here.

Wherein, those in quantities of two including those in quantities of two or two more including $Z_2$, q, $Z_1$, $q_1$, $R_{O1}$, $Z_8$, $q_8$, $Z_7$, $q_7$, $R_{O2}$, $L_0$, $g_0$, $L_{O2}$ and $g_{O2}$ are each independently identical in one molecule.

Wherein, $g_1$ and $g_2$ are each independently 0 or 1, and can be the same or different from each other in one molecule.

Wherein, $k_5$, $k_6$, $k_7$ and $k_8$ are each independently an integer of 1 or from 2 to 250.

When $g_1=0$, $k_5=k_6=1$. When $g_1=1$, $k_5$ and $k_6$ are each independently an integer from 2 to 250, and can be the same or different from each other in one molecule, preferably $k_5$ and $k_6$ are equal.

When $g_2=0$, $k_7=k_8=1$. When $g_2=1$, $k_7$ and $k_8$ are each independently an integer from 2 to 250, and can be the same or different from each other in one molecule, preferably $k_7$ and $k_8$ are equal.

The definitions of $G_5$, $G_6$, $G_7$ and $G_8$ are the same as G, each independently a linking group of trivalence or higher valence with a valence of $k_5+1$, $k_6+1$, $k_7+1$, $k_8+1$, respectively.

In one molecule, the structure type of $G_5$ and $G_6$ are the same, preferably $G_5$ and $G_6$ are identical wherein $k_5$ and $k_6$ are equal; the structure type of $G_7$ and $G_8$ are the same, preferably $G_7$ and $G_8$ are equal wherein $k_7=k_8$. The structure type of $G_5$ and $G_7$ can be the same or different from each other.

In one molecule, LPEG, $U_1$, $U_2$, $U_{O1}$, $U_{O2}$, $L_1$, $L_2$, $L_3$, $L_4$, $L_5$, $L_6$, $Z_1$, $Z_2$, $L_0$, $G_5$, $G_6$, $G_7$, $G_8$, $L_{O2}$, $Z_8$, $Z_7$, and the joint linking group formed by any said group with its adjacent heterosubstituted group each independently can be either stable or degradable.

Wherein, $R_{O1}$ and $R_{O2}$ are each independently an unprotected functional group and they are different.

Wherein, at least one of $R_{O1}$ and $R_{O2}$ is a hydroxyl group, a protected hydroxyl group, a targeting group or a photosensitive group, and the other one is an unprotected or protected functional end-group which is different from the former one, so as to obtain a heterofunctional pair ($R_{O1}$, $R_{O2}$); preferable manners of these heterofunctional pairs are the same as those in part 1.3.

For instance, provided that one of $R_{O1}$ and $R_{O2}$ is a hydroxyl group, when $g_1=g_2=0$, general formula (22) can be equivalent to general formula (23). When $g_1=1$ and $g_2=0$,

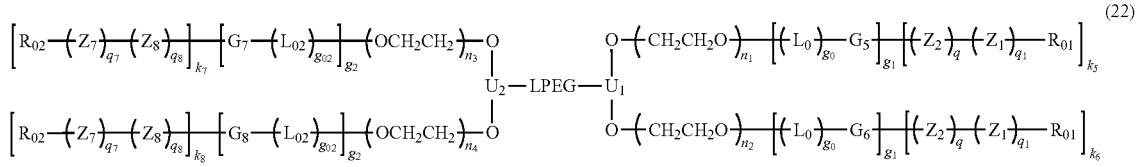
(22)

general formula (22) can be equivalent to general formula (24) or (25). When $g_1=g_2=1$, general formula (22) can be equivalent to general formula (26).

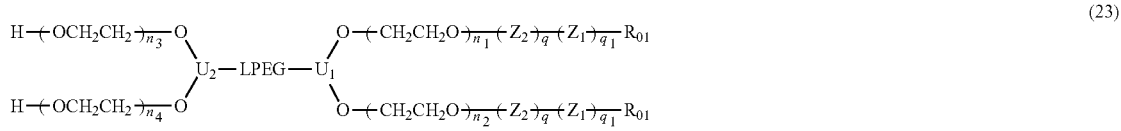

(23)

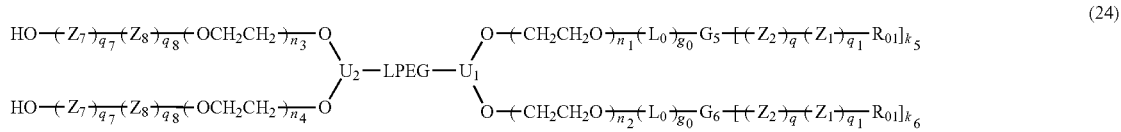

(24)

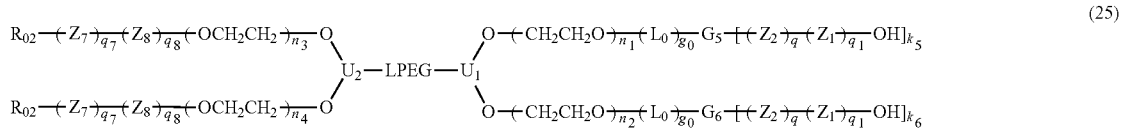

(25)

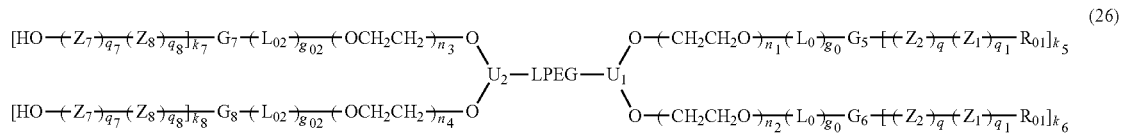

(26)

The above-said hydroxyl group and protected hydroxyl group are not particularly limited, including but not limited to functional groups and protected forms thereof in above-said Group H.

The targeting groups are not particularly limited, including but not limited to functional groups above-listed in Group I, polypeptide ligands, small molecule ligands, other ligands and ligand variants that can be recognized by cell surface receptors, ligands targeting tumor-associated angiogenesis, ligands targeting tumor cell apoptosis, disease cell cycle targeting ligands, disease receptor targeting ligands, kinase inhibitors or protease inhibitors, PI3K/Akt/mTOR inhibitors, angiogenesis inhibitors, cytoskeletal signaling inhibitors, stem cells and Wnt-inhibitors, protease inhibitors, tyrosine kinase inhibitors, apoptosis inhibitors, MAPK inhibitors, cell cycle inhibitors, TGF-beta/Smad inhibitors, nerve signal inhibiting peptides, endocrine and hormone inhibitors, metabolic inhibitors, microbial inhibitors, epigenetic inhibitors, JAK/STAT inhibitors, DNA damage inhibitors, NF-κB inhibitors, GPCR & G protein inhibitors, transmembrane transport protein inhibitors, autophagy inhibitors, ubiquitin inhibitors, multitarget inhibitors, receptors, antibodies, gene targeting molecules, viruses, vaccines, biomacromolecular targeting factors, vitamins, targeting drugs and the like.

The source of the targeting molecule can be a monomer (i.e., itself), a dimer, a multimer, a subunit and fragments thereof, a precursor, an activated form, a derivative, an isomer, a mutant, an analogue, a mimetics, a polymorph, a pharmaceutically acceptable salt, a fusion protein, a chemically modified substance, a genetic recombinant substance or the like, and can also be a corresponding agonist, activating agent, activator, inhibitor, antagonist, modulator, receptor, ligand or aptamer, antibody and fragment thereof or the like. Prior to or after combing a functionalized polyethylene glycol, the targeting molecule is allowed to covalently contain given molecules, tags or delivery carriers.

The target sites of targeting factors include but are not limited to CD3, CD11, CD20, CD22, CD25, CD30, CD33, CD41, CD44, CD52, CD6, CD3, CD11a, Her2, GpIIb/IIIa, RANKL, CTLA-4, CO17-1A, IL-1β, IL-12/23, IL6, IL13, IL-17, Blys, RSV, IgE-25, integrin-α4, respiratory syncytial virus F-protein, tumor necrosis factor α (TNFα), vascular endothelial growth factors, epidermal growth factor receptors (EGFR), FGR3, EGFL-7, interferon-α and the like.

Targeting factors are not particularly limited. They can have a single or multiple target sites (mono-target or multi-target). They can be an individual molecule or a conjugate of multiple molecules. The targeting factors can be themselves, molecules modified with targeting factors, conjugates of multiple molecules, self-assembled substances, nanoparticles, liposomes, vesicles, drugs, etc.

The target sites are not particularly limited, including but not limited to brain, lung, kidney, stomach, liver, pancreas, breast, prostate, thyroid, uterus, ovary, nasopharynx, esophagus, rectum, colon, small intestine, gall bladder, bladder, bone, glands, skin, blood vessel, lymph, joints, soft tissues and other sites.

The target tissues are not specifically limited, including but not limited to tumor tissue, inflammatory tissue, diseased tissue, etc.

Specific examples of targeting factors include but are not limited to:

Peptide ligands, such as RGD peptides and RGD cyclic peptides, LPR peptides, NGR peptides, tumor vascular targeting peptide GX1, transferrin receptor binding peptide, GE11, H24, LINGO-1 peptide, somatostatin analogue RC160, bombesin, gastrin-releasing peptides (e.g., GRP peptide), SynB3 decapeptide, oligopeptide (K) 16GRGD-SPC, dhvar5, FHS001, octreotide, cell-penetrating peptides CPPs (such as TAT peptide and ACPP peptide), vasoactive intestinal peptide (VIP), LyP-1 (CGNKRTRGC), angiogenic homing peptides (e.g., GPLPLR and APRPG), Angiopep-2, F3 peptide, PR-b peptide, ARA peptide, etc.;

Small molecule ligands, such as carnitine, doxorubicin, amifostine, bortezomib, bile acids (such as cisplatin-glycocholiate chelates, cisplatin-ursodeoxycholate chelates), GDC-0449, triptolide, etc.;

Ligands and ligand variants that can be recognized by cell surface receptors, such as phosphorescent iridium complexes targeting integrin αvβ3 on tumor cell surfaces, tumor-targeting tumor necrosis factor-related apoptosis-inducing ligand variants and so on;

Tumor angiogenesis targeting ligands, for example, include endogenous anti-angiogenic molecules (e.g., angiostatin), endostatin (e.g., endostar), fumagillin derivatives (TNP-470), thalidomide, cyclooxygenase-2 (COX-2), zactima (ZD6474), NGR, COX-2, anti-EGF, herceptin, angiostatin, cadherin antagonists, alphastatin, PSMA, anti-CD44, endoglin, endosialin, matrix metalloproteinase (such as MMP2 and MMP9), VCAM-1 E-selectin, tissue factor phosphatidylserine, cediramb and the like;

Disease cell cycle targeting ligands, such as adenosine, penciclovir, FIAU, FIRU, IVFRU, GCV, PCV, FGCV, FPCV, PHPG, PHBG, guanine and the like;

Tumor cell apoptosis targeting ligands include but are not limited to TRAIL, caspase-3, etc.;

Disease receptor targeting ligands, such as estrogen, testosterone, luteinizing hormone, transferrin, progesterone, etc., Kinase inhibitors or protease inhibitors include tyrosine kinase inhibitors (e.g., imatinib, gefitinib, erlotinib, sorafenib, dasatinib, sunitinib, lapatinib, nilotinib, pazopanib, vandetanib and the like;

PI3K/Akt/mTOR inhibitors, include but are not limited to ATM/ATR inhibitors (such as KU-55933 (ATM kinase inhibitor), KU-55933, KU-60019, VE-821, CP-466722, VE-822, AZ20, ETP-46464, chloroquine phosphate and CGK 733), PI3K inhibitors (such as PI-103, GDC-0980, CH5132799, CAL-101, GDC-0941, LY294002, BKM120, HS-173, CZC24832, NU7441, TGX-221, IC-87114, Wortmannin, XL147, ZSTK474, BYL719, AS-605240, PIK-75, 3-methyladenine, A66, PIK-93, PIK-90, AZD6482, GDC-0980, IPI-145, TG100-115, AS-252424, CUDC-907, PIK-294, AS-604850, GSK2636771, BAY 80-6946, YM201636, CH5132799, CAY10505, PIK-293 and TG100713), mTOR inhibitors (such as CCI-779, ridaforolimus, rapamycin, everolimus, AZD8055, KU-0063794, XL388, PP242, INK128, Torin 1, GSK2126458, OSI-027, WYE-354, AZD2014, Torin 2, WYE-125132, Palomid 529, WYE-687, WAY-600, chrysophanic acid and GDC-0349), Akt inhibitors (such as A-674563, MK-2206, perifosine, GSK690693, ipatasertib, AZD5363, PF-04691502, AT7867, triciribine, CCT128930, PHT-427, miltefosine, honokiol, TIC10 and triciribine phosphate), GSK-3 inhibitors (such as CHIR-99021 HCl, SB216763, CHIR-98014, TWS119, tideglusib, 1-azakenpaullone, AR-A014418, BIO, AZD2858, SB415286, AZD1080 and indirubin), DNA-PK inhibitors (such as NU7441, NU7026, KU-0060648 and PIK-75), PDK-1 inhibitors (such as OSU-03012, BX-795, BX-912 and GSK2334470), S6 kinase inhibitors (such as BI-D1870 and PF-4708671);

Angiogenesis inhibitors, include but are not limited to Bcr-Abl inhibitors (such as imatinib, punatinib, nilotinib, saracatinib, degrasyn, dasatinib, bafetinib, PD173955, GNF-5, danusertib, DCC-2036, GNF-2, GZD824, etc.), Src inhibitors (such as dasatinib, saracatinib, bosutinib, KX2-391, PP2 and PP1), vascular endothelial growth factor receptor inhibitors (e.g., endostatin, simvastatin, squalamine, thalidomide, combretastatin A-4 disodium phosphate, Endostar, vandetanib, vatalanib, bevacizumab, PTK787/ZK2222584, apatinib, thrombospondins, SU5416, Orantinib, ZD4190, Zactima, AEE788, enzastaurin, motesanib, cabozantinib, cediranib, nintedanib, SKLB1002, foretinib, linifanib, RAF265, brivanib, OSI-930, Ki8751, telatinib, semaxanib, ZM 306416, ZM 323881 HCl, tivozanib/AV-951, etc.), EGFR inhibitors (such as erlotinib HCl, gefitinib, afatinib, canertinib, lapatinib, AZD9291, CO-1686, AG-1478/tyrphostin, neratinib, AG-490, CP-724714, dacomitinib/PF299804, WZ4002, AZD8931/sapitinib, PD153035 HCl, pelitinib, AC480/BMS-599626, AEE788, OSI-420, WZ3146, WZ8040, ARRY-380, AST-1306, genistein, varlitinib, icotinib, desmethyl erlotinib, tyrphostin 9, CNX-2006, AG-18, etc.), anaplastic lymphoma kinase inhibitors (ALK inhibitors, such as TAE684, alectinib, LDK378, AP26113, GSK1838705A, ASP3026 and AZD3463), Syk inhibitors (such as R406, R788 (fostamatinib) disodium, PRT062607, fostamatinib, GS-9973 and piceatannol), HER2 inhibitors (such as CP-724714, sapitinib, mubritinib, AC480/BMS-599626, ARRY-380, etc.), fibroblast growth factor receptor inhibitors (FGFR inhibitors, such as BGJ398, PD173074, AZD4547, SSR128129E and brivanib alaninate), HIF inhibitors (such as FG-459, 2-methoxyestradiol, IOX2 and BAY 87-2243), VDA inhibitors (such as DMXAA/vadimezan and plinabulin), JAK inhibitors (such as ruxolitinib/INCB018424, tofacitinib, AZD1480, TG101348, GLPG0634, pacritinib, XL019, momelotinib, TG101209, LY2784544, NVP-BSK805 2HCl, baricitinib, AZ 960, CEP-33779, S-ruxolitinib and ZM 39923 HCl), platelet-derived growth factor receptor inhibitors (PDGFR inhibitors, such as crenolanib/CP-868596, CP-673451, nintedanib/BIBF 1120, masitinib/AB1010, TSU-68/SU6668/orantinib and tyrphostin AG 1296), FLT3 inhibitors (such as quizartinib, tandutinib, KW-2449, TCS 359, ENMD-2076 and L-(+)-tartaric acid), FAK inhibitors (such as PF-00562271, PF-562271, PF-573228, TAE226 and PF-562271 HCl), BTK inhibitors (such as ibrutinib, AVL-292, CNX-774 and CGI1746);

Cell skeleton signal inhibitors, include integrin inhibitors (such as cilengitide and RGD (Arg-Gly-Asp) peptides), dynamin inhibitors (such as dynasore and Mdivi-1), Bcr-Abl inhibitor, Wnt/beta-catenin inhibitors (such as XAV-939, ICG-001, IWR-1-endo, Wnt-C59, LGK-974, FH535, IWP-2, IWP-L6 and KY02111), PAK inhibitors (such as IPA-3 and PF-3758309), Akt inhibitors, HSP inhibitors (such as HSP90 inhibitors, e.g., tanespimycin, AUY922, alvespimycin, ganetespib, elesclomol, VER-50589, CH5138303, PU-H71, NMS-E973, VER-49009, BIIB021, AT13387, NVP-BEP800, geldanamycin, SNX-2112, PF-04929113, KW-2478 and XL888), kinesin inhibitors (such as ispinesib, SB743921, GSK923295, and MPI-0479605), tubulin-related inhibitors (such as paclitaxel, docetaxel, vincristine, epothilone B, ABT-751, INH6, INH1, vinorelbine tartrate, CK-636, CW069, nocodazole, vinblastine, CYT997, epothilone, fosbretabulin, vinflunine tartrate and griseofulvin), PKC inhibitors (such as enzastaurin, sotrastaurin, staurosporine, Go 6983, GF109203X, Ro 31-8220 mesylate and dequalinium chloride), FAK inhibitor;

Stem cells and Wnt inhibitors, include but are not limited to Wnt/beta-catenin inhibitor, Hedgehog/Smoothened inhibitors (e.g., vismodegib, cyclopamine, LDE225, LY2940680, purmorphamine, BMS-833923, PF-5274857, GANT61 and SANT-1), GSK-3 inhibitors (e.g., CHIR-99021, CHIR-99021, CHIR-98014, TWS119, tideglusib, AR-A014418, AZD2858 and SB415286), JAK inhibitor, STAT inhibitors (e.g., S3I-201, fludarabine, niclosamide, Stattic, cryptotanshinone and HO-3867), ROCK inhibitors (e.g., Y-27632 2HCl, thiazovivin, GSK429286A and RKI-1447), TGF-beta/Smad inhibitors (e.g., SB431542, LY2157299, LY2109761, SB525334, DMH1, LDN-212854, ML347, LDN193189 HCl, K02288, SB505124, pirfenidone, GW788388, LY364947 and RepSox), γ-secretase inhibitors (e.g., DAPT, RO4929097, semagacestat, MK-0752, avagacestat, FLI-06, YO-01027 and LY411575);

Protease inhibitors, include but are not limited to DPP-4 inhibitors (e.g., sitagliptin phosphate monohydrate, linagliptin, vildagliptin, glimepiride, saxagliptin, trelagliptin and alogliptin), HIV protease inhibitors (e.g., ritonavir, lopinavir, atazanavir sulfate, darunavir ethanolate, amprenavir amd nelfinavir mesylate), MMP inhibitors (e.g., sulfamerazine, batimastat, NSC 405020, ilomastat and SB-3CT), caspase inhibitors (e.g., VX-765, PAC-1, apoptosis activator 2, tasisulam and Z-VAD-FMK), serine protease inhibitors (e.g., Avelestat, AEBSF HCl, aprotinin and gabexate mesylate), γ-secretase inhibitor, proteasome inhibitors (such as bortezomib, MG-132, carfilzomib, MLN9708, MLN2238, PI-1840, ONX-0914, oprozomib, CEP-18770 and nafamostat mesylate), HCV protease inhibitors (e.g., daclatasvir, telaprevir, VX-222 and danoprevir), cysteine protease inhibitors (e.g., odanacatib, E-64, aloxistatin, Z-FA-FMK, loxistatin Acid (E-64C), leupeptin hemisulfate), Fms-like tyrosine kinase inhibitors, Aurora kinase inhibitors, Abelson kinase inhibitors and the like;

Tyrosine kinase inhibitors, include but are not limited to Axl inhibitors (e.g., R428/BGB324, BMS-777607 and cabozantinib malate), c-kit inhibitors (such as dasatinib), Tie-2 inhibitors (such as Tie2 kinase inhibitor), CSF-1R inhibitors (e.g., GW2580), ephrin receptor inhibitors, vascular endothelial growth factor receptor inhibitors, EGFR inhibitors, IGF-1R inhibitors (e.g., OSI-906, NVP-AEW541, GSK1904529A, NVP-ADW742, BMS-536924, GSK1838705A, AG-1024, BMS-754807 and PQ 401), c-Met inhibitors (e.g., crizotinib, foretinib, PHA-665752, SU11274, SGX-523, EMD 1214063, JNJ-38877605, tivantinib, PF-04217903, INCB28060, BMS-794833, AMG-208, AMG-458 and NVP-BVU972), ALK inhibitors, HER2 inhibitors, FGFR inhibitors, PDGFR inhibitors, c-RET inhibitors, FLT3 inhibitors, Trk receptor inhibitors (e.g., GW441756);

Cell apoptosis inhibitors, include but are not limited to Caspase inhibitor, Bcl-2 inhibitors (e.g., ABT-737, ABT-263, obatoclax mesylate, TW-37, ABT-199, AT101, HA14-1 and BAM7), p53 inhibitors (e.g., JNJ-26854165, pifithrin-α, RITA, Tenovin-1, NSC 319726, Tenovin-6, pifithrin-μ and NSC 207895), survivin inhibitors (e.g., YM155), TNF-alpha inhibitors (e.g., lenalidomide, pomalidomide, thalidomide, necrostatin-1 and QNZ), PERK inhibitors (e.g., GSK2606414, GSK2656157 and ISRIB), Mdm2 inhibitors (e.g., nutlin-3, nutlin-3a, nutlin-3b and YH239-EE), c-RET inhibitor, IAP inhibitors (e.g., birinapant, GDC-0152, embelin and BV6);

MAPK inhibitors, include but are not limited to Raf inhibitors (e.g., vemurafenib, PLX-4720, dabrafenib, GDC-0879, encorafenib, TAK-632, SB590885, ZM 336372, GW5074 and Raf265 derivative), ERK inhibitors (e.g., XMD8-92, SCH772984 and FR 180204), MEK inhibitors (e.g., selumetinib, PD0325901, trametinib, U0126-EtOH, PD184352, RDEA119, MEK162, PD98059, BIX 02189 and pimasertib), p38 MAPK inhibitors (e.g., SB203580, BIRB 796, SB202190, LY2228820, VX-702, losmapimod, skepinone-L, PH-797804, VX-745, TAK-715 and asiatic acid), JNK inhibitors (e.g., SP600125, JNK-IN-8 and JNK inhibitor IX);

Cell cycle inhibitors, include but are not limited to c-Myc inhibitors (e.g., 10058-F4), Wee1 inhibitors (e.g., MK-1775), Rho inhibitors (e.g., zoledronic Acid, NSC 23766, EHop-016, ZCL278, K-Ras(G12C) inhibitor 6 and EHT 1864), Aurora kinase inhibitors (e.g., Alisertib, VX-680, barasertib, ZM 447439, MLN8054, danusertib, hesperadin, Aurora A inhibitor, SNS-314 mesylate, PHA-680632, MK-5108, AMG-900, CCT129202, PF-03814735, GSK1070916, TAK-901 and CCT137690), CDK inhibitors (e.g., palbociclib, roscovitine, SNS-032, dinaciclib, flavopiridol, XL413, LDC000067, ML167, LEE011, TG003, AT7519, flavopiridol HCl, JNJ-7706621, AZD5438, MK-8776, PHA-793887, BS-181 HCl, palbociclib, A-674563, LY2835219, BMS-265246, PHA-767491, milciclib, R547, NU6027 and P276-00), Chk inhibitors (e.g., AZD7762, LY2603618, MK-8776 and CHIR-124), ROCK inhibitor, PLK inhibitors (e.g., BI 2536, volasertib, rigosertib, GSK461364, HMN-214, Ro3280 and MLN0905), APC inhibitors (e.g., TAME);

TGF-beta/Smad inhibitors, include but are not limited to Bcr-ablinhibitors, ROCK inhibitors, TGF-beta/Smad inhibitors and PKC inhibitors;

Nerve signaling inhibitors, include BACE inhibitors (e.g., LY2811376), dopamine receptor inhibitors (e.g., quetiapine fumarate, benztropine mesylate, chlorpromazine HCl, amantadine HCl, domperidone, alizapride, olanzapine, amfebutamone HCl, amisulpride, paliperidone, rotundine, chlorprothixene, pramipexole 2HCl monohydrate, levosulpiride, lurasidone HCl, pramipexole, dopamine HCl, pergolide mesylate and PD128907 HCl), COX inhibitors (e.g., celecoxib, ibuprofen, rofecoxib, bufexamac, piroxicam, etodolac, ketoprofen, diclofenac sodium, ibuprofen lysine, ketorolac, naproxen, lornoxicam, lumiracoxib, asaraldehyde, acemetacin, tolfenamic acid, zaltoprofe, valdecoxib, phenacetin, nimesulide, licofelone, nabumetone, flunixin meglumin, triflusal, ampiroxicam and mefenamic acid), GluR inhibitors (e.g., LY404039, MK-801, (−)-MK 801 maleate, CTEP, riluzole, ADX-47273, ifenprodil, VU 0357121, MPEP, IEM 1754 dihydrobromide, NMDA, VU 0364439, VU 0364770 and VU 0361737), γ-aminobutyric acid receptor inhibitors (e.g., valproic acid sodium salt, flumazenil, gabapentin HCl, etomidate, gabapentin, (+)-bicuculline, nefiracetam, niflumic acid, (R)-baclofen and ginkgolide A), γ-secretase inhibitor, adrenergic receptor inhibitors (e.g., salbutamol sulfate, doxazosin mesylate, doxazosin mesylate, mirabegron, alfuzosin HCl, carteolol HCl, brimonidine tartrate, asenapine, indacaterol maleateisoprenaline HCl, formoterol hemifumarate, silodosin, nebivolol, epinephrine bitartrate, clonidine HCl, oxymetazoline HCl, phentolamine mesylate, propranolol HCl bisoprolol fumarate, $_L$-adrenaline, dexmedetomidine, naftopidil diHCl, naftopidil, maprotiline HCl, phenylephrine HCl, carvedilol, metoprolol tartrate, terazosin HCl, phenoxybenzamine HCl, sotalol, naphazoline HCl, ritodrine HCl, dexmedetomidine HCl, synephrine HCl, guanabenz acetate, timolol maleate, tizanidine HCl, synephrine, betaxolol HCl, detomidine HCl, epinephrine HCl, medetomidine HCl, acebutolol HCl, scopine, DL-adrenaline, ivabradine HCl, betaxolol, cisatracurium besylate, adrenalone HCl, tetrahydrozoline HCl, tolazoline HCl and terbutaline sulfate), opioid receptor inhibitors (e.g., loperamide HCl, naloxone HCl, JTC-801, ADL5859 HCl, naltrexone HCl, (+)-matrine, racecadotril and trimebutine), 5-HT receptor inhibitors (e.g., clozapine, olanzapine, ketanserin, fluoxetine HCl, tianeptine sodium, RS-127445, agomelatine, sumatriptan succinate, prucalopride, dapoxetine HCl, paroxetine, risperidone, WAY-100635 maleate, aripiprazole, naratriptan, blonanserin, vortioxetine, rizatriptan benzoate, zolmitriptan, fluvoxamine maleate, granisetron HCl, mosapride citrate, BRL-15572, SB269970 HCl, SB742457, PRX-08066 maleic acid, lorcaserin HCl, ondansetron HCl, tropisetron, lamotrigine, eletriptan HBr, sertraline HCl, desvenlafaxine, duloxetine HCl, azasetron HCl, escitalopram oxalate, ondansetron, almotriptan malate, amitriptyline HCl, SB271046, LY310762 trazodone HCl, urapidil HCl, atomoxetine HCl, BRL-54443, palonosetron HCl, VUF 10166 and desvenlafaxine succinate), P-gp inhibitors (e.g., Zosuquidar, Tariquidar), P2 receptor inhibitors (e.g., prasugrel, clopidogrel, MRS 2578, ticagrelor, GW791343 HCl, ticlopidine HCl), MT receptor inhibitors (e.g., ramelteon), AChR inhibitors (e.g., donepezil HCl, tiotropium bromide hydrate, pancuronium dibromide tolterodine tartrate, fesoterodine fumarate, (−)-huperzine A (HupA, oxybutynin, PNU-120596, solifenacin succinate, varenicline tartrate, galanthamine HBr, atropine, trospium chloride, rocuronium bromide, methscopolamine, aclidinium bromide, bethanechol chloride, scopolamine HBr, otilonium bromide, biperiden HCl, pyridostigmine bromide, irsogladine, gallamine triethiodide, arecoline, 5-hydroxymethyl tolterodine, rivastigmine tartrate, neostigmine bromide, darifenacin HBr, acetylcholine chloride, tropicamide, orphenadrine citrate, oxybutynin chloride, hyoscyamine, homatropine methylbromide, homatropine bromide, flavoxate HCl, diphemanil methylsulfate, hexamethonium bromide, decamethonium bromide and succinylcholine chloride dihydrate), histamine receptor inhibitors (e.g., clemastine fumarate, loratadine, mianserin HCl, ranitidine, azelastine HCl, ebastinea, latrepirdine, bepotastine besilate, cetirizine diHCl, hesperetin, chlorpheniramine maleate, mizolastine, ciproxifan, desloratadine, nizatidine, cimetidine, lafutidine, tripelennamine HCl, fexofenadine HCl, lidocaine, olopatadine HCl, brompheniramine hydrogen maleate, ketotifen fumarate, cyproheptadine HCl, azatadine dimaleate, rupatadine fumarate, JNJ-7777120, hydroxyzine 2HCl, buclizine HCl, famotidine, roxatidine acetate, betahistine 2HCl, pemirolast potassium, histamine 2HCl, levodropropizine and cyclizine 2HCl), OX receptor inhibitors (e.g., suvorexant, SB408124 and almorexant HCl), beta amyloid inhibitors (e.g., EUK 134, RO4929097 and LY2811376);

Endocrine and hormone inhibitors, include but are not limited to androgen receptor inhibitors (e.g., enzalutamide, bicalutamide, MK-2866, ARN-509, Andarine, AZD3514, galeterone, flutamide, dehydroepiandrosterone and cyproterone acetate), estrogen/progestogen receptor inhibitors (e.g., fulvestrant, tamoxifen citrate, raloxifene HCl, Erteberel, mifepristone, ospemifene, toremifene citrate, dienogest, bazedoxifene HCl, gestodene, clomifene citrate, medroxyprogesterone acetate, equol, drospirenone, hexestrol, epiandrosterone, estriol, pregnenolone, estradiol valerate, estrone, bazedoxifene acetate, altrenogest, tamoxifen, ethisterone, ethynodiol diacetate and estradiol cypionate), aromatase inhibitors, RAAS inhibitors (e.g., candesartan, aliskiren hemifumarate, losartan potassium, enalaprilat dihydrate, telmisartan, PD123319, irbesartan, valsartan, perindopril erbumine, benazepril HCl, olmesartan medoxomil, ramipril, enalapril maleate, candesartan cilexetil, captopril, lisinopril, cilazapril monohydrate, moexipril HCl, azilsartan medoxomil, quinapril HCl, temocapril HCl, temocapril imidapril HCl, fosinopril sodium and azilsartan), opioid receptor inhibitors, 5α-reductase inhibitors (e.g., dutasteride and finasteride), GPR inhibitors (e.g., TAK-875, GSK1292263, GW9508, AZD1981 and OC000459);

Metabolic inhibitors, include but are not limited to IDO inhibitors (e.g., NLG919), aminopeptidase (e.g., tosedostat), procollagen C-proteinase inhibitors (e.g., UK 383367), phospholipase inhibitors (e.g., varespladib and darapladib), FAAH inhibitors (e.g., URB597, PF-3845, JNJ-1661010), Factor Xa inhibitors (e.g., rivaroxaban, apixaban, ozagrel and edoxaban), PDE inhibitors (e.g., roflumilast, sildenafil citrate, cilomilast, tadalafil, vardenafil HCl trihydrate, pimobendan, GSK256066, PF-2545920, rolipram, apremilast, cilostazol, icariin, avanafil, S-(+)-rolipram, aminophylline, anagrelide HCl, dyphylline and luteolin), dihydrofolate reductase inhibitors (e.g., pemetrexed, methotrexate, pralatrexate and pyrimethamine), carbonic anhydrase inhibitors (e.g., dorzolamide HCl, topiramate, U-104, tioxolone, brinzolamide and methazolamide), MAO inhibitors (e.g., safinamide mesylate, rasagiline mesylate, tranylcypromine (2-PCPA) HCl and moclobemide), PPAR inhibitors (e.g., rosiglitazone maleate, rosiglitazone, GW9662, T0070907, WY-14643, FH535, GSK3787 inhibitor GW0742, ciprofibrate and rosiglitazone HCl), CETP inhibitors (e.g., anacetrapib, torcetrapib, evacetrapib and dalcetrapib), HMG-CoA reductase inhibitors (e.g., rosuvastatin calcium, lovastatin, fluvastatin sodium, atorvastatin calcium, pravastatin sodium and clinofibrate), transferase inhibitors (e.g., tipifarnib, lonafarnib, FK866A922500, tolcapone, PF-04620110, LB42708, RG108), ferroptosis inhibitors (e.g., erastin, Ferrostatin-1), HSP inhibitors (e.g., HSP90 inhibitor), P450 inhibitors (abiraterone, abiraterone acetate, voriconazole, avasimibe, ketoconazole, apigenin, TAK-700, galeterone, clarithromycin, baicalein, cobicistat, naringenin, pioglitazone HCl, alizarin, sodium danshensu and PF-4981517), hydroxylase inhibitors (e.g., nepicastat (SYN-117) HCl, isotretinoin, mildronate, telotristat etiprate, (R)-nepicastat HCl and DMOG), dehydrogenase inhibitors (e.g., mycophenolate mofetil, CPI-613, AGI-5198, MK-8245, trilostane, AGI-6780, PluriSln #1 and gimeracil);

Microbial inhibitors, include but are not limited to CCR inhibitors (e.g., maraviroc), HIV protease inhibitors, reverse transcriptase inhibitors (e.g., tenofovir, tenofovir disoproxil fumarate, emtricitabine, adefovir dipivoxil, nevirapine, rilpivirine, didanosine, lamivudine, stavudine, etravirine, zidovudine, zalcitabine, abacavir sulfate and dapivirine), HCV protease inhibitors, integrase inhibitors (e.g., raltegravir, elvitegravir, dolutegravir, BMS-707035 and MK-2048);

Epigenetic inhibitors, include but are not limited to histone demethylase inhibitors (e.g., GSK J4 HCl, OG-L002 and JIB-04, IOX1), Pim inhibitors (e.g., SGI-1776, SMI-4a, AZD1208 and CX-6258 HCl), histon transmethylase inhibitors (e.g., EPZ5676, EPZ005687, GSK343, BIX 01294, EPZ-6438, MM-102, UNC1999, EPZ004777, 3-deazaneplanocin A, EPZ004777 HCl, SGC 0946 and entacapone), epigenetic reader domain inhibitors (e.g., (+)-JQ1, I-BET151, PFI-1, I-BET-762, RVX-208, CPI-203, OTX015, UNC669, SGC-CBP30, UNC1215 and bromosporine), histon acetyltransferase inhibitors (e.g., C646 and MG149), HIF inhibitors (e.g., FG-4592, 2-methoxyestradiol, IOX2 and BAY 87-2243), JAK inhibitor, HDAC inhibitors (e.g., vorinostat, entinostat, panobinostat, trichostatin A, mocetinostat, TMP269, nexturastat A, RG2833, RGFP966, belinostat, romidepsin, MC1568, tubastatin A HCl, givinostat, LAQ824, CUDC-101, quisinostat, pracinostat, PCI-34051, droxinostat, PCI-24781, AR-42, rocilinostat, valproic acid sodium salt, CI994, CUDC-907, tubacin, M344, resminostat, Scriptaid, sodium phenylbutyrate and tubastatin A), deacetylase inhibitors (e.g., SRT1720, EX 527, resveratrol and sirtinol), Aurora kinase inhibitors, PARP inhibitors (e.g., olaparib, veliparib, rucaparib, iniparib, BMN 673, 3-aminobenzamide, ME0328, PJ34 HCl, AG-14361, INO-1001, A-966492, PJ34, UPF 1069 and AZD2461), DNA transmethylase inhibitors (e.g., decitabine, azacitidine, RG108, thioguanine, zebularine, SGI-1027 and lomeguatrib);

JAK/STAT inhibitors, include but are not limited to Pim inhibitors, EGFR inhibitors, JAK inhibitors and STAT inhibitors;

DNA damage inhibitors, include but are not limited to ATM/ATR inhibitors, DNA-PK inhibitors (e.g., NU7441, NU7026, KU-0060648 and PIK-75), HDAC inhibitors, deacetylase (sirtuin) inhibitors, PARP inhibitors, topoisomerase inhibitors (e.g., doxorubicin, etoposide, camptothecin, topotecan HCl, irinotecan, voreloxin, beta-lapachone, idarubicin HCl, epirubicin HCl, moxifloxacin HCl, irinotecan HCl trihydrate, SN-38, amonafide, genistein, mitoxantrone, pirarubicin, ofloxaci, ellagic acid, betulinic acid, (S)-10-hydroxycamptothecin, flumequine and pefloxacin mesylate dihydrate), telomerase inhibitors (e.g., BIBR 1532, daunorubicin HCl and costunolide), DNA/RNA synthesis inhibitors (e.g., cisplatin, gemcitabine HCl, bleomycin sulfate, carboplatin, oxaliplatin, CRT0044876, triapine, pemetrexed, fludarabine, CX-5461, fluorouracil capecitabine, fludarabine phosphate, cytarabine, gemcitabine, nelarabine, cladribine, raltitrexed, clofarabine, ifosfamide, NSC 207895, dacarbazine, floxuridine, mercaptopurine, flupirtine maleate, mizoribine, carmofur, procarbazine HCl, daphnetin, FT-207, adenine, adenine HCl, adenine sulfate and uridine);

NF-κB inhibitors, include but are not limited to NOD1 inhibitors (e.g., ML130), HDAC inhibitor, NF-κB inhibitors (e.g., QNZ, sodium 4-aminosalicylate, JSH-23, caffeic acid phenethyl ester and SC75741), IκB/IKK inhibitors (e.g., IKK-16, TPCA-1IMD 0354, bardoxolone methyl, BAY 11-7085, BMS-345541, BX-795 and SC-514);

GPCR & G protein inhibitors, include but are not limited to protease-activated receptor inhibitors, CGRP receptor inhibitors (e.g., MK-3207 HCl), Hedgehog/Smoothened inhibitors (e.g., vismodegib, cyclopamine, LDE225, LY2940680, purmorphamine, BMS-833923, PF-5274857, GANT61 and SANT-1), LPA receptor inhibitors (e.g., Ki16425 and Ki16198), PAFR inhibitors (e.g., ginkgolide B), CaSR inhibitors (e.g., cinacalcet HCl and NPS-2143), vasopressin receptor inhibitors (e.g., tolvaptan and mozavaptan), adenosine receptor inhibitors (e.g., CGS 21680 HCl and istradefylline), endothelin receptor inhibitors (e.g., Zibotentan, bosentan hydrate, macitentan, sitaxentan sodium and bosentan), S1P receptor inhibitors (e.g., fingolimod, SKI II and PF-543), adrenergic receptor inhibitor, cannabinoid receptor inhibitors (e.g., rimonabant, AM1241, AM251, otenabant (CP-945598) HCl, GW842166X, BML-190 and Org 27569), SGLT inhibitors (e.g., dapagliflozin, canagliflozin and empagliflozin), opioid receptor inhibitors, dopamine inhibitors, 5-HT receptor inhibitors, MT receptor inhibitors, histamine receptor inhibitors, OX receptor inhibitors, CXCR inhibitors (e.g., plerixafor 8HCl, plerixafor and WZ811), cAMP inhibitors (e.g., forskolin and bupivacaine HCl);

Transmembrane transport inhibitors, include CRM1 inhibitors (e.g., Selinexor, KPT-185 and KPT-276), CFTR inhibitors (e.g., ataluren, ivacaftor, VX-809, VX-661, CFTRinh-172 and IOWH032), sodium channel inhibitors (e.g., riluzole, rufinamide, carbamazepine, phenytoin sodium, amiloride HCl dehydrate, A-803467, phenytoin, lamotrigine, ambroxol HCl, ouabain, oxcarbazepine, propafenone HCl, proparacaine HCl, vinpocetine, ibutilide fumarate, procaine HCl, dibucaine HCl and triamterene), ATPase inhibitors (e.g., omecamtiv mecarbil, oligomycin A, brefeldin A, (−)-blebbistatin, sodium orthovanadate, BTB06584, golgicide A, milrinone, ciclopirox ethanolamine, esomeprazole sodium and PF-3716556), potassium channel inhibitors (e.g., amiodarone HCl, repaglinide, TRAM-34, nicorandil, tolbutamide, chlorpromazine HCl, gliquidone, nateglinide, TAK-438, ML133 HCl, gliclazide and mitiglinide calcium), γ-aminobutyric acid receptor inhibitor, calcium channel inhibitors (e.g., amlodipine besylate, cilnidipine, ranolazine 2HCl, felodipine, isradipine, amlodipine, manidipine 2HCl, manidipine, nimodipine, nilvadipine, lacidipine, clevidipine butyrate, benidipine HCl, flunarizine 2HCl, nitrendipine, tetracaine HCl, strontium ranelate, azelnidipine and tetrandrine), proton pump inhibitors (e.g., lansoprazole, omeprazole, esomeprazole magnesium, zinc pyrithione, PF-3716556 and tenatoprazole), P-gp inhibitor;

Autophagy inhibitors, e.g., temozolomide, metformin HCl, trifluoperazine 2HCl, divalproex sodium, azithromycin, dexamethasone and sulfacetamide sodium;

Ubiquitin inhibitors, include but are not limited to p97 inhibitors (e.g., NMS-873, DBeQ and MNS), E1 activating inhibitors (e.g., PYR-41), proteasome inhibitors, DUB inhibitors (e.g., PR-619, P5091, IU1, LDN-57444, TCID, ML323, degrasyn and P22077), E2 conjugating inhibitors (e.g., NSC697923), E3 ligase inhibitors (e.g., (−)-parthenolide, Nutlin-3, JNJ-26854165, thalidomide, NSC 207895, TAME and RITA);

Multitarget inhibitors, include but are not limited to KU-60019, CUDC-101, TAK-285, WHI-P154, chrysophanic acid, PD168393, butein, sunitinib malate, imatinib (STI571), PP121, sorafenib tosylate, imatinib mesylate (STI571), ponatinib (AP24534), axitinib, pazopanib HCl (GW786034 HCl), dovitinib (TKI-258, CHIR-258), linifanib (ABT-869), tivozanib (AV-951), motesanib diphosphate (AMG-706), amuvatinib (MP-470), dilactic acid, MK-2461, WP1066, WHI-P154, ponatinib, neratinib (HKI-272), lapatinib, TAK-285, tyrphostin AG 879, KW-2449, cabozantinib, R406, amuvatinib, PF-03814735, WIKI4, AZ 3146, fasudil, vatalanib, MGCD-265, golvatinib, regorafenib, RAF265, CEP-32496, AZ 628, NVP-BHG712, AT9283, ENMD-2076, ENMD-2076, CYC116, ENMD-2076 $_L$-(+)-tartaric acid, PF-477736, BMY 7378, clomipramine HCl, latrepirdine, CUDC-907, quercetin and BAY 11-7082;

Receptors, such as HER2 receptors, anti-EGFR receptors (such as gefitinib, Erbitux, erlotinib, pelitinib, lapatinib, canertinib), hepatocyte growth factor receptors (HGFR, c-Met) and RON, tumor necrosis factor receptors, vascular endothelial growth factor receptors (such as Flt-1, KDR, Flt4), interleukin receptors, transferrin receptors, lipoprotein receptors, insulin-like growth factor receptors (IGFR), lectin receptors (including asialoglycoprotein receptors and mannose receptors), scavenger receptors, folate receptors, galactose receptors (asialoglycoprotein receptors, ASGPR) (e.g. β-D-galactose, galactosylceramide, cholesteryl trigalactoside, galactosyl phosphatidylethanolamine, asialofetuin and synthesized glycoproteins thereof), I-type transmembrane tyrosine kinase growth factor (ErbB) receptors, Toll-like receptors (including TLR-1, TLR-2, TLR-3, TLR-4, TLR-5, TLR-6, TLR-7, TLR-8 and TLR-9), leptin receptors, diphtheria toxin receptors, integrin αvβ3, nucleolar protein, p32 receptors, somatostatin receptors, vasoactive intestinal peptide receptors, cholecystokinin receptors, endothelium selectins, and the like;

Antibodies include but are not limited to all the above-said antibodies, no more repeated here;

Targeting drugs include but are not limited to tamoxifen, raloxifene, toremifene, fulvestrant, icotinib, flumatinib, famitinib, fruquintinib, cipatinib, sulfatinib, anlotinib, allitinib, puquitinib, epitinib, rofecoxib, sildenafil, imatinib, dasatinib, nilotinib, gefitinib, erlotinib, everolimus, vandetanib, lapatinib, vorinostat, romidepsin, bexarotene, alitretinoin, bortezomib, pralatrexate, sorafenib, sunitinib, pazopanib, ipilimumab, denileukin-2, Glivec, tofacitinib, temsirolimus, apatinib, motesanib, endostain, ziv-aflibercept, brivanib, linifanib, tivozanib, vatalanib, CDP791, crizotinib, navitoclax, gossypol, iniparib, perifosine, AN-152, vemurafenib, dabrafenib, trametinib, binimetinib, encorafenib, palbociclib, LEE011, salinomycin, vintafolide, afatinib, neratinib, axitinib, masitinib, Toc vorinostat eranib, lestaurtinib, cediranib, regorafenib, semaxanib, ponatinib, bosutinib, Jakafi (ruxolitinib), cabozantinib, ceritinib, ibrutinib, capecitabine, Tegafur-containing, combretastatin disodium phosphate, vismodegib, anastrozole, arimidex, exemestane, letrozole, denosumab, lenalidomide, pomalidomide, carfilzomib, belinostat, cabazitaxel, abiraterone acetate, dichloride radium 233 injection, luteinizing hormone releasing hormone, midostaurin, oblimersen, saracatinib, marimastat, fucosyl-GM1 compound, alvocidib, havopiridol, vincristine, tipifarnib, panitumumab, rituximab, alemtuzumab, ofatumumab, tositumomab, ibritumomab tiuxetan, depsipeptide, BSU21051, cationic porphyrin compounds, UCN-01, ICR-62, pelitinib, PKI-166, canertinib, PD158780, HKI-357, ZD6126, amifostine, ombrabulin, combretastatin, soblidotin, denibulin, tozasertib, decitabine, AEE788, orantinib, SU5416, enzastaurin, oxaliplatin, celecoxib, aspirin, obatoclax, AT-101, tanomastat, biricodar, NS-398, SC-58125, batimastat, prinomastat, metastat, neovastat, BMS-275291, lonafarnib, SCH44342, SCH54429, L-778123, BMS-214662, BMS-185878, BMS-186511, BZA-5B, BzA-2B, L-735, L-739, L-750, L-744832, B581, Cys-4-ABA-Met, Cys-AMBAMet, FTI276, FTI277, B956, B1096, limonene, manumycin, trihydroxyisoflavon (or genistein), erbstatin, lavendustin A, herbimycin A, tyrphostin, PD169540, CL-387785, CP-358744, CGP59326, CGP59326-A, fungicidin, valinomycin A and its derivatives, lupinane derivatives, CGS27023A, squalamine, thalidomide, cilengitide, carboxylaminoimidazole, suramin, IM862, DS-4152, CM-101, simvastatin, PD98059, PD184352, azatyrosine, antipain, MT477, benzoquinone ansamycin, geldanamycin, neocarzinostatin, azacitidine, aclacinomycin A, cholesterol derivatives, thioguanine, MCC465, liver-targeting primaquinum, liver targeting ricin, etoposide, teniposide, poloxamer, dexamethasone, taribavirin, BIBW-2992, all the other above-mentioned monoclonal antibody drugs, etc.

Gene targeting molecules, such as nucleic acid aptamers, cyclins, antisense oligonucleotides (such as c-Myc, c-Myb, Bcl-2, N-Ras, K-Ras, H-Ras, c-Jun, c-Fos, CDC-2, c-Mos, etc.), genetically modified rhizobia, p53 negative regulatory molecules (e.g., PACT), gene-transduced DC (such as AAV-BA46-DC), gene-transduced TIL (e.g., IL-2, TNF-α), intracellular signaling molecules and transcription factors, MDM2 oncogenes;

Viruses, such as anti-cancer recombinant oncolytic adenovirus, human T-lymphotropic viruses, Rous sarcoma virus, ONXY2 015, herpes simplex virus I (HSV-I), recombinant adenovirus serotypes (e.g., rAAV2, rAAV8) and so on;

Vaccines, such as tumor cell vaccines, genetically modified vaccines, dendritic cell vaccines, fusion cell vaccines), viral vaccines, protein/peptide vaccines, DNA vaccines (such as tumor-targeting recombinant DNA vaccines), anti-idiotypic vaccines, heterologous vaccines, human recombinant EGF-P64K vaccine, conjugate of BEC-2 and Bacillus Calmette-Guéri, fucosyl-GM1 conjugate, HPV quadrivalent vaccine of Gar dasil, bivalent vaccine of Cervarix, etc., Biomacromolecular targeting factors include but are not limited to proteins (such as transferrin, low density lipoprotein, hemochromatosis proteins, lectin, cytoskeletal proteins, such as vimentin and heat shock protein), low-relative-mass proteins (such as lysozyme and streptavidin) and the like;

Vitamins include such as folic acid, biotins and the like.

The above-mentioned targeting group is preferably any functional group of group I or protected form thereof.

The above mentioned photosensitive group is not particularly limited, preferably the residue of a dye or a fluorescent substance.

Specifically, dyes include but are not limited to trypan blue, Coomassie Brilliant Blue, crystal violet, pyrogallol red, phenylamyl ketone, etc.

Fluorescent substances can be used for chemical staining, immunofluorescent staining and the like, or be used for fluorescent labeling and tracing. Fluorescent substances include but are not limited to fluorescent proteins (such as green fluorescent protein, red fluorescent protein, etc.), rhodamines (e.g., TRITC, Texas Red, HAMRA, R101, RB200, etc.), phalloidin and derivatives thereof, cyanine dyes (such as thiazole orange, oxazole orange), acridines (such as acridine red, acridine yellow, acridine orange, etc.), phycoerythrin, phycocyanin, methyl green, alizarin red, aniline blue, pyronin, fluoresceins (including but not limited to standard fluorescein, fluorescein isothiocyanate (FITC), fluorescein diacetate (FDA), FAM, TET, HEX, JOE, etc.), hematoxylin, eosin, neutral red, fuchsin, Alexa Fluor dyes, Oregon green dyes, BODIPY dyes, Cy3, Cy3.5, Cy5, Cy5.5, Cy7, Cy7.5, Hex, PerCP, DAPI, Hoechst dyes, Cascade blue, Astrazon dyes, SYTO dyes, stilbene dyes, naphthalimide dyes, coumarin dyes, pyrene dyes, phenanthridine dyes, porphyrin dyes, indole dyes, chromomycin A, ethidium bromide, purpurin and the like. All the fluorescent substances disclosed in patent documents of CN1969190A, CN101679849B and U.S. Ser. No. 14/526,901 (US20150119281A1) are incorporated by reference into the present invention herein. Rhodamine derivatives disclosed in document "Progress in Chemistry, 2010, 22 (10): 1929-1939" and cited references therein are also incorporated by reference into the present invention herein. Said coumarin dyes also include but not limited to 4,5,7-trihydroxyl coumarin. Functional groups in Group J and Applicable for general formula (1) also fall into the scope of bio-related substances.

The above-mentioned photosensitive group is preferably any functional group in Group J or protected form thereof.

2. Production Methods 2.1. The present invention also discloses a production method of multifunctionalized polyethylene glycol. The H-shaped multifunctionalized polyethylene glycol (1) can also be represented by general formula (7), general formula (8) or general formula (9) as follows;

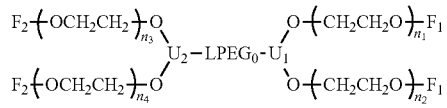

(7)

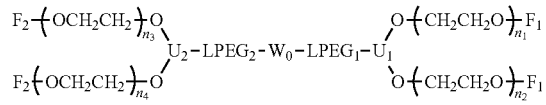

(8)

(9)

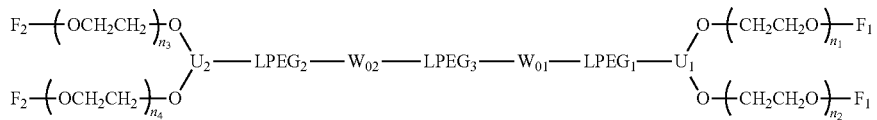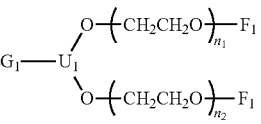

Wherein, the structure of $F_1$ and $F_2$ are each independently and correspondingly represented by respective

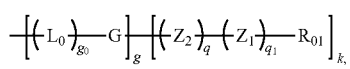

and $F_1$ and $F_2$ can be the same or different from each other in one molecule.

Wherein, the definitions of $n_1$, $n_2$, $n_3$, $n_4$, $U_1$, $U_2$, $F_1$, $F_2$, k, G, g, $L_0$, $g_0$, $Z_1$, $R_{01}$, q, $m_1$, $m_2$, $m_3$, $F_1$ and $F_2$ are the same as those in the general formula (1), and no more repeated here.

Wherein, LPEG corresponds to $-LPEG_0-$, $-LPEG_2-W_0-LPEG_1-$ and $-LPEG_2-W_{02}-LPEG_3-W_{01}-LPEG_1-$, respectively; wherein, $LPEG_0$, $LPEG_1$ and $LPEG_2$ are each independently a linear PEG monoblock segment or a PEG segment consisting of 2 to 150 PEG blocks (a PEG 2- to 150-block), and each independently contains at least one oxyethylene group unit (EO unit); $LPEG_0$, $LPEG_1$ and $LPEG_2$ are each independently a stable or degradable sement.

$LPEG_0$ is preferably

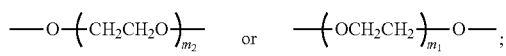

$LPEG_1$ is preferably

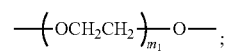

$LPEG_2$ is preferably

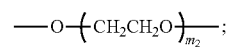

$LPEG_3$ is preferably

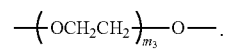

The production method of said multifunctionalized polyethylene glycol involves an intermediate compound A which contains a skeleton selected from IM, IM-1, IM-2 and IM-3; wherein, the definitions of $n_1$, $n_2$, $n_3$, $n_4$, $U_1$, $U_2$, $F_1$, $F_2$ and LPEG are the same as those in general formula (1), and no more repeated here.

IM

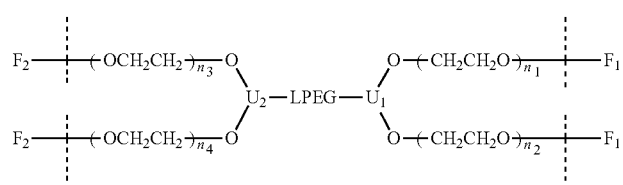

IM-1

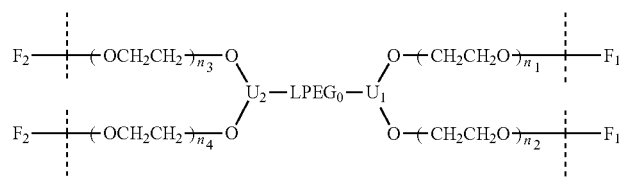

IM-2

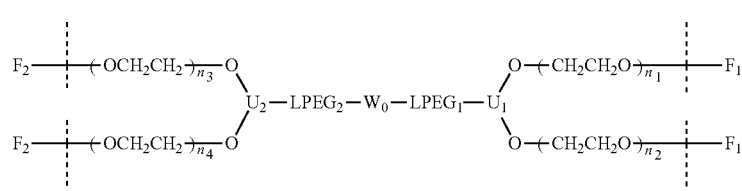

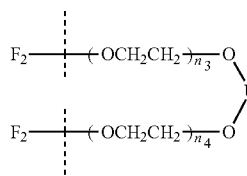 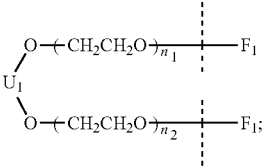

IM-3

Wherein, the dashed lines represent that the terminal residue groups of the skeleton would be linked to the said terminal group $F_1$ or $F_2$ as shown in the general formulas. In the intermediate compound A, the termini marked by the dashed line can connect with a hydrogen atom (corresponding to a terminal hydroxyl group), a non-objective unprotected or protected functional group, or an objective unprotected or protected functional group (also referred to as an objective active or protected functional group, or a given active or protected functional group).

The process to convert a hydroxyl group or a non-objective functional group at the ends of polyethylene glycol chains into corresponding $F_t$ thereof, the objective unprotected or protected functional group thereof, via modification is termed as terminal functionalization or end-functionalization, including linear end-functionalization (also terminal linear-functionalization) and branched end-functionalization (also terminal branched-functionalization). Said unprotected or protected functional groups include but are not limited to those listed in functional Groups from Group A to Group J and protected forms thereof.

The end-functionalization process corresponding to g of zero is termed as linear end-functionalization, while the corresponding G is absent, and the number of corresponding $R_{01}$ at PEG-chain terminus k is 1; the end-functionalization process corresponding to g of unity is termed as branched end-functionalization, while the corresponding k is an integer from 2 to 250, the valence of corresponding G is k+1, and the number of corresponding $R_{01}$ at PEG-chain terminus is k.

An H-shaped multifunctionalized polyethylene glycol with objective unprotected or protected functional groups can be obtained by modifying an intermediate compound A which contains a skeleton of IM, IM-1, IM-2 or IM-3 via linear or branched end-functionalization;

when k of $F_1$ or $F_2$ is equal to 1, the corresponding PEG chain terminus of intermediate compound A should be linearly end-functionalized;

when k of $F_1$ or $F_2$ is greater than 1, the corresponding PEG chain terminus of intermediate compound A should be branchedly end-functionalized;

the linear end-functionalization can be carried out prior to, after or along with obtaining said intermediate compound A.

An intermediate to be branchedly end-functionalized should have a V-, Y- or H-shaped structure. Said V-shaped structure has two PEG branch chains with an unprotected or protected functional group between the two PEG chains; said Y-shaped structure has a PEG main chain as well as two PEG branch chains with an unprotected or protected functional group at the main chain end; said H-shaped structure has a PEG main chain and four PEG branch chains with two branch chains at each end of the main chain. The above-said end-functionalization process can be carried out at the two branch-chain terminals of a V-shaped structure, the main-chain terminal of a Y-shaped structure, two branch-chain terminals linked to a common branching center of an H-shaped structure, or two branch-chain terminals linked with different branching centers of an H-shaped structure.

In the present invention, any polyethylene glycol segment of any used polyethylene glycol reagent of a linear, V-shaped or Y-shaped structure can be independently either polydisperse or monodisperse.

When using monodisperse reagents, the resulting product would have a more homogeneous molecular-weight distribution, however most molecular weights are not available due to the limitation of production methods. The advantage of polydisperse reagents is to provide a broader range for molecule-weight modulation, also referring to the above-mentioned definitions of LPEG, $n_1$, $n_2$, $n_3$ and $n_4$, respectively.

2.1.1. The Linear End-Functionalization Towards Polyethylene Glycol Chain Termini The method for linear end-functionalization is not particularly limited, but related to the type of objective unprotected or protected terminal functional group. The method can be a linear end-functionalization based on the terminal hydroxyl group of polyethylene chains, conversion of a reactive group towards the objective unprotected or protected functional group, or combination of above-said two manners. All prior art can be used by reference. Conditions such as reaction temperature, reaction time, feeding amount and the like are well known to those skilled in the art, or can be obtained through a finite number of experiments for optimization purposes, no more repeated here. We generally describe reaction mechanism, reagents, reaction routes and the like herein.

Typical examples include the unprotected or protected functional end-groups in above-said Groups from Group A to Group J, wherein production methods for corresponding linear end-functionalization based on the terminal hydroxyl group of polyethylene glycol chains are described herein, starting from said terminal hydroxyl group to generate unprotected or protected functional groups of Group A to Group J via end-functionalization. The reaction formula is as follows:

$$\text{—PEG—OH} \longrightarrow$$

IF1

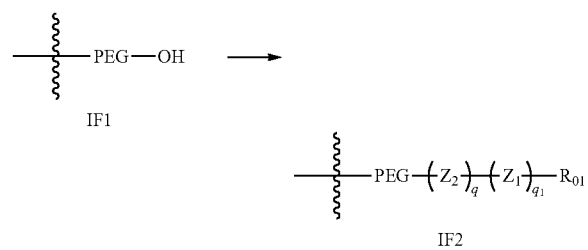

IF2

Wherein, the structure of PEG-OH is $(CH_2CH_2O)_nCH_2CH_2OH$, n is $n_1-1$, $n_2-1$, $n_3-1$ or $n_4-1$; the definitions of q, $Z_2$, $q_1$, $Z_1$ and $R_{01}$ are the same as above-mentioned. Wherein, PEG-OH is a moiety of the terminal-hydroxyl-containing intermediate (IF1) present in the process of producing H-shaped multifunctionalized polyethylene glycol; said terminal-hydroxyl-containing intermediate can contain one, two, three or four polyethylene glycol chains; PEG-OH can come from the polyethylene glycol main chain, or one of the polyethylene glycol branch chains.

In the following production methods for linear end-functionalization based on the terminal hydroxyl groups of PEG chains, it is preferably that q is 0, $q_1$ is 1 and $Z_1$ is a 1.2-methylene group. What should be noted is that, the molar equivalent of the hydroxyl group of the intermediate IF1 is 1, if without particular illustrations. When q is not 0 and a linking group such as an amino acid linkage or a succinyl group is present between PEG and $R_{O1}$, the prior art capable of generating $Z_2$ or $Z_1$ can be used, including alkylation, condensation, click reactions and the like), and be carried out referring to the following linear end-functionalization methods.

2.1.1.1. Group A: End-Functionalization Towards $R_{O1}$ in Group A

The functional groups in Group A are mainly active ester groups or analogues thereof.

Active ester derivatives (A4, A6, A7, A9, A10, A16 and A18) can be obtained through condensation reactions under a basic condition between terminal-hydroxyl-containing intermediates and corresponding carbonates (e.g., N,N'-disuccinimidyl carbonate, bis(p-nitrophenyl)carbonate, bis(o-nitrophenyl)carbonate, di(benzotriazol-1-yl)carbonate, etc.), haloformates (e.g., p-nitrophenyl chloroformate, o-nitrophenyl chloroformate, trichlorophenyl chloroformate, etc.) and N,N'-carbonyldiimidazole. Substituted derivatives with substituents on the ring can also be obtained in a similar manner, for example, 2-methylimidazole derivative can be obtained by reacting with 1,1'-carbonylbis(2-methylimidazole). Said haloformates are a chloride, a bromide or an iodide, preferably a chloride. The resulting product can be purified by a purification means such as extraction, recrystallization, adsorption treatment, precipitation, reverse precipitation, membrane dialysis, supercritical extraction or the like.

Active esters (A1-A3, A5, A8, A11, A15 and A17) can also be obtained through a condensation reaction. The terminal hydroxyl group can be converted into a terminal carboxyl group through a one-step or multi-step reaction, and then reacts with corresponding alcohols (e.g., N-hydroxysuccinimide, p-nitrophenol, o-nitrophenol, trichlorophenol, 1-hydroxybenzotriazole, etc.) to obtain corresponding active esters in the presence of condensing agents.

Analogs of active esters (A11-A14) can be obtained through a condensation reaction between terminal carboxyl groups and corresponding amines (such as thiazolidine-2-thione, pyrrolidine-2-thione, benzo[d]thiazol-2(3H)-thione, 4-oxo-2-thiothiazolidine, etc.) to obtain corresponding amides in the presence of condensing agents. Substituted derivatives with substituents on the ring can also be obtained in a similar manner, for example, active ester analogs can be obtained by reacting with 4-isopropyl-1,3-thiazolidine-2-thione, (R)-4-isopropylthiazolidine-2-thione, 4-phenylthiazoline-2-thione or the like. The condensing agent is not particularly limited, but is preferably N,N'-dicyclohexylcarbodiimide (DCC), 1-ethyl-(3-dimethylaminopropyl)carbodiimide hydrochloride (EDC.HCl), 2-(7-azobenzotriazole-N,N,N',N'-tetramethyluronium hexafluorophosphate (HATU), (benzotriazol-1-yl)-N,N,N',N'-tetramethyluronium hexafluorophosphate (HBTU), and most preferably DCC.

The solvent can be no solvent or an aprotic solvent. As used herein, the base is usually an organic base, and preferably triethylamine or pyridine.

2.1.1.2. Group B: End-Functionalization Towards $R_{O1}$ in Group B a. The sulfonate (B1) and sulfinate (B2) derivatives can be obtained via the esterification reaction under a basic condition between the terminal hydroxyl group and a sulfonyl chloride or a sulfinyl chloride that contains a leaving group $Y_1$.

b. The sulfone (B3) and sulfoxide (B4) derivatives can be obtained via the oxidation reaction with a sulfoxide intermediate or a thioether intermediate that contains a leaving group $Y_1$. The oxidizing agent is not particularly limited as long as it is a compound or a combination of multiple compounds capable of increasing the valence of the substrate. The solvent can be no solvent or an aprotic solvent.

c. The sulfone (B3) derivative can be obtained via the addition reaction between the terminal hydroxyl group and a base followed by an additional reaction with vinylsulfone.

d. The disulfone (B5) derivative and variant form thereof (B6) can be obtained with the method disclosed in the literature "Advanced Drug Delivery Reviews, 2008, 60, 3-12".

2.1.1.3. Group C: End-Functionalization Towards $R_{O1}$ in Group C

The hydroxylamine compound (C1) can be obtained via the reaction under a strong basic condition between the terminal hydroxyl group and excess hydroxylamine hydrochloride (e.g., diphenylmethyl potassium).

The thiol derivative (C2) can be obtained by the reaction between the terminal hydroxyl group and a thiourea compound. The reaction can be carried out in a solvent or without any solvent. The solvent is not limited, preferably water, toluene, benzene, xylene, acetonitrile, ethyl acetate, diethyl ether, methyl tert-butyl ether, tetrahydrofuran, chloroform, methylene chloride, dimethyl sulfoxide, dimethylformamide or dimethylacetamide, and more preferably water, tetrahydrofuran, dichloromethane or acetonitrile.

The thiol derivative (C2) can also be obtained via the reaction between a sulfonate and xanthate potassium compound followed by decomposition treatment with primary amine. This reaction can be carried out without any solvent or in a solvent, and the solvent is not limited, preferably an aprotic solvent.

The sulfide compound (C7) as a protected thiol can be obtained via the reaction between corresponding thiol compound (C2) and corresponding protective agent. The production method is not limited, including but not limited to the following manners: Manner a, sulfides (C7) of a thioether species can be prepared via the reaction between thiol compounds and corresponding alkylating agents containing a leaving group under a basic condition. The solvent can be no solvent or an aprotic solvent. Manner b, thioester compounds (C7 and C17) can be prepared via the reaction between thiol compounds and corresponding acyl halides under a basic condition. The solvent can be no solvent or an aprotic solvent.

The amine derivative (C3) can be synthesized in the following manner: the intermediate containing a terminal hydroxyl group is coupled with acrylonitrile or the like via base catalysis in advance, and then the cyano group of the resulting compound is reduced to the corresponding amine compound by using palladium or nickel as a catalyst in a high-pressure reactor. The reaction can be carried out in a solvent or without any solvent. The solvent is not particularly limited, but is preferably water, 1,4-dioxane or combination thereof. The base can be an organic base or an inorganic base, preferably an inorganic base, and more preferably sodium hydroxide or potassium hydroxide.

The amine derivative (C3) can also be obtained via the reaction between a sulfonate compound (B1) and ammonia water.

The protected amine derivative (C6 and C16) can be prepared via the reaction between corresponding amines (C3) and corresponding protective agents. The production method is not limited, including but not limited to the following manners:

Manner a, carbamate compounds can be prepared via the reaction between amines and corresponding haloformates in the presence of base. The solvent can be no solvent or an aprotic solvent. The base can be an organic base or an inorganic base, preferably an organic base, and more preferably triethylamine or pyridine.

Manner b, amide compounds can be prepared via the reaction between amines and corresponding acyl halides under a basic condition.

Manner c, alkylamine compounds can be prepared via the reaction between amines and corresponding alkylating agents that contain a leaving group under a basic condition. The solvent can be no solvent or an aprotic solvent. The base can be an organic base or an inorganic base, preferably an organic base, and more preferably triethylamine, pyridine, sodium hydride, DPMK, potassium hydride and sodium alkoxide.

Manner d, alkylamine compounds can also be prepared by reacting an amine with corresponding aldehyde or ketone to generate an imine compound and then the resulting imine (Schiff base) is reduced to the corresponding alkylamine compound (C6) in the presence of reducing agent. Said aldehyde or ketone is not particularly limited. The solvent can be a protic solvent or an aprotic solvent, preferably toluene, benzene, xylene, acetonitrile, ethyl acetate, diethyl ether, methyl t-butyl ether, tetrahydrofuran, methanol, dimethylformamide or dimethylacetamide, and more preferably tetrahydrofuran, methanol or ethyl acetate. The reducing agent is not particularly limited as long as it can reduce the resulting Schiff base formed by an amine and an aldehyde or ketone to an amino group, preferably sodium borohydride, sodium cyanoborohydride, lithium aluminum hydride, borane, diborane, diisobutylaluminum hydride, diisopinocampheylborane, lithium borohydride, zinc borohydride, borane-pyridine, borane-methyl sulfide, borane-tetrahydrofuran, the like or combination thereof, and more preferably sodium cyanoborohydride.

The azide compound (C4), halide compound (C5), tetramethylpiperidinyloxy compound (C8) and dioxapiperidinyloxy compound (C9) can be prepared by reacting a sulfonate compound (B1) with corresponding halogeno salt, 2,2,6,6-tetramethylpiperidine-N-oxyl and 3,5-dioxo-1-cyclohexylamine, respectively. The bromide salt is not limited as long as free bromide ions exist in the solvent, preferably sodium bromide or potassium bromide. The azide salt is not limited as long as free azide ions exist in the solvent, preferably sodium azide or potassium azide. The solvent used for preparing the azide compound (C4) is not limited, preferably water, ethanol, acetonitrile, dimethyl sulfoxide, dimethylformamide or dimethylacetamide, and more preferably water and dimethylformamide.

The halide compound (C5) can also be obtained via the reaction between the terminal hydroxyl group and a halogenated agent. The halogenated agent is not particularly limited as long as it can convert a hydroxyl group to corresponding halogen atom, preferably dichlorosulfone, phosphorus trichloride, phosphorus tribromide, dibromosulfoxide, the like or combination thereof. The solvent can be no solvent or an aprotic solvent.

The ester compound or thiocarboxylate compound (C17) can be obtained via the condensation reaction between the terminal hydroxyl group or a mercapto group and a carboxyl group or an acyl halide, and the acid halide is preferably an acyl chloride.

The thioester compound (C17) can also be obtained via the reaction between a mercapto group rand an active ester, referring to the literature of "Journal of Controlled Release, 2014, 194: 301-309".

The carbonate or thiocarbonate compound (C18) can be obtained via the condensation reaction between the terminal hydroxyl group or a mercapto group and an oxycarbonyl-chloride compound. E.g., ethyl chloroformate and ethyl thiocarbamate.

The trithiocarbonate derivative (C18) can also be prepared via the coupling reaction between a trithioester-containing small molecule compound (such as 3-(benzylthio-thiocarbonylthio)propionate) and a functionalized polyethylene glycol containing a suitable functional group.

The haloacetamide compound (C10) can be obtained by reacting haloacetic acid with a polyethylene glycol amine derivative (C3) in the presence of condensing agent to form an amide bond.

The lipoic acid derivative can be obtained via the condensation reaction between lipoic acid and corresponding alcohol (H1) or amine (C3).

2.1.1.4. Group D: End-Functionalization Towards $R_{01}$ in Group D

The ester compound (D11) and the thiocarboxylate compound (D13, D16 and D17) can be obtained by deprotonating the terminal hydroxyl groups followed by a substitution reaction with an α-halogenated ester compound, respectively, e.g., ethyl chloroacetate and ethyl bromoacetate.

The thioester compound (D13) can also be obtained via the reaction between a corresponding ester (D11) and a thiol compound.

The amide compound (D1), hydrazide compound (D2) and carboxylic acid compound (D4) can be obtained via the hydrolysis or aminolysis reaction between the ester compound (D11) and corresponding nucleophile reagents respectively. The ester compound (D11) can be hydrolyzed with a basic solution to obtain a carboxylic acid compound (D4), or be treated with ammonia water, hydrazine hydrate to obtain the amide compound (D1) and the hydrazide compound (D2), respectively.

The acyl halide compound (D6) can be obtained via the reaction between the carboxylic acid compound (D4) and a halide agent. The halide agent is not particularly limited as long as it can convert the hydroxyl group of carboxyl group to corresponding halogen atom, preferably thionyl chloride (also referred to as dichlorosulfoxide), phosphorus trichloride, phosphorus tribromide, dibromosulfoxide, the like or combination thereof. The solvent can be no solvent or an aprotic solvent.

The anhydride derivative (D11) can be obtained via the reaction between the carboxylic acid derivative (D4) and an acyl halide, a small molecule anhydride or a mixture of small molecule anhydrides. The acyl halide, small molecule anhydride and mixture of small molecule anhydrides are not particularly limited as long as they can convert the carboxyl group to corresponding anhydride group, preferably $C_{1-10}$ acyl chloride, $C_{1-10}$ acyl bromide, $C_{1-10}$ acyl anhydride, the like or combination thereof.

The acetaldehyde derivative (D5) can be obtained by directing oxidizing the terminal hydroxyl group. The oxidizing agent is not particularly limited, preferably PDC, PCC, "DCC+DMSO" or $MnO_2$, and more preferably "DCC+DMSO". The reaction solvent is not particularly limited, but preferably an aprotic solvent. In addition, the salt of a weakly acidic which should be added to the reaction is not particularly limited, preferably pyridine trifluoroacetate, triethylamine trifluoroacetate, pyridine hydrochloride, triethylamine hydrochloride, pyridine sulfate, triethylamine sulfate or the like, and more preferably pyridine trifluoroacetate.

The propionaldehyde derivative and other aldehyde derivatives (D5) can be obtained by deprotonating terminal hydroxyl group followed by the reaction with halides to get corresponding acetal intermediates (D7), and then the compounds (D7) are hydrolyzed to obtain corresponding aldehydes under an acidic condition. The base used for deprotonation is not particularly limited, preferably sodium, potassium, sodium hydride, potassium hydride, sodium methoxide, potassium t-butoxide or diphenylmethyl potassium, and more preferably sodium hydride or diphenylmethyl potassium. The reaction solvent is not particularly limited, preferably an aprotic solvent. The deprotection of the acetal intermediates is carried out under an acidic condition, and the pH of the solution is preferably 1 to 4. The acid is not particularly limited, preferably acetic acid, phosphoric acid, sulfuric acid, hydrochloric acid or nitric acid, and more preferably hydrochloric acid. The reaction solvent is not particularly limited as far as it can dissolve the reagents and the product, preferably water.

The acetal derivative (D7) can also be obtained via the reaction between the polyethylene glycol aldehyde derivative (D5) and corresponding alcohol via acid catalysis. Wherein, the acid is not particularly limited and can be a protonic acid or a Lewis acid, preferably hydrochloric acid, sulfuric acid, trifluoroacetic acid, trifluoromethanesulfonic acid, p-toluenesulfonic acid, aluminum trichloride, tin chloride or the like. The acid is preferably a protonic acid, and more preferably hydrochloric acid, sulfuric acid, trifluoroacetic acid, trifluoromethanesulfonic acid, phosphoric acid or nitric acid. The alcohol is not particularly limited and can be a monool, a diol or a multiol, preferably methanol, ethanol, propanol, butanol, pentanol, ethylene glycol, 1,3-propanediol, 1,4-butanediol or the like. The solvent can be no solvent or an aprotic solvent.

The isocyanate (D9) and thioisocyanate (D10) derivatives can be obtained via the reaction between the alcoholic derivative (H1) or amine derivative (C3) and excess diisocyanate or dithioisocyanate. The diisocyanate and dithioisocyanate are not particularly limited, preferably a $C_{1-10}$ diisocyanate and a $C_{1-10}$ dithioisocyanate, respectively. The solvent can be no solvent or an aprotic solvent. The diisocyanate can be but not limited to 1,6-hexamethylene diisocyanate, dimethylbiphenyl diisocyanate, di-p-phenylmethane diisocyanate, p-phenyl diisocyanate, toluene-2,4-diisocyanate, 1,5-naphthalene diisocyanate, m-xylylene isocyanate, isophorone diisocyanate, 4,4-diisocyanatodicyclohexylmethane, or bis(2-isocyanato)-5-norbornene-2,3-diformate.

The squarate derivative (D24) can be obtained via the reaction between the amine derivative (C3) and squaryl diester.

The sulfonic acid derivative (D25) can be obtained via the alkylation reaction between the haloalkylsulfonic acid (e.g., 2-bromoethylsulfonic acid) and the terminal hydroxyl group.

The oxycarbonylchloride derivative (D29) can be obtained via the reaction between the terminal hydroxyl group (H1) and triphosgene under a basic condition. The base is preferably an organic base, such as dimethylaminopyridine. The solvent is preferably an aprotic solvent, such as dichloromethane.

2.1.1.5. Group E: End-Functionalization Towards $R_{01}$ in Group E

The maleimide derivative (E1) can be obtained via the ring-opening reaction between the amine compound (C3) and maleic anhydride to get a maleic intermediate (E6), followed by a ring-closing condensation reaction by using acetic anhydride or sodium acetate as a catalyst. The reaction solvent is not particularly limited, preferably an aprotic solvent. In the ring-closing condensation reaction, the solvent is not limited, preferably the above-mentioned aprotic solvent or acetic anhydride.

The maleimide derivative (E1) can also be obtained via the condensation reaction between the amine compound (C3) and a maleimido-containing acid or active ester (MAL-containing). The MAL-containing acids include but are not limited to 3-maleimidopropionic acid, 4-maleimidobenzoic acid, 6-maleimidohexanoic acid, 11-(maleimido)undecanoic acid and the like. The MAL-containing active esters include but are not limited to N-succinimidyl maleimidoacetate, N-succinimidyl-3-maleimidopropinate, N-succinimidyl-6-maleimidohexanoate N-(3-maleimidobenzoyloxy)succinamide, N-succinimidyl-4-(N-maleimidomethyl)cyclohexane-1-carboxylate, N-succinimidyl-4-(4-maleimidophenyl)butyrate, N-succinimidyl 11-(maleimido)undecanoate and N-(4-Maleimidebutyryloxy)succinimide. Similarly, the diazamaleimide derivative (E6) can also be obtained via the condensation reaction between the amine compound (C3) and corresponding acid or active ester.

The maleimide derivative (E1) can also be obtained via the condensation reaction between the active ester derivative (functional groups A1 to A10 or functional groups A15 to A18) and MAL-containing amine compound. MAL-containing amines include but are not limited to N-(2-aminoethyl)maleimide and N-(4-aminophenyl)maleimide.

The protected maleimide compound (E4) can be obtained via the substitution reaction between the activated terminal alcoholic hydroxyl group and furan-protected maleimide. The maleimide derivative E1 can be obtained by removing the protection of protected-maleimide derivative (E4) at high temperature. Wherein, the alcoholic hydroxyl activator is not particularly limited and preferably the combination of diisopropyl azodicarboxylate and triphenylphosphine. The reaction solvent is not particularly limited, preferably an aprotic solvent.

The α,β-unsaturated esters (E2, E3) can be obtained by deprotonating the terminal hydroxyl group followed by the reaction with the corresponding halides. The deprotonating base is not particularly limited, preferably sodium, potassium, sodium hydride, potassium hydride, sodium methoxide, potassium t-butoxide or diphenylmethyl potassium, and more preferably sodium hydride or diphenylmethyl potassium. The reaction solvent is not limited, preferably an aprotic solvent. Examples of halides are acryloyl chloride and methacryloyl chloride.

The maleamic acid derivative (E6) can also be obtained via the reaction between the amine derivative (C3) and corresponding dicarboxylic to form an amide bong in the presence of a condensing agent. The condensing agent is not particularly limited, preferably DCC, EDC.HCl, HATU or HBTU, and most preferably DCC. The solvent can be no solvent or an aprotic solvent. The base is generally an organic base, preferably triethylamine or pyridine.

2.1.1.6. Group F: End-Functionalization Towards $R_{o1}$ Selected from Group F The nitrile compound (F1) can be obtained via the addition reaction between the terminal hydroxyl group and acrylonitrile under a basic condition. Alternatively, it can also be obtained in the following manner: the amine derivative (C3) is treated by ammonia in advance and by hydrogen subsequently by using palladium or nickel as a catalyst under a high-pressure condition, and then is dehydrogenated at a high temperature.

Functionalized derivatives (F2, F3, F4 and F5) can be obtained by deprotonating the terminal hydroxyl group followed by a reaction with corresponding halides. The deprotonating base is not particularly limited, preferably sodium, potassium, sodium hydride, potassium hydride, sodium methoxide, potassium tert-butoxide or diphenylmethyl potassium, and more preferably sodium hydride or diphenylmethyl potassium. The reaction solvent is not particularly limited, preferably an aprotic solvent. The halide corresponding to the epoxide compound (F5) can be epichlorohydrin, 2-chloromethyl-2-methyloxirane, 3-chlorophenyloxirane, epifluorohydrin, epibromohydrin, 4-bromo-1,2-epoxybutane, 6-bromo-1,2-epoxyhexane or the like, preferably epichlorohydrin. The halide corresponding to the vinyl-containing compound (F2) can be 3-chloroethene or 3-bromoethene. The halide corresponding to the ethynyl-containing compound can be 3-bromopropyne. The halide corresponding to the protected ethyne compound can be (3-bromo-1-propynyl)trimethylsilane or (3-bromoprop-1-yn-1-yl)(tert-butyl)dimethylsilane.

The nitrile oxide (F11) can be obtained via the reaction between an aldehyde derivative (D5) and hydroxylamine to form an oxime (F12) followed by an oxidization reaction. With respect to the reaction forming the oxime, the solvent can be no solvent or an aprotic solvent. In the oxidation process, the oxidizing agent is not particularly limited, preferably N-iodosuccinimide, N-chlorosuccinimide, N-bromosuccinimide, the like or combination thereof. The solvent can be no solvent or an aprotic solvent.

2.1.1.7. Group G: End-Functionalization Towards $R_{o1}$ Selected from Group G The cyclic alkyne compounds (functional groups G1 to G3 and G19 to G22), cyclodiene compounds (G12 and G9) and furan compound (G5) can be obtained via the reaction between corresponding ring-containing alcohol, carboxylic acid, amine, amide or methyl ester derivative and corresponding reactive groups through condensation reactions, while resulting linking groups include but are not limited to an ester bond, an amide bond, a carbamate bond, a carbonate bond, a hydrazide bond and the like. Examples of reagents are as follows:

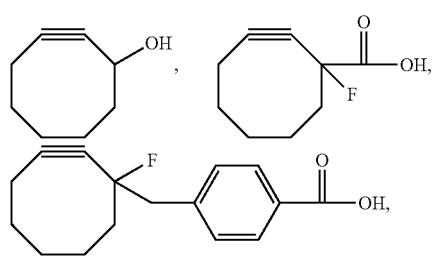

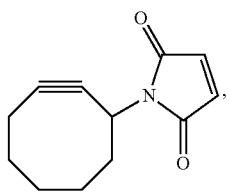

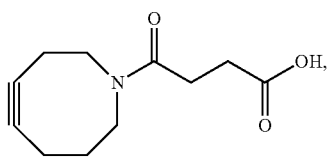

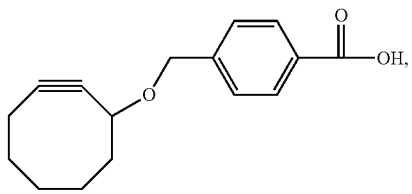

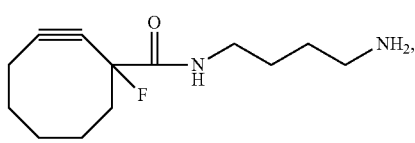

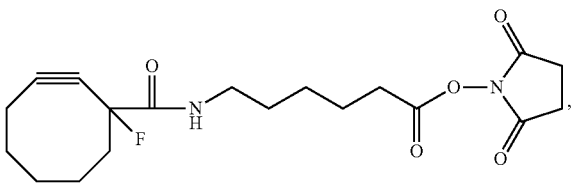

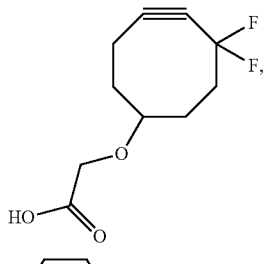

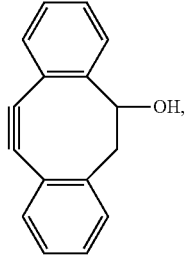

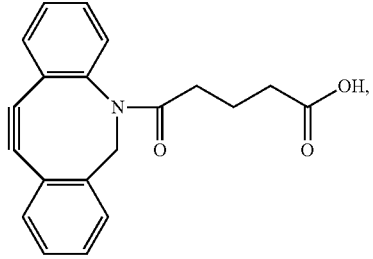

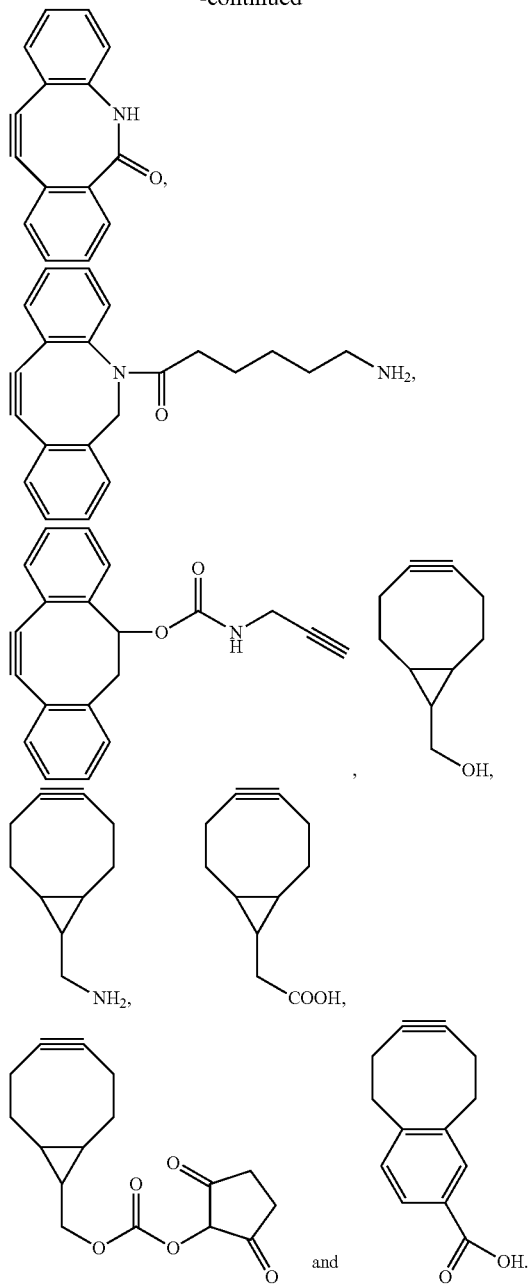

2.1.1.8. Group H: End-Functionalization Towards $R_{O1}$ Selected from Group H

The resulting product obtained after the polymerization of ethylene oxide is a mixture of alcohols and oxygen anions, and can be protonated to obtain polyethylene glycol chains with terminal hydroxyl groups.

The alcohol derivative with a terminal hydroxyl group (H1) can also be obtained by modifying a non-hydroxyl reactive group, e.g., the alcohol having a structure of —NH—CH(=O)CH$_2$CH$_2$OH can be formed via the reaction between vinyl carbonate and a secondary amine.

The alcohol derivative with a terminal hydroxyl group (H1) can also be obtained by treating the amine derivative (C3) with nitrite via the diazotization reaction followed by hydrolysis reaction under a low-temperature and acidic condition. Wherein, the acid is not particularly limited and can be a protonic acid or a Lewis acid, preferably a protonic acid, and more preferably hydrochloric acid, sulfuric acid, trifluoroacetic acid, trifluoromethanesulfonic acid, phosphoric acid or nitric acid. Said low temperature is preferably about 0° C.

The protected hydroxyl group (H2) can be obtained via the reaction between the terminal hydroxyl group and a protective agent. Generally, the protective agent is not particularly limited, preferably a halosilane, a carboxylic acid, an acyl chloride, an anhydride, a halohydrocarbon, a sulfonyl chloride, an alkenyl ether, a carbonyl-containing compound or the like.

A. In general, the terminal hydroxyl group can react with halosilanes, acyl chlorides, anhydrides, sulfonyl chlorides or halohydrocarbons to obtain a protected form (H2) under a neutral or basic condition. The solvent can be no solvent or an aprotic solvent. The base can be an organic base or an inorganic base, preferably an organic base, and more preferably triethylamine and pyridine. Said protected form OPG$_4$ of an ether structure is defined as above.

B. The terminal hydroxyl group can react with a carboxylic acid in the presence of a base and a condensing agent to obtain the compound (H2). The reaction conditions are similar to those for preparing the active ester as a $R_{O1}$ selected from Group A.

C. The terminal hydroxyl group can undergo an addition reaction with an alkenyl ether under an acidic condition to obtain the compound (H2). The alkenyl ether is not particularly limited, preferably ethyl vinyl ether or tetrahydropyran. Wherein, the acid is not particularly limited and it can be a protonic acid or a Lewis acid. The solvent can be no solvent or an aprotic solvent.

D. The terminal hydroxyl group can react with t-butyldimethylchlorosilane, ethyl vinyl ether, dihydropyran, benzyl bromide and di-t-butyl dicarbonate to form hydroxyl groups protected by a silyl group, a 2-ethoxyethyl group, a dihydropyryl group, a benzyl group and a Boc group, respectively.

The protected terminal dihydroxyl group (H3) can be obtained through methods including but not limited to those disclosed in the literature of "Macromol. Biosci. 2011, 11, 1570-1578" and "J. Am. Chem. Soc., Vol. 123, No. 25, 2001".

The photoreactive groups (H6) and (H7) which can be converted to an enolic hydroxyl group can be prepared with the methods disclosed in the literature U.S. Ser. No. 14/021,040.

2.1.1.9. Group I: End-Functionalization Towards $R_{O1}$ Selected from Group I

The pegylated folic acid (I1) can be obtained via the condensation reaction between the carboxyl group of folic acid and a polyethylene glycol or alcoholic derivative thereof (H1) or an amine derivative (C4). Wherein, the condensing agent is not particularly limited, preferably DCC, EDC.HCl, HATU or HBTU, and most preferably DCC. Generally, the molar equivalent of the condensing agent is 1 to 20 folds of folic acid, preferably 5 to 10 folds. Suitable catalyst such as 4-dimethylaminopyridine can be added to the reaction. The solvent can be no solvent or an aprotic solvent. The base is generally an organic base, preferably triethylamine or pyridine.

The pegylated cholesterol derivative (I2) can be obtained via the condensation reaction between the terminal hydroxyl group of polyethylene glycol and corresponding cholesterol derivative of a carboxylic acid (D4), an acyl halide (D6), a sulfonyl chloride (D27), an isocyanate (D9), an isothiocyanate (D10) or the like. The pegylated cholesterol can also be obtained via the coupling reaction between a cholesterol derivative and a compound with a suitable reactive group. Take cholesterol succinate for example, it can be obtained via the condensation reaction with the terminal hydroxyl group of polyethylene glycol.

The pegylated biotin derivative (I3) can be obtained via the condensation reaction between the carboxyl group of biotin and a polyethylene glycol or its alcoholic derivative (H1) or amine derivative (C3). The reaction conditions are the same as those for the above-mentioned reaction between the carboxyl group and a hydroxyl group. Biotin derivatives such as D-dethiobiotin and 2-iminobiotin can also be obtained via the condensation reaction between the carboxyl group and a polyethylene glycol or its alcoholic derivative (H1) or an amine derivative (C3).

The pegylated biotin derivative (I3) can also be obtained via the coupling reaction between any of the above-mentioned biotin derivatives and a suitable polyethylene glycol or derivative thereof such as an alcoholic derivative of polyethylene glycol, an amine derivative (C3), an alkyne derivative (F3, G1-G3 or G19-G22), a carboxylic acid derivative (D4), an acyl halide derivative (D6), an aldehyde derivative (D5) or the like. Wherein, the amine derivative and alcoholic derivative of biotin can also be obtained via the alkylation reaction with corresponding polyethylene glycol sulfonate or polyethylene glycol halide.

2.1.1.10. Group J: End-Functionalization Towards $R_{01}$ Selected from Group J

Regarding this Group, fluorescein and derivatives thereof (including but not limited to J1 and J3), rhodamine the and derivatives thereof (including but not limited to J2), anthracene and derivatives thereof (J4), pyrene and derivatives thereof (J5), coumarin and derivatives thereof (including but not limited to J6), fluorescent yellow 3G and derivatives thereof (including but not limited to J7), carbazole and derivatives thereof (J8), imidazole and derivatives thereof (J9), and indole and derivatives thereof (J10), can be obtained via the coupling reaction between the reactive group thereof such as a succinimidyl active ester group (A1 and A6), a carboxyl group (D4), a primary amino group (C3), a secondary amino group (C14), a hydrazino or substituted hydrazino group (C12, N-aminocarbazole), a cyano group (F1), the unsaturated bond of maleimide (E1), a maleimido group (D35), an aldehyde group (D5), an acrylate group (E2), a methacrylate group (E3), an oxime group (F12) and a hydroxyl group, coupled and functionalized polyethylene glycol to obtain a bio-related substance modified with polyethylene glycol. The coupling reactions include but are not limited to the above-mentioned coupling reactions. Wherein, reagents for functional groups (J1 to J10) include but are not limited to the above-mentioned fluorescent agents in the present invention.

2.1.1.11. Conversion Based on Reactive Groups to the Objective Unprotected or Protected Functional Groups (Also Referred to as Objective Active or Protected Functional Groups)

This can be achieved in any of the following approaches:

Approach 1: direct modification based on a reactive group to get the objective unprotected or protected functional group. For example, the conversion of the carboxyl group to an acyl halide group, a hydrazide group, an ester group, a thioester group or a dithioester group, the conversion of involving a hydroxyl group, a mercapto group, an alkynyl group, an amino group, a carboxyl group, or the like to corresponding protected form thereof, the modification to a hydroxyl group, an amino group or the like with an anhydride, and the like.

Approach 2: a coupling reaction between two reactive groups, using a heterofunctional reagent which contains a reactive group and an objective unprotected or protected functional group as the reagent to introduce the objective unprotected or protected functional group via the reaction between said reactive group and a terminal reactive group of polyethylene glycol chains. The reaction manner and reaction method between above-said two reactive groups are not particularly limited. The reaction conditions are related to the type of divalent linking groups formed after the reaction. The available prior art such as alkylation reaction, addition reaction of alkenes, addition reaction of alkynes, combination of a Schiff base reaction and a reduction reaction, condensation reaction, and the like can be used herein. Wherein, the alkylation reaction is preferably based on a mercapto group or an amino group, corresponding to the formation of a thioether bond, and a secondary amino group or a tertiary amino group, respectively. Wherein, the condensation reaction includes but is not limited to reactions forming an ester bond, a thioester bond, an amide bond, an imine bond (—C=N—), a hydrazone bond, a carbamate bond and the like. For another example, the objective unprotected or protected functional group can be introduced via click reactions by using heterofunctional reagents which contain an azido group, an alkynyl group, an alkenyl group, a trithioester group, a mercapto group, a dienyl group, a furyl group, a 1,2,4,5-tetrazinyl group, a cyanate group or the like. The reaction between two reactive groups brings the formation of new bonds. The representative newly formed divalent linking groups include an amide bond, a urethane bond, an ester bond, a secondary amino bond, a thioether bond, a triazole linkage and the like.

Approach 3: the combination of direct modifications and coupling reactions to obtain the objective unprotected or protected functional group.

2.1.2. The Branched End-Functionalization of Polyethylene Glycol Chains

The branched end-functionalization refers to introducing an end-branching group to link multiple functional or protected functional end-groups to the terminal end of an individual polyethylene glycol chain. Herein, the number of functional or protected functional end-groups of the polyethylene glycol chain terminal is greater than 1. The polyethylene glycol chain terminal to be connected with the end-branching group can be a hydroxyl group or a linear end-functionalized reactive group.

2.1.2.1. Methods for Branched End-Functionalization

Wherein, when $g_0$ is 0 or 1, the end-functionalization includes the following two processes: one process is the introduction of an end-branching group, and the other process is the introduction of multiple functional or protected functional end-groups. The sequence of these two processes is no particularly limited. Herein, the branched end-functionalization can be achieved in the following manners: (1) direct reaction of functionalized end-branching group with the terminal hydroxyl group of polyethylene glycol chains; (2) functionalization of the terminal hydroxyl group of the polyethylene glycol main chain in advance which is followed by the reaction with a functionalized end-branching group; (3) introduction of an end-branching group firstly and functionalization of the branching group subsequently. Wherein, the introduction of the end-branching group can form or do not form the linking group $L_0$. Take the terminal hydroxyl group of polyethylene glycol chains for example: with respect to the introduction of an end-branching group via an alkylation reaction that form a connection of ether type, the reagent that provides the end-branching group loses a leaving group, the hydroxyl group loses a hydrogen atom, and it is regarded that no new linking group is generated. For another example, with respect to reaction of the terminal hydroxyl group of polyethylene glycol chains with reactive groups such as an isocyanato group, a carboxyl group and the like, the whole moiety of the newly formed bonds such as —NHCOO—, —COO— and the like or only partial moiety thereof such as —NHCO—, —CO— and the like are respectively included in $L_0$. Further for another example, the reaction between polyethylene glycol chain ends functionalized with a succinic acid group and the end-branching reagent would form a linking group containing a succinyl group. Modification methods for functionalizing the above-said end-branching groups are not particularly limited, including end-functionalization based on a hydroxyl group and the conversion of a non-hydroxyl reactive group to the objective functional or protected functional end-group.

When $g_0$ is greater than 1, the branched end-functionalization includes the following three processes: introduction of the linking group, introduction of the end-branching group, and introduction of the objective unprotected or protected functional end-groups. Said linking group is not particularly limited, for example, it can contain segments consisting of repeat units such as amino acids, peptides or the like. Starting from the polyethylene glycol terminal hydroxyl group or above-said linear end-functionalized group, and the sequence and combination of above-aid three processes are each independently not particularly limited. Take the branched end-functionalization of polyethylene glycol main chain for example, production methods include but are not limited to the following four manners: (1) introduce the linking group, the end-branching group and the objective unprotected or protected functional end-groups by merely one step; (2) introduce the linking group in the first step and then the end-branching group and the objective unprotected or protected functional end-groups in the second step; (3) introduce the linking group in the first step, then the end-branching group in the second step, and later the objective unprotected or protected functional end-groups in the third step; (4) introduce the linking group and the branching group in the first group, and then the objective unprotected or protected functional end-groups in the second step.

The method for introducing the above-mentioned end-branching groups is not particularly limited. The available prior art in the chemistry field can be applied as long as a covalent bond can be formed, including but not limited to various coupling reactions involving the conversion of a reactive group to the objective unprotected or protected functional end-group. For example, the preparation methods of comb-like structures in the literatures of "Macromolecules 2013, 46, 3280-3287", "Macromol. Chem. Phys. 2014, 215, 566-571", "Macromolecules, 2012, 45, 3039-3046", "Polym. Chem., 2012, 3, 1714-1721", "U.S. Pat. Nos. 5,811,510, 7,790,150", "7,838,619", etc, the preparation methods of hyperbranched structures in the literatures of "Journal of Polymer Science, Part A: Polymer Chemistry, 2013, 51, 995-1019", "Macromol. Biosci. 2011, 11, 1553-1562", "Macromol. Rapid Commun. 2010, 31, 1811-1815", "Langmuir 2010, 26(11), 8875-8881", etc, the preparation methods of dendritic structures in the literatures of "Nanoscale Research Letters, 2014, 9:247", "J. Movellan et al. Biomaterials 35 (2014) 7940-7950", "Chem. Soc. Rev., 2011, 40, 2673-2703", "Macromolecules, Vol. 33, No. 12, 2000", "Chem. Soc. Rev., 2011, 40, 2673-2703", "Biomacromolecules 2012, 13, 4089-4097", etc.

Functionalization methods of the terminals of the end-branching group are not particularly limited, including but not limited to the above-mentioned linear end-functionalization methods.

2.1.2.2. Reagents for Branched End-Functionalization

With respect to terminal bifunctionalization, also referred to as end-bifunctionalization, the applicable reagents are preferably heterofunctional small molecules (htriSM) which contain one above-said trivalent core structure, epoxy-containing aldehydes, epoxy-containing alcohols (e.q., 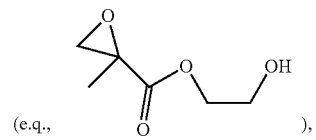 ), epoxy-containing sulfonates, epoxy-containing halides, compounds that contain one epoxy group and another different reactive group, combination compounds formed by one molecule primary amine and two molecules of acrylic acid ester of the Michael addition reaction of. It also can use the lipoic acid as terminal, then the reduction and ring-opening reactions of the disulfide bond are carried out to obtain two terminal mercapto groups.

Wherein, said htriSM contains two different kinds of functional groups, wherein one kind functional group is 1 in quantities, and the other kind functional group is 2. The pairs of heterofunctional groups which can be present meanwhile include but are not limited to the pairs listed in the above-mentioned part 1.1.4.

Said htriSM molecules include but are not limited to small molecule compounds which contain two unprotected or protected hydroxyl groups (e.g., triethanolamine p-toluenesulfonate, glycerol monomercaptoacetate, 2-Chloro-3',4'-dihydroxyacetophenone and hydroxyl-protected forms thereof), two unprotected or protected mercapto groups (e.g., dimercapto-propanol and its mercapto-protected form), two primary amino groups, two secondary amino groups, two protected primary amino groups or two protected secondary amino groups, wherein said small molecule compounds include alcohols, thiols, primary amines, secondary amines, sulfonates and halides. Said htriSM molecules include but are not limited to htriSMs used in the polymerization process of the present invention. Wherein, one example of alcohols containing two primary amino groups is 1,3-diamino-2-propanol.

Said htriSM molecules also include but are not limited to primary amines containing two hydroxyl groups, aldehydes containing two protected hydroxyl groups, aldehydes containing an epoxy group, primary amines containing an epoxy group, secondary amines containing two primary amino groups, sulfonic acids containing two hydroxyl groups, carboxylic acids containing two hydroxyl groups, azides containing two hydroxyl groups, and hydroxyl-protected forms of the above-said compounds. The primary amines containing two hydroxyl groups include but are not limited to 2-amino-1,3-propanediol, 2-amino-2-methyl-1,3-propanediol, N,N-bis(2-hydroxyethyl)ethylenediamine, 3-amino-1,2-propanediol, 2-amino-1-[4-(methylthio)phenyl]-1,3-propanediol, 2-amino-1-phenyl-1,3-propanediol, 2-(3,4-dihydroxylphenyl)ethylamine, 2-amino-1,3-benzenediol and the like. The secondary amines containing two primary amino groups include but are not limited to diethylenetriamine, N-(3-aminopropyl)-1,4-butanediamine, 3,3'- diaminodipropylamine, N-(2-aminoethyl)-1,3-propanediamine, 3,6-diaminocarbazole and the like. The sulfonic acids containing two hydroxyl groups include but are not limited to 6,7-dihydroxynaphthalene-2-sulfonic acid, 1,4-dihydroxyanthraquinone-2-sulfonic acid, and the like. The carboxylic acids containing two hydroxyl groups include but are not limited to 2,3-dihydroxypropionic acid, 2,2-bis(hydroxymethyl)propionic acid, 2,4-dihydroxy-3,3-dimethylbutanoic acid, N,N-bis(hydroxyethyl)glycine, 2,3-dihydroxybenzoic acid, 2,4-dihydroxybenzoic acid, 2,5-dihydroxybenzoic acid, 2,6-dihydroxybenzoic acid, 3,4-dihydroxybenzoic acid, 3,5-dihydroxybenzoic acid, 3,4-dihydroxyphenylacetic acid, 3,5-dihydroxyphenylacetic acid, 3,4-dihydroxycinnamic acid, 2,6-dihydroxypyridine-4-carboxylic acid and 4,8-dihydroxyquinoline-2-carboxylic acid. The azides containing two hydroxyl groups include but are not limited to 3-azido-2,3-dideoxyl-1-O-(t-butyldimethylsilyl)-β-D-Arabino-pyranose and azidohexyl 2,2-bis(hydroxymethyl)propionate. Wherein, with respect to protected forms of two hydroxyl groups, take dihydroxyl-protecting for example,

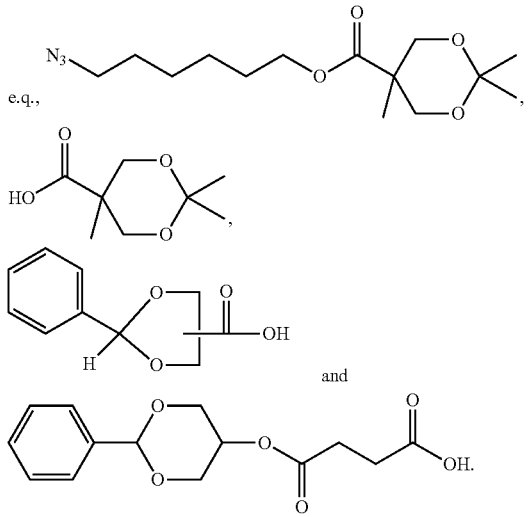

Said htriSM molecules also include but are not limited to 3-allyloxy-1,2-propanediol, 5-norbornene-2,3-dicarboxylic acid, 3-(2-propynyloxy)propane-1,2-diol, 3-cyano-2,6-dihydroxy-4-methylpyridine, 1,3-dibromo-2-propanol, 2,3-dibromo-1-propanol, 1,4-dibromo-2-butanol, 1,4-diazido-2-butanol, 1,3-dichloro-2-propanol, 4,4'-dichlorobenzhydrol, 2-bromo-malonaldehyde, 2-hydroxyhexanedialdehyde, 2-(4-chlorophenyl)malondialdehyde, 2-(5-carboxypyridin-2-yl)malondialdehyde, 7-amino-1,3-naphthalenedisulfonic acid, 4-chloro-1,2-phenylenediamine, 4-bromo-o-phenylenediamine, 6,8-dimercaptoctanoic acid, 4-chloro-1,3-benzenedithiol, 2,6-bis(p-azidobenzal)-4-carboxycyclohexanone, hydroxyl dicarboxylic acids which contain two carboxyl groups and one hydroxyl groups (including but not limited to tartronic acid, L-malic acid, D-malic acid, butanedioic acid and 3-hydroxylpentanedioic acid), amino dicarboxylic acids which contain two carboxyl groups and one amino group (including but not limited to 2-aminomalonic acid, diethyl 2-aminomalonate and 3-aminoglutaric acid), mercapto dicarboxylic acids which contain two carboxyl groups and one mercapto group (including but not limited to mercaptosuccinic acid), 4-chlorophthalic acid, 2-bromosuccinic acid, methylenesuccinic acid, 4-amino-2-(2-aminoethylamino)butyric acid, 4-amino-2-(2-aminoethylamino)butyric acid with two amino groups to be protected, glycerol dimethacrylate, 2,2-di(allyloxymethyl)-1-butanol,

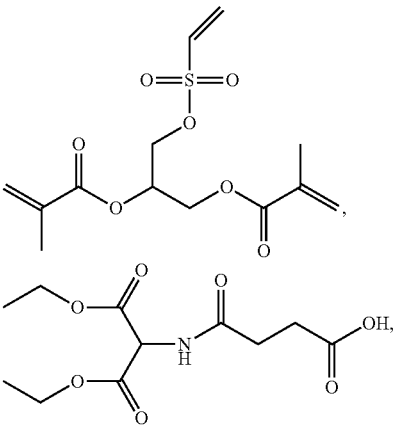

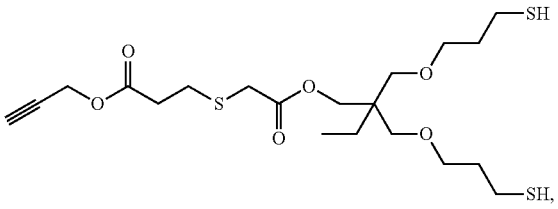

the like, and protected forms of any above-said htriSM with the two identical functional groups to be protected.

Said htriSM molecules also include but are not limited to lysine, lysine with two amino groups to be protected, glutamic acid and aspartic acid.

Since both the two hydrogen atoms of the primary amine can be substituted to form a trivalent N-branching center, then heterofunctional small molecules containing a primary amino group and another reactive group can be used as htriSM. For example, diglycolamine, 2-[(2-aminoethyl)thio]ethanol, 1-amino-2-propanol, 4-hydroxyphenylthylamine, mercaptoethylamine, N-methyl-1,3-propanediamine, N-ethyl-1,3-propanediamine and N-isopropyl-1,3-diaminopropane.

With respect to terminal trifunctionalization, the applicable reagents include but are not limited to tetrafunctionalized small molecules (htetraSM) which contain three hydroxyl groups and one different kind of reactive group. Said htetraSM molecules include but are not limited to N-tris(hydroxymethyl)methyl-2-aminoethanesulfonic acid, 3-[tris(hydroxymethyl)methylamino]-1-propanesulfonic acid, methyl 6-O-tosyl-α-D-glucopyranoside, 2-(bromomethyl)-2-(hydroxymethyl)-1,3-propanediol, tris(hydroxymethyl)aminomethane, 2-amino-1,3,4-octadecanetriol, 3-aminopropylsilanetriol, 4-(2-amino-1-hydroxylethyl)-1,2-benzenediol, 4-[1-hydroxy-2-(propan-2-ylamino)ethyl]benzene-1,2-diol, 3,4-dihydroxy-alpha-(methylaminomethyl)benzyl alcohol, 2,5-anhydro-1-azido-1-deoxy-D-glucitol, 2,3,4-trihydroxybutanal (L-erythrose, D-erythrose, L-(+)-threose and D-(+)-threose), 2,3,4-trihydroxybenzaldehyde, 3,4,5-trihydroxybenzaldehyde, N-[tris(hydroxymethyl)methyl]glycine, 2,3,4-trihydroxybutyric acid (including but not limited to erythorbic acid and threonic acid), 2,4,6-trihydroxybenzoic acid, shikimic acid, 3,4,5-trihydroxybenzoic acid, 2,3,4-trihydroxybenzoic acid, arjunolic acid, 1,4,7-tris(tert-butoxycarbonyl)-1,4,7,10-tetraazacyclododecane, tri-(t-butoxycarbonyl)spermine, the like, and hydroxyl-protected forms of above-said htetraSM molecules. The htetraSM molecules can also be citric acid, laricic acid, N-(2-hydroxyethyl)ethylenediamine-triacetic acid, pentaerythritol triacrylate, 4-amino-4-(2-carboxyehtyl)-heptanedioic acid, di-tert-butyl 4-amino-4-(3-(tert-butoxy)-3-oxopropyl)heptanedioate or the like. The resulting compound formed via the reaction based on an alkenyl, trichlorosilane and allylmagnesium chloride, along with the formation of a tetravalent silicon-atom branching center, referring to the literature "Macromolecules, Vol. 33, No. 12, 2000", is also included. Trifunctionalized small molecules, such as 1,4,7-tris(t-butoxycarbonylmethyl)-1,4,7,10-azacyclotetradecane (NOTA), are also included and require an excess amount in the reaction.

With respect to terminal tetrafunctionalization, the applicable reagents can be pentafunctional compounds such as xylitol, 1,5-anhydroglucitol, bis(2-hydroxyethyl)iminotris(hydroxymethyl)methane, miglitol, D-(+)-talose, arbutin, diethylenetriaminepentaacetic acid and the like, but preferably heteropentafunctional small molecules that contain two different kinds of functional groups, including but not limited to compounds with four protected hydroxyl groups and one reactive group such as 1,2:5,6-di-O-isopropylidene-α-D-isofuranose, 2,3:5,6-di-O-cyclohexylidene-α-D-mannofuranose, 2-azido-1,3-bis(2,2-dimethyl-1,3-dioxan-5-yl)oxy]propane and the like. Said pentafunctional compounds also include but are not limited to molecules which contain two epoxy groups and one reactive group-containing molecule. Said pentafunctional compounds can also be preferably pentafunctional small molecules (hpentSM) that contain two kinds of functional groups, wherein one kind functional group is four in quantities and the other kind functional group is one, such as 2-(2-hydroxyethylamino)-2-hydroxymethyl-1,3-propanediol, 2-hydroxymethyl-piperidine-3,4,5-triol, 6-amino-4-(hydroxymethyl)-4-cyclohexane-[4H,5H]-1,2,3-triol, fenoterol, benserazide, 1-azido-1-deoxy-β-D-galactopyranoside, 2-azidoethyl β-D-glucopyranoside, 2,3,4,5-tetrahydroxypentanal (including but not limited to ribose, arabinose, xylose and lyxose), 2,3,4,5-tetrahydroxypentanoic acid (including but not limited to ribonucleic acid, arabinonic acid, lignic acid and lysuccinic acid), diethylenetriamine, N-(3-aminopropyl)-1,4-diaminebutane, the like, and protected forms of any said hpentSM molecule wherein functional groups is quantities of four are protected.

With respect to terminal pentafunctionalization, the applicable reagents are preferably hexafunctional small molecule (hhexaSM) which contain two kinds of functional groups, wherein one kind functional group is five in quantities and the other kind functional group is one, including but not limited to sorbitol, mannitol, D-talitol, D-glucamine, 1-thio-D-glucitol, N-methyl-D-glucamine, 2,3,4,5,6-pentahydroxyhexanal (including, but not limited to β-D-allose, D-altrose, D-anhydrousglucose D-(+)-mannose, L-(−)-mannose, D-gluconose, idose, D-galactose, L(−)-talose and D-(+)-talose), 2,3,4,5,6-pentahydroxyhexanoic acid (including but not limited to allonic acid, altronic acid, gluconic acid, mannonic acid, gulonic acid, idonic acid, galactonic acid and talonic acid), D-sorbitol 3-phosphate, the like, and protected forms of any said hhexaSM molecules wherein functional groups in quantities of five are protected.

The applicable reagents for providing dendritic end-branching groups can be but not limited to htriSM molecules, htetraSM molecules, hpentSM molecules, hhexaSM molecules, heterofunctional molecules containing an epoxy group and another kind of reactive group, htriSM molecules containing two unprotected or protected ethynyl groups and another kind of reactive group, diallyl(methyl)silane, the combination of acrylates and diamines (repeating Michael addition reaction between a primary amine and two molecules of acrylates and amidation reaction of the ester group), the combination of propargyl glycidyl ether and mercaptoethylamine, mercaptoethylamine hydrochloride or amino-protected mercaptoethylamine (repeating the addition reaction between a primary amino group and an epoxy group and click reaction of an alkynyl group with two mercapto groups), a diallylmethylsilyl group and the like. Specific examples include

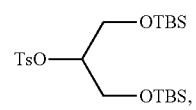

epichlorohydrin, lysine with two amino groups being protected, glutamic acid, aspartic acid, N,N-bis(2-hydroxyethyl)glycine and hydroxyl-protected form thereof with two hydroxyl groups being protected, dihydroxy monocarboxylic acids and hydroxyl-protected forms thereof, hydroxy dicarboxylic acids and hydroxyl-protected forms thereof, amino dicarboxylic acids and amino-protected protected forms thereof, mercaptodicarboxylic acids and mercapto-protected forms thereof, glyceraldehyde and hydroxyl-protected form thereof, Methyl 6-O-tosyl-alpha-D-galactopyranoside, 3-aminopropylsilanetriol, 2,3,4-trihydroxybutanal, 2,3,4-trihydroxybutanoic acid, citric acid, N-(2-hydroxyethyl)ethylenediaminetriacetic acid,

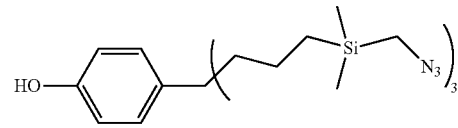

2-azido-1,3-bis[(2,2-dimethyl-1,3-dioxan-5-yl)oxo]propane, etc. Wherein, the dihydroxy monocarboxylic acid is preferably 2,2-bis(hydroxymethyl)propionic acid. The hydroxy dicarboxylic acid is preferably a malic acid or a 3-hydroxypentanedioic acid.

The Applicable monomers used for the preparing hyperbranched end-branching structures include but are not limited to those disclosed in the literature "Journal of Polymer Science, Part A: Polymer Chemistry, 2013, 51, 995-1019", for example, glycidol,

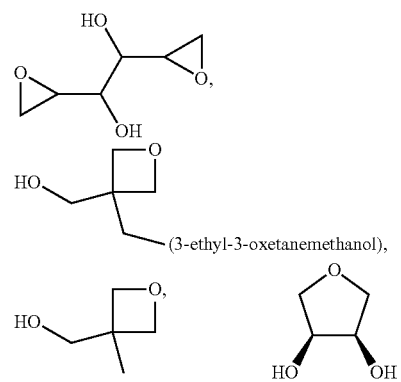

(3-ethyl-3-oxetanemethanol),

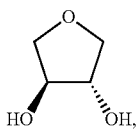 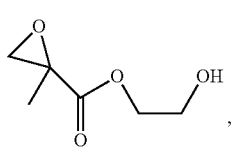

combinations of acrylates and diamines, and the like.

The Applicable monomers used for the preparing comb-like end-branching structures containing repeat units include but are not limited to glycerol with a protected 2-hydroxyl group form a multiglycidyl ether, pentaerythritol with two protected hydroxyl groups (e.g., the monomer of benzaldehyde monopentaerythritolacetel to form multipentaerythrityl ether),

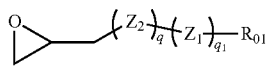

(the definitions of $Z_1$, $q_1$ and $R_{01}$ are in accord with those above-mentioned, preferably a protected form, and one preferable form is protected hydroxyl group $OPG_4$; e.g., 1-ethoxyethyl (2,3-epoxy)propyl ether, benzyl glycidyl ether, t-butyl glycidyl ether, allyl glycidyl ether, propargyl glycidyl ether, glycidyl methacrylate,

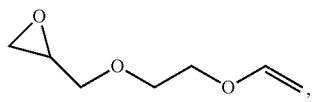

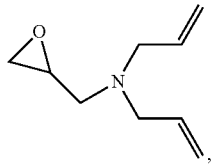

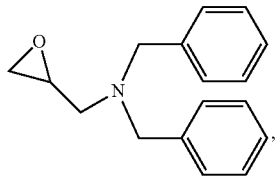

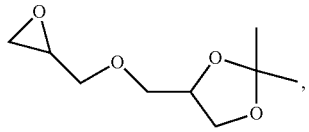

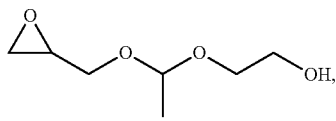

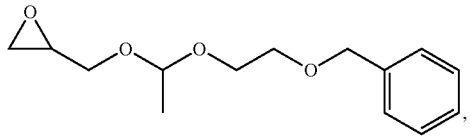

etc)

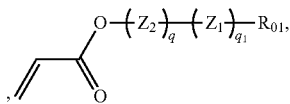 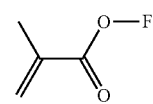

(e.g., azidopropyl methacrylate), the combination of carbon dioxide and

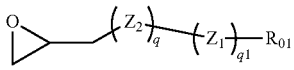

(e.g., "Macromolecules 2013, 46, 3280-3287"; e.g., the combination of carbon dioxide and

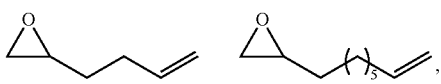

propargyl glycidyl ether, or the like), the combination of a diisocyanate and a diol having one unprotected or protected reactive group),

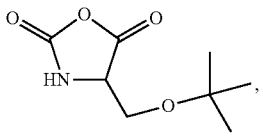

the combination of

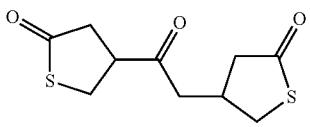 [SMILES: O=C1CC(CC(=O)C2CSC(=O)C2)CS1]

and a diamine (to form a comb-like structure with multiple pendent mercapto groups, referring to "Macromol. Rapid Commun. 2014, 35, 1986-1993"), D-glucopyranose (to form glycan of acetal structure, such as (1→6)polyhexose, (2→1) polyfructosan; specific examples include glucan and oxidized structures thereof and polyfructoses disclosed in the literature of U.S. Pat. Nos. 5,811,510, 7,790,150 and 7,838,619), lysine, aspartic acid, glutamic acid and the like. Other triols, tri- or tetra-ols with one hydroxyl group being protected, tetraols with two hydroxyl groups being protected, multiols with only two active hydroxyl groups and other hydroxyl groups being protected can also be used as reagents for preparing comb-like end-branching structures. In addition, the comb-like structure can be a non-repeated structure, e.g., peptide structures formed by using some amino acids such as glycine as the spacer group and using more than two amino acids selected from lysine, aspartic acid and glutamic acid as branching unit. Moreover, said monomers also include but are not limited to 2,3,4,5-tetrahydroxy-petanal, 2,3,4,5-tetrahydroxy-pentanoic acid, 2,3,4,5,6-pentahydroxy-hexanal, 2,3,4,5,6-pentahydroxy-hexanoic acid, D-glucamine, 1-thio-glucitol, N-methyl-D-glucamine, D-sorbitol-3-phosphate and the like can directly serve as reagents for preparing comb-like branched terminals.

The applicable reagents for the preparing cyclic end-branching structures include but are not limited to 2,5-anhydro-1-azido-1-deoxy-D-glucitol, 1,4,7-tris-(t-butoxycarbonyl)-1,4,7,10-tetraazacyclododecane, 2-hydroxymethyl-piperidine-3,4,5-triol, 6-amino-4-(hydroxymethyl)-4-cyclohexane-[4H,5H]-1,2,3-triol, 1-azido-1-deoxy-β-D-galactopyranoside, 2-azidoethyl β-D-glucopyranoside, propargyl α-D-mannopyranoside, propargyl α-L-fucopyranoside, propargyl β-D-lactoside, monofunctionalized cyclodextrin (e.g., mono-6-O-(azido)-6-deoxy-β-cyclodextrin, mono-6-O-(p-toluenesulfonye-γ-cyclodextrin, mono-2-O-(p-toluenesulfonyl)-γ-cyclodextrin, mono-6-O-(p-toluenesulfonyl)-β-cyclodextrin, mono-2-O-(p-toluenesulfonyl)-α-cyclodextrin, etc.) and the like.

2.1.3. The Coupling Reactions

The types of coupling reactions described in the present method are not particularly limited as long as two identical or different reactive groups can form a covalent linking group after reaction. The reaction conditions are related to the types of resulting covalent linking groups, and the prior art can be introduced herein. Coupling reactions in the present invention include but are not limited to all available reactions to form covalent linking group involving all the above-mentioned functional groups from Group A to Group H, as well as all the above-mentioned reaction types. The valence of the covalent linking groups can be either divalent or trivalent, and mainly divalent.

The coupling reaction can form stable or degradable groups.

Generally, for example, an amino group can react with an active ester, an active formate, a sulfonate ester, an aldehyde, an α,β-unsaturated compound, a carboxylic acid, an epoxide, an isocyanate and an isothiocyanate to obtain a divalent linking group of an amide bond a urethane bond, an amino bond an imide bond (which can be further reduced to a secondary amino group), an amino bond, an amide bond, a hydroxyalkylamino bond, a urea bond (a carbamide bond or a ureido bond) and a thiourea bond, respectively; a mercapto group can react with an active ester, an active formate, a sulfonate group, a mercapto group, a maleimido group, an aldehyde group, an α,β-unsaturated bond, a carboxyl group, an iodoacetamide group and an anhydride group to obtain a divalent linking group of a thioester bond, a thiocarbonate bond, a thioether bond, a disulfide bond, a thioether bond, a thiohemiacetal linkage, a thioether bond, a thioester bond, a thioether bond and an imide linkage, respectively; an unsaturated bond can react with a mercapto group to obtain a thioether group; a carboxyl group or an acyl halide can react with a mercapto group and an amino group to obtain a thioester bond and an amide bond, respectively; a hydroxyl group can react with a carboxyl group, an isocyanate, an epoxide or a chlorocarbonyloxy group to obtain a divalent linking group of an ester bond, a carbamate bond, an ether bond and a carbonate group, respectively; a carbonyl group or an aldehyde group can react with an amino group, a hydrazine and a hydrazide to obtain a divalent linking group of an imine bond, a hydrazone bond and an acylhydrazone bond, respectively; a reactive group of an azido group, an alkynyl group, an alkenyl group, a mercapto group, an azido group, a dienyl group, a maleimido group, a 1,2,4-triazoline-3,5-dione group, a dithioester group, a hydroxylamine, a hydrazide, an acrylate, an allyloxy group, an isocyanate, a tetrazole or the like can undergo click reactions to form various linking groups including but not limited to a triazole linkage, an isoxazole linkage, a thioether bond and the like. Linking groups formed via click reactions disclosed in the literature "Adv. Funct. Mater., 2014, 24, 2572" and cited references therein are incorporated by reference into the present invention. Specifically, such as azide-alkyne cycloaddition reactions, Diels-Alder addition reactions, reactions with the formation of oximes or acylhydrazones, thiol-ene addition reactions, thiol-yne addition reactions, thiol-isocyanate reactions, 1,3-dipolar cycloaddition reactions and the like. Coupling reaction in the present invention also include but are not limited to cycloaddition reactions, Diels-Alder addition reactions, 1,3-dipolar cycloaddition reactions and the like which can be conducted via functional groups in Group G. The primary amines can react with one molecule of sulfonate, halide, epoxide,α,β-unsaturated compound to obtain a divalent secondary amino group, or react with two molecules of above-said reagents to form a trivalent t-amino group. Another example is the reaction between a functional group B5 or B6 with a disulfide bond to form a trivalent linking group.

Typical examples of resulting divalent linking groups include an amide bond, a urethane bond, an ester bond, a secondary amino bond, a thioether bond, a triazole linkage and the like. When forming an amide bond (—CONH—) or an imide bond (—CON(-)$_2$), the reactions can be conducted, including but not limited to, through the following methods: (1) via the condensation reaction between an amino group and a carboxyl group; (2) via the reaction between an amino group and a carboxylic acid derivative; (3) via the amidation reaction of an amine substrate with an acyl halide, and the acyl halide is preferably an acyl chloride. When forming a urethane bond (—OCONH—), it can be obtained via the condensation reaction between a terminal amino group and a terminal active carbonate derivative, wherein, the active carbonate can be derivatives which are capable of reacting with an amino group to obtain a urethane bond, including but not limited to succinimidyl carbonate (SC), p-nitrophenol carbonate (p-NPC), 2,4,6-trichlorophenol carbonate, imidazole carbonate, N-hydroxybenzotriazole carbonate, and preferably succinimidyl carbonate (SC), o-nitrophenol carbonate (o-NPC) or the like; a urethane bond can also be obtained via the reaction between a hydroxyl group and an isocyanate. When forming a thio- or dithio-carbamate bond, the reactions can be carried out between a terminal amino group and a terminal thio(oxycarbonyl) chloride (—O—C(=S)Cl, —S—C(=O)Cl or —S—C(=S)Cl), between a hydroxyl or mercapto group and an isothiocyanate, or between a mercapto group and an isocyanate. When forming an ester bond (—OCO—), it can be obtained via the condensation reaction between a terminal hydroxyl group and a terminal carboxyl group or an acyl halide, and the acyl halide is preferably an acyl chloride. When forming a secondary amino bond (—CH$_2$NHCH$_2$—), it can be obtained by the condensation reaction and subsequent reduction reaction of an aldehyde and an amino group, it can also be obtained via the alkylation reaction of a primary amine with a sulfonate or a halide. When forming a thioether bond (>CHS—), it can be obtained via the addition reaction between a terminal mercapto group and a maleimido group or other reactive groups containing unsaturated-bonds ("Angew. Chem. Int. Ed., 2010, 49, 3415-3417"), or be obtained via the alkylation reaction between a terminal mercapto group and a sulfonate or a halide. When forming a triazole linkage, it can be obtained via click reactions between an alkynyl group and an azido group. When forming a 4,5-dihydroisoxazole linkage, it can be obtained via 1,3-dipolar cycloaddition reactions between a nitrile oxide and an alkynyl group.

Typical reaction to form a stable divalent linking group is alkylation reactions, including but not limited to alkylation reactions between a hydroxyl group, a mercapto group or an amino group and a sulfonate or a halide, corresponding to the formation of an ether bond, a thioether bond, a secondary amino bond or a tertiary amino bond, respectively Production methods in the present invention also allow small molecules containing two identical or different functional groups (biSM) as reagents, as the linking groups between a tetraSM moiety and a htriSM moiety, or as the linking groups between a htriSM moiety and main, branch PEG, or as the linking groups between PEG blocks in LPEG. The biSM molecules are preferably heterofunctional biSM (biheteroSM) molecules. Typical examples include amino acids and derivatives thereof, and preferably neutral amino acids and derivatives thereof, such as glycine, alanine, β-alanine and the like. Examples of biheteroSM molecules include but are not limited to 2-mercaptoethanol, aminoethylethanolamine, 2-(2-aminoethoxy)ethanol, 2-(2-aminoethylthio)ethanol, 1-amino-2-propanol, 4-hydroxyphenylethylamine, 2-azidoethanol, 2-(2-(2-azidoethoxy)ethoxy)ethanol, hydroxycitronellal diethylacetal, hydroxycarboxylic acids, hydroxycarboxylic acids substituted with an aralkyl group or an aryl group, N-hydroxymaleimide, N-(2-hydroxyethyl)maleimide, 3-hydroxybutyronitrile, 4-hydroxy-1-naphthalenesulfonic acid, 8-hydroxyquinoline-5-sulfonic acid, 2-(p-toluenesulfonyl)ethanol, 2-hydroxy-2-phenylethyl 4-methylbenzenesulfonate, 2-aminonaphthalene-1-sulfonic acid, 1-naphthylamine-8-sulfonic acid, 4-amino-1-naphthalenesulfonic acid, 5-amino-naphthalenesulfonic acid, 2-(methylsulfonyl) ethylsuccinimidyl carbonate, 2-chloro-1-(p-toluenesulfonyl)ethane, N-succinimidyl 3-(2-pyridyldithio)propionate, 4-(toluenesulfonyl)acetonitrile, 2-(thien-2-yl)ethyl 4-methylbenzenesulfonate, mercaptoethylamine, mercaptoethylamine hydrochloride, mercaptoacetic acid, 2-mercaptopropionic acid, 2-aminoethanethiol, 2-azidoethanamine, O-(2-aminoethyl)-O'-(2-azidoethyl)pentaethylene glycol, 1-azido-2(2-(2-chloroethoxy)ethoxy)ethanol, 4-bromophenylsulfonyl chloride, 3-chloropropanesulfonyl chloride, 3-chloropropionyl chloride, 4-(chloromethyl)benzoyl chloride, 4-bromobutyryl chloride, iodoacetic acid, 3-chloropropyl isocyanate, 3-chloro-4-methylphenyl isocyanate, 3-bromophenyl isocyanate, p-cyanophenyl isocyanate, 3-cyanophenyl isocyanate, 2-cyanophenyl isocyanate, Boc-piperazine-2-carboxylic acid, morpholine-3,4-dicarboxylic acid 4-tert-butyl ester, 2,4-morpholinedicarboxylic acid 4-(1,1-dimethylethyl) ester, N-benzylmaleamic acid, 4-carboxybenzenesulfonyl azide, 2-azido-2-methylpropionic acid, 4-azidobenzoic acid, N-succinimidyl 4-azido-2,3,5,6-tetrafluorobenzoate, Fmoc-4-azidobutyric acid, acrolein diethyl acetal, bromoacetaldehyde diethyl acetal, 3-bromopropionaldehyde dimethyl acetal; 2-bromobenzaldehyde diethyl acetal, 3-(2,2-diethoxy)propyne, (3,3-diethoxy-1-propynyl)trimethylsilane, succinimidyl maleimidoacetate, N-succinimidyl 3-maleimidopropionate, N-succinimidyl 6-maleimidohexanoate, N-(3-maleimidobenzoyloxy)succinamide, N-succinimidyl 4-(N-maleimidomethyl)cyclohexane-1-carboxylate, N-succinimidyl 4-(4-maleimidophenhyl)butyrate, N-succinimidyl 11-(maleimido)undecanoate, N-succinimidyl 4-(maleimido)butanoate, 3-maleimidopropionic acid, 4-maleimidobenzoic acid, 6-maleimidocaproic acid, 11-maleamidoundecanoic acid, N-(2-aminoethyl)maleimide, N-(4-aminophenyl)maleimide, N-succinimidyl 4-pentynoate, propargyl chloroformate, 2-butyn-1-yl chloroformate, 3-butyn-1-yl chloroformate, 4-ethynylaniline, 2-ethynylaniline, 4-ethynylbenzaldehyde, 4-[(trimethylsilyl)ethynyl]benzaldehyde, 2-[(trimethylsilyl)ethynyl]benzaldehyde, 3-cyano-2-hydroxypyridine, 3-hdroxyenzonitrile, N-2-cyanoethylsuccinimide, cyanomethyl benzenesulfonate, cyanomethyl p-toluenesulfonate, 2-(chloromethyl)benzonitrile, 3-(chloromethyl)benzonitrile, 4-(chloromethyl)benzonitrile, 2-chloro-3-cyanopyridine, p-iodobenzonitrile, 4'-amino-4-cyanobiphenyl, 2-amino-5-methylbenzonitrile, 1-methyl-4-cyano-5-amino-1,2-pyrazole, 2-amino-5-trifluoromethylbenzonitrile, 2-amino-2-cyanoacetamide, cyanoacetic acid, p-cyanobenzoic acid, m-cyanobenzoic acid, o-cyanobenzoic acid, 1-cyano-1-cyclopropanecarboxylic acid, methyl 4-cyanobenzoate, 4-cyanobenzoyl chloride, 4-cyanobenzaldehyde, cyanoacetaldehyde diethylacetal, allyl cyanide, 5-norbornene-2-methanol, 5-norbornene-2-carboxamide, 5-norbornene-2-carbonitrile, 5-norbornene-2-methylamine, allyl chloride, propargyl chloroformate, allyl chloroformate, 2-hydroxyethyl methacrylate (HEMA), the like, and protected forms of any said compound with one functional group to be protected. Wherein, typical examples of hydroxycarboxylic acids include 2-hydroxycarboxylic acids and 3-hydroxycarboxylic acids. Examples of 2-hydroxycarboxylic acids include but are not limited to 2-hydroxypropionic acid, 2-hydroxybutyric acid, 2-hydroxypentanoic acid, 2-hydroxyhexanoic acid, 2-hydroxyheptanoic acid, 2-hydroxyoctanoic acid, 2-hydroxynonanoic acid, 2-hydroxydecanoic acid, 2-hydroxyundecanoic acid, 2-hydroxylauric acid, 2-hydroxymyristic acid, 2-hydroxypalmitic acid, 2-hydroxystearic acid, 2-hydroxyoleic acid, 2-hydroxyelaidic acid, 2-hydroxylinolenic acid, 2-hydroxyarachidic acid, 2-hydroxyarachidonic acid, 2-hydroxyundecanoic acid, 2-hydroxydocosanoic acid, 2-hydroxydocosenoic acid, 2-hydroxylignoceric acid, 2-hydroxytetracosenoic acid, 2-hydroxyhexacosanoic acid, 2-hydroxyoctacosanoic acid, 2-hydroxytriacontanoic acid and 2-hydroxydotriacontanoic acid, preferably $C_{3-20}$ 2-hydroxycarboxylic acids, more preferably $C_{3-20}$ 2-hydroxycarboxylic acids, and more preferably $C_{3-6}$ 2-hydroxycarboxylic acids. Wherein, 2-hydroxlcarboxylic acids substituted with an arylalkyl group or an aryl group include but are not limited to mandelic acid, 2,2-diphenyl-2-hydroxyacetic acid, 3-phenyl-2-hydroxypropionic acid and 2-phenyl-2-methyl-2-hydroxyacetic acid. Said 3-hydroxylcarboxylic acids include but are not limited to salicylic acid and 2-phenyl-3-hydroxypropionic acid. In addition, reagents of hydroxycarboxylic acids can also be in the form of salt or lactone.

With respect to the reaction between an alkynyl group and two mercapto groups along with the formation of a trivalent linking group, reaction conditions can refer to the prior art, such as the following literatures including "Macromolecules, 2010, 43, 4937-4942", "Angew. Chem. Int. Ed., 2010, 49, 3415-3417" and "Chem. Commun., 2011, 47, 11086-11088", and cited references therein.

2.1.4. Preparation of Linear Polyethylene Glycol Intermediates

The monodisperse linear polyethylene glycol intermediates involving with the preparation routes, approaches or methods in the present invention include monodisperse linear polyethylene glycols and their bi- or hetero-functionalized derivatives. The preparation methods of monodisperse polyethylene glycol chains refer to the following literatures "J. Org. Chem. 2006, 71, 9884-9886", "Angew. Chem. 2009, 121, 1274-1278" and "Expert Rev. Mol. Diagn. 2013, 13 (4), 315-319", and cited references therein.

The characterization methods of the structure, molecular weight and molecular weight distribution of the key intermediates and products including but not limited to NMR, electrophoresis, UV-visible spectrophotometer, FTIR, AFM, GPC, HPLC and MALDI-TOF. With respect to monodisperse polyethylene glycol derivatives, the molecular weight is preferably determined by MALDI-TOF.

2.1.5. Purification of Intermediates and Products

The intermediates and products involved in the present invention can be purified by a purification means such as extraction, recrystallization, adsorption treatment, precipitation, reverse precipitation, membrane dialysis, supercritical extraction or the like.

2.2. The H-Shaped Multifunctionalized Polyethylene Glycol can be Produced by Any of the Following Routes:

Concerning the production process, polyethylene glycol segments or blocks of a linear, V-shaped or Y-shaped PEG reagent are each independently either polydisperse or monodisperse.

2.2.1. Route-1, direct polymerization method is applicable when $F_1$ and $F_2$ have the same $R_{01}$ groups, and production steps of Route-1 are as follows:

Step (a): preparation of a branched intermediate with a linear main chain: prepare an intermediate (35) which contains four unprotected hydroxyl groups and a skeleton shown as IM1; wherein, $U_1$ and $U_2$ are identical, and also denoted as U;

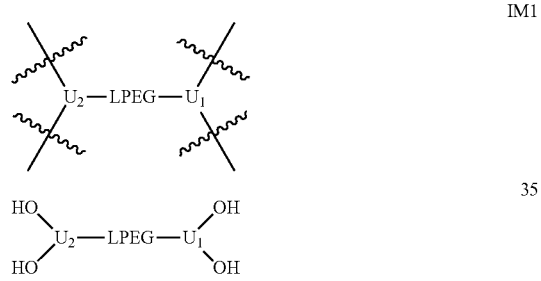

IM1

Step (b): preparation of compound (36) with an H-shaped skeleton via the polymerization of ethylene oxide which is initiated from four unprotected hydroxyl groups of the intermediate (35) to generate four polyethylene glycol branch chains both end-capped with a hydroxyl group;

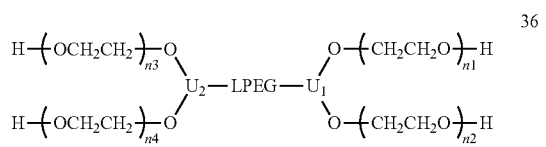

36

Step (c): end-functionalization of the four PEG branch-chains to obtain an H-shaped multifunctionalized polyethylene glycol compound which contains the objective unprotected or protected functional groups including objective $R_{01}$ groups as represented by general formula (13); if the objective terminal functional group of the H-shaped multifunctionalized polyethylene glycol compound is $CH_2CH_2OH$, this step can be omitted; wherein, general formula (13) can be represented by general formula (10), (11), (12), (14), (15), (16), (17) or (18).

2.2.1.1. As for Step (a), the Preparation of Intermediate Compound (35) can be Achieved Through Any of the Following Methods:

Method-1: starting from a linear polyethylene glycol HO-PEG-OH (compound 37), reacting with a branching reagent $X_{12}$—$U(OPG_4)_2$ (compound 39) to obtain an intermediate compound (40) containing four protected hydroxyl groups, further removing the hydroxyl protecting groups to obtain a compound (35) containing four unprotected groups; wherein, $X_{12}$ is a reactive group;

Method-2: starting from a linear bifunctionalized polyethylene glycol $X_{11}$-PEG-$X_{11}$ (compound 38), reacting with a branching reagent $X_{12}$—$U(OPG_4)_2$ (compound 39) to form an intermediate compound (40) containing four protected hydroxyl groups, further removing the hydroxyl protecting groups to obtain a compound (35) containing four unprotected groups; wherein, $X_{11}$ is a non-hydroxyl reactive group;

Method-3: starting from a linear bifunctionalized polyethylene glycol $X_{11}$-PEG-$X_{11}$ (compound 38), and reacting with a branching reagent $X_{12}$—$U(OH)_2$ (compound 41) to obtain a compound (35) containing four unprotected hydroxyl groups; and Method-4: starting from a linear bifunctionalized polyethylene glycol $X_{11}$-PEG-$X_{11}$ (compound 38), reacting with a branching reagent $X_{12}$—U (compound 42) to obtain a compound U-PEG-U (43), and carrying out chemical modification to generate two unprotected hydroxyl group at each end respectively and meanwhile obtain a compound (35);

The reaction processes of Method-1 to Method-4 are as follows:

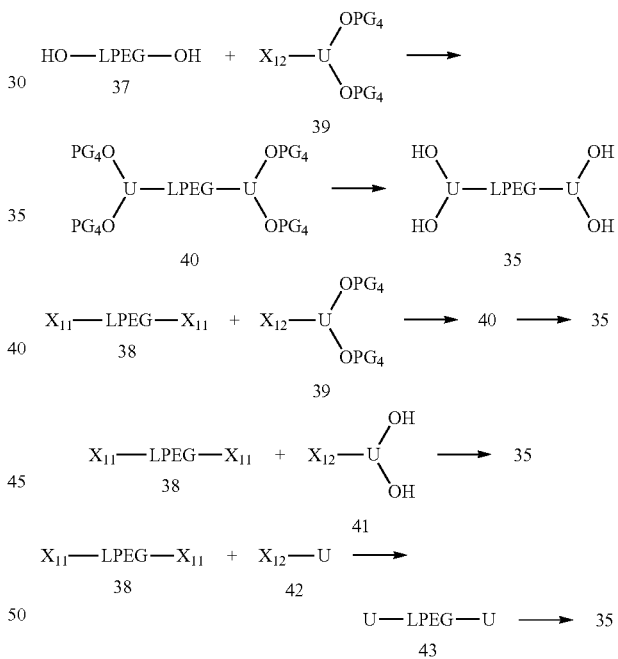

In the Method-4, the method to chemically modify the U group of compound (43) to obtain compound (35) is not particularly limited. For example, when the terminal group of U is an epoxy group, two unprotected hydroxyl groups can be obtained via the ring-opening reaction. The ring-opening reaction of the epoxy group should be carried out under a basic condition. The base can be an organic base (such as triethylamine, pyridine, 4-dimethylaminopyridine, imidazole or diisopropylethylamine) or an inorganic base (such as sodium carbonate, sodium hydroxide, sodium hydrogencarbonate, sodium acetate, potassium carbonate or potassium hydroxide), preferably an inorganic base. The solvent is preferably water. One example consists of the following steps including starting from a polyethylene glycol, connecting two glycidyloxy groups via linear end-functionalization, and then carrying out the ring-opening reaction under a basic condition to generate two unprotected hydroxyl groups at each end, referring to the following reaction conditions.

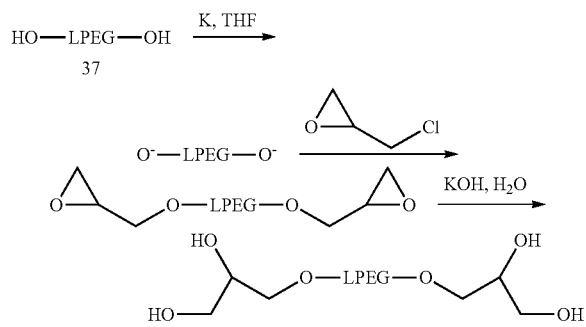

When the terminal group of U is an alkynyl group (corresponding to compound 38b), unprotected hydroxyl groups can be obtained via the click reaction with reagent (44) which has a terminal mercapto group and a terminal hydroxyl group as shown in the following formula. Wherein, $L_{12}$ is a divalent linking group which can remain stable under anionic polymerization conditions.

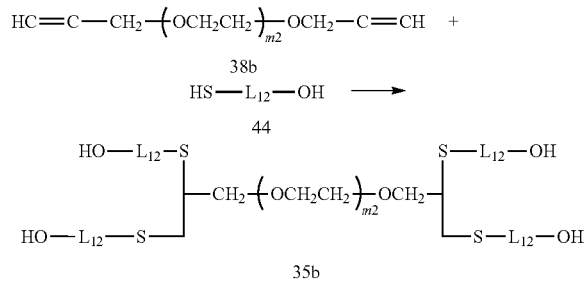

When the terminal group of U is an alkynyl group, an intermediate (46) in which each of the two semiH-branching centers connects two protected hydroxyl groups can be obtained via the reaction between reagent (45) with a terminal mercapto group and a terminal protected hydroxyl group and a linear bifunctionalized polyethylene glycol (38b); after removing the protection of the two hydroxyl groups at each semiH-branching center, an intermediate (35b) can be obtained.

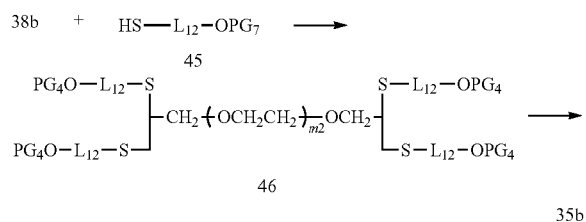

The polyethylene glycol blocks within LPEG can be either polydisperse or be monodisperse.

Wherein, the reactions between a hydroxyl-containing compound or a compound containing a non-hydroxyl reactive group and branching reagents to introduce branching groups include but are not limited to alkylation reaction, addition reaction of alkenes, addition reaction of alkynes, combination of a Schiff base reaction and a reduction reaction (Schiff-base/reduction reaction), etc. Wherein, the alkylation reaction is preferably based on a hydroxyl group, a mercapto group or an amino group, corresponding to the formation of an ether bond, a thioether bond, and a secondary amino group or a tertiary amino group, respectively. Wherein, the addition reaction of alkenes includes but is not limited to the click reaction between a maleimide and a thiol; addition reaction of alkynes includes but is not limited to the click reaction between an alkynyl group and a mercapto group; said Schiff-base/reduction reaction includes the following two processes: formation of an imino bond (—C=N—) and reduction of the imino bond into a secondary amino bond.

In Step (a), the deprotection of hydroxyl groups is related to the types of hydroxyl protecting groups. Said types of hydroxyl protecting groups are not particularly limited, including benzyl ether, silyl ether, acetal, ketal, tert-butyl ether and the like, and the deprotection method can be carried out correspondingly in the following four ways:

A: Deprotection of the Benzyl Group

The deprotection of the benzyl group can be achieved via hydrogenation by using a hydrogenative reduction catalyst and a hydrogen donor. As used herein, the water content should be less than 1% in order to facilitate the reaction. When the water content is more than 1%, the decomposition reaction of the polyethylene glycol chain occurs. The resulting low-molecular-weight polyethylene glycol with a hydroxyl group, which can participate in the subsequent polymerization reaction or functionalization reaction, will introduce impurities into the target product. Such impurities may even react with the bio-related substance and change the property of the preparation.

The hydrogenative reduction catalyst is not particularly limited, preferably palladium and nickel. The carrier is not particularly limited, but is preferably alumina or carbon, more preferably carbon. The amount of palladium is 1% to 100% by weight, preferably 1% to 20% by weight to the hydroxyl-containing compound. When the amount of palladium is less than 1% by weight, the rate and the conversion of deprotection decrease. For the compounds that are not deprotected, subsequent polymerization or functionalization is not allowed to proceed, which will result in low ratio of functionalization of the final product. However, when the amount of palladium exceeds 100% by weight, the polyethylene glycol chain tends to undergo a decomposition reaction.

The reaction solvent is not particularly limited as far as it allows the reagents and the product to be dissolved. Preferable solvents include methanol, ethanol, ethyl acetate, tetrahydrofuran, and more preferable is methanol. The hydrogen donor is not particularly limited, but is preferably hydrogen, cyclohexene, 2-propanol, ammonium formate, or the like. The reaction temperature is preferably 25 to 40° C. When the temperature is higher than 40° C., the decomposition reaction of the polyethylene glycol chain may occur. The reaction time is not particularly limited as far as it is negatively correlated with the amount of catalyst, preferably 1 to 5 hours. When the reaction time is shorter than one hour, the conversion is relatively low. When the reaction time is longer than 5 hours, the polyethylene glycol chain may undergo a decomposition reaction B: The Deprotection of an Acetal or Ketal Structure The acetal or ketal compound used a protecting such a hydroxyl group is preferably ethyl vinyl ether, tetrahydropyran, acetone, 2,2-dimethoxypropane, benzaldehyde or the like. The deprotection reaction should be carried out under an acidic condition, and the pH of the solution is preferably 0 to 4. When the pH is higher than 4, the acidity is too weak for the protecting group to be completely removed. When the pH is lower than 0, the acidity is too strong so that the polyethylene glycol chain tends to undergo a decomposition reaction. The acid is not particularly limited, but is preferably acetic acid, phosphoric acid, sulfuric acid, hydrochloric acid or nitric acid, more preferably hydrochloric acid. The reaction solvent is not particularly limited as long as it allows the reagents and the product to be dissolved. The solvent is preferably water. The reaction temperature is preferably 0 to 30° C. When the temperature is lower than 0° C., the reaction rate is relatively slow, and the protecting group cannot be completely removed. When the temperature is higher than 30° C., the decomposition reaction of the polyethylene glycol chain tends to occur under an acidic condition C: The Deprotection of a Silyl Group The protected hydroxyl group of a silyl ether type is preferably trimethylsilyl ether, triethylsilyl ether, tert-butyldimethylsilyl ether, tert-butyldiphenylsilyl ether or the like. The deprotection of such a silyl ether structure involves a fluorinion-containing compound which is preferably tetrabutylammonium fluoride, tetraethylammonium fluoride, hydrofluoric acid or potassium fluoride, more preferably tetrabutylammonium fluoride or potassium fluoride. The amount of the fluorine-containing compound is 5 to 20 molar equivalents, preferably 8 to 15 molar equivalents relative to the initiator. When the amount of the fluorine-containing compound is less than 5 molar equivalents to the initiator, the deprotonation reaction cannot sufficiently proceed. When the amount exceeds 20 molar equivalents to the initiator, the excess reagent tends to cause difficulty in the purification process and result in side reactions in the subsequent steps. The reaction solvent is not particularly limited as long as it can dissolve the reagents and the product. The solvent is preferably an aprotic solvent, more preferably tetrahydrofuran or dichloromethane. The reaction temperature is preferably 0° C. to 30° C. When the temperature is lower than 0° C., the reaction rate is relatively slow, and the protective group cannot be completely removed.

D: The Deprotection of a t-Butyl Group

The deprotection of the tert-butyl group is carried out under an acidic condition, and the pH of the solution is preferably 0 to 4. When the pH is higher than 4, the acidity is too weak for the protecting group to be completely removed. When the pH is lower than 0, the acidity is too strong, and there is a tendency for the polyethylene glycol chain to undergo a decomposition reaction. The acid is not particularly limited, but is preferably acetic acid, phosphoric acid, sulfuric acid, hydrochloric acid or nitric acid, more preferably hydrochloric acid. The reaction solvent is not particularly limited as far as it can dissolve the reagents and the product. The solvent is preferably water. The reaction temperature is preferably 0° C. to 30° C. When the temperature is lower than 0° C., the reaction rate is relatively slow, and the protective group cannot be completely removed. When the temperature is higher than 30° C., the decomposition reaction of the polyethylene glycol chain tends to occur.

The resulting product can be purified by a purification means such as extraction, recrystallization, adsorption treatment, precipitation, reverse precipitation, membrane dialysis or supercritical extraction to obtain a compound with an unprotected hydroxyl group.

2.2.1.2. In the step (b), the polymerization process of ethylene oxide initiated from unprotected hydroxyl groups consists of the following two steps (i) and (ii). Step (i): deprotonation of unprotected hydroxyl groups to form oxyanions; Step (ii): polymerization of ethylene oxide. These two steps can be carried out in a solvent or without any solvent. The solvent is not particularly limited, but is preferably an aprotic solvent, such as toluene, benzene, xylene, acetonitrile, ethyl acetate, tetrahydrofuran, chloroform, dichloromethane, dimethyl sulfoxide, dimethylformamide or dimethylacetamide, and more preferably toluene or tetrahydrofuran. The resulting polyethylene glycol chain is polydisperse.

When producing polyethylene glycol branch chains, the amount of ethylene oxide is in accord with corresponding degree of polymerization. Take polyethylene branch chains for example, according to the value of $n_1$, $n_2$, $n_3$ and $n_4$, ethylene oxide should be added in an amount of 2 to 2000 molar equivalents relative to initiator, preferably 5 to 2000 molar equivalents, more preferably 5 to 1000 molar equivalents, more preferably 10 to 1000 molar equivalents, more preferably 20 to 1000 molar equivalents, more preferably 20 to 500 molar equivalents, and more preferably 50 to 500 molar equivalents. The amount of ethylene oxide is determined by the value of $m_1$, $m_2$ and $m_3$ when generating the PEG main chain.

Step (i): The Deprotonation of Unprotected Hydroxyl Groups

The oxyanions formed after deprotonating the hydroxyl groups act as initiators to start the polymerization of ethylene oxide and to form a coinitiator system together with a base.

The deprotonation of unprotected hydroxyl groups is carried out under a basic condition. The base used for deprotonation is not particularly limited, but is preferably sodium, potassium, sodium hydride, potassium hydride, sodium methoxide, potassium methoxide, naphthalene-lithium, n-butyllithium, t-butyllithium, potassium t-butanoate or diphenylmethyl potassium, more preferably sodium, potassium or diphenylmethyl potassium, most preferably diphenylmethyl potassium. The catalyst amount is 5% to 80% by mole. When the catalyst amount is less than 5% by mole, the polymerization rate is low and heat history increases to result in the formation of impurities such as a terminal vinyl ether compound formed by vinyl etherification of the terminal hydroxyl group. Under a solvent-free condition, when the catalyst amount exceeds 50% by mole, the viscosity of the reaction solution increases or the liquid solidifies, and thus the reaction becomes inhomogeneous and purification thereof tends to be difficult. In the case that toluene or tetrahydrofuran is used as solvent, the problem of viscosity increasing or liquid solidification can be solved so that the catalyst amount can be increased up to 80% by mole.

The deprotonation is commonly conducted at 10° C. to 50° C., preferably 25° C. to 50° C. When the temperature is lower than 10° C., the deprotonation does not sufficiently proceed, and the base as a nucleophile reagent participates in the anionic polymerization to form a low-molecular-weight impurity having a molecular weight 0.5 time that of the target compound. There is a possibility that such an impurity may react with a bio-related substance and change the physical properties of the resulting preparation. If initiators for polymerizing ethylene oxide contain a protecting group, when the temperature is higher than 50° C., a decomposition of the protective group occurs resulting in a high-molecular-weight impurity having a molecular weight greater than that of the target compound. When the modification to a drug or the like is carried out with such impurities in presence, the resulting preparation becomes inhomogeneous and hence the quality tends to be varied. Also, the requirement for a highly pure product cannot be satisfied.

The deprotonation time is preferably 10 minutes to 24 hours and varies with the base to be used. A weak base or a base with relatively low solubility in an organic solvent (e.g. sodium methoxide, potassium methoxide, sodium hydride, potassium hydride or the like) usually calls for a long deprotonation time of 1 hour to 24 hours. A strong base with good solubility in an organic solvent (e.g. diphenylmethyl potassium, n-butyllithium, tert-butyllithium or the like) can be mutually fully miscible with small molecule initiators even under solvent-free conditions, and has a fast deprotonation rate. The deprotonation time of such a strong base is usually 10 minutes to 24 hours, preferably 20 minutes to 1 hour. When the deprotonation time is short, the deprotonation does not sufficiently proceed, and the base as a nucleophile reagent takes part in the anionic polymerization to form a low-molecular-weight impurity having a molecular weight 0.5 folds that of the target compound. If initiators for polymerizing ethylene oxide contain a protecting group, when the deprotonation time is longer than 24 hours, there is a possibility that a decomposition of the protective group may occur resulting in a high-molecular-weight impurity having a molecular weight greater than that of the target compound, which cannot satisfy the requirement for the modification of highly pure drugs.

Potassium methoxide, potassium tert-butoxide or sodium methoxide, preferably potassium methoxide is added as a catalyst in an amount of 5% to 80% by mole, and the reaction is carried out at 25° C. to 80° C., preferably 50° C. to 60° C. What's more, a pressure-reducing operation should be conducted in order to facilitate the exchange of protons. Potassium methoxide, potassium t-butoxide or sodium methoxide can react with ethylene oxide during the polymerization to form a mono-etherified polyethylene glycol derivative having a molecular weight 0.5 folds that of the target compound. Such a polyethylene glycol derivative will interfere with the subsequent reaction to form by-products.

So, the reaction should be conducted at a relatively high temperature to ensure complete protonation, preferably 50° C. to 60° C., and meanwhile a pressure-reducing operation is needed to remove lower alcohols.

Step (ii): Polymerization of Ethylene Oxide

The amount of ethylene oxide is determined by the designed molecular weight of the polyethylene glycol chain, and ethylene oxide should be added in a calculated amount.

When the polymerization is conducted in an aprotic solvent, the temperature is preferably 50° C. to 70° C. When the temperature is lower than 50° C., as the molecular weight gradually increases with the proceeding of polymerization, the viscosity of the reaction solution increases or the liquid solidifies, and hence the reaction becomes inhomogeneous and the resulting product has a broad distribution which is not suitable for the modification aimed to get highly pure drugs. When the temperature is higher than 70° C., there is a possibility that explosive polymerization or side reactions may occur, such as the vinyl etherification of the terminal hydroxyl group to generate a terminal vinyl ether compound.

When the polymerization is conducted under a solvent-free condition, the temperature is preferably 50° C. to 130° C., more preferably 80° C. to 110° C. When the temperature is lower than 50° C., the polymerization rate is low and heat history increases to result in a tendency to reduce the quality of the target product. When the temperature is higher than 130° C., side reactions tend to occur such as vinyl etherification of the terminal hydroxyl group to form a terminal vinyl ether compound. Alike, during the polymerization, as the molecular weight gradually increases, the viscosity of the reaction solution increases or the liquid solidifies, and hence the reaction becomes inhomogeneous and the distribution of the resulting product gets broad. As a result, the polymerization is preferably carried out in an aprotic solvent, preferably tetrahydrofuran or toluene.

The resulting polymerized product after Step (b) is a mixture of alcohol and oxygen anions. When the polymerization is carried out to a certain extent, a hydroxyl-terminated intermediate having a given degree of polymerization can be obtained after the addition of proton source. Wherein, the proton source is not particularly limited as long as it can increase the reactivity of the active hydrogen. Preferable proton source is methanol, ethanol, water or acetic acid.

2.2.1.3. In step (c), an H-shaped multifunctionalized polyethylene glycol with a structure as represented by general formula (14) can be obtained by carrying out linear end-functionalization reaction; while an H-shaped multi-functionalized polyethylene glycol with a structure as represented by general formula (15) can be obtained by carrying out branched end-functionalization reaction. The methods for conducting linear end-functionalization refer to part 2.1.1, and the methods for conducting branched end-functionalization refer to part 2.1.2, no more repeated here.

2.2.2. Route-2, "main-then-branch" polymerization method is applicable when $F_1$ and $F_2$ have identical or different $R_{01}$ groups, and production steps of Route-2 are as follows:

Step (a): preparation of an intermediate with a linear main chain: prepare an intermediate (47), (48) or (49) which contains a skeleton of either IM1 or IM14; wherein, $X_{13}$ is an unprotected or protected functional group which can remain stable under anionic polymerization conditions.

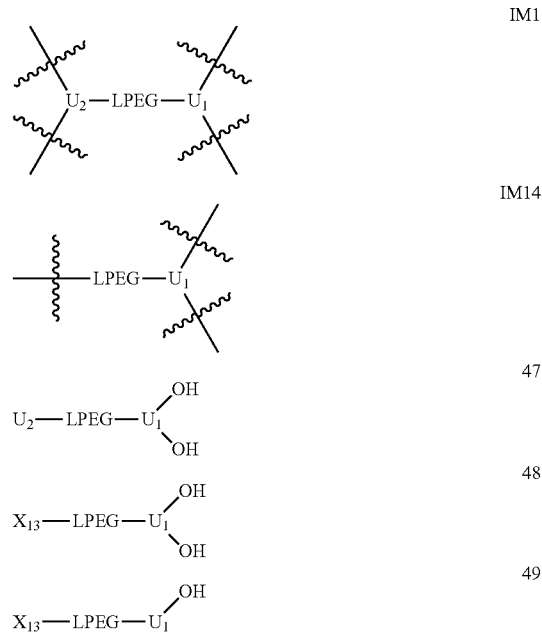

With respect to the functional group which can remain stable under anionic polymerization conditions, the corresponding $R_{01}$ is preferably selected from, but not limited to, the following functional groups:

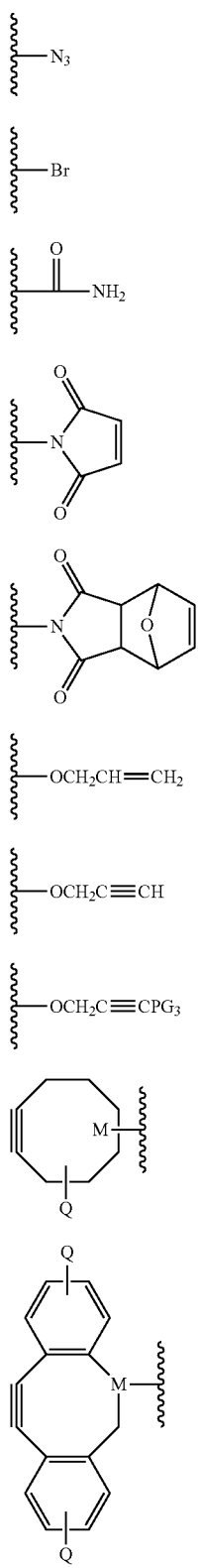

C4

C5

D1

E1

E4

F2

F3

F4

G1

G2

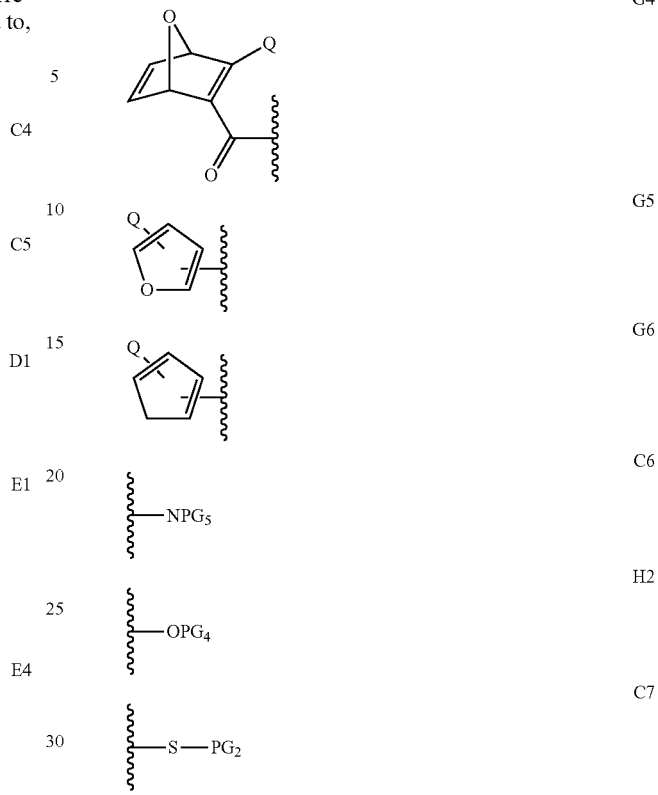

G4

G5

G6

C6

H2

C7

Q is a hydrogen atom or a substituting group that can favor inductive effect, conjugation effect, or both inductive and conjugation effects of electrons of unsaturated bonds;

M is a carbon atom or a nitrogen atom, and acts as a ring-membering atom.

Wherein, the polyethylene glycol segment can be either polydisperse or monodisperse;

Step (b): preparation of an intermediate (51) or (52) which contains a skeleton IM3, two commonly branched PEG chains and a linear main chain; in the present invention, two PEG branch chains linked together via a common trivalent semiH-branching center ($U_1$ or $U_2$) are also referred to as commonly branched PEG chains, while two PEG branch chains linked separately and telechelically to two trivalent semiH-branching centers ($U_1$ and $U_2$) are also referred to as telechelically branched PEG chains or separately branched PEG chains.

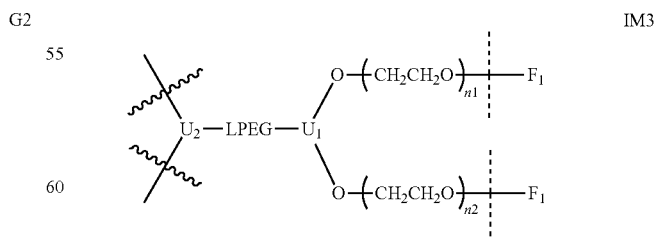

IM3

Step (b) can be achieved through any of the following methods:

Method-1: starting from a linear polyethylene glycol with two unprotected hydroxyl groups (47), initiating the polymerization of ethylene oxide to obtain a Y-shaped intermediate (50) which contains three PEG chains and two branch chains thereof are both terminated with a hydroxyl group, and carrying out linear end-functionalization reaction to terminal hydroxyl groups to introduce unprotected or protected functional groups ($X_{15}$) to obtain an intermediate (51); wherein, $X_{15}$ is stable under anionic polymerization conditions; $X_{15}$ can be the same as or different from the objective unprotected or protected functional group;

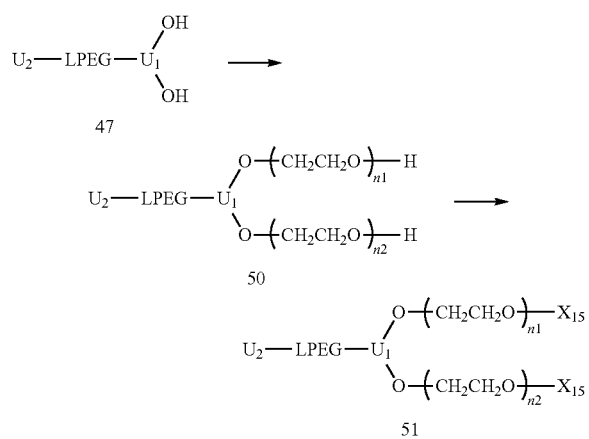

Method-2: starting from a linear polyethylene glycol containing two unprotected hydroxyl groups (47), initiating the polymerization of ethylene oxide to obtain a Y-shaped intermediate (50) which contains three PEG chains wherein two branch chains both have a terminal hydroxyl group, and carrying out branched end-functionalization reaction to terminal hydroxyl groups to introduce end-branching groups $G_5$ and $G_6$ as well as unprotected or protected functional groups ($X_{15}$) to obtain an intermediate (52); wherein, $X_{15}$ can remain stable under anionic polymerization conditions;

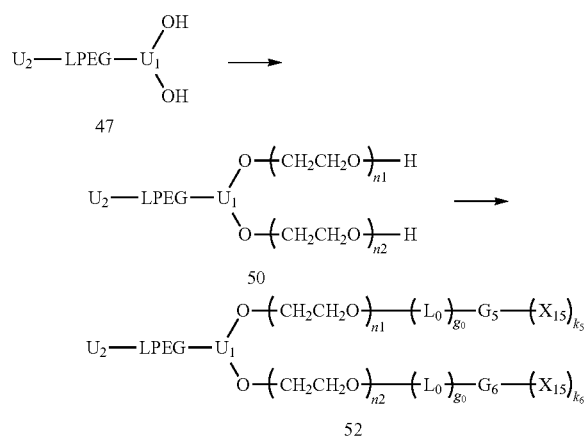

Method-3: starting from a linear polyethylene glycol containing two unprotected hydroxyl groups (48), initiating the polymerization of ethylene oxide to obtain a Y-shaped intermediate (53) which contains a PEG main chain and two hydroxyl-terminated PEG branch chains, carrying out linear end-functionalization reaction to terminal hydroxyl groups to introduce unprotected or protected functional groups ($X_{15}$) to obtain an intermediate (54); and the semiH-branching group $U_2$ is introduced by referring to Route-1 to obtain an intermediate (51); wherein, $X_{15}$ can remain stable under anionic polymerization conditions;

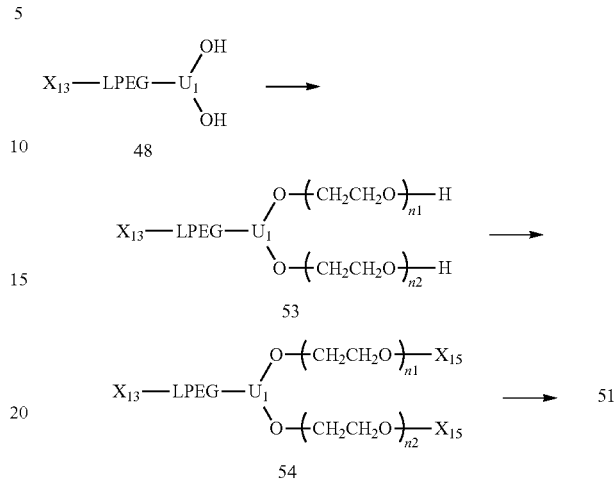

Method-4: starting from a linear polyethylene glycol containing two unprotected hydroxyl groups (48), initiating the polymerization of ethylene oxide to obtain a Y-shaped intermediate (53) which contains a PEG main chain and two hydroxyl-terminated PEG branch chains, carrying out branched end-functionalization reaction to terminal hydroxyl groups to introduce end-branching groups $G_5$ and $G_6$ as well as unprotected or protected functional groups ($X_{15}$) to obtain an intermediate (55); and a semiH-branching group $U_2$ is further introduced by referring to Route-1 to obtain an intermediate (52); wherein, $X_{15}$ is stable under anionic polymerization conditions;

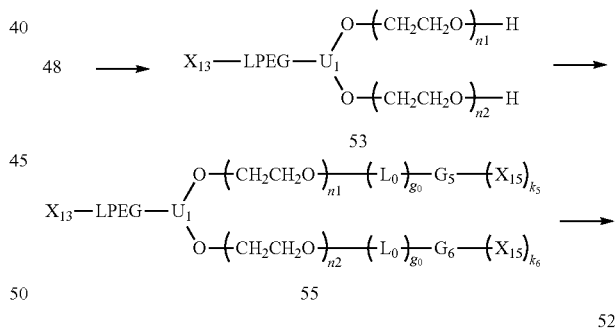

Method-5: starting from a linear polyethylene glycol containing one unprotected hydroxyl groups (49), initiating the polymerization of ethylene oxide to obtain a V-shaped intermediate (56) which contains a PEG main chain and one hydroxyl-terminated PEG branch chain, carrying out chemical modification to introduce a PEG main chain which has an unprotected hydroxyl group at semiH-branching center $U_1$ to obtain an intermediate compound (53), initiating the polymerization of ethylene oxide and conducting linear or branched end-functionalization to obtain an intermediate (54) or (55), and further introducing another semiH-branching group $U_2$ to obtain an intermediate (51) or (52) respectively;

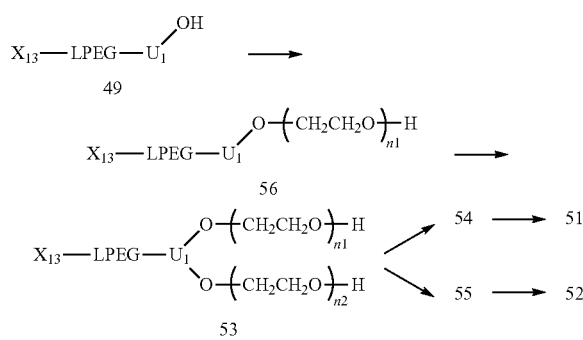

Step (c): preparation of a Y-shaped intermediate with two unprotected hydroxyl groups: carrying out chemical modification to the terminal branching group $U_2$ of the intermediate obtained in Step (b) to introduce two unprotected hydroxyl groups and thus a Y-shaped intermediate (51b) or (52b) which has a PEG main chain, two PEG branch chains, and two unprotected hydroxyl groups at the non-pegylated terminal of the main chain corresponding to (51) or (52) respectively;

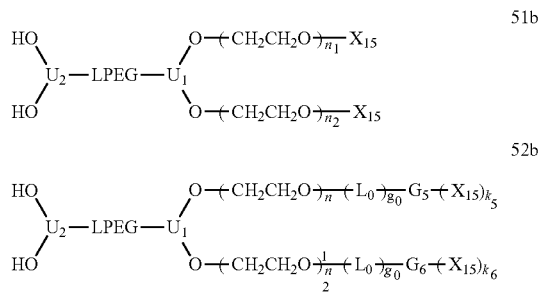

Step (d): preparation of an H-shaped intermediate: starting from the two unprotected hydroxyl groups of the Y-shaped intermediate obtained in step (c), initiating the polymerization of ethylene oxide to form an H-shaped intermediate (51c) or (52c) which contains a PEG main chain and four PEG branch chains and has two hydroxyl-terminated PEG branch chains at one H-membering tribranching center and two other PEG branch chains terminated with unprotected or protected functional groups ($X_{15}$) at the other H-membering tribranching center corresponding to (51b) or (52b), respectively; wherein, $X_{15}$ remains stable under anionic polymerization conditions;

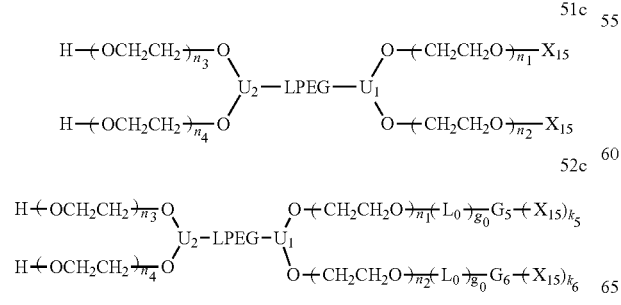

step (e): carrying out end-functionalization reactions to the PEG-chain terminals of the H-shaped intermediate obtained in Step (d) respectively to obtain an H-shaped multifunctionalized polyethylene glycol containing objective unprotected or protected functional groups; wherein, said functionalization reactions refer to linear or branched end-functionalization reactions;

the resulting H-shaped multifunctionalized polyethylene glycol by starting from intermediate (51c) can be represented by general formulas (1), (19), (20), (21), (22), (23), (24), (25) or (26);

while the resulting H-shaped multifunctionalized polyethylene glycol by starting from intermediate (52c) can be represented by general formula (20), (21), (22), (24), (25) or (26).

In Route-2, the reactions between a hydroxyl-containing compound or a compound containing a non-hydroxyl reactive group and branching reagents to introduce branching groups include but are not limited to alkylation reaction, addition reaction of alkenes, addition reaction of alkynes, combination of a Schiff base reaction and a reduction reaction (Schiff-base/reduction reaction), etc., referring to Step (a) of Route-1, such as reactions to introduce semiH-branching groups $U_1$ and $U_2$ including but not limited to reactions with branching reagents of $X_{12}$—$U(OPG_4)_2$, $X_{12}$—$U(OH)_2$ and $X_{12}$—$U$, wherein, U is identical to $U_1$ or $U_2$.

Similarly, reactions to introduce other branching groups in other part of the present invention include but are not limited to alkylation reactions, addition reactions of alkenes, addition reactions of alkynes, combinations of Schiff base reactions and reduction reactions (Schiff-base/reduction reaction), etc., and no more repeated here.

2.2.3. Route-3, "branch-then-main" polymerization method is applicable when $F_1$ and $F_2$ have the same or different $R_{01}$ groups, and production steps of Route-3 are as follows:

Step (a): preparation of a V-shaped intermediate (58b) or (59b) with two PEG branch chains, which is conducted through one of the following two methods:

Method-1: starting from a small molecule initiator IN3 which contains two unprotected hydroxyl groups and one protected hydroxyl group, initiating the polymerization of ethylene oxide to obtain an intermediate (57) which contains two terminal hydroxyl groups, further carrying out linear or branched end-functionalization to obtain a V-shaped intermediate (58) or (59), and removing the protecting group of the protected hydroxyl group to obtain a V-shaped intermediate (58b) or (59b) which contains one unprotected hydroxyl group and two PEG branch chains;

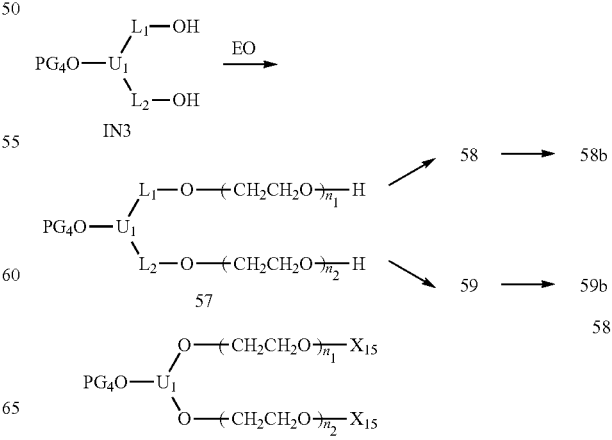

-continued

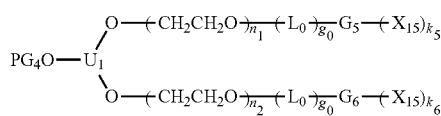
59

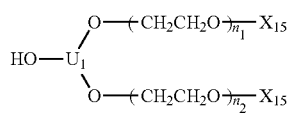
58b

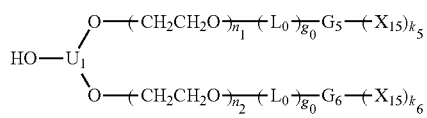
59b

Method-2: starting from a small molecule initiator IN4 with two unprotected hydroxyl groups, initiating the polymerization of ethylene oxide to obtain an intermediate (57c) which contains two terminal hydroxyl groups, further carrying out linear or branched end-functionalization to obtain a V-shaped intermediate (58c) or (59c) which has two unprotected or protected functional groups ($X_{15}$), then conducting chemical modification to the center-branching group of the V-shaped intermediate to generate an unprotected hydroxyl group and thus a V-shaped intermediate (58b) or (59b) which contain one unprotected hydroxyl group and two PEG branch chains; wherein, $X_{15}$ can be the same as or different from the objective unprotected or protected functional group;

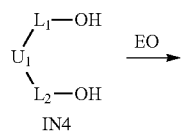
IN4

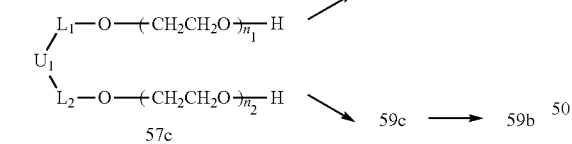

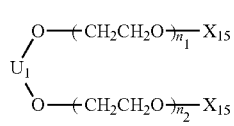
58c

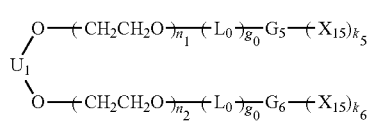
59c

Step (b): preparation of a Y-shaped intermediate with a PEG main chain and two PEG branch chains: starting from a V-shaped intermediate which contains one unprotected hydroxyl group and two PEG branch chains, then initiating the polymerization of ethylene oxide to obtain a Y-shaped intermediate (58d) or (59d) which contains a PEG main chain and two PEG branch chains;

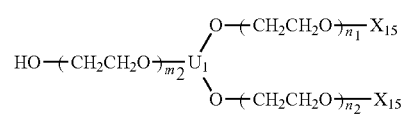
58d

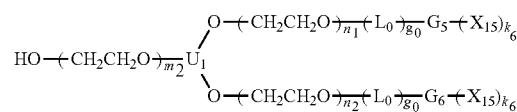
59d

Step (c): preparation of a Y-shaped intermediate with two unprotected hydroxyl groups: carrying out chemical modification reaction to the terminal hydroxyl group of the PEG main chain to introduce a branching group $U_2(OH)_2$ which contains two unprotected hydroxyl groups and thus obtain a Y-shaped intermediate (58e) or (59e); wherein, the chemical modification reaction to introduce the branching group includes but is not limited to alkylation reactions, addition reactions of alkenes, addition reactions of alkynes, combinations of Schiff base reactions and reduction reactions (Schiff-base/reduction reaction), etc., referring to Step (a) of Route-1, and can be a one-step reaction or a multi-step reaction.

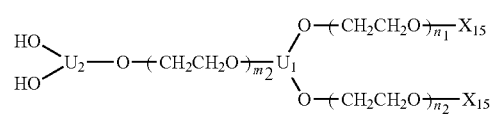
58e

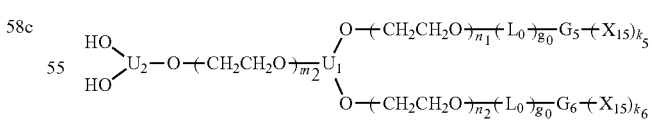
59e

Step (d): preparation of an H-shaped polyethylene glycol intermediate: starting from the Y-shaped intermediate with two unprotected hydroxyl groups prepared in Step (c), initiating the polymerization of ethylene oxide to obtain an H-shaped polyethylene glycol intermediate (58f) or (59f) which contains two hydroxyl groups on one branching center side and two unprotected or protected functional groups ($X_{15}$) on the other branching center side;

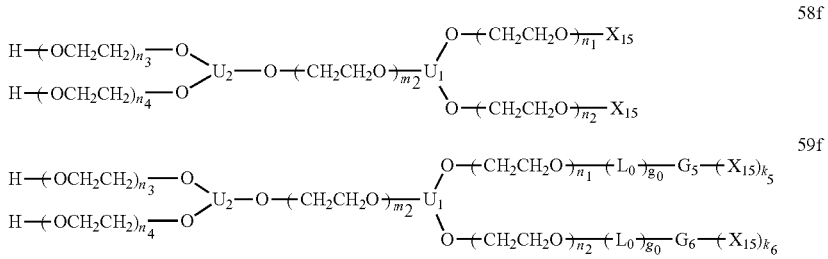

58f

59f

Step (e): carrying out linear or branched end-functionalization reactions to the PEG-chain terminals of the H-shaped intermediate obtained in Step (d) respectively to obtain an H-shaped multifunctionalized polyethylene glycol derivative which contains objective unprotected or protected functional end-groups $R_{O1}$ and $R_{O2}$; wherein, $R_{O1}$ and $R_{O2}$ can be the same or different from each other in one molecule;

the resulting H-shaped multifunctionalized polyethylene glycol by starting from intermediate (58f) can be represented by general formula (60), (61), (62), (63) or (64);

the resulting H-shaped multifunctionalized polyethylene glycol by starting from intermediate (59f) can be represented by general formula (60), (62) or (64).

groups, initiating the polymerization of ethylene oxide to form an intermediate (65) which contains two telechelically branched PEG branch chains and a linear main chain, carrying out chemical modification to the terminal hydroxyl groups of two telechelically branched PEG branch chains to introduce unprotected or protected functional groups ($X_{15}$) and thus obtain an intermediate (66); in the LPEG segment, polyethylene glycol blocks can be either polydisperse or monodisperse; $X_{15}$ can be the same as or different from the objective unprotected or protected functional group;

Step (b): preparation of an intermediate which contains a linear PEG main chain, two PEG branch chains, and one hydroxyl group at each branching center of the main chain:

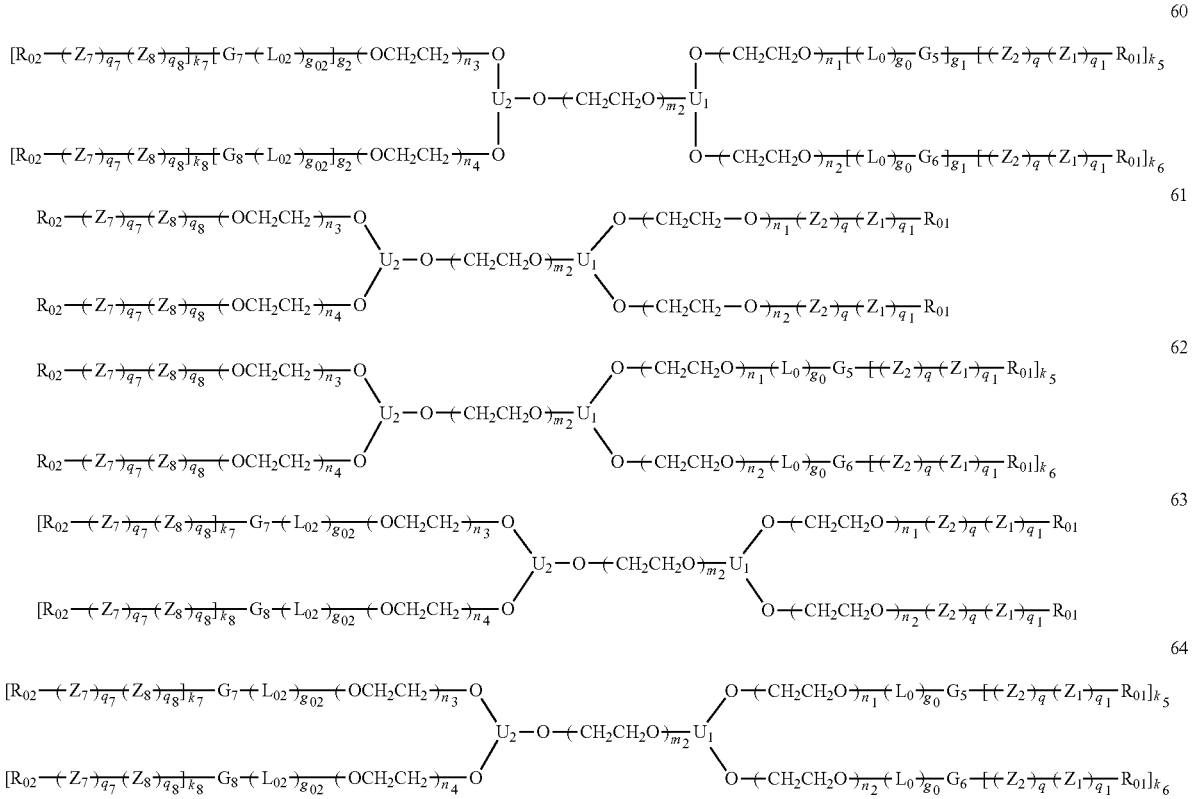

2.2.4. Route-4 is applicable when $F_1$ and $F_2$ have the same $R_{O1}$ groups, and production steps of Route-4 are as follows:

Step (a): preparation of an intermediate which contains two telechelically branched PEG branch chains and a linear main chain: starting from an initiator IN5 which contains a linear main chain LPEG and two unprotected hydroxyl starting from the intermediate (66) obtained in Step (a), and initiating the polymerization of ethylene oxide to form an H-shaped polyethylene glycol intermediate (67);

Step (c): carrying out end-functionalization reactions to the PEG-chain terminals of the H-shaped intermediate obtained in Step (b) respectively to obtain an H-shaped multifunctionalized polyethylene glycol which contains objective unprotected or protected functional groups ($R_{01}$); the structure of resulting H-shaped multifunctionalized polyethylene glycol can be represented by general formula (13), (14), (15) or (16).

When the structure of IN5 is

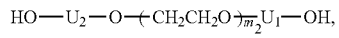

the structure of resulting H-shaped multifunctionalized polyethylene glycol obtained in Step (c) can be represented by general formula (10), (11), (12), (17) or (18).

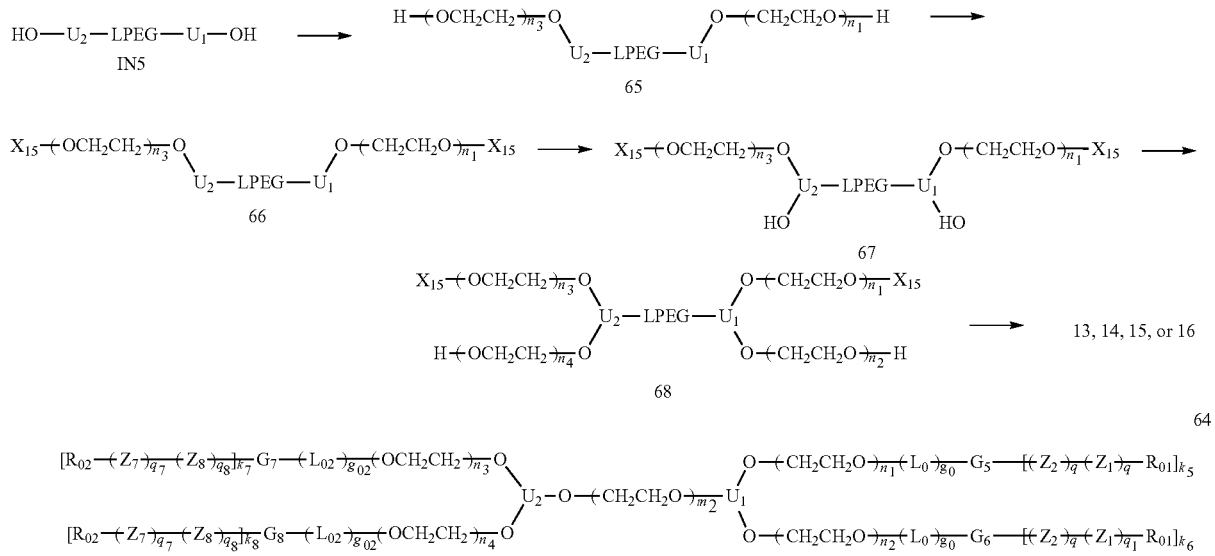

2.2.5. Route-5, "coupling-of-branches" method is applicable when $F_1$ and $F_2$ have the same or different $R_{01}$ groups. When V-shaped polyethylene glycols (containing two PEG branch chains, such as the following compound (69), (69b), (73) and (73b)) or/and Y-shaped polyethylene glycols (containing a PEG main chain and two PEG branch chains, such as compound (77), (77c), (78), (78c), (79), (79b), (79c), (83), (83b) and (83c)) are used as reagents, two identical or different reagent molecules can be coupled together directly, or be coupled to the two terminal ends of a small molecule compound, or be coupled to the two terminal ends of a linear polyethylene glycol molecule to form an H-shaped polyethylene glycol derivative which contains a PEG main chain and four PEG branch chains, and after end-functionalization, an H-shaped multifunctionalized polyethylene glycol derivative which contains the objective unprotected or protected functional groups can be obtained.

Wherein, the unprotected or protected functional groups ($X_{15}$ and $X_{16}$) at the terminal ends of PEG branch chains of said V-shaped and Y-shaped PEG reagents can be each independently the same or different from corresponding objective unprotected or protected functional group.

Wherein, the two terminal functional groups of said small molecule compound can be the same or different from each other in one molecule; and the two terminal functional groups of said linear polyethylene glycol molecule can be the same or different from each other in one molecule.

Wherein, the direct coupling reaction is not particularly limited, for example, including but not limited to condensation reactions (such as esterification reactions, amidation reactions, etc.), alkylation reactions, Schiff-base reactions, combinations of a Schiff-base reaction and a reduction reaction, as well as reactions involving the formation of a divalent linking group such as a disulfide bond, a urea bond, a thiourea bond, etc. Wherein, said esterification reactions include but are not limited to carbonyl-based esterification, sulfonatification forming a sulfonate, thioesterification forming a thioester, thiocarbonatification forming a thiocarbonate, carbamatification forming a carbamate, etc., and said amidation reactions include but are not limited to carbonyl-based amidation, sulfonamidation forming a sulfonamide, phosphamidation forming a phosphamide, etc.

Specifically, Route-5 can be achieved by using approaches including but not limited to the following 21 methods. What should be noted is that, in the following reactions, the coupling reactions to the two terminal ends of a small molecule compound or a linear polyethylene glycol molecule can be each independently conducted, and the sequence is not particularly limited, even including simultaneous coupling to the two terminal ends of a small molecule compound or a linear polyethylene glycol molecule via a one-step reaction.

2.2.5.1. Method-1, coupling two V-shaped polyethylene glycol molecules (69) and (69b) containing unprotected or protected functional groups $X_{15}$ and $X_{16}$ respectively to the two terminal ends of a linear polyethylene glycol molecule (70) via a pair of reactive groups $X_{18}$ and $X_{17}$ to obtain an H-shaped polyethylene glycol intermediate (71), carrying out linear or branched end-functionalization to terminal groups $X_{15}$ and $X_{16}$ respectively to obtain an H-shaped multifunctional polyethylene glycol as represented by general formula (1); wherein, $X_{15}$ and $X_{16}$ can be the same or different from each other; $X_{15}$ and $X_{16}$ are each independently identical to or different from corresponding objective unprotected or protected functional group. According to the combination of linear and branched end-functionalization reactions, specifically, the resulting H-shaped multifunctionalized polyethylene glycol as represented by general formula (1) can be represented by formula (19), (20), (21) or (22).

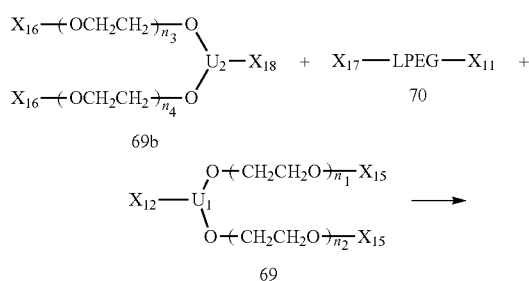

69b

70

69

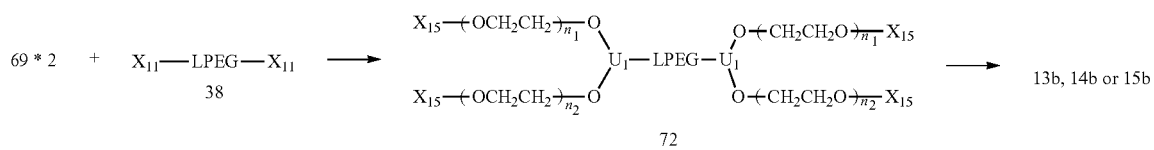

71

With respect to this method, when (69) and (69b) are identical, it is equivalent to coupling two molecules of V-shaped polyethylene glycol (69) as a single reagent to the two terminal ends of a bifunctionalized polyethylene glycol (38) to obtain an H-shaped polyethylene glycol intermediate (72), followed by linear or branched end-functionalization to terminal groups $X_{15}$ to obtain an H-shaped multifunctionalized polyethylene glycol as represented by formula (13b), (14b) or (15b); wherein, $X_{15}$ can be the same as or different from the objective unprotected or protected functional group. When $G_5=G_6=G_7=G_8$ and $k_5=k_6=k_7=k_8$, general formula (15b) is equivalent to the general formula (16).

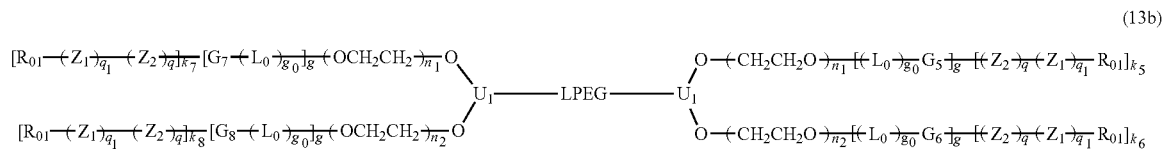

72

13b, 14b or 15b (13b)

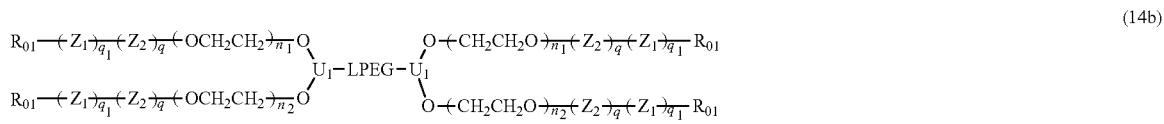

(14b)

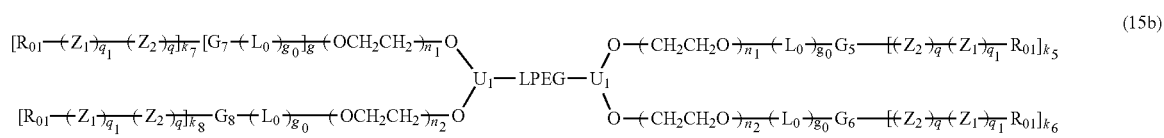

(15b)

2.2.5.2. Method-2 coupling a V-shaped polyethylene glycol molecule (73) which contains a branched terminal and unprotected or protected functional groups $X_{15}$ as well as a V-shaped polyethylene glycol molecule (69) which contains protected functional groups $X_{16}$ to the two terminal ends of the a linear polyethylene glycol molecule (70) respectively to obtain an H-shaped polyethylene glycol intermediate (74), and independently carrying out linear or branched end-functionalization to terminal groups $X_{16}$ as well as linear end-functionalization to terminal groups $X_{15}$ to obtain an H-shaped multifunctionalized polyethylene glycol as represented by formula (20) or (21); wherein, $X_{15}$ and $X_{16}$ can be the same or different from each other; $X_{15}$ and $X_{16}$ are each independently identical to or different from corresponding objective unprotected or protected functional group.

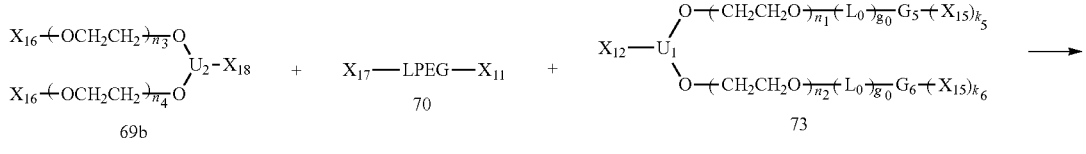

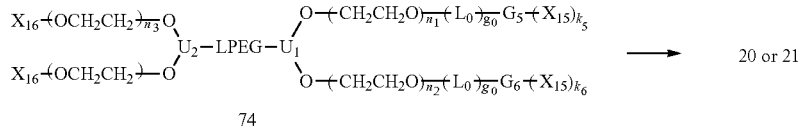

2.2.5.3. Method-3 coupling two V-shaped polyethylene glycol molecules (73) and (73b) both containing a branched terminal and respective two unprotected or protected functional groups $X_{15}$ and $X_{16}$ to the two terminal ends of a linear polyethylene glycol molecule (70) respectively to obtain an H-shaped polyethylene glycol intermediate (75), and carrying out linear end-functionalization to terminal groups $X_{15}$ and $X_{16}$ respectively to obtain an H-shaped multifunctionalized polyethylene glycol as represented by formula (21); wherein, $X_{15}$ and $X_{16}$ can be the same or different from each other; $X_{15}$ and $X_{16}$ are each independently identical to or different from corresponding objective unprotected or protected functional group.

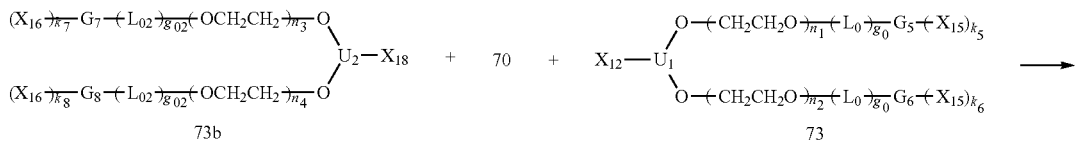

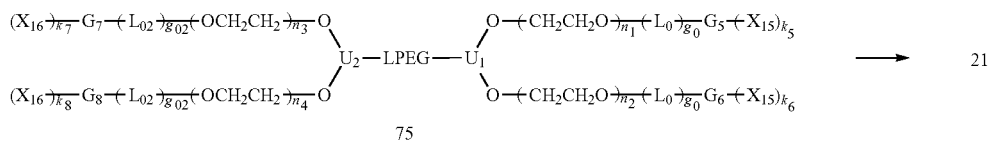

With respect to this method, when (73) and (73b) are identical, it is equivalent to coupling two molecules of V-shaped polyethylene glycol (73) as a single reagent to the two terminal ends of a bifunctionalized polyethylene glycol (38) to obtain a polyethylene glycol intermediate (76), followed by linear end-functionalization to terminal groups $X_{15}$ to obtain an H-shaped multifunctionalized polyethylene glycol as represented by formula (15c); wherein, $X_{15}$ can be the same as or different from the objective unprotected or protected functional group. When $G_5=G_6=G_7=G_8$ and $k_5=k_6=k_7=k_8$, general formula (15c) is equivalent to the general formula (16).

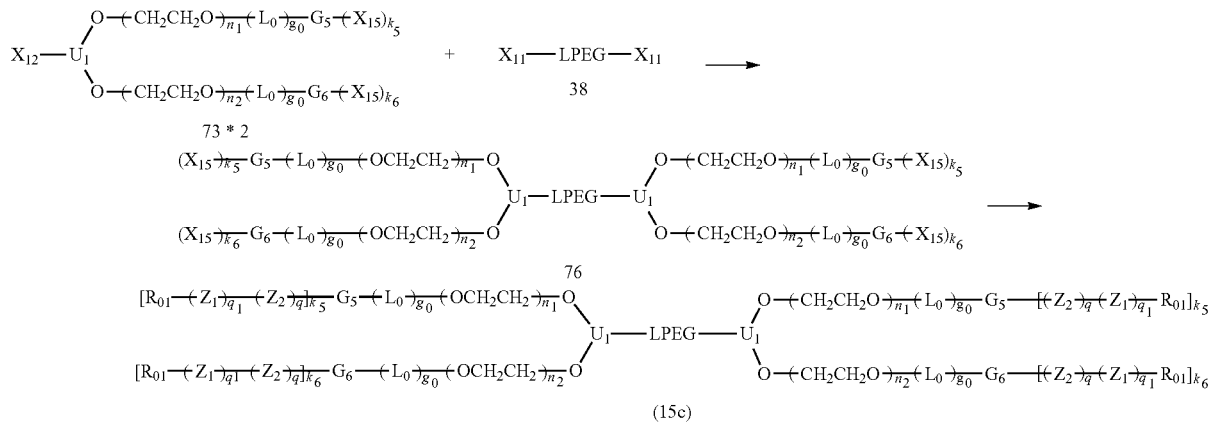

(15c)

2.2.5.4. Method-4, carrying out the coupling reaction between a V-shaped polyethylene glycol molecule (69b) with unprotected or protected functional groups $X_{16}$ and a Y-shaped polyethylene glycol molecule (77) with unprotected or protected functional groups $X_{15}$ to form an H-shaped polyethylene glycol compound (71), and carrying out linear or branched end-functionalization to terminal groups $X_{15}$ and $X_{16}$ respectively to obtain an H-shaped multifunctionalized polyethylene glycol as represented by formula (1); wherein, $X_{15}$ and $X_{16}$ can be the same or different from each other; $X_{15}$ and $X_{16}$ are each independently identical to or different from corresponding objective unprotected or protected functional group. According to the combination of linear and branched end-functionalization reactions, specifically, the resulting H-shaped multifunctionalized polyethylene glycol as represented by general formula (1) can be represented by formula (19), (20), (21) or (22).

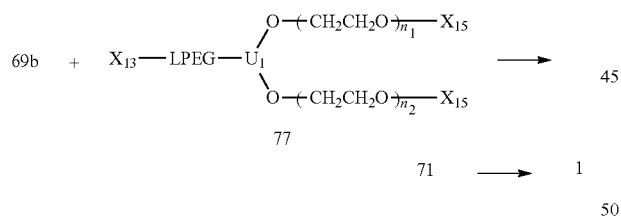

2.2.5.5. Method-5, reacting a V-shaped polyethylene glycol molecule (69b) containing unprotected or protected functional groups $X_{16}$ with a Y-shaped polyethylene glycol molecule (78) containing a branched terminal and unprotected or protected functional groups $X_{15}$ to form an H-shaped polyethylene glycol compound (74), and independently carrying out linear or branched end-functionalization to terminal groups $X_{16}$ as well as linear end-functionalization to terminal groups $X_{15}$ to obtain an H-shaped multifunctionalized polyethylene glycol as represented by formula (20) or (21); wherein, $X_{15}$ and $X_{16}$ can be the same or different from each other; $X_{15}$ and $X_{16}$ are each independently identical to or different from corresponding objective unprotected or protected functional group.

69b +

$X_{13}$—LPEG—$U_1$$\begin{matrix}O\text{—}(CH_2CH_2O)_{\overline{n_1}}(L_0)_{\overline{g_0}}G_5\text{—}(X_{15})_{k_5}\\O\text{—}(CH_2CH_2O)_{\overline{n_2}}(L_0)_{\overline{g_0}}G_6\text{—}(X_{15})_{k_6}\end{matrix}$

78

74 ⟶ 20 or 21

2.2.5.6. Method-6, reacting a V-shaped polyethylene glycol molecule (73b) containing a branched terminal and unprotected or protected functional groups $X_{16}$ with a Y-shaped polyethylene glycol molecule (78) containing a branched terminal and unprotected or protected functional groups $X_{15}$ to form an H-shaped polyethylene glycol compound (75), and carrying out linear end-functionalization to terminal groups $X_{15}$ and $X_{16}$ respectively to obtain an H-shaped multifunctionalized polyethylene glycol as represented by formula (15); wherein, $X_{15}$ and $X_{16}$ can be the same or different from each other; $X_{15}$ and $X_{16}$ are each independently identical to or different from corresponding objective unprotected or protected functional group.

73b +

$X_{13}$—LPEG—$U_1$$\begin{matrix}O\text{—}(CH_2CH_2O)_{\overline{n_1}}(L_0)_{\overline{g_0}}G_5\text{—}(X_{15})_{k_5}\\O\text{—}(CH_2CH_2O)_{\overline{n_2}}(L_0)_{\overline{g_0}}G_6\text{—}(X_{15})_{k_6}\end{matrix}$

78

75 ⟶ 15

2.2.5.7. Method-7, coupling a V-shaped polyethylene glycol molecule (69b) containing unprotected or protected functional groups $X_{16}$ with a Y-shaped polyethylene glycol molecule (79) containing unprotected or protected functional groups $X_{15}$ to the two terminal ends of a linear bifunctionalized polyethylene glycol (81) respectively to obtain an H-shaped polyethylene glycol derivative (80) which has a linear main chain consisting of at least two PEG blocks ($LPEG_1$ and $LPEG_2$), and carrying out linear or branched end-functionalization to terminal groups $X_{15}$ and $X_{16}$ respectively to obtain an H-shaped multifunctionalized polyethylene glycol as represented by formula (8); wherein, $X_{15}$ and $X_{16}$ can be the same or different from each other; $X_{15}$ and $X_{16}$ are each independently identical to or different from corresponding objective unprotected or protected functional group.

2.2.5.9. Method-9, coupling a V-shaped polyethylene glycol molecule (73b) containing a branched terminal and unprotected or protected functional groups $X_{16}$ with a Y-shaped polyethylene glycol molecule (83) containing a

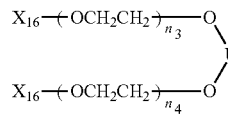
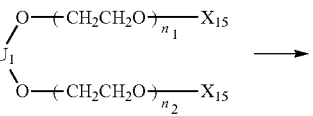

69b     81     79

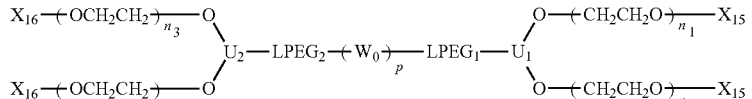

80 → 8

2.2.5.8. Method-8, coupling a V-shaped polyethylene glycol molecule (69b) containing unprotected or protected functional groups $X_{16}$ with a Y-shaped polyethylene glycol molecule (83) containing a branched terminal and unprotected or protected functional groups $X_{15}$ to the two terminal ends of a linear bifunctionalized polyethylene glycol (81) respectively to obtain an H-shaped polyethylene glycol derivative (84) which has a linear main chain consisting of at least two PEG blocks ($LPEG_1$ and $LPEG_2$), and independently carrying out linear or branched end-functionalization to terminal groups $X_{16}$ as well as linear end-functionalization to terminal groups $X_{15}$ to obtain an H-shaped multifunctionalized polyethylene glycol as represented by formula (20b) or (21b); wherein, $X_{15}$ and $X_{16}$ can be the same or different from each other; $X_{15}$ and $X_{16}$ are each independently identical to or different from corresponding objective unprotected or protected functional group.

branched terminal and unprotected or protected functional groups $X_{15}$ to the two terminal ends of a linear bifunctionalized polyethylene glycol (81) respectively to obtain an H-shaped polyethylene glycol derivative (86) which has a linear main chain consisting of at least two PEG blocks ($LPEG_1$ and $LPEG_2$), and carrying out linear end-functionalization to terminal groups $X_{15}$ and $X_{16}$ respectively to obtain an H-shaped multifunctionalized polyethylene glycol as represented by formula (21b); wherein, $X_{15}$ and $X_{16}$ can be the same or different from each other; $X_{15}$ and $X_{16}$ are each independently identical to or different from corresponding objective unprotected or protected functional group.

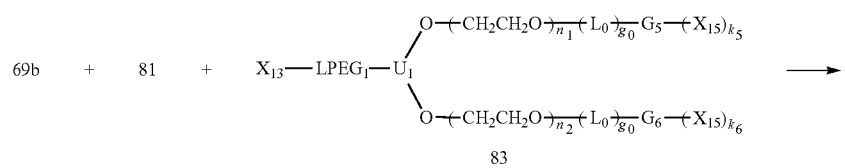

69b + 81 + 83

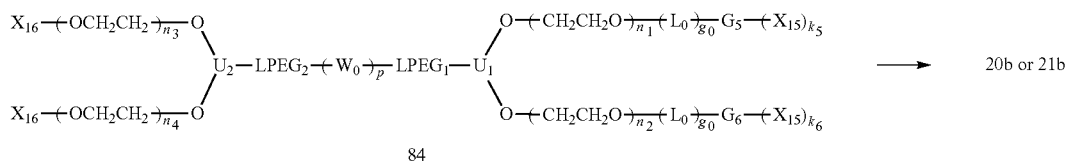

84 → 20b or 21b

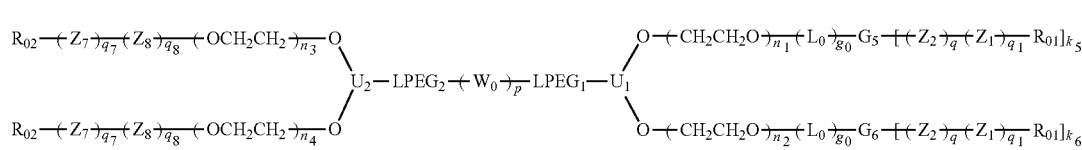

20b

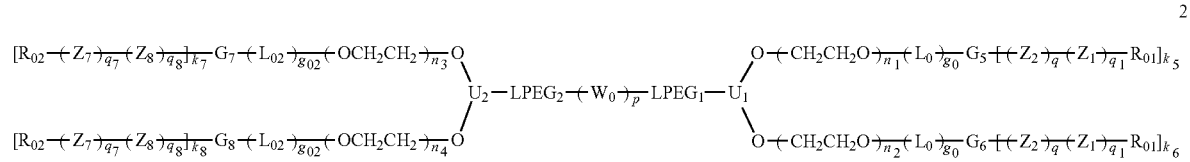

21b

73b + 81 + 83 ⟶

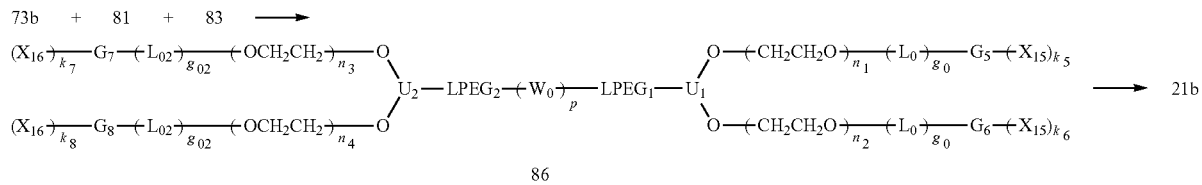

86

2.2.5.10. Method-10, coupling two Y-shaped polyethylene glycol molecules (79) and (79b) containing respective unprotected or protected functional groups $X_{15}$ and $X_{16}$ to obtain an H-shaped polyethylene glycol derivative as (80) which has a linear main chain consisting of at least two PEG blocks ($LPEG_1$ and $LPEG_2$), and carrying out linear or branched end-functionalization to terminal groups $X_{15}$ and $X_{16}$ respectively to obtain an H-shaped multifunctionalized polyethylene glycol as represented by formula (8); wherein, $X_{15}$ and $X_{16}$ can be the same or different from each other; $X_{15}$ and $X_{16}$ are each independently identical to or different from corresponding objective unprotected or protected functional group.

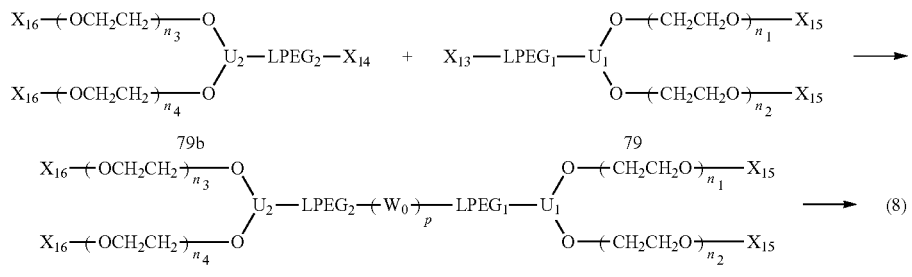

With respect to this method, when (79) and (79b) are identical, it is equivalent to coupling two molecules of Y-shaped polyethylene glycol (79) with two unprotected or protected functional groups $X_{15}$ as a single reagent into one molecule to obtain an H-shaped polyethylene glycol derivative (88) which has a linear main chain consisting of at least two PEG blocks ($LPEG_1$ and $LPEG_2$), followed by linear or branched end-functionalization to terminal groups $X_{15}$ to obtain an H-shaped multifunctionalized polyethylene glycol as represented by formula (8b); wherein, $X_{15}$ can be the same as or different from the objective unprotected or protected functional group.

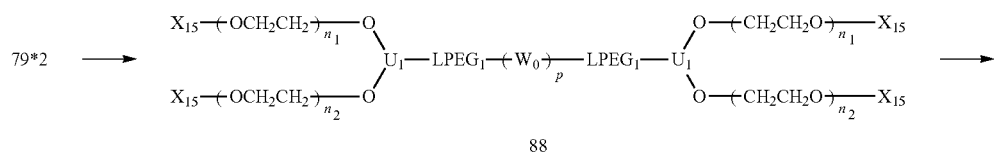

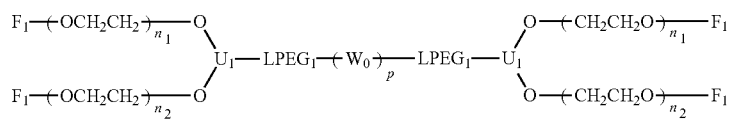

2.2.5.11. Method-11, coupling two Y-shaped polyethylene glycol molecules (79) and (79b) containing respective two unprotected or protected functional groups $X_{15}$ and $X_{16}$ to the two terminal ends of a linear bifunctionalized polyethylene glycol (81) respectively to obtain an H-shaped polyethylene glycol derivative (82) which has a linear main chain consisting of at least three PEG blocks ($LPEG_1$, $LEGP_2$ and $LPEG_3$), and carrying out linear or branched end-functionalization to terminal groups $X_{15}$ and $X_{16}$ respectively to obtain an H-shaped multifunctionalized polyethylene glycol as represented by formula (9); wherein, $X_{15}$ and $X_{16}$ can be the same or different from each other; $X_{15}$ and $X_{16}$ are each independently identical to or different from corresponding objective unprotected or protected functional group.

2.2.5.12. Method-12, coupling a Y-shaped polyethylene glycol molecule (79b) containing two unprotected or protected functional groups $X_{16}$ with a Y-shaped polyethylene glycol molecule (83) containing a branched terminal and unprotected or protected functional groups $X_{15}$ to obtain an H-shaped polyethylene glycol derivative (84) which has a linear main chain consisting of at least two PEG blocks ($LPEG_1$ and $LPEG_2$), and independently carrying out linear or branched end-functionalization to terminal groups $X_{16}$ as well as linear end-functionalization to terminal groups $X_{15}$ to obtain an H-shaped multifunctionalized polyethylene glycol as represented by formula (20b) or (21b); wherein, $X_{15}$ and $X_{16}$ can be the same or different from each other;

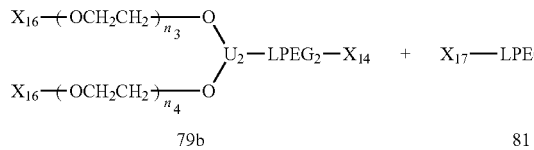
79b
81
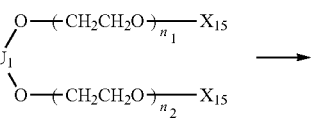
79

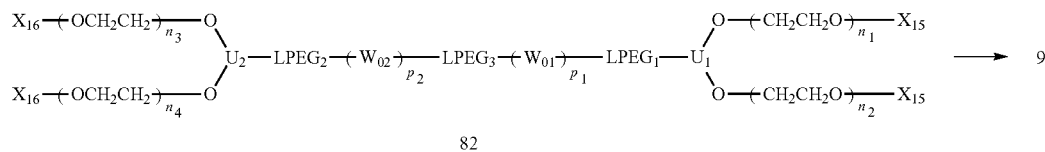
82

With respect to this method, when (79) and (79b) are identical, it is equivalent to coupling two molecules of Y-shaped polyethylene glycol (79) with two unprotected or protected functional groups $X_{15}$ as a single reagent to the two terminal ends of a linear bifunctionalized polyethylene glycol (89) respectively to obtain an H-shaped polyethylene glycol derivative (90) which has a linear main chain consisting of at least three PEG blocks ($LPEG_1$, $LEGP_2$ and $LPEG_3$), followed by linear or branched end-functionalization to terminal groups $X_{15}$ to obtain an H-shaped multifunctionalized polyethylene glycol as represented by formula (9b); wherein, $X_{15}$ can be the same as or different from the objective unprotected or protected functional group.

$X_{15}$ and $X_{16}$ are each independently identical to or different from corresponding objective unprotected or protected functional group.

79*2 + $X_{11}$—$LPEG_3$—$X_{11}$ ⟶
89

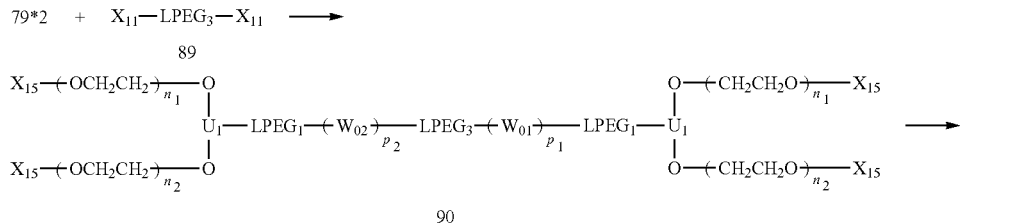
90

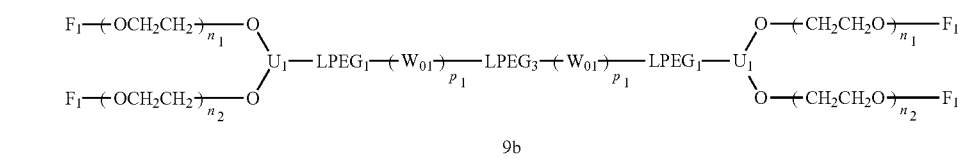
9b

-continued

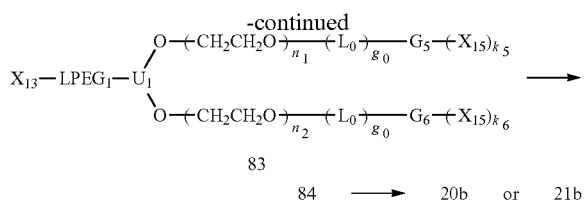

83

84 ⟶ 20b or 21b 2.2.5.13. Method-13, coupling a Y-shaped polyethylene glycol molecule (79b) containing two unprotected or protected functional groups $X_{16}$ with a Y-shaped polyethylene glycol molecule (83) containing a branched terminal and unprotected or protected functional groups $X_{15}$ to the two terminal ends of a linear bifunctionalized polyethylene glycol (81) respectively to obtain an H-shaped polyethylene glycol derivative (85) which has a linear main chain consisting of at least three PEG blocks (LPEG$_1$, LEGP$_2$ and LPEG$_3$), and independently carrying out linear or branched end-functionalization to terminal groups $X_{16}$ as well as linear end-functionalization to terminal groups $X_{15}$ to obtain an H-shaped multifunctionalized polyethylene glycol as represented by formula (20c) or (21c); wherein, $X_{15}$ and $X_{16}$ can be the same or different from each other; $X_{15}$ and $X_{16}$ are each independently identical to or different from corresponding objective unprotected or protected functional group.

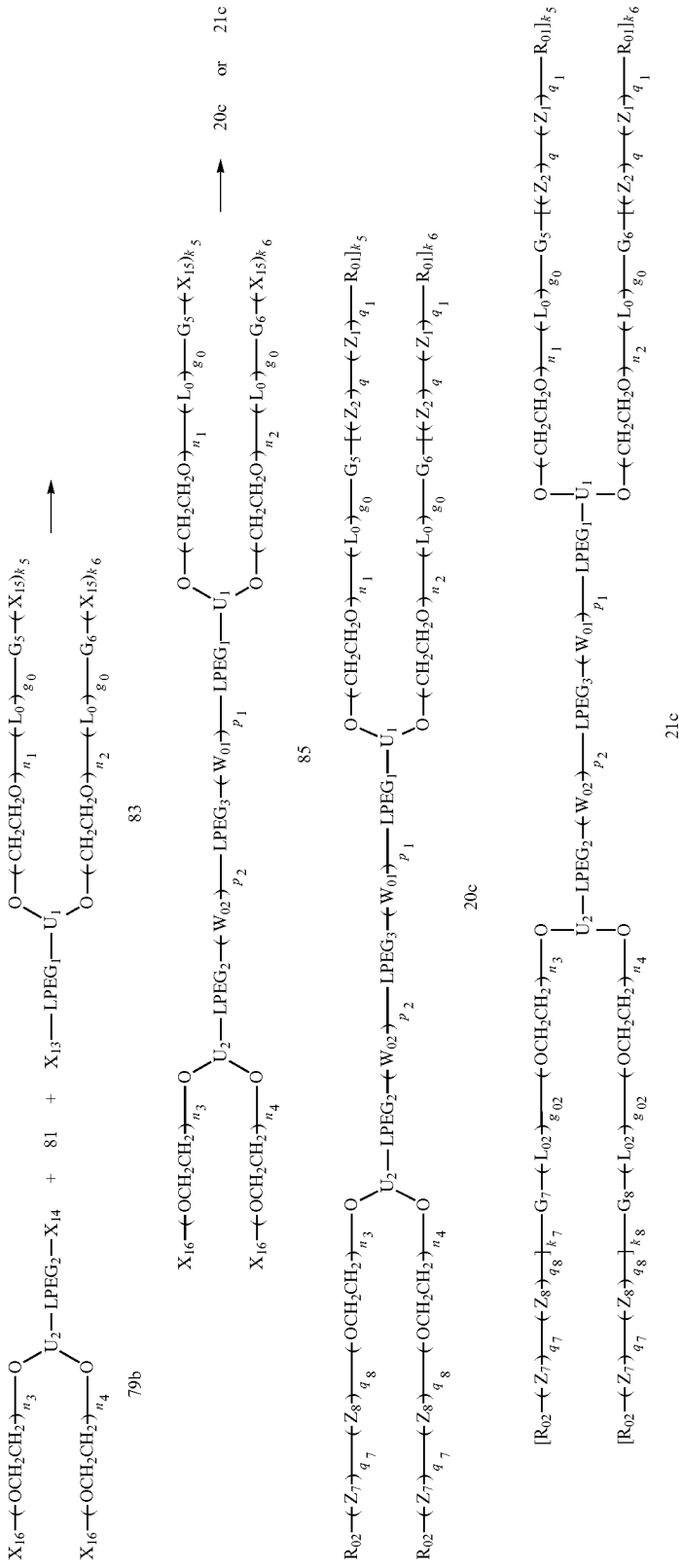

2.2.5.14. Method-14, reacting two Y-shaped polyethylene glycol molecules (83) and (83b) containing respective branched terminal and respective two unprotected or protected functional groups $X_{15}$ and $X_{16}$ via coupling reaction to obtain an H-shaped polyethylene glycol derivative (86) which has a linear main chain consisting of at least two PEG blocks ($LPEG_1$ and $LPEG_2$), and carrying out linear end-functionalization to terminal groups $X_{15}$ and $X_{16}$ respectively to obtain an H-shaped multifunctionalized polyethylene glycol as represented by formula (21b); wherein, $X_{15}$ and $X_{16}$ can be the same or different from each other; $X_{15}$ and $X_{16}$ are each independently identical to or different from corresponding objective unprotected or protected functional group.

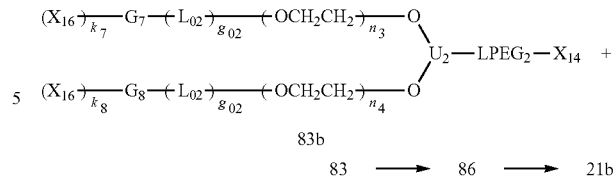

With respect to this method, when (83) and (83b) are identical, it is equivalent to coupling two molecules of Y-shaped polyethylene glycol (83) containing a branched terminal and two unprotected or protected functional groups $X_{15}$ as a single reagent into one molecule to obtain an H-shaped polyethylene glycol derivative (91) which has a linear main chain consisting of at least two PEG blocks ($LPEG_1$ and $LPEG_2$), followed by linear end-functionalization to terminal groups $X_{15}$ to obtain an H-shaped multifunctionalized polyethylene glycol as represented by formula (21d); wherein, $X_{15}$ can be the same as or different from the objective unprotected or protected functional group.

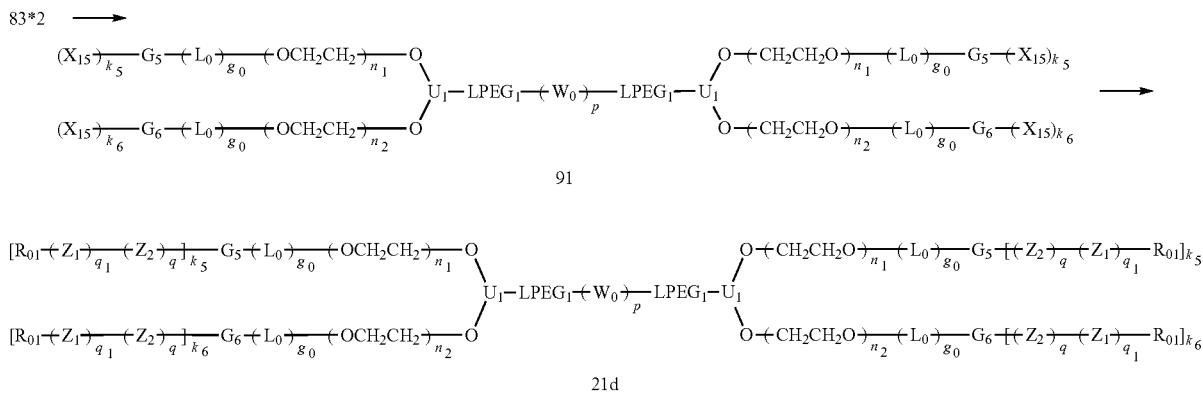

2.2.5.15. Method-15, coupling two Y-shaped polyethylene glycol molecules (83) and (83b) containing respective branched terminal and respective two unprotected or protected functional groups $X_{15}$ and $X_{16}$ to the two terminal ends of a linear bifunctionalized polyethylene glycol (81) respectively to obtain an H-shaped polyethylene glycol derivative (87) which has a linear main chain consisting of at least three PEG blocks ($LPEG_1$, $LEGP_2$ and $LPEG_3$), and carrying out linear end-functionalization to terminal groups $X_{15}$ and $X_{16}$ respectively to obtain an H-shaped multifunctionalized polyethylene glycol as represented by formula (21c); wherein, $X_{15}$ and $X_{16}$ can be the same or different from each other; $X_{15}$ and $X_{16}$ are each independently identical to or different from corresponding objective unprotected or protected functional group.

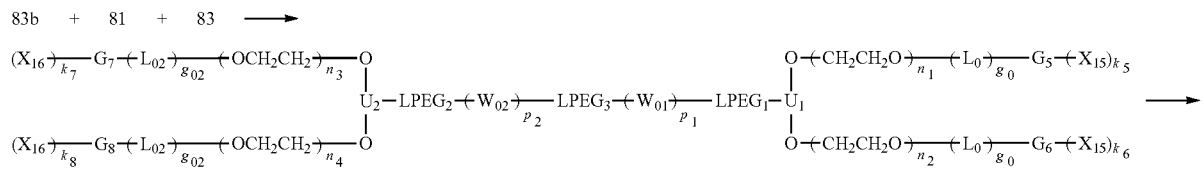

With respect to this method, when (83) and (83b) are identical, it is equivalent to coupling two molecules of Y-shaped polyethylene glycol (83) containing a branched terminal and two unprotected or protected functional groups $X_{15}$ as a single reagent to the two terminal ends of a linear bifunctionalized polyethylene glycol (81) respectively to obtain an H-shaped polyethylene glycol derivative (92) which has a linear main chain consisting of at least three PEG blocks ($LPEG_1$, $LEGP_2$ and $LPEG_3$), followed by linear end-functionalization to terminal groups $X_{15}$ to obtain an H-shaped multifunctionalized polyethylene glycol as represented by formula (21e); wherein, $X_{15}$ can be the same as or different from the objective unprotected or protected functional group.

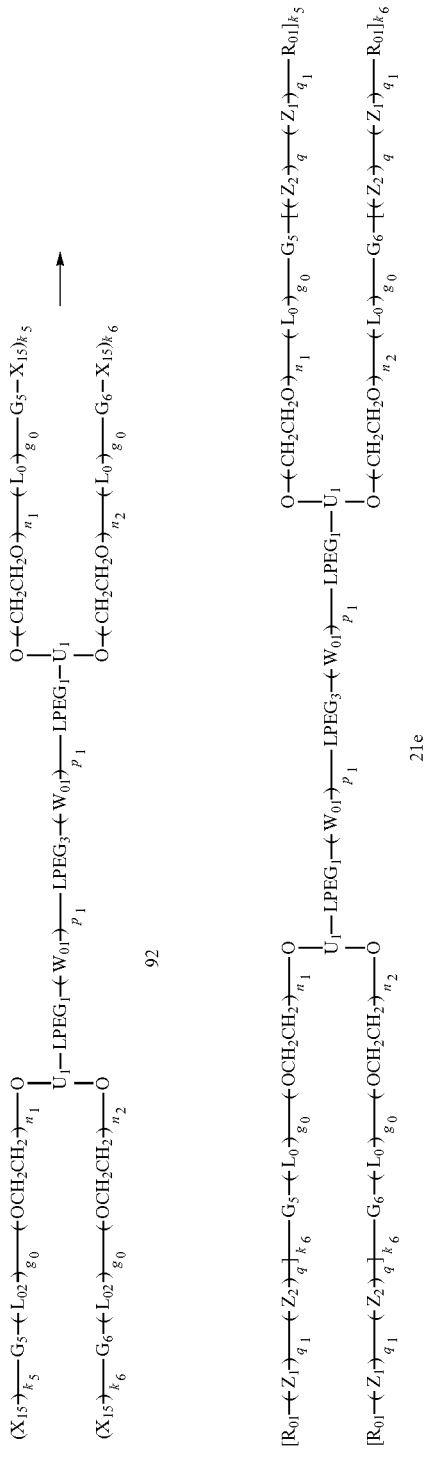
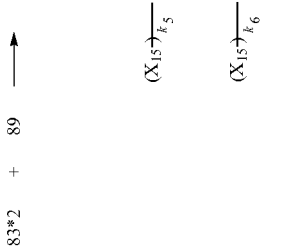

2.2.5.16. Method-16, coupling a V-shaped polyethylene glycol molecule (69b) containing unprotected or protected functional groups $X_{16}$ with a Y-shaped polyethylene glycol molecule (77c) containing unprotected or protected functional groups $X_{15}$ to the two terminal ends of a small molecule compound (93) to obtain an H-shaped polyethylene glycol derivative (71) which has a linear main chain consisting of at least one PEG block (LPEG), and carrying out linear or branched end-functionalization to terminal groups $X_{15}$ and $X_{16}$ respectively to obtain an H-shaped multifunctionalized polyethylene glycol as represented by formula (1); wherein, $X_{15}$ and $X_{16}$ can be the same or different from each other; $X_{15}$ and $X_{16}$ are each independently identical to or different from corresponding objective unprotected or protected functional group; wherein, said LPEG include residues of $LPEG_0$ and $W_0$. According to the combination of linear and branched end-functionalization reactions, specifically, the resulting H-shaped multifunctionalized polyethylene glycol as represented by general formula (1) can be represented by formula (19), (20), (21) or (22).

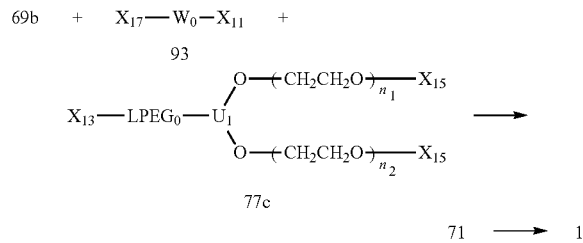

2.2.5.17. Method-17, coupling a V-shaped polyethylene glycol molecule (69b) containing unprotected or protected functional groups $X_{16}$ with a Y-shaped polyethylene glycol molecule (78c) containing a branched terminal and unprotected or protected functional groups $X_{15}$ to the two terminal ends of a small molecule compound (93) to obtain an H-shaped polyethylene glycol derivative (74) which has a linear main chain consisting of at least one PEG block (LPEG), and independently carrying out linear or branched end-functionalization to terminal groups $X_{16}$ as well as linear end-functionalization to terminal groups $X_{15}$ to obtain an H-shaped multifunctionalized polyethylene glycol as represented by formula (20) or (21); wherein, $X_{15}$ and $X_{16}$ can be the same or different from each other; $X_{15}$ and $X_{16}$ are each independently identical to or different from corresponding objective unprotected or protected functional group.

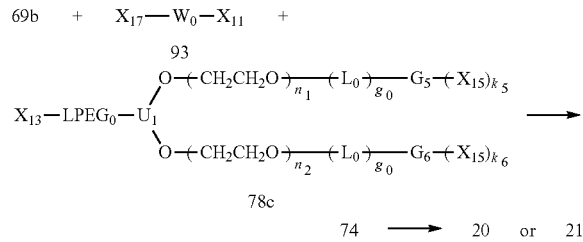

2.2.5.18. Method-18, coupling a Y-shaped polyethylene glycol molecule (73b) containing a branched terminal and unprotected or protected functional groups $X_{16}$ with a Y-shaped polyethylene glycol molecule (78c) containing a branched terminal and unprotected or protected functional groups $X_{15}$ to the two terminal ends of a small molecule compound (93) to obtain an H-shaped polyethylene glycol derivative (75) which has a linear main chain consisting of at least one PEG block (LPEG), and carrying out linear end-functionalization to terminal groups $X_{15}$ and $X_{16}$ respectively to obtain an H-shaped multifunctionalized polyethylene glycol as represented by formula (15); wherein, $X_{15}$ and $X_{16}$ can be the same or different from each other; $X_{15}$ and $X_{16}$ are each independently identical to or different from corresponding objective unprotected or protected functional group; wherein, said LPEG include residues of $LPEG_0$ and $W_0$.

2.2.5.19. Method-19, coupling two Y-shaped polyethylene glycol molecules (79) and (79b) containing respective two unprotected or protected functional groups $X_{15}$ and $X_{16}$ to the two terminal ends of a small molecule compound (93) to obtain an H-shaped polyethylene glycol derivative (80) which has a linear main chain consisting of at least two PEG blocks ($LPEG_1$ and $LPEG_2$), and carrying out linear or branched end-functionalization to terminal groups $X_{15}$ and $X_{16}$ respectively to obtain an H-shaped multifunctionalized polyethylene glycol as represented by formula (8); wherein, $X_{15}$ and $X_{16}$ can be the same or different from each other; $X_{15}$ and $X_{16}$ are each independently identical to or different from corresponding objective unprotected or protected functional group; wherein, said LPEG include residues of $LPEG_0$ and $W_0$.

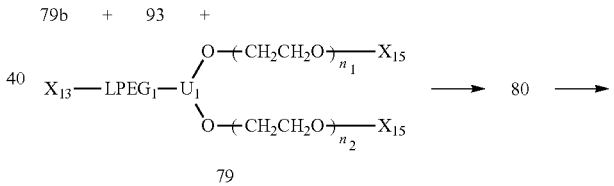

With respect to this method, when (79) and (79b) are identical, it is equivalent to coupling two molecules of Y-shaped polyethylene glycol (79) containing two unprotected or protected functional groups $X_{15}$ as a single reagent to the two terminal ends of a small molecule compound (93) respectively to obtain an H-shaped polyethylene glycol derivative (80) which has a linear main chain consisting of at least two PEG blocks ($LPEG_1$ and $LPEG_2$), followed by linear or branched end-functionalization to terminal groups $X_{15}$ to obtain an H-shaped multifunctionalized polyethylene glycol as represented by formula (8b); wherein, $X_{15}$ can be the same as or different from the objective unprotected or protected functional group; wherein, said LPEG include residues of $LPEG_0$ and $W_0$.

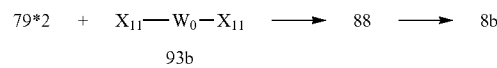

2.2.5.20. Method-20, coupling a Y-shaped polyethylene glycol molecule (79b) containing unprotected or protected functional groups $X_{16}$ with a Y-shaped polyethylene glycol molecule (83) containing a branched terminal and unprotected or protected functional groups $X_{15}$ to the two terminal ends of a small molecule compound (93) to obtain an H-shaped polyethylene glycol derivative (84) which has a linear main chain consisting of at least two PEG blocks (LPEG$_1$ and LPEG$_2$), and carrying out linear or branched end-functionalization to terminal groups $X_{15}$ and $X_{16}$ respectively to obtain an H-shaped multifunctionalized polyethylene glycol as represented by formula (20b) or (21b); wherein, $X_{15}$ and $X_{16}$ can be the same or different from each other; $X_{15}$ and $X_{16}$ are each independently identical to or different from corresponding objective unprotected or protected functional group.

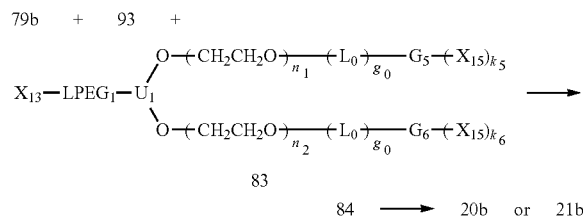

2.2.5.21. Method-21, coupling two Y-shaped polyethylene glycol molecules (83) and (83b) containing respective branched terminal and respective two unprotected or protected functional groups $X_{15}$ and $X_{16}$ to the two terminal ends of a small molecule compound (93) to obtain an H-shaped polyethylene glycol derivative (86) which has a linear main chain consisting of at least two PEG blocks (LPEG$_1$ and LPEG$_2$), and carrying out linear end-functionalization to terminal groups $X_{15}$ and $X_{16}$ respectively to obtain an H-shaped multifunctionalized polyethylene glycol as represented by formula (21b); wherein, $X_{15}$ and $X_{16}$ can be the same or different from each other; $X_{15}$ and $X_{16}$ are each independently identical to or different from corresponding objective unprotected or protected functional group.

83b+93+83→86→21b

With respect to this method, when (83) and (83b) are identical, it is equivalent to coupling two molecules of Y-shaped polyethylene glycol (83) containing a branched terminal and two unprotected or protected functional groups $X_{15}$ as a single reagent to the two terminal ends of a small molecule compound (93) respectively to obtain an H-shaped polyethylene glycol derivative (91) which has a linear main chain consisting of at least two PEG blocks (LPEG$_1$ and LPEG$_2$), followed by linear end-functionalization to terminal groups $X_{15}$ to obtain an H-shaped multifunctionalized polyethylene glycol as represented by formula (21d); wherein, $X_{15}$ can be the same as or different from the objective unprotected or protected functional group.

83*2+93b→91→21d 2.2.6. Route-6, step-by-step coupling method is applicable when $F_1$ and $F_2$ have identical or different $R_{01}$ groups, and production steps of Route-6 are as follows:

Step (a): preparation of an intermediate containing two telechelically branched PEG branch chains and a linear main chain: coupling one molecule of linear polyethylene glycol derivative (94) with an unprotected or protected functional group $X_{15}$ and a reactive group $X_{19}$ to each terminal end of a linear bifunctionalized polyethylene glycol (96a, containing two semiH-branching groups $U_1$ and $U_2$ or precursors thereof) to obtain a polyethylene glycol intermediate (66) which contains a PEG main chain and two telechelically branched PEG branch chains; wherein, $X_{15}$ can be the same as or different from the objective unprotected or protected functional group $F_1$;

Step (b): preparation of an H-shaped polyethylene glycol intermediate: coupling one molecule of linear polyethylene glycol (94b) with an unprotected or protected functional group $X_{15}$ and a reactive group $X_{19}$ to the two semiH-branching groups ($U_1$ and $U_2$ or precursors thereof) respectively to obtain an H-shaped polyethylene glycol intermediate (95);

Step (c): carrying out linear or branched end-functionalization to the terminal unprotected or protected functional groups $X_{15}$ to obtain an H-shaped multifunctionalized polyethylene glycol derivative (8c) which has objective unprotected or protected functional groups; when $X_{15}$ is identical to the objective unprotected or protected functional group $F_1$, this end-functionalization step should be omitted; linear end-functionalization of $X_{15}$ corresponds to a resulting formula (14b) while branched end-functionalization of $X_{15}$ corresponds to a resulting formula (15b).

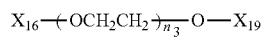

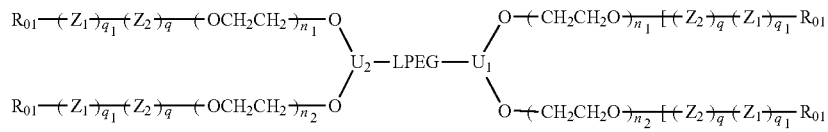

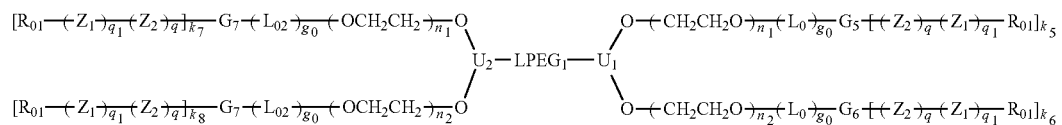

-continued

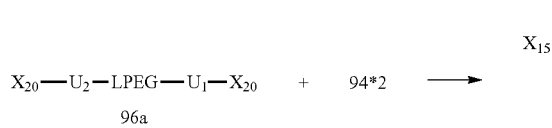
96a

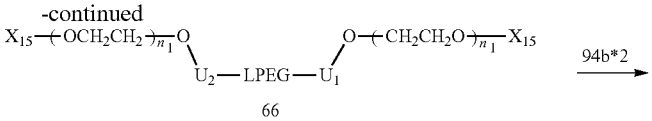
66

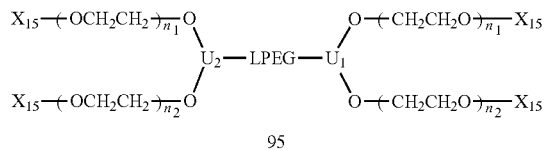
95

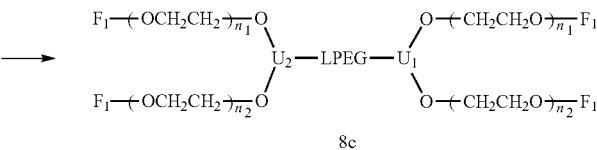
8c 2.2.7. Route-7, coupling method based on an H-branched intermediate is applicable when $F_1$ and $F_2$ have the same $R_{01}$ groups, and production steps of Route-7 are as follows:

Step (a): preparation of a branched intermediate containing a linear main chain: coupling two molecules of linear polyethylene glycol derivative (94) containing an unprotected or protected functional group $X_{15}$ to each terminal end of a linear polyethylene glycol derivative (96b, containing two semiH-branching groups $U_1$ and $U_2$ and four reactive groups $X_{20}$) to obtain an H-shaped polyethylene glycol intermediate (95b); wherein, $X_{15}$ can be the same as or different from the objective unprotected or protected functional group $F_1$;

Step (b): carrying out linear or branched end-functionalization to the terminal unprotected or protected functional groups $X_{15}$ to obtain an H-shaped multifunctionalized polyethylene glycol derivative (8d) which contains the objective unprotected or protected functional groups; if $X_{15}$ is identical to the objective unprotected or protected functional group $F_1$, omitting this end-functionalization step; linear end-functionalization of $X_{15}$ corresponds to a resulting formula (14c) while branched end-functionalization of $X_{15}$ corresponds to a resulting formula (15c).

Y-shaped polyethylene glycol derivatives as reagent, and coupling with a linear polyethylene glycol derivative to obtain an H-shaped polyethylene glycol derivative; the branch-chain terminals of said Y-shaped polyethylene glycol derivatives can be linearly or branchedly functionalized, while the two terminals of said linear polyethylene glycol derivative are both linearly functionalized.

The approaches to achieve Route-8 include but are not limited to the following four methods:

Method-1: starting from a Y-shaped polyethylene glycol (79c) with unprotected or protected functional groups $X_{15}$ at two branch-chain terminals, introducing two reactive sites $X_{20}$ via chemical modification to obtain a Y-shaped intermediate (97), coupling two molecules of linear polyethylene glycol derivative (94c) with a terminal unprotected or protected functional group $X_{16}$ to the main-chain terminal end of Y-shaped intermediate (97) to obtain an H-shaped polyethylene glycol intermediate (95c), and carrying out linear or branched end-functionalization to terminal groups $X_{15}$ and $X_{16}$ respectively to obtain an H-shaped multifunctionalized polyethylene glycol as represented by formula (8e); wherein, $X_{15}$ and $X_{16}$ can be the same or different from each

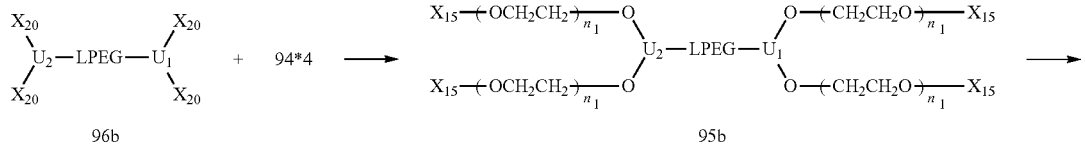
96b        95b

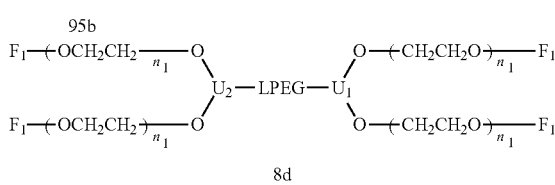
8d

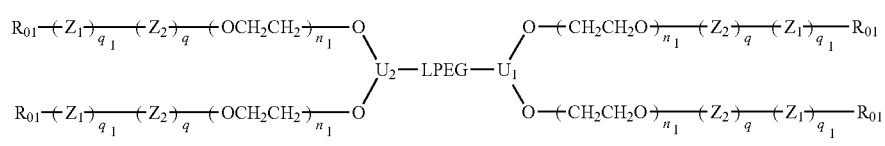
14c

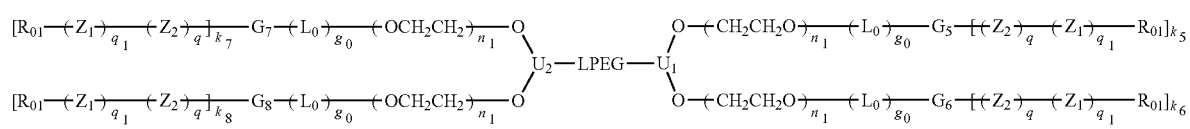
15c 2.2.8. Route-8, step-by-step coupling method is applicable when $F_1$ and $F_2$ have the same or different from $R_{01}$ groups. Route-8 is achieved in the following manner: using other; $X_{15}$ and $X_{16}$ are each independently identical to or different from corresponding objective unprotected or protected functional group.

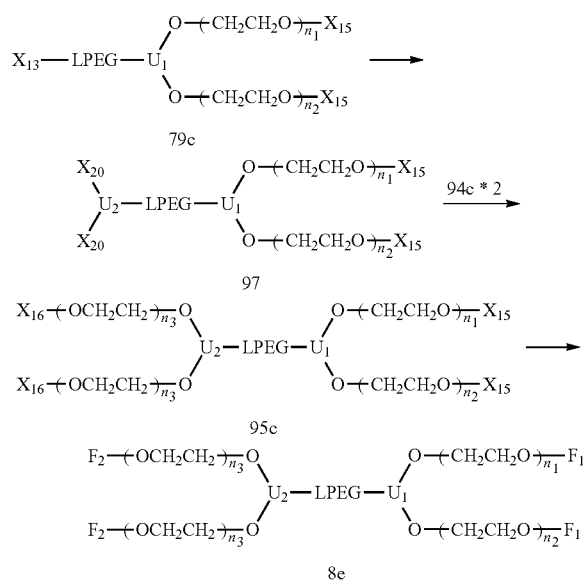

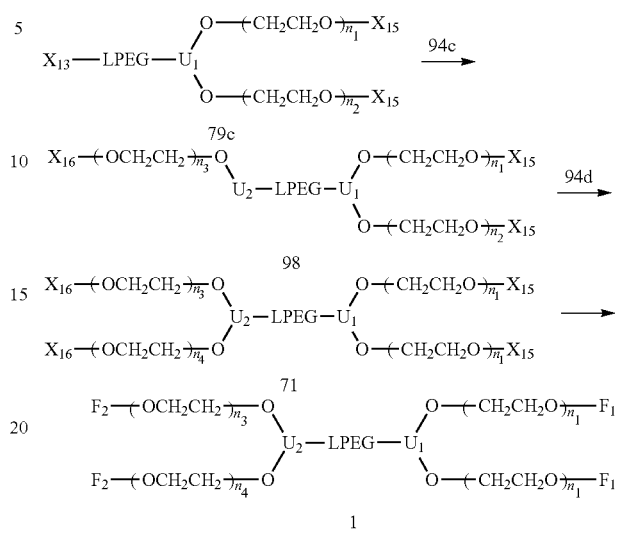

as represented by general formula (1) can be represented by formula (19), (20), (21) or (22).

Method-2: starting from a Y-shaped polyethylene glycol (79c) with two terminal unprotected or protected functional groups $X_{15}$, introducing a third branch chain with a terminal unprotected or protected functional group $X_{16}$ via coupling reaction to obtain an intermediate as shown by formula (98), further introducing the fourth branch chain with a terminal unprotected or protected functional group $X_{16}$ via coupling reaction to obtain an H-shaped polyethylene glycol intermediate (71), and carrying out linear or branched end-functionalization to terminal groups $X_{15}$ and $X_{16}$ respectively to obtain an H-shaped multifunctionalized polyethylene glycol as represented by formula (1); wherein, $X_{15}$ and $X_{16}$ can be the same or different from each other; $X_{15}$ and $X_{16}$ are each independently identical to or different from corresponding objective unprotected or protected functional group. According to the combination of linear and branched end-functionalization reactions, specifically, the resulting H-shaped multifunctionalized polyethylene glycol Method-3: starting from a Y-shaped polyethylene glycol (83c) containing a branched end terminated with unprotected or protected functional groups $X_{15}$, introducing two reactive sites $X_{20}$ via chemical modification to obtain a Y-shaped intermediate (99), coupling two molecules of linear polyethylene glycol derivative (94c) with a terminal unprotected or protected functional group $X_{16}$ to the main-chain terminal end of Y-shaped intermediate (99) to obtain an H-shaped polyethylene glycol intermediate (84c), and independently carrying out linear or branched end-functionalization to terminal groups $X_{16}$ as well as linear end-functionalization to terminal groups $X_{15}$ to obtain an H-shaped multifunctionalized polyethylene glycol as represented by formula (20f) or (21f); wherein, $X_{15}$ and $X_{16}$ can be the same or different from each other; $X_{15}$ and $X_{16}$ are each independently identical to or different from corresponding objective unprotected or protected functional group.

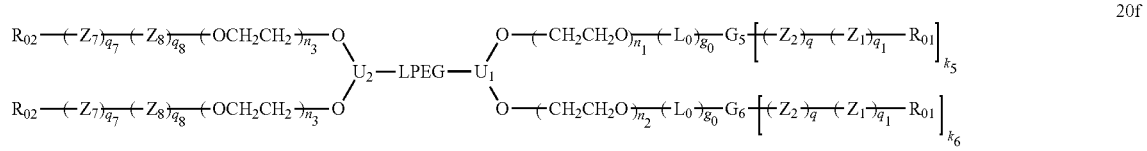

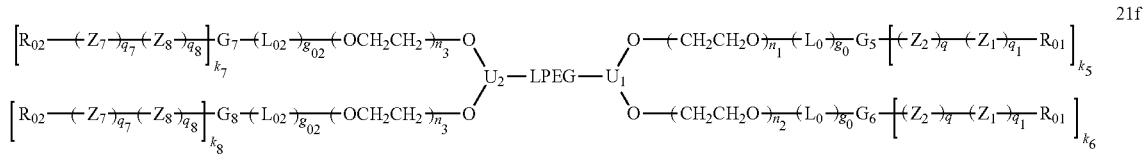

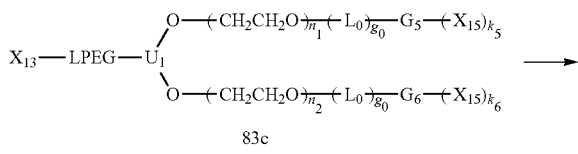

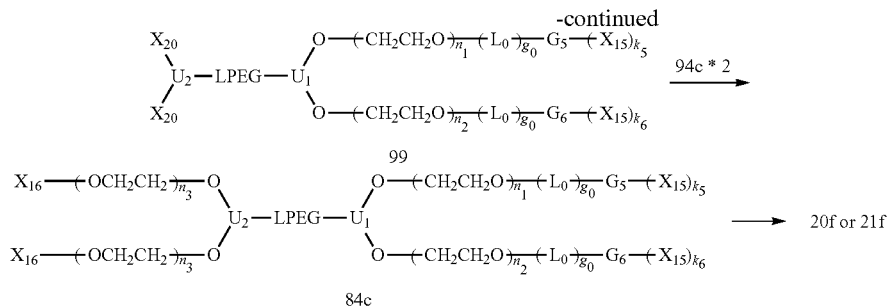

Method-4:
starting from a Y-shaped polyethylene glycol (83c) containing a branched end terminated with unprotected or protected functional groups $X_{15}$, introducing a third branch chain with a terminal unprotected or protected functional group $X_{16}$ via the coupling reaction with (94c) to obtain an intermediate as shown by formula (100), further introducing the fourth branch chain with a terminal unprotected or protected functional group $X_{16}$ via coupling reaction with (94d) to obtain an H-shaped polyethylene glycol intermediate (84), and independently carrying out linear or branched end-functionalization to terminal groups $X_{16}$ as well as linear end-functionalization to terminal groups $X_{15}$ to obtain an H-shaped multifunctionalized polyethylene glycol as represented by formula (20e) or (21e); wherein, $X_{15}$ and $X_{16}$ can be the same or different from each other; $X_{15}$ and $X_{16}$ are each independently identical to or different from corresponding objective unprotected or protected functional group. According to the combination of linear and branched end-functionalization reactions, specifically, the resulting H-shaped multifunctionalized polyethylene glycol as represented by general formula (1) can be represented by formula (19), (20), (21) or (22).

The production methods of said V-shaped polyethylene glycol intermediates (73) and (73b) containing a respective terminal branch and respective unprotected or protected functional groups $X_{15}$ and $X_{16}$, which are involved in above-described various routes and methods, include two steps of the formation of a V-shaped structure and branched end-functionalization, such as the preparation method of (59b) and (59c) in the Step (a) of Route-3. Wherein, the preparation method of the V-shaped structure refers to the formation of (69) and (69b).

The production methods of said Y-shaped polyethylene glycol intermediate (79) and (79b) containing terminal unprotected or protected functional groups $X_{15}$ or $X_{16}$ respectively, which are involved in above-described various routes and methods, are not particularly limited, including polymerization of ethylene oxide, coupling reactions by using linear polyethylene glycol chains, or the combination of polymerization and coupling reactions. For example, the preparation method of (53), (54) and (58d) in the Step (b) of Route-2, or the preparation of (79) via chemical modification to the terminal hydroxyl group of PEG main chain of (58d) prepared in the Step (b) of Route-3, or preparation of

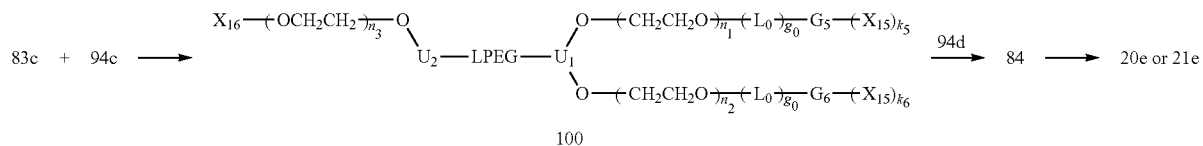

2.2.9. Preparation of Important Intermediates

Any of the linear polyethylene glycol intermediates in the above-mentioned routes and methods can be either polydisperse or monodisperse, e.g., such as IN5, (70), (38), (81), (89), (94), (94b), (94c), (94d), (96a) and (96b), etc. Wherein, the production method of PEG segments or blocks is not particularly limited, e.g. via polymerization of ethylene oxide to form a polydisperse segment, or via organic synthesis, or by using purchased reagents which are either polydisperse or monodisperse.

The production methods of said V-shaped polyethylene glycol intermediates (69) and (69b) containing terminal unprotected or protected functional groups $X_{15}$ and $X_{16}$ respectively, which are involved in above-described various routes and methods, are not particularly limited, including polymerization of ethylene oxide and coupling reactions by using linear polyethylene glycol chains. In addition, compound (69) and (69b) can also be prepared by starting from compound (58b) or (58c) obtained from Step (a) of Route-3, or be prepared by coupling two molecules of linear polyethylene glycol to the branching group $U_1$ and $U_2$ respectively via a one-step or stepwise reaction.

a Y-shaped polyethylene glycol derivative by the coupling reaction between a V-shaped polyethylene glycol derivative such as (69) or (69b) and a linear polyethylene glycol chain followed by suitable end-functionalization.

The production methods of said Y-shaped polyethylene glycol intermediates (83) and (83b) containing a respective terminal branch and respective unprotected or protected functional groups $X_{15}$ and $X_{16}$, which are involved in above-described various routes and methods, e.g., including the production method as preparing (55) in Step (b) of Route-2, chemical modification to the terminal hydroxyl group of PEG main chain of the intermediate prepared in the Step (b) of Route-3, coupling reaction of (73) and (73b) respectively with a linear polyethylene glycol derivative followed by suitable chemical modification, or branched end-functionalization of branch-chain terminals of (79) and (79b) respectively.

What should be noted is that, with respect to the formulas (72), (13b), (14b), (15b), (76), (15c), (88), (8b), (90), (9b), (91), (21d), (92), (21e), (66), (95), (8c), (14c), (15c), (95b), (8d), (95c), (8e), (84c), (20f), (21f), etc., when the number of one of $n_1$, $n_2$, $n_3$, $n_4$, $m_1$ and $m_2$ in one molecule is an integer such as 2, 3 or 4, it does not mean that the average EO-unit number of corresponding polyethylene glycol chain is strictly equal to said integer in terms of value, but refers to deriving from the same reagent and thus being close to said integer in terms of value. When the reagent is a monodisperse compound, they may be strictly equal in terms of value.

2.2.10. Reactions Between Two Unprotected or Protected Functional Groups

The reactions between two unprotected or protected functional groups involved in the above-said Route-5, Route-6, Route-7 and Route-8 are not particularly limited in the present invention. For example, said two unprotected or protected functional groups can be a functional-group pair such as $(X_{11}, X_{12})$, $(X_{11}, X_{13})$, $(X_{18}, X_{17})$, $(X_{14}, X_{17})$, $(X_{18}, X_{13})$, $(X_{14}, X_{13})$, $(X_{18}, X_{12})$, $(X_{14}, X_{12})$ or $(X_{20}, X_{19})$. The reaction conditions are related to the types of the resulting divalent linking groups, and the prior art can be incorporated. Typical examples of the newly formed divalent linking groups include an amide bond, a urethane bond, an ester bond, a secondary amino bond, a thioether bond, a triazole linkage and the like, also referring to part 2.1.3, and no more repeated here.

Step (c): removing the hydroxyl protecting groups of the intermediate (203) to obtain an intermediate (204) with four unprotected hydroxyl groups;

Step (d): initiating the polymerization of ethylene oxide from the terminal hydroxyl groups of the intermediate (204) to form oxyanion-terminated PEG branch chains, and then carrying out protonation to obtain an intermediate (205) with terminal hydroxyl groups;

Step (e): carrying out end-functionalization to the terminal hydroxyl groups of the PEG branch chains of intermediate (205) to obtain an H-shaped multifunctionalized polyethylene glycol as represented by general formula (6).

Wherein, the definitions of $n_1$, $n_2$, $n_3$, $n_4$, $m_1$, $m_2$, $W_0$, $U_1$, $U_2$, $F_1$ and $F_2$ are the same as those in above-mentioned general formula (6), and no more repeated here. Herein, $U_1$ and $U_2$ are identical, $F_1$ and $F_2$ are identical, and $PG_4$ is a hydroxyl protecting group, for example, including but not limited to a silyl group, a benzyl group, an acetal group, a ketal group and a t-butyl group.

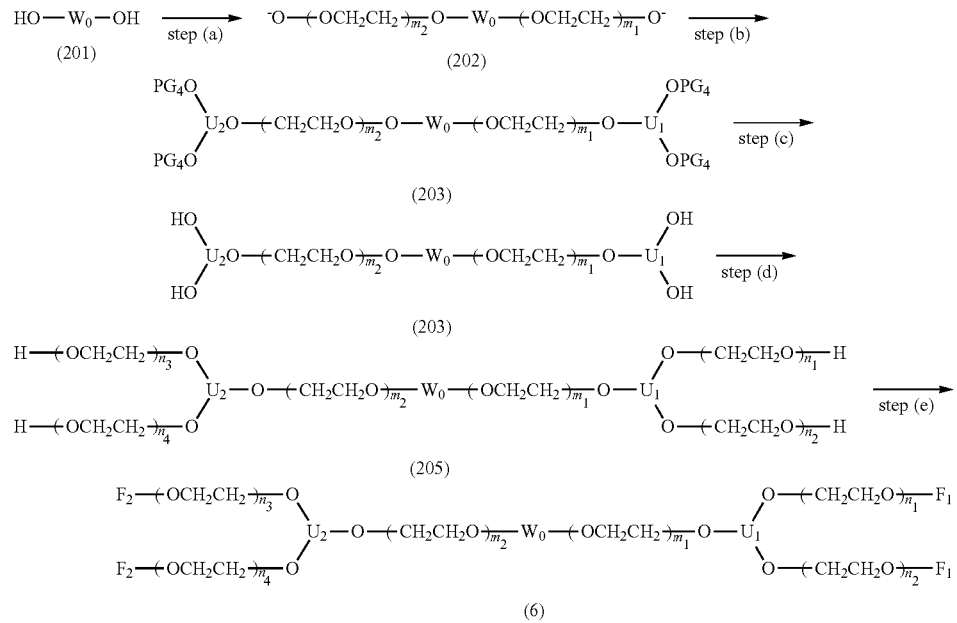

(6)

2.3. Specifically, the Present Invention also Discloses the Following Methods for Producing H-Shaped Multifunctionalized Polyethylene Glycol Derivatives.

Wherein, polyethylene glycol segments and blocks of any PEG reagent with a linear, V-shaped or Y-shaped structure involved in the production processes can be each independently polydisperse or monodisperse.

2.3.1. Method-1 Consisting of the Following Steps:

Step (a): using a coinitiator system which contains a small molecule initiator (201) with two unprotected hydroxyl groups and a base, then initiating the polymerization of ethylene oxide to form a linear polyethylene glycol chain consisting of two polyethylene glycol blocks and thus obtain an oxyanion intermediate (202);

Step (b): reacting the oxyanion intermediate (202) with a branching reagent (206) containing two protected hydroxyl groups to obtain an intermediate (203);

2.3.1.1. Preparation of Polyethylene Glycol Anion Intermediate (202) (Step a)

The preparation of the intermediate (202) includes the following two steps: polymerization between small molecule initiator and ethylene oxide, and subsequent deprotonation of the polymerized product. Wherein, the intermediate (202) is polydisperse, and the reaction conditions refer to Step (b) of Route-1 (2.2.1.2.), and no more repeated here.

The compound (201) is a diol. The diol can be a diol derived from a $C_{2-20}$ hydrocarbyl group, or an oligomer or polymer of small molecule diols, preferably a monomer of diols. Said oligomer or polymer of small molecule diols is an oligomer or polymer of ethanediol (that is ethylene glycol), and can be polydisperse or monodisperse, preferably monodisperse. With respect to the oligomer or polymer of ethanediol, for a monodisperse compound, the EO-unit number $j_2$ is from 2 to 70, preferably from 2 to 50, more preferably from 2 to 32, more preferably from 2 to 16, more preferably from 2 to 6, more preferably 2, 3 or 4. The spacer groups used for indirect combinations are preferably above-mentioned $L_{10}$ groups, and the number of $L_{10}$ can be one or more. When containing two or two more $L_{10}$ spacer groups, they can be the same or different. The two hydroxyl groups of diols are each independently an alcoholic hydroxyl group, a phenolic hydroxyl group, the hydroxyl group of a hemiacetal, an enolic hydroxyl group and the like, preferably an alcoholic hydroxyl group. For example, the diols include but are not limited to ethylene glycol, tetraethylene glycol, diethylene glycol (also diglycol), 1,2-dipheyl-1,2-ethanediol, 1,2-dicyclohexyl-1,2-ethanediol, 1-(naphthalen-1-yl)ethane-1,2-diol, 1-phenyl-1,2-ethanediol, 1,2-di(naphthalen-1-yl)ethane-1,2-diol, 1,1,2-triphenylethane-1,2-diol, 1,1,2,2-tetra-p-tolylethane-1,2-diol, 1,1,2,2-tetrakis(4-methoxyphenyl)ethane-1,2-diol, 1,2-diphenyl-1,2-di-p-tolylethane-1,2-diol, 1,3-propanediol, 1,2-propanediol, 1-phenyl-1,3-propanediol, 2,2-dioctyl-1,3-propanediol, 2,2-diisobutyl-1,3-propanediol, 2,2-diisopentyl-1,3-propanediol, 2,2-di-n-butyl-1,3-propanediol, 2-phenyl-1,3-propanediol, 2-benzyloxy-1,3-propanediol, 2-butyl-1,3-propanediol, 2-butyl-2-ethyl-1,3-propanediol, 2-methyl-1,3-propanediol, 2-methyl-2-propyl-1,3-propanediol, 3-phenoxy-1,2-propanediol, 3-benzyloxy-1,2-propanediol, 2-phenyl-1,2-propanediol, 3-L-menthoxy-2-methylpropane-1,2-diol, 3-((2-isopropyl-5-methylcyclohexyl)oxy)propane-1,2-diol (also 3-L-menthoxy-1,2-propanediol), 3-methoxy-1,2-propanediol, 3-ethoxy-1,2-propanediol, 3-(isooctadecyloxy)-1,2-propanediol, 3-octyloxy-1,2-propanediol, 1,4-butanediol, 1,2-butanediol, 1,3-butanediol, 2,3-butanediol, 2-methyl-1,4-butanediol, 2,3-dimethyl-2,3-butanediol, 2-butyne-1,4-diol, 1,5-pentanediol, 2-methyl-2,4-pentanediol, 2,2-dimethyl-1,3-propanediol, 2,2,4-trimethyl-1,3-pentanediol, 3-methyl-1,5-pentanediol, 1,2-pentanediol, dipropylene glycol, triethylene glycol, 1,6-hexanediol, 1,5-hexanediol, 2-ethyl-1,3-hexanediol, 2,5-dimethyl-2,5-hexanediol, trimethyl-1,6-hexanediol, 2,5-hexanediol, 1,2-hexanediol, 2,5-dimethyl-3-hexyne-2,5-diol, 3-hexyne-2,5-diol, 5-norbornene-2,2-dimethanol, 5-norbornene-2,3-dimethanol, 1,3-cyclohexanediol, 1,4-cyclohexanediol, 1,2-cyclohexanediol, 1,10-decanediol, 1,2-decanediol, 2,4,7,9-tetramethyl-5-decyne-4,7-diol, 1,3-bis(2-hydroxyethoxy)benzene, hydroquinone bis(2-hydroxyethyl)ether, 1,4-benzenediol, 2,5-di-tert-butylhydroquinone, 2,3,5-trimethylhydroquinone, 2-methoxyhydroquinone, 2,5-bis(1,1,3,3-tetramethylbutyl)hydroquinone, 2-t-octylhydroquinone, t-butylhydroquinone, 2,5-bis(1,1-dimethylpropyl)hydroquinone, 2,5-diphenylhydroquinone, 2,5-diisooctylhydroquinone, 2-(hexadecan-2-yl)-5-methylbenzene-1,4-diol, 2,3-dimethoxy-5-methyl-1,4-hydroquinone, 2,6-dimethoxyhydroquinone, biphenyl-4,4'-diol, 2,2',6,6'-tetramethyl-4,4'-biphenol, p-tert-butylcatechol, 1,2-benzenediol, 4-methylcatechol, 3,5-di-tert-butylcatechol, 4-butylcatechol, tert-butylcatechol, 3-methoxycatechol, 1,3-benzenediol, 3,5-dihydroxytoluene, 4-hexyl-1,3-benzenediol, 5-pentylresorcinol, 5-heptylresorcinol, 2-methylresorcinol, 4-ethylresorcinol, 4-propylresorcinol, 4-butylresorcinol, 4-isopropylresorcinol, 1,4-bis(hydroxymethyl)cyclohexane, 1,2-cyclohexanedimethanol, 5',5-diallyl-2,2'-biphenydiol, estradiol, 3,5-di-tert-butyl-4-hydroxybenzyl alcohol, 3,6-dihydroxybenzonorbornane, 3-dimethylamino-1,2-propanediol, 3-diethylamino-1,2-propanediol, 3-piperidinyl-1,2-propanediol, isosorbide and the like. The diols can be a cis- or trans-structure. The above-said diols containing two alcoholic hydroxyl groups are preferable. Wherein, the dimethylamino group acts as a pendant group of 3-dimethylamino-1,2-propanediol; however, the N atom of N-butyldiethanolamine acts as a divalent linking group, and therefore it should not be included.

Specific examples of diol compound (201) are as follows:

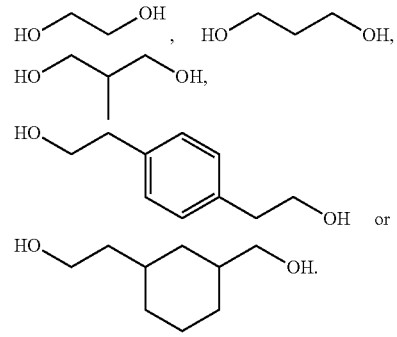

2.3.1.2. Deprotonation of Polyethylene Glycol Anion Intermediate (202) (Step b) (also Referred to End-Capping, Termination and Alkyl-Etherification)

The aim of this step is to branch the two terminals of a linear polyethylene glycol intermediate as to introduce two unprotected hydroxyl groups respectively to initiate the polymerization of ethylene oxide to form PEG branch chains.

The alkyl-etherification of the terminal ends of the polyethylene glycol anion intermediate (202) can be achieved through any of the following approaches:

Approach-1: reacting the polyethylene glycol anion intermediate (202) with a compound (206) of an alkyl halide, an alkyl sulfonate or the like which contains a leaving group.

(206)

Wherein, U is $U_1$ or $U_2$; $PG_4$ is a hydroxyl protecting group, such as a silyl group, a benzyl group, an acetal group, a ketal group or a t-butyl group; $LG_1$ is a leaving group, including but not limited to a chlorine atom, a bromine atom, an iodine atom, a mesyl group, a tosyl group or a 2,2,2-trifluoroethylsulfonyl group, preferably an iodine atom.

With respect to the compound (206) which contains a leaving group, such as an alkyl halide, an alkyl sulfonate or the like, the amount of such an end-capping reagent (also referred to as a terminating agent) is generally 5 to 20 molar equivalents, preferably 8 to 15 molar equivalents relative to the initiator. When the end-capping reagent is in an amount less than 5 molar equivalents to the initiator, the terminals of the branch chains are not completely end-capped, and the terminal oxygen anions will participate in the subsequent polymerization reaction to form an impurity having a molecular weight higher than the target compound. Therefore, the distribution of molecular weight becomes broad and a multifunctional impurity is generated. When such impurities are contained, the activity of the resulting modified drugs may be reduced or completely lost. When the amount of the capping reagent exceeds 20 molar equivalents to the initiator, the excess reagent tends to cause difficulty in purification process, and result in side reactions in the subsequent steps. The temperature of the end-capping reaction is not particularly limited, but preferably 25° C. to 50° C.

Approach-2: adding an activating reagent into the polyethylene glycol anion intermediate (202) to obtain a corresponding polyethylene glycol sulfonate, and followed by a substitution reaction with a deprotonated alcohol (207) shown as follows to obtain a compound (203). Commonly used activating reagents include methanesulfonyl chloride, p-toluenesulfonic acid and 2,2,2-trifluoroethylsulfonyl chloride.

(207)

Wherein, U is $U_1$ or $U_2$; $PG_4$ is a hydroxyl protecting group, such as a silyl group, a benzyl group, an acetal group, a ketal group or a t-butyl group.

Wherein, the compound (207) is the variant form of a triol while two hydroxyl groups thereof are protected and the third hydroxyl group thereof is deprotected. Said triols include but are not limited to glycerol, 2-hydroxymethyl-2-methyl-1,3-propanediol, 1,1,1-trihydroxymethylolpropane, 2-hydroxymethyl-1,3-butanediol, 1,2,4-butanetriol, 1,2,3-butanetriol, 2-benzyloxy-1,3,4-butanetriol, 1,2,5-pentanetriol, 3-methyl-1,3,5-pentanetriol, 1,2,3-hexanetriol, 1,2,6-hexanetriol, 1,2,7-heptanetriol, 1,2,8-octanetriol, 1,2,9-nonanetriol, 1,2,10-decatriol, 1,3,5-cyclohexanetriol, 1,3,5-benzenetrimethanol, 2-hydroxy-5-methyl-1,3-benzenedimethanol, 1,2,3-benzenetriol, 1,3,5-benzenetriol, 1,2,4-benzenetriol, dimethylphloroglucinol and the like. The triol can be an isomeric form of cis- or trans-structure, for example, a 1,2,4-butanetriol can be (S)-1,2,4-butanetriol, (R)-1,2,4-butanetriol or the like. The triol can also be an etherified form of any above-said triol with a diol, such an oligomer of polymer of 1,2-propanediol or a 1,2,6-hexanetriol triether. Said triols also allow the existence of a hydroxyl group of a hemiacetal, such as benzaldehyde glycerol acetal and phenylacetaldehyde glycerol acetal. For example, the compound (207) can has a structure of

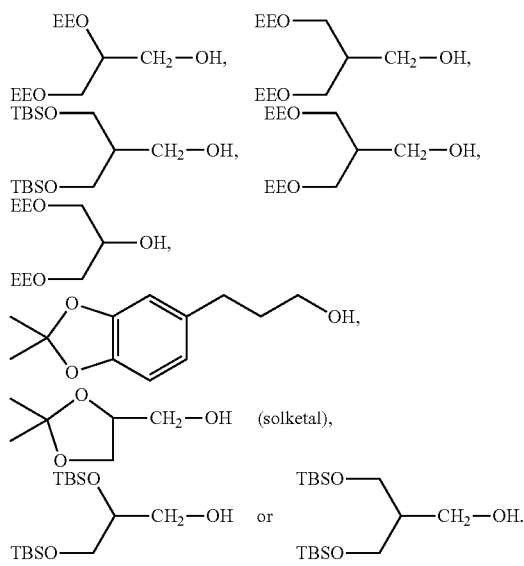

Wherein, EE is a 1-ethoxyethyl group derived from an ethyl vinyl ether and TBS is a t-butyldimethylsilyl group.

Complete end-capping can be achieved by both Approach (1) and Approach (2). In the case of Approach (1), the alkyl-etherification reaction can be conducted in the same reactor as polymerization reaction while the production method is simple and convenient in process, so Approach (1) is more preferable.

The resulting product can be purified by a purification means such as extraction, recrystallization, adsorption treatment, precipitation, reverse precipitation, membrane dialysis or supercritical extraction to obtain an intermediate compound (203).

2.3.1.3. Deprotection of the Intermediate Compound (203) (Step c)

The methods of deprotecting the intermediate compounds refer to Step (a) of above-said Route-1 (2.2.1.1), related to the type of protecting groups. The protecting group is preferably a benzyl group, a silyl group, an acetal group or a t-butyl group, accordingly, this step preferably involves deprotection of a benzyl group, a silyl group, an acetal group or a t-butyl group. Specific reaction conditions are not repeated herein.

The intermediate obtained in this step can be purified by a purification means such as extraction, recrystallization, adsorption treatment, precipitation, reverse precipitation, membrane dialysis or supercritical extraction to obtain an intermediate compound (204).

Generally describing, the intermediate compound (204) can be prepared through the following steps from step (a) to step (c): initiating the polymerization of ethylene oxide in an amount of 2-fold to 2000-fold by mole relative to the compound (201) which contains two unprotected hydroxyl groups, adding the deprotonation reagent in excess to generate a linear polyethylene glycol oxyanion intermediate (202) containing two PEG blocks, then reacting the terminal oxyanions with a branching reagent (206) containing two protected hydroxyl groups to obtain an intermediate (203), and subsequently removing the protection to obtain an intermediate (204), corresponding to the above-said step (a) to step (c). Wherein, the branching reagent (206) is preferably a compound containing a leaving group such as a halide or a sulfonate.

2.3.1.4. Polymerization of Intermediate (204) with Ethylene Oxide (Step d)

This step consists of two steps including (A) deprotonation of the terminal hydroxyl groups of the main chain via base catalysis and (B) polymerization with ethylene oxide, similar to the polymerization process of 2.2.1.2, and no more repeated here.

When the polymerization proceeds to a certain degree, an intermediate compound (205) which has a given degree of polymerization and terminal hydroxyl groups can be obtained after adding proton source. Wherein, the proton source is not particularly limited as long as it can increase the reactivity of the active hydrogen. Preferable proton source is methanol, ethanol, water or acetic acid.

2.3.1.5. End-Functionalization of the Terminal Ends of PEG Branch Chains (step e)

The end-functionalization of the terminal ends of PEG branch chains includes linear end-functionalization and branched end-functionalization, while the linear end-functionalization corresponds to the g of $F_1$ or $F_2$ with a value of 0, and the branched end-functionalization corresponds to the g of $F_1$ or $F_2$ with a value of 1. There are described in detailed before, and no more repeated here.

2.3.2. Method-2:

Method-2 is achieved in the following manner: reacting a Y-shaped polyethylene glycol derivative (208) containing unprotected or protected functional groups $F_1$ with a Y-shaped polyethylene glycol derivative (209) containing unprotected or protected functional groups $F_2$ to obtain an H-shaped multifunctionalized polyethylene glycol as represented by formula (6);

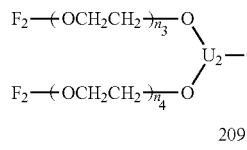
209

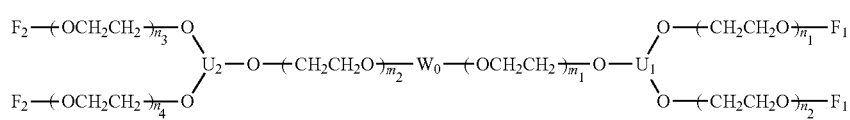
208

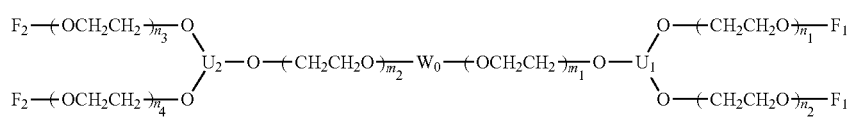
6 wherein, $X_{21}$ and $X_{22}$ are each independently a reactive group; $X_{21}$ and $X_{22}$ can be the same or different from each other; the definitions of $n_1$, $n_2$, $n_3$, $n_4$, $m_1$, $m_2$, $W_0$, $U_1$, $U_2$, $F_1$ and $F_2$ are the same as those in general formula (6l), and no more repeated here.

The H-shaped multifunctionalized polyethylene glycol as represented by formula (6) can be prepared via the reaction between two Y-shaped polyethylene molecules along with the formation of a divalent linking group $W_0$. The reaction between $X_{21}$ and $X_{22}$ is not particularly limited, and can be the reaction between any two unprotected or protected functional groups wherein a hydroxyl group is also allowable can refer to part 2.1.3. and part 2.1.4; when one of them is a protected form, the reaction can be conducted after deprotection. Typical examples include alkylation reactions, and reactions involving a divalent linking group $W_0$ containing an amide bond, a urethane bond, an ester bond, a secondary amino bond, a thioether bond, a triazole linkage or the like, and no more repeated here.

2.3.3. Method-3:

Method-3 is achieved in the following manner: reacting a Y-shaped polyethylene glycol derivative (208) containing unprotected or protected functional groups $F_1$ with a V-shaped polyethylene glycol derivative (210) containing unprotected or protected functional groups $F_2$ to generate a divalent linking group $W_0$ and meanwhile obtain an H-shaped multifunctionalized polyethylene glycol as represented by formula (5);

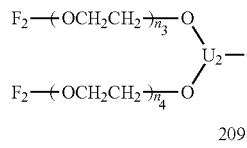
209

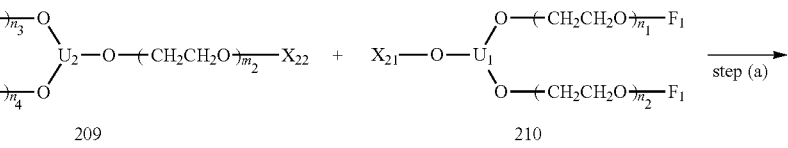
210

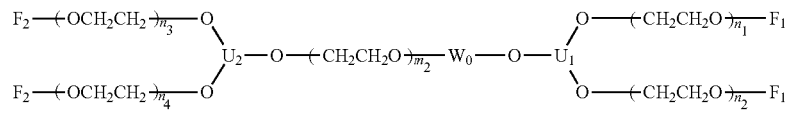
5 wherein, $X_{21}$ and $X_{22}$ are each independently a reactive group; $X_{21}$ and $X_{22}$ can be the same or different from each other; the definitions of $n_1$, $n_2$, $n_3$, $n_4$, $m_1$, $m_2$, $W_0$, $U_1$, $U_2$, $F_1$ and $F_2$ are the same as those in the general formula (5l), and no more repeated here.

The reaction between $X_{21}$ and $X_{22}$ to form the divalent linking group $W_0$ is not particularly limited, and can be the reaction between any two unprotected or protected functional groups wherein a hydroxyl group is also allowable can refer to part 2.1.3. and part 2.1.4; when one of them is a protected form, the reaction can be conducted after deprotection. Typical examples include alkylation reactions, and reactions involving a divalent linking group $W_0$ containing an amide bond, a urethane bond, an ester bond, a secondary amino bond, a thioether bond, a triazole linkage or the like, and no more repeated here.

2.3.4. Method-4 Including the Following Steps:

Step (a): using a coinitiator system which contains a small molecule initiator (201) with two unprotected hydroxyl groups and a base, then initiating the polymerization of ethylene oxide to form a linear polyethylene glycol oxyanion intermediate, followed by protonation to obtain an intermediate (211);

Step (b): reacting the intermediate (211) with a sulfonyl chloride to obtain a sulfonate, and then adding ammonia water to a polyethylene glycol diamine intermediate (212) through the substitution reaction;

Step (c): carrying out alkylation reaction between terminal amino groups of the intermediate (212) and the unprotected or protected functional group $X_{15}$ of a linear polyethylene glycol derivative to obtain an intermediate (213); wherein, $X_{15}$ can be identical to or different from the objective unprotected or protected functional group;

Step (d): carrying out alkylation or amidation reaction between the intermediate (213) and a linear polyethylene glycol derivative containing an unprotected or protected functional group $X_{15}$ to obtain an H-shaped multifunctionalized polyethylene glycol (214); wherein, the linear polyethylene glycol can be either polydisperse or monodisperse;

Step (e): when $X_{15}$ is different from the objective unprotected or protected functional group, this step should be conducted via linear or branched end-functionalization to obtain an H-shaped multifunctionalized polyethylene glycol as represented by formula (215), and otherwise this step would be omitted.

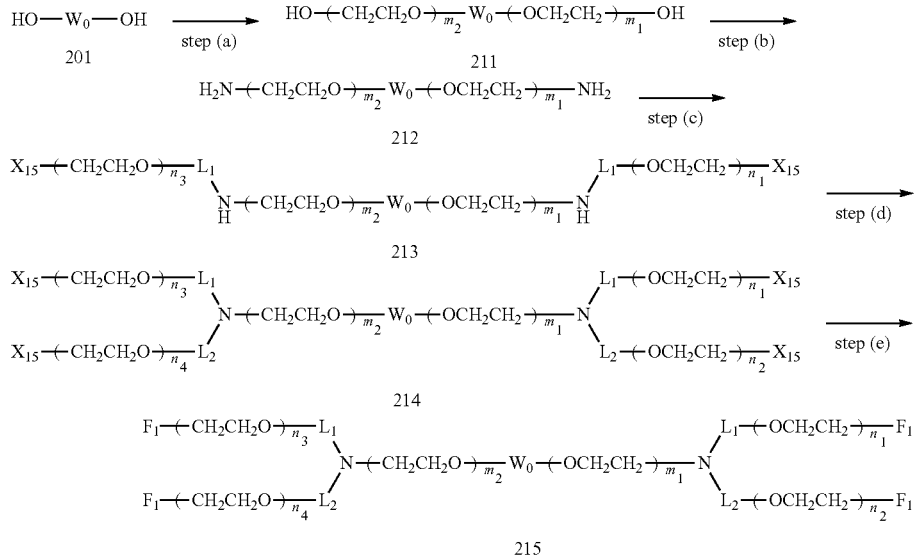

Wherein, the definitions of $n_1$, $n_2$, $n_3$, $n_4$, $m_1$, $m_2$, $W_0$, $L_1$, $L_2$ and $F_1$ are the same as those in general formula (6), and no more repeated here.

2.3.4.1. Preparation of Intermediate Compound (211) (Step a)

The intermediate compound (211) can be prepared in the following manner: initiating the polymerization of ethylene oxide in an amount of 2 to 2000 molar equivalents relative to compound (201) which contains two unprotected hydroxyl groups, then adding the protonation reagent to generate an intermediate (211). Wherein, the preparation method of polyethylene glycol intermediate (211) is similar to the above-mentioned polymerization reaction, also referring to part 2.3.1.1 and part 2.2.1.2, and no more repeated here.

2.3.4.2. Preparation of Polyethylene Glycol Diamine Intermediate Compound (212) (Step b)

The polyethylene glycol intermediate reacts with a sulfonyl chloride to form a sulfonate derivative and meanwhile obtain an intermediate (216) which contains two leaving groups $LG_1$. The reaction conditions refer to part 2.1.1.2, and no more repeated here. The leaving group $LG_1$ of polyethylene glycol intermediate (216) can be but not limited to a mesyl group, a tosyl group or a 2,2,2-trifluoroethylsulfonyl group.

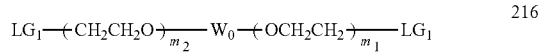

The process for preparing polyethylene glycol diamine intermediate (212) by using the polyethylene glycol intermediate (216) with two leaving groups refers to the preparation methods of amine derivatives in the part 2.1.1.3, and no more repeated here.

2.3.4.3. Preparation of Intermediate Compound (213, Step c) Via the Alkylation of Polyethylene Glycol Intermediate (212)

It can be achieved by the following Method (A) or Method (B).

Method (A): conducting alkylation reaction between the substrate diamine (212) and sulfonate or halide derivative of polyethylene glycol.

The diamine intermediate (213) can be obtained via the nucleophilic substitution between the substrate diamine (212) and sulfonate or halide derivative of polyethylene glycol under a basic condition. The amount of the sulfonate or halide derivative is 2 to 100 molar equivalents, preferably 2 to 10 molar equivalents relative to substrate diamine (212). When the amount of the sulfonate or halide derivative is less than 2 molar equivalents to substrate diamine (212), the substitution may not sufficiently proceed and purification thereof tends to be difficult. When the amount of the sulfonate or halide derivative exceeds 100 molar equivalents to substrate diamine (212), the excess reagent tends to cause difficulty in the purification process and result in side reactions in the subsequent steps.

The resulting product is a mixture of di-secondary-amine intermediate (213) and excess polyethylene glycol sulfonate or halide, and can be purified by a purification means such as cation exchange resin, osmosis treatment, ultrafiltration treatment or the like. Wherein, the anion exchange resin is not particularly limited as long as the target product can undergo ion-exchange and adsorption with the resin, preferably ion exchange resin of a tertiary amine or quaternary ammonia salt based on dextran, agarose, polyacrylate, polystyrene, poly(diphenylethylene) or the like. The solvents used for osmosis treatment and ultrafiltration treatment are not limited, generally water or an organic solvent. Said organic solvent is not particularly limited as long as the product can be dissolved therein, preferably dichloromethane, chloroform or the like.

The reaction solvent is not limited, preferably an aprotic solvent, such as toluene, benzene, xylene, acetonitrile, ethyl acetate, tetrahydrofuran, chloroform, dichloromethane, dimethylsulfoxide, dimethylformamide or dimethylacetamide, and more preferably dimethylformamide, dichloromethane, dimethylsulfoxide or tetrahydrofuran.

The base can be an organic base (such as triethylamine, pyridine, 4-dimethylaminopyridine, imidazole or diisopropylethylamine) or an inorganic base (such as sodium carbonate, sodium hydroxide, sodium bicarbonate, sodium acetate, potassium carbonate or potassium hydroxide), preferably an organic base, more preferably triethylamine or pyridine. The amount of the base is 1 to 50 molar equivalents, preferably 1 to 10 molar equivalents, and more preferably 3 to 5 molar equivalents relative to the sulfonate or halide.

Method (B): conducting alkylation reaction between the substrate diamine (212) and polyethylene glycol aldehyde derivative.

After reacting the substrate diamine (212) with polyethylene glycol aldehyde derivative to obtain a diimine intermediate, the intermediate (213) can be obtained via reduction reaction by the reduction reagent. Wherein, the amount of the polyethylene glycol aldehyde derivative is 2 to 40 molar equivalents, preferably 2 to 4 molar equivalents, and more preferably 2 to 3 molar equivalents relative to substrate diamine (212). When the amount of polyethylene glycol aldehyde exceeds 40 molar equivalents to substrate diamine (212), the excess reagent tends to cause difficulty in the purification process and result in side reactions in the subsequent steps. When the amount of polyethylene glycol aldehyde is less than 2 molar equivalents to substrate diamine (212), the substitution may not sufficiently proceed and purification thereof tends to be difficult. Wherein, the resulting product can be purified by a purification means such as cation exchange resin, osmosis treatment, ultrafiltration treatment or the like to obtain an intermediate (213). Said cation exchange resin is not particularly limited as long as it can facilitate ion-exchange with quaternary ammonium cation to achieve isolation. The solvents used for osmosis treatment and ultrafiltration treatment are not limited, generally water or an organic solvent. Said organic solvent is not particularly limited as long as the product can be dissolved therein, preferably dichloromethane, chloroform or the like.

The reaction solvent is not limited, preferably an organic solvent, such as methanol, ethanol, water, toluene, benzene, xylene, acetonitrile, ethyl acetate, tetrahydrofuran, chloroform, dichloromethane, dimethylsulfoxide, dimethylformamide or dimethylacetamide or the like, more preferably water or methanol.

The reduction reagent is not particularly limited, as long as the diimine can be reduced to a diamine (a di-secondary-amine), preferably sodium borohydride, lithium aluminum hydride, sodium cyanoborohydride, Zn/AcOH or the like, and more preferably sodium cyanoborohydride. The amount of the reduction reagent is generally 1-fold to 100-fold by mole, more preferably 2-fold to 20-fold by mole relative to polyethylene glycol aldehyde derivative.

2.3.4.4. Preparation of Intermediate Compound (214, Step d) Via Alkylation or Amidation of Polyethylene Glycol Intermediate (213)

When introducing two PEG chains to a primary amine, the first chain should be introduced via alkylation reaction, while the second chain can be introduced to the intermediate (213) with an alkylation or amidation method, wherein the alkylation method is similar to the part 2.3.4.3, and no more repeated here. When introducing the second branch chain through the alkylation method, for example, the structure of intermediate (214) is as follows:

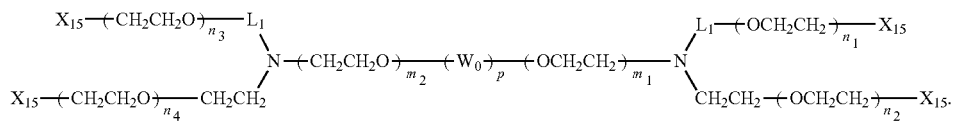

The amidation reaction can be achieved via the reaction between the substrate diamine (213) and polyethylene glycol acyl chloride derivative.

The intermediate (214) can be obtained via the reaction between the substrate di-secondary-amine (213) and polyethylene glycol acyl chloride under a basic condition. The amount of polyethylene glycol acyl chloride is 2 to 40 molar equivalents, preferably 2 to 4 molar equivalents, and more preferably 2 to 3 molar equivalents relative to substrate di-secondary-amine (213). When the amount of polyethylene glycol acyl chloride exceeds 40 molar equivalents to the substrate di-secondary-amine (213), the excess reagent tends to cause difficulty in the purification process and result in side reactions in the subsequent steps. When the amount of polyethylene glycol acyl chloride is less than 2 molar equivalents to the substrate di-secondary-amine (213), the reaction may not sufficiently proceed and purification thereof tends to be difficult. Wherein, the excess polyethylene glycol acyl chloride can be converted into corresponding acid via hydrolysis treatment, and then be purified by a purification means such as anion exchange resin, osmosis treatment, ultrafiltration treatment or the like to obtain an intermediate (213). Said anion exchange resin is not particularly limited as long as it can facilitate ion-exchange with anions to achieve isolation, preferably ion exchange resin of a tertiary amine or quaternary ammonia salt based on dextran, agarose, polyacrylate, polystyrene, poly(diphenylethylene) or the like. The solvents used for osmosis treatment and ultrafiltration treatment are not limited, generally water or an organic solvent. Said organic solvent is not particularly limited as long as the product can be dissolved therein, preferably dichloromethane, chloroform or the like.

The reaction solvent is not limited, preferably an aprotic solvent, such as toluene, benzene, xylene, acetonitrile, ethyl acetate, tetrahydrofuran, chloroform, dichloromethane, dimethylsulfoxide, dimethylformamide or dimethylacetamide, and more preferably dimethylformamide, dichloromethane, dimethylsulfoxide or tetrahydrofuran.

The base can be an organic base (such as triethylamine, pyridine, 4-dimethylaminopyridine, imidazole or diisopropylethylamine) or an inorganic base (such as sodium carbonate, sodium hydroxide, sodium bicarbonate, sodium acetate, potassium carbonate or potassium hydroxide), preferably an organic base, more preferably triethylamine or pyridine. The amount of the base is 2 to 100 molar equivalents, preferably 2 to 20 molar equivalents, and more preferably 6 to 10 molar equivalents relative to the substrate di-secondary-amine (213).

When introducing the second branch chain to the di-secondary-amine through the amidation method, for example, the structure of intermediate (214) is as follows:

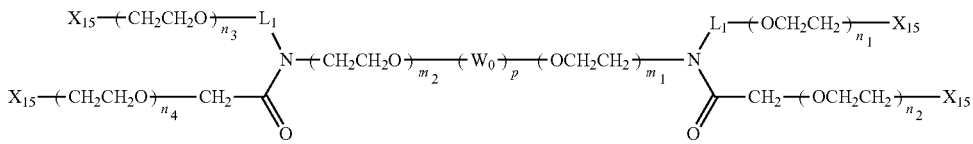

2.3.4.5. Preparation of an H-Shaped Multifunctionalized Polyethylene Glycol (215) (Step e)

The method for linear end-functionalization refers to steps of part 2.1.1, method for branched end-functionalization refers to steps of part 2.1.2.

2.3.5. Method-5 Including the Following Steps:

Step (a): using a coinitiator system which contains a small molecule initiator (217) with one unprotected hydroxyl groups and a base, and then initiating the polymerization of ethylene oxide to form a linear polyethylene glycol oxyanion intermediate (218);

Step (b): reacting the polyethylene glycol oxyanion intermediate (218) with a compound (206) having a leaving group such as halide, sulfonate or the like, and then removing the protection of hydroxyl groups to obtain an intermediate (219);

Step (c): initiating the polymerization of ethylene oxide from the terminal hydroxyl groups of the intermediate (219) followed by protonation, further conducting end-functionalization to introduce terminal $F_3$ groups and thus obtain an intermediate (220); wherein, $F_3$ is an unprotected or protected group which is linearly or branchedly functional, can remain stable under anionic polymerization conditions, and has one or one more terminal unprotected or protected groups;

Step (d): removing the protection of terminal hydroxyl group of the PEG main chain of the intermediate (220) to obtain a Y-shaped polyethylene glycol intermediate (221) which has an unprotected hydroxyl group;

Step (e): initiating the polymerization of ethylene oxide from the terminal hydroxyl group of the intermediate (221) followed by the addition of deprotonation reagent to obtain a Y-shaped polyethylene glycol intermediate (222);

Step (f): reacting the polyethylene glycol oxyanion intermediate (222) with a compound having a leaving group (206) such as halide, sulfonate or the like, and then removing the protection of hydroxyl groups to obtain an intermediate (223) which has two unprotected hydroxyl groups;

Step (g): initiating the polymerization of ethylene oxide from the terminal hydroxyl groups of the intermediate (223) followed by protonation to obtain an H-shaped polyethylene glycol intermediate (224);

Step (h): carrying out linear or branched end-functionalization to the terminal hydroxyl groups and terminal $F_3$ groups of the intermediate (224) respectively to obtain an H-shaped multifunctionalized polyethylene glycol as represented by general formula (6); wherein, $F_3$ can be identical to or different from $F_1$.

Wherein, the formation of polyethylene glycol chains in Steps (a), (c), (e) and (f) consists of the following two steps: (A) deprotonation of the terminal hydroxyl group under a basic condition; (B) polymerization of ethylene oxide. The resulting product after step (B) is a polyethylene glycol oxyanion intermediate, after adding proton source to conduct protonation, a polyethylene glycol derivative with terminal hydroxyl groups can be obtained. The reaction conditions refer to part 2.2.1.2., and no more repeated herein.

Wherein, the preparation method of introducing two unprotected hydroxyl groups into one terminal end of a linear polyethylene glycol in the Step (b) and Step (f) refers to part 2.3.1.2, and no more repeated here.

Wherein, the preparation method of deprotecting hydroxyl protecting groups refers to part 2.2.1.1, and no more repeated here.

The production process of Method-5 is represented as follows:

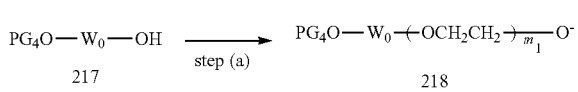 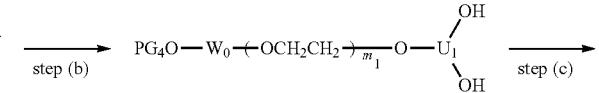

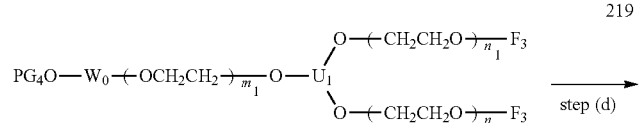

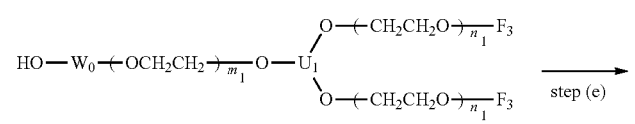

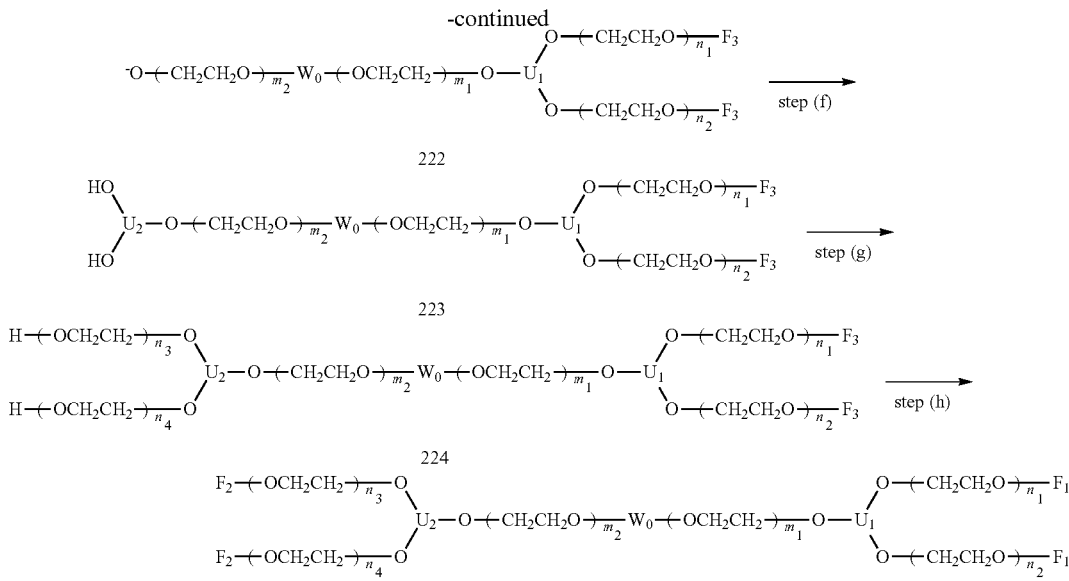

Wherein, the definitions of $n_1$, $n_2$, $n_3$, $n_4$, $m_1$, $m_2$, $W_0$, $U_1$, $U_2$, $F_1$ and $F_2$ are the same as those in general formula (6), and no more repeated here. $PG_4$ is a hydroxyl protecting group, preferably a silyl group, a benzyl group, an acetal group, a ketal group or a t-butyl group. The definition of $F_3$ is the same as $F_1$, with a structure of

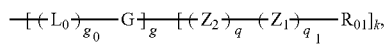

wherein, the definitions of g, k, $L_0$, $g_0$, G, $Z_2$, q, $Z_1$, $q_1$ and $R_{01}$ are the same as those in the general formula (1).

Specifically, the reaction conditions of Method-5 are as follows: initiating the polymerization of ethylene oxide in an amount of 1-fold to 2000-fold by mole relative to the compound (217) which contains one unprotected hydroxyl group, adding the deprotonation reagent to generate a linear polyethylene glycol oxyanion intermediate (218); then reacting the terminal oxyanions with a compound having a leaving group (206) such as halide, sulfonate or the like, removing the hydroxyl protecting groups to obtain an intermediate (219) which has two unprotected hydroxyl groups; initiating the polymerization of ethylene oxide in an amount of 2-fold to 2000-fold by mole relative to the unprotected hydroxyl groups of intermediate (219), followed by protonation and linear or branched end-functionalization in sequence to introduce terminal unprotected or protected functional groups $F_3$ and thus obtain an intermediate (220); removing the hydroxyl protecting group of the intermediate (220) to obtain a compound (221) which has an unprotected hydroxyl group; initiating the polymerization of ethylene oxide in an amount of 1-fold to 2000-fold by mole relative to the intermediate (221) followed by the addition of deprotonation reagent to obtain a polyethylene glycol oxyanion intermediate (222); then reacting the terminal oxyanion with a compound having a leaving group (206) such as halide, sulfonate or the like to obtain an intermediate (223); initiating the polymerization of ethylene oxide in an amount of 2 to 2000 molar equivalents relative to the unprotected hydroxyl groups of the intermediate (223) to obtain an H-shaped polyethylene glycol intermediate (224); carrying out linear or branched end-functionalization to terminal hydroxyl groups and terminal $F_3$ groups respectively to obtain an H-shaped multifunctionalized polyethylene glycol as represented by general formula (6). This preparation method is similar to above-said reactions, no more repeated herein.

Wherein, the compound (217) has an unprotected hydroxyl group at one terminal and a protected hydroxyl group at the other terminal, the typical structures include as follows:

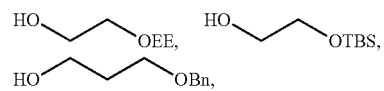

wherein, EE is a 1-ethoxyethyl group

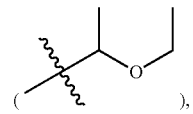 [SMILES: *C(C)OCC]

TBS is a t-butyldimethylsilyl group, and Bn is a benzyl group.

2.3.6. Method-6 Including the Following Steps:

Step (a): using a coinitiator system which contains a small molecule initiator (225) which has one protected and two unprotected hydroxyl groups and a base, then initiating the polymerization of ethylene oxide to form two polyethylene glycol branch chains, followed by protonation and end-functionalization in sequence to introduce terminal $F_3$ groups, then removing the hydroxyl protecting group to obtain a V-shaped intermediate (226); wherein, $F_3$ is an unprotected or protected group which is linearly or branchedly functional, can remain stable under anionic polymerization conditions, and has one or one more terminal unprotected or protected groups;

Step (b): initiating the polymerization of ethylene oxide from the unprotected hydroxyl group of the V-shaped intermediate (226), then reacting with a compound (230) of a halide or sulfonate derivative which has a leaving group and a protected hydroxyl group at the other end, and then removing the hydroxyl protecting group to obtain a Y-shaped intermediate (221);

Step (c): initiating the polymerization of ethylene oxide from the unprotected hydroxyl group of the Y-shaped intermediate (221) to obtain a Y-shaped polyethylene glycol oxyanion intermediate (227);

Step (d): reacting the polyethylene glycol oxyanion intermediate (227) with a compound having a leaving group (206) such as halide, sulfonate or the like, and then removing the protection of hydroxyl groups to obtain an intermediate (228) which has two unprotected hydroxyl groups;

Step (e): initiating the polymerization of ethylene oxide from the unprotected hydroxyl groups of the intermediate (228) followed by protonation to obtain an H-shaped polyethylene glycol intermediate (229);

Step (f): carrying out linear or branched end-functionalization to the terminal hydroxyl groups and terminal $F_3$ groups of the intermediate (229) respectively to obtain an H-shaped multifunctionalized polyethylene glycol as represented by general formula (6); wherein, $F_3$ can be identical to or different from $F_1$.

Wherein, the formation of polyethylene glycol chains via initiating polymerization of ethylene oxide from hydroxyl groups, such as Steps (a), (b), (c) and (e), consists of the following two steps: (A) deprotonation of the terminal hydroxyl group under a basic condition; (B) polymerization of ethylene oxide. The resulting product after step (B) is a polyethylene glycol oxyanion intermediate, after adding proton source to conduct protonation, a polyethylene glycol derivative with terminal hydroxyl groups can be obtained. The reaction conditions refer to part 2.2.1.2., and no more repeated herein.

Wherein, the preparation method of introducing two unprotected hydroxyl groups into one terminal end of a linear polyethylene glycol in the Step (d) refers to part 2.3.1.2, and no more repeated here.

Wherein, the preparation method of deprotecting hydroxyl protecting groups in the Step (a), (b) and (d) refers to part 2.2.1.1, and no more repeated here.

Generally speaking, the reaction conditions of Method-6 are as follows: initiating the polymerization of ethylene oxide in an amount of 2-fold to 2000-fold by mole relative to the small molecule compound (225) which has one protected and two unprotected hydroxyl groups, terminating with linearly or branchedly functional groups $F_3$, removing the hydroxyl protecting group to obtain a V-shaped intermediate (226); then initiating the polymerization of ethylene oxide in an amount of 1-fold to 2000-fold by mole and subsequently terminating with a compound (230) such as halide, sulfonate or the like, which has a leaving group at one end and a protected hydroxyl group at the other end, and then removing the hydroxyl protecting group to obtain a Y-shaped intermediate (221); initiating the polymerization of ethylene oxide in an amount of 1-fold to 2000-fold by mole to obtain a Y-shaped polyethylene glycol oxyanion intermediate (227); then reacting with a compound having a leaving group (206) such as halide, sulfonate or the like followed by removal of the hydroxy protecting group to obtain an intermediate (228); initiating the polymerization of ethylene oxide in an amount of 2-fold to 2000-fold by mole to obtain an H-shaped polyethylene glycol intermediate (229); carrying out linear or branched end-functionalization to terminal hydroxyl groups and terminal $F_3$ groups respectively to obtain an H-shaped multifunctionalized polyethylene glycol as represented by general formula (6). This preparation method is similar to above-said reactions, no more repeated herein.

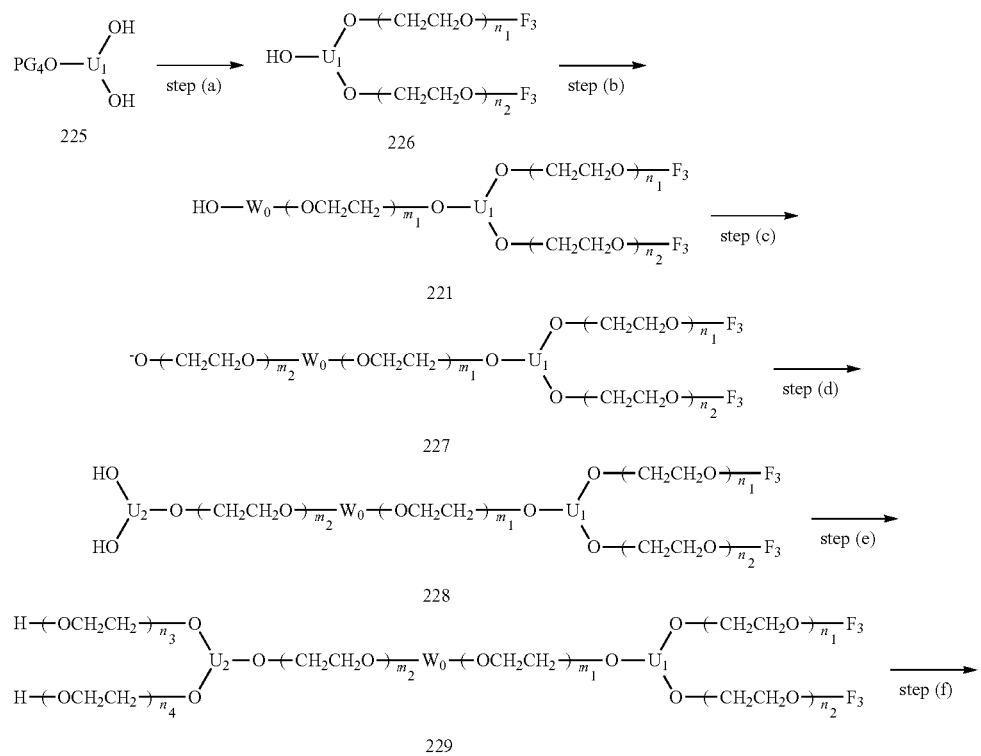

-continued

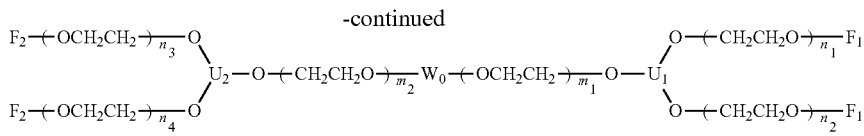

Wherein, the definitions of $n_1$, $n_2$, $n_3$, $n_4$, $m_1$, $m_2$, $W_0$, $U_1$, $U_2$, $F_1$ and $F_2$ are the same as those in the general formula (6), and no more repeated here. $PG_4$ is a hydroxyl protecting group, preferably a silyl group, a benzyl group, an acetal group, a ketal group or a tertiary butyl group.

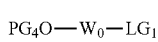

230

Wherein, the compound (225) is a small molecule initiator which contains one protected hydroxyl group and two unprotected hydroxyl groups, for example, including but not limited to:

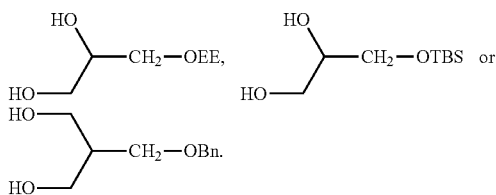

2.3.7. Method-7 Including the Following Steps:

Step (a): using a coinitiator system which contains a small molecule initiator (201) with two unprotected hydroxyl groups and a base, then initiating the polymerization of ethylene oxide to form a linear polyethylene glycol chain consisting of two polyethylene glycol blocks and thus obtain an oxyanion intermediate (202);

Step (b): reacting the intermediate (202) with a compound such as halide, sulfonate or the like (236) which has a leaving group and two different protected hydroxyl groups $OPG_{4A}$ and $OPG_{4B}$ to obtain an intermediate (231);

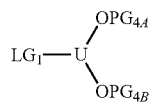

(236)

Step (c): removing the hydroxyl protecting groups $PG_{4A}$ of the intermediate (231) to obtain an intermediate (232);

Step (d): initiating the polymerization of ethylene oxide to form the terminal hydroxyl groups of the intermediate (232), followed by protonation and termination with $F_3$ groups in sequence to obtain an intermediate (233); wherein, $F_3$ is an unprotected or protected group which is linearly or branchedly functional, can remain stable under anionic polymerization conditions, and has one or one more terminal unprotected or protected groups;

Step (e): removing the hydroxyl protecting group $PG_{4B}$ of the intermediate (233) to obtain an intermediate (234);

Step (f): initiating the polymerization of ethylene oxide to form the terminal hydroxyl groups of the intermediate (234), followed by protonation and termination with $F_3$ groups in sequence to obtain an H-shaped polyethylene glycol derivative (235);

Step (g): when $F_3$ is different from the objective unprotected or protected functional group $F_1$, further carrying out linear or branched end-functionalization to obtain an H-shaped multifunctionalized polyethylene glycol as represented by general formula (6b); otherwise this step is not conducted.

In this production method, with respect to steps including the formation of polyethylene glycol chains via initiating polymerization of ethylene oxide from hydroxyl groups, reactions with derivatives containing a leaving groups such as a halide, a sulfonate or the like to introduce protected or unprotected hydroxyl groups, removal of hydroxyl protecting groups, linear or branched end-functionalization reactions and the like, the conditions are similar as above-mentioned, and no more repeated here.

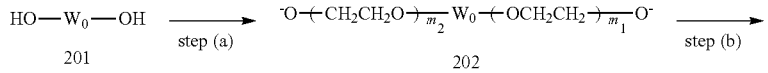

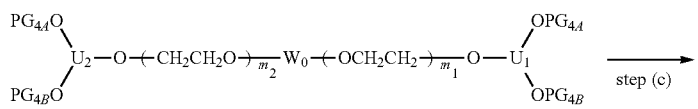

231

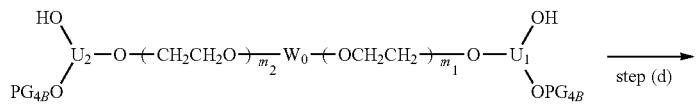

232

-continued

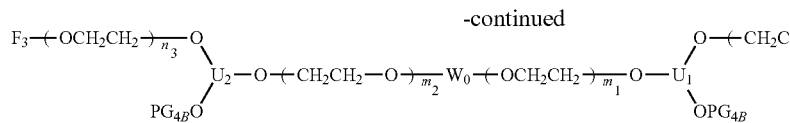

233

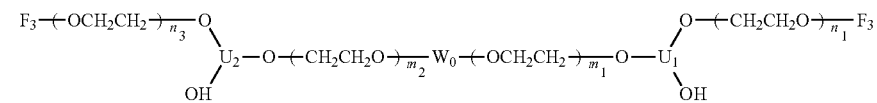

234

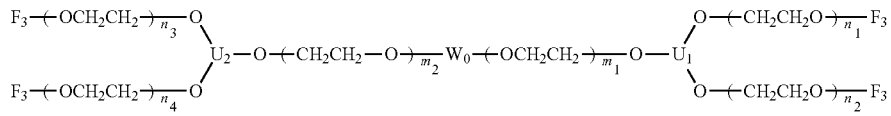

235

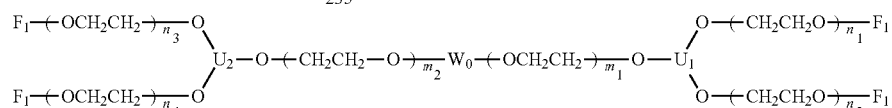

6b

Wherein, the definitions of $n_1$, $n_2$, $n_3$, $n_4$, $m_1$, $m_2$, $W_0$, $U_1$, $U_2$ and $F_1$ are the same as those in general formula (6), and no more repeated here. $PG_4$ is a hydroxyl protecting group, preferably a silyl group, a benzyl group, an acetal group, a ketal group or a t-butyl group.

2.3.8. Method-8 Including the Following Steps:

Step (a): reacting a linear polyethylene glycol derivative (237) which has a terminal protected hydroxyl group and a terminal reactive group $X_{11}$, with a Y-shaped polyethylene glycol derivative (238) in which the two branch chains are end-capped with linearly or branched functional groups $F_3$ and the main chain is end-capped with a reactive group $X_{13}$, to generate a divalent linking group $W_{01}$ and thus obtain a Y-shaped polyethylene glycol intermediate (239);

Step (b): removing the hydroxyl protecting group at the main chain terminal of the Y-shaped polyethylene glycol intermediate (239), and carrying out linear end-functionalization to obtain an intermediate (240);

Step (c): reacting the Y-shaped polyethylene glycol intermediate (240) with a Y-shaped polyethylene glycol derivative (209) in which the two branch chains are end-capped with linearly or branched functional groups $F_2$ and the main chain is end-capped with a reactive group $X_{14}$, to generate a divalent linking group $W_{02}$ and thus obtain an H-shaped polyethylene glycol intermediate (241);

Step (d): when $F_3$ is identical to $F_1$, this step would be omitted; otherwise, when $F_3$ is different from $F_1$, further carrying out linear or branched end-functionalization to obtain an H-shaped multifunctionalized polyethylene glycol as represented by general formula (3).

The production process of Method-8 is presented as follows:

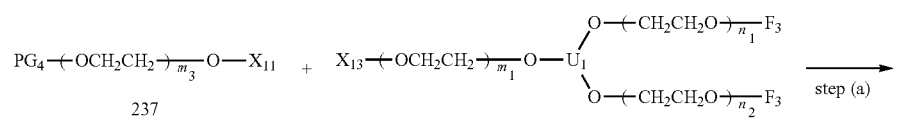

238

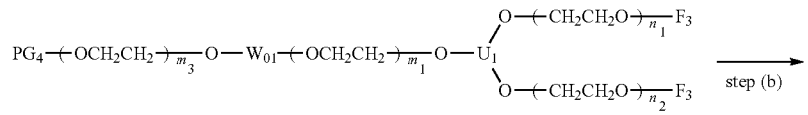

239

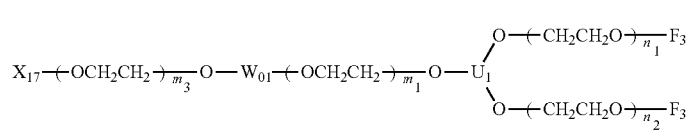

240

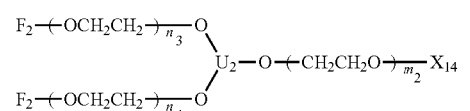

209

-continued

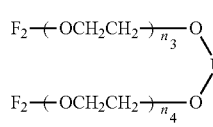 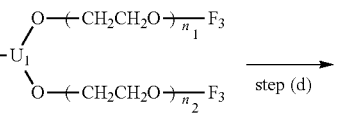

241 step (d)

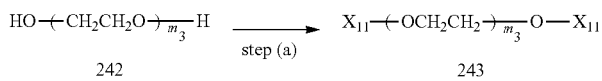

Wherein, the definitions of $X_{11}$, $X_{13}$, $X_{14}$ and $X_{17}$ are each independently a reactive group, and $X_{11}$, $X_{13}$, $X_{14}$ and $X_{17}$ can be the same or different; the definitions of $n_1$, $n_2$, $n_3$, $n_4$, functional groups $F_1$ and the main chain is end-capped with a reactive group $X_{13}$, to obtain an H-shaped multifunctionalized polyethylene glycol as represented by formula (3b);

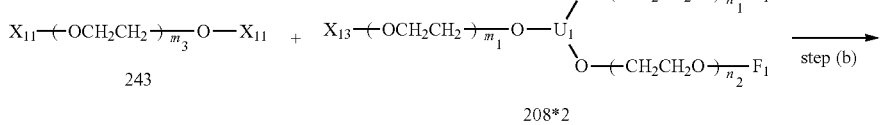

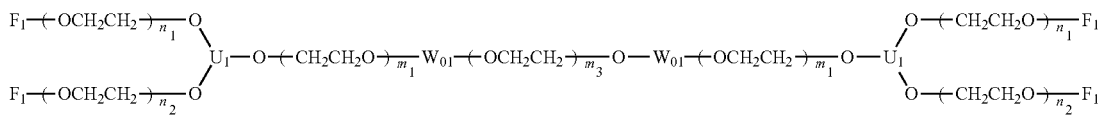

3b $m_1$, $m_2$, $m_3$, $W_{01}$, $W_{02}$, $U_1$, $U_2$, $F_1$ and $F_2$ are the same as those in general formula (3), and no more repeated here. Wherein, $F_1$ and $F_2$ can be the same or different from each other; $PG_4$ is a hydroxyl protecting group, preferably a silyl group, a benzyl group, an acetal group, a ketal group or a t-butyl group.

The compound (237) can be either polydisperse or monodisperse.

The reactions between two reactive groups in the above production process such as ($X_{11}$, $X_{13}$) and ($X_{14}$, $X_{17}$) are not particularly limited. The reaction between any two unprotected or protected functional groups wherein a hydroxyl group is also allowable can refer to part 2.1.3. and part 2.1.4; when one of them is a protected form, the reaction can be conducted after deprotection. Typical examples include alkylation reactions, and reactions involving a divalent linking group $W_0$ containing an amide bond, a urethane bond, an ester bond, a secondary amino bond, a thioether bond, a triazole linkage or the like, and no more repeated here.

With respect to steps including removal of hydroxyl protecting groups, linear or branched end-functionalization reactions and the like, the conditions are similar as abovementioned, and no more repeated here.

2.3.9. Method-9 Including the Following Steps:

Step (a): carrying out linear end-functionalization to the two hydroxyl groups of a linear polyethylene glycol (242) to obtain a bifunctionalized polyethylene glycol intermediate (243) which has two reactive groups $X_{11}$; wherein, the compound (242) can be either polydisperse or monodisperse;

Step (b): reacting the intermediate (243) with a Y-shaped polyethylene glycol derivative (208) in which the two branch chains are end-capped with linearly or branched functional groups $F_1$ and the main chain is end-capped with a reactive group $X_{13}$, to obtain an H-shaped multifunctionalized polyethylene glycol as represented by formula (3b);

Wherein, $X_{11}$ and $X_{13}$ are each independently a reactive group, and $X_{11}$ and $X_{13}$ can be the same or different from each other; the definitions of $n_1$, $n_2$, $m_1$, $m_3$, $W_{01}$, $U_1$ and $F_1$ are the same as those in general formula (3), and no more repeated here. Referring to part 2.2.9, two $n_1$s in the molecule are close to each other in terms of value, and are allowed to be not strictly equal; also two $n_2$s in the molecule are close to each other in terms of value, and are allowed to be not strictly equal.

2.3.10. Method-10 Including the Following Steps:

Step (a): using a coinitiator system which contains a small molecule initiator (217) with one unprotected hydroxyl groups and a base, and then initiating the polymerization of ethylene oxide to form a linear polyethylene glycol oxyanion intermediate (218);

Step (b): reacting the polyethylene glycol oxyanion intermediate (218) with a compound (206) having a leaving group such as halide, sulfonate or the like, and then removing the protection of hydroxyl groups to obtain an intermediate (219);

Step (c): initiating the polymerization of ethylene oxide from the terminal hydroxyl groups of the intermediate (219) followed by protonation, further conducting end-functionalization to introduce terminal $F_3$ groups and thus obtain an intermediate (220); wherein, $F_3$ is an unprotected or protected group which is linearly or branchedly functional, can remain stable under anionic polymerization conditions, and has one or one more terminal unprotected or protected groups;

Step (d): removing the protection of terminal hydroxyl group of the PEG main chain of the intermediate (220) to obtain a Y-shaped polyethylene glycol intermediate (221) which has an unprotected hydroxyl group;

Step (e): reacting the intermediate (221) with a compound having a leaving group (206) such as halide, sulfonate or the like, and then removing the protection of hydroxyl groups to obtain an intermediate (244) which has two unprotected hydroxyl groups;

Step (f): initiating the polymerization of ethylene oxide from the terminal hydroxyl groups of the intermediate (244) followed by protonation to obtain an H-shaped polyethylene glycol intermediate (245);

Step (g): carrying out linear or branched end-functionalization to the terminal hydroxyl groups and terminal $F_3$ groups of the intermediate (245) respectively to obtain an H-shaped multifunctionalized polyethylene glycol as represented by general formula (5b); wherein, $F_3$ can be identical to or different from $F_1$.

The production process of Method-10 is represented as follows:

Wherein, the definitions of $n_1$, $n_2$, $n_3$, $n_4$, $m_1$, $W_0$, $U_1$, $U_2$, $F_1$ and $F_2$ are the same as those in the general formula (5b), and no more repeated here. $PG_4$ is a hydroxyl protecting group, preferably a silyl group, a benzyl group, an acetal group, a ketal group or a t-butyl group.

This production method is similar to the above part 2.3.5, and no more repeated here.

2.3.11. Method-11 Including the Following Steps:

By using a linear polyethylene glycol derivative (246) or (246b) which has a terminal protected hydroxyl group and an unprotected hydroxyl group to replace the intermediate (218), repeat Steps (b) to (g) of Method-10, to obtain an H-shaped multifunctionalized polyethylene glycol as represented by general formula (4) or (4b). The production processes are represented as follows, respectively. Compounds (246) and (246b) can be either polydisperse or monodisperse.

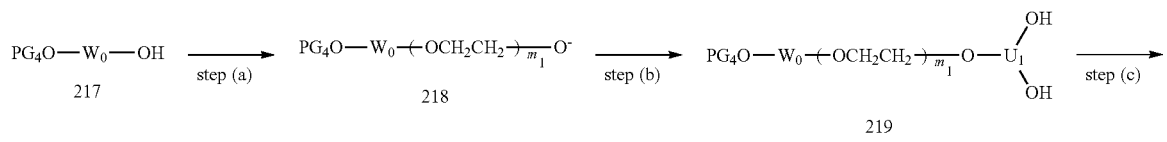

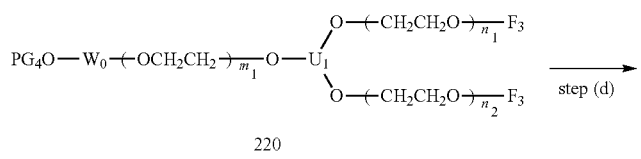
220

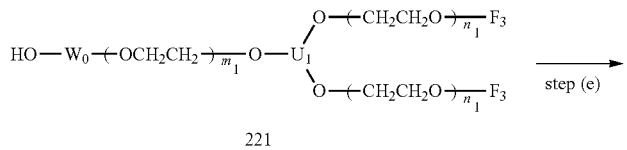
221

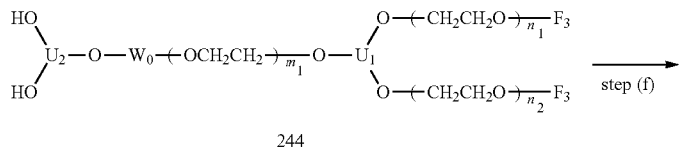
244

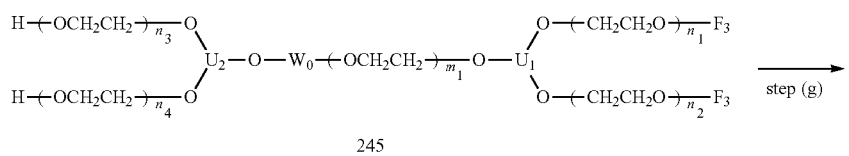
245

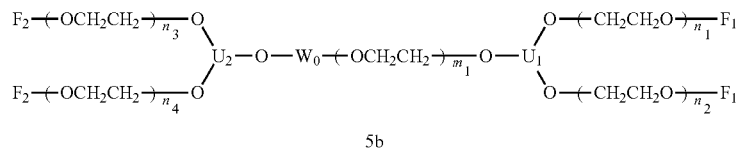
5b

The production method to obtain compound (4) by using compound (246) as reagent is as follows:

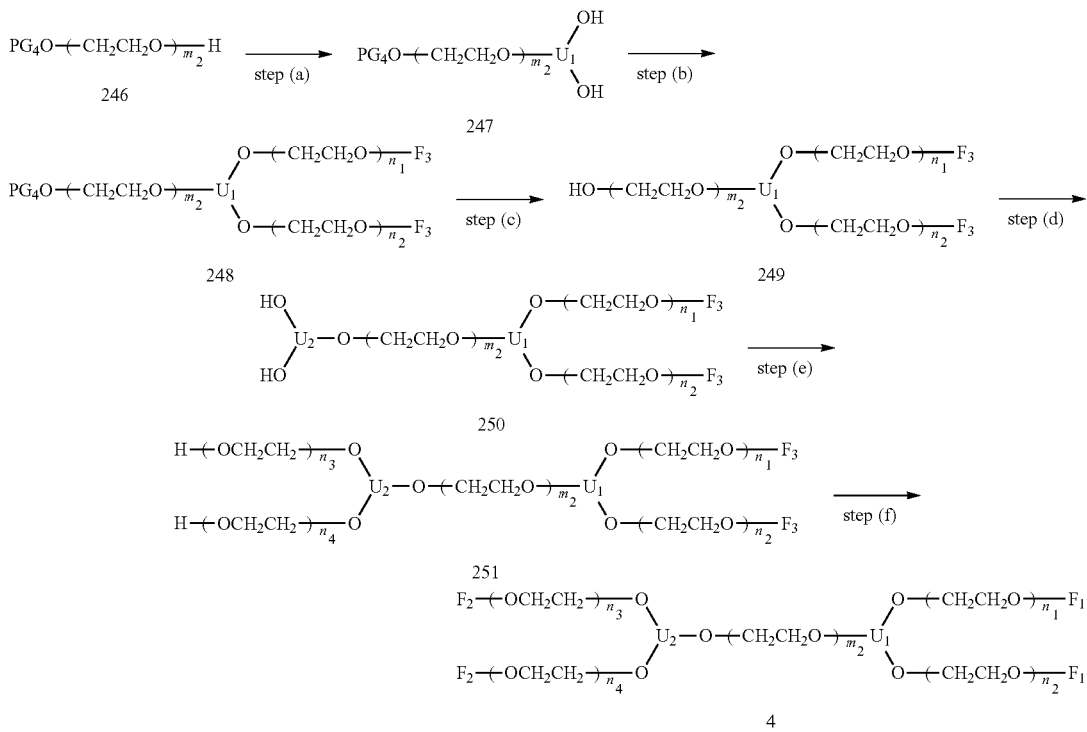

Wherein, the definitions of $n_1$, $n_2$, $n_3$, $n_4$, $m_2$, $U_1$, $U_2$, $F_1$ and $F_2$ are the same as those in general formula (4), and no more repeated here. $PG_4$ is a hydroxyl protecting group, preferably a silyl group, a benzyl group, an acetal group, a ketal group or a t-butyl group. This production method is similar to the above part 2.3.10 (Method-10), and no more repeated here.

The production method to obtain compound (4b) by using compound (246b) as reagent is as follows:

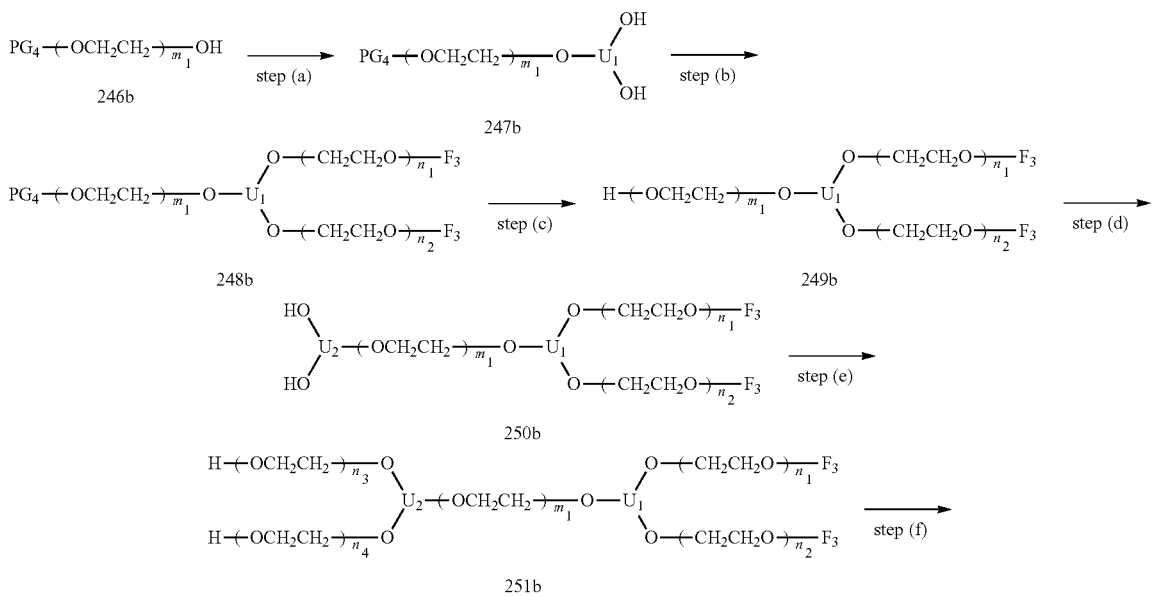

-continued

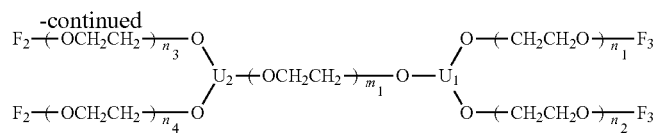

4b

Wherein, the definitions of $n_1$, $n_2$, $n_3$, $n_4$, $m_1$, $U_1$, $U_2$, $F_1$ and $F_2$ are the same as those in general formula (4b), and no more repeated here. $PG_4$ is a hydroxyl protecting group, preferably a silyl group, a benzyl group, an acetal group, a ketal group or a t-butyl group. This production method is similar to the above part 2.3.10, and no more repeated here.

Wherein, the production process of compounds (246) and (246b) can start from a mono-protected diol with one protected and one unprotected hydroxyl group (such as

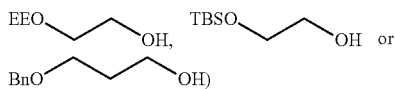

to initiate the polymerization of ethylene oxide, and after protonation, a polydisperse compound can be obtained; a monodisperse compound can be obtained via organic synthesis, or be purchased.

2.3.12. Method-12

Step (a) and Step (b) are the same as Step (a) and Step (b) of part 2.3.6. (Method-6) respectively, Step (c), Step (d), Step (e) are the same as Step (e), Step (f) and Step (g) of part 2.3.10 (Method-10), respectively.

Method-12 can be achieved through the following steps:

Step (a): using a coinitiator system which contains a small molecule initiator (225) which has one protected and two unprotected hydroxyl groups and a base, then initiating the polymerization of ethylene oxide to form two polyethylene glycol branch chains, followed by protonation and end-functionalization in sequence to introduce terminal $F_3$ groups, then removing the hydroxyl protecting group to obtain a V-shaped intermediate (226); wherein, $F_3$ is an unprotected or protected group which is linearly or branchedly functional, can remain stable under anionic polymerization conditions, and has one or one more terminal unprotected or protected groups;

Step (b): initiating the polymerization of ethylene oxide from the unprotected hydroxyl group of the V-shaped intermediate (226), then reacting with a compound having a leaving group (230) such as halide, sulfonate or the like, then removing the hydroxyl protecting group to obtain a Y-shaped intermediate (221);

Step (c): reacting the intermediate (221) with a compound having a leaving group (206) such as halide, sulfonate or the like, and then removing the protection of hydroxyl groups to obtain an intermediate (244) which has two unprotected hydroxyl groups;

Step (d): initiating the polymerization of ethylene oxide from the terminal hydroxyl groups of the intermediate (244) followed by protonation to obtain an H-shaped polyethylene glycol intermediate (245);

Step (e): carrying out linear or branched end-functionalization to the terminal hydroxyl groups and terminal $F_3$ groups of the intermediate (245) respectively to obtain an H-shaped multifunctionalized polyethylene glycol as represented by general formula (5b); wherein, $F_3$ can be identical to or different from $F_1$.

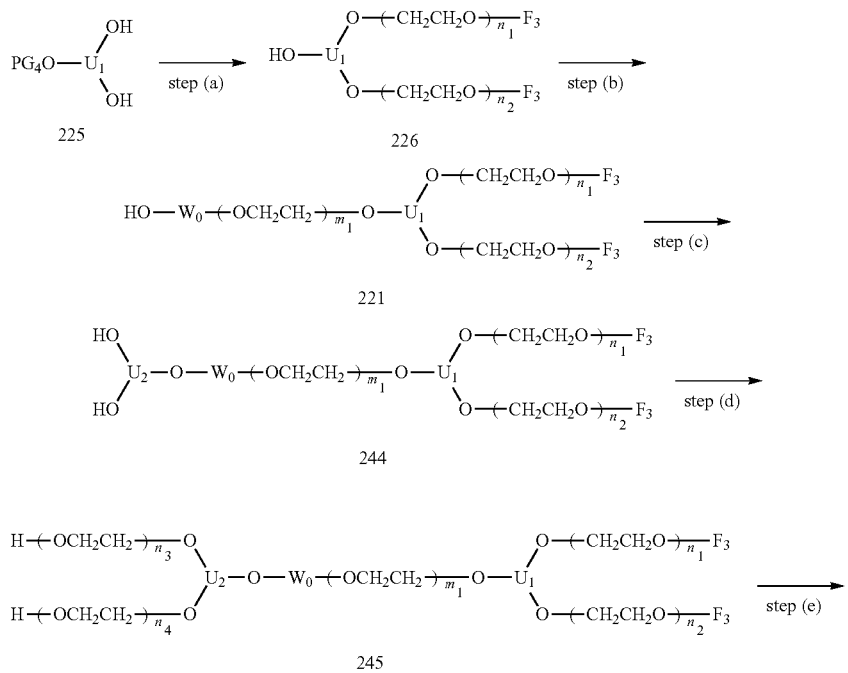

-continued

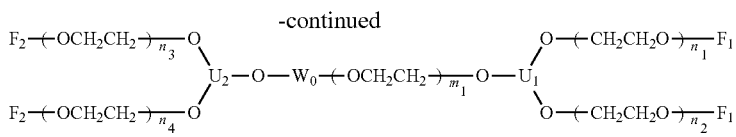

5b

Wherein, the definitions of $n_1$, $n_2$, $n_3$, $n_4$, $m_1$, $W_0$, $U_1$, $U_2$, $F_1$ and $F_2$ are the same as those in general formula (5b), and no more repeated here. $PG_4$ is a hydroxyl protecting group, preferably a silyl group, a benzyl group, an acetal group, a ketal group or a t-butyl group.

2.3.13. Method-13

Using a polyethylene glycol (252) or (252b) containing two unprotected hydroxyl groups at the two ends as reagent, which can be either polydisperse or monodisperse, to prepare an H-shaped multifunctionalized polyethylene glycol as represented by formula (4c) or formula (4d).

The production method to obtain compound (4c) by using compound (252) as reagent is as follows:

Step (a): reacting a polyethylene glycol (252) containing two terminal unprotected hydroxyl groups with a compound having a leaving group and two protected hydroxyl groups (206) such as halide, sulfonate or the like, to obtain an intermediate (253) which has four protected hydroxyl groups;

Step (b): removing the hydroxyl protecting groups of intermediate (253) to obtain an intermediate (254) containing four unprotected hydroxyl groups;

Step (c): initiating the polymerization of ethylene oxide from the terminal hydroxyl groups of the intermediate (254) followed by protonation to obtain an H-shaped polyethylene glycol intermediate (255);

Step (d): carrying out linear or branched end-functionalization to the intermediate (255) to obtain an H-shaped multifunctionalized polyethylene glycol as represented by general formula (4c).

Wherein, the definitions of $n_1$, $n_2$, $n_3$, $n_4$, $m_2$, $U_1$ and $F_1$ are the same as those in general formula (4), and no more repeated here. $PG_4$ is a hydroxyl protecting group, preferably a silyl group, a benzyl group, an acetal group, a ketal group or a t-butyl group.

The production method to obtain compound (4d) by using compound (252b) as reagent is as follows:

Step (a): reacting a polyethylene glycol (252b) containing two terminal unprotected hydroxyl groups with a compound having a leaving group and two protected hydroxyl groups (206) such as halide, sulfonate or the like, to obtain an intermediate (253b) which has four protected hydroxyl groups;

Step (b): removing the hydroxyl protecting groups of intermediate (253b) to obtain an intermediate (254b) containing four unprotected hydroxyl groups;

Step (c): initiating the polymerization of ethylene oxide from the terminal hydroxyl groups of the intermediate (254b) followed by protonation to obtain an H-shaped polyethylene glycol intermediate (255b);

Step (d): carrying out linear or branched end-functionalization to the intermediate (255b) to obtain an H-shaped multifunctionalized polyethylene glycol as represented by general formula (4d).

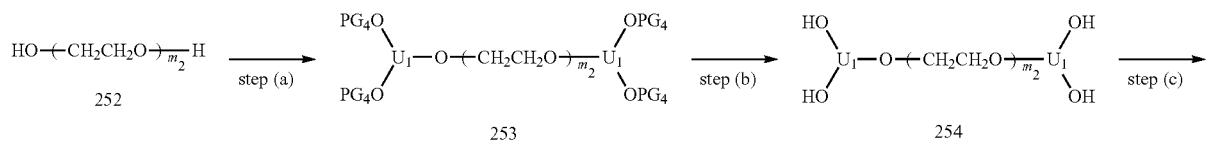

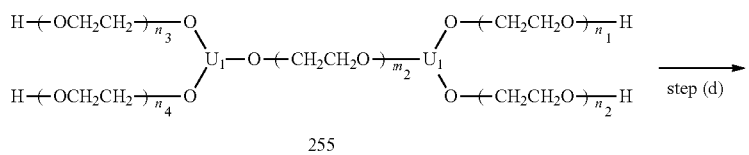

255

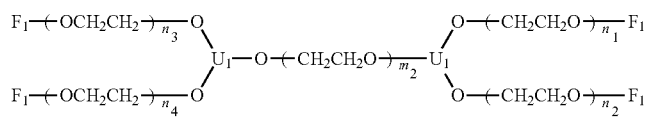

4c

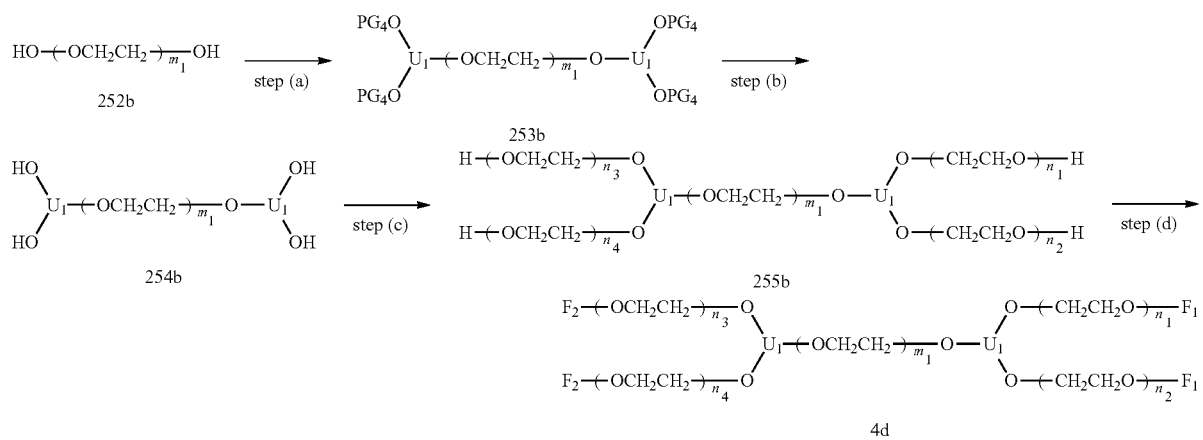

4d

Wherein, the definitions of $n_1$, $n_2$, $n_3$, $n_4$, $m_1$, $U_1$ and $F_1$ are the same as those in general formula (4b), and no more repeated here. $PG_4$ is a hydroxyl protecting group, preferably a silyl group, a benzyl group, an acetal group, a ketal group or a t-butyl group.

The compounds (252) and (252b) can also be obtained by starting from ethylene glycol to initiate the polymerization of ethylene oxide followed by protonation to obtain a polydisperse compound; a monodisperse compound can be obtained via organic synthesis, or be purchased.

2.3.14. The Reaction of Obtaining Two Unprotected Hydroxyl Groups by Starting from the Terminal Ends of Linear Polyethylene Glycol The methods of generating two unprotected hydroxyl groups from one terminal of a linear polyethylene glycol, include not only the above-mentioned method by reacting with a compound such as halide, sulfonate or the like (206) which has a leaving group and two unprotected hydroxyl groups, but also can refer to the ring-opening reaction in part 2.2.1.1., the reaction between an alkynyl group and a mercapto group in part 2.2.1.1., etc. All the aforementioned can refer to the prior art, and no more repeated here.

The above-provided routes and methods are typical embodiments in a descriptive sense. Other suitable production methods in the art can also be incorporated, no more repeated here. Those skilled in the art can choose suitable methods according to specific needs.

In the following, H-shaped multifunctionalized polyethylene glycols and production methods thereof are described more specifically with reference to EXAMPLES in the present invention. The specific examples are disclosed to further illustrate the invention, but should not be regarded as a limitation of the scope of present invention.

With respect to the nomenclature of bifunctional or multifunctional compounds involved in the EXAMPLES, sometimes, only the nature of the functionality is illustrated while the degree of functionality is not particularly indicated in their chemical names for simplicity, which should not be considered as limitation. Similar description may also occur in other context of the present invention. For instance, the compound B1-B1-1 which has four sulfonate groups in Example-2 is just denoted as a sulfonate derivative.

With respect to EXAMPLES, characteristics involving polydispersity, such as $n_1$, $n_2$, $n_3$, $n_4$, $m_1$, $m_2$, $m_3$, PDI, $M_n$ and the like, refer to the resulting substance produced with the method, which is composed of molecules deriving from a common general formula, if without particular illustration.

Therefore, a lot of "≈" symbols were used for parameters related to molecular weight or degree of polymerization such as $n_1$, $n_2$, $n_3$, $n_4$ and the like to indicate the polydispersity of the resulting polymeric substance.

EXAMPLE-1

Preparation of an H-Shaped Polyethylene Glycol Derivative Containing Terminal Hydroxyl Groups Synthesis of Derivative with Hydroxyl Groups H1-H1-1

Herein, the structural design of H-shaped polyethylene glycol derivative was given as follows: $F_1=F_2=-CH_2CH_2OH$,

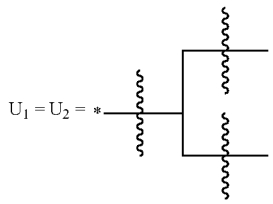

($U_1$ and $U_2$ are of a symmetrical type,

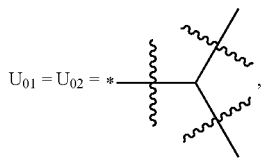

$L_1=L_2=L_3=L_4=CH_2$, and without $L_5$ and $L_6$) j=1, $W_0$ is $-CH_2CH_2-$ and $m_1=0$ in the present example. The designed total molecular weight is approximately 25000 Da, wherein, the molecular weight of four branch chains is approximately 4×5000=20000 Da corresponding to $n_1 \approx n_2 \approx n_3 \approx n_4 \approx 114$, and the molecular weight of the main chain is approximately 5000 Da corresponding to $m_2 \approx 113$.

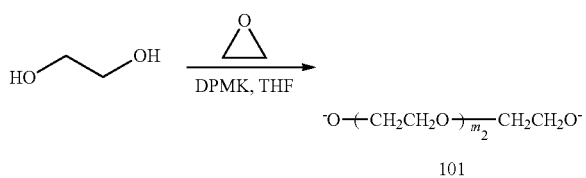

101

Step (a): Into a sealed reactor under an anhydrous and oxygen-free atmosphere, tetrahydrofuran (250 mL), ethylene glycol (2.532 mmol) and diphenylmethyl potassium (4.0 mmol) were added in sequence.

Step (b): After the addition of a calculated amount of ethylene oxide (570 mmol), the whole was heated stepwisely to 60° C., followed by reaction at 60° C. for 48 hours.

Step (c): After completion of the reaction, excess diphenylmethyl potassium (40 mmol) and excess compound 102 (100 mmol, OTs is a tosyl group) were added in sequence, followed by reaction at 30° C. for 12 hours. After completion of the reaction, open the reactor. The product in the solvent was concentrated, and then precipitated with absolute ether at 0° C. The crystals were collected by filtration and dried, and then an H-shaped polyethylene glycol intermediate 103 containing four terminal hydroxyl groups protected with silyl groups was obtained.

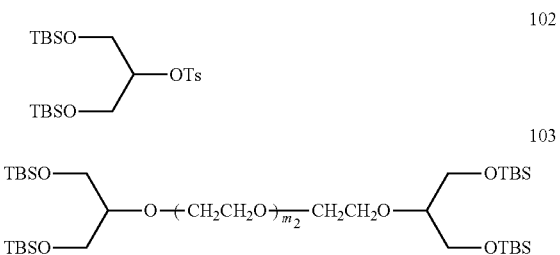

102

103

$^1$H-NMR spectrum data of the intermediate 103 were as follows: $^1$H NMR (CDCl$_3$) δ (ppm): 0.21 (—Si(CH$_3$)$_2$), 0.98 (—SiC(CH$_3$)$_3$), 2.90-3.00 (—OCH(CH$_2$O—)$_2$), 3.40-3.80 (—CH$_2$CH$_2$O—), 3.90-4.00 (—OCH(CH$_2$O—)$_2$).

Step (d): Into a dry and clean container, the intermediate 103 obtained from step (c) was added and then dissolved with tetrahydrofuran. Tetra-t-butyl ammonium fluoride (TBAF) was added, thereafter the reaction was conducted overnight, and then an H-shaped polyethylene glycol intermediate 104 containing four unprotected hydroxyl groups was obtained.

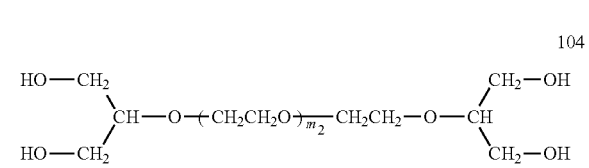

104

$^1$H-NMR spectrum data of the intermediate 104 were as follows: $^1$HNMR (CDCl$_3$) δ (ppm): 2.90-3.00 (—OCH(CH$_2$O—)$_2$), 3.40-3.50 (—OCH(CH$_2$O—)$_2$), 3.40-3.80 (—CH$_2$CH$_2$O—); M$_n$≈5000 Da, PDI=1.02.

Step (e): Step (a) and (b) were repeated, and then excess proton source (methanol) was added to obtain an intermediate compound H1-H1-1. Wherein, F$_1$=F$_2$=—CH$_2$CH$_2$OH (g=0, k=1, q=0, q$_1$=1, Z$_1$=CH$_2$CH$_2$, R$_{01}$=H).

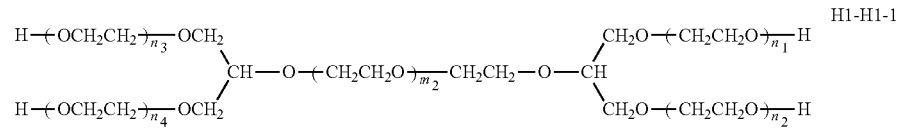

H1-H1-1

$^1$H-NMR spectrum data of the compound (H1-H1-1) were as follows: $^1$H NMR (CDCl$_3$) δ (ppm): 3.40-3.80 (—CH$_2$CH$_2$O—, —OCH(CH$_2$O—)$_2$); M$_n$≈25000 Da, PDI=1.02 (total molecular weight is approximately 4×5000+5000=25000 Da, molecular weight of the main chain is approximately 5000 Da).

EXAMPLE-2

Preparation of an H-Shaped Polyethylene Glycol Sulfonate Derivative

Synthesis of Sulfonate Derivative B1-B1-1

Herein, the structural design of H-shaped polyethylene glycol derivative was given as follows: F$_1$=F$_2$=Ts (a tosyl group),

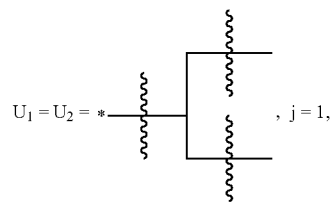

W$_0$ is CH$_2$CH$_2$, m$_1$=0. The designed total molecular weight is approximately 25000 Da, wherein, the molecular weight of four branch chains is approximately 4×5000=20000 Da corresponding to n$_1$≈n$_2$≈n$_3$≈n$_4$≈114, and the molecular weight of the main chain is approximately 5000 Da corresponding to m$_2$≈113.

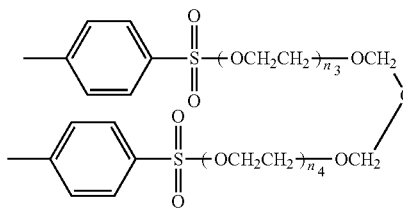
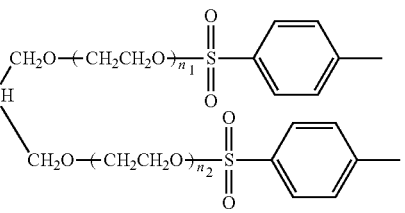

B1-B1-1

Into a dry and clean 1 L round-bottom flask, 40 g of tetrahydroxyl-containing H-shaped branched polyethylene glycol compound H1-H1-1 which has symmetrical branches obtained in Example-1 was added. Using nitrogen protecweight of four branch chains is approximately 4×5000= 20000 Da corresponding to $n_1 \approx n_2 \approx n_3 \approx n_4 \approx 114$, and the molecular weight of the main chain is approximately 5000 Da corresponding to $m_2 \approx 113$.

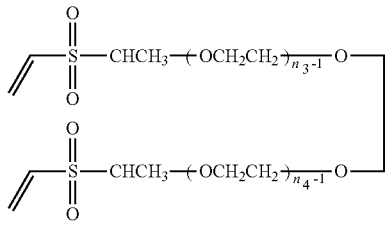
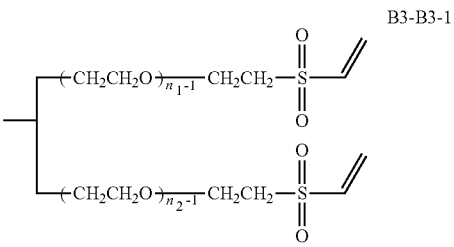

B3-B3-1 tion, anhydrous and oxygen-free dichloromethane (500 mL), 20 mL of pyridine and 5 g of p-toluenesulfonyl chloride were added, followed by reaction at room temperature for 24 hours. The resulting solution was adjusted to pH <7 with 1 mol/L HCl. The aqueous phase was washed with dichloromethane (50 mL trice), then the organic phase was collected, washed with saturated salt solutions, dried with anhydrous $Na_2SO_4$, filtrated, concentrated and recrystallized, and then a sulfonate derivative B1-B1-1 was obtained.

$^1$H-NMR spectrum data of the sulfonate derivative B1-B1-1 were as follows: $^1$H NMR (CDCl$_3$) δ (ppm): 2.35 ($CH_3C_6H_4SO_2$—), 3.40-3.80 (—$CH_2CH_2O$—), 4.20 (—$OCH_2CH_2OSO_2$—), 7.30 ($CH_3C_6H_4SO_2$—), 7.80 ($CH_3C_6H_4SO_2$—); $M_n \approx 25000$ Da, PDI=1.02.

EXAMPLE-3

Preparation of an H-Shaped Polyethylene Glycol Sulfone Derivative

Synthesis of Sulfone Derivative B3-B3-1

Herein, the structural design of H-shaped polyethylene glycol derivative was given as follows: $F_1$ and $F_2$ is —$CH_2CH_2SO_2CH$=$CH_2$,

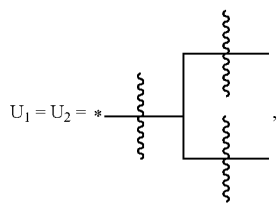

$j=1$, $W_0$ is $CH_2CH_2$ and $m_1=0$. The designed total molecular weight is approximately 25000 Da, wherein, the molecular Into a dry and clean 1 L round-bottom flask, 0.32 g of sodium hydride (60 wt %, in oil) was added. Using nitrogen protection, 400 mL of anhydrous tetrahydrofuran was added, and 30 g of tetrahydroxyl-containing H-shaped branched polyethylene glycol compound H1-H1-1 (treated by azeotropic removal of water with toluene) which has symmetrical branches obtained in Example-1 dissolved in tetrahydrofuran was added slowly in an ice bath, followed by stirring at room temperature for 3 hours, then 1 g of divinylsulfone was added, followed by reaction at room temperature for 24 hours. After completion of the reaction, a small amount of saturated ammonium chloride solution was added to quench the reaction. Then the solution was concentrated, dissolved in dichloromethane (400 mL), washed with saturated salt solutions (100 mL trice), dried, concentrated and recrystallized, and then an H-shaped polyethylene glycol sulfone derivative B3-B3-1 in a white solid state was obtained.

$^1$H-NMR spectrum data of the sulfone derivative B3-B3-1 were as follows: $^1$H NMR (CDCl$_3$) δ (ppm): 3.40-3.90 (—$CH_2CH_2O$—, —$OCH(CH_2O$—$)_2$, —$SO_2CH_2CH_2O$—), 6.19-6.81 (—$SO_2CH$=$CH_2$); $M_n \approx 25000$ Da, PDI=1.02.

EXAMPLE-4

Preparation of an H-Shaped Polyethylene Thiol Derivative

Synthesis of Thiol Derivative C2-C2-1

Herein, the structural design of H-shaped polyethylene glycol derivative was given as follows: $F_1$=$F_2$=— $CH_2CH_2SH$ (g=0, k=1, q=0, $q_1$=1, $Z_1$=$CH_2CH_2$, $R_{01}$=SH),

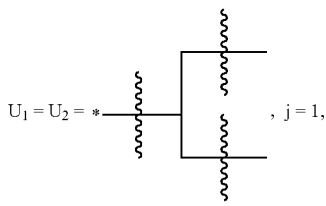

$U_1 = U_2 = $ , $j = 1$, $W_0$ is $CH_2CH_2$ and $m_1=0$. The designed total molecular weight is approximately 25000 Da, wherein, the molecular weight of four branch chains is approximately $4\times5000=20000$ Da corresponding to $n_1 \approx n_2 \approx n_3 \approx n_4 \approx 114$, and the molecular weight of the main chain is approximately 5000 Da corresponding to $m_2 \approx 113$.

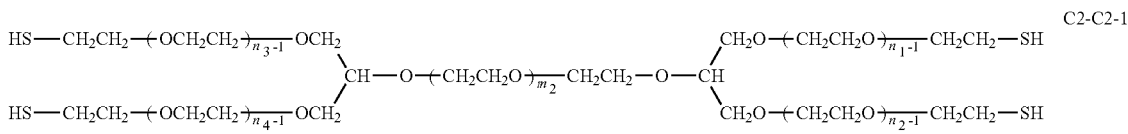

C2-C2-1

Step (a): Into a dry and clean round-bottom flask, 40 g of H-shaped polyethylene glycol sulfonate B1-B1-1 obtained in Example-2 was added. Using nitrogen protection, 400 mL of tetrahydrofuran and 16 mL of DMF were added. The whole was stirred till dissolution, then 10 g of potassium ethylxanthate

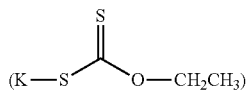

was added, followed by reaction at room temperature for 24 hours. After completion of the reaction, the solution was concentrated, and 400 mL of dichloromethane was added. The undissolved substances were removed by filtration, washed with saturated salt solutions (100 mL trice), dried, concentrated and recrystallized from isopropanol, and then an intermediate C7-C7-1 in white or yellowish was obtained.

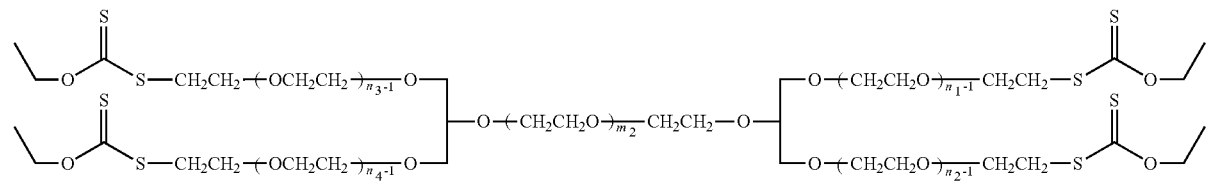

C7-C7-1

$^1$H-NMR spectrum data of the intermediate C7-C7-1 were as follows: $^1$H NMR (CDCl$_3$) δ (ppm): 0.90-1.20 (CH$_3$CH$_2$OC(=S)—)), 2.90-3.10 (—OCH$_2$CH$_2$S—), 3.40-3.80 (—CH$_2$CH$_2$O—, —OCH(CH$_2$O—)$_2$, CH$_3$CH$_2$OC(=S)—), 3.90-4.10, (—SCH$_2$CH$_2$O—); M$_n$≈25000 Da, PDI=1.02.

Step (b): Into a dry and clean round-bottom flask, 20 g of polyethylene glycol dithiocarbonate derivative C7-C7-1 obtained in step (a) was added. Using nitrogen protection, 200 mL of tetrahydrofuran was added. The whole was stirred till dissolution, and 10 mL of n-propylamine was added, followed by reaction at room temperature for 24 hours. The resulting mixture was concentrated and recrystallized from deoxygenated isopropanol to obtain a dithiol derivative in a white or yellowish solid state. The intermediate was treated with sodium borohydride in tetrahydrofuran. After quenching the reaction with ammonium chloride, the solution was concentrated, dissolved in 400 mL of dichloromethane, washed with saturated salt solution (100 mL trice), dried, concentrated and recrystallized, and then an H-shaped polyethylene glycol thiol derivative C2-C2-1 in a white solid state was obtained.

$^1$H-NMR spectrum data of the thiol derivative C2-C2-1 were as follows: $^1$H NMR (CDCl$_3$) δ (ppm): 2.70-2.85 (—OCH$_2$CH$_2$SH), 3.40-3.80 (—CH$_2$CH$_2$O—, —OCH(CH$_2$O—)$_2$, —SCH$_2$CH$_2$O—); $M_n$≈25000 Da, PDI=1.02.

EXAMPLE-5

Preparation of an H-Shaped Polyethylene Glycol Thiocarbonate Derivative

Synthesis of Thiocarbonate Derivative C7-C7-2

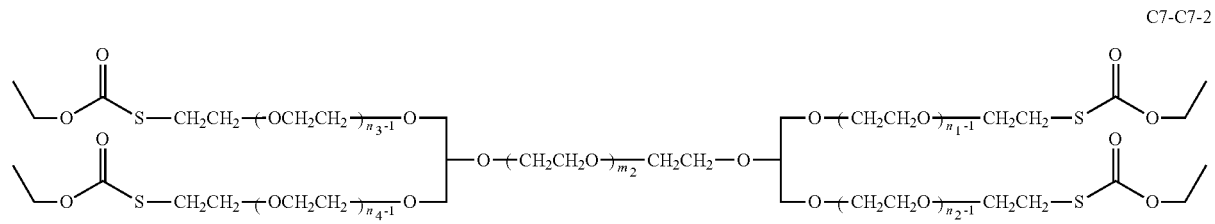

Herein, the structural design of H-shaped polyethylene glycol derivative was given as follows: $F_1=F_2=$—CH$_2$CH$_2$SCOOCH$_2$CH$_3$,

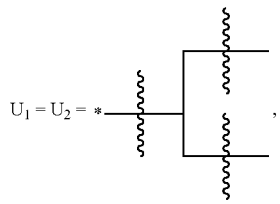

j=1, $W_0$ is CH$_2$CH$_2$, $m_1$=0, p=0, j=1 and $m_1$=1. The designed total molecular weight is approximately 25000 Da, wherein, the molecular weight of four branch chains is approximately 4×5000=20000 Da corresponding to $n_1$≈$n_2$≈$n_3$≈$n_4$≈114, and the molecular weight of the main chain is approximately 5000 Da corresponding to $m_2$≈113.

Into a dry and clean 1 L round-bottom flask, 50 g of H-shaped polyethylene glycol thiol derivative C2-C2-1 obtained in Example-4 and dichloromethane (500 mL) were added in sequence. The whole was stirred till dissolution, and subsequently 8 g of triethylamine and 10 g of ethyl chloroformate were added in sequence. The reaction was conducted overnight at room temperature, thereafter added with saturated sodium bicarbonate solution, extracted with dichloromethane (250 mL trice). The organic phase was combined and washed with saturated salt solutions, dried, filtrated, concentrated and recrystallized, and then a thiocarbonate derivative C7-C7-2 in a white solid state was obtained.

$^1$H-NMR spectrum data of the compound C7-C7-2 were as follows: $^1$H NMR (CDCl$_3$) δ (ppm): 1.20-1.40 (CH$_3$CH$_2$OC(=O)—), 2.90-3.10 (—OCH$_2$CH$_2$S—), 3.40-3.80 (—CH$_2$CH$_2$O—, —OCH(CH$_2$O—)$_2$), 3.90-4.10, (—SCH$_2$CH$_2$O—), 4.10-4.30 (CH$_3$CH$_2$OC(=O)—); $M_n$≈25000 Da, PDI=1.02.

EXAMPLE-6

Preparation of H-Shaped Polyethylene Glycol Thioacetate Derivative

Synthesis of Thioacetate Derivative C7-C7-3

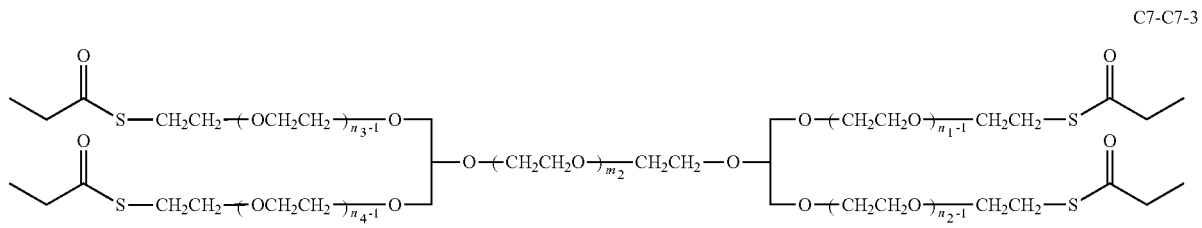

Herein, the structural design of H-shaped polyethylene glycol derivative was given as follows: $F_1=F_2=$—$CH_2CH_2SCOCH_2CH_3$,

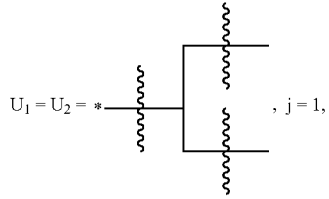, $j=1$, $W_0$ is $CH_2CH_2$ and $m_1=0$. The designed total molecular weight is approximately 25000 Da, wherein, the molecular weight of four branch chains is approximately $4\times5000=20000$ Da corresponding to $n_1\approx n_2\approx n_3\approx n_4\approx114$, and the molecular weight of the main chain is approximately 5000 Da corresponding to $m_2\approx113$.

Into a dry and clean 1 L round-bottom flask, 50 g of H-shaped polyethylene glycol thiol derivative C2-C2-1 obtained in Example-4 was added. After the addition of dichloromethane (500 mL), the whole was stirred till dissolution, and then 8 g of triethylamine and 10 g of propionyl chloride were added in sequence. The reaction was conducted overnight at room temperature, thereafter added with saturated sodium bicarbonate solution, extracted with dichloromethane (250 mL trice). The organic phase was combined and washed with saturated salt solutions, dried, filtrated, concentrated and recrystallized, and then a thioester derivative C7-C7-3 in a white solid state was obtained.

$^1$H-NMR spectrum data of the compound C7-C7-3 were as follows: $^1$H NMR (CDCl$_3$) δ (ppm): 1.00-1.30 (CH$_3$CH$_2$C(=O)—)), 2.30-2.50 (CH$_3$CH$_2$C(=O)—), 2.90-3.10 (—OCH$_2$CH$_2$S—), 3.40-3.80 (—CH$_2$CH$_2$O—, —OCH(CH$_2$O—)$_2$), 3.90-4.10 (—SCH$_2$CH$_2$O—); $M_n\approx25000$ Da, PDI=1.02.

EXAMPLE-7

Preparation of H-Shaped Polyethylene Glycol Thioate Derivative

Synthesis of Alkanethioate Derivative H2-H2-1

Herein, the structural design of H-shaped polyethylene glycol derivative was given as follows: $F_1=F_2=$—$CH_2CH_2OC(=S)CH(CH_3)_2$,

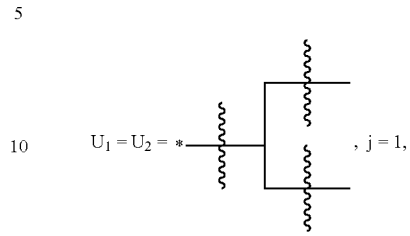, $j=1$, $W_0$ is $CH_2CH_2$ and $m_1=0$. The designed total molecular weight is approximately 25000 Da, wherein, the molecular weight of four branch chains is approximately $4\times5000=20000$ Da corresponding to $n_1\approx n_2\approx n_3\approx n_4\approx114$, and the molecular weight of the main chain is approximately 5000 Da corresponding to $m_2\approx113$.

Into a dry and clean 1 L round-bottom flask, 50 g of H-shaped polyethylene glycol compound H1-H1-1 obtained in Example-1 was added. After the addition of dichloromethane (500 mL), the whole was stirred till dissolution, and then 8 g of triethylamine and 10 g of 2-methylpropanethioyl chloride were added in sequence. The reaction was conducted overnight at room temperature, thereafter added with saturated sodium bicarbonate solution, extracted with dichloromethane (250 mL trice). The organic phase was combined and washed with saturated salt solutions, dried, filtrated, concentrated and recrystallized, and then a 2-methylpropanethioate derivative H2-H2-1 in a white solid state was obtained.

$^1$H-NMR spectrum data of the compound H2-H2-1 were as follows: $^1$H NMR (CDCl$_3$) δ (ppm): 1.00-1.40 (CH$_3$CH$_2$C(=S)—), —CH(CH$_3$)$_2$), 2.30-2.50 (CH$_3$CH$_2$C(=S)—), 3.00-3.40 (—CH(CH$_3$)$_2$), 3.40-3.80 (—CH$_2$CH$_2$O—, —OCH(CH$_2$O—)$_2$); $M_n\approx25000$ Da, PDI=1.02.

EXAMPLE-8

Preparation of H-Shaped Polyethylene Glycol Amine Derivative

Synthesis of Amine Derivative C3-C3-1

Herein, the structural design of H-shaped polyethylene glycol derivative was given as follows: $F_1=F_2=$—$CH_2CH_2NH_2$,

H2-H2-1

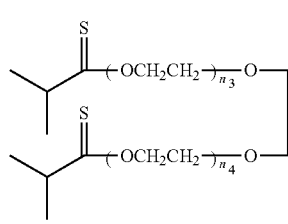

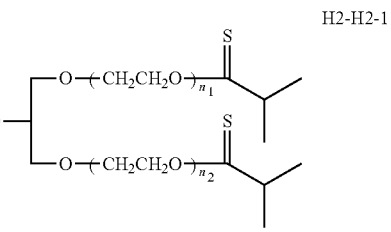

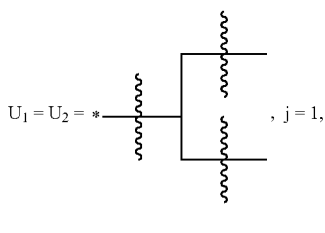

$U_1 = U_2 = *$—, $j = 1$, $W_0$ is $CH_2CH_2$ and $m_1=0$. The designed total molecular weight is approximately 25000 Da, wherein, the molecular weight of four branch chains is approximately 4×5000=20000 Da corresponding to $n_1 \approx n_2 \approx n_3 \approx n_4 \approx 114$, and the molecular weight of the main chain is approximately 5000 Da corresponding to $m_2 \approx 113$.

Into a dry and clean 1 L round-bottom flask, 40 g of H-shaped polyethylene glycol sulfonate derivative B1-B1-1 obtained in Example-2 and 800 mL of ammonia water (40 wt %) were added in sequence. The whole was stirred till dissolution. Thereafter, the reaction was conducted at room temperature for a week. After completion of the reaction, the resulting product was extracted with dichloromethane (200 mL trice). The organic phase was collected, washed with saturated salt solutions, dried, filtrated, concentrated and recrystallized, and then an amine derivative C3-C3-1 in a white solid state was obtained.

$^1$H-NMR spectrum data of the amine derivative C3-C3-1 were as follows: $^1$H NMR (CDCl$_3$) δ (ppm): 2.70-2.85 (—CH$_2$CH$_2$NH$_2$—), 3.40-3.80 (—CH$_2$CH$_2$O—, —OCH(CH$_2$O—)$_2$, —OCH$_2$CH$_2$NH$_2$); $M_n \approx$25000 Da, PDI=1.02.

EXAMPLE-9

Preparation of H-Shaped Polyethylene Glycol Boc-Protected Amine Derivative

Synthesis of Boc-Protected Amine Derivative C6-C6-1

Herein, the structural design of H-shaped polyethylene glycol derivative was given as follows: $F_1=F_2=$—CH$_2$CH$_2$NHBoc,

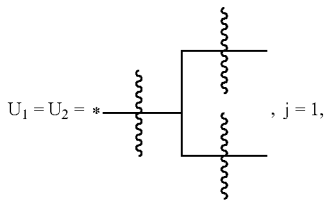

$U_1 = U_2 = *$—, $j = 1$, $W_0$ is $CH_2CH_2$ and $m_1=0$. The designed total molecular weight is approximately 25000 Da, wherein, the molecular weight of four branch chains is approximately 4×5000=20000 Da corresponding to $n_1 \approx n_2 \approx n_3 \approx n_4 \approx 114$, and the molecular weight of the main chain is approximately 5000 Da corresponding to $m_2 \approx 113$.

Into a dry and clean 1 L round-bottom flask, 40 g of H-shaped polyethylene glycol ethylamine C3-C3-1 was added, and then 500 mL of dichloromethane and di-tert-butyl dicarbonate (20 g) were added in sequence. Thereafter, the reaction was conducted at room temperature overnight. After completion of the reaction, saturated sodium bicarbonate solution was added and then the resulting product was extracted with dichloromethane (200 mL trice). The organic phase was collected, washed with saturated salt solutions, dried, filtrated, concentrated and recrystallized, and then a Boc-protected amine derivative C6-C6-1 in a white solid state was obtained.

$^1$H-NMR spectrum data of the compound C6-C6-1 were as follows: $^1$H NMR (CDCl$_3$) δ (ppm): 1.38 (—C(CH$_3$)$_3$), 3.00-3.20 (—CH$_2$CH$_2$NH—), 3.40-3.80 (—CH$_2$CH$_2$O—, —OCH(CH$_2$O—)$_2$, —OCH$_2$CH$_2$NH); $M_n \approx$25000 Da, PDI=1.02.

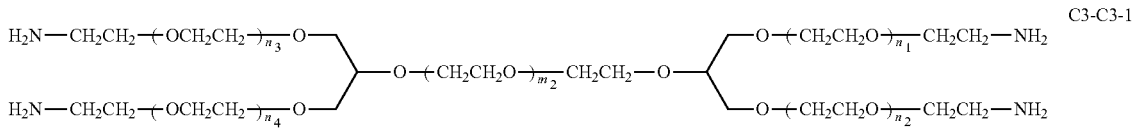

C3-C3-1

BocHN—CH$_2$CH$_2$—(OCH$_2$CH$_2$)$_{n_3}$—O\
BocHN—CH$_2$CH$_2$—(OCH$_2$CH$_2$)$_{n_4}$—O—O—(CH$_2$CH$_2$O)$_{m_2}$—CH$_2$CH$_2$—O—O—(CH$_2$CH$_2$O)$_{n_1}$—CH$_2$CH$_2$—NHBoc\
O—(CH$_2$CH$_2$O)$_{n_2}$—CH$_2$CH$_2$—NHBoc

C6-C6-1

EXAMPLE-10

Modification of Biotin with H-Shaped Polyethylene Glycol Amine Derivative

Synthesis of Biotin Derivative I3-I3-1

Herein, the structural design of H-shaped polyethylene glycol derivative was given as follows:

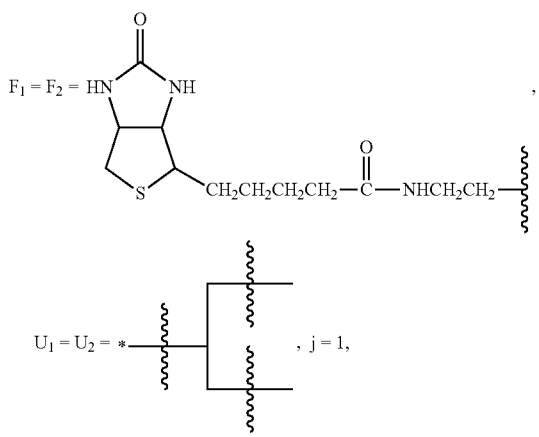

$W_0$ is $CH_2CH_2$ and $m_1=0$. The designed total molecular weight is approximately 25000 Da, wherein, the molecular weight of four branch chains is approximately 4×5000=20000 Da corresponding to $n_1 \approx n_2 \approx n_3 \approx n_4 \approx 114$, and the molecular weight of the main chain is approximately 5000 Da corresponding to $m_2 \approx 113$.

Into a dry and clean 150 mL round-bottom flask, 2 g of H-shaped polyethylene glycol amine derivative C3-C3-1 (treated by azeotropic removal of water with toluene), 1 g of biotin and 480 mg of DMAP were added. Using nitrogen protection, anhydrous dichloromethane (50 mL) was added, and the whole was stirred till all were dissolved. Subsequently, 120 mg of dicyclohexylcarbodiimide (DCC) was added thereinto, followed by reaction at room temperature for 24 hours. The resulting mixture was filtrated to remove undissolved substances, concentrated and recrystallized from isopropanol, and then a biotin derivative I3-I3-1 modified by polyethylene glycol was obtained.

$^1$H-NMR spectrum data of the biotin derivative I3-I3-1 were as follows: $^1$H NMR (CDCl$_3$) δ (ppm): 1.25-1.62 (—CH$_2$CH$_2$CH$_2$CH$_2$CONH—), 2.11 (—CH$_2$CONH—), 2.70-3.50 (—CHSCH$_2$—, —CH$_2$CH$_2$NH—), 3.40-3.80 (—CH$_2$CH$_2$O—, —OCH(CH$_2$O—)$_2$, —OCH$_2$CH$_2$NH), 4.55-4.60 (—CHNHC(=O)NHCH—); $M_n \approx 25000$ Da, PDI=1.02.

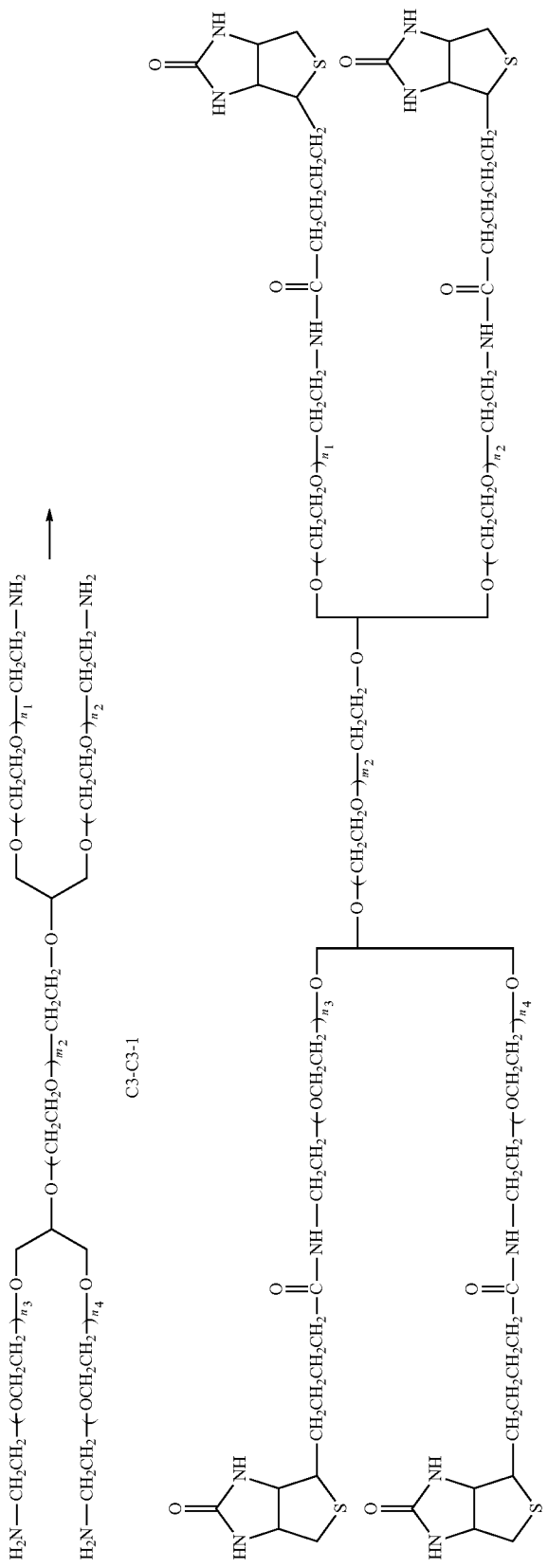

EXAMPLE-11

Modification of Rhodamine B with H-Shaped Polyethylene Glycol Amine Derivative

Synthesis of Rhodamine B Derivative J2-J2-1

Herein, the structural design of H-shaped polyethylene glycol derivative was given as follows:

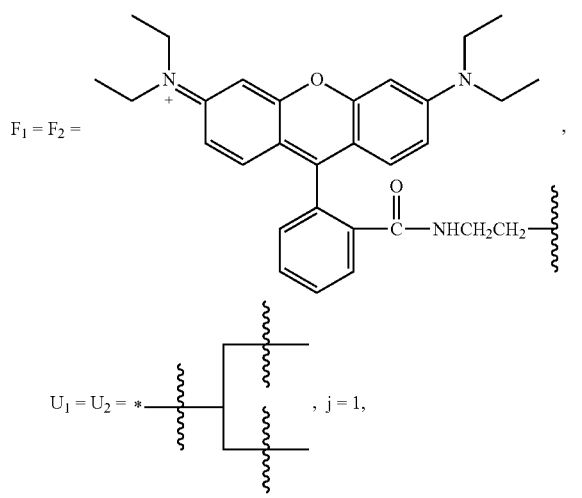

$W_0$ is $CH_2CH_2$ and $m_1=0$. The designed total molecular weight is approximately 27000 Da, wherein, the molecular weight of four branch chains is approximately $4 \times 5000 = 20000$ Da corresponding to $n_1 \approx n_2 \approx n_3 \approx n_4 \approx 114$, and the molecular weight of the main chain is approximately 5000 Da corresponding to $m_2 \approx 113$.

Into a dry and clean 150 mL round-bottom flask, 2 g of H-shaped polyethylene glycol amine derivative C3-C3-1 (treated by azeotropic removal of water with toluene), 2 g of rhodamine B and 480 mg of DMAP were added. Using nitrogen protection, anhydrous dichloromethane (50 mL) was added, and the whole was stirred till all were dissolved. Thereafter, 120 mg of dicyclohexylcarbodiimide (DCC) was added thereinto, followed by reaction at room temperature for 24 hours. The resulting mixture was filtrated to remove undissolved substances, concentrated and recrystallized from isopropanol, and then a rhodamine B derivative modified by polyethylene glycol J2-J2-1 was obtained.

$^1$H-NMR spectrum data of the rhodamine B derivative J2-J2-1 were as follows: $^1$H NMR (CDCl$_3$) δ (ppm): 1.10-1.30 (—NCH$_2$CH$_3$), 3.20-3.50 (—CH$_2$CH$_2$NH—), 3.40-3.80 (—CH$_2$CH$_2$O—, —OCH(CH$_2$O—)$_2$, —OCH$_2$CH$_2$NH), 3.50-3.80 (—NCH$_2$CH$_3$), 6.80-7.20 (—ArH), 7.40-7.60 (—ArH), 7.60-7.80 (—ArH), 8.10-8.30 (—ArH); $M_n \approx 27000$ Da, PDI=1.02.

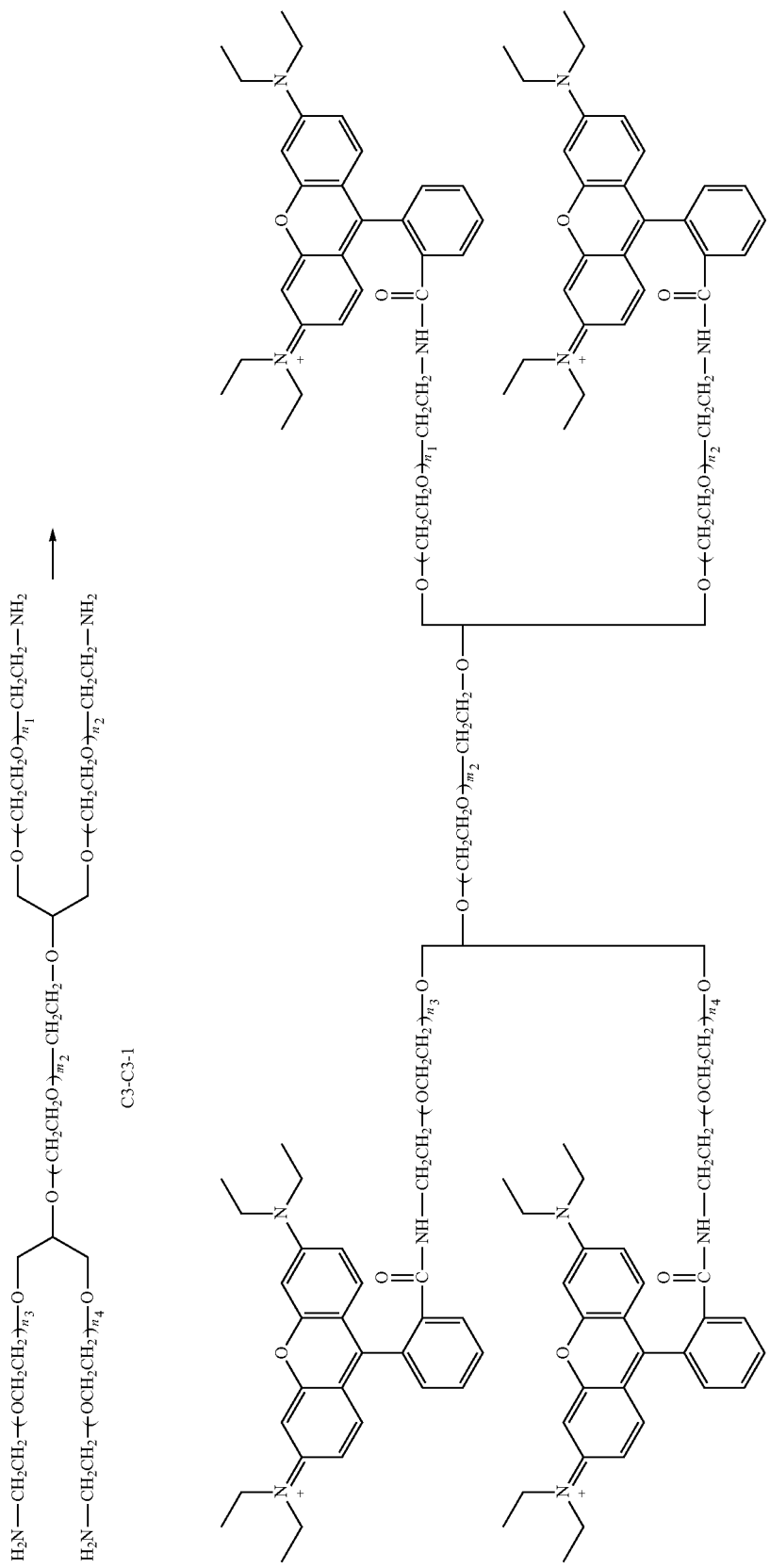

EXAMPLE-12

Preparation of H-Shaped Polyethylene Glycol Amine Derivative

Synthesis of Amine Derivative C14-C14-1

Herein, the structural design of H-shaped polyethylene glycol derivative was given as follows:

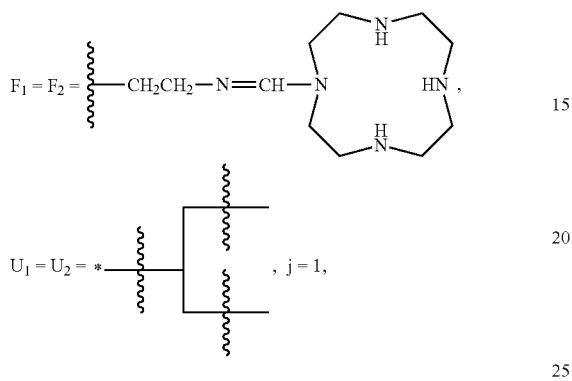

$W_0$ is $CH_2CH_2$ and $m_1=0$. The designed total molecular weight is approximately 25000 Da, wherein, the molecular weight of four branch chains is approximately $4\times5000=20000$ Da corresponding to $n_1 \approx n_2 \approx n_3 \approx n_4 \approx 114$, and the molecular weight of the main chain is approximately 5000 Da corresponding to $m_2 \approx 113$.

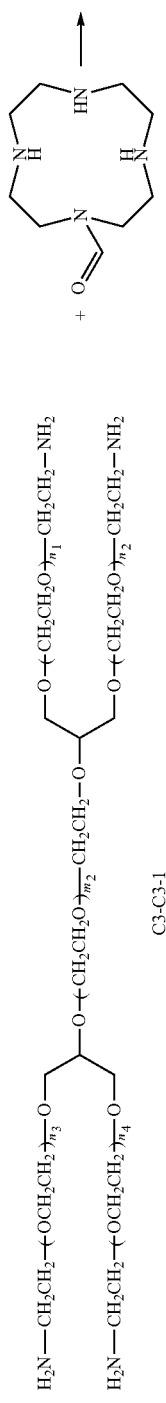
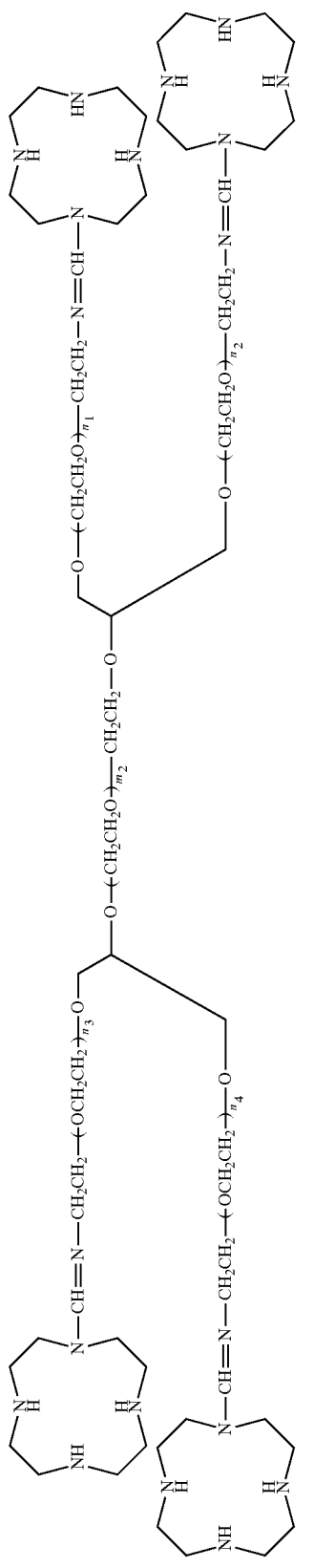
C3-C3-1
C14-C14-1

Into a round-bottom flask under an anhydrous and oxygen-free atmosphere, H-shaped polyethylene glycol amine derivative C3-C3-1 (2.5 mmol) and methanol (250 mL) were added in sequence. 1,4,7,10-tetraazacyclododecanecarbaldehyde (100 mmol) was added, followed by reaction at 25° C. for 24 hours. After completion of the reaction, the resulting mixture was concentrated, extracted, dried, concentrated and recrystallized, and then an amine derivative C14-C14-1 was obtained.

$^1$H-NMR spectrum data of the amine derivative C14-C14-1 were as follows: $^1$H NMR (CDCl$_3$) δ (ppm): 2.50-2.70 (—NCH$_2$CH$_2$N—), 3.40-3.80 (—CH$_2$CH$_2$O—, —OCH(CH$_2$O—)$_2$, —NCH$_2$CH$_2$O—), 7.40-7.60 (—N=CH—); M$_n$≈25000 Da, PDI=1.02.

EXAMPLE-13

Preparation of H-Shaped Polyethylene Glycol Carbamate Derivative

Synthesis of Carbamate Derivative C6-C6-2

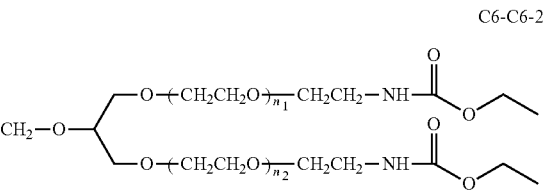

C6-C6-2

Herein, the structural design of H-shaped polyethylene glycol derivative was given as follows: F$_1$=F$_2$=—CH$_2$CH$_2$NHCOOCH$_2$CH$_3$,

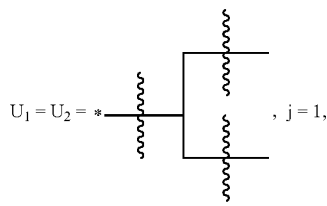

$W_0$ is CH$_2$CH$_2$ and m$_1$=0. The designed total molecular weight is approximately 25000 Da, wherein, the molecular weight of four branch chains is approximately 4×5000=20000 Da corresponding to n$_1$≈n$_2$≈n$_3$≈n$_4$≈114, and the molecular weight of the main chain is approximately 5000 Da corresponding to m$_2$≈113.

Into a dry and clean 1 L round-bottom flask, 50 g of H-shaped polyethylene glycol amine derivative C3-C3-1 obtained in Example-8 and dichloromethane (500 mL) were added in sequence. The whole was stirred till dissolution, and subsequently 8 g of triethylamine and 10 g of ethyl chloroformate were added. The reaction was conducted overnight at room temperature, added with saturated sodium bicarbonate solution, extracted with dichloromethane (250 mL trice). The organic phase was collected, washed with saturated salt solutions, dried, filtrated, concentrated and recrystallized, and then a carbamate derivative C6-C6-2 in a white solid state was obtained.

$^1$H-NMR spectrum data of the compound C6-C6-2 were as follows: $^1$H NMR (CDCl$_3$) δ (ppm): 1.20-1.40 (CH$_3$CH$_2$OC(=O)—), 3.00-3.20 (—OCH$_2$CH$_2$N—), 3.40-3.80 (—CH$_2$CH$_2$O—, —OCH(CH$_2$O—)$_2$, —NCH$_2$CH$_2$O—), 4.00-4.20 (CH$_3$CH$_2$OC(=O)—); M$_n$≈25000 Da, PDI=1.02.

EXAMPLE-14

Preparation of H-Shaped Polyethylene Glycol Maleimide Derivative

Synthesis of Maleimide Derivative E1-E1-1

Herein, the structural design of H-shaped polyethylene glycol derivative was given as follows:

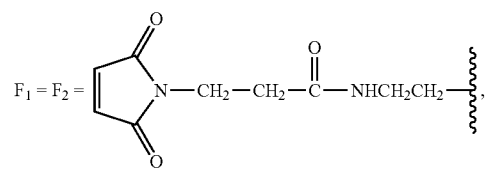

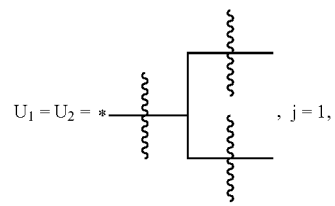

$W_0$ is CH$_2$CH$_2$ and m$_1$=0. The designed total molecular weight is approximately 25000 Da, wherein, the molecular weight of four branch chains is approximately 4×5000=20000 Da corresponding to n$_1$≈n$_2$≈n$_3$≈n$_4$≈114, and the molecular weight of the main chain is approximately 5000 Da corresponding to m$_2$≈113.

E1-E1-1

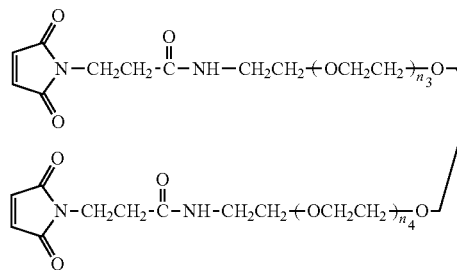 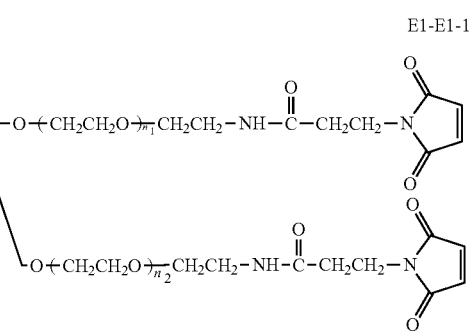

Into a dry and clean 1 L round-bottom flask, 50 g of H-shaped polyethylene glycol amine derivative C3-C3-1 (treated by azeotropic removal of water with toluene) obtained in Example-8 and 48 g of β-maleimidopropionic acid E11 were added. Using nitrogen protection, dichloromethane (700 mL) was added, the whole was stirred till dissolution, and then 110 mL of triethylamine and 110 g of dicyclohexylcarbodiimide (DCC) were added in sequence, followed by reaction at room temperature for 24 hours. The resulting mixture was filtrated to remove undissolved substances, concentrated and recrystallized from isopropanol, and then a maleimide derivative E1-E1-1 in a white solid state was obtained.

E11

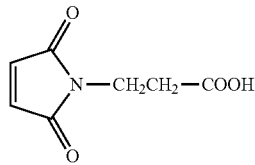

$^1$H-NMR spectrum data of maleimide derivative E1-E1-1 were as follows: $^1$H NMR (CDCl$_3$) δ (ppm): 2.60-2.70 (—NHC(=O)CH$_2$CH$_2$—), 3.40-3.80 (—CH$_2$CH$_2$O—, —OCH(CH$_2$O—)$_2$, —NCH$_2$CH$_2$O—), 3.92 (—NHCOCH$_2$CH$_2$N—), 6.81 (—CH=CH—); M$_n$≈25000 Da, PDI=1.02.

EXAMPLE-15

Preparation of H-Shaped Polyethylene Glycol Diazamaleimide Derivative

Synthesis of Diazamaleimide Derivative E7-E7-1

Herein, the structural design of H-shaped polyethylene glycol derivative was given as follows:

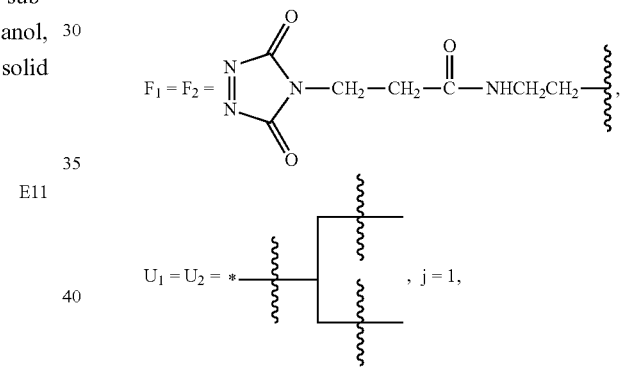

W$_0$ is CH$_2$CH$_2$ and m$_1$=0. The designed total molecular weight is approximately 25000 Da, wherein, the molecular weight of four branch chains is approximately 4×5000=20000 Da corresponding to n$_1$≈n$_2$≈n$_3$≈n$_4$≈114, and the molecular weight of the main chain is approximately 5000 Da corresponding to m$_2$≈113.

E7-E7-1

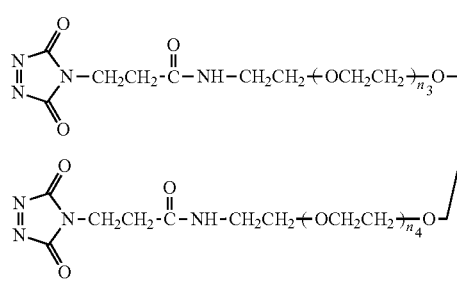 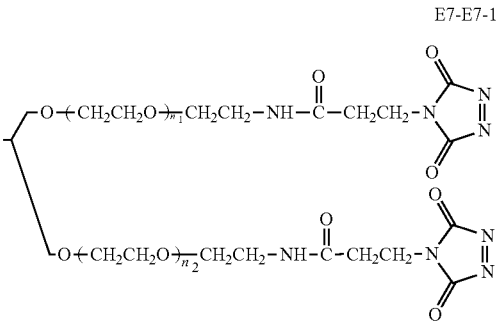

Into a dry and clean 1 L round-bottom flask, 50 g of H-shaped polyethylene glycol amine derivative C3-C3-1 (treated by azeotropic removal of water with toluene) obtained in Example-8 and 48 g of 3-(3,5-dioxo-3H-1,2,4-triazol-4(5H)-yl)propanoic acid (β-diazamaleimidopropionic acid) E71 were added. Using nitrogen protection, dichloromethane (700 mL), was added, thereafter the whole was stirred till dissolution, and then 110 mL of triethylamine and 110 g of dicyclohexylcarbodiimide (DCC) were added in sequence, followed by reaction at room temperature for 24 hours. The resulting mixture was filtrated to remove undissolved substances, concentrated and recrystallized from isopropanol, and then a diazamaleimide derivative E7-E7-1 in a white solid state was obtained.

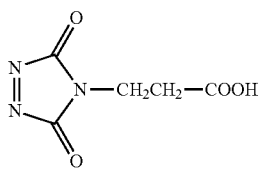

E71

$^1$H-NMR spectrum data of derivative E7-E7-1 were as follows: $^1$H NMR (CDCl$_3$) δ (ppm): 2.60-2.70 (—NHC(=O)CH$_2$CH$_2$—), 3.40-3.80 (—CH$_2$CH$_2$O—, —OCH(CH$_2$O—)$_2$, —NCH$_2$CH$_2$O—), 3.92 (—NHCOCH$_2$CH$_2$N—); $M_n$≈25000 Da, PDI=1.02.

EXAMPLE-16

Preparation of H-Shaped Polyethylene Glycol Carboxylic Acid Derivative

Synthesis of Carboxylic Acid Derivative D4-D4-1

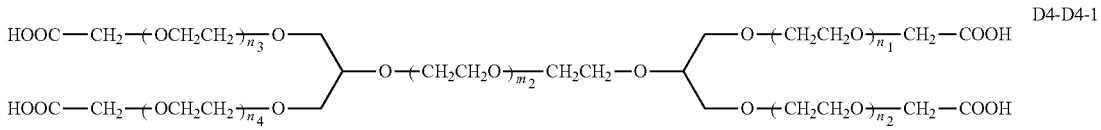

D4-D4-1

Herein, the structural design of H-shaped polyethylene glycol derivative was given as follows: $F_1=F_2=$ —CH$_2$COOH,

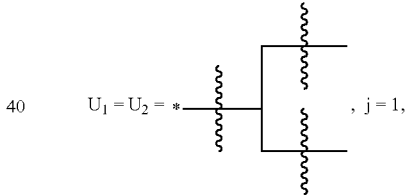

$W_0$ is CH$_2$CH$_2$ and $m_1=0$. The designed total molecular weight is approximately 25000 Da, wherein, the molecular weight of four branch chains is approximately 4×5000=20000 Da corresponding to $n_1≈n_2≈n_3≈n_4≈114$, and the molecular weight of the main chain is approximately 5000 Da corresponding to $m_2≈113$.

Step (a): Into a dry and clean 1 L round-bottom flask, 1.6 g of sodium hydride (60 wt %, in oil) was added. Using nitrogen protection, 500 mL of anhydrous tetrahydrofuran was added, and then 50 g of H-branched polyethylene glycol H1-H1-1 (treated by azeotropic removal of water with toluene) obtained in the Example-1 dissolved in the tetrahydrofuran was added slowly in an ice bath, followed by stirring at room temperature for 3 hours, thereafter 1 mL of bromoethyl acetate was added, followed by reaction at room temperature for 24 hours. After completion of the reaction, a small amount of saturated ammonium chloride was added to quench the reaction. The product in the solvent was concentrated, added with 400 mL of dichloromethane, washed with saturated salt solutions (120 mL trice), dried, concentrated and recrystallized, and then an H-shaped polyethylene glycol carboxylate derivative D11-D11-1 in a white solid state was obtained.

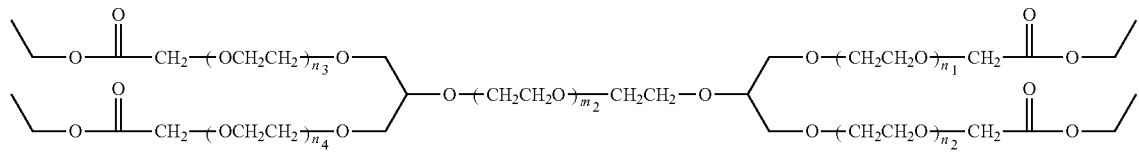

D11-D11-1

$^1$H-NMR spectrum data of the carboxylate D11-D11-1 were as follows: $^1$H NMR (CDCl$_3$) δ (ppm): 1.31 (—C(=O)OCH$_2$CH$_3$), 3.40-3.80 (—CH$_2$CH$_2$O—, —OCH(CH$_2$O—)$_2$, —OCH$_2$CH$_3$), 4.53 (—OCH$_2$C(=O)O—); $M_n$≈25000 Da, PDI=1.02.

Step (b): Into a dry and clean 500 mL flask, the polyethylene glycol carboxylate D11-D11-1 and 200 mL of aqueous sodium hydroxide (1 mol/L) were added in sequence. The whole was stirred till dissolution. Thereafter, the reaction was conducted at 80° C. for 24 hours. After completion of the reaction, the reaction solution was acidified with HCl (3 mol/L) until pH 3 in an ice bath, and the aqueous phase was extracted with dichloromethane (100 mL trice). The organic phase was collected, washed with saturated salt solutions, dried, filtrated, concentrated and recrystallized, and then a carboxylic acid derivative (D4-D4-1) in a white solid state was obtained.

$^1$H-NMR spectrum data of the carboxylic acid derivative D4-D4-1 were as follows: $^1$H NMR (CDCl$_3$) δ (ppm): 3.40-3.80 (—CH$_2$CH$_2$O—, —OCH(CH$_2$O—)$_2$), 4.35 (—OCH$_2$C(=O)O—); $M_n$≈25000 Da, PDI=1.02.

EXAMPLE-17

Preparation of H-Shaped Polyethylene Glycol Acyl Chloride Derivative

Synthesis of Acyl Chloride Derivative D6-D6-1

Herein, the structural design of H-shaped polyethylene glycol derivative was given as follows: $F_1=F_2=$—CH$_2$COCl,

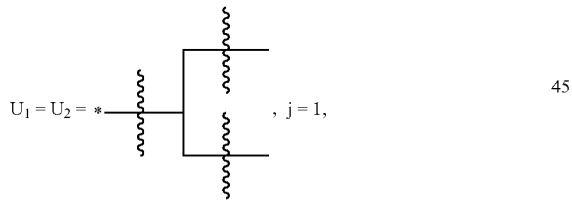

$W_0$ is CH$_2$CH$_2$ and $m_1$=0. The designed total molecular weight is approximately 25000 Da, wherein, the molecular weight of four branch chains is approximately 4×5000=20000 Da corresponding to $n_1$≈$n_2$≈$n_3$≈$n_4$≈114, and the molecular weight of the main chain is approximately 5000 Da corresponding to $m_2$≈113.

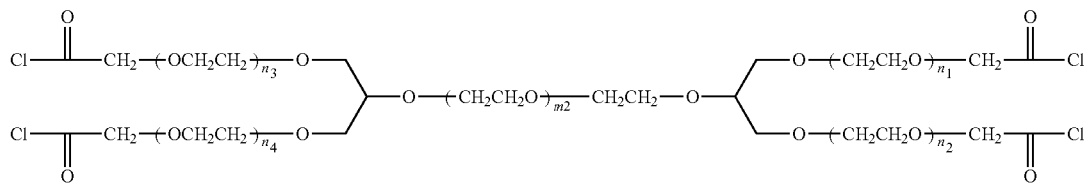

D6-D6-1

Into a dry and clean 1 L round-bottom flask, 50 g of polyethylene glycol carboxylic acid derivative D4-D4-1 obtained in Example-16 (treated by azeotropic removal of water with toluene) was added. Using nitrogen protection, 500 mL of anhydrous tetrahydrofuran was added, and then 5 mL of sulfur dichloride was added slowly at 20° C., followed by stirring reaction at room temperature for 3 hours. After completion of the reaction, the solvent was removed by rotary evaporation, thereafter the resulting solid was dried by oil pump vacuum and recrystallized. Then, an H-shaped polyethylene glycol acyl chloride derivative D6-D6-1 in a yellowish solid state was obtained.

$^1$H-NMR spectrum data of the chloroacetate derivative D6-D6-1 were as follows: $^1$H NMR (CDCl$_3$) δ (ppm): 3.40-3.80 (—CH$_2$CH$_2$O—, —OCH(CH$_2$O—)$_2$), 4.80-5.00 (—OCH$_2$C(=O)Cl); $M_n$≈25000 Da, PDI=1.02.

EXAMPLE-18

Preparation of H-Shaped Polyethylene Glycol Active Ester Derivative

Synthesis of Active Ester Derivative A1-A1-1

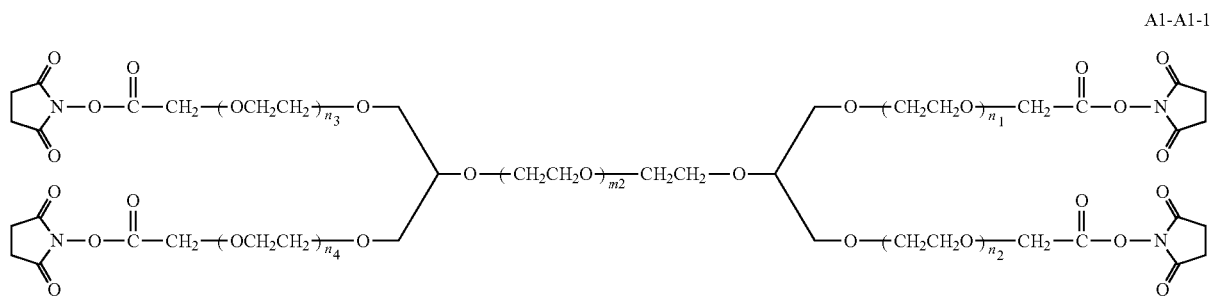

A1-A1-1

Herein, the structural design of H-shaped polyethylene glycol derivative was given as follows: $F_1=F_2=$ —CH$_2$CONHS,

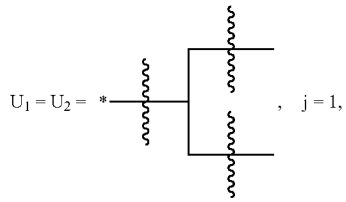

$U_1=U_2=$ *—..., j=1, $W_0$ is CH$_2$CH$_2$ and $m_1$=0. The designed total molecular weight is approximately 25000 Da, wherein, the molecular weight of four branch chains is approximately 4×5000= 20000 Da corresponding to $n_1$≈$n_2$≈$n_3$≈$n_4$≈114, and the molecular weight of the main chain is approximately 5000 Da corresponding to $m_2$≈113.

Into a dry and clean 1 L round-bottom flask, 50 g of polyethylene glycol acetic acid derivative D4-D4-1 obtained in Example-16, 100 mL of triethylamine and 36 g of N-hydroxysuccinimide (NHS) were added in sequence. Using nitrogen protection, after the addition of dichloromethane (600 mL), the whole was stirred till dissolution, thereafter 100 g of dicyclohexylcarbodiimide (DCC) dissolved in dichloromethane was added thereinto, followed by reaction at room temperature for 24 hours. The resulting mixture was filtrated to remove undissolved substances, concentrated and recrystallized from isopropanol, and then an active ester A1-A1-1 in a white solid state was obtained.

$^1$H-NMR spectrum data of the active ester A1-A1-1 were as follows: $^1$H NMR (CDCl$_3$) δ (ppm): 2.70-2.85 (—(O=) CCH$_2$CH$_2$C(=O)—), 3.40-3.80 (—CH$_2$CH$_2$O—, —OCH (CH$_2$O—)$_2$), 4.35 (—OCH$_2$C(=O)—); $M_n$≈25000 Da, PDI=1.02.

EXAMPLE-19

Preparation of H-Shaped Polyethylene Glycol Aldehyde Derivative

Synthesis of Aldehyde Derivative D5-D5-1

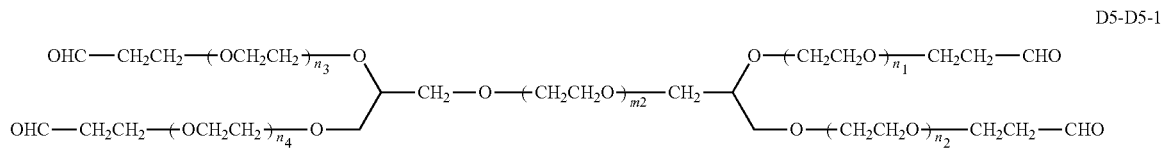

D5-D5-1

Herein, the structural design of H-shaped polyethylene glycol derivative was given as follows: $F_1=F_2=$—$CH_2CH_2CHO$,

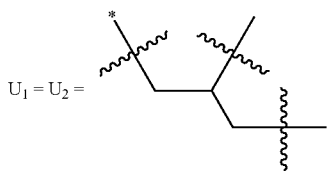

(both $U_1$ and $U_2$ are of an asymmetrical structure type,

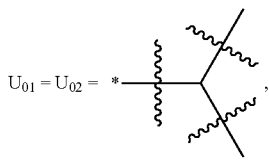

without $L_1$ and $L_3$, $L_2=L_4=CH_2$, $L_5=L_6=CH_2$), $j=1$, $W_0$ is $CH_2CH_2$ and $m_1=0$. The designed total molecular weight is approximately 25000 Da, wherein, the molecular weight of four branch chains is approximately $4\times5000=20000$ Da corresponding to $n_1\approx n_2\approx n_3\approx n_4\approx114$, and the molecular weight of the main chain is approximately 5000 Da corresponding to $m_2\approx113$.

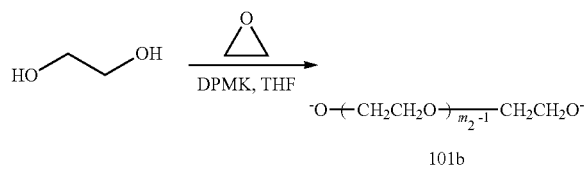

Step (a): Into a sealed reactor under an anhydrous and oxygen-free atmosphere, tetrahydrofuran (250 mL), ethylene glycol (2.532 mmol) and diphenylmethyl potassium (4.0 mmol) were added in sequence.

Step (b): After the addition of a calculated amount of ethylene oxide (580 mmol), the whole was heated step-wisely to 60° C., followed by reaction at 60° C. for 48 hours.

Step (c): After completion of the reaction, excess diphenylmethyl potassium (40 mmol) and excess compound 105 (100 mmol) were added, followed by reaction at 30° C. for 12 hours. After completion of the reaction, open the reactor. The product in the solvent was concentrated, precipitated with absolute ether at 0° C. The crystals were collected by filtration and dried, and then a polyethylene glycol intermediate 106 with terminal silyl-protected hydroxyl groups was obtained.

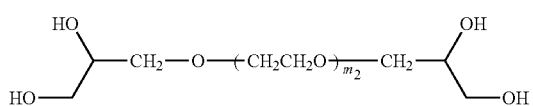

105

106

$^1$H-NMR spectrum data of the intermediate 106 were as follows: $^1$H NMR (CDCl$_3$) δ (ppm): 0.21 (—Si(CH$_3$)$_2$), 0.98 (—SiC(CH$_3$)$_3$), 3.40-3.80 (—CH$_2$CH$_2$O—, —OCH$_2$CHCH$_2$OSi—), 3.80-4.00 (—OCH$_2$CHCH$_2$OSi—); $M_n\approx$ 5000 Da, PDI=1.02.

Step (d): Into a dry and clean container, the intermediate 106 was added and then dissolved with tetrahydrofuran. After the addition of tetra-t-butyl ammonium fluoride (TBAF), the reaction was conducted overnight, and a polyethylene glycol intermediate 107 containing four unprotected hydroxyl groups was obtained.

107

$^1$H-NMR spectrum data of the intermediate 107 were as follows: $^1$H NMR (CDCl$_3$) δ (ppm): 3.40-3.60 (—OCH$_2$CHCH$_2$O—), 3.60-3.80 (—OCH$_2$CHCH$_2$O—), 3.40-3.80 (—CH$_2$CH$_2$O—); $M_n\approx$5000 Da, PDI=1.02.

Step (e): Step (a) and step (b) were repeated, then excess proton source (methanol) was added to obtain a compound H1-H1-2 (wherein $F_1=F_2=$—CH$_2$CH$_2$OH (g=0, k=1, q=0, $q_1$=1, $Z_1$=CH$_2$CH$_2$, $R_{01}$=OH).

$^1$H-NMR spectrum data of the compound H1-H1-2 were as follows: $^1$H NMR (CDCl$_3$) δ (ppm): 3.40-3.60 (—OCH(CH$_2$O—)$_2$), 3.40-3.80 (—CH$_2$CH$_2$O—); $M_n\approx$25000 Da, PDI=1.02 (with a molecular weight of $4\times5000+5000\approx25000$ Da and a molecular weight of main chain of 5000 Da).

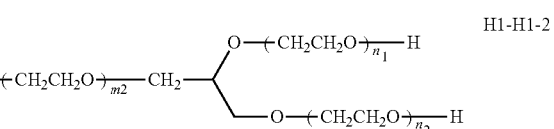

H1-H1-2

Step (f): Into a dry and clean 1 L round-bottom flask, 40 g of H-shaped polyethylene glycol H1-H1-2 and 15 g of sodium hydroxide were added in sequence. Using nitrogen protection, toluene (400 mL) was added, thereafter 6 mL of 2-(2-bromoethyl)-1,3-dioxane was added dropwisely, and subsequently the whole was heated until reflux followed by reaction for 24 hours. After completion of the reaction, 400 mL of deionized water was added for hierarchical extraction.

The aqueous phase was extracted with dichloromethane (200 mL trice), then the organic phase was collected, washed with saturated salt solutions, dried, concentrated and recrystallized, and then an H-shaped polyethylene glycol acetal intermediate D7-D7-1 in a white solid state was obtained.

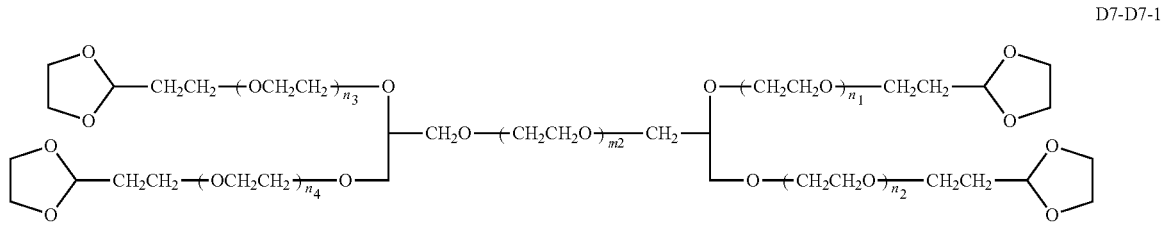

D7-D7-1

$^1$H-NMR spectrum data of the polyethylene glycol acetal intermediate D7-D7-1 were as follows: $^1$H NMR (CDCl$_3$) δ (ppm): 1.91 (—OCH$_2$CH$_2$CHO(O)—), 3.40-3.80 (—CH$_2$CH$_2$O—, —OCH(CH$_2$O—)$_2$, —OCH$_2$CH$_2$CHO (O)—), 4.89 (—OCH$_2$CH$_2$CHO(O)—); M$_n$≈25000 Da, PDI=1.02 (with a molecular weight of 4×5000+5000≈25000 Da and a molecular weight of main chain of 5000 Da).

Step (g): Into a dry and clean 1 L round-bottom flask, 40 g of polyethylene glycol acetal intermediate D7-D7-1 and 400 mL of deionized water were added in sequence. The whole was stirred till dissolution, and the solution was adjusted to pH 1.0 with HCl of 1 mol/L in an ice bath, followed by reaction at room temperature for 4 hours. After completion of the reaction, the aqueous phase was extracted with dichloromethane (200 mL trice). Then the organic phase was collected, washed with saturated salt solutions, dried, filtrated, concentrated and recrystallized, and then an H-shaped polyethylene glycol aldehyde derivative D5-D5-1 in a white solid state was obtained.

$^1$H-NMR spectrum data of the polyethylene glycol propionaldehyde derivative D5-D5-1 were as follows: $^1$H NMR (CDCl$_3$) δ (ppm): 1.91 (—OCH$_2$CH$_2$CHO), 3.40-3.80 (—CH$_2$CH$_2$O—, —OCH(CH$_2$O—)$_2$, —OCH$_2$CH$_2$CHO), 9.75 (—OCH$_2$CH$_2$CHO); M$_n$≈25000 Da, PDI=1.02.

EXAMPLE-20

Preparation of H-Shaped Polyethylene Glycol Nitrile Oxide Derivative

Synthesis of Nitrile Oxide Derivative E11-E11-1

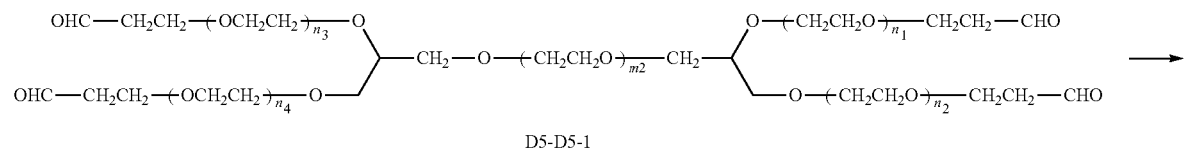

D5-D5-1

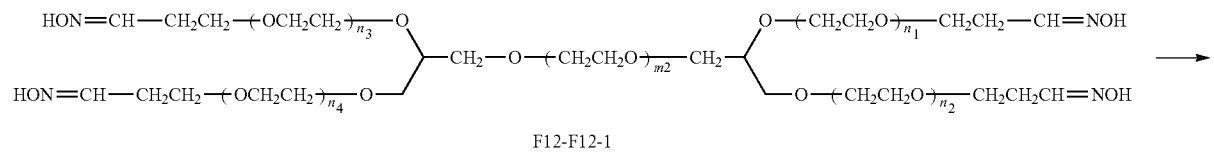

F12-F12-1

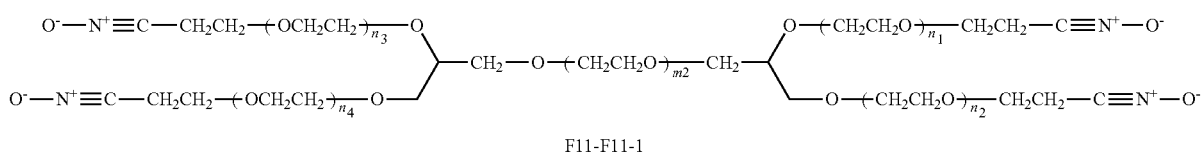

F11-F11-1

Herein, the structural design of H-shaped polyethylene glycol derivative was given as follows:

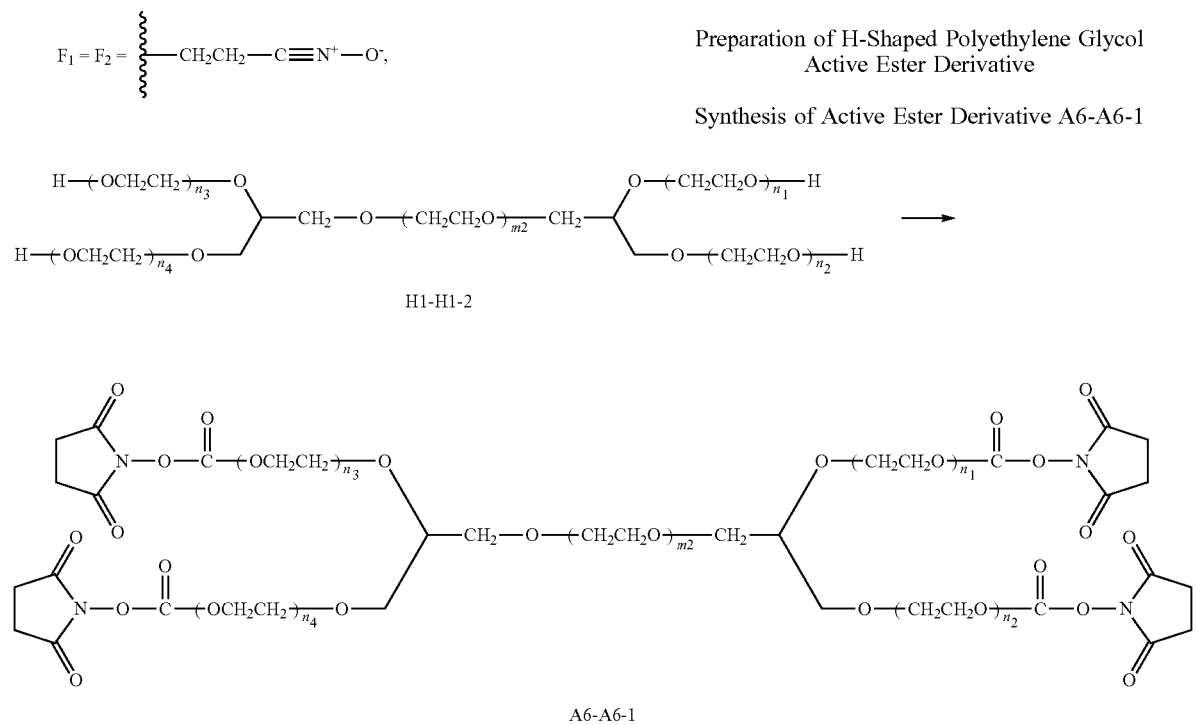

$W_0$ is $CH_2CH_2$ and $m_1=0$. The designed total molecular weight is approximately 25000 Da, wherein, the molecular weight of four branch chains is approximately 4×5000= 20000 Da corresponding to $n_1 \approx n_2 \approx n_3 \approx n_4 \approx 114$, and the molecular weight of the main chain is approximately 5000 Da corresponding to $m_2 \approx 113$. The product in this example, $M_n \approx 25000$ Da, PDI=1.02.

Into a dry and clean 50 mL round-bottom flask, the H-shaped polyethylene glycol propionaldehyde D5-D5-1 (0.4 mmol) and acetonitrile were added in sequence, and the whole was stirred till dissolution. Under nitrogen gas protection, hydroxylamine hydrochloride (16 mmol) was added, the solution was adjusted to pH 8 with sodium acetate, and then the reaction was conducted overnight. The resulting product was concentrated, precipitated with ether and to be used in the next step reaction after such rough purification.

Into a dry and clean round-bottom flask, the-above obtained crude product was dissolved with N,N-dimethyl-formamide (80 mL). With introducing nitrogen gas there-into, solid NCS (16 mmol) was added, and the reaction was conducted overnight, Thereafter, saturated sodium bicarbonate solution (80 mL) was added, followed by stirring reaction for 4 hours. The solution was diluted with large amounts of dichloromethane, washed with saturated salt solutions, dried, concentrated and precipitated with ether.

EXAMPLE-21

Preparation of H-Shaped Polyethylene Glycol Active Ester Derivative

Synthesis of Active Ester Derivative A6-A6-1

Herein, the structural design of H-shaped polyethylene glycol derivative was given as follows:

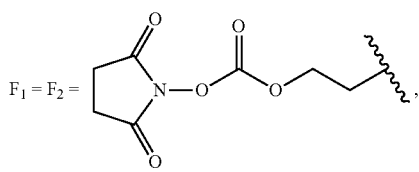

$W_0$ is $CH_2CH_2$ and $m_1=0$. The designed total molecular weight is approximately 25000 Da, wherein, the molecular weight of four branch chains is approximately 4×5000=20000 Da corresponding to $n_1 \approx n_2 \approx n_3 \approx n_4 \approx 114$, and the molecular weight of the main chain is approximately 5000 Da corresponding to $m_2 \approx 113$.

Into a dry and clean round-bottom flask, 40 g of H-shaped polyethylene glycol H1-H1-2 (treated by azeotropic removal of water with toluene) obtained in Example-20 was added. Subsequently, 500 mL of acetonitrile, 40 mL of triethylamine and 10 g of N,N'-disuccinimidyl carbonate were added thereinto, followed by reaction at room temperature for 24 hours. After completion of the reaction, the resulting product was concentrated and recrystallized from isopropanol, and then an active ester derivative A6-A6-1 in a white solid state was obtained.

$^1$H-NMR spectrum data of the active ester derivative A6-A6-1 were as follows: $^1$H NMR (CDCl$_3$) δ (ppm): 2.70-2.85 (—(O═)CCH$_2$CH$_2$C(═O)—), 3.40-3.80 (—CH$_2$CH$_2$O—, —OCH(CH$_2$O—)$_2$, —COOCHCH$_2$O—), 4.30-4.40 (—CH$_2$OCO—); $M_n$≈25000 Da, PDI=1.02.

EXAMPLE-22

Preparation of H-Shaped Polyethylene Glycol Glycidyl Ether Derivative

Synthesis of Glycidyl Ether Derivative F5-F5-1

F5-F5-1

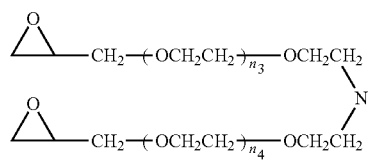

Herein, the structural design of H-shaped polyethylene glycol derivative was given as follows:

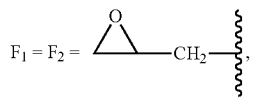

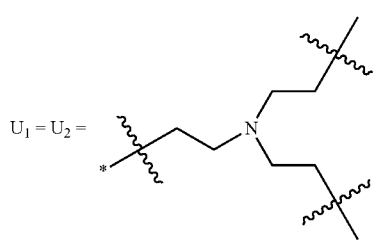

(both U$_1$ and U$_2$ are of a symmetrical structure type,

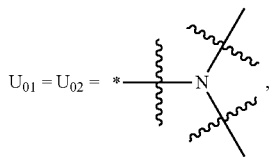

$L_1=L_2=L_3=L_4=CH_2CH_2$, $L_5=L_6=CH_2CH_2$), $W_0=CH_2CH_2$ and j=1. The designed total molecular weight is approximately 3000 Da, wherein, the molecular weight of four branch chains is approximately 4×500=2000 Da corresponding to $n_1≈n_2≈n_3≈n_4≈11$, and the molecular weight of the main chain is approximately 2×500≈1000 Da corresponding to $m_1≈m_2≈11$.

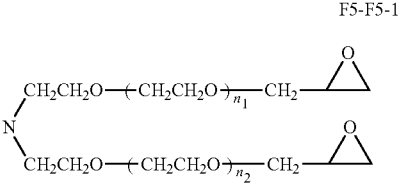

108

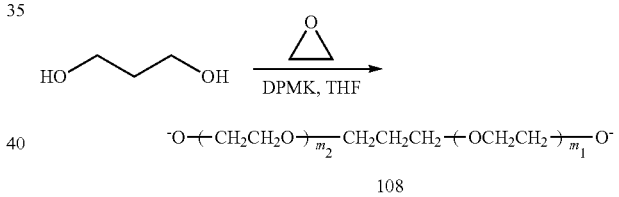

Step (a): Into a sealed reactor under an anhydrous and oxygen-free atmosphere, tetrahydrofuran (250 mL), propylene glycol (2.532 mmol) and diphenylmethyl potassium (4.0 mmol) were added in sequence;

Step (b): After a calculated amount of ethylene oxide (115 mmol) was added, the whole was heated stepwisely to 60° C., followed by reaction at 60° C. for 48 hours.

Step (c): After completion of the reaction, excess diphenylmethyl potassium (40 mmol) and excess compound 109 (100 mmol) were added, followed by reaction at 30° C. for 12 hours. After completion of the reaction, open the reactor. The product in the solvent was concentrated, precipitated with absolute ether at 0° C. The crystals were collected by filtration and dried, and a polyethylene glycol intermediate 110 with terminal silyl-protecting hydroxyl groups was obtained.

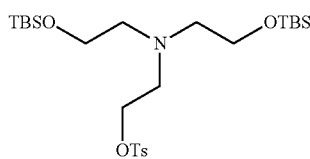

109

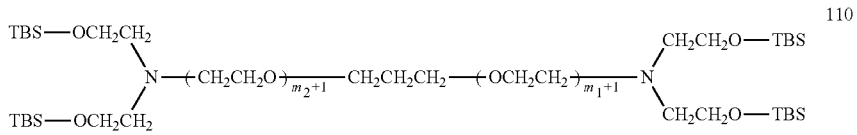

110

$^1$H-NMR spectrum data of the intermediate 110 were as follows: $^1$H NMR (CDCl$_3$) δ (ppm): 0.21 (—Si(CH$_3$)$_2$), 0.98 (—SiC(CH$_3$)$_3$), 1.60-1.70 (—CH$_2$CH$_2$CH$_2$—), 2.45-2.65 (—NCH$_2$CH$_2$O—), 3.30-3.90 (—OCH$_2$CH$_2$O—, —CH$_2$CH$_2$CH$_2$—, —NCH$_2$CH$_2$O—); M$_n$≈1000 Da, PDI=1.02.

Step (d): Into a dry and clean container, the intermediate 110 was added and then dissolved with tetrahydrofuran, followed by addition of tetra-t-butyl ammonium fluoride (TBAF), thereafter the reaction was conducted overnight, and a polyethylene glycol intermediate 111 containing four unprotected hydroxyl groups was obtained.

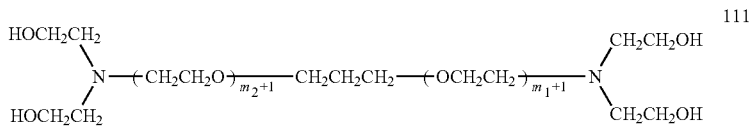

111

$^1$H-NMR spectrum data of the intermediate 111 were as follows: $^1$H NMR (CDCl$_3$) δ (ppm): 1.60-1.70 (—CH$_2$CH$_2$CH$_2$—), 2.45-2.65 (—NCH$_2$CH$_2$O—), 3.30-3.90 (—OCH$_2$CH$_2$O—, —CH$_2$CH$_2$CH$_2$—, —NCH$_2$CH$_2$O—); M$_n$≈1000 Da, PDI=1.02.

Step (e): Step (a) and step (b) were repeated, excess diphenylmethyl potassium (100 mmol) and excess epichlorohydrin (100 mmol) were added in sequence, followed by reaction at 30° C. for 12 hours. After completion of the reaction, open the reactor. The product in the solvent was concentrated, precipitated with absolute ether at 0° C. The crystals were collected by filtration and dried, and then a compound F5-F5-1 was obtained.

$^1$H-NMR spectrum data of the compound F5-F5-1 were as follows: $^1$H NMR (CDCl$_3$) δ (ppm): 1.60-1.70 (—CH$_2$CH$_2$CH$_2$—), 2.38 (—CH$_2$CH(O)CH$_2$O—), 2.45-2.65 (—NCH$_2$CH$_2$O—), 3.30-3.90 (—OCH$_2$CH$_2$O—, —CH$_2$CH$_2$CH$_2$—, —NCH$_2$CH$_2$O—, —CH$_2$CH(O)CH$_2$O—); The designed total molecular weight is approximately 3000 Da, wherein, the molecular weight of four branch chains is approximately 4×500=2000 Da corresponding to n$_1$≈n$_2$≈n$_3$≈n$_4$≈11, and the molecular weight of the main chain is approximately 2×500≈1000 Da corresponding to m$_1$≈m$_2$≈11, PDI=1.02.

In this example, an H-shaped polyethylene glycol of the same general formula was also prepared by changing the reagent amount. The designed total molecular weight is approximately 30000 Da, wherein, the molecular weight of four branch chains is approximately 4×5000=20000 Da corresponding to n$_1$≈n$_2$≈n$_3$≈n$_4$≈114, and the molecular weight of the main chain is approximately 2×5000≈10000 Da corresponding to m$_1$≈m$_2$≈114. The structure was determined by $^1$H NMR.

EXAMPLE-23

Preparation of H-Shaped Polyethylene Glycol Hydroxylamine Derivative

Synthesis of Hydroxylamine Derivative C1-C1-1

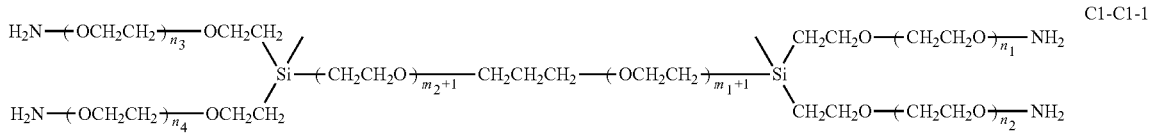

C1-C1-1

Herein, the structural design of H-shaped polyethylene glycol derivative was given as follows:

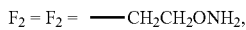

$F_2 = F_2' = $ —CH$_2$CH$_2$ONH$_2$,

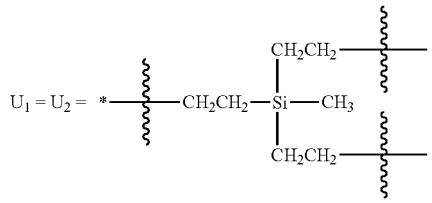

($U_1$ and $U_2$ are of a symmetrical structure type,

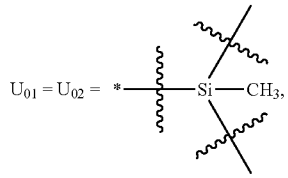

$L_1=L_3=CH_2CH_2$, $L_2=L_4=CH_2CH_2$, $L_5=L_6=CH_2CH_2$), $W_0=CH_2CH_2CH_2$ and $j=1$. The designed total molecular weight is approximately 3000 Da, wherein, the molecular weight of four branch chains is approximately 4×500=2000 Da corresponding to $n_1 \approx n_2 \approx n_3 \approx n_4 \approx 11$, and the molecular weight of the main chain is approximately 2×500≈1000 Da corresponding to $m_1 \approx m_2 \approx 11$.

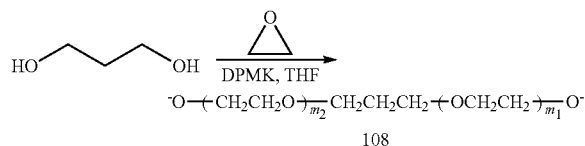

108

Step (a): Into a sealed reactor under an anhydrous and oxygen-free atmosphere, tetrahydrofuran (250 mL), propylene glycol (2.532 mmol) and diphenylmethyl potassium (4.0 mmol) were added in sequence.

Step (b): After a calculated amount of ethylene oxide (55 mmol) was added, the whole was heated stepwisely to 60° C., followed by reaction at 60° C. for 48 hours.

Step (c): After completion of the reaction, excess diphenylmethyl potassium (40 mmol) and excess compound 112 (100 mmol) were added, followed by reaction at 30° C. for 12 hours. After completion of the reaction, open the reactor. The product was concentrated by solvent evaporation, and then precipitated with absolute ether at 0° C. The crystals were collected by filtration and dried, and a polyethylene glycol intermediate 113 with terminal silyl-protected hydroxyl groups was obtained.

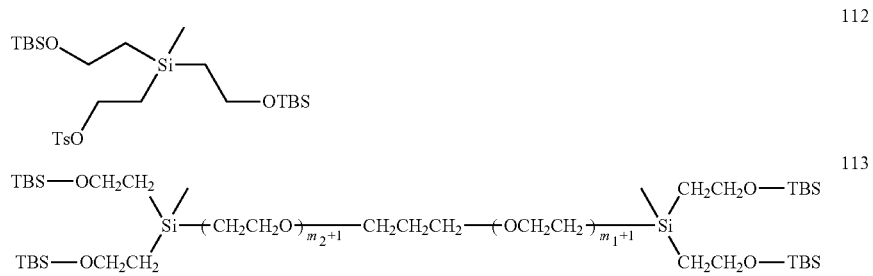

$^1$H-NMR spectrum data of the intermediate 113 were as follows: $^1$H NMR (CDCl$_3$) δ (ppm): 0-0.21 (—Si(CH$_3$), —Si(CH$_3$)$_2$), 0.70-1.00 (—SiCH$_2$CH$_2$O—, —SiC(CH$_3$)$_3$), 1.60-1.70 (—CH$_2$CH$_2$CH$_2$—), 3.30-3.90 (—OCH$_2$CH$_2$O—, —CH$_2$CH$_2$CH$_2$—, —SiCH$_2$CH$_2$O—).

Step (d): Into a dry and clean container, the intermediate 113 was added and then dissolved with tetrahydrofuran, followed by the addition of tetra-t-butyl ammonium fluoride (TBAF). Thereafter, the reaction was conducted overnight, and a polyethylene glycol intermediate containing four unprotected hydroxyl groups 114 was obtained.

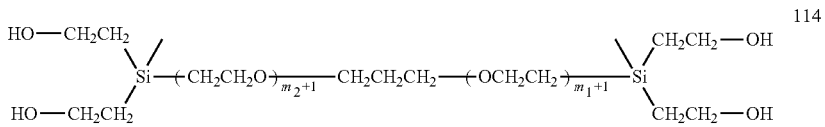

$^1$H-NMR spectrum data of the intermediate 114 were as follows: $^1$H NMR (CDCl$_3$) δ (ppm): 0-0.21 (—Si(CH$_3$)), 0.70-1.00 (—SiCH$_2$CH$_2$O—), 1.60-1.70 (—CH$_2$CH$_2$CH$_2$—), 3.30-3.90 (—OCH$_2$CH$_2$O—, —CH$_2$CH$_2$CH$_2$—, —SiCH$_2$CH$_2$O—); $M_n \approx 1000$ Da, PDI=1.02.

Step (e): Step (a) and step (b) were repeated, excess diphenylmethyl potassium (100 mmol) and excess hydroxylamine hydrochloride (100 mmol) were added in sequence, followed by reaction at 30° C. for 12 hours. After completion of the reaction, open the reactor. The product in the solvent was concentrated, precipitated with absolute ether at 0° C. The crystals were collected by filtration and dried, and a compound C1-C1-1 was obtained.

$^1$H-NMR spectrum data of the compound C1-C1-1 were as follows: $^1$H NMR (CDCl$_3$) δ (ppm): 0-0.21 (—Si(CH$_3$)), 0.70-1.00 (—SiCH$_2$CH$_2$O—), 1.60-1.70 (—CH$_2$CH$_2$CH$_2$—), 3.30-3.90 (—CH$_2$CH$_2$O—, —CH$_2$CH$_2$CH$_2$—, —SiCH$_2$CH$_2$O—, —CH$_2$CH$_2$ONH$_2$); the designed total molecular weight is approximately 3000 Da, wherein, the molecular weight of four branch chains is approximately 4×500=2000 Da corresponding to $n_1 \approx n_2 \approx n_3 \approx n_4 \approx 11$, and the molecular weight of the main chain is approximately 1000 Da corresponding to $m_1 \approx m_2 \approx 11$, PDI=1.02.

EXAMPLE-24

Preparation of H-Shaped Polyethylene Glycol Derivative with TBS-Protected Hydroxyl Groups Synthesis of Derivative with TBS-Protected Hydroxyl Groups

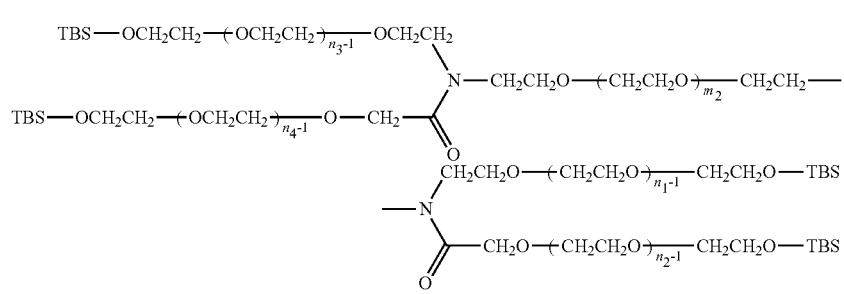

Herein, the structural design of H-shaped polyethylene glycol derivative was given as follows: $F_1=F_2=$ —CH$_2$CH$_2$OTBS,

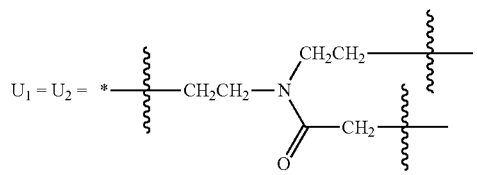

($U_1$ and $U_2$ are of an asymmetrical type,

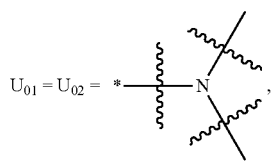

$L_1=L_3=$CH$_2$CH$_2$, $L_2=L_4=$—C(═O)CH$_2$—, $L_5=L_6=$CH$_2$CH$_2$), j=0 and $m_1=0$. The designed total molecular weight is approximately 400000 Da, wherein, the molecular weight of four branch chains is approximately 4×80000=320000 Da corresponding to $n_1 \approx n_2 \approx 1818$ and $n_3 \approx n_4 \approx 1818$, and the molecular weight of the main chain is approximately 80000 Da corresponding to $m_2 \approx 1818$.

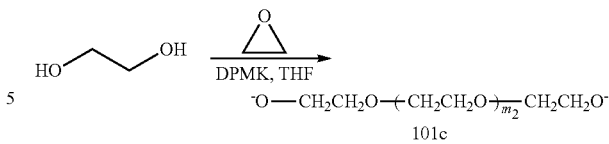

Step (a): Into a sealed reactor under an anhydrous and oxygen-free atmosphere, tetrahydrofuran (250 mL), ethylene glycol (2.532 mmol) and diphenylmethyl potassium (4.0 mmol) were added in sequence.

Step (b): After a calculated amount of ethylene oxide (9100 mmol) was added, the whole was heated stepwise to 60° C., followed by reaction at 60° C. for 48 hours.

Step (c): After completion of the reaction, excess diphenylmethyl potassium (40 mmol) and excess TsCl (100 mmol) were added, followed by reaction at 30° C. for 12 hours. After completion of the reaction, open the reactor. The product in the solvent was concentrated, precipitated with absolute ether at 0° C. The crystals were collected by filtration and dried, and a linear polyethylene glycol intermediate 115 with terminal sulfonate groups was obtained.

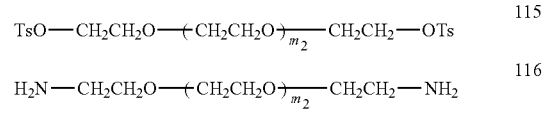

$^1$H-NMR spectrum data of the sulfonate derivative 115 were as follows: $^1$H NMR (CDCl$_3$) δ (ppm): 2.35 (CH$_3$C$_6$H$_4$SO$_2$—), 3.40-3.80 (—CH$_2$CH$_2$O—), 4.20 (—OCH$_2$CH$_2$OSO$_2$—), 7.30 (CH$_3$C$_6$H$_4$SO$_2$—), 7.80 (CH$_3$C$_6$H$_4$SO$_2$—).

Step (d): Into a dry and clean round-bottom flask, 40 g of H-shaped polyethylene glycol sulfonate 115 obtained in Example-3 and 800 mL of ammonia water (40 wt %) were added in sequence. The whole was stirred till dissolution. Thereafter, the reaction was conducted at room temperature for a week. After completion of the reaction, the resulting product was extracted with dichloromethane (200 mL trice). The organic phase was collected, washed with saturated salt solutions, dried, filtrated, concentrated and recrystallized, and then an amine derivative 116 (diamine) in a white solid state was obtained.

$^1$H-NMR spectrum data of the amine derivative 116 were as follows: $^1$H NMR (CDCl$_3$) δ (ppm): 2.70-2.85 (—OCH$_2$CH$_2$NH$_2$), 3.40-3.80 (—CH$_2$CH$_2$O—, —OCH$_2$CH$_2$NH$_2$); $M_n \approx 80000$ Da, PDI=1.02.

Step (e): Into a round-bottom flask under an anhydrous and oxygen-free atmosphere, polyethylene glycol amine derivative 116 (7.5 mmol), dichloromethane (250 mL) and triethylamine (10 mmol) were added in sequence. Then polyethylene glycol sulfonate derivative 117 (15 mmol, $M_n$=80000 Da, PDI=1.02) dissolved in dichloromethane (50 mL) was added slowly, followed by reaction at room temperature for 24 hours. The resulting product was washed by aqueous solutions, dried, concentrated and precipitated with ether, and a secondary amine intermediate 118 was obtained.

$^1$H-NMR spectrum data of the secondary amine intermediate 118 were as follows: $^1$H NMR (CDCl$_3$) δ (ppm): 0.21 (—Si(CH$_3$)$_2$), 0.98 (—SiC(CH$_3$)$_3$), 2.70-2.80 (—NHCH$_2$CH$_2$O—), 3.40-3.80 (—CH$_2$CH$_2$O—, —NHCH$_2$CH$_2$O—, —OCH$_2$CH$_2$Si—), 3.80-4.00 (—OCH$_2$CH$_2$Si—); $M_n$≈240000 Da, PDI=1.03. Wherein, $n_1$≈$n_3$.

Step (f): Into a round-bottom flask under an anhydrous and oxygen-free atmosphere, the secondary intermediate 118 (2.0 mmol), dichloromethane (250 mL) and triethylamine (10 mmol) were added in sequence, then polyethylene acyl chloride derivative 119 (5.0 mmol, $M_n$=80000 Da, PDI=1.02) dissolved in dichloromethane (50 mL) was slowly added dropwise, followed by reaction at 25° C. for 24 hours. After completion of the reaction, the product was washed by aqueous solutions, dried, concentrated and purified by an anion exchange resin, and a derivative H2-H2-2 was obtained.

$^1$H-NMR spectrum data of the compound H2-H2-2 were as follows: $^1$H NMR (CDCl$_3$) δ (ppm): 0.21 (—Si(CH$_3$)$_2$), 0.98 (—SiC(CH$_3$)$_3$), 3.25-3.45 (—NCH$_2$CH$_2$O—), 3.40-3.80 (—CH$_2$CH$_2$O—, —NCH$_2$CH$_2$O—), 3.80-4.00 (—OCH$_2$CH$_2$Si—), 4.15-4.25 (—NC(=O)CH$_2$—O—); $M_n$≈400000 Da, PDI=1.04. Wherein, $n_1$≈$n_3$≈$n_2$≈$n_4$.

Herein, the structural design of H-shaped polyethylene glycol derivative was given as follows:

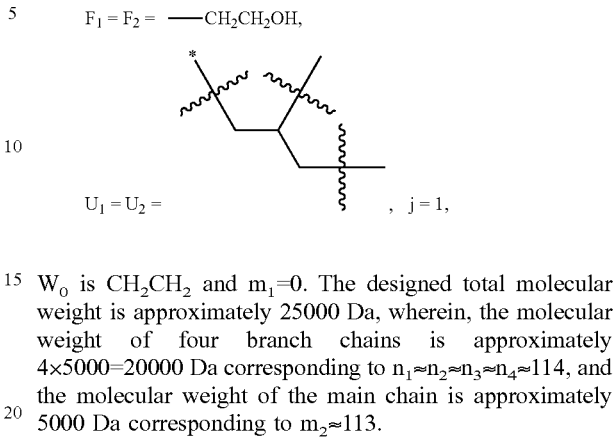

$F_1 = F_2 =$ ——CH$_2$CH$_2$OH, $U_1 = U_2 =$ , j = 1, $W_0$ is CH$_2$CH$_2$ and $m_1$=0. The designed total molecular weight is approximately 25000 Da, wherein, the molecular weight of four branch chains is approximately 4×5000=20000 Da corresponding to $n_1$≈$n_2$≈$n_3$≈$n_4$≈114, and the molecular weight of the main chain is approximately 5000 Da corresponding to $m_2$≈113.

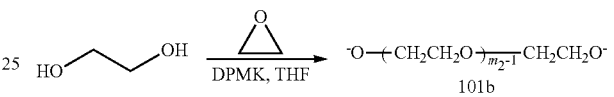

101b

Step (a): Into a sealed reactor under an anhydrous and oxygen-free atmosphere, tetrahydrofuran (250 mL), ethylene glycol (2.532 mmol) and diphenylmethyl potassium (4.0 mmol) were added in sequence.

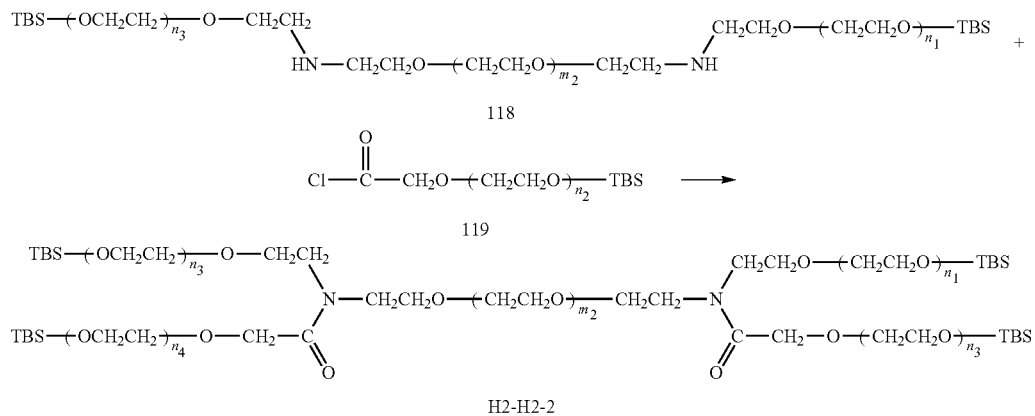

H2-H2-2

EXAMPLE-25

Preparation of Hydroxyl-Terminated H-Shaped Polyethylene Glycol Derivative

Synthesis of Hydroxyl-Terminated Derivative H1-H1-2

Step (b): After a calculated amount of ethylene oxide (570 mmol) was added, the whole was heated stepwisely to 60° C., followed by reaction at 60° C. for 48 hours.

Step (c): After completion of the reaction, excess diphenylmethyl potassium (40 mmol) and excess compound 120 (100 mmol) were added, followed by reaction at 30° C. for 12 hours. After completion of the reaction, open the reactor.

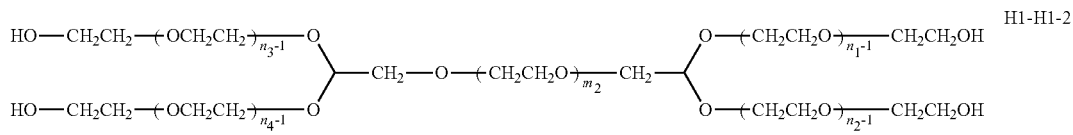

H1-H1-2

The product in the solvent was concentrated, precipitated with absolute ether at 0° C. The crystals were collected by filtration and dried, and an H-shaped polyethylene glycol intermediate 121 with silyl-protected terminal hydroxyl groups was obtained.

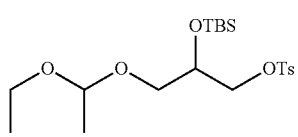

120

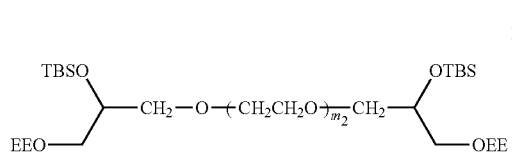

121

¹H-NMR spectrum data of the intermediate 121 were as follows: ¹H NMR (CDCl$_3$) δ (ppm): 0.21 (—Si(CH$_3$)$_2$), 0.98 (—SiC(CH$_3$)$_3$), 1.22 (—OCH$_2$CH$_3$), 1.36 (—OCH(O)CH$_3$), 3.40-3.80 (—CH$_2$CH$_2$O—, —OCH$_2$CHCH$_2$O—, OCH$_2$CH$_3$), 3.80-4.00 (—OCH$_2$CHCH$_2$O—), 4.75 (—OCHCH$_3$(OCH$_2$)); M$_n$≈5000 Da, PDI=1.02.

Step (d): Into a dry and clean container, the intermediate 121 was added and then dissolved with tetrahydrofuran, followed by the addition of tetra-t-butyl ammonium fluoride (TBAF) thereinto, thereafter the reaction was conducted overnight, and an H-shaped polyethylene glycol intermediate 122 containing two unprotected hydroxyl groups was obtained.

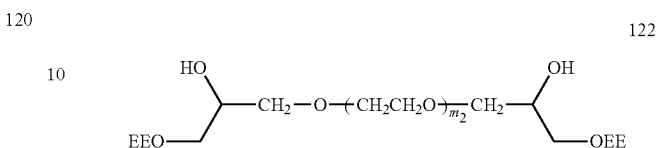

122

¹H-NMR spectrum data of the intermediate 122 were as follows: ¹H NMR (CDCl$_3$) δ (ppm): 1.22 (—OCH$_2$CH$_3$), 1.36 (—OCH(O)CH$_3$), 3.40-3.80 (—CH$_2$CH$_2$O—, —OCH$_2$CHCH$_2$O—, OCH$_2$CH$_3$), 3.80-4.00 (—OCH$_2$CHCH$_2$O—), 4.75 (—OCHCH$_3$(OCH$_2$)).

Step (e): Step (a) and step (b) were repeated, excess diphenylmethyl potassium (40 mmol) and excess TBSCl (100 mmol) were added in sequence, followed by reaction at 30° C. for 12 hours. After completion of the reaction, open the reactor. The product in the solvent was concentrated, precipitated with absolute ether at 0° C. The crystals were collected by filtration and dried, and a polyethylene glycol intermediate 123, wherein terminal hydroxyl groups were protected with silyl ether groups was obtained.

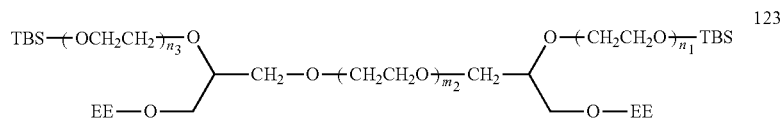

123

¹H-NMR spectrum data of the intermediate 123 were as follows: ¹H NMR (CDCl$_3$) δ (ppm): 0.21 (—Si(CH$_3$)$_2$), 0.98 (—SiC(CH$_3$)$_3$), 1.22 (—OCH$_2$CH$_3$), 1.36 (—OCH(O)CH$_3$), 3.40-3.80 (—CH$_2$CH$_2$O—, OCH$_2$CH$_3$, —OCH$_2$CHCH$_2$O—), 3.80-4.00 (—OCH$_2$CHCH$_2$O—, —OCH$_2$CH$_2$OSi—), 4.75 (—OCHCH$_3$(OCH$_2$)).

Step (f): Into a dry and clean container, the polyethylene glycol intermediate 123 was added and then dissolved with methanol. The reaction solution was adjusted to pH 3.5 with the addition of hydrochloric acid (1 M), followed by reaction for 4 hours, and a polyethylene glycol intermediate 124 containing two telechelically located unprotected hydroxyl groups was obtained.

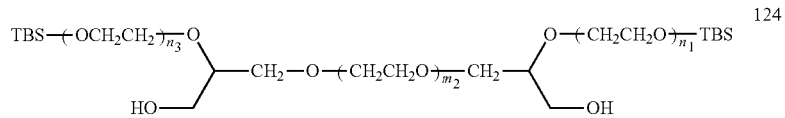

124

¹H-NMR spectrum data of the intermediate 124 were as follows: ¹H NMR (CDCl$_3$) δ (ppm): 0.21 (—Si(CH$_3$)$_2$), 0.98 (—SiC(CH$_3$)$_3$), 3.15-3.35 (—OCH$_2$CHCH$_2$O—), 3.40-3.80 (—CH$_2$CH$_2$O—, —OCH$_2$CHCH$_2$O—), 3.80-4.00 (—OCH$_2$CH$_2$OSi—); M$_n$≈15000 Da, PDI=1.02.

Step (g): Step (a) and step (b) were repeated, then excess proton source (methanol) was added, and a compound 125 was obtained.

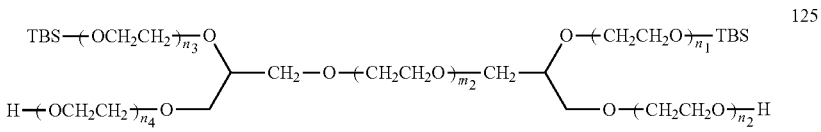

125

$^1$H-NMR spectrum data of the intermediate 125 were as follows: $^1$H NMR (CDCl$_3$) δ (ppm): 0.21 (—Si(CH$_3$)$_2$), 0.98 (—SiC(CH$_3$)$_3$), 3.40-3.80 (—CH$_2$CH$_2$O—, —OCH (CH$_2$O—)$_2$, —OCH$_2$CH$_2$OSi—), 3.80-4.00 (—OCH$_2$CH$_2$OSi—); $M_n$≈25000 Da, PDI=1.02.

Step (h): Into a dry and clean container, the intermediate 125 was added and then dissolved with tetrahydrofuran, followed by the addition of tetra-t-butyl ammonium fluoride (TBAF), thereafter the reaction was conducted overnight, and an H-shaped polyethylene glycol compound H1-H1-2 containing four unprotected hydroxyl groups was obtained.

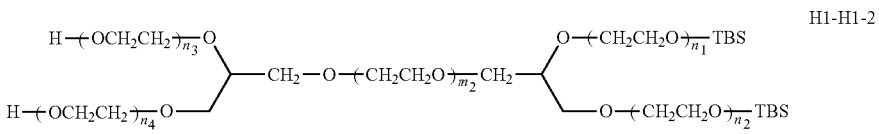

H1-H1-2

$^1$H-NMR spectrum data of the compound H1-H1-2 were as follows: $^1$H NMR (CDCl$_3$) δ (ppm): 3.40-3.80 (—CH$_2$CH$_2$O—, —OCH(CH$_2$O—); $M_n$≈25000 Da, PDI=1.02 (with a molecular weight of 4×5000+5000≈25000 and a molecular weight of main chain of 5000 Da).

EXAMPLE-26

Preparation of H-Shaped Polyethylene Glycol Derivative with Terminal Hydroxyl Groups Synthesis of Derivative H1-H2-1 with Terminal Hydroxyl Groups

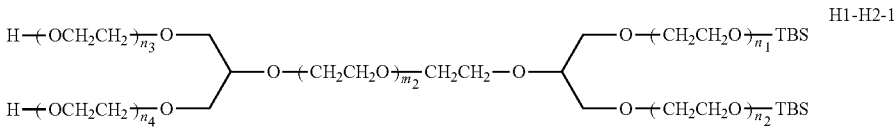

H1-H2-1

Herein, the structural design of H-shaped polyethylene glycol derivative was given as follows: $F_1$=—CH$_2$CH$_2$OTBS (g=0, k=1, q=0, q$_1$=1, Z$_1$=CH$_2$CH$_2$, R$_{01}$=OPG$_4$, PG$_4$ is TBS), $F_2$=—CH$_2$CH$_2$OH (g=0, k=1, q=0, q$_1$=1, Z$_1$=CH$_2$CH$_2$, R$_{01}$=OH),

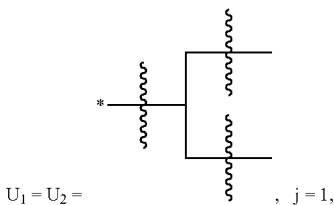

$U_1 = U_2 =$ , j=1, $W_0$ is —CH$_2$CH$_2$ and m$_1$=0. The designed total molecular weight is approximately 60000 Da, wherein, the molecular weight of four branch chains is approximately 2×5000+2× 20000=50000 Da corresponding to n$_1$≈n$_2$≈114, n$_3$≈n$_4$≈455, and the molecular weight of the main chain is approximately 10000 Da corresponding to m$_2$≈227.

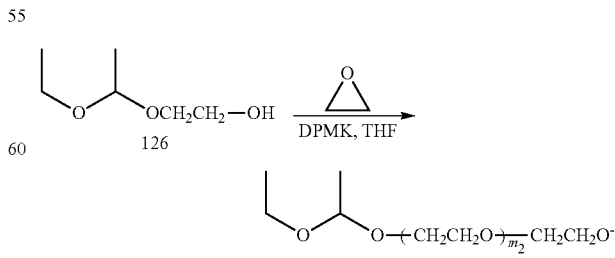

126

127

Step (a): Into a sealed reactor under an anhydrous and oxygen-free atmosphere, tetrahydrofuran (125 mL), EE-monoprotected ethylene glycol 126 (2.5 mmol) and diphenylmethyl potassium (2.0 mmol) were added in sequence.

Step (b): After a calculated amount of ethylene oxide (1100 mmol) was added, the whole was heated stepwisely to 60° C., followed by reaction at 60° C. for 48 hours.

Step (c): After completion of the reaction, excess diphenylmethyl potassium (20 mmol) and excess compound 102 (50 mmol) were added in sequence, followed by reaction at 30° C. for 12 hours. After completion of the reaction, open the reactor. The product in the solvent was concentrated and then precipitated with absolute ether at 0° C. The crystals were collected by filtration and dried, and a Y-shaped polyethylene glycol intermediate 128 was obtained, wherein two terminal hydroxyl groups were protected with silyl groups and one terminal hydroxyl group was protected with EE groups (i.e., 1-ethoxyethyl groups).

$^1$H-NMR spectrum data of the intermediate 128 were as follows: $^1$H NMR (CDCl$_3$) δ (ppm): 0.21 (—Si(CH$_3$)$_2$), 0.98 (—SiC(CH$_3$)$_3$), 1.22 (—OCH$_2$CH$_3$), 1.36 (—OCH(O)CH$_3$), 2.90-3.00 (—OCH(CH$_2$O—)$_2$), 3.40-3.80 (—CH$_2$CH$_2$O—, OCH$_2$CH$_3$), 3.90-4.00 (—OCH(CH$_2$O—)$_2$), 4.75 (—OCHCH$_3$(OCH$_2$)); M$_n$≈10000 Da, PDI=1.02.

Step (d): Into a dry and clean container, the intermediate 128 was added and then dissolved with tetrahydrofuran, followed by the addition of tetra-t-butyl ammonium fluoride (TBAF), thereafter the reaction was conducted overnight, and a polyethylene glycol intermediate 129 containing two unprotected hydroxyl groups was obtained.

$^1$H-NMR spectrum data of the intermediate 129 were as follows: $^1$H NMR (CDCl$_3$) δ (ppm): 1.22 (—OCH$_2$CH$_3$), 1.36 (—OCH(O)CH$_3$), 2.90-3.00 (—OCH(CH$_2$O—)$_2$), 3.40-3.80 (—CH$_2$CH$_2$O—, OCH$_2$CH$_3$, —OCH(CH$_2$O—)$_2$), 4.75 (—OCHCH$_3$(OCH$_2$)); M$_n$≈10000 Da, PDI=1.02.

Step (e): Step (a) and step (b) were repeated, then excess proton source (DPMK) was added, followed by the addition of TBSCl, and a compound 130 was obtained.

130

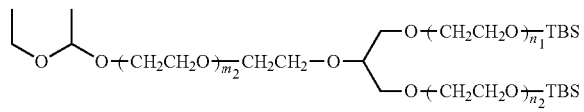

$^1$H-NMR spectrum data of the intermediate 130 were as follows: $^1$H NMR (CDCl$_3$) δ (ppm): 0.21 (—Si(CH$_3$)$_2$), 0.98 (—SiC(CH$_3$)$_3$), 1.22 (—OCH$_2$CH$_3$), 1.36 (—OCH(O)CH$_3$), 3.40-3.80 (—CH$_2$CH$_2$O—, —OCH$_2$CH$_2$OSi—, OCH$_2$CH$_3$, —OCH(CH$_2$O—)$_2$), 3.80-4.00 (—OCH$_2$CH$_2$OSi—), 4.75 (—OCHCH$_3$(OCH$_2$)); M$_n$≈20000 Da, PDI=1.02.

Step (f): Into a dry and clean container, the Y-shaped polyethylene glycol 130 was added and then dissolved with methanol. The reaction solution was added with hydrochloric acid (1 M) until pH 3.5, followed by reaction for 4 hours, and a Y-shaped polyethylene glycol intermediate 131 containing an unprotected hydroxyl group was obtained.

$^1$H-NMR spectrum data of the intermediate 131 were as follows: $^1$H NMR (CDCl$_3$) δ (ppm): 0.21 (—Si(CH$_3$)$_2$), 0.98 (—SiC(CH$_3$)$_3$), 3.40-3.80 (—CH$_2$CH$_2$O—, —OCH$_2$CH$_2$OSi—, —OCH(CH$_2$O—)$_2$), 3.80-4.00 (—OCH$_2$CH$_2$OSi—); M$_n$≈20000 Da, PDI=1.02.

Step (g): Into a solution of tetrahydrofuran, the intermediate 131 (2.5 mmol), excess diphenylmethyl potassium (40 mmol) and excess compound 132 (100 mmol) were added in sequence, followed by reaction at 30° C. for 12 hours. After completion of the reaction, open the reactor. The product in the solvent was concentrated, precipitated with absolute ether at 0° C. The crystals were collected by filtration and dried, and a polyethylene glycol intermediate 133 was obtained, wherein two terminal hydroxyl groups were protected with silyl groups and two terminal hydroxyl groups were protected with EE.

132

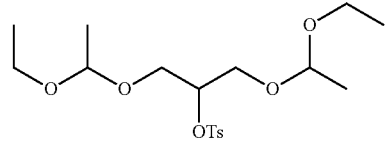

133

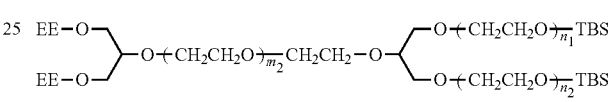

$^1$H-NMR spectrum data of the compound 133 were as follows: $^1$H NMR (CDCl$_3$) δ (ppm): 0.21 (—Si(CH$_3$)$_2$), 0.98 (—SiC(CH$_3$)$_3$), 1.22 (—OCH$_2$CH$_3$), 1.36 (—OCH(O)CH$_3$), 3.40-3.80 (—CH$_2$CH$_2$O—, —OCH$_2$CH$_2$OSi—, OCH$_2$CH$_3$, —OCH(CH$_2$O—)$_2$), 3.80-4.00 (—OCH$_2$CH$_2$OSi—), 4.75 (—OCHCH$_3$(OCH$_2$)); M$_n$≈50000 Da, PDI=1.02.

Step (h): Step (f), step (a) and step (b) were repeated to remove EE protection and a polyethylene glycol intermediate containing two unprotected hydroxyl groups was obtained. After completion of deprotonation, the polymerization of ethylene oxide was initiated, and an H-shaped polyethylene glycol compound H1-H2-1 with two terminal silyl-protected hydroxyl groups was obtained.

$^1$H-NMR spectrum data of the compound H1-H2-1 were as follows: $^1$H NMR (CDCl$_3$) δ (ppm): 0.21 (—Si(CH$_3$)$_2$), 0.98 (—SiC(CH$_3$)$_3$), 3.40-3.80 (—CH$_2$CH$_2$O—, —OCH$_2$CH$_2$OSi—, —OCH(CH$_2$O—)$_2$,), 3.80-4.00 (—OCH$_2$CH$_2$OSi—); M$_n$≈60000 Da, PDI=1.02.

EXAMPLE-27

Preparation of H-Shaped Polyethylene Glycol Derivative

Synthesis of Acrylate-Methacrylate Derivative E2-E3-1

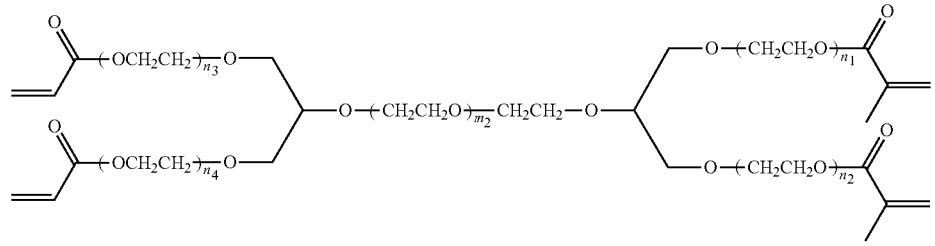

Herein, the structural design of H-shaped polyethylene glycol derivative was given as follows: $F_1$ is —COC($CH_3$)=$CH_2$, $F_2$ is —COCH=$CH_2$,

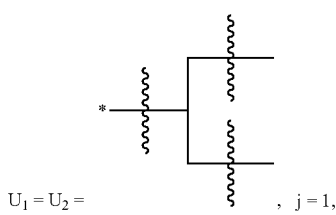

$U_1 = U_2 =$ , $j = 1$, $W_0$ is —$CH_2CH_2$— and $m_1=0$. The designed total molecular weight is approximately 60000 Da, wherein, the molecular weight of four branch chains is approximately $2\times5000+2\times20000=50000$ Da corresponding to $n_1 \approx n_2 \approx 114$, $n_3 \approx n_4 \approx 455$, and the molecular weight of the main chain is approximately 10000 Da corresponding to $m_2 \approx 227$.

Step (a): Into a dry and clean 1 L round-bottom flask, 10 g of polyethylene glycol compound containing two unprotected hydroxyl groups H1-H2-1 (treated by azeotropic removal of water with toluene), 10 mL of triethylamine and 5 g of acrylic acid were added. Using nitrogen protection, anhydrous dichloromethane (200 mL) was added, and the whole was stirred until all were dissolved. Then 20 g of dicyclohexylcarbodiimide (DCC) was added thereinto, followed by reaction at room temperature for 24 hours. The resulting mixture was filtrated to remove undissolved substances, concentrated, and recrystallized from isopropanol, and an H-shaped polyethylene glycol compound E2-H2-1 in a white solid state was obtained.

E2-H2-1

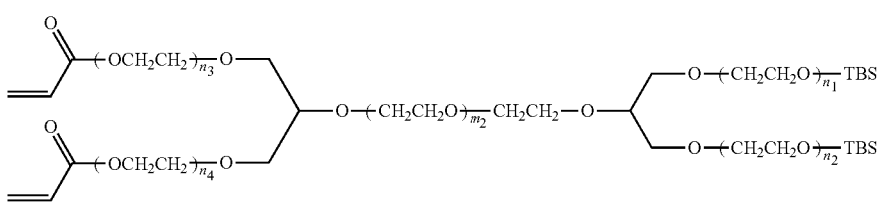

$^1$H-NMR spectrum data of the intermediate E2-H2-1 were as follows: $^1$H NMR (CDCl$_3$) δ (ppm): 0.21 (—Si(CH$_3$)$_2$), 0.98 (—SiC(CH$_3$)$_3$), 3.40-3.80 (—CH$_2$CH$_2$O—, —OCH$_2$CH$_2$OSi—, —OCH(CH$_2$O—)$_2$, COOCH$_2$CH$_2$), 3.80-4.00 (—OCH$_2$CH$_2$OSi—), 4.20-4.40 (COOCH$_2$CH$_2$), 5.80-6.10 (COCH=CH$_2$, COCH=CH$_2$), 6.30-6.50 (COCH=CH$_2$).

Step (b): Into a dry and clean container, the intermediate E2-H2-1 was added and then dissolved with tetrahydrofuran, followed by the addition of tetra-t-butyl ammonium fluoride (TBAF), thereafter the reaction was conducted overnight, and an H-shaped polyethylene glycol intermediate E2-H1-1 containing two unprotected hydroxyl groups was obtained.

E2-H1-1

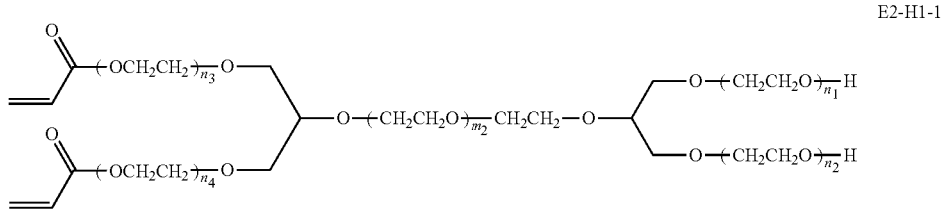

Step (c): Into a dry and clean 1 L round-bottom flask, 10 g of polyethylene glycol intermediate E2-H1-1 (treated by azeotropic removal of water with toluene), 10 mL of triethylamine and 5 g of acrylic acid were added. Using nitrogen protection, anhydrous dichloromethane (200 mL) was added, and the whole was stirred till all were dissolved. Then 20 g of dicyclohexylcarbodiimide (DCC) was added thereinto, followed by reaction at room temperature for 24 hours. The resulting mixture was filtrated to remove undissolved substances, concentrated and recrystallized from isopropanol, and an H-shaped polyethylene glycol compound E2-E3-1 in a white solid state was obtained.

$^1$H-NMR spectrum data of the compound E2-E3-1 were as follows: $^1$H NMR (CDCl$_3$) δ (ppm): 1.80-1.90 (COC(CH3)=CH$_2$), 3.40-3.80 (—CH$_2$CH$_2$O—, —OCH(CH$_2$O—)$_2$, COOCH$_2$CH$_2$), 4.20-4.40 (COOCH$_2$CH$_2$), 5.40-5.60 (COCH=CH$_2$), 6.20-6.30 (COCH=CH$_2$); $M_n$≈60000 Da, PDI=1.02.

EXAMPLE-28

Preparation of H-Shaped Polyethylene Glycol Derivative

Synthesis of Derivative G7-H2-1

Herein, the structural design of H-shaped polyethylene glycol derivative was given as follows:

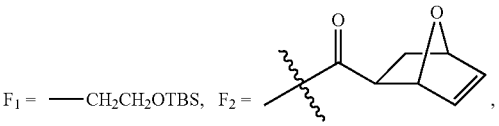

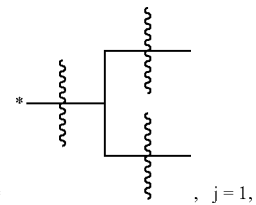

$W_0$ is —CH$_2$CH$_2$— and $m_1$=0. The designed total molecular weight is approximately 60000 Da, wherein, the molecular weight of four branch chains is approximately 2×5000+2×20000=50000 Da corresponding to $n_1$≈$n_2$≈114, $n_3$≈$n_4$≈455, and the molecular weight of the main chain is approximately 10000 Da corresponding to $m_2$≈227.

G7-H2-1

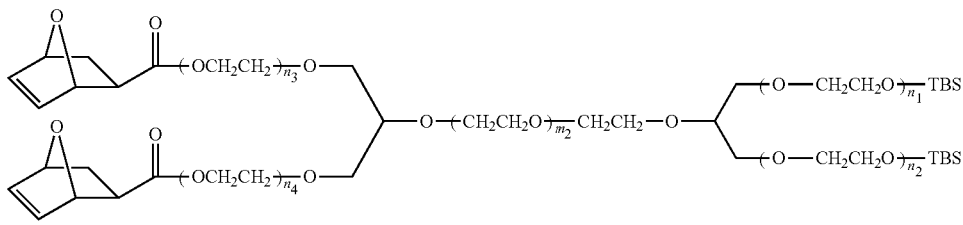

Into a dry and clean 500 mL round-bottom flask, the H-shaped polyethylene glycol acrylate derivative E2-H2-1 and acetonitrile were added in sequence. The whole was stirred until dissolution, then furan/acetonitrile solution (100 mL) was slowly added dropwisely, and thereafter boron trifluoride-diethyl etherate was added dropwisely, followed by reaction at room temperature for 3 days. After completion of the reaction, the resulting product was concentrated and recrystallized from isopropanol, and a compound G7-H2-1 was obtained.

$^1$H-NMR spectrum data of the compound G7-H2-1 were as follows: $^1$H NMR (CDCl$_3$) δ (ppm): 0.21 (—Si(CH$_3$)$_2$), 0.98 (—SiC(CH$_3$)$_3$), 2.00-2.80 (—CHCHCH= CHCHCH$_2$—), 3.40-3.80 (—CH$_2$CH$_2$O—, —OCH(CH$_2$O—)$_2$, —COOCH$_2$CH$_2$), 3.90-4.00 (—OCH(CH$_2$O—)$_2$), 4.20-4.40 (—COOCH$_2$CH$_2$—), 4.90-5.15 (—CHCHCH= CHCHCH$_2$—), 4.30-4.65 (—CHCHCH=CHCHCH$_2$—), 5.60-5.90 (—CHCHCH=CHCHCH$_2$—); $M_n$≈60000 Da, PDI=1.02.

EXAMPLE-29

Preparation of H-Shaped Polyethylene Glycol Derivative

Synthesis of Derivative F1-H2-1

F1-H2-1

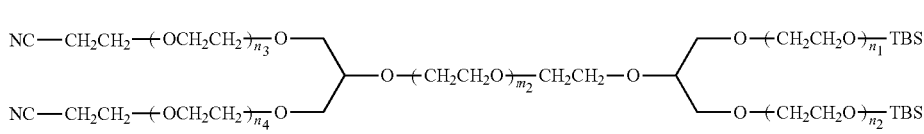

Herein, the structural design of H-shaped polyethylene glycol derivative was given as follows: $F_1=$ —$CH_2CH_2OTBS$, $F_2=$—$CH_2CH_2CN$,

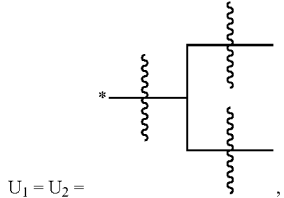

$U_1 = U_2 =$ , $j=1$, $W_0$ is —$CH_2CH_2$— and $m_1=0$. The designed total molecular weight is approximately 60000 Da, wherein, the molecular weight of four branch chains is approximately $2\times5000+2\times20000=50000$ Da corresponding to $n_1\approx n_2\approx 114$, $n_3\approx n_4\approx 455$, and the molecular weight of the main chain is approximately 10000 Da corresponding to $m_2\approx 227$.

Into a dry and clean 1 L round-bottom flask, 40 g of H-shaped polyethylene glycol H1-H2-1 was added. Using nitrogen protection, 500 mL of 1,4-dioxane was added, and the whole was stirred till dissolution. 5 g of 50% potassium hydroxide was added in an ice bath, and then acrylonitrile was added dropwisely, followed by reaction at room temperature for 24 hours. After completion of the reaction, the solution was adjusted to pH 7 with hydrochloric acid (1 M) and was concentrated to remove 1,4-dioxane. The product was added with 400 mL of deionized water, and then the aqueous phase was washed with dichloromethane (200 mL trice). The organic phase was collected, washed with saturated salt solutions, dried with anhydrous sodium sulfate, filtrated, concentrated and precipitated, and a derivative (F1-H2-1) was obtained.

$^1$H-NMR spectrum data of the compound F1-H2-1 were as follows: $^1$H NMR (CDCl$_3$) δ (ppm): 0.21 (—Si(CH$_3$)$_2$), 0.98 (—SiC(CH$_3$)$_3$), 2.60 (—CH$_2$CH$_2$CN), 3.40-3.80 (—CH$_2$CH$_2$O—, —OCH(CH$_2$O—)$_2$, —OCH$_2$CH$_2$CN)); $M_n\approx 60000$ Da, PDI=1.02.

EXAMPLE-30

Preparation of H-Shaped Polyethylene Glycol Ester Derivative

Synthesis of Carboxylate Derivative D11-H2-1

Herein, the structural design of H-shaped polyethylene glycol derivative was given as follows: $F_1=$ —$CH_2CH_2OTBS$, $F_2=$—$CH_2CH_2CN$,

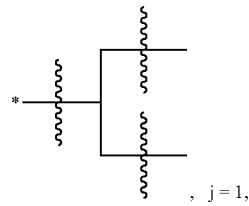

$U_1 = U_2 =$ , $j=1$, $W_0$ is —$CH_2CH_2$— and $m_1=0$. The designed total molecular weight is approximately 60000 Da, wherein, the molecular weight of four branch chains is approximately $2\times5000+2\times20000=50000$ Da corresponding to $n_1\approx n_2\approx 114$, $n_3\approx n_4\approx 455$, and the molecular weight of the main chain is approximately 10000 Da corresponding to $m_2\approx 227$.

Into a dry and clean 1 L round-bottom flask, 0.32 g of sodium hydride (60 wt %, in oil) was added. Using nitrogen protection, 400 mL of anhydrous tetrahydrofuran was added, and 40 g of H-shaped polyethylene glycol H1-H2-1 (treated by azeotropic removal of water with toluene) dissolved in the tetrahydrofuran was slowly added dropwisely in an ice bath, followed by stirring at room temperature for 3 hours, then 2.2 mL of ethyl bromoacetate was added, followed by reaction at room temperature for 24 hours. After completion of the reaction, a small amount of saturated ammonium chloride was added to quench the reaction. The product in the solvent was concentrated, and added with 400 mL of dichloromethane. The organic phase was washed with saturated salt solutions (100 mL trice), dried, concentrated and recrystallized from isopropanol, and a polyethylene glycol carboxylate derivative D11-H2-1 in a white solid state was obtained.

$^1$H-NMR spectrum data of the carboxylate compound D11-H2-1 were as follows: $^1$H NMR (CDCl$_3$) δ (ppm): 0.21 (—Si(CH$_3$)$_2$), 0.98 (—SiC(CH$_3$)$_3$), 1.31 (COOCH$_2$CH$_3$), 3.40-3.80 (—CH$_2$CH$_2$O—, —OCH$_2$CH$_2$OSi—, —OCH (CH$_2$O—)$_2$, 3.80-4.00 (—OCH$_2$CH$_2$OSi—), 4.00-4.40 (COCH$_2$O, COOCH$_2$CH$_3$); $M_n\approx 60000$ Da, PDI=1.02.

D11-H2-1

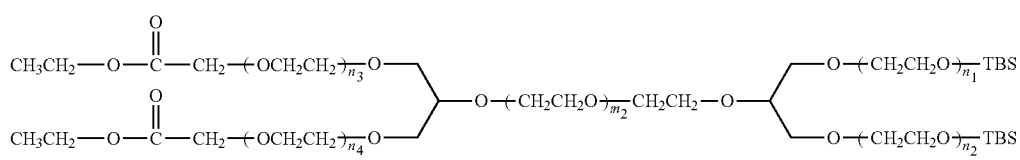

EXAMPLE-31

Preparation of H-Shaped Polyethylene Glycol Derivative

Synthesis of Hydrazide Derivative D2-H2-1

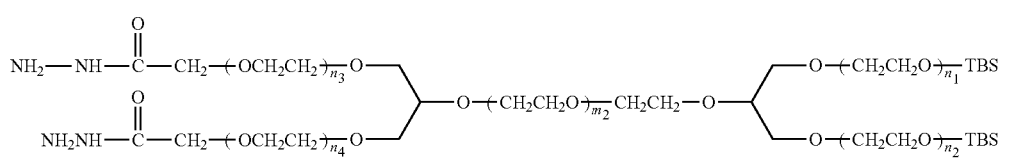

D2-H2-1

Herein, the structural design of H-shaped polyethylene glycol derivative was given as follows: $F_1$=—$CH_2CH_2OTBS$, $F_2$=—$CH_2CONHNH_2$,

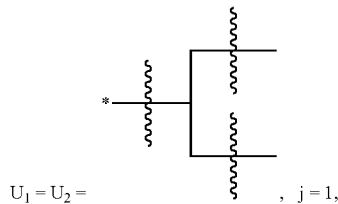

$U_1 = U_2 = $ , $j = 1$, $W_0$ is —$CH_2CH_2$— and $m_1=0$. The designed total molecular weight is approximately 60000 Da, wherein, the molecular weight of four branch chains is approximately 2×5000+2×20000=50000 Da corresponding to $n_1 \approx n_2 \approx 114$, $n_3 \approx n_4 \approx 455$, and the molecular weight of the main chain is approximately 10000 Da corresponding to $m_2 \approx 227$.

Into a dry and clean 500 mL round-bottom flask, 40 g of H-shaped polyethylene glycol carboxylate D11-H2-1 and 200 mL of 80% hydrazine hydrate were added in sequence. The whole was stirred till dissolution. Thereafter, the reaction was conducted at room temperature for 24 hours. After completion of the reaction, 200 mL of deionized water was added, and the mixture was extracted with dichloromethane (100 mL trice). The organic phase was collected, washed with saturated salt solutions, dried, filtrated, concentrated and recrystallized, and a hydrazide compound D2-H2-1 was obtained.

$^1$H-NMR spectrum data of the hydrazide compound D2-H2-1 were as follows: $^1$H NMR (CDCl$_3$) δ (ppm): 0.21 (—Si(CH$_3$)$_2$), 0.98 (—SiC(CH$_3$)$_3$), 2.21 (—OCH$_2$CONH$_2$NH$_2$) 3.40-3.80 (—CH$_2$CH$_2$O—, —OCH(CH$_2$O—)$_2$), 4.26 (—OCH$_2$CONHNH$_2$); $M_n \approx 60000$ Da, PDI=1.02.

EXAMPLE-32

Preparation of H-Shaped Polyethylene Glycol Amide Derivative

Synthesis of Amide Derivative D1-H2-1

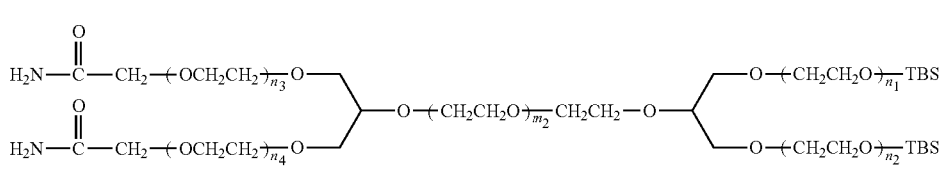

D1-H2-1

Herein, the structural design of H-shaped polyethylene glycol derivative was given as follows: $F_1$=—$CH_2CH_2OTBS$, $F_2$=—$CH_2CONH_2$,

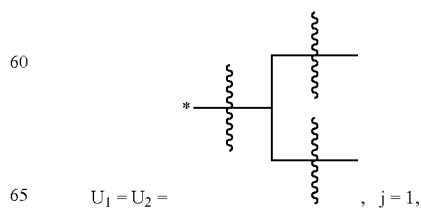

$U_1 = U_2 = $ , $j = 1$, $W_0$ is —$CH_2CH_2$— and $m_1$=0. The designed total molecular weight is approximately 60000 Da, wherein, the molecular weight of four branch chains is approximately 2×5000+2×20000=50000 Da corresponding to $n_1 \approx n_2 \approx 114$, $n_3 \approx n_4 \approx 455$, and the molecular weight of the main chain is approximately 10000 Da corresponding to $m_2 \approx 227$.

Into a dry and clean 500 mL high-pressure reactor, 40 g of H-shaped polyethylene glycol carboxylate D11-H2-1 and 200 mL of 34% ammonia water were added in sequence. The whole was stirred till dissolution. Thereafter, the reaction was conducted at 80° C. for 24 hours. After completion of the reaction, 200 mL of deionized water was added, and the solution was extracted with dichloromethane (100 mL trice). The organic phase was collected, washed with saturated salt solutions, dried, filtrated, concentrated and recrystallized, and an amide compound D1-H2-1 in a white solid state was obtained.

$^1$H-NMR spectrum data of the amide compound D1-H2-1 were as follows: $^1$H NMR (CDCl$_3$) δ (ppm): 0.21 (—Si(CH$_3$)$_2$), 0.98 (—SiC(CH$_3$)$_3$), 3.40-3.80 (—CH$_2$CH$_2$O—, —OCH(CH$_2$O—)$_2$), 4.30 (—OCH$_2$CONH$_2$); $M_n \approx 60000$ Da, PDI=1.02.

EXAMPLE-33

Preparation of H-Shaped Polyethylene Glycol Carboxylic Acid Derivative

Synthesis of Carboxylic Acid Derivative D4-H2-1

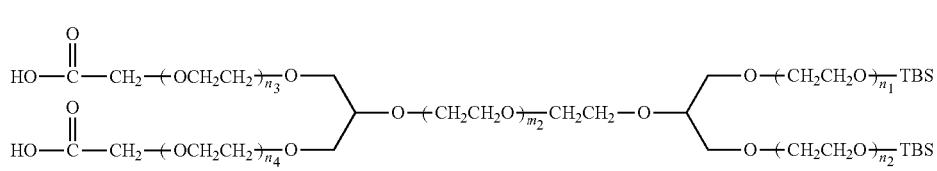

Herein, the structural design of H-shaped polyethylene glycol derivative was given as follows: $F_1$=—CH$_2$CH$_2$OTBS, $F_2$=—CH$_2$COOH,

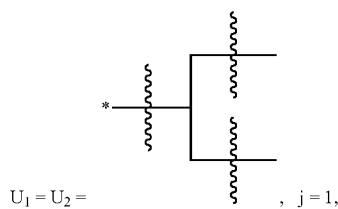

$U_1 = U_2 = $ , j = 1, $W_0$ is —$CH_2CH_2$— and $m_1$=0. The designed total molecular weight is approximately 60000 Da, wherein, the molecular weight of four branch chains is approximately 2×5000+2×20000=50000 Da corresponding to $n_1 \approx n_2 \approx 114$, $n_3 \approx n_4 \approx 455$, and the molecular weight of the main chain is approximately 10000 Da corresponding to $m_2 \approx 227$.

Into a dry and clean 500 mL high-pressure reactor, 40 g of H-shaped polyethylene glycol amide derivative D1-H2-1 and 200 mL of sodium hydroxide solution (1 mol/L) were added in sequence. The whole was stirred till dissolution. Thereafter, the reaction was conducted at 80° C. for 24 hours, and acidified with HCl (3 mol/L) until pH 3. The aqueous phase was extracted with dichloromethane (100 mL trice), then the organic phase was collected, washed with saturated salt solutions, dried, filtrated, concentrated and recrystallized, and a carboxylic acid derivative D4-H2-1 in a white solid state was obtained.

$^1$H-NMR spectrum data of the carboxylic acid derivative D4-H2-1 were as follows: $^1$H NMR (CDCl$_3$) δ (ppm): 0.21 (—Si(CH$_3$)$_2$), 0.98 (—SiC(CH$_3$)$_3$), 3.40-3.80 (—CH$_2$CH$_2$O—, —OCH(CH$_2$O—)$_2$), 4.35 (—OCH$_2$COOH); $M_n \approx 60000$ Da, PDI=1.02.

EXAMPLE-34

Preparation of H-Shaped Polyethylene Glycol Isocyanate Derivative

Synthesis of Isocyanate Derivative D9-H2-1

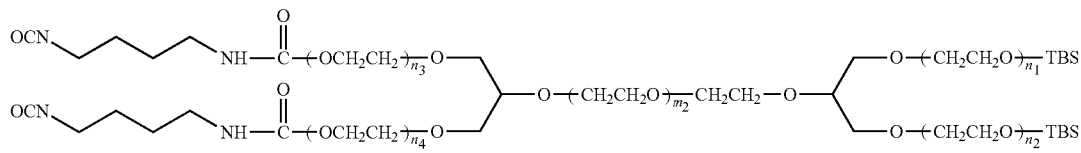

D9-H2-1

Herein, the structural design of H-shaped polyethylene glycol derivative was given as follows: $F_1$=—$CH_2CH_2$OTBS, $F_2$=—$CONHCH_2CH_2CH_2CH_2NCO$,

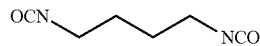

134

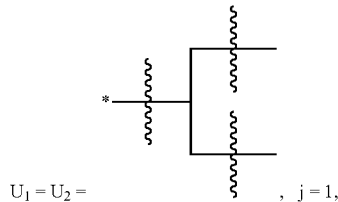

$W_0$ is —$CH_2CH_2$— and $m_1$=0. The designed total molecular weight is approximately 60000 Da, wherein, the molecular weight of four branch chains is approximately 2×5000+2×20000=50000 Da corresponding to $n_1 \approx n_2 \approx 114$, $n_3 \approx n_4 \approx 455$, and the molecular weight of the main chain is approximately 10000 Da corresponding to $m_2 \approx 227$.

Into a dry and clean 1 L round-bottom flask, 10 g of H-shaped polyethylene glycol H1-H2-1 and anhydrous dichloromethane (200 mL) were added in sequence, and then the whole was stirred till dissolution. Thereafter, 5 mL of triethylamine and 4 g of compound 134 were added in sequence, followed by 8 hours of reaction at room temperature. The resulting mixture was concentrated, precipitated with ether, and an isocyanate derivative D9-H2-1 in a white solid state was obtained.

$^1$H-NMR spectrum data of the compound D9-H2-1 were as follows: $^1$H NMR (CDCl$_3$) δ (ppm): 0.21 (—Si(CH$_3$)$_2$), 0.98 (—SiC(CH$_3$)$_3$), 1.32-1.55 (—CH$_2$CH$_2$CH$_2$CH$_2$—), 2.70-3.15 (NCOCH$_2$CH$_2$CH$_2$—, —OCONHCH$_2$—), 3.40-3.80 (—CH$_2$CH$_2$O—, —OCH$_2$CH$_2$OSi—, —OCH(CH$_2$O—)$_2$), 3.80-4.00 (—OCH$_2$CH$_2$OSi—); $M_n \approx 60000$ Da, PDI=1.02.

EXAMPLE-35

Preparation of Furan-Protected Maleimide Derivative of H-Shaped Polyethylene Glycol Synthesis of Furan-Protected Maleimide Derivative E4-H2-1

Herein, the structural design of H-shaped polyethylene glycol derivative was given as follows: $F_1$=—$CH_2CH_2OTBS$, $F_2$ = 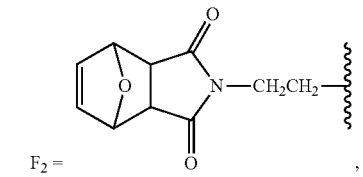

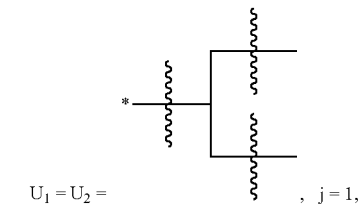

$W_0$ is —$CH_2CH_2$— and $m_1$=0. The designed total molecular weight is approximately 60000 Da, wherein, the molecular weight of four branch chains is approximately 2×5000+2×20000=50000 Da corresponding to $n_1 \approx n_2 \approx 114$, $n_3 \approx n_4 \approx 455$, and the molecular weight of the main chain is approximately 10000 Da corresponding to $m_2 \approx 227$.

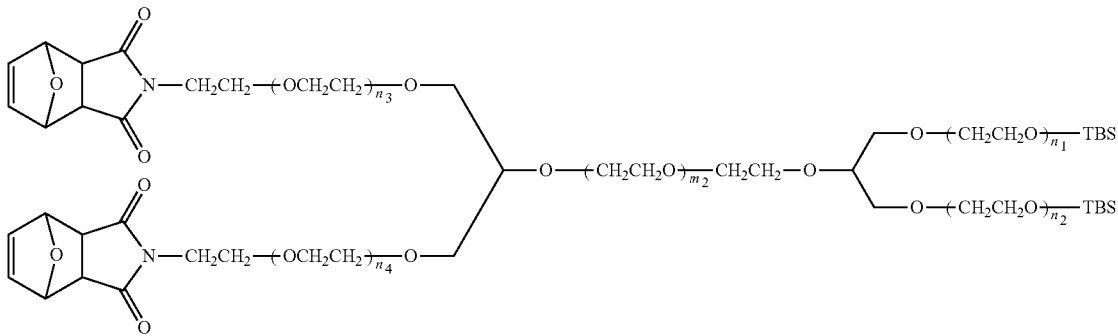

E4-H2-1

Into a dry and clean 1 L round-bottom flask, 40 g of H-shaped polyethylene glycol H1-H2-1 (treated by azeotropic removal of water with toluene) and 10.4 g of triphenylphosphine were added. Using nitrogen protection, 600 mL of anhydrous and oxygen-free tetrahydrofuran was added, and the whole was stirred at room temperature till dissolution. Subsequently 8 mL of diisopropyl azodiformate was added, followed by reaction at room temperature for 3 hours. Thereafter, 10 g of small molecules of furan-protected maleimide was added, followed by reaction at room temperature for 48 hours. After completion of the reaction, 600 mL of deionized water was added, the mixture was extracted with dichloromethane (200 mL trice). Then the organic phase was collected, washed with saturated salt solutions (200 mL), dried, concentrated and recrystallized, and a polyethylene glycol compound E4-H2-1 in a white solid state was obtained.

$^1$H-NMR spectrum data of the compound E4-H2-1 were as follows: $^1$H NMR (CDCl$_3$) δ (ppm): 0.21 (—Si(CH$_3$)$_2$), 0.98 (—SiC(CH$_3$)$_3$), 2.70-2.80 (—NCH$_2$CH$_2$O—), 3.07 (—CHCHCO—), 3.40-3.80 (—CH$_2$CH$_2$O—, —OCH$_2$CH$_2$OSi—, —OCH(CH$_2$O—)$_2$, —NCH$_2$CH$_2$O—), 3.80-4.00 (—OCH$_2$CH$_2$OSi—), 4.65 (—CHCHO—), 5.78 (—CH=CH—); $M_n$≈60000 Da, PDI=1.02.

EXAMPLE-36

Preparation of H-Shaped Polyethylene Glycol Azide Derivative

Synthesis of Azide Derivative C4-H2-1

Herein, the structural design of H-shaped polyethylene glycol derivative was given as follows: F$_1$=—CH$_2$CH$_2$OTBS, F$_2$=—CH$_2$CH$_2$N$_3$,

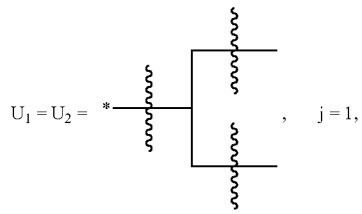

$W_0$ is —CH$_2$CH$_2$— and $m_1$=0. The designed total molecular weight is approximately 60000 Da, wherein, the molecular weight of four branch chains is approximately 2×5000+2×20000=50000 Da corresponding to $n_1$≈$n_2$≈114, $n_3$≈$n_4$≈455, and the molecular weight of the main chain is approximately 10000 Da corresponding to $m_2$≈227.

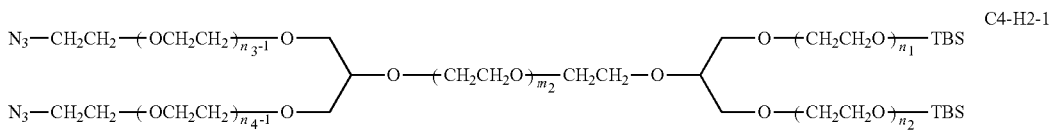

C4-H2-1

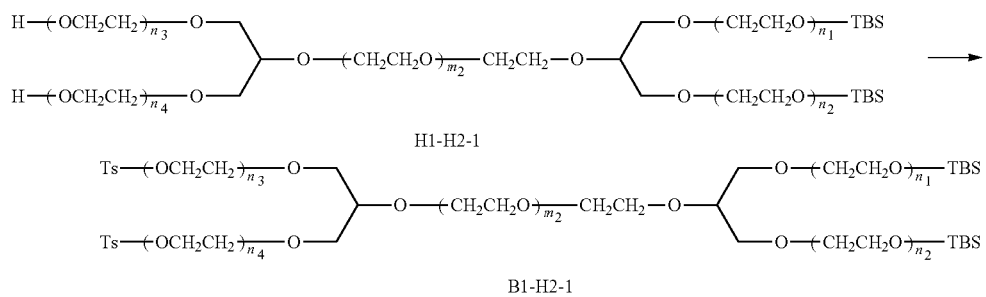

H1-H2-1

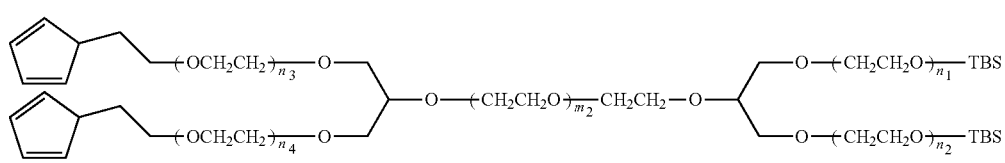

B1-H2-1

Step (a): Into a dry and clean 1 L round-bottom flask, 30 g of tetrahydroxyl H-shaped polyethylene glycol H1-H2-1 which has symmetrical branches obtained in Example-1 was added. Using nitrogen protection, 600 mL of anhydrous and oxygen-free dichloromethane, 10 mL of pyridine and 5 g of p-toluenesulfonyl chloride were added, followed by reaction at room temperature for 24 hours. After completion of the reaction, the solution was adjusted to pH lower than 7 with hydrochloric acid (1 mol/L), and the aqueous phase was washed with dichloromethane (50 mL trice). The organic phase was collected, washed with saturated salt solutions, dried with anhydrous sodium sulfate, filtrated, concentrated and recrystallized, and a polyethylene glycol sulfonate derivative B1-H2-1 was obtained.

$^1$H-NMR spectrum data of the compound B1-H2-1 were as follows: $^1$H NMR (CDCl$_3$) δ (ppm): 0.21 (—Si(CH$_3$)$_2$), 0.98 (—SiC(CH$_3$)$_3$), 2.35 (CH$_3$C$_6$H$_4$SO$_2$—), 3.40-3.80 (—CH$_2$CH$_2$O—, —OCH$_2$CH$_2$OSi—, —OCH(CH$_2$O—)$_2$), 3.80-4.00 (—OCH$_2$CH$_2$OSi—), 4.20 (—OCH$_2$CH$_2$OSO$_2$—), 7.30 (CH$_3$C$_6$H$_4$SO$_2$—), 7.80 (CH$_3$C$_6$H$_4$SO$_2$—); $M_n$≈60000 Da, PDI=1.02.

Step (b): Into a dry and clean 1 L round-bottom flask, 9 g of H-shaped polyethylene glycol sulfonate B1-H2-1 and 200 mL of tetrahydrofuran were added in sequence. The whole was stirred till dissolution, and then 4 g of sodium azide was added, followed by reaction at room temperature for a week. The mixture was extracted with dichloromethane (100 mL trice). The organic phase was collected, washed with saturated salt solutions, dried, filtrated, concentrated at low temperature and recrystallized, and an azide derivative C4-H2-1 in a white solid state was obtained.

$^1$H-NMR spectrum data of the azide derivative C4-H2-1 were as follows: $^1$H NMR (CDCl$_3$) δ (ppm): 0.21 (—Si(CH$_3$)$_2$), 0.98 (—SiC(CH$_3$)$_3$), 1.30-1.50 (—CH$_2$CH$_2$N$_3$), 3.40-3.80 (—CH$_2$CH$_2$O—, —OCH$_2$CH$_2$OSi—, —OCH$_2$CH$_2$N$_3$, —OCH(CH$_2$O—)$_2$), 3.80-4.00 (—OCH$_2$CH$_2$OSi—); $M_n$≈60000 Da, PDI=1.02.

EXAMPLE-37

Preparation of H-Shaped Polyethylene Glycol Cyclopentadiene Derivative

Synthesis of Cyclopentadiene Derivative G6-H2-1

Herein, the structural design of H-shaped polyethylene glycol derivative was given as follows: $F_1$=—CH$_2$CH$_2$OTBS,

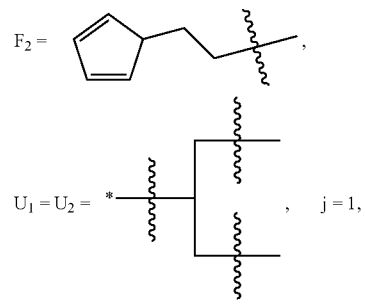

$W_0$ is —CH$_2$CH$_2$— and $m_1$=0. The designed total molecular weight is approximately 60000 Da, wherein, the molecular weight of four branch chains is approximately 2×5000+2×20000=50000 Da corresponding to $n_1$≈$n_2$≈114, $n_3$≈$n_4$≈455, and the molecular weight of the main chain is approximately 10000 Da corresponding to $m_2$≈227.

G6-H2-1

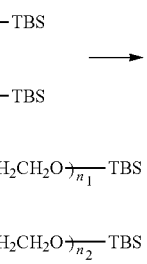

Into a dry and clean 1 L round-bottom flask, 9 g of H-shaped polyethylene glycol sulfonate B1-H2-1 and 200 mL of tetrahydrofuran were added in sequence. The whole was stirred till dissolution, and LiCp (6 mmol) dissolved in tetrahydrofuran was added dropwisely, followed by reaction at room temperature for a week. The mixture was extracted with dichloromethane (100 mL trice). The organic phase was collected, washed with saturated salt solutions, dried, filtrated, concentrated at low temperature and recrystallized, and a cyclopentadiene derivative (G6-H2-1) in a white solid state was obtained.

$^1$H-NMR spectrum data of the cyclopentadiene derivative G6-H2-1 were as follows: $^1$H NMR (CDCl$_3$) δ (ppm): 0.21 (—Si(CH$_3$)$_2$), 0.98 (—SiC(CH$_3$)$_3$), 1.40-1.60 (—OCH$_2$CH$_2$Cp-), 2.80-3.00 (—CH═CHCH—), 3.25-

3.47 (—OCH$_2$CH$_2$Cp-), 3.40-3.80 (—CH$_2$CH$_2$O—, —OCH$_2$CH$_2$—OSi—, —OCH(CH$_2$O—)$_2$), 3.80-4.00 (—OCH$_2$CH$_2$OSi—), 6.30-6.60 (—CH=CHCH—); $M_n \approx 60000$ Da, PDI=1.02.

EXAMPLE-38

Preparation of H-Shaped Polyethylene Glycol Alkyne Derivative

Synthesis of Alkyne Derivative F3-H1-1

Herein, the structural design of H-shaped polyethylene glycol derivative was given as follows: $F_1$==—CH$_2$CH$_2$OH,

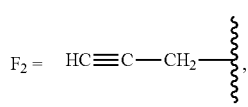

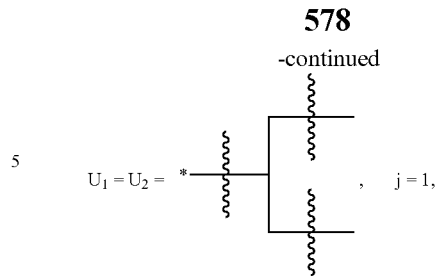

$W_0$ is —CH$_2$CH$_2$— and $m_1=0$. The designed total molecular weight is approximately 60000 Da, wherein, the molecular weight of four branch chains is approximately 2×5000+2×20000=50000 Da corresponding to $n_1 \approx n_2 \approx 114$, $n_3 \approx n_4 \approx 455$, and the molecular weight of the main chain is approximately 10000 Da corresponding to $m_2 \approx 227$.

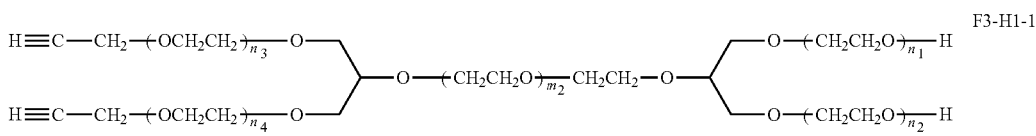

F3-H1-1

Step (a): Into a dry and clean 1 L round-bottom flask, 0.32 g of sodium hydride (60 wt %, in oil) was added. Using nitrogen protection, 400 mL of anhydrous tetrahydrofuran was added, and 40 g of H-shaped polyethylene glycol H1-H2-1 (treated by azeotropic removal of water with toluene) dissolved in the tetrahydrofuran was added slowly in an ice bath, followed by stirring at room temperature for 3 hours, thereafter 5 mL of TBS-protected propargyl bromide was added, followed by reaction at room temperature for 24 hours. After completion of the reaction, a small amount of saturated ammonium chloride solution was added to quench the reaction. The product in the solvent was concentrated, added with 600 mL of dichloromethane, then washed with saturated salt solutions (200 mL trice), dried, concentrated and recrystallized, and a TBS-protected polyethylene glycol alkyne derivative F4-H2-1 in a white solid state was obtained.

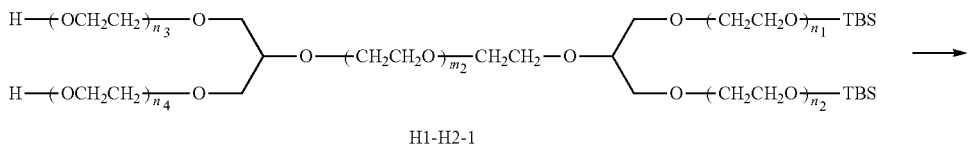

H1-H2-1

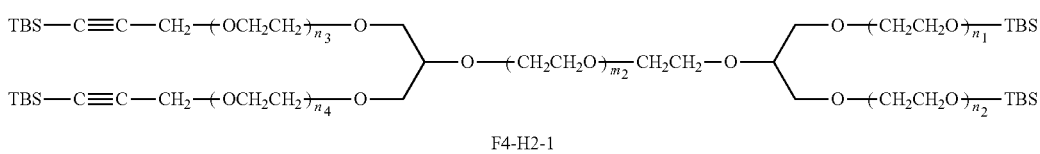

F4-H2-1

¹H-NMR spectrum data of the TBS-protected alkyne derivative F4-H2-1 were as follows: ¹H NMR (CDCl₃) δ (ppm): 0.21 (—Si(CH₃)₂), 0.98 (—SiC(CH₃)₃), 3.40-3.80 (—CH₂CH₂O—, —OCH₂CH₂OSi—, —OCH(CH₂O—)₂), 3.80-4.00 (—OCH₂CH₂OSi—), 4.15-4.35 (—C≡CCH₂O—).

Step (b): Into a dry and clean container, the compound F4-H2-1 was added and then dissolved with tetrahydrofuran, followed by the addition of tetra-t-butyl ammonium fluoride (TBAF), thereafter the reaction was conducted overnight, and an H-shaped polyethylene glycol alkyne derivative F3-H1-1 was obtained.

¹H-NMR spectrum data of the alkyne derivative F3-H1-1 were as follows: ¹H NMR (CDCl₃) δ (ppm): 2.40-2.60 (HC≡CCH₂O—), 3.40-3.80 (—OCH₂CH₂OSi—, —CH₂CH₂O—, —OCH(CH₂O—)₂), 3.80-4.00 (—OCH₂CH₂OSi—), 4.05-4.25 (HC≡CCH₂O—); $M_n \approx 60000$ Da, PDI=1.02.

EXAMPLE-39

Preparation of H-Shaped Polyethylene Glycol Cyclodextrin Derivative

Synthesis of Cyclodextrin Derivative H1-H1-3

Herein, the structural design of H-shaped polyethylene glycol derivative was given as follows: $F_1$=—CH₂CH₂OH, $F_2$=β-cyclodextrin,

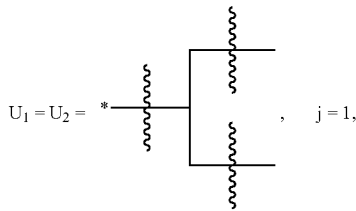

$W_0$ is —CH₂CH₂— and $m_1$=0. The designed total molecular weight is approximately 60000 Da, wherein, the molecular weight of four branch chains is approximately 2×5000+2×20000=50000 Da corresponding to $n_1 \approx n_2 \approx 114$, $n_3 \approx n_4 \approx 455$, and the molecular weight of the main chain is approximately 10000 Da corresponding to $m_2 \approx 227$.

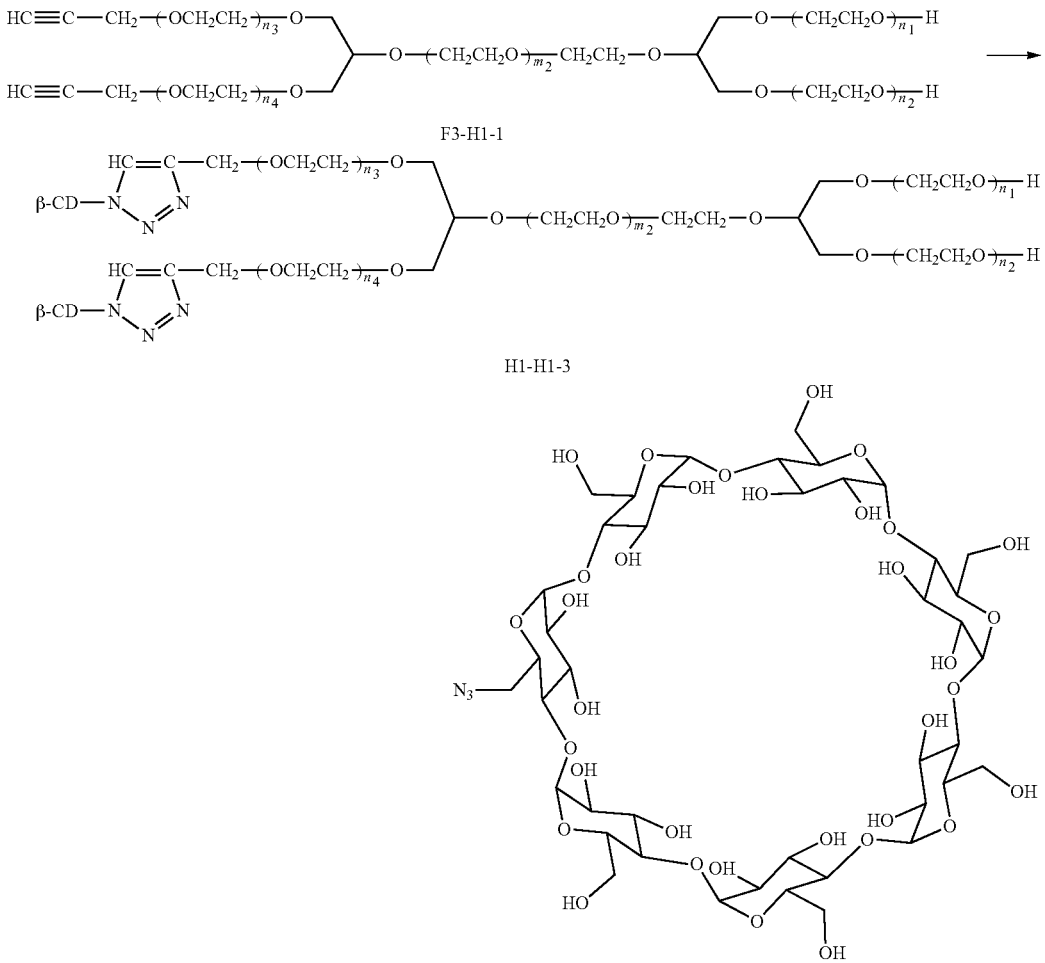

-continued

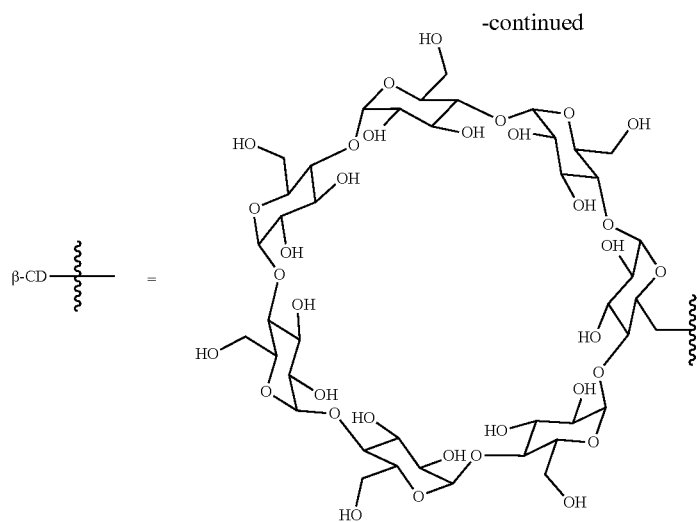

Into a dry and clean 1 L round-bottom flask, 10 g of alkynyl-containing polyethylene glycol derivative F3-H1-1 and 10 g of azido-containing cyclodextrin derivative 135 (β-CD-N$_3$) were added. Using nitrogen protection, 200 mL of tetrahydrofuran was added. The whole was stirred till dissolution, followed by reaction at room temperature for 24 hours. The resulting mixture was concentrated and recrystallized from isopropanol, and then an H-shaped polyethylene glycol cyclodextrin derivative H1-H1-3 in a white solid state was obtained.

$^1$H-NMR spectrum data of the cyclodextrin derivative H1-H1-3 were as follows: $^1$H NMR (CDCl$_3$) δ (ppm): 2.90-3.10 ((—O)$_2$CHCHCHCH—), 3.40-4.10 (—CH$_2$CH$_2$O—, —OCH(CH$_2$O—)$_2$, —NCH$_2$CH—, —OCHCH$_2$OH, (—O)$_2$CHCHCHCH—), 4.05-4.25 (—HC≡CCH$_2$O—), 4.90-5.10 ((—O)$_2$CHCHCHCH—), 7.10-7.40 (—HC≡CCH$_2$O—); M$_n$≈62000 Da, PDI=1.02.

EXAMPLE-40

Preparation of H-Shaped Polyethylene Glycol Lipoic Acid Derivative

Synthesis of Lipoic Acid Derivative C13-H1-1

Herein, the structural design of H-shaped polyethylene glycol derivative was given as follows:

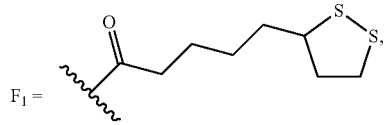

-continued

F$_2$ = HC≡C—CH$_2$—

U$_1$ = U$_2$ = *  , j = 1,

W$_0$ is —CH$_2$CH$_2$— and m$_1$=0. The designed total molecular weight is approximately 60000 Da, wherein, the molecular weight of four branch chains is approximately 2×5000+2×20000=50000 Da corresponding to n$_1$≈n$_2$≈114, n$_3$≈n$_4$≈455, and the molecular weight of the main chain is approximately 10000 Da corresponding to m$_2$≈227.

F3-C13-1

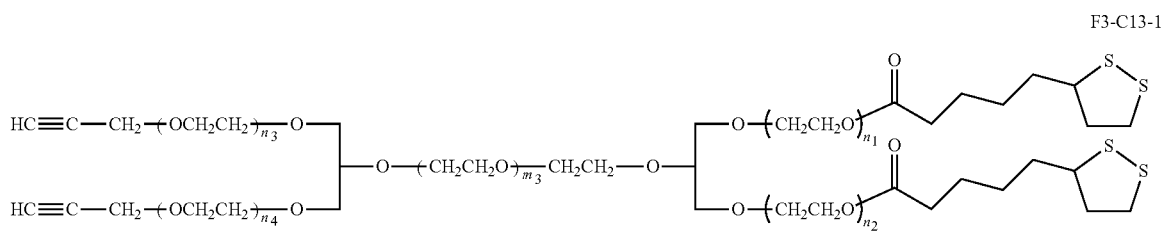

Into a dry and clean 1 L round-bottom flask, 10 g of polyethylene glycol derivative with two unprotected hydroxyl groups F3-H1-1 (treated by azeotropic removal of water with toluene), 10 mL of triethylamine and 15 g of lipoic acid were added. Using nitrogen protection, dichloromethane (200 mL) was added, thereafter the whole was stirred till dissolution, and 20 g of dicyclohexylcarbodiimide (DCC) was added, followed by reaction at room temperature for 24 hours and removal of the undissolved substances by filtration. The resulting mixture was concentrated and recrystallized from isopropanol, and an H-shaped polyethylene glycol lipoic acid compound F3-C13-1 in a white solid state was obtained.

$^1$H-NMR spectrum data of the lipoic acid derivative F3-C13-1 were as follows: $^1$H NMR (CDCl$_3$) δ (ppm): 1.20-1.40 (—COCH$_2$CH$_2$CH$_2$CH$_2$CHSS), 1.45-1.80 (—COCH$_2$CH$_2$CH$_2$CH$_2$CHSS), 1.70-2.30 (—COCH$_2$CH$_2$CH$_2$CH$_2$CHSS, —SSCH$_2$CH$_2$—), 2.40-2.70 (HC≡CCH$_2$O—, —COCH$_2$CH$_2$CH$_2$CH$_2$CHSS, —SSCH$_2$CH$_2$—), 3.40-3.80 (—CH$_2$CH$_2$O—, —OCH(CH$_2$O—)$_2$, —COOCH$_2$CH$_2$O—), 4.05-4.35 (HC≡CCH$_2$O—, —COOCH$_2$CH$_2$O—); $M_n$≈60000 Da, PDI=1.02.

EXAMPLE-41

Preparation of H-Shaped Polyethylene Glycol Active Cylcoalkyne Derivative

Synthesis of Active Cylcoalkyne Derivative G2-H2-1

Herein, the structural design of H-shaped polyethylene glycol derivative was given as follows: $F_1$=—CH$_2$CH$_2$OTBS,

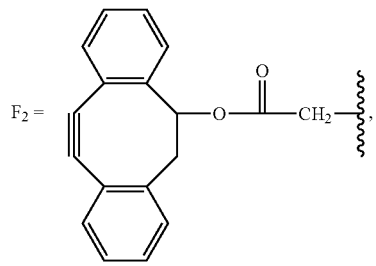

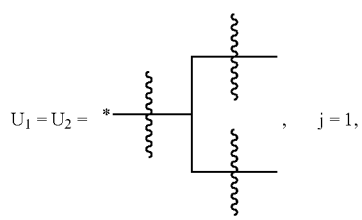

$W_0$ is —CH$_2$CH$_2$— and $m_1$=0. The designed total molecular weight is approximately 60000 Da, wherein, the molecular weight of four branch chains is approximately 2×5000+2×20000=50000 Da corresponding to $n_1$≈$n_2$≈114, $n_3$≈$n_4$≈455, and the molecular weight of the main chain is approximately 10000 Da corresponding to $m_2$≈227.

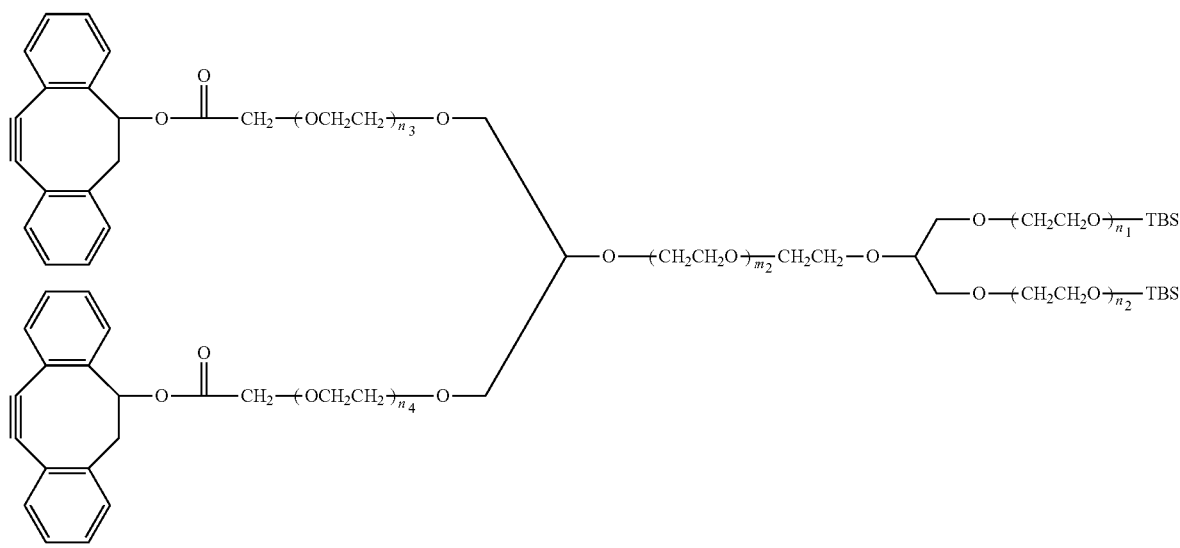

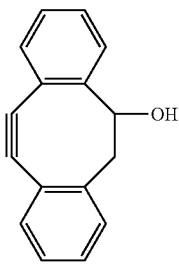

136

Into a dry and clean 1 L round-bottom flask, 40 g of branched polyethylene glycol acetic acid derivative D4-H2-1 (treated by azeotropic removal of water with toluene), 20 mL of triethylamine and 10 g of cycloalkynyl-alcohol 136 were added. Using nitrogen protection, dichloromethane (200 mL) was added, thereafter the whole was stirred till dissolution, and then 20 g of dicyclohexylcarbodiimide (DCC) was added, followed by reaction at room temperature for 24 hours and removal of the undissolved substances by filtration. The resulting mixture was concentrated and recrystallized from isopropanol, and a cycloalkyne derivative G2-H2-1 in a white solid state was obtained.

$^1$H-NMR spectrum data of the cycloalkyne compound G2-H2-1 were as follows: $^1$H NMR (CDCl$_3$) δ (ppm): 0.21 (—Si(CH$_3$)$_2$), 0.98 (—SiC(CH$_3$)$_3$), 2.91-3.15 (PhCH$_2$CH—), 3.40-3.80 (—CH$_2$CH$_2$O—, —OCH$_2$CH$_2$OSi—, —OCH(CH$_2$O—)$_2$), 3.80-4.00 (—OCH$_2$CH$_2$OSi—), 4.53 (—OCH$_2$COO—), 5.63 (PhCH$_2$CH—), 7.32-7.54 (C$_6$H$_4$—); M$_n$≈60000 Da, PDI=1.02.

EXAMPLE-42

Preparation of H-Shaped Polyethylene Glycol Active Cycloalkyne Derivative

Synthesis of Cycloalkyne Derivative G3-H2-1

Herein, the structural design of H-shaped polyethylene glycol derivative was given as follows: F$_1$=—CH$_2$CH$_2$OTBS,

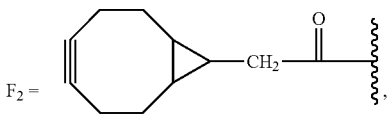

$U_1$=$U_2$=—CH(CH$_2$)$_2$—, p=0, j=1 and m$_1$=1. The designed total molecular weight is approximately 60000 Da, wherein, the molecular weight of four branch chains is approximately 2×5000+2×20000=50000 Da corresponding to n$_1$≈n$_2$≈114, n$_3$≈n$_4$≈455, and the molecular weight of the main chain is approximately 10000 Da corresponding to m$_2$≈227.

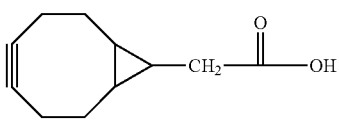

137

Into a dry and clean 1 L round-bottom flask, 8 g of polyethylene glycol compound containing two unprotected hydroxyl groups H1-H2-1 (treated by azeotropic removal of water with toluene), 10 mL of triethylamine and 5 g of compound 137 were added. Using nitrogen protection, dichloromethane (160 mL) was added, the whole was stirred till dissolution, thereafter 10 g of dicyclohexylcarbodiimide (DCC) was added, followed by reaction at room temperature for 24 hours, and then the undissolved substances were removed by filtration. The resulting mixture was concentrated and recrystallized from isopropanol, and an H-shaped polyethylene glycol cycloalkyne derivative G3-H2-1 in a white solid state was obtained.

$^1$H-NMR spectrum data of the cycloalkyne derivative G3-H2-1 were as follows: $^1$H NMR (CDCl$_3$) δ (ppm): 0.21 (—Si(CH$_3$)$_2$), 0.73-1.00 (—CH(CH—)$_2$—), 0.98 (—SiC(CH$_3$)$_3$), 1.30-1.50 (—CCCH$_2$CH$_3$—), 1.80-2.10 (—CCCH$_2$CH$_3$—), 2.10-2.30 (—CH$_2$COO—), 3.40-3.80 (—CH$_2$CH$_2$O—, —OCH$_2$CH$_2$OSi—, —OCH(CH$_2$O—)$_2$, —COOCH$_2$CH$_2$—), 3.80-4.00 (—OCH$_2$CH$_2$OSi—), 4.10-4.30 (—COOCH$_2$CH$_2$—); M$_n$≈60000 Da, PDI=1.02.

G3-H2-1

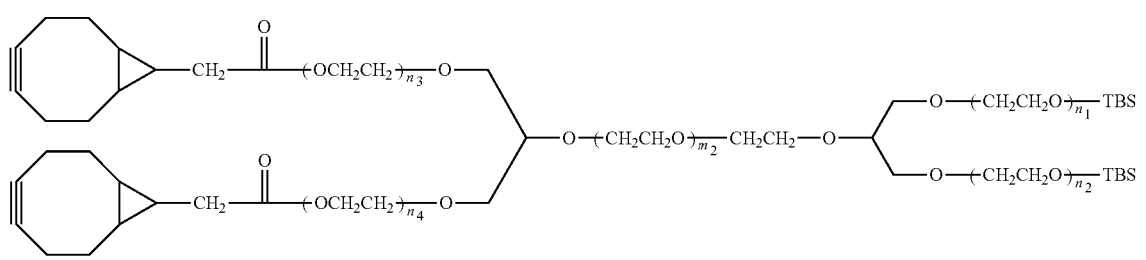

EXAMPLE-43

Preparation of H-Shaped Polyethylene Active Cycloalkyne Derivative

Synthesis of Active Cycloalkyne Derivative G1-H2-1

Herein, the structural design of H-shaped polyethylene glycol derivative was given as follows: $F_1$=—$CH_2CH_2OTBS$,

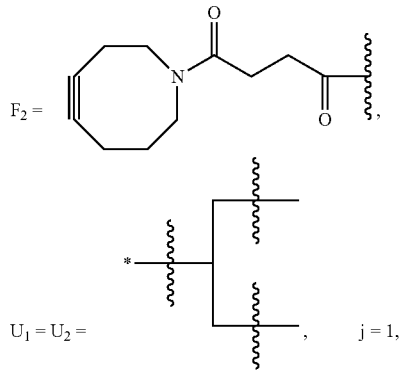

$W_0$ is —$CH_2CH_2$— and $m_1$=0. The designed total molecular weight is approximately 60000 Da, wherein, the molecular weight of four branch chains is approximately 2×5000+2×20000=50000 Da corresponding to $n_1 \approx n_2 \approx 114$, $n_3 \approx n_4 \approx 455$, and the molecular weight of the main chain is approximately 10000 Da corresponding to $m_2 \approx 227$.

Into a dry and clean 1 L round-bottom flask, 8 g of polyethylene glycol compound containing two unprotected hydroxyl groups H1-H2-1 (treated by azeotropic removal of water with toluene), 10 mL of triethylamine and 5 g of compound 138 were added. Using nitrogen protection, dichloromethane (160 mL) was added, the whole was stirred till dissolution, thereafter 10 g of dicyclohexylcarbodiimide (DCC) was added, followed by reaction at room temperature for 24 hours, and then the undissolved substances were removed by filtration. The resulting mixture was concentrated and recrystallized from isopropanol, and an H-shaped polyethylene glycol cycloalkyne derivative G1-H2-1 in a white solid state was obtained.

$^1$H-NMR spectrum data of the cycloalkyne derivative G1-H2-1 were as follows: $^1$H NMR (CDCl$_3$) δ (ppm): 0.21 (—Si(CH$_3$)$_2$), 0.98 (—SiC(CH$_3$)$_3$), 1.60-2.10 (—C≡CCH$_2$CH$_2$CH$_2$N—), 2.10-2.70 (—C≡CCH$_2$CH$_2$N—, —NC(=O)CH$_2$CH$_2$C(=O)O—), 3.10-3.50 (—C≡CCH$_2$CH$_2$N—, —C≡CCH$_2$CH$_2$CH$_2$N—), 3.40-3.80 (—CH$_2$CH$_2$O—, —OCH$_2$CH$_2$OSi—, —OCH(CH$_2$O—)$_2$, —COOCH$_2$CH$_2$O—), 3.80-4.00 (—OCH$_2$CH$_2$OSi—), 4.15-4.35 (—COOCH$_2$CH$_2$O—); $M_n \approx 60000$ Da, PDI≈1.02.

G1-H2-1

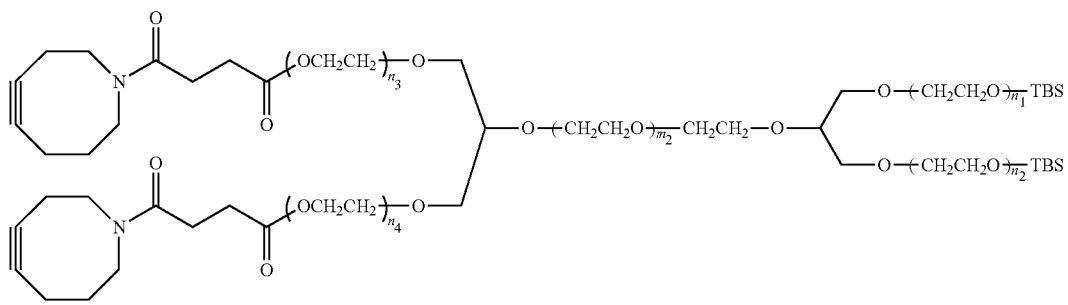

138

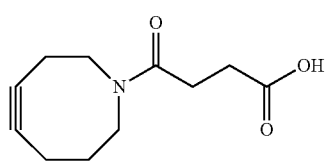

EXAMPLE-44

Preparation of H-Shaped Polyethylene Glycol with TBS-Protected Hydroxyl Groups

Synthesis of Derivative with TBS-Protected Hydroxyl Groups H2-H2-3

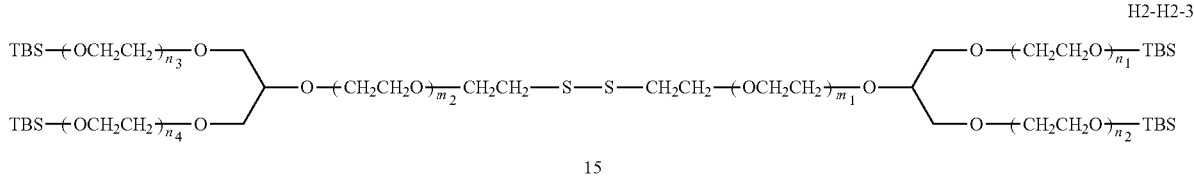

H2-H2-3

Herein, the structural design of H-shaped polyethylene glycol derivative was given as follows: $F_1=F_2=$—$CH_2CH_2OTBS$,

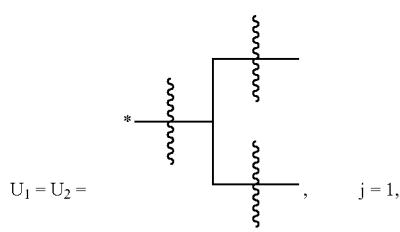

$W_0$ is —$CH_2CH_2$—S—S—$CH_2CH_2$—. The designed total molecular weight is approximately 40000 Da, wherein, the molecular weight of four branch chains is approximately 4×5000=20000 Da corresponding to $n_1 \approx n_2 \approx n_3 \approx n_4 \approx 114$, and the molecular weight of the main chain is approximately 20000 Da corresponding to $m_1 \approx m_2 \approx 227$.

Step (a): Into a dry and clean 1 L round-bottom flask, 40 g of Y-shaped branched polyethylene glycol 131 with one hydroxyl group obtained in Example-26 was added. Using nitrogen protection, 500 mL of anhydrous and oxygen-free dichloromethane was added, thereafter 20 mL of pyridine and 5 g of p-toluenesulfonyl chloride were added, followed by reaction at room temperature for 24 hours. After completion of the reaction, the solution was adjusted to pH less than 7 with hydrochloric acid (1 mol/L), and the aqueous phase was washed with dichloromethane (50 mL trice). The organic phase was collected, washed with saturated salt solutions, dried with anhydrous sodium sulfate, filtrated, concentrated and recrystallized, and a polyethylene glycol sulfonate derivative 139 was obtained.

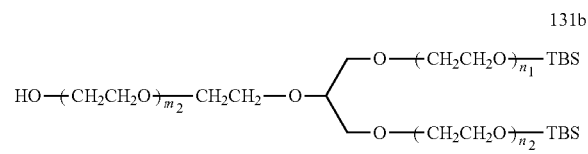

131b

-continued

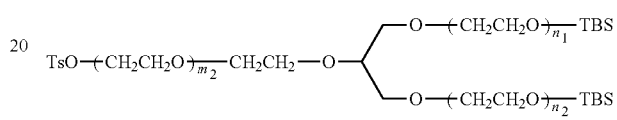

139

$^1$H-NMR spectrum data of the sulfonate derivative 139 were as follows: $^1$H NMR (CDCl$_3$) δ (ppm): 0.21 (—Si(CH$_3$)$_2$), 0.98 (—SiC(CH$_3$)$_3$), 2.35 (CH$_3$C$_6$H$_4$SO$_2$—), 3.40-3.80 (—CH$_2$CH$_2$O—, —OCH$_2$CH$_2$—OSi—, —OCH(CH$_2$O—)$_2$), 3.80-4.00 (—OCH$_2$CH$_2$OSi—), 4.20 (—OCH$_2$CH$_2$OSO$_2$—), 7.30 (CH$_3$C$_6$H$_4$SO$_2$—), 7.80 (CH$_3$C$_6$H$_4$SO$_2$—); $M_n \approx 20000$ Da, PDI=1.02.

Step (b): Into a dry and clean 1 L round-bottom flask, 40 g of H-shaped polyethylene glycol sulfonate 139 was added. Using nitrogen protection, 400 mL of tetrahydrofuran and 16 mL of DMF were added, thereafter the whole was stirred till dissolution, and then 5 g of potassium ethylxanthate

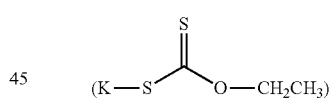

was added, followed by reaction at room temperature for 24 hours. After completion of the reaction, the solution was concentrated, and 400 mL of dichloromethane was added, followed by removal of the undissolved substances by filtration. The mixture washed with saturated salt solutions (100 mL trice), dried, concentrated and recrystallized from isopropanol, and a compound 140 in a white or yellowish solid state was obtained.

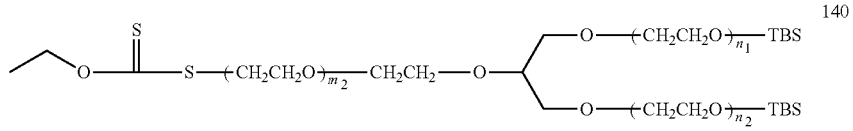

140

$^1$H-NMR spectrum data of the compound 140 were as follows: $^1$H NMR (CDCl$_3$) δ (ppm): 0.21 (—Si(CH$_3$)$_2$), 0.9 (CH$_3$CH$_2$OC(=S)—), —OCH$_2$CH$_2$S—), 0.98 (—SiC(CH$_3$)$_3$), 3.40-3.80 (—CH$_2$CH$_2$O—, —OCH$_2$CH$_2$OSi—, —OCH(CH$_2$O—)$_2$, —SCH$_2$CH$_2$O—), 3.80-4.00 (—OCH$_2$CH$_2$OSi—), 4.50 (CH$_3$CH$_2$OC(=S)—).

Step (c): Into a dry and clean 400 mL round-bottom flask, 20 g of branched polyethylene glycol dithiocarbonate derivative 140 was added. Using nitrogen protection, 200 mL of tetrahydrofuran was added, thereafter the whole was stirred till dissolution, and then 10 mL of n-propylamine was added, followed by reaction at room temperature for 24 hours. After completion of the reaction, the resulting mixture was concentrated and recrystallized from deoxygenated isopropanol, and a disulfide derivative H2-H2-3 in a white or yellowish solid state was obtained.

$^1$H-NMR spectrum data of the disulfide derivative H2-H2-3 were as follows: $^1$H NMR (CDCl$_3$) δ (ppm): 0.21 (—Si(CH$_3$)$_2$), 2.60-2.80 (—OCH$_2$CH$_2$S—), 0.98 (—SiC(CH$_3$)$_3$), 3.40-3.80 (—CH$_2$CH$_2$O—, —OCH$_2$CH$_2$OSi—, —OCH(CH$_2$O—)$_2$, —OCH$_2$CH$_2$S—), 3.80-4.00 (—OCH$_2$CH$_2$OSi—); $M_n$≈40000 Da, PDI=1.02.

EXAMPLE-45

Preparation of H-Shaped Polyethylene Glycol Phosphate Derivative

Synthesis of Derivative with TBS-Protected Hydroxyl Groups and a Divalent Phosphate Linkage H2-H2-4

Herein, the structural design of H-shaped polyethylene glycol derivative was given as follows: $F_1$=$F_2$=—CH$_2$CH$_2$OTBS,

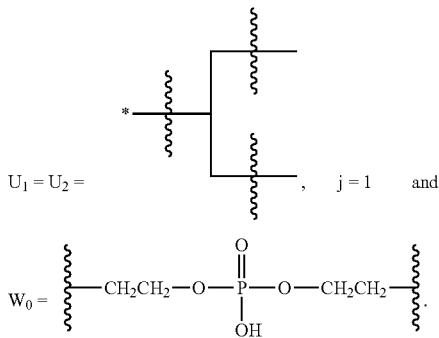

The designed total molecular weight is approximately 40000 Da, wherein, the molecular weight of four branch chains is approximately 4×5000=20000 Da corresponding to $n_1$≈$n_2$≈$n_3$≈$n_4$≈114, and the molecular weight of the main chain is approximately 20000 Da corresponding to $m_1$≈$m_2$≈227.

Into a 1 L reactor, POCl$_3$ (8 mmol), TEA (24 mmol) and 50 mL THF were added, a Y-shaped polyethylene glycol compound 131 (16 mmol) dissolved in THF (50 mL) was added dropwisely in an ice bath, and then the whole was stirred at 25° C. for 5 hours. After completion of the reaction, the resulting mixture was concentrated and recrystallized from isopropanol, and an H-shaped polyethylene glycol phosphate derivative H2-H2-4 in a white solid state was obtained.

$^1$H-NMR spectrum data of the phosphate derivative H2-H2-4 were as follows: $^1$H NMR (CDCl$_3$) δ (ppm): 0.21 (—Si(CH$_3$)$_2$), 0.98 (—SiC(CH$_3$)$_3$), 3.40-3.80 (—CH$_2$CH$_2$O—, —OCH$_2$CH$_2$—OSi—, —OCH(CH$_2$O—)$_2$, —POCH$_2$CH$_2$), 3.80-4.00 (—OCH$_2$CH$_2$OSi—), 4.10-4.30 (—POCH$_2$CH$_2$); $M_n$≈40000 Da, PDI=1.02.

EXAMPLE-46

Preparation of H-Shaped Polyethylene Glycol Phosphate Derivative

Synthesis of Derivative with TBS-Protected Hydroxyl Groups and a Trivalent Phosphate Linkage H2-H2-5

Herein, the structural design of H-shaped polyethylene glycol derivative was given as follows: $F_1$=$F_2$=—CH$_2$CH$_2$OTBS,

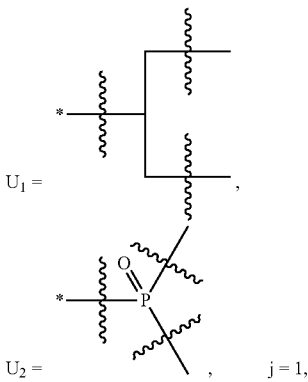

$W_0$ is —CH$_2$CH$_2$— and $m_1$=0. The designed total molecular weight is approximately 180000 Da, wherein, the molecular weight of four branch chains is approximately 2×5000+2×80000=170000 Da corresponding to $n_1$≈$n_2$≈114, $n_3$≈$n_4$≈1818, and the molecular weight of the main chain is approximately 10000 Da corresponding to $m_2$≈227.

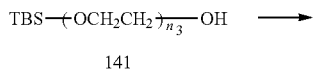

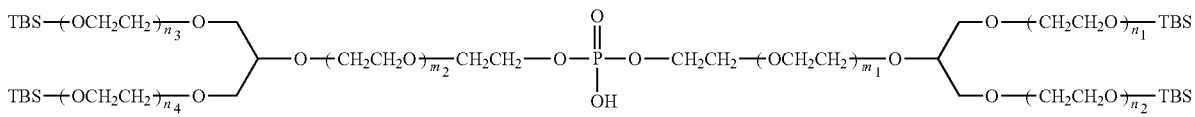

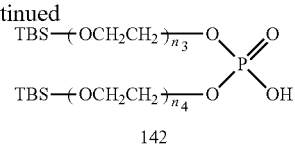

142

Step (a): Into a 1 L reactor, $POCl_3$ (0.2 mmol), TEA (10 mmol) and 50 mL THF were added, linear polyethylene glycol compound 141 (0.5 mmol) dissolved in THF (500 mL) was added dropwisely in an ice bath, and then the reaction was conducted with stirring at 25° C. for 5 hours. After completion of the reaction, the resulting mixture was concentrated and recrystallized from isopropanol, and a V-shaped polyethylene glycol phosphoric acid derivative 142 in a white solid state was obtained.

$^1$H-NMR spectrum data of the compound 142 were as follows: $^1$H NMR ($CDCl_3$) δ (ppm): 0.21 (—Si($CH_3$)$_2$), 0.98 (—SiC($CH_3$)$_3$), 3.40-3.80 (—$CH_2CH_2O$—, —$OCH_2CH_2OSi$—, —$POCH_2CH_2$), 3.80-4.00 (—$OCH_2CH_2OSi$—), 4.10-4.30 (—$POCH_2CH_2$); $M_n$≈160000 Da, PDI=1.03.

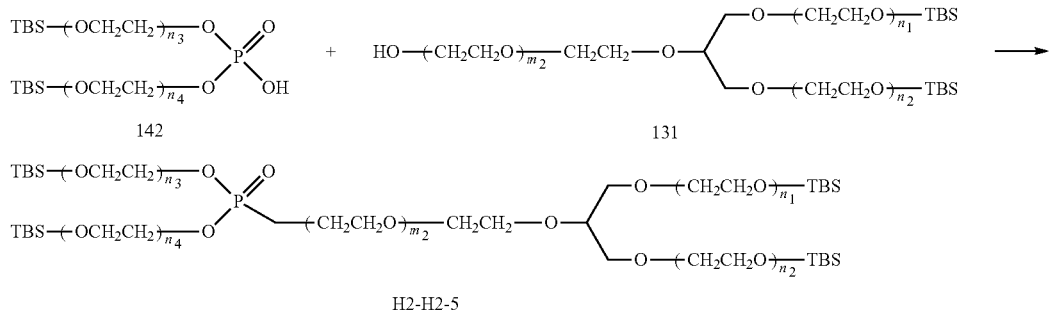

H2-H2-5

Step (b): Into a dry and clean 1 L round-bottom flask, Y-shaped polyethylene glycol compound with one unprotected hydroxyl group 131 (0.2 mmol, treated by azeotropic removal of water with toluene), 2 mL of triethylamine and Y-shaped polyethylene glycol phosphoric acid derivative 142 synthesized in step (a) (0.2 mmol) were added. Using nitrogen protection, dichloromethane (400 mL) was added, thereafter the whole was stirred till dissolution, and then 2 g of dicyclohexylcarbodiimide (DCC) was added, followed by reaction at room temperature for 24 hours and removal of the undissolved substances by filtration. The resulting mixture was concentrated and recrystallized from isopropanol, and an H-shaped polyethylene glycol phosphate derivative H2-H2-5 containing a trivalent phosphate linkage in a white solid state was obtained.

$^1$H-NMR spectrum data of the phosphate derivative H2-H2-5 were as follows: $^1$H NMR ($CDCl_3$) δ (ppm): 0.21 (—Si($CH_3$)$_2$), 0.98 (—SiC($CH_3$)$_3$), 3.40-3.80 (—$CH_2CH_2O$—, —$OCH_2CH_2OSi$—, —$OCH(CH_2O$—)$_2$, —$POCH_2CH_2$), 3.80-4.00 (—$OCH_2CH_2OSi$—), 4.10-4.30 (—$POCH_2CH_2$); $M_n$≈180000 Da, PDI=1.03.

EXAMPLE-47

Preparation of H-Shaped Polyethylene Glycol Derivative

Synthesis of Derivative with TBS-Protected Hydroxyl Groups H2-H2-6

H2-H2-6

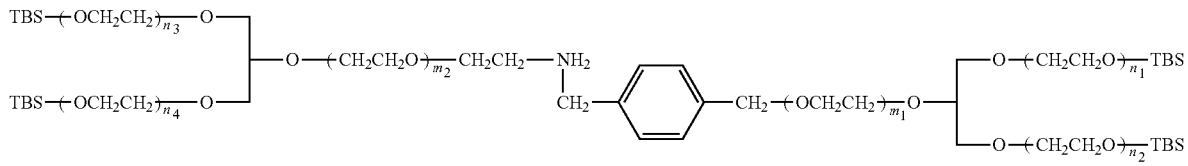

Herein, the structural design of H-shaped polyethylene glycol derivative was given as follows: $F_1=F_2=$ —$CH_2CH_2OTBS$, $U_1 = U_2 =$ 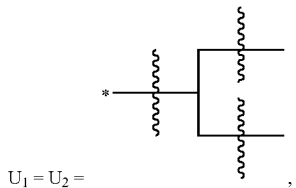

$W_0=$—$CH_2CH_2NHCH_2PhCH_2$— and j=1. The designed total molecular weight is approximately 40000 Da, wherein, the molecular weight of four branch chains is approximately 4×5000=20000 Da corresponding to $n_1 \approx n_2 \approx n_3 \approx n_4 \approx 114$, and the molecular weight of the main chain is approximately 20000 Da corresponding to $m_1 \approx m_2 \approx 227$.

Step (a): Into a dry and clean 1 L round-bottom flask, 40 g of Y-shaped polyethylene glycol sulfonate 139 obtained in the Example-3 and 800 mL of ammonia water (40 wt %) were added in sequence, and then the whole was stirred till dissolution. Thereafter, the reaction was conducted at room temperature for a week. After completion of the reaction, the resulting product was extracted with dichloromethane (200 mL trice). The organic phase was collected, washed with saturated salt solutions, dried, filtrated, concentrated and recrystallized, and an amine derivative 143 in a white solid state was obtained.

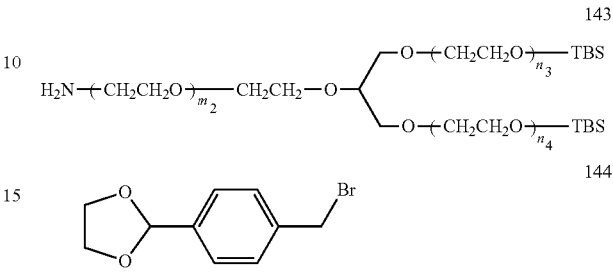

143

144

$^1$H-NMR spectrum data of the amine derivative 143 were as follows: $^1$H NMR (CDCl$_3$) δ (ppm): 0.21 (—Si(CH$_3$)$_2$), 0.98 (—SiC(CH$_3$)$_3$), 2.70-2.85 (—CH$_2$CH$_2$NH$_2$), 3.40-3.80 (—CH$_2$CH$_2$O—, —OCH$_2$CH$_2$OSi—, —OCH(CH$_2$O—)$_2$, —OCH$_2$CH$_2$NH$_2$), 3.80-4.00 (—OCH$_2$CH$_2$OSi—); $M_n \approx 20000$ Da, PDI=1.02.

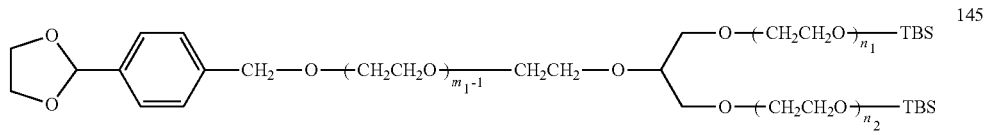

145

Step (b): Into a dry and clean 1 L round-bottom flask, 35 g of branched polyethylene glycol compound 131 and 4 g of sodium hydroxide were added in sequence. Using nitrogen protection, after the addition of toluene (350 mL), 3 mL of 4-bromomethyl-2-phenyl-1,3-dioxane 144 was added dropwisely. Thereafter, the whole was heated till reflux, and the reaction was carried out for 24 hours. After completion of the reaction, 400 mL of deionized water was added for hierarchical extraction, and the aqueous phase was extracted with dichloromethane (200 mL trice). Then the organic phase was collected, washed with saturated salt solutions (100 mL trice), dried, concentrated and recrystallized, and a Y-shaped polyethylene glycol acetal compound 145 in a white solid state was obtained.

Step (c): Into a dry and clean 1 L round-bottom flask, 35 g of above-obtained branched polyethylene glycol acetal derivative and 400 mL of deionized water were added, and then the whole was stirred till dissolution. The solution was adjusted to pH 1.0 with HCl (1 mol/L) in an ice bath, followed by reaction at room temperature for 4 hours. The aqueous phase was extracted with dichloromethane (200 mL trice), thereafter the organic phase was collected, washed with saturated salt solutions, dried, filtrated, concentrated and recrystallized, and a polyethylene glycol aldehyde derivative 146 in a white solid state was obtained.

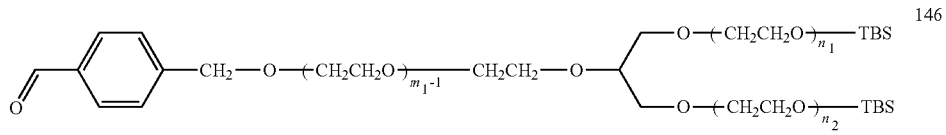

146

¹H-NMR spectrum data of the aldehyde derivative 146 were as follows: ¹H NMR (CDCl₃) δ (ppm): 0.21 (—Si(CH₃)₂), 0.98 (—SiC(CH₃)₃), 3.40-3.80 (—CH₂CH₂O—, —OCH₂CH₂OSi—, —OCH(CH₂O—)₂), 3.80-4.00 (—OCH₂CH₂OSi—), 4.50-4.60 (-PhCH₂—), 7.30-7.80 (-Ph-H), 9.80 (—OCH₂CHO); $M_n \approx 20000$ Da, PDI=1.02.

Step (d): Into a round-bottom flask under an anhydrous and oxygen-free atmosphere, polyethylene glycol amine derivative 143 (7.5 mmol), methanol (250 mL) and polyethylene glycol aldehyde derivative 146 (7.5 mmol) were added in sequence, and then the reaction was carried out at 25° C. for 24 hours. Thereafter the resulting mixture was concentrated, extracted, dried, concentrated and recrystallized, and a compound H2-H2-7 was obtained.

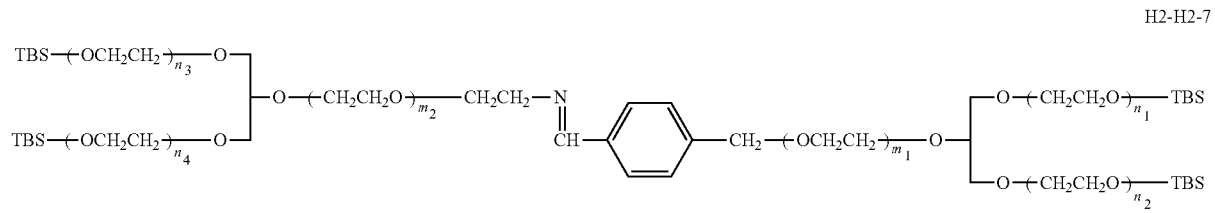

H2-H2-7

¹H-NMR spectrum data of the aldehyde derivative H2-H2-7 were as follows: ¹H NMR (CDCl₃) δ (ppm): 0.21 (—Si(CH₃)₂), 0.98 (—SiC(CH₃)₃), 3.40-3.80 (—CH₂CH₂O, —OCH₂CH₂OSi—, —OCH(CH₂O—)₂, —NCH₂CH₂O—), 3.80-4.00 (—OCH₂CH₂OSi—), 4.50-4.60 (-PhCH₂O—), 7.20-7.50 (-Ph-H), 8.00-8.15 (—N=CHPh-); $M_n \approx 40000$ Da, PDI=1.02.

Step (e): Into a round-bottom flask under an anhydrous and oxygen-free atmosphere, polyethylene glycol amine derivative H2-H2-6 (7.5 mmol) and methanol (250 mL) were added in sequence. Then sodium cyanoborohydride was added, and then the reaction was carried out at 25° C. for 24 hours. The resulting mixture was washed with water, dried, concentrated and dialyzed in the water, and a compound H2-H2-6 was obtained.

¹H-NMR spectrum data of the compound H2-H2-6 were as follows: ¹H NMR (CDCl₃) δ (ppm): 0.21 (—Si(CH₃)₂), 0.98 (—SiC(CH₃)₃), 2.60-2.70 (—NHCH₂CH₂O—), 3.40-3.80 (—CH₂CH₂O—, —OCH₂CH₂OSi—, —OCH(CH₂O—)₂, —NHCH₂CH₂O—, —NHCH₂Ph-), 3.80-4.00 (—OCH₂CH₂OSi—), 4.50-4.60 (-PhCH₂O—), 6.90-7.00 (-Ph-H); $M_n \approx 40000$ Da, PDI=1.02.

EXAMPLE-48

Preparation of H-Shaped Polyethylene Glycol Derivative

Synthesis of Derivative with TBS-Protected Hydroxyl Groups H2-H2-8

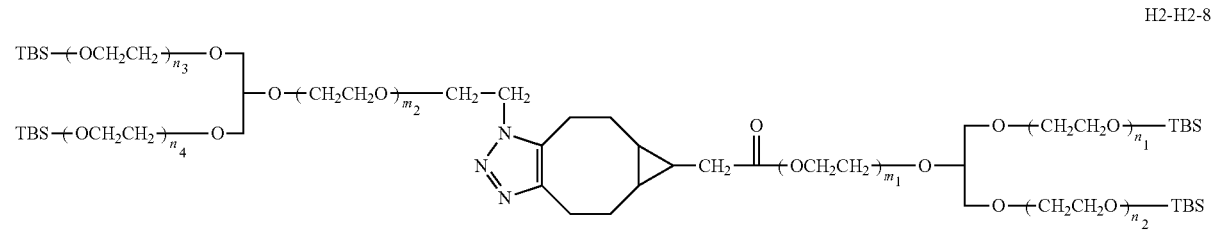

H2-H2-8

Herein, the structural design of H-shaped polyethylene glycol derivative was given as follows: $F_1=F_2=-CH_2CH_2OTBS$,

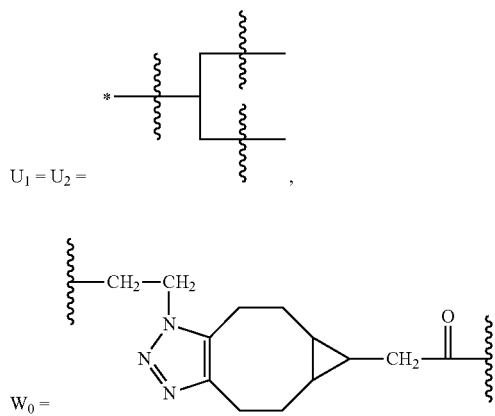

and j=1. The designed total molecular weight is approximately 40000 Da, wherein, the molecular weight of four branch chains is approximately 4×5000=20000 Da corresponding to $n_1 \approx n_2 \approx n_3 \approx n_4 \approx 114$, and the molecular weight of the main chain is approximately 20000 Da corresponding to $m_1 \approx m_2 \approx 227$.

147

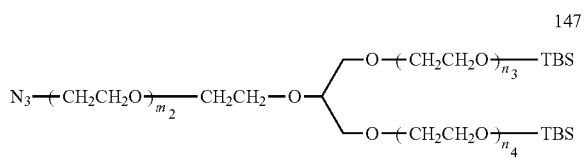

Step (a): Into a dry and clean 1 L round-bottom flask, 50 g of Y-shaped polyethylene glycol sulfonate 139 obtained in Example-3 and 600 mL of tetrahydrofuran were added in sequence. The whole was stirred till dissolution, and then 4 g of sodium azide was added, followed by reaction at room temperature for a week. The mixture was extracted with dichloromethane (200 mL trice), subsequently the organic phase was collected, washed with saturated salt solutions, dried, filtrated, concentrated at low temperature and recrystallized, and an azide derivative 147 in a white solid state was obtained.

$^1$H-NMR spectrum data of the azide derivative 147 were as follows: $^1$H NMR (CDCl$_3$) δ (ppm): 0.21 (—Si(CH$_3$)$_2$), 0.98 (—SiC(CH$_3$)$_3$), 1.30-1.50 (—CH$_2$CH$_2$N$_3$), 3.40-3.80 (—CH$_2$CH$_2$O—, —OCH$_2$CH$_2$OSi—, —OCH(CH$_2$O—)$_2$, —OCH$_2$CH$_2$N$_3$), 3.80-4.00 (—OCH$_2$CH$_2$OSi—); $M_n \approx$ 20000 Da, PDI=1.02.

Step (b): Into a dry and clean 1 L round-bottom flask, 10 g of hydroxyl-containing polyethylene glycol compound 131 (treated by azeotropic removal of water with toluene), 10 mL of triethylamine and 5 g of compound 137 were added. Using nitrogen protection, dichloromethane (200 mL) was added, and then the whole was stirred until all were dissolved. Thereafter 10 g of dicyclohexylcarbodiimide (DCC) was added, followed by reaction at room temperature for 24 hours. The resulting mixture was filtrated to remove undissolved substances, concentrated and recrystallized from isopropanol, and an H-shaped polyethylene cycloalkyne glycol compound 148 in a white solid state was obtained.

148

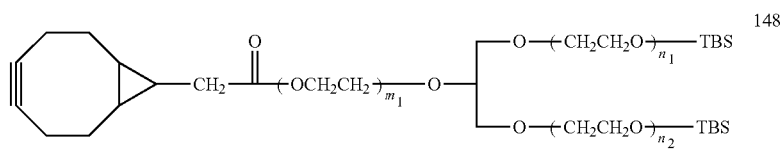

$^1$H-NMR spectrum data of the cycloalkyne derivative 148 were as follows: $^1$H NMR (CDCl$_3$) δ (ppm): 0.21 (—Si(CH$_3$)$_2$), 0.73-1.00 (—CH(CH—)$_2$—), 0.98 (—SiC(CH$_3$)$_3$), 1.30-1.50 (—CCCH$_2$CH$_3$—), 1.80-2.10 (—CCCH$_2$CH$_3$—), 2.10-2.30 (—CH$_2$COO—), 3.40-3.80 (—CH$_2$CH$_2$O—, —OCH$_2$CH$_2$OSi—, —OCH(CH$_2$O—)$_2$, —COOCH$_2$CH$_2$—), 3.80-4.00 (—OCH$_2$CH$_2$OSi—), 4.10-4.30 (—COOCH$_2$CH$_2$—); $M_n \approx$ 20000 Da, PDI=1.02.

Step (c): Into a dry and clean 1 L round-bottom flask, 10 g of alkynyl-containing polyethylene glycol compound 148, and 10 g of azido-containing polyethylene glycol derivative 147 were added. Using nitrogen protection, tetrahydrofuran (200 mL) was added, and then the whole was stirred until all were dissolved, followed by reaction at room temperature for 24 hours. The resulting mixture was concentrated and recrystallized from isopropanol, and an H-shaped polyethylene glycol compound H2-H2-8 in a white solid state was obtained.

$^1$H-NMR spectrum data of the H-shaped polyethylene glycol derivative H2-H2-8 were as follows: $^1$H NMR (CDCl$_3$) δ (ppm): 0.21 (—Si(CH$_3$)$_2$), 0.73-1.00 (—CH(CH)$_2$—), 0.98 (—SiC(CH$_3$)$_3$), 1.40-1.70 (—CCCH$_2$CH$_3$—), 2.40-2.70 (—CCCH$_2$CH$_3$—), 2.10-2.30 (—CH$_2$COO—), 3.40-3.80 (—CH$_2$CH$_2$O—, —OCH$_2$CH$_2$OSi—, —OCH(CH$_2$O—)$_2$, —COOCH$_2$CH$_2$—), 3.80-4.00 (—OCH$_2$CH$_2$OSi—), 3.80-4.00 (—OCH$_2$CH$_2$N—), 4.10-4.30 (—COOCH$_2$CH$_2$—); $M_n \approx$ 40000 Da, PDI=1.02.

EXAMPLE-49

Preparation of H-Shaped Polyethylene Glycol Derivative Containing Amide Bond Synthesis of Derivative with TBS-Protected Hydroxyl Groups and an Amide Bond H2-H2-9

Herein, the structural design of H-shaped polyethylene glycol derivative was given as follows: $F_1=F_2=-CH_2CH_2OTBS$,

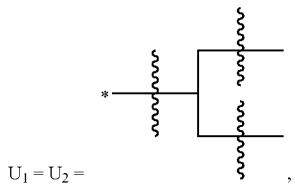

$W_0=-CH_2CH_2NHCOCH_2-$, $j=1$ and $m_3 \approx 0$. The designed total molecular weight is approximately 40000 Da, wherein, the molecular weight of four branch chains is approximately 4×5000=20000 Da corresponding to $n_1 \approx n_2 \approx n_3 \approx n_4 \approx 114$, and the molecular weight of the main chain is approximately 20000 Da corresponding to $m_1 \approx m_2 \approx 227$.

H2-H2-9

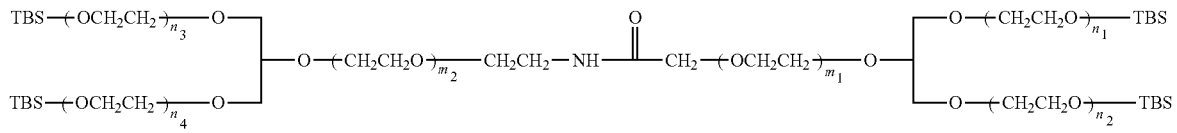

Step (a): Using polyethylene glycol compound containing one hydroxyl group 131 as reagent, a Y-shaped polyethylene glycol carboxylic acid 149 was prepared by using the method in Example-16.

149

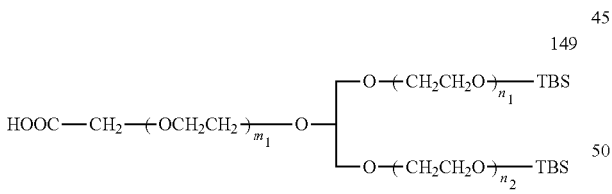

$^1$H-NMR spectrum data of the intermediate 149 were as follows: $^1$H NMR (CDCl$_3$) δ (ppm): 0.21 (—Si(CH$_3$)$_2$), 0.98 (—SiC(CH$_3$)$_3$), 3.40-3.80 (—CH$_2$CH$_2$O—, —OCH(CH$_2$O—)$_2$), 4.35 (—OCH$_2$COOH); $M_n \approx 20000$ Da, PDI=1.02.

Step (b): Into a dry and clean 1 L round-bottom flask, 10 g of carboxyl-containing Y-shaped polyethylene glycol derivative 149 (treated by azeotropic removal of water with toluene), 5 mL of triethylamine and 10 g of mono-amino-terminated Y-shaped polyethylene glycol derivative 143 obtained in Example-47 were added. Using nitrogen protection, dichloromethane (200 mL) was added, and then the whole was stirred until all were dissolved. Thereafter 5 g of dicyclohexylcarbodiimide (DCC) was added, followed by reaction at room temperature for 24 hours. The resulting mixture was filtrated to remove undissolved substances, concentrated and recrystallized from isopropanol, and thereafter an H-shaped polyethylene glycol compound H2-H2-9 containing an amide bond in a white solid state was obtained.

$^1$H-NMR spectrum data of the amide derivative H2-H2-9 were as follows: $^1$H NMR (CDCl$_3$) δ (ppm): 0.21 (—Si(CH$_3$)$_2$), 0.9-1.0 (—SiC(CH$_3$)$_3$), 3.27-3.47 (—OCH$_2$CH$_2$NHCO—), 3.40-3.80 (—CH$_2$CH$_2$O—, —OCH(CH$_2$O—)$_2$, —OCH$_2$CH$_2$NHCO—), 4.15-4.35 (—OCH$_2$C(=O)—); $M_n \approx 40000$ Da, PDI=1.02.

EXAMPLE-50

Preparation of H-Shaped Polyethylene Glycol Derivative

Synthesis of Derivative with TBS-Protected Hydroxyl Groups H2-H2-10

Herein, the structural design of H-shaped polyethylene glycol derivative was given as follows: $F_1=F_2=-CH_2CH_2OTBS$,

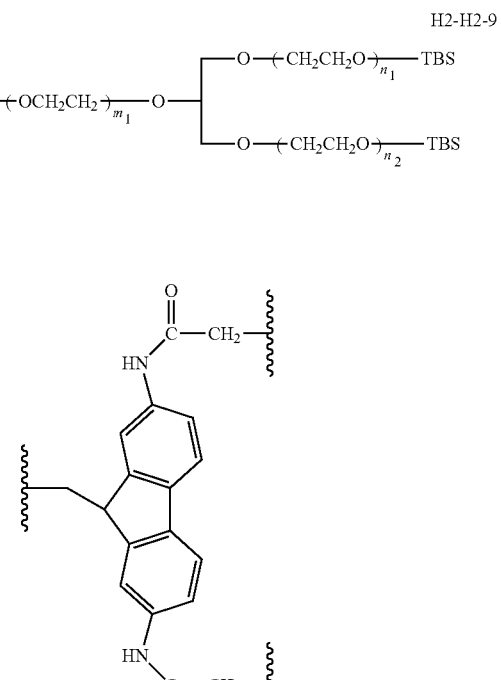

$W_0$=CH$_2$CO and $m_1 \approx 0$. The designed total molecular weight is approximately 180000 Da, wherein, the molecular weight of four branch chains is approximately 2×80000+2×5000=170000 Da corresponding to $n_1 \approx n_2 \approx 1818$, $n_3 \approx n_4 \approx 114$, and the molecular weight of the main chain is approximately 10000 Da corresponding to $m_2 \approx 227$.

Step (a): Into an anhydrous and oxygen-free atmosphere round-bottom flask, the amine compound 151 (2.0 mmol), dichloromethane (250 mL) and triethylamine (10 mmol) were added in sequence, subsequently polyethylene acyl chloride derivative 119 (5 mmol, molecular weight about 80000, PDI=1.03) dissolved in dichloromethane (50 mL) was slowly added dropwisely, followed by reaction at 25° C. for 24 hours. After completion of the reaction, the mixture was washed with water, dried, concentrated and purified by an anion exchange resin, and a compound 150b was obtained. Into a dry and clean container, the compound 150b was added and then dissolved with methanol. The solution was adjusted to pH 3.5 with hydrochloric acid (1 M), followed by reaction for 4 hours, and a V-shaped polyethylene glycol compound 150 containing one unprotected hydroxyl group was obtained.

$^1$H-NMR spectrum data of the compound 150 were as follows: $^1$H NMR (CDCl$_3$) δ (ppm): 0.21 (—Si(CH$_3$)$_2$), 0.98 (—SiC(CH$_3$)$_3$), 3.40-3.80 (—CH$_2$CH$_2$O—, —OCH$_2$CH$_2$—OSi—), 3.80-4.00 (—OCH$_2$CH$_2$OSi—), 3.90-4.30 (OCH$_2$CHPh), 4.32 (—NC(=O)CH$_2$—O—), 7.6-8.00 (Ph-H); $M_n \approx 160000$ Da, PDI=1.03.

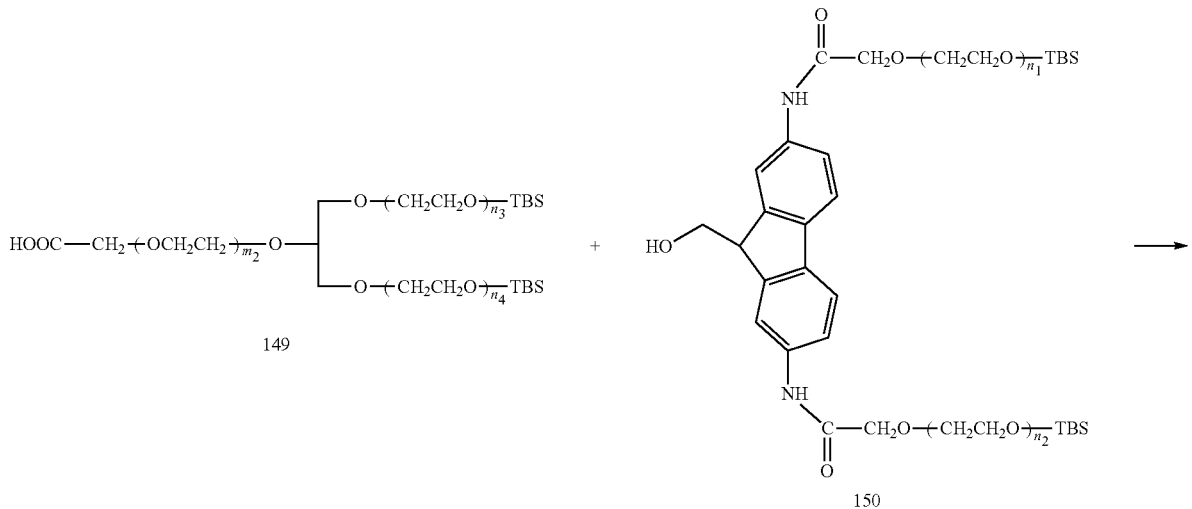

149

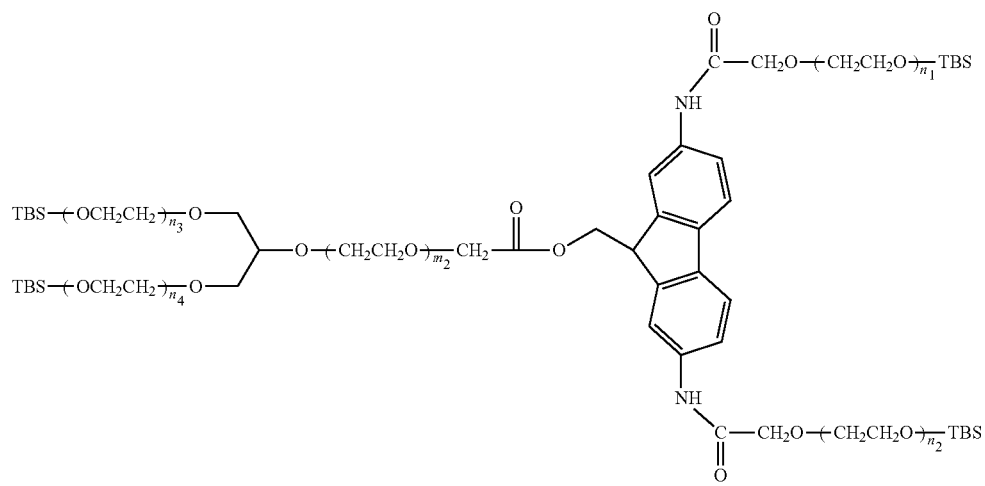

H2-H2-10

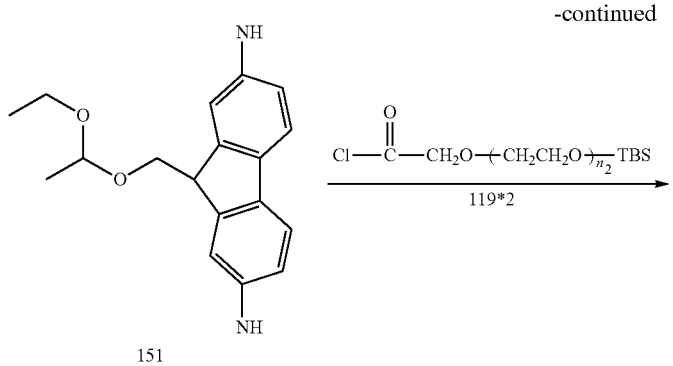

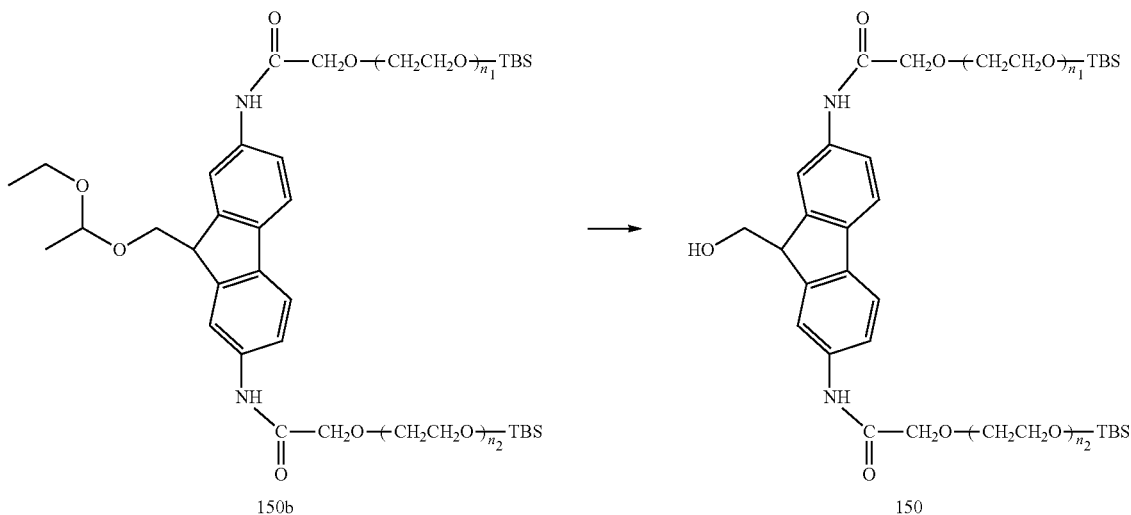

Step (b): Into a dry and clean 1 L round-bottom flask, 10 g of carboxyl-containing Y-shaped polyethylene glycol derivative 149 (treated by azeotropic removal of water with toluene), 5 mL of triethylamine and 10 g of mono-hydroxyl-containing Y-shaped polyethylene glycol derivative 150 (obtained by acidification of the product from the above step) were added. Using nitrogen protection, dichloromethane (200 mL) was added, and then the whole was stirred until all were dissolved. Thereafter 5 g of dicyclohexylcarbodiimide (DCC) was added, followed by reaction at room temperature for 24 hours. The resulting mixture was filtrated to remove undissolved substances, concentrated, recrystallized from isopropanol and finally dialyzed, and an H-shaped polyethylene glycol compound H2-H2-10 containing an Fmoc linkage in a white solid state was obtained.

$^1$H-NMR spectrum data of the compound H2-H2-10 were as follows: $^1$H NMR (CDCl$_3$) δ (ppm): 0.21 (—Si(CH$_3$)$_2$), 0.98 (—SiC(CH$_3$)$_3$), 3.40-3.80 (—CH$_2$CH$_2$O—, —OCH$_2$CH$_2$OSi—, —OCH(CH$_2$O—)$_2$), 3.80-4.00 (—OCH$_2$CH$_2$OSi—), 4.35-4.80 (OCH$_2$CHPh), 4.32 (—C(=O)CH$_2$—O—), 7.6-8.00 (Ph-H); $M_n$≈180000 Da, PDI=1.03.

EXAMPLE-51

Preparation of H-Shaped Polyethylene Glycol Derivative with a C—S Bond

Synthesis of Derivative with a C—S Bond H2-H2-11

H2-H2-11

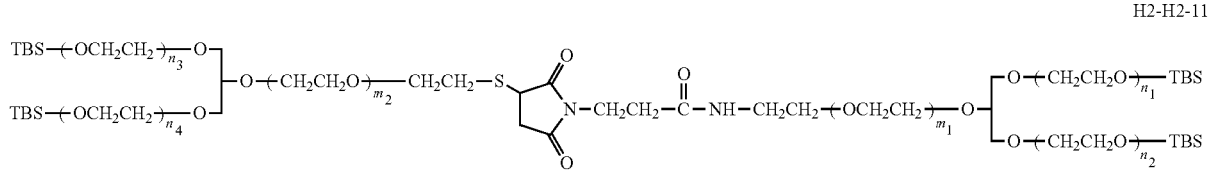

Herein, the structural design of H-shaped polyethylene glycol derivative was given as follows: $F_1=F_2=$ —$CH_2CH_2OTBS$,

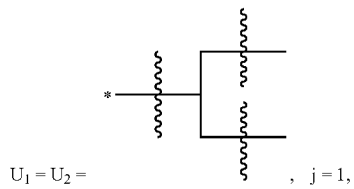

$U_1 = U_2 = $ , $j = 1$,

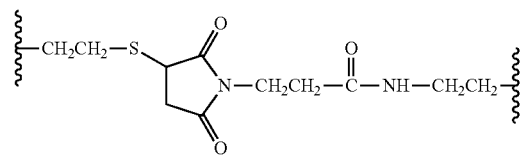

$W_0 = $ .

The designed total molecular weight is approximately 40000 Da, wherein, the molecular weight of four branch chains is approximately $4\times5000=20000$ Da corresponding to $n_1\approx n_2\approx n_3\approx n_4\approx 114$, and the molecular weight of the main chain is approximately 20000 Da corresponding to $m_1\approx m_2\approx 227$.

Into a dry and clean 500 mL round-bottom flask, Y-shaped polyethylene glycol thiol derivative 152 (10 g) dissolved in 100 mL of phosphate buffered solution (pH=7.4) was added, and then 10 g of Y-shaped polyethylene glycol maleimide derivative 153 was added, followed by reaction at 4° C. for 24 hours. After completion of the reaction, the solution was diluted with distilled water, extracted with dichloromethane, dried, concentrated and recrystallized from isopropanol, and a compound H2-H2-11 containing a thioether bond (>CHS—) was obtained. The reagent can be obtained by modifying corresponding Y-shaped polyethylene glycol derivative with an unprotected hydroxyl group, referring to Example-14.

$^1$H-NMR spectrum data of the compound H2-H2-11 were as follows: $^1$H NMR (CDCl$_3$) δ (ppm): 0.21 (—Si(CH$_3$)$_2$), 0.9-1.0 (—SiC(CH$_3$)$_3$), 2.30-2.70 (—NCH$_2$CH$_2$CONH—, —OCH$_2$CH$_2$S—), 2.50-3.50 (—SCHCH$_2$CON—, —OCH$_2$CH$_2$S—, —OCH$_2$CH$_2$NHCO—), 3.40-3.90 (—CH$_2$CH$_2$O—, —OCH(CH$_2$O—)$_2$, —NCH$_2$CH$_2$CONH—, —OCH$_2$CH$_2$S—, —SCHCH$_2$CON—, —OCH$_2$CH$_2$NHCO—); $M_n\approx 40000$ Da, PDI=1.02.

EXAMPLE-52

Preparation of H-Shaped Polyethylene Glycol Derivative with a Thioester Linkage

Synthesis of Derivative Containing a Thioester Bond H2-H2-12

Herein, the structural design of H-shaped polyethylene glycol derivative was given as follows: $F_1=F_2=$—$CH_2CH_2OTBS$,

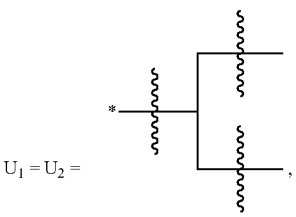

$U_1 = U_2 = $ , $j=1$ and $W_0$=—$CH_2CH_2SCOCH_2CH_2$—. The designed total molecular weight is approximately 40000 Da, wherein, the molecular weight of four branch chains is approximately $4\times5000=20000$ Da corresponding to $n_1\approx n_2\approx n_3\approx n_4\approx 114$, and the molecular weight of the main chain is approximately 20000 Da corresponding to $m_1\approx m_2\approx 227$.

152

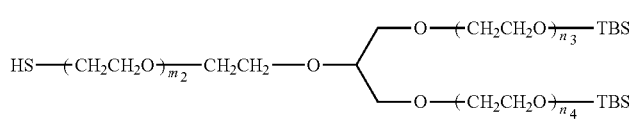

153

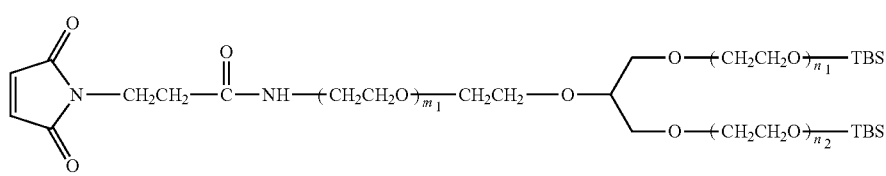

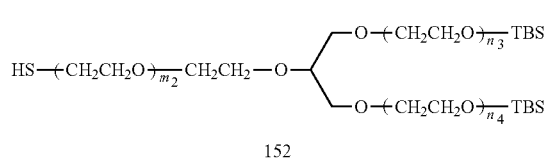

152

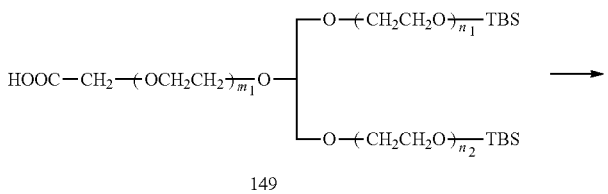

149

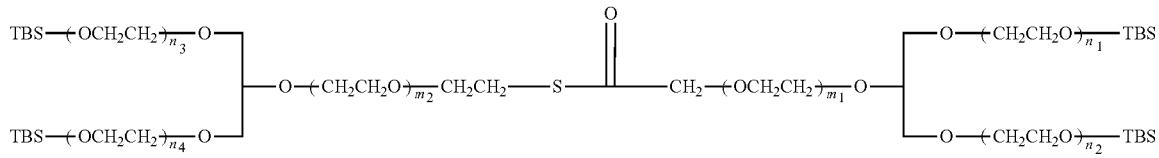

H2-H2-12

$^1$H-NMR spectrum data of the compound H2-H2-12 were as follows: $^1$H NMR (CDCl$_3$) δ (ppm): 0.21 (—Si(CH$_3$)$_2$), 0.9-1.0 (—SiC(CH$_3$)$_3$), 2.90-3.10 (—OCH$_2$CH$_2$SCO—), 3.40-3.80 (—CH$_2$CH$_2$O—, —OCH$_2$CH$_2$OSi—, —OCH(CH$_2$O—)$_2$), 3.80-4.00 (—OCH$_2$CH$_2$OSi—), 3.90-4.60 (—OCH$_2$C(=O), —OCH$_2$CH$_2$SCO—); $M_n$≈40000 Da, PDI=1.02.

EXAMPLE-53

Preparation of H-Shaped Polyethylene Glycol Derivative with A Sulfonamide Bond

Synthesis of Derivative with a Sulfonamide Bond H2-H2-13

Herein, the structural design of H-shaped polyethylene glycol derivative was given as follows: $F_1$=$F_2$=—CH$_2$CH$_2$OTBS,

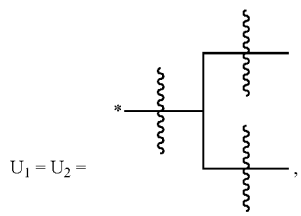

j=1 and W$_0$=—CH$_2$CH$_2$NHSO$_2$CH$_2$CH$_2$—. The designed total molecular weight is approximately 40000 Da, wherein, the molecular weight of four branch chains is approximately 4×5000=20000 Da corresponding to $n_1$≈$n_2$≈$n_3$≈$n_4$≈114, and the molecular weight of the main chain is approximately 20000 Da corresponding to $m_1$≈$m_2$≈227.

Step (a): Into a dry and clean 1 L round-bottom flask, 0.25 g of sodium hydride (60 wt %, in oil) was added. Using nitrogen protection, after the addition of anhydrous tetrahydrofuran (400 mL), and 30 g of Y-shaped branched polyethylene glycol derivative 131 (treated by azeotropic removal of water with toluene) dissolved in the tetrahydrofuran was added slowly in an ice bath, followed by stirring at room temperature for 3 hours. Thereafter, 1 g of 2-bromoethanesulfonic acid was added, followed by reaction at room temperature for 24 hours. After completion of the reaction, a small amount of saturated ammonium chloride was added to quench the reaction, and then the solution was adjusted to pH 2 with 1 N hydrochloric acid. The product in the solvent was concentrated, added with 400 mL of dichloromethane, washed with saturated salt solutions (100 mL trice), dried, concentrated and recrystallized from isopropanol, and a Y-shaped polyethylene glycol sulfonic acid derivative 154 in a white solid state was obtained.

$^1$H-NMR spectrum data of the intermediate 154 were as follows: $^1$H NMR (CDCl$_3$) δ (ppm): 0.21 (—Si(CH$_3$)$_2$), 0.98 (—SiC(CH$_3$)$_3$), 3.40-3.80 (—CH$_2$CH$_2$O—, —OCH$_2$CH$_2$OSi—, —OCH(CH$_2$O—)$_2$, —OCH$_2$CH$_2$SO$_2$OH), 3.80-4.00 (—OCH$_2$CH$_2$OSi—), 4.35 (—OCH$_2$CH$_2$SO$_2$OH); $M_n$≈30000 Da, PDI=1.02.

Step (b): Into a dry and clean 150 mL round-bottom flask, 2 g of Y-shaped polyethylene glycol amine derivative 143 (treated by azeotropic removal of water with toluene), 2 g of Y-shaped polyethylene glycol sulfonic acid derivative 154 and 480 mg DMAP were added. Using nitrogen protection, after the addition of anhydrous dichloromethane (50 mL), and the whole was stirred until all were dissolved. Then 120 mg of dicyclohexylcarbodiimide (DCC) was added, followed by reaction at room temperature for 24 hours. The resulting mixture was filtrated to remove undissolved substances, concentrated, recrystallized from isopropanol and

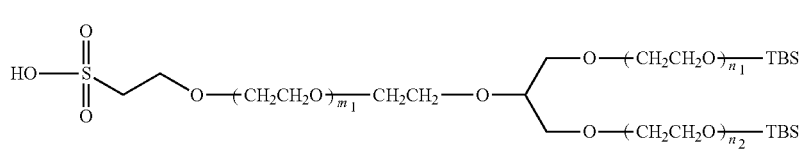

154 dialyzed, and then an H-shaped polyethylene glycol derivative containing a sulfonamide bond H2-H2-13 was obtained.

$^1$H-NMR spectrum data of the compound H2-H2-13 were as follows: $^1$H NMR (CDCl$_3$) δ (ppm): 0.21 (—Si(CH$_3$)$_2$), 0.9-1.0 (—SiC(CH$_3$)$_3$), 2.72-2.92 (—OCH$_2$CH$_2$NHSO$_2$—), 3.40-3.80 (—CH$_2$CH$_2$O—, —OCH$_2$CH$_2$OSi—, —OCH(CHO—)$_2$, —OCH$_2$CH$_2$NHSO$_2$—, —OCH$_2$CH$_2$SO$_2$—), 3.80-4.00 (—OCH$_2$CH$_2$SO$_2$—, —OCH$_2$CH$_2$OSi—); $M_n$≈40000 Da, PDI=1.02.

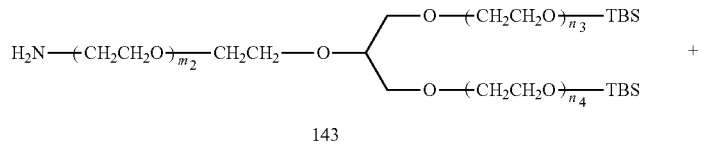

143

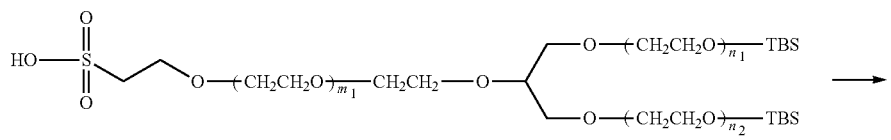

154

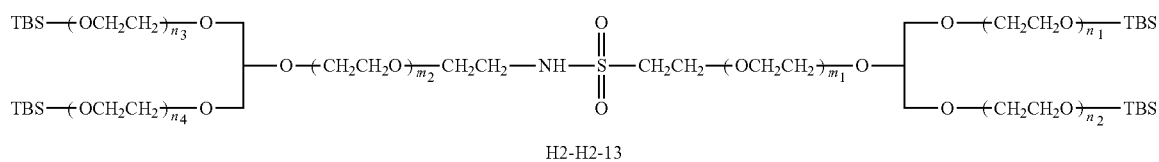

H2-H2-13

EXAMPLE-54

Preparation of H-Shaped Polyethylene Glycol Derivative with a Sulfonate Bond

Synthesis of Derivative with a Sulfonate Bond H2-H2-14

Herein, the structural design of H-shaped polyethylene glycol derivative was given as follows: F$_1$=F$_2$=—CH$_2$CH$_2$OTBS, $U_1 = U_2 =$ 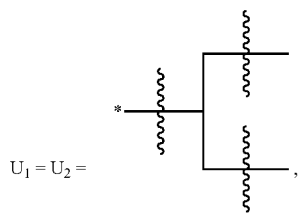, j=1 and W$_0$=—CH$_2$CH$_2$OSO$_2$CH$_2$CH$_2$—. The designed total molecular weight is approximately 40000 Da, wherein, the molecular weight of four branch chains is approximately 4×5000=20000 Da corresponding to $n_1$≈$n_2$≈$n_3$≈$n_4$≈114, and the molecular weight of the main chain is approximately 20000 Da corresponding to $m_1$≈$m_2$≈227.

Into a dry and clean 150 mL round-bottom flask, 2 g of Y-shaped polyethylene glycol alcohol derivative 131 (treated by azeotropic removal of water with toluene, obtained in Example-26), 2 g of Y-shaped polyethylene glycol sulfonic acid derivative 154 and 480 mg DMAP were added. Using nitrogen protection, after the addition of anhydrous dichloromethane (50 mL), and the whole was stirred until all were dissolved. Then 120 mg of dicyclohexylcarbodiimide (DCC) was added, followed by reaction at room temperature for 24 hours. The resulting mixture was filtrated to remove undissolved substances, concentrated, recrystallized from isopropanol and dialyzed, and an H-shaped polyethylene glycol derivative with a sulfonate bond H2-H2-14 was obtained.

$^1$H-NMR spectrum data of the compound H2-H2-14 were as follows: $^1$H NMR (CDCl$_3$) δ (ppm): 0.21 (—Si(CH$_3$)$_2$), 0.9-1.0 (—SiC(CH$_3$)$_3$), 3.40-3.80 (—CH$_2$CH$_2$O—, —OCH$_2$CH$_2$OSi—, —OCH$_2$CH$_2$OSO$_2$—, —OCH(CHO—)$_2$, —OCH$_2$CH$_2$SO$_2$—), 3.80-4.00 (—OCH$_2$CH$_2$SO$_2$—, —OCH$_2$CH$_2$OSi—); $M_n$≈40000 Da, PDI=1.02.

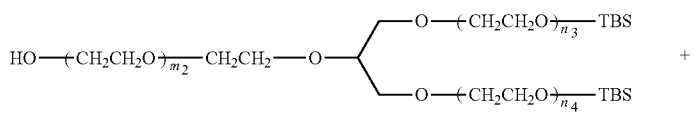

131

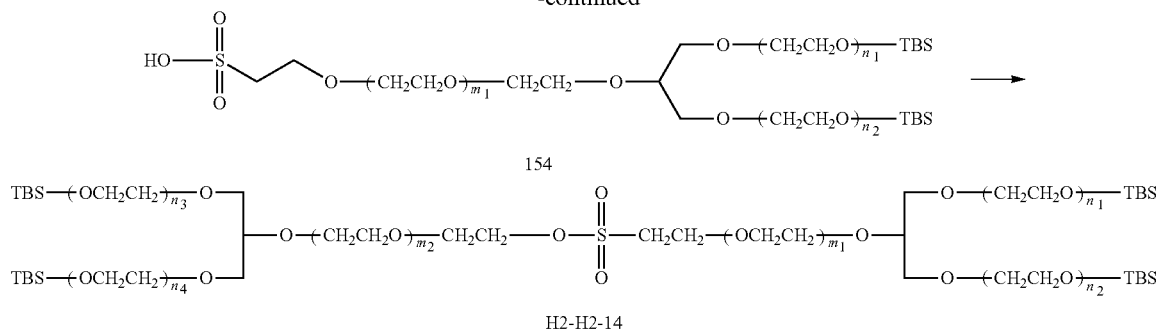

154

H2-H2-14

EXAMPLE-55

Preparation of H-Shaped Polyethylene Glycol Derivative with a Carbimide Bond (i.e., a Urea Bond)

Synthesis of Derivative with a Carbimide Bond H2-H2-15

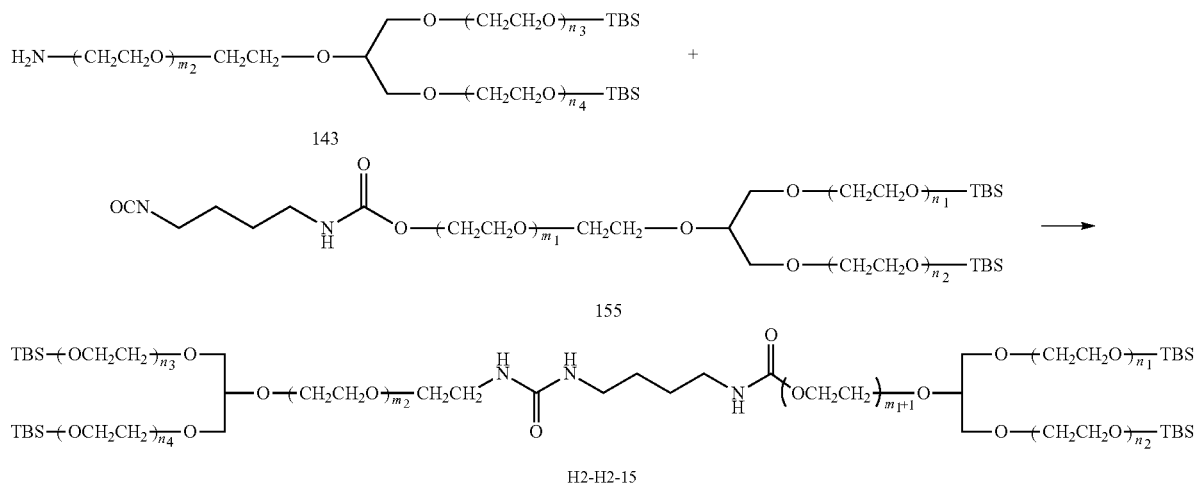

H2-H2-15

Herein, the structural design of H-shaped polyethylene glycol derivative was given as follows: $F_1=F_2=-CH_2CH_2OTBS$,

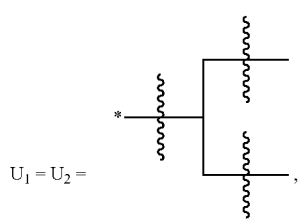

$j=1$ and $W_0=-CH_2CH_2NH(C=O)NH(CH_2)_4NHCO-$. The designed total molecular weight is approximately 40000 Da, wherein, the molecular weight of four branch chains is approximately $4 \times 5000 = 20000$ Da corresponding to $n_1 \approx n_2 \approx n_3 \approx n_4 \approx 114$, and the molecular weight of the main chain is approximately 20000 Da corresponding to $m_1 \approx m_2 \approx 227$.

Into a dry and clean 1 L round-bottom flask, 10 g of Y-shaped polyethylene glycol amine derivative 143 and 10 g of Y-shaped polyethylene glycol isocyanate derivative 155 were added followed by the addition of anhydrous dichloromethane (200 mL), and then the whole was stirred until all were dissolved. Thereafter, 5 mL of triethylamine was added, followed by reaction at room temperature for 8 hours. After completion of the reaction, the resulting mixture was concentrated, precipitated with absolute ether and dialyzed, and a urea derivative H2-H2-15 in a white solid state was obtained. The Y-shaped polyethylene glycol isocyanate derivative was obtained by modifying corresponding Y-shaped polyethylene glycol derivative by using the method in Example-34.

$^1$H-NMR spectrum data of the compound H2-H2-15 were as follows: $^1$H NMR (CDCl$_3$) δ (ppm): 0.21 (—Si(CH$_3$)$_2$), 0.98 (—SiC(CH$_3$)$_3$), 1.32-1.55 (—CH$_2$CH$_2$CH$_2$CH$_2$—), 2.70-3.15 (NCOCH$_2$CH$_2$—, —OCONHCH$_2$—), 3.40-3.80 (—CH$_2$CH$_2$O—, —OCH$_2$CH$_2$OSi—, —OCH(CH$_2$O—)$_2$), 3.80-4.00 (—OCH$_2$CH$_2$OSi—); $M_n \approx 40000$ Da, PDI=1.02.

EXAMPLE-56

Preparation of H-Shaped Polyethylene Glycol Derivative Containing 4,5-dihydroisoxazole Linkage

Synthesis of Derivative with a 4,5-dihydroisoxazole Linkage H2-H2-16

Herein, the structural design of H-shaped polyethylene glycol derivative was given as follows: $F_1=F_2=-CH_2CH_2OTBS$,

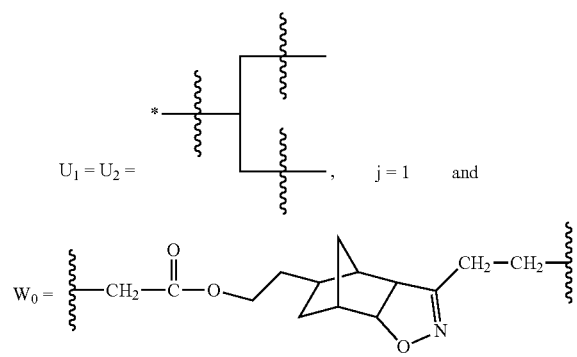

The designed total molecular weight is approximately 40000 Da, wherein, the molecular weight of four branch chains is approximately 4×5000=20000 Da corresponding to $n_1 \approx n_2 \approx n_3 \approx n_4 \approx 114$, and the molecular weight of the main chain is approximately 20000 Da corresponding to $m_1 \approx m_2 \approx 227$.

Step (a): Into a dry and clean 1 L round-bottom flask, 10 g of carboxyl-containing Y-shaped polyethylene glycol derivative 149 (treated by azeotropic removal of water with toluene), 5 mL of triethylamine and 5 g of compound 157 were added. Using nitrogen protection, dichloromethane (200 mL) was added, subsequently the whole was stirred till dissolution, and then 5 g of dicyclohexylcarbodiimide (DCC) was added, followed by reaction at room temperature for 24 hours and removal of the undissolved substances by filtration. The resulting mixture was concentrated and recrystallized from isopropanol, and an H-shaped polyethylene glycol norbornene derivative 156 in a white solid state was obtained.

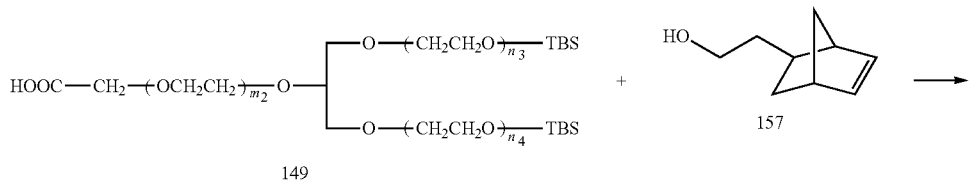

149     157

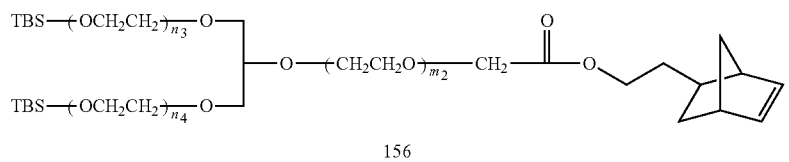

156

$^1$H-NMR spectrum data of the compound 156 were as follows: $^1$H NMR (CDCl$_3$) δ (ppm): 0.21 (—Si(CH$_3$)$_2$), 0.98 (—SiC(CH$_3$)$_3$), 1.30-2.10 (—COOCH$_2$CH$_2$CH—, —CH$_2$CH(CH$_2$)CH=CHCH—), 2.15-2.35 (—CH$_2$CH(CH$_2$)CH=CHCH—), 3.40-3.80 (—CH$_2$CH$_2$O—, —OCH$_2$CH$_2$OSi—, —OCH(CH$_2$O—)$_2$), 3.90-4.20 (—COOCH$_2$CH$_2$CH—), 4.20-4.45 (—OCH$_2$COO—), 5.40-5.70 (—CH$_2$CH(CH$_2$)CH=CHCH—); $M_n \approx 20000$ Da, PDI=1.02.

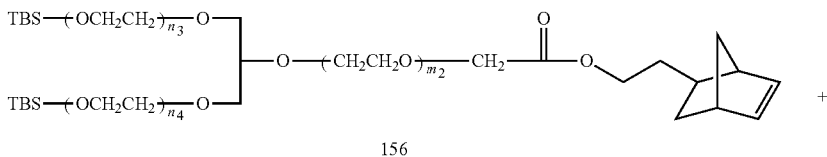

156

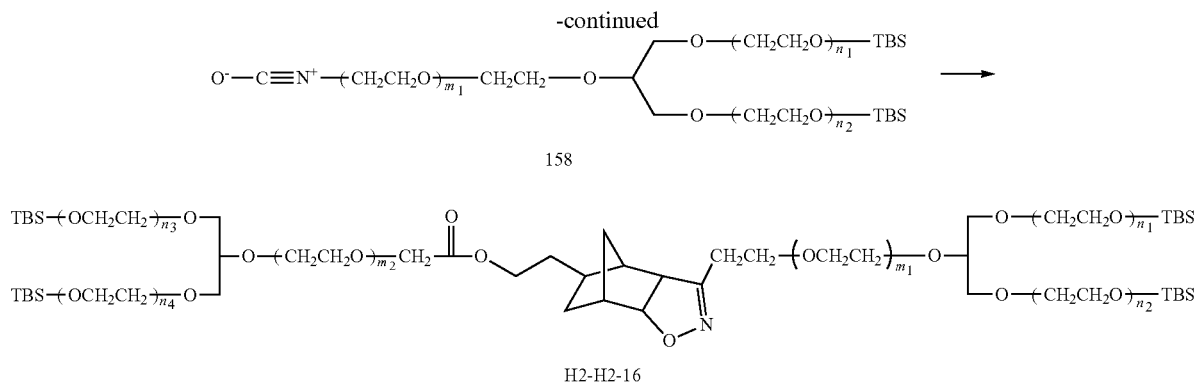

H2-H2-16

Step (b): Into a dry and clean 500 mL round-bottom flask, Y-shaped polyethylene glycol nitrile oxide compound 158 (starting from corresponding Y-shaped polyethylene glycol 131, prepared by using the method in Example-20) and acetonitrile were added in sequence. The whole was stirred at room temperature till dissolution, thereafter polyethylene glycol norbornene derivative 156 dissolved in acetonitrile (100 mL) was slowly added dropwisely, and the reaction was conducted at room temperature for 4 hours. The resulting mixture was concentrated and recrystallized from isopropanol, and a derivative H2-H2-16 was obtained.

$^1$H-NMR spectrum data of the derivative H2-H2-16 were as follows: $^1$H NMR (CDCl$_3$) δ (ppm): 0.21 (—Si(CH$_3$)$_2$), 0.98 (—SiC(CH$_3$)$_3$), 1.30-2.10 (—COOCH$_2$CH$_2$CH—, —CH$_2$CH(CH$_2$)CHCHCH—, —C(═N)CH$_2$CH$_2$O—), 3.40-3.80 (—CH$_2$CH$_2$O—, —OCH$_2$CH$_2$OSi—, —OCH(CH$_2$O—)$_2$, —C(═N)CH$_2$CH$_2$O—), 3.80-4.00 (—OCH$_2$CH$_2$OSi—), 3.90-4.20 (—COOCH$_2$CH$_2$CH—, C(═N)CH$_2$CH$_2$O—), 4.20-4.45 (—OCH$_2$COO—); $M_n$≈40000 Da, PDI=1.02.

EXAMPLE-56-2

Preparation of H-Shaped Polyethylene Glycol Derivative with Two Different Trivalent Branching Centers Synthesis of Hetero-Branching H-Shaped Derivative H1-H2-2

Step (a): Into a sealed reactor under an anhydrous and oxygen-free atmosphere, tetrahydrofuran (125 mL), EE-monoprotected ethylene glycol 158 (2.5 mmol) and diphenylmethyl potassium (2.0 mmol) were added in sequence.

Step (b): After a calculated amount of ethylene oxide (1100 mmol) was added, the whole was heated stepwisely to 60° C., followed by reaction at 60° C. for 48 hours.

Step (c): After completion of the reaction, excess diphenylmethyl potassium (20 mmol) and excess TBSCl (100 mmol) were added in sequence, followed by reaction at 30° C. for 12 hours. After completion of the reaction, open the reactor. The product in the solvent was concentrated, and then precipitated with absolute ether at 0° C. The crystals were collected by filtration and dried, and a V-shaped polyethylene glycol compound 159 with two silyl-protected hydroxyl groups was obtained.

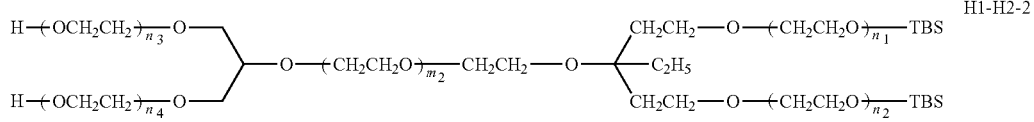

H1-H2-2

Herein, the structural design of H-shaped polyethylene glycol derivative was given as follows: $F_1$=—CH$_2$CH$_2$OTBS, $F_2$=—CH$_2$CH$_2$OH, $U_1$=—C(CH$_2$CH$_3$)(CH$_2$CH$_2$—)$_2$, $U_2$=—CH(CH$_2$—)$_2$, j=1, $W_0$ is CH$_2$CH$_2$ and $m_1$≈0. The designed total molecular weight is approximately 25000 Da, wherein the molecular weight of four branch chains is approximately 4×5000=20000 Da corresponding to $n_1$≈$n_2$≈$n_3$≈$n_4$≈114, and the molecular weight of the main chain is approximately 5000 Da corresponding to $m_2$≈113.

$^1$H-NMR spectrum data of the compound 159 were as follows: $^1$H NMR (CDCl$_3$) δ (ppm): 0.21 (—Si(CH$_3$)$_2$), 0.9-1.0 (CCH$_2$CH$_3$, —SiC(CH$_3$)$_3$), 1.22 (—OCH$_2$CH$_3$), 1.3-1.6 (—OCH(O)CH$_3$), CCH$_2$CH$_3$, CCH$_2$CH$_2$), 3.40-3.80 (—CH$_2$CH$_2$O—, OCH$_2$CH$_3$, —OCH$_2$CH$_2$OSi—, CCH$_2$CH$_2$), 3.80-4.00 (—OCH$_2$CH$_2$OSi—), 4.75 (—OCHCH$_3$(OCH$_2$)); $M_n$≈10000 Da, PDI=1.02.

Step (d): Into a dry and clean container, the V-shaped polyethylene glycol compound 159 was added and then dissolved with methanol. The solution was adjusted to pH 3.5 with hydrochloric acid (1 M), followed by reaction for 4 hours, and a V-shaped polyethylene glycol compound 160 containing an unprotected hydroxyl group was obtained.

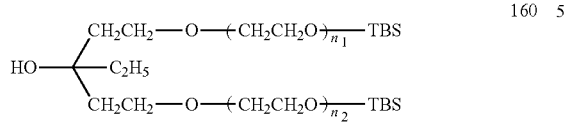

160

$^1$H-NMR spectrum data of the intermediate 160 were as follows: $^1$H NMR (CDCl$_3$) δ (ppm): 0.21 (—Si(CH$_3$)$_2$), 0.9-1.0 (CCH$_2$CH$_3$, —SiC(CH$_3$)$_3$), 1.3-1.6 (CCH$_2$CH$_3$, CCH$_2$CH$_2$), 3.40-3.80 (—CH$_2$CH$_2$O—, —OCH$_2$CH$_2$OSi—, CCH$_2$CH$_2$), 3.80-4.00 (—OCH$_2$CH$_2$OSi—).

Step (e): Step (a) and step (b) were repeated, then excess proton source (e.g., DPMK) and excess compound 132 (100 mmol) were added thereinto in sequence, followed by reaction at 30° C. for 12 hours. After completion of the reaction, open the reactor. The product in the solvent was concentrated, and then precipitated with absolute ether at 0° C. The crystals were collected by filtration and dried, and a polyethylene glycol derivative 161 with two EE-protected hydroxyl groups was obtained.

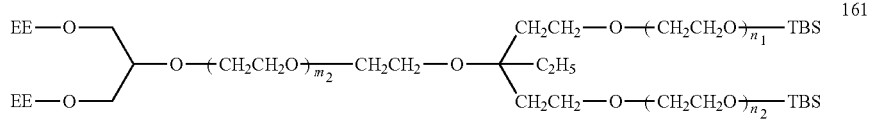

161

$^1$H-NMR spectrum data of the compound 161 were as follows: $^1$H NMR (CDCl$_3$) δ (ppm): 0.21 (—Si(CH$_3$)$_2$), 0.9-1.0 (CCH$_2$CH$_3$, —SiC(CH$_3$)$_3$), 1.22 (—OCH$_2$CH$_3$), 1.3-1.6 (—OCH(O)CH$_3$), CCH$_2$CH$_3$, CCH$_2$CH$_2$), 3.40-3.80 (—CH$_2$CH$_2$O—, —OCH$_2$CH$_2$OSi—, —OCH(CH$_2$O—)$_2$, OCH$_2$CH$_3$, CCH$_2$CH$_2$), 3.80-4.00 (—OCH$_2$CH$_2$OSi—), 4.75 (—OCHCH$_3$(OCH$_2$)); M$_n$≈15000 Da, PDI=1.02.

Step (f): Step (d), step (a) and step (b) were repeated, and the EE groups were removed to obtain a polyethylene glycol intermediate containing two unprotected hydroxyl groups. After deprotonation, the polymerization of ethylene oxide was initiated, and an H-shaped polyethylene glycol derivative H1-H2-2 with two terminal silyl-protected hydroxyl groups was obtained.

$^1$H-NMR spectrum data of the compound H1-H2-2 were as follows: $^1$H NMR (CDCl$_3$) δ (ppm): 0.21 (—Si(CH$_3$)$_2$), 0.9-1.0 (CCH$_2$CH$_3$, —SiC(CH$_3$)$_3$), 1.3-1.6 (CCH$_2$CH$_3$, CCH$_2$CH$_2$), 3.40-3.80 (—CH$_2$CH$_2$O—, —OCH$_2$CH$_2$OSi—, —OCH(CH$_2$O—)$_2$, CCH$_2$CH$_2$), 3.80-4.00 (—OCH$_2$CH$_2$OSi—); M$_n$≈25000 Da, PDI=1.02.

EXAMPLE-57

Preparation of H-Shaped Polyethylene Glycol Derivative with Ester Bonds

Synthesis of Derivative with Two Ester Bonds H2-H2-17

Herein, the structural design of H-shaped polyethylene glycol derivative was given as follows: F$_1$=F$_2$=—CH$_2$CH$_2$OTBS, U$_1$=U$_2$=—CH$_2$COO—C(CH$_2$CH$_3$)(CH$_2$—)$_2$, j=1 and W$_0$ is CH$_2$CH$_2$. The designed total molecular weight is approximately 60000 Da, wherein, the molecular weight of four branch chains is approximately 4×5000=20000 Da corresponding to n$_1$≈n$_2$≈n$_3$≈n$_4$≈114, and the molecular weight of the main chain is approximately 40000 Da corresponding to m$_2$≈909.

Into a dry and clean 1 L round-bottom flask, 10 g of polyethylene glycol compound 160 with one unprotected hydroxyl group (treated by azeotropic removal of water with toluene), 10 mL of triethylamine and 2.5 g of linear polyethylene glycol derivative 161 containing two terminal carboxyl groups were added. Using nitrogen protection, dichloromethane (200 mL) was added, thereafter the whole was stirred till dissolution, and then 10 g of dicyclohexylcarbodiimide (DCC) was added, followed by reaction at room temperature for 24 hours and removal of the undissolved substances by filtration. The resulting mixture was concentrated and recrystallized from isopropanol, and an H-shaped polyethylene glycol compound H2-H2-17 in a white solid state was obtained.

$^1$H-NMR spectrum data of the compound H2-H2-17 were as follows: $^1$H NMR (CDCl$_3$) δ (ppm): 0.21 (—Si(CH$_3$)$_2$), 0.9-1.0 (CCH$_2$CH$_3$, —SiC(CH$_3$)$_3$), 1.3-1.6 (CCH$_2$CH$_3$, CCH$_2$CH$_2$), 3.40-3.80 (—CH$_2$CH$_2$O—, —OCH$_2$CH$_2$OSi—, CCH$_2$CH$_2$), 3.80-4.00 (—OCH$_2$CH$_2$OSi—), 4.53 (—OCH$_2$C(=O)O—); M$_n$≈60000 Da, PDI=1.02.

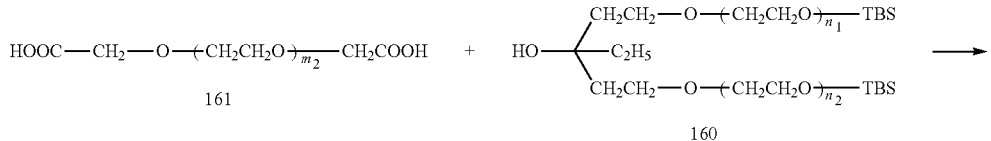

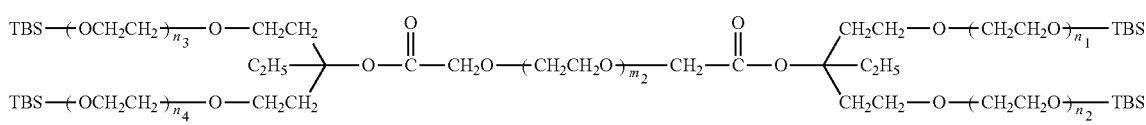

H2-H2-17

EXAMPLE-58

Preparation of H-Shaped Polyethylene Glycol Derivative with Ester Bonds

Synthesis of Derivative with Two Ester Bonds H2-H2-18

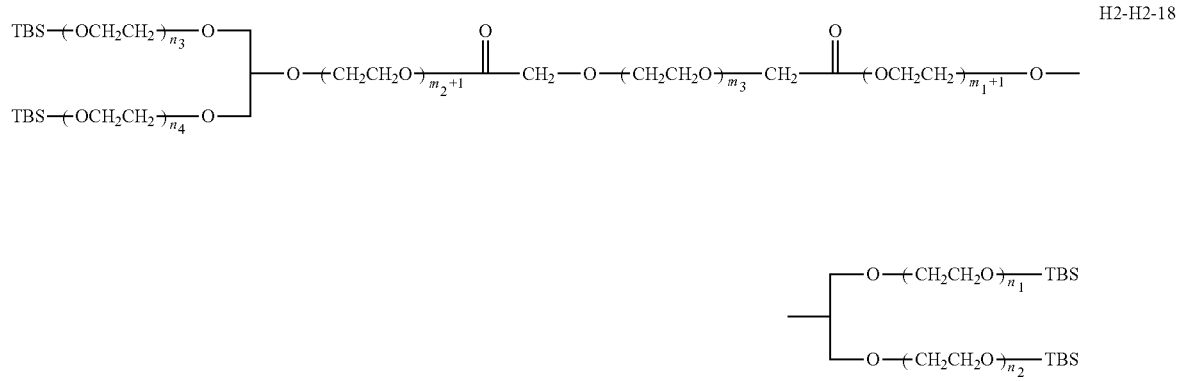

H2-H2-18

Herein, the structural design of H-shaped polyethylene glycol derivative was given as follows: $F_1=F_2=$—$CH_2CH_2OTBS$, $U_1=U_2=$—$CH(CH_2—)_2$, $W_{01}=CH_2CO$ and $W_{02}=COCH_2$. The designed total molecular weight is approximately 80000 Da, wherein, the molecular weight of four branch chains is approximately 4×5000=20000 Da corresponding to $n_1 \approx n_2 \approx n_3 \approx n_4 \approx 114$, and the molecular weight of the main chain is approximately 60000 Da corresponding to $m_2 \approx 909$, $m_1 \approx m_2 \approx 227$.

Into a dry and clean 1 L round-bottom flask, 10 g of Y-shaped polyethylene glycol compound 131 with one unprotected hydroxyl group (treated by azeotropic removal of water with toluene), 10 mL of triethylamine and 1.5 g of linear polyethylene glycol derivative 161 containing two terminal carboxyl groups (the molecular weight was about 40000 and $m_3 \approx 909$) were added. Using nitrogen protection, dichloromethane (200 mL) was added, thereafter the whole was stirred till dissolution, and then 10 g of dicyclohexylcarbodiimide (DCC) was added, followed by reaction at room temperature for 24 hours and removal of the undissolved substances by filtration. The resulting mixture was concentrated and recrystallized from isopropanol, and an H-shaped polyethylene glycol compound H2-H2-18 in a white solid state was obtained.

$^1$H-NMR spectrum data of the compound H2-H2-18 were as follows: $^1$H NMR (CDCl$_3$) δ (ppm): 0.21 (—Si(CH$_3$)$_2$), 0.9-1.0 (—SiC(CH$_3$)$_3$), 3.40-3.80 (—CH$_2$CH$_2$O—, —OCH$_2$CH$_2$OSi—, —OCH(CHO—)$_2$, —OCH$_2$CH$_2$OCO—), 3.80-4.00 (—OCH$_2$CH$_2$OSi—), 4.15-4.50 (—OCH$_2$C(=O)O—, —OCH$_2$CH$_2$OCO—); $M_n \approx 80000$ Da, PDI=1.03.

EXAMPLE-59

Preparation of H-Shaped Polyethylene Glycol Derivative with Ester Bonds

Synthesis of Derivative with Four Ester Bonds at Branch Chains H2-H2-19

Herein, the structural design of H-shaped polyethylene glycol derivative was given as follows: $F_1=F_2=$—$CH_2CH_2OTBS$, $U_1=U_2=$—$CH(CH_2OOCCH_2—)_2$, j=1, $W_0$ is $CH_2CH_2$ and $m_1 \approx 0$. The designed total molecular weight is approximately 10000 Da, wherein, the molecular weight of four branch chains is approximately 4×2000=8000 Da corresponding to $n_1=n_2=n_3=n_4=44$, and the molecular weight of the main chain is approximately 2000 Da corresponding to $m_2 \approx 43$.

By using the production method in Example-1 and changing the amount of ethylene oxide, a polyethylene glycol compound 104b containing four unprotected hydroxyl groups was obtained, wherein the compound 104b has the same structural general formula as above-obtained compound 104, but has a molecular weight of 2000 Da and an oxyethylene-unit number of $m_2 \approx 43$.

Into a dry and clean 1 L round-bottom flask, 10 g of polyethylene glycol compound 104b containing four hydroxyl groups (treated by azeotropic removal of water with toluene), 20 mL of triethylamine and 40 g of monodisperse polyethylene glycol chloroacetate derivative 162 with one terminal TBS-protected hydroxyl group and an EO-unit number of 44 were added. Using nitrogen protection, dichloromethane (200 mL) was added, thereafter the whole was stirred till dissolution, and then 20 g of dicyclohexylcarbodiimide (DCC) was added, followed by reaction at room temperature for 24 hours. Then the undissolved substances were removed by filtration, the resulting mixture was concentrated and recrystallized from isopropanol, and an H-shaped polyethylene glycol compound H2-H2-19 in a white solid state was obtained.

$^1$H-NMR spectrum data of the compound H2-H2-19 were as follows: $^1$H NMR (CDCl$_3$) δ (ppm): 0.21 (—Si(CH$_3$)$_2$), 0.9-1.0 (CCH$_2$CH$_3$, —SiC(CH$_3$)$_3$), 3.40-3.80 (—CH$_2$CH$_2$O—, —OCH$_2$CH$_2$OSi—), 3.80-4.00 (—OCH$_2$CH$_2$OSi—), 3.90-4.00 (—OCH(CH$_2$O—)$_2$), 4.20-4.30 (—OCH(CH$_2$O—)$_2$), 4.30-4.40 (—CH$_2$COO—); $M_n \approx 10000$ Da, PDI=1.02.

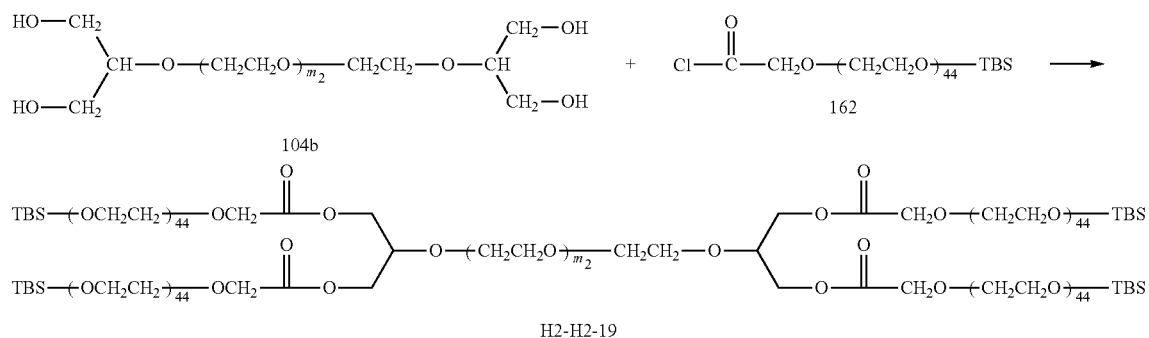

EXAMPLE-60

Preparation of H-Shaped Polyethylene Glycol Derivative in Which Branch Chains Have Glycerol-Branching Terminals Synthesis of H-Shaped Polyethylene Glycol Derivative H2-H2-20 with Glycerol-Branching Branch-Chain Terminals

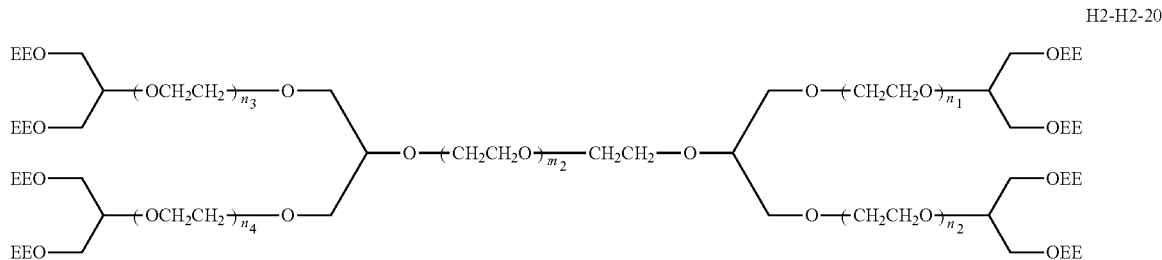

Herein, the structural design of H-shaped polyethylene glycol derivative was given as follows: $F_1=F_2=-CH(CH_2OEE)_2$ (g=1, k=2, $g_0=0$,

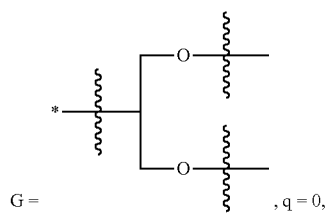

without $Z_2$, $q_1=1$, $Z_1=CH_2$, $R_{01}=OPG_4$, $PG_4$ is EE),

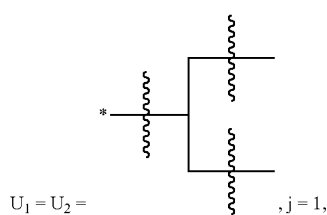

$W_0$ is $CH_2CH_2$ and $m_1\approx 0$. The designed total molecular weight is approximately 26000 Da, wherein, the molecular weight of four branch chains is approximately 4×5000=20000 Da corresponding to $n_1\approx n_2\approx n_3\approx n_4\approx 114$, and the molecular weight of the main chain is approximately 5000 Da corresponding to $m_2\approx 113$.

132

TsO—⟨—OEE / —OEE⟩

H-shaped polyethylene glycol compound H1-H1-1 (2.5 mmol) was dissolved in tetrahydrofuran, subsequently added with excess diphenylmethyl potassium (80 mmol), and then excess compound 132 (200 mmol) was added thereinto, followed by reaction at 30° C. for 12 hours. After completion of the reaction, open the reactor. The product in the solvent was concentrated and then precipitated with absolute ether at 0° C. The crystals were collected by filtration and dried, and a polyethylene glycol derivative H2-H2-20 with eight terminal EE-protected hydroxyl groups was obtained.

$^1$H-NMR spectrum data of the compound H2-H2-20 were as follows: $^1$H NMR (CDCl$_3$) δ (ppm): 1.22 (—OCH$_2$CH$_3$), 1.36 (—OCH(O)CH$_3$), 3.40-3.80 (—CH$_2$CH$_2$O—, —OCH (CH$_2$O—)$_2$, OCH$_2$CH$_3$), 4.75 (—OCHCH$_3$(OCH$_2$)); $M_n\approx 26000$ Da, PDI=1.02.

EXAMPLE-61

Preparation of H-Shaped Polyethylene Glycol Derivative Having Branched Chain-Terminals Synthesis of Polyethylene Glycol Derivative H2-H2-21 Having Branched Chain-Terminals Wherein Each Terminal has Three Active Sites

H2-H2-21

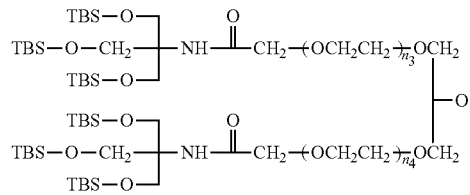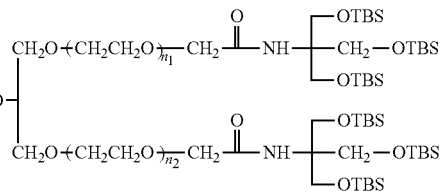

Herein, the structural design of H-shaped polyethylene glycol derivative was given as follows: $F_1=F_2=-CH_2CONHC(CH_2OTBS)_3$ (g=1, k=3, $g_0=0$, $L_0=CH_2CONH$,

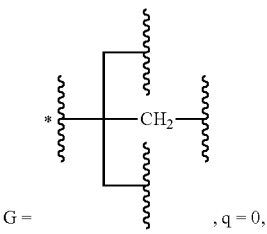

without $Z_2$, $q_1=0$, without $Z_1$, $R_{01}=OPG_4$, $PG_4$ is TBS)

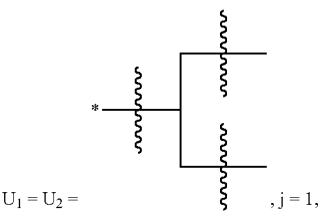

$W_0$ is $CH_2CH_2$ and $m_1\approx 0$. The designed total molecular weight is approximately 25000 Da, wherein, the molecular weight of four branch chains is approximately 4×5000=20000 Da corresponding to $n_1\approx n_2\approx n_3\approx n_4\approx 114$, and the molecular weight of the main chain is approximately 5000 Da corresponding to $m_2\approx 113$.

Into a dry and clean 1 L round-bottom flask, 10 g of H-shaped polyethylene glycol compound containing four carboxyl groups D4-D4-1 (treated by azeotropic removal of water with toluene), 20 mL of triethylamine and 80 g of compound 163 were added. Using nitrogen protection, dichloromethane (400 mL) was added, thereafter the whole was stirred till dissolution, and then 40 g of dicyclohexylcarbodiimide (DCC) was added, followed by reaction at room temperature for 24 hours and removal of the undissolved substances by filtration. The resulting mixture was concentrated and recrystallized from isopropanol, and an H-shaped polyethylene glycol compound H2-H2-21 in a white solid state was obtained.

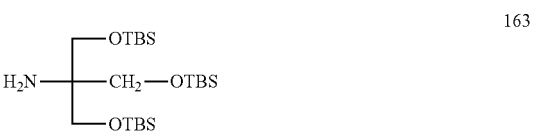 [SMILES: CC(C)(C)[Si](C)(C)OCC(N)(CO[Si](C)(C)C(C)(C)C)CO[Si](C)(C)C(C)(C)C]

$^1$H-NMR spectrum data of the compound H2-H2-21 were as follows: $^1$H NMR (CDCl$_3$) δ (ppm): 0.21 (—Si(CH$_3$)$_2$), 0.98 (—SiC(CH$_3$)$_3$), 3.40-3.80 (—CH$_2$CH$_2$O—, —OCH(CH$_2$O—)$_2$), 3.90-4.20 (—NHCCH$_2$O—), 4.10-4.30 (—OCH$_2$CO—); $M_n\approx 27000$ Da, PDI=1.02.

EXAMPLE-62

Preparation of H-Shaped Multifunctionalized Polyethylene Glycol with Comb-Like Branched Chain-Terminals Synthesis of H-Shaped Multifunctionalized Polyethylene Glycol H2-H2-22 with Comb-Like Branched Chain-Terminals Herein, the structural design of H-shaped polyethylene glycol derivative was given as follows:

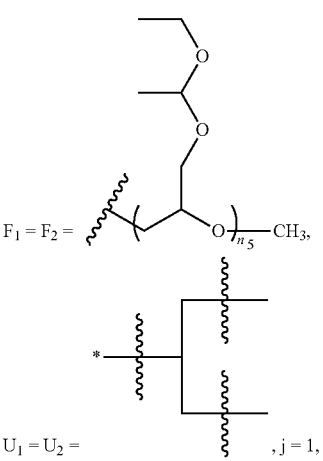

$W_0$ is $CH_2CH_2$ and $m_1\approx 0$. The designed total molecular weight is approximately 45000 Da, wherein, the molecular weight of four branch chains is approximately 4×5000=20000 Da corresponding to $n_1 \approx n_2 \approx n_3 \approx n_4 \approx 114$, and the molecular weight of $F_1$ is approximately 5000 Da corresponding to $n_5 \approx 34$, and the molecular weight of the main chain is approximately 5000 Da corresponding to $m_2 \approx 113$.

Step (a): Into a sealed reactor under an anhydrous and oxygen-free atmosphere, tetrahydrofuran (125 mL), the H-shaped polyethylene glycol H1-H1-1 containing four hydroxyl groups (2.5 mmol) and diphenylmethyl potassium (8.0 mmol) were added in sequence.

Step (b): After a calculated amount of EEGE164 (Ethoxy ethyl glycidyl ether) (100 mL, 2000 mmol,

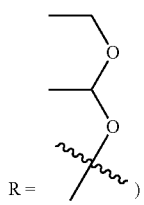 [SMILES: *OC(C)OCC]

was added, thereafter the whole was heated stepwisely to 60° C., followed by reaction at 60° C. for 48 hours.

Step (c): After completion of the reaction, excess diphenylmethyl potassium (20 mmol) and excess methyl iodide (50 mmol) were added in sequence, followed by reaction at 30° C. for 12 hours. After completion of the reaction, open the reactor. The product in the solvent was concentrated and then precipitated with absolute ether at 0° C. The crystals were collected by filtration and dried, and an H-shaped polyethylene glycol derivative H2-H2-22 was obtained.

$^1$H-NMR spectrum data of the compound H2-H2-22 were as follows: $^1$H NMR (CDCl$_3$) δ (ppm): 1.22 (—OCH$_2$CH$_3$), 1.36 (—OCH(O)CH$_3$), 3.35 (CH$_3$O—), 3.40-3.80 (—CH$_2$CH$_2$O—, —OCH(CH$_2$O—)$_2$, OCH$_2$CH$_3$), 4.75 (—OCHCH$_3$(OCH$_2$)); $M_n \approx 45000$ Da, PDI=1.02.

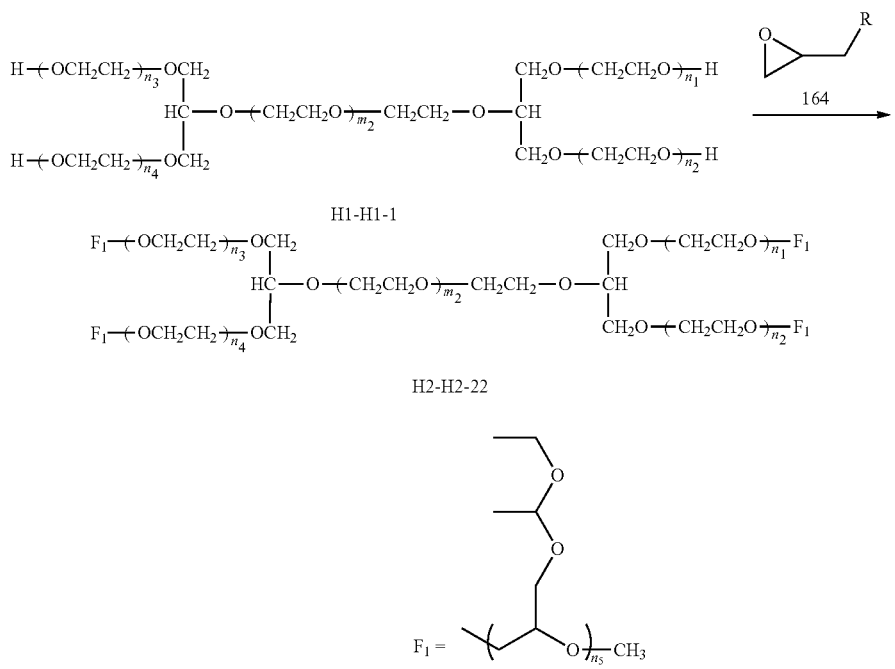

EXAMPLE-63

Preparation of H-Shaped Polyethylene Glycol Derivative with Hyperbranched Branch-Chain Terminals Synthesis of Derivative H1-H1-4 with Hyperbranched Branch-Chain Terminals

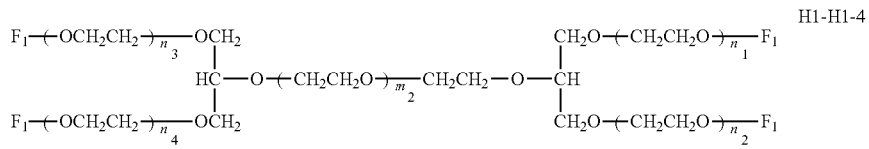

-continued

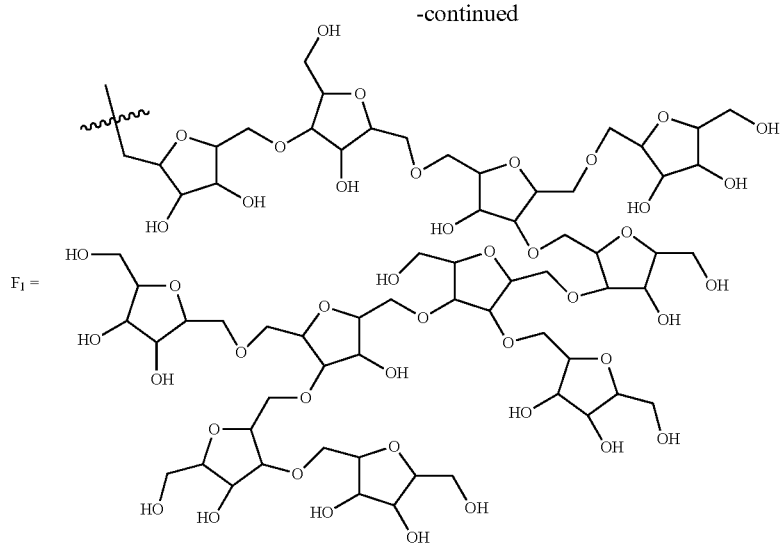

Herein, the structural design of H-shaped polyethylene glycol derivative was given as follows: $F_1$ and $F_2$ are the same as those of H1-H1-4, respectively

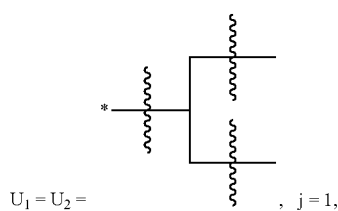

$W_0$ is $CH_2CH_2$ and $m_1 \approx 0$. The designed total molecular weight is approximately 45000 Da, wherein, the molecular weight of four branch chains is approximately $4 \times 5000 = 20000$ Da corresponding to $n_1 \approx n_2 \approx n_3 \approx n_4 \approx 114$, and the molecular weight of the main chain is approximately 5000 Da corresponding to $m_2 \approx 113$.

165

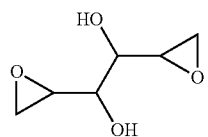

Step (a): Into a sealed reactor under an anhydrous and oxygen-free atmosphere, tetrahydrofuran (125 mL), H-shaped polyethylene glycol H1-H1-1 containing four hydroxyl groups (2.5 mmol) and diphenylmethyl potassium (8.0 mmol) were added in sequence.

Step (b): After a calculated amount of compound 165 (100 mL, 2000 mmol) was added, the whole was heated step-wisely to 60° C., followed by reaction at 60° C. for 48 hours.

Step (c): After completion of the reaction, excess methanol was added thereinto. The product in the solvent was concentrated and then precipitated with absolute ether at 0° C. The crystals were collected by filtration and dried, and an H-shaped polyethylene glycol derivative H1-H1-4 was obtained.

1H-NMR spectrum data of the compound H1-H1-4 were as follows: $^1H$ NMR (CDCl$_3$) δ (ppm): 3.40-3.80 (—CH$_2$CH$_2$O—, —OCH(CH$_2$O—)$_2$, —OCH$_2$CH(O)CH(O)—), 3.85-4.40 (—OCH$_2$CH(O)CH(O)—); $M_n \approx 45000$ Da, PDI=1.02.

EXAMPLE-64

Preparation of H-Shaped Polyethylene Glycol Derivative with Hyperbranched Branch-Chain Terminals Synthesis of Derivative H1-H1-5 with Hyperbranched Branch-Chain Terminals

H1-H1-5

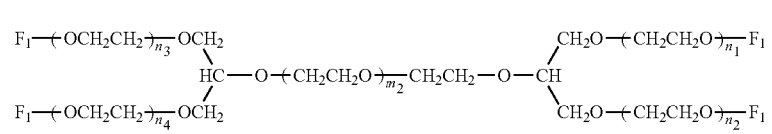

$F_1 =$

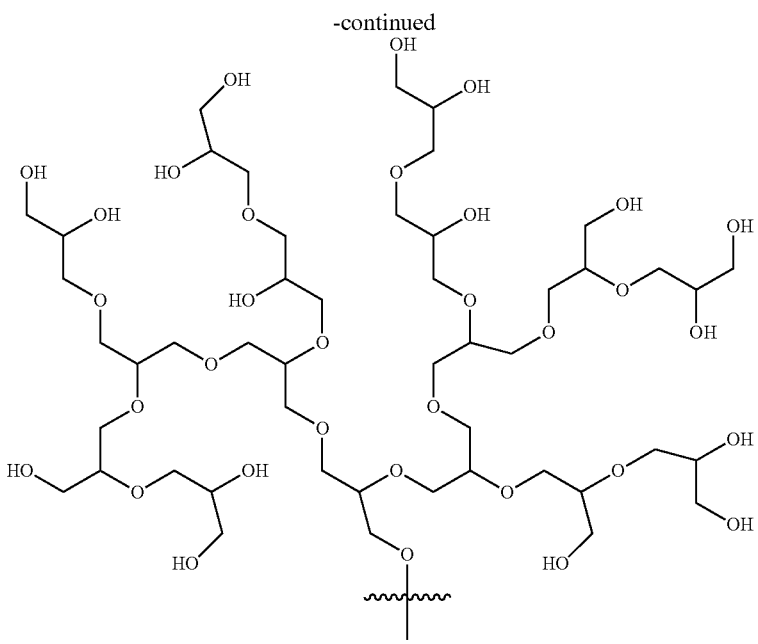

Herein, the structural design of H-shaped polyethylene glycol derivative was given as follows: $F_1$ and $F_2$ are the same as those of H1-H1-5, respectively,

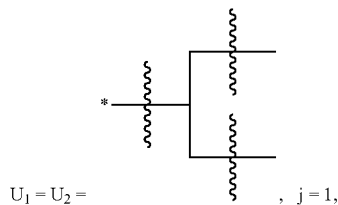

$W_0$ is $CH_2CH_2$ and $m_1 \approx 0$. The designed total molecular weight is approximately 45000 Da, wherein, the molecular weight of four branch chains is approximately $4 \times 5000 = 20000$ Da corresponding to $n_1 \approx n_2 \approx n_3 \approx n_4 \approx 114$, and the molecular weight of the main chain is approximately 5000 Da corresponding to $m_2 \approx 113$.

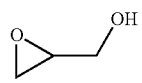

166

Step (a): Into a sealed reactor under an anhydrous and oxygen-free atmosphere, tetrahydrofuran (125 mL), H-shaped polyethylene glycol H1-H1-1 (2.5 mmol) containing four hydroxyl groups and diphenylmethyl potassium (8.0 mmol) were added in sequence.

Step (b): After a calculated amount of glycidol 166 (100 mL, 2000 mmol) was added, the whole was heated stepwisely to 60° C., followed by reaction at 60° C. for 48 hours.

Step (c): After completion of the reaction, excess methanol was added thereinto. The product in the solvent was concentrated and then precipitated with absolute ether at 0° C. The crystals were collected by filtration and dried, and then an H-shaped polyethylene glycol derivative H1-H1-5 was obtained.

$^1$H-NMR spectrum data of the compound H1-H1-5 were as follows: $^1$H NMR (CDCl$_3$) δ (ppm): 3.40-3.85 (—CH$_2$CH$_2$O—, —OCH(CH$_2$O—)$_2$); M$_n \approx$ 45000 Da, PDI=1.02.

EXAMPLE-65

Preparation of H-Shaped Polyethylene Glycol Derivative with Dendritic Branch-Chain Terminals Synthesis of Derivative H2-H2-23 with Dendritic Branch-Chain Terminals

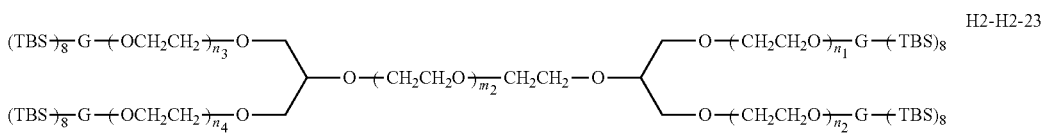

G =

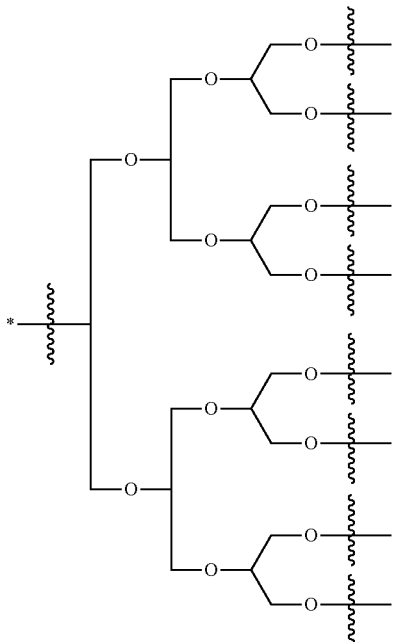

Herein, the structural design of H-shaped polyethylene glycol derivative was given as follows: $F_1=F_2=G(TBS)_8$ (wherein, g=1, $g_0=0$, k=8, G is the same of that in H2-H2-23, q=0, without $Z_2$, $q_1=0$, without $Z_1$, $R_{O1}$=TBS), $U_1 = U_2 =$ , j = 1, $W_0$ is $CH_2CH_2$ and $m_1 \approx 0$. The designed total molecular weight is approximately 45000 Da, wherein, the molecular weight of four branch chains is approximately 4×5000=20000 Da corresponding to $n_1 \approx n_2 \approx n_3 \approx n_4 \approx 114$, and the molecular weight of the main chain is approximately 5000 Da corresponding to $m_2 \approx 113$.

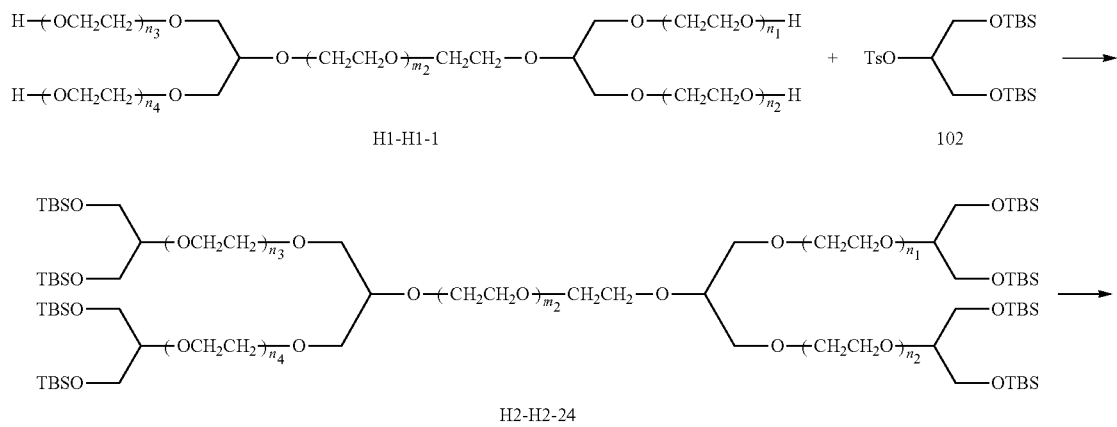

-continued

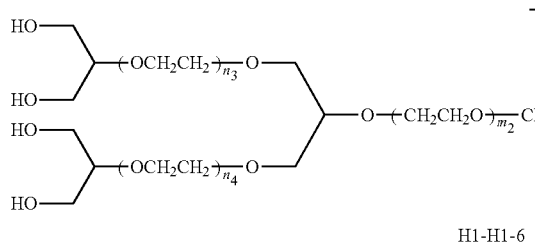

H1-H1-6 → H2-H2-23

Step (a): Into the reactor, H-shaped polyethylene glycol H1-H1-1 (2.532 mmol) containing four unprotected hydroxyl groups was added, and thereafter excess diphenylmethyl potassium (80 mmol) and excess compound 102 (200 mmol) were added in sequence, followed by reaction at 30° C. for 12 hours. After completion of the reaction, open the reactor. The product in the solvent was concentrated and precipitated with absolute ether at 0° C. The crystals were collected by filtration and dried, and a polyethylene glycol intermediate H2-H2-21 containing two terminal silyl-protected hydroxyl groups was obtained.

Step (b): Into a dry and clean container, the intermediate H2-H2-21 was added and then dissolved with tetrahydrofuran, followed by the addition of tetra-t-butyl ammonium fluoride (TBAF), thereafter the reaction was conducted overnight, and an H-shaped polyethylene glycol intermediate H1-H1-6 containing eight unprotected hydroxyl groups was obtained.

Step (c): Step (a) and step (b) were repeated twice, and thereafter a dendritic H-shaped polyethylene glycol derivative H2-H2-23 containing terminal TBS-protected hydroxyl groups was obtained.

$^1$H-NMR spectrum data of the compound H2-H2-23 were as follows: $^1$H NMR (CDCl$_3$) δ (ppm): 0.21 (—Si(CH$_3$)$_2$), 0.98 (—SiC(CH$_3$)$_3$), 2.90-3.10 (—OCHCH$_2$OSi—), 3.40-3.80 (—CH$_2$CH$_2$O—, —OCH(CH$_2$O—)$_2$), 3.80-4.10 (—OCHCH$_2$OSi—); $M_n$≈27000 Da, PDI=1.03.

EXAMPLE-66

Preparation of H-Shaped Polyethylene Glycol Succinimidyl Succinate Derivative (H-PEG-SS)

Synthesis of H-Shaped Polyethylene Glycol Succinimidyl Succinate Derivative A1-A1-2

Herein, the structural design of H-shaped polyethylene glycol derivative was given as follows: $F_1$=$F_2$=COCH$_2$CH$_2$CONHS,

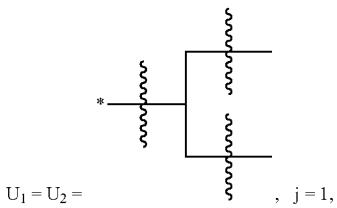

$U_1 = U_2 =$ , $j = 1$, $W_0$ is CH$_2$CH$_2$ and $m_1$=0. The designed total molecular weight is approximately 21000 Da, wherein, the molecular weight of four branch chains is approximately 4×5000=20000 Da corresponding to $n_1$≈$n_2$≈$n_3$≈$n_4$≈114, and the main chain polyethylene glycol is monodisperse corresponding to $m_2$=5.

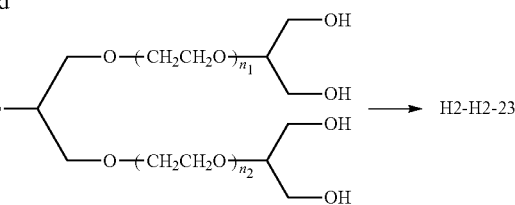

101c → 103b

Step (a): Into the reactor, monodisperse polyethylene glycol 101c (2.5 mmol, with an oxyethylene-unit number of 6) was added, and thereafter excess diphenylmethyl potassium (40 mmol) and excess compound 102 (100 mmol, OTs is a tosyl group) were added in sequence, followed by reaction at 30° C. for 12 hours. After completion of the reaction, open the reactor. The product in the solvent was concentrated and precipitated with absolute ether at 0° C. The crystals were collected by filtration and dried, and a polyethylene glycol intermediate 103b with four TBS-protected hydroxyl groups was obtained.

$^1$H-NMR spectrum data of the intermediate 103b were as follows: $^1$H NMR (CDCl$_3$) δ (ppm): 0.21 (—Si(CH$_3$)$_2$), 0.98 (—SiC(CH$_3$)$_3$), 2.90-3.00 (—OCH(CH$_2$O—)$_2$), 3.40-3.80 (—CH$_2$CH$_2$O—), 3.90-4.00 (—OCH(CH$_2$O—)$_2$).

Step (b): Into a dry and clean container, the intermediate 103b was added and then dissolved with tetrahydrofuran, followed by the addition of tetra-t-butyl ammonium fluoride (TBAF). Thereafter, the reaction was conducted overnight, and an H-shaped polyethylene glycol intermediate 104c with four unprotected hydroxyl groups was obtained.

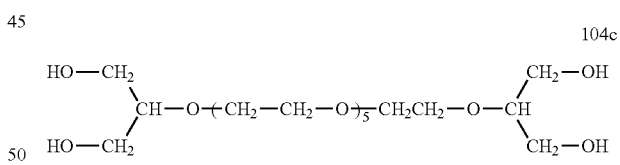

104c $^1$H-NMR spectrum data of the intermediate 104c were as follows: $^1$H NMR (CDCl$_3$) δ (ppm): 2.90-3.00 (—OCH(CH$_2$O—)$_2$), 3.40-3.80 (—CH$_2$CH$_2$O—, —OCH(CH$_2$O—)$_2$).

Step (c): Into a sealed reactor under an anhydrous and oxygen-free atmosphere, tetrahydrofuran (250 mL), the polyethylene glycol intermediate 104c (2.532 mmol) and diphenylmethyl potassium (4.0 mmol) were added in sequence.

Step (d): After a calculated amount of ethylene oxide (2300 mmol) was added, the whole was heated stepwise to 60° C., followed by reaction for 48 hours. After completion of reaction, excess proton source (methanol) was added, and an intermediate compound H1-H1-7 was obtained. Wherein, $F_1$=$F_2$=—CH$_2$CH$_2$OH (g=0, k=1, q=0, $q_1$=1, $Z_1$=CH$_2$CH$_2$, $R_{01}$=OH).

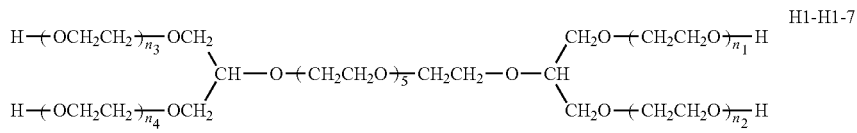

H1-H1-7

$^1$H-NMR spectrum data of the compound H1-H1-7 were as follows: $^1$H NMR (CDCl$_3$) δ (ppm): 3.40-3.80 (—CH$_2$CH$_2$O—, —OCH(CH$_2$O—)$_2$); M$_n$≈20000 Da, PDI=1.02.

Step (e): Into the reactor H-shaped polyethylene glycol compound H1-H1-7 (2.5 mmol) containing four terminal unprotected hydroxyl groups was added, and thereafter toluene (500 mL) and excess succinic anhydride (200 mmol) were added in sequence, followed by reaction at 50° C. for 12 hours. After completion of the reaction, open the reactor. The product in the solvent was concentrated, and then precipitated with absolute ether at 0° C. The crystals were collected by filtration and dried, and then an H-shaped polyethylene glycol carboxylic acid intermediate derivative D4-D4-2 containing four terminal carboxyl groups was obtained.

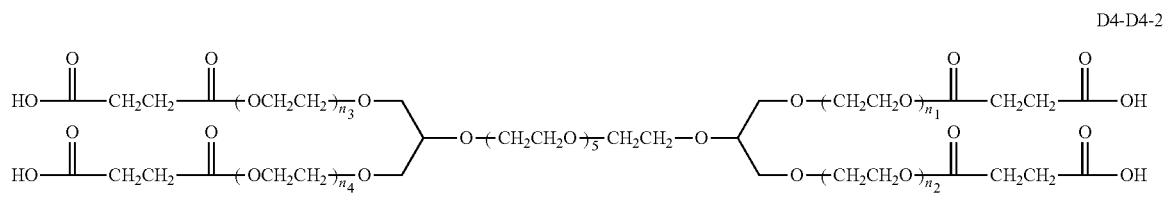

D4-D4-2

$^1$H-NMR spectrum data of the compound D4-D4-2 were as follows: $^1$H NMR (CDCl$_3$) δ (ppm): 2.40-2.70 (—OCOCH$_2$CH$_2$COO—), 3.40-3.80 (—CH$_2$CH$_2$O—, —OCH(CH$_2$O—)$_2$, —OCH$_2$CH$_2$OCO—), 4.15-4.35 (—OCH$_2$CH$_2$OCO—); M$_n$≈21000 Da, PDI=1.02.

Step (f): Into a dry and clean 1 L round-bottom flask, 50 g of polyethylene glycol carboxylic acid derivative D4-D4-2, 100 mL of triethylamine and 36 g of N-hydroxysuccinimide (NHS) were added in sequence. Using nitrogen protection, dichloromethane (600 mL) was added, thereafter the whole was stirred till dissolution, and then 100 g of dicyclohexylcarbodiimide (DCC) dissolved in dichloromethane was added, followed by reaction at room temperature for 24 hours and removal of the undissolved substances by filtration. The resulting mixture was concentrated and recrystallized from isopropanol, and an active ester A1-A1-2 in a white solid state was obtained.

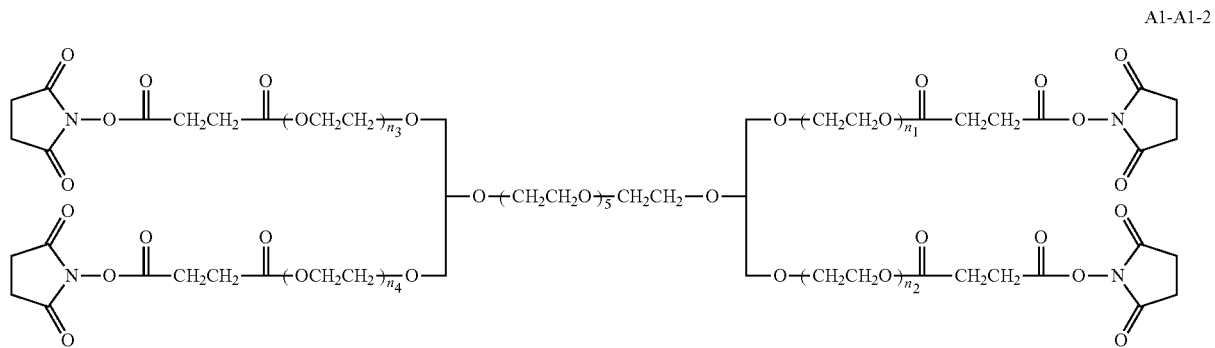

A1-A1-2

$^1$H-NMR spectrum data of the compound A1-A1-2 were as follows: $^1$H NMR (CDCl$_3$) δ (ppm): 2.40-2.70 (—OCOCH$_2$CH$_2$COO—), 2.70-2.85 (—(O=)CCH$_2$CH$_2$C(=O)N—), 3.40-3.80 (—CH$_2$CH$_2$O—, —OCH(CH$_2$O—)$_2$, —OCH$_2$CH$_2$OCO—), 4.15-4.35 (—OCH$_2$CH$_2$OCO—).

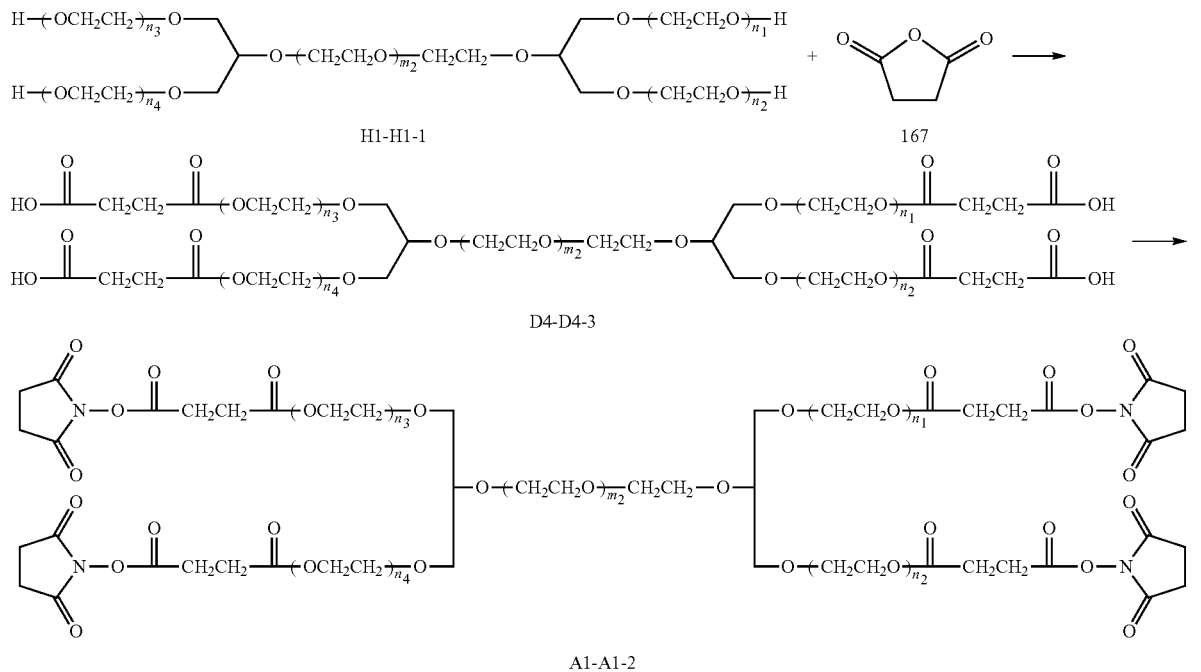

EXAMPLE-67

Preparation of Protected-Amine Derivative of H-Shaped Polyethylene Glycol (H-PEG-NPG$_5$)

Synthesis of Boc-Glycine-Terminated H-Shaped Polyethylene Glycol Derivative (C6-C6-3)

Herein, the structural design of H-shaped polyethylene glycol derivative was given as follows: $F_1=F_2=COCH_2NH-Boc$,

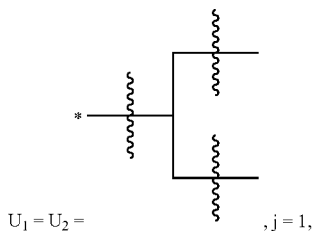

$W_0$ is CH$_2$CH$_2$ and $m_1$=0. The designed total molecular weight is approximately 21000 Da, wherein, the molecular weight of four branch chains is approximately 4×5000=20000 Da corresponding to $n_1 \approx n_2 \approx n_3 \approx n_4 \approx 114$, and the main chain polyethylene glycol is monodisperse with ethylene oxide units of 12 corresponding to $m_2 \approx 11$.

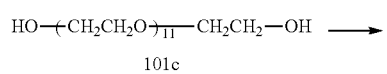

Step (a): Into the reactor, monodisperse polyethylene glycol 101c (2.5 mmol, with an oxyethylene-unit number of 12, $m_2$=11) was added, and then excess diphenylmethyl potassium (40 mmol) and excess compound 102 (100 mmol, OTs is a tosyl group) were added in sequence, followed by reaction at 30° C. for 12 hours. After completion of the reaction, open the reactor. The product in the solvent was concentrated and precipitated with absolute ether at 0° C. The crystals were collected by filtration and dried, and a polyethylene glycol intermediate 103b with four TBS-protected hydroxyl groups was obtained.

$^1$H-NMR spectrum data of the intermediate 103b were as follows: $^1$H NMR (CDCl$_3$) δ (ppm): 0.21 (—Si(CH$_3$)$_2$), 0.98 (—SiC(CH$_3$)$_3$), 2.90-3.00 (—OCH(CH$_2$O—)$_2$), 3.40-3.80 (—CH$_2$CH$_2$O—), 3.90-4.00 (—OCH(CH$_2$O—)$_2$).

Step (b): Into a dry and clean container, the intermediate 103b was added and then dissolved with tetrahydrofuran, followed by the addition of tetra-t-butyl ammonium fluoride (TBAF). Thereafter the reaction was conducted overnight, and an H-shaped polyethylene glycol intermediate 104c containing four unprotected hydroxyl groups was obtained.

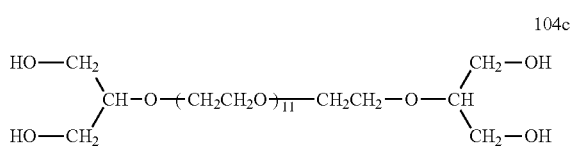

104c $^1$H-NMR spectrum data of the intermediate 104c were as follows: $^1$H NMR (CDCl$_3$) δ (ppm): 2.90-3.00 (—OCH(CH$_2$O—)$_2$), 3.40-3.80 (—CH$_2$CH$_2$O—, —OCH(CH$_2$O—)$_2$).

Step (c): Into a sealed reactor under an anhydrous and oxygen-free atmosphere, tetrahydrofuran (250 mL), the polyethylene glycol intermediate 104c (2.532 mmol) and diphenylmethyl potassium (4.0 mmol) were added in sequence.

Step (d): After a calculated amount of ethylene oxide (2300 mmol) was added, the whole was heated stepwisely to 60° C., followed by reaction for 48 hours. After completion of reaction, excess proton source (methanol) was added, and a compound H1-H1-8 was obtained. Wherein, $F_1=F_2=$ —CH$_2$CH$_2$OH (g=0, k=1, q=0, q$_1$=1, Z$_1$=CH$_2$CH$_2$, R$_{01}$=OH).

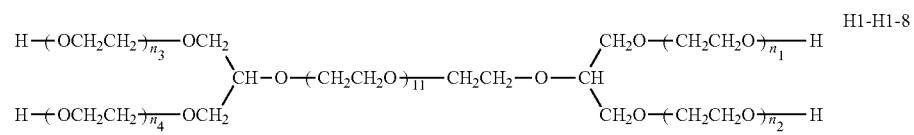

H1-H1-8

$^1$H-NMR spectrum data of the compound H1-H1-8 were as follows: $^1$H NMR (CDCl$_3$) δ (ppm): 3.40-3.80 (—CH$_2$CH$_2$O—, —OCH(CH$_2$O—)$_2$); M$_n$≈20000 Da, PDI=1.02.

Step (e): Into a dry and clean round-bottom, 10 g of the H-shaped polyethylene glycol intermediate H1-H1-8 containing four terminal unprotected hydroxyl groups (treated by azeotropic removal of water with toluene), 20 mL of triethylamime and Boc-protected glycine 168 (16 mmol) were added in sequence. Using nitrogen protection, dichloromethane (200 mL) was added, thereafter the whole was stirred till dissolution, and then 40 g of dicyclohexylcarbodiimide (DCC) was added, followed by reaction at room temperature for 24 hours. After completion of the reaction, the undissolved substances were removed by filtration. The resulting mixture was concentrated and recrystallized from isopropanol, and an H-shaped polyethylene glycol compound C6-C6-3 in a white solid state was obtained.

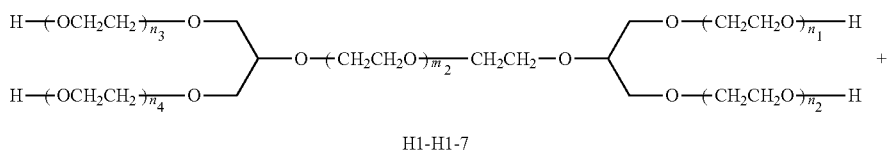

H1-H1-7

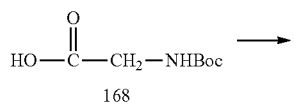

168

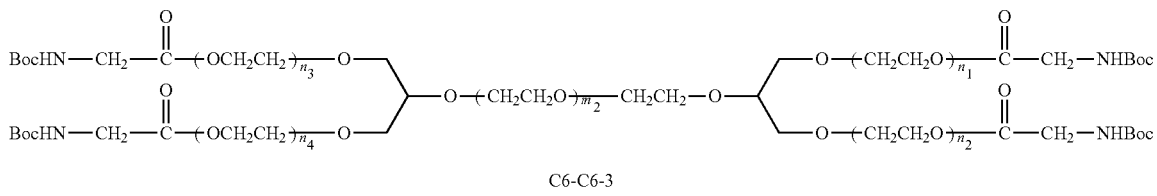

C6-C6-3

¹H-NMR spectrum data of the compound C6-C6-3 were as follows: ¹H NMR (CDCl₃) δ (ppm): 1.38 (—C(CH₃)₃), 3.40-3.80 (—CH₂CH₂O—, —OCH(CH₂O—)₂, —OCH₂CH₂OCO—), 3.80-4.00 (—COCH₂N—), 4.15-4.35 (—OCH₂CH₂OCO—); $M_n \approx 21000$ Da, PDI=1.02.

EXAMPLE 68

Preparation of Lysine-Branching Polyethylene Glycol Derivative

Synthesis of Lysine-Branching H-Shaped Polyethylene Glycol Derivative (H2-H2-25)

In this lysine-branching H-shaped polyethylene glycol derivative (H2-H2-25), $F_1=F_2=CH_2CH_2OTBS$, $U_1=U_2=$

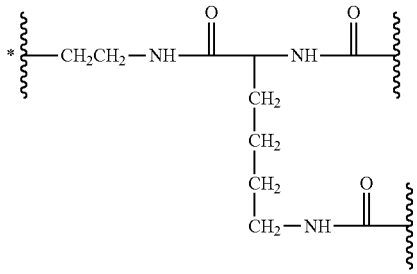

and j=0. The designed total molecular weight is approximately 9000 Da, wherein, the four branch chains are monodisperse corresponding to $n_1=n_2=n_3=n_4=48$, and the main chain polyethylene glycol is monodisperse corresponding to $m_2 \approx 22$.

Step (a): Into a dry and clean 1 L round-bottom flask, monodisperse amino polyethylene glycol 116b (2.5 mmol, with an EO-unit number of 24, treated by azeotropic removal of water with toluene), 8 mL of triethylamine and 40 mol of Boc-protected amino acid derivative 169 were added in sequence. Using nitrogen protection, dichloromethane (600 mL) was added, thereafter the whole was stirred till dissolution, and then 10 g of dicyclohexylcarbodiimide (DCC) was added, followed by reaction at room temperature for 24 hours. After completion, the undissolved substances were removed by filtration, the resulting mixture was concentrated and recrystallized from isopropanol, and a polyethylene glycol compound 170 in a white solid state was obtained.

¹H-NMR spectrum data of the intermediate 170 were as follows: ¹H NMR (CDCl₃) δ (ppm): 1.20-1.60 (—NCH₂CH₂CH₂CH₂CHCO—, —OC(CH₃)₃), 1.70-1.90 (—NCH₂CH₂CH₂CH₂CHCO—), 2.90-3.10 (—NCH₂CH₂CH₂CH₂CHCO—), 3.30-3.80 (—CH₂CH₂O—, —NCH₂CH₂O—), 4.40-4.60 (—NCH₂CH₂CH₂CH₂CHCO—); the molecular weight was determined by MALDI-TOF.

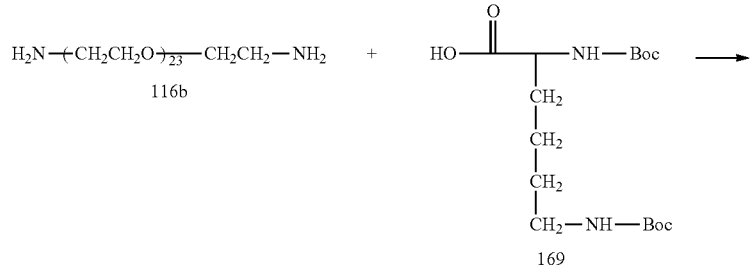

116b    169

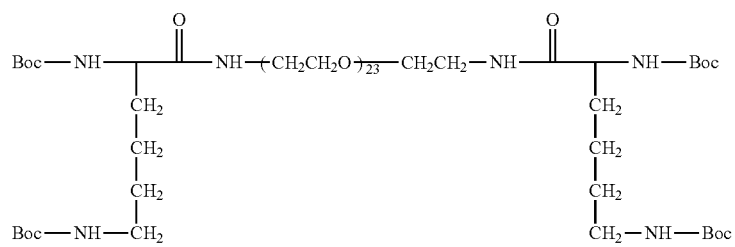

170

Step (b): Into a dry and clean container, the polyethylene glycol intermediate 170 was added and then dissolved with methanol. Thereafter, hydrochloric acid (1 M) was added, followed by reaction for 4 hours, and a polyethylene glycol intermediate 171 containing four unprotected amino groups was obtained.

$^1$H-NMR spectrum data of the intermediate 171 were as follows: $^1$H NMR (CDCl$_3$) δ (ppm): 1.20-1.60 (—NCH$_2$CH$_2$ CH$_2$CH$_2$CHCO—), 1.70-1.90 (—NCH$_2$CH$_2$CH$_2$ CH$_2$CHCO—), 2.55-2.75 (—NCH$_2$CH$_2$CH$_2$CH$_2$CHCO—), 3.30-3.90 (—CH$_2$CH$_2$O—, —NCH$_2$CH$_2$O—, —NCH$_2$CH$_2$CH$_2$CH$_2$CHCO—).

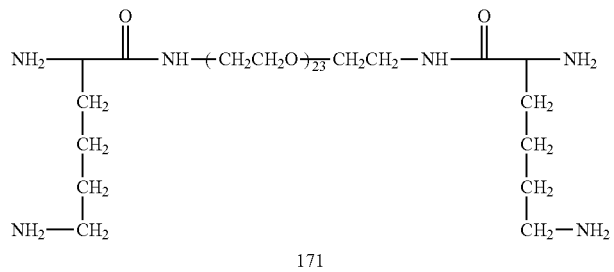

171

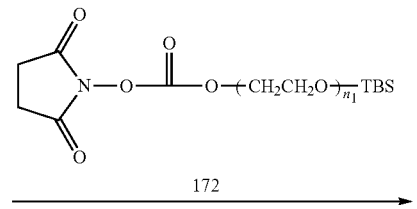

172

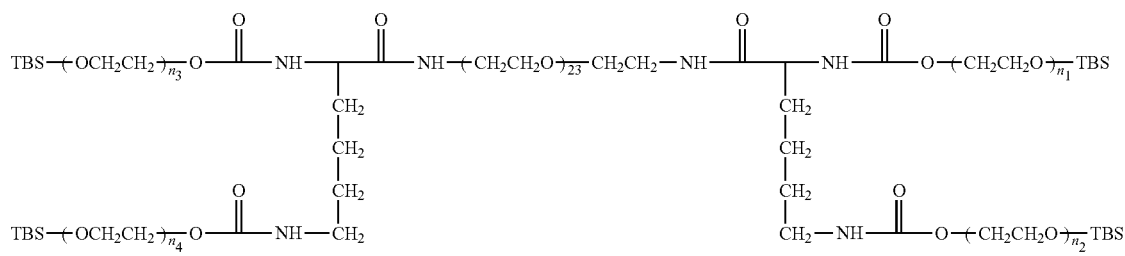

H2-H2-25

Step (c): Into a dry and clean 1 L round-bottom flask, the polyethylene glycol intermediate 171 (2.5 mmol, treated by azeotropic removal of water with toluene), 8 mL of triethylamine and 12 mol of monodisperse polyethylene glycol 172 (with an EO-unit number of 48) were added in sequence. Using nitrogen protection, tetrahydrofuran (600 mL) was added, thereafter the whole was stirred till dissolution, followed by reaction at room temperature for 24 hours. The resulting mixture was concentrated, dialyzed and recrystallized from isopropanol, and an H-shaped polyethylene glycol compound H2-H2-25 in a white solid state was obtained.

$^1$H-NMR spectrum data of the compound H2-H2-25 were as follows: $^1$H NMR (CDCl$_3$) δ (ppm): 0.21 (—Si(CH$_3$)$_2$), 0.98 (—SiC(CH$_3$)$_3$), 1.20-1.60 (—NCH$_2$CH$_2$CH$_2$CH$_2$CHCO—), 1.70-1.90 (—NCH$_2$CH$_2$CH$_2$CH$_2$CHCO—), 2.90-3.10 (—NCH$_2$CH$_2$CH$_2$CH$_2$CHCO—), 3.30-3.80 (—CH$_2$CH$_2$O—, —NCH$_2$CH$_2$O—, —NCOOCH$_2$CH$_2$—, —OCH$_2$CHCH$_2$OSi—), 3.80-4.00 (—OCH$_2$CHCH$_2$OSi—); 4.15-4.35 (—NCOOCH$_2$CH$_2$—), 4.40-4.60 (—NCH$_2$CH$_2$CH$_2$CH$_2$CHCO—); the molecular weight was determined by MALDI-TOF.

The above-described embodiments are provided in a generic and descriptive sense only, and are not for the purpose of limitation. Any modification of equivalent structures or equivalent routes according to the present invention, which may be applied in other related art in a direct or an indirect way, should be included into the scope of the present invention.

What is claimed is:
1. A multifunctionalized polyethylene glycol compound represented by the following general formula (1):

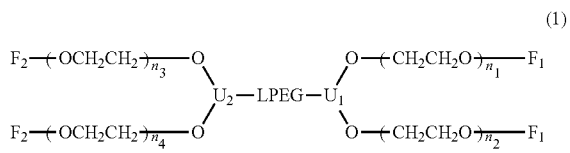

(1)

said multifunctionalized polyethylene glycol compound has an H-shaped structure consisting of one linear main chain LPEG and four PEG branch chains corresponding to $n_1$, $n_2$, $n_3$ and $n_4$, and the total oxyethylene-unit number of both main and branch chains is no more than 5000;
wherein, LPEG is a polyethylene glycol segment which contains two, three or 4 to 150 polyethylene glycol blocks; the oxyethylene-unit number of LPEG is an integer from 10 to 1000; said LPEG has a structure of J or

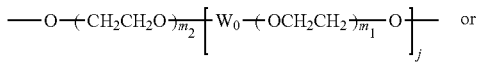

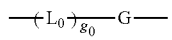

wherein, $W_0$, $W_{01}$ and $W_{02}$ are each independently a linking group containing 1 to 100 atoms and the structure of $W_0$, $W_{01}$ and $W_{02}$ is a linear structure or a branched structure; $m_1$, $m_2$ and $m_3$ are each independently selected from 0 to 1000, and in one molecule, they can be identical or not identical; j is an integer of 1 or from 2 to 100;

wherein, $n_1$, $n_2$, $n_3$ and $n_4$ are each independently a value from 5 to 2000, and can be identical or not identical in one molecule;

wherein, $U_1$ and $U_2$ are each independently a trivalent branching linking group connecting LPEG and respective two PEG branch chains;

the structure of $U_1$ is

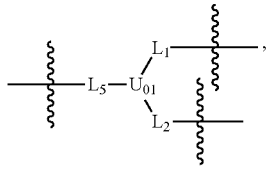

and the structure of $U_2$ is

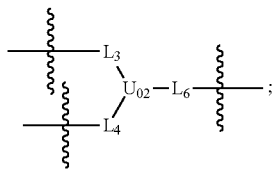

wherein, $U_{01}$ and $U_{02}$ are each independently a trivalent linking group; $L_1$, $L_2$, $L_3$, $L_4$, $L_5$ and $L_6$ are each independently a divalent linking group which can be either present or absent, and $L_1$, $L_2$, $L_3$, $L_4$, $L_5$ and $L_6$ can be identical or not identical in one molecule;

wherein, $F_1$ and $F_2$ are each independently an unprotected or protected functional group, and each independently represented as respective

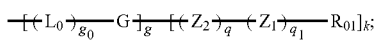

in one molecule, $F_1$ and $F_2$ can be identical or different, but the two $F_1$ groups have the same g, $L_0$, $g_0$, $Z_2$, q, $Z_1$, $q_1$ and $R_{01}$, and the two $F_2$ groups have the same g, $L_0$, $g_0$, $Z_2$, q, $Z_1$, $q_1$ and $R_{01}$;

wherein, $$-(L_0)_{g_0}-G-$$

is a linking group that connects with corresponding PEG branch chain; wherein, k is an integer of 1 or from 2 to 250; g is 0 or 1; G is a linking group of trivalence or higher valence; when g is 0, k is equal to 1; when g is 1, k is an integer from 2 to 250, and the valence of corresponding G is k+1; $L_0$ is a divalent linking group; $g_0$ is 0 or 1, or an integer from 2 to 1000; q and $q_1$ are each independently 0 or 1; $Z_1$ and $Z_2$ are each independently a divalent linking group; $R_{01}$ is the unprotected or protected form of a functional end-group capable of generating a covalent bond, a dynamic covalent bond, dihydrogen-bonding, multiple hydrogen bonding, therapeutic targeting binding or photoreactive response; in one molecule, k, G, g, $L_0$, $g_0$, $Z_2$, q, $Z_1$, $q_1$ and $R_{01}$ of $F_1$ are each independently the same as or different from that of $F_2$.

2. The multifunctionalized polyethylene glycol compound according to claim 1, wherein, one linking group selected from LPEG, $U_1$, $U_2$, $U_{01}$, $U_{02}$, $L_1$, $L_2$, $L_3$, $L_4$, $L_5$, $L_6$, $L_0(F_1)$, $G(F_1)$, $Z_1(F_1)$, $Z_2(F_1)$, $L_0(F_2)$, $G(F_2)$, $Z_1(F_2)$ and $Z_2(F_2)$, or the joint linking group formed by said group with its adjacent heterosubstituted group is independently either a STAG group or a DEGG group; wherein, said STAG group is a linking group which keeps covalently linking adjacent groups along the backbone thereof under a condition of light illumination, heat, an enzymatic condition, an oxidation-reduction condition, an acidic condition, a basic condition, a physiological condition or a simulated physiological environment in vitro, and said DEGG group is a linking group which can be degraded into at least two separate individual subgroups under a condition of light illumination, heat, an enzymatic condition, an oxidation-reduction condition, an acidic condition, a basic condition, a physiological condition or a simulated physiological environment in vitro.

3. The multifunctionalized polyethylene glycol compound according to claim 1, wherein, said multifunctionalized polyethylene glycol compound has a structure correspondingly represented by general formula (6)

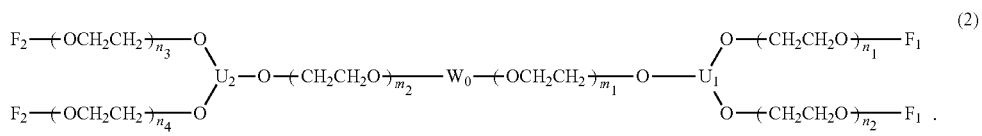

(2)

4. The multifunctionalized polyethylene glycol compound according to claim 2, wherein, said multifunctionalized polyethylene glycol compound has at least one DEGG group; the distribution of said DEGG linkages is selected from the following Groups:
  Group (1): wherein, one of $U_{01}$-$L_1$-O and $U_{01}$-$L_2$-O contains at least one DEGG group, and one of $U_{02}$-$L_3$-O and $U_{02}$-$L_4$-O contains at least one DEGG group;
  Group (2): wherein, $U_{01}$-$L_5$-O contains at least one DEGG group, and $U_{02}$-$L_6$-O contains at least one DEGG group;
  Group (3): wherein, $U_{01}$, or $U_{02}$ has a trivalent core structure $CC_3$, and $CC_3$ contains at least one DEGG group;
  Group (4): wherein, LPEG contains at least one DEGG group;
  Group (5): wherein, the joint linkage of one —$(Z_2)_q$—$(Z_1)_{q1}$— group with its adjacent group towards the PEG side contains at least one DEGG group;
  Group (6): wherein, one said g is equal to 1, linkages including corresponding $(L_0)_{g0}$, O-$(L_0)_{g0}$ and $(L_0)_{g0}$-G contains at least one DEGG group;
  Group (7): wherein, one said g is equal to 1, corresponding G contains at least one DEGG group.

5. The multifunctionalized polyethylene glycol compound according to claim 1, wherein, the total oxyethylene-unit number of both main and branch chains is no more than 2500.

6. The multifunctionalized polyethylene glycol compound according to claim 1, wherein, the oxyethylene-unit number of said LPEG is from 20 to 500.

7. The multifunctionalized polyethylene glycol compound according to claim 1, said $n_1$, $n_2$, $n_3$ and $n_4$ are each independently a value from 20 to 1000 or a value from 10 to 2000.

8. The multifunctionalized polyethylene glycol compound according to claim 1, wherein, the molecular weight of LPEG main chain, PEG branches or combination thereof is selected from one of the following Groups:
  Group (1): the molecular weight of LPEG is about 500, 600, 700, 800, 900, 1000, 1500, 2000, 2500, 3000, 3350, 3500, 4000, 5000, 5500, 6000, 6500, 7000, 7500, 8000, 8500, 9000, 9500, 10000, 11000, 12000, 13000, 14000, 15000, 16000, 17000, 18000, 19000, 20000, 25000, 30000, 35000, 40000, 50000 or 60000, in units of Da; and the oxyethylene-unit of all the PEG branch chains are selected from 5 to 1000;
  Group (2): said LPEG has two PEG blocks and an oxyethylene-unit number of 10 to 140;
  Group (3): said LPEG has three PEG blocks and an oxyethylene-unit number of 10 to 210;
  Group (4): said LPEG has four or more than four PEG blocks and an oxyethylene-unit number of 10 to 500;
  Group (5): the molecular weight of one PEG branch chain is about 500, 600, 700, 800, 900, 1000, 1500, 2000, 2500, 3000, 3350, 3500, 4000, 5000, 5500, 6000, 6500, 7000, 7500, 8000, 8500, 9000, 9500, 10000, 11000, 12000, 13000, 14000, 15000, 16000, 17000, 18000, 19000, 20000, 25000, 30000, 35000, 40000, 50000 or 60000, in units of Da;
  Group (6): the oxyethylene-unit of one PEG branch chain is selected from 5 to 70;
  Group (7): the molecular weight of all the PEG branch chains are about 500, 600, 700, 800, 900, 1000, 1500, 2000, 2500, 3000, 3350, 3500, 4000, 5000, 5500, 6000, 6500, 7000, 7500, 8000, 8500, 9000, 9500, 10000, 11000, 12000, 13000, 14000, 15000, 16000, 17000, 18000, 19000, 20000, 25000, 30000, 35000, 40000, 50000 or 60000, in units of Da; and the oxyethylene-unit of LPEG is selected from 10 to 70;
  Group (8): the molecular weight of two of the PEG branch chains are about 500, 600, 700, 800, 900, 1000, 1500, 2000, 2500, 3000, 3350, 3500, 4000, 5000, 5500, 6000, 6500, 7000, 7500, 8000, 8500, 9000, 9500, 10000, 11000, 12000, 13000, 14000, 15000, 16000, 17000, 18000, 19000, 20000, 25000, 30000, 35000, 40000, 50000 or 60000, in units of Da; and the oxyethylene-unit of the other two PEG branch chains are selected from 5 to 70;
  Group (9): the oxyethylene-unit of all the PEG branch chains are selected from 5 to 70; and the molecular weight of LPEG is about 500, 600, 700, 800, 900, 1000, 1500, 2000, 2500, 3000, 3350, 3500, 4000, 5000, 5500, 6000, 6500, 7000, 7500, 8000, 8500, 9000, 9500, 10000, 11000, 12000, 13000, 14000, 15000, 16000, 17000, 18000, 19000, 20000, 25000, 30000, 35000, 40000, 50000 or 60000, in units of Da;
  Group (10): the molecular weight of all the PEG branch chains and LPEG are about 500, 600, 700, 800, 900, 1000, 1500, 2000, 2500, 3000, 3350, 3500, 4000, 5000, 5500, 6000, 6500, 7000, 7500, 8000, 8500, 9000, 9500, 10000, 11000, 12000, 13000, 14000, 15000, 16000, 17000, 18000, 19000, 20000, 25000, 30000, 35000, 40000, 50000 or 60000, in units of Da;
  Group (11): the oxyethylene-unit of all the PEG branch chains and LPEG are selected from 10 to 70;
  Group (12): the oxyethylene-unit of LPEG is from 10 to 1000 and the oxyethylene-unit of all the PEG branch chains are selected from 5 to 1000;
  Group (13): the oxyethylene-unit of LPEG is from 10 to 210 or from 10 to 500, and the oxyethylene-unit of all the PEG branch chains are selected from 5 to 1000.

9. The multifunctionalized polyethylene glycol compound according to claim 1, wherein, said $U_{01}$ and $U_{02}$ are each independently of a branched structure or a ring-containing structure.

10. The multifunctionalized polyethylene glycol compound according to claim 1, wherein, said $U_{01}$ and $U_{02}$ each independently contains a trivalent core selected from an atom core $CM_3$, an unsaturated bond core $CB_3$ and a cyclic core $CC_3$; wherein,
  said $CM_3$ is a carbon atom core, a nitrogen atom core, a silicon atom core, an oxo-phosphorus atom core, or a thioxo-phosphorus atom core;
  said $CB_3$ is a trivalent imine bond, a trivalent carbon-carbon double bond or >C=C=N—;
  said $CC_3$ is derived from one of the following cyclic structures: a furanose ring, a pyranose ring, benzene, tetrahydrofuran, pyrrolidine, thiazolidine, cyclohexane, cyclohexene, tetrahydropyran, piperidine, 1,4-dioxane, pyridine, pyridazine, pyrimidine, pyrazine, 1,3,5-triazine, 1,4,7-triazacyclononane, cyclotripeptides, indene, indane, indole, isoindole, purine, naphthalene, dihydroanthracene, xanthene, thioxanthene, dihydrophenanthrene, 10,11-dihydro-5H-dibenzo[a,d]cycloheptane, dibenzocycloheptene, 5-dibenzosuberenone, quinoline, isoquinoline, fluorene, carbazole, iminodibenzyl, acenaphthene, dibenzocyclooctyne, aza-dibenzocyclooctyne, the substituted form of any cyclic structure thereof, and the heterosubstituted form of any cyclic structure of the foregoing.

11. The multifunctionalized polyethylene glycol compound according to claim 1, wherein, said $U_{01}$ and $U_{02}$ each independently contains one of the following trivalent structures:
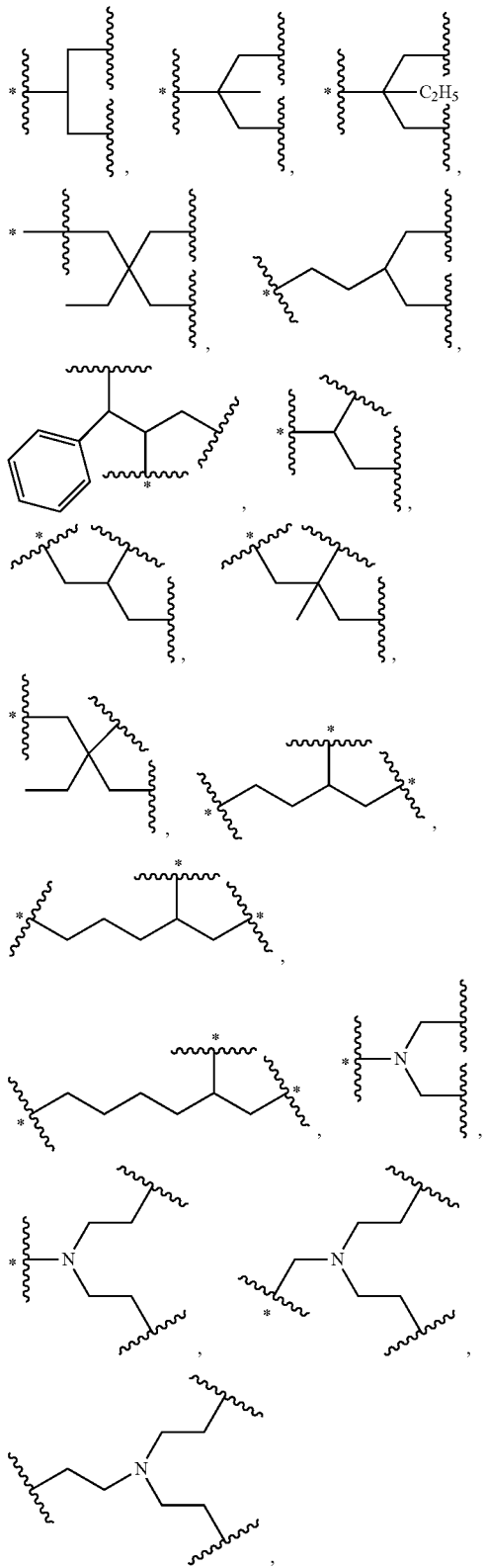
-continued
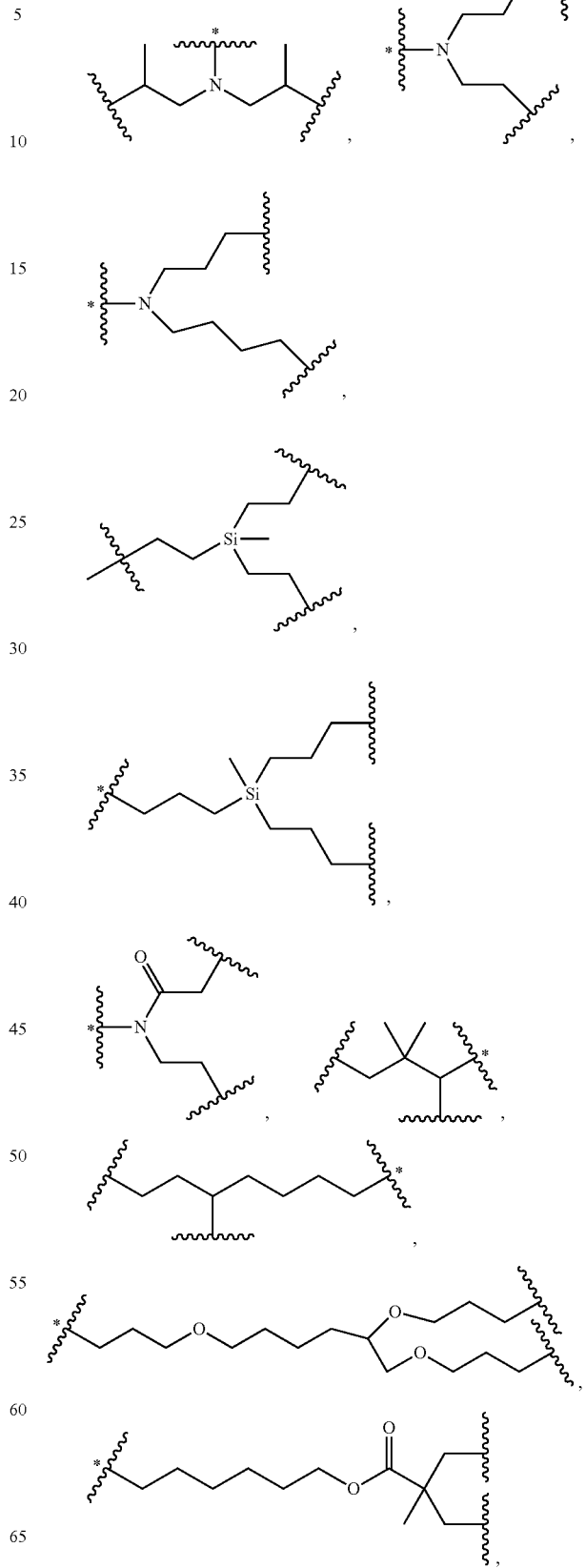

-continued

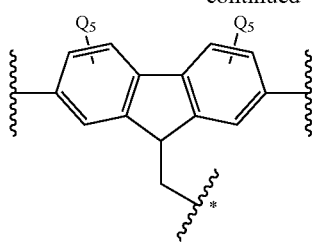

and

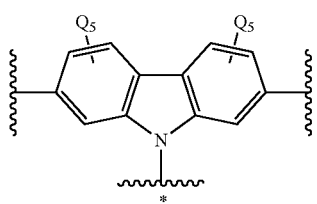

;

wherein, $Q_5$ is a hydrogen atom or a substituent of the ring; the number of $Q_5$ is one or more in quantities, when more than one, the $Q_5$ groups are identical in structure or are the combination of two or two more different structures; wherein, any said trivalent structure is independently end-capped or not, the number of the end-groups for end-capping is one, two or three, the end-groups are selected from an oxy group, a thioxy group, a secondary amino group, a divalent t-amino group and a carbonyl group, and the end-groups can be identical or not identical; wherein, the asterisk "*" in the structural formulas indicates the available radical ends to be connected towards LPEG.

12. The multifunctionalized polyethylene glycol compound according to claim 1, wherein, said $U_{01}$ and $U_{02}$ are each independently any trivalent structure selected from Group (1) and Group (2):

Group (1) consisting of:

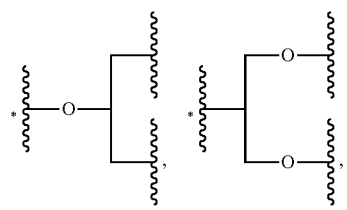

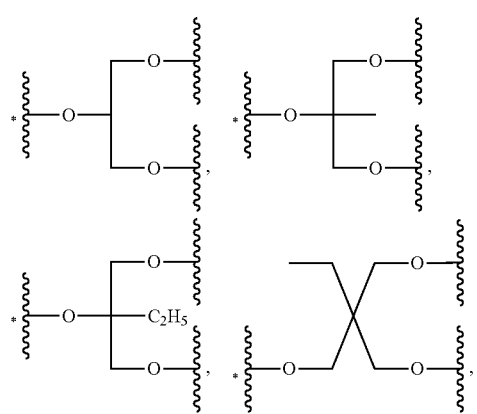

-continued

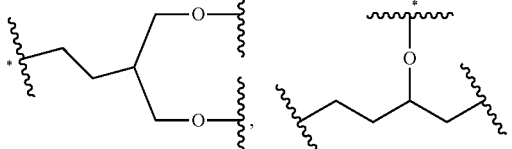

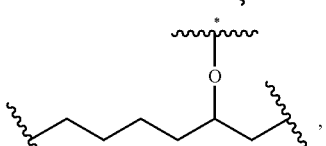

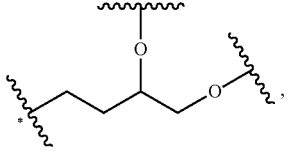

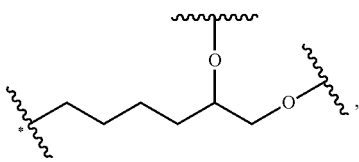

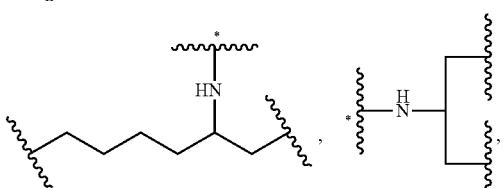

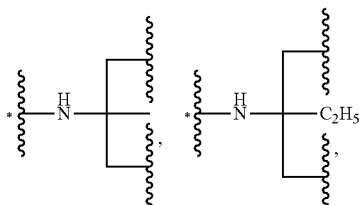

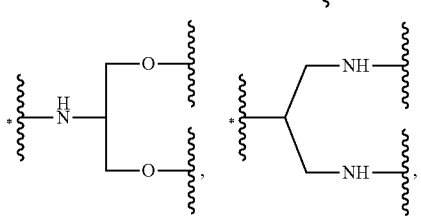

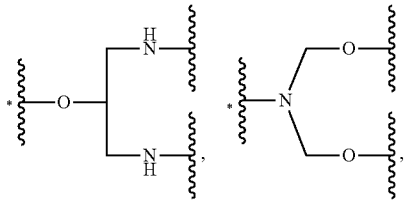

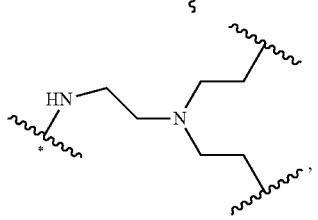
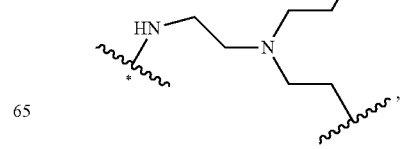

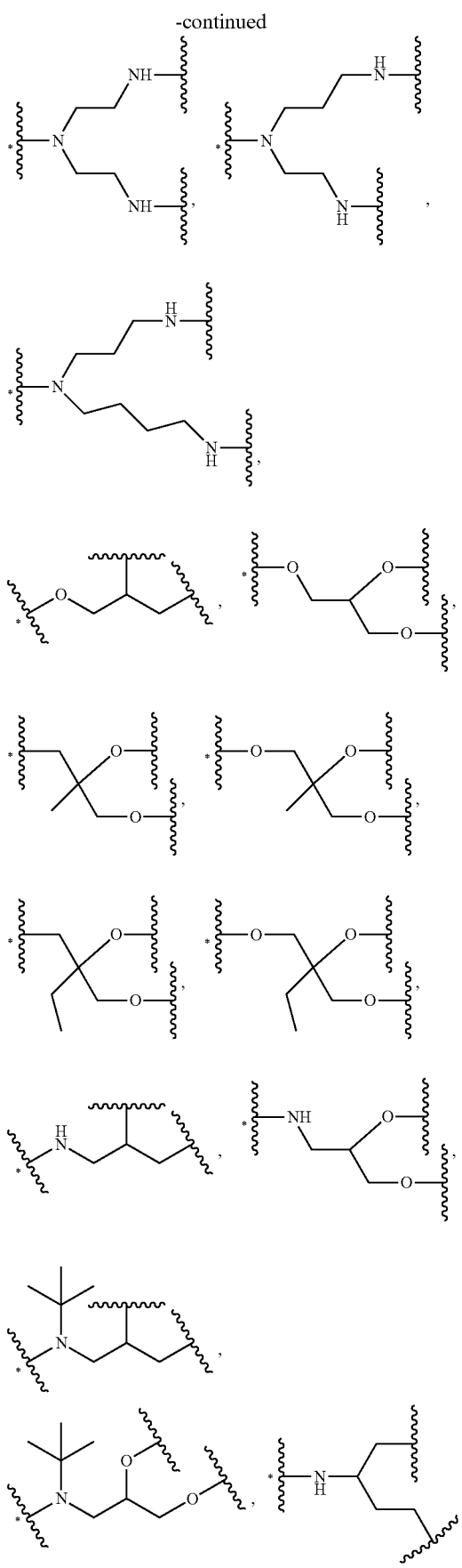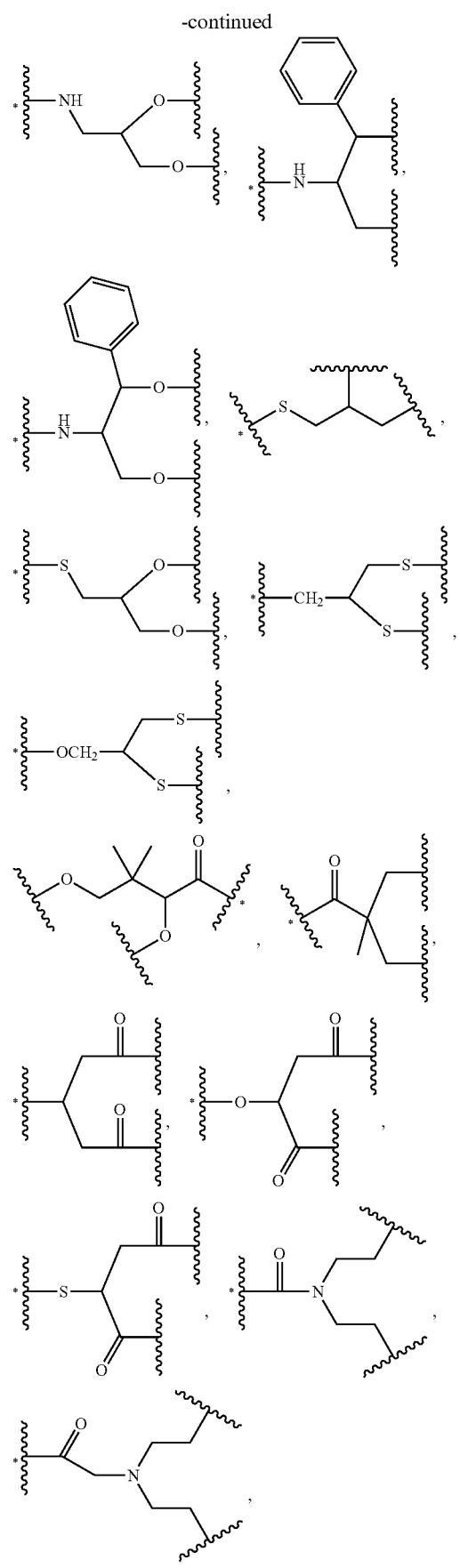

657

-continued

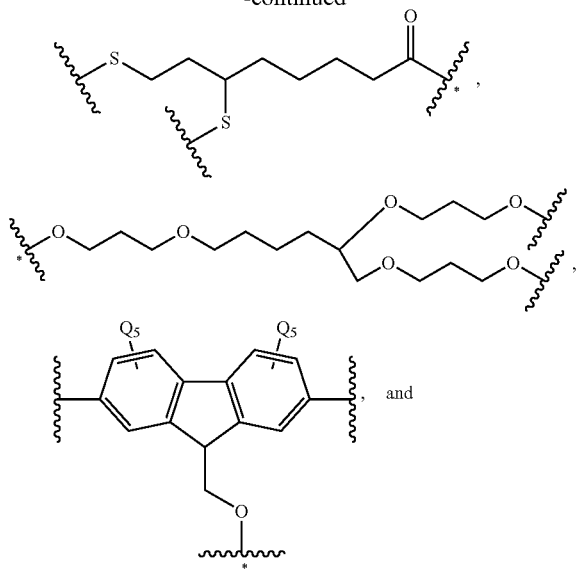

658

-continued

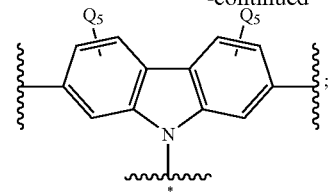

wherein, $Q_5$ is a hydrogen atom, a atom substituent or a group substituent, and located on the ring; the number of $Q_5$ is one or more in quantities, when more than one, the $Q_5$ groups have the same structure or are the combination of two or two more different structures; wherein, the asterisk "*" indicates the available radical ends to be connected towards LPEG; and Group (2) consisting of trivalent skeleton structures of amino acids and derivatives thereof.

13. The multifunctionalized polyethylene glycol compound according to claim 1, wherein, said $U_1$ and $U_2$ are each independently a trivalent structure selected from the group consisting of:

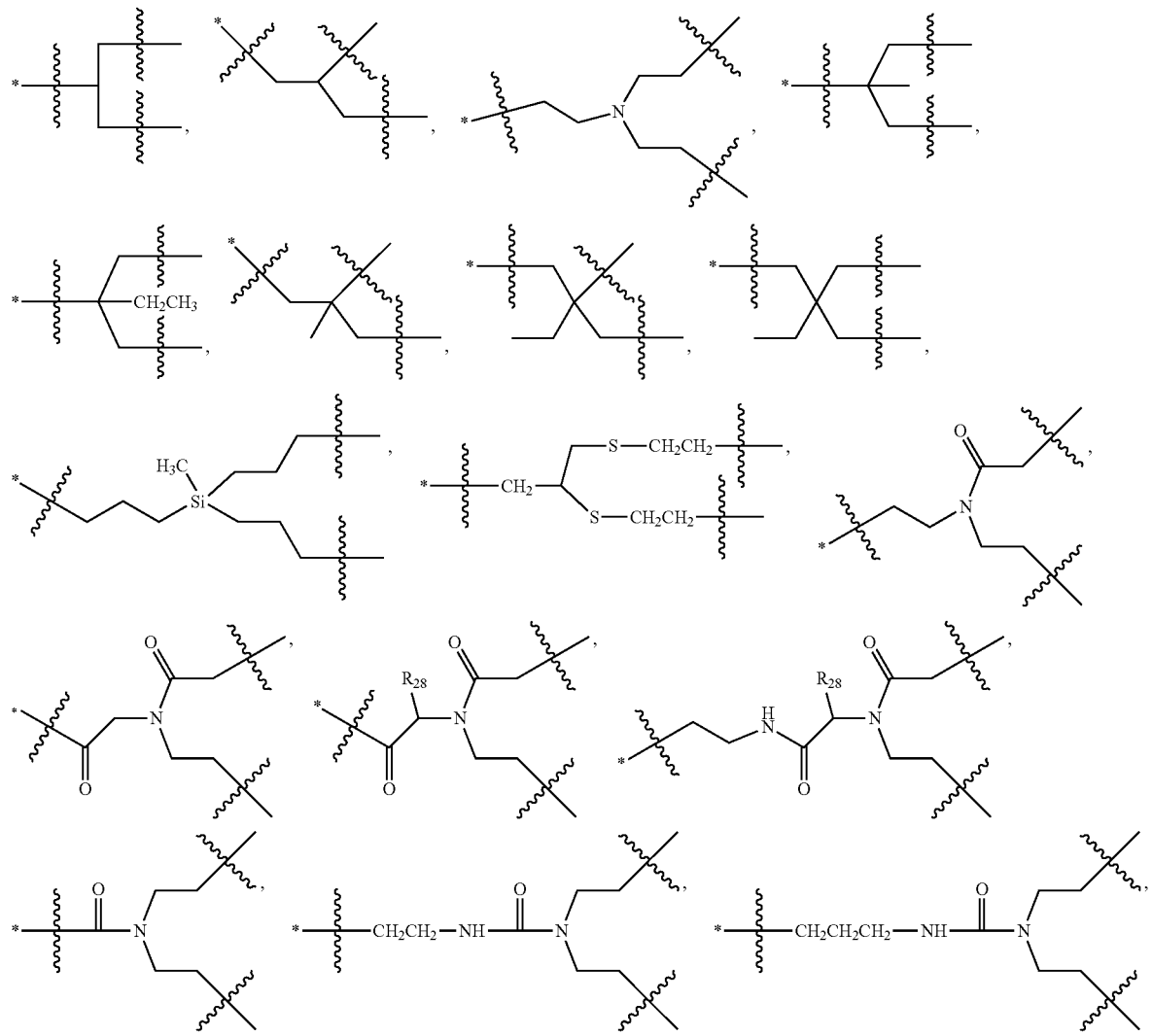

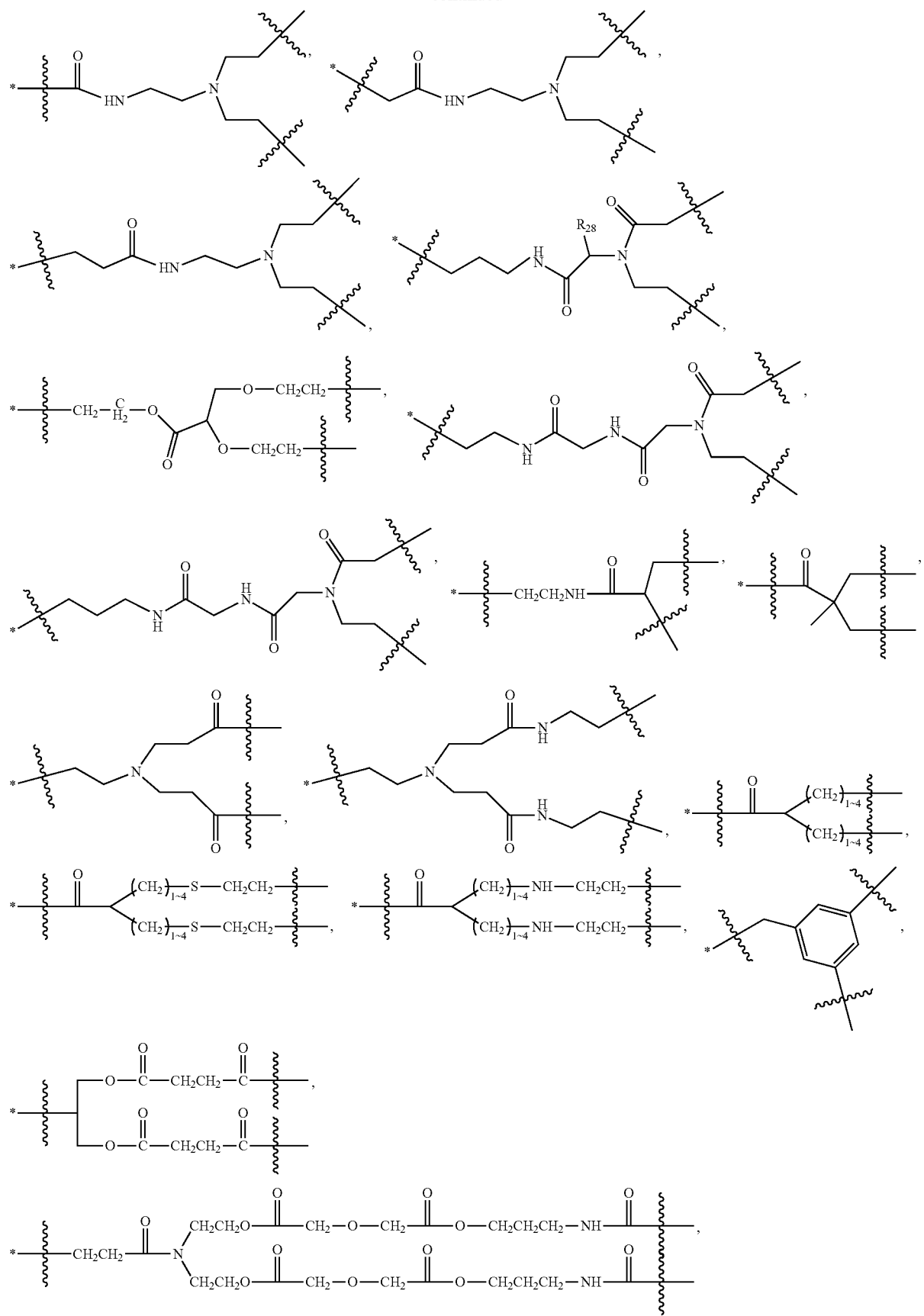

-continued
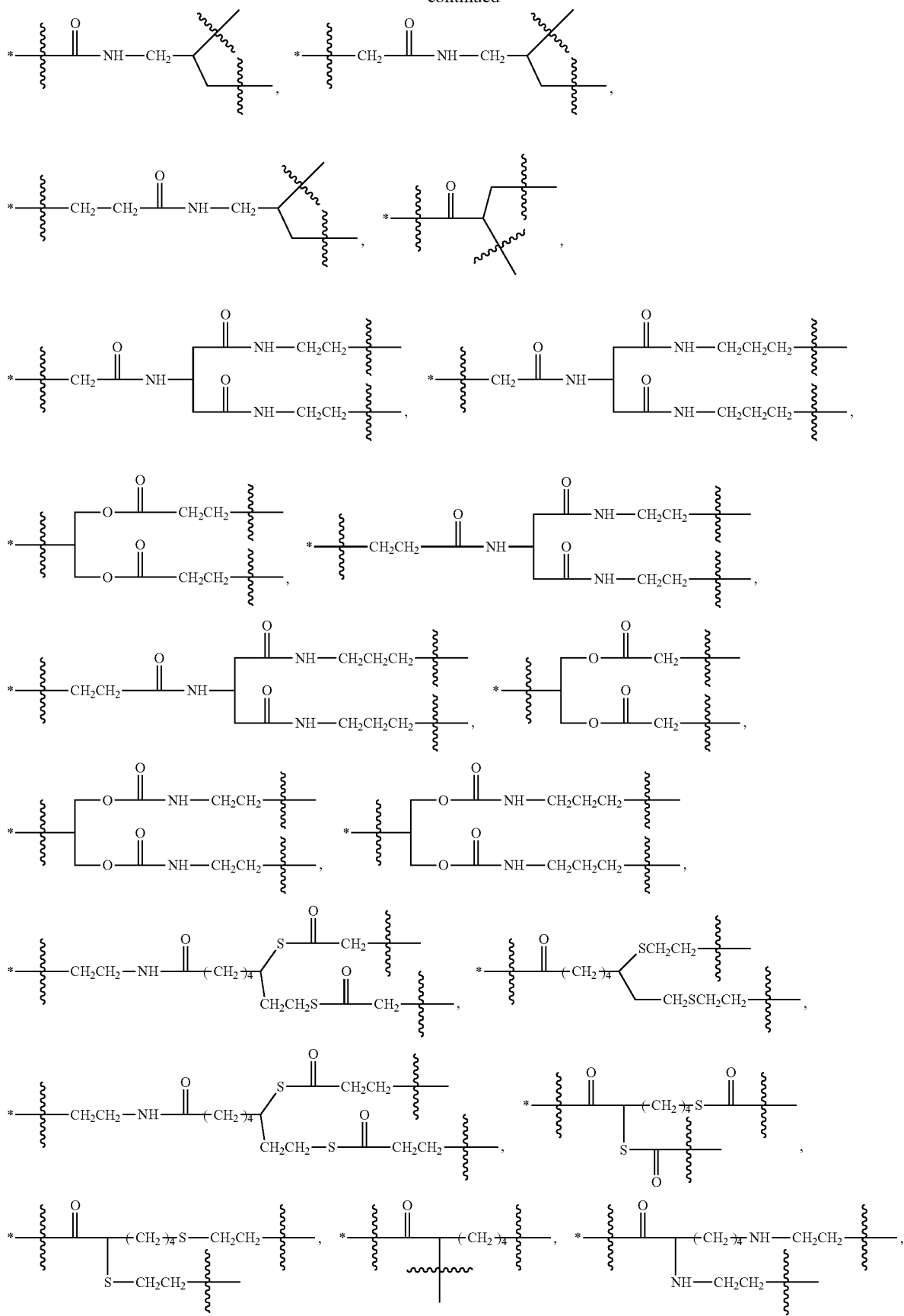

-continued
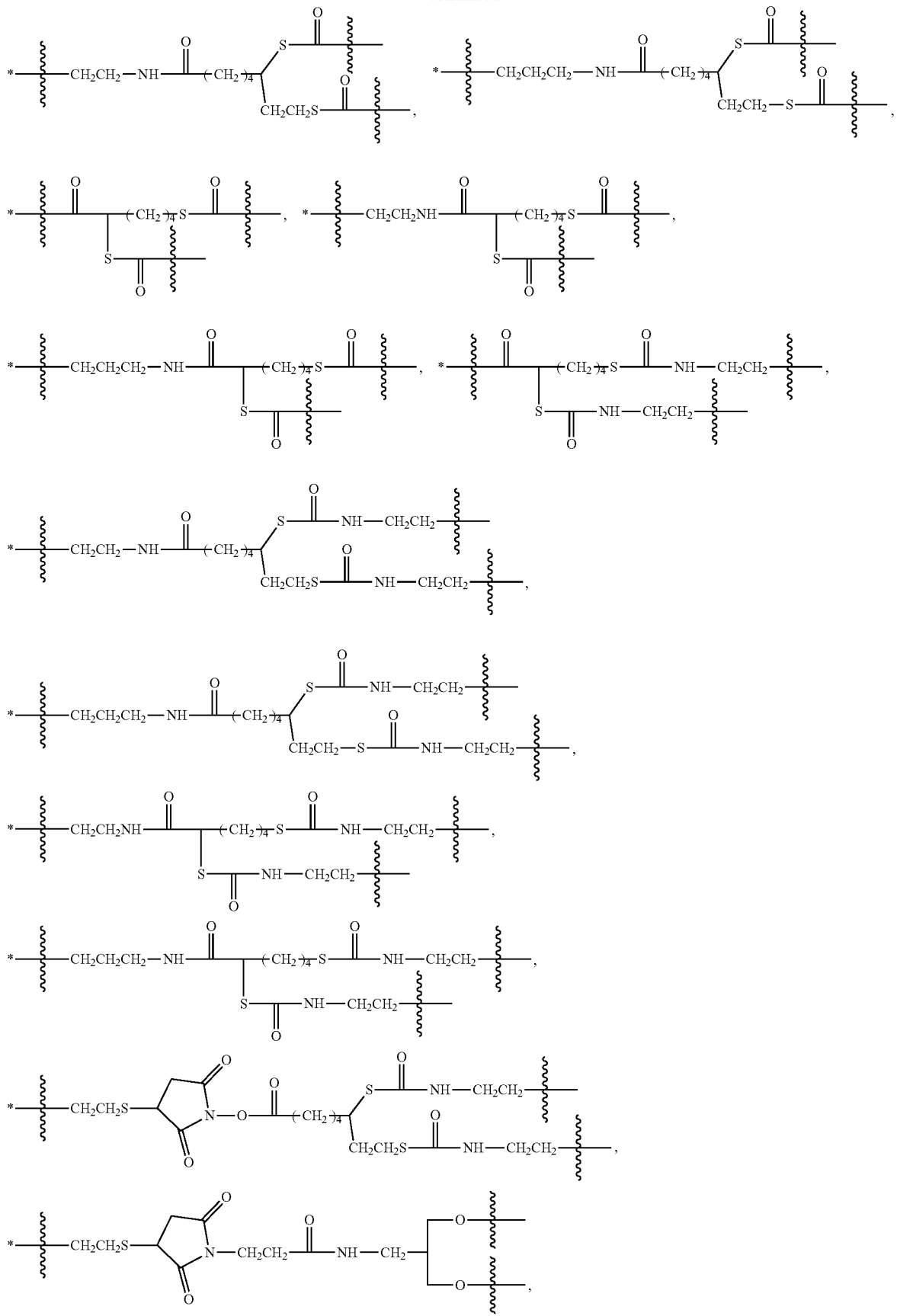

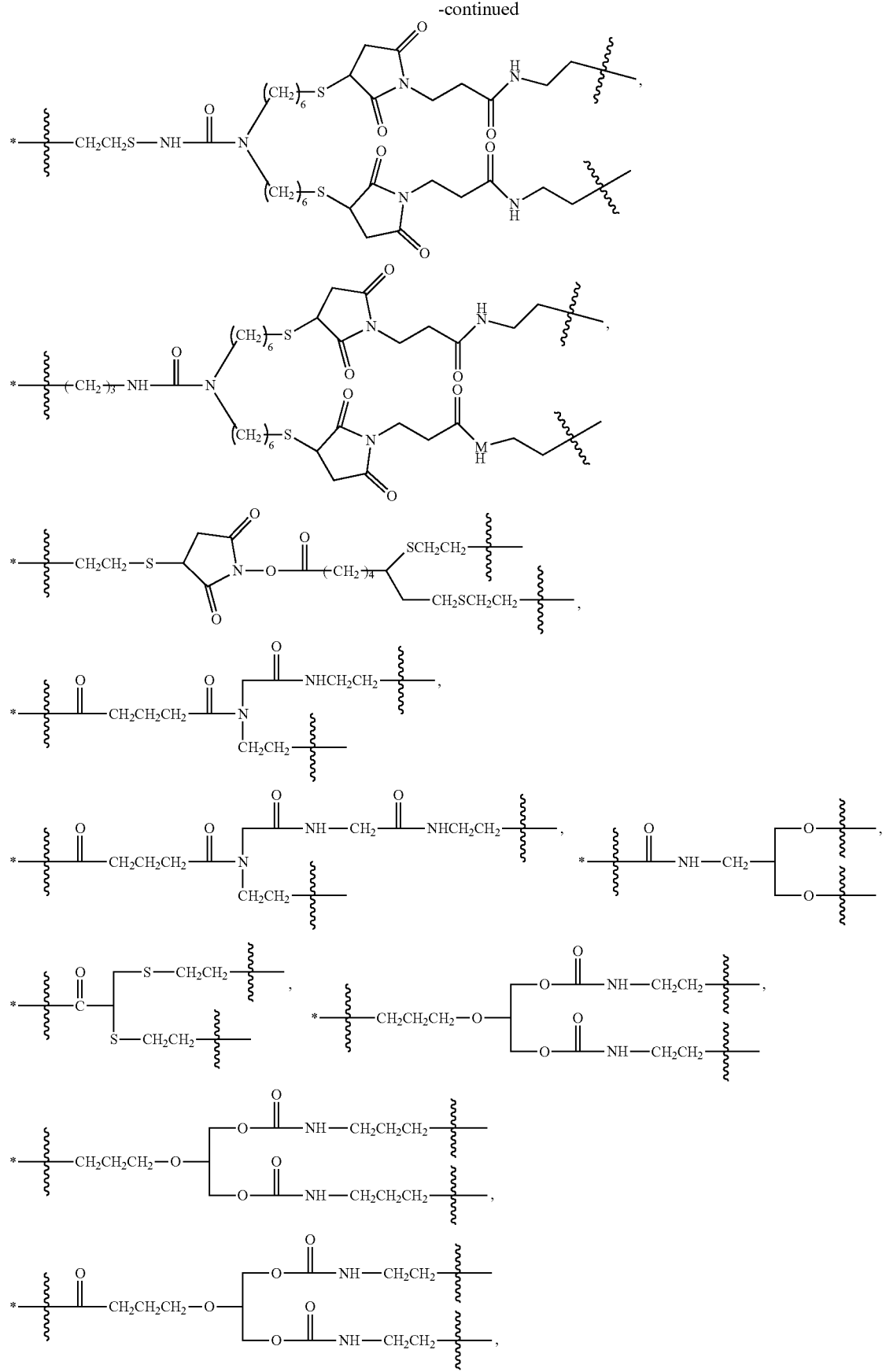

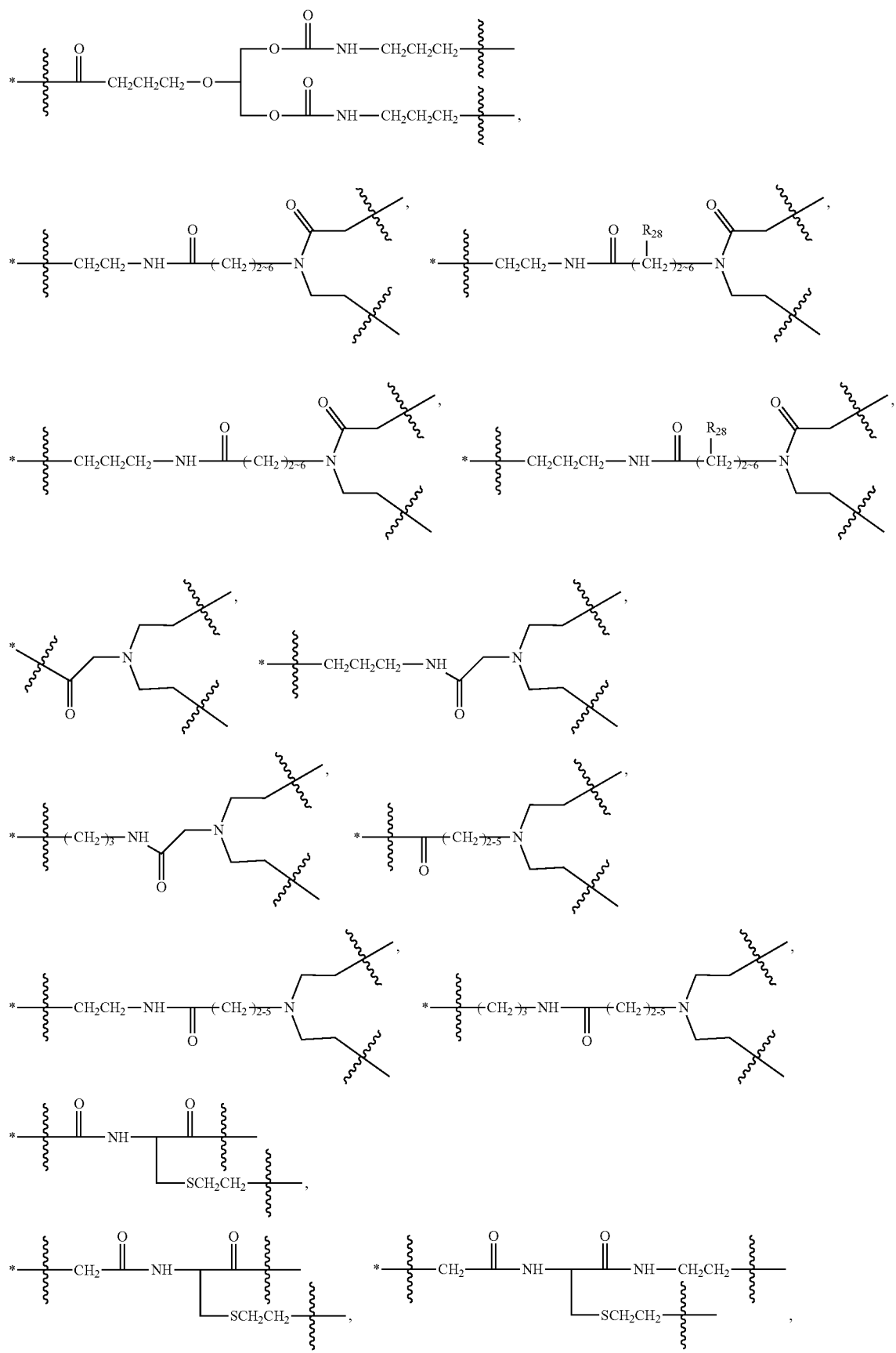

-continued
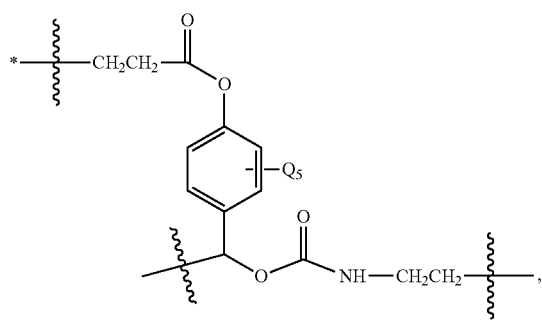
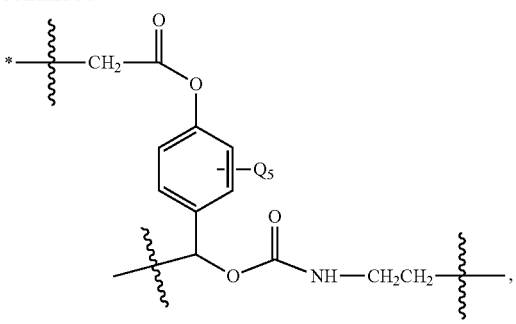
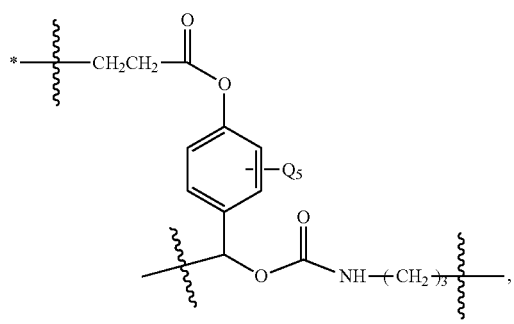
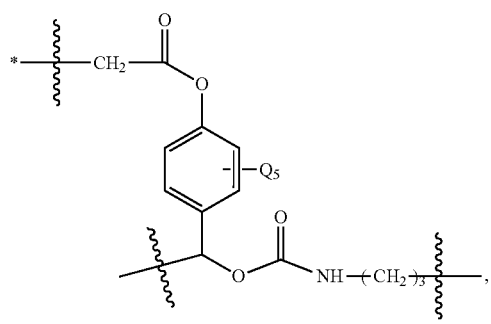
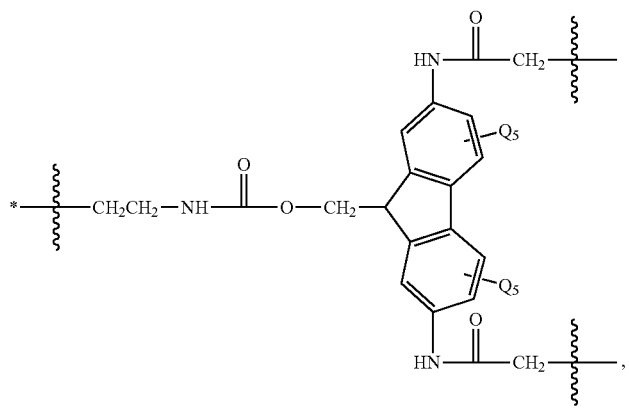
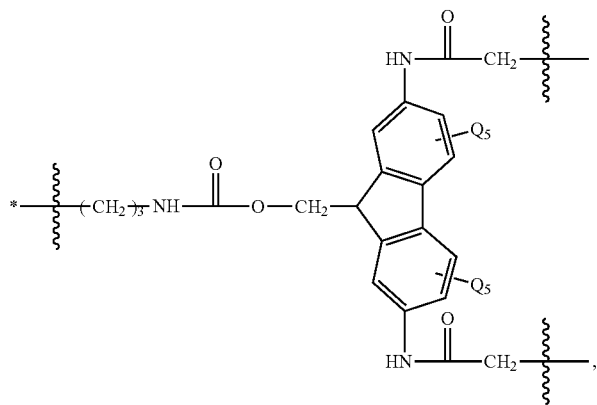

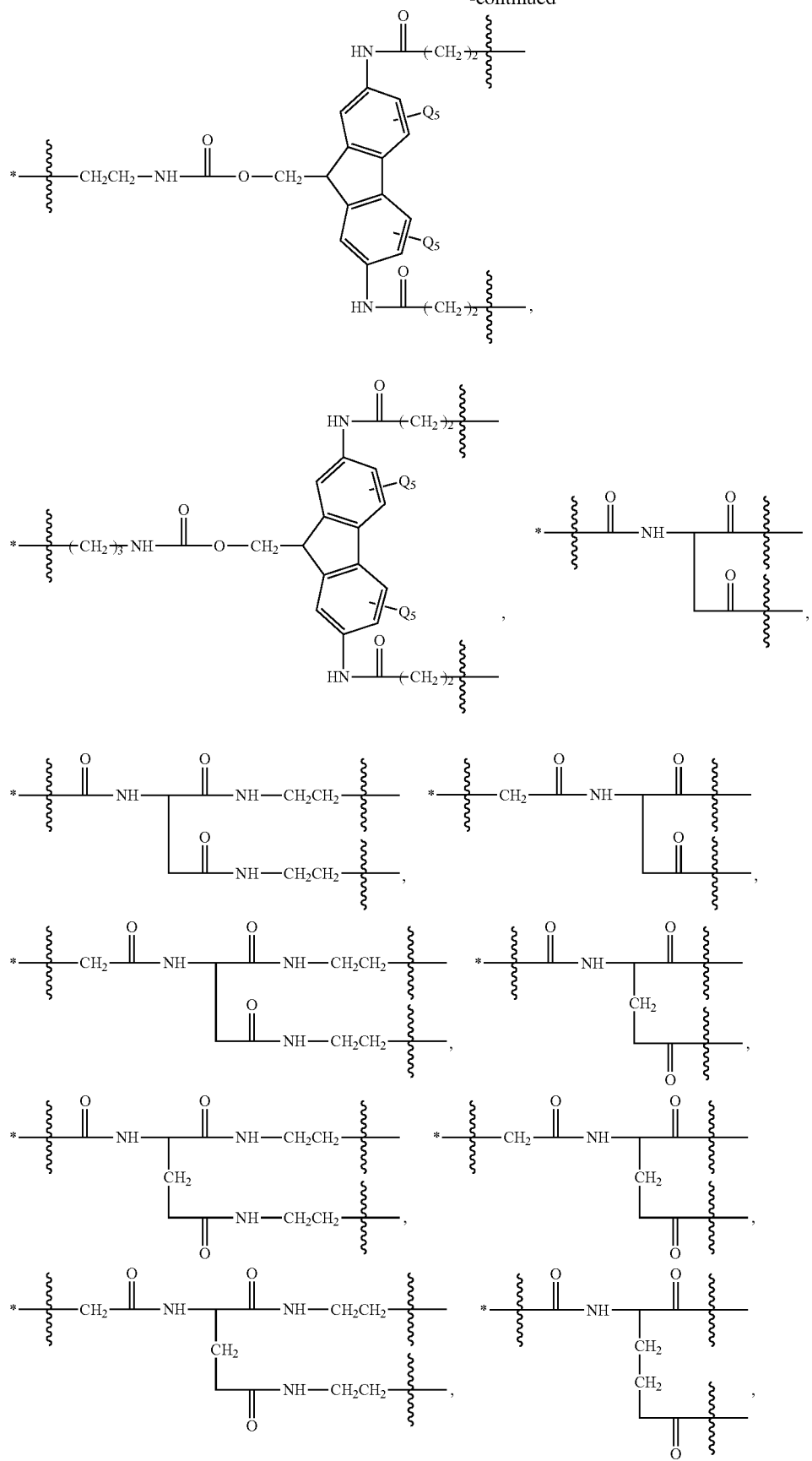

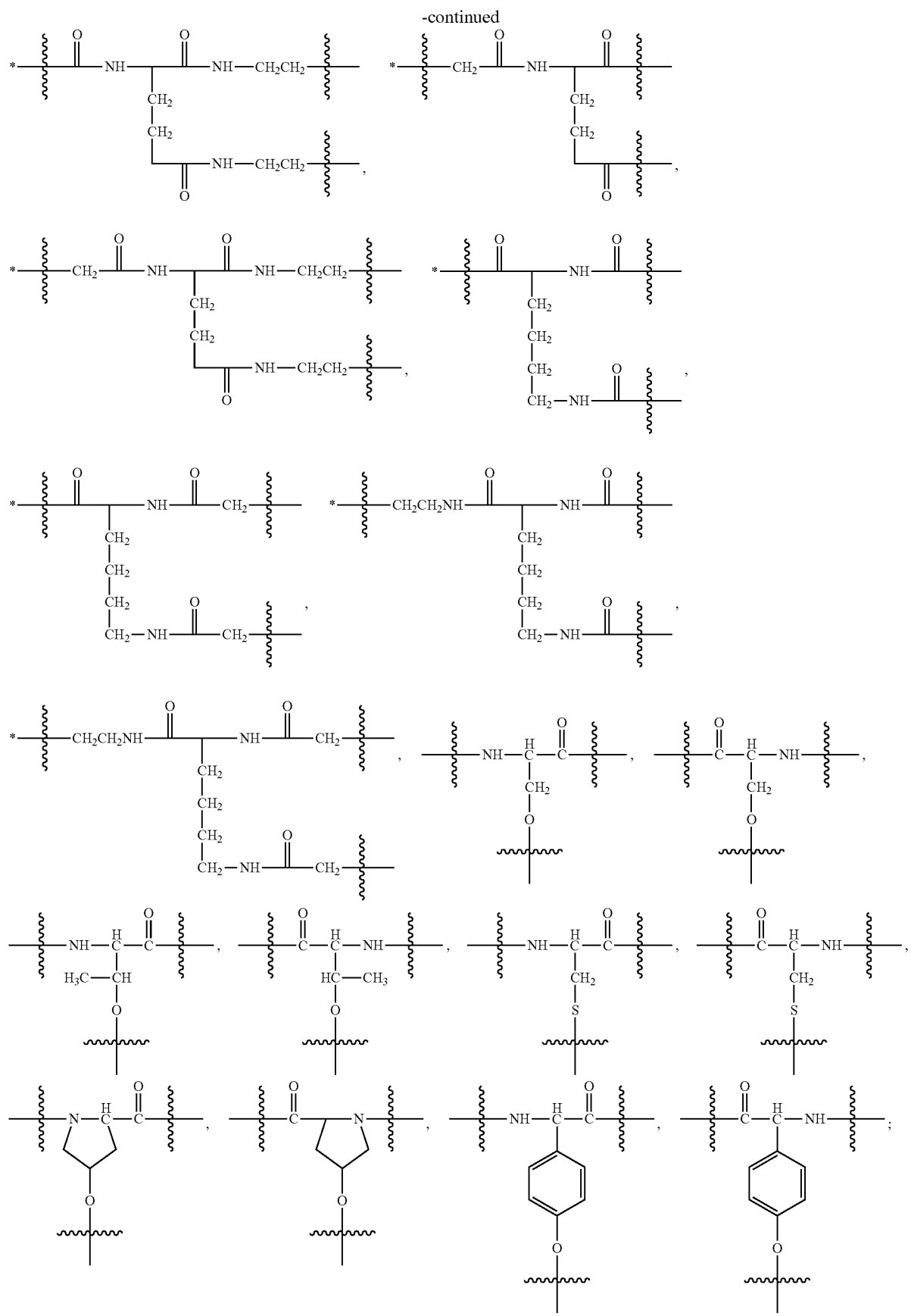

wherein, $Q_5$ is a hydrogen atom, a methyl group, an ethyl group or a propyl group, and QS is located on the ring; the number of $Q_5$ is one or more in quantities, when more than one, the $Q_5$ groups are identical or are the combination of two or two more different structures;
wherein, $R_{28}$ is a methyl group, an isopropyl group or an isobutyl group;
wherein, the asterisk "*" indicates the available radical ends to be connected towards LPEG.

14. The multifunctionalized polyethylene glycol compound according to claim 2, wherein, the combination of $U_1$ and $U_2$ is selected from the following Groups:
   Group (1): when $U_{01}$ and $U_{02}$ are not identical each a trivalent nitrogen atom core, both $U_1(O—)_3$ and $U_2(O—)_3$ contain no DEGG linkages;
   Group (2): when $U_{01}$ and $U_{02}$ are not identical each a trivalent nitrogen atom core, both $U_1(O—)_3$ and $U_2(O—)_3$ contain at least one DEGG linkage;
   Group (3): when $U_{01}$ and $U_{02}$ are not identical each a trivalent nitrogen atom core, $U_1(O—)_3$ contains no DEGG linkages, and $U_2(O—)_3$ contains at least one DEGG linkage;
   Group (4): when $U_{01}$ and $U_{02}$ are not identical each a trivalent nitrogen atom core, $U_1(O—)_3$ contains at least one DEGG linkage, and $U_2(O—)_3$ contains no DEGG linkages.

15. The multifunctionalized polyethylene glycol compound according to claim 1, wherein, at least one said g of

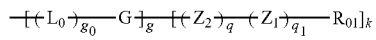

structures is equal to 1, and corresponding G group is of a branched structure, a ring-containing structure, a comb-like structure, a dendritic structure or a hyperbranched structure.

16. The multifunctionalized polyethylene glycol compound according to claim 10, wherein, at least one said g of

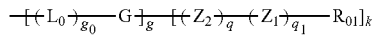

structures is equal to 1, and corresponding G group is selected from one of the following Groups:
   Group (1): corresponding k is equal to 2, corresponding linking group $(L_0)_{g0}$-G contains one structure selected from the group consisting of all applicable $U_{01}$ groups, all applicable $U_{02}$ groups, all applicable $U_1$ groups and all applicable $U_2$ groups;
   Group (2): corresponding k is equal to 3, corresponding linking group G contains a tetravalent core selected from an atom core $CM_4$, an unsaturated bond core $CB_4$ and a cyclic core $CC_4$, or contains two trivalent cores; wherein, said $CM_4$ is a tetravalent carbon atom core or a tetravalent silicon atom core;
said $CB_4$ is a tetravalent carbon-carbon double bond or >C=C=C<;
said $CC_4$ is derived from one of the following cylcic structures: a furanose ring, a pyranose ring, cycleanine, a cyclic tetrapeptide, tetrahydrofuran, pyrrolidine, thiazolidine, cyclohexane, benzene, cyclohexene, tetrahydropyran, piperidine, 1,4-dioxane, pyridine, pyridazine, pyrimidine, pyrazine, indene, indane, indole, isoindole, purine, naphthalene, dihydroanthracene, xanthene, thioxanthene, dihydrophenanthrene, 10,11-5H-dihydro-dibenzo[a,d]cycloheptane, dibenzocycloheptene, 5-dibenzosuberenone, quinoline, isoquinoline, fluorene, carbazole, iminodibenzyl, tetramethyl tetrahydroindene, dipyridamole skeleton, tetravalent triethanedial dehydrate skeleton, tetravalent six-membered ring of D-sorbitol skeleton with 2-, and 4-hydroxyl groups being protected, the substituted form of any said cyclic structure thereof, and the heterosubstituted form of any cyclic structure of the foregoing;
   Group (3): corresponding k is equal to or greater than 3, corresponding G has a valence equal to or higher than 4, and contains a (k+1)-valent core structure, or is combined directly by lower-valent groups with a valence from 3 to k in quantities of 2 to k−1, or is combined indirectly via one or more divalent spacer groups; said lower-valent groups of 3- to k-valence can be identical or not identical in structure, and can independently be identical or not identical in valence; when containing two or two more spacer groups, these spacer groups can be identical or not identical;
   Group (4): corresponding k is equal to or greater than 4, corresponding G is a (k+1)-valent group, and contains a (k+1)-valent core of a cyclic structure;
   Group (5): corresponding k is equal to or greater than 4, corresponding G is a (k+1)-valent group, and is constituted via a direct or indirect combination, wherein the combination manner is comb-like, dendritic, branched, hyperbranched, or cyclic.

17. The multifunctionalized polyethylene glycol compound according to claim 11, wherein, at least one said g of

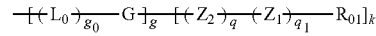

structures is equal to 1, and corresponding G group is selected from one of the following Groups:
   Group (1): corresponding k is equal to 2, and corresponding linking group $(L_0)_{g0}$-G contains one structure selected from the group consisting of all applicable $U_{01}$ groups, all applicable $U_{02}$ groups, all applicable $U_1$ groups, all applicable $U_2$ groups,

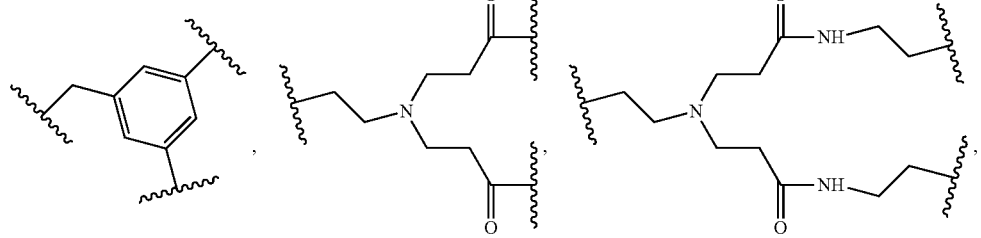

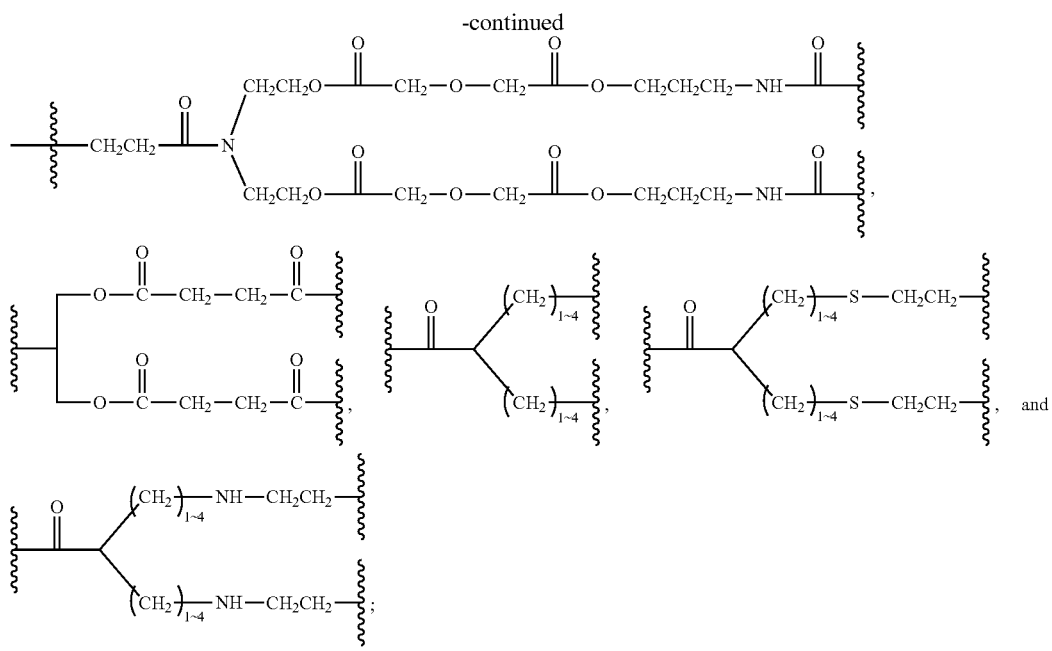
Group (2): corresponding k is equal to 3, and corresponding linking group $(L_o)_{go}$-G contains one structure selected from the group consisting of:
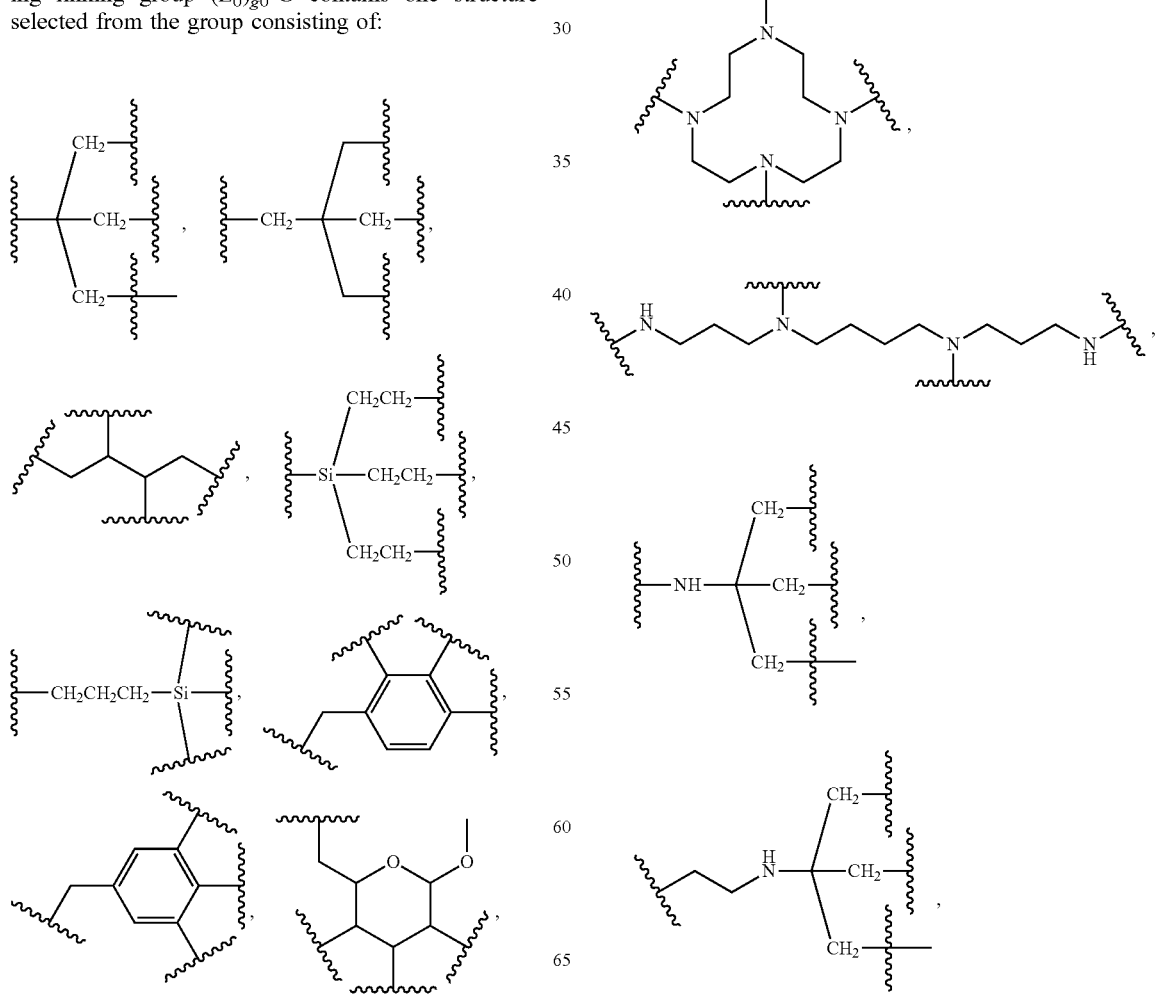

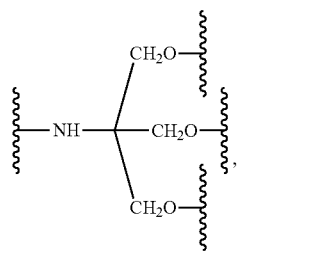
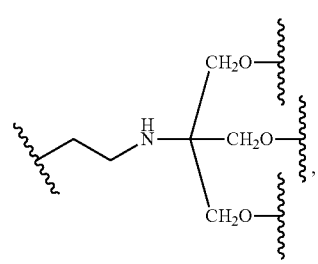
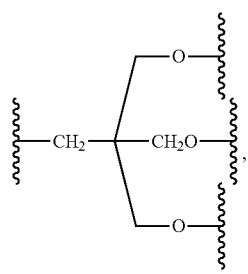
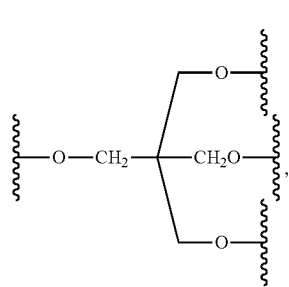
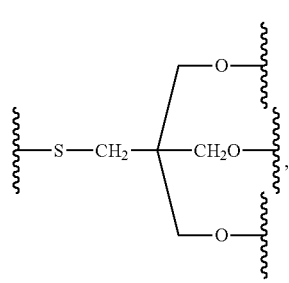
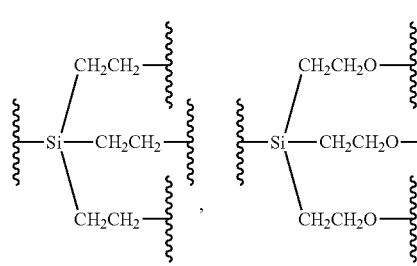
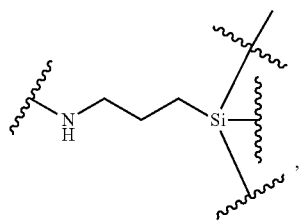
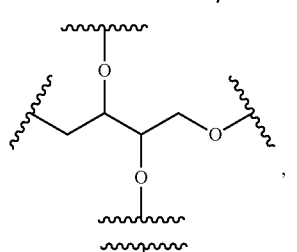
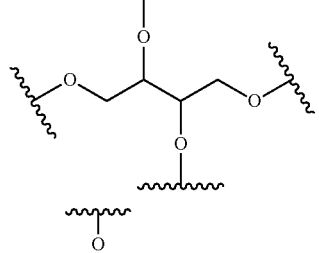
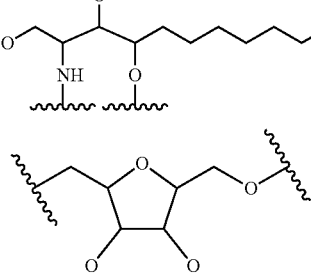
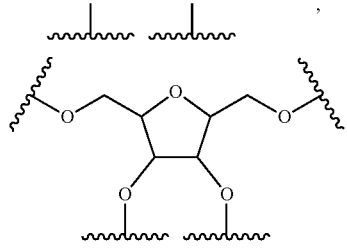
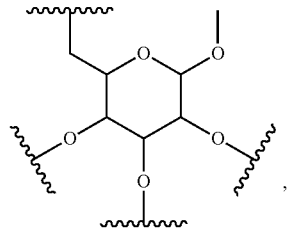
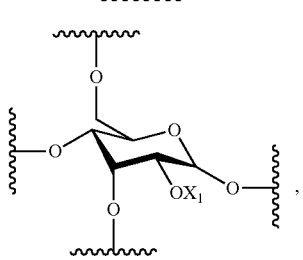

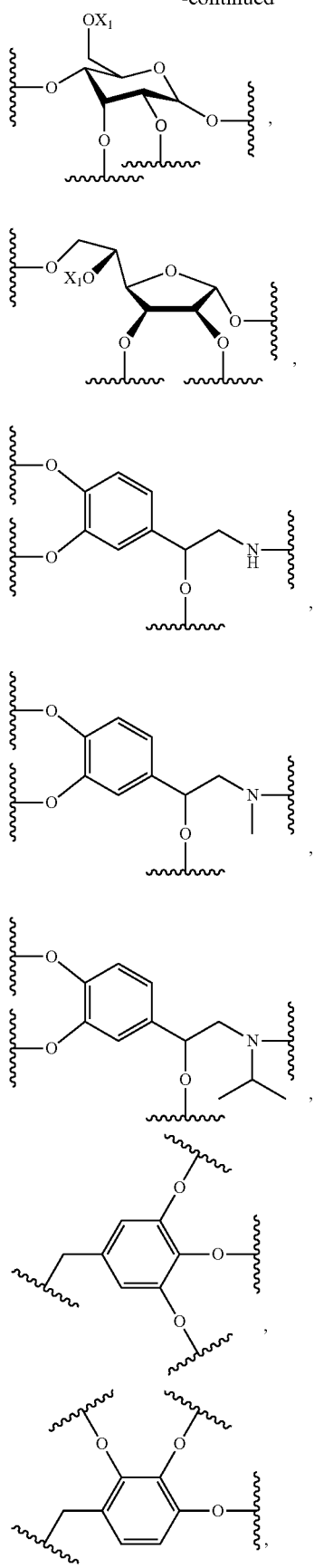
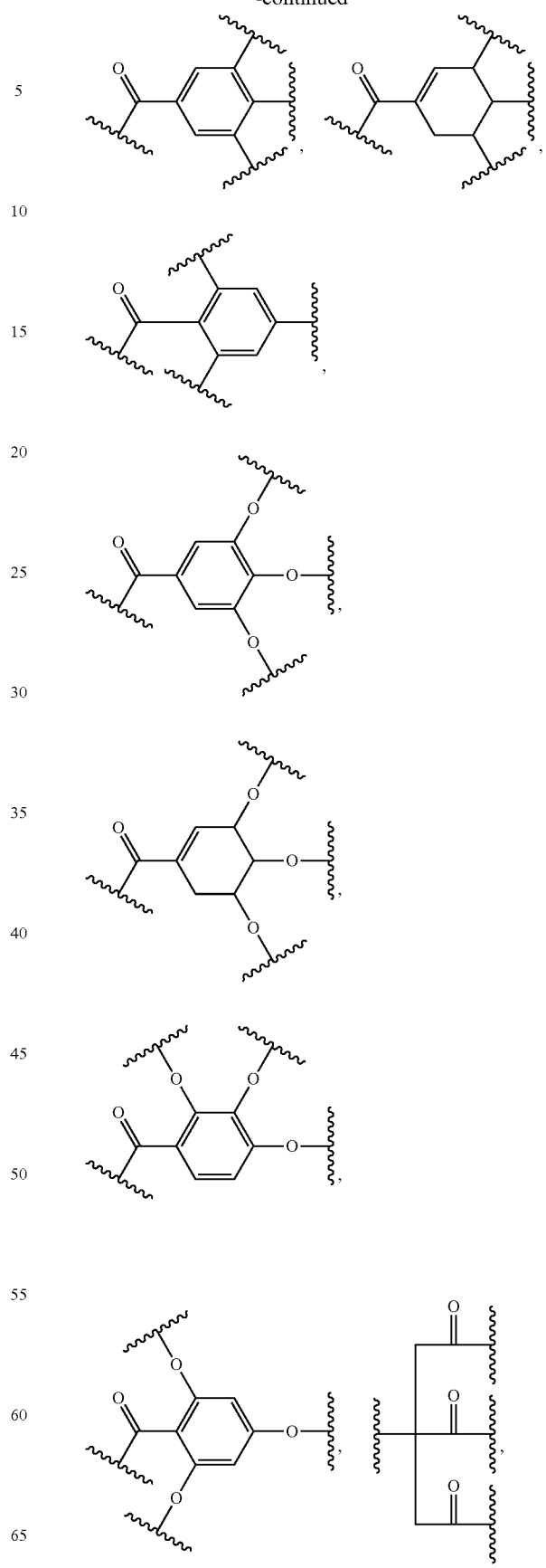

683
-continued

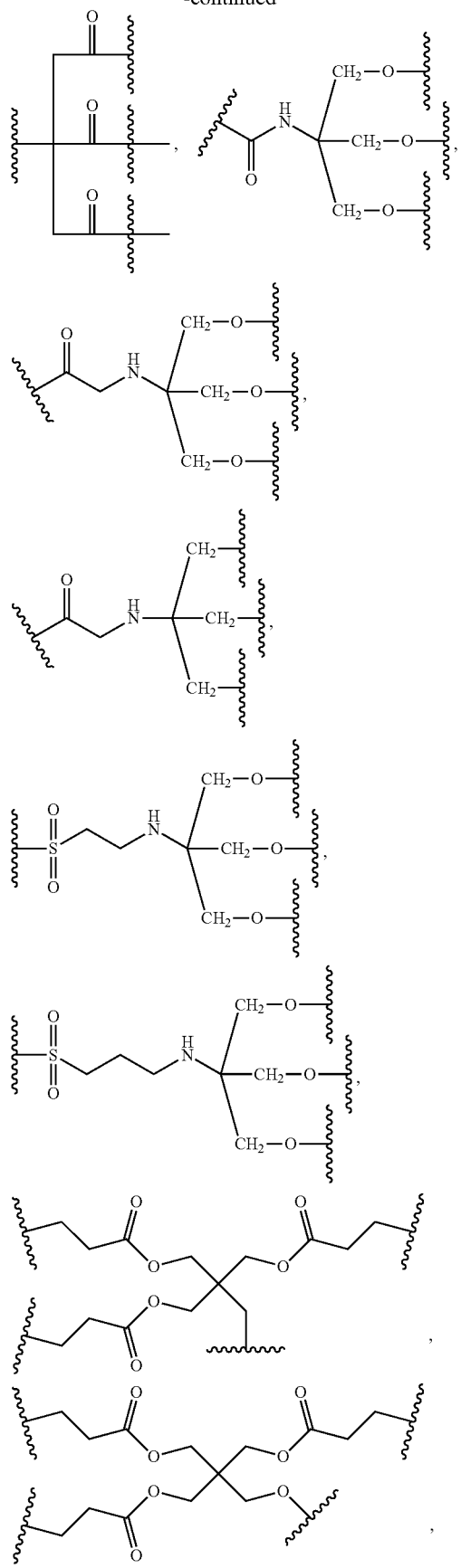

684
-continued

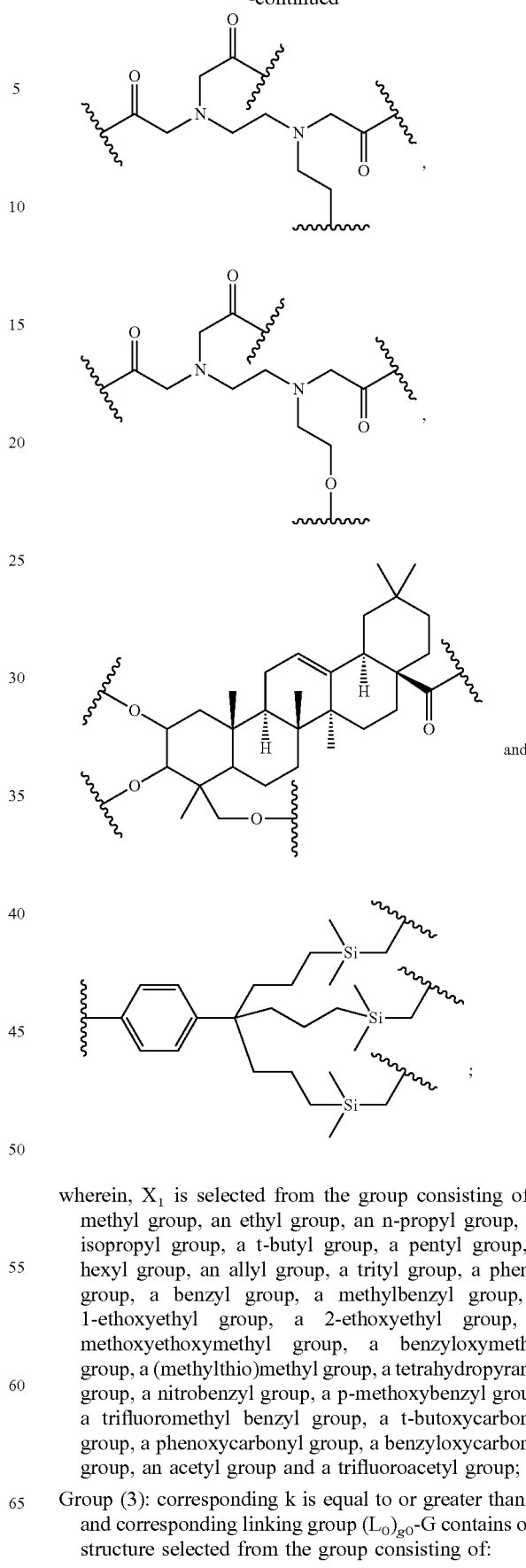

wherein, $X_1$ is selected from the group consisting of a methyl group, an ethyl group, an n-propyl group, an isopropyl group, a t-butyl group, a pentyl group, a hexyl group, an allyl group, a trityl group, a phenyl group, a benzyl group, a methylbenzyl group, a 1-ethoxyethyl group, a 2-ethoxyethyl group, a methoxyethoxymethyl group, a benzyloxymethyl group, a (methylthio)methyl group, a tetrahydropyranyl group, a nitrobenzyl group, a p-methoxybenzyl group, a trifluoromethyl benzyl group, a t-butoxycarbonyl group, a phenoxycarbonyl group, a benzyloxycarbonyl group, an acetyl group and a trifluoroacetyl group;

Group (3): corresponding k is equal to or greater than 4, and corresponding linking group $(L_O)_{gO}$-G contains one structure selected from the group consisting of:

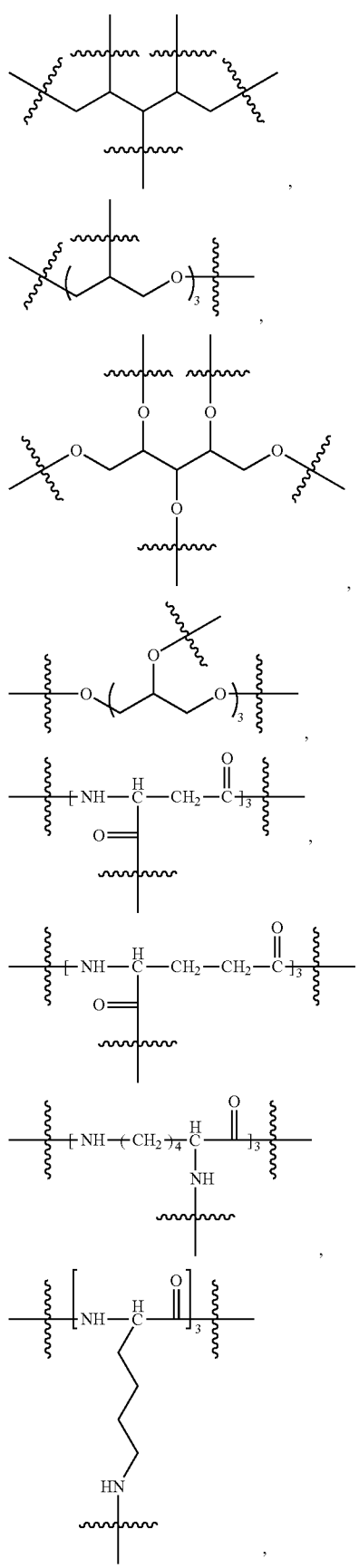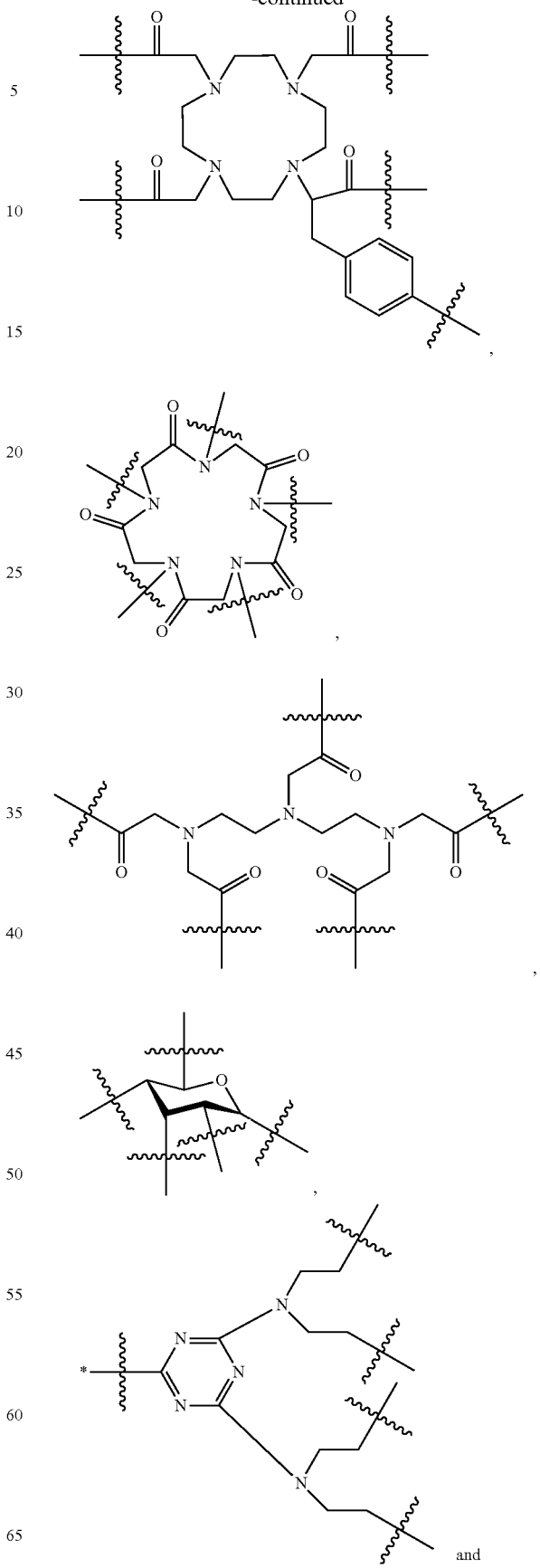

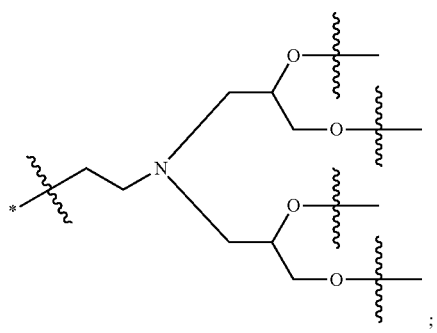
Group (4): corresponding k is equal to 5, and corresponding linking group $(L_O)_{g0}$-G contains one structure selected from the group consisting of:
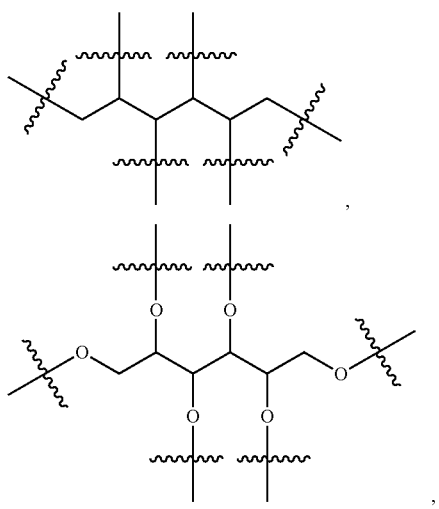
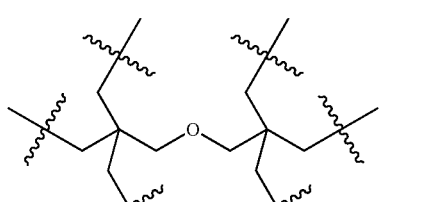
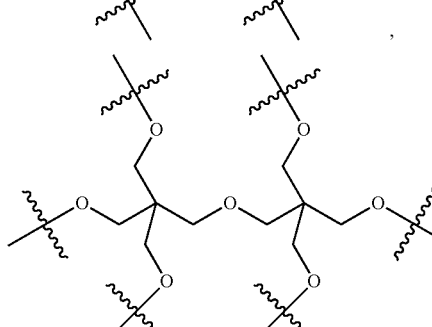
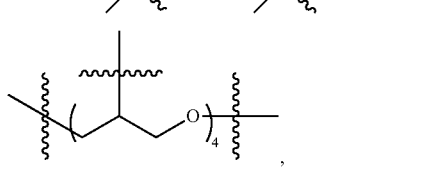
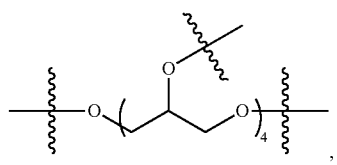
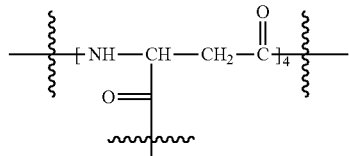
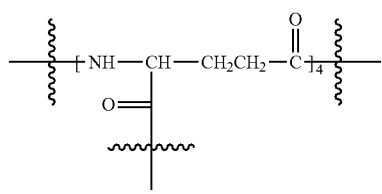
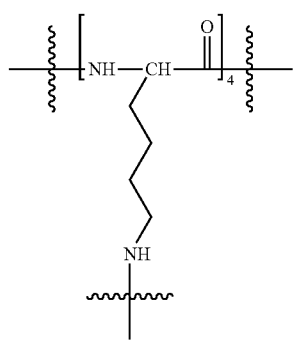
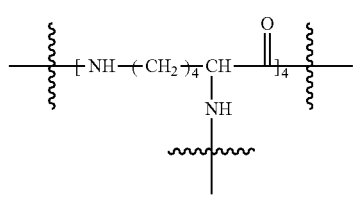
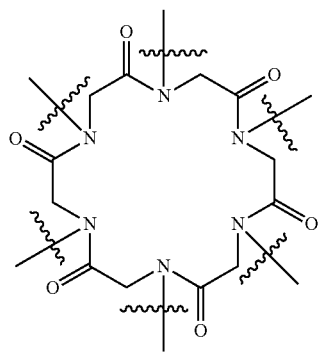
and -continued

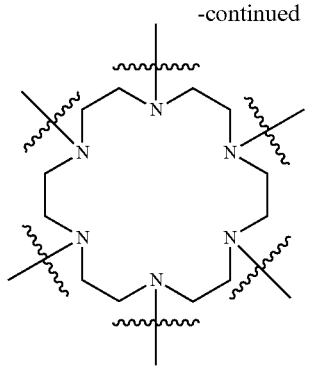

;

Group (5): corresponding k is equal to 6, and corresponding linking group $(L_O)_{gO}$-G contains one structure selected from the group consisting of:

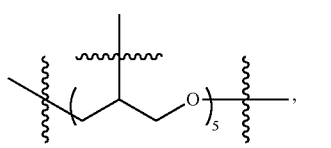

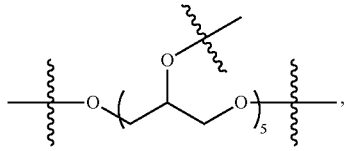

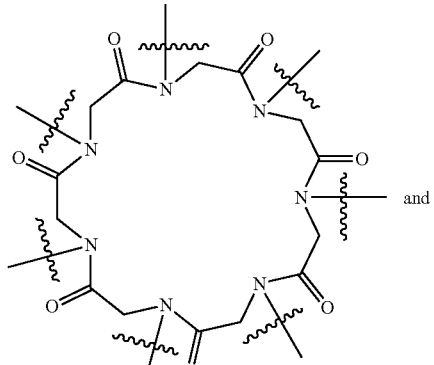

and

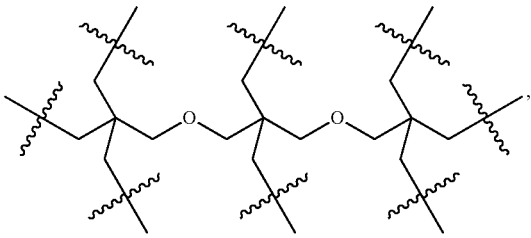

;

Group (6): corresponding k is equal to 7, and corresponding linking group $(L_O)_{gO}$-G contains one structure selected from the group consisting of:

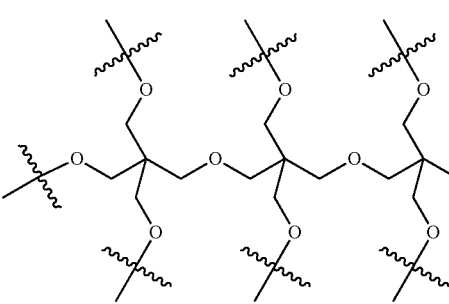

,

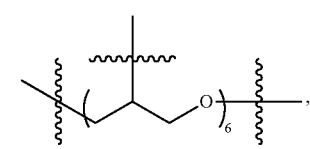

,

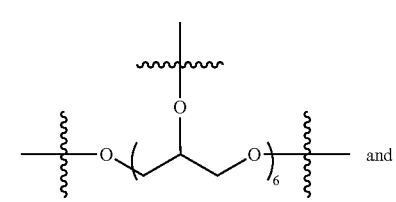

and

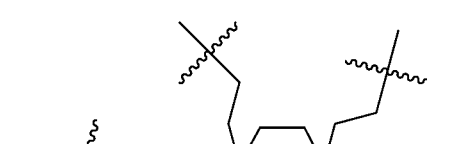

;

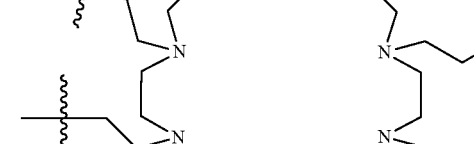

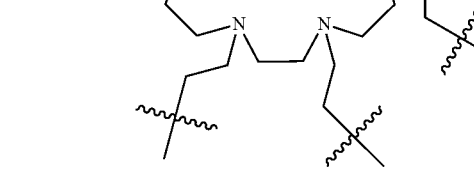

Group (7): corresponding k is equal to or greater than 4, and corresponding G is a (k+1)-valent group, and is constituted via a direct or indirect combination, wherein the combination manner is comb-like, dendritic, branched, hyperbranched, or cyclic;

wherein, said G group via a dendritic combination is selected from the following structures:

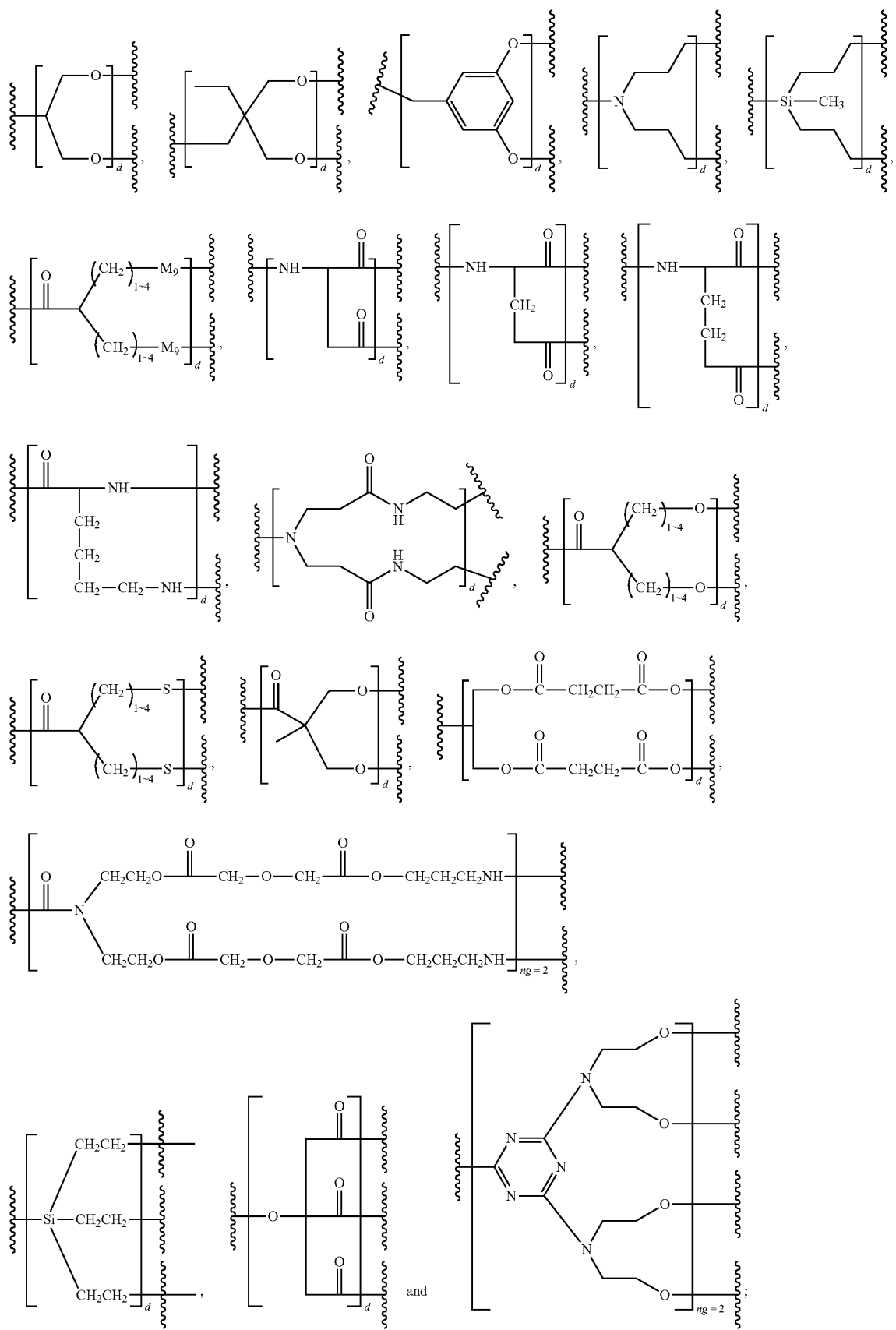

wherein, d represents a generation number of 2, 3, 4, 5 or 6;
wherein, Mg is an oxy bond, a thioxy bond or an amino bond;
  wherein, said G group via a branched or hyperbranched combination is formed by using trivalent or tetravalent structural units, and is a hybrid combination of said structural units mixed with lower-valent form thereof;
  wherein, said G group via a comb-like combination is formed by using tri-, tetra- or pentavalent structural units; wherein, G is constructed by one kind of structural units derived from any of the following structures: glycerol, pentaerythritol, substituted epoxypropane, the combination of substituted epoxypropane with carbon dioxide, acrylate and derivatives thereof, methacrylate and derivatives thereof, acetal-containing structural units, hydroxyl- or mercapto-containing amino acids and derivatives thereof, acidic amino acids and derivatives thereof, basic amino acids and derivatives thereof, or G is constructed as an acetalated-dextran structure or an oxidized form thereof; and
  wherein, said G group via a cyclic combination is selected from the following structures: residues of cyclopeptides and derivatives thereof, residues of monosaccharides and derivatives thereof, residue of polysaccharides and derivatives thereof, the skeleton of 1,4,7-tri-t-butoxycarbonyl-1,4,7,10-tetraazacyclododecane, the skeleton of 2-hydroxymethylpiperidine-3,4,5-triol, and the skeleton of 6-amino-4-(hydroxymethyl)-4-cyclohexyl-[4H,5H]-1,2,3-triol.

18. The multifunctionalized polyethylene glycol compound according to claim 1, wherein, at least one said g of

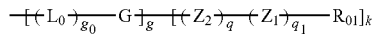

structures is equal to 1, and corresponding $L_0$ group is selected from one of the following Group (1) and Group (2):
  Group (1): $L_0$ contains an oligopeptide or peptide segment;
  Group (2): $L_0$ contains a linkage selected from $-(L_{11}O)_{nj}-$, $-(OL_{11})_{nj}-$, $-(R_{29}O)_{nj}-$, $-(OR_{29})_{nj}-$, $-(CH_2CH_2O)_{nj}-$ and $-(OCH_2CH_2)_{nj}-$; wherein, $R_{29}$ is a $C_{3-20}$ alkylene group, $L_{11}$ is a hydrocarbylene group or a substituted hydrocarbylene group, nj is an integer selected from 2 to 20.

19. The multifunctionalized polyethylene glycol compound according to claim 1, wherein, said $R_{01}$ is selected from functional end-groups.

20. The multifunctionalized polyethylene glycol compound according to claim 19, wherein, said $R_{01}$ is a functional group selected from Group A to Group H or a variant form of said functional group, a functional group selected from the Group I and Group J or a derivative form of said functional group, or a functional group selected from the Group (A-H)' or a variant form of said functional group; wherein,
  Group A: active ester groups;
  Group B: a sulfonate group, a sulfinate group, a sulfonyl group, a sulfoxide group, a 1,3-disulfonyl-2-propylcarbonylphenyl group and a (2-sulfonylmethyl)acryl group;
  Group C: a hydroxylamino group, a mercapto group, a primary or secondary amino group, an azido group, a halohydrocarbyl group, a haloacetylamino group, a tetramethylpiperidinyloxy group, a dioxapiperidinyloxy group, an ammonia salt group, a hydrazino group and a cyclodisulfide group;
  Group D: an amido group, an acylhydrozino group, an acyl-hydroxylamino group, a carboxyl group, an aldehyde group, a glyoxalgroup, an haloacyl group, an acetal group, a hemiacetal group, a hydrated aldehyde group, a ketal group, a hemiketal group, a hydrated ketone group, an orthoester group, a cyanate group, an isocyanato group, an ester group, a silyloxy group, a silicate group, a silyl group, a thioestergroup, a thioate group, a dithioester group, a trithioester group, a thiohemiacetal group, a monothiohydrate group, a dithiohydrate group, a disulfide group, a thiol hydrate group, a thione group, a thioacetal group, a thione hydrate group, a thioketal group, a dithioketal group, a thiohemiketal group, a dihydrooxazole group, an isothiocyanato group, a mercapto group, a ureido group, a thioureido group, a guanidino group, an anhydride group, a squaryl group and a squarate group;
  Group E: a maleimido group, an acrylamide group, an acrylate group, an N-methacrylamide group, a methacrylate group, a norbornenyl-2,3-dicarboximide group, a maleamic acid group, a protected maleimido group, a 1,2,4-triazoline-3,5-dione group and a substituted maleimido group;
  Group F: a cyano group, an alkenyl group, an alkenyl-hydrocarbyl groups, a cycloalkenyl group, an alkynyl group, an alkynyl-hydrocarbyl group, an epoxy groups, a linear or cyclic azo group, a diazo group, a dienyl group, a dienyl-hydrocarbyl group, a tetrazole group, a linear conjugated dienyl group and a nitrile oxide group;
  Group G: a cycloalkynyl group, a heterosubstituted cycloalkynyl group, a cyclodienyl group, a heterosubstituted conjugated dienyl group with a skeleton-membering heteroatom and a 1,2,4,5-tetrazinyl group;
  Group H: a hydroxyl group, a protected hydroxyl group, a siloxy group, a protected dihydroxyl group, a trihydroxysilyl group and a protected trihydroxysilyl group;
  Group (A-H)': an imide group, a sulfonylhydrazino group, a hydrazone group, an imino group, an enamino group, an alkynylamino group, a xanthate group, a perthiocarbonate group, a dithiobis(thionoformate) group, a sulfonic acid group, a sulfenic acid group, a hydroxamic acid group, a thiohydroxamic acid group, a xanthogenic acid group, a chlorosulfonyl group, an orthoacid group, a cyanate group, a thiocyanate group, a monothiocarboxylic acid group, a dithiocarboxylic acid group, an amidino group and protonated form thereof, a semi-squaric acid group, a semi-squarate group, an N-carbamoyl-3-imidazole group, an N-carbamoyl-3-methylimidazolium iodide group, an imidic acid group, an imidic ester group, a nitrone group, an oximino group, a urea group, a thiourea group, a pseudourea group, an isocyano group, an aldoxime group, a diazo group, a diazonium group, an azoxy group, a nitrilimine group, an N-aldimine oxide group, a tetrazole group, a 4-acetyl-2-methoxy-5-nitrophenoxy group and its diazo form, and other functional groups involving 1,3-dipolar cycloaddition reactions;
  Group I: therapeutic targeting groups and pharmaceutically acceptable salts thereof;
  Group J: fluorescent groups.

21. The multifunctionalized polyethylene glycol compound according to claim 19, wherein, said $R_{01}$ is one functional group selected from the Group A to Group H or variant form of said functional group, or one functional group selected from the Group I and Group J or functional derivative of said functional group; wherein,
Group A consists of:
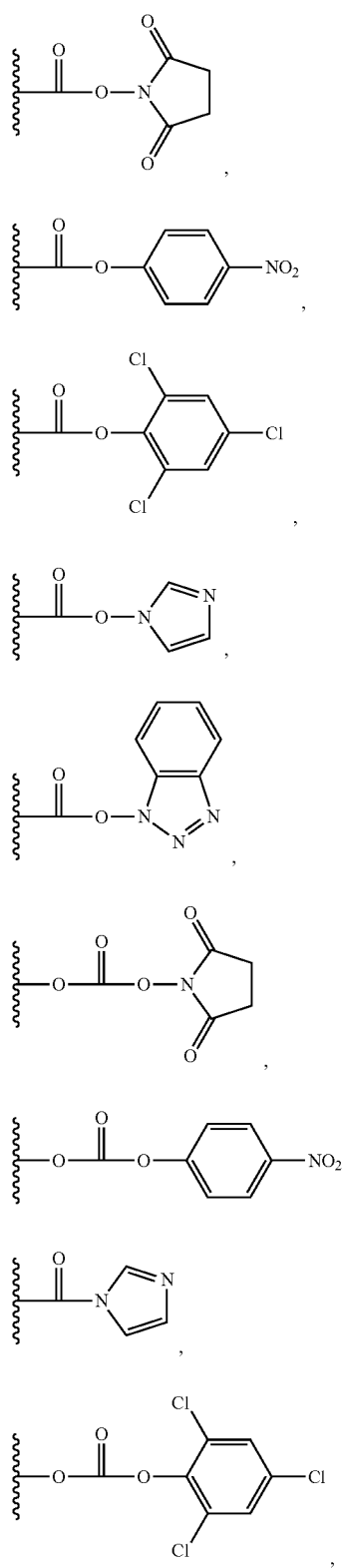
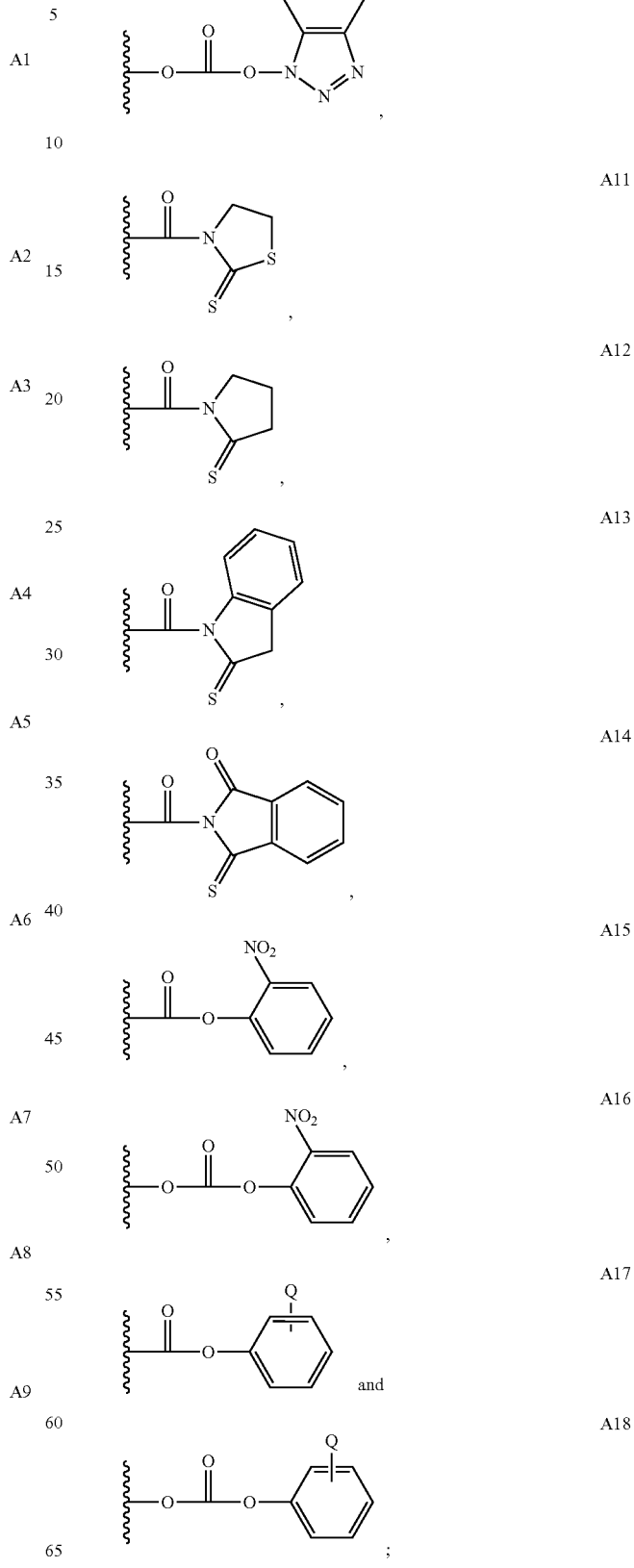

Group B consists of:
B1 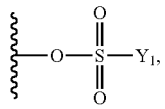
B2 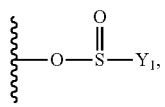
B3 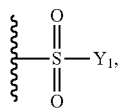
B4 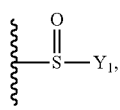
B5 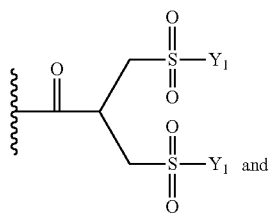
B6 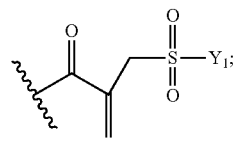
Group C consists of:
C1 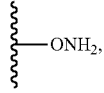
C2 
C3 
C4 
C5 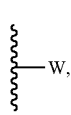
-continued
C6 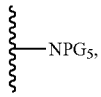
C7 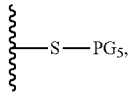
C8 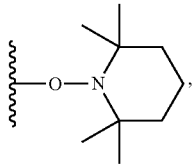
C9 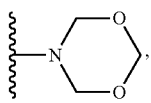
C10 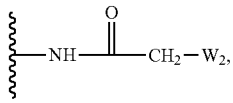
C11 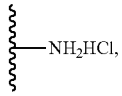
C12 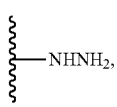
C13 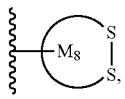
C14 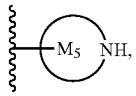
C15 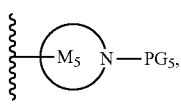
C16 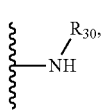
C17 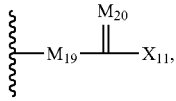
C18 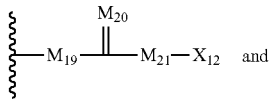 and

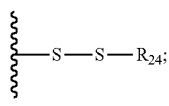
Group D consists of:
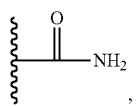
D1
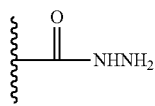
D2
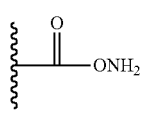
D3
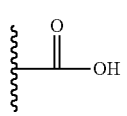
D4
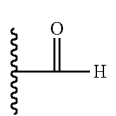
D5
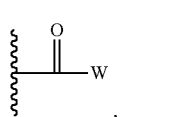
D6
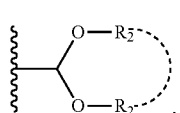
D7
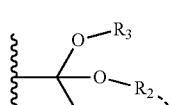
D8
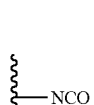
D9
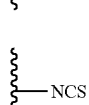
D10
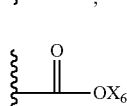
D11
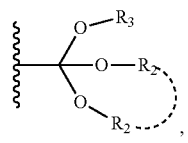
D12
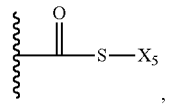
D13
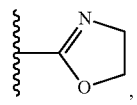
D14
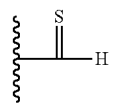
D15
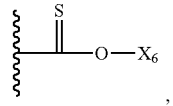
D16
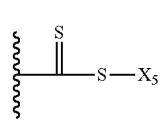
D17
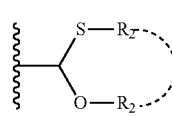
D18
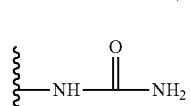
D19
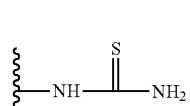
D20
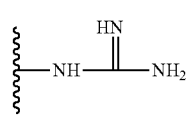
D21
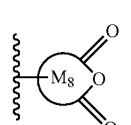
D22
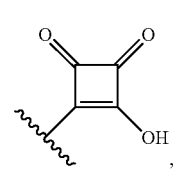
D23

701
-continued
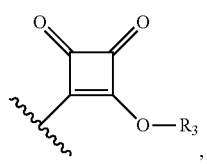
D24
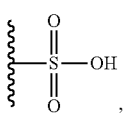
D25
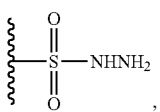
D26
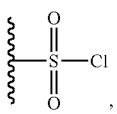
D27
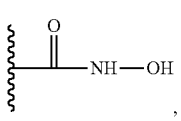
D28
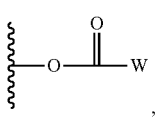
D29
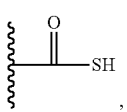
D30
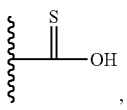
D31
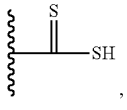
D32
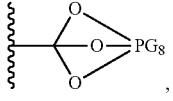
D33
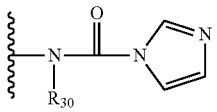
D34
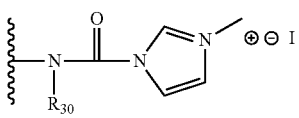
and
702
-continued
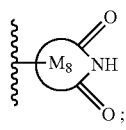
D35
Group E consists of:
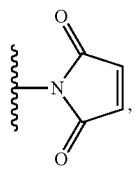
E1
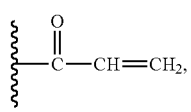
E2
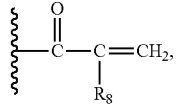
E3
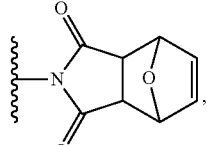
E4
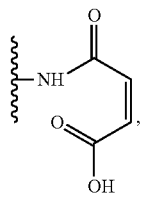
E6
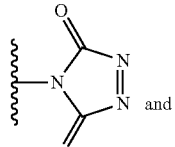
E7
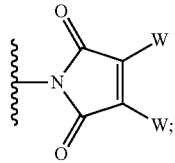
E8
and
Group F consists of:
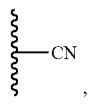
F1

703
-continued
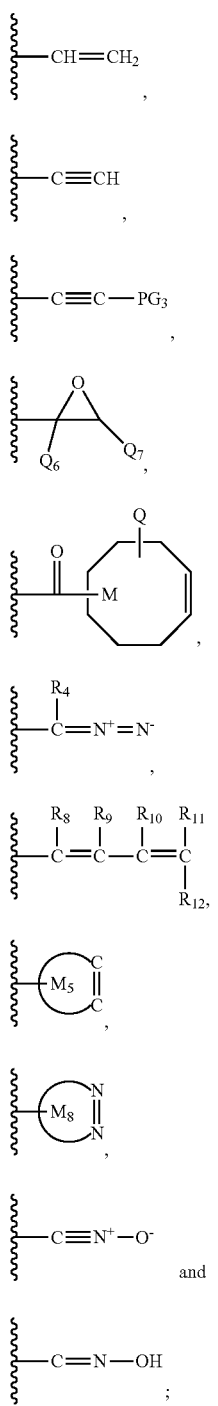
Group G consists of:
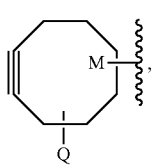
704
-continued
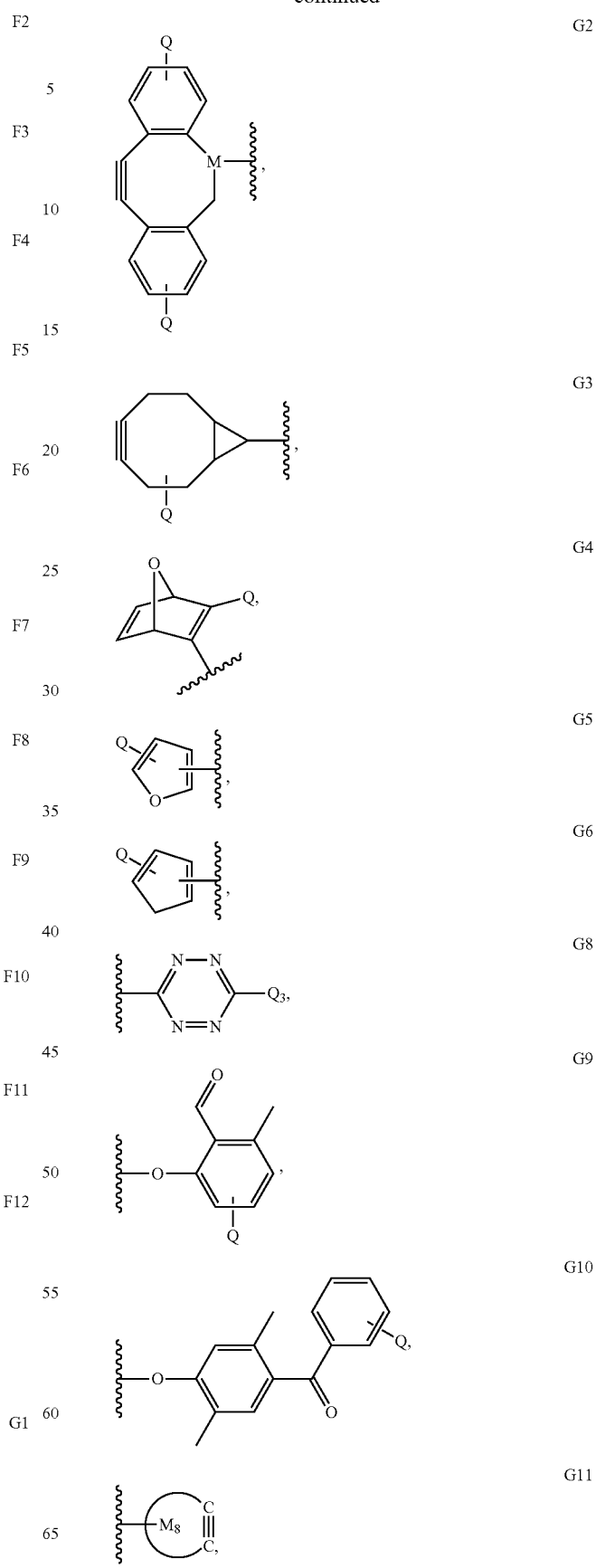

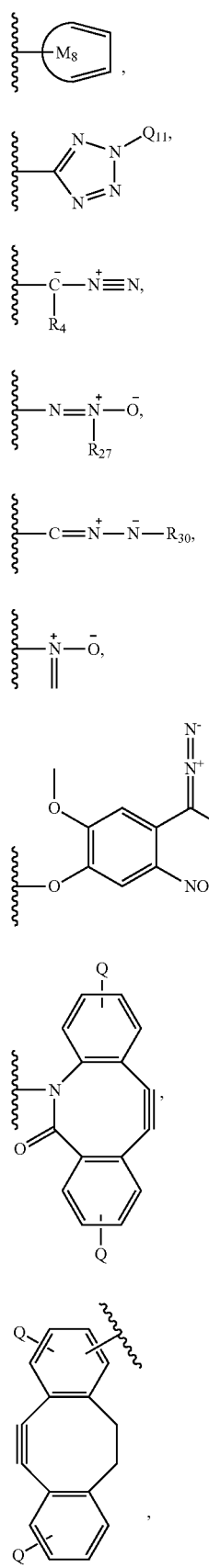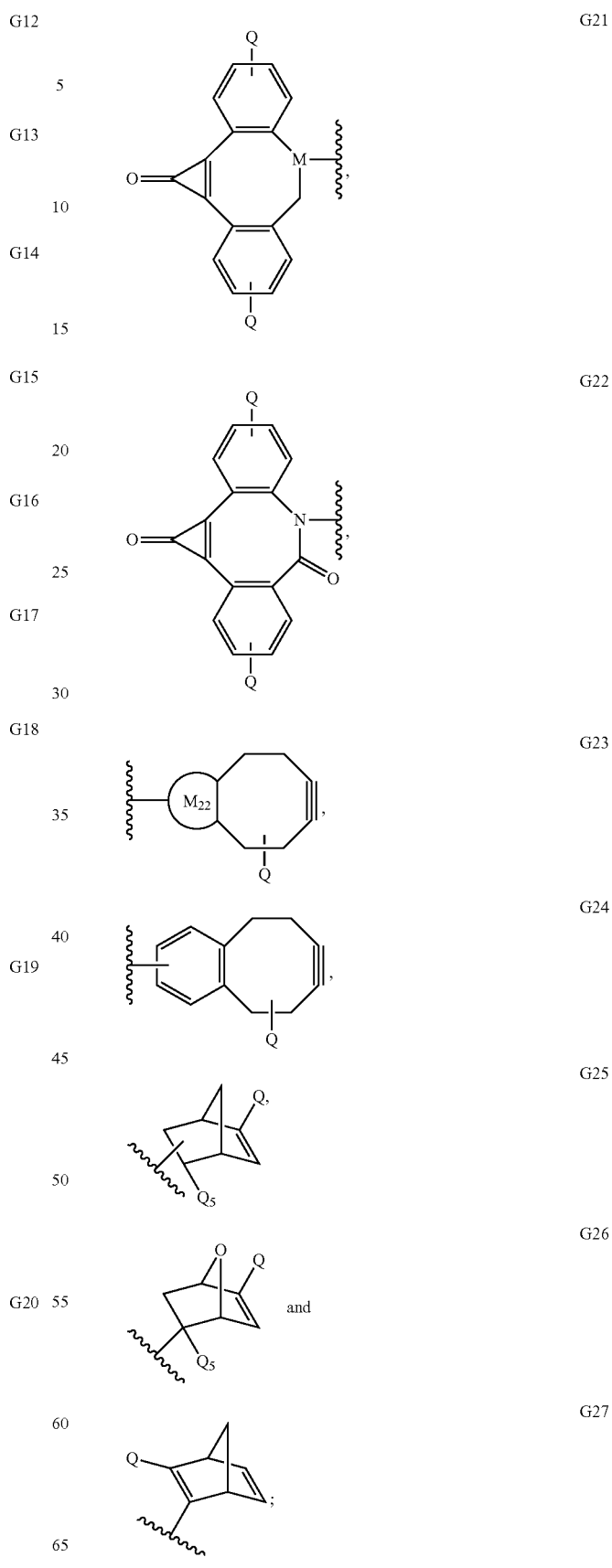

Group H consists of:
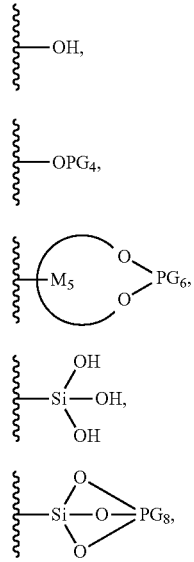
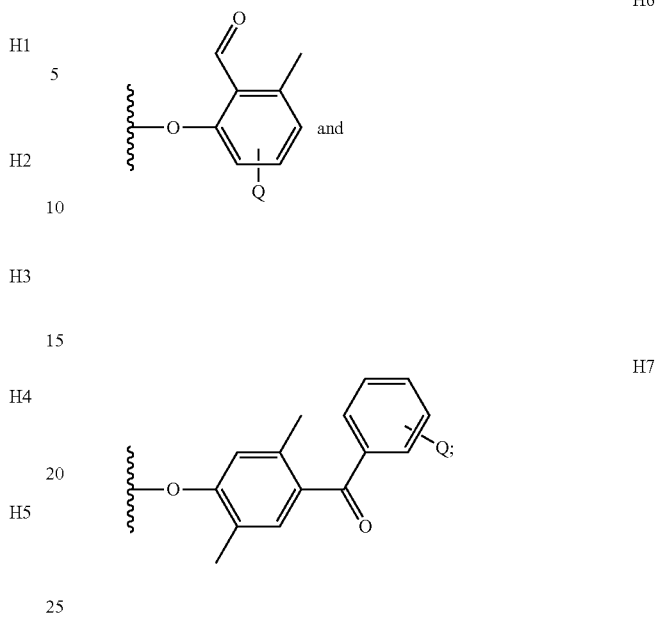
Group I consists of:
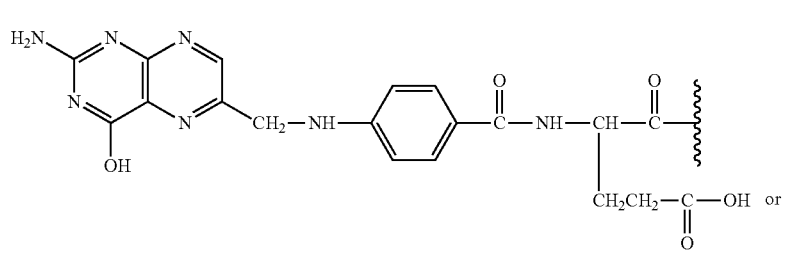
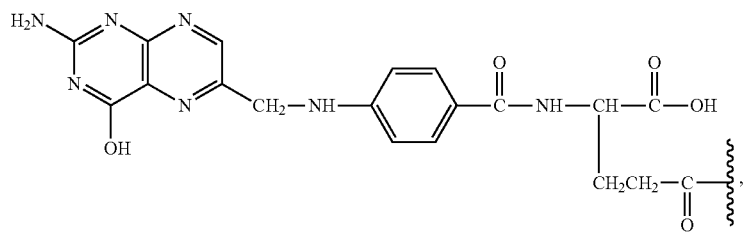
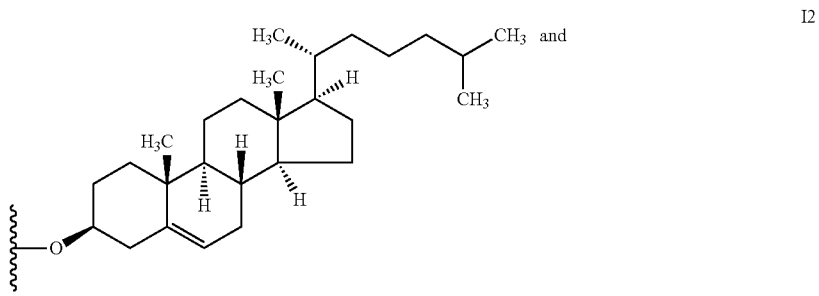

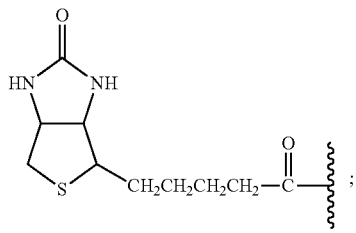
Group J consists of:
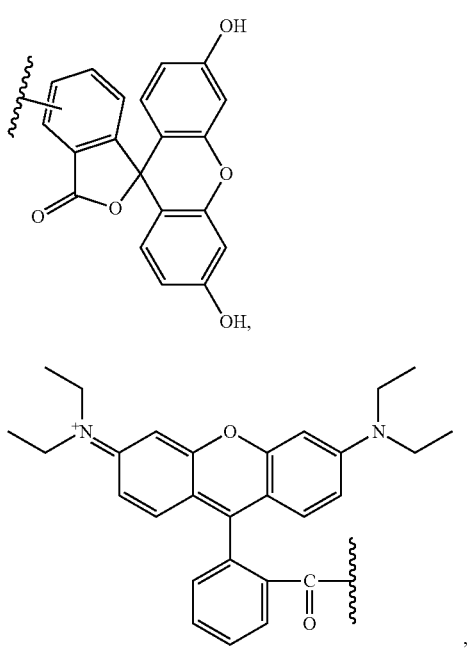
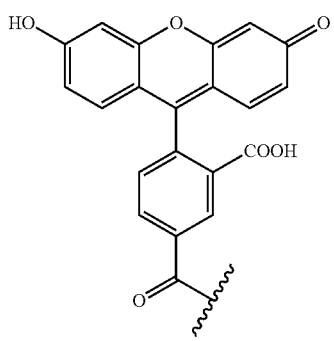
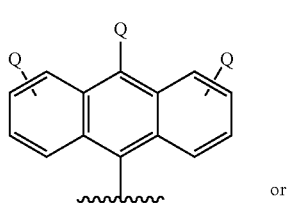 or
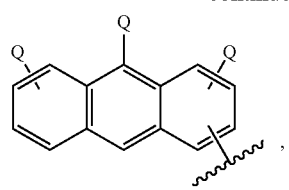
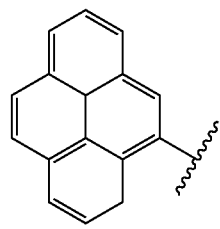 or 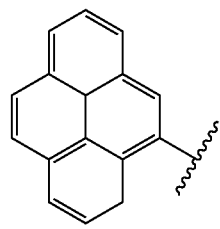,
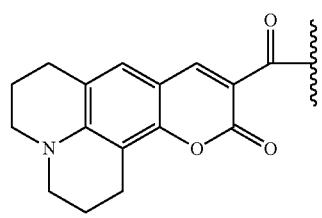,
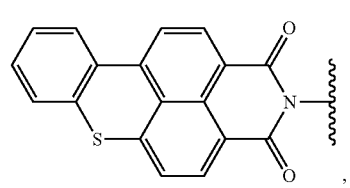,
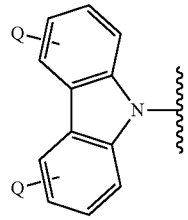,
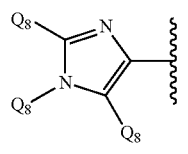 or -continued

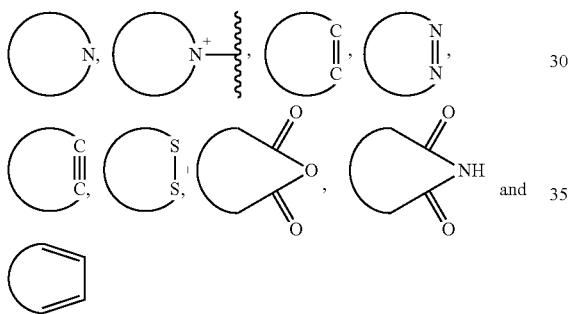

wherein, Yi is a leaving group selected from the group consisting of a methyl group, an ethyl group, an n-propyl group, an isopropyl group, a butyl group, a pentyl group, a hexyl group, a heptyl group, an octyl group, a nonyl group, a decyl group, a vinyl group, a phenyl group, a benzyl group, a p-methylphenyl group, a 4-(trifluoromethoxy)phenyl group, a trifluoromethyl group and a 2,2,2-trifluoroethyl group;

wherein, W is F, Cl, Br or I;

wherein, $W_2$ is F, Cl, Br or I;

Wherein, and are cyclic structures wherein the ring skeleton contains a nitrogen atom, a nitrogen cation, a carbon-carbon double bond, an azo bond, a carbon-carbon triple bond, a disulfide bond, an anhydride group, an imide group and a dienylene group, respectively;

wherein, M is ring-membering atom selected from a carbon atom and a heteroatom;

wherein, $M_5$ is a ring-membering atom selected from a carbon atom, a nitrogen atom, a phosphorus atom and a silicon atom, and said $M_5$-membered ring is 3- to 50-membered;

wherein, $M_8$ is a ring-membering atom selected from a carbon atom, a nitrogen atom, a phosphorus atom and a silicon atom, and said $M_8$-membered ring is 4- to 32-membered;

wherein, $M_{19}$, $M_{20}$ and $M_{21}$ are each independently an oxygen atom or a sulfur atom, and in one molecule they can be identical or not identical;

wherein, $M_{22}$ is a ring-membering atom selected from a carbon atom, a nitrogen atom, a phosphorus atom and a silicon atom, and said $M_{22}$-membered ring is 4-, 5-, 6-, 7-, or 8-membered;

wherein, $R_2$ is a monovalent group or a divalent linking group that connects with an oxygen atom or a sulfur atom, and selected from a hydrogen atom, a divalent group $R_{21}$ or a monovalent group $R_3$;

said $R_{21}$ is a ring-membering divalent linking group selected from the group consisting of a methylene group, an ethylene group, a propylene group, a butylene group, a pentylene group, a hexylene group, a heptylene group, an octylene group, a nonylene group, a decylene group, a 1,2-phenylene group, a benzylene group, a $C_{1-20}$ oxa-alkylene group, a $C_{1-20}$ thia-alkylene group, a $C_{1-20}$ aza-alkylene group, an aza-arylhydrocarbylene group, the substituted form of any said group thereof, and the combination of any two or two more identical or different said groups or substituted forms thereof;

said $R_3$ is a monovalent group connecting with an oxy group or a thioxy group, and selected from the group consisting of a methyl group, an ethyl group, an n-propyl group, an isopropyl group, a butyl group, a pentyl group, a hexyl group, a heptyl group, an octyl group, a nonyl group, a decyl group, a benzyl group, an allyl group, and the substituted form of any said group thereof;

wherein, $R_4$ is selected from the group consisting of a hydrogen atom, a methyl group, an ethyl group, an n-propyl group, an isopropyl group, a butyl group, a pentyl group, a hexyl group, a heptyl group, an octyl group, a nonyl group, a decyl group, an allyl group, a propenyl group, an ethenyl group, a phenyl group, a methylphenyl group, a butylphenyl group and a benzyl group;

wherein, $R_8$, $R_9$, $R_{10}$, $R_{11}$ and $R_{12}$ are each independently a hydrogen atom, a fluorine atom or a methyl group; in one molecule, $R_8$, $R_9$, $R_{10}$, $R_{11}$ and $R_{12}$ can be identical or not identical; and in Group E3, $R_8$ is a methyl group;

wherein, $R_{24}$ is a monovalent group selected from a $C_{1-20}$ alkyl group, an aryl group, an arylhydrocarbyl group and a heterosubstituted phenyl group containing one or more ring-membering heteroatoms;

wherein, $R_{27}$ is a group substituent selected from a phenyl group, a substituted phenyl group and a heterosubstituted phenyl group containing one or more ring-membering heteroatoms;

wherein, $R_{30}$ is a hydrocarbyl group;

wherein, $X_5$ is a monovalent group selected from a mercapto protecting group and a group $LG_2$;

said $LG_2$ is selected from the group consisting of a $C_{1-20}$ alkyl group, an aryl group, an arylalkyl group, a $C_{1-20}$ heteroalkyl group, a heteroaryl group, a heteroarylalkyl group, a $C_{1-20}$ alkylthio group, an arylthio group, an arylalkylthio group, a $C_{1-20}$ heteroalkyl thio group, a heteroarylthio group, a heteroarylalkylthio group, a $C_{1-20}$ alkylcarbonyl group, an arylcarbonyl group, an arylalkylcarbonyl group, a $C_{1-20}$ heteroalkylcarbonyl group, a heteroarylcarbonyl group, a heteroarylalkylcarbonyl group, a $C_{1-20}$ alkoxycarbonyl group, an aryloxycarbonyl group, an arylalkoxycarbonyl group, a $C_{1-20}$ (alkylthio)carbonyl group, an (arylthio)carbonyl group, an (arylalkylthio)carbonyl group, a $C_{1-20}$ alkylaminocarbonyl group, an arylaminocarbonyl group, an arylalkylaminocarbonyl group, a $C_{1-20}$ heteroalkoxycarbonyl group, a heteroaryloxycarbonyl group, a heteroarylalkoxycarbonyl group, a $C_{1-20}$ hetero(alkylthio)carbonyl group, a hetero(arylthio)carbonyl group, a hetero(arylalkylthio)carbonyl group, a $C_{1-20}$ heteroalkylaminocarbonyl group, a heteroarylaminocarbonyl group, a heteroarylalkylaminocarbonyl group, a $C_{1-20}$ alkyl-thiocarbonyl group, an aryl-thiocarbonyl group, an arylalkyl-thiocarbonyl group, a $C_{1-20}$ heteroalkyl-thiocarbonyl group, a heteroaryl-thiocarbonyl group, a heteroarylalkyl-thiocarbonyl group, a $C_{1-20}$ alkoxy-thiocarbonyl group, an aryloxy-thiocarbonyl group, an arylalkoxy-thiocarbonyl group, a $C_{1-20}$ (alkylthio)thiocarbonyl group, an (arylthio)thiocarbonyl group, an (arylalkylthio)thiocarbonyl group, a $C_{1-20}$ alkylaminothiocarbonyl group, an arylaminothiocarbonyl group, an arylalkylaminothiocarbonyl group, a $C_{1-20}$ heteroalkyloxy-thiocarbonyl group, a heteroaryloxy-thiocarbonyl group, a heteroarylalkoxy-thiocarbonyl group, a $C_{1-20}$ hetero(alkylthio)thiocarbonyl group, a hetero(arylthio)thiocarbonyl group, a hetero(arylalkylthio)thiocarbonyl group, a $C_{1-20}$ heteroalkylaminothiocarbonyl group, a heteroarylaminothiocarbonyl group, a heteroarylalkylaminothiocarbonyl group and the substituted form of any said group thereof;

wherein, $X_6$ is a monovalent group selected from a hydroxyl protecting group and a group $LG_4$;

said $LG_4$ is selected from the group consisting of a $C_{1-20}$ alkyl group, a $C_{3-20}$ alkenylhydrocarbyl group, an aryl group, an arylalkyl group, a $C_{1-20}$ heteroalkyl group, a heteroaryl group, a heteroarylalkyl group, a $C_{1-20}$ alkylcarbonyl group, an arylcarbonyl group, an arylalkylcarbonyl group, a $C_{1-20}$ heteroalkylcarbonyl group, a heteroarylcarbonyl group, a heteroarylalkylcarbonyl group, a $C_{1-20}$ alkoxycarbonyl group, an aryloxycarbonyl group, an arylalkoxycarbonyl group, a $C_{1-20}$ (alkylthio)carbonyl group, an (arylthio)carbonyl group, an (arylalkylthio)carbonyl group, a $C_{1-20}$ alkylaminocarbonyl group, an arylaminocarbonyl group, an arylalkylaminocarbonyl group, a $C_{1-20}$ heteroalkoxycarbonyl group, a heteroaryloxycarbonyl group, a heteroarylalkoxycarbonyl group, a $C_{1-20}$ hetero(alkylthio)carbonyl group, a hetero(arylthio)carbonyl group, a hetero(arylalkylthio)carbonyl group, a $C_{1-20}$ heteroalkylaminocarbonyl group, a heteroarylaminocarbonyl group, a heteroarylalkylaminocarbonyl group, a $C_{1-20}$ alkyl-thiocarbonyl group, an aryl-thiocarbonyl group, an arylalkyl-thiocarbonyl group, a $C_{1-20}$ heteroalkyl-thiocarbonyl group, a heteroaryl-thiocarbonyl group, a heteroarylalkyl-thiocarbonyl group, a $C_{1-20}$ alkoxy-thiocarbonyl group, an aroxy-thiocarbonyl group, an arylalkoxy-thiocarbonyl group, a $C_{1-20}$ (alkylthio)thiocarbonyl group, an (arylthio)thiocarbonyl group, an (arylalkylthio)thiocarbonyl group, a $C_{1-20}$ alkylaminothiocarbonyl group, an arylaminothiocarbonyl group, an arylalkylaminothiocarbonyl group, a $C_{1-20}$ heteroalkoxy-thiocarbonyl group, a heteroaryloxy-thiocarbonyl group, a heteroarylalkoxy-thiocarbonyl group, a $C_{1-20}$ hetero(alkylthio)thiocarbonyl group, a hetero(arylthio)thiocarbonyl group, a hetero(arylalkylthio)thiocarbonyl group, a $C_{1-20}$ heteroalkylaminothiocarbonyl group, a heteroarylaminothiocarbonyl group, a heteroarylalkylaminothiocarbonyl group and substituted forms thereof;

wherein, $X_{11}$ is a $C_{1-20}$ alkyl group;

wherein, $X_{12}$ is a $C_{1-20}$ hydrocarbyl group;

wherein, Q is a hydrogen atom or a substituent of ring; the number of Q is one or more in quantities, when more than one, the Q groups have the same structure or are a combination of two or two more different structures;

wherein, $Q_3$ is a hydrogen atom or a substituent of ring, and selected from the group consisting of a hydrogen atom, a halogen atom, a $C_{1-20}$ alkyl group, a $C_{2-20}$ alkenyl group, a $C_{3-20}$ open-chain alkenyl-hydrocarbyl group, a $C_{3-20}$ cycloalkenyl group, an aryl group, an arylhydrocarbyl group, a $C_{1-20}$ heteroalkyl group, a heteroaryl group, a heteroarylalkyl group, a $C_{1-20}$ alkoxy group, an aryloxy group, an arylhydrocarbyloxy group, a $C_{1-20}$ heteroalkoxy group, a heteroaryloxy group, a heteroarylhydrocarbyloxy group, a $C_{1-20}$ heteroalkylthio group, a heteroarylthio group, a heteroarylhydrocarbylthio group, a $C_{1-20}$ haloalkyl group and the substituted form of any said group thereof;

wherein, $Q_5$ is a hydrogen atom, a methyl group, an ethyl group or a propyl group;

wherein, $Q_6$ is a hydrogen atom or a methyl group, and $Q_7$ is a hydrogen atom, a methyl group, a phenyl group, or a substituted phenyl group; in one molecule, $Q_6$ and $Q_7$ can be identical or different from each other;

wherein, $Q_8$ is selected from a hydrogen atom, a methyl group, an ethyl group, a propyl group, a butyl group and a phenyl group; the number of $Q_8$ is one or more in quantities, when more than one, the $Q_8$ groups have the same structure or are a combination of two or two more different structures;

wherein, $Q_{11}$ is a phenyl group, a substituted phenyl group or an azaphenyl group;

wherein, $PG_2$ is a mercapto protecting group;

wherein, $PG_3$ is an alkynyl protecting group;

wherein, $PG_4$ is a hydroxyl protecting group;

wherein, $PG_5$ is an amino protecting group;

wherein, $PG_6$ is a dihydroxyl protecting group;

wherein, $PG_8$ is a protecting group for orthocarbonic acid or orthosilicic acid.

22. The multifunctionalized polyethylene glycol according to claim 1, wherein, said $F_1$ and $F_2$ have different $R_{01}$ groups, and such a heterofunctional group pair, also denoted as "$R_{01}$ pair", is selected from the group consisting of a hydroxyl group with a protected hydroxyl group, an unprotected or protected hydroxyl group with a non-hydroxyl reactive group, an unprotected or protected hydroxyl group with a therapeutic targeting or derivative thereof, an unprotected or protected hydroxyl group with a photosensitive functional group or derivative thereof, an active ester group or an active ester analog with a maleimido group, an active ester group or an active ester analog with an aldehyde group, an active ester group or an active ester analog with an azido group, an active ester group or an active ester analog with an unprotected or protected alkynyl group, an active ester group or an active ester analog with an acrylate group, an active ester group or an active ester analog with a methacrylate group, an active ester group or an active ester analog with an acrylic acid group, a maleimido group with an azido group, a maleimido group with an unprotected or protected alkynyl group, a maleimido group with an acrylate group, a maleimido group with a methacrylate group, a maleimido group with an acrylic acid group, a maleimido group with a carboxyl group, a maleimido group with an unprotected or protected amino group or an amine salt group, a maleimido group with an isocyanato group, a maleimido group with a protected mercapto group, an aldehyde group with an azido group, an aldehyde group with an acrylate group, an aldehyde group with a methacrylate group, an aldehyde group with an acrylic acid group, an aldehyde group with an epoxy group, an aldehyde group with a carboxyl group, an aldehyde group with an unprotected or protected alkynyl group, an azido group with a mercapto group or a protected mercapto group, an azido group with an unprotected or protected amino group or an amine salt group, an azido group with an acrylate group, an azido group with a methacrylate group, an azido group with an acrylic acid group, an azido group with a carboxyl group, an acrylate group with an unprotected or protected amino group or an amine salt group, an acrylate group with an isocyanato group, an acrylate group with an epoxy group, an acrylate group with a methacrylate group, an acrylate group with a carboxyl group, a methacrylate group with a carboxyl group, a methacrylate group with an unprotected or protected amino group or an amine salt group, a methacrylate group with an isocyanato group, a methacrylate group with an epoxy group, an unprotected or protected alkynyl group with an amino or a protected amino group or an amine salt group, an unprotected or protected alkynyl group with an isocyanato group, an unprotected or protected alkynyl group with an acrylate group, an unprotected or protected alkynyl group with a methacrylate group, an unprotected or protected alkynyl group with acrylic acid group, an unprotected or protected alkynyl group with an epoxy group, an unprotected or protected alkynyl group with a carboxyl group, a protected alkynyl group with an azido group, an acrylic acid group with an isocyanato group, an acrylic acid group with an acrylate group, an acrylic acid group with an epoxy group, an acrylic acid group with a carboxyl group, a carboxyl group with a mercapto group or a protected mercapto group, a carboxyl group with an unprotected or protected amino group or an amine salt group, a carboxyl group with an isocyanato group, a carboxyl group with an epoxy group, an unprotected or protected amino group or an amine salt group with an unprotected or protected mercapto group, a therapeutic targeting group with a non-hydroxyl reactive group and a photosensitive group with a non-hydroxyl reactive group.

23. The multifunctionalized polyethylene glycol according to claim 2, wherein, divalent linking groups including $L_0(F_1), L_0(F_2), L_0, L_2, L_3, L_4, L_5, L_6, W_0, W_{01}, W_{02}, Z_1(F_1), Z_2(F_1), Z_1(F_2)$ and $Z_2(F_2)$ are each independently identical or not identical in one molecule; one divalent linking group thereof, or the joint linking group formed by said group with its adjacent heterosubstituted group is independently either a STAG group or a DEGG group.

24. The multifunctionalized polyethylene glycol compound according to claim 2, wherein, said STAG group is selected from the group consisting of an alkylene group, a divalent heteroalkyl group, a carbon-carbon double bond, a carbon-carbon triple bond, a divalent dienyl group, a divalent cycloalkyl group, a divalent cycloalkenyl group, a divalent cycloalkenylhydrocarbyl group, a divalent cycloalkynyl group, an arylene group, an aliphatic-derived heteroring group, a heterophenylene group with one or more heteroatoms as ring-membering atom, an arylheteroring group, a heterocondensed heteroring group, a substituted alkylene group, a substituted heteroalkylene group, a substituted double bond, a substituted divalent dienyl group, a substituted divalent cycloalkyl group, a substituted divalent cycloalkenyl group, a substituted divalent cycloalkenylhydrocarbyl group, a substituted divalent cycloalkynyl group, a substituted arylene group, a substituted aliphatic-derived heteroring group, a substituted heterophenylene group, a substituted aryloheterorings group, a substituted herocondensed heteroring group, an ether bond, a thioether bond, a urea bond, a thiourea bond, a carbamate bond, a thiocarbamate bond, a linkage containing a —P(=O)-moiety, a linkage containing a —P(=S)-moiety, a divalent silyl group without active hydrogen atoms, a boron-containing divalent linking group, a secondary amino bond, a tertiary amino bond, a carbonyl group, a thiocarbonyl group, a —S(=O)$_2$— linkage, a —S(=O)— linkage, a 1,1-ring linkage, an amide bond, a thioamide bond, a sulfonamide bond, an enamino group, a triazole linkage, a 4,5-dihydroisoxazole linkage, the skeleton of an amino acid and derivatives thereof, and divalent linking groups formed by the combination of any two or two more divalent linkages of the foregoing; and independently, said DEGG group contains at least one divalent linkage selected from the group consisting of a disulfide bond, a vinylether bond, an ester bond, a thioester bond, a thioate bond, a dithioester bond, a carbonate bond, a thiocarbonate bond, a dithiocarbonate bond, a trithiocarbonate bond, a carbamate bond, a thiocarbamate bond, a dithiocarbamate bond, an acetal linkage, a cycloacetal linkage, a mercaptal linkage, an azaacetal linkage, an azacycloacetal linkage, an azathiaacetal linkage, a dithioacetal linkage, a hemiacetal linkage, a thiohemiacetal linkage, an azahemiacetal linkage, a ketal linkage, a thioketal linkage, an azaketal linkage, an azacycloketal linkage, an azathiaketal linkage, an imine bond, a hydrazone bond, an acylhydrazone bond, an oxime bond, a thiooxime bond, a semicarbazone bond, a thiosemicarbazone bond, a hydrazino bond, an acylhydrazino bond, a thiocarbonyl-hydrazino bond, an azocarbonyl-hydrazino linkage, an azo-thiocarbonyl-hydrazino linkage, a hydrazino formate linkage, a hydrazino thioformate linkage, a carbohydrazide bond, a thiocarbohydrazide bond, an azo bond, an isourea bond, an isothiourea bond, an allophanate linkage, a thioallophanate linkage, a guanidino linkage, an amidino linkage, an aminoguanidino linkage, an aminoamidino linkage, an iminocarbonyl-oxy linkage, an iminocarbonyl-thioxy linkage, a sulfonate linkage, a sulfinate linkage, a sulfonylhydrazino linkage, a sulfonylureido linkage, a maleimide linkage, an orthoester linkage, a phosphate linkage, a phosphirate linkage, a phosphinate linkage, a phosphonate linkage, a phosphosilicate linkage, a silicate linkage, an amide bond, a thioamide bond, a sulfonamide bond, a polyamide linkage, a phosphamide linkage, a phosphiramide linkage, a phosphinamide linkage, a phosphonamide linkage, a pyrophosphamide linkage, a cyclophosphamide linkage, an ifosfamide linkage, a thiophosphamide linkage, an aconityl linkage, a benzyloxycarbonyl linkage, a peptide fragment, the skeleton of a nucleotide and derivatives thereof, the skeleton of a deoxynucleotide and derivatives thereof, and divalent linking groups via the combination of any two or two more divalent linkages of the foregoing.

25. The multifunctionalized polyethylene glycol compound according to claim 2, wherein, said DEGG group contains at least one linkage selected from the group consisting of —S—S—, CH=CH—O—, —O—CH=CH—, —C(=O)—O—, —O—C(=O)—, —C(=O)—O—CH$_2$—, —CH$_2$—O—C(=O)—, —C(=O)—O—CH$_2$—O—C(=O)—, —C(=O)—O—CH$_2$—NH—C(=O)—, —O—C(=O)—R$_5$—C(=O)—O—, —C(=O)—S—, —S—C(=O)—, —C(=S)—O—, —O—C(=S)—, —C(=S)—S—, —S—C(=S)—, —O—C(=O)—O—, —S—C(=O)—O—, —O—C(=S)—O—, —O—C(=O)—S—, —S—C(=S)—O—, —O—C(=S)—S—, —S—C(=O)—S—, S—C(=S)—S—, —NH—C(=O)—O—, —O—C(=O)—NH—, —NH—C(=S)—O—, —O—C(=S)—NH—, —NH—C(=O)—S—, —S—C(=O)—NH—, —NH—C(=S)—S—, —S—C(=S)—NH—, —CH(OR$_3$)—O—, —O—CH(OR$_3$)—, —CH(OR$_3$)—S—, —S—CH(OR$_3$)—, —CH(SR$_3$)—O—, —O—CH(SR$_3$)—, —CH(SR$_3$)—S—, —S—CH(SR$_3$)—, —CH(OR$_3$)—NH—, —NH—CH(OR$_3$)—, —CH(NPG$_5$)-O—, —O—CH(NH$_2$)—, —CH(NH$_2$)—NH—, —NH—CH(NH$_2$)—, —(NH$_2$)C(SR$_3$)—, —CH(SR$_3$)—NH—, —NH—CH(SR$_3$)—, —CH(NH$_2$)—S—, —S—CH(NH$_2$)—, —CH (OH)—NH—, —NH—CH(OH)—, —CH(NH₂)—O—, —CH(OH)—O—, —O—CH(OH)—, —CH(OH)—S—, —S—CH(OH)—, —HC=N—, —N=CH—, —HC=N—NH—, —NH—N=CH—, —HC=N—NH—C(=O)—, —C(=O)—NH—N=CH—, —HC=N—O—, —O—N=CH—, —HC=N—S—, —S—N=CH—, —NH—C(=O)—NH—N=CH—, —HC=N—NH—C(=O)—NH—, —NH—C(=S)—NH—N=CH—, —HC=N—NH—C(=S)—NH—, —NH—NH—, —NH—NH—C(=O)—, —C(=O)—NH—NH—, —NH—NH—C(=S)—, —C(=S)—NH—NH—, —NH—NH—C(=O)—N=N—, —N=N—C(=O)—NH—NH—, —NH—NH—C(=S)—N=N—, —N=N—C(=S)—NH—NH—, —NH—NH—C(=O)—O—, —O—C(=O)—NH—NH—, —NH—NH—C(=S)—O—, —O—C(=S)—NH—NH—, —NH—NH—C(=O)—S—, —S—C(=O)—NH—NH—, —NH—NH—C(=S)—S—, —S—C(=S)—NH—NH—, —NH—NH—C(=O)—NH—NH—, —NH—NH—C(=S)—NH—NH—, —N=N—, —O—C(=NH)—NH—, —NH—C(=NH)—O—, —O—C(=NH₂⁺)—NH—, —NH—C(=NH₂⁺)—O—, —NH—C(=NH)—S—, —S—C(=NH)—NH—, —NH—C(=NH₂⁺)—S—, —S—C(=NH₂⁺)—NH—, —NH—C(=O)—NH—C(=O)—O—, —O—C(=O)—NH—C(=O)—NH—, —NH—C(=S)—NH—C(=O)—O—, —O—C(=O)—NH—C(=S)—NH—, —NH—C(=NH)—NH—, —NH—C(=NH₂⁺)—NH—NH—C(=O)—NH—C(=O)—O—, —NH—C(=NH₂⁺)—NH—, —C(=NH)—NH—, —NH—C(=NH)—, —NH—C(=NH₂⁺)—, —C(=NH₂⁺)—NH—, —NH—NH—C(=NH)—NH—, —NH—C(=NH)—NH—NH—, —NH—NH—C(=NH₂⁺)—NH—, —NH—C(=NH₂⁺)—NH—NH—, —C(=NH)—NH—NH—, —NH—NH—C(=NH)—, —NH—NH—C(=NH₂⁺)—, —C(=NH₂⁺)—NH—NH—, —C(=NH)—O—, —O—C(=NH)—, —O—C(=NH₂⁺)—, —C(=NH₂⁺)—O—, —C(=NH)—S—, —S—C(=NH)—, —S—C(=NH₂⁺)—, —C(=NH₂⁺)—S—, —S(=O)₂—O—, —O—S(=O)₂—, —S(=O)—O—, —O—S(=O)—, —S(=O)₂—NH—, —NH—S(=O)₂—, —NH—S(=O)₂—NH—, —S(=O)₂—NH—NH—, —NH—NH—S(=O)₂—, —S(=O)₂—NH—C(=O)—NH—, —NH—C(=O)—NH—S(=O)₂—, —NH—(CH₂)ᵣ₃—O—C(=O)—, —N(CH₃)—(CH₂)ᵣ₃—O—C(=O)—, —O—Si(R₄₁R₄₂)—O—, an orthocarbonate linkage, an orthosilicate linkage, an orthophosphate linkage, an orthosulfate linkage, an orthotellurate linkage, a phosphate linkage, a phosphirate linkage, a phosphinate linkage, a phosphonate linkage, a phosphosilicate linkage, a silicate linkage, an amide bond, a thioamide bond, a sulfonamide bond, a polyamide linkage, a phosphamide linkage, a phosphiramide linkage, a phosphinamide linkage, a phosphonamide linkage, a pyrophosphamide linkage, a cyclophosphamide linkage, an ifosfamide linkage, a thiophosphamide linkage, an aconityl linkage, a benzyloxycarbonyl linkage, a peptide fragment, divalent linkages deriving from a nucleotide and derivatives thereof, divalent linkages deriving from a deoxynucleotide and derivatives thereof,

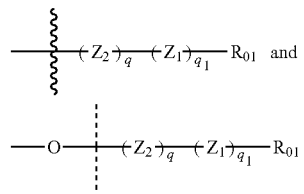

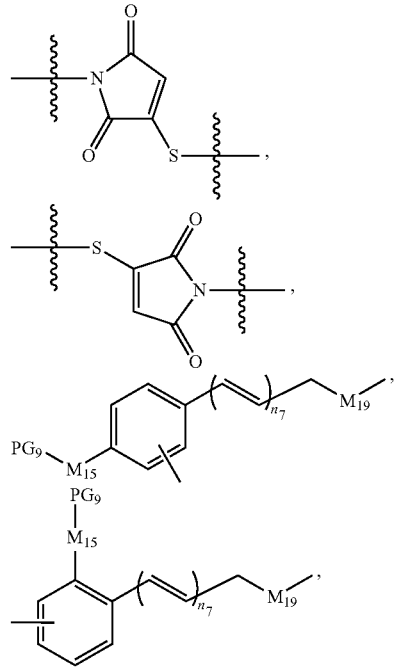

the substituted form of any divalent linkage thereof, and divalent linking groups via the combination of any two or two more divalent linkages of the foregoing;

wherein, r3 is 2, 3, 4, 5 or 6;

wherein, $R_5$ is a hydrocarbylene group or a substituted hydrocarbylene group;

wherein, $R_3$ is selected from the group consisting of a methyl group, an ethyl group, an n-propyl group, an isopropyl group, a butyl group, a pentyl group, a hexyl group, a heptyl group, an octyl group, a nonyl group, a decyl group, a benzyl group, an allyl group, and the substituted form of any said group thereof;

wherein, $PG_5$ is an amino protecting group;

wherein, $R_{41}$ and $R_{42}$ are each independently a $C_{1-20}$ alkyl group, a phenyl group, a benzyl group, a phenyl group substituted with a $C_{1-20}$ alkyl substituent, a benzyl group substituted with a $C_{1-20}$ alkyl substituent, or a $C_{1-20}$ alkoxy group;

wherein, $M_{15}$ is a heteroatom selected from an oxygen atom, a sulfur atom and a nitrogen atom; $PG_9$ is the protecting group for $M_{15}$, corresponding to a hydroxyl protecting group, a mercapto protecting group or an amino protecting group, respectively;

wherein, $M_{19}$ is an oxygen atom or a sulfur atom;

wherein, $n_7$ is zero or an integer from 1 to 10.

26. The multifunctionalized polyethylene glycol compound according to claim 1, wherein, $$\underset{\xi}{\xi}-(Z_2)_q-(Z_1)_{q_1}-R_{01} \text{ and}$$

$$-O-\mid-(Z_2)_q-(Z_1)_{q_1}-R_{01}$$

are the unprotected or protected form of a function group deriving from one structure selected from the group consisting of active esters, analogs of active esters, an acetic acid, a propionic acid, a butyric acid, a pentanoic acid, a hexanoic acid, an oxalic acid, a malonic acid, a methylmalonic acid, an ethylmalonic acid, a butylmalonic acid, a succinic acid, a 2-methylsuccinic acid, a 2,2-dimethylsuccinic acid, a 2-ethyl-2-methylsuccinic acid, a 2,3-dimethylsuccinic acid, a glutaric acid, a 2-methylglutaric acid, a 3-methylglutaric acid, a 2,2-dimethylglutaric acid, a 2,3-dimethylglutaric acid, a 3,3-dimethylglutaric acid, an adipic acid, a maleic acid, a fumaric acid, an amino acid, apeptide acid, a poly(amino acid), a squaric acid, an acetaldehyde, a propionaldehyde, a butanal, a pentanal, a hexanal, a benzaldehyde, a tolunaldehyde, a methanol, an ethanol, a propanol, a butanol, a pentanol, a hexanol, a propylene, a propyne, an ethanthiol, a propanthiol, a butanthiol, a pentanthiol, a hexanthiol, a propionitrile, a cyanacetic acid, a vinylsulfone, a vinyl sulfoxide, a p-methylphenylsulfone, a p-methylphenylsulfoxide, a vinylsulfonyl-ethyl group, a vinylsulfoxide-ethyl group, a p-methylphenylsulfonyl-ethyl group, a p-methylphenylsulfoxide-ethyl group, a p-methylbenzenesulfonate, a hydroxylamine, an azidoethyl group, an azidopropyl group, an azidobutyl group, an azidopentyl group, an azidohexyl group, an orthopyridyldisulfide group, a lipoic acid, an acetamide, a propanamide, a butyramide, a pentanamide, a hexanamide, an acethydrazide, a daminozide, a pentanehydrazide, a hexanohydrazide, an acetylhydroxylamine, a propionylhydroxylamine, a butyrylhydroxylamine, a pentanoylhydroxylamine, a hexanoylhydroxylamine, a heptanoylhydroxylamine, an isoxazolylethyl group, a tetrazolylethyl group, an isocyanatoethyl group, an isothiocyanatoethyl group, a glycidyl group, a maleimide, an acrylate, a methyl acrylate, a propynoate, a squarate, a carbonate, a trithiocarbonate-ethyl group, an acetate, an ethanethioate, an alkyloxy(thiocarbonyl) group, an alkylthio(thiocarbonyl) group, a chloroformyloxy group, an acetylchloride, an acetylbromide, an iodoacetamidopropyl group, an ethylamine, a propylamine, a butylamine, a pentylamine, a hexylamine, amino acid esters, a cyclooctenyl group, a norbornenyl-azo group, a diazo group, a dienyl group, a dienylhydrocarbyl group, a tetrazolylgroup, a cyclopentadienyl group, a 2,5-norbomadienyl group, a dicycloheptadienyl group, a 7-oxabicyclo[2.2.1]hept-5-en-2-yl group, a furyl group, a 1,2,4,5-tetrazinyl group, a cycloalkynyl group and a benzocycloalkynyl group.

27. The multifunctionalized polyethylene glycol compound according to claim 19, wherein, said multifunctionalized polyethylene glycol compound has a structure represented by any of the following general formulas including general formula (13), general formula (14), general formula (15), general formula (16), general formula (17) and general formula (18);

wherein, said identical structure types mean that all are of a tribranched type, a tetrabranched type, a comb-like type, a dendritic type, a hyperbranched type, or a ring-containing structure type;

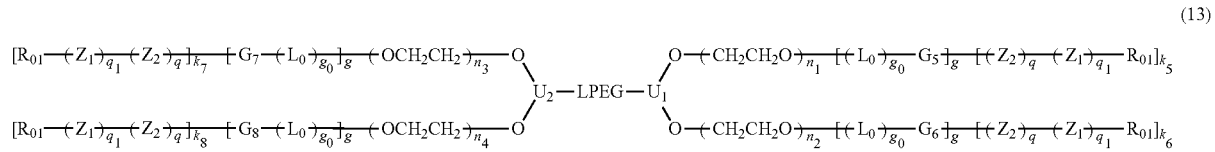

(13)

wherein, in general formula (13), those in quantities of four or four more including $Z_2$, q, $Z_1$, $q_1$, $R_{01}$, $L_0$, $g_0$ and g are each independently identical in one molecule; $k_5$, $k_6$, $k_7$ and $k_8$ are each independently an integer from 2 to 250, and can be identical or not identical in one molecule; the definitions of $G_5$, $G_6$, $G_7$ and $G_8$ are each independently a linking group of trivalence or higher valence with a valence of $k_5+1$, $k_6+1$, $k_7+1$ and $k_8+1$, respectively;

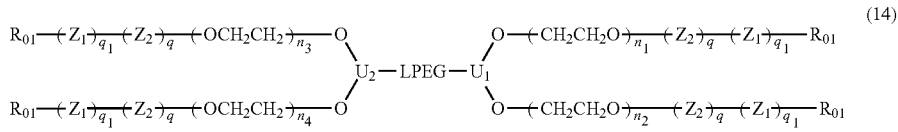

(14)

wherein, in general formula (14), those in quantities of four or four more including $Z_2$, q, $Z_1$, $q_1$ and $R_{01}$ are each independently identical in one molecule;

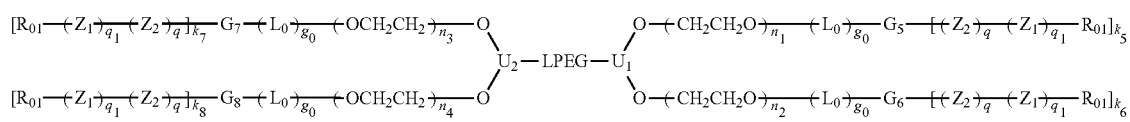

(15)

wherein, in general formula (15), those in quantities of four or four more including $Z_2$, q, $Z_1$, $q_1$, $R_{01}$, $L_0$ and $g_0$ are each independently identical in one molecule; $k_5$, $k_6$, $k_7$, $k_8$, $G_5$, $G_6$, $G_7$ and $G_5$ are defined the same as those in general formula (13), but $G_5$, $G_6$, $G_7$ and $G_8$ have identical structure types;

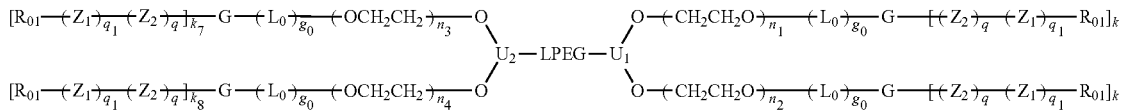
(16)

wherein, in general formula (16), those in quantities of four or four more including $Z_2$, $q$, $Z_1$, $q_1$, $R_{01}$, $k$, $L_0$ and $g_0$ are each independently identical in one molecule; $k$ is an integer from 2 to 250 and four G groups have identical structure types.

28. The multifunctionalized polyethylene glycol compound according to claim 19, wherein, said multifunctionalized polyethylene glycol compound has a structure represented by any of the following general formulas including general formula (19), general formula (20) and general formula (21);

wherein, the definitions of $L_{02}$, $g_{02}$, $Z_8$, $q_8$, $Z_7$, $q_7$ and Roz are the same as $L_0$, $g_0$, $Z_2$, $q$, $Z_1$, $q_1$ and $R_{01}$, respectively; $k_5$, $k_6$, $k_7$ and $k_8$ are each independently an integer from 2 to 250, and can be identical or not identical in one molecule; $G_5$, $G_6$, $G_7$ and $G_8$ are each independently a linking group of trivalence or higher valence with a valence of $k_5+1$, $k_6+1$, $k_7+1$, $k_8+1$, respectively;

wherein, said identical structure types mean that all are of a tribranched type, a tetrabranched type, a comb-like type, a dendritic type, a hyperbranched type, or a ring-containing structure type;

wherein, in general formula (21), those in quantities of two or two more including $Z_2$, $q$, $Z_1$, $q_1$, $R_{01}$, $Z_8$, $q_8$, $Z_7$, $q_7$, $R_{02}$, $L_0$, $g_0$, $L_{02}$ and $g_{02}$ are each independently identical in one molecule; in one molecule, the structure type of $G_5$ and $G_6$ are identical; the structure type of $G_7$ and $G_8$ are identical; the structure type of $G_5$ and $G_7$ can be identical or different;

in general formula (19), (20) and (21),

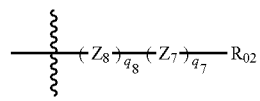

is different from

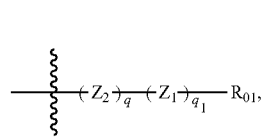

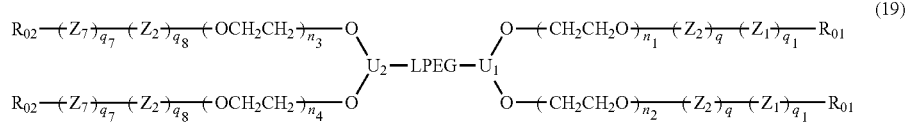
(19)

wherein, in general formula (19), those in quantities of two or two more including $Z_2$, $q$, $Z_1$, $q_1$, $R_{01}$, $Z_8$, $q_8$, $Z_7$, $q_7$ and Roz are each independently identical in one molecule;

but $L_{02}$ and $L_0$, $g_{02}$ and $g_0$, $Z_8$ and $Z_2$, $q_8$ and $q$, $Z_7$ and $Z_1$, $q_7$ and $q_1$, $R_{02}$ and $R_{01}$, are each independently identical or different, respectively.

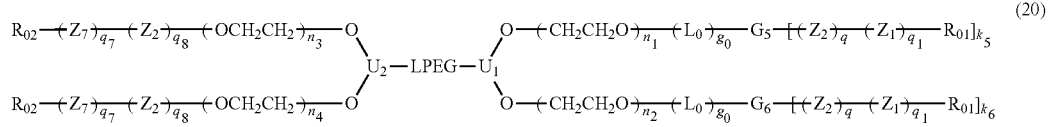
(20)

wherein, in general formula (20), those in quantities of two or two more including $Z_2$, $q$, $Z_1$, $q_1$, $R_{01}$, $Z_8$, $q_8$, $Z_7$, $q_7$, $R_{02}$, $L_0$ and $g_0$ are each independently identical in one molecule; $G_5$ and $G_6$ have identical structure types;

29. The multifunctionalized polyethylene glycol compound according to claim 28, wherein, said Roz and $R_{01}$ are different.

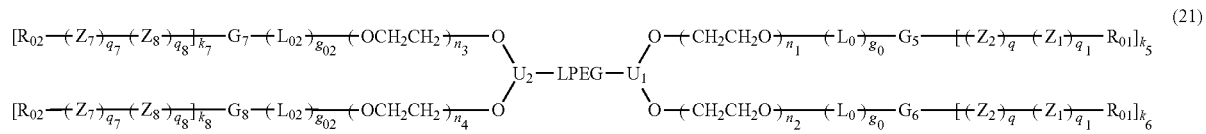
(21)

30. The multifunctionalized polyethylene glycol compound according to claim 1, wherein, said multifunctionalized polyethylene glycol compound has a structure represented by general formula (22);

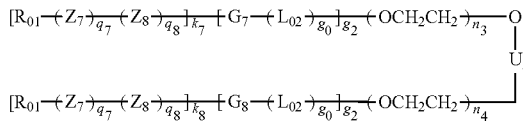
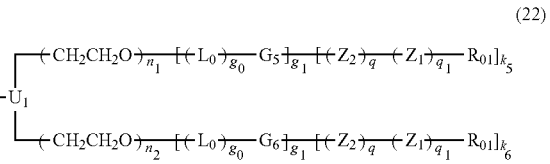

(22)

wherein, the definitions of $L_{02}$, $g_{02}$, $Z_8$, $q_8$, $Z_7$, $q_7$ and $R_{02}$ are the same as $L_0$, $g_0$, $Z_2$, $q$, $Z_1$, $q_1$ and $R_{01}$, respectively;

wherein, those in quantities of two including those in quantities of two or two more including $Z_2$, q, $Z_1$, $q_1$, $R_{01}$, $Z_8$, $q_8$, $Z_7$, $q_7$, $R_{02}$, $L_0$, $g_0$, $L_{02}$ and $g_{02}$ are each independently identical in one molecule;

wherein, $g_1$ and $g_2$ are each independently 0 or 1, and can be identical or different in one molecule;

wherein, $k_5$, $k_6$, $k_7$ and $k_8$ are each independently an integer of 1 or from 2 to 250, and can be identical or not identical in one molecule;

wherein, $G_5$, $G_6$, $G_7$ and $G_8$ are each independently a linking group of trivalence or higher valence with a valence of $k_5+1$, $k_6+1$, $k_7+1$, $k_8+1$, respectively;

when $g_1$ is 0, both $k_5$ and $k_6$ are equal to 1; when $g_1$ is 1, $k_5$ and $k_6$ are each independently an integer from 2 to 250, and can be identical or different in one molecule;

when $g_2$ is 0, both $k_7$ and $k_8$ are equal to 1; when $g_2$ is 1, $k_7$ and $k_8$ are each independently an integer from 2 to 250, and can be identical or different in one molecule;

in one molecule, the structure type of $G_5$ and $G_6$ are identical; the structure type of $G_7$ and $G_8$ are identical; the structure type of $G_5$ and $G_7$ can be identical or different;

wherein, $R_{01}$ and $R_{02}$ are each independently an unprotected or protected functional group; $R_{01}$ and $R_{02}$ are different, and at least one of $R_{01}$ and $R_{02}$ is a hydroxyl group, a protected hydroxyl group, a therapeutic targeting group or a photosensitive group.

31. The multifunctionalized polyethylene glycol compound according to claim 30, wherein, said therapeutic targeting group is one targeting group deriving from one of the following Groups (1) to (7), or is a functional derivative of said targeting group; wherein, Group (1) consists of targeting moieties selected from polypeptide ligands, small molecule ligands, viruses, vaccines, biomacromolecular targeting factors, vitamins and targeting drugs;

Group (2) consists of targeting factors that have a target site selected from the group consisting of CD3, CD11, CD20, CD22, CD25, CD30, CD33, CD41, CD44, CD52, CD6, CD3, CD11a, Her2, GpIIb/IIIa, RANKL, CTLA-4, CO17-1A, IL-1β, IL-12/23, IL6, IL13, IL-17, Blys, RSV, IgE-25, integrin-a4, respiratory syncytial virus F-protein, tumor necrosis factor α, vascular endothelial growth factors, epidermal growth factor receptors, FGR3, EGFL-7 and interferon-α;

Group (3) consists of targeting factors that are directed to a tissue or organ selected from the group consisting of brain, lung, kidney, stomach, liver, pancreas, breast, prostate, thyroid, uterus, ovary, nasopharynx, esophagus, rectum, colon, small intestine, gall bladder, bladder, bone, glands, skin, blood vessel, lymph, joints and soft tissues;

Group (4) consists of targeting factors that are directed to tumor tissue, inflammatory tissue or diseased tissue;

Group (5) consists of ligands that can be recognized by cell surface receptors and ligand variants, ligands targeting tumor-associated angiogenesis, ligands targeting tumor cell apoptosis, disease cell cycle targeting ligands, disease receptor targeting ligands, kinase inhibitors or protease inhibitors, PI3K/Akt/mTOR inhibitors, angiogenesis inhibitors, cytoskeletal signaling inhibitors, stem cells and Wnt-inhibitors, protease inhibitors, tyrosine kinase inhibitors, apoptosis inhibitors, MAPK inhibitors, cell cycle inhibitors, TGF-beta/Smad inhibitors, nerve signal inhibiting peptides, endocrine and hormone inhibitors, metabolic inhibitors, microbial inhibitors, epigenetic inhibitors, JAK/STAT inhibitors, DNA damage inhibitors, NF-κB inhibitors, GPCR & G protein inhibitors, transmembrane transport protein inhibitors, autophagy inhibitors, ubiquitin inhibitors, multitarget inhibitors, receptors, antibodies and gene targeting molecules;

Group (6) consists of targeting moieties selected from agonists, activating agents, activators, inhibitors, antagonists, modulators, receptors, ligands or aptamers, antibodies and fragments of any of the foregoing targeting moieties in Group (1) to (5);

Group (7) consists of targeting moieties selected from a monomer, a dimer, a multimer, a subunit and fragments thereof, a precursor, an activated form, a derivative, an isomer, a mutant, an analogue, a mimetics, a polymorph, a pharmaceutically acceptable salt, a fusion protein, a chemically modified substance and a genetic recombinant substance of any of the foregoing targeting moieties in Group (1) to (6).

32. The multifunctionalized polyethylene glycol compound according to claim 30, wherein, said photosensitive group is one functional group deriving from Group (1) and Group (2), or is a functional derivative of said photosensitive group;

wherein, Group (1) consists of trypan blue, Coomassie Brilliant Blue, crystal violet, pyrogallol red and phenylamyl ketone;

Group (2) consists of fluorescent proteins, rhodamines and derivatives thereof, phalloidin and derivatives thereof, cyanine dyes, acridines, phycoerythrin, phycocyanin, methyl green, alizarin red, aniline blue, pyronin, fluoresceins, hematoxylin, eosin, neutral red, fuchsin, Alexa Fluor dyes, Oregon green dyes, BODIPY dyes, Cy3, Cy3.5, Cy5, Cy5.5, Cy7, Cy7.5, Hex, PerCP, DAPI, Hoechst dyes, Cascade blue, Astrazon dyes, SYTO dyes, stilbene dyes, naphthalimide dyes, coumarin dyes, pyrene dyes, phenanthridine dyes, porphyrin dyes, indole dyes, chromomycin A, ethidium bromide and purpurin.

33. The multifunctionalized polyethylene glycol compound according to claim 1, wherein, said multifunctionalized polyethylene glycol compound has a structure as follows:

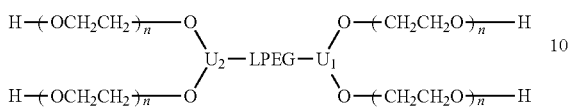

wherein, n is an integer from 5 to 2000.

34. A multifunctionalized polyethylene glycol compound represented by the following general formula (1):

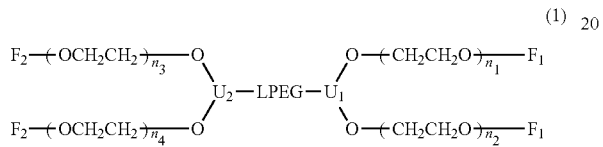

wherein, $F_1$ and $F_2$ are each independently an unprotected or protected functional group which contains at least one $R_{01}$ group, wherein the two $F_1$ groups have identical or different $R_{01}$ groups, the two $F_2$ groups have identical or different $R_{01}$ groups, but the combination of $R_{01}$ groups of $F_1$ are the same of that of $F_2$;

wherein, LPEG, $U_1$, $U_2$, $n_1$, $n_2$, $n_3$, $n_4$ and $R_{01}$ are the same as those defined in the general formula (1) of claim 1.

35. A substance composed of multifunctionalized polyethylene glycol molecules according to claim 1, wherein, the PDI value of the whole substance is equal to or greater than 1.

36. The substance composed of multifunctionalized polyethylene glycol molecules according to claim 35, wherein, the PDI value of LPEG main chain, PEG branches or combination thereof is selected from one of the following Groups:

Group (1): the PDI value of LPEG is greater than 1 corresponding to a number average degree of polymerization selected from 10 to about 1000;

Group (2): the PDI value of LPEG consisting of two PEG blocks is equal to 1 corresponding to an oxyethylene-unit number selected from 10 to 140;

Group (3): the PDI value of LPEG consisting of three PEG blocks is equal to 1 corresponding to an oxyethylene-unit number selected from 10 to 210;

Group (4): the PDI value of LPEG consisting of four or four more PEG blocks is equal to 1 corresponding to an oxyethylene-unit number selected from 10 to 500;

Group (5): the PDI value of one PEG branch chain is greater than 1 corresponding to a number average degree of polymerization selected from 5 to about 2000;

Group (6): the PDI value of one PEG branch chain is equal to 1 corresponding to an oxyethylene-unit number selected from 5 to 70;

Group (7): the PDI value of all the PEG branch chains are greater than 1 corresponding to a number average degree of polymerization selected from 5 to about 2000; and the PDI value of LPEG equal to 1 corresponding to an oxyethylene-unit number selected from 10 to 140, from 10 to 210 or from 10 to 500;

Group (8): the PDI value of two of the PEG branch chains are greater than 1 corresponding to a number average degree of polymerization selected from 5 to about 2000; and the PDI value of the other two PEG branch chains are equal to 1 corresponding to an oxyethylene-unit number selected from 5 to 70;

Group (9): the PDI value of all the PEG branch chains are equal to 1 corresponding to an oxyethylene-unit number selected from 5 to 70; and the PDI value of LPEG is greater than 1 corresponding to a number average degree of polymerization selected from 10 to about 1000;

Group (10): the PDI value of LPEG is greater than 1 corresponding to a number average degree of polymerization selected from 10 to about 1000, and the PDI value of all the PEG branch chains are greater than 1 corresponding to a number average degree of polymerization selected from 5 to about 2000;

Group (11): the PDI value of all the PEG branch chains are equal to 1 corresponding to an oxyethylene-unit number selected from 5 to 70, and the PDI value of LPEG is equal to 1 corresponding to an oxyethylene-unit number selected from 10 to 140, from 10 to 210 or from 10 to 500.

* * * * *